US012478621B2

(12) United States Patent
Schmees et al.

(10) Patent No.: US 12,478,621 B2
(45) **Date of Patent: *Nov. 25, 2025**

(54) SUBSTITUTED AMINOQUINOLONES AS DGKALPHA INHIBITORS FOR IMMUNE ACTIVATION

(71) Applicants: Bayer Aktiengesellschaft, Leverkusen (DE); Bayer Pharma Aktiengesellschaft, Berlin (DE); Deutsches Krebsforschungszentrum, Heidelberg (DE)

(72) Inventors: Norbert Schmees, Berlin (DE); Lars Wortmann, Biberbach an der Riß (DE); Dennis Kirchhoff, Berlin (DE); Thi Thanh Uyen Nguyen, Berlin (DE); Nicolas Werbeck, Freiburg (DE); Ulf Bömer, Glienicke (DE); Kirstin Petersen, Berlin (DE); Christina Kober, Lollar (DE); Detlef Stöckigt, Potsdam (DE); Christian Lechner, Berlin (DE); Robin Michael Meier, Wain (DE); Simon Anthony Herbert, Berlin (DE); Isabel Patrizia Kerschgens, Zürich (CH); Dirk Kosemund, Berlin (DE); Rienk Offringa, Heidelberg (DE); Mareike Grees, Berlin (DE); Benjamin Bader, Berlin (DE)

(73) Assignees: Deutsches Krebsforschungszentrum (DE); Bayer Pharma Aktiengesellschaft (DE); Bayer Aktiengesellschaft (DE)

( * ) Notice: Subject to any disclaimer, the term of this patent is extended or adjusted under 35 U.S.C. 154(b) by 529 days.

This patent is subject to a terminal disclaimer.

(21) Appl. No.: 17/780,890

(22) PCT Filed: Nov. 24, 2020

(86) PCT No.: PCT/EP2020/083198

§ 371 (c)(1),
(2) Date: May 27, 2022

(87) PCT Pub. No.: WO2021/105117

PCT Pub. Date: Jun. 3, 2021

(65) Prior Publication Data

US 2023/0148194 A1 May 11, 2023

(30) Foreign Application Priority Data

Nov. 28, 2019 (EP) .................................... 19212252
Jun. 19, 2020 (EP) .................................... 20181065

(51) Int. Cl.
*A61K 31/4545* (2006.01)
*A61K 31/4709* (2006.01)
(Continued)

(52) U.S. Cl.
CPC ...... *A61K 31/4545* (2013.01); *A61K 31/4709* (2013.01); *A61K 31/4725* (2013.01);
(Continued)

(58) Field of Classification Search
CPC ............ A61K 31/4545; A61K 31/4709; A61K 31/4725; A61K 31/496; A61K 31/498;
(Continued)

(56) References Cited

U.S. PATENT DOCUMENTS 5,679,689 A 10/1997 Petersen et al.
10,357,484 B2 7/2019 Kaieda
(Continued)

FOREIGN PATENT DOCUMENTS

CN 1126211 A 7/1996
CN 1867335 A 11/2006
(Continued)

OTHER PUBLICATIONS

Lipson et al., Antagonists of PD-1 and PD-L1 in Cancer Treatment, Seminars in Oncology, vol. 42, No. 4, 587-600, Aug. 1, 2016 (Year: 2016).*
(Continued)

*Primary Examiner* — Sarah Pihonak
*Assistant Examiner* — Padmaja S Rao
(74) *Attorney, Agent, or Firm* — MORRISON & FOERSTER LLP

(57) ABSTRACT

The present invention covers aminoquinolone compounds of general formula (I), in which R1, R2, R3, R4, R5, R6, R7, R8 and n are as defined herein, methods of preparing said compounds, intermediate compounds useful for preparing said compounds, pharmaceutical compositions and combinations comprising said compounds and the use of said compounds for manufacturing pharmaceutical compositions for the treatment and/or prophylaxis of diseases, in particular of diacylglycerol kinase alpha regulated disorders, as a sole agent or in combination with other active ingredients.

(I)

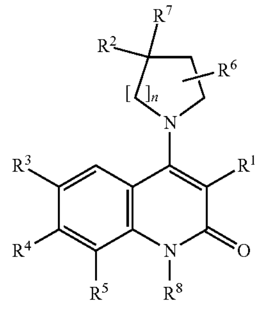

17 Claims, 5 Drawing Sheets

Specification includes a Sequence Listing.

(51) Int. Cl.

| | |
|---|---|
| ***A61K 31/4725*** | (2006.01) |
| ***A61K 31/496*** | (2006.01) |
| ***A61K 31/498*** | (2006.01) |
| ***A61K 31/55*** | (2006.01) |
| ***A61K 45/06*** | (2006.01) |
| ***A61P 35/00*** | (2006.01) |
| ***A61P 37/04*** | (2006.01) |
| ***C07D 401/04*** | (2006.01) |
| ***C07D 401/14*** | (2006.01) |
| ***C07D 405/14*** | (2006.01) |
| ***C07D 413/14*** | (2006.01) |
| ***C07D 417/14*** | (2006.01) |

(52) U.S. Cl.

CPC .......... *A61K 31/496* (2013.01); *A61K 31/498* (2013.01); *A61K 31/55* (2013.01); *A61K 45/06* (2013.01); *A61P 35/00* (2018.01); *A61P 37/04* (2018.01); *C07D 401/04* (2013.01); *C07D 401/14* (2013.01); *C07D 405/14* (2013.01); *C07D 413/14* (2013.01); *C07D 417/14* (2013.01)

(58) Field of Classification Search

CPC ...... A61K 31/55; A61K 45/06; A61K 31/497; A61K 31/5377; A61K 31/541; A61P 35/00; A61P 37/04; C07D 215/22; C07D 215/54; C07D 401/04; C07D 401/14; C07D 405/12; C07D 405/14; C07D 409/14; C07D 413/14; C07D 417/14; C07D 513/04; C07D 215/227

See application file for complete search history.

(56) References Cited

U.S. PATENT DOCUMENTS

| | | | |
|---|---|---|---|
| 10,889,591 | B2 | 1/2021 | Wu et al. |
| 11,542,492 | B2 | 1/2023 | Petter |
| 11,998,539 | B2 | 6/2024 | Schmees |
| 2005/0009838 | A1 | 1/2005 | Barta et al. |
| 2007/0015802 | A1 | 1/2007 | Lal et al. |
| 2013/0053362 | A1 | 2/2013 | Castro et al. |
| 2015/0232481 | A1 | 8/2015 | Naidu et al. |
| 2021/0277004 | A1 | 9/2021 | Chupak et al. |
| 2022/0064141 | A1 | 3/2022 | Fang et al. |
| 2022/0081409 | A1 | 3/2022 | Wan et al. |
| 2022/0089593 | A1 | 3/2022 | Wu |
| 2023/0062100 | A1 | 3/2023 | Schmees et al. |
| 2023/0064809 | A1 | 3/2023 | Schmees et al. |
| 2023/0148194 | A1 | 5/2023 | Schmees et al. |
| 2023/0201186 | A1 | 6/2023 | Schmees et al. |

FOREIGN PATENT DOCUMENTS

| | | | |
|---|---|---|---|
| CN | 102812167 | A | 12/2012 |
| CN | 103002738 | A | 3/2013 |
| EP | 0705828 | A1 | 4/1996 |
| EP | 3939588 | A1 | 1/2022 |
| JP | 2005-170792 | A | 6/2005 |
| WO | 0018761 | A1 | 4/2000 |
| WO | 2004004632 | A2 | 1/2004 |
| WO | 2004074218 | A2 | 9/2004 |
| WO | 2005018641 | A2 | 3/2005 |
| WO | 2005087752 | A2 | 9/2005 |
| WO | 2006011040 | A1 | 2/2006 |
| WO | 2007030061 | A1 | 3/2007 |
| WO | 2007109251 | A2 | 9/2007 |
| WO | 2010042867 | A2 | 4/2010 |
| WO | 2011070080 | A1 | 6/2011 |
| WO | 2011146882 | A1 | 11/2011 |
| WO | 2012009649 | A1 | 1/2012 |
| WO | 2012142498 | A2 | 10/2012 |
| WO | 2013032591 | A1 | 3/2013 |
| WO | 2015074064 | A2 | 5/2015 |
| WO | 2016044772 | A1 | 3/2016 |
| WO | 2016197027 | A1 | 12/2016 |
| WO | 2017014170 | A1 | 1/2017 |
| WO | 2017019723 | A1 | 2/2017 |
| WO | 2017101763 | A1 | 6/2017 |
| WO | 2017106607 | A1 | 6/2017 |
| WO | 2017158619 | A1 | 9/2017 |
| WO | 2019062733 | A1 | 4/2019 |
| WO | 2019111218 | A1 | 6/2019 |
| WO | 2019125849 | A1 | 6/2019 |
| WO | 2019241157 | A1 | 12/2019 |
| WO | 2020006016 | A1 | 1/2020 |
| WO | 2020006018 | A1 | 1/2020 |
| WO | 2020025517 | A1 | 2/2020 |
| WO | 2020143626 | A1 | 7/2020 |
| WO | 2020151636 | A1 | 7/2020 |
| WO | 2020182076 | A1 | 9/2020 |
| WO | 2020207991 | A1 | 10/2020 |
| WO | 2021041588 | A1 | 3/2021 |

OTHER PUBLICATIONS

Riese et al., Diacylglycerol Kinases (DGKs): Novel Targets for Improving T Cell Activity in Cancer, Frontiers in Cell and Developmental Biology, vol. 4, No. 108, Oct. 17, 2016 (Year: 2016).*

Arranz-Nicolas et al. (2018). "Diacylglycerol kinase a inactivation is an integral component of the costimulatory pathway that amplifies TCR signals," Canc Immun, Immunother 67(6), 965-980.

Ashford, M.E. et al. (2014). "Synthesis and in vitro evaluation oftetrahydroisoquinolines with pendent aromatics as sigma-2 (σ2) selective ligands," Org. Biomol. Chem., 12:783-794.

B. K. Singh et al., (Sep. 3, 2019) "Diacylglycerol kinase ζ promotes allergic airway inflammation and airway hyperresponsiveness through distinct mechanisms," Sci. Signal; 12:1-13.

Bacchiocchi, R. at al., (Sep. 15, 2005) "Activation of α-diacylglycerol kinase is critical for the mitogenic propertiesof anaplastic lymphoma kinase," Blood, 106(6):2175-2182.

C. L. Dominguez et al., (Jul. 2013) "Diacylglycerol kinase alpha is a critical signaling node and novel therapeutic target in glioblastoma and other cancers," Cancer Discov.; 3(7):782-797.

Conway, R.J. et al. (2012). "Synthesis and SAR study of 4-arylpiperidines and 4-aryl-1,2,3,6-tetrahydropyridines as 5-HT2C agonists," 22: 2560-2564.

Culkin, D.A., et al. (2002). "Synthesis, Characterization, and Reactivity of Arylpalladium Cyanoalkyl Complexes: Selection of Catalysts for the a-Arylation of Nitriles," J. Am. Chem. Soc., 124:9330-9331.

D. R. Jones et al., (Jun. 11, 1999) "Interleukin-2 Causes an Increase in Saturated/Monounsaturated Phosphatidic Acid Derived from 1,2-Diacylglycerol and 1-O-Alkyl-2-acylglycerol," Journal of Biological Chemistry; 274(24):16846-16852.

de Chaffoy de Courcelles, D. et.al. (1985). "R 59 022, a Diacylglycerol Kinase Inhibitor," J. Biol. Chem. 260 (29):15762-15770.

Duan, Z. et al. (2016). "Nickel-Catalyzed Reductive Cross-Coupling of Aryl Bromides with Alkyl Bromides: Et3N as the Terminal Reductant" Org. Lett. 18:4012-4015.

E. J. Quann et al., (2011) "A Cascade of Protein Kinase C Isozymes Promotes Cytoskeletal Polarization in T Cells," Nay Immunol; 12(7):647-654.

E. Rainero et al., (Jun. 2014) "The Diacylglycerol Kinase α/Atypical PKC/β1 Integrin Pathway in SDF-1α Mammary Carcinoma Invasiveness," Plos One; 9(6):1-15.

E. Ruffo et al., "Inhibition of diacylglycerol kinase alpha restores restimulation-induced cell death and reduces immunopathology in XLP-1," Sci Transl Med.; 8(321):1-27.

Filigheddu, N. et al., (2007) "Diacylglycerol Kinase is Required for HGF-induced Invasiveness and Anchorage-Independent Growth of MDA-MB-231 Breast Cancer Cells," Anticancer Research; 27:1489-1492.

G. Baldanzi et al. (2008) "Diacylglycerol kinase-α phosphorylation by Src on Y335is required for activation, membrane recruitment and Hgf-induced cell motility," Oncogene, 27:942-956.

(56) References Cited

OTHER PUBLICATIONS

Hao, X. et al., (Mar. 15, 2004) "Differential Gene and Protein Expression in Primary Breast Malignancies and Their Lymph Node Metastases as Revealed by Combined cDNA Microarray and Tissue Microarray Analysis," American Cancer Society, 100(6):1110-1122.
Huang, G. et al., (2014) "A simple heterocyclic fusion reaction and its application for expeditious syntheses of rutaecarpine and its analogs, " Tetrahedron Letters; 55:3607-3609.
J. Chen et al., (2019) "The diacylglycerol kinase α (DGKα)/Akt/NF-κB feedforward loop promotes esophageal squamous cell carcinoma (ESCC) progression via FAK-dependent and FAK-independent manner," Oncogene, 38:2533-2550.
Joshi, R.P., et al. (2013). "Diacylglycerol Kinases: Regulated Controllers of T Cell Activation, Function, and Development," Int. J. Mol. Sci. 14: 6649-6673.
Jung, I-Y. et al., (2018) "Unleashing the Therapeutic Potential of CAR-T Cell Therapy Using Gene-Editing Technologies," Mol. Cells; 41(8):712-723.
Jung, I-Y. et al., (Aug. 15, 2018) "CRISPR/Cas9-Mediated Knockout of DGK Improves Antitumor Activities of Human T Cells," Cancer Res; 78(16):4692-4703.
K. Takeishi et al., (2012) "Diacylglycerol kinase alpha enhances hepatocellular carcinoma progression by activation of Ras-Raf-MEK-ERK pathway," Journal of Hepatology; 57:77-83.
K. Yanagisawa et al., (2007) "Diacylglycerol kinase α suppresses tumor necrosis factor-α-induced apoptosis of human melanoma cells through NF-κB activation," Biochimica et Biophysica Acta; 1771:462-474.
Keir, M.E. et al. (2008, e-pub. Jan. 2, 2008). "PD-1 and Its Ligands in Tolerance and Immunity," Annu. Rev. Immunol. 26:677-704.
Kobayashi, T. et al., (2006). "Synthesis of 2,4,6-Trisubstituted ChiralPiperidines and (−)-Dendroprimine by One-Pot Asymmetric Azaelectrocyclization Protocol," Organic Letters, 8(17):3813-3816.
Krishna, S. et al., (Jul. 2013) "Regulation of lipid signaling by diacylglycerol kinases during T cell development and function," T Cell Biology; 4:1-14.
Lambert-Van Der Brempt, C. et al. (1994). "Conformational Analysis of 5-Lipoxygenase Inhibitors: Role of the Substituents in Chiral Recognition and on the Active Conformations of the (Methoxyalkyl)thiazole and Methoxytetrahydropyran Series," J. Med. Chem., 37:113-124.
M. J. Riese et al., (Feb. 18, 2011) "Decreased Diacylglycerol Metabolism Enhances ERK Activation and Augments CD8+ T Cell Functional Responses," Journal of Biological Chemistry; 286(7):5254-5265.
Martin, R. et al. (2008). "An Improved Protocol for the Pd-catalyzed a-Arylation of Aldehydes with Aryl Halides," Org Lett. 10(20):4561-4564.
Munoz, J. et al. (2011). "Application of flow chemistry to the reduction of nitriles to aldehydes," Tetrahedron Letters, 52:6058-6060.
Nantermet, P.G. et al. (2000). "Selective 1a Adrenergic Receptor Antagonists Based on 4-Aryl-3,4-dihydropyridine-2-ones" Bioorganic & Medicinal Chemistry Letters, 10: 1625-1628.
Olenchock, B. A. et al., (Nov. 2006) "Disruption of diacylglycerol metabolism impairs the induction of T cell anergy," Nature Immunology; 7(11)1174-1181.
P. U. Prinz et al., (May 9, 2012) "High DGK-α and Disabled MAPK Pathways Cause Dysfunction of Human Tumor-Infiltrating CD8+ T Cells That Is Reversible by Pharmacologic Intervention," J Immunol; 188:5990-6000.
Park, J.S. et al. (2016). "Discovery and SAR of N-(1-((substituted piperidin-4-yl)methyl)-3-methoxypiperidin-4-yl)-2-methoxybenzamide derivatives: 5-Hydroxytryptamine receptor 4 agonist as a potent prokinetic agent," European Journal of Medicinal Chemistry, 109:75-88.
Phelan, J.P. et al. (2018). "Redox-Neutral Photocatalytic Cyclopropanation via Radical/Polar Crossover," J. Am. Chem. Soc. 140:8037-8047.
Prinz, P.U. et al. (2012). "High DGK-α and Disabled MAPK Pathways Cause Dysfunction of Human Tumor-Infiltrating CD8+ T Cells Thatis Reversible by Pharmacologic Intervention," J. Immunol 188: 5990-6000.
Rainero, E. et al., (2012) "Diacylglycerol kinase α controls RCP-dependent integrin trafficking to promote invasive migration," JCB; 196(2):277-295.
Rhoden, J.B. et al. (2005). "Structure-activity studies of 3'-4'-dichloro-meperidine analogues at dopamine and serotonin transporters," Bioorganic & Medicinal Chemistry, 13:5623-5634.
Riese, M. J. et al., (Jun. 13, 2013) "Enhanced Effector Responses in Activated CD8+ T Cells Deficient in Diacylglycerol Kinases," Cancer Res; 73(12):3566-3577.
S. Boroda et al., (Jan. 1, 2017) "Dual activities of ritanserin and R59022 as DGKα inhibitors and serotonin receptor antagonists," Biochem Pharmacol.; 123:29-39.
S. Degorce et al., (2016) "Discovery of Novel 3-Quinoline Carboxamides as Potent, Selective, and Orally Bioavailable Inhibitors of Ataxia Telangiectasia Mutated (ATM) Kinase," J. Med. Chem., 59:6281-6292.
S. Gao et al., (2014) "Palladium-Catalyzed Carbonylation of o-Iodoanilines for Synthesis of Isatoic Anhydrides," J. Org. Chem., 79:4196-4200.
Sakane, F. et al. (Liu, K.) (2016) "A novel diacylglycerol kinase α-selective inhibitor, CU-3, induces cancer cell apoptosis and enhances immune response," Journal of Lipid Research; 57:368-379.
Shin, J. et al., (2012) "Differential Regulation of Primary and Memory CD8 T Cell Immune Responses by Diacylglycerol Kinases," J. Immunol; 188:2111-2117.
Singla, P. et al. (2017). "Novel pyrazolo[3,4-d]pyrimidine with 4-(1H-benzimidazol-2-yl)-phenylamine as broad spectrum anticancer agents: Synthesis, cellbased assay, topoisomerase inhibition, DNA intercalation and bovineserum albumin studies," European Journal of Medicinal Chemistry, 126:24-35.
T. O. Eichmann et al., (2015) "DAG tales: the multiple faces of diacylglycerol—stereochemistry, metabolism, and signaling," Cell. Mol. Life Sci.; 72:3931-3952.
T. Sasaki et al., "Diacylglycerol kinase α exacerbates cardiac injuryafter ischemia/reperfusion," Heart Vessels; 29:110-118.
Velnati, S. et al., (2019) "Identification of a novel DGKα inhibitor for XLP-1 therapy by virtual screening," European Journal of Medicinal Chemistry;164:378-390.
Verma, C. et al., (2013) "A phosgene and peroxide-free one-pot tandem synthesis of isatoic anhydrides involving anthranilic acid, Boc anhydride, and 2-chloro-N-methyl pyridinium iodide," Tetrahedron Letters; 54:6897-6899.
Y. Zha (Nov. 2006) "T cell anergy is reversed by active Ras and is regulated by diacylglycerol kinase-α," Nature Immunology; 7(11):1166-1343.
Zhang, P. et al. (2016). "Silyl Radical Activation of Alkyl Halides in Metallaphotoredox Catalysis: A Unique Pathway for Cross-Electrophile Coupling" J. Am. Chem. Soc. 138:8084-8087.
Zhong, X-P. et al., (Sep. 2003) "Enhanced T cell responses due to diacylglycerol kinase ζ deficiency," Nature Immunology; 4(9):882-890.
International Search Report and Written Opinion mailed Mar. 17, 2021 for PCT Application No. PCT/EP2020/083196, filed Nov. 24, 2020, 9 pages.
International Search Report and Written Opinion mailed Mar. 17, 2021 for PCT Application No. PCT/EP2020/083197, filed Nov. 24, 2020, 9 pages.
International Search Report and Written Opinion mailed Mar. 22, 2021 for PCT Application No. PCT/EP2020/083198 filed Nov. 24, 2020, 9 pages.
U.S. Appl. No. 17/780,890, filed May 27, 2022 for Norbert Schmees, et al. (U.S. Patent Application is not submitted herewith pursuant to the waiver of 37 C.F.R. §1.98(a)(2)(iii) issued by the Office on Sep. 21, 2004.).
U.S. Appl. No. 18/072,490, filed Nov. 30, 2022 for Norbert Schmees, et al. (U.S. Patent Application is not submitted herewith pursuant to the waiver of 37 C.F.R. §1.98(a)(2)(iii) issued by the Office on Sep. 21, 2004.).

(56) References Cited

OTHER PUBLICATIONS

U.S. Appl. No. 17/780,903, filed May 27, 2022 for Norbert Schmees, et al. (U.S. Patent Application is not submitted herewith pursuant to the waiver of 37 C.F.R. §1.98(a)(2)(iii) issued by the Office on Sep. 21, 2004.).

U.S. Appl. No. 17/780,814, filed May 27, 2022 for Norbert Schmees, et al. (U.S. Patent Application is not submitted herewith pursuant to the waiver of 37 C.F.R. §1.98(a)(2)(iii) issued by the Office on Sep. 21, 2004.).

Banu, S. et al. (2018). "A novel templates of piperazinyl-1,2-dihydroquinoline-3-carboxylates: Synthesis, anti-microbial evaluation and molecular docking studies," Bioorganic & Medicinal Chemistry Letters, 28:116-1170.

E. G. Corley et al., (2004) "Direct Synthesis of 4-Arylpiperidines viaPalladium/Copper(I)-Cocatalyzed Negishi Coupling of a 4-Piperidylzinc Iodide with Aromatic Halides and Triflates," J. Org. Chem., 69:5120-5123.

L. Gonnard et al., (2015) "Cobalt-Catalyzed Cross-Coupling of 3- and 4-Iodopiperidines with Grignard Reagents," Chem. Eur. J.,21, 12797-12803.

Q. Wang et al., "Discovery of N (3-((1-Isonicotinoylpiperidin-4-yl)oxy)-4-methylphenyl)-3-(trifluoromethyl)benzamide (CHMFL-KIT-110) as a Selective, Potent, and Orally Available Type II c KIT KinaseInhibitor for Gastrointestinal Stromal Tumors (GISTs)," J. Med. Chem.; 59:3964-3979.

R. Nirogi et al., (2016) "Benzamide derivatives and their constrained analogs as histamine H3 receptor antagonists," European Journal of Medicinal Chemistry; 108:655-662.

R. S. R. Vidadala et al., (2014) "Development of potent and selective Plasmodium falciparum calcium-dependent protein kinase 4 (PfCDPK4) inhibitors that block the transmission of malaria to mosquitoes," European Journal of Medicinal Chemistry; 74:562-573.

S. Fletcher (2015) "The Mitsunobu reaction in the 21st century," Org. Chem. Front., 2:739-752.

S. Imamura et al., (2006) "Discovery of a Piperidine-4-carboxamide CCR5 Antagonist (TAK-220) with Highly Potent Anti-HIV-1 Activity," J. Med. Chem. 45:2784-2793.

Y. E. Kwon et al., "Synthesis, in vitro assay, and molecular modeling of new piperidine derivatives having dual inhibitory potency against acetylcholinesterase and Aβ1-42 aggregation for Alzheimer's disease therapeutics;" Bioorganic & Medicinal Chemistry; 15:6596-6607.

Zak, M. et al. (Feb. 1, 2015, e-pub. Dec. 17, 2014) "Identification of Nicotinamide Phosphoribosyltransferase (NAMPT) Transferase Inhibitors With No Evidence of CYP3A4 Time-Dependent Inhibition and Improved Aqueous Solubility," Bioorg. Med. Chem. Lett. 25(3):529-541.

PubChem. (Dec. 4, 2007). "CID No. 19095573. 4-(2-Thienyl)piperidine Hydrochloride," located at <https://pubchem.ncbi.nlm.nih.gov/compound/19095573>, last visited on Feb. 11, 2025, 10 pages.

Registry of STN. Entered STN before Nov. 26, 2019, 6 pages.

PubChem. (Jul. 19, 2005). "CID No. 2785748. 4-Chloro-1-methyl-2-oxo-1,2-dihydroquinoline-3-carbonitrile," located at <https://pubchem.ncbi.nlm.nih.gov/compound/2785748>, last visited on Sep. 17, 2025, 11 pages.

* cited by examiner

Figure 1

```
Met Ala Lys Glu Arg Gly Leu Ile Ser Pro Ser Asp Phe Ala Gln Leu
1               5                   10                  15
Gln Lys Tyr Met Glu Tyr Ser Thr Lys Lys Val Ser Asp Val Leu Lys
            20                  25                  30
Leu Phe Glu Asp Gly Glu Met Ala Lys Tyr Val Gln Gly Asp Ala Ile
        35                  40                  45
Gly Tyr Glu Gly Phe Gln Gln Phe Leu Lys Ile Tyr Leu Glu Val Asp
    50                  55                  60
Asn Val Pro Arg His Leu Ser Leu Ala Leu Phe Gln Ser Phe Glu Thr
65                  70                  75                  80
Gly His Cys Leu Asn Glu Thr Asn Val Thr Lys Asp Val Val Cys Leu
                85                  90                  95
Asn Asp Val Ser Cys Tyr Phe Ser Leu Leu Glu Gly Gly Arg Pro Glu
            100                 105                 110
Asp Lys Leu Glu Phe Thr Phe Lys Leu Tyr Asp Thr Asp Arg Asn Gly
        115                 120                 125
Ile Leu Asp Ser Ser Glu Val Asp Lys Ile Ile Leu Gln Met Met Arg
    130                 135                 140
Val Ala Glu Tyr Leu Asp Trp Asp Val Ser Glu Leu Arg Pro Ile Leu
145                 150                 155                 160
Gln Glu Met Met Lys Glu Ile Asp Tyr Asp Gly Ser Gly Ser Val Ser
                165                 170                 175
Gln Ala Glu Trp Val Arg Ala Gly Ala Thr Thr Val Pro Leu Leu Val
            180                 185                 190
Leu Leu Gly Leu Glu Met Thr Leu Lys Asp Asp Gly Gln His Met Trp
        195                 200                 205
Arg Pro Lys Arg Phe Pro Arg Pro Val Tyr Cys Asn Leu Cys Glu Ser
    210                 215                 220
Ser Ile Gly Leu Gly Lys Gln Gly Leu Ser Cys Asn Leu Cys Lys Tyr
225                 230                 235                 240
Thr Val His Asp Gln Cys Ala Met Lys Ala Leu Pro Cys Glu Val Ser
                245                 250                 255
Thr Tyr Ala Lys Ser Arg Lys Asp Ile Gly Val Gln Ser His Val Trp
            260                 265                 270
Val Arg Gly Gly Cys Glu Ser Gly Arg Cys Asp Arg Cys Gln Lys Lys
        275                 280                 285
Ile Arg Ile Tyr His Ser Leu Thr Gly Leu His Cys Val Trp Cys His
    290                 295                 300
Leu Glu Ile His Asp Asp Cys Leu Gln Ala Val Gly His Glu Cys Asp
305                 310                 315                 320
Cys Gly Leu Leu Arg Asp His Ile Leu Pro Pro Ser Ser Ile Tyr Pro
                325                 330                 335
Ser Val Leu Ala Ser Gly Pro Asp Arg Lys Asn Ser Lys Thr Ser Gln
            340                 345                 350
Lys Thr Met Asp Asp Leu Asn Leu Ser Thr Ser Glu Ala Leu Arg Ile
        355                 360                 365
Asp Pro Val Pro Asn Thr His Pro Leu Leu Val Phe Val Asn Pro Lys
    370                 375                 380
Ser Gly Gly Lys Gln Gly Gln Arg Val Leu Trp Lys Phe Gln Tyr Ile
385                 390                 395                 400
Leu Asn Pro Arg Gln Val Phe Asn Leu Leu Lys Asp Gly Pro Glu Ile
                405                 410                 415
```

Figure 1 (continued)

```
Gly Leu Arg Leu Phe Lys Asp Val Pro Asp Ser Arg Ile Leu Val Cys
            420                 425                 430
Gly Gly Asp Gly Thr Val Gly Trp Ile Leu Glu Thr Ile Asp Lys Ala
        435                 440                 445
Asn Leu Pro Val Leu Pro Pro Val Ala Val Leu Pro Leu Gly Thr Gly
    450                 455                 460
Asn Asp Leu Ala Arg Cys Leu Arg Trp Gly Gly Gly Tyr Glu Gly Gln
465                 470                 475                 480
Asn Leu Ala Lys Ile Leu Lys Asp Leu Glu Met Ser Lys Val Val His
                485                 490                 495
Met Asp Arg Trp Ser Val Glu Val Ile Pro Gln Gln Thr Glu Glu Lys
            500                 505                 510
Ser Asp Pro Val Pro Phe Gln Ile Ile Asn Asn Tyr Phe Ser Ile Gly
        515                 520                 525
Val Asp Ala Ser Ile Ala His Arg Phe His Ile Met Arg Glu Lys Tyr
    530                 535                 540
Pro Glu Lys Phe Asn Ser Arg Met Lys Asn Lys Leu Trp Tyr Phe Glu
545                 550                 555                 560
Phe Ala Thr Ser Glu Ser Ile Phe Ser Thr Cys Lys Lys Leu Glu Glu
                565                 570                 575
Ser Leu Thr Val Glu Ile Cys Gly Lys Pro Leu Asp Leu Ser Asn Leu
            580                 585                 590
Ser Leu Glu Gly Ile Ala Val Leu Asn Ile Pro Ser Met His Gly Gly
        595                 600                 605
Ser Asn Leu Trp Gly Asp Thr Arg Arg Pro His Gly Asp Ile Tyr Gly
    610                 615                 620
Ile Asn Gln Ala Leu Gly Ala Thr Ala Lys Val Ile Thr Asp Pro Asp
625                 630                 635                 640
Ile Leu Lys Thr Cys Val Pro Asp Leu Ser Asp Lys Arg Leu Glu Val
                645                 650                 655
Val Gly Leu Glu Gly Ala Ile Glu Met Gly Gln Ile Tyr Thr Lys Leu
            660                 665                 670
Lys Asn Ala Gly Arg Arg Leu Ala Lys Cys Ser Glu Ile Thr Phe His
        675                 680                 685
Thr Thr Lys Thr Leu Pro Met Gln Ile Asp Gly Glu Pro Trp Met Gln
    690                 695                 700
Thr Pro Cys Thr Ile Lys Ile Thr His Lys Asn Gln Met Pro Met Leu
705                 710                 715                 720
Met Gly Pro Pro Pro Arg Ser Thr Asn Phe Phe Gly Phe Leu Ser Asp
                725                 730                 735
Tyr Lys Asp Asp Asp Asp Lys

            740
```

Figure 2

```
Met Thr Ser His His His His His His Ser Ser Met Gly Ser Arg Gly
1               5                   10                  15
Ile Glu Gly Arg Gly Gly Leu Asn Asp Ile Phe Glu Ala Gln Lys Ile
            20                  25                  30
Glu Trp His Glu Gly Ser Arg Thr Ser Leu Tyr Lys Lys Ala Gly Ser
        35                  40                  45
Ala Thr Met Ala Lys Glu Arg Gly Leu Ile Ser Pro Ser Asp Phe Ala
    50                  55                  60
Gln Leu Gln Lys Tyr Met Glu Tyr Ser Thr Lys Lys Val Ser Asp Val
65                  70                  75                  80
Leu Lys Leu Phe Glu Asp Gly Glu Met Ala Lys Tyr Val Gln Gly Asp
                85                  90                  95
Ala Ile Gly Tyr Glu Gly Phe Gln Gln Phe Leu Lys Ile Tyr Leu Glu
            100                 105                 110
Val Asp Asn Val Pro Arg His Leu Ser Leu Ala Leu Phe Gln Ser Phe
        115                 120                 125
Glu Thr Gly His Cys Leu Asn Glu Thr Asn Val Thr Lys Asp Val Val
    130                 135                 140
Cys Leu Asn Asp Val Ser Cys Tyr Phe Ser Leu Leu Glu Gly Gly Arg
145                 150                 155                 160
Pro Glu Asp Lys Leu Glu Phe Thr Phe Lys Leu Tyr Asp Thr Asp Arg
                165                 170                 175
Asn Gly Ile Leu Asp Ser Ser Glu Val Asp Lys Ile Ile Leu Gln Met
            180                 185                 190
Met Arg Val Ala Glu Tyr Leu Asp Trp Asp Val Ser Glu Leu Arg Pro
        195                 200                 205
Ile Leu Gln Glu Met Met Lys Glu Ile Asp Tyr Asp Gly Ser Gly Ser
    210                 215                 220
Val Ser Gln Ala Glu Trp Val Arg Ala Gly Ala Thr Thr Val Pro Leu
225                 230                 235                 240
Leu Val Leu Leu Gly Leu Glu Met Thr Leu Lys Asp Asp Gly Gln His
                245                 250                 255
Met Trp Arg Pro Lys Arg Phe Pro Arg Pro Val Tyr Cys Asn Leu Cys
            260                 265                 270
Glu Ser Ser Ile Gly Leu Gly Lys Gln Gly Leu Ser Cys Asn Leu Cys
        275                 280                 285
Lys Tyr Thr Val His Asp Gln Cys Ala Met Lys Ala Leu Pro Cys Glu
    290                 295                 300
Val Ser Thr Tyr Ala Lys Ser Arg Lys Asp Ile Gly Val Gln Ser His
305                 310                 315                 320
Val Trp Val Arg Gly Gly Cys Glu Ser Gly Arg Cys Asp Arg Cys Gln
                325                 330                 335
Lys Lys Ile Arg Ile Tyr His Ser Leu Thr Gly Leu His Cys Val Trp
            340                 345                 350
Cys His Leu Glu Ile His Asp Asp Cys Leu Gln Ala Val Gly His Glu
        355                 360                 365
Cys Asp Cys Gly Leu Leu Arg Asp His Ile Leu Pro Pro Ser Ser Ile
    370                 375                 380
Tyr Pro Ser Val Leu Ala Ser Gly Pro Asp Arg Lys Asn Ser Lys Thr
385                 390                 395                 400
Ser Gln Lys Thr Met Asp Asp Leu Asn Leu Ser Thr Ser Glu Ala Leu
                405                 410                 415
Arg Ile Asp Pro Val Pro Asn Thr His Pro Leu Leu Val Phe Val Asn
            420                 425                 430
```

Figure 2 (continued)

```
Pro Lys Ser Gly Gly Lys Gln Gly Gln Arg Val Leu Trp Lys Phe Gln
        435                 440                 445
Tyr Ile Leu Asn Pro Arg Gln Val Phe Asn Leu Leu Lys Asp Gly Pro
    450                 455                 460
Glu Ile Gly Leu Arg Leu Phe Lys Asp Val Pro Asp Ser Arg Ile Leu
465                 470                 475                 480
Val Cys Gly Gly Asp Gly Thr Val Gly Trp Ile Leu Glu Thr Ile Asp
                485                 490                 495
Lys Ala Asn Leu Pro Val Leu Pro Pro Val Ala Val Leu Pro Leu Gly
            500                 505                 510
Thr Gly Asn Asp Leu Ala Arg Cys Leu Arg Trp Gly Gly Gly Tyr Glu
        515                 520                 525
Gly Gln Asn Leu Ala Lys Ile Leu Lys Asp Leu Glu Met Ser Lys Val
    530                 535                 540
Val His Met Asp Arg Trp Ser Val Glu Val Ile Pro Gln Gln Thr Glu
545                 550                 555                 560
Glu Lys Ser Asp Pro Val Pro Phe Gln Ile Ile Asn Asn Tyr Phe Ser
                565                 570                 575
Ile Gly Val Asp Ala Ser Ile Ala His Arg Phe His Ile Met Arg Glu
            580                 585                 590
Lys Tyr Pro Glu Lys Phe Asn Ser Arg Met Lys Asn Lys Leu Trp Tyr
        595                 600                 605
Phe Glu Phe Ala Thr Ser Glu Ser Ile Phe Ser Thr Cys Lys Lys Leu
    610                 615                 620
Glu Glu Ser Leu Thr Val Glu Ile Cys Gly Lys Pro Leu Asp Leu Ser
625                 630                 635                 640
Asn Leu Ser Leu Glu Gly Ile Ala Val Leu Asn Ile Pro Ser Met His
                645                 650                 655
Gly Gly Ser Asn Leu Trp Gly Asp Thr Arg Arg Pro His Gly Asp Ile
            660                 665                 670
Tyr Gly Ile Asn Gln Ala Leu Gly Ala Thr Ala Lys Val Ile Thr Asp
        675                 680                 685
Pro Asp Ile Leu Lys Thr Cys Val Pro Asp Leu Ser Asp Lys Arg Leu
    690                 695                 700
Glu Val Val Gly Leu Glu Gly Ala Ile Glu Met Gly Gln Ile Tyr Thr
705                 710                 715                 720
Lys Leu Lys Asn Ala Gly Arg Arg Leu Ala Lys Cys Ser Glu Ile Thr
                725                 730                 735
Phe His Thr Thr Lys Thr Leu Pro Met Gln Ile Asp Gly Glu Pro Trp
            740                 745                 750
Met Gln Thr Pro Cys Thr Ile Lys Ile Thr His Lys Asn Gln Met Pro
        755                 760                 765
Met Leu Met Gly Pro Pro Pro Arg Ser Thr Asn Phe Phe Gly Phe Leu
    770                 775                 780
Ser Asp Tyr Lys Asp Asp Asp Asp Lys
785                 790
```

Figure 3

```
Ser Ile Ile Asn Phe Glu Lys Leu
1               5
```

Figure 4

```
GCCACC
```

Figure 5

```
Asp Tyr Lys Asp Asp Asp Asp Lys
1               5
```

Figure 6

```
Ser Met Leu Val Leu Leu Pro Asp Glu Val Ser Gly Leu Glu Gln Leu
1               5                   10                  15
Glu Ser Ile Ile Asn Phe Glu Lys Leu Thr Glu Trp Thr Ser
            20                  25                  30
```

SUBSTITUTED AMINOQUINOLONES AS DGKALPHA INHIBITORS FOR IMMUNE ACTIVATION

CROSS REFERENCE TO RELATED APPLICATIONS

This application is a national stage application under 35 U.S.C. § 371 of International Application No. PCT/EP2020/083198, filed internationally on Nov. 24, 2020, which claims benefit of European Application Nos.: 19212252.1, filed on Nov. 28, 2019, and 20181065.2, filed on Jun. 19, 2020.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052065200SEQLIST.TXT, date recorded: May 25, 2022, size: 14,143 bytes).

The present invention covers substituted aminoquinolone compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of diacylglycerol kinase alpha (DGKalpha, DGKα) regulated disorders, as a sole agent or in combination with other active ingredients.

The compounds of general formula (I) inhibit DGKα and enhance T cell mediated immune response. This is a new strategy to use the patient's own immune system to overcome immunoevasive strategies utilized by many neoplastic disorders, respectively cancer and by this enhancing anti-tumor immunity. Furthermore, said compounds are used in particular to treat disorders such as viral infections or conditions with dysregulated immune responses or other disorders associated with aberrant DGKα signaling.

The present invention further relates to the use, respectively to the use of the compounds of general formula (I) for manufacturing pharmaceutical compositions for enhancement of T cell mediated immune response.

The present invention further relates to the use, respectively to the use of the compounds of general formula (I) for manufacturing pharmaceutical compositions for the treatment of cancer.

The present invention further relates to the use, respectively to the use of the compounds of general formula (I) for manufacturing pharmaceutical compositions for the treatment or prophylaxis of fibrotic disorders, virus infections, cardiac diseases and lymphoproliferative disorders.

BACKGROUND

Diacylglycerol kinases (DGKs) represent a family of enzymes that catalyze phosphorylation of the membrane lipid sn-1,2 diacylglycerol (DAG) to form phosphatidic acid (PA) (Eichmann and Lass, Cell Mol Life Sci. 2015; 72: 3931). In T cells, DAG is formed downstream of the T cell receptor (TCR) after activation of the gamma 1 isoform of phospholipase C (PLCγ1) and cleavage of phosphatidylinositol 4,5-biphosphate (PIP2) into DAG and an additional second messenger, inositol 1,4,5-triphosphate (IP3) (Krishna and Zhong, Front. Immunol 2013, 4, 178). Whereas, IP3 is important in facilitating release of calcium from the endoplasmic reticulum, DAG interacts with other proteins important in TCR signal transduction, such as Protein kinase Cθ (Quann et al., Nat Immunol 2011(7), 647) and the Ras activating protein RasGRP1 (Krishna and Zhong, Front. Immunol 2013, 4:178). Although, three isoforms of DGK are known to be present within T cells [DGKα (DGKalpha), DGK6 (DGKdelta), and DGKζ (DGKzeta)], only two, DGKα and DGKζ, are thought to play an important role in facilitating DAG metabolism downstream of the TCR (Joshi and and Koretzky, Int. J. Mol. Sci. 2013, 14, 6649).

Targeting the activity of DGKα in T cells, either by germline deletion, or with chemical inhibitors, results in enhanced and sustained signaling downstream of T cells, as assessed by prolonged phosphorylation of downstream molecules, such as extracellular signal-related kinases 1/2 (ERK1/2 (Zhong et al., Nat Immunol 2003, 4, 882; Olenchock et al., Nat Immunol 2006, 7, 1174; Riese et al., J. Biol. Chem 2011, 286, 5254). Furthermore, the overexpression of DGKα induces a state of decreased functional activity resembling an anergy-like state (Zha et al., Nat Immunol 2006, 7, 1166). In contrast, deletion of DGKα in T cells with enhanced production of effector cytokines, such as IL2 and IFNγ, and enhanced proliferation (Zhong et al., Nat Immunol 2003, 4, 882 Olenchock et al., Nat Immunol 2006, 7, 1174).

These findings suggest that DGKa might serve as a useful target for enhancing T cell anti-tumor activity. The role of DGKα in anti-tumor responses was studied recently in human tumor-infiltrating CD8+ T cells (CD8-TILs) from patients with renal cell carcinoma (RCC) (Prinz et al., J. Immunol 2012, 188, 5990). CD8-TILs from RCCs were defective in lytic granule exocytosis and their ability to kill target cells. While proximal signaling events were intact in response to TCR engagement, CD8-TILs exhibited decreased phosphorylation of ERK when compared to non-tumor-infiltrating CD8+ T cells. Treatment of CD8-TILs with an inhibitor of DGKα activity rescued killing ability of target cells, increased basal levels of phosphorylation of ERK, and increased PMA/ionomycin-stimulated phosphorylation of ERK.

In addition, Arranz-Nicolas et al show that DGK inhibitors promoted not only Ras/ERK signaling but also AP-1 (Activator protein-1) transcription, facilitated DGKα membrane localization, reduced the requirement for costimulation, and cooperated with enhanced activation following DGKζ silencing/deletion. In contrast with enhanced activation triggered by pharmacological inhibition, DGKα silencing/genetic deletion led to impaired Lck (lymphocyte-specific protein tyrosine kinase) activation and limited costimulation responses. (Arranz-Nicolas et al., Canc Immun, Immunother 2018, 67(6), 965).

In addition, antigen-specific CD8+ T cells from $DGK\alpha^{-/-}$ and $DGK\zeta^{-/-}$ mice show enhanced expansion and increased cytokine production following (Lymphocytic choriomeningitis virus): infection (Shin et al. J. Immunol, 2012).

Additionally, the adoptive transfer of CAR (chimeric antigen receptor)-T cells deficient in DGKα demonstrated increased efficacy compared to wild type CAR T cells T cells in the treatment of murine mesothelioma (Riese et al., Cancer Res 2013, 73(12), 3566) and a glioblastoma xenograft mouse model (Jung et al. Cancer Res. 2018, 78(16), 4692).

Apart from T-cell regulation, DGKα also plays a role in cancer, mediating numerous aspects of cancer cell progression including survival (Bacchiocchi et al., Blood, 2005, 106(6), 2175; Yanagisawa et al. Biochim Biophys Acta 2007, 1771, 462), migration and invasion of cancer cells (Baldanzi et al., Oncogene 2008, 27, 942; Filigheddu et al., Anticancer Res 2007, 27, 1489; Rainero et al., J Cell Biol 2012, 196(2): 277). In particular, it has been reported that DGKα is over expressed in hepatocellular carcinoma (Takeishi et al., J Hepatol 2012, 57, 77) and melanoma cells (Yanagisawa et al., Biochim Biophys Acta 2007, 1771, 462) while other reports suggested that the growth of colon and breast cancer cell lines was significantly inhibited by DGKα-siRNA16 and DGKα/atypical PKC/b1 integrin signalling pathway was crucial for matrix invasion of breast carcinoma cells (Rainero et al., PLoS One 2014, 9(6): e97144) In addition, expression is also higher in lymphonodal metastasis than in breast original tumour (Hao et al., Cancer 2004, 100, 1110).

Additionally, a study testing the importance of DGKα in glioblastoma multiforme (GBM) cells found that concurrent administration of the relatively non-specific DGKα inhibitor R59022 resulted in decreased growth of intracranially injected GBM tumors. (Dominguez et al. Cancer Discov 2013, 3(7): 782).

Also, DGKα promotes esophageal squamous cell carcinoma (ESCC) progression, supporting DGKα as a potential target for ESCC therapy (Chen et al., Oncogene, 2019, 38 (14) 2533).

In addition, pharmacological inhibition of DGK diminished both airway inflammation and airway hyperresponsiveness in mice and also reduced bronchoconstriction of human airway samples in vitro by blocking T helper 2 ($T_H2$) differentiation (Singh et al., Sci Signal. 2019, 12, eaax3332). Furthermor, inhibition of DGKα has the potential to reverse the life-threatening Epstein-Barr virus (EBV)-associated immunopathology that occurs in patients X-linked lymphoproliferative disease (XLP-1) patients (Ruffo et al., Sci Transl Med. 2016, 13, 8, 321; Velnati et al., Eur J Med Chem. 2019, 164,378).

In addition, DGKα exacerbates cardiac injury after ischemia/reperfusioncardiac diseases (Sasaki et al., Heart Vessels, 2014, 29,110).

Taken together, the findings from these studies argue that restraining DGKα activity in T cells and tumor cells may prove valuable in generating more vigorous immune responses against pathogens and tumors and in amoiroting Th2 driven (ato) immune deseases (in re-balancing the immune-systeme). In addition, inhibiting DGKα activity has a therapeutic potential in targeting tumors directly as well as addressing fibrotic disorders, virus infection associated pathologies, cardiac diseases and lymphoproliferative disorders.

PRIOR ART

DGKα inhitors were reported in the literature. R59022 (A) was identified to act on DGKα in red blood cells (de Chaffoy de Courcelles et. al., J. Biol. Chem. Vol 260, No. 29, (1985), p 15762-70). Structurally related R59949 (B) was identified to act on DGKα in T-lymphocytes by inhibiting the transformation of 1,2-diacylglycerols to their respective phosphatidic acids (Jones et. al., J. Biol. Chem. Vol 274, No. 24, (1999), p 16846-52). Ritanserin (C), originally identified as a serotonine receptor antagonist, showed comparable activity on DGKα such as the two cpds (A) and (B): (Boroda et. al., BioChem. Pharm. 123, (2017), 29-39).

(A)

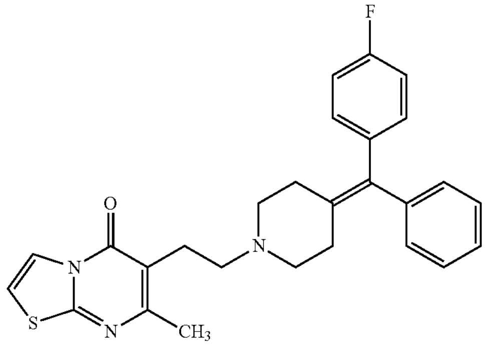

(B)

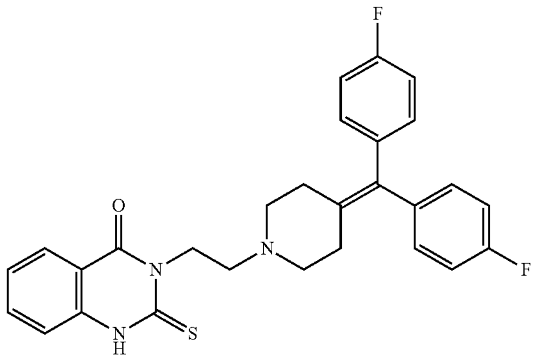

(C)

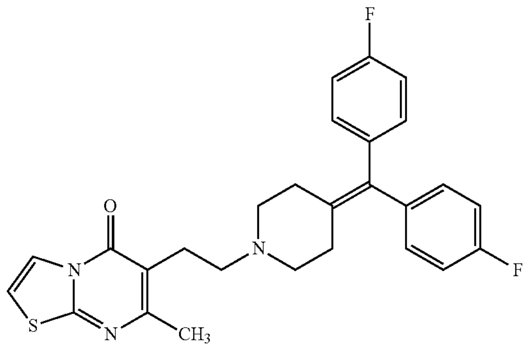

A further structure, CU-3 (D) was identified as a first compound with sub-micromolar inhibitory activity on DGKα (Sakane et. al., J. Lipid Res. Vol 57, (2016), p 368-79).

(D)

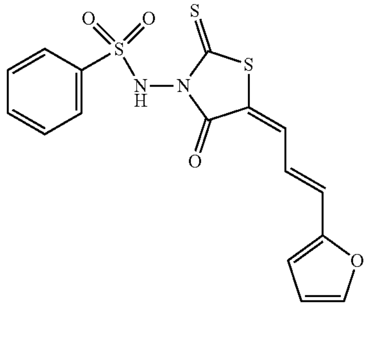

AMB639752 (E) was describe as a further DGKα selective inhibitor with micromolar activity (S. Velnati et al. Eur J. Med. Chem 2019, 164, p 378-390.).

(E)

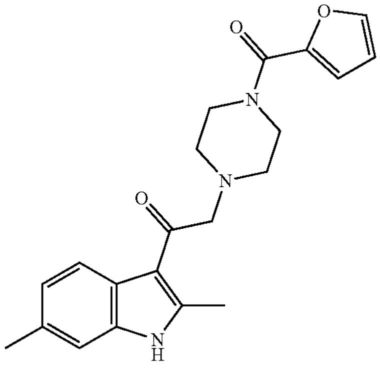

WO2020/151636 relates to azaquinolinones as PDE9 inhibitor compounds for treatment of PDE9 mediated diseases.

WO2020/143626 relates to quinolinones as PDE9 inhibitor compounds for treatment of PDE9 mediated diseases.

WO2020/182076 relates to the use of phosphodiesterase inhibitor compounds in the preparation of drugs for treating heart failure in mammals.

WO2020/006016 and WO2020/006018 describe Naphthydrinone compounds as T cell activators, which inhibit the activity of DGKα and/or DGKζ, for treatment of viral infections and proliferative disorders, such as cancer.

WO2017/019723 A1 relates to azacyanoquinolinone compounds which may be useful as therapeutic agents for the treatment of central nervous system disorders associated with phosphodiesterase 9 (PDE9). It also relates to the use of the compounds compounds for treating neurological and psychiatric disorders.

WO2004/074218 describes MIF-inhibitors and multiple uses thereof, among others for treatment of cancer.

WO2007/109251 describes the use of TNFα inhibitors for treatment of diseases, among others for treatment of cancer.

WO 2012/142498 and WO2012/009649 describe MIF-inhibitors and multiple uses thereof, among others in cancer therapy. These patent applications claim an extremely high number of compounds. However, many of these theoretical compounds are not specifically disclosed.

However, the state of the art does not describe:

- the specific substituted aminoquinolone compounds of general formula (I) of the present invention as described and defined herein, i.e. compounds having a 2-oxo-1,2-dihydroquinoline core bearing:
  - in its 1-position a methyl- or an ethyl group,
  - in its 3-position a cyano-, carbamoyl-, alkylcarbamoyl-, dialkylcarbamoyl- or alkoxycarbonyl group,
  - in its 4-position a pyrolidinyl-, piperidinyl- or azepanyl group; and
  - as a substituent of said pyrolidinyl-, piperidinyl- or azepanyl group a phenyl-, naphthyl-
  - or 5- to 10-membered heteroaryl group,
  - or stereoisomers, tautomers, N-oxides, hydrates, solvates, salts thereof, or mixtures of same, as described and defined herein, and as hereinafter referred to as "compounds of general formula (I)" or "compounds of the present invention",
- or their pharmacological activity.

It is desirable to provide novel compounds having prophylactic and therapeutic properties.

Accordingly, it is an object of the present invention to provide compounds and pharmaceutical compositions comprising these compounds used for prophylactic and therapeutic use in DGKα regulated disorders in a T cell immune-stimulatory or immune-modifying manner. DGKα regulated disorders comprise conditions with dysregulated immune responses, particularly in an immunologically suppressed tumor microenvironment in cancer, autoimmune diseases, viral infections as well as other disorders associated with aberrant DGKα signalling, e.g. fibrotic diseases. Said compounds can be used as sole agent or in combination with other active ingredients.

It has now been found, and this constitutes the basis of the present invention, that the compounds of the present invention have surprising and advantageous properties.

In particular, the compounds of the present invention have surprisingly been found to effectively inhibit the DGKα protein and enhance T-cell mediated immunity. Accordingly, they provide novel structures for the therapy of human and animal disorders, in particular of cancers, and may therefore be used for the treatment or prophylaxis of hyperproliferative disorders, such as cancer, for example.

DESCRIPTION OF THE INVENTION

In accordance with a first aspect, the present invention covers compounds of general formula (I):

(I)

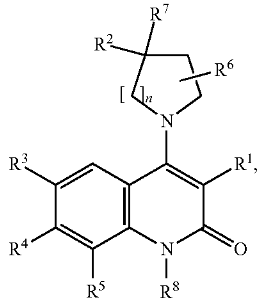

in which $R^1$ represents a group selected from cyano, $—C(=O)NH_2$, $—C(=O)N(H)CH_3$, $—C(=O)N(H)C_2H_5$, $—C(=O)N(CH_3)_2$ and $—C(=O)OR^{15}$, $R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_6$-cycloalkyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_6$-haloalkoxy, $C_3$-$C_6$-cycloalkyloxy, phenoxy, $—SR^{14}$, $—S(=O)R^{14}$, $—S(=O)_2R^{14}$, $—P(=O)(R^{14})_2$, cyano, hydroxy, $—N(R^9)(R^{10})$, $—C(=O)N(R^9)(R^{10})$, $—C(=O)R^{11}$, $—N(R^{12})C(=O)R^{13}$, $—N(R^{12})S(=O)_2R^{14}$, $—N=S(=NH)(R^{14})_2$, $—N=S(=O)(R^{14})_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from $—(CH_2)_3—$, $—CH_2—CH(OH)—CH_2—$, $—(CH_2)_4—$, $—O—(CH_2)_2—$, $—(CH_2)_2—O—$, $—CH_2—CH(CH_3)—O—$, $—CH_2—O—CH_2—$, $—O—(CH_2)_3—$, $—(CH_2)_3—O—$, $—CH_2—O—(CH_2)_2—$, $—(CH_2)_2O—CH_2—$, $—O—CH_2—O—$, $—O—C(CH_3)_2—O—$, $—O—(CH_2)_2—O—$, $—N(R^{18})—C(═O)—(C(R^1)(R^{19}))_m—$, $—N(R^{18})—C(═O)—(C(CH_3)_2)—$, $—N(R^{18})—(C(R^{18})(R^{19}))_m—$, $—N(R^{18})—C(═O)—O—$ and $—N(R^{18})—C(═O)—N(R^{18})—$, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, $—N(R^9)(R^{10})$ and oxo, and wherein said $C_1$-$C_6$-alkyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, $—N(R^9)(R^{10})$ and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $—N(R^9)(R^{10})$, and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $—N(R^9)(R^{10})$:

$R^3$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, $C_3$-$C_6$-cycloalkyloxy, phenoxy, $—SR^{14}$, $—S(═O)R^{14}$, $—S(═O)_2R^{14}$, cyano, hydroxy, $—N(R^9)(R^{10})$, $—C(═O)N(R^9)(R^{10})$, $—C(═O)R^{11}$, $—N(R^{12})C(═O)R^{13}$, $—N(R^{12})S(═O)_2R^{14}$, $—N═S(═NH)(R^{14})_2$, $—N═S(═O)(R^{14})_2$, $—P(═O)(R^{14})_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, $—N(R^9)(R^{10})$ and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, $—N(R^9)(R^{10})$ and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $—N(R^9)(R^{10})$, and which $C_3$-$C_4$-cycloalkyl group is optionally substituted, one or two times, each substituent indepen dently selected from a halogen atom or a group selected from cyano and hydroxy, and wherein said $C_2$-$C_6$-alkenyl group is optionally substituted with a $C_1$-$C_4$-haloalkyl group, and wherein said $C_3$-$C_6$-cycloalkyl and $C_4$-$C_6$-cycloalkenyl group is optionally substituted, one or two times, each substituent independently selected from a halogen atom or a group selected from $C_1$-$C_4$-alkyl and $C_1$-$C_4$-haloalkyl, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^4$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, —O—($C_1$-$C_4$-alkyl)-C(═O)O$R^{15}$, —O—($C_1$-$C_4$-alkyl)-C(═O)N($R^9$)($R^{10}$), $C_3$-$C_6$-cycloalkyloxy, —S(═O)$R^{14}$, —S(═O)$_2R^{14}$, cyano, nitro, hydroxy, —N($R^9$)($R^{10}$), —N($R^{16}$)($R^{17}$), —N($R^{16}$)($R^{20}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_1$-$C_6$-alkoxy group is optionally substituted with a oxiran-2-yl group, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^5$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_2$-$C_6$-alkoxy)-, $C_1$-$C_4$-haloalkoxy, $C_3$-$C_6$-cycloalkyloxy, phenoxy, —S$R^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$—P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^6$ represents a hydrogen atom, or a fluorine atom or a group selected from $C_1$-$C_4$-alkyl, $C_1$-$C_4$-hydroxyalkyl, $C_1$-$C_4$-alkoxy, hydroxy and oxo, $R^7$ represents a hydrogen atom or a halogen atom or a group selected from $C_1$-$C_4$-alkyl, $C_1$-$C_4$-alkoxy, hydroxy and cyano, $R^8$ represents a group selected from methyl and ethyl, $R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)-, $C_3$-$C_4$-cycloalkyl and $C_2$-$C_4$-haloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, $R^{11}$ represents a hydrogen atom or group selected from $C_1$-$C_4$-alkyl, $C_1$-$C_4$-hydroxyalkyl, $C_1$-$C_4$-haloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^{12}$ represents a hydrogen atom or a $C_1$-$C_4$-alkyl group, $R^{13}$ represents a hydrogen atom or a group selected from $C_1$-$C_6$-alkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^{14}$ represents a group selected from $C_1$-$C_6$-alkyl, $C_1$-$C_6$-haloalkyl, $C_3$-$C_6$-cycloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^{15}$ represents a hydrogen atom or a $C_1$-$C_4$-alkyl group, $R^{16}$ represents a hydrogen atom or a group selected from $C_1$-$C_4$-alkyl, $C_3$-$C_4$-cycloalkyl and $C_2$-$C_4$-haloalkyl, $R^{17}$ represents a 4- to 7-membered heterocycloalkyl group, wherein said 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, and wherein said 4- to 7-membered heterocycloalkyl group is connected to the rest of the molecule via a carbon atom of the 4- to 7-membered heterocycloalkyl group, $R^{18}$ represents a hydrogen atom or a group selected from methyl and ethyl, $R^{19}$ represents a hydrogen atom or a group selected from methyl and ethyl, $R^{20}$ represents a (4- to 7-membered heterocycloalkyl)-($C_1$-$C_4$-alkyl)- group, wherein the (4- to 7-membered heterocycloalkyl) part of said group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, m represents an integer selected from 1, 2 and 3, and n represents an integer selected from 1, 2 and 3, and stereoisomers, tautomers, N-oxides, hydrates, solvates, and salts thereof, and mixtures of same.

In accordance with a variant of the first aspect, the present invention covers compounds of general formula (I), supra, in which:

$R^1$ represents a group selected from cyano, —C(═O)$NH_2$, —C(═O)N(H)$CH_3$, —C(═O)N(H)$C_2H_5$, —C(═O)N($CH_3$)$_2$ and —C(═O)O$R^{15}$, $R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_6$-cycloalkyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_6$-haloalkoxy, $C_3$-$C_6$-cycloalkyloxy, phenoxy, —$SR^{14}$, —S(═O)$R^{14}$, —S(═O)$_2R^{14}$, —P(═O)($R^{14}$)$_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)($R^{14}$)$_2$, —N═S(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from —($CH_2$)$_3$—, —($CH_2$)$_4$—, —O—($CH_2$)$_2$—, —($CH_2$)$_2$—O—, —$CH_2$—O—$CH_2$—, —O—($CH_2$)$_3$—, —($CH_2$)$_3$—O—, —$CH_2$—O—($CH_2$)$_2$—, —($CH_2$)$_2$ O—$CH_2$—, —O—$CH_2$—O— and —O—($CH_2$)$_2$—O—, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^3$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, $C_3$-$C_6$-cycloalkyloxy, phenoxy, —$SR^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^4$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, $C_3$-$C_6$-cycloalkyloxy, —S(═O)$R^{14}$, —S(═O)$_2R^{14}$, cyano, hydroxy, —N($R^9$)($R^{10}$), —N($R^{16}$)($R^{17}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

$R^5$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_2$-$C_6$-alkoxy)-, $C_1$-$C_4$-haloalkoxy, $C_3$-$C_6$-cycloalkyloxy, phenoxy, —S$R^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$—P(═O)($R^{14}$)$_2$4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, $R^6$ represents a hydrogen atom, or a fluorine atom or a group selected from $C_1$-$C_4$-alkyl, $C_1$-$C_4$-hydroxyalkyl, $C_1$-$C_4$-alkoxy, hydroxy and oxo, $R^7$ represents a hydrogen atom or a halogen atom or a group selected from $C_1$-$C_4$-alkyl, $C_1$-$C_4$-alkoxy, hydroxy and cyano, $R^8$ represents a group selected from methyl and ethyl, $R^9$ and $R^{10}$ represent, independently from each occurrence, a hydrogen atom or a group selected from $C_1$-$C_4$-alkyl, ($C_1$-$C_4$-alkoxy)-($C_2$-$C_4$-alkyl)-, $C_3$-$C_4$-cycloalkyl and $C_2$-$C_4$-haloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, $R^{11}$ represents a hydrogen atom or group selected from $C_1$-$C_4$-alkyl, $C_1$-$C_4$-hydroxyalkyl, $C_1$-$C_4$-haloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$:

$R^{12}$ represents a hydrogen atom or a $C_1$-$C_4$-alkyl group, $R^{13}$ represents a hydrogen atom or a group selected from $C_1$-$C_6$-alkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, $R^{14}$ represents a group selected from $C_1$-$C_6$-alkyl, $C_1$-$C_6$-haloalkyl, $C_3$-$C_6$-cycloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$:

$R^{15}$ represents a hydrogen atom or a $C_1$-$C_4$-alkyl group, $R^{16}$ represents a hydrogen atom or a group selected from $C_1$-$C_4$-alkyl, $C_3$-$C_4$-cycloalkyl and $C_2$-$C_4$-haloalkyl, $R^{17}$ represents a 4- to 7-membered heterocycloalkyl group, wherein said 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, and wherein said 4- to 7-membered heterocycloalkyl group is connected to the rest of the molecule via a carbon atom of the 4- to 7-membered heterocycloalkyl group, and n represents an integer selected from 1, 2 and 3, and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3 or 4, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents, particularly with one substituent.

As used herein, an oxo substituent represents an oxygen atom, which is bound to a carbon atom or to a sulfur atom via a double bond.

Should a composite substituent be composed of more than one part, e.g. ($C_1$-$C_2$-alkoxy)-($C_1$-$C_6$-alkyl)-, it is possible for a given part to be attached at any suitable position of said composite substituent, e.g. it is possible for the $C_1$-$C_2$-alkoxy part to be attached to any suitable carbon atom of the $C_1$-$C_6$-alkyl part of said ($C_1$-$C_2$-alkoxy)-($C_1$-$C_6$-alkyl)-group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings: The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3, 4 or 5 carbon atoms ("$C_1$-$C_5$-alkyl"), e.g. a methyl, ethyl, propyl, isopropyl, butyl, sec-butyl isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl group. More particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group, more particularly 1 or 2 carbon atoms ("$C_1$-$C_2$-alkyl"), e.g. a methyl or ethyl group.

The term "$C_2$-$C_4$-alkyl" means a linear or branched, saturated, monovalent hydrocarbon group having 2, 3 or 4 carbon atoms, e.g. an ethyl, propyl, isopropyl, butyl, sec-butyl, isobutyl or tert-butyl group.

The term "$C_1$-$C_6$-hydroxyalkyl" means a linear or branched, saturated, monovalent hydrocarbon group in which the term "$C_1$-$C_6$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl, 1-hydroxybutyl, 2-hydroxybutyl, 3-hydroxybutyl, 4-hydroxybutyl group, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, 6-hydroxyhexyl group, or an isomer thereof. Particularly, said group has 1, 2, 3 or 4 carbon atoms ("$C_1$-$C_4$-hydroxyalkyl"), e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl, 1-hydroxybutyl, 2-hydroxybutyl, 3-hydroxybutyl, 4-hydroxybutyl group, or an isomer thereof.

The term "$C_2$-$C_4$-hydroxyalkyl" means a linear or branched, saturated, monovalent hydrocarbon group having 2, 3 or 4 carbon atoms, in which the term "$C_2$-$C_4$-alkyl" is defined supra, and in which 1 or 2 hydrogen atoms are replaced with a hydroxy group, e.g. a 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl, 1-hydroxybutyl, 2-hydroxybutyl, 3-hydroxybutyl or 4-hydroxybutyl group, or an isomer thereof.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl, 1,3-difluoropropan-2-yl, 4,4,4-trifluorobutyl, 5,5,5-trifluoropentyl or 6,6,6-trifluorohexyl. Particularly, said group has 1, 2, 3 or 4 carbon atoms ("$C_1$-$C_4$-haloalkyl"), e.g. a fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl, 1,3-difluoropropan-2-yl or 4,4,4-trifluorobutyl group.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof. Particularly, said group has 1, 2, 3 or 4 carbon atoms ("$C_1$-$C_4$-alkoxy"), e.g. a methoxy, ethoxy, n-propoxy, isopropoxy, n-butoxy, sec-butoxy, isobutoxy or tert-butoxy group.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy.

The term "$C_2$-$C_6$-alkenyl" means a linear or branched, monovalent hydrocarbon group, which contains one or two double bonds, and which has 2, 3, 4, 5 or 6 carbon atoms, it being understood that in the case in which said alkenyl group contains two double bonds, then it is possible for said double bonds to be conjugated with each other, or to form an allene. Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut- 2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1,5-dienyl group.

The term "$C_2$-$C_6$-alkynyl" means a linear or branched, monovalent hydrocarbon group which contains one triple bond, and which contains 2, 3, 4, 5 or 6 carbon atoms, particularly 2, 3 oder 4 carbon atoms ("$C_2$-$C_4$-alkynyl"). Said $C_2$-$C_6$-alkynyl group is, for example, ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methyl-pent-4-ynyl, 2-methylpent-3-ynyl, 1-methylpent-3-ynyl, 4-methylpent-2-ynyl, 1-methyl-pent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group.

The term "$C_3$-$C_6$-cycloalkyl" means a saturated, monovalent, monocyclic hydrocarbon ring which contains 3, 4, 5 or 6 carbon atoms. Said $C_3$-$C_6$-cycloalkyl group is for example a cyclopropyl, cyclobutyl, cyclopentyl or cyclohexyl group. Particularly, said group has 3, 4 or 5 carbon atoms ("$C_3$-$C_5$-cycloalkyl"), e.g. a cyclopropyl, cyclobutyl or cyclopentyl group. Particularly, said group has 3 or 4 carbon atoms ("$C_3$-$C_4$-cycloalkyl"), e.g. a cyclopropyl or cyclobutyl group.

The term "$C_4$-$C_6$-cycloalkenyl" means a monocyclic hydrocarbon ring which contains 4, 5 or 6 carbon atoms and one double bond. Particularly, said ring contains 5 or 6 carbon atoms ("$C_5$-$C_6$-cycloalkenyl"). Said $C_4$-$C_6$-cycloalkenyl group is for example, a monocyclic hydrocarbon ring, e.g. a cyclobutenyl, cyclopentenyl, cyclohexenyl or cycloheptenyll group.

The term "$C_3$-$C_6$-cycloalkyloxy" means a saturated, monovalent group of formula ($C_3$-$C_6$-cycloalkyl)-O—, in which the term "$C_3$-$C_6$-cycloalkyl" is as defined supra, e.g. a cyclopropyloxy, cyclobutyloxy, cyclopentyloxy or cyclohexyloxy group.

The term "4- to 7-membered heterocycloalkyl" means a monocyclic, saturated heterocycle with 4, 5, 6 or 7 ring atoms in total, which contains one or two identical or different ring heteroatoms from the series N, O and S.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

The term "5- to 7-membered heterocycloalkenyl" means a monocyclic, unsaturated, non-aromatic heterocycle with 5, 6 or 7 ring atoms in total, which contains one or two double bonds and one or two identical or different ring heteroatoms from the series N, O and S.

Said heterocycloalkenyl group is, for example, 4H-pyranyl, 2H-pyranyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl.

The term "(4- to 7-membered heterocycloalkyl)oxy" means a monocyclic, saturated heterocycloalkyl of formula (4- to 7-membered heterocycloalkyl)-O— in which the term "4- to 7-membered heterocycloalkyl" is as defined supra.

The term "nitrogen containing 4- to 7-membered heterocycloalkyl group" means a monocyclic, saturated heterocycle with 4, 5, 6 or 7 ring atoms in total, which contains one ring nitrogen atom and optionally one further ring heteroatom from the series N, O and S.

Said nitrogen containing 4- to 7-membered heterocycloalkyl group, without being limited thereto, can be a 4-membered ring, such as azetidinyl, for example; or a 5-membered ring, such as pyrrolidinyl, imidazolidinyl, pyrazolidinyl, 1,2-oxazolidinyl, 1,3-oxazolidinyl or 1,3-thiazolidinyl, for example; or a 6-membered ring, such as piperidinyl, morpholinyl, thiomorpholinyl, piperazinyl, or 1,2-oxazinanyl, for example, or a 7-membered ring, such as azepanyl, 1,4-diazepanyl or 1,4-oxazepanyl, for example.

The term "heteroaryl" means a monovalent, monocyclic or bicyclic aromatic ring having 5, 6, 8, 9 or 10 ring atoms (a "5- to 10-membered heteroaryl" group), which contains at least one ring heteroatom and optionally one, two or three further ring heteroatoms from the series: N, O and/or S, and which is bound via a ring carbon atom.

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a 9-membered heteroaryl group, such as, for example, benzofuranyl, benzothienyl, benzoxazolyl, benzisoxazolyl, benzimidazolyl, benzothiazolyl, benzotriazolyl, thiazolopyridinyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_6$-cycloalkyl", means a cycloalkyl group having a finite number of carbon atoms of 3 to 6, i.e. 3, 4, 5 or 6 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as 2H (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm. 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol. 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208): and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In another embodiment the present invention concerns a deuterium-containing compound of general formula (I) having 1, 2, 3 or 4 deuterium atoms, particularly with 1, 2 or 3 deuterium atoms.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, the compounds of the present invention may contain an amide moiety and can exist as an amide, or an imidic acid, or even a mixture in any amount of the two tautomers, namely:

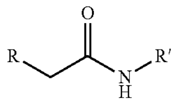
amide

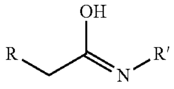
imidic acid

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the "Experimental Section", for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

The invention further includes all possible cyclodextrin clathrates, i.e alpha-, beta-, or gamma-cyclodextrins, hydroxypropyl-beta-cyclodextrins, methylbetacyclodextrins.

In accordance with a second embodiment of the first aspect, the present invention covers compounds of general formula (I), supra, in which:

$R^1$ represents a group selected from cyano, $—C(=O)NH_2$, $—C(=O)N(H)CH_3$, $—C(=O)N(H)C_2H_5$, $—C(=O)N(CH_3)_2$ and $—C(=O)OR^{15}$, $R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_6$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, $—SR^{14}$, $—S(=O)R^{14}$, $—S(=O)_2R^{14}$, $—P(=O)(R^{14})_2$, cyano, hydroxy, $—N(R^9)(R^{10})$, $—C(=O)N(R^9)(R^{10})$, $—C(=O)R^{11}$, $—N(R^{12})C(=O)R^{13}$, $—N(R^{12})S(=O)_2R^{14}$, $—N=S(=NH)(R^{14})_2$, $—N=S(=O)(R^{14})_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from $(CH_2)_3—$, $—CH_2—CH(OH)—CH_2—$, $—(CH_2)_4—$, $—O—(CH_2)_2—$, $—(CH_2)_2—O—$, $—CH_2—CH(CH_3)—O—$, $—CH_2—O—CH_2—$, $—O—(CH_2)_3—$, $—(CH_2)_3—O—$, $—CH_2—O—(CH_2)_2—$, $—(CH_2)_2O—CH_2—$, $—O—CH_2—O—$, $—O—C(CH_3)_2—O—$, $—O—(CH_2)_2—O—$, $—N(R^{18})—C(=O)—(C(R^{18})(R^{19}))—$, $—N(R^{18})—C(=O)—(C(CH_3)_2)—$, $—N(R^{18})—(C(R^{18})(R^{19}))_m—$, $—N(R^{18})—C(=O)—O—$ and $—N(R^{18})—C(=O)—N(R^{18})—$, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

$R^3$ represents a hydrogen atom or a halogen atom or a group selected from $C_1$-$C_6$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_2$-$C_4$-alkenyl group is optionally substituted with a $C_1$-$C_4$-haloalkyl group, and wherein said $C_3$-$C_5$-cycloalkyl and $C_4$-$C_5$-cycloalkenyl group is optionally substituted, one or two times, each substituent independently selected from a halogen atom or a group selected from $C_1$-$C_4$-alkyl and $C_1$-$C_4$-haloalkyl, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^4$ represents a hydrogen atom or a halogen atom or a group selected from $C_1$-$C_6$-alkyl, $C_1$-$C_6$-haloalkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_5$-hydroxyalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, —O—($C_1$-$C_4$-alkyl)-C(═O)O$R^{15}$, —O—

($C_1$-$C_4$-alkyl)-C(═O)N($R^9$)($R^{10}$), $C_3$-$C_5$-cycloalkyloxy, —S(═O)$R^{14}$, —S(═O)$_2R^{14}$, cyano, nitro, hydroxy, —N($R^9$)($R^{10}$), —N($R^{16}$)($R^{17}$), —N($R^{16}$)($R^{20}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^5$ represents a hydrogen atom or a halogen atom or a group selected from $C_1$-$C_5$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_2$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$—P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_5$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl and $C_4$-$C_5$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^6$ represents a hydrogen atom, or a fluorine atom or a group selected from $C_1$-$C_4$-alkyl, $C_1$-$C_4$-hydroxyalkyl, $C_1$-$C_4$-alkoxy, hydroxy and oxo, $R^7$ represents a hydrogen atom or a halogen atom or a group selected from $C_1$-$C_4$-alkyl, $C_1$-$C_4$-alkoxy, hydroxy and cyano, $R^8$ represents a group selected from methyl and ethyl, $R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)-, $C_3$-$C_4$-cycloalkyl and $C_2$-$C_4$-haloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, $R^{11}$ represents a hydrogen atom or group selected from $C_1$-$C_4$-alkyl, $C_1$-$C_4$-hydroxyalkyl, $C_1$-$C_4$-haloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

$R^{12}$ represents a hydrogen atom or a $C_1$-$C_4$-alkyl group, $R^{13}$ represents a hydrogen atom or a group selected from $C_1$-$C_4$-alkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^{14}$ represents a group selected from $C_1$-$C_4$-alkyl, $C_1$-$C_4$-haloalkyl, $C_3$-$C_5$-cycloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^{15}$ represents a hydrogen atom or a $C_1$-$C_4$-alkyl group, $R^{16}$ represents a hydrogen atom or a group selected from $C_1$-$C_4$-alkyl, $C_3$-$C_4$-cycloalkyl and $C_2$-$C_4$-haloalkyl, $R^{17}$ represents a 4- to 7-membered heterocycloalkyl group, wherein said 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, and wherein said 4- to 7-membered heterocycloalkyl group is connected to the rest of the molecule via a carbon atom of the 4- to 7-membered heterocycloalkyl group, $R^{18}$ represents a hydrogen atom or a group selected from methyl and ethyl, $R^{19}$ represents a hydrogen atom or a group selected from methyl and ethyl, $R^{20}$ represents a (4- to 7-membered heterocycloalkyl)-($C_1$-$C_4$-alkyl)- group, wherein the (4- to 7-membered heterocycloalkyl) part of said group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, m represents an integer selected from 1, 2 and 3, and n represents an integer selected from 1, 2 and 3, and stereoisomers, tautomers, N-oxides, hydrates, solvates, and salts thereof, and mixtures of same.

In accordance with a variant of the second embodiment of the first aspect, the present invention covers compounds of general formula (I), supra, in which:

$R^1$ represents a group selected from cyano, —C(═O)$NH_2$, —C(═O)N(H)$CH_3$, —C(═O)N(H)$C_2H_5$, —C(═O)N($CH_3$)$_2$ and —C(═O)O$R^{15}$, $R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_6$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2R^{14}$, —P(═O)($R^{14}$)$_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)($R^{14}$)$_2$, —N═S(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from ($CH_2$)$_3$—, —($CH_2$)$_4$—, —O—($CH_2$)$_2$—, —($CH_2$)$_2$—O—, —$CH_2$—O—$CH_2$—, —O—($CH_2$)$_3$—, —($CH_2$)$_3$—O—, —$CH_2$—O—($CH_2$)$_2$—, —($CH_2$)$_2$ O—$CH_2$—, —O—$CH_2$—O— and —O—($CH_2$)$_2$—O—, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

$R^3$ represents a hydrogen atom or a halogen atom or a group selected from $C_1$-$C_6$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl and $C_4$-$C_5$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^4$ represents a hydrogen atom or a halogen atom or a group selected from $C_1$-$C_6$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_5$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$- haloalkoxy, $C_3$-$C_5$-cycloalkyloxy, —S(=O)$R^{14}$, —S(=O)$_2R^{14}$, cyano, hydroxy, —N($R^9$)($R^{10}$), —N($R^{16}$)($R^{17}$), —C(=O)N($R^9$)($R^{10}$), —C(=O)$R^1$, —N($R^{12}$)C(=O)$R^{13}$, —N($R^{12}$)S(=O)$_2R^{14}$, —N=S(=NH)($R^{14}$)$_2$, —N=S(=O)($R^{14}$)$_2$, —P(=O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^5$ represents a hydrogen atom or a halogen atom or a group selected from $C_1$-$C_5$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_2$-$C_4$-alkoxy)-, $C_1$-$C_4$-haloalkoxy, $C_3$-$C_5$-cycloalkyloxy, phenoxy, —$SR^{14}$, —S(=O)$R^{14}$, —S(=O)$_2R^{14}$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2R^{14}$, —N=S(=NH)($R^{14}$)$_2$, —N=S(=O)($R^{14}$)$_2$, —P(=O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_5$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl and $C_4$-$C_5$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^6$ represents a hydrogen atom, or a fluorine atom or a group selected from $C_1$-$C_4$-alkyl, $C_1$-$C_4$-hydroxyalkyl, $C_1$-$C_4$-alkoxy, hydroxy and oxo, $R^7$ represents a hydrogen atom or a halogen atom or a group selected from $C_1$-$C_4$-alkyl, $C_1$-$C_4$-alkoxy, hydroxy and cyano, $R^8$ represents a group selected from methyl and ethyl, $R^9$ and $R^{10}$ represent, independently from each occurrence, a hydrogen atom or a group selected from $C_1$-$C_4$-alkyl, ($C_1$-$C_4$-alkoxy)-($C_2$-$C_4$-alkyl)-, $C_3$-$C_4$-cycloalkyl and $C_2$-$C_4$-haloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, $R^{11}$ represents a hydrogen atom or group selected from $C_1$-$C_4$-alkyl, $C_1$-$C_4$-hydroxyalkyl, $C_1$-$C_4$-haloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $-N(R^9)(R^{10})$, $R^{12}$ represents a hydrogen atom or a $C_1$-$C_4$-alkyl group, $R^{13}$ represents a hydrogen atom or a group selected from $C_1$-$C_4$-alkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $-N(R^9)(R^{10})$, $R^{14}$ represents a group selected from $C_1$-$C_4$-alkyl, $C_1$-$C_4$-haloalkyl, $C_3$-$C_5$-cycloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $-N(R^9)(R^{10})$, $R^{15}$ represents a hydrogen atom or a $C_1$-$C_4$-alkyl group, $R^{16}$ represents a hydrogen atom or a group selected from $C_1$-$C_4$-alkyl, $C_3$-$C_4$-cycloalkyl and $C_2$-$C_4$-haloalkyl, $R^{17}$ represents a 4- to 7-membered heterocycloalkyl group, wherein said 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, and wherein said 4- to 7-membered heterocycloalkyl group is connected to the rest of the molecule via a carbon atom of the 4- to 7-membered heterocycloalkyl group, and n represents an integer selected from 1, 2 and 3, and stereoisomers, tautomers, N-oxides, hydrates, solvates, and salts thereof, and mixtures of same.

In accordance with a third embodiment of the first aspect, the present invention covers compounds of general formula (I), supra, in which:

$R^1$ represents a group selected from cyano, $-C(=O)NH_2$, $-C(=O)N(H)CH_3$, $-C(=O)N(H)C_2H_5$, $-C(=O)N(CH_3)_2$ and $-C(=O)OR^{15}$, $R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, $-S(=O)_2R^{14}$, $-P(=O)(R^{14})_2$, cyano, hydroxy, $-N(R^9)(R^{10})$, $-C(=O)N(R^9)(R^{10})$, $-C(=O)R^{11}$, $-N(R^{12})C(=O)R^{13}$, $-N(R^{12})S(=O)_2R^{14}$, $-N=S(=O)(R^{14})_2$, 4- to 7-membered heterocycloalkyl, phenyl and 5- or 6-membered heteroaryl, or two substituents of said phenyl group, when they are attached to adjacent ring atoms, are optionally linked to one another in such a way that they jointly form a group selected from $-CH_2-CH(OH)-CH_2-$, $-CH_2-CH(CH_3)-O-$, $-O-C(CH_3)_2-O-$, $-N(R^{18})-C(=O)-(C(R^{18})(R^{19}))_m-$, $-N(R^{18})-C(=O)-(C(CH_3)_2)-$, $-N(R^{18})-(C(R^{18})(R^{19}))_m-N(R^{18})-C(=O)-O-$ and $-N(R^{18})-C(=O)-N(R^{18})-$, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from phenyl and 4- to 7-membered heterocycloalkyl, wherein said 4- to 7-membered heterocycloalkyl group is connected to the rest of the molecule via a carbon atom of said 4- to 7-membered heterocycloalkyl group, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $-N(R^9)(R^{10})$, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^3$ represents a hydrogen atom or a halogen atom or a group selected from $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2$$R^{14}$, cyano, hydroxy, —N($R^9$)($R^{10}$), —C(═O)N($R^9$)($R^{10}$), —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_2$-$C_4$-alkenyl group is optionally substituted with a $C_1$-$C_4$-haloalkyl group, and wherein said $C_3$-$C_5$-cycloalkyl group is optionally substituted, one or two times, each substituent independently selected from a halogen atom or a group selected from $C_1$-$C_4$-alkyl and $C_1$-$C_4$-haloalkyl, $R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—($C_1$-$C_4$-alkyl)-C(═O)O$R^{15}$, —O—($C_1$-$C_4$-alkyl)-C(═O)N($R^9$)($R^{10}$), $C_3$-$C_5$-cycloalkyloxy, —S(═O)$_2$$R^{14}$, cyano, nitro, hydroxy, —N($R^9$)($R^{10}$), —N($R^{16}$)($R^{17}$), —N($R^{16}$)($R^{20}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl group is optionally substituted, one or two times, each substituent independently selected from a halogen atom or a $C_1$-$C_4$-alkyl group, and wherein said phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(═O)$_2$$R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$$R^{14}$, —N═S(═NH)($R^{14}$)$_2$, —N═S(═O)($R^{14}$)$_2$, —P(═O)($R^{14}$)$_2$, 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_5$-alkyl, $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, $R^6$ represents a hydrogen atom or a group selected from $C_1$-$C_4$-alkyl, $C_1$-$C_4$-hydroxyalkyl, $C_1$-$C_4$-alkoxy, hydroxy and oxo, $R^7$ represents a hydrogen atom or a halogen atom or a group selected from $C_1$-$C_4$-alkyl, $C_1$-$C_4$-alkoxy and hydroxy, $R^3$ represents a group selected from methyl and ethyl, $R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, $R^{11}$ represents a hydrogen atom or a group selected from $C_1$-$C_4$-alkyl and $C_1$-$C_4$-haloalkyl, $R^{12}$ represents a hydrogen atom, $R^{13}$ represents a phenyl group, $R^{14}$ represents a group selected from $C_1$-$C_4$-alkyl and phenyl, wherein said phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R_9$)($R^{10}$), $R^{15}$ represents a hydrogen atom or a $C_1$-$C_4$-alkyl group, and $R^{16}$ represents a hydrogen atom or a $C_1$-$C_4$-alkyl group, $R^{17}$ represents a 4- to 7-membered heterocycloalkyl group, wherein said 4- to 7-membered heterocycloalkyl group is optionally substituted, one or two times, with a $C_1$-$C_4$-alkyl group, and wherein said 4- to 7-membered heterocycloalkyl group is connected to the rest of the molecule via a carbon atom of the 4- to 7-membered heterocycloalkyl group, $R^{18}$ represents a hydrogen atom or a methyl group, $R^{19}$ represents a hydrogen atom or a methyl group, $R^{20}$ represents a (4- to 7-membered heterocycloalkyl)-($C_1$-$C_4$-alkyl)- group, wherein the (4- to 7-membered heterocycloalkyl) part of said group is optionally substituted, one or two times, with a $C_1$-$C_4$-alkyl group, m represents an integer selected from 1 and 2, and n represents an integer selected from 1, 2 and 3, and stereoisomers, tautomers, N-oxides, hydrates, solvates, and salts thereof, and mixtures of same.

In accordance with a variant of the third embodiment of the first aspect, the present invention covers compounds of general formula (I), supra, in which:

$R^1$ represents a group selected from cyano, —C(═O)$NH_2$, —C(═O)N(H)$CH_3$, —C(═O)N(H)$C_2H_5$, —C(═O)N($CH_3$)$_2$ and —C(═O)$OR^{15}$, $R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(═O)$_2R^{14}$, —P(═O)($R^{14}$)$_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2R^{14}$, —N=S(=O)($R^{14}$)$_2$ and phenyl, wherein said $C_1$-$C_4$-alkoxy group is optionally substituted with a phenyl group, which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^3$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —S(=O)$_2R^{14}$, cyano, hydroxy, —N($R^9$)($R^{10}$), —P(=O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, $R^4$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —S(=O)$_2$ $R^{14}$, cyano, —N($R^9$)($R^{10}$), —N($R^{16}$)($R^{17}$), —N=S(=NH)($R^{14}$)$_2$, —N=S(=O)($R^{14}$)$_2$, —P(=O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(=O)$_2R^{14}$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2R^{14}$, —N=S(=NH)($R^{14}$)$_2$, —N=S(=O)($R^{14}$)$_2$, —P(=O)($R^{14}$)$_2$, 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, and wherein said 4- to 7-membered heterocycloalkyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_5$-alkyl, $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, $R^6$ represents a hydrogen atom or a group selected from $C_1$-$C_4$-alkyl, $C_1$-$C_4$-hydroxyalkyl, $C_1$-$C_4$-alkoxy, hydroxy and oxo, $R^7$ represents a hydrogen atom or a halogen atom or a group selected from $C_1$-$C_4$-alkyl and hydroxy, $R^3$ represents a group selected from methyl and ethyl, $R^9$ and $R^{10}$ represent, independently from each occurrence, a hydrogen atom or $C_1$-$C_4$-alkyl group, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, $R^{11}$ represents a hydrogen atom or a $C_1$-$C_4$-haloalkyl group, $R^{12}$ represents a hydrogen atom, $R^{13}$ represents a phenyl group, $R^{14}$ represents a group selected from $C_1$-$C_4$-alkyl and phenyl, wherein said phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), $R^{15}$ represents a hydrogen atom or a $C_1$-$C_4$-alkyl group, $R^{16}$ represents a hydrogen atom or a $C_1$-$C_4$-alkyl group, $R^{17}$ represents a 4- to 7-membered heterocycloalkyl group, wherein said 4- to 7-membered heterocycloalkyl group is optionally substituted, one or two times, with a $C_1$-$C_4$-alkyl group, and wherein said 4- to 7-membered heterocycloalkyl group is connected to the rest of the molecule via a carbon atom of the 4- to 7-membered heterocycloalkyl group, and n represents an integer selected from 1, 2 and 3, and stereoisomers, tautomers, N-oxides, hydrates, solvates, and salts thereof, and mixtures of same.

In accordance with a fourth embodiment of the first aspect, the present invention covers compounds of general formula (I), supra, in which:

$R^1$ represents a group selected from cyano, —C(═O)$NH_2$, —C(═O)N(H)$CH_3$ and —C(═O)N($CH_3$)$_2$, $R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(═O)$_2R^{14}$, —P(═O)($R^{14}$)$_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═O)($R^{14}$)$_2$, 4- to 7-membered heterocycloalkyl, phenyl and 5- or 6-membered heteroaryl, or two substituents of said phenyl group, when they are attached to adjacent ring atoms, are optionally linked to one another in such a way that they jointly form a group selected from —$CH_2$—CH(OH)—$CH_2$—, —$CH_2$—CH($CH_3$)—O—, —O—C($CH_3$)$_2$—O—, —N($R^{18}$)—C(═O)—(C($R^{18}$)($R^{19}$))$_m$—, —N($R^{18}$)—C(═O)—(C($CH_3$)$_2$)—, —N($R^{18}$)—(C($R^{18}$)($R^{19}$))$_m$—, —N($R^{18}$)—C(═O)—O— and —N($R^{18}$)—C(═O)—N($R^{18}$)—, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from 4- to 7-membered heterocycloalkyl and phenyl, wherein said 4- to 7-membered heterocycloalkyl group is connected to the rest of the molecule via a carbon atom of said 4- to 7-membered heterocycloalkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl and $C_1$-$C_2$-alkoxy, $R^3$ represents a hydrogen atom or a halogen atom or a group selected from $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2$R$^{14}$, cyano, hydroxy, —N(R$^9$)(R$^{10}$), —C(═O)N(R$^9$)(R$^{10}$), —P(═O)(R$^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, with a cyano group, and wherein said $C_2$-$C_4$-alkenyl group is optionally substituted with a $C_1$-$C_4$-haloalkyl group, and wherein said $C_3$-$C_5$-cycloalkyl group is optionally substituted, one or two times, each substituent independently selected from a halogen atom or a group selected from $C_1$-$C_4$-alkyl and $C_1$-$C_4$-haloalkyl, $R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—($C_1$-$C_4$-alkyl)-C(═O)OR$^{15}$, —O—($C_1$-$C_4$-alkyl)-C(═O)N(R$^9$)(R$^{10}$), $C_3$-$C_5$-cycloalkyloxy, —S(═O)$_2$R$^{14}$, cyano, nitro, hydroxy, —N(R$^9$)(R$^{10}$), —N(R$^{16}$)(R$^{17}$), —N(R$^{16}$)(R$^{20}$), —N═S(═NH)(R$^{14}$)$_2$, —N═S(═O)(R$^{14}$)$_2$, —P(═O)(R$^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and, 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl is optionally substituted, one or two times, each substituent independently selected from a halogen atom or a $C_1$-$C_4$-alkyl group, $R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(═O)$_2$R$^{14}$, cyano, hydroxy, —N(R$^9$)(R$^{10}$), 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, $R^6$ represents a hydrogen atom or a group selected from $C_1$-$C_4$-alkyl and $C_1$-$C_4$-hydroxyalkyl, $R^7$ represents a hydrogen atom or a halogen atom or a group selected from $C_1$-$C_4$-alkyl, $C_1$-$C_4$-alkoxy and hydroxy, $R^8$ represents a group selected from methyl and ethyl, $R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, $R^{11}$ represents a group selected from $C_1$-$C_4$-alkyl and $C_1$-$C_4$-haloalkyl, $R^{12}$ represents a hydrogen atom, $R^{13}$ represents a phenyl group, $R^{14}$ represents a group selected from $C_1$-$C_4$-alkyl and phenyl, $R^{15}$ represents a hydrogen atom or a $C_1$-$C_4$-alkyl group,
$R^{16}$ represents a hydrogen atom or a $C_1$-$C_4$-alkyl group,
$R^{17}$ represents a 4- to 7-membered heterocycloalkyl group,
wherein said 4- to 7-membered heterocycloalkyl group is optionally substituted, one or two times, with a $C_1$-$C_4$-alkyl group,
and
wherein said 4- to 7-membered heterocycloalkyl group is connected to the rest of the molecule via a carbon atom of the 4- to 7-membered heterocycloalkyl group,
$R^{18}$ represents a hydrogen atom or a methyl group,
$R^{19}$ represents a hydrogen atom or a methyl group,
$R^{20}$ represents a (4- to 7-membered heterocycloalkyl)-($C_1$-$C_4$-alkyl)- group,
wherein the (4- to 7-membered heterocycloalkyl) part of said group is optionally substituted, one or two times, with a $C_1$-$C_4$-alkyl group,
m represents an integer selected from 1 and 2,
and
n represents an integer selected from 1, 2 and 3,
and stereoisomers, tautomers, N-oxides, hydrates, solvates, and salts thereof, and mixtures of same.

In accordance with a variant of the fourth embodiment of the first aspect, the present invention covers compounds of general formula (I), supra, in which:
$R^1$ represents a group selected from cyano, $—C(=O)NH_2$, $—C(=O)N(H)CH_3$ and $—C(=O)N(CH_3)_2$,
$R^2$ represents a group selected from phenyl, naphthyl and 5- to 10-membered heteroaryl,
which 5- to 10-membered heteroaryl group is connected to the rest of the molecule via a carbon atom of said 5- to 10-membered heteroaryl group,
and
which phenyl, naphthyl and 5- to 10-membered heteroaryl group is optionally substituted, one, two, three or four times, each substituent independently selected from a halogen atom or a group selected from
$C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, $—S(=O)_2R^{14}$, $—P(=O)(R^{14})_2$, cyano, hydroxy, $—N(R^9)(R^{10})$, $—C(=O)N(R^9)(R^{10})$, $—C(=O)R^{11}$, $—N(R^{12})C(=O)R^{13}$, $—N(R^{12})S(=O)_2R^{14}$, $—N=S(=O)(R^{14})_2$ and phenyl,
wherein said $C_1$-$C_4$-alkoxy group is optionally substituted with a phenyl group,
$R^3$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, $—S(=O)_2R^{14}$, cyano, hydroxy, $—N(R^9)(R^{10})$, 4- to 7-membered heterocycloalkyl, 5- to 7-membered heterocycloalkenyl, (4- to 7-membered heterocycloalkyl)oxy and phenyl,
wherein said 4- to 7-membered heterocycloalkyl group and
5- to 7-membered heterocycloalkenyl group is connected to the rest of the molecule via a carbon atom of said 4- to 7-membered heterocycloalkyl group and 5- to 7-membered heterocycloalkenyl group,
and
wherein said $C_1$-$C_6$-alkyl and $C_1$-$C_4$-alkoxy group is optionally substituted with a group selected from
$C_3$-$C_4$-cycloalkyl and 4- to 7-membered heterocycloalkyl,
wherein said 4- to 7-membered heterocycloalkyl group is connected to the rest of the molecule via a carbon atom of said 4- to 7-membered heterocycloalkyl group,
and
which $C_3$-$C_4$-cycloalkyl group is optionally substituted, one or two times, with a cyano group,
and
wherein said $C_3$-$C_5$-cycloalkyl group is optionally substituted, one or two times, with a halogen atom,
$R^4$ represents a hydrogen atom or a halogen atom or a group selected from
$C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, $—S(=O)_2R^{14}$, cyano, $—N(R^9)(R^{10})$, $—N(R^{16})(R^{17})$, $—N=S(=NH)(R^{14})_2$, $—N=S(=O)(R^{14})_2$, 4- to 7-membered heterocycloalkyl,
5- to 7-membered heterocycloalkenyl, (4- to 7-membered heterocycloalkyl)oxy and phenyl,
wherein said 4- to 7-membered heterocycloalkyl group and
5- to 7-membered heterocycloalkenyl group is connected to the rest of the molecule via a carbon atom of said 4- to 7-membered heterocycloalkyl group and 5- to 7-membered heterocycloalkenyl group,
and
wherein said $C_1$-$C_6$-alkyl and $C_1$-$C_4$-alkoxy group is optionally substituted with a group selected from
$C_3$-$C_4$-cycloalkyl and 4- to 7-membered heterocycloalkyl,
wherein said 4- to 7-membered heterocycloalkyl group is connected to the rest of the molecule via a carbon atom of said 4- to 7-membered heterocycloalkyl group,
and
which $C_3$-$C_4$-cycloalkyl group is optionally substituted, one or two times, each substituent independently selected from a halogen atom or a group selected from
cyano and hydroxy,
and
wherein said $C_3$-$C_5$-cycloalkyl is optionally substituted, one or two times, each substituent independently selected from a halogen atom or a $C_1$-$C_4$-alkyl group,
$R^5$ represents a hydrogen atom or a halogen atom or a group selected from
$C_1$-$C_5$-alkyl, $C_3$-$C_5$-cycloalkyl, $C_1$-$C_4$-alkoxy, $C_3$-$C_5$-cycloalkyloxy, $—S(=O)_2R^{14}$, cyano, hydroxy, $—N(R^9)(R^{10})$, 4- to 7-membered heterocycloalkyl and (4- to 7-membered heterocycloalkyl)oxy,
wherein said 4- to 7-membered heterocycloalkyl group is connected to the rest of the molecule via a carbon atom of said 4- to 7-membered heterocycloalkyl group,
$R^6$ represents a hydrogen atom or a group selected from
$C_1$-$C_4$-alkyl and $C_1$-$C_4$-hydroxyalkyl,
$R^7$ represents a hydrogen atom or a halogen atom or a group selected from
$C_1$-$C_4$-alkyl and hydroxy,
$R^8$ represents a group selected from methyl and ethyl,
$R^9$ and $R^{10}$ represent, independently from each occurrence, a hydrogen atom or $C_1$-$C_4$-alkyl group,
or
$R^9$ and $R^{10}$ together with the nitrogen to which they are attached represent a nitrogen containing 4- to 7-membered heterocycloalkyl group,
wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, $R^{11}$ represents a $C_1$-$C_4$-haloalkyl group, $R^{12}$ represents a hydrogen atom, $R^{13}$ represents a phenyl group, $R^{14}$ represents a group selected from $C_1$-$C_4$-alkyl and phenyl, $R^{16}$ represents a hydrogen atom or a $C_1$-$C_4$-alkyl group, $R^{17}$ represents a 4- to 7-membered heterocycloalkyl group, wherein said 4- to 7-membered heterocycloalkyl group is optionally substituted, one or two times, with a $C_1$-$C_4$-alkyl group, and wherein said 4- to 7-membered heterocycloalkyl group is connected to the rest of the molecule via a carbon atom of the 4- to 7-membered heterocycloalkyl group, and n represents an integer selected from 1, 2 and 3, and stereoisomers, tautomers, N-oxides, hydrates, solvates, and salts thereof, and mixtures of same.

In accordance with a fifth embodiment of the first aspect, the present invention covers compounds of general formula (I), supra, in which:

$R^1$ represents a group selected from cyano, —C(═O)$NH_2$, —C(═O)N(H)$CH_3$ and —C(═O)N($CH_3$)$_2$, $R^2$ represents a group selected from phenyl, 1-naphthyl, 2-naphthyl and 5- to 10-membered heteroaryl, which 5- to 10-membered heteroaryl group is selected from pyrazolyl, 1,2,4-oxadiazol, 1,3,4-oxadiazol, 1H-1,2,3-triazolyl, 2H-1,2,3-triazolyl, 1,3-thiazolyl, pyridinyl, pyrazinyl, indolyl, benzothiophenyl, benzofuranyl, 1,3-benzoxazolyl, indazolyl, benzimidazolyl, 1,3-benzothiazolyl, pyrrolo[2,3-b]pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which phenyl, 1-naphthyl, 2-naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(═O)$_2R^{14}$, —P(═O)($R^{14}$)$_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═O)($R^{14}$)$_2$, 4- to 7-membered heterocycloalkyl, phenyl and pyridinyl, or two substituents of said phenyl group, when they are attached to adjacent ring atoms, are optionally linked to one another in such a way that they jointly form a group selected from —$CH_2$—CH(OH)—$CH_2$—, —$CH_2$—CH($CH_3$)—O—, —O—C($CH_3$)$_2$—O—, —NH—C(═O)—CH($CH_3$)—, —N($CH_3$)—C(═O)—C($CH_3$)$_2$—, —NH—C(═O)—(C($CH_3$)$_2$)—, —NH—$CH_2$—C($CH_3$)$_2$—, —N($CH_3$)—C(═O)—O— and —N($CH_3$)—C(═O)—N($CH_3$)—, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from 4- to 7-membered heterocycloalkyl and phenyl, wherein said 4- to 7-membered heterocycloalkyl group is connected to the rest of the molecule via a carbon atom of said 4- to 7-membered heterocycloalkyl group, and wherein said phenyl group is optionally substituted, one or two times, each substituent independently selected from a halogen atom or a group selected from $C_1$-$C_2$-alkyl, $C_1$-$C_2$-haloalkyl and $C_1$-$C_2$-alkoxy, $R^3$ represents a hydrogen atom or a halogen atom or a group selected from $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2R^{14}$, cyano, hydroxy, —N($R^9$)($R^{10}$), —C(═O)N($R^9$)($R^{10}$), —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, with a cyano group, and wherein said $C_2$-$C_4$-alkenyl group is optionally substituted with a $C_1$-$C_4$-haloalkyl group, and wherein said $C_3$-$C_5$-cycloalkyl group is optionally substituted, one or two times, with a halogen atom or a group selected from $C_1$-$C_4$-alkyl and $C_1$-$C_4$-haloalkyl, $R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—$CH_2$—C(═O)O$R^{15}$, —O—$CH_2$—C(═O)N($R^9$)($R^{10}$), $C_3$-$C_5$-cycloalkyloxy, —S(═O)$_2R^{14}$, cyano, nitro, hydroxy, —N($R^9$)($R^{10}$), —N($R^{16}$)($R^{17}$), —N($R^{16}$)($R^{20}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl group is optionally substituted, one or two times, each substituent independently selected from a halogen atom or a $C_1$-$C_4$-alkyl group, $R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(=O)$_2$R$^{14}$, cyano, hydroxy, —N(R$^9$)(R$^{10}$), 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, $R^6$ represents a hydrogen atom or a group selected from $C_1$-$C_4$-alkyl and $C_1$-$C_4$-hydroxyalkyl, $R^7$ represents a hydrogen atom or a halogen atom or a group selected from $C_1$-$C_4$-alkyl, $C_1$-$C_4$-alkoxy and hydroxy, $R^8$ represents a group selected from methyl and ethyl, $R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, $R^{11}$ represents a group selected from $C_1$-$C_4$-alkyl and $C_1$-$C_4$-haloalkyl, $R^{12}$ represents a hydrogen atom, $R^{13}$ represents a phenyl group, $R^{14}$ represents a group selected from $C_1$-$C_4$-alkyl and phenyl, $R^{15}$ represents a hydrogen atom or a $C_1$-$C_4$-alkyl group, $R^{16}$ represents a hydrogen atom or a $C_1$-$C_4$-alkyl group, $R^{17}$ represents a 4- to 7-membered heterocycloalkyl group, wherein said 4- to 7-membered heterocycloalkyl group is connected to the rest of the molecule via a carbon atom of the 4- to 7-membered heterocycloalkyl group, $R^{20}$ represents a (4- to 7-membered heterocycloalkyl)-($C_1$-$C_4$-alkyl)- group, and n represents an integer selected from 1, 2 and 3, and stereoisomers, tautomers, N-oxides, hydrates, solvates, and salts thereof, and mixtures of same.

In accordance with a variant of the fifth embodiment of the first aspect, the present invention covers compounds of general formula (I), supra, in which:

$R^1$ represents a group selected from cyano, —C(=O)NH$_2$, —C(=O)N(H)CH$_3$ and —C(=O)N(CH$_3$)$_2$, $R^2$ represents a group selected from phenyl, 1-naphthyl, 2-naphthyl and 5- to 10-membered heteroaryl, which 5- to 10-membered heteroaryl group is selected from pyrazolyl, 1,2,4-oxadiazol, 1,3,4-oxadiazol 1,3-thiazolyl, pyridinyl, pyrazinyl, indolyl, benzothiophenyl, benzofuranyl, 1,3-benzoxazolyl, indazolyl, benzimidazolyl, 1,3-benzothiazolyl, pyrrolo[2,3-b]pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which phenyl, 1-naphthyl, 2-naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(=O)$_2$R$^{14}$, —P(=O)(R$^{14}$)$_2$, cyano, hydroxy, —N(R$^9$)(R$^{10}$), —C(=O)N(R$^9$)(R$^{10}$), —C(=O)R$^{11}$, —N(R$^{12}$)C(=O)R$^{13}$, —N(R$^{12}$)S(=O)$_2$R$^{14}$, —N=S(=O)(R$^{14}$)$_2$, 4- to 7-membered heterocycloalkyl, phenyl and pyridinyl, or two substituents of said phenyl group, when they are attached to adjacent ring atoms, are optionally linked to one another in such a way that they jointly form a group selected from —CH$_2$—CH(OH)—CH$_2$—, —CH$_2$—CH(CH$_3$)—O—, —O—C(CH$_3$)$_2$—O—, —NH—C(=O)—CH(CH$_3$)—, —N(CH$_3$)—C(=O)—C(CH$_3$)$_2$—, —NH—C(=O)—(C(CH$_3$)$_2$)—, —NH—CH$_2$—C(CH$_3$)$_2$—, —N(CH$_3$)—C(=O)—O— and —N(CH$_3$)—C(=O)—N(CH$_3$)—, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from 4- to 7-membered heterocycloalkyl and phenyl, wherein said 4- to 7-membered heterocycloalkyl group is connected to the rest of the molecule via a carbon atom of said 4- to 7-membered heterocycloalkyl group, and wherein said phenyl group is optionally substituted, one or two times, each substituent independently selected from a halogen atom or a group selected from $C_1$-$C_2$-alkyl, $C_1$-$C_2$-haloalkyl and $C_1$-$C_2$-alkoxy, $R^3$ represents a hydrogen atom or a halogen atom or a group selected from $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2$$R^{14}$, cyano, hydroxy, —N($R^9$)($R^{10}$), —C(═O)N($R^9$)($R^{10}$), —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, with a cyano group, and wherein said $C_2$-$C_4$-alkenyl group is optionally substituted with a $C_1$-$C_4$-haloalkyl group, and wherein said $C_3$-$C_5$-cycloalkyl group is optionally substituted, one or two times, with a halogen atom or a group selected from $C_1$-$C_4$-alkyl and $C_1$-$C_4$-haloalkyl, $R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—$CH_2$—C(═O)O$R^{15}$, —O—$CH_2$—C(═O)N($R^9$)($R^{10}$), $C_3$-$C_5$-cycloalkyloxy, —S(═O)$_2$$R^{14}$, cyano, nitro, hydroxy, —N($R^9$)($R^{10}$), —N($R^{16}$)($R^{17}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl group is optionally substituted, one or two times, each substituent independently selected from a halogen atom or a $C_1$-$C_4$-alkyl group, $R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(═O)$_2$$R^{14}$, cyano, hydroxy, —N($R^9$)($R^{10}$), 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, $R^6$ represents a hydrogen atom or a group selected from $C_1$-$C_4$-alkyl and $C_1$-$C_4$-hydroxyalkyl, $R^7$ represents a hydrogen atom or a halogen atom or a group selected from $C_1$-$C_4$-alkyl, $C_1$-$C_4$-alkoxy and hydroxy, $R^8$ represents a group selected from methyl and ethyl, $R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, $R^{11}$ represents a group selected from $C_1$-$C_4$-alkyl and $C_1$-$C_4$-haloalkyl, $R^{12}$ represents a hydrogen atom, $R^{13}$ represents a phenyl group, $R^{14}$ represents a group selected from $C_1$-$C_4$-alkyl and phenyl, $R^{15}$ represents a hydrogen atom or a $C_1$-$C_4$-alkyl group, $R^{16}$ represents a hydrogen atom or a $C_1$-$C_4$-alkyl group, $R^{17}$ represents a 4- to 7-membered heterocycloalkyl group, wherein said 4- to 7-membered heterocycloalkyl group is connected to the rest of the molecule via a carbon atom of the 4- to 7-membered heterocycloalkyl group, and n represents an integer selected from 1, 2 and 3, and stereoisomers, tautomers, N-oxides, hydrates, solvates, and salts thereof, and mixtures of same.

In accordance with a further variant of the fifth embodiment of the first aspect, the present invention covers compounds of general formula (I), supra, in which:

$R^1$ represents a group selected from cyano, —C(═O)$NH_2$, —C(═O)N(H)$CH_3$ and —C(═O)N$(CH_3)_2$, $R^2$ represents a group selected from phenyl, 1-naphthyl and 5- to 10-membered heteroaryl, which 5- to 10-membered heteroaryl group is selected from pyrazolyl, 1,2,4-oxadiazol, 1,3-thiazolyl, pyridinyl, pyrazinyl, indolyl, benzofuranyl, 1,3-benzoxazolyl, benzimidazolyl, 1,3-benzothiazolyl, pyrrolo[2,3-b]pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which phenyl, 1-naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(═O)$_2R^{14}$, —P(═O)$(R^{14})_2$, cyano, hydroxy, —N$(R^9)(R^{10})$, —C(═O)N$(R^9)(R^{10})$, —C(═O)$R^{11}$, —N$(R^{12})$C(═O)$R^{13}$, —N$(R^{12})$S(═O)$_2R^{14}$, —N═S(═O)$(R^{14})_2$ and phenyl, wherein said $C_1$-$C_4$-alkoxy group is optionally substituted with a phenyl group, $R^3$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —S(═O)$_2$ $R^{14}$, cyano, hydroxy, —N$(R^9)(R^{10})$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, with a cyano group, and wherein said $C_3$-$C_5$-cycloalkyl group is optionally substituted, one or two times, with a halogen atom, $R^4$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —S(═O)$_2R^{14}$, cyano, —N$(R^9)(R^{10})$, —N$(R^{16})(R^{17})$, —N═S(═NH)$(R^{14})_2$, —N═S(═O)$(R^{14})_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, $R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(═O)$_2R^{14}$, cyano, hydroxy, —N$(R^9)(R^{10})$, 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, $R^6$ represents a hydrogen atom or a group selected from $C_1$-$C_4$-alkyl and $C_1$-$C_4$-hydroxyalkyl, $R^7$ represents a hydrogen atom or a halogen atom or a group selected from $C_1$-$C_4$-alkyl and hydroxy, $R^8$ represents a group selected from methyl and ethyl, $R^9$ and $R^{10}$ represent, independently from each occurrence, a hydrogen atom or $C_1$-$C_4$-alkyl group, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, $R^{11}$ represents a $C_1$-$C_4$-haloalkyl group, $R^{12}$ represents a hydrogen atom, $R^{13}$ represents a phenyl group, $R^{14}$ represents a group selected from $C_1$-$C_4$-alkyl and phenyl, $R^{16}$ represents a hydrogen atom or a $C_1$-$C_4$-alkyl group, $R^{17}$ represents a 4- to 7-membered heterocycloalkyl group, wherein said 4- to 7-membered heterocycloalkyl group is connected to the rest of the molecule via a carbon atom of the 4- to 7-membered heterocycloalkyl group, and n represents an integer selected from 1, 2 and 3, and stereoisomers, tautomers, N-oxides, hydrates, solvates, and salts thereof, and mixtures of same.

In accordance with a sixth embodiment of the first aspect, the present invention covers compounds of general formula (I), supra, in which:

$R^1$ represents a group selected from cyano, —C(═O)$NH_2$, —C(═O)N(H)$CH_3$ and —C(═O)N$(CH_3)_2$, $R^2$ represents a group selected from phenyl, 1-naphthyl, 2-naphthyl, 1H-pyrazol-3-yl, 1H-pyrazol-4-yl, 1H-pyrazol-5-yl, 1,2,4-oxadiazol-5-yl, 1,3,4-oxadiazol-2-yl, 1H-1,2,3-triazol-4-yl, 2H-1,2,3-triazol-4-yl, 1,3-thiazol-2-yl, pyridin-3-yl, pyrazin-2-yl, 1H-indol-5-yl, 1-benzofuran-4-yl, 1-benzofuran-7-yl, 1H-indol-6-yl, benzothiophen-2-yl, 1,3-benzoxazol-2-yl, 1,3-benzoxazol-5-yl, 1,3-benzoxazol-6-yl, 1,3-benzoxazol-7-yl, 1H-indazol-5-yl, 1H-benzimidazol-2-yl, 1H-benzimidazol-4-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1H-pyrrolo[2,3-b]pyridin-3-yl, quinolin-2-yl, quinolin-4-yl, quinolin-6-yl, quinolin-7-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, methoxymethyl, 2-methoxyethyl, benzyloxy, trifluormethoxy, 2,2,2-trifluoroethoxy, phenoxy, (oxolan-2-yl)methoxy, (tetrahydrofuran-2-yl)methoxy, methanesulfonyl, dimethylphosphoryl, cyano, hydroxy, dimethylamino, oxetan-3-yl, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, acetyl, trifluoroacetyl, benzamido, benzenesulfonamido, [dimethyl(oxido)-$\lambda^6$-sulfanylidene]amino, phenyl, 3-chlorophenyl, 4-chlorophenyl, 2-methylphenyl, 3-methylphenyl, 4-methylphenyl, 3-trifluoromethylphenyl, 2-methoxyphenyl, 3-methoxyphenyl, 4-methoxyphenyl and pyridin-3-yl, or two substituents of said phenyl group, when they are attached to adjacent ring atoms, are linked to one another in such a way that they jointly form a group selected from —$CH_2$—CH(OH)—$CH_2$—, —$CH_2$—CH($CH_3$)—O—, —O—C$(CH_3)_2$—O—, —NH—C(═O)—CH($CH_3$)—, —N($CH_3$)—C(═O)—C$(CH_3)_2$—, —NH—C(═O)—(C$(CH_3)_2$)—, —NH—$CH_2$—C$(CH_3)_2$—, —N($CH_3$)—C(═O)—O— and —N($CH_3$)—C(═O)—N($CH_3$)—, $R^3$ represents a hydrogen atom or a fluorine, chlorine or bromine atom or a group selected from methyl, sec-butyl, (oxetan-3-yl)methyl, 3,3,3-trifluoroprop-1-en-2-yl, cyclopropyl, (trifluoromethyl)cyclopropyl, cyclobutyl, 2,2-dimethylcyclobutyl, 3,3-difluorocyclobutyl, methoxymethyl, methoxy, ethoxy, propoxy, 2,2-difluoroethoxy, 2,2-difluoropropoxy, cyclopropylmethoxy, (1-cyanocyclopropyl)methoxy, cyclopropyloxy, cyclobutyloxy, methanesulfonyl, cyano, hydroxy, 4-hydroxy-2-oxo-pyrrolidin-1-yl, 7-oxo-2-oxa-6-azaspiro[3.4]octan-6-yl, carbamoyl, dimethylphosphoryl, oxetan-3-yl, 3,6-dihydro-2H-pyran-4-yl, (oxetan-3-yl)oxy and phenyl, $R^4$ represents a hydrogen atom or a fluorine, chlorine or bromine atom or a group selected from methyl, sec-butyl, (oxetan-3-yl)methyl, trifluoromethyl, cyclopropyl, 3,3-difluorocyclobutyl, methoxymethyl, methoxy, propoxy, 2-methoxyethoxy, (1-hydroxycyclopropyl)methoxy, (1-cyanocyclopropyl)methoxy, (oxiran-2-yl)methoxy, carboxymethoxy, 2-tert-butoxy-2-oxo-ethoxy, 2-amino-2-oxo-ethoxy, cyclopropyloxy, cyclobutyloxy, methanesulfonyl, dimethylphosphoryl, cyano, nitro, hydroxy, (cyanomethyl)(methyll)amino, (2-hydroxyethyl)amino, (2-hydroxyethyl)(methyl)amino, (2-methoxyethyl)amino, (2-methoxyethyl)(methyl)amino, cyclopropylamino, (oxetan-3-yl)amino, methyl(oxetan-3-yl)amino, methyl(oxolan-3-yl)amino, 3-hydroxyazetidin-1-yl, 2-oxopyrrolidin-1-yl, morpholino, 1,1-dioxidothiomorpholin-4-yl, 4-hydroxy-2-oxo-pyrrolidin-1-yl, 7-oxo-2-oxa-6-azaspiro[3.4]octan-6-yl, 2,2-dimethyl-2$\lambda^6$-diazathia-1,2-dien-1-yl, [dimethyl(oxido)-$\lambda^6$-sulfanylidene]amino, methyl(tetrahydrofuran-3-yl)amino, tetrahydrofuran-3-ylmethoxy, (tetrahydrofuran-3-ylmethyl)amino, oxetan-3-yl, 3,6-dihydro-2H-pyran-4-yl, (oxetan-3-yl)oxy, (tetrahydrofuran-3-yl)oxy, (tetrahydro-2H-pyran-3-yl)oxy, (tetrahydro-2H-pyran-4-yl)oxy and phenyl, $R^5$ represents a hydrogen atom or a fluorine, chlorine or bromine atom or a group selected from methyl, cyclopropyl, methoxy, propoxy, cyclopropyloxy, methanesulfonyl, cyano, hydroxy, oxetan-3-yl and oxetan-3-yloxy, $R^6$ represents a hydrogen atom or a group selected from methyl and hydroxymethyl, $R^7$ represents a hydrogen atom or a fluorine atom or a group selected from methyl, ethyl, methoxy and hydroxy, $R^8$ represents a group selected from methyl and ethyl, and n represents an integer selected from 1, 2 and 3, and stereoisomers, tautomers, N-oxides, hydrates, solvates, and salts thereof, and mixtures of same.

In accordance with a variant of the sixth embodiment of the first aspect, the present invention covers compounds of general formula (I), supra, in which:

$R^1$ represents a group selected from cyano, —C(═O)$NH_2$, —C(═O)N(H)$CH_3$ and —C(═O)N$(CH_3)_2$, $R^2$ represents a group selected from phenyl, 1-naphthyl, 2-naphthyl, 1H-pyrazol-3-yl, 1H-pyrazol-4-yl, 1H-pyrazol-5-yl, 1,2,4-oxadiazol-5-yl, 1,3,4-oxadiazol-2-yl, 1,3-thiazol-2-yl, pyridin-3-yl, pyrazin-2-yl, 1H-indol-5-yl, 1-benzofuran-4-yl, 1-benzofuran-7-yl, 1H-indol-6-yl, benzothiophen-2-yl, 1,3-benzoxazol-2-yl, 1,3-benzoxazol-5-yl, 1,3-benzoxazol-6-yl, 1,3-benzoxazol-7-yl, 1H-indazol-5-yl, 1H-benzimidazol-2-yl, 1H-benzimidazol-4-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1H-pyrrolo[2,3-b]pyridin-3-yl, quinolin-2-yl, quinolin-4-yl, quinolin-6-yl, quinolin-7-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, methoxymethyl, 2-methoxyethyl, benzyloxy, trifluormethoxy, 2,2,2-trifluoroethoxy, phenoxy, (oxolan-2-yl)methoxy, (tetrahydrofuran-2-yl) methoxy, methanesulfonyl, dimethylphosphoryl, cyano, hydroxy, dimethylamino, oxetan-3-yl, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, acetyl, trifluoroacetyl, benzamido, benzenesulfonamido, [dimethyl(oxido)-$\lambda^6$-sulfanylidene]amino, phenyl, 3-chlorophenyl, 4-chlorophenyl, 2-methylphenyl, 3-methylphenyl, 4-methylphenyl, 3-trifluoromethylphenyl, 2-methoxyphenyl, 3-methoxyphenyl, 4-methoxyphenyl and pyridin-3-yl, or two substituents of said phenyl group, when they are attached to adjacent ring atoms, are linked to one another in such a way that they jointly form a group selected from $—CH_2—CH(OH)—CH_2—$, $—CH_2—CH(CH_3)—O—$, $—O—C(CH_3)_2—O—$, $—NH—C(=O)—CH(CH_3)—$, $—N(CH_3)—C(=O)—C(CH_3)_2—$, $—NH—C(=O)—(C(CH_3)_2)—$, $—NH—CH_2—C(CH_3)_2—$, $—N(CH_3)—C(=O)—O—$ and $—N(CH_3)—C(=O)—N(CH_3)—$, $R^3$ represents a hydrogen atom or a fluorine, chlorine or bromine atom or a group selected from methyl, sec-butyl, (oxetan-3-yl)methyl, 3,3,3-trifluoroprop-1-en-2-yl, cyclopropyl, (trifluoromethyl)cyclopropyl, cyclobutyl, 2,2-dimethylcyclobutyl, 3,3-difluorocyclobutyl, methoxymethyl, methoxy, ethoxy, propoxy, 2,2-difluoroethoxy, 2,2-difluoropropoxy, cyclopropylmethoxy, (1-cyanocyclopropyl)methoxy, cyclopropyloxy, cyclobutyloxy, methanesulfonyl, cyano, hydroxy, 4-hydroxy-2-oxo-pyrrolidin-1-yl, 7-oxo-2-oxa-6-azaspiro[3.4]octan-6-yl, carbamoyl, dimethylphosphoryl, oxetan-3-yl, 3,6-dihydro-2H-pyran-4-yl, (oxetan-3-yl)oxy and phenyl, $R^4$ represents a hydrogen atom or a fluorine, chlorine or bromine atom or a group selected from methyl, sec-butyl, (oxetan-3-yl)methyl, trifluoromethyl, cyclopropyl, 3,3-difluorocyclobutyl, methoxymethyl, methoxy, propoxy, 2-methoxyethoxy, (1-hydroxycyclopropyl)methoxy, (1-cyanocyclopropyl)methoxy, (oxiran-2-yl)methoxy, carboxymethoxy, 2-tert-butoxy-2-oxo-ethoxy, 2-amino-2-oxo-ethoxy, cyclopropyloxy, cyclobutyloxy, methanesulfonyl, dimethylphosphoryl, cyano, nitro, hydroxy, (cyanomethyl)(methyll)amino, (2-hydroxyethyl)amino, (2-hydroxyethyl)(methyl)amino, (2-methoxyethyl)amino, (2-methoxyethyl)(methyl)amino, cyclopropylamino, (oxetan-3-yl)amino, methyl(oxetan-3-yl)amino, methyl (oxolan-3-yl)amino, 3-hydroxyazetidin-1-yl, 2-oxopyrrolidin-1-yl, morpholino, 1,1-dioxidothiomorpholin-4-yl, 4-hydroxy-2-oxo-pyrrolidin-1-yl, 7-oxo-2-oxa-6-azaspiro [3.4]octan-6-yl, 2,2-dimethyl-2$\lambda^6$-diazathia-1,2-dien-1-yl, [dimethyl(oxido)-$\lambda^6$-sulfanylidene]amino, methyl(tetrahydrofuran-3-yl)amino, oxetan-3-yl, 3,6-dihydro-2H-pyran-4-yl, (oxetan-3-yl)oxy, (tetrahydrofuran-3-yl)oxy, (tetrahydro-2H-pyran-3-yl)oxy, (tetrahydro-2H-pyran-4-yl)oxy and phenyl, $R^5$ represents a hydrogen atom or a fluorine, chlorine or bromine atom or a group selected from methyl, cyclopropyl, methoxy, propoxy, cyclopropyloxy, methanesulfonyl, cyano, hydroxy, oxetan-3-yl and oxetan-3-yloxy, $R^6$ represents a hydrogen atom or a group selected from methyl and hydroxymethyl, $R^7$ represents a hydrogen atom or a fluorine atom or a group selected from methyl, ethyl, methoxy and hydroxy, $R^8$ represents a group selected from methyl and ethyl, and n represents an integer selected from 1, 2 and 3, and stereoisomers, tautomers, N-oxides, hydrates, solvates, and salts thereof, and mixtures of same.

In accordance with a further variant of the sixth embodiment of the first aspect, the present invention covers compounds of general formula (I), supra, in which:

$R^1$ represents a group selected from cyano, $—C(=O)NH_2$, $—C(=O)N(H)CH_3$ and $—C(=O)N(CH_3)_2$, $R^2$ represents a group selected from phenyl, 1-naphthyl, 1H-pyrazol-5-yl, 1,2,4-oxadiazol-5-yl, 1,3-thiazol-2-yl, pyridin-3-yl, pyrazin-2-yl, 1H-indol-5-yl, 1-benzofuran-4-yl, 1-benzofuran-7-yl, 1,3-benzoxazol-2-yl, 1,3-benzoxazol-5-yl, 1,3-benzoxazol-7-yl, 1H-benzimidazol-2-yl, 1H-benzimidazol-4-yl, 1,3-benzothiazol-2-yl, 1,3-benzothiazol-4-yl, 1,3-benzothiazol-7-yl, 1H-pyrrolo[2,3-b] pyridin-3-yl, quinolin-4-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, benzyloxy, trifluormethoxy, 2,2,2-trifluoroethoxy, phenoxy, methanesulfonyl, dimethylphosphoryl, cyano, hydroxy, dimethylamino, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, trifluoroacetyl, benzamido, benzenesulfonamido, [dimethyl (oxido)-$\lambda^6$-sulfanylidene]amino and phenyl, $R^3$ represents a hydrogen atom or a fluorine, chlorine or bromine atom or a group selected from methyl, sec-butyl, (oxetan-3-yl)methyl, cyclopropyl, 3,3-difluorocyclobutyl, methoxymethyl, methoxy, propoxy, (1-cyanocyclopropyl) methoxy, cyclopropyloxy, cyclobutyloxy, methanesulfonyl, cyano, hydroxy, 4-hydroxy-2-oxo-pyrrolidin-1-yl, 7-oxo-2-oxa-6-azaspiro[3.4]octan-6-yl, oxetan-3-yl, 3,6-dihydro-2H-pyran-4-yl, (oxetan-3-yl)oxy and phenyl, $R^4$ represents a hydrogen atom or a fluorine, chlorine or bromine atom or a group selected from methyl, sec-butyl, (oxetan-3-yl)methyl, cyclopropyl, 3,3-difluorocyclobutyl, methoxymethyl, methoxy, propoxy, (1-hydroxycyclopropyl)methoxy, (1-cyanocyclopropyl)methoxy, cyclopropyloxy, cyclobutyloxy, methanesulfonyl, cyano, 2-oxopyrrolidin-1-yl, morpholino, 1,1-dioxidothiomorpholin-4-yl, 4-hydroxy-2-oxo-pyrrolidin-1-yl, 7-oxo-2-oxa-6-azaspiro [3.4]octan-6-yl, 2,2-dimethyl-2$\lambda^6$-diazathia-1,2-dien-1-yl, [dimethyl(oxido)-$\lambda^6$-sulfanylidene]amino, methyl(tetrahydrofuran-3-yl)amino, oxetan-3-yl, 3,6-dihydro-2H-pyran-4-yl, (oxetan-3-yl)oxy, (tetrahydrofuran-3-yl)oxy, (tetrahydro-2H-pyran-3-yl)oxy, (tetrahydro-2H-pyran-4-yl)oxy and phenyl, $R^5$ represents a hydrogen atom or a fluorine, chlorine or bromine atom or a group selected from methyl, cyclopropyl, methoxy, propoxy, cyclopropyloxy, methanesulfonyl, cyano, hydroxy, oxetan-3-yl and oxetan-3-yloxy, $R^6$ represents a hydrogen atom or a group selected from methyl and hydroxymethyl, $R^7$ represents a hydrogen atom or a fluorine atom or a group selected from methyl, ethyl and hydroxy, $R^8$ represents a group selected from methyl and ethyl, and n represents an integer selected from 1, 2 and 3, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano, $—C(=O)NH_2$, $—C(=O)N(H)CH_3$, $—C(=O)N(H)C_2H_5$, $—C(=O)N(CH_3)_2$ and $—C(=O)OR^{15}$, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano, $—C(=O)NH_2$, $—C(=O)N(H)CH_3$, $—C(=O)N(H)C_2H_5$ and $—C(=O)N(CH_3)_2$, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano, $—C(=O)NH_2$, $—C(=O)N(H)CH_3$ and $—C(=O)N(CH_3)_2$, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a cyano group, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from $—C(=O)NH_2$, $—C(=O)N(H)CH_3$, $—C(=O)N(H)C_2H_5$ and $—C(=O)N(CH_3)_2$, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from $—C(=O)NH_2$, $—C(=O)N(H)CH_3$ and $—C(=O)N(CH_3)_2$, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_6$-cycloalkyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_6$-haloalkoxy, $C_3$-$C_6$-cycloalkyloxy, phenoxy, $—SR^{14}$, $—S(=O)R^{14}$, $—S(=O)_2R^{14}$, $—P(=O)(R^{14})_2$, cyano, hydroxy, $—N(R^9)(R^{10})$, $—C(=O)N(R^9)(R^{10})$, $—C(=O)R^{11}$, $—N(R^{12})C(=O)R^{13}$, $—N(R^{12})S(=O)_2R^{14}$, $—N=S(=NH)(R^{14})_2$, $—N=S(=O)(R^{14})_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from $—CH_2)_3—$, $—CH_2—CH(OH)—CH_2—$, $—(CH_2)_4—$, $—O—(CH_2)_2—$, $—(CH_2)_2—O—$, $—CH_2—CH(CH_3)—O—$, $—CH_2—O—CH_2—$, $—O—(CH_2)_3—$, $—(CH_2)_3—O—$, $—CH_2—O—(CH_2)_2—$, $—(CH_2)_2O—CH_2—$, $—O—CH_2—O—$, $—O—C(CH_3)_2—O—$, $—O—(CH_2)_2—O—$, $—N(R^{18})—C(=O)—(C(R^1)(R^{19}))_m—$, $—N(R^{18})—C(=O)—(C(CH_3)_2)—$, $—N(R^{18})—(C(R^{18})(R^{19}))_m—$, $—N(R^{18})—C(=O)—O—$ and $—N(R^{18})—C(=O)—N(R^{18})—$, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, $—N(R^9)(R^{10})$ and oxo, and wherein said $C_1$-$C_6$-alkyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, $—N(R^9)(R^{10})$ and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and $—N(R^9)(R^{10})$, and which $C_3$-$C_4$-cycloalkyl group is optionally substituted, one or two times, each substituent indepen dently selected from a halogen atom or a group selected from cyano and hydroxy, and wherein said $C_3$-$C_6$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_6$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —$SR^{14}$, —S(=O)$R^{14}$, —S(=O)$_2R^{14}$, —P(=O)($R^{14}$)$_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2$ $R^{14}$, —N=S(=NH)($R^{14}$)$_2$, —N=S(=O)($R^{14}$)$_2$, 4- to 7-membered heterocycloalkyl, 5- to 7-membered heterocycloalkenyl, (4- to 7-membered heterocycloalkyl) oxy, phenyl and 5- or 6-membered heteroaryl, or two substituents of said phenyl group, when they are attached to adjacent ring atoms, are optionally linked to one another in such a way that they jointly form a group selected from —$(CH_2)_3$—, —$CH_2$—CH(OH)—$CH_2$—, —$(CH_2)_4$—, —O—$(CH_2)_2$—, —$(CH_2)_2$—O—, —$CH_2$—CH($CH_3$)—O—, —$CH_2$—O—$CH_2$—, —O—$(CH_2)_3$—, —$(CH_2)_3$—O—, —$CH_2$—O—$(CH_2)_2$—, —$(CH_2)_2$ O—$CH_2$—, —O—$CH_2$—O—, —O—C$(CH_3)_2$—O—, —O—$(CH_2)_2$—O—, —N($R^{18}$)—C(=O)—(C($R^1$)($R^{19}$))—, —N($R^{18}$)—C(=O)—(C$(CH_3)_2$)—, —N($R^{18}$)—(C($R^{18}$)($R^{19}$))$_m$—, —N($R^{18}$)—C(=O)—O— and —N($R^{18}$)—C(=O)—N($R^{18}$)—, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(=O)$_2R^{14}$, —P(=O)($R^{14}$)$_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2$ $R^{14}$, —N=S(=O)($R^{14}$)$_2$, 4- to 7-membered heterocycloalkyl, phenyl and 5- or 6-membered heteroaryl, or two substituents of said phenyl group, when they are attached to adjacent ring atoms, are optionally linked to one another in such a way that they jointly form a group selected from —$CH_2$—CH(OH)—$CH_2$—, —$CH_2$—CH($CH_3$)—O—, —O—C($CH_3$)$_2$—O—, —N($R^{18}$)—C(═O)—(C($R^{18}$)($R^{19}$))$_m$—, —N($R^{18}$)—C(═O)—(C($CH_3$)$_2$)—, —N($R^{18}$)—(C($R^{18}$)($R^{19}$))$_m$—, —N($R^{18}$)—C(═O)—O— and —N($R^{18}$)—C(═O)—N($R^{18}$)—, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from 4- to 7-membered heterocycloalkyl and phenyl, wherein said 4- to 7-membered heterocycloalkyl group is connected to the rest of the molecule via a carbon atom of said 4- to 7-membered heterocycloalkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl and $C_1$-$C_2$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, 1-naphthyl, 2-naphthyl and 5- to 10-membered heteroaryl, which 5- to 10-membered heteroaryl group is selected from pyrazolyl, 1,2,4-oxadiazol, 1,3,4-oxadiazol, 1H-1,2,3-triazolyl, 2H-1,2,3-triazolyl, 1,3-thiazolyl, pyridinyl, pyrazinyl, indolyl, benzothiophenyl, benzofuranyl, 1,3-benzoxazolyl, indazolyl, benzimidazolyl, 1,3-benzothiazolyl, pyrrolo[2,3-b]pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which phenyl, 1-naphthyl, 2-naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(═O)$_2$$R^{14}$, —P(═O)($R^{14}$)$_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═O)($R^{14}$)$_2$, 4- to 7-membered heterocycloalkyl, phenyl and pyridinyl, or two substituents of said phenyl group, when they are attached to adjacent ring atoms, are optionally linked to one another in such a way that they jointly form a group selected from —$CH_2$—CH(OH)—$CH_2$—, —$CH_2$—CH($CH_3$)—O—, —O—C($CH_3$)$_2$—O—, —NH—C(═O)—CH($CH_3$)—, —N($CH_3$)—C(═O)—C($CH_3$)$_2$—, —NH—C(═O)—(C($CH_3$)$_2$)—, —NH—$CH_2$—C($CH_3$)$_2$—, —N($CH_3$)—C(═O)—O— and —N($CH_3$)—C(═O)—N($CH_3$)—, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from 4- to 7-membered heterocycloalkyl and phenyl, wherein said 4- to 7-membered heterocycloalkyl group is connected to the rest of the molecule via a carbon atom of said 4- to 7-membered heterocycloalkyl group, and wherein said phenyl group is optionally substituted, one or two times, each substituent independently selected from a halogen atom or a group selected from $C_1$-$C_2$-alkyl, $C_1$-$C_2$-haloalkyl and $C_1$-$C_2$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from 5- to 10-membered heteroaryl, which 5- to 10-membered heteroaryl group is selected from pyrazolyl, 1,2,4-oxadiazol, 1,3,4-oxadiazol, 1H-1,2,3-triazolyl, 2H-1,2,3-triazolyl, 1,3-thiazolyl, pyridinyl, pyrazinyl, indolyl, benzothiophenyl, benzofuranyl, 1,3-benzoxazolyl, indazolyl, benzimidazolyl, 1,3-benzothiazolyl, pyrrolo[2,3-b]pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(═O)$_2$$R^{14}$, —P(═O)($R^{14}$)$_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═O)($R^{14}$)$_2$, 4- to 7-membered heterocycloalkyl, phenyl and pyridinyl, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from 4- to 7-membered heterocycloalkyl and phenyl, wherein said 4- to 7-membered heterocycloalkyl group is connected to the rest of the molecule via a carbon atom of said 4- to 7-membered heterocycloalkyl group, and wherein said phenyl group is optionally substituted, one or two times, each substituent independently selected from a halogen atom or a group selected from $C_1$-$C_2$-alkyl, $C_1$-$C_2$-haloalkyl and $C_1$-$C_2$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, 1-naphthyl, 2-naphthyl and 5- to 10-membered heteroaryl, which 5- to 10-membered heteroaryl group is selected from pyrazolyl, 1,2,4-oxadiazol, 1,3,4-oxadiazol 1,3-thiazolyl, pyridinyl, pyrazinyl, indolyl, benzothiophenyl, benzofuranyl, 1,3-benzoxazolyl, indazolyl, benzimidazolyl, 1,3-benzothiazolyl, pyrrolo[2,3-b] pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which phenyl, 1-naphthyl, 2-naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, $—S(=O)_2R^{14}$, $—P(=O)(R^{14})_2$, cyano, hydroxy, $—N(R^9)(R^{10})$, $—C(=O)N(R^9)(R^{10})$, $—C(=O)R^{11}$, $—N(R^{12})C(=O)R^{13}$, $—N(R^{12})S(=O)_2R^{14}$, $—N=S(=O)(R^{14})_2$, 4- to 7-membered heterocycloalkyl, phenyl and pyridinyl, or two substituents of said phenyl group, when they are attached to adjacent ring atoms, are optionally linked to one another in such a way that they jointly form a group selected from $—CH_2—CH(OH)—CH_2—$, $—CH_2—CH(CH_3)—O—$, $—O—C(CH_3)_2—O—$, $—NH—C(=O)—CH(CH_3)—$, $—N(CH_3)—C(=O)—C(CH_3)_2—$, $—NH—C(=O)—(C(CH_3)_2)—$, $—NH—CH_2—C(CH_3)_2—$, $—N(CH_3)—C(=O)—O—$ and $—N(CH_3)—C(=O)—N(CH_3)—$, wherein said 4- to 7-membered heterocycloalkyl group is connected to the rest of the molecule via a carbon atom of said 4- to 7-membered heterocycloalkyl group, and wherein said $C_1$-$C_4$-alkoxy group is optionally substituted with a group selected from 4- to 7-membered heterocycloalkyl and phenyl, wherein said 4- to 7-membered heterocycloalkyl group is connected to the rest of the molecule via a carbon atom of said 4- to 7-membered heterocycloalkyl group, and wherein said phenyl group is optionally substituted, one or two times, each substituent independently selected from a halogen atom or a group selected from $C_1$-$C_2$-alkyl, $C_1$-$C_2$-haloalkyl and $C_1$-$C_2$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, 1-naphthyl, 2-naphthyl, 1H-pyrazol-3-yl, 1H-pyrazol-4-yl, 1H-pyrazol-5-yl, 1,2,4-oxadiazol-5-yl, 1,3,4-oxadiazol-2-yl, 1H-1,2,3-triazol-4-yl, 2H-1,2,3-triazol-4-yl, 1,3-thiazol-2-yl, pyridin-3-yl, pyrazin-2-yl, 1H-indol-5-yl, 1-benzofuran-4-yl, 1-benzofuran-7-yl, 1H-indol-6-yl, benzothiophen-2-yl, 1,3-benzoxazol-2-yl, 1,3-benzoxazol-5-yl, 1,3-benzoxazol-6-yl, 1,3-benzoxazol-7-yl, 1H-indazol-5-yl, 1H-benzimidazol-2-yl, 1H-benzimidazol-4-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1H-pyrrolo[2,3-b]pyridin-3-yl, quinolin-2-yl, quinolin-4-yl, quinolin-6-yl, quinolin-7-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, methoxymethyl, 2-methoxyethyl, benzyloxy, trifluormethoxy, 2,2,2-trifluoroethoxy, phenoxy, (oxolan-2-yl)methoxy, (tetrahydrofuran-2-yl) methoxy, methanesulfonyl, dimethylphosphoryl, cyano, hydroxy, dimethylamino, oxetan-3-yl, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, acetyl, trifluoroacetyl, benzamido, benzenesulfonamido, [dimethyl(oxido)-$\lambda^6$-sulfanylidene]amino, phenyl, 3-chlorophenyl, 4-chlorophenyl, 2-methylphenyl, 3-methylphenyl, 4-methylphenyl, 3-trifluoromethylphenyl, 2-methoxyphenyl, 3-methoxyphenyl, 4-methoxyphenyl and pyridin-3-yl, or two substituents of said phenyl group, when they are attached to adjacent ring atoms, are linked to one another in such a way that they jointly form a group selected from $—CH_2—CH(OH)—CH_2—$, $—CH_2—CH(CH_3)—O—$, $—O—C(CH_3)_2—O—$, $—NH—C(=O)—CH(CH_3)—$, $—N(CH_3)—C(=O)—C(CH_3)_2—$, $—NH—C(=O)—(C(CH_2)_3)—$, $—NH—CH_2—C(CH_3)_2—$, $—N(CH_3)—C(=O)—O—$ and $—N(CH_3)—C(=O)—N(CH_3)—$, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from 1H-pyrazol-3-yl, 1H-pyrazol-4-yl, 1H-pyrazol-5-yl, 1,2,4-oxadiazol-5-yl, 1,3,4-oxadiazol-2-yl, 1H-1,2,3-triazol-4-yl, 2H-1,2,3-triazol-4-yl, 1,3-thiazol-2-yl, pyridin-3-yl, pyrazin-2-yl, 1H-indol-5-yl, 1-benzofuran-4-yl, 1-benzofuran-7-yl, 1H-indol-6-yl, benzothiophen-2-yl, 1,3-benzoxazol-2-yl, 1,3-benzoxazol-5-yl, 1,3-benzoxazol-6-yl, 1,3-benzoxazol-7-yl, 1H-indazol-5-yl, 1H-benzimidazol-2-yl, 1H-benzimidazol-4-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1H-pyrrolo[2,3-b]pyridin-3-yl, quinolin-2-yl, quinolin-4-yl, quinolin-6-yl, quinolin-7-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, methoxymethyl, 2-methoxyethyl, benzyloxy, trifluormethoxy, 2,2,2-trifluoroethoxy, phenoxy, (oxolan-2-yl)methoxy, (tetrahydrofuran-2-yl) methoxy, methanesulfonyl, dimethylphosphoryl, cyano, hydroxy, dimethylamino, oxetan-3-yl, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, acetyl, trifluoroacetyl, benzamido, benzenesulfonamido, [dimethyl(oxido)-$\lambda^6$-sulfanylidene]amino, phenyl, 3-chlorophenyl, 4-chlorophenyl, 2-methylphenyl, 3-methylphenyl, 4-methylphenyl, 3-trifluoromethylphenyl, 2-methoxyphenyl, 3-methoxyphenyl, 4-methoxyphenyl and pyridin-3-yl, or two substituents of said phenyl group, when they are attached to adjacent ring atoms, are linked to one another in such a way that they jointly form a group selected from $-CH_2-CH(OH)-CH_2-$, $-CH_2-CH(CH_3)-O-$, $-O-C(CH_3)_2-O-$, $-NH-C(=O)-CH(CH_3)-$, $-N(CH_3)-C(=O)-C(CH_3)_2-$, $-NH-C(=O)-(C(CH_3)_2)-$, $-NH-CH_2-C(CH_3)_2-$, $-N(CH_3)-C(=O)-O-$ and $-N(CH_3)-C(=O)-N(CH_3)-$, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, 1-naphthyl, 2-naphthyl, 1H-pyrazol-3-yl, 1H-pyrazol-4-yl, 1H-pyrazol-5-yl, 1,2,4-oxadiazol-5-yl, 1,3,4-oxadiazol-2-yl, 1,3-thiazol-2-yl, pyridin-3-yl, pyrazin-2-yl, 1H-indol-5-yl, 1-benzofuran-4-yl, 1-benzofuran-7-yl, 1H-indol-6-yl, benzothiophen-2-yl, 1,3-benzoxazol-2-yl, 1,3-benzoxazol-5-yl, 1,3-benzoxazol-6-yl, 1,3-benzoxazol-7-yl, 1H-indazol-5-yl, 1H-benzimidazol-2-yl, 1H-benzimidazol-4-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1H-pyrrolo[2,3-b]pyridin-3-yl, quinolin-2-yl, quinolin-4-yl, quinolin-6-yl, quinolin-7-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, methoxymethyl, 2-methoxyethyl, benzyloxy, trifluormethoxy, 2,2,2-trifluoroethoxy, phenoxy, (oxolan-2-yl)methoxy, (tetrahydrofuran-2-yl) methoxy, methanesulfonyl, dimethylphosphoryl, cyano, hydroxy, dimethylamino, oxetan-3-yl, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, acetyl, trifluoroacetyl, benzamido, benzenesulfonamido, [dimethyl(oxido)-$\lambda^6$-sulfanylidene]amino, phenyl, 3-chlorophenyl, 4-chlorophenyl, 2-methylphenyl, 3-methylphenyl, 4-methylphenyl, 3-trifluoromethylphenyl, 2-methoxyphenyl, 3-methoxyphenyl, 4-methoxyphenyl and pyridin-3-yl, or two substituents of said phenyl group, when they are attached to adjacent ring atoms, are linked to one another in such a way that they jointly form a group selected from $-CH_2-CH(OH)-CH_2-$, $-CH_2-CH(CH_3)-O-$, $-O-C(CH_3)_2-O-$, $-NH-C(=O)-CH(CH_3)-$, $-N(CH_3)-C(=O)-C(CH_3)_2-$, $-NH-C(=O)-(C(CH_3)_2)-$, $-NH-CH_2-C(CH_3)_2-$, $-N(CH_3)-C(=O)-O-$ and $-N(CH_3)-C(=O)-N(CH_3)-$, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_6$-cycloalkyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_6$-haloalkoxy, $C_3$-$C_6$-cycloalkyloxy, phenoxy, $-SR^{14}$, $-S(=O)R^{14}$, $-S(=O)_2R^{14}$, $-P(=O)(R^{14})_2$, cyano, hydroxy, $-N(R^9)(R^{10})$, $-C(=O)N(R^9)(R^{10})$, $-C(=O)R^{11}$, $-N(R^{12})C(=O)R^{13}$, $-N(R^{12})S(=O)_2R^{14}$, $-N=S(=NH)(R^{14})_2$, $-N=S(=O)(R^{14})_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from $-(CH_2)_3-$, $-(CH_2)_4-$, $-O-(CH_2)_2-$, $-(CH_2)_2-O-$, $-CH_2-O-CH_2-$, $-O-(CH_2)_3-$, $-(CH_2)_3-O-$, $-CH_2-O-(CH_2)_2-$, $-(CH_2)_2O-CH_2-$, $-O-CH_2-O-$ and $-O-(CH_2)_2-O-$, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, $-N(R^9)(R^{10})$ and oxo, and wherein said $C_1$-$C_6$-alkyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_6$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2R^{14}$, —P(═O)($R^{14}$)$_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)($R^{14}$)$_2$, —N═S(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from —($CH_2$)$_3$—, —($CH_2$)$_4$—, —O—($CH_2$)$_2$—, —($CH_2$)$_2$—O—, —$CH_2$—O—$CH_2$—, —O—($CH_2$)$_3$—, —($CH_2$)$_3$—O—, —$CH_2$—O—($CH_2$)$_2$—, —($CH_2$)$_2$ O—$CH_2$—, —O—$CH_2$—O— and —O—($CH_2$)$_2$—O—, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(=O)$_2$R$^{14}$, —P(=O)(R$^{14}$)$_2$, cyano, hydroxy, —N(R$^9$)(R$^{10}$), —C(=O)N(R$^9$)(R$^{10}$), —C(=O)R$^{11}$, —N(R$^{12}$)C(=O)R$^{13}$, —N(R$^{12}$)S(=O)$_2$R$^{14}$, —N=S(=O)(R$^{14}$)$_2$ and phenyl, wherein said $C_1$-$C_4$-alkoxy group is optionally substituted with a phenyl group, which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N(R$^9$)(R$^{10}$), and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, naphthyl and 5- to 10-membered heteroaryl, which 5- to 10-membered heteroaryl group is connected to the rest of the molecule via a carbon atom of said 5- to 10-membered heteroaryl group, and which phenyl, naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(=O)$_2$R$^{14}$, —P(=O)(R$^{14}$)$_2$, cyano, hydroxy, —N(R$^9$)(R$^{10}$), —C(=O)N(R$^9$)(R$^{10}$), —C(=O)R$^{11}$, —N(R$^{12}$)C(=O)R$^{13}$, —N(R$^{12}$)S(=O)$_2$R$^{14}$, —N=S(=O)(R$^{14}$)$_2$ and phenyl, wherein said $C_1$-$C_4$-alkoxy group is optionally substituted with a phenyl group, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, 1-naphthyl and 5- to 10-membered heteroaryl, which 5- to 10-membered heteroaryl group is selected from pyrazolyl, 1,2,4-oxadiazol, 1,3-thiazolyl, pyridinyl, pyrazinyl, indolyl, benzofuranyl, 1,3-benzoxazolyl, benzimidazolyl, 1,3-benzothiazolyl, pyrrolo[2,3-b]pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which phenyl, 1-naphthyl and 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(=O)$_2$R$^{14}$, —P(=O)(R$^{14}$)$_2$, cyano, hydroxy, —N(R$^9$)(R$^{10}$), —C(=O)N(R$^9$)(R$^{10}$), —C(=O)R$^{11}$, —N(R$^{12}$)C(=O)R$^{13}$, —N(R$^{12}$)S(=O)$_2$R$^{14}$, —N=S(=O)(R$^{14}$)$_2$ and phenyl, wherein said $C_1$-$C_4$-alkoxy group is optionally substituted with a phenyl group, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl, 1-naphthyl, 1H-pyrazol-5-yl, 1,2,4-oxadiazol-5-yl, 1,3-thiazol-2-yl, pyridin-3-yl, pyrazin-2-yl, 1H-indol-5-yl, 1-benzofuran-4-yl, 1-benzofuran-7-yl, 1,3-benzoxazol-2-yl, 1,3-benzoxazol-5-yl, 1,3-benzoxazol-7-yl, 1H-benzimidazol-2-yl, 1H-benzimidazol-4-yl, 1,3-benzothiazol-2-yl, 1,3-benzothiazol-4-yl, 1,3-benzothiazol-7-yl, 1H-pyrrolo[2,3-b]pyridin-3-yl, quinolin-4-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, benzyloxy, trifluormethoxy, 2,2,2-trifluoroethoxy, phenoxy, methanesulfonyl, dimethylphosphoryl, cyano, hydroxy, dimethylamino, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, trifluoroacetyl, benzamido, benzenesulfonamido, [dimethyl(oxido)-$\lambda^6$-sulfanylidene]amino and phenyl, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a 5- to 10-membered heteroaryl group, which 5- to 10-membered heteroaryl group is connected to the rest of the molecule via a carbon atom of said 5- to 10-membered heteroaryl group, and which 5- to 10-membered heteroaryl group is optionally substituted, one, two, three or four times, each substituent independently selected from a halogen atom or a group selected from $C_1$-$C_6$-alkyl, $C_3$-$C_6$-cycloalkyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_6$-haloalkoxy, $C_3$-$C_6$-cycloalkyloxy, phenoxy, —SR$^{14}$, —S(=O)R$^{14}$, —S(=O)$_2$R$^{14}$, —P(=O)(R$^{14}$)$_2$, cyano, hydroxy, —N(R$^9$)(R$^{10}$), —C(=O)N(R$^9$)(R$^{10}$), —C(=O)R$^{11}$, —N(R$^{12}$)C(=O)R$^{13}$, —N(R$^{12}$)S(=O)$_2$R$^{14}$, —N=S(=NH)(R$^{14}$)$_2$, —N=S(=O)(R$^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —$N(R^9)(R^{10})$ and oxo, and wherein said $C_1$-$C_6$-alkyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —$N(R^9)(R^{10})$ and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a 5- to 10-membered heteroaryl group, which 5- to 10-membered heteroaryl group is connected to the rest of the molecule via a carbon atom of said 5- to 10-membered heteroaryl group, and which 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_6$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —$SR^{14}$, —$S(=O)R^{14}$, —$S(=O)_2R^{14}$, —$P(=O)(R^{14})_2$, cyano, hydroxy, —$N(R^9)(R^{10})$, —$C(=O)N(R^9)(R^{10})$, —$C(=O)R^{11}$, —$N(R^{12})C(=O)R^{13}$, —$N(R^{12})S(=O)_2R^{14}$, —$N{=}S(=NH)(R^{14})_2$, —$N{=}S(=O)(R^{14})_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —$N(R^9)(R^{10})$ and oxo, and wherein said $C_1$-$C_6$-alkyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —$N(R^9)(R^{10})$ and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a 5- to 10-membered heteroaryl, which 5- to 10-membered heteroaryl group is connected to the rest of the molecule via a carbon atom of said 5- to 10-membered heteroaryl group, and which 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(═O)$_2$R$^{14}$, —P(═O)(R$^{14}$)$_2$, cyano, hydroxy, —N(R$^9$)(R$^{10}$), —C(═O)N(R$^9$)(R$^{10}$), —C(═O)R$^{11}$, —N(R$^{12}$)C(═O)R$^{13}$, —N(R$^{12}$)S(═O)$_2$R$^{14}$, —N═S(═O)(R$^{14}$)$_2$ and phenyl, wherein said $C_1$-$C_4$-alkoxy group is optionally substituted with a phenyl group, which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N(R$^9$)(R$^{10}$), and stereoisomers, tautomers, N-oxides, hydrates, solvates, and salts thereof, and mixtures of same.

In a further embodiment of the first aspect, the present invention covers compounds of formula (I), supra, in which: $R^2$ represents a 5- to 10-membered heteroaryl group, which 5- to 10-membered heteroaryl group is connected to the rest of the molecule via a carbon atom of said 5- to 10-membered heteroaryl group, and which 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(═O)$_2$R$^{14}$, —P(═O)(R$^{14}$)$_2$, cyano, hydroxy, —N(R$^9$)(R$^{10}$), —C(═O)N(R$^9$)(R$^{10}$), —C(═O)R$^{11}$, —N(R$^{12}$)C(═O)R$^{13}$, —N(R$^{12}$)S(═O)$_2$R$^{14}$, —N═S(═O)(R$^{14}$)$_2$ and phenyl, wherein said $C_1$-$C_4$-alkoxy group is optionally substituted with a phenyl group, and stereoisomers, tautomers, N-oxides, hydrates, solvates, and salts thereof, and mixtures of same.

In a further embodiment of the first aspect, the present invention covers compounds of formula (I), supra, in which: $R^2$ represents a 5- to 10-membered heteroaryl group, which 5- to 10-membered heteroaryl group is selected from pyrazolyl, 1,2,4-oxadiazol, 1,3-thiazolyl, pyridinyl, pyrazinyl, indolyl, benzofuranyl, 1,3-benzoxazolyl, benzimidazolyl, 1,3-benzothiazolyl, pyrrolo[2,3-b]pyridinyl, quinolinyl, isoquinolinyl, quinoxalinyl and 1,3-thiazolo[5,4-b]pyridinyl, and which 5- to 10-membered heteroaryl group is connected to the rest of the molecule via a carbon atom of said 5- to 10-membered heteroaryl group, and which 5- to 10-membered heteroaryl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(═O)$_2$R$^{14}$, —P(═O)(R$^{14}$)$_2$, cyano, hydroxy, —N(R$^9$)(R$^{10}$), —C(═O)N(R$^9$)(R$^{10}$), —C(═O)R$^{11}$, —N(R$^{12}$)C(═O)R$^{13}$, —N(R$^{12}$)S(═O)$_2$R$^{14}$, —N═S(═O)(R$^{14}$)$_2$ and phenyl, wherein said $C_1$-$C_4$-alkoxy group is optionally substituted with a phenyl group, and stereoisomers, tautomers, N-oxides, hydrates, solvates, and salts thereof, and mixtures of same.

In a further embodiment of the first aspect, the present invention covers compounds of formula (I), supra, in which: $R^2$ represents a group selected from 1H-pyrazol-5-yl, 1,2,4-oxadiazol-5-yl, 1,3-thiazol-2-yl, pyridin-3-yl, pyrazin-2-yl, 1H-indol-5-yl, 1-benzofuran-4-yl, 1-benzofuran-7-yl, 1,3-benzoxazol-2-yl, 1,3-benzoxazol-5-yl, 1,3-benzoxazol-7-yl, 1H-benzimidazol-2-yl, 1H-benzimidazol-4-yl, 1,3-benzothiazol-2-yl, 1,3-benzothiazol-4-yl, 1,3-benzothiazol-7-yl, 1H-pyrrolo[2,3-b]pyridin-3-yl, quinolin-4-yl, isoquinolin-5-yl, isoquinolin-7-yl, isoquinolin-8-yl, quinoxalin-2-yl, quinoxalin-5-yl and 1,3-thiazolo[5,4-b]pyridin-2-yl, which group is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, benzyloxy, trifluormethoxy, 2,2,2-trifluoroethoxy, phenoxy, methanesulfonyl, dimethylphosphoryl, cyano, hydroxy, dimethylamino, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, trifluoroacetyl, benzamido, benzenesulfonamido, [dimethyl(oxido)-λ$^6$-sulfanylidene]amino and phenyl, and stereoisomers, tautomers, N-oxides, hydrates, solvates, and salts thereof, and mixtures of same.

In a further embodiment of the first aspect, the present invention covers compounds of formula (I), supra, in which: $R^2$ represents a group selected from phenyl and naphthyl, which phenyl and naphthyl group is optionally substituted, one, two, three or four times, each substituent independently selected from a halogen atom or a group selected from $C_1$-$C_6$-alkyl, $C_3$-$C_6$-cycloalkyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_6$-haloalkoxy, $C_3$-$C_6$-cycloalkyloxy, phenoxy, —SR$^{14}$, —S(═O)R$^{14}$, —S(═O)$_2$R$^{14}$, —P(═O)(R$^{14}$)$_2$, cyano, hydroxy, —N(R$^9$)(R$^{10}$), —C(═O)N(R$^9$)(R$^{10}$), —C(═O)R$^{11}$, —N(R$^{12}$)C(═O)R$^{13}$, —N(R$^{12}$)S(═O)$_2$R$^{14}$, —N═S(═NH)(R$^{14}$)$_2$, —N═S(═O)(R$^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from —$(CH_2)_3$—, —$(CH_2)_4$—, —O—$(CH_2)_2$—, —$(CH_2)_2$—O—, —$CH_2$—O—$CH_2$—, —O—$(CH_2)_3$—, —$(CH_2)_3$—O—, —$CH_2$—O—$(CH_2)_2$—, —$(CH_2)_2$O—$CH_2$—, —O—$CH_2$—O— and —O—$(CH_2)_2$—O—, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from phenyl and naphthyl, which phenyl and naphthyl group is optionally substituted, one, two, three or four times, each substituent independently selected from a halogen atom or a group selected from $C_1$-$C_6$-alkyl, $C_3$-$C_5$-cycloalkyl, $C_1$-$C_6$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —S$R^{14}$, —S(=O)$R^{14}$, —S(=O)$_2R^{14}$, —P(=O)($R^{14}$)$_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2$ $R^{14}$, —N=S(=NH)($R^{14}$)$_2$, —N=S(=O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, or two substituents of said phenyl group, when they are attached to adjacent ring atoms, are optionally linked to one another in such a way that they jointly form a group selected from $-(CH_2)_3-$, $-(CH_2)_4-$, $-O-(CH_2)_2-$, $-(CH_2)_2-O-$, $-CH_2-O-CH_2-$, $-O-(CH_2)_3-$, $-(CH_2)_3-O-$, $-CH_2-O-(CH_2)_2-$, $-(CH_2)_2O-CH_2-$, $-O-CH_2-O-$ and $-O-(CH_2)_2-O-$, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and stereoisomers, tautomers, N-oxides, hydrates, solvates, and salts thereof, and mixtures of same.

In a further embodiment of the first aspect, the present invention covers compounds of formula (I), supra, in which: $R^2$ represents a group selected from phenyl and naphthyl, which phenyl and naphthyl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(=O)$_2$$R^{14}$, —P(=O)($R^{14}$)$_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2$$R^{14}$, —N=S(=O)($R^{14}$)$_2$ and phenyl, wherein said $C_1$-$C_4$-alkoxy group is optionally substituted with a phenyl group, which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and stereoisomers, tautomers, N-oxides, hydrates, solvates, and salts thereof, and mixtures of same.

In a further embodiment of the first aspect, the present invention covers compounds of formula (I), supra, in which: $R^2$ represents a group selected from phenyl and naphthyl, which phenyl and naphthyl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(=O)$_2$$R^{14}$, —P(=O)($R^{14}$)$_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2$$R^{14}$, —N=S(=O)($R^{14}$)$_2$ and phenyl, wherein said $C_1$-$C_4$-alkoxy group is optionally substituted with a phenyl group, and stereoisomers, tautomers, N-oxides, hydrates, solvates, and salts thereof, and mixtures of same.

In a further embodiment of the first aspect, the present invention covers compounds of formula (I), supra, in which: $R^2$ represents a group selected from phenyl and 1-naphthyl, which phenyl and 1-naphthyl group is optionally substituted, one, two, three or four times, each substituent independently selected from a halogen atom or a group selected from $C_1$-$C_6$-alkyl, $C_3$-$C_5$-cycloalkyl, $C_1$-$C_4$-haloalkyl, $C_1$-$C_4$-alkoxy, $C_1$-$C_4$-haloalkoxy, phenoxy, —S(=O)$_2$$R^{14}$, —P(=O)($R^{14}$)$_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2$$R^{14}$, —N=S(=O)($R^{14}$)$_2$ and phenyl, wherein said $C_1$-$C_4$-alkoxy group is optionally substituted with a phenyl group, and stereoisomers, tautomers, N-oxides, hydrates, solvates, and salts thereof, and mixtures of same.

In a further embodiment of the first aspect, the present invention covers compounds of formula (I), supra, in which: $R^2$ represents a group selected from phenyl, 1-naphthyl which phenyl and naphthyl group is is optionally substituted, one or two times, each substituent independently selected from a fluorine, chlorine or bromine atom or a group selected from methyl, propyl, isopropyl, tert-butyl, cyclopropyl, difluoromethyl, trifluoromethyl, methoxy, ethoxy, propoxy, (propan-2-yl)oxy, benzyloxy, trifluormethoxy, 2,2,2-trifluoroethoxy, phenoxy, methanesulfonyl, dimethylphosphoryl, cyano, hydroxy, dimethylamino, 2-oxopyrrolidin-1-yl, 4-methyl-2-oxopiperazin-1-yl, 4-methyl-3-oxopiperazin-1-yl, morpholino-4-yl, 7-oxo-2-oxa-6-azaspiro[3.4]octan-6-yl, 8-methyl-3-oxo-2,8-diazaspiro[4.5]decan-2-yl, carbamoyl, trifluoroacetyl, benzamido, benzenesulfonamido, [dimethyl(oxido)-$\lambda^6$-sulfanylidene]amino and phenyl, and stereoisomers, tautomers, N-oxides, hydrates, solvates, and salts thereof, and mixtures of same.

In a further embodiment of the first aspect, the present invention covers compounds of formula (I), supra, in which: $R^3$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, $C_3$-$C_6$-cycloalkyloxy, phenoxy, —S$R^{14}$, —S(=O)$R^{14}$, —S(=O)$_2$$R^{14}$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2$$R^{14}$, —N=S(=NH)($R^{14}$)$_2$, —N=S(=O)($R^{14}$)$_2$, —P(=O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_2$-$C_6$-alkenyl group is optionally substituted with a $C_1$-$C_4$-haloalkyl group, and wherein said $C_3$-$C_6$-cycloalkyl and $C_4$-$C_6$-cycloalkenyl group is optionally substituted, one or two times, each substituent independently selected from a halogen atom or a group selected from $C_1$-$C_4$-alkyl and $C_1$-$C_4$-haloalkyl, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_2$-$C_4$-alkenyl group is optionally substituted with a $C_1$-$C_4$-haloalkyl group, and wherein said $C_3$-$C_5$-cycloalkyl and $C_4$-$C_5$-cycloalkenyl group is optionally substituted, one or two times, each substituent independently selected from a halogen atom or a group selected from $C_1$-$C_4$-alkyl and $C_1$-$C_4$-haloalkyl, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2R^{14}$, cyano, hydroxy, —N($R^9$)($R^{10}$), —C(═O)N($R^9$)($R^{10}$), —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_2$-$C_4$-alkenyl group is optionally substituted with a $C_1$-$C_4$-haloalkyl group, and wherein said $C_3$-$C_5$-cycloalkyl group is optionally substituted, one or two times, each substituent independently selected from a halogen atom or a group selected from $C_1$-$C_4$-alkyl and $C_1$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2$$R^{14}$, cyano, hydroxy, —N($R^9$)($R^{10}$), —C(═O)N($R^9$)($R^{10}$), —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, with a cyano group, and wherein said $C_2$-$C_4$-alkenyl group is optionally substituted with a $C_1$-$C_4$-haloalkyl group, and wherein said $C_3$-$C_5$-cycloalkyl group is optionally substituted, one or two times, each substituent independently selected from a halogen atom or a group selected from $C_1$-$C_4$-alkyl and $C_1$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2$$R^{14}$, cyano, hydroxy, —N($R^9$)($R^{10}$), —C(═O)N($R^9$)($R^{10}$), —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, with a cyano group, and wherein said $C_2$-$C_4$-alkenyl group is optionally substituted with a $C_1$-$C_4$-haloalkyl group, and wherein said $C_3$-$C_5$-cycloalkyl group is optionally substituted, one or two times, with a halogen atom or a group selected from $C_1$-$C_4$-alkyl and $C_1$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a fluorine, chlorine or bromine atom or a group selected from methyl, sec-butyl, (oxetan-3-yl)methyl, 3,3,3-trifluoroprop-1-en-2-yl, cyclopropyl, (trifluoromethyl)cyclopropyl, cyclobutyl, 2,2-dimethylcyclobutyl, 3,3-difluorocyclobutyl, methoxymethyl, methoxy, ethoxy, propoxy, 2,2-difluoroethoxy, 2,2-difluoropropoxy, cyclopropylmethoxy, (1-cyanocyclopropyl)methoxy, cyclopropyloxy, cyclobutyloxy, methanesulfonyl, cyano, hydroxy, 4-hydroxy-2-oxo-pyrrolidin-1-yl, 7-oxo-2-oxa-6-azaspiro[3.4]octan-6-yl, carbamoyl, dimethylphosphoryl, oxetan-3-yl, 3,6-dihydro-2H-pyran-4-yl, (oxetan-3-yl)oxy and phenyl, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, $C_3$-$C_6$-cycloalkyloxy, phenoxy, —$SR^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^1$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —$SR^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent indepen dently selected from a halogen atom or a group selected from cyano and hydroxy, and wherein said $C_3$-$C_5$-cycloalkyl and $C_4$-$C_5$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —S(═O)$_2$$R^{14}$, cyano, hydroxy, —N($R^9$)($R^{10}$), —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —S(═O)$_2$$R^{14}$, cyano, hydroxy, —N($R^9$)($R^{10}$), 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, with a cyano group, and wherein said $C_3$-$C_5$-cycloalkyl group is optionally substituted, one or two times, with a halogen atom, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a fluorine, chlorine or bromine atom or a group selected from methyl, sec-butyl, (oxetan-3-yl)methyl, cyclopropyl, 3,3-difluorocyclobutyl, methoxymethyl, methoxy, propoxy, (1-cyanocyclopropyl) methoxy, cyclopropyloxy, cyclobutyloxy, methanesulfonyl, cyano, hydroxy, 4-hydroxy-2-oxo-pyrrolidin-1-yl, 7-oxo-2-oxa-6-azaspiro[3.4]octan-6-yl, oxetan-3-yl, 3,6-dihydro-2H-pyran-4-yl, (oxetan-3-yl)oxy and phenyl, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, —O—($C_1$-$C_4$-alkyl)-C(═O)O$R^{15}$, —O—($C_1$-$C_4$-alkyl)-C(═O)N($R^9$)($R^{10}$), $C_3$-$C_6$-cycloalkyloxy, —S(═O)$R^{14}$, —S(═O)$_2$$R^{14}$, cyano, nitro, hydroxy, —N($R^9$)($R^{10}$), —N($R^{16}$)($R^{17}$), —N($R^{16}$)($R^{20}$), —C(═O)N($R^9$)($R^{10}$), —C(═O)$R^{11}$, —N($R^{12}$)C(═O)$R^{13}$, —N($R^{12}$)S(═O)$_2$$R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_1$-$C_6$-alkoxy group is optionally substituted with a oxiran-2-yl group, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_1$-$C_6$-haloalkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_5$-hydroxyalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, —O—($C_1$-$C_4$-alkyl)-C(═O)O$R^{15}$, —O—($C_1$-$C_4$-alkyl)-C(═O)N($R^9$)($R^{10}$), $C_3$-$C_5$-cycloalkyloxy, —S(═O)$R^{14}$, —S(═O)$_2R^{14}$, cyano, nitro, hydroxy, —N($R^9$)($R^{10}$), —N($R^{16}$)($R^{17}$), —N($R^{16}$)($R^{20}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—($C_1$-$C_4$-alkyl)-C(═O)$OR^{15}$, —O—($C_1$-$C_4$-alkyl)-C(═O)N($R^9$)($R^{10}$), $C_3$-$C_5$-cycloalkyloxy, —S(═O)$_2R^{14}$, cyano, nitro, hydroxy, —N($R^9$)($R^{10}$), —N($R^{16}$)($R^{17}$), —N($R^{16}$)($R^{20}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl group is optionally substituted, one or two times, each substituent independently selected from a halogen atom or a $C_1$-$C_4$-alkyl group, and wherein said phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—($C_1$-$C_4$-alkyl)-C(═O)$OR^{15}$, —O—($C_1$-$C_4$-alkyl)-C(═O)N($R^9$)($R^{10}$), $C_3$-$C_5$-cycloalkyloxy, —S(═O)$_2R^{14}$, cyano, nitro, hydroxy, —N($R^9$)($R^{10}$), —N($R^{16}$)($R^{17}$), —N($R^{16}$)($R^{20}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and, 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl is optionally substituted, one or two times, each substituent independently selected from a halogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—$CH_2$—C(═O)$OR^{15}$, —O—$CH_2$—C(═O)N($R^9$)($R^{10}$), $C_3$-$C_5$-cycloalkyloxy, —S(═O)$_2R^{14}$, cyano, nitro, hydroxy, —N($R^9$)($R^{10}$), —N($R^{16}$)($R^{17}$), —N($R^{16}$)($R^{20}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl group is optionally substituted, one or two times, each substituent independently selected from a halogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—$CH_2$—C(═O)$OR^{15}$, —O—$CH_2$—C(═O)N($R^9$)($R^{10}$), $C_3$-$C_5$-cycloalkyloxy, —S(═O)$_2R^{14}$, cyano, nitro, hydroxy, —N($R^9$)($R^{10}$), —N($R^{16}$)($R^{17}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_1$-$C_4$-alkoxy group is optionally substituted with a oxiran-2-yl group, and wherein said $C_3$-$C_5$-cycloalkyl group is optionally substituted, one or two times, each substituent independently selected from a halogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a fluorine, chlorine or bromine atom or a group selected from methyl, sec-butyl, (oxetan-3-yl)methyl, trifluoromethyl, cyclopropyl, 3,3-difluorocyclobutyl, methoxymethyl, methoxy, propoxy, 2-methoxyethoxy, (1-hydroxycyclopropyl)methoxy, (1-cyanocyclopropyl)methoxy, (oxiran-2-yl)methoxy, carboxymethoxy, 2-tert-butoxy-2-oxo-ethoxy, 2-amino-2-oxo-ethoxy, cyclopropyloxy, cyclobutyloxy, methanesulfonyl, dimethylphosphoryl, cyano, nitro, hydroxy, (cyanomethyl)(methyll)amino, (2-hydroxyethyl)amino, (2-hydroxyethyl)(methyl)amino, (2-methoxyethyl)amino, (2-methoxyethyl)(methyl)amino, cyclopropylamino, (oxetan-3-yl)amino, methyl(oxetan-3-yl)amino, methyl(oxolan-3-yl)amino, 3-hydroxyazetidin-1-yl, 2-oxopyrrolidin-1-yl, morpholino, 1,1-dioxidothiomorpholin-4-yl, 4-hydroxy-2-oxo-pyrrolidin-1-yl, 7-oxo-2-oxa-6-azaspiro[3.4]octan-6-yl, 2,2-dimethyl-2λ$^6$-diazathia-1,2-dien-1-yl, [dimethyl(oxido)-λ$^6$-sulfanylidene]amino, methyl(tetrahydrofuran-3-yl)amino, oxetan-3-yl, 3,6-dihydro-2H-pyran-4-yl, (oxetan-3-yl)oxy, (tetrahydrofuran-3-yl)oxy, (tetrahydro-2H-pyran-3-yl)oxy, (tetrahydro-2H-pyran-4-yl)oxy and phenyl, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, $C_3$-$C_6$-cycloalkyloxy, —S(═O)$R^{14}$, —S(═O)$_2R^{14}$, cyano, hydroxy, —N($R^9$)($R^{10}$), —N($R^{16}$)($R^1$), —C(═O)N($R^9$)($R^{10}$), —C(═O)$R^1$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_5$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, —S(═O)$R^{14}$, —S(═O)$_2R^{14}$, cyano, hydroxy, —N($R^9$)($R^{10}$), —N($R^{16}$)($R^1$), —C(═O)N($R^9$)($R^{10}$), —C(═O)$R^1$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl and $C_4$-$C_6$-cycloalkenyl group is optionally substituted, one or two times, each substituent independently selected from a halogen atom or a $C_1$-$C_4$-alkyl group, and wherein said phenyl and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —S(═O)$_2R^{14}$, cyano, —N($R^9$)($R^{10}$), —N($R^{16}$)($R^{17}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —$N(R^9)(R^{10})$ and oxo, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and wherein said phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_6$-alkyl, $C_3$-$C_5$-cycloalkyl, ($C_1$-$C_2$-alkoxy)-($C_1$-$C_4$-alkyl)-, $C_1$-$C_4$-alkoxy, $C_3$-$C_5$-cycloalkyloxy, —$S(=O)_2R^{14}$, cyano, —$N(R^9)(R^{10})$, —$N(R^{16})(R^{17})$, —$N{=}S(=NH)(R^{14})_2$, —$N{=}S(=O)(R^{14})_2$, 4- to 7-membered heterocycloalkyl, 5- to 7-membered heterocycloalkenyl, (4- to 7-membered heterocycloalkyl)oxy and phenyl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said $C_1$-$C_6$-alkyl and $C_1$-$C_4$-alkoxy group is optionally substituted with a group selected from $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl is optionally substituted, one or two times, each substituent independently selected from a halogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a fluorine, chlorine or bromine atom or a group selected from methyl, sec-butyl, (oxetan-3-yl)methyl, trifluoromethyl, cyclopropyl, 3,3-difluorocyclobutyl, methoxymethyl, methoxy, propoxy, 2-methoxyethoxy, (1-hydroxycyclopropyl)methoxy, (1-cyanocyclopropyl)methoxy, (oxiran-2-yl)methoxy, carboxymethoxy, 2-tert-butoxy-2-oxo-ethoxy, 2-amino-2-oxo-ethoxy, cyclopropyloxy, cyclobutyloxy, methanesulfonyl, dimethylphosphoryl, cyano, nitro, hydroxy, (cyanomethyl)(methyll)amino, (2-hydroxyethyl)amino, (2-hydroxyethyl)(methyl)amino, (2-methoxyethyl)amino, (2-methoxyethyl)(methyl)amino, cyclopropylamino, (oxetan-3-yl)amino, methyl(oxetan-3-yl)amino, methyl (oxolan-3-yl)amino, 3-hydroxyazetidin-1-yl, 2-oxopyrrolidin-1-yl, morpholino, 1,1-dioxidothiomorpholin-4-yl, 4-hydroxy-2-oxo-pyrrolidin-1-yl, 7-oxo-2-oxa-6-azaspiro [3.4]octan-6-yl, 2,2-dimethyl-2$\lambda^6$-diazathia-1,2-dien-1-yl, [dimethyl(oxido)-$\lambda^6$-sulfanylidene]amino, methyl(tetrahydrofuran-3-yl)amino, tetrahydrofuran-3-ylmethoxy, (tetrahydrofuran-3-ylmethyl)amino, oxetan-3-yl, 3,6-dihydro-2H-pyran-4-yl, (oxetan-3-yl)oxy, (tetrahydrofuran-3-yl)oxy, (tetrahydro-2H-pyran-3-yl)oxy, (tetrahydro-2H-pyran-4-yl)oxy and phenyl, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a fluorine, chlorine or bromine atom or a group selected from methyl, sec-butyl, (oxetan-3-yl)methyl, cyclopropyl, 3,3-difluorocyclobutyl, methoxymethyl, methoxy, propoxy, (1-hydroxycyclopropyl)methoxy, (1-cyanocyclopropyl)methoxy, cyclopropyloxy, cyclobutyloxy, methanesulfonyl, cyano, 2-oxopyrrolidin-1-yl, morpholino, 1,1-dioxidothiomorpholin-4-yl, 4-hydroxy-2-oxo-pyrrolidin-1-yl, 7-oxo-2-oxa-6-azaspiro [3.4]octan-6-yl, 2,2-dimethyl-2$\lambda^6$-diazathia-1,2-dien-1-yl, [dimethyl(oxido)-$\lambda^6$-sulfanylidene]amino, methyl(tetrahydrofuran-3-yl)amino, oxetan-3-yl, 3,6-dihydro-2H-pyran-4-yl, (oxetan-3-yl)oxy, (tetrahydrofuran-3-yl)oxy, (tetrahydro-2H-pyran-3-yl)oxy, (tetrahydro-2H-pyran-4-yl)oxy and phenyl, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a halogen atom or a group selected from $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_2$-$C_6$-alkoxy)-, $C_1$-$C_4$-haloalkoxy, $C_3$-$C_6$-cycloalkyloxy, phenoxy, —$SR^{14}$, —$S(=O)R^{14}$, —$S(=O)_2R^{14}$, cyano, hydroxy, —$N(R^9)(R^{10})$, —$C(=O)N(R^9)(R^{10})$, —$C(=O)R^{11}$, —$N(R^{12})C(=O)R^{13}$, —$N(R^{12})S(=O)_2R^{14}$, —$N{=}S(=NH)(R^{14})_2$, —$N{=}S(=O)(R^{14})_2$—$P(=O)(R^{14})_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_6$-alkyl, $C_2$-$C_6$-alkenyl, $C_2$-$C_6$-alkynyl and $C_1$-$C_6$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_3$-$C_6$-cycloalkyl and $C_4$-$C_6$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a halogen atom or a group selected from $C_1$-$C_5$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_2$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═NH)($R^{14}$)$_2$, —N═S(═O)($R^{14}$)$_2$—P(═O)($R^{14}$)$_2$, 4- to 7-membered heterocycloalkyl, 5- to 7-membered heterocycloalkenyl, (4- to 7-membered heterocycloalkyl)oxy, phenyl and 5- or 6-membered heteroaryl, wherein said 4- to 7-membered heterocycloalkyl group and 5- to 7-membered heterocycloalkenyl group is connected to the rest of the molecule via a carbon atom of said 4- to 7-membered heterocycloalkyl group and 5- to 7-membered heterocycloalkenyl group, and wherein said 4- to 7-membered heterocycloalkyl group, 5- to 7-membered heterocycloalkenyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_5$-alkyl, $C_2$-$C_4$-alkenyl, $C_2$-$C_4$-alkynyl and $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl and $C_4$-$C_5$-cycloalkenyl group is optionally substituted, one or two times, each substituent independently selected from a halogen atom or a $C_1$-$C_4$-alkyl group, and wherein said phenyl, phenoxy and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(═O)$_2$$R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$$R^{14}$, —N═S(═NH)($R^{14}$)$_2$, —N═S(═O)($R^{14}$)$_2$, —P(═O)($R^{14}$)$_2$, 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, and wherein said 4- to 7-membered heterocycloalkyl group and (4- to 7-membered heterocycloalkyl)oxy group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and wherein said $C_1$-$C_5$-alkyl, $C_1$-$C_4$-alkoxy group is optionally substituted with a group selected from $C_3$-$C_4$-cycloalkyl, phenyl and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two or three times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$) and oxo, and which phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and which $C_3$-$C_4$-cycloalkyl group is optionally substituted, one or two times, each substituent independently selected from a halogen atom or a group selected from cyano and hydroxy, and wherein said $C_3$-$C_5$-cycloalkyl group is optionally substituted, one or two times, each substituent independently selected from a halogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a halogen atom or a group selected from $C_1$-$C_5$-alkyl, $C_3$-$C_5$-cycloalkyl, $C_1$-$C_4$-alkoxy, $C_3$-$C_5$-cycloalkyloxy, —S(═O)$_2$$R^{14}$, cyano, hydroxy, —N($R^9$)($R^{10}$), 4- to 7-membered heterocycloalkyl and (4- to 7-membered heterocycloalkyl)oxy, wherein said 4- to 7-membered heterocycloalkyl group is connected to the rest of the molecule via a carbon atom of said 4- to 7-membered heterocycloalkyl group, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a fluorine, chlorine or bromine atom or a group selected from methyl, cyclopropyl, methoxy, propoxy, cyclopropyloxy, methanesulfonyl, cyano, hydroxy, oxetan-3-yl and oxetan-3-yloxy, and stereoisomers, tautomers, N-oxides, hydrates, solvates, and salts thereof, and mixtures of same.

In a further embodiment of the first aspect, the present invention covers compounds of formula (I), supra, in which:

$R^6$ represents a hydrogen atom, or a fluorine atom or a group selected from $C_1$-$C_4$-alkyl, $C_1$-$C_4$-hydroxyalkyl, $C_1$-$C_4$-alkoxy, hydroxy and oxo, and stereoisomers, tautomers, N-oxides, hydrates, solvates, and salts thereof, and mixtures of same.

In a further embodiment of the first aspect, the present invention covers compounds of formula (I), supra, in which:

$R^6$ represents a hydrogen atom or a group selected from $C_1$-$C_4$-alkyl and $C_1$-$C_4$-hydroxyalkyl, and stereoisomers, tautomers, N-oxides, hydrates, solvates, and salts thereof, and mixtures of same.

In a further embodiment of the first aspect, the present invention covers compounds of formula (I), supra, in which:

$R^6$ represents a hydrogen atom or a group selected from methyl and hydroxymethyl, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a hydrogen atom or a halogen atom or a group selected from $C_1$-$C_4$-alkyl, $C_1$-$C_4$-alkoxy and hydroxy, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a hydrogen atom or a fluorine atom or a group selected from methyl, ethyl, methoxy and hydroxy, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a hydrogen atom or a halogen atom or a group selected from $C_1$-$C_4$-alkyl, $C_1$-$C_4$-alkoxy, hydroxy and cyano, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a hydrogen atom or a halogen atom or a group selected from $C_1$-$C_4$-alkyl and hydroxy, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a hydrogen atom or a fluorine atom or a group selected from ethyl, ethyl and hydroxy, and stereoisomers, tautomers, N-oxides, hydrates, solvates, and salts thereof, and mixtures of same.

In a further embodiment of the first aspect, the present invention covers compounds of formula (I), supra, in which:

$R^8$ represents a group selected from methyl and ethyl, and stereoisomers, tautomers, N-oxides, hydrates, solvates, and salts thereof, and mixtures of same.

In a further embodiment of the first aspect, the present invention covers compounds of formula (I), supra, in which:

$R^8$ represents a methyl group, and stereoisomers, tautomers, N-oxides, hydrates, solvates, and salts thereof, and mixtures of same.

In a further embodiment of the first aspect, the present invention covers compounds of formula (I), supra, in which:

$R^8$ represents an ethyl group, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)-, $C_3$-$C_4$-cycloalkyl and $C_2$-$C_4$-haloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, $C_2$-$C_4$-hydroxyalkyl, N═C—($C_1$-$C_4$-alkyl)-, ($C_1$-$C_4$-alkoxy)-($C_2$-$C_4$-alkyl)-, $C_3$-$C_4$-cycloalkyl and $C_2$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, ($C_1$-$C_4$-alkoxy)-($C_2$-$C_4$-alkyl)-, $C_3$-$C_4$-cycloalkyl and $C_2$-$C_4$-haloalkyl, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, ($C_1$-$C_4$-alkoxy)-($C_2$-$C_4$-alkyl)-, $C_3$-$C_4$-cycloalkyl and $C_2$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or $C_1$-$C_4$-alkyl group, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, each substituent independently selected from a halogen atom or a group selected from $C_1$-$C_4$-alkyl, $C_3$-$C_4$-cycloalkyl, $C_1$-$C_4$-haloalkyl, hydroxy and oxo, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a methyl group, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or $C_1$-$C_4$-alkyl group, or $R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ together with the nitrogen to which they are attached represent a nitrogen containing 4- to 7-membered heterocycloalkyl group, wherein said nitrogen containing 4- to 7-membered heterocycloalkyl group is optionally substituted, one, two or three times, each substituent independently selected from a halogen atom or a group selected from $C_1$-$C_4$-alkyl, hydroxy and oxo, or two substituents, which are attached to the same carbon atom of said nitrogen containing 4- to 7-membered heterocycloalkyl group, together with the carbon atom to which they are attached, represent a 4- to 7-membered heterocycloalkyl group, wherein said 4- to 7-membered heterocycloalkyl group is optionally substituted, one or two times, with a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a hydrogen atom or a group selected from $C_1$-$C_4$-alkyl and $C_1$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a group selected from $C_1$-$C_4$-alkyl and $C_1$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a group selected from methyl and trifluoromethyl, and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a methyl group, and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a hydrogen atom or group selected from $C_1$-$C_4$-alkyl, $C_1$-$C_4$-hydroxyalkyl, $C_1$-$C_4$-haloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a hydrogen atom or a $C_1$-$C_4$-haloalkyl group, and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a $C_1$-$C_4$-haloalkyl group, and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents a trifluoromethy group, and stereoisomers, tautomers, N-oxides, hydrates, solvates, and salts thereof, and mixtures of same.

In a further embodiment of the first aspect, the present invention covers compounds of formula (I), supra, in which:

$R^{12}$ represents a hydrogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{12}$ represents a hydrogen atom, and stereoisomers, tautomers, N-oxides, hydrates, solvates, and salts thereof, and mixtures of same.

In a further embodiment of the first aspect, the present invention covers compounds of formula (I), supra, in which:

$R^{13}$ represents a hydrogen atom or a group selected from $C_1$-$C_6$-alkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^{13}$ represents a hydrogen atom or a group selected from $C_1$-$C_4$-alkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$), and stereoisomers, tautomers, N-oxides, hydrates, solvates, and salts thereof, and mixtures of same.

In a further embodiment of the first aspect, the present invention covers compounds of formula (I), supra, in which:

$R^{13}$ represents a phenyl group, and stereoisomers, tautomers, N-oxides, hydrates, solvates, and salts thereof, and mixtures of same.

In a further embodiment of the first aspect, the present invention covers compounds of formula (I), supra, in which:

$R^{14}$ represents a group selected from $C_1$-$C_6$-alkyl, $C_1$-$C_6$-haloalkyl, $C_3$-$C_6$-cycloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$):

and stereoisomers, tautomers, N-oxides, hydrates, solvates, and salts thereof, and mixtures of same.

In a further embodiment of the first aspect, the present invention covers compounds of formula (I), supra, in which:

$R^{14}$ represents a group selected from $C_1$-$C_4$-alkyl, $C_1$-$C_4$-haloalkyl, $C_3$-$C_5$-cycloalkyl, phenyl and 5- or 6-membered heteroaryl, wherein said phenyl group and 5- or 6-membered heteroaryl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, and stereoisomers, tautomers, N-oxides, hydrates, solvates, and salts thereof, and mixtures of same.

In a further embodiment of the first aspect, the present invention covers compounds of formula (I), supra, in which:

$R^{14}$ represents a group selected from $C_1$-$C_4$-alkyl and phenyl, wherein said phenyl group is optionally substituted, one or two times, each substituent independently selected from a halogen atom or a group selected from $C_1$-$C_2$-alkyl, $C_1$-$C_2$-haloalkyl, cyano, hydroxy, $C_1$-$C_2$-alkoxy, $C_3$-$C_4$-cycloalkyl and —$N(R^9)(R^{10})$, and stereoisomers, tautomers, N-oxides, hydrates, solvates, and salts thereof, and mixtures of same.

In a further embodiment of the first aspect, the present invention covers compounds of formula (I), supra, in which:

$R^{14}$ represents a group selected from $C_1$-$C_4$-alkyl and phenyl, and stereoisomers, tautomers, N-oxides, hydrates, solvates, and salts thereof, and mixtures of same.

In a further embodiment of the first aspect, the present invention covers compounds of formula (I), supra, in which:

$R^{14}$ represents a group selected from methyl and phenyl, and stereoisomers, tautomers, N-oxides, hydrates, solvates, and salts thereof, and mixtures of same.

In a further embodiment of the first aspect, the present invention covers compounds of formula (I), supra, in which:

$R^{15}$ represents a hydrogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{16}$ represents a hydrogen atom or a group selected from $C_1$-$C_4$-alkyl, $C_3$-$C_4$-cycloalkyl and $C_2$-$C_4$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^{16}$ represents a hydrogen atom or a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{17}$ represents a 4- to 7-membered heterocycloalkyl group, wherein said 4- to 7-membered heterocycloalkyl group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, and wherein said 4- to 7-membered heterocycloalkyl group is connected to the rest of the molecule via a carbon atom of the 4- to 7-membered heterocycloalkyl group, and stereoisomers, tautomers, N-oxides, hydrates, solvates, and salts thereof, and mixtures of same.

In a further embodiment of the first aspect, the present invention covers compounds of formula (I), supra, in which:

$R^{17}$ represents a 4- to 7-membered heterocycloalkyl group, wherein said 4- to 7-membered heterocycloalkyl group is optionally substituted, one or two times, with a $C_1$-$C_4$-alkyl group, and wherein said 4- to 7-membered heterocycloalkyl group is connected to the rest of the molecule via a carbon atom of the 4- to 7-membered heterocycloalkyl group, and stereoisomers, tautomers, N-oxides, hydrates, solvates, and salts thereof, and mixtures of same.

In a further embodiment of the first aspect, the present invention covers compounds of formula (I), supra, in which:

$R^{17}$ represents a 4- to 7-membered heterocycloalkyl group, wherein said 4- to 7-membered heterocycloalkyl group is connected to the rest of the molecule via a carbon atom of the 4- to 7-membered heterocycloalkyl group, and stereoisomers, tautomers, N-oxides, hydrates, solvates, and salts thereof, and mixtures of In a further embodiment of the first aspect, the present invention covers compounds of formula (I), supra, in which:

$R^{18}$ represents a hydrogen atom or a group selected from methyl and ethyl, and stereoisomers, tautomers, N-oxides, hydrates, solvates, and salts thereof, and mixtures of same.

In a further embodiment of the first aspect, the present invention covers compounds of formula (I), supra, in which:

$R^{18}$ represents a hydrogen atom or a methyl group, and stereoisomers, tautomers, N-oxides, hydrates, solvates, and salts thereof, and mixtures of same.

In a further embodiment of the first aspect, the present invention covers compounds of formula (I), supra, in which:

$R^{19}$ represents a hydrogen atom or a group selected from methyl and ethyl, and stereoisomers, tautomers, N-oxides, hydrates, solvates, and salts thereof, and mixtures of same.

In a further embodiment of the first aspect, the present invention covers compounds of formula (I), supra, in which:

$R^{19}$ represents a hydrogen atom or a methyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a (4- to 7-membered heterocycloalkyl)-($C_1$-$C_4$-alkyl)- group, wherein the (4- to 7-membered heterocycloalkyl) part of said group is optionally substituted, one, two or three times, each substituent independently selected from a halogen atom or a group selected from $C_1$-$C_4$-alkyl, $C_3$-$C_4$-cycloalkyl, $C_1$-$C_4$-alkoxy, hydroxy and oxo, and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a (4- to 7-membered heterocycloalkyl)-($C_1$-$C_4$-alkyl)- group, wherein the (4- to 7-membered heterocycloalkyl) part of said group is optionally substituted, one or two times, with a $C_1$-$C_4$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^{20}$ represents a (4- to 7-membered heterocycloalkyl)-($C_1$-$C_4$-alkyl)- group, and stereoisomers, tautomers, N-oxides, hydrates, solvates, and salts thereof, and mixtures of same.

In a further embodiment of the first aspect, the present invention covers compounds of formula (I), supra, in which:

m represents an integer selected from 1, 2 and 3, and stereoisomers, tautomers, N-oxides, hydrates, solvates, and salts thereof, and mixtures of same.

In a further embodiment of the first aspect, the present invention covers compounds of formula (I), supra, in which:

m represents an integer selected from 1 and 2, and stereoisomers, tautomers, N-oxides, hydrates, solvates, and salts thereof, and mixtures of same.

In a further embodiment of the first aspect, the present invention covers compounds of formula (I), supra, in which:

m represents an integer selected from 1 and 3, and stereoisomers, tautomers, N-oxides, hydrates, solvates, and salts thereof, and mixtures of same.

In a further embodiment of the first aspect, the present invention covers compounds of formula (I), supra, in which:

m represents an integer selected from 2 and 3, and stereoisomers, tautomers, N-oxides, hydrates, solvates, and salts thereof, and mixtures of same.

In a further embodiment of the first aspect, the present invention covers compounds of formula (I), supra, in which:

m represents an integer of 1, and stereoisomers, tautomers, N-oxides, hydrates, solvates, and salts thereof, and mixtures of same.

In a further embodiment of the first aspect, the present invention covers compounds of formula (I), supra, in which:

m represents an integer of 2, and stereoisomers, tautomers, N-oxides, hydrates, solvates, and salts thereof, and mixtures of same.

In a further embodiment of the first aspect, the present invention covers compounds of formula (I), supra, in which:

m represents an integer of 3, and stereoisomers, tautomers, N-oxides, hydrates, solvates, and salts thereof, and mixtures of same.

In a further embodiment of the first aspect, the present invention covers compounds of formula (I), supra, in which:

n represents an integer selected from 1, 2 and 3, and stereoisomers, tautomers, N-oxides, hydrates, solvates, and salts thereof, and mixtures of same.

In a further embodiment of the first aspect, the present invention covers compounds of formula (I), supra, in which:

n represents an integer selected from 1 and 2, and stereoisomers, tautomers, N-oxides, hydrates, solvates, and salts thereof, and mixtures of same.

In a further embodiment of the first aspect, the present invention covers compounds of formula (I), supra, in which:

n represents an integer selected from 1 and 3, and stereoisomers, tautomers, N-oxides, hydrates, solvates, and salts thereof, and mixtures of same.

In a further embodiment of the first aspect, the present invention covers compounds of formula (I), supra, in which:

n represents an integer selected from 2 and 3, and stereoisomers, tautomers, N-oxides, hydrates, solvates, and salts thereof, and mixtures of same.

In a further embodiment of the first aspect, the present invention covers compounds of formula (I), supra, in which:

n represents an integer of 1, and stereoisomers, tautomers, N-oxides, hydrates, solvates, and salts thereof, and mixtures of same.

In a further embodiment of the first aspect, the present invention covers compounds of formula (I), supra, in which:

n represents an integer of 2, and stereoisomers, tautomers, N-oxides, hydrates, solvates, and salts thereof, and mixtures of same.

In a further embodiment of the first aspect, the present invention covers compounds of formula (I), supra, in which:

n represents an integer of 3, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano and —C(═O)NH$_2$, $R^2$ represents a 5- to 10-membered heteroaryl group, which 5- to 10-membered heteroaryl group is connected to the rest of the molecule via a carbon atom of said 5- to 10-membered heteroaryl group, and which 5- to 10-membered heteroaryl group is optionally substituted with a group selected from $C_1$-$C_4$-alkyl and phenyl, wherein said phenyl group is optionally substituted with a $C_1$-$C_2$-alkyl group, $R^3$ represents a hydrogen atom or a halogen atom or a group selected from $C_1$-$C_6$-alkyl and cyano, $R^4$ represents a hydrogen atom or a group selected from —N($R^9$)($R^{10}$) and (4- to 7-membered heterocycloalkyl)oxy, $R^5$ represents a hydrogen atom, $R^6$ represents a hydrogen atom, $R^7$ represents a hydrogen atom, $R^8$ represents a methyl group, $R^9$ and $R^{10}$ represent, independently from each occurrence, a hydrogen atom or a group selected from $C_1$-$C_4$-alkyl, $C_2$-$C_4$-hydroxyalkyl and ($C_1$-$C_4$-alkoxy)-($C_2$-$C_4$-alkyl)-, and n represents an integer of 2, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano and —C(═O)NH$_2$, $R^2$ represents a group selected from 1,2,4-oxadiazol-5-yl, 1H-pyrazol-3-yl and 1,3-benzoxazol-2-yl, which group is optionally substituted with a group selected from $C_1$-$C_4$-alkyl and phenyl, wherein said phenyl group is optionally substituted with a $C_1$-$C_2$-alkyl group, $R^3$ represents a hydrogen atom or a fluorine atom or a group selected from methyl and cyano, $R^4$ represents a hydrogen atom or a group selected from (2-hydroxyethyl)amino, (2-hydroxyethyl)(methyl)amino, (2-methoxyethyl)amino and (tetrahydrofuran-3-yl)oxy, $R^5$ represents a hydrogen atom, $R^6$ represents a hydrogen atom, $R^7$ represents a hydrogen atom, $R^8$ represents a methyl group, and n represents an integer of 2, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano and —C(═O)NH$_2$, $R^2$ represents a group selected from 1,2,4-oxadiazol-5-yl, 1H-pyrazol-3-yl and 1,3-benzoxazol-2-yl, which group is optionally substituted with a group selected from methyl and phenyl, wherein said phenyl group is optionally substituted with a methyl group, $R^3$ represents a hydrogen atom or a fluorine atom or a group selected from methyl and cyano, $R^4$ represents a hydrogen atom or a group selected from (2-hydroxyethyl)amino, (2-hydroxyethyl)(methyl)amino, (2-methoxyethyl)amino and (tetrahydrofuran-3-yl)oxy, $R^5$ represents a hydrogen atom, $R^6$ represents a hydrogen atom, $R^7$ represents a hydrogen atom, $R^8$ represents a methyl group, and n represents an integer of 2, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano and —C(═O)$NH_2$, $R^2$ represents a group selected from 1,2,4-oxadiazol-5-yl, 1H-pyrazol-3-yl and 1,3-benzoxazol-2-yl, which group is substituted with a group selected from methyl and phenyl, wherein said phenyl group is substituted with a methyl group, $R^3$ represents a hydrogen atom or a fluorine atom or a group selected from methyl and cyano, $R^4$ represents a hydrogen atom or a group selected from (2-hydroxyethyl)amino, (2-hydroxyethyl)(methyl)amino, (2-methoxyethyl)amino and (tetrahydrofuran-3-yl)oxy, $R^5$ represents a hydrogen atom, $R^6$ represents a hydrogen atom, $R^7$ represents a hydrogen atom, $R^8$ represents a methyl group, and n represents an integer of 2, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from cyano and —C(═O)$NH_2$, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a 5- to 10-membered heteroaryl group, which 5- to 10-membered heteroaryl group is connected to the rest of the molecule via a carbon atom of said 5- to 10-membered heteroaryl group, and which 5- to 10-membered heteroaryl group is optionally substituted with a group selected from $C_1$-$C_4$-alkyl and phenyl, wherein said phenyl group is optionally substituted with a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from 1,2,4-oxadiazol-5-yl, 1H-pyrazol-3-yl and 1,3-benzoxazol-2-yl, which group is optionally substituted with a group selected from $C_1$-$C_4$-alkyl and phenyl, wherein said phenyl group is optionally substituted with a $C_1$-$C_2$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from 1,2,4-oxadiazol-5-yl, 1H-pyrazol-3-yl and 1,3-benzoxazol-2-yl, which group is optionally substituted with a group selected from methyl and phenyl, wherein said phenyl group is optionally substituted with a methyl group, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from 1,2,4-oxadiazol-5-yl, 1H-pyrazol-3-yl and 1,3-benzoxazol-2-yl, which group is substituted with a group selected from methyl and phenyl, wherein said phenyl group is substituted with a methyl group, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_6$-alkyl and cyano, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a fluorine atom or a group selected from methyl and cyano, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a group selected from —N($R^9$)($R^{10}$) and (4- to 7-membered heterocycloalkyl)oxy, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a group selected from (2-hydroxyethyl)amino, (2-hydroxyethyl)(methyl)amino, (2-methoxyethyl)amino and (tetrahydrofuran-3-yl)oxy, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom, and stereoisomers, tautomers, N-oxides, hydrates, solvates, and salts thereof, and mixtures of same.

In a further embodiment of the first aspect, the present invention covers compounds of formula (I), supra, in which:

$R^6$ represents a hydrogen atom, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a hydrogen atom, and stereoisomers, tautomers, N-oxides, hydrates, solvates, and salts thereof, and mixtures of same.

In a further embodiment of the first aspect, the present invention covers compounds of formula (I), supra, in which:

$R^9$ and $R^{10}$ represent, independently from each occurrence, a hydrogen atom or a group selected from $C_1$-$C_4$-alkyl, $C_2$-$C_4$-hydroxyalkyl and ($C_1$-$C_4$-alkoxy)-($C_2$-$C_4$-alkyl)-, and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

In a particular further embodiment of the first aspect, the present invention covers combinations of two or more of the above mentioned embodiments.

The present invention covers any sub-combination within any embodiment or aspect of the present invention of compounds of general formula (I), supra.

The present invention covers the compounds of general formula (I) which are disclosed in the Example Section of this text, infra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively inhibit DGKα and it is possible therefore that said compounds be used for the treatment or prophylaxis of diseases, preferably conditions with dysregulated immune responses, particularly cancer or other disorders associated with aberrant DGKα signaling, in humans and animals.

Disorders and conditions particularly suitable for treatment with an DGKα inhibitor of the present invention are liquid and solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, glioblastoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Examples of ovarian cancer include, but are not limited to serous tumour, endometrioid tumour, mucinous cystadenocarcinoma, granulosa cell tumour, Sertoli-Leydig cell tumour and arrhenoblastoma.

Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumours of the digestive tract include, but are not limited to, anal, colon, colorectal, esophageal, gallbladder, gastric, pancreatic, rectal, small-intestine, and salivary gland cancers.

Examples of esophageal cancer include, but are not limited to esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumours.

Tumours of the urinary tract include, but are not limited to, bladder, penile, kidney, renal pelvis, ureter, urethral and human papillary renal cancers.

Examples of kidney cancer include, but are not limited to renal cell carcinoma, urothelial cell carcinoma, juxtaglomerular cell tumour (reninoma), angiomyolipoma, renal oncocytoma, Bellini duct carcinoma, clear-cell sarcoma of the kidney, mesoblastic nephroma and Wilms' tumour.

Examples of bladder cancer include, but are not limited to transitional cell carcinoma, squamous cell carcinoma, adenocarcinoma, sarcoma and small cell carcinoma.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies, 4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention are used in combination with radiation: i.e. radiation treatment sensitizes cancers to anti-tumor immune responses by induction of tumor cell death and subsequent presentation of tumor neoantigens to tumor-reactive Tcells. As DGKα is enhancing the antigen specific activation of T cells, the overall effect results in a much stronger cancer cell attack as compared to irradiation treatment alone.

Thus, the present invention also provides a method of killing a tumor, wherein conventional radiation therapy is employed previous to administering one or more of the compounds of the present invention.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with:

131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, alpharadin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, cemiplimab, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tislelizumab, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention can further be combined with other reagents targeting the immune system, such as immune checkpoint inhibitors, e.g. a PD-1/L1 axis antagonists. PD-1, along with its ligands PD-L1 and PD-L2, function as negative regulators of T cell activation. DGKα suppresses immune cell function. PD-L1 is overexpressed in many cancers and overexpression of PD-1 often occurs concomitantly in tumor infiltrating T cells. This results in attenuation of T cell activation and evasion of immune surveillance, which contributes to impaired antitumor immune responses. (Keir M E et al. (2008) Annu. Rev. Immunol. 26:677).

In accordance with a further aspect, the present invention covers combinations comprising one or more of the compounds of general formula (I), as described herein, or stereoisomers, tautomers, N-oxides, hydrates, solvates, and salts thereof, particularly pharmaceutically acceptable salts thereof, or mixtures of same, and one or more immune checkpoint inhibitors. Preferably, the immune checkpoint inhibitor is a PD-1/L1 axis antagonist.

The compounds of the invention can further be combined with chimeric antigen receptor T cells (CAR-T cells), such as Axicabtagen-Ciloleucel or Tisagenlecleucel. The activity of CAR-T cells can be suppressed by the tumor micro environment (TME). Knock out of DGKα by techniques such as Crispr had been shown to enhance CAR-T cell activity in a suppressive TME (Mol. Cells 2018; 41(8): 717-723).

In accordance with a further aspect, the present invention covers combinations comprising one or more compounds of general formula (I), as described herein, or stereoisomers, tautomers, N-oxides, hydrates, solvates, and salts thereof, particularly pharmaceutically acceptable salts thereof, or mixtures of same, with chimeric antigen receptor T cells, (CAR-T cells), CAR-NKT cells or CAR-NK cells.

Preferably, the chimeric antigen receptor T cells (CAR-T cells) are Axicabtagen-Ciloleucel or Tisagenlecleucel.

The present invention further provides the use of the compounds according to the invention for expansion of T cells including CAR-T and tumor infiltrated lymphocytes ex-vivo. Inhibition of DGKα was shown to reactivate ex vivo treated T cells (Prinz et al. (2012) J. Immunol).

In accordance with a further aspect, the present invention covers compounds of general formula (I), as described herein, or stereoisomers, tautomers, N-oxides, hydrates, solvates, and salts thereof, particularly pharmaceutically acceptable salts thereof, or mixtures of same, for use in the expansion of T cells including CAR-T cells, CAR-NKT cells or CAR-NK cells and tumor infiltrated lymphocytes ex-vivo.

Hence, the present invention also relates to the use of the compounds according to the invention for the expansion of T cells, including CAR-T cell, CAR-NKT cells or CAR-NK cells and tumor infiltrated lymphocytes, ex-vivo.

The present invention also comprises an ex-vivo method for the expansion of T cells, including CAR-T cells, CAR-NKT cells or CAR-NK cells and tumor infiltrated lymphocytes, contacting said T cells with compounds according to the invention.

The compounds of the invention can further be combined with inhibitors of DGK, such as those inhibitors of DGK disclosed in WO2020/006016 and WO2020/006018. As DGK(in T cells operates in a similar fashion as DGKα, a dual inhibition profoundly enhances T cell effector functions compared with cells with deletion of either DGK isoform alone or wild-type cells (Riese et al., Cancer Res 2013, 73(12), 3566).

Compounds of the present invention can be utilized to inhibit, block, reduce or decrease DGKα activity resulting in the modulation of dysregulated immune responses e.g. to block immunosuppression and increase immune cell activation and infiltration in the context of cancer and cancer immunotherapy that will eventually lead to reduction of tumour growth.

This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder. The present invention also provides methods of treating a variety of other disorders wherein DGKα is involved such as, but not limited to, disorders with dysregulated immune responses, inflammation, vaccination for infection & cancer, viral infections, obesity and diet-induced obesity, adiposity, metabolic disorders, fibrotic disorders, cardiac diseases and lymphoproliferative disorders.

These disorders have been well characterized in humans, but also exist with a similar etiology in other mammals, and can be treated by administering pharmaceutical compositions of the present invention.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular cancer or conditions with dysregulated immune responses or other disorders associated with aberrant DGKα signaling.

The pharmaceutical activity of the compounds according to the invention can be explained by their activity as DGKα inhibitors.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular cancer or conditions with dysregulated immune responses or other disorders associated with aberrant DGKα signaling, particularly liquid and solid tumours.

In accordance with a further aspect, the present invention covers the compounds of general formula (I), as described supra, or stereoisomers, tautomers, N-oxides, hydrates, solvates, and salts thereof, particularly pharmaceutically acceptable salts thereof, or mixtures of same, for the use of treatment or prophylaxis of diseases, in particular cancer or conditions with dysregulated immune responses or other disorders associated with aberrant DGKα signaling, particularly liquid and solid tumours.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer or conditions with dysregulated immune responses or other disorders associated with aberrant DGKα signaling, particularly liquid and solid tumours.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular cancer or conditions with dysregulated immune responses or other disorders associated with aberrant DGKα signaling, particularly liquid and solid tumours.

In accordance with a further aspect, the present invention covers a method of treatment or prophylaxis of diseases, in particular cancer or conditions with dysregulated immune responses or other disorders associated with aberrant DGKα signaling, particularly liquid and solid tumours, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of cancer or conditions with dysregulated immune responses or other disorders associated with aberrant DGKα signaling, particularly liquid and solid tumours.

Particularly, the present invention covers a pharmaceutical combination, which comprises:

one or more first active ingredients, in particular compounds of general formula (I) as defined supra, and one or more further active ingredients, in particular in particular immune checkpoint inhibitors.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

Based upon standard laboratory techniques known to evaluate compounds useful for the treatment of cancer or conditions with dysregulated immune responses or other disorders associated with aberrant DGKα signaling, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Syntheses of Compounds

The compounds according to the invention of general formula (I) can be prepared according to the following schemes 1-19. The schemes and procedures described below illustrate synthetic routes to the compounds of general formula (I) of the invention and are not intended to be limiting. It is clear to the person skilled in the art that the order of transformations as exemplified in schemes 1-19 can be modified in various ways. The order of transformations exemplified in these schemes is therefore not intended to be limiting. In addition, interconversion of any of the substituents, $R^1$, $R^2$, $R^3$, $R^4$, $R^5$, $R^6$, $R^7$ or $R^3$, can be achieved before and/or after the exemplified transformations. These modifications can be such as the introduction of protecting groups, cleavage of protecting groups, reduction or oxidation of functional groups, halogenation, metalation or substitution known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 4th edition, Wiley 2006). Specific examples are described in the subsequent paragraphs.

Isatoic anhydrides 1 are widely available from commercial suppliers or described in the literature. For example the isatoic anhydrides 1 can be prepared from 2-aminobenzoic acids 2 (in analogy to the procedure in *Tetrahedron Lett.* 2014, 55, 3607-3609) using triphosgene in an organic solvent such as THF or 1,4-dioxane or (in analogy to the procedure in *Tetrahedron Lett.* 2013, 54, 6897-6899) using di-tert-butyl dicarbonate and a base such as NaOH followed by treatment with 2-chloromethylpyridinium iodide and subsequent acidic workup (Scheme 1).

Alternatively, preparation of the isatoic anhydrides 1 can also be achieved (for example in analogy to the procedure in *J. Org. Chem.* 2014, 79, 4196-4200) using Pd-catalyzed oxidative double carbonylation of o-iodoanilines 3.

The obtained isatoic anhydrides 1 can then be alkylated at the nitrogen to obtain compounds of the general formula 4. Typically an alkylating agent such as for example an alkylbromide, alkyliodide or alkylsulfonate, a base such as diisopropylethylamine, $K_2CO_3$ or KOtBu in an organic solvent is used.

Alternatively the alkylated isatoic anhydrides 4 can be prepared directly from secondary anilines 5 (in analogy to the procedure in *Tetrahedron Lett.* 2014, 55, 3607-3609) using triphosgene in an organic solvent such as THF or 1,4-dioxane or (in analogy to the procedure in *Tetrahedron Lett.* 2013, 54, 6897-6899) using di-tert-butyl dicarbonate and a base such as NaOH followed by treatment with 2-chloromethylpyridinium iodide and subsequent acidic workup.

Scheme 1: Route for the preparation of compounds of the general formula 4, wherein $R^3$, $R^4$, $R^5$ and $R^8$ have the meaning as given for the general formula (I), supra.

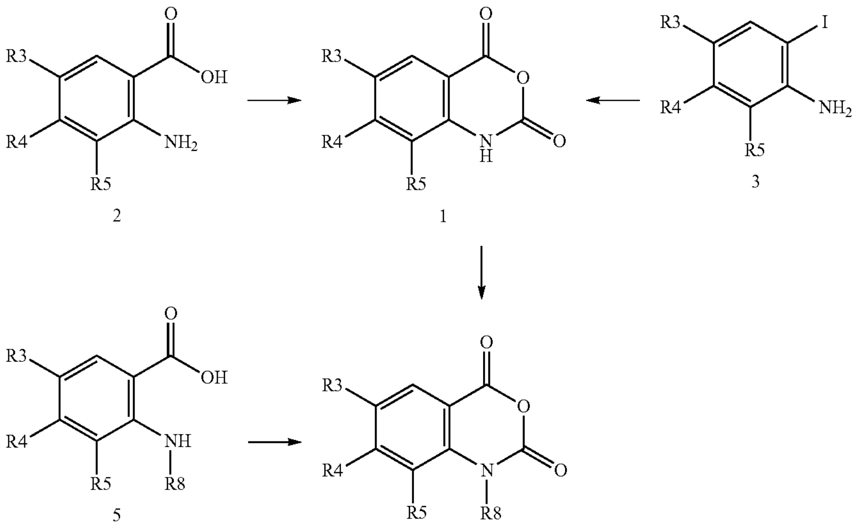

2, 1, 3, 5, 4

Isatoic anhydrides 4 can be converted to the corresponding quinolones 7 using ethyl acetate derivatives 6 such as for example ethylcyano acetate (for $R^1$=CN), a base such as for example triethylamine in an organic solvent such as for example THF (Scheme 2).

Hydroxy quinolones 7 can be converted to the corresponding halides 8 using for example phosphoryl chloride (X=chloro) or phosphoryl bromide (Hal=bromo).

Scheme 2: Route for the preparation of compounds of the general formula 8, wherein $R^1$, $R^3$, $R^4$, $R^5$, and $R^8$ have the meaning as given for the general formula (I), supra and X has the meaning as chloro or bromo.

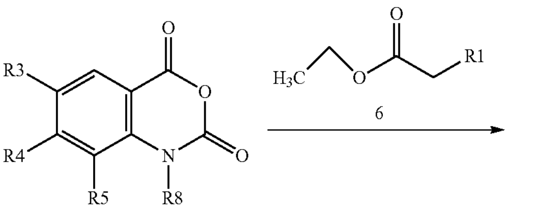

4

6

-continued

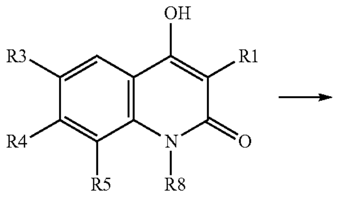

7

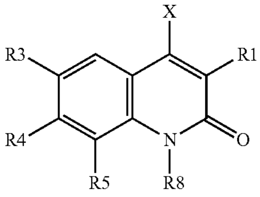

8

Halides of the general formula 8 can be reacted with amines 9 to yield compounds of the general formula 10. Typically the reaction is performed in an organic solvent such as for example isopropanol and a base such as for example diisopropylethylamine or triethylamine. Many amines of the general formula 9 are commercially available or described in the literature (Scheme 3).

Scheme 3: Route for the preparation of compounds of general formula 10, wherein $R^1$, $R^2$, $R^3$, $R^4$, $R^5$, $R^6$, $R^7$, $R^8$ and n have the meaning as given for the general formula (I), supra and X has the meaning as chloro or bromo.

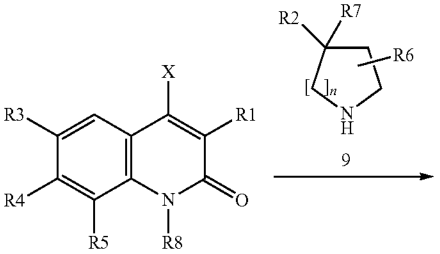

8

9

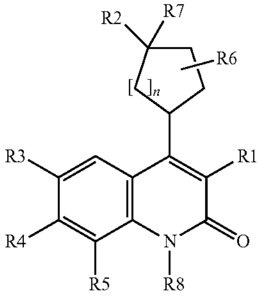

10

Nitriles of the general formula 11 can be converted to the amides of the general formula 12. Typically the reaction is performed with palladium(II)acetate and acetaldoxime in an organic solvent such as for example ethanol (see for example *J. Med. Chem.* 2016, 59, 6281ff, Degorce et al.) (Scheme 4).

Scheme 4: Route for the preparation of compounds of general formula 12, wherein $R^2$, $R^3$, $R^4$, $R^5$, $R^6$, $R^7$, $R^8$ and n having the meaning as given for the general formula (I), supra.

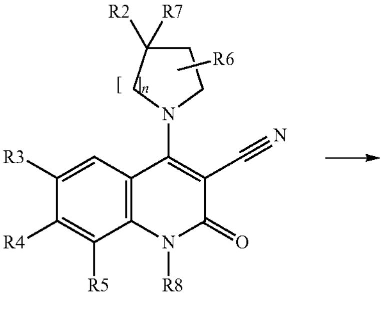

11

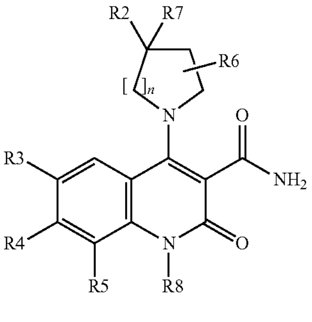

12

Compounds of the general formula 15 can be formed from compounds of the general formula 13 and compounds of the general formula 14 (which are commercially available or described in the literature) by a light promoted, nickel catalyzed reaction as described in J. Am. Chem. Soc. 2016, 138, 8084-8087 and Org. Lett. 2016, 18, 4012, and known to one skilled in the art (Scheme 5). Preferentially, compounds of general formula 13 are reacted with compounds of the general formula 14 in the presence of a photoredox catalyst such as Ir(4',6'-dF-5-$CF_3$-ppy)$_2$(4,4'-dtbbpy)$PF_6$, a nickel precatalyst such as nickel II chloride dimethoxyethane adduct, and a ligand such as 4,4'-Di-tert-butyl-2,2'-bipyridine, with a base such as sodium carbonate, 2,6-dimethoxypyridine, 2,2,6,6-tertramethylpiperidine or lithium carbonate, with additives such as tris(trimehylsilyl) silane, in a solvent or solvent mixture such as dimethoxyethane, N,N-dimethylacetamide/trifluorotoluene or 1,3-dimethyl-2-imidazolidinone/trifluorotoluene, irradiated with light generated by two 40 W Kessil LED aquarium lights, at a temperature between 0° C. and the boiling point of the respective solvent. Ideally the reaction is performed between room temperature and 35° C. to afford compounds of general formula 15.

Scheme 5: Route for the preparation of compounds of general formula 15, wherein $R^1$, $R^2$, $R^3$, $R^4$, $R^5$, $R^6$, $R^7$, $R^8$ and n having the meaning as given for the general formula (I), supra.

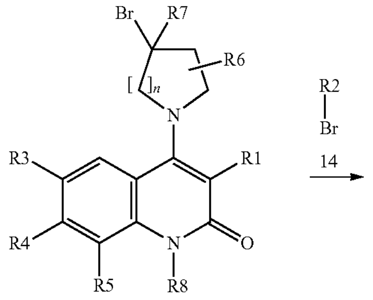

13

14

-continued

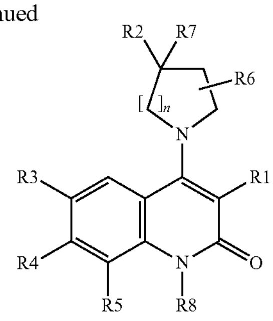

15

Isatoic anhydrides 4 can be converted to the corresponding quinolones 16 using diethylmalonate, a base such as for example triethylamine in an organic solvent such as for example THF (Scheme 6).

Hydroxy quinolones 16 can be converted to the corresponding halides 17 using for example phosphoryl chloride (X=chloro) or phosphoryl bromide (X=bromo).

Halides of the general formula 17 can be reacted with amines 9 to yield compounds of the general formula 18. Typically the reaction is performed in an organic solvent such as for example isopropanol and with a base such as for example diisopropylethylamine.

Scheme 6: Route for the preparation of compounds of general formula 18, wherein $R^2$, $R^3$, $R^4$, $R^5$, $R^6$, $R^7$, $R^8$ and n having the meaning as given for the general formula (I), supra supra and X has the meaning as chloro or bromo.

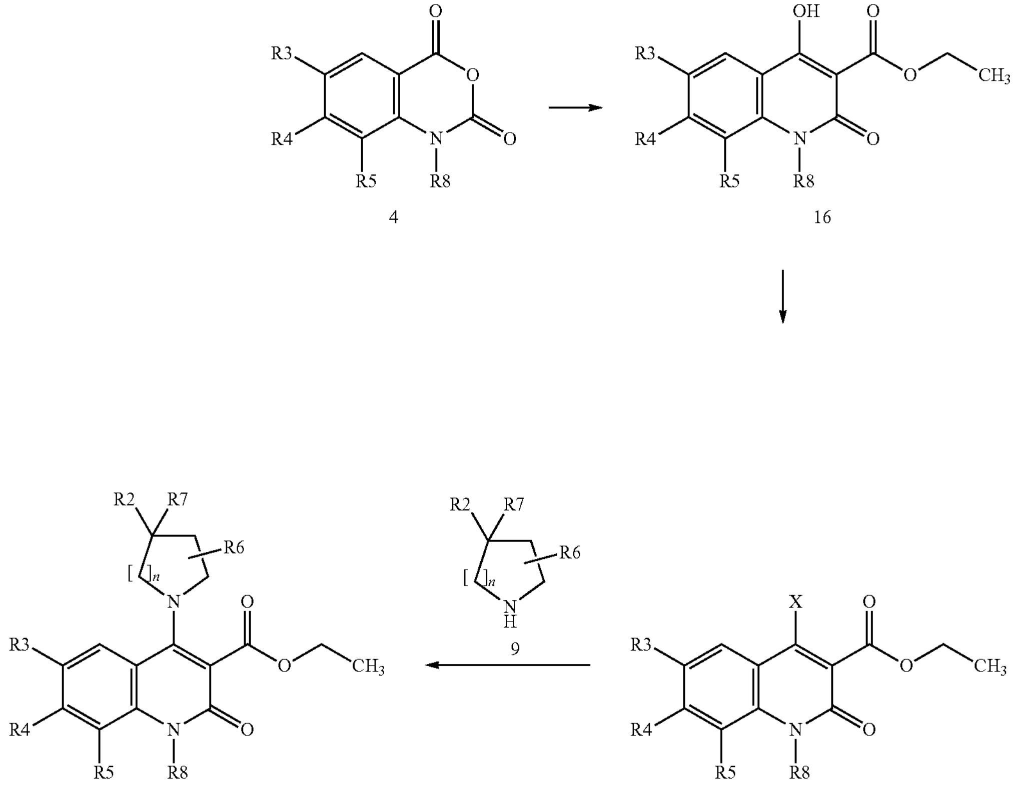

4

16

9

18

17

Esters of the general formula 18 can be converted to the corresponding carboxylic acids 19 using classical ester hydrolysis conditions. Typically LiOH, KOH or NaOH in water/ethanol/THF at elevated temperatures is used for this reaction (Scheme 7).

The carboxylic acids of the general formula 19 and amines of general formula 20 can be converted to the corresponding amides 21 using standard amide forming reaction known to the person skilled in the art. For a review see for example *Chem. Rev.* 2011, 111, 6557-6602. Compounds of general formula 20 are commercially available or described in the literature.

Scheme 7: Route for the preparation of compounds of general formula 21, wherein $R^2$, $R^3$, $R^4$, $R^5$, $R^6$, $R^7$, $R^8$ and n having the meaning as given for the general formula (I), supra, and the amine of general formula 20 has the meaning of $NH_3$, $H_2NCH_3$, $HNC_2H_5$ or $HN(CH_3)_2$.

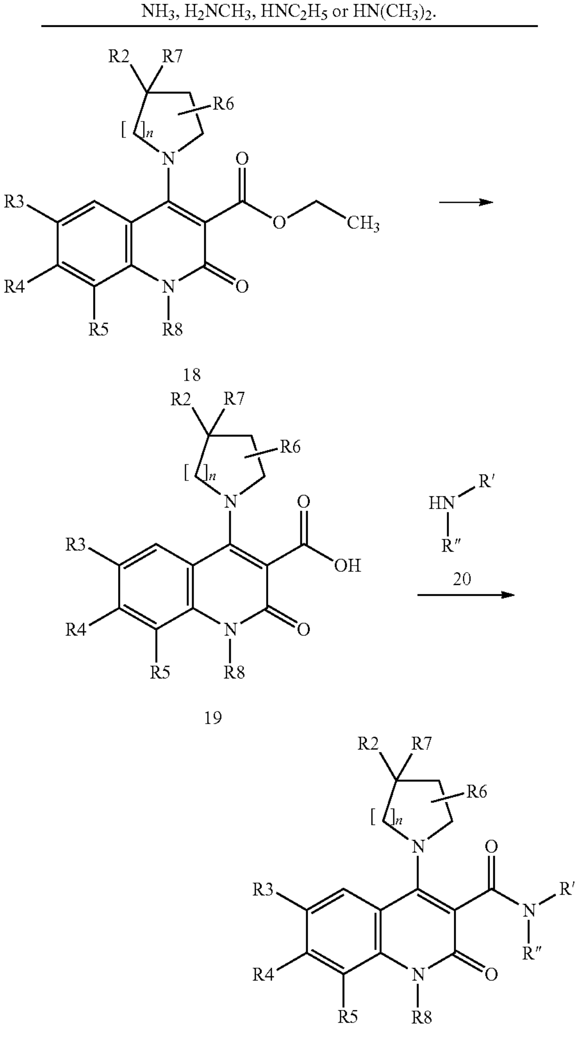

18

19

21

Compounds of the general formula 26 can be prepared from ketones 22 via formation of the corresponding sulfonates 23 followed by a Suzuki coupling leading to compounds of the general formula 24 (Scheme 8). Subsequent hydrogenation to compounds of the general formula 25 followed by cleavage of the tertbutyloxycarbonyl protecting group leads to amines of the general formula 26. All reaction types are known to the person skilled in the art. Instead of a tertbutyloxycarbonyl other suitable protecting groups can be used for this sequence known to the skilled person (see for example P. G. M. Wuts and T. W. Greene in "Protective Groups in Organic Synthesis", $4^{th}$ edition, Wiley 2006). Compounds of general formula 22 are commercially available or described in the literature.

Typical conditions for the conversion of 22 to compounds of the general formula 23 are known to the skilled person. For example, 22 is reacted with a sulfonylation reagent such as for example nonafluorobutanesulfonyl fluoride (for LG-O=[(nonafluorobutyl)sulfonyl]oxy or N,N-phenylbistrifluoromethane-sulfonimide (for LG-O=[(trifluoromethyl)sulfonyl]oxy, a base such as bis-(trimethylsilyl)-lithiumamid in an organic solvent such as THF (see for example procedure in WO2017/158619).

Typical conditions for the Suzuki reaction converting compounds of the general formula 23 to compounds of the general formula 24 are known to the skilled person. For example, 23 can be reacted with a boronic acid derivative $R^2$—$B(OR)_2$ to give a compound of formula 24. The boronic acid derivative may be a boronic acid (R=—H) or an ester of the boronic acid, e.g. its isopropyl ester (R=—$CH(CH_3)_2$), preferably an ester derived from pinacol in which the boronic acid intermediate forms a 2-aryl-4, 4, 5,5-tetramethyl-1,3,2-dioxaborolane (R—R=—$C(CH_3)_2$—$C(CH_2)_2$—). The coupling reaction is catalyzed by palladium catalysts, e.g. by Pd(0) catalysts such as tetrakis(triphenylphosphine)palladium(0) $[Pd(PPh_3)_4]$, tris(dibenzylideneacetone)di-palladium(0): $[Pd_2(dba)_3]$, or by Pd(II) catalysts such as dichlorobis(triphenylphosphine)-palladium(II): $[Pd(PPh_3)_2Cl_2]$, palladium(II) acetate and triphenylphosphine or 4,5-bis(diphenylphosphosphino)-9,9-dimethylxanthene as a ligand or by [1,1'-bis(diphenylphosphino)ferrocene]palladium dichloride. The reaction is preferably carried out in a mixture of a solvent such as 1,2-dimethoxyethane, dioxane, DMF, DME, THF, or isopropanol with water and in the presence of a base like potassium carbonate, sodium bicarbonate or potassium phosphate. For a review see D. G. Hall, Boronic Acids, 2005 WILEY-VCH Verlag GmbH & Co. KGaA, Weinheim, ISBN 3-527-30991-8 and references cited therein). The reaction is performed at temperatures ranging from room temperature (i.e. approx. 20° C.) to the boiling point of the respective solvent. Further on, the reaction can be performed at temperatures above the boiling point using pressure tubes and a microwave oven. The reaction is preferably completed after 1 to 36 hours of reaction time.

Typical conditions for the hydrogenation reaction converting compounds of the general formula 24 to compounds of the general formula 25 are known to the skilled person. For example, 24 can be reacted with hydrogen and a catalyst such as 10% palladium on activated carbon in an organic solvent such as methanol or ethanol (see for example *Bioorganic and medicinal chemistry letters,* 2000, 10, 1625-1628).

Compounds of the general formula 26 can be prepared from the Boc protected amines 25 via removal of the tertbutyloxycarbonyl protecting group under acidic conditions (for example with trifluoroacetic acid or hydrochloric acid) known to the person skilled in the art. Instead of a tertbutyloxycarbonyl other suitable protecting groups can be used for this sequence known to the skilled person (see for example P. G. M. Wuts and T. W. Greene in "Protective Groups in Organic Synthesis", $4^{th}$ edition, Wiley 2006).

Scheme 8: Route for the preparation of compounds of general formula 26, wherein $R^2$, $R^6$ and n having the meaning as given for the general formula (I), supra and

LG—O has the meaning of a sulfonyloxy leaving group such as for example [(trifluoromethyl)sulfonyl]oxy or [(nonafluoro-butyl)sulfonyl]oxy.

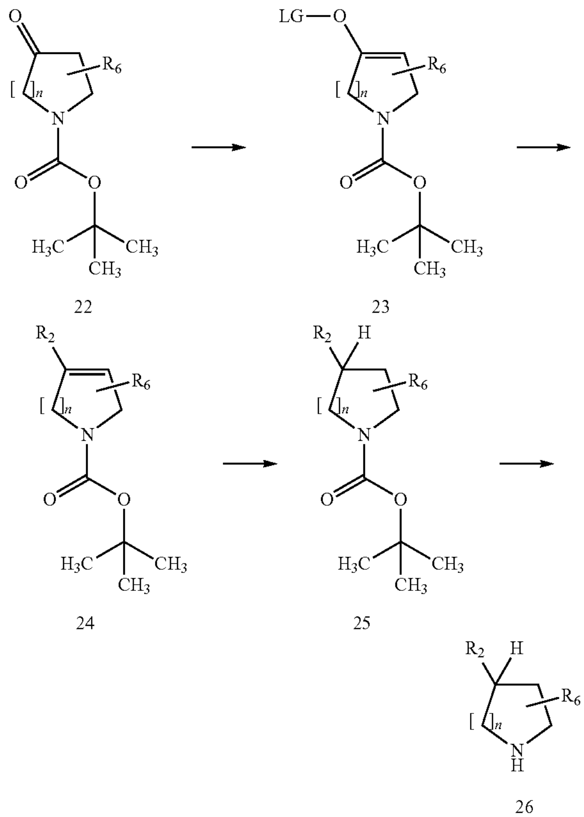

22, 23, 24, 25, 26

Alternatively compounds of the general formula 26 can be prepared from ketones 22 via a Grignard type reaction (via compounds of general formula 27) known to the skilled person followed by reductive removal of the hydroxyl group (via compounds of general formula 28) and removal of the tertbutyloxycarbonyl protecting group under acidic conditions (for example with trifluoroacetic acid or hydrochloric acid) known to the person skilled in the art (Scheme 9). Instead of a tertbutyloxycarbonyl other suitable protecting groups can be used for this sequence known to the skilled person (see for example P. G. M. Wuts and T. W. Greene in "Protective Groups in Organic Synthesis", 4th edition, Wiley 2006). Compounds of general formula 22 are commercially available or described in the literature.

For example, the compounds of the general formula 22 can be reacted with an organometallic reagent $R^2$-[Metal] such as for example [Metal]=MgBr or MgCl or Li in an organic solvent such as THF or diethyl ether to yield compounds of the general formula 27 (see for example procedure in *Bioorganic and Medicinal Chemistry Letters,* 2012, 22, 2560-2564).

In a subsequent reaction hydroxyl compounds of the general formula 27 can be converted to compounds of the general formula 28. Procedures are known to the skilled person. For example triethylsilane, trifluoroacetic acid in an organic solvent such as dichloromethane (see for example procedures in US2005/9838) or hydrogenation conditions such as hydrogen on 10% Pd/C in an alcohol such as for example methanol (see for example WO2011/70080) can be used.

In a subsequent step compounds of the general formula 26 can be prepared from the Boc protected amines 28 via removal of the tertbutyloxycarbonyl protecting group under acidic conditions (for example with trifluoroacetic acid or hydrochloric acid) known to the person skilled in the art.

Scheme 9: Alternative route for the preparation of compounds of general formula 26, wherein $R^2$, $R^6$ and n having the meaning as given for the general formula (I), supra.

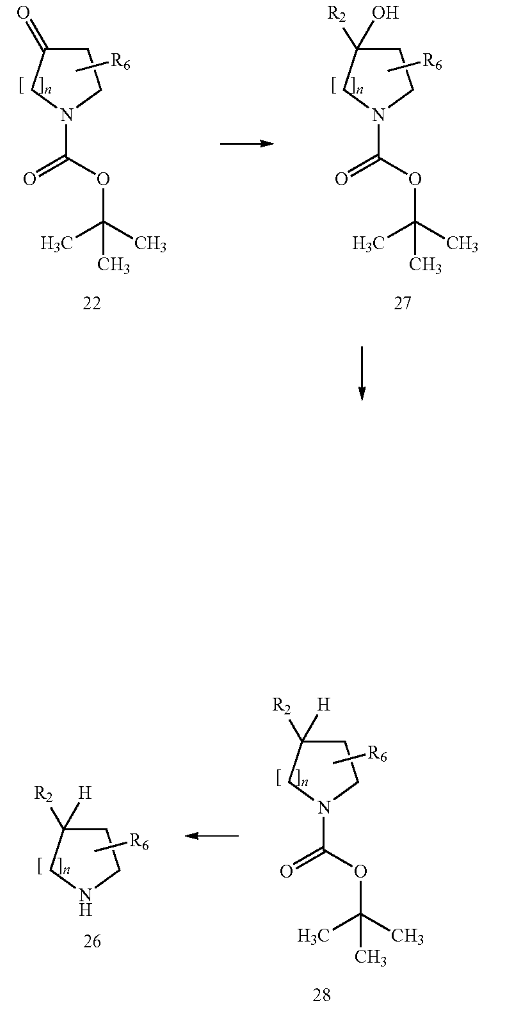

22, 27, 26, 28

Hydroxy compounds of the general formula 29 can be prepared from the Boc protected amines 27 via removal of the tertbutyloxycarbonyl protecting group under acidic conditions (for example with trifluoroacetic acid or hydrochloric acid) known to the person skilled in the art (Scheme 10). Instead of a tertbutyloxycarbonyl other suitable protecting groups can be used for this sequence known to the skilled person (see for example P. G. M. Wuts and T. W. Greene in "Protective Groups in Organic Synthesis", 4th edition, Wiley 2006).

Scheme 10: Route for the preparation of compounds of general formula 29, wherein $R^2$, $R^6$ and n having the meaning as given for the general formula (I), supra.

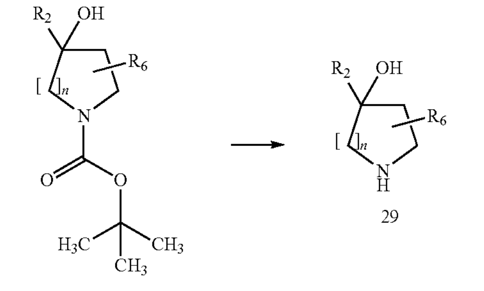

27

29

Fluoro compounds of the general formula 31 can be prepared from alcohols 27 via a fluorination reaction followed by removal of the tertbutyloxycarbonyl protecting group under acidic conditions (for example with trifluoroacetic acid or hydrochloric acid) known to the person skilled in the art (Scheme 11). Instead of a tertbutyloxycarbonyl other suitable protecting groups can be used for this sequence known to the skilled person (see for example P. G. M. Wuts and T. W. Greene in "Protective Groups in Organic Synthesis", $4^{th}$ edition, Wiley 2006). For example, the alcohols 27 can be reacted with a fluorination reagent such as diethylamino-sulfur trifluoride in an organic solvent such as dichloromethane to yield compounds of the general formula 30 (see for example procedure in WO2015/74064).

Scheme 11: Route for the preparation of compounds of general formula 31, wherein $R^2$, $R^6$ and n having the meaning as given for the general formula (I), supra.

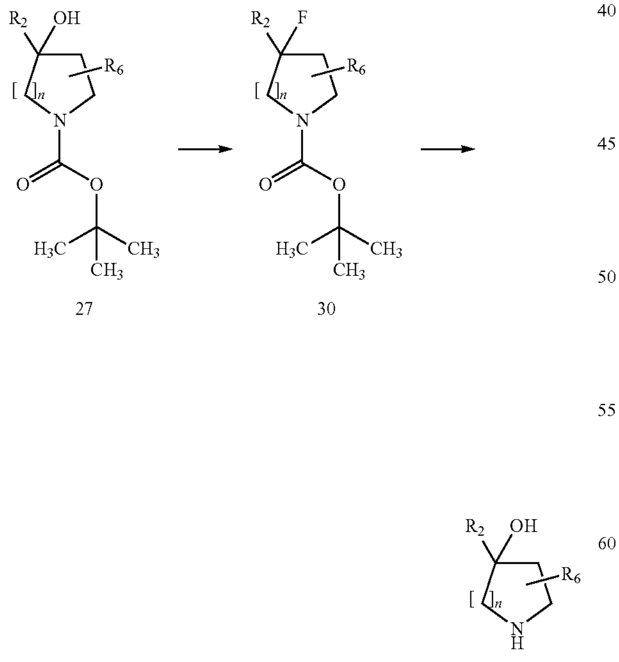

27

30

29

Compounds of the general formula 37 can be prepared from the corresponding esters of general formula 32 via arylation to compounds of the general formula 33 (Scheme 12). The esters 33 can be transformed to the corresponding aldehydes 34 and subsequently converted to olefins 35 via an olefination reaction such as for example a Wittig type reaction. Compounds of the general formula 35 can then be hydrogenated to furnish compounds of the general formula 36. Removal of the tertbutyloxycarbonyl protecting group under acidic conditions (for example with trifluoroacetic acid or hydrochloric acid) furnishes compounds of general formula 37. Instead of a tertbutyloxycarbonyl other suitable protecting groups can be used for this sequence known to the skilled person (see for example P. G. M. Wuts and T. W. Greene in "Protective Groups in Organic Synthesis", $4^{th}$ edition, Wiley 2006). All reactions of this sequence are known to the person skilled in the art. Compounds of general formula 32 are commercially available or described in the literature.

Typical conditions for the conversion of esters 32 to esters 33 are for example a base such as n-butyllithium and N-cyclohexyl-cyclohexanamine, a palladium catalyst such as tris(dibenzylideneacetone)dipalladium(0) chloroform complex and a ligand such as tris tert-butylphosphoniumtetrafluoroborate in an organic solvent such as toluene at elevated temperature (see for example procedure in WO2005/87752).

The conversion of the esters 33 to the aldehydes 34 is typically performed in a two-step procedure. In the first step the ester is reduced to the corresponding alcohols. Typical reaction conditions are a reducing agent such as for example $LiAlH_4$/diethyl ether in an organic solvent such as for example THF or diethylether (see for example *Journal of Medicinal Chemistry,* 1994, 37, 113-124). In the second step the alcohols are oxidized to the corresponding aldehydes 34. Typical reaction conditions are for example Swern oxidation conditions such as DMSO, oxalyl chloride, a base such as trimethylamine in an organic solvent such as dichloromethane (see for example *Journal of Medicinal Chemistry,* 1994, 37, 113-124). Alternative reduction/oxidation conditions are known to the persons skilled in the art.

Typical reaction conditions for the conversion of aldehydes 34 to olefins 35 are known to the skilled person. For example, Wittig type reaction conditions such as an alkyltriphenylphosphonium bromide, a base such as sodium t-butanolate in an organic solvent such as tetrahydrofuran can be used (see for example *Organic Letters,* 2008, 10, 4561-4564).

Typical hydrogenation conditions for the conversion of olefins 35 to alkanes 36 are known to the skilled person. For example, hydrogen a catalyst such as 10% palladium on activated carbon in an organic solvent such as for example methanol or ethanol (see for example *Bioorganic and Medicinal Chemistry,* 2005, 13, 5623-5634).

Typical reaction conditions for the deprotection of the tertbutyloxycarbonyl protecting group in compounds of the general formula 36 are an acid such as for example trifluoroacetic acid or hydrochloric acid giving rise to compound of the general formula 37.

Scheme 12: Route for the preparation of compounds of general formula 37, wherein $R^2$, $R^6$ and n having the meaning as given for the general formula (I), supra and R has the meaning of methyl, ethyl or tertbutyl and Y has the meaning of methyl and ethyl. Alternatively compounds of the general formula 34 can be prepared from the corresponding nitriles 38 via arylation with bromides 14 to compounds of the general formula 39 and subsequent reduction of the nitriles 39 to aldehydes 34. All reactions are known to the person skilled in the art (Scheme 13).

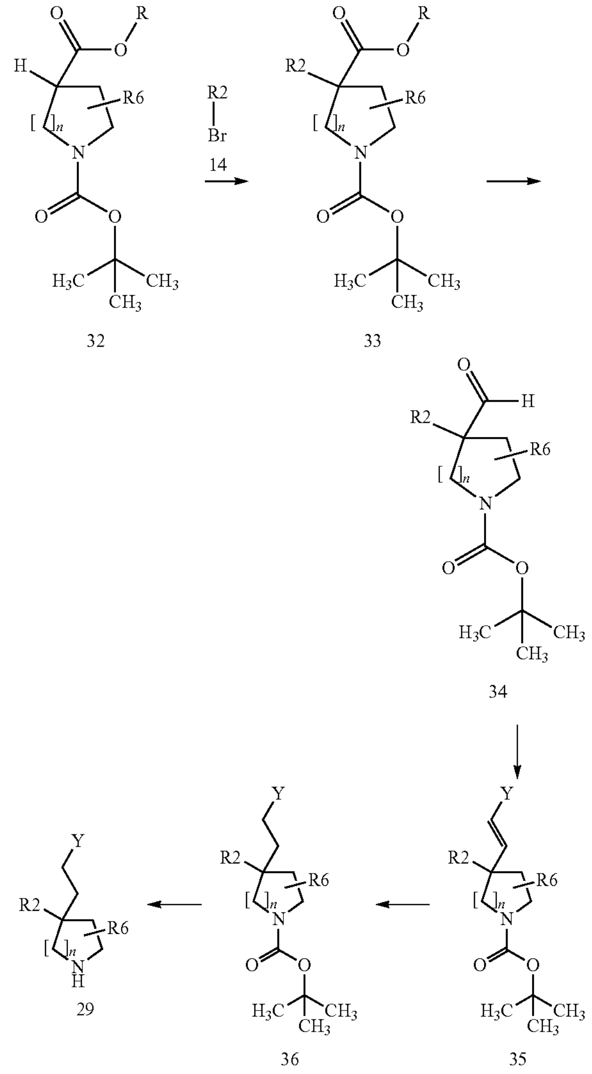

32 33 34 35 36 29

Typical conditions for the conversion of nitriles 38 to nitriles 39 are for example a base such as sodium hexamethyldisilazane in an organic solvent such as toluene and subsequent addition of bromides 14, a palladium catalyst such as palladium diacetate and a ligand such as 2,2'-bis-(diphenylphosphino)-1,1'-binaphthyl in an organic solvent such as toluene (see for example *Journal of the American Chemical Society,* 2002, 124, 9330-9331).

Typical reaction conditions for the conversion of nitriles 38 to aldehydes 34 are a reducing agent such as diisobutylaluminium hydride in an organic solvent such as toluene (see for example *Tetrahedron Letters,* 2011, 52, 6058-6060).

Scheme 13: Route for the preparation of compounds of general formula 34, wherein $R^2$, $R^6$ and n having the meaning as given for the general formula (I), supra.

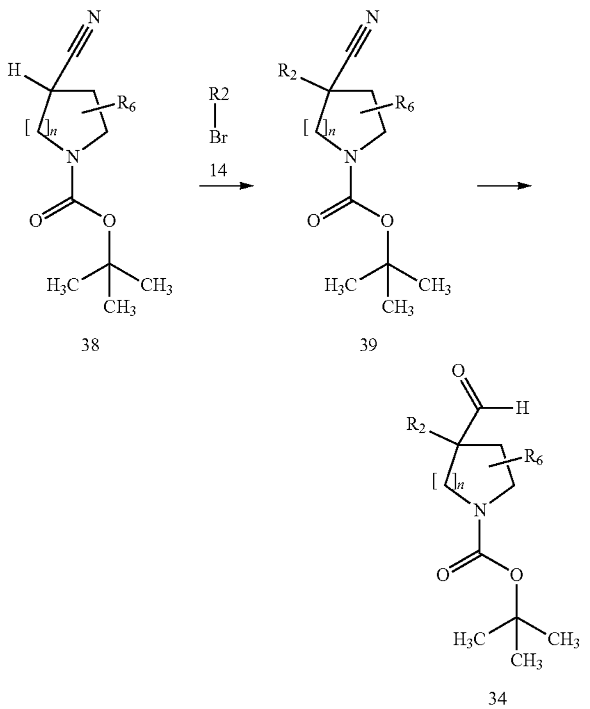

38 39 34

Compounds of the general formula 43 can be prepared from aldehydes 34 via reduction of aldehydes 34 to their corresponding alcohols 35 and subsequent transformation to halides 41 (X=Br, I) (Scheme 14). Halides 41 can then be reduced to the compounds of the general formula 42. Removal of the tertbutyloxycarbonyl protecting group under acidic conditions (for example with trifluoroacetic acid or hydrochloric acid) furnishes compounds of general formula 43. Instead of a tertbutyloxycarbonyl other suitable protecting groups can be used for this sequence known to the skilled person (see for example P. G. M. Wuts and T. W. Greene in "Protective Groups in Organic Synthesis", $4^{th}$ edition, Wiley 2006). All reactions of this sequence are known to the person skilled in the art.

In the first step the aldehydes 34 are reduced to the corresponding alcohols 40. Typical reaction conditions are a reducing agent such as for example $LiAlH_4$/diethyl ether in an organic solvent such as for example THF or diethylether (see for example *Journal of Medicinal Chemistry,* 1994, 37, 113-124).

The reaction conditions for the conversion of alcohols of the general formula 40 to the corresponding halides 41 are known to the skilled person. For X=Br typically a bromination reagent such as N-Bromosuccinimide, triphenylphosphine in an organic solvent such as dichloromethane is used (see for example *European Journal of Medicinal Chemistry,* 2016, 109, 75-88 or procedures in WO2006/50506). For Hal=I typically an iodination reagent such as iodine, triphenylphosphine with or without a base such as 1H-imidazole in an organic solvent such as THF, dichloromethane or toluene is used (see for example *Organic and* Biomolecular *Chemistry,* 2014, 12, 783-794).

The reaction conditions for the conversion of halides 41 to the corresponding compounds of general formula 42 are known to the skilled person. Typically for example for Hal=bromo a hydrogen source such as sodium tetrahydroborate in an organic solvent such as dimethyl sulfoxide is used (see for example *Organic Letters,* 2006, 8, 3813-3816). Typically for example for X=iodo a hydrogen source such as hydrogen, a catalyst such as 10% palladium on activated carbon, a base such as triethylamine in an organic solvent such as methanol or ethanol is used (see for example procedure in patent US2015/232481).

Typical reaction conditions for the deprotection of the tertbutyloxycarbonyl protecting group in compounds of the general formula 42 are an acid such as for example trifluoroacetic acid or hydrochloric acid giving rise to compound of the general formula 43.

Scheme 14: Route for the preparation of compounds of general formula 43, wherein $R^2$, $R^6$ and n having the meaning as given for the general formula (I), supra and X has the meaning of iodo or bromo.

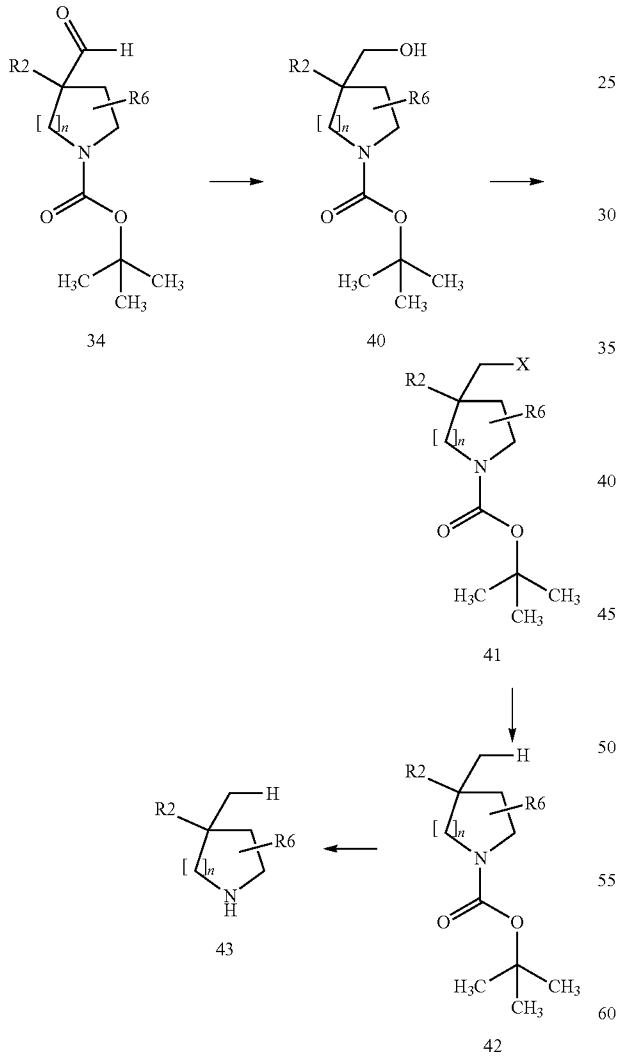

34

40

41

42

43

Benzoxazoles of the general formula 46 can be prepared from carboxylic acids 44 and 2-aminophenols 45 via a condensation reaction followed by removal of the tertbutyloxycarbonyl protecting group under acidic conditions (for example with trifluoroacetic acid or hydrochloric acid) known to the person skilled in the art (Scheme 15). Instead of a tertbutyloxycarbonyl other suitable protecting groups can be used for this sequence known to the skilled person (see for example P. G. M. Wuts and T. W. Greene in "Protective Groups in Organic Synthesis", $4^{th}$ edition, Wiley 2006). For example, the carboxylic acid 44 and the 2-aminophenols 45 can be reacted in polyphosphoric acid at elevated temperature to yield compounds of the general formula 46. Compounds of general formula 44 or 45 are commercially available or described in the literature.

Scheme 15: Route for the preparation of compounds of general formula 46, wherein $R^6$, $R^7$ and n having the meaning as given for the general formula (I), supra, p represents an integer of 0, 1, 2 or 3 and R′ represents a substituent of the heteroaryl group $R^2$, as defined for the compounds of general formula (I), supra.

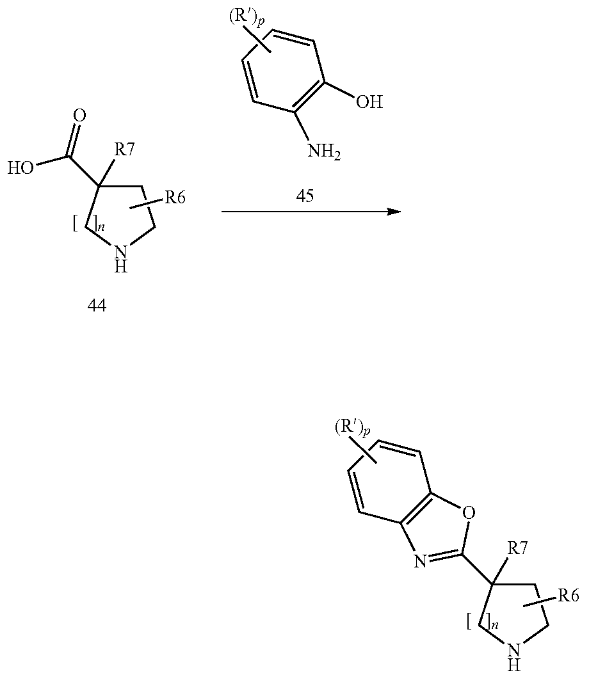

44

45

46

Benzothiazoles of the general formula 50 can be prepared from carboxylic acids 47 and 2-aminothiophenols 48 via a condensation reaction followed by removal of the tertbutyloxycarbonyl protecting group under acidic conditions (for example with trifluoroacetic acid or hydrochloric acid) known to the person skilled in the art (Scheme 16). Instead of a tertbutyloxycarbonyl other suitable protecting groups can be used for this sequence known to the skilled person (see for example P. G. M. Wuts and T. W. Greene in "Protective Groups in Organic Synthesis", $4^{th}$ edition, Wiley 2006). For example, the carboxylic acid 47 and the 2-aminophenols 48 can be reacted with a base such as triethylamine or diisopropylethylamine and propylphosphonic anhydride (T3P) at elevated temperature to yield compounds of the general formula 49. Compounds of general formula 47 or 48 are commercially available or described in the literature.

Scheme 16: Route for the preparation of compounds of general formula 50, wherein $R^6$, $R^7$ and n having the meaning as given for the general formula (I), supra, p represents an integer of 0, 1, 2 or 3 and R′ represents a substituent of the heteroaryl group $R^2$, as defined for the compounds of general formula (I), supra.

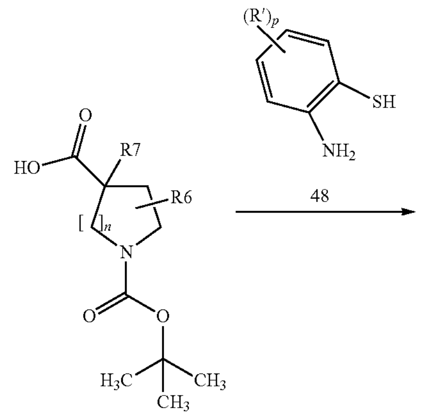

48

47

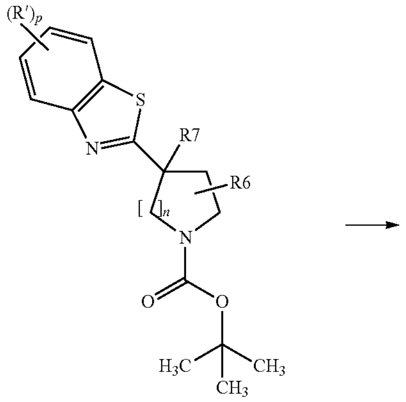

49

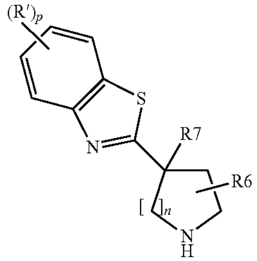

50

Benzimidazoles of the general formula 52 can be prepared from carboxylic acids 44 and 1,2-diaminobenzoles 51 via a condensation known to the person skilled in the art (Scheme 17). For example, the carboxylic acid 44 and the 1,2-diaminobenzoles 51 can be reacted in polyphosphoric acid at elevated temperature to yield compounds of the general formula 52 (see for example *European Journal of Medicinal Chemistry,* 2017, 126, 24-35). Compounds of general formula 44 or 51 are commercially available or described in the literature.

Scheme 17: Route for the preparation of compounds of general formula 52, wherein $R^6$, $R^7$ and n having the meaning as given for the general formula (I), supra, p represents an integer of 0, 1, 2 or 3 and R′ represents a substituent of the heteroaryl group $R^2$, as defined for the compounds of general formula (I), supra.

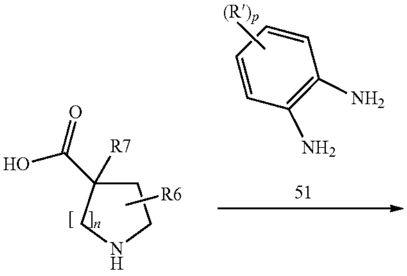

51

44

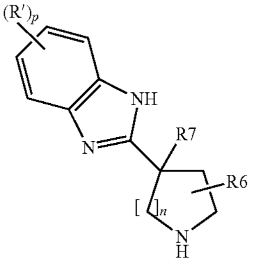

52

Generally, the order of synthetic steps to generate inventive compounds of formula (I) or to to build up the amine parts of inventive compounds of formula (I) such as 26 (Schemes 8, 9), 29 (Scheme 10), 31 (Scheme 11), 37 (Scheme 12), 43 (Scheme 14), 46 (Scheme 15), 50 (Scheme 16) or 52 (Scheme 17) could be exchanged. The synthetic conditions necessary to do transformations from 53 to 56 are usually comparable or could easily be adjusted by a person skilled in the art (Scheme 18 and 19). Precursors such as 53 or 57 can be generated according to the procedures described before (Schemes 3 and 6).

Scheme 18: Route for the preparation of compounds of general formula 56, wherein $R^1$, $R^2$, $R^3$, $R^4$, $R^5$, $R^6$, $R^7$, $R^8$ and n having the meaning as given for the general formula (I), supra.

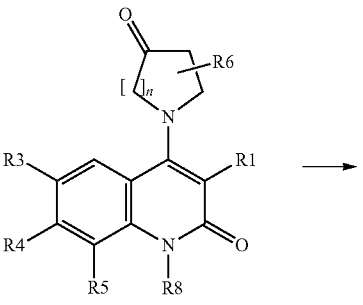

53

-continued

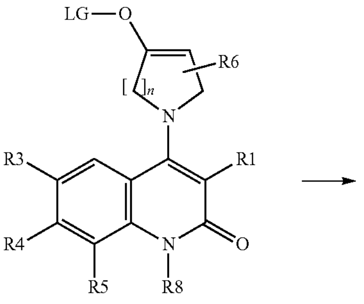

54

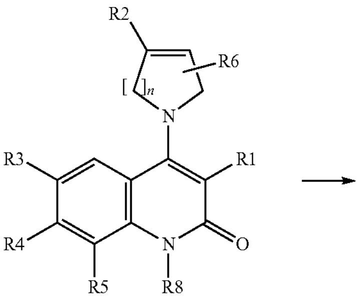

55

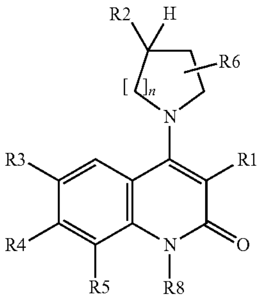

56

Scheme 19: Route for the preparation of compounds of general formula 59, wherein $R^1$, $R^2$, $R^3$, $R^4$, $R^5$, $R^6$, $R^7$, $R^8$ and n have the meaning as given for the general formula (I), supra, p represents an integer of 0, 1, 2 or 3, and R′ represents a substituent of the heteroaryl group $R^2$, as defined for the compounds of general formula (I), supra, and V represents a group selected from from NH, NR′, O and SH, wherein R′ represents a substituent of the heteroaryl group $R^2$, as defined for the compounds of general formula (I), supra.

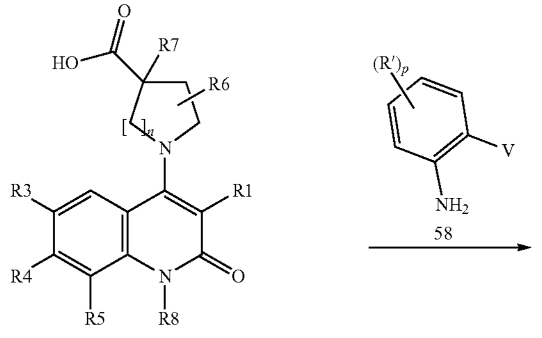

57

-continued

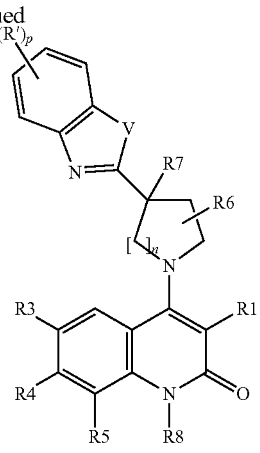

59

In accordance with a second aspect, the present invention covers methods of preparing compounds of general formula (I), said methods comprising the step of allowing an intermediate compound of general formula (II):

(II)

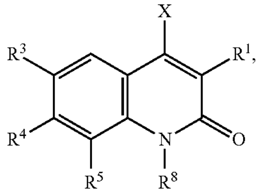

in which $R^1$, $R^3$, $R^4$, $R^5$ and $R^8$ are as defined for the compound of general formula (I) as defined supra, and X has the meaning of chloro or bromo, to react with a compound of general formula (III):

(III)

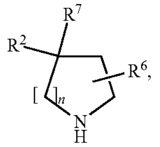

in which $R^2$, $R^6$, $R^7$, and n are as defined for the compound of general formula (I) as defined supra, thereby giving a compound of general formula (I):

(I)

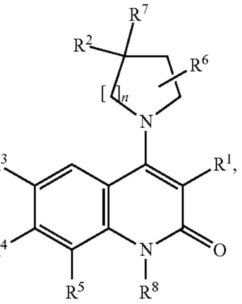

in which $R^1$, $R^2$, $R^3$, $R^4$, $R^5$, $R^6$ $R^7$, $R^8$ and n are as defined supra.

In accordance with a second embodiment of the second aspect, the present invention covers methods of preparing compounds of general formula (I-b), which are compounds of general formula (I) in which $R^2$, $R^3$, $R^4$, $R^5$, $R^6$ $R^7$, $R^8$ and n are as defined for the compound of general formula (I) as defined supra, and $R^1$ represents a carbamoyl group, said methods comprising the step of allowing a compound of general formula (I-a):

(I-a)

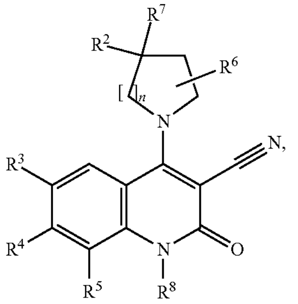

which is a compound of general formula (I) in which $R^2$, $R^3$, $R^4$, $R^5$, $R^6$ $R^7$, $R^8$ and n are as defined for the compound of general formula (I) as defined supra, and $R^1$ represents a cyano group, to react with palladium(II)acetate and acetaldoxime, thereby giving a compound of general formula (I-b):

(I-b)

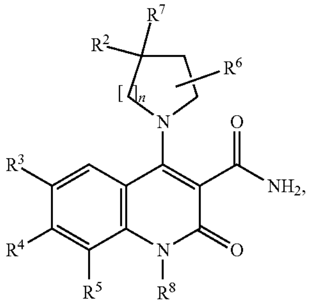

in which $R^2$, $R^3$, $R^4$, $R^5$, $R^6$ $R^7$, $R^8$ and n are as defined supra, and $R^1$ represents a carbamoyl group.

In accordance with a third embodiment of the second aspect, the present invention covers methods of preparing compounds of general formula (I), said methods comprising the step of allowing an intermediate compound of general formula (IV):

(IV)

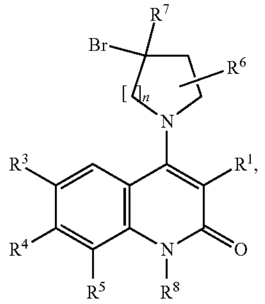

in which $R^1$, $R^3$, $R^4$, $R^5$, $R^6$ $R^7$, $R^8$ and n are as defined for the compound of general formula (I): as defined supra, to react with a compound of general formula (V):

$R^2$—Br (V), in which $R^2$ is as defined for the compound of general formula (I) as defined supra, in the presence of a photoredox catalyst and a nickel precatalyst, thereby giving a compound of general formula (I):

(I)

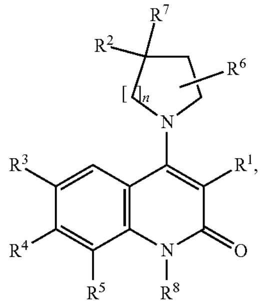

in which $R^1$, $R^2$, $R^3$, $R^4$, $R^5$, $R^6$ $R^7$, $R^8$ and n are as defined supra.

In accordance with a fourth embodiment of the second aspect, the present invention covers methods of preparing compounds of general formula (I-d), which are compounds of general formula (I) in which $R^2$, $R^3$, $R^4$, $R^5$, $R^6$ $R^7$, $R^8$ and n are as defined for the compound of general formula (I) as defined supra, and $R^1$ represents a —C(═O)$NH_2$, —C(═O)N(H)$CH_3$, —C(═O)N(H)$C_2H_5$ or —C(═O)N$(CH_3)_2$ group, said methods comprising the step of allowing a compound of general formula (I-c):

(I-c)

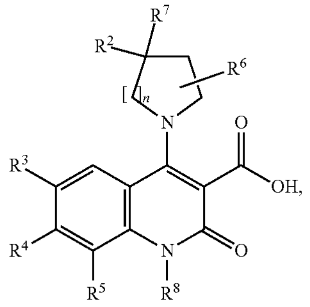

which is a compound of general formula (I) in which $R^2$, $R^3$, $R^4$, $R^5$, $R^6$ $R^7$, $R^a$ and n are as defined for the compound of general formula (I) as defined supra, and $R^1$ represents a carboxyl group, to react with a compound of general formula (VI):

(VI)

which compound is $NH_3$, $H_2NCH_3$, $H_2NCH_2CH_3$ or $HN(CH_3)_2$, or salts thereof, thereby giving a compound of general formula (I-d):

(I-d)

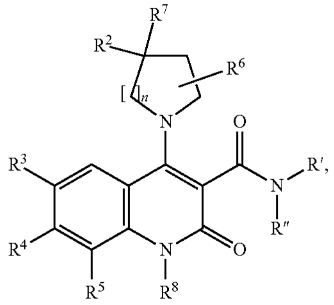

which is a compound of general formula (I) in which $R^2$, $R^3$, $R^4$, $R^5$, $R^6$ $R^7$, $R^8$ and n are as defined supra, and $R^1$ represents a group —C(═O)$NH_2$, —C(═O)N(H)$CH_3$, —C(═O)N(H)$C_2H_5$ or —C(═O)N$(CH_3)_2$.

In accordance with a fifth embodiment of the second aspect, the present invention covers methods of preparing compounds of general formula (I-e), which are compounds of general formula (I) in which $R^1$, $R^3$, $R^4$, $R^5$, $R^6$ $R^7$, $R^8$ and n are as defined supra, and $R^2$ represents a group

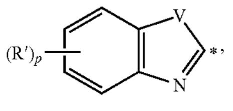

in which "*" represents the point of attachment of said group to the rest of the molecule, V represents a group O, S, NH or NR', R' represents a substituent of the group $R^2$ as defined for the compounds of formula (I) as defined supra, and p represents an integer of 0, 1, 2 or 3, said methods comprising the step of allowing a compound of general formula (VII):

(VII)

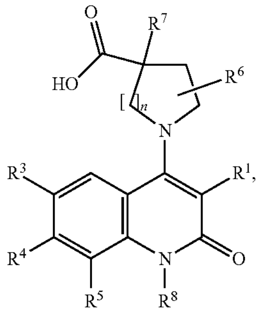

in which $R^1$, $R^3$, $R^4$, $R^5$, $R^6$ $R^7$, $R^8$ and n are as defined for the compound of general formula (I): as defined supra, to react with a compound of general formula (VIII):

(VIII)

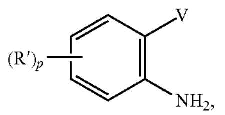

in which R' represents a substituent of the group $R^2$ as defined for the compounds of formula (I): as defined supra, p represents an integer of 0, 1, 2 or 3, V represents a group OH, SH, $NH_2$ or N(H)R', and R' represents a substituent of the group $R^2$ as defined for the compounds of formula (I) as defined supra, thereby giving a compound of general formula (I-e):

(I-e)

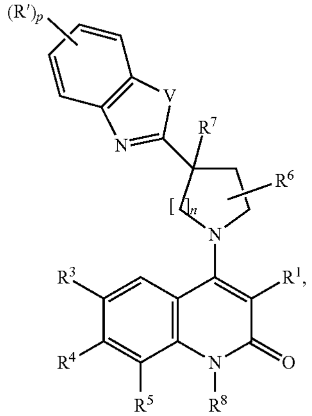

in which $R^1$, $R^3$, $R^4$, $R^5$, $R^6$ $R^7$, $R^8$ and n are as defined supra, and $R^2$ represents a group

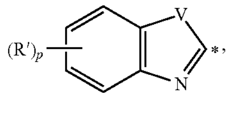

in which "*" represents the point of attachment of said group to the rest of the molecule, V represents a group O, S, NH or NR', R' represents a substituent of the group $R^2$ as defined for the compounds of formula (I) as defined supra, and p represents an integer of 0, 1, 2 or 3.

In accordance with a third aspect, the present invention covers methods of preparing compounds of general formula (I), said methods comprising the step of allowing an intermediate compound of general formula (II):

(II)

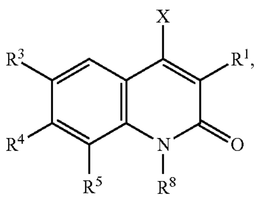

in which $R^1$, $R^3$, $R^4$, $R^5$ and $R^8$ are as defined for the compound of general formula (I) as defined supra, and X has the meaning of chloro or bromo, to react with a compound of general formula (III):

(III)

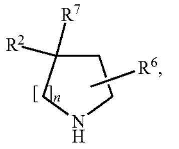

in which $R^2$, $R^6$, $R^7$, and n are as defined for the compound of general formula (I) as defined supra, thereby giving a compound of general formula (I):

(I)

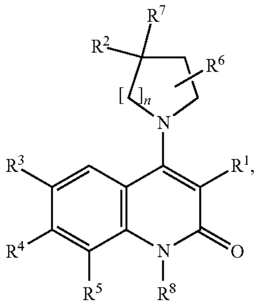

in which $R^1$, $R^2$, $R^3$, $R^4$, $R^5$, $R^6$ $R^7$, $R^8$ and n are as defined supra, then optionally converting said compound into solvates, salts and/or solvates of such salts using the corresponding (i) solvents and/or (ii) bases or acids.

In accordance with a second embodiment of the third aspect, the present invention covers methods of preparing compounds of general formula (I-b), which are compounds of general formula (I) in which $R^2$, $R^3$, $R^4$, $R^5$, $R^6$ $R^7$, $R^8$ and n are as defined for the compound of general formula (I) as defined supra, and $R^1$ represents a carbamoyl group, said methods comprising the step of allowing a compound of general formula (I-a):

(I-a)

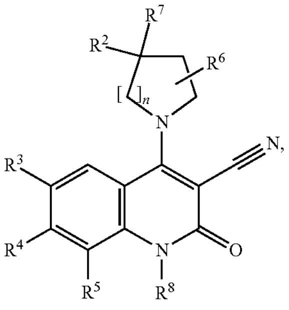

which is a compound of general formula (I) in which $R^2$, $R^3$, $R^4$, $R^5$, $R^6$ $R^7$, $R^8$ and n are as defined for the compound of general formula (I) as defined supra, and $R^1$ represents a cyano group, to react with with palladium(II)acetate and acetaldoxime, thereby giving a compound of general formula (I-b):

(I-b)

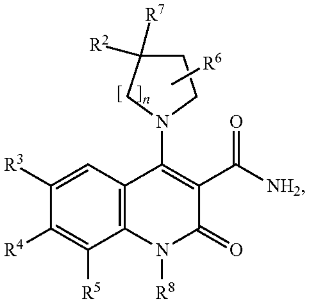

in which $R^2$, $R^3$, $R^4$, $R^5$, $R^6$ $R^7$, $R^a$ and n are as defined supra, and $R^1$ represents a carbamoyl group, then optionally converting said compound into solvates, salts and/or solvates of such salts using the corresponding (i) solvents and/or (ii) bases or acids.

In accordance with a third embodiment of the third aspect, the present invention covers methods of preparing compounds of general formula (I), said methods comprising the step of allowing an intermediate compound of general formula (IV):

(IV)

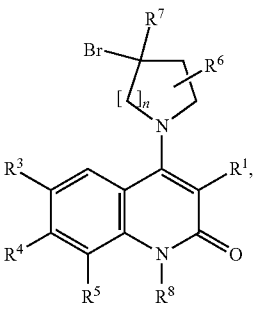

in which $R^1$, $R^3$, $R^4$, $R^5$, $R^6$ $R^7$, $R^8$ and n are as defined for the compound of general formula (I): as defined supra, to react with a compound of general formula (V):

$R^2$—Br (V), in which $R^2$ is as defined for the compound of general formula (I) as defined supra, in the presence of a photoredox catalyst and a nickel precatalyst, thereby giving a compound of general formula (I):

(I)

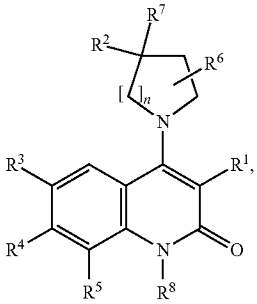

in which $R^1$, $R^2$, $R^3$, $R^4$, $R^5$, $R^6$ $R^7$, $R^8$ and n are as defined supra, then optionally converting said compound into solvates, salts and/or solvates of such salts using the corresponding (i) solvents and/or (ii) bases or acids.

In accordance with a fourth embodiment of the third aspect, the present invention covers methods of preparing compounds of general formula (I-d), which are compounds of general formula (I) in which $R^2$, $R^3$, $R^4$, $R^5$, $R^6$ $R^7$, $R^8$ and n are as defined for the compound of general formula (I) as defined supra, and $R^1$ represents a $-C(=O)NH_2$, $-C(=O)N(H)CH_3$, $-C(=O)N(H)C_2H_5$ or $-C(=O)N(CH_3)_2$ group, said methods comprising the step of allowing a compound of general formula (I-c):

(I-c)

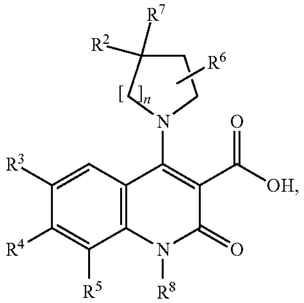

which is a compound of general formula (I) in which $R^2$, $R^3$, $R^4$, $R^5$, $R^6$ $R^7$, $R^8$ and n are as defined for the compound of general formula (I) as defined supra, and $R^1$ represents a carboxyl group, to react with a compound of general formula (VI):

(VI)

which compound is $NH_3$, $H_2NCH_3$, $H_2NCH_2CH_3$ or $HN(CH_3)_2$, or salts thereof, thereby giving a compound of general formula (I-d):

(I-d)

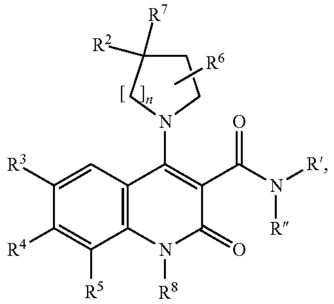

which is a compound of general formula (I) in which $R^2$, $R^3$, $R^4$, $R^5$, $R^6$ $R^7$, $R^a$ and n are as defined supra, and $R^1$ represents a group $-C(=O)NH_2$, $-C(=O)N(H)CH_3$, $-C(=O)N(H)C_2H_5$ or $-C(=O)N(CH_3)_2$, then optionally converting said compound into solvates, salts and/or solvates of such salts using the corresponding (i) solvents and/or (ii) bases or acids.

In accordance with a fifth embodiment of the second aspect, the present invention covers methods of preparing compounds of general formula (I-e), which are compounds of general formula (I) in which $R^1$, $R^3$, $R^4$, $R^5$, $R^6$ $R^7$, $R^8$ and n are as defined supra, and $R^2$ represents a group

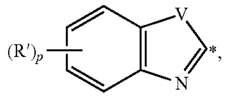

in which "*" represents the point of attachment of said group to the rest of the molecule, V represents a group O, S, NH or NR', R' represents a substituent of the group $R^2$ as defined for the compounds of formula (I) as defined supra, and p represents an integer of 0, 1, 2 or 3, said methods comprising the step of allowing a compound of general formula (VII):

(VII)

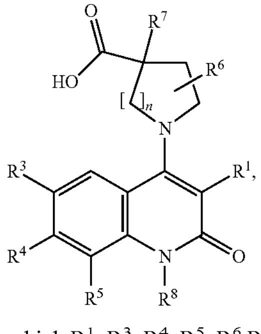

in which $R^1$, $R^3$, $R^4$, $R^5$, $R^6$ $R^7$, $R^a$ and n are as defined for the compound of general formula (I): as defined supra, to react with a compound of general formula (VIII):

(VIII)

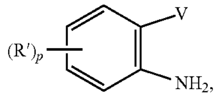

in which R' represents a substituent of the group $R^2$ as defined for the compounds of formula (I): as defined supra, p represents an integer of 0, 1, 2 or 3, V represents a group OH, SH, $NH_2$ or N(H)R', and R' represents a substituent of the group $R^2$ as defined for the compounds of formula (I) as defined supra, thereby giving a compound of general formula (I-e):

(I-e)

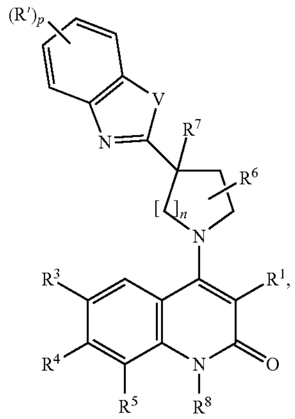

in which $R^1$, $R^3$, $R^4$, $R^5$, $R^6$ $R^7$, $R^8$ and n are as defined supra, and $R^2$ represents a group

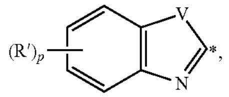

in which "*" represents the point of attachment of said group to the rest of the molecule, V represents a group O, S, NH or NR', R' represents a substituent of the group $R^2$ as defined for the compounds of formula (I) as defined supra, and p represents an integer of 0, 1, 2 or 3, then optionally converting said compound into solvates, salts and/or solvates of such salts using the corresponding (i) solvents and/or (ii) bases or acids.

The present invention covers methods of preparing compounds of the present invention of general formula (I), said methods comprising the steps as described in the Experimental Section herein.

In accordance with a fourth aspect, the present invention covers intermediate compounds which are useful for the preparation of the compounds of general formula (I), supra.

Particularly, the inventions covers the intermediate compounds of general formula (II):

(II)

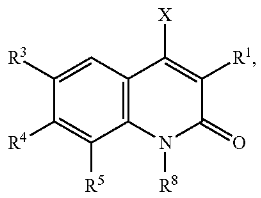

in which $R^1$, $R^3$, $R^4$, $R^5$ and $R^8$ are as defined for the compound of general formula (I) as defined supra, and X has the meaning of chloro or bromo.

In accordance with a fifth aspect, the present invention covers the use of intermediate compounds for the preparation of a compound of general formula (I) as defined supra.

Particularly, the inventions covers the use of intermediate compounds of general formula (II):

(II)

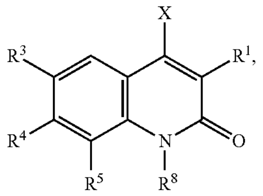

in which $R^1$, $R^3$, $R^4$, $R^5$ and $R^8$ are as defined for the compound of general formula (I) as defined supra, and X has the meaning of chloro or bromo, for the preparation of a compound of general formula (I) as defined supra.

Particularly, the inventions covers the use of intermediate compounds of general formula (III):

(III)

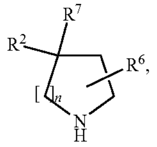

in which $R^2$, $R^6$, $R^7$, and n are as defined for the compound of general formula (I) as defined supra, for the preparation of a compound of general formula (I) as defined supra.

Particularly, the inventions covers the use of intermediate compounds of general formula (IV):

(IV)

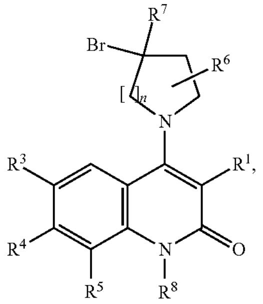

in which $R^1$, $R^3$, $R^4$, $R^5$, $R^6$ $R^7$, $R^8$ and n are as defined for the compound of general formula (I): as defined supra, for the preparation of a compound of general formula (I) as defined supra.

Particularly, the inventions covers the use of intermediate compounds of general formula (V):

$R^2$—Br (V), in which $R^2$ is as defined for the compound of general formula (I) as defined supra, for the preparation of a compound of general formula (I) as defined supra.

Particularly, the inventions covers the use of intermediate compounds of general formula (VI):

(VI)

which compounds are $NH_3$, $H_2NCH_3$, $H_2NCH_2CH_3$ or $HN(CH_3)_2$, or salts thereof, for the preparation of a compound of general formula (I) as defined supra.

Particularly, the inventions covers the use of intermediate compounds of general formula (VII):

(VII)

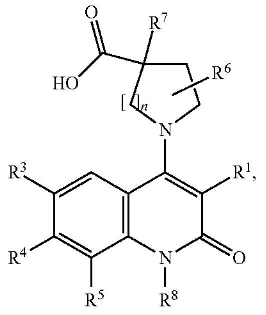

in which $R^1$, $R^3$, $R^4$, $R^5$, $R^6$ $R^7$, $R^8$ and n are as defined for the compound of general formula (I): as defined supra, for the preparation of a compound of general formula (I) as defined supra.

Particularly, the inventions covers the use of intermediate compounds of general formula (VIII):

(VIII)

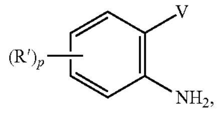

in which R' represents a substituent of the group $R^2$ as defined for the compounds of formula (I): as defined supra, p represents an integer of 0, 1, 2 or 3, V represents a group OH, SH, $NH_2$ or N(H)R', and R' represents a substituent of the group $R^2$ as defined for the compounds of formula (I) as defined supra, for the preparation of a compound of general formula (I) as defined supra.

The present invention covers the intermediate compounds which are disclosed in the Example Section of this text, infra.

The present invention covers the use of intermediate compounds which are disclosed in the Example Section of this text, infra.

The present invention covers any sub-combination within any embodiment or aspect of the present invention of intermediate compounds of general formulae (II), (III), (IV), (V), (VI), (VII): and (VIII), supra.

DESCRIPTION OF THE FIGURES

FIG. 1: human DGKa M1 to S735 plus C-terminal Flag-Tag, DGKa_hu_1, as described under SEQ ID No. 1.

FIG. 2: human DGKa M1 to S735 plus N-terminal Avi-Tag and C-terminal Flag-Tag, DGKa_hu_1Avi, as described under SEQ ID No. 2.

FIG. 3: SIINFEKL amino acid sequence, as described under SEQ ID No. 3.

FIG. 4: GCCACC DNA sequence.

FIG. 5: Flag-Tag sequence, as described under SEQ ID No. 4.

FIG. 6: OVA-30 peptide sequence, as described under SEQ ID No. 5.

EXPERIMENTAL SECTION

NMR peak forms are stated as they appear in the spectra, possible higher order effects have not been considered. The multiplicities are stated according to the signal form which appears in the spectrum, NMR-spectroscopic effects of a higher order were not taken into consideration. Multiplicity of the NMR signals: s=singlet, d=doublet, t=triplet, q=quartet, quin=quintet, spt=septed, br=broad signal, m=multiplet. NMR signals: shift in [ppm]. Combinations of multiplicity could be e.g. dd=doublet from doublet.

Chemical names were generated using the ACD/Name software from ACD/Labs. In some cases generally accepted names of commercially available reagents were used in place of ACD/Name generated names.

Table 1 lists the abbreviations used in this paragraph and in the Examples section as far as they are not explained within the text body. Other abbreviations have their meanings customary per se to the skilled person.

TABLE 1

| Abbreviations | |
|---|---|
| ACN | acetonitrile |
| AcOH | acetic acid |
| ADP | adenosine diphosphate |
| AMP | adenosine monophosphate |
| ATP | adenosine triphosphate |
| BOC | tert-butoxycarbonyl |
| $CaCl_2$ | calcium chloride |
| cAMP | cyclic adenosine monophosphate |
| $CDCl_3$ | deuterochloroform |
| CFSE | carboxyfluorescein succinimidyl ester |
| DAD | diode array detector |
| DEA | diethylamine |
| 4',6'-dF-5-$CF_3$-ppy | 2-(2,4-difluorophenyl)-5-(trifluoromethyl)pyridine |
| DMF | N,N-dimethylformamide |
| DMSO-d6 | deuterated dimethyl sulfoxide |
| DMSO | dimethyl sulfoxide |
| dtbbpy | 4-tert-butyl-2-(4-tert-butyl-2-pyridyl)pyridine |
| DTT | dithiothreitol |
| ELSD | evaporative light scattering detector |
| ESIpos | electrospray ionization positive |
| Expl. | Example |
| FBS | fetal bovine serum |
| HATU | (7-aza-1H-benzotriazol-1-yl)-1,1,3,3-tetramethyluronium hexafluorophosphate |
| HBTU | O-benzotriazole-N,N,N',N'-tetramethyluronium hexafluorophosphate |
| HPLC | high-pressure liquid chromatography |
| LCMS | liquid chromatography coupled with mass spectrometry |
| LPS | lipopolysaccharide |
| $MgCl_2$ | magnesium chloride |
| mL | milliliter |
| min. | minute(s) |
| MTBE | methyl tert-butyl ether |
| NaCl | sodium chloride |
| NP-40 | nonyl phenoxypolyethoxylethanol |
| PBMC | peripheral blood mononuclear cells |
| PyBOP | (benzotriazol-1-yl)oxytripyrrolidinophosphonium hexafluorophosphate |
| RP-HPLC | reverse-phase high-pressure liquid chromatography |
| Rt | retention time |
| RT, rt | room temperature |
| sat. | saturated |

TABLE 1-continued

| Abbreviations | |
|---|---|
| T3P | 2,4,6-tripropyl-1,3,5,2,4,6-trioxatriphosphorinane 2,4,6-trioxide |
| THF | tetrahydrofurane |
| TFA | trifluoroacetic acid |
| TLC | thin layer chromatography |
| TNFα | tumour necrosis factor alpha |
| μM | micromolar |
| UPLC | Ultra high performance chromatography |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP—NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Chromatographic Conditions:

LC-MS (Method 1): Instrument: Waters Acquity UPLCMS SingleQuad; column: Acquity UPLC BEH C18 1.7 μm, 50×2.1 mm; eluent A: water+0.1 vol. % formic acid (99%), eluent B: acetonitrile; gradient: 0-1.6 min. 1-99% B, 1.6-2.0 min. 99% B; flow 0.8 ml/min; temperature: 60° C.; DAD scan: 210-400 nm.

LC-MS (Method 2): Instrument: Waters Acquity UPLCMS SingleQuad; column: Acquity UPLC BEH C18 1.7 μm, 50×2.1 mm; eluent A: water+0.2 vol. % aqueous ammonia (32%), eluent B: acetonitrile; gradient: 0-1.6 min. 1-99% B, 1.6-2.0 min. 99% B; flow 0.8 ml/min; temperature: 60° C.; DAD scan: 210-400 nm.

LC-MS (Method 3): Instrument: Agilent 1290 UPLCMS 6230 TOF; column: BEH C 18 1.7 μm, 50×2.1 mm; eluent A: water+0.05 vol. % formic acid (99%); eluent B: acetonitrile+0.05 vol. % formic acid (99%); gradient: 0-1.7 min. 2-90% B, 1.7-2.0 min. 90% B; flow 1.2 ml/min; temperature: 60° C.; DAD scan: 190-400 nm.

Experimental Section—Intermediates

Intermediate 1

2-(4-methylpiperidin-4-yl)-1,3-benzoxazole

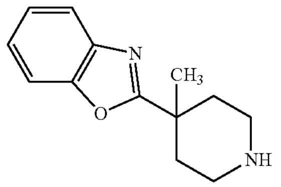 [SMILES: CC1(c2nc3ccccc3o2)CCNCC1]

A mixture of 500 mg 4-methylpiperidine-4-carboxylic acid (3.5 mmol, CAS 919354-20-4) and 381 mg 2-aminophenol (3.5 mmol, CAS 95-55-6) in 1.14 g polyphosphoric acid was stirred for 5 h at 180° C. Water was added carefully at about 80° C. and after cooling to rt, sodium hydroxide solution was added to get to pH=10. The solution was extracted 3 times with ethyl acetate. The combined organic phases were washed with water and brine and dried over sodium sulfate. After evaporation of the solvent, 230 mg of the title compound were obtained (29% yield).

$^1$H-NMR (400 MHz, DMSO-d6) δ[ppm]: 1.35 (s, 3H); 1.53-1.62 (n, 2H); 2.15-2.24 (n, 2H); 2.56-2.60 (i, 2H); 2.77-2.85 (i, 2H); 7.31-7.38 (n, 2H); 7.66-7.73 (n, 2H).

TABLE 2

The intermediates of table 2 were prepared in analogy to intermediate 1 from 4-piperidine-4-carboxylic acid or 4-methylpiperidine-4-carboxylic acid and aminophenols which are either commercially available or described in the art.

| Intermediate | structure | IUPAC-Name | analytics |
|---|---|---|---|
| 2 | 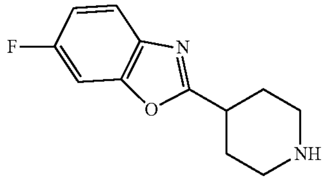 [SMILES: Fc1ccc2nc(C3CCNCC3)oc2c1] | 6-fluoro-2-(piperidin-4-yl)-1,3-benzoxazole | $^1$H-NMR (400 MHz, DMSO-d6) δ [ppm]: 1.65-1.75 (m, 2H); 1.97-2.07 (m, 2H); 2.62-2.71 (m, 2H); 3.00-3.17 (m, 3H); 7.18-7.25 (m, 1H); 7.68 (dd, 1H); 7.71 (dd, 1H). |
| 3 | 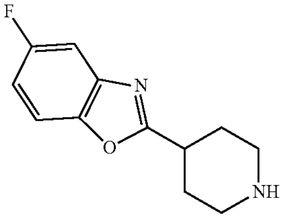 [SMILES: Fc1ccc2oc(C3CCNCC3)nc2c1] | 5-fluoro-2-(piperidin-4-yl)-1,3-benzoxazole | $^1$H-NMR (400 MHz, DMSO-d6) δ [ppm]: 1.66 (dq, 2H); 1.98 (dd, 2H); 2.59 (dt, 2H); 2.98 (td, 2H); 3.07 (tt, 1H); 7.21 (ddd, 1H); 7.58 (dd, 1H); 7.71 (dd, 1H). |
| 4 | 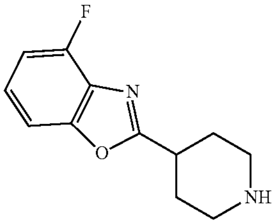 [SMILES: Fc1cccc2oc(C3CCNCC3)nc12] | 4-fluoro-2-(piperidin-4-yl)-1,3-benzoxazole | $^1$H-NMR (400 MHz, DMSO-d6) δ [ppm]: 1.67 (dq, 2H); 1.99 (dd, 2H); 2.60 (dt, 2H); 2.99 (td, 2H); 3.10 (tt, 1H); 7.21 (ddd, 1H); 7.37 (td, 1H); 7.56 (dd, 1H). |
| 5 | 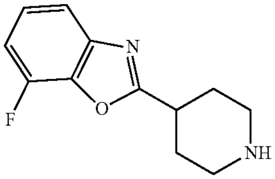 [SMILES: Fc1cccc2nc(C3CCNCC3)oc12] | 7-fluoro-2-(piperidin-4-yl)-1,3-benzoxazole | $^1$H-NMR (400 MHz, DMSO-d6) δ [ppm]: 1.68 (dq, 2H); 2.00 (dd, 2H); 2.60 (dt, 2H); 2.99 (td, 2H); 3.12 (tt, 1H); 7.26-7.38 (m,2H); 7.55 (dd, 1H). |
| 6 | 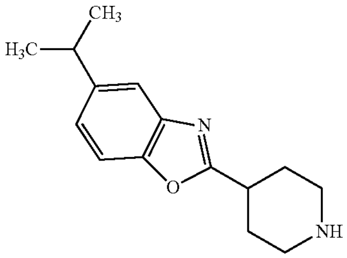 [SMILES: CC(C)c1ccc2oc(C3CCNCC3)nc2c1] | 5-isopropyl-2-(piperidin-4-yl)-1,3-benzoxazole | $^1$H-NMR (400 MHz, DMSO-d6) δ [ppm]: 1.23 (d, 6H); 1.66 (dq, 2H); 1.96 (dd, 2H); 2.59 (dt, 2H); 2.94-3.08 (m, 4H); 7.22 (dd, 1H); 7.53 (s, 1H); 7.55 (d, 1H). |
| 7 | 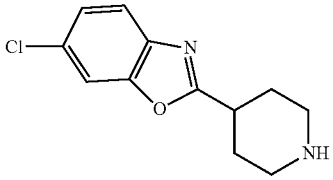 [SMILES: Clc1ccc2nc(C3CCNCC3)oc2c1] | 6-chloro-2-(piperidin-4-yl)-1,3-benzoxazole | $^1$H-NMR (400 MHz, DMSO-d6) δ [ppm]: 1.66 (dq, 2H); 1.94-2.02 (m, 2H); 2.59 (dt, 2H); 2.98 (td, 2H); 3.08 (tt, 1H); 7.39 (dd, 1H); 7.71 (d, 1H); 7.89 (d, 1H). |
| 8 | 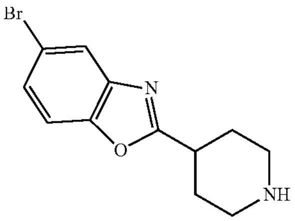 | 5-bromo-2-(piperidin-4-yl)-1,3-benzoxazole | $^1$H-NMR (400 MHz, DMSO-d6) δ [ppm]: 1.66 (dq, 2H); 1.94-2.02 (m, 2H); 2.59 (dt, 2H); 2.98 (td, 2H); 3.08 (tt, 1H); 7.51 (dd, 1H); 7.67 (dd, 1H); 7.94 (d, 1H). |

TABLE 2-continued

The intermediates of table 2 were prepared in analogy to intermediate 1 from 4-piperidine-4-carboxylic acid or 4-methylpiperidine-4-carboxylic acid and aminophenols which are either commercially available or described in the art.

| Intermediate | structure | IUPAC-Name | analytics |
| --- | --- | --- | --- |
| 9 | 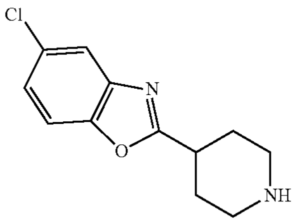 [SMILES: Clc1ccc2oc(C3CCNCC3)nc2c1] | 5-chloro-2-(piperidin-4-yl)-1,3-benzoxazole | $^1$H-NMR (400 MHz, DMSO-d6) δ [ppm]: 1.66 (dq, 2H); 1.94-2.02 (m, 2H); 2.59 (dt, 2H); 2.98 (td, 2H); 3.08 (tt, 1H); 7.40 (dd, 1H); 7.72 (d, 1H); 7.81 (d, 1H). |
| 10 | 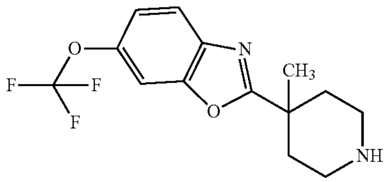 [SMILES: CC1(c2nc3ccc(OC(F)(F)F)cc3o2)CCNCC1] | 2-(4-methylpiperidin-4-yl)-6-(trifluoromethoxy)-1,3-benzoxazole | $^1$H-NMR (400 MHz, DMSO-d6) δ [ppm]: 1.36 (s, 3H); 1.54-1.64 (m, 2H); 2.14-2.23 (m, 2H); 2.52-2.62 (m, 2H); 2.75-2.86 (m, 2H); 7.35-7.40 (m, 1H); 7.81 (d, 1H); 7.88-7.92 (m, 1H). |
| 11 | 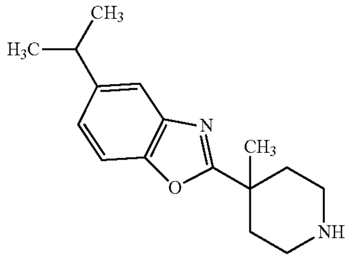 [SMILES: CC(C)c1ccc2oc(C3(C)CCNCC3)nc2c1] | 5-isopropyl-2-(4-methylpiperidin-4-yl)-1,3-benzoxazole | $^1$H-NMR (400 MHz, DMSO-d6) δ [ppm]: 1.24 (d, 6H); 1.33 (s, 3H); 1.51-1.60 (m, 2H); 2.14-2.22 (m, 2H); 2.53-2.60 (m, 2H); 2.81 (td, 2H); 3.00 (spt, 1H); 7.23 (dd, 1H); 7.54-7.58 (m, 2H). |
| 12 | 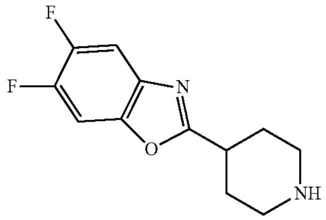 [SMILES: Fc1cc2nc(C3CCNCC3)oc2cc1F] | 5,6-difluoro-2-(piperidin-4-yl)-1,3-benzoxazole | $^1$H-NMR (400 MHz, DMSO-d6) δ [ppm]: 1.65 (dq, 2H); 1.92-2.02 (m, 2H); 2.59 (dt, 2H); 2.98 (td, 2H); 3.07 (tt, 1H); 7.87 (dd, 1H); 7.99 (dd, 1H). |
| 13 | 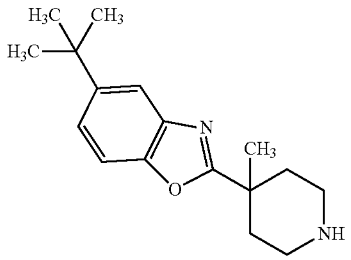 [SMILES: CC(C)(C)c1ccc2oc(C3(C)CCNCC3)nc2c1] | 5-tert-butyl-2-(4-methylpiperidin-4-yl)-1,3-benzoxazole | $^1$H-NMR (400 MHz, DMSO-d6) δ [ppm]: 1.33 (s, 9H); 1.35 (s, 3H); 1.52-1.62 (m, 2H); 2.15-2.24 (m, 2H); 2.52-2.61 (m, 2H); 2.76-2.85 (m, 2H); 7.40 (dd, 1H); 7.57 (d, 1H); 7.70 (s, 1H). |
| 14 | 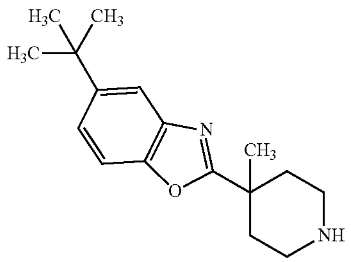 [SMILES: CC(C)(C)c1ccc2oc(C3(C)CCNCC3)nc2c1] | 2-(4-methylpiperidin-4-yl)-5-(methylsulfonyl)-1,3-benzoxazole | $^1$H-NMR (400 MHz, DMSO-d6) δ [ppm]: 1.38 (s, 3H); 1.56-1.65 (m, 2H); 2.17-2.25 (m, 2H); 2.52-2.62 (m, 2H); 2.82 (td, 2H); 3.26 (s, 3H); 7.93 (dd, 1H); 7.98 (dd, 1H); 8.28 (dd, 1H). |

Intermediate 15

Ethyl 1-(3-cyano-1-methyl-2-oxo-1,2-dihydroquinolin-4-yl)piperidine-4-carboxylate

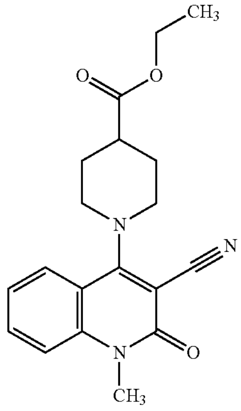 [SMILES: CCOC(=O)C1CCN(c2c(C#N)c(=O)n(C)c3ccccc23)CC1]

To a solution of 3 g 4-chloro-1-methyl-2-oxo-1,2-dihydroquinoline-3-carbonitrile (13.7 mmol, CAS 150617-68-8, Synthesis described in WO2012009649, example 1—compound III) and 7.2 mL N,N-diisopropylethylamine (41 mmol) in 60 mL 2-propanol was added 2.5 mL ethyl piperidine-4-carboxylate (16 mmol, CAS 1126-09-6) and the reaction was stirred for 2 h at 90° C. After this time, water was added and the reaction was extracted with dichloromethane. The organic phase dried over sodium sulfate and concentrated under reduced pressure. The residue was purified by flash chromatography (silica, dichloromethane/ethanol gradient 0-3%) to give 4.22 g of the title compound (91% yield).

$^1$H NMR (400 MHz, CHLOROFORM-d) δ ppm: 1.32 (m, 3H), 2.03 (m, 2H), 2.16 (m, 2H), 2.64 (m, 1H), 3.50 (m, 2H), 3.69 (s, 3H), 3.80 (dt, 2H), 4.22 (m, 2H), 7.26 (m, 1H), 7.37 (m, 1H), 7.65 (m, 1H), 7.81 (m, 1H).

LC-MS (Method 1): $R_t$=1.10 min; MS (ESIpos): m/z=340 $[M+H]^+$

Intermediate 16

1-(3-cyano-1-methyl-2-oxo-1,2-dihydroquinolin-4-yl)piperidine-4-carboxylic Acid

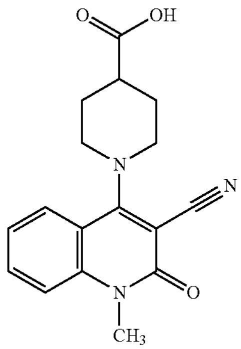 [SMILES: Cn1c(=O)c(C#N)c(N2CCC(C(=O)O)CC2)c2ccccc21]

To 4.21 g ethyl 1-(3-cyano-1-methyl-2-oxo-1,2-dihydroquinolin-4-yl)piperidine-4-carboxylate (12.4 mmol, intermediate 15) in 350 mL THF and 80 mL ethanol was added 74 mL lithium hydroxide (1.0 M, 74 mmol) and the mixture was stirred for 3 h at rt. The reaction mixture was diluted with water, and adjusted to pH=3-4 with hydrogen chloride (4M) and extracted with dichloromethane. The combined organic phases were washed with brine, dried over sodium sulfate and concentrated under reduced pressure. 3.81 g of the title compound were obtained (94% yield, 95% purity).

$^1$H NMR (400 MHz, DMSO-$d_6$) δ ppm: 1.86 (m, 2H), 2.02 (br dd, 2H), 2.64 (m, 1H), 3.44 (m, 2H), 3.57 (s, 3H), 3.72 (m, 2H), 7.34 (m, 1H), 7.56 (m, 1H), 7.73 (m, 1H), 7.82 (m, 1H), 12.37 (br s, 1H).

LC-MS (Method 1): $R_t$=0.84 min; MS (ESIpos): m/z=312 $[M+H]^+$

Intermediate 17

Ethyl 1-(3-cyano-1-methyl-2-oxo-1,2-dihydroquinolin-4-yl)-4-fluoropiperidine-4-carboxylate

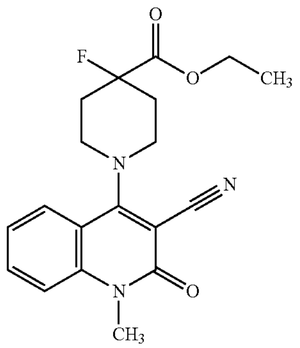 [SMILES: CCOC(=O)C1(F)CCN(c2c(C#N)c(=O)n(C)c3ccccc23)CC1]

To a solution of 1 g 4-chloro-1-methyl-2-oxo-1,2-dihydroquinoline-3-carbonitrile (4.57 mmol, CAS 150617-68-8, Synthesis described in WO2012009649, example 1—compound III) and 2.4 mL N,N-diisopropylethylamine (14 mmol) in 17 mL 2-propanol was added 1.06 g ethyl 4-fluoropiperidine-4-carboxylate hydrogen chloride salt (1:1) (5.03 mmol, CAS 845909-49-1) and the reaction was stirred for 2 h at 90° C. in the microwave. The reaction was allowed to cool to rt and poured into water. The precipitate was filtered off, washed with ethanol and dried in vacuum.

The title compound was obtained in 78% yield (1.34 g, 95% purity).

$^1$H NMR (400 MHz, DMSO-$d_6$) δ ppm: 1.27 (t, 3H), 2.13 (m, 2H), 2.32 (m, 2H), 3.58 (s, 3H), 3.68 (m, 4H), 4.25 (q, 2H), 7.35 (td, 1H), 7.58 (m, 1H), 7.75 (m, 1H), 7.87 (m, 1H).

LC-MS (Method 1): $R_t$=1.09 min; MS (ESIpos): m/z=358 $[M+H]^+$

Intermediate 18

1-(3-cyano-1-methyl-2-oxo-1,2-dihydroquinolin-4-yl)-4-fluoropiperidine-4-carboxylic Acid

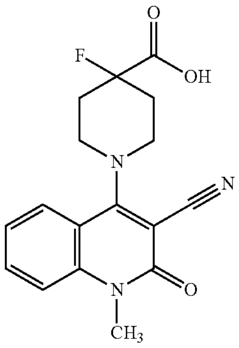 [SMILES: Cn1c(=O)c(C#N)c(N2CCC(F)(C(=O)O)CC2)c2ccccc21]

To 1 g of ethyl 1-(3-cyano-1-methyl-2-oxo-1,2-dihydroquinolin-4-yl)-4-fluoropiperidine-4-carboxylate (2.8 mmol, intermediate 17) in 80 mL THF and 20 mL ethanol was added 17 mL lithium hydroxide (1.0 M, 17 mmol) and the mixture was stirred for 3 h at rt. The reaction was diluted with water and adjusted to pH=3-4 with hydrogen chloride (4M). The organic solvents were evaporated, the precipitate was filtered off, washed with water and dried in vacuum. 782 mg of the title compound were obtained (81% yield, 95% purity).

$^1H$ NMR (400 MHz, DMSO-$d_6$) δ ppm: 2.10 (m, 2H), 2.33 (m, 2H), 3.58 (s, 3H), 3.67 (m, 4H), 7.35 (m, 1H), 7.58 (m, 1H), 7.75 (m, 1H), 7.86 (m, 1H), 13.49 (m, 1H).

LC-MS (Method 1): $R_t$=0.79 min; MS (ESIpos): m/z=330 $[M+H]^+$

Intermediate 19

7-bromo-1-methyl-2H-3,1-benzoxazine-2,4(1H)-dione

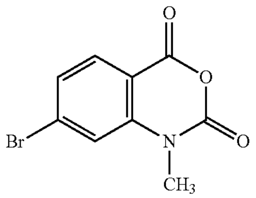

To a solution of 50 g 7-bromo-2H-3,1-benzoxazine-2,4(1H)-dione (207 mmol, CAS 76561-16-5): and 72 mL N,N-diisopropylethylamine (413 mmol) in 400 mL N,N-dimethylacetamide was added 39 mL iodomethane (620 mmol) at rt and was stirred overnight. The reaction was cooled to 0° C. and 200 mL water was slowly added. The solid that precipitated from this procedure was collected by filtration, washed with water and dried in an oven at 50° C. 48.1 g of the title compound were obtained (91% yield).

$^1H$-NMR (400 MHz, DMSO-d6) δ[ppm]: 3.46 (s, 3H); 7.52 (dd, 1H); 7.70 (d, 1H); 7.90 (d, 1H).

Intermediate 20

7-bromo-4-hydroxy-1-methyl-oxo-1,2-dihydroquinoline-3-carbonitrile

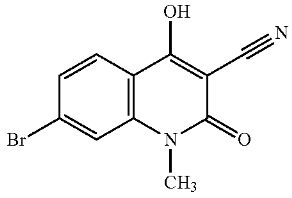

A solution of 40 g 7-bromo-1-methyl-2H-3,1-benzoxazine-2,4(1H)-dione (156 mmol, intermediate 19) in 320 mL THF was slowly treated with 170 mL triethylamine (1.2 mol) followed by the addition of 25 mL ethyl cyanoacetate (234 mmol, CAS 105-56-6) at rt. The reaction was heated at 60° C. and stirred at that temperature over night. Further 25 mL ethyl cyanoacetate (234 mmol) were added and the reaction was stirred at 70° C. for further 5 h. After cooling to rt, water was added and THF was evaporated in vacuum. The mixture was acidified to pH=1 by addition of hydrochloric acid (2 M) and extracted with ethyl acetate 3 times. The combined organic layers were evaporated in vacuum and the residue was stirred first with hexane, decanted and then stirred with a small amount ethyl acetate/hexane. The residue was filtered and 46 g of the title material were obtained in two crops (106% yield).

$^1H$-NMR (400 MHz, DMSO-d6) δ[ppm]: 3.51 (s, 3H); 6.67 (bs, 1H); 7.46 (dd, 1H); 7.71 (d, 1H); 7.96 (d, 1H).

Intermediate 21

7-bromo-4-chloro-1-methyl-2-oxo-1,2-dihydroquinoline-3-carbonitrile

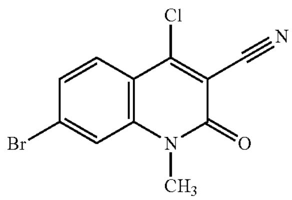 [SMILES: Cn1c(=O)c(C#N)c(Cl)c2ccc(Br)cc21]

A mixture of 16 g 7-bromo-4-hydroxy-1-methyl-2-oxo-1,2-dihydroquinoline-3-carbonitrile (57 mmol, intermediate 20) and 100 mL phosphorus trichloride (1.05 mol) was stirred at 90° C. overnight. After cooling to rt, hexane was added and the reaction was filtered. The solid was washed with sat. sodium bicarbonate solution and water. The obtained residue was dried in an oven at 50° C. overnight to give 13.2 g of the title compound (77% yield).

$^1H$-NMR (400 MHz, DMSO-d6) δ[ppm]: 3.64 (s, 3H); 7.66 (dd, 1H); 7.94-7.98 (m, 2H).

Intermediate 22

Tert-Butyl 4-[4-(2,2,2-trifluoroethoxy)phenyl]piperidine-1-carboxylate

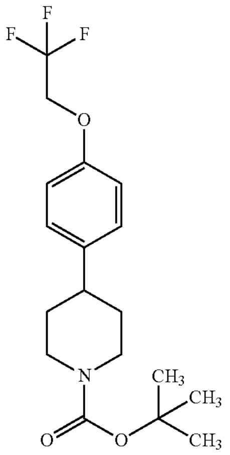 [SMILES: CC(C)(C)OC(=O)N1CCC(c2ccc(OCC(F)(F)F)cc2)CC1]

A mixture of 4 g 1-bromo-4-(2,2,2-trifluoroethoxy)benzene (15.7 mmol, CAS 106854-77-7), 8.29 g tert-butyl 4-bromopiperidine-1-carboxylate (31.4 mmol, CAS 180695-79-8), 4.8 mL 1,1,1,3,3,3-hexamethyl-2-(trimethylsilyl)trisilane (16 mmol), 176 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (157 μmol, CAS 870987-63-6), 11 mL 2,2,6,6-tetramethylpiperidine (63 mmol), 103 mg 1,2-dimethoxyethane-dichloronickel (1:1) (471 μmol) and 126 mg 4,4'-di-tert-butyl-2,2'-bipyridine (471 μmol) was stirred in a mixture of 150 mL N,N-dimethylacetamide and 300 mL (trifluoromethyl)benzene and degassed with argon. The reaction was stirred and irradiated at 455 nm for 6 h. The mixture was concentrated under reduced pressure, 500 mL water was added and extracted with ethyl acetate (3×). The combined organic phases were washed with water, dried and concentrated under reduced pressure. The residue was purified by flash chromatography (silica, hexane/ethyl acetate gradient 0-30%) to give 1.9 g of the title compound (34% yield).

$^1$H NMR (400 MHz, CHLOROFORM-d) δ ppm: 1.49 (m, 9H), 1.58 (m, 2H), 1.80 (br d, 2H), 2.61 (m, 1H), 2.80 (m, 2H), 4.23 (m, 2H), 4.34 (m, 2H), 6.91 (m, 2H), 7.15 (m, 2H).

LC-MS (Method 2): $R_t$=1.48 min; MS (ESIpos): m/z=304.3 $[M+H]^+$

Intermediate 23

4-[4-(2,2,2-trifluoroethoxy)phenyl]piperidine

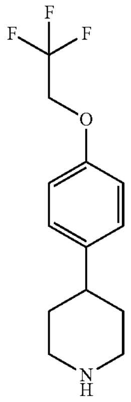 [SMILES: FC(F)(F)COc1ccc(C2CCNCC2)cc1]

To a solution of 1.8 g tert-butyl 4-[4-(2,2,2-trifluoroethoxy)phenyl]piperidine-1-carboxylate (4.76 mmol, intermediate 22) in 31 mL dichloromethane was added 3.7 mL trifluoroacetic acid (48 mmol) and the mixture was stirred overnight at rt. The mixture was cooled down to rt, concentrated under reduced pressure and the residue was diluted with toluene (2×). The solvent was evaporated to give 2.0 g TFA salt of the title compound (154% yield).

$^1$H NMR (400 MHz, DMSO-$d_6$) δ ppm: 1.83 (m, 4H), 2.80 (m, 1H), 3.01 (m, 2H), 3.37 (m, 2H), 4.71 (m, 2H), 7.01 (m, 2H), 7.18 (m, 2H), 8.67 (m, 1H).

LC-MS (Method 2): $R_t$=1.15 min; MS (ESIpos): m/z=260.7 $[M+H]^+$

Intermediate 24

Tert-Butyl 4-{4-[(propan-2-yl)oxy]phenyl}piperidine-1-carboxylate

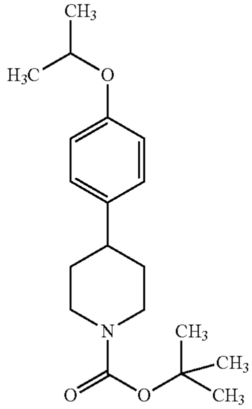 [SMILES: CC(C)Oc1ccc(C2CCN(C(=O)OC(C)(C)C)CC2)cc1]

A mixture of 4.3 g 1-bromo-4-[(propan-2-yl)oxy]benzene (19.0 mmol, CAS 6967-88-0), 10 g tert-butyl 4-bromopiperidine-1-carboxylate (38.0 mmol, CAS 180695-79-8), 5.9 mL 1,1,1,3,3,3-hexamethyl-2-(trimethylsilyl)trisilane (19 mmol), 213 mg bis{3,5-difluoro-2-[5-(trifluoromethyl)pyridin-2-yl]phenyl}iridium(I)hexafluorophosphate-4,4'-di-tert-butyl-2,2'-bipyridine (1:1:1) (190 μmol, CAS 870987-63-6), 13 mL 2,2,6,6-tetramethylpiperidine (76 mmol), 125 mg 1,2-dimethoxyethane-dichloronickel (1:1) (570 μmol) and 153 mg 4,4'-di-tert-butyl-2,2'-bipyridine (570 μmol) was stirred in a mixture of 150 mL N,N-dimethylacetamide and 300 mL (trifluoromethyl)benzene and degassed with argon. The reaction was stirred and irradiated at 455 nm 50% (~223 W) for 10 h. The mixture was concentrated under reduced pressure, 500 mL water was added and extracted with ethyl acetate (3×). The combined organic phases were washed with water, dried and concentrated under reduced pressure. The residue was purified by flash chromatography (silica, hexane/ethyl acetate gradient 0-50%) to give 3.3 g of the title compound (54% yield).

$^1$H NMR (400 MHz, CHLOROFORM-d) δ ppm: 1.32 (d, 6H); 1.48 (s, 9H); 1.53-1.61 (m, 2H); 1.75-1.83 (m, 2H); 2.57 (tt, 1H); 3.28-3.37 (m, 2H); 3.62-3.73 (m, 2H); 4.50 (spt, 1H); 6.80-6.85 (m, 2H); 7.06-7.12 (m, 2H).

LC-MS (Method 2): $R_t$=1.54 min; MS (ESIpos): m/z=320.3 [M+H]$^+$

Intermediate 25

4-{4-[(propan-2-yl)oxy]phenyl}piperidine

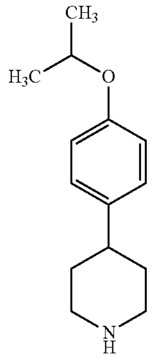 [SMILES: CC(C)Oc1ccc(C2CCNCC2)cc1]

To a solution of 3.3 g tert-butyl 4-{4-[(propan-2-yl)oxy] phenyl}piperidine-1-carboxylate (9.81 mmol, intermediate 24) in 63 mL dichloromethane was added 7.6 mL trifluoroacetic acid (98 mmol) and the mixture was stirred overnight at rt. The mixture was cooled down to rt, concentrated under reduced pressure and the residue was diluted with toluene (2×). The solvent was evaporated to give 3.9 g TFA salt of the title compound (85% purity, 154% yield).

$^1$H NMR (400 MHz, DMSO-$d_6$) δ ppm: 1.24 (d, 6H); 1.51-1.69 (m, 2H); 1.85-1.93 (m, 2H); 2.75 (tt, 1H); 3.16-3.27 (m, 2H); 3.31-3.40 (m, 2H); 4.51-4.60 (m, 1H); 6.86 (d, 2H); 7.11 (d, 2H).

LC-MS (Method 2): $R_t$=1.23 min; MS (ESIpos): m/z=220.8 [M+H]$^+$

Intermediate 26

4-(4-bromopiperidin-1-yl)-1-methyl-2-oxo-1,2-dihydroquinoline-3-carbonitrile

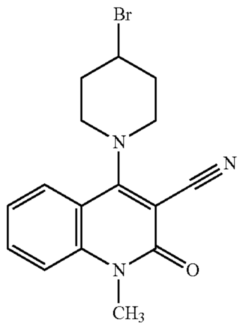 [SMILES: Cn1c(=O)c(C#N)c(N2CCC(Br)CC2)c2ccccc21]

A solution of 2.58 g 4-chloro-1-methyl-2-oxo-1,2-dihydroquinoline-3-carbonitrile (11.8 mmol, CAS 150617-68-8, Synthesis described in WO2012009649, example 1—compound III), 8.66 g 4-bromopiperidine hydrogen bromide salt (1:1) (35.4 mmol, CAS 54288-70-9) and 4.9 mL triethylamine (35 mmol) in 77 mL 2-propanol was stirred for 6 h at 90° C. After this time, the solvent was removed by evaporation and the residue was concentrated by flash chromatography (silica, dichloromethane/methanol gradient 0-3%). The fractions containing the desired material were pooled and the solvent was removed by evaporation. The residue was taken up into ethyl acetate at 50° C. The title compound was obtained by fractionated crystallization of this solution. 3.65 g of the title compound was obtained (85% yield).

$^1$H NMR (400 MHz, DMSO-$d_6$) δ ppm: 2.10-2.23 (m, 2H); 2.33-2.44 (m, 2H); 3.48-3.60 (m+s, 5H); 3.67-3.78 (m, 2H); 4.69-4.78 (m, 1H); 7.31-7.37 (m, 1H); 7.57 (d, 1H); 7.71-7.77 (m, 1H); 7.85 (dd, 1H).

Intermediate 27

Tert-Butyl 4-[4-(propan-2-yl)phenyl]piperidine-1-carboxylate

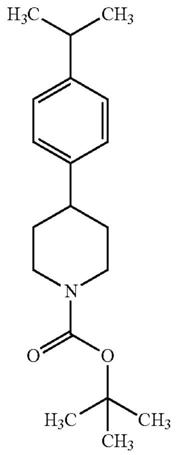 [SMILES: CC(C)c1ccc(C2CCN(C(=O)OC(C)(C)C)CC2)cc1]

In analogy to intermediate 24, 2 mL 1-bromo-4-(propan-2-yl)benzene (13 mmol, CAS 586-61-8): and 7 g tert-butyl 4-bromopiperidine-1-carboxylate (26.5 mmol, CAS 180695-79-8) were converted in 10 h. After workup, purification was performed by flash chromatography (silica, hexane/ethyl acetate gradient 0-50%) to give 1.88 g of the title compound (47% yield, 80% purity).

$^{1}H$ NMR (400 MHz, CHLOROFORM-d) δ ppm: 1.24 (d, 6H); 1.54-1.60 (m, 2H); 1.77-1.86 (m, 2H); 2.61 (tt, 1H); 2.73-2.84 (m, 2H); 2.88 (spt, 1H); 4.15-4.29 (m, 2H); 7.10-7.20 (m, 4H).

Intermediate 28

4-[4-(propan-2-yl)phenyl]piperidine

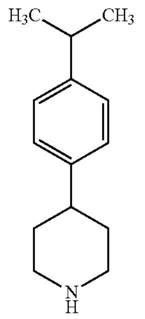

A solution of 1.8 g tert-butyl 4-[4-(propan-2-yl)phenyl]piperidine-1-carboxylate (5.6 mmol, intermediate 27) in 36 mL dichloromethane and 4.3 mL trifluoroacetic acid (56 mmol) was stirred for 14 h at 70° C. The solvent was evaporated and the residue was taken up into 100 mL methanol. 1 g palladium on charcoal (10%) was added and the suspension was shaked under a hydrogen atmosphere for several hours. The catalyst was filtered off, the solvent was evaporated and 1.1 g of the title compound was obtained (95% purity):

$^{1}H$ NMR (400 MHz, DMSO-$d_6$) δ ppm: 1.17 (d, 6H); 1.51-1.59 (m, 2H); 1.69-1.82 (m, 2H); 1.87-1.96 (m, 2H); 2.73-2.90 (m, 2H); 3.32-3.41 (m, 2H); 7.10-7.16 (m, 2H); 7.17-7.23 (m, 2H).

Intermediate 29

Tert-Butyl 4-(1-methyl-1H-indol-5-yl)piperidine-1-carboxylate

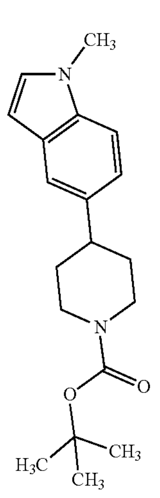 [SMILES: Cn1ccc2cc(C3CCN(C(=O)OC(C)(C)C)CC3)ccc21]

A mixture of 600 mg 5-bromo-1-methyl-1H-indole (2.85 mmol, CAS 10075-52-2), 1.51 g tert-butyl 4-bromopiperidine-1-carboxylate (5.7 mmol, CAS 180695-79-8), 0.88 mL 1,1,1,3,3,3-hexamethyl-2-(trimethylsilyl)trisilane (2.9 mmol), 64.1 mg bis{3,5-difluoro-2-[5-(trifluoromethyl)pyridin-2-yl]phenyl}iridium(I)hexafluorophosphate-4,4'-di-tert-butyl-2,2'-bipyridine (1:1:1) (57.1 μmol, CAS 870987-63-6), 0.67 mL 2,6-dimethylpyridine (5.7 mmol), 3.14 mg 1,2-dimethoxyethane-dichloronickel (1:1) (14.3 μmol) and 3.8 mg 4,4'-di-tert-butyl-2,2'-bipyridine (14 μmol) was stirred in 60 mL 1,2-dimethoxyethane and degassed with argon. The reaction was stirred and irradiated at 455 nm 50% (~223 W) for 16 h. The mixture was diluted with half concentrated sodium bicarbonate solution and extracted with ethyl acetate (3×). The combined organic phases were washed with water, dried and concentrated under reduced pressure. The residue was purified by RP-HPLC (column: X-Bridge C18 5 μm 100×30 mm, mobile phase: acetonitrile/water gradient) to give 570 mg of the title compound (48% yield).

$^{1}H$ NMR (400 MHz, DMSO-$d_6$) δ ppm: 1.42 (s, 9H); 1.46-1.58 (m, 2H); 1.72-1.83 (m, 2H); 2.72 (tt, 1H); 2.76-2.91 (m, 2H); 3.75 (s, 3H); 4.00-4.16 (m, 2H); 6.33 (dd, 1H); 7.03 (dd, 1H); 7.26 (d, 1H); 7.31-7.35 (m, 1H); 7.35-7.39 (m, 1H).

Intermediate 30

1-methyl-5-(piperidin-4-yl)-1H-indole

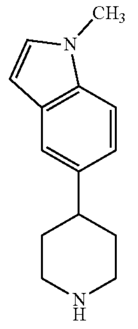 [SMILES: Cn1ccc2cc(C3CCNCC3)ccc21]

A solution of 570 mg tert-butyl 4-(1-methyl-1H-indol-5-yl)piperidine-1-carboxylate (1.7 mmol, intermediate 29) in 11 mL dichloromethane and 1.3 mL trifluoroacetic acid (17.2 mmol) was stirred overnight at rt. The reaction mixture was concentrated under reduced pressure, the residue was treated with toluene and the mixture was evaporated to dryness to give 450 mg of the title compound (85% purity, 104% yield).

$^{1}H$ NMR (400 MHz, DMSO-$d_6$) δ ppm: 1.62-1.73 (m, 1H); 1.74-1.92 (m, 2H); 1.89-2.05 (m, 1H); 2.72-2.97 (m, 2H); 2.98-3.11 (m, 1H); 3.20-3.34 (m, 2H); 3.32-3.50 (m, 1H); 6.85-6.97 (m, 1H); 6.97-7.12 (m, 1H); 7.23-7.39 (m, 1H); 8.19-8.40 (m, 1H); 8.53-8.72 (m, 1H).

TABLE 3

The intermediates of table 3 were prepared according to intermediate 29 with modifications stated and from starting materials listed.

| Inter-mediates | Structure | IUPAC-Name | Starting Materials | Analytics |
|---|---|---|---|---|
| 31 | 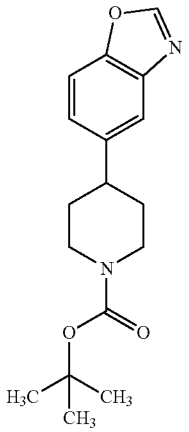 [SMILES: CC(C)(C)OC(=O)N1CCC(c2ccc3ocnc3c2)CC1] | tert-butyl 4-(1,3-benzoxazol-5-yl)piperidine-1-carboxylate | In analogy to intermediate 29 but N,N-dimethylacetamide and benzotrifluoride as solvent and with 5-bromo-1,3-benzoxazole (CAS 132244-31-6) | $^1$H NMR (400 MHz, DMSO-$d_6$) δ ppm: 1.42 (s, 9H); 1.49-1.62 (m, 2H); 1.78 (br d, 2H); 2.72-2.94 (m, 3H); 4.09 (br d, 2H); 7.33 (dd, 1H); 7.65-7.69 (m, 2H); 8.70 (s, 1H). |
| 32 | 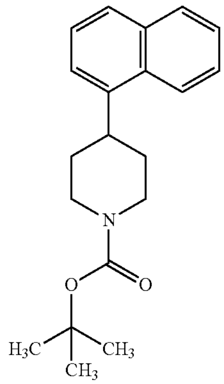 [SMILES: CC(C)(C)OC(=O)N1CCC(c2cccc3ccccc23)CC1] | tert-butyl 4-(naphthalen-1-yl)piperidine-1-carboxylate | In analogy to intermediate 29 but sodium carbonate as base and with 1-bromonaphthalene (CAS 90-11-9) | $^1$H NMR (400 MHz, DMSO-$d_6$) δ ppm: 1.43 (s, 9H); 1.59 (dq, 2H); 1.85 (br d, 2H); 2.74-2.97 (m, 3H); 4.11 (br d, 2H); 7.42-7.50 (m, 3H); 7.72-7.75 (m, 1H); 7.83-7.88 (m, 3H). |
| 33 | 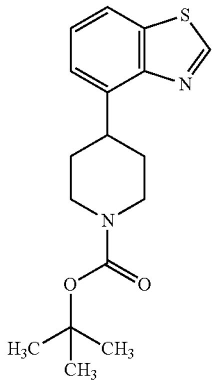 [SMILES: CC(C)(C)OC(=O)N1CCC(c2cccc3scnc23)CC1] | tert-butyl 4-(1,3-benzothiazol-4-yl)piperidine-1-carboxylate | In analogy to intermediate 32 with 4-bromo-1,3-benzothiazole (CAS 767-68-0) | $^1$H NMR (400 MHz, DMSO-$d_6$) δ ppm: 1.32-1.38 (m, 9 H) 1.57-1.72 (m, 2 H) 1.72-1.83 (m, 2 H) 2.66-2.99 (m, 2 H) 3.52-3.63 (m, 1 H) 3.92-4.14 (m, 2 H) 7.31-7.42 (m, 2 H) 7.94 (dd, 1 H) 9.30 (s, 1 H). |

TABLE 3-continued

The intermediates of table 3 were prepared according to intermediate 29 with modifications stated and from starting materials listed.

| Inter-mediates | Structure | IUPAC-Name | Starting Materials | Analytics |
|---|---|---|---|---|
| 34 | 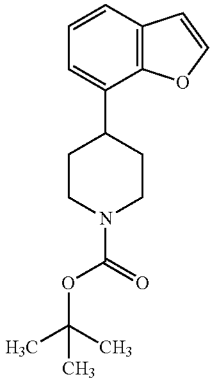 [SMILES: CC(C)(C)OC(=O)N1CCC(c2cccc3ccoc23)CC1] | tert-butyl 4-(1-benzofuran-7-yl)piperidine-1-carboxylate | In analogy to intermediate 32 with 7-bromo-1-benzofuran (CAS 133720-60-2) | $^1$H NMR (400 MHz, DMSO-$d_6$) δ ppm: 1.43 (s, 9H); 1.70 (qd, 2H); 1.79-1.89 (m, 2H); 2.77-3.01 (m, 2H); 3.16 (tt, 1H); 4.11 (br d, 2H); 6.94 (d, 1H); 7.16-7.23 (m, 2H); 7.49 (s, 1H); 7.98 (d, 1H). |
| 35 | 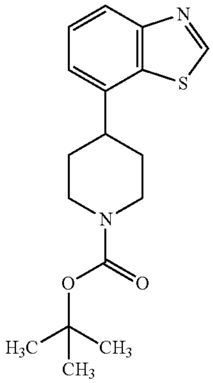 [SMILES: CC(C)(C)OC(=O)N1CCC(c2cccc3ncsc23)CC1] | tert-butyl 4-(1,3-benzothiazol-7-yl)piperidine-1-carboxylate | In analogy to intermediate 32 with 7-bromo-1,3-benzothiazole (CAS 767-70-4) | $^1$H NMR (400 MHz, DMSO-$d_6$) δ ppm: 1.40-1.45 (m, 9 H) 1.62-1.75 (m, 2 H) 1.88 (brd, 2 H) 2.80-3.04 (m, 3 H) 4.11 (br d, 2 H) 7.39 (d, 1 H) 7.52 (t, 1 H) 7.96 (dd, 1 H) 9.40 (s, 1 H). |
| 36 | 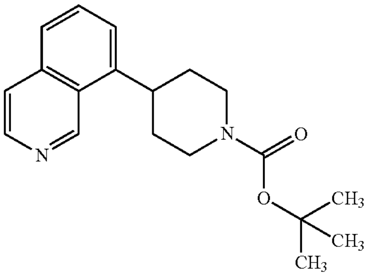 [SMILES: CC(C)(C)OC(=O)N1CCC(c2cccc3ccncc23)CC1] | tert-butyl 4-(isoquinolin-8-yl)piperidine-1-carboxylate | In analogy to intermediate 31 but sodium carbonate as base and with 8-bromoisoquinoline (CAS 63927-22-0) | $^1$H NMR (400 MHz, DMSO-$d_6$): δ ppm: 1.43 (s, 9H); 1.65 (qd, 2H); 1.89 (br d, 2H); 3.05 (br s, 2H); 3.78 (tt, 1H); 4.13 (d, 2H); 7.56 (d, 1H); 7.72 (t, 1H); 7.85-7.81 (m, 2H); 8.52 (d, 1H); 9.67 (s, 1H). |
| 37 | 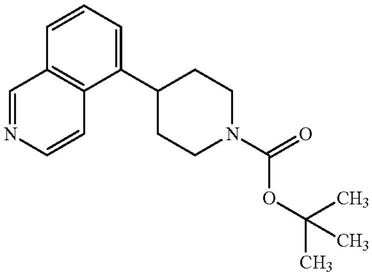 [SMILES: CC(C)(C)OC(=O)N1CCC(c2cccc3cnccc23)CC1] | tert-butyl 4-(isoquinolin-5-yl)piperidine-1-carboxylate | In analogy to intermediate 36 with 5-bromoisoquinoline (CAS 34784-04-8) | $^1$H NMR (400 MHz, DMSO-$d_6$): δ ppm: 1.43 (s, 9H); 1.61 (br qd, 2H); 1.84 (br d, 2H); 3.00 (br s, 2H); 3.52 (tt, 1H); 4.13 (br d, 2H); 7.71-7.60 (m, 2H); 7.98 (d, 1H); 8.07 (d, 1H); 8.54 (d, 1H); 9.31 (s, 1H). |

TABLE 3-continued

The intermediates of table 3 were prepared according to intermediate 29 with modifications stated and from starting materials listed.

| Inter-mediates | Structure | IUPAC-Name | Starting Materials | Analytics |
|---|---|---|---|---|
| 38 | 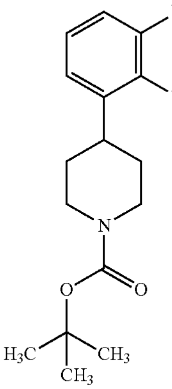 | tert-butyl 4-(quinoxalin-5-yl)piperidine-1-carboxylate | In analogy to intermediate 36 with 5-bromoquinoxaline (CAS 76982-23-5) | $^1$H-NMR (400 MHz, DMSO-$d_6$): δ ppm: 2H); 1.84 (br d, 2H); 2.93 (br s, 2H); 4.04 (tt, 1H); 4.14 (br d, 2H); 7.76 (dd, 1H); 7.82 (t, 1H); 7.96 (dd, 1H); 8.98 (q, 2H). |
| 39 | 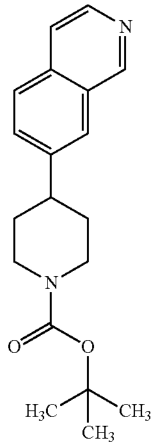 [SMILES: CC(C)(C)OC(=O)N1CCC(c2ccc3ccncc3c2)CC1] | tert-butyl 4-(isoquinolin-7-yl)piperidine-1-carboxylate | In analogy to intermediate 36 with 7-bromoisoquinoline (CAS 58794-09-5) | $^1$H-NMR (400 MHz, DMSO-$d_6$): δ ppm: 1.43 (s, 9H); 1.60 (br qd, 2H); 1.87 (br d, 2H); 2.97-2.74 (m, 3H); 4.12 (br d, 2H); 7.73 (dd, 1H); 7.78 (d, 1H); 7.91 (d, 1H); 7.95 (s, 1H); 8.45 (d, 1H); 9.26 (s, 1H). |
| 40 | 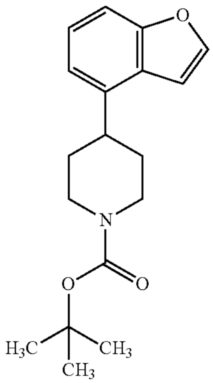 [SMILES: CC(C)(C)OC(=O)N1CCC(c2cccc3occc23)CC1] | tert-butyl 4-(1-benzofuran-4-yl)piperidine-1-carboxylate | In analogy to intermediate 32 with 4-bromo-1-benzofuran (CAS 128868-60-0) | $^1$H-NMR (400 MHz, DMSO-$d_6$): δ ppm: 1.43 (s, 9H); 1.59 (qd, 2H); 1.81 (br d, 2H); 2.89 (br s, 2H); 3.08 (tt, 1H); 4.10 (br d, 2H); 7.11-7.08 (m, 2H); 7.25 (t, 1H); 7.43 (d, 1H); 7.97 (d, 1H). |

TABLE 4

The intermediates of table 4 were prepared in in analogy to intermediate 30.

| Inter-mediates | Structure | IUPAC-Name | Starting Materials | Analytics |
|---|---|---|---|---|
| 41 | 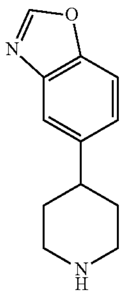 [SMILES: c1nc2cc(C3CCNCC3)ccc2o1] | 5-(piperidin-4-yl)-1,3-benzoxazole | tert-butyl 4-(1,3-benzoxazol-5-yl)piperidine-1-carboxylate (intermediate 31) | 1H NMR (400 MHz, DMSO-d6) δ ppm: 1.83 (m, 2H); 1.95-2.05 (m, 2H); 2.93-3.12 (m, 3H); 3.38 (br d, 2H); 7.32 (dd, 1H); 7.64 (d, 1H); 7.74 (d, 1H); 8.74 (s, 1H). |
| 42 | 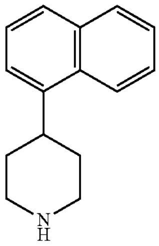 [SMILES: c1ccc2c(C3CCNCC3)cccc2c1] | 4-(naphthalen-1-yl)piperidine | tert-butyl 4-(1-naphthyl) piperidine-1-carboxylate (intermediate 32) | $^{1}$H NMR (400 MHz, DMSO-$d_6$) δ ppm: 1.80-1.96 (m, 2 H) 1.99-2.11 (m, 2 H) 2.95-3.17 (m, 3 H) 3.35-3.48 (m, 2 H) 7.37-7.57(m, 3 H) 7.66-7.79 (m, 1 H) 7.83-7.96 (m, 3H). |
| 43 | 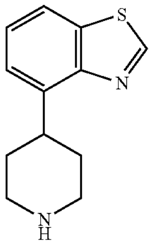 [SMILES: c1cc(C2CCNCC2)c2ncsc2c1] | 4-(piperidin-4-yl)-1,3-benzothiazole | tert-butyl 4-(1,3-benzothiazol-4-yl)piperidine-1-carboxylate (intermediate 33) | $^{1}$H-NMR (400 MHz, DMSO-$d_6$) δ ppm: 1.99-2.12 (m, 2H); 3.02-3.23 (m, 2H); 3.36-3.48 (m, 3H); 3.72-3.87 (m, 2H); 7.28-7.42 (m, 1H); 7.44-7.58 (m, 1H); 7.96-8.17 (m, 1H); 9.30-9.49 (m, 1H). |
| 44 | 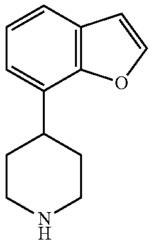 [SMILES: c1cc(C2CCNCC2)c2occc2c1] | 4-(1-benzofuran-7-yl)piperidine | tert-butyl 4-(1-benzofuran-7-yl)piperidine-1-carboxylate (intermediate 34) | $^{1}$H NMR (400 MHz, DMSO-$d_6$) δ ppm: 1.96-2.11 (m, 4H); 2.70-2.93 (m, 1H); 3.02-3.19 (m, 2H); 3.24-3.52 (m, 4H); 6.93-7.04 (m, 1 H); 7.09-7.19 (m, 1H); 7.19-7.31 (m, 1H) 7.47-7.58 (m, 1 H); 7.92-8.12 (m, 1H). |
| 45 | 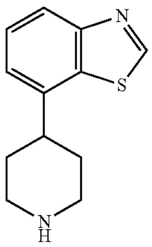 [SMILES: c1cc(C2CCNCC2)c2scnc2c1] | 7-(piperidin-4-yl)-1,3-benzothiazole | tert-butyl 4-(1,3-benzothiazol-7-yl)piperidine-1-carboxylate (intermediate 35) | $^{1}$H NMR (400 MHz, DMSO-$d_6$) δ ppm: 1.91-2.01 (m, 1H); 2.00-2.00 (m, 1H); 2.02-2.11 (m, 3H); 2.21-2.33 (m, 1H); 3.02-3.31 (m, 2H); 3.08-3.22 (m, 4H); 3.43 (br d, 3H); 7.35 (d, 1H); 7.58 (t, 1H); 8.01 (dd, 1H); 9.33-9.47 (m, 1H). |

TABLE 4-continued

The intermediates of table 4 were prepared in in analogy to intermediate 30.

| Inter-mediates | Structure | IUPAC-Name | Starting Materials | Analytics |
|---|---|---|---|---|
| 46 | 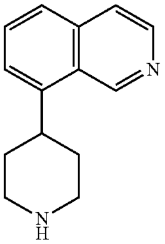 [SMILES: c1cc(C2CCNCC2)c2cnccc2c1] | 8-(piperidin-4-yl)isoquinoline | tert-butyl 4-(isoquinolin-8-yl)piperidine-1-carboxylate (intermediate 36) | $^1$H NMR (400 MHz, DMSO-$d_6$) δ ppm: 1.91-2.02 (m, 2H); 2.03-2.12 (m, 2H); 3.14-3.29 (m, 2H); 3.40-3.55 (m, 2H); 3.88-4.03 (m, 1H); 4.47-4.64 (m, 1H); 7.71 (d, 1H); 7.96-8.05 (m, 1H); 8.04-8.13 (m, 1H); 8.24 (d, 1H); 8.66 (d, 1H); 9.84-9.96 (m, 1H). |
| 47 | 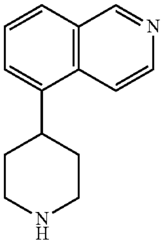 [SMILES: c1cc(C2CCNCC2)c2ccncc2c1] | 5-(piperidin-4-yl)isoquinoline | tert-butyl 4-(isoquinolin-5-yl)piperidine-1-carboxylate (intermediate 37) | $^1$H NMR (400 MHz, DMSO-$d_6$) δ ppm: 1.87-2.08 (m, 4 H) 3.13-3.32 (m, 2 H) 3.40-3.52 (m, 2 H) 3.69-3.84 (m, 1 H) 7.79-7.91 (m, 2H) 8.24 (dd, 1 H) 8.43 (d, 1 H) 8.68 (d, 1 H) 9.63 (s, 1 H). |
| 48 | 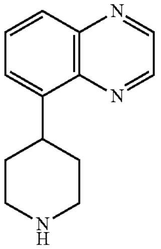 [SMILES: c1cc(C2CCNCC2)c2nccnc2c1] | 5-(piperidin-4-yl)quinoxaline | tert-butyl 4-(quinoxalin-5-yl)piperidine-1-carboxylate (Intermediate 38) | $^1$H NMR (400 MHz, DMSO-$d_6$) δ ppm: 1.87-2.02 (m, 2H); 2.02-2.10 (m, 2H); 3.11-3.25 (m, 2H); 3.44 (br d, 2H); 4.09-4.21 (m, 1H); 7.71 (dd, 1H); 7.88 (dd, 1H); 8.01 (dd, 1H); 8.88-9.11 (m, 2H). |
| 49 | 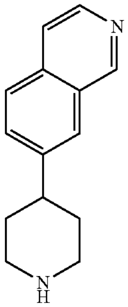 [SMILES: c1cc2ccc(C3CCNCC3)cc2cn1] | 7-(piperidin-4-yl)isoquinoline | tert-butyl 4-(isoquinolin-7-yl)piperidine-1-carboxylate (intermediate 39) | $^1$H NMR (400 MHz, DMSO-$d_6$) δ ppm: 1.48-1.72 (m, 1H); 1.81-1.99 (m, 2H); 2.03-2.17 (m, 2H); 3.02-3.23 (m, 3H); 3.45 (br d, 2H); 7.92 (dd, 1H); 8.12-8.23 (m, 3H); 8.59 (d, 1H); 9.46-9.73 (m, 1H). |
| 50 | 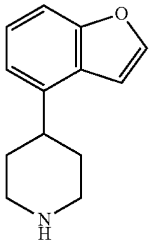 [SMILES: c1cc(C2CCNCC2)c2ccoc2c1] | 4-(1-benzofuran-4-yl)piperidine | tert-butyl 4-(1-benzofuran-4-yl)piperidine-1-carboxylate (intermediate 40) | $^1$H NMR (400 MHz, DMSO-$d_6$) δ ppm: 1.91-2.01 (m, 4 H) 3.01-3.32 (m, 3 H) 3.38-3.47 (m, 2 H) 7.02-7.09 (m, 1 H) 7.15-7.22 (m, 1 H) 7.26-7.32 (m, 1 H) 7.45-7.54 (m, 1 H) 8.00-8.08 (m, 1 H). |

Intermediate 51

2-(4-ethylpiperidin-4-yl)-1,3-benzoxazole

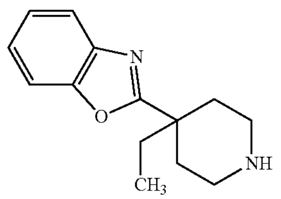 [SMILES: CCC1(c2nc3ccccc3o2)CCNCC1]

A mixture of 1.5 g 4-ethylpiperidine-4-carboxylic acid (9.54 mmol, CAS 1227465-48-6) and 1.04 g 2-aminophenol (9.54 mmol, CAS 95-55-6) in 5.54 g polyphosphoric acid was stirred for 2 h at 180° C. Water was added carefully and after cooling to rt, an aqueous solution of potassium hydroxide was added to adjusted pH=10. The solution was extracted with ethyl acetate 3 times. The combined organic phases were washed with water and brine, dried over sodium sulfate and the filtrate was concentrated under reduced pressure to give 740 mg of the title compound (93% purity, 31% yield).

$^1H$ NMR (400 MHz, DMSO-$d_6$) δ ppm: 0.64 (t, 3H); 1.45-1.62 (m, 2H); 1.66-1.82 (m, 2H); 2.18-2.33 (m, 2H); 2.82 (dt, 2H); 7.12-7.44 (m, 1H); 7.26-7.41 (m, 1H); 7.44-7.53 (m, 1H); 7.51-7.99 (m, 1H); 7.59-7.93 (m, 1H).

Intermediate 52

5-methyl-2-(4-methylpiperidin-4-yl)-1,3-benzoxazole

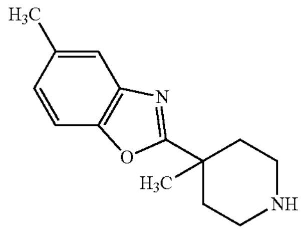 [SMILES: Cc1ccc2oc(C3(C)CCNCC3)nc2c1]

A mixture of 3.08 g 2-amino-4-methylphenol (25.0 mmol, CAS 95-84-1) and 4.50 g 4-methylpiperidine-4-carboxylic acid hydrogen chloride salt (1:1) (25.0 mmol, CAS 919354-20-4): in 24 mL polyphosphoric acid was stirred for 2 h at 180° C. Water was added carefully and after cooling to rt, an aqueous solution of potassium hydroxide was added to adjusted pH=10. The solution was extracted with ethyl acetate two times. The combined organic phases were washed with water and brine, dried over sodium sulfate and the filtrate was concentrated under reduced pressure to give 2.20 g of the title compound (95% purity, 36% yield).

$^1H$ NMR (400 MHz, DMSO-$d_6$) δ [ppm]: 1.33 (s, 3H); 1.49-1.70 (m, 2H); 2.07-2.28 (m, 2H); 2.41 (s, 3H); 2.51-2.61 (m, 2H); 2.74-2.89 (m, 2H); 7.15 (dt, 1H); 7.42-7.61 (m, 2H).

Intermediate 53

5-methyl-2-(3-methylpiperidin-4-yl)-1,3-benzoxazole

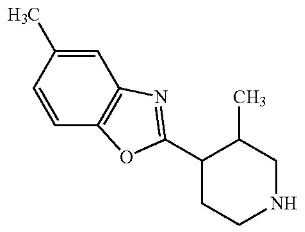 [SMILES: Cc1ccc2oc(C3CCNCC3C)nc2c1]

A mixture of 430 mg 2-amino-4-methylphenol (3.49 mmol, CAS 95-84-1) and 500 mg 3-methylpiperidine-4-carboxylic acid (3.49 mmol, CAS 885951-69-9) in 6 mL polyphosphoric acid was stirred for 2 h at 180° C. Water was added carefully and after cooling to rt, an aqueous solution of potassium hydroxide was added to adjusted pH=10. The solution was extracted with ethyl acetate two times. The combined organic phases were washed with water and brine, dried over sodium sulfate and the filtrate was concentrated under reduced pressure to give 550 mg of the title compound (90% purity, 62% yield).

$^1H$ NMR (400 MHz, DMSO-$d_6$) δ [ppm]: 1.33 (s, 3H); 1.48-1.67 (m, 2H); 2.07-2.28 (m, 2H); 2.41 (s, 3H); 2.51-2.62 (m, 2H); 2.67-2.85 (m, 2H); 7.07-7.24 (m, 1H); 7.40-7.67 (m, 2H).

Intermediate 54

(Rac)-Tert-Butyl 4-[4-(propan-2-yl)phenyl]azepane-1-carboxylate

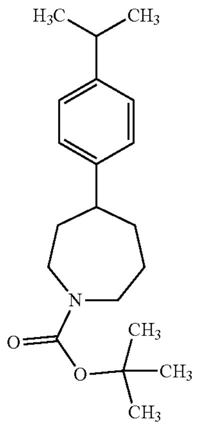 [SMILES: CC(C)c1ccc(C2CCCN(C(=O)OC(C)(C)C)CC2)cc1]

A mixture of 1.8 g tert-butyl 4-hydroxyazepane-1-carboxylate (8.36 mmol, CAS 478832-21-2): and 2.12 g oxalylchloride was stirred in 61 mL diethyl ether at 0° C. for 30 minutes and rt for 14 hours. Then, the reaction was colled again to 0° C. and water was added very carefully. After warming to rt, the two phases were separated and the aqueous layer was extracted with diethyl ether (3×). The combined organic layers were evaporate in vacuum to obtain 2.24 g [1-(tert-butoxycarbonyl)azepan-4-yl]oxy}(oxo)acetic acid. 800 mg of this [1-(tert-butoxycarbonyl)azepan-4-yl]oxy}(oxo)acetic acid (2.78 mmol), 280 μL 1-bromo-4-(propan-2-yl)benzene (1.9 mmol, CAS 586-61-8), 720 mg cesium carbonate (3.71 mmol), 20.3 mg bis{3,5-difluoro-2-[5-(trifluoromethyl)pyridin-2-yl]phenyl}iridium(I) hexafluorophosphat, 24.9 mg 4,4'-di-tert-butyl-2,2'-bipyridine (92.8 μmol) and 20.3 mg 1,2-dimethoxyethane-dibromonickel (1:1): (471 μmol) was stirred in a mixture of 46 mL tetrahydropyran and 9.2 mL dimethylsulfoxide and degassed with argon. The reaction was stirred and irradiated at 455 nm for 6 h at 70° C. The mixture was concentrated under reduced pressure, 500 mL water was added and extracted with ethyl acetate (3×). The combined organic phases were washed with water, dried and concentrated under reduced pressure. The residue was purified by flash chromatography (silica, hexane/ethyl acetate gradient 0-25%). The impure product was purified by RP-HPLC (column: Chromatorex 125×30 mm, 10 μm mobile phase: acetonitrile/water (0.2 vol. % ammonia 32%)-gradient) to give 116 mg of the title compound (100% purity, 20% yield).

$^1$H NMR (400 MHz, DMSO-$d_6$) δ [ppm]: 1.17 (d, 6); 1.19-1.28 (m, 1H); 1.42 (d, 9H); 1.45-1.48 (m, 1H): 1.47-1.71 (m, 2H); 1.72-1.93 (m, 3H); 2.53-2.64 (m, 1H); 2.77-2.93 (m, 1H); 3.09-3.30 (m, 1H); 3.34-3.46 (m, 2H); 3.48-3.73 (m, 1H); 6.92-7.27 (m, 4H).

Intermediate 55

(rac)-4-[4-(propan-2-yl)phenyl]azepane

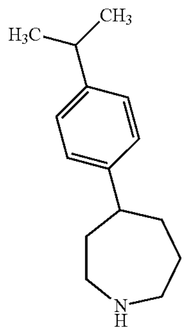 [SMILES: CC(C)c1ccc(C2CCCNCC2)cc1]

To a solution of 110 mg tert-butyl 4-[4-(propan-2-yl)phenyl]azepane-1-carboxylate (3.29 mmol, intermediate 54) in 2 mL dichloromethane was added 254 μL trifluoroacetic acid (3.29 mmol): and the mixture was stirred overnight at rt. The mixture was concentrated under reduced pressure and the residue was diluted with toluene (2×). The solvent was evaporated to give 145 mg TFA salt of the title compound (95% purity, 193% yield).

$^1$H NMR (400 MHz, DMSO-$d_6$) δ [ppm]: 1.13-1.21 (m, 6H) 1.63-2.01 (m, 6H) 2.72-2.91 (m, 2H) 3.06-3.32 (m, 4H) 7.11-7.22 (m, 4H).

Intermediate 56

(rac)-2-(azepan-4-yl)-1,3-benzoxazole

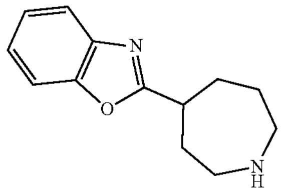 [SMILES: c1ccc2oc(C3CCCNCC3)nc2c1]

449 mg 2- aminophenol (4.11 mmol, CAS 95-55-6) and 1.00 g 1-(tert-butoxycarbonyl)azepane-4-carboxylic acid (4.11 mmol, CAS 868284-36-0) were solubilised in 0.72 mL polyphosphoric acid and the mixture was stirred for 3 h at 180° C. The reaction mixture was cooled down to rt, treated with water and the mixture was adjusted to pH=10 with an aqueous solution of potassium hydroxide. The aqueous phase was extracted with ethyl acetate two times, the combined organic phases were washed with water and brine, filtered through a waterresistant filter, the filtrate was concentrated under reduced pressure to give 460 mg of the title compound (95% purity, 49% yield).

$^1$H NMR (400 MHz, DMSO-$d_6$) δ [ppm]: 1.54-1.66 (m, 1H) 1.70-1.80 (m, 1H) 1.87-1.97 (m, 2H) 2.09-2.19 (m, 2H) 2.64-2.94 (m, 4H) 3.21-3.30 (m, 2H) 7.27-7.41 (m, 2H) 7.62-7.72 (m, 2H).

Intermediate 57

(Rac)-Tert-Butyl 4-{4-[(propan-2-yl)oxy]phenyl}azepane-1-carboxylate

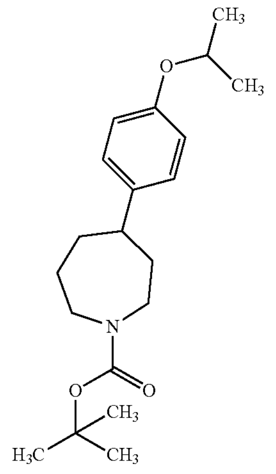 [SMILES: CC(C)Oc1ccc(C2CCCN(C(=O)OC(C)(C)C)CC2)cc1]

A mixture of 230 μL 1-bromo-4-[(propan-2-yl)oxy]benzene (1.4 mmol, CAS 1852254-64-8), 1.16 g tert-butyl 4-bromoazepane-1-carboxylate (4.18 mmol), 430 μL 1,1,1,3,3,3-hexamethyl-2-(trimethylsilyl)trisilane (1.4 mmol), 31.3 mg bis{3,5-difluoro-2-[5-(trifluoromethyl)pyridin-2-yl]phenyl}iridium(I)hexafluorophosphate (27.9 μmol), 1.87 mg 4,4'-di-tert-butyl-2,2'-bipyridine (1:1:1) (6.97 μmol, CAS 870987-63-6), 591 mg sodium carbonate (5.58 mmol), 1.53 g 1,2-dimethoxyethane-dichloronickel (1:1) (6.97

μmol) was stirred in 9 mL N,N-dimethylacetamide and 28 mL trifluorotoluene and degassed under argon. The reaction was stirred and irradiated by two Kessil LED Aquarium lights (each 40 W) 455 nm for 14 h at 35° C. The mixture was concentrated under reduced pressure, water was added and the aqueous phase was extracted with ethyl acetate two times. The combined organic phases were washed with an aqueous solution of sodium bicarbonate and water, dried over sodium sulfate and the filtrate was concentrated under reduced pressure. The residue was purified by flash chromatography (silica, hexane/ethyl acetate gradient 0-20%) to give 351 mg of the title compound (85% purity, 44% yield).

$^1$H NMR (400 MHz, DMSO-$d_6$) δ [ppm]: 1.23 (d, 6H) 1.42 (d, 9H) 1.47-1.61 (m, 2H) 1.62-1.75 (m, 2H) 1.77-1.92 (m, 2H) 2.51-2.61 (m, 2H) 3.11-3.25 (m, 1H) 3.35-3.47 (m, 2H) 3.48-3.62 (m, 1H) 4.53 (dt, 1H) 6.76-6.86 (m, 2H) 7.02-7.10 (m, 2H).

Intermediate 58

(rac)-4-{4-[(propan-2-yl)oxy]phenyl}azepane

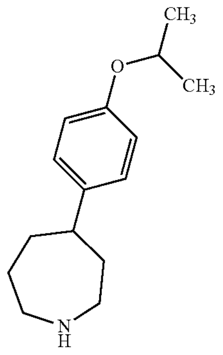 [SMILES: CC(C)Oc1ccc(C2CCCNCC2)cc1]

300 mg of tert-butyl 4-{4-[(propan-2-yl)oxy]phenyl}azepane-1-carboxylate (intermediate 57, 855 μmol) was solubilised in 5.5 mL dichloromethane, treated with 660 μL triflouroacetic acid (8.5 mmol) and the mixture was stirred overnight at rt. The reaction mixture was concentrated under reduced pressure, to the residue was added toluene and the solution was evaporated to give 400 mg of the title compound, which was obtained as a TFA salt (85% purity, 170% yield).

$^1$H-NMR (400 MHz, DMSO-$d_6$): δ [ppm]: 1.23 (d, 6H), 1.55-1.73 (m, 1H), 1.83-1.96 (m, 4H), 2.69-2.84 (m, 1H), 3.00-3.46 (m, 5H), 4.54 (dt, 1H), 6.71-6.96 (m, 2H), 6.97-7.26 (m, 2H), 8.41-8.78 (m, 2H).

Intermediate 59

Tert-Butyl 5-[(1,1,2,2,3,3,4,4,4-nonafluorobutane-1-sulfonyl)oxy]-2,3,4,7-tetrahydro-1H-azepine-1-carboxylate

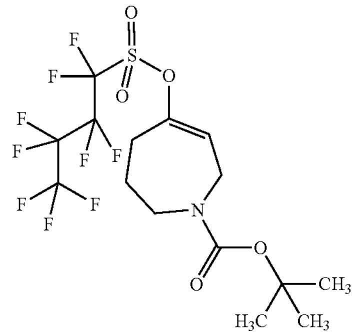 [SMILES: CC(C)(C)OC(=O)N1CC=C(OS(=O)(=O)C(F)(F)C(F)(F)C(F)(F)C(F)(F)F)CCC1]

5.00 g of tert-butyl 4-oxoazepane-1-carboxylate (22.3 mmol, CAS 188975-88-4) was solubilised in 350 mL tetrahydrofurane, 33 mL bis-(trimethylsilyl)-lithiumamide (1.0 M in THF, 33 mmol) was added dropwise at −70° C. and the solution was stirred for 45 min. at −70° C. 6 mL nonafluorobutane-1-sulfonyl fluoride (33 mmol, CAS 375-72-4) was added dropwise and the solution was stirred overnight at rt. The reaction mixture was quenched with an aqueous solution of sodium bicarbonate and extracted with ethyl acetate three times. The combined organic phases were washed with water and brine, dried over sodium sulfate and the filtrate was concentrated under reduced pressure to give 13.0 g of the title compound (95% purity, 112% yield).

$^1$H-NMR (400 MHz, DMSO-$d_6$): δ [ppm]: 1.29-1.44 (m, 9H), 1.77-1.91 (m, 1H), 2.51-2.64 (m, 2H), 3.47 (t, 2H), 3.90 (br dd, 1H), 3.94-4.15 (m, 1H), 6.07 (t, 1H).

Intermediate 60

Tert-Butyl 5-(4-methoxyphenyl)-2,3,4,7-tetrahydro-1H-azepine-1-carboxylate

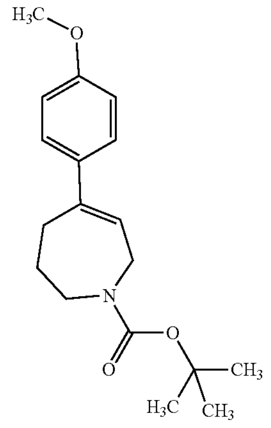 [SMILES: COc1ccc(C2=CCN(C(=O)OC(C)(C)C)CCC2)cc1]

1.00 g tert-butyl 5-[(1,1,2,2,3,3,4,4,4-nonafluorobutane-1-sulfonyl)oxy]-2,3,4,7-tetrahydro-1H-azepine-1-carboxylate (intermediate 59, 1.92 mmol) and 379 mg (4-methoxyphenyl)boronic acid (2.49 mmol, CAS 5720-07-0) were solubilised in 24 mL toluene and 4.9 mL ethanol, 1.9 mL sodium carbonate solution (2.0 M in water, 3.8 mmol), 163 mg lithium chloride (3.84 mmol) and 222 mg tetrakis (triphenylphosphine)palladium(0) (192 μmol) were added and the mixture was heated for 7 h at 90° C. The reaction mixture was diluted with water and the aqueous phase was extracted with ethyl acetate three times. The combined organic layers were washed with water and brine, dried over sodium sulfate, filterated and the filtrate was concentrated under reduced pressure. The residue was purified by flash chromatography (silica, hexane/ethyl acetate gradient 0-25%) to give 405 mg of the title compound (95% purity, 66% yield).

$^1$H-NMR (400 MHz, DMSO-$d_6$): δ [ppm]: 1.32-1.44 (m, 9H), 1.72-1.85 (m, 2H), 2.54-2.63 (m, 2H), 3.52 (t, 2H), 3.73 (s, 3H), 3.94 (br dd, 2H), 6.87 (d, 2H), 7.16-7.38 (m, 2H).

Intermediate 61

(Rac)-Tert-Butyl 4-(4-methoxyphenyl)azepane-1-carboxylate

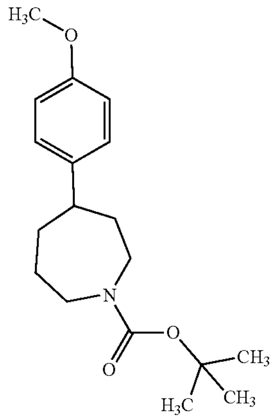 [SMILES: COc1ccc(C2CCCN(C(=O)OC(C)(C)C)CC2)cc1]

400 mg tert-butyl 5-(4-methoxyphenyl)-2,3,4,7-tetrahydro-1H-azepine-1-carboxylate (intermediate 60, 1.25 mmol) was dissolved in 10 mL methanol, 40 mg palladium on carbon (10%, 376 μmol) was added and the mixture was stirred under hydrogen atmosphere for 4 h at rt. The reaction mixture was filtered through celite (celite pad prewashed with water), the filter cake was washed with less methanol three times. The filtrate was concentrated under reduced pressure to give 370 mg of the title compound (95% purity, 92% yield).

$^1$H-NMR (400 MHz, DMSO-$d_6$): δ [ppm]: 1.42 (d, 9H), 1.52-1.95 (m, 6H), 2.52-2.62 (m, 1H), 3.12-3.26 (m, 1H), 3.38-3.47 (m, 1H), 3.49-3.65 (m, 1H), 3.70 (s, 3H), 6.83 (dd, 2H), 7.01-7.24 (m, 2H).

Intermediate 62

(rac)-4-(4-methoxyphenyl)azepane

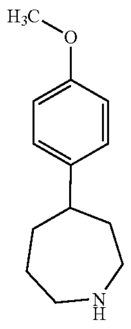

To a solution of 360 mg tert-butyl 4-(4-methoxyphenyl) azepane-1-carboxylate (intermediate 61, 1.12 mmol) in 7.2 mL dichloromethane was added 860 μL trifluoroacetic acid (110 mmol) and the mixture was stirred overnight at rt. The mixture was concentrated under reduced pressure and the residue was diluted with toluene (2×). The solvent was evaporated to give 400 mg of the title compound as a TFA salt (85% purity, 148% yield).

$^1$H-NMR (400 MHz, DMSO-$d_6$): δ [ppm]: 1.55-1.82 (m, 2H), 1.83-2.04 (m, 4H), 2.69-2.86 (m, 1H), 3.00-3.19 (m, 2H), 3.20-3.41 (m, 3H), 3.71 (s, 3H), 6.62-6.96 (m, 2H), 7.05-7.26 (m, 2H).

Intermediate 63

Tert-Butyl 5-(4-chlorophenyl)-2,3,4,7-tetrahydro-1H-azepine-1-carboxylate

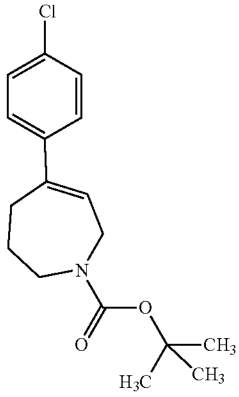 [SMILES: CC(C)(C)OC(=O)N1CC=C(c2ccc(Cl)cc2)CCC1]

1.00 g tert-butyl 5-[(1,1,2,2,3,3,4,4,4-nonafluorobutane-1-sulfonyl)oxy]-2,3,4,7-tetrahydro-1H-azepine-1-carboxylate (intermediate 59, 1.92 mmol) and 390 mg (4-chlorophenyl)boronic acid (2.49 mmol, CAS 1679-18-1) were solubilised in 24 mL toluene and 4.9 mL ethanol, 1.9 mL sodium carbonate solution (2.0 M in water, 3.8 mmol), 163 mg lithium chloride (3.84 mmol) and 222 mg tetrakis (triphenylphosphine)palladium(0) (192 μmol) were added and the mixture was heated for 7 h at 90° C. The reaction mixture was diluted with water and the aqueous phase was extracted with ethyl acetate three times. The combined organic layers were washed with water and brine, dried over sodium sulfate, filterated and the filtrate was concentrated under reduced pressure. The residue was purified by flash chromatography (silica, hexane/ethyl acetate gradient 0-25%) to give 277 mg of the title compound (95% purity, 45% yield).

$^1$H-NMR (400 MHz, DMSO-$d_6$): δ [ppm]: 1.38 (br d, 9H), 1.76-1.88 (m, 2H), 2.56-2.62 (m, 2H), 3.52 (t, 2H), 3.96 (br dd, 2H), 5.91-6.23 (m, 1H), 7.23-7.55 (m, 4H).

Intermediate 64

(Rac)-Tert-Butyl 4-(4-chlorophenyl)azepane-1-carboxylate

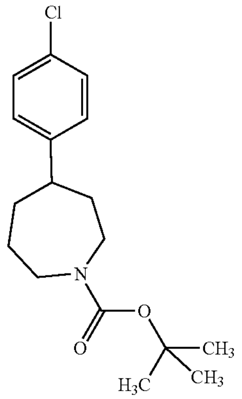 [SMILES: CC(C)(C)OC(=O)N1CCCC(c2ccc(Cl)cc2)CC1]

420 mg tert-butyl 5-(4-chlorophenyl)-2,3,4,7-tetrahydro-1H-azepine-1-carboxylate (intermediate 63, 1.36 mmol) was dissolved in 10 mL methanol, 42 mg palladium on carbon (10%, 250 μmol): was added and the mixture was stirred under hydrogen atmosphere for 1 h at rt. The reaction mixture was filtered through celite (celite pad prewashed with water), the filter cake was washed with less methanol three times. The filtrate was concentrated under reduced pressure to give 220 mg of the title compound (95% purity, 49% yield).

$^1$H NMR (400 MHz, DMSO-$d_6$) δ ppm: 1.42 (s, 9H), 1.53-1.95 (m, 6H), 2.55-2.70 (m, 1H), 3.12-3.26 (m, 1H), 3.33-3.48 (m, 2H), 3.50-3.65 (m, 1H), 7.16-7.24 (m, 2H), 7.28-7.36 (m, 2H).

Intermediate 65

(rac)-4-(4-chlorophenyl)azepane

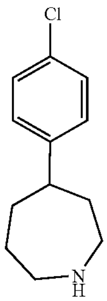 [SMILES: Clc1ccc(C2CCCNCC2)cc1]

To a solution of 205 mg tert-butyl 4-(4-chlorophenyl) azepane-1-carboxylate (intermediate 64, 629 μmol) in 4.0 mL dichloromethane was added 480 μL trifluoroacetic acid (6.3 mmol) and the mixture was stirred overnight at rt. The mixture was concentrated under reduced pressure and the residue was diluted with toluene (2×). The solvent was evaporated to give 175 mg of the title compound as a TFA salt (85% purity, 113% yield).

$^1$H NMR (400 MHz, DMSO-$d_6$) δ ppm: 1.62-2.03 (m, 6H), 2.77-2.89 (m, 1H), 3.05-3.20 (m, 2H), 3.20-3.37 (m, 2H), 7.23-7.29 (m, 2H), 7.34-7.40 (m, 2H).

Intermediate 66

2-(4-ethylpiperidin-4-yl)-5-methyl-1,3-benzoxazole

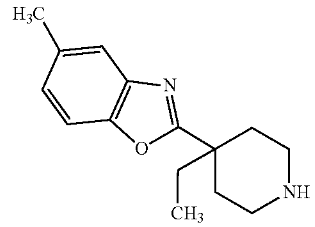 [SMILES: CCC1(c2nc3cc(C)ccc3o2)CCNCC1]

1.18 g 2-amino-4-methylphenol (9.54 mmol, CAS 95-84-1) and 1.50 g 4-ethylpiperidine-4-carboxylic acid (9.54 mmol, CAS 1227465-48-6) were solubilised in 3.0 mL polyphosphoric acid and the mixture was stirred for 2 h at 180° C. The reaction mixture was cooled down to rt, treated with water and the mixture was adjusted to pH=10 with an aqueous solution of potassium hydroxide. The aqueous phase was extracted with ethyl acetate two times, the combined organic phases were washed with water and brine and filtered through a waterresistant filter. The filtrate was concentrated under reduced pressure to give 840 mg of the title compound (97% purity, 35% yield).

$^1$H NMR (400 MHz, DMSO-$d_6$) δ ppm: 0.63 (t, 3H), 1.53 (ddd, 2H), 1.69 (q, 2H), 2.23 (br d, 2H), 2.41 (s, 3H), 2.45-2.50 (m, 2H), 2.81 (dt, 2H), 3.33 (br s, 1H), 7.13-7.17 (m, 1H), 7.47-7.52 (m, 1H), 7.49-7.57 (m, 1H).

Intermediate 67

Tert-Butyl 4-[(1,1,2,2,3,3,4,4,4-nonafluorobutane-1-sulfonyl)oxy]-3,6-dihydropyridine-1(2H)-carboxylate

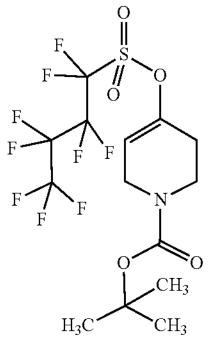

5.30 g tert-butyl 4-oxopiperidine-1-carboxylate (25.3 mmol, CAS 79099-07-3) was solubilised in 400 mL tetrahydrofurane, 38 mL bis-(trimethylsilyl)-lithiumamide (1.0 M in THF, 38 mmol) was added dropwise at −70° C. and the solution was stirred for 45 min. at −70° C. 6.8 mL nonafluorobutane-1-sulfonyl fluoride (38 mmol, CAS 375-72-4) was added dropwise and the solution was stirred overnight at rt. The reaction mixture was quenched with an aqueous solution of sodium bicarbonate and extracted with ethyl acetate three times. The combined organic phases were washed with water and brine, dried over sodium sulfate and the filtrate was concentrated under reduced pressure to give 13.0 g of the title compound (93% purity, 99% yield).

$^1H$ NMR (400 MHz, DMSO-$d_6$) δ ppm: 1.42 (s, 9H), 2.31-2.37 (m, 2H), 2.38-2.44 (m, 2H), 3.58-3.63 (m, 2H), 3.95-4.00 (m, 1H).

Intermediate 68

Tert-Butyl 6-methoxy-3',6'-dihydro[3,4'-bipyridine]-1'(2'H)-carboxylate

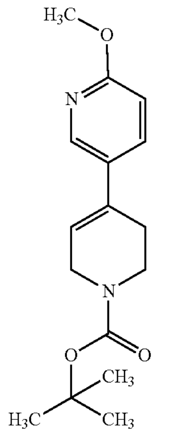

1.50 g tert-butyl 4-[(1,1,2,2,3,3,4,4,4-nonafluorobutane-1-sulfonyl)oxy]-3,6-dihydropyridine-1(2H)-carboxylate (intermediate 67, 2.96 mmol) and 589 mg (6-methoxypyridin-3-yl)boronic acid (3.85 mmol, CAS 163105-89-3) were solubilised in 37 mL toluene and 7.5 mL ethanol, 3.0 mL sodium carbonate solution (2.0 M in water, 5.9 mmol), 251 mg lithium chloride (5.92 mmol) and 342 mg tetrakis (triphenylphosphine)palladium(0) (296 μmol) were added and the mixture was heated for 7 h at 90° C. The reaction mixture was diluted with water and the aqueous phase was extracted with ethyl acetate three times. The combined organic layers were washed with water and brine, dried over sodium sulfate and filterated. The filtrate was concentrated under reduced pressure. The residue was purified by flash chromatography (silica, dichloromethane/ethanol gradient 0-3%) to give 420 mg of the title compound (80% purity, 48% yield).

$^1H$ NMR (400 MHz, DMSO-$d_6$) δ ppm: 1.38-1.47 (m, 11H), 2.41-2.47 (m, 2H), 3.53 (br t, 1H), 3.57-3.63 (m, 1H), 3.84 (s, 3H), 3.98 (br s, 1H), 6.08-6.16 (m, 1H), 6.72-6.83 (m, 1H), 7.80 (dd, 1H), 8.22 (d, 1H).

Intermediate 69

6-methoxy-1',2',3',6'-tetrahydro-3,4'-bipyridine

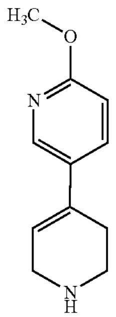

To a solution of 350 mg tert-butyl 6-methoxy-3',6'-dihydro[3,4'-bipyridine]-1'(2'H)-carboxylate (intermediate 68, 1.15 mmol) in 7.4 mL dichloromethane was added 880 μL trifluoroacetic acid (11 mmol) and the mixture was stirred for 4 h at rt. The mixture was concentrated under reduced pressure and the residue was diluted with toluene (2×). The solvent was evaporated to give 330 mg of the title compound as a TFA salt (85% purity, 128% yield).

LC-MS (Method 2): Rt=0.85 min; MS (ESIpos): m/z=191.7 [M+H]+

Intermediate 70

4-(6-methoxy-3',6'-dihydro[3,4'-bipyridin]-1'(2'H)-yl)-1-methyl-2-oxo-1,2-dihydroquinoline-3-carbonitrile

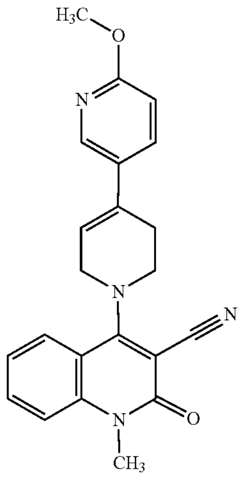 [SMILES: COc1ccc(C2=CCN(c3c(C#N)c(=O)n(C)c4ccccc34)CC2)cn1]

167 mg 4-chloro-1-methyl-2-oxo-1,2-dihydroquinoline-3-carbonitrile (765 μmol, CAS 150617-68-8), 218 mg 6-methoxy-1',2',3',6'-tetrahydro-3,4'-bipyridine (1.15 mmol, intermediate 69) and 210 μL triethylamine (1.5 mmol) were solubilised in 5.0 mL 2-propanol and the mixture was stirred for 4 h at 90° C. The reaction mixture was diluted with ethyl acetate, the organic layer was washed with water and brine, dried over sodium sulfate, filtered and the filtrate was concentrated under reduced pressure to give 30 mg of the title compound (95% purity, 10% yield).

$^1$H NMR (400 MHz, DMSO-$d_6$) δ ppm: 2.81 (br s, 2H), 3.58 (s, 3H), 3.82-3.87 (m, 5H), 4.34 (br d, 2H), 6.33 (s, 1H), 6.85 (d, 1H), 7.34 (s, 1H), 7.56-7.61 (m, 1H), 7.75 (s, 1H), 7.85-7.92 (m, 2H), 8.32 (d, 1H).

Intermediate 71

Tert-Butyl 6-methyl-3',6'-dihydro[3,4'-bipyridine]-1'(2'H)-carboxylate

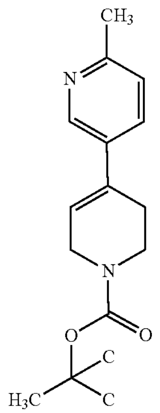

1.00 g tert-butyl 4-[(1,1,2,2,3,3,4,4,4-nonafluorobutane-1-sulfonyl)oxy]-3,6-dihydropyridine-1(2H)-carboxylate (intermediate 67, 1.97 mmol) and 351 mg (6-methylpyridin-3-yl)boronic acid (2.57 mmol, CAS 659742-21-9) were solubilised in 25 mL toluene and 5 mL ethanol, 2.0 mL sodium carbonate solution (2.0 M in water, 3.9 mmol), 167 mg lithium chloride (3.95 mmol) and 228 mg tetrakis (triphenylphosphine)palladium(0) (197 μmol) were added and the mixture was heated for 6 h at 90° C. The reaction mixture was diluted with water and the aqueous phase was extracted with ethyl acetate three times. The combined organic layers were washed with water and brine, dried over sodium sulfate, filterated and the filtrate was concentrated under reduced pressure. The residue was purified by flash chromatography (silica, dichloromethane/ethanol gradient 0-1%) to give 155 mg of the title compound (95% purity, 27% yield).

$^1$H NMR (400 MHz, DMSO-$d_6$) δ ppm: 1.42 (s, 9H), 2.43-2.47 (m, 5H), 3.54 (t, 2H), 3.99 (br s, 2H), 6.20 (br s, 1H), 7.22 (d, 1H), 7.53-7.65 (m, 2H), 7.71 (dd, 1H).

Intermediate 72

6-methyl-1',2',3',6'-tetrahydro-3,4'-bipyridine

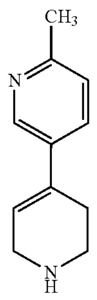

To a solution of 150 mg tert-butyl 6-methyl-3',6'-dihydro [3,4'-bipyridine]-1'(2'H)-carboxylate (519 μmol, intermediate 71) in 3.3 mL dichloromethane was added 400 μL trifluoroacetic acid (5.2 mmol) and the mixture was stirred for 4 h at rt. The mixture was concentrated under reduced pressure and the residue was diluted with toluene (2×). The solvent was evaporated to give 210 mg of the title compound as a TFA salt (95% purity, 220% yield).

LC-MS (Method 2): Rt=0.75 min; MS (ESIpos): m/z=175.6 [M+H]+

Intermediate 73

1-methyl-4-(6-methyl-3',6'-dihydro[3,4'-bipyridin]-1'(2'H)-yl)-2-oxo-1,2-dihydroquinoline-3-carbonitrile

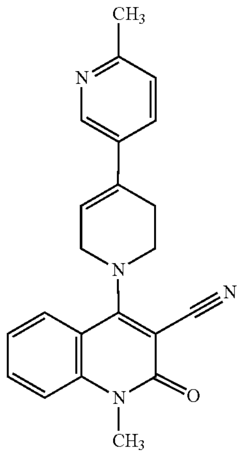 [SMILES: Cc1ccc(C2=CCN(c3c(C#N)c(=O)n(C)c4ccccc34)CC2)cn1]

167 mg 4-chloro-1-methyl-2-oxo-1,2-dihydroquinoline-3-carbonitrile (765 μmol, CAS 150617-68-8), 200 mg 6-methyl-1',2',3',6'-tetrahydro-3,4'-bipyridine (1.15 mmol, intermediate 72) and 210 μL triethylamine (1.5 mmol) were solubilised in 4.2 mL 2-propanol and the mixture was stirred for 4 h at 90° C. The reaction mixture was diluted with ethyl acetate, the organic layer was washed with water and brine, dried over sodium sulfate, filtered and the filtrate was concentrated under reduced pressure to give 41 mg of the title compound (95% purity, 14% yield).

$^1$H NMR (400 MHz, DMSO-$d_6$) δ ppm: 2.47 (s, 3H), 2.83 (br d, 2H), 3.59 (s, 3H), 3.85 (t, 2H), 4.36 (br d, 2H), 6.39-6.43 (m, 1H), 7.27 (d, 1H), 7.31-7.37 (m, 1H), 7.58 (d, 1H), 7.75 (ddd, 1H), 7.82 (dd, 1H), 7.88 (dd, 1H), 8.62 (d, 1H).

Intermediate 74

Tert-Butyl 3',6'-dihydro[3,4'-bipyridine]-1'(2'H)-carboxylate

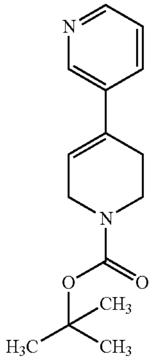

1.00 g tert-butyl 4-[(1,1,2,2,3,3,4,4,4-nonafluorobutane-1-sulfonyl)oxy]-3,6-dihydropyridine-1(2H)-carboxylate (1.97 mmol, intermediate 67) and 315 mg pyridin-3-ylboronic acid (2.57 mmol, CAS 1692-25-7) were solubilised in 25 mL toluene and 5 mL ethanol, 2.0 mL sodium carbonate solution (2.0 M in water, 3.9 mmol), 167 mg lithium chloride (3.95 mmol) and 228 mg tetrakis(triphenylphosphine)palladium(0) (197 μmol) were added and the mixture was heated for 4 h at 90° C. The reaction mixture was diluted with water and the aqueous phase was extracted with ethyl acetate three times. The combined organic layers were washed with water and brine, dried over sodium sulfate, filterated and the filtrate was concentrated under reduced pressure. The residue was purified by flash chromatography (silica, dichloromethane/ethanol gradient 0-1%) to give 155 mg of the title compound (95% purity, 27% yield).

LC-MS (Method 2): Rt=1.12 min; MS (ESIpos): m/z=261.8 [M+H]+

Intermediate 75

1',2',3',6'-tetrahydro-3,4'-bipyridine

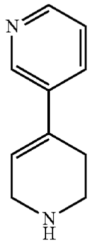 [SMILES: C1=C(c2cccnc2)CCNC1]

To a solution of 170 mg tert-butyl 6-methyl-3',6'-dihydro[3,4'-bipyridine]-1'(2'H)-carboxylate (intermediate 74, 62 μmol) in 4.0 mL dichloromethane was added 480 μL trifluoroacetic acid (6.2 mmol) and the mixture was stirred overnight at rt. The mixture was concentrated under reduced pressure and the residue was diluted with toluene (2×). The solvent was evaporated to give 250 mg of the title compound as a TFA salt (90% purity, 226% yield).

LC-MS (Method 2): Rt=0.64 min; MS (ESIpos): m/z=161.5 [M+H]+

Intermediate 76

4-(3',6'-dihydro[3,4'-bipyridin]-1'(2'H)-yl)-1-methyl-2-oxo-1,2-dihydroquinoline-3-carbonitrile

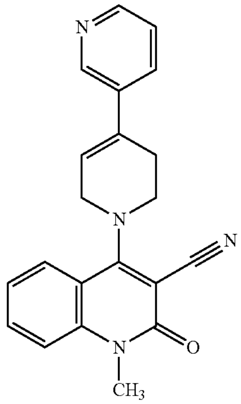 [SMILES: Cn1c(=O)c(C#N)c(N2CC=C(c3cccnc3)CC2)c2ccccc21]

167 mg 4-chloro-1-methyl-2-oxo-1,2-dihydroquinoline-3-carbonitrile (765 μmol, CAS 150617-68-8), 184 mg 1',2',3',6'-tetrahydro-3,4'-bipyridine (intermediate 75, 1.15 mmol) and 210 μL triethylamine (1.5 mmol) were solubilised in 4.2 mL 2-propanol and the mixture was stirred for 4 h at 90° C. The reaction mixture was diluted with ethyl acetate, the organic layer was washed with water and brine, dried over sodium sulfate, filtered and the filtrate was concentrated under reduced pressure. The residue was purified by flash chromatography (silica, dichloromethane/ethanol gradient 0-3%) to give 62 mg of the title compound (95% purity, 22% yield).

$^1$H NMR (400 MHz, DMSO-$d_6$) δ ppm: 2.08 (s, 1H), 2.86 (br s, 2H), 3.59 (s, 3H), 3.85 (t, 2H), 4.37 (br d, 2H), 6.47 (br s, 1H), 7.30-7.46 (m, 2H), 7.58 (d, 1H), 7.70-7.80 (m, 1H), 7.85-7.96 (m, 2H), 8.51 (dd, 1H), 8.77 (d, 1H).

Intermediate 77

4-[4-(1,3-benzothiazol-2-yl)piperidin-1-yl]-1-methylquinolin-2(1H)-one

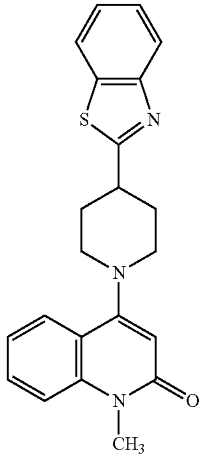 [SMILES: Cn1c(=O)cc(N2CCC(c3nc4ccccc4s3)CC2)c2ccccc21]

1.00 g 4-chloro-1-methylquinolin-2(1H)-one (5.16 mmol, CAS 32262-17-2) was solubilised in 40 mL dimethylsulfoxide, 2.7 mL N,N-diisopropylethylamine (15 mmol) and 6.77 g 2-(piperidin-4-yl)-1,3-benzothiazole (31.0 mmol, CAS 51784-73-7) were added and the mixture was stirred overnight at 110° C. The reaction mixture was was diluted with water and the aqueous phase was extracted with dichloromethane three times. The combined organic layers were washed with water and brine, dried over sodium sulfate, filtered and the filtrate was concentrated under reduced pressure. The residue was purified by flash chromatography (silica, dichloromethane/methanol gradient 0-50%) to give 1.64 g of the title compound (85% yield).

$^{1}$H NMR (400 MHz, DMSO-$d_6$) δ ppm: 2.07-2.21 (m, 2H), 2.24-2.33 (m, 2H), 2.86-2.98 (m, 2H), 3.37-3.47 (m, 1H), 3.57 (m+s, 5H), 6.07 (s, 1H), 7.29 (td, 1H), 7.40-7.46 (m, 1H), 7.48-7.55 (m, 2H), 7.58-7.65 (m, 1H), 7.83 (dd, 1H), 7.96-8.01 (m, 1H), 8.10 (dd, 1H).

Intermediate 78

4-[4-(1,3-benzothiazol-2-yl)piperidin-1-yl]-3-bromo-1-methylquinolin-2(1H)-one

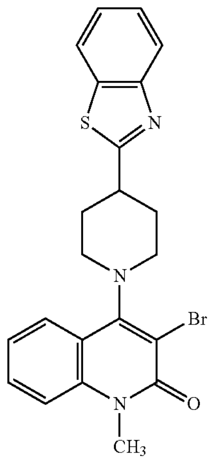 [SMILES: Cn1c(=O)c(Br)c(N2CCC(c3nc4ccccc4s3)CC2)c2ccccc21]

1.00 g 4-[4-(1,3-benzothiazol-2-yl)piperidin-1-yl]-1-methylquinolin-2(1H)-one (intermediate 77, 2.66 mmol) was solubilised in 45 mL acetonitrile, 569 mg N-bromosuccinimide (3.20 mmol) was added and the mixture was stirred for 3.5 h at rt. The reaction mixture was concentrated under reduced pressure and the residue was purified by flash chromatography (silica, dichloromethane/methanol gradient 0-10%) to give 1.00 g of the title compound (83% yield).

LC-MS (Method 1): $R_t$=1.43 min; MS (ESIpos): m/z=454 $[M+H]^+$ $^{1}$H NMR (400 MHz, DMSO-$d_6$) δ ppm 2.13 (qd, 2H) 2.22-2.31 (m, 2H) 3.37-3.49 (m, 1H): 3.57-3.67 (m, 2H) 3.69 (s, 3H) 7.34-7.40 (m, 1H) 7.41-7.46 (m, 1H) 7.49-7.55 (m, 1H): 7.56-7.61 (m, 1H) 7.65-7.72 (m, 1H) 7.96-8.02 (m, 1H) 8.03-8.08 (m, 1H) 8.08-8.14 (m, 1H).

Intermediate 79

Methyl 4-[4-(1,3-benzothiazol-2-yl)piperidin-1-yl]-1-methyl-2-oxo-1,2-dihydroquinoline-3-carboxylate

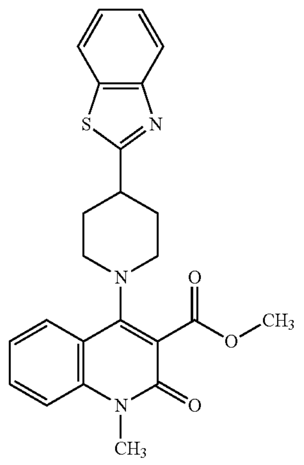 [SMILES: COC(=O)c1c(N2CCC(c3nc4ccccc4s3)CC2)c2ccccc2n(C)c1=O]

357 mg 4-[4-(1,3-benzothiazol-2-yl)piperidin-1-yl]-3-bromo-1-methylquinolin-2(1H)-one (intermediate 78, 786 μmol) was dissolved in 12 mL methanol and 1.2 mL tetrahydrofurane, 65 mg 1,1'bis(diphenylphosphino)ferrocene-palladium(II)dichloride-dichloromethane complex (1.6 mmol) and 220 μL triethylamie (1.6 mmol) were added and the mixture was stirred for 22 h at 100° C. (15 bar) under carbon monooxide atmosphere. The reaction mixture was cooled down to rt and atmospheric pressure, diluted with dichloromethane and the suspension was filtered. The filter cake was washed with less dichloromethane three times and the filtrate was concentrated under reduced pressure. The residue was purified by flash chromatography (silica, dichloromethane/methanol gradient 0-5%) to give 312 mg of the title compound (92% yield).

$^{1}$H NMR (400 MHz, DMSO-$d_6$) δ ppm 2.05-2.19 (m, 2H) 2.21-2.30 (m, 2H) 3.05 (br t, 2H): 3.38-3.48 (m, 3H) 3.59 (s, 3H) 3.84 (s, 3H) 7.32-7.40 (m, 1H) 7.40-7.47 (m, 1H) 7.48-7.54 (m, 1H) 7.56 (d, 1H) 7.65-7.73 (m, 1H) 7.94 (dd, 1H) 7.99 (d, 1H) 8.07-8.15 (m, 1H).

LC-MS (Method 1): $R_t$=1.34 min; MS (ESIpos): m/z=435 $[M+H]^+$

Intermediate 80

4-[4-(1,3-benzothiazol-2-yl)piperidin-1-yl]-1-methyl-2-oxo-1,2-dihydroquinoline-3-carboxylic Acid

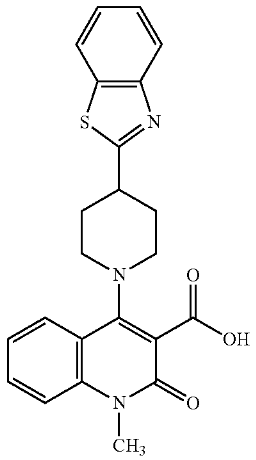 [SMILES: Cn1c(=O)c(C(=O)O)c(N2CCC(c3nc4ccccc4s3)CC2)c2ccccc21]

254 mg methyl 4-[4-(1,3-benzothiazol-2-yl)piperidin-1-yl]-1-methyl-2-oxo-1,2-dihydroquinoline-3-carboxylate (intermediate 79, 586 μmol) was dissolved in 20 mL tetrahydrofurane and 20 mL ethanol, 12 mL lithium hydroxide solution (1.0 M in water, 12 mmol) and the mixture was stirred for 12 h at 80° C. The reaction mixture was cooled d own to rt, diluted with water and adjusted to pH=5 with hydrogen chloride solution (1 M in water) and the aqueous phase was extracted with dichloromethane three times. The combined organic layers were washed with brine, dried over sodium sulfate, filtered and the filtrate was concentrated under reduced pressure. The residue was purified by flash chromatography (silica, dichloromethane/methanol gradient 0-3%) to give 100 mg of the title compound (41% yield).

$^1$H NMR (400 MHz, DMSO-$d_6$) δ ppm 1.98-2.23 (m, 3H) 2.25-2.36 (m, 2H) 2.86-2.99 (m, 1H): 3.53 (br d, 2H) 3.55-3.61 (m, 3H) 7.22-7.32 (m, 1H) 7.38-7.46 (m, 1H) 7.47-7.58 (m, 2H) 7.59-7.66 (m, 1H) 7.91 (dd, 1H) 7.84 (dd, 1H) 7.79-7.88 (m, 1H) 7.95-8.02 (m, 1H): 8.07-8.15 (m, 1H).

Intermediate 81

8-fluoro-1-methyl-2H-3,1-benzoxazine-2,4(1H)-dione

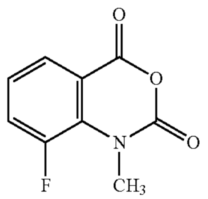

5.00 g 8-fluoro-2H-3,1-benzoxazine-2,4(1H)-dione (26.2 mmol, CAS174463-53-7) was dissolved in 200 mL dimethyl formamide, cooled down to 0° C., 2.4 mL iodomethane (39 mmol): and then 1.45 g sodium hydride (65% purity, 39.3 mmol) were added dropwise and the mixture was stirred overnight at rt. The reaction mixture was diluted with water, the aqueous phase was extracted with ethyl acetate two times. The combined organic layers were washed with water and brine, dried over sodium sulfate, filtered and the filtrate was concentrated under reduced pressure. The residue was purified by flash chromatography (silica, hexane/ethyl acetate gradient 0-25%) to give 2.40 g of the title compound (95% purity, 45% yield).

$^1$H NMR (400 MHz, DMSO-$d_6$) δ ppm: 3.61 (d, 3H), 7.33 (td, 1H), 7.76 (ddd, 1H), 7.80-7.92 (m, 1H).

Intermediate 82

8-fluoro-4-hydroxy-1-methyl-2-oxo-1,2-dihydroquinoline-3-carbonitrile

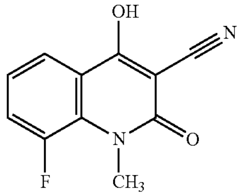 [SMILES: Cn1c(=O)c(C#N)c(O)c2cccc(F)c21]

2.40 g 8-fluoro-1-methyl-2H-3,1-benzoxazine-2,4(1H)-dione (intermediate 81, 11.7 mmol) was solubilised in 27 mL tetrahydrofurane and 13 mL triethylamine (93 mmol) was added dropwise at rt. Then 1.9 mL ethyl cyanoacetate (18 mmol) was added and the mixture was stirred overnight at 70 C. The reaction mixture was cooled down to rt and concentrated under reduced pressure. The residue was diluted with less ethyl acetate and water, the mixture was adjusted to pH=1 with hydrogen chloride solution (2 M in water) and the resulting solid was filtered off. The filter cake was washed with less water and dried in vacuum to give 2.40 g of the title compound (95% purity, 99% yield).

$^1$H NMR (400 MHz, DMSO-$d_6$) δ ppm: 3.68 (d, 3H), 7.25 (td, 1H), 7.58 (ddd, 1H), 7.89 (dt, 1H).

Intermediate 83

4-chloro-8-fluoro-1-methyl-2-oxo-1,2-dihydroquinoline-3-carbonitrile

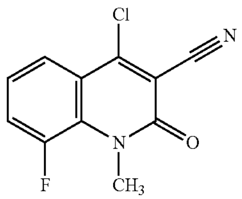 [SMILES: Cn1c(=O)c(C#N)c(Cl)c2cccc(F)c21]

1.80 g 8-fluoro-4-hydroxy-1-methyl-2-oxo-1,2-dihydroquinoline-3-carbonitrile (intermediate 82, 7.84 mmol) was suspended in 7.3 mL phosphoryl chloride (78 mmol) and the mixture was stirred for 20 h at 90° C. The reaction mixture was cooled d own to rt, diluted with ice water and adjusted to pH=10 with sodium bicarbonate (solid). The resulting solid was filtered off to give 1.50 g of the title compound (95% purity, 77% yield).

$^1H$ NMR (400 MHz, DMSO-$d_6$) δ ppm: 3.80 (d, 3H), 7.48 (td, 1H), 7.77-7.84 (m, 1H), 7.95 (dt, 1H).

Intermediate 84

8-bromo-1-methyl-2H-3,1-benzoxazine-2,4(1H)-dione

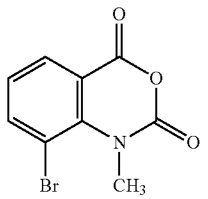

90.0 g 8-bromo-2H-3,1-benzoxazine-2,4(1H)-dione (372 mmol, CAS 331646-98-1) was solubilised in 720 mL N,N-dimethylacetamide, 130 mL N,N-diisopropylethylamine and 69 mL iodomethane (1.1 mol) was added and the suspension was stirred overnight at rt. The reaction mixture was diluted with 3 L water and the resulting solid was filtered off. The filter cake was washed with ethanol and then with hexane to give 86.1 g of the title compound (90% yield).

$^1H$ NMR (400 MHz, DMSO-$d_6$) δ ppm: 3.64 (s, 3H), 7.26 (t, 1H), 8.00 (dd, 1H), 8.09 (dd, 1H).

Intermediate 85

8-bromo-4-hydroxy-1-methyl-2-oxo-1,2-dihydroquinoline-3-carbonitrile

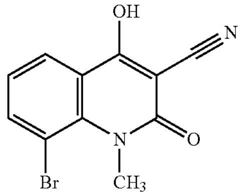

40 g 8-bromo-1-methyl-2H-3,1-benzoxazine-2,4(1H)-dione (intermediate 84, 156 mmol) was dissolved in 320 mL tetrahydrofurane, 170 mL triethylamine (1.2 mol) and then 50 mL ethyl cyanoacetate (470 mmol) were added and the mixture was stirred for 24 h at 70° C. The reaction mixture was cooled down to rt and concentrated under reduced pressure. The residue was diluted with water and ethyl acetate and the mixture was adjusted to pH=1 with hydrogen chloride solution (2 N in water). The suspension was filtered and the filter cake was washed with water and less ethyl acetate to give 36.01 g of the tilte compound (83% yield).

$^1H$ NMR (400 MHz, DMSO-$d_6$) δ ppm 3.63-3.73 (m, 3H) 6.09-6.42 (m, 1H) 7.21 (dt, 1H) 7.83-8.12 (m, 2H).

Intermediate 86

8-bromo-4-chloro-1-methyl-2-oxo-1,2-dihydroquinoline-3-carbonitrile

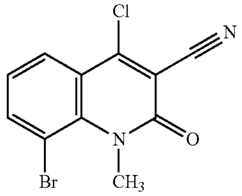 [SMILES: Cn1c(=O)c(C#N)c(Cl)c2cccc(Br)c21]

35.6 g 8-bromo-4-hydroxy-1-methyl-2-oxo-1,2-dihydroquinoline-3-carbonitrile (intermediate 85, 127 mmol) was suspended in 120 mL phosphoryl chloride (1.3 mol) and the mixture was stirred overnight at 90° C. The reaction mixture was cooled down to rt, diluted with 125 mL hexane and the suspension was filtered. The filter cake was diluted carefully with sodium bicarbonate solution (2 M in water) and the suspension was stirred for 10 min. at rt. The basic suspension was filtered, the filter cake was washed with water and ethyl acetate and dried in a vacuum oven at 50° C. The solid was suspended in dichloromethane and cristallized, filtered the solid off and dried the solid in vacuum at 100° C. to give 6.12 g of the title compound (16% yield).

$^1H$ NMR (400 MHz, DMSO-$d_6$) δ ppm 3.80 (s, 3H) 7.29-7.51 (m, 1H) 8.01-8.32 (m, 2H).

Intermediate 87

8-chloro-1-methyl-2H-3,1-benzoxazine-2,4(1H)-dione

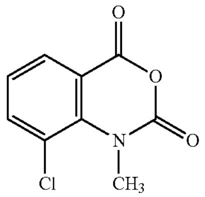

4.00 g 8-fluoro-2H-3,1-benzoxazine-2,4(1H)-dione (19.2 mmol, CAS 63497-60-9) was dissolved in 33 mL dimethyl formamide, cooled down to 0° C., 6.7 mL N,N-diisoprpylamine and then 3.6 mL iodomethane (58 mmol) were added dropwise and the mixture was stirred overnight at rt. The suspension was concentrated under reduced pressure (to half-amount), then diluted with ice water and the resulting solid was filtered. The filter cake was washed with water and then with less hexane and concentrated in vacuum to give 4.40 g of the title compound (90% purity, 97% yield).

$^1H$ NMR (400 MHz, DMSO-$d_6$) δ ppm 3.64 (s, 3H) 7.34 (t, 1H) 7.79-8.06 (m, 2H).

Intermediate 88

8-chloro-4-hydroxy-1-methyl-2-oxo-1,2-dihydroquinoline-3-carbonitrile

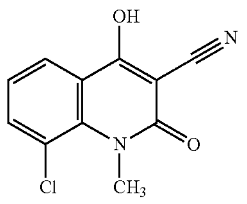

4.35 g 8-chloro-1-methyl-2H-3,1-benzoxazine-2,4(1H)-dione (intermediate 87, 18.5 mmol) was solubilised in 45 mL 2-methyl tetrahydrofurane, 21 mL triethylamine (150 mmol) and then 7.9 mL ethyl cyanoacetate (74 mmol) were added carefully and the suspension was stirred for 18 h at 80° C. The reaction mixture was concentrated under reduced pressure, the residue was diluted with water and ethyl acetate and the mixture was adjusted to pH=1 with hydrogen chloride solution (2 M in water). The resulting solid was filtered and the filter cake was washed with less hexane to give 3.87 g of the title compound (99% purity, 88% yield).

$^1$H NMR (400 MHz, DMSO-$d_6$) δ ppm 3.68 (s, 3H) 7.25 (t, 1H) 7.75 (dd, 1H) 7.91-8.10 (m, 1H).

Intermediate 89

4,8-dichloro-1-methyl-2-oxo-1,2-dihydroquinoline-3-carbonitrile

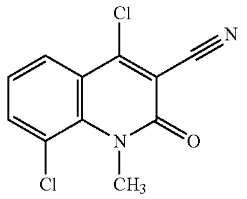 [SMILES: Cn1c(=O)c(C#N)c(Cl)c2cccc(Cl)c21]

3.80 g 8-chloro-4-hydroxy-1-methyl-2-oxo-1,2-dihydroquinoline-3-carbonitrile (intermediate 88, 16.2 mmol) was suspended in 23 mL phosphoryl chloride (16.2 mmol) and the mixture was stirred overnight at 90° C. The reaction mixture was cooled down to rt, diluted with 400 mL ice water and the aqueous phase was extracted with dichloromethane three times. The combined organic phases were washed with sodium bicarbonate solution (2 M in water, filtered through a waterresistant filter and the filtrate was concentrated under reduced pressure. The residue was suspended in a mixture of 25 mL dichloromethane and of 25 mL ethanol and the suspension was stirred for 1 h at rt. The solid was filtered off and dried in vacuum oven to give 1.66 g of the title compound (94% purity, 38% yield).

$^1$H NMR (400 MHz, DMSO-$d_6$) δ ppm 3.81 (s, 3H) 7.40-7.62 (m, 1H) 7.95-8.03 (m, 1H) 8.05-8.19 (m, 1H).

Intermediate 90

1,6-dimethyl-2H-3,1-benzoxazine-2,4(1H)-dione

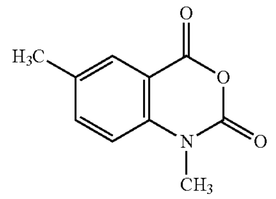

10.0 g 6-methyl-2H-3,1-benzoxazine-2,4(1H)-dione (53.6 mmol, CAS 4692-99-3) was solubilised in 100 mL N,N-dimethylacetamide, 19 mL N,N-diisoprpylethylamine (110 mmol) and 10 mL iodomethane (160 mmol) was added and the suspension was stirred overnight at rt. The reaction mixture was diluted with water and the resulting solid was filtered off. The filter cake was washed with ethanol and then with hexane to give 9.10 g of the title compound (95% purity, 85% yield).

$^1$H NMR (400 MHz, DMSO-$d_6$) δ ppm: 2.37 (s, 3H), 3.44 (s, 3H), 7.35 (d, 1H), 7.68 (dd, 1H), 7.82 (d, 1H).

Intermediate 91

4-hydroxy-1,6-dimethyl-2-oxo-1,2-dihydroquinoline-3-carbonitrile

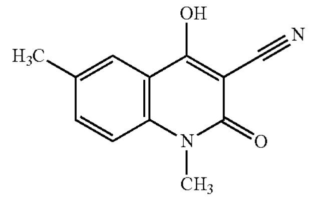 [SMILES: Cc1ccc2c(c1)c(Cl)c(C#N)c(=O)n2C]

9.10 g 1,6-dimethyl-2H-3,1-benzoxazine-2,4(1H)-dione (intermediate 90, 45.2 mmol) was solubilised in 100 mL tetrahydrofurane, 50 mL triethylamine (360 mmol) and then 7.2 mL ethyl cyanoacetate (68 mmol) were added carefully and the suspension was stirred for 24 h at 70° C. The reaction mixture was diluted with water and ethyl acetate and the mixture was adjusted to pH=1 with hydrogen chloride solution (2 N in water). The resulting solid was filtered and the filter cake was washed with less hexane to give 8.00 g of the title compound (95% purity, 78% yield).

$^1$H NMR (400 MHz, DMSO-$d_6$) δ ppm: 2.38 (s, 3H), 3.53 (s, 6H), 7.45 (d, 1H), 7.59 (dd, 1H), 7.90 (d, 1H).

Intermediate 92

4-chloro-1,6-dimethyl-2-oxo-1,2-dihydroquinoline-3-carbonitrile

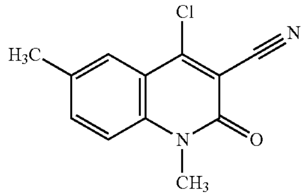

8.00 g 4-hydroxy-1,6-dimethyl-2-oxo-1,2-dihydroquinoline-3-carbonitrile (intermediate 91, 35.5 mmol) was suspended in 33 mL phosphoryl chloride (350 mmol) and the mixture was stirred overnight at 90° C. The reaction mixture was cooled down to rt, diluted with 4 L ice water and the aqueous phase was adjusted to pH=10 with sodium bicarbonate (solid). The resulting solid was filtered off, the filter cake was washed with less water and ethyl acetate. The impure solid was purified by flash chromatography (silica, dichloromethane/ethanol gradient 0-1%) to give 2.90 g of the title compound (94% purity, 38% yield).

$^1$H NMR (400 MHz, DMSO-$d_6$) δ ppm: 2.44 (s, 3H), 3.65 (s, 3H), 7.65 (d, 1H), 7.79 (br d, 1H), 7.86-7.90 (m, 1H).

Intermediate 93

6-bromo-1-methyl-2H-3,1-benzoxazine-2,4(1H)-dione

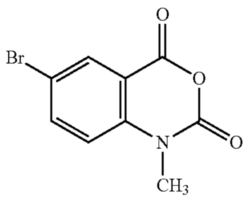

20.0 g 6-bromo-2H-3,1-benzoxazine-2,4(1H)-dione (82.6 mmol, CAS 4692-98-2) was solubilised in 160 mL N,N-dimethylacetamide, 29 mL N,N-diisoprpylethylamine (170 mmol) and 15 mL iodomethane (250 mmol) were added and the suspension was stirred for 72 h at rt. The reaction mixture was diluted with water and the resulting solid was filtered off. The filter cake was washed with ethanol and dried in a vacuum oven at 100° C. to give 20.7 g of the title compound (98% yield).

$^1$H NMR (400 MHz, DMSO-$d_6$) δ ppm 3.45 (s, 3H) 7.42 (d, 1H) 7.98-8.04 (m, 1H) 8.06-8.11 (m, 1H).

LC-MS (Method 1): $R_t$=0.95 min; MS (ESIpos): m/z=256 $[M+H]^+$

Intermediate 94

6-bromo-4-hydroxy-1-methyl-2-oxo-1,2-dihydroquinoline-3-carbonitrile

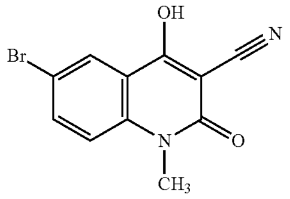 [SMILES: Cn1c(=O)c(C#N)c(O)c2cc(Br)ccc21]

4.42 g 6-bromo-1-methyl-2H-3,1-benzoxazine-2,4(1H)-dione (intermediate 93, 17.3 mmol) was solubilised in 35 mL tetrahydrofurane, 19 mL triethylamine (140 mmol) and then 3.5 mL ethyl cyanoacetate (33 mmol) were added carefully and the suspension was stirred 72 h at 90° C. The reaction mixture was cooled down to rt, diluted with water and ethyl acetate (1:1) and the mixture was adjusted to pH=1 with hydrogen chloride solution (2 M in water). The resulting solid was filtered and the filter cake was washed with less water and ethyl acetate to give 3.24 g of the title compound (67% yield).

$^1$H NMR (400 MHz, DMSO-$d_6$) δ ppm 3.49 (s, 3H) 7.44 (d, 1H) 7.75-7.92 (m, 1H) 8.06-8.38 (m, 1H).

LC-MS (Method 1): $R_t$=0.75 min; MS (ESIpos): m/z=279 [M+H]+

Intermediate 95

6-bromo-4-chloro-1-methyl-2-oxo-1,2-dihydroquinoline-3-carbonitrile

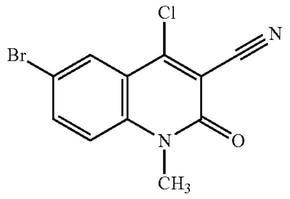 [SMILES: Cn1c(=O)c(C#N)c(Cl)c2cc(Br)ccc21]

3.23 g 6-bromo-4-hydroxy-1-methyl-2-oxo-1,2-dihydroquinoline-3-carbonitrile (intermediate 94, 11.6 mmol) was suspended in 22 mL phosphoryl chloride (230 mmol) and the mixture was stirred overnight at 90° C. The reaction mixture was cooled down to rt, diluted with 4 L ice water and the aqueous phase was adjusted to pH=10 with sodium bicarbonate (solid). The resulting solid was filtered off, the filter cake was washed with less water and ethanol and dried in a vacuum oven at 100° C. to give 3.10 g of the title compound (94% purity, 90% yield).

$^1$H NMR (400 MHz, DMSO-$d_6$) δ ppm 3.65 (s, 4H) 7.70 (d, 1H) 8.06 (dd, 1H) 8.11-8.28 (m, 1H).

LC-MS (Method 1): $R_t$=1.14 min; MS (ESIpos): m/z=297 $[M+H]^+$

Intermediate 96

6-methyl-2-(4-methylpiperidin-4-yl)-1,3-benzoxazole

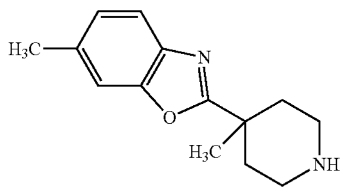 [SMILES: Cc1ccc2nc(C3(C)CCNCC3)oc2c1]

860 mg 2-amino-5-methylphenol (6.98 mmol, CAS 2835-98-5) and 1.00 g 4-methylpiperidine-4-carboxylic acid (6.98 mmol, CAS 162648-32-0) were suspended in 10 mL polyphosphoric acid and the mixture was stirred for 4 h at 180€C. The hot reaction mixture was added dropwise into water and the mixture was adjusted to pH=10 with potassium hydroxide solution (1 M in water). The aqueous phase was extracted with ethyl acetate three times, the combined organic phases were washed with brine, filtered through a waterresistant filter and the filtrate was concentrated under reduced pressure to give 880 mg of the title compound (95% purity, 52% yield).

$^1$H NMR (400 MHz, DMSO-$d_6$) δ ppm: 1.33 (s, 3H), 1.56 (ddd, 2H), 2.17 (dt, 2H), 2.42 (s, 3H), 2.52-2.60 (m, 2H), 2.74-2.85 (m, 2H), 7.13-7.17 (m, 1H), 7.48-7.50 (m, 1H), 7.56 (d, 1H).

Intermediate 97

6-methoxy-1-methyl-2H-3,1-benzoxazine-2,4(1H)-dione

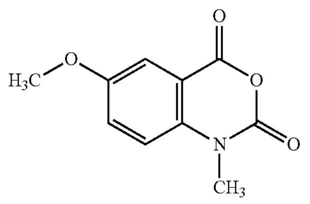

To a solution of 4.6 g 6-methoxy-2H-3,1-benzoxazine-2,4(1H)-dione (22.6 mmol, CAS 37795-77-0) and 7.9 mL N,N-diisopropylethylamine (45 mmol) in 42 mL N,N-dimethylacetamide was added 4.2 mL iodomethane (68 mmol) at rt and was stirred overnight. The reaction was added to 1000 mL water. The solid that precipitated from this procedure was collected by filtration, washed with water, ethanol and hexane and dried in vacuum. 4.3 g of the title compound were obtained (87% yield).

$^1$H NMR (DMSO-$d_6$) δ [ppm]: 3.45 (s, 3H); 3.84 (s, 3H); 7.39-7.49 (m, 3H).

Intermediate 98

4-hydroxy-6-methoxy-1-methyl-2-oxo-1,2-dihydroquinoline-3-carbonitrile

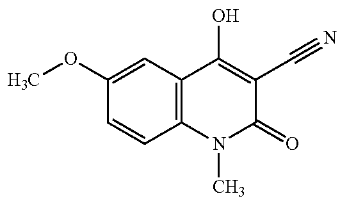 [SMILES: COc1ccc2c(c1)c(Cl)c(C#N)c(=O)n2C]

A suspension of 4.3 g 6-methoxy-1-methyl-2H-3,1-benzoxazine-2,4(1H)-dione (intermediate 97, 19.7 mmol) in 45 mL THF was slowly treated with 22 mL triethylamine (160 mmol) followed by the addition of 3.2 mL ethyl cyanoacetate (30 mmol) and was stirred for 24 h at 70° C. After cooling to rt, ethyl acetate and water were added and the mixture was acidified to pH=1 by addition of hydrochloric acid (2 N). The resulting precipitate was collected by filtration to give 2.7 g of the title compound (57% yield).

$^1$H NMR (400 MHz, DMSO-$d_6$) δ [ppm]: 3.53 (s, 3H); 3.83 (s, 3H); 7.38 (dd, 1H); 7.47-7.51 (m, 1H); 7.57 (d, 1H).

Intermediate 99

4-chloro-6-methoxy-1-methyl-2-oxo-1,2-dihydroquinoline-3-carbonitrile

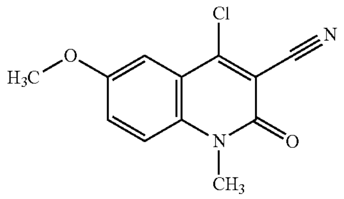

A mixture of 2.7 g 4-hydroxy-6-methoxy-1-methyl-2-oxo-1,2-dihydroquinoline-3-carbonitrile (intermediate 98, 11.7 mmol) and 11 mL phosphoric trichloride (120 mmol) was stirred for 10 h at 90° C. After cooling to rt, ice water (2000 ml) w as added carefully and the mixture was adjusted to pH=10 with sodium carbonate. The precipitate was collected by filtration to obtain 2.6 g of a crude solid. This solid was purified by flash chromatography (silica; dichloromethane/methanol gradient 0-3%) to give 700 mg of the title compound (23% yield).

$^1$H NMR (400 MHz, DMSO-$d_6$) δ [ppm]: 3.66 (s, 3H); 3.89 (s, 3H); 7.42 (d, 1H); 7.56 (dd, 1H); 7.70 (d, 1H).

Intermediate 100

4,6-dichloro-1-methyl-2-oxo-1,2-dihydroquinoline-3-carbonitrile

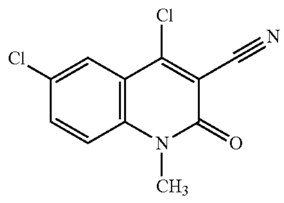

Intermediate 100 was isolated as a by product of the synthesis of intermediate 99. After flash chromatography (silica, dichloromethane/methanol gradient 0-3%), 180 mg of the title compound (6% yield) was obtained.

$^1H$ NMR (400 MHz, DMSO-$d_6$) δ [ppm]: 4.00 (s, 3H); 7.51 (d, 1H); 7.75 (dd, 1H); 8.06 (d, 1H).

Intermediate 101

6-fluoro-1-methyl-2H-3,1-benzoxazine-2,4(1H)-dione

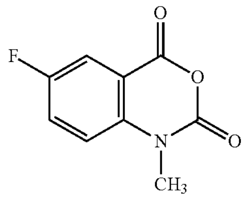

To a solution of 5.00 g 6-fluoro-2H-3,1-benzoxazine-2,4 (1H)-dione (26.8 mmol, CAS 321-69-7): and 9.3 mL N,N-diisopropylethylamine (54 mmol) in 40 mL dimethylformamide was added 5.1 mL iodomethane (80 mmol) at rt and the mixture was stirred overnight. The reaction mixture was diluted with 1000 mL water and the resulting solid was collected by filtration, the filter cake was washed with water and dried in vacuum to give 4.93 g of the title compound (99% purity, 93% yield).

$^1H$ NMR (400 MHz, DMSO-$d_6$) δ ppm 3.47 (s, 3H), 7.40-7.61 (m, 1H), 7.69-7.93 (m, 2H).

Intermediate 102

6-fluoro-4-hydroxy-1-methyl-2-oxo-1,2-dihydroquinoline-3-carbonitrile

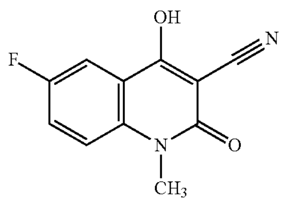

4.85 g 6-fluoro-1-methyl-2H-3,1-benzoxazine-2,4(1H)-dione (intermediate 101, 24.6 mmol) was solubilised in 50 mL tetrahydrofurane, 34 mL triethylamine (250 mmol) and then 15.1 mL ethyl cyanoacetate (133 mmol) were added carefully and the suspension was stirred 72 h at 90° C. The reaction mixture was cooled down to rt, concentrated under reduced pressure, the residue was diluted with water and ethyl acetate (1:1) and the mixture was adjusted to pH=1 with hydrogen chloride solution (2 M in water). The resulting solid was filtered and the filter cake was washed with less water and ethyl acetate to give 4.40 g of the title compound (100% purity, 82% yield).

$^1H$ NMR (400 MHz, DMSO-$d_6$) δ ppm 3.34 (br s, 3H), 7.01-7.44 (m, 2H), 7.51-7.70 (m, 1H).

Intermediate 103

4-chloro-6-fluoro-1-methyl-2-oxo-1,2-dihydroquinoline-3-carbonitrile

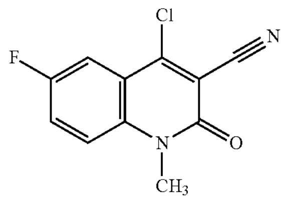 [SMILES: Cn1c(=O)c(C#N)c(Cl)c2cc(F)ccc21]

A mixture of 4.40 g 6-fluoro-4-hydroxy-1-methyl-2-oxo-1,2-dihydroquinoline-3-carbonitrile (intermediate 102, 20.0 mmol) and 19 mL phosphoric trichloride (200 mmol) was stirred overnight at 90° C. The reaction mixture was cooled down to rt, diluted with hexane and the resulting solid was filtered. The filter cake was carefully added to a half saturated solution of sodium bicarbonate, the resulting suspension was filtered, the solid was washed with water, ethyl acetate and then with ethanol and dried in vacuum to give 4.17 g of the title compound (100% purity, 88% yield).

$^1H$ NMR (400 MHz, DMSO-$d_6$) δ ppm 3.67 (s, 3H); 7.58-8.09 (m, 3H).

Intermediate 104

1,7-dimethyl-2H-3,1-benzoxazine-2,4(1H)-dione

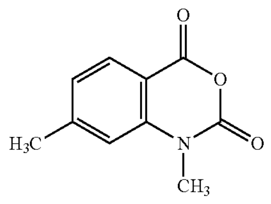

To a solution of 4.78 g 7-methyl-2H-3,1-benzoxazine-2,4(1H)-dione (27 mmol, CAS 63480-11-5) and 9.4 mL N,N-diisopropylethylamine (54 mmol) in 45 mL DMF was added 5.1 mL iodomethane (81 mmol) and was stirred overnight at rt. To the mixture was added ice water (300 ml). The solid that precipitated from this procedure was collected by filtration, washed with water and hexane and dried in vacuum to give 4.92 g of the title compound (95% purity, 91% yield).

$^1$H NMR (DMSO-$d_6$) δ: 7.89 (d, 1H), 7.29 (s, 1H), 7.15-7.19 (m, 1H), 3.45 (s, 3H), 2.46 (s, 3H).

LC-MS (Method 1): $R_t$=0.87 min; MS (ESIpos): m/z=192.1 $[M+H]^+$

Intermediate 105

4-hydroxy-1,7-dimethyl-2-oxo-1,2-dihydroquinoline-3-carbonitrile

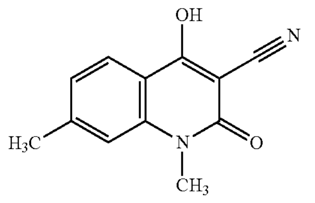 [SMILES: Cc1ccc2c(O)c(C#N)c(=O)n(C)c2c1]

A suspension of 4.8 g 1,7-dimethyl-2H-3,1-benzoxazine-2,4(1H)-dione (25.1 mmol, intermediate 104) in 65 mL 2-methyltetrahydrofuran was slowly treated with 28 mL triethylamine (200 mmol): followed by the addition of 11 mL ethyl cyanoacetate (100 mmol) and was stirred for 113 h at 80° C. After cooling to rt, the solvent was evaporated in vacuum, water/ethyl acetate (200 ml, 1:1) was added and the mixture was acidified to pH=1 by addition of hydrochloric acid (2 M). The solid that precipitated from this procedure was collected by filtration, washed with water, ethyl acetate and hexane and dried in vacuum to give 5.55 g of the title compound (98% purity, 101% yield).

$^1$H NMR (DMSO-$d_6$) δ: 7.97 (d, 1H), 7.38 (s, 1H), 7.16 (dd, 1H), 3.54 (s, 3H), 2.46 (s, 3H).

LC-MS (Method 1): $R_t$=0.72 min; MS (ESIpos): m/z=215.2 $[M+H]^+$

Intermediate 106

4-chloro-1,7-dimethyl-2-oxo-1,2-dihydroquinoline-3-carbonitrile

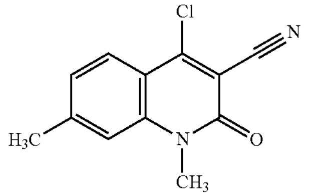 [SMILES: Cc1ccc2c(Cl)c(C#N)c(=O)n(C)c2c1]

A mixture of 5.45 g 4-hydroxy-1,7-dimethyl-2-oxo-1,2-dihydroquinoline-3-carbonitrile (24.9 mmol, intermediate 105) and 35 mL phosphoric trichloride (370 mmol) was stirred overnight at 90° C. After cooling to rt, ice water (400 ml) was added and the mixture was extracted with dichloromethane (3×). The combined organic phases were washed with brine, filtered (using a waterresistant filter) and concentrated under reduced pressure. The residue was stirred in dichloromethane and ethanol, the precipitate was collected by filtration, washed with dichloromethane and dried in vacuum. 2.4 g of the title compound were obtained (31% yield, 74% purity).

$^1$H NMR (DMSO-$d_6$) δ: 7.90-7.99 (m, 1H), 7.51-7.62 (m, 1H), 7.31-7.35 (m, 1H), 3.61-3.68 (m, 3H), 2.52-2.54 (m, 3H).

LC-MS (Method 1): $R_t$=1.07 min; MS (ESIpos): m/z=233.2 $[M+H]^+$

Intermediate 107

8-bromo-1,6-dimethyl-2H-3,1-benzoxazine-2,4(1H)-dione

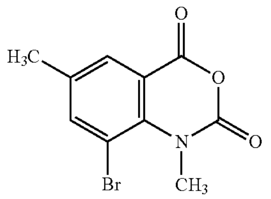

To a solution of 10 g 8-bromo-6-methyl-2H-3,1-benzoxazine-2,4(1H)-dione (39.1 mmol, CAS 177970-27-3) and 14 mL N,N-diisopropylethylamine (78 mmol) in 100 mL N,N-dimethylacetamide was added 7.3 mL iodomethane (120 mmol) at rt and was stirred overnight.

To the reaction was added 2000 mL water. The solid that precipitated from this procedure was collected by filtration, washed with water, ethanol and hexane and dried in vacuum. 7.2 g of the title compound were obtained (95% purity, 65% yield).

$^1$H NMR (DMSO-$d_6$) δ: 7.91-7.99 (m, 1H), 7.79-7.85 (m, 1H), 3.63 (s, 3H), 2.34 (s, 3H).

Intermediate 108

8-bromo-4-hydroxy-1,6-dimethyl-2-oxo-1,2-dihydroquinoline-3-carbonitrile

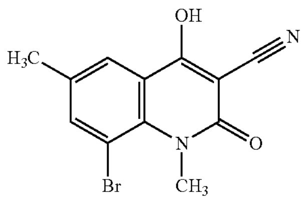 [SMILES: Cc1cc(Br)c2c(c1)c(O)c(C#N)c(=O)n2C]

A suspension of 7.2 g 8-bromo-1,6-dimethyl-2H-3,1-benzoxazine-2,4(1H)-dione (25.3 mmol, intermediate 107) in 150 mL THF was slowly treated with 28 mL triethylamine (200 mmol): followed by the addition of 4.1 mL ethyl cyanoacetate (38 mmol) and was stirred for 8 h at 70° C. After cooling to rt, ethyl acetate and water were added and the mixture was acidified to pH=1 by addition of hydrochloric acid (2 N). The mixture was extracted with ethyl acetate (2×). The combined organic phases were washed with brine and water, dried and concentrated under reduced pressure. The residue was stirred in ethyl acetate, the solid that precipitated from this procedure was collected by filtration to give 4.49 g of the title compound (95% purity, 57% yield).

$^1$H NMR (DMSO-$d_6$) δ: 7.71-7.90 (m, 2H), 3.55-3.71 (m, 3H), 2.26-2.38 (m, 3H).

LC-MS (Method 2): $R_t$=0.61 min; MS (ESIpos): m/z=294.0 $[M+H]^+$

Intermediate 109

8-bromo-4-chloro-1,6-dimethyl-2-oxo-1,2-dihydro-quinoline-3-carbonitrile

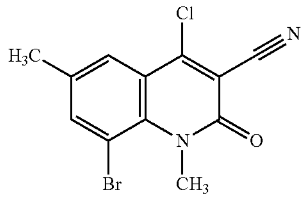 [SMILES: Cc1cc(Br)c2c(c1)c(Cl)c(C#N)c(=O)n2C]

A mixture of 4.49 g 8-bromo-4-hydroxy-1,6-dimethyl-2-oxo-1,2-dihydroquinoline-3-carbonitrile (15.3 mmol, intermediate 108) and 14 mL phosphoric trichloride (150 mmol) was stirred for 10 h at 90° C. After cooling to rt, ice water (1500 ml) w as added carefully and the mixture was adjusted to pH=10 with sodium carbonate. The mixture was extracted with dichloromethane (3×). The combined organic phases were washed with water, dried and concentrated under reduced pressure. The residue was purified by flash chromatography (silica, dichloromethane/methanol gradient 0-1%) to give 2.9 g of the title compound (95% purity, 58% yield).

$^1H$ NMR (DMSO-$d_6$) δ: 8.01-8.11 (m, 1H), 7.89-7.94 (m, 1H), 3.78 (s, 3H), 2.41 (s, 3H).

LC-MS (Method 2): $R_t$=1.19 min; MS (ESIpos): m/z=311.3 $[M+H]^+$

Intermediate 110

7-chloro-1-methyl-2H-3,1-benzoxazine-2,4(1H)-dione

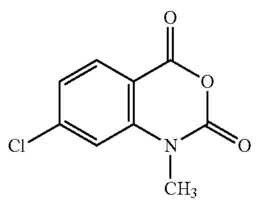

To a solution of 2 g 7-chloro-2H-3,1-benzoxazine-2,4(1H)-dione (9.82 mmol, CAS 40928-13-0): and 3.4 mL N,N-diisopropylethylamine (20 mmol) in 15 mL DMF was added 1.9 mL iodomethane (29 mmol) and was stirred overnight at rt. To the mixture was added ice water. The solid that precipitated from this procedure was collected by filtration, washed with water and hexane and dried in vacuum to give 2.50 g of the title compound (98% purity, 118% yield).

$^1H$ NMR (DMSO-$d_6$) δ: 8.00 (d, 1H), 7.59 (d, 1H), 7.39 (dd, 1H), 3.46 (s, 3H).

LC-MS (Method 1): $R_t$=0.90 min; MS (ESIpos): m/z=212.1 $[M+H]^+$

Intermediate 111

7-chloro-4-hydroxy-1-methyl-2-oxo-1,2-dihydroquinoline-3-carbonitrile

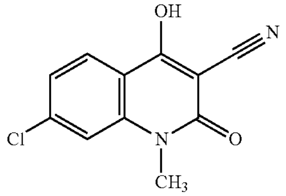 [SMILES: Cn1c(=O)c(C#N)c(Cl)c2ccc(Cl)cc21]

A suspension of 2.5 g 7-chloro-1-methyl-2H-3,1-benzoxazine-2,4(1H)-dione (11.6 mmol, intermediate 110) in 25 mL 2-methyltetrahydrofuran was slowly treated with 13 mL triethylamine (93 mmol) followed by the addition of 4.9 mL ethyl cyanoacetate (46 mmol) and was refluxed for 65 h. After cooling to rt, the solvent was evaporated in vacuum, water/ethyl acetate (1:1) was added and the mixture was acidified to pH=1 by addition of hydrochloric acid (2 M). The solid that precipitated from this procedure was collected by filtration, washed with water, ethyl acetate and hexane and dried in vacuum to give 2.55 g of the title compound (100% purity, 94% yield).

$^1H$ NMR (DMSO-$d_6$) δ: 8.05 (d, 1H), 7.59 (d, 1H), 7.34 (dd, 1H), 3.52 (s, 3H).

LC-MS (Method 2): $R_t$=0.57 min; MS (ESIneg): m/z=233.1 $[M-H]^-$

Intermediate 112

4,7-dichloro-1-methyl-2-oxo-1,2-dihydroquinoline-3-carbonitrile

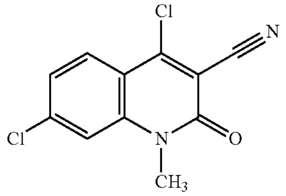

A mixture of 2.48 g 7-chloro-4-hydroxy-1-methyl-2-oxo-1,2-dihydroquinoline-3-carbonitrile (10.6 mmol, intermediate 111) and 15 mL phosphoric trichloride (160 mmol) was stirred overnight at 90° C. After cooling to rt, dichloromethane (20 ml) and ice water (500 ml) were added and the mixture was extracted with dichloromethane (3×). The combined organic phases were washed with brine, filtered (using a waterresistant filter) and concentrated under reduced pressure to give 2.46 g of the title compound (95% purity, 87% yield).

$^1H$ NMR (DMSO-$d_6$) δ: 8.07 (d, 1H), 7.85 (d, 1H), 7.55 (dd, 1H), 3.65 (s, 3H).

LC-MS (Method 1): $R_t$=1.10 min; MS (ESIpos): m/z=253.1 $[M+H]^+$

Intermediate 113

5-methyl-2-[(2S,4S)-2-methylpiperidin-4-yl]-1,3-benzoxazole

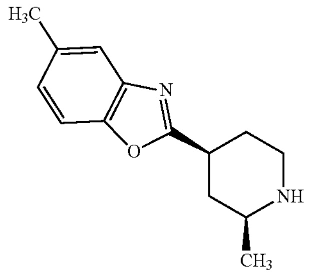 [SMILES: Cc1ccc2oc([C@H]3CCN[C@@H](C)C3)nc2c1]

686 mg 2-amino-4-methylphenol (5.57 mmol, CAS 95-84-1) and 1.00 g (2S,4S)-2-methylpiperidine-4-carboxylic acid hydrogen chloride salt (1:1) (5.57 mmol, CAS 1820569-68-3): were suspended in polyphosphoric acid and the mixture was stirred for 90 min. at 180° C. The hot reaction mixture was added dropwise into water and the mixture was adjusted to pH=10 with potassium hydroxide solution. The aqueous phase was extracted with ethyl acetate (2×), the combined organic phases were washed with brine and water, filtered through a waterresistant filter and the filtrate was concentrated under reduced pressure to give 970 mg of the title compound (95% purity, 72% yield).

$^1$H NMR (400 MHz, DMSO-$d_6$) δ ppm 0.97-1.05 (m, 3H) 1.20-1.32 (m, 1H) 1.45-1.60 (m, 1H): 1.90-2.03 (m, 2H) 2.40 (s, 3H) 2.58-2.70 (m, 2H) 2.94-3.06 (m, 2H) 7.14 (d, 1H) 7.46-7.54 (m, 2H).

LC-MS (Method 2): $R_t$=1.04 min; MS (ESIpos): m/z=231.8 $[M+H]^+$

Intermediate 114

7-fluoro-1-methyl-2H-3,1-benzoxazine-2,4(1H)-dione

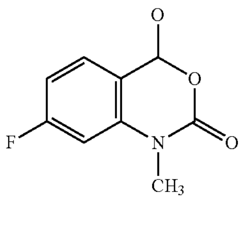

To a solution of 5 g 7-fluoro-2H-3,1-benzoxazine-2,4(1H)-dione (26.2 mmol, CAS 321-50-6) and 9.1 mL N,N-diisopropylethylamine (52 mmol) in 400 mL DMF was added 4.9 mL iodomethane (79 mmol) and was stirred overnight at rt. To the mixture was added ice water. The solid that precipitated from this procedure was collected by filtration, washed with water and hexane and dried in vacuum to give 3.75 g of the title compound (95% purity, 70% yield).

$^1$H NMR (DMSO-$d_6$) δ: 8.08 (dd, 1H), 7.40 (dd, 1H), 7.19 (td, 1H), 3.44 (s, 3H).

LC-MS (Method 1): $R_t$=0.79 min; MS (ESIpos): m/z=196.1 $[M+H]^+$

Intermediate 115

7-fluoro-4-hydroxy-1-methyl-2-oxo-1,2-dihydroquinoline-3-carbonitrile

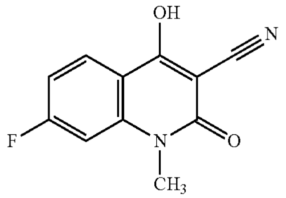

A suspension of 3.7 g 7-fluoro-1-methyl-2H-3,1-benzoxazine-2,4(1H)-dione (18 mmol, intermediate 114) in 40 mL 2-methyltetrahydrofuran was slowly treated with 20 mL triethylamine (144 mmol) followed by the addition of 7.7 mL ethyl cyanoacetate (72 mmol) and was refluxed for 73 h. After cooling to rt, the solvent was evaporated in vacuum, water and ethyl acetate was added and the mixture was acidified to pH=1 by addition of hydrochloric acid (2 M). The solid that precipitated from this procedure was collected by filtration, washed with water and hexane and dried in vacuum to give 3.09 g of the title compound (100% purity, 73% yield).

$^1$H NMR (DMSO-$d_6$) δ: 8.11 (dd, 1H), 7.37 (dd, 1H), 7.16 (td, 1H), 3.49 (s, 3H).

LC-MS (Method 1): $R_t$=0.68 min; MS (ESIneg): m/z=217.1 $[M-H]^-$

Intermediate 116

4-chloro-7-fluoro-1-methyl-2-oxo-1,2-dihydroquinoline-3-carbonitrile

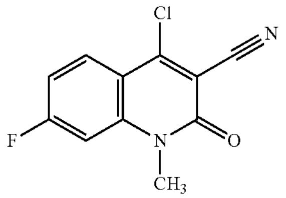 [SMILES: Cn1c(=O)c(C#N)c(Cl)c2ccc(F)cc21]

A mixture of 3 g 7-fluoro-4-hydroxy-1-methyl-2-oxo-1,2-dihydroquinoline-3-carbonitrile (13.7 mmol, intermediate 115) and 20 mL phosphoric trichloride (208 mmol) was stirred for 67 h at 70° C. and 4 h at 90° C. After cooling to rt, dichloro methane and ice water were added and the mixture was extracted with dichloromethane (3×). The combined organic phases were washed with brine, filtered (using a waterresistant filter) and concentrated under reduced pressure to give 2.46 g of the title compound (96% purity, 73% yield).

$^1$H NMR (DMSO-$d_6$) δ: 8.15 (dd, 1H), 7.67 (dd, 1H), 7.35-7.42 (m, 1H), 3.63 (s, 3H).

LC-MS (Method 1): $R_t$=1.00 min; MS (ESIneg): m/z=235.1 $[M-H]^-$

Intermediate 117

4-bromo-2-(piperidin-4-yl)-1,3-benzoxazole

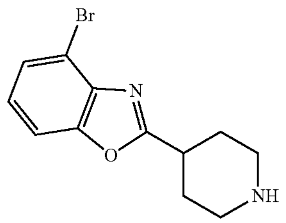 [SMILES: Brc1cccc2oc(C3CCNCC3)nc12]

3 g 2-amino-3-bromophenol (16 mmol, CAS 116435-77-9) and 2.06 g piperidine-4-carboxylic acid (16 mmol, CAS 498-94-2) were suspended in polyphosphoric acid and the mixture was stirred for 90 h at 180° C. The hot reaction mixture was added dropwise into water and the mixture was adjusted to pH=10 with potassium hydroxide solution. The aqueous phase was extracted with ethyl acetate (2×), the combined organic phases were washed with brine and water, filtered through a waterresistant filter and the filtrate was concentrated under reduced pressure to give 3 g of the title compound (90% purity, 60% yield).

$^{1}$H NMR (400 MHz, DMSO-$d_6$) δ ppm 0.97-1.04 (m, 3H) 1.19-1.31 (m, 1H) 1.45-1.59 (m, 1H): 1.90-2.04 (m, 2H) 2.40 (s, 3H) 2.58-2.70 (m, 2H) 2.94-3.06 (m, 2H) 7.14 (d, 1H) 7.46-7.54 (m, 2H).

LC-MS (Method 2): $R_t$=1.00 min; MS (ESIpos): m/z=283.3 $[M+H]^+$

Intermediate 118

Tert-Butyl 4-(4-bromo-1,3-benzoxazol-2-yl)piperidine-1-carboxylate

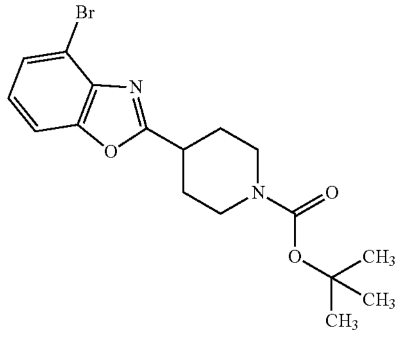 [SMILES: CC(C)(C)OC(=O)N1CCC(c2nc3c(Br)cccc3o2)CC1]

To a mixture of 1.50 g 4-bromo-2-(piperidin-4-yl)-1,3-benzoxazole (intermediate 117, 5.34 mmol), 4.6 mL N,N-diisopropylethylamine (27 mmol) and 1 mg N,N-dimethylpyridin-4-amine in 15 mL dichloromethane were added 2.3 g di-tert-butyl dicarbonate (10.7 mmol) in 5 mL dichloromethane. The mixture was stirred for 18 h at rt. The reaction mixture was diluted with water and the aqueous phase was extracted with dichloromethane. The combined organic layers were washed with water and brine, filtered and the filtrate was concentrated under reduced pressure. The residue was purified by flash chromatography (silica, dichloromethane/methanol gradient 0-3%) to give 1.4 g of the title compound (95% purity, 65% yield).

$^{1}$H NMR (400 MHz, DMSO-$d_6$) δ ppm 1.41 (s, 9H) 1.62-1.73 (m, 2H) 2.09 (br dd, 2H) 2.97 (br s, 2H) 3.23-3.31 (m, 1H) 3.97 (br d, 2H) 7.32 (t, 1H) 7.58 (dd, 1H) 7.73 (dd, 1H).

Intermediate 119

Tert-Butyl 4-[4-(2-methoxyethyl)-1,3-benzoxazol-2-yl]piperidine-1-carboxylate

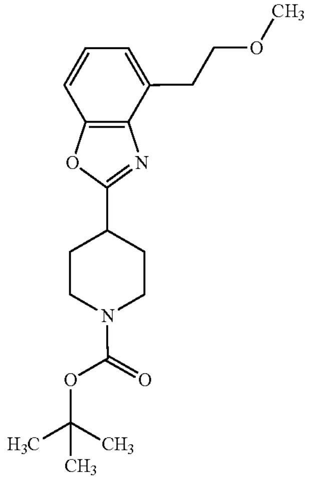 [SMILES: COCCc1cccc2oc(C3CCN(C(=O)OC(C)(C)C)CC3)nc12]

300 mg tert-butyl 4-(4-bromo-1,3-benzoxazol-2-yl)piperidine-1-carboxylate (787 μmol, intermediate 118), 17.7 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (15.7 μmol, CAS 870987-63-6) and 349 mg dilithium carbonate (4.72 μmol) were dissolved in the reaction vial in 4.5 mL N,N-dimethylacetamide and 14 mL (trifluoromethyl)benzene. In a separate vial the Ni-catalyst was prepared by dissolving 8.64 mg 1,2-dimethoxyethane-dichloronickel (1:1) (39.3 μmol) and 10.6 mg 4,4-di-tert-butyl-2,2-bipyridine (39.3 μmol) in N,N-dimethylacetamide followed by stirring for 5 min. The catalyst solution was syringed to the sealed reaction vial and was degassed with argon for 5 min., then 240 μL 1,1,1,3,3,3-hexamethyl-2-(trimethylsilyl)trisilane (790 μmol, CAS 1873-77-4) and 330 μL 1-bromo-2-methoxyethane (3.5 mmol) were added. The vial was placed in a water bath (to keep the temperature below 35° C.) and was subsequently irradiated by two 40 W Kessil LED Aquarium lamps for 18 h. The reaction was quenched with water, extracted with ethyl acetate, dried over sodium sulfate and concentrated in vacuum. The crude material was purified by flash chromatography (silica, dichloromethane/methanol gradient 0-2%). 170 mg of the title compound were obtained (98% purity, 59% yield).

$^{1}$H NMR (400 MHz, DMSO-$d_6$) δ ppm 1.38 (s, 9H) 1.58-1.71 (m, 2H) 2.05 (br dd, 2H) 2.94 (br s, 2H) 2.99-3.11 (m, 2H) 3.17-3.28 (m, 4H) 3.63 (t, 2H) 3.93 (br d, 2H) 7.16-7.26 (m, 2H): 7.48 (dd, 1H).

LC-MS (Method 2): $R_t$=1.38 min; MS (ESIpos): m/z=361.6 $[M+H]^+$

Intermediate 120

4-(2-methoxyethyl)-2-(piperidin-4-yl)-1,3-benzoxazole

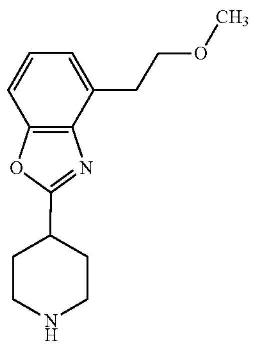 [SMILES: COCCc1cccc2oc(C3CCNCC3)nc12]

To a solution of 170 mg tert-butyl 4-[4-(2-methoxyethyl)-1,3-benzoxazol-2-yl]piperidine-1-carboxylate (intermediate 119, 472 μmol) in 6 mL dichloromethane was added 730 μL trifluoroacetic acid (9.4 mmol) and the mixture was stirred for 4 h at rt. The mixture was concentrated under reduced pressure and the residue was diluted with toluene (2×). The solvent was evaporated to give 300 mg of the title compound as a TFA salt (244% yield).

$^1$H NMR (400 MHz, DMSO-$d_6$) δ ppm 1.93-2.05 (m, 2H) 2.23-2.32 (m, 2H) 3.04-3.17 (m, 4H): 3.23-3.28 (m, 3H) 3.32-3.44 (m, 3H) 3.67 (t, 2H) 7.21-7.32 (m, 2H) 7.53 (dd, 1H) 8.63 (br s, 1H).

LC-MS (Method 2): Rt=0.98 min; MS (ESIpos): m/z=261.5 $[M+H]^+$

Intermediate 121

Tert-Butyl 4-(5-bromo-1,3-benzoxazol-2-yl)piperidine-1-carboxylate

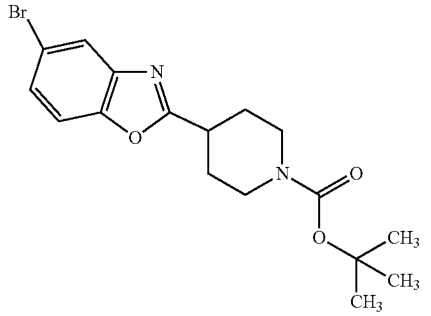 [SMILES: CC(C)(C)OC(=O)N1CCC(c2nc3cc(Br)ccc3o2)CC1]

To a mixture of 1.30 g 5-bromo-2-(piperidin-4-yl)-1,3-benzoxazole (intermediate 8, 4.62 mmol), 4.0 mL N,N-diisopropylethylamine (23 mmol) and 1 mg N,N-dimethylpyridin-4-amine in 15 mL dichloromethane were added 2.0 g di-tert-butyl dicarbonate (9.2 mmol) in 5 mL dichloromethane. The mixture was stirred for 18 h at rt. The reaction mixture was diluted with water and the aqueous phase was extracted with dichloromethane. The combined organic layers were washed with water and brine, filtered and the filtrate was concentrated under reduced pressure.

The residue was purified by flash chromatography (silica, dichloromethane/methanol gradient 0-3%) to give 1.3 g of the title compound (95% purity, 70% yield).

$^1$H NMR (400 MHz, DMSO-$d_6$) δ ppm 1.41 (s, 9H) 1.56-1.71 (m, 2H) 2.07 (br dd, 2H) 2.98 (br s, 2H) 3.25 (tt, 1H) 3.94 (br d, 2H) 7.53 (dd, 1H) 7.69 (d, 1H) 7.96 (d, 1H).

LC-MS (Method 2): Rt=1.46 min; MS (ESIpos): m/z=383.3 [M+H]+

Intermediate 122

Tert-Butyl 4-[5-(2-methoxyethyl)-1,3-benzoxazol-2-yl]piperidine-1-carboxylate

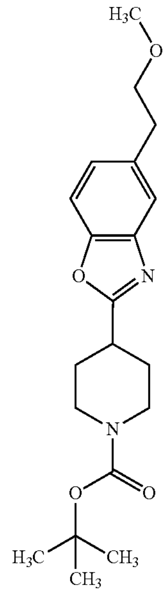 [SMILES: COCCc1ccc2oc(C3CCN(C(=O)OC(C)(C)C)CC3)nc2c1]

300 mg tert-butyl 4-(5-bromo-1,3-benzoxazol-2-yl)piperidine-1-carboxylate (787 μmol, intermediate 121), 17.7 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (15.7 μmol, CAS 870987-63-6) and 349 mg dilithium carbonate (4.72 μmol) were dissolved in the reaction vial in 4.5 mL N,N-dimethylacetamide and 14 mL (trifluoromethyl)benzene. In a separate vial the Ni-catalyst was prepared by dissolving 8.64 mg 1,2-dimethoxyethane-dichloronickel (1:1) (39.3 μmol) and 10.6 mg 4,4-di-tert-butyl-2,2-bipyridine (39.3 μmol) in N,N-dimethylacetamide followed by stirring for 5 min. The catalyst solution was syringed to the sealed reaction vial and was degassed with argon for 5 min., then 240 μL 1,1,1,3,3,3-hexamethyl-2-(trimethylsilyl)trisilane (790 μmol, CAS 1873-77-4) and 330 μL 1-bromo-2-methoxyethane (3.5 mmol) were added. The vial was placed in a water bath (to keep the temperature below 35° C.): and was subsequently irradiated by two 40 W Kessil LED Aquarium lamps for 18 h. The reaction was quenched with water, extracted with ethyl acetate, dried over sodium sulfate and concentrated in vacuum. The crude material was purified by flash chromatography (silica, dichloromethane/methanol gradient 0-2%). 90 mg of the title compound were obtained (98% purity, 31% yield).

$^1$H NMR (400 MHz, DMSO-$d_6$) δ ppm 1.41 (s, 9H) 1.56-1.71 (m, 2H) 2.06 (br dd, 2H) 2.86-3.10 (m, 4H) 3.17-3.28 (m, 4H) 3.54 (t, 2H) 3.94 (br d, 2H) 7.22 (dd, 1H) 7.56 (d, 1H) 7.55 (s, 1H).

LC-MS (Method 2): $R_t$=1.33 min; MS (ESIpos): m/z=361.6 $[M+H]^+$

Intermediate 123

5-(2-methoxyethyl)-2-(piperidin-4-yl)-1,3-benzoxazole

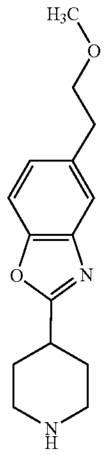 [SMILES: COCCc1ccc2oc(C3CCNCC3)nc2c1]

To a solution of 90 mg tert-butyl 4-[5-(2-methoxyethyl)-1,3-benzoxazol-2-yl]piperidine-1-carboxylate (intermediate 122, 250 µmol) in 3 mL dichloromethane was added 380 µL trifluoroacetic acid (5 mmol) and the mixture was stirred for 4 h at rt. The mixture was concentrated under reduced pressure and the residue was diluted with toluene (2×). The solvent was evaporated to give 130 mg of the title compound as a TFA salt (180% yield).

$^1$H NMR (400 MHz, DMSO-$d_6$) δ ppm 1.92-2.03 (m, 2H) 2.25 (br dd, 2H) 2.91 (t, 2H) 3.03-3.14 (m, 2H) 3.21-3.26 (m, 3H) 3.32-3.47 (m, 3H) 3.55 (t, 2H) 7.24 (dd, 1H) 7.58 (d, 1H): 7.57 (s, 1H).

LC-MS (Method 2): Rt=0.93 min; MS (ESIpos): m/z=261.5 [M+H]+

Intermediate 124

6-bromo-2-(piperidin-4-yl)-1,3-benzoxazole

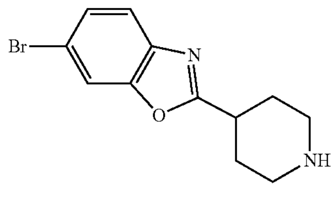 [SMILES: Brc1ccc2nc(C3CCNCC3)oc2c1]

4.5 g 2-amino-5-bromophenol (23.9 mmol, CAS 38191-34-3) and 3.09 g piperidine-4-carboxylic acid (23.9 mmol, CAS 498-94-2) were suspended in 13.9 g polyphosphoric acid and the mixture was stirred for 3 h at 180° C. The hot reaction mixture was added dropwise into water and the mixture was adjusted to pH=10 with potassium hydroxide solution. The aqueous phase was extracted with ethyl acetate (2×), the combined organic phases were washed with brine and water, filtered through a waterresistant filter and the filtrate was concentrated under reduced pressure. The residue was purified by flash chromatography (basic silica, hexane/dichloromethane gradient 0-100%). The impure product was purified by RP-HPLC (labomatic HD3000, AS-3000, Labcol Vario 4000 Plus, Knauer DAD 2600; column: Waters XBrigde C18 5µ 100×50 mm; eluent A: water+0.2 vol. % aq. ammonia (32%), eluent B: acetonitrile; gradient: 0.00-0.50 min. 28% B (100→150 mL/min.), 0.50-7.00 min. 28-40% B (150 mL/min.); DAD 254 nm) to give 640 mg of the title compound (98% purity, 9% yield).

$^1$H NMR (400 MHz, DMSO-$d_6$) δ ppm 1.60-1.71 (m, 2H) 1.97 (br dd, 2H) 2.12 (br s, 1H): 2.54-2.64 (m, 2H) 2.98 (dt, 2H) 3.07 (tt, 1H) 7.49-7.53 (m, 1H) 7.66 (d, 1H) 8.01 (d, 1H).

LC-MS (Method 2): Rt=1.06 min; MS (ESIpos): m/z=281.4 [M+H]+

Intermediate 125

Tert-Butyl 4-(6-bromo-1,3-benzoxazol-2-yl)piperidine-1-carboxylate

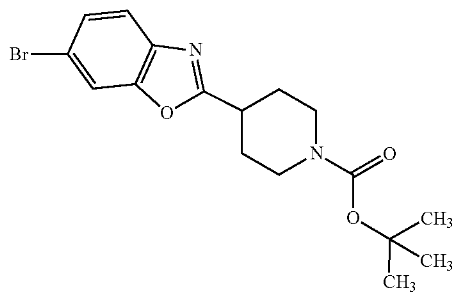 [SMILES: CC(C)(C)OC(=O)N1CCC(c2nc3ccc(Br)cc3o2)CC1]

To a mixture of 640 mg 6-bromo-2-(piperidin-4-yl)-1,3-benzoxazole (intermediate 124, 2.28 mmol), 2.0 mL N,N-diisopropylethylamine (11 mmol) and 1 mg N,N-dimethylpyridin-4-amine in 10 mL dichloromethane were added 0.99 g di-tert-butyl dicarbonate (4.6 mmol) in 5 mL dichloromethane. The mixture was stirred for 18 h at rt. The reaction mixture was diluted with water and the aqueous phase was extracted with dichloromethane. The combined organic layers were washed with water and brine, filtered and the filtrate was concentrated under reduced pressure. The residue was purified by flash chromatography (silica, dichloromethane/methanol gradient 0-3%) to give 860 mg of the title compound (99% purity, 98% yield).

$^1$H NMR (400 MHz, DMSO-$d_6$) δ ppm 1.41 (s, 9H) 1.59-1.71 (m, 2H) 2.07 (br dd, 2H) 2.98 (br s, 2H) 3.16-3.32 (m, 1H) 3.94 (br d, 2H) 7.52 (dd, 1H) 7.67 (d, 1H) 8.03 (d, 1H).

LC-MS (Method 2): Rt=1.46 min; MS (ESIpos): m/z=381.3 [M+H]+

Intermediate 126

Tert-Butyl 4-[6-(2-methoxyethyl)-1,3-benzoxazol-2-yl]piperidine-1-carboxylate

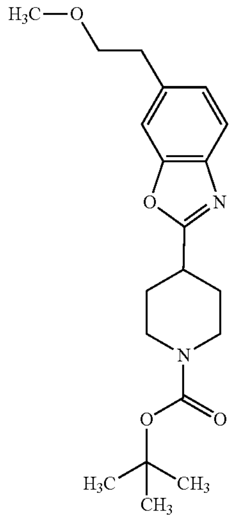 [SMILES: COCCc1ccc2nc(C3CCN(C(=O)OC(C)(C)C)CC3)oc2c1]

300 mg tert-butyl 4-(6-bromo-1,3-benzoxazol-2-yl)piperidine-1-carboxylate (787 µmol, intermediate 125), 17.7 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (15.7 µmol, CAS 870987-63-6) and 349 mg dilithium carbonate (4.72 µmol) were dissolved in the reaction vial in 4.5 mL N,N-dimethylacetamide and 14 mL (trifluoromethyl)benzene. In a separate vial the Ni-catalyst was prepared by dissolving 8.64 mg 1,2-dimethoxyethane-dichloronickel (1:1) (39.3 µmol) and 10.6 mg 4,4-di-tert-butyl-2,2-bipyridine (39.3 µmol) in N,N-dimethylacetamide followed by stirring for 5 min. The catalyst solution was syringed to the sealed reaction vial and was degassed with argon for 5 min., then 240 µL 1,1,1,3,3,3-hexamethyl-2-(trimethylsilyl)trisilane (790 µmol, CAS 1873-77-4) and 330 µL 1-bromo-2-methoxyethane (3.5 mmol) were added. The vial was placed in a water bath (to keep the temperature below 35° C.): and was subsequently irradiated by two 40 W Kessil LED Aquarium lamps for 12 h. The reaction was quenched with water, extracted with ethyl acetate, dried over sodium sulfate and concentrated in vacuum. The crude material was purified by flash chromatography (silica, dichloromethane/methanol gradient 0-2%). 100 mg of the title compound were obtained (98% purity, 34% yield).

$^{1}$H NMR (400 MHz, DMSO-$d_6$) δ ppm 1.41 (s, 9H) 1.56-1.75 (m, 2H) 2.06 (br dd, 2H) 2.89-3.07 (m, 4H) 3.17-3.25 (m, 4H) 3.55 (t, 2H) 3.94 (br d, 2H) 7.21 (dd, 1H) 7.54 (s, 1H) 7.58 (d, 1H).

LC-MS (Method 2): $R_t$=1.32 min; MS (ESIpos): m/z=361.6 $[M+H]^+$

Intermediate 127

6-(2-methoxyethyl)-2-(piperidin-4-yl)-1,3-benzoxazole

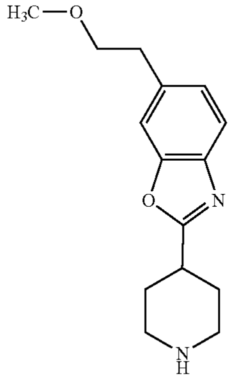 [SMILES: COCCc1ccc2nc(C3CCNCC3)oc2c1]

To a solution of 100 mg tert-butyl 4-[6-(2-methoxyethyl)-1,3-benzoxazol-2-yl]piperidine-1-carboxylate (intermediate 126, 277 µmol) in 3 mL dichloromethane was added 430 µL trifluoroacetic acid (5.5 mmol) and the mixture was stirred for 4 h at rt. The mixture was concentrated under reduced pressure and the residue was diluted with toluene (2×). The solvent was evaporated to give 160 mg of the title compound as a TFA salt (199% yield).

$^{1}$H NMR (400 MHz, DMSO-$d_6$) δ ppm 1.91-2.02 (m, 2H) 2.22-2.32 (m, 2H) 2.93 (t, 2H) 3.03-3.15 (m, 2H) 3.21-3.27 (m, 3H) 3.31-3.42 (m, 3H) 3.56 (t, 2H) 7.23 (dd, 1H) 7.56 (s, 1H): 7.60 (d, 1H).

LC-MS (Method 2): Rt=0.93 min; MS (ESIpos): m/z=261.5 [M+H]+

Intermediate 128

Tert-Butyl 4-[5-(oxetan-3-yl)-1,3-benzoxazol-2-yl]piperidine-1-carboxylate

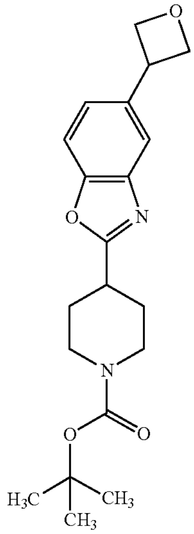 [SMILES: CC(C)(C)OC(=O)N1CCC(c2nc3cc(C4COC4)ccc3o2)CC1]

300 mg tert-butyl 4-(5-bromo-1,3-benzoxazol-2-yl)piperidine-1-carboxylate (787 μmol, intermediate 121), 17.7 mg bis{3,5-difluoro-2-[5-(trifluoromethyl)pyridin-2-yl]phenyl}iridium-(I)hexafluorophosphate-4,4-di-tert-butyl-2,2-bipyridine (1:1:1) (15.7 μmol, CAS 870987-63-6): and 113 mg lithium hydroxide (4.72 μmol) were dissolved in the reaction vial in 14 mL 1,2-dimethoxyethane. In a separate vial the Ni-catalyst was prepared by dissolving 8.64 mg 1,2-dimethoxyethane-dichloronickel (1:1) (39.3 μmol) and 10.6 mg 4,4-di-tert-butyl-2,2-bipyridine (39.3 μmol) in 1,2-dimethoxyethane followed by stirring for 5 min. The catalyst solution was syringed to the sealed reaction vial and was degassed with argon for 5 min., then 240 μL 1,1,1,3,3,3-hexamethyl-2-(trimethylsilyl)trisilane (790 μmol, CAS 1873-77-4) and 485 mg 3-bromooxetane (3.54 mmol) were added. The vial was placed in a water bath (to keep the temperature below 35° C.) and was subsequently irradiated by two 40 W Kessil LED Aquarium lamps for 12 h. The reaction was quenched with water, extracted with ethyl acetate, dried over sodium sulfate and concentrated in vacuum. The crude material was purified by flash chromatography (silica, dichloromethane/methanol gradient 0-2%). The impure product was purified by RP-HPLC (column: X-Bridge C18 5 μm 100x30 mm, mobile phase: acetonitrile/water (0.2 vol. % ammonia 32%)-gradient). 50 mg of the title compound were obtained (99% purity, 18% yield).

$^1$H NMR (400 MHz, DMSO-$d_6$) δ ppm 1.41 (s, 9H) 1.61-1.72 (m, 2H) 2.04-2.11 (m, 2H) 2.98 (br s, 2H) 3.15-3.31 (m, 1H) 3.94 (br d, 2H) 4.33-4.41 (m, 1H) 4.65 (dd, 2H) 4.96 (dd, 2H): 7.39 (dd, 1H) 7.66 (d, 1H) 7.74 (d, 1H).

Intermediate 129

5-(oxetan-3-yl)-2-(piperidin-4-yl)-1,3-benzoxazole

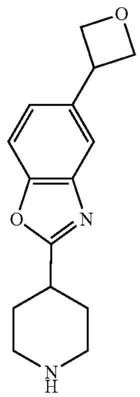 [SMILES: c1cc2oc(C3CCNCC3)nc2cc1C1COC1]

To a solution of 50 mg tert-butyl 4-[5-(oxetan-3-yl)-1,3-benzoxazol-2-yl]piperidine-1-carboxylate (intermediate 128, 139 μmol) in 1.5 mL dichloromethane was added 210 μL trifluoroacetic acid (2.8 mmol) and the mixture was stirred for 4 h at rt. The mixture was concentrated under reduced pressure and the residue was diluted with toluene (2×). The solvent was evaporated to give 80 mg of the title compound as a TFA salt (200% yield).

LC-MS (Method 2): Rt=0.82 min; MS (ESIpos): m/z=259.5 [M+H]+

Intermediate 130

1-methyl-7-(trifluoromethyl)-2H-3,1-benzoxazine-2,4(1H)-dione

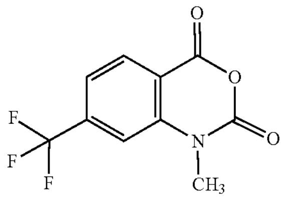 [SMILES: Cn1c(=O)oc(=O)c2ccc(C(F)(F)F)cc21]

To a solution of 2 g 7-(trifluoromethyl)-2H-3,1-benzoxazine-2,4(1H)-dione (8.22 mmol, CAS 97928-01-3) and 2.9 mL N,N-diisopropylethylamine (16 mmol) in 15 mL DMF was added 1.6 mL iodomethane (25 mmol) and was stirred overnight at rt. To the mixture was added ice water. The solid that precipitated from this procedure was collected by filtration, washed with water and hexane and dried in vacuum to give 1.90 g of the title compound (96% purity, 91% yield).

$^1$H NMR (400 MHz, DMSO-$d_6$) δ ppm 3.53 (s, 3H) 7.66 (dd, 1H) 7.74 (s, 1H) 8.20 (d, 1H).

LC-MS (Method 1): $R_t$=1.01 min; MS (ESIpos): m/z=246.1 $[M+H]^+$

Intermediate 131

4-hydroxy-1-methyl-2-oxo-7-(trifluoromethyl)-1,2-dihydroquinoline-3-carbonitrile

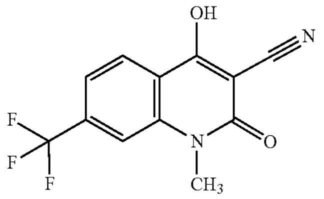 [SMILES: Cn1c(=O)c(C#N)c(O)c2ccc(C(F)(F)F)cc21]

A suspension of 1.87 g 1-methyl-7-(trifluoromethyl)-2H-3,1-benzoxazine-2,4(1H)-dione (7.32 mmol, intermediate 130) in 22 mL 2-methyltetrahydrofuran was slowly treated with 8.2 mL triethylamine (59 mmol) followed by the addition of 3.1 mL ethyl cyanoacetate (29 mmol) and was refluxed for 86 h. After cooling to rt, the solvent was evaporated in vacuum, water and ethyl acetate (1:1) was added and the mixture was acidified to pH=1 by addition of hydrochloric acid (2 M). The solid that precipitated from this procedure was collected by filtration, washed with water, ethyl acetate and less hexane and dried in vacuum to give 1.06 g of the title compound (100% purity, 54% yield).

$^1$H NMR (400 MHz, DMSO-$d_6$) δ ppm 3.56 (s, 3H) 7.55 (dd, 1H) 7.70 (s, 1H) 8.22 (d, 1H). LC-MS (Method 1): $R_t$=0.84 min; MS (ESIneg): m/z=267.2 $[M-H]^-$ Intermediate 132

4-chloro-1-methyl-2-oxo-7-(trifluoromethyl)-1,2-dihydroquinoline-3-carbonitrile

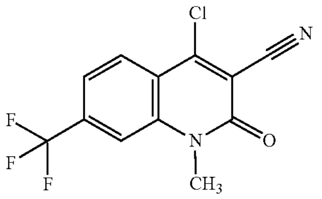 [SMILES: Cn1c(=O)c(C#N)c(Cl)c2ccc(C(F)(F)F)cc21]

A mixture of 1.02 g 4-hydroxy-1-methyl-2-oxo-7-(trifluoromethyl)-1,2-dihydroquinoline-3-carbonitrile (3.82 mmol, intermediate 131) and 5.3 mL phosphoric trichloride (57 mmol) was stirred overnight at 90° C. After cooling to rt, ice water was added and the mixture was extracted with dichloromethane (3×). The combined organic phases were washed with brine, filtered (using a waterresistant filter) and concentrated under reduced pressure to give 916 mg of the title compound (80% purity, 67% yield).

$^1$H NMR (400 MHz, DMSO-$d_6$) δ ppm 3.73 (s, 3H) 7.81 (dd, 1H) 8.00 (s, 1H) 8.29 (d, 1H).

LC-MS (Method 1): $R_t$=1.16 min; MS (ESIpos): m/z=287.2 $[M+H]^+$

Intermediate 133

7-methoxy-1-methyl-2H-3,1-benzoxazine-2,4(1H)-dione

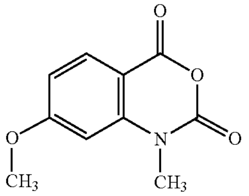

To a solution of 420 g potassium carbonate in 300 mL DMF was added 235 g 7-methoxy-2H-3,1-benzoxazine-2,4(1H)-dione (1.22 mol, CAS 128076-63-1) and 259 g iodomethane (1.82 mol, 113 ml). The mixture was stirred at 20° C. for 1 2 h. The reaction was monitored by LC-MS until complete consumption of 7-methoxy-2H-3,1-benzoxazine-2,4(1H)-dione. The reaction mixture was added to ice water (2000 ml), stirred for 0.5 h and filtered and concentrated under vacuum to give 218 g of the title compound (87% yield) as yellow solid.

$^1$H-NMR (400 MHz, DMSO-d6) δ[ppm]: 7.92 (d, 3H); 6.91 (dd, 1H); 6.83 (d, 1H); 3.93 (s, 3H); 3.45 (s, 3H).

Intermediate 134

4-hydroxy-7-methoxy-1-methyl-2-oxo-1,2-dihydroquinoline-3-carbonitrile

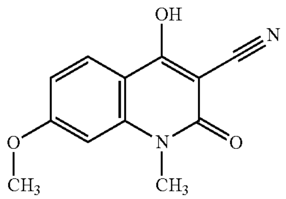 [SMILES: COc1ccc2c(Cl)c(C#N)c(=O)n(C)c2c1]

To a solution of 218 g 7-methoxy-1-methyl-2H-3,1-benzoxazine-2,4(1H)-dione (intermediate 133) and 159 g ethyl cyanoacetate in 2 L DMF was added 264 g potassium tert-butoxide. The mixture was stirred at 120° C. for 12 h. The reaction mixture was poured into 1000 mL water, extracted with ethyl acetate, the aqueous phase was adjusted pH=2~3 with 6 M hydrochloric acid (400 ml) and stirred for 1 h at 0° C., then filtered and dried over sodium sulfate and evaporated in vacuum to give 130 g of the title compound (48% yield) as a yellow solid.

$^1$H-NMR (400 MHz, DMSO-d6) δ[ppm]: 8.03 (d, 1H); 6.96-6.92 (m, 2H); 3.93 (s, 3H); 3.54 (s, 3H).

Intermediate 135

7-bromo-4-chloro-1-methyl-2-oxo-1,2-dihydroquinoline-3-carbonitrile

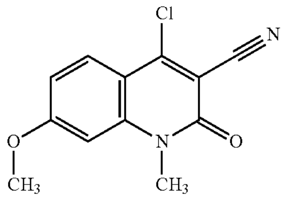

A solution of 50 g 4-hydroxy-7-methoxy-1-methyl-2-oxo-1,2-dihydroquinoline-3-carbonitrile (intermediate 134) in 430 mL phosphoric trichloride was stirred at 110° C. for 12 h. The solvent was removed in vacuum and to the residue was added 500 mL ice water and stirred for 12 h. The reaction mixture was filtered and concentrated under vacuum to give 47.5 g of the title compound (88% yield) as a brown solid.

$^1$H-NMR (400 MHz, DMSO-d6) δ[ppm]: 7.97 (d, 1H); 7.11 (dd, 1H); 7.05 (d, 1H); 3.99 (s, 3H); 3.64 (s, 3H).

Intermediate 136

4-chloro-7-hydroxy-1-methyl-2-oxo-1,2-dihydroquinoline-3-carbonitrile

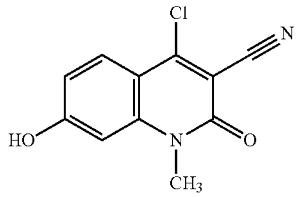 [SMILES: Cn1c(=O)c(C#N)c(Cl)c2ccc(O)cc21]

To a solution of 15 g 7-bromo-4-chloro-1-methyl-2-oxo-1,2-dihydroquinoline-3-carbonitrile (intermediate 135) in 350 mL dichloromethane at −40° C. was added 117 g boron tribromide (45.0 ml). Then the mixture was stirred at 20° C. for 12 h. The conversion was checked by LC-MS to indicate ~10% of left starting material. The residue was poured into 6 L ice water and filtered. To the reaction mixture was added 1.5 L sat. aqueous sodium bicarbonate solution and the mixture was stirred for 2 h, then the mixture was filtered and dried over sodium sulfate. The solvent was removed in vacuum and to the resulting residue was added 500 mL DMSO. The mixture was stirred for 3 h, then filtered and washed with water (100 ml, 3×), the product was dried in vacuum to give 3.34 g of the title compound (24% yield) as a light brown solid.

$^1$H-NMR (400 MHz, DMSO-d6) δ[ppm]: 11.28 (brs, 1H); 7.89 (d, 1H); 6.94 (dd, 1H); 6.85 (s, 1H); 3.55 (s, 3H).

Intermediate 137

Tert-Butyl 4-(quinoxalin-2-yl)piperidine-1-carboxylate

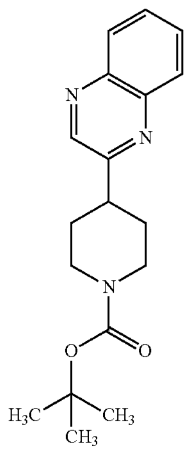 [SMILES: CC(C)(C)OC(=O)N1CCC(c2cnc3ccccc3n2)CC1]

4 times in parallel 2-bromoquinoxaline (150 mg, 718 μmol), tert-butyl 4-bromopiperidine-1-carboxylate (569 mg, 2.15 mmol), $Ir[dF(CF_3)ppy]_2(dtbbpy)PF_6$ (16.1 mg, 14.4 μmol), TTMSS (220 μl, 720 μmol, CAS:1873-77-4) and sodium carbonate (304 mg, 2.87 mmol) were dissolved in the reaction vial in 6 mL (N,N-dimethylacetamide:benzotrifluoride 1:2). In a separate vial, the Nickel catalyst was prepared by dissolving Nickel (II) chloride dimethoxyethane adduct (790 μg, 3.6 μmol, CAS: 29046-78-4) and the 4,4'-Di-tert-butyl-2,2'-bipyridine (960 μg, 3.6 μmol; CAS: 72914-19-3) in solvent (100-fold amount in 10 mL) followed by stirring for 5 min. The catalyst solution (0.1 mL) was syringed to the sealed reaction vial and Ar was bubbled through the solution for another 5 min. The MW-vial was placed in a water bath (to keep the temp. below 35° C.) and was subsequently irradiated by two 40 W Kess il LED lamps. After 5 h the reaction was quenched with ½ sat. sodium bicarbonate aqueous solution, extracted three times with ethyl acetate, dried over sodium sulphate and concentrated in vacuo. The crude material was purificated by RP-HPLC. Combined product fractions were evaporated and lyophilized to obtain 203 mg of the title compound (81% yield).

$^1$H NMR (400 MHz, DMSO-$d_6$) δ ppm 1.43 (s, 10H) 1.72 (br qd, 2H) 1.96 (br d, 2H) 2.91 (br s, 2H) 3.21 (br tt, 1H) 4.12 (br d, 2H) 7.77-7.86 (m, 2H) 8.00-8.10 (m, 2H) 8.96 (s, 1H):

LC-MS Method 2): $R_t$=1.30 min; MS (ESIpos): m/z=314 $[M+H]^+$

Intermediate 138

2-(piperidin-4-yl)quinoxaline

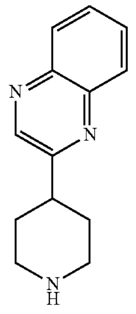 [SMILES: c1ccc2nc(C3CCNCC3)cnc2c1]

A solution of 190 mg tert-butyl 4-(quinoxalin-2-yl)piperidine-1-carboxylate (0.58 mmol, intermediate 137) in 3.7 mL dichloromethane was treated with 0.44 mL TFA (5.8 mmol) at room temperature and stirred over night. After complete consumption of starting material the reaction mixture was evaporated in vacuo at 70° C. For complete removal of remaining TFA the crude product was coevaporated with toluene (2×). The product was obtained as the TFA salt in quantitative yield.

$^1$H NMR (400 MHz, DMSO-$d_6$) δ ppm 1.96-2.10 (m, 2H) 2.13-2.23 (m, 2H) 3.03-3.17 (m, 2H): 3.33-3.49 (m, 5H) 7.80-7.90 (m, 2H) 8.01-8.06 (m, 1H) 8.07-8.12 (m, 1H) 8.28-8.44 (m, 1H) 8.58-8.72 (m, 1H) 8.95 (s, 1H):

Intermediate 139

Tert-Butyl 4-(1-methyl-1H-pyrazol-4-yl)-3,6-dihydropyridine-1(2H)-carboxylate

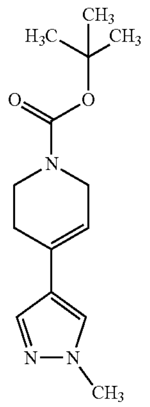 [SMILES: Cn1cc(C2=CCN(C(=O)OC(C)(C)C)CC2)cn1]

To a solution of 200 mg tert-butyl 4-(4,4,5,5-tetramethyl-1,3,2-dioxaborolan-2-yl)-3,6-dihydropyridine-1(2H)-carboxylate (0.65 mmol, CAS 286961-14-6) in 3.7 mL 1,4-dioxane was added 38 mg 4-bromo-1-methyl-1H-pyrazole (67 μmol, CAS 15803-02-8). The mixture was sparged with argon for 5 min. Then 38 mg tetrakis(triphenylphosphine) palladium (32 μmol, CAS 14221-01-3), 268 mg potassium carbonate (1.94 mmol) and 0.43 mL water were added. The reaction mixture was stirred overnight at 80° C.

The reaction mixture was diluted with water and extracted 3× with diethylether. The combined organic layers were washed with water and brine, dried and concentrated under reduced pressure. The crude product was purified by RP-HPLC. After evaporation and lyophilization 106 mg of the title compound (35% yield) were obtained.

1H-NMR (400 MHz, DMSO-d6): δ [ppm]=1.37-1.44 (m, 9H), 2.23-2.33 (m, 2H), 3.48 (t, 2H), 3.77-3.82 (m, 3H), 3.91 (br s, 2H), 5.90 (br s, 1H), 7.55 (d, 1H), 7.73 (s, 1H). LC-MS Method 2): $R_t$=1.07 min; MS (ESIpos): m/z=264 $[M+H]^+$ Intermediate 140

4-(1-methyl-1H-pyrazol-4-yl)-1,2,3,6-tetrahydropyridine

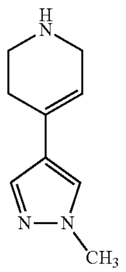

To a icebath cooled solution of 106 mg tert-butyl 4-(1-methyl-1H-pyrazol-4-yl)-3,6-dihydropyridine-1(2H)-carboxylate (0.225 mmol, intermediate 139) in 2 mL dichloromethane was added 0.17 mL TFA (2.3 mmol). The reaction mixture stirred overnight at room temperature. After consumption of starting material the reaction mixture was basified with 10 eq. aqueous ammonia (33%) and then concentrated under reduced pressure. The crude product (179 mg) was directly used in the next step.

LC-MS Method 2): $R_t$=0.61 min; MS (ESIpos): m/z=164 $[M+H]^+$

Intermediate 141

1-methyl-4-[4-(1-methyl-1H-pyrazol-4-yl)-3,6-dihydropyridin-1(2H)-yl]-2-oxo-1,2-dihydroquinoline-3-carbonitrile

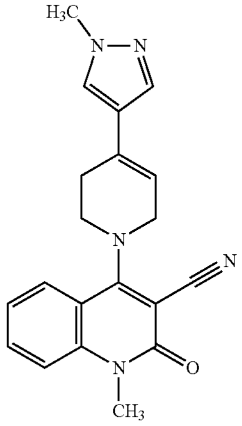 [SMILES: Cn1cc(C2=CCN(c3c(C#N)c(=O)n(C)c4ccccc34)CC2)cn1]

To a suspension of 48 mg 4-chloro-1-methyl-2-oxo-1,2-dihydroquinoline-3-carbonitrile (0.22 mmol) in 0.77 mL DMSO was added 0.11 mL N,N-diisopropylethylamine (0.66 mmol) and 179 mg 4-(1-methyl-1H-pyrazol-4-yl)-1,2,3,6-tetrahydropyridine (0.22 mmol, intermediate 140). The reaction mixture was stirred for 2 h at 90° C. Upon complete consumption of starting material the solvents were evaporated and the crude product was purified by RP-HPLC. The title compound was obtained in 28 mg (34% yield).

1H-NMR (400 MHz, DMSO-d6): 5 [ppm]=2.67 (br s, 2H), 3.58 (s, 3H), 3.77-3.84 (m, 5H), 4.27 (br d, 2H), 6.09 (t, 1H), 7.29-7.37 (m, 1H), 7.57 (dd, 1H), 7.63 (d, 1H), 7.74 (ddd, 1H), 7.81-7.86 (m, 2H). LC-MS (Method 1): $R_t$=0.92 min; MS (ESIpos): m/z=346 $[M+H]^+$ Intermediate 142

Tert-Butyl 4-(3,4-dimethoxyphenyl)-3,6-dihydropyridine-1(2H)-carboxylate

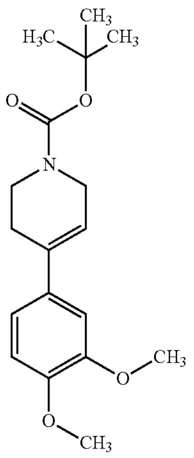 [SMILES: COc1ccc(C2=CCN(C(=O)OC(C)(C)C)CC2)cc1OC]

To a solution of 200 mg tert-butyl 4-(4,4,5,5-tetramethyl-1,3,2-dioxaborolan-2-yl)-3,6-dihydropyridine-1(2H)-carboxylate (0.65 mmol, CAS 286961-14-6) in 3.7 mL 1,4-dioxane was added 93 µl 4-bromo-1,2-dimethoxybenzene (0.65 mmol, CAS 2859-78-1). The mixture was sparged with argon for 5 min. Then Then 38 mg tetrakis(triphenylphosphine)palladium (32 µmol), 268 mg potassium carbonate (1.9 mmol) and 0.43 mL water were added. The reaction mixture was stirred overnight at 80° C. The reaction mixture was diluted with water and extracted 3× with diethylether. The combined organic layers were washed with water and brine, dried and concentrated under reduced pressure. The crude product was purified by RP-HPLC. The received fractions were concentrated under reduced pressure. The product was obtained in 61% yield (135 mg).

1H-NMR (400 MHz, DMSO-d6): 5 [ppm]=1.42 (s, 9H), 2.44 (br d, 2H), 3.52 (t, 2H), 3.74 (s, 3H), 3.77 (s, 3H), 3.94-4.01 (m, 2H), 6.07 (br s, 1H), 6.88-6.96 (m, 2H), 7.01 (d, 1H).

LC-MS Method 2): $R_t$=1.30 min; MS (ESIpos): m/z=320 $[M+H]^+$

Intermediate 143

4-(3,4-dimethoxyphenyl)-1,2,3,6-tetrahydropyridine

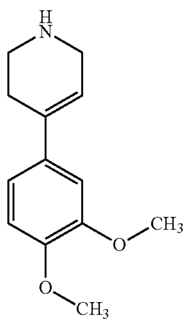 [SMILES: COc1ccc(C2=CCNCC2)cc1OC]

To a icebath cooled solution of 160 mg tert-butyl 4-(3,4-dimethoxyphenyl)-3,6-dihydropyridine-1(2H)-carboxylate (0.5 mmol, intermediate 142) in 10 mL dichloromethane was added 0.39 mL TFA (5 mmol). The reaction mixture stirred overnight at room temperature. The reaction mixture was basified with 10 eq. ammonia (aqueous 33%-solution) and then concentrated under reduced pressure. The crude product was directly used in the next step.

$^1$H-NMR (400 MHz, DMSO-d6): 5 [ppm]=2.66 (dt, 2H), 3.28-3.36 (m, 2H), 3.74-3.76 (m, 2H), 6.13 (t, 1H), 6.92-7.01 (m, 2H), 7.04 (d, 1H). LC-MS Method 2): $R_t$=0.88 min; MS (ESIpos): m/z=220 $[M+H]^+$ Intermediate 144

4-[4-(3,4-dimethoxyphenyl)-3,6-dihydropyridin-1(2H)-yl]-1-methyl-2-oxo-1,2-dihydroquinoline-3-carbonitrile

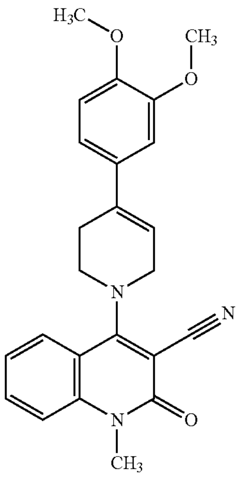 [SMILES: COc1ccc(C2=CCN(c3c(C#N)c(=O)n(C)c4ccccc34)CC2)cc1OC]

To a suspension of 108 mg 4-chloro-1-methyl-2-oxo-1,2-dihydroquinoline-3-carbonitrile (0.5 mmol) in 1.7 mL DMSO was added N,N-diisopropylethylamine and 247 mg 4-(3,4-dimethoxyphenyl)-1,2,3,6-tetrahydropyridine (intermediate 144, 44% purity, 0.5 mmol). The reaction mixture was stirred 2 h at 90° C. The product was isolated by RP-HPLC (87 mg, 43% yield).

$^1$H-NMR (400 MHz, DMSO-d6): δ [ppm]=2.82 (br s, 2H), 3.58 (s, 3H), 3.76 (s, 3H), 3.80 (s, 3H), 3.83 (t, 2H), 4.35 (br d, 2H), 6.28 (s, 1H), 6.92-6.99 (m, 1H), 7.02-7.08 (m, 1H), 7.12 (d, 1H), 7.30-7.37 (m, 1H), 7.58 (d, 1H), 7.75 (ddd, 1H), 7.87 (dd, 1H).

Intermediate 145

5-methyl-2-[(2S,4S)-2-methylpiperidin-4-yl]-1,3-benzoxazole

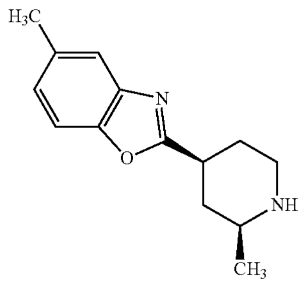 [SMILES: Cc1ccc2oc([C@H]3CCN[C@@H](C)C3)nc2c1]

686 mg 2-amino-4-methylphenol (5.6 mmol, CAS 95-84-1) and 1 g (2S,4S)-2-methylpiperidine-4-carboxylic acid hydrogen chloride (5.57 mmol, CAS 1820569-68-3) were treated with 3.23 g polyphosphoric acid at 180° C. oil bath temperature f or 90 min. The reaction mixture was poured into water and basified with aqueous potassium hydroxide solution. The aqueous layer was extracted with diethylether (2×) and the combined organic layers were washed with brine and water. The organic layers were dried and the solvent was evaporated. The title compound was obtained in 72% yield (970 mg).

LC-MS Method 2): $R_t$=1.04 min; MS (ESIpos): m/z=231 $[M+H]^+$

Intermediate 146

Tert-Butyl 4-(3-cyanophenyl)-3,6-dihydropyridine-1(2H)-carboxylate

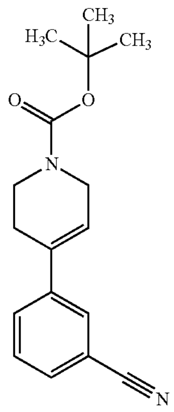 [SMILES: CC(C)(C)OC(=O)N1CC=C(c2cccc(C#N)c2)CC1]

To a solution of 200 mg tert-butyl 4-[(1,1,2,2,3,3,4,4,4-nonafluorobutane-1-sulfonyl)oxy]-3,6-dihydropyridine-1(2H)-carboxylate (intermediate 67, 0.42 mmol) in 3.6 mL 1,4-dioxane was added 64 mg (3-cyanophenyl)boronic acid (0.44 mmol, CAS 150255-96-2). The mixture was sparged with argon for 5 min. Then 24 mg tetrakis(triphenylphosphine)palladium (20.8 μmol, CAS 14221-01-3), 172 potassium carbonate (1.25 mmol) and 0.4 mL water were added. The reaction mixture was stirred overnight at 80° C. The reaction mixture was diluted with water and extracted 3× with dichloromethane. The combined organic layers were washed with water and brine, dried and concentrated under reduced pressure.

The crude product was purified my RP-HPLC (basic with 0.1% ammonia in water; gradient: 50-70% ACN). The product was obtained in 26% yield (33 mg):

1H-NMR (400 MHz, DMSO-d6): δ [ppm]=1.41-1.47 (m, 10H), 3.53 (t, 2H), 4.01 (br s, 2H), 6.32 (br s, 1H), 7.52-7.59 (m, 1H), 7.73 (dt, 1H), 7.76-7.82 (m, 1H), 7.90 (t, 1H).

LC-MS Method 2): $R_t$=1.31 min; MS (ESIpos): m/z=185 $[M+H]^+$

Intermediate 147

3-(1,2,3,6-tetrahydropyridin-4-yl)benzonitrile

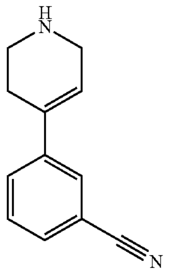 [SMILES: N#Cc1cccc(C2=CCNCC2)c1]

To a icebath cooled solution of 100 mg tert-butyl 4-(3-cyanophenyl)-3,6-dihydropyridine-1(2H)-carboxylate (0.35 mmol, intermediate 146) in 3 mL dichloromethane was added 0.2 mL TFA (2.6 mmol, CAS 76-05-1). The reaction mixture was stirred overnight at room temperature. The reaction mixture was filtered over an amino cased column and washed with dichloromethane. The filtrate was concentrated under reduced pressure and the crude product was used in the next step (98 mg, 121% of TFA salt).

1H-NMR (400 MHz, DMSO-d6): δ [ppm]=2.66-2.73 (m, 2H), 3.79 (br s, 2H), 6.38 (dt, 1H), 7.61 (t, 1H), 7.75-7.87 (m, 2H), 7.97 (t, 1H), 8.85 (br s, 1H).

LC-MS Method 2): $R_t$=0.87 min; MS (ESIpos): m/z=185 $[M+H]^+$

Intermediate 148

4-[4-(3-cyanophenyl)-3,6-dihydropyridin-1(2H)-yl]-1-methyl-2-oxo-1,2-dihydroquinoline-3-carbonitrile

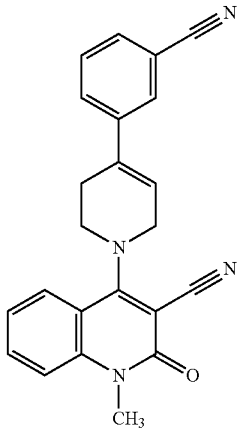 [SMILES: Cn1c(=O)c(C#N)c(N2CC=C(c3cccc(C#N)c3)CC2)c2ccccc21]

To a suspension of 98 mg 3-(1,2,3,6-tetrahydropyridin-4-yl)benzonitrile (intermediate 147, 80% purity, 0.42 mmol) in 0.51 mL 2-propanol was added 62 mg 4-chloro-1-methyl-2-oxo-1,2-dihydroquinoline-3-carbonitrile (0.28 mmol) as solid. Then N,N-diisopropylethylamine was added and the reaction mixture stirred overnight at 80° C. The suspension was filtered and the solid was washed with ethanol. The solid product was dried and obtained in 81% yield (89 mg). 1H-NMR (400 MHz, DMSO-d6): δ [ppm]=2.82-2.88 (m, 2H), 3.59 (s, 3H), 3.84 (t, 2H), 4.34-4.40 (m, 2H), 6.53 (t, 1H), 7.34 (t, 1H), 7.56-7.64 (m, 2H), 7.71-7.82 (m, 2H), 7.88 (t, 2H), 8.00 (t, 1H).

LC-MS (Method 1): $R_t$=1.16 min; MS (ESIpos): m/z=367 $[M+H]^+$

Intermediate 149

1-ethyl-2H-3,1-benzoxazine-2,4(1H)-dione

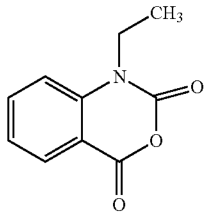

A solution of 20 g 2H-3,1-benzoxazine-2,4(1H)-dione (123 mmol, CAS 118-48-9) in 350 mL dry DMF was cooled to 0° C. and treated portionwise with 5.4 g sodium hydride (60% dispersion in mineral oil, 135 mmol). The reaction mixture was warmed to room temperature and 10 mL bromoethane (130 mmol) were added. The reaction mixture was stirred at room temperature overnight. The reaction mixture was carefully poured over ice/water and the formed crystals were filtered, washed with water and dried. The crude product was purified by column chromatography and the product was obtained in 67% yield (15.6 g).

MS (ESIpos): m/z=192.0.

$^1$H NMR (400 MHz, DMSO-$d_6$) δ 8.02 (dd, 1H), 7.85 (ddd, 1H), 7.51 (d, 1H), 7.33 (t, 1H), 4.06 (q, 2H), 1.23 (t, 3H).

Intermediate 150

1-ethyl-4-hydroxy-2-oxo-1,2-dihydroquinoline-3-carbonitrile

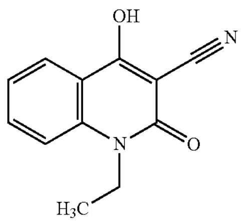 [SMILES: CCn1c(=O)c(C#N)c(O)c2ccccc21]

To a solution of 15.6 g 1-ethyl-2H-3,1-benzoxazine-2,4(1H)-dione (intermediate 152, 73.4 mmol): in 150 mL THF was added 82 mL triethylamine (590 mmol) and 12 ml ethyl cyanoacetate (110 mmol). The reaction mixture was heated to 60° C. over night. Additional 12 ml ethyl cyanoacetate (110 mmol) were added and the reaction was stirred under reflux for two days. Additional 12 ml ethyl cyanoacetate (110 mmol) and 20.5 mL triethylamine (147 mmol) were added and the reaction was stirred under reflux for one week. The reaction was cooled to ambient temperature and the solvent was removed under reduced pressure. The residue was dissolved in water/ethyl acetate (1:1) and the pH value was adjusted to one by addition of aqueous hydrochloric acid (2M). The resulting precipitate was collected by filtration, the filter cake was washed with water and ethyl acetate and dried in vacuo at 80° C.

MS (ESIpos): m/z=215.1.

$^1$H NMR (400 MHz, DMSO-$d_6$) δ 8.11 (dd, 1H), 7.76 (ddd, 1H), 7.60 (d, 1H), 7.32 (t, 1H), 4.81 (br s, 1H), 4.40 (br d, 1H), 4.23 (q, 2H), 1.18 (t, 3H).

Intermediate 151

4-chloro-1-ethyl-2-oxo-1,2-dihydroquinoline-3-carbonitrile

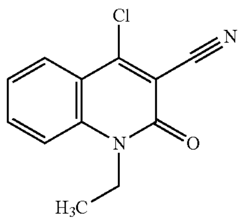 [SMILES: CCn1c(=O)c(C#N)c(Cl)c2ccccc21]

A mixture of 1-ethyl-4-hydroxy-2-oxo-1,2-dihydroquinoline-3-carbonitrile (12.3 g, 57.2 mmol) and phosphorus oxychloride (53 ml, 570 mmol, CAS-RN:[10025-87-3]) was stirred at 90° C. for one day. The reaction mixture was cooled to ambient temperature, poured into ice-cooled water and neutralized by addition of sodium carbonate (solid). The resulting precipitate was collected by filtration, washed with water and dried in vacuo at 80° C. Yield: 12.9 g (78% with 80% purity).

MS (ESIpos): m/z=233.0.

Intermediate 152

Tert-Butyl 4-[5-(2-oxopyrrolidin-1-yl)-1,3-benzoxazol-2-yl]piperidine-1-carboxylate

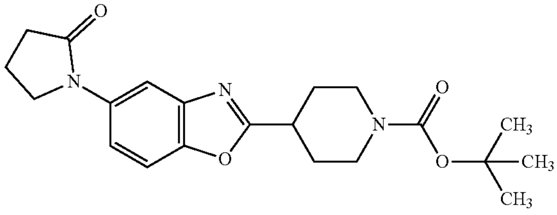 [SMILES: CC(C)(C)OC(=O)N1CCC(c2nc3cc(N4CCCC4=O)ccc3o2)CC1]

300 mg tert-butyl 4-(5-bromo-1,3-benzoxazol-2-yl)piperidine-1-carboxylate (0.79 mmol), 18 mg $Ir[dF(CF_3)(ppy)]_2(dtbbpy)PF_6$ (16 μmol), 167 mg sodium carbonate (157 mmol) and 47 mg 4,4'-dimethoxybenzophenone (39 μmol, CAS 72914-19-3) were dissolved in 13 mL pyrrolidinone. In a separate vial, the Ni-catalyst was prepared by dissolving 11.4 mg nickel(II) nitrate hexahydrate (39 μmol, CAS 13478-00-7) and 10.6 mg of the 4,4'-di-tert-butyl-2,2'-bipyridine (39 μmol, CAS 72914-19-3) in 1 mL pyrrolidinone followed by heating (50° C.) for 10 min. The catalyst solution (1 mL) was syringed to the sealed reaction vial followed by sparging with Ar for 10 min. The MW-vial was placed in a water bath (to keep the temp. below 35° C.) and was subsequently irradiated by two 40 W Kessil LED aquarium lamps. The crude product was purified by RP-HPLC chromatography and 81 mg of the title compound was obtained.

$^1$H NMR (600 MHz, DMSO-$d_6$) δ ppm 1.38-1.45 (m, 10H) 1.63-1.71 (m, 2H) 2.05-2.11 (m, 4H) 2.52 (dd, 2H) 2.88-3.10 (m, 2H) 3.20-3.27 (m, 1H) 3.87-3.91 (m, 2H) 3.91-3.99 (m, 2H) 7.67 (dd, 2H) 7.92 (dd, 1H).

Intermediate 153

1-[2-(piperidin-4-yl)-1,3-benzoxazol-5-yl]pyrrolidin-2-one

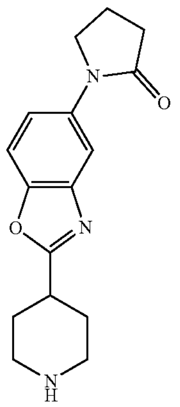 [SMILES: O=C1CCCN1c1ccc2oc(C3CCNCC3)nc2c1]

A solution of 70 mg tert-butyl 4-[5-(2-oxopyrrolidin-1-yl)-1,3-benzoxazol-2-yl]piperidine-1-carboxylate (intermediate 152, 182 μmol) was treated with 0.28 mL TFA (3.6 mmol) and stirred at room temperature for 4 h. The solvents were removed by rotary evaporation and the reaction mixture was coevaported with toluene for removal of remaining TFA. The title compound was obtained as the TFA salt (90 mg) and directly used in the next step.

$^1$H NMR (400 MHz, DMSO-$d_6$) δ ppm 1.91-2.03 (m, 2H) 2.04-2.13 (m, 2H) 2.22-2.31 (m, 2H): 3.03-3.16 (m, 2H) 3.32-3.45 (m, 3H) 3.86-3.91 (m, 2H) 7.65-7.72 (m, 2H) 7.95-7.98 (m, 1H).

Intermediate 154

Tert-Butyl 4-(4-acetylphenyl)-4-methylpiperidine-1-carboxylate

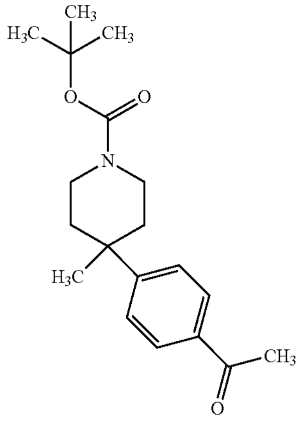 [SMILES: CC(=O)c1ccc(C2(C)CCN(C(=O)OC(C)(C)C)CC2)cc1]

Preparation for this compound has been described in the literature: J. Am. Chem. Soc. 2018 140,11317.

281 mg 1-(4-iodophenyl)ethan-1-one (1.14 mmol), 152 mg Fe(dmp)$_3$ (0.25 mmol), 42 mg Mn (0.76 mmol) and 27 mg NiBr$_2$(diglyme) (76.0 μmol, CAS 312696-09-6) were placed in a dried flask and evacuated and backfilled with nitrogen (3×). 3.6 mL 1,2-dichloroethane was added followed by 280 mg tert-butyl 4-methylidenepiperidine-1-carboxylate (0.76 mmol) and 3.6 mL 1-methyl-2-pyrrolidinone and the solution was stirred at maximum stirr rate under nitrogen for 1.5 h at RT. 132 mg manganese dioxide (1.52 mmol) and 0.14 mL of phenyl[(propan-2-yl)oxy]silane (0.76 mmol) was added und air and it was stirred at room temperature. After 1 h a second eq. of phenyl[(propan-2-yl)oxy]silane (0.14 mL, 0.76 mmol) was added and stirred overnight at room temperature.

The reaction mixture was filtered over Celite, washed with ethyl acetate and the filtrate was concentrated under reduced pressure. Purification was performed by column chromatography (hexane 100→hexane:ethyl acetate 70:30). The product was obtained in 29% yield (71 mg).

$^1$H NMR (400 MHz, DMSO-$d_6$) δ ppm 1.21 (s, 3H) 1.35-1.40 (m, 10H) 1.53-1.73 (m, 2H): 1.91-2.03 (m, 2H) 2.56 (s, 3H) 3.19-3.30 (m, 2H) 3.35-3.48 (m, 2H) 7.51-7.56 (m, 2H): 7.91 (d, 1H) 7.89-7.94 (m, 1H).

Intermediate 155

1-[4-(4-methylpiperidin-4-yl)phenyl]ethan-1-one, salt with trifluoroacetic acid

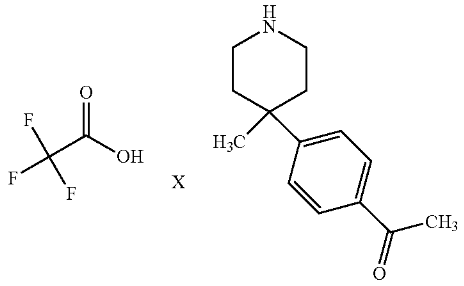

A solution of 65 mg tert-butyl 4-(4-acetylphenyl)-4-methylpiperidine-1-carboxylate (intermediate 154, 205 μmol) in 1.1 mL dichloromethane was treated with 0.39 mL TFA (5.1 mmol) and was stirred at room temperature overnight. The mixture was concentrated under reduced pressure and the crude product (90 mg) was directly used in the next step.

$^1$H NMR (400 MHz, DMSO-$d_6$) δ ppm 1.84-1.95 (m, 2H) 2.17-2.28 (m, 2H) 2.55-2.59 (m, 3H): 2.85-2.98 (m, 2H) 3.14-3.27 (m, 2H) 7.53-7.58 (m, 2H) 7.92-7.98 (m, 2H).

Intermediate 156

Tert-Butyl 4-(3-chlorophenyl)-4-hydroxypiperidine-1-carboxylate

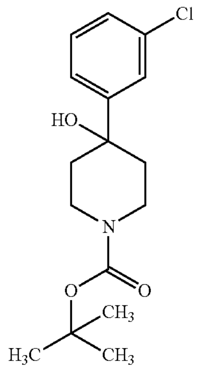

160 mg LiCl (3.76 mmol) was placed in a flask and dried under vacuum. 7.5 mL 3-chlorophenylmagnesium bromide (7.5 ml, 0.50 M in THF, 3.8 mmol) was added under nitrogen and stirred 15 min. Then a solution of 250 mg tert-butyl 4-oxopiperidine-1-carboxylate (1.25 mmol, CAS 79099-07-3) in 6.3 mL THF was added and the mixture was stirred 2.5 h at RT. The reaction mixture was quenched with saturated aq. ammoniumchloride and extracted 3× with ethyl acetate. The combined org. layers were filtered over a waterresistant filter and concentrated under reduced pressure. The crude product was purified by column chromatography using (dichloromethane 100→dichloromethane: ethanol: 30). The product was obtained in 59% yield (241 mg).

$^1$H NMR (400 MHz, DMSO-$d_6$) δ ppm 1.41 (s, 9H) 1.55 (br d, 2H) 1.79 (br td, 2H) 2.98-3.22 (m, 2H) 3.85 (br d, 2H) 7.26-7.30 (m, 1H) 7.35 (t, 1H) 7.39-7.43 (m, 1H) 7.53 (t, 1H).

Intermediate 157

Tert-Butyl 4-(3-chlorophenyl)-4-methoxypiperidine-1-carboxylate

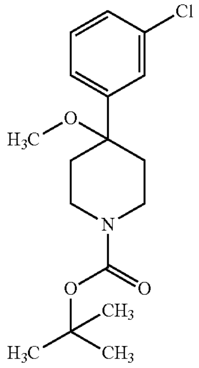 [SMILES: COC1(c2cccc(Cl)c2)CCN(C(=O)OC(C)(C)C)CC1]

To a solution of 240 mg tert-butyl 4-(3-chlorophenyl)-4-hydroxypiperidine-1-carboxylate (0.770 mmol, intermediate 156) in 4.9 mL DMF was added 46 mg sodium hydride (60% dispersion in mineral oil, 1.15 mmol) and it was stirred for 5 min. 96 μl iodomethane (1.5 mmol, CAS 74-88-4) was added to the reaction mixture and it was stirred for 3 h at room temperature. The reaction mixture was diluted with water and extracted 3× with ethyl acetate. The org. layer was filtered over a WA-Filter and concentrated under reduced pressure. The crude product was purified by column chromatography using (hexanes/ethyl acetate gradient 0-50%). The product was obtained in 82% yield (210 mg).

$^1$H NMR (400 MHz, DMSO-$d_6$) δ ppm 1.40 (s, 9H) 1.75 (td, 2H) 1.95 (br d, 2H) 2.90 (s, 3H): 2.93-3.14 (m, 2H) 3.83 (br d, 2H) 7.34-7.45 (m, 4H).

Intermediate 158

4-(3-chlorophenyl)-4-methoxypiperidine, Salt with Trifluoroacetic Acid

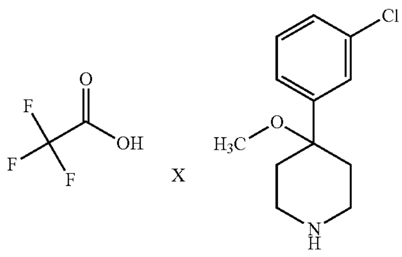

1.2 mL TFA was added to a solution of 210 mg tert-butyl 4-(3-chlorophenyl)-4-methoxypiperidine-1-carboxylate (intermediate 160, 0.64 mmol) in 3.3 mL dichloromethane and stirred 2 h at room temperature. The mixture was concentrated under reduced pressure and the crude product (353 mg) was directly used in the next step.

$^{1}H$ NMR (400 MHz, DMSO-$d_6$) δ ppm 1.94-2.06 (m, 2H) 2.13-2.23 (m, 2H) 2.87-2.94 (m, 3H): 3.02-3.15 (m, 2H) 3.19-3.29 (m, 2H) 7.33-7.38 (m, 1H) 7.38-7.44 (m, 2H) 7.44-7.50 (m, 1H).

Intermediate 159

Tert-Butyl 4-[3-methyl-2-oxo-2,3-dihydro-1H-indol-5-yl]piperidine-1-carboxylate

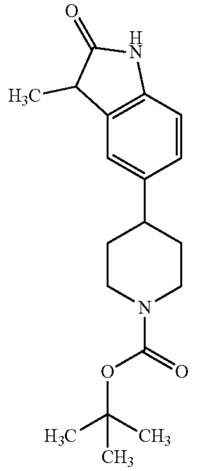

A solution of 150 mg tert-butyl 4-(4,4,5,5-tetramethyl-1,3,2-dioxaborolan-2-yl)-3,6-dihydropyridine-1(2H)-carboxylate (0.485 mmol), 110 mg 5-bromo-3-methyl-1,3-dihydro-2H-indol-2-one (0.485 mmol) and 0.31 mL water was degassed with argon for 5 min. Then 3.8 mg chloro(2-dicyclohexylphosphino-2',4',6'-triisopropyl-1,1'-biphenyl)[2-(2'-amino-1,1'-biphenyl)]palladium(II) (4.85 μmol) and 309 mg tripotassium phosphate (1.46 mmol) were added to the solution and the mixture was stirred for 2 h at 80° C. and 2 d at room temperature. To the mixture was added 62 mg palladium on carbon (10% on carbon, 0.058 mmol) and a solution of 305 mg ammonium formate (4.8 mmol) in 3.9 mL methanol. The reaction mixture was stirred overnight at room temperature. The reaction mixture was filtered (45μ filter) and the filtrate was concentrated under reduced pressure. The crude product was purified by RP-HPLC and the combined fractions were concentrated under reduced pressure. The product was obtained in 61% yield (98 mg).

1H-NMR (400 MHz, DMSO-d6): δ [ppm]=1.30 (d, 3H), 1.36-1.53 (m, 11H), 1.71 (br d, 2H), 2.55-2.92 (m, 4H), 3.97-4.17 (m, 2H), 6.72 (d, 1H), 7.02 (d, 1H), 7.15 (s, 1H), 10.23 (s, 1H).

LC-MS Method 2): $R_t$=1.18 min; MS (ESIneg): m/z=329 $[M-H]^-$

Intermediate 160

3-methyl-5-(piperidin-4-yl)-1,3-dihydro-2H-indol-2-one

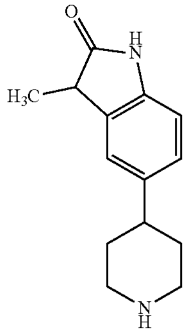 [SMILES: CC1C(=O)Nc2ccc(C3CCNCC3)cc21]

To a suspension of 96 mg tert-butyl 4-[3-methyl-2-oxo-2,3-dihydro-1H-indol-5-yl]piperidine-1-carboxylate (0.29 mmol, intermediate 159) in 0.42 mL methanol was added 0.36 mL 4N hydrochloric acid in dioxane (CAS 7647-01-0). The reaction mixture stirred overnight at room temperature until complete consumption of starting material (UPLC-MS). The reaction mixture was concentrated under reduced pressure and the crude product was directly used in the next step (87 mg).

LC-MS Method 2): $R_t$=0.77 min; MS (ESIpos): m/z=231 $[M+H]^+$

Intermediate 161

Tert-Butyl 4-[3-(4-methoxyphenyl)-1,2,4-oxadiazol-5-yl]piperidine-1-carboxylate

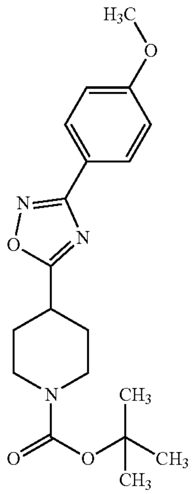 [SMILES: COc1ccc(-c2noc(C3CCN(C(=O)OC(C)(C)C)CC3)n2)cc1]

A solution of 1.66 g 1-(tert-butoxycarbonyl)piperidine-4-carboxylic acid (7.22 mmol), 800 mg N-hydroxy-4-methoxybenzene-1-carboximidamide (4.81 mmol), 4.3 mL 1-propanephosphonic anhydride solution (50% in ethyl acetate, 7.2 mmol; CAS 68957-94-8) and 2 mL triethylamine (14 mmol) in 33 mL ethyl acetate and heated to 80° C. for 6 h. The reaction mixture was diluted with ethyl acetate and washed with water and brine, dried and the solvents were evaporated. The crude product was purified by column chromatography (dichloromethane/0% methanol-2% methanol). The product was obtained in 31% yield (840 mg).

1H NMR (400 MHz, DMSO-d6) δ ppm 1.25-1.51 (m, 9H) 1.54-1.77 (m, 2H) 1.97-2.17 (m, 3H) 2.82-3.17 (m, 2H) 3.78-3.87 (m, 3H) 3.89-4.07 (m, 2H) 6.98-7.22 (m, 2H) 7.79-8.03 (m, 2H):

Intermediate 162

4-[3-(4-methoxyphenyl)-1,2,4-oxadiazol-5-yl]piperidine

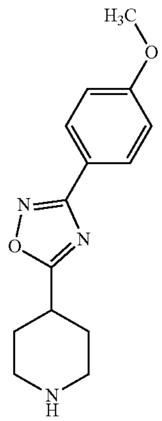 [SMILES: COc1ccc(-c2noc(C3CCNCC3)n2)cc1]

A solution of 830 mg tert-butyl 4-[3-(4-methoxyphenyl)-1,2,4-oxadiazol-5-yl]piperidine-1-carboxylate (intermediate 161, 2.31 mmol) in 15 mL dichloromethane was treated with 1.8 mL trifluoroacetic acid (23 mmol) and stirred at RT until full conversion of starting material. The solvents were evaporated and the crude product was directly used in the next step.

$^1$H NMR (400 MHz, DMSO-$d_6$) δ ppm 1.90-2.03 (m, 2H) 2.21-2.31 (m, 2H) 3.02-3.15 (m, 2H): 3.32-3.42 (m, 2H) 3.48 (tt, 1H) 3.81-3.86 (m, 3H) 7.07-7.15 (m, 2H) 7.90-8.00 (m, 2H):

Intermediate 163

Tert-Butyl 4-[3-(3-methylphenyl)-1,2,4-oxadiazol-5-yl]piperidine-1-carboxylate

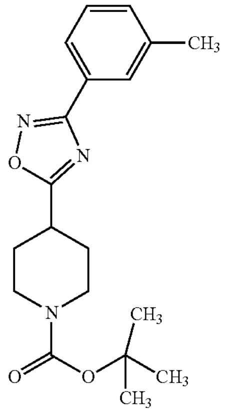 [SMILES: Cc1cccc(-c2noc(C3CCN(C(=O)OC(C)(C)C)CC3)n2)c1]

The reaction was performed in analogy to intermediate 161 using 1.66 g 1-(tert-butoxycarbonyl)piperidine-4-carboxylic acid (7.22 mmol, CAS 84358-13-4) and 723 mg N-hydroxy-3-methylbenzene-1-carboximidamide (4.81 mmol, CAS 40067-82-1). The product was obtained in 23% yield (600 mg).

$^1$H NMR (400 MHz, DMSO-d6) δ ppm 1.34-1.45 (m, 9H) 1.60-1.77 (m, 2H) 2.02-2.14 (m, 2H): 2.36-2.42 (m, 3H) 2.89-3.09 (m, 2H) 3.89-4.00 (m, 2H) 7.37-7.48 (m, 2H) 7.75-7.85 (m, 2H).

Intermediate 164

4-[3-(3-methylphenyl)-1,2,4-oxadiazol-5-yl]piperidine

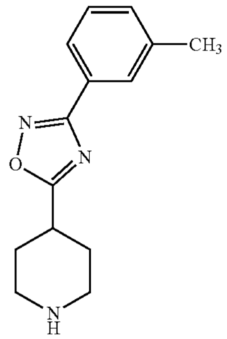 [SMILES: Cc1cccc(-c2noc(C3CCNCC3)n2)c1]

The reaction was performed in analogy to intermediate 162 using 600 mg tert-butyl 4-[3-(3-methylphenyl)-1,2,4-oxadiazol-5-yl]piperidine-1-carboxylate (1.75 mmol, intermediate 163).

$^1$H NMR (400 MHz, DMSO-d6) δ ppm 1.84-2.10 (m, 2H) 2.14-2.34 (m, 2H) 2.35-2.44 (m, 3H): 2.95-3.19 (m, 2H) 3.33-3.43 (m, 2H) 3.43-3.65 (m, 1H) 7.30-7.60 (m, 2H) 7.74-7.91 (m, 2H).

Intermediate 165

Tert-Butyl 4-[2-(2-methylbenzoyl)hydrazinecarbonyl]piperidine-1-carboxylate

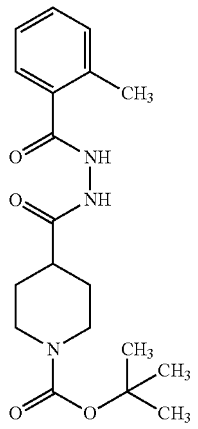 [SMILES: Cc1ccccc1C(=O)NNC(=O)C1CCN(C(=O)OC(C)(C)C)CC1]

To a solution of 2 g 1-(tert-butoxycarbonyl)piperidine-4-carboxylic acid (2.00 g, 8.72 mmol) in 50 mL DMF was added 4.6 mL Di-isopropylethylamine (26 mmol), 4.98 g HATU (13.1 mmol, CAS 148893-10-1) and 1.44 g 2-methylbenzohydrazide (9.60 mmol). The reaction mixture was stirred at room temperature overnight. The reaction mixture was diluted with ethyl acetate and water, the layer were separated and the aqueous layer was extracted with ethyl acetate (2×). The combined organic layers were evaporated and the crude product was directly used in the next step (including remaining reagents and by-products).

$^1$H NMR (400 MHz, DMSO-$d_6$) δ ppm 1.38-1.43 (m, 10H) 1.43-1.53 (m, 2H) 1.72 (br dd, 2H): 2.34-2.38 (m, 3H) 2.43 (tt, 1H) 2.70-2.89 (m, 2H) 3.95 (br d, 2H) 7.20-7.30 (m, 2H) 7.31-7.41 (m, 2H) 9.89 (d, 1H) 9.97 (d, 1H).

Intermediate 166

4-[5-(2-methylphenyl)-1,3,4-oxadiazol-2-yl]piperidine

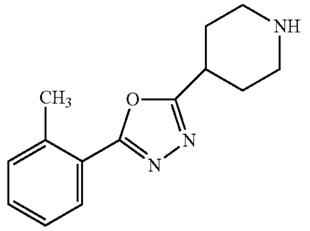 [SMILES: Cc1ccccc1-c1nnc(C2CCNCC2)o1]

To a solution of 2.2 g tert-butyl 4-[2-(2-methylbenzoyl)hydrazinecarbonyl]piperidine-1-carboxylate (6.09 mmol, intermediate 165) in 60 mL acetonitrile was added 5.7 mL phosphoryl chloride (61 mmol, 10025-87-3). The reaction mixture was stirred at 120° C. for 7 h. The reaction mixture was poured over water and treated with solid sodium carbonate until pH>7. The mixture was extracted with ethyl acetate (3×) and the combined organic layers were washed with brine and water. The organic layer was dried and the solvents removed in vacuo. 1.6 g of the title compound were obtained.

$^1$H NMR (400 MHz, DMSO-$d_6$) δ ppm 1.59-1.72 (m, 2H) 1.93-2.01 (m, 2H) 2.55-2.65 (m, 5H): 2.89-3.07 (m, 2H) 3.11 (s, 1H) 7.37-7.52 (m, 3H) 7.88 (dd, 1H).

Intermediate 167

Tert-Butyl 4-[2-(4-methylbenzoyl)hydrazinecarbonyl]piperidine-1-carboxylate

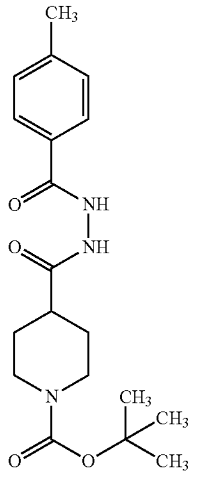 [SMILES: Cc1ccc(C(=O)NNC(=O)C2CCN(C(=O)OC(C)(C)C)CC2)cc1]

The reaction was carried out in analogy to intermediate 165 by using 2 g 1-(tert-butoxycarbonyl)piperidine-4-carboxylic acid (8.72 mmol) and 1.44 g 4-methylbenzohydrazide (9.60 mmol). 3 g of the title compound were obtained.

$^1$H NMR (400 MHz, DMSO-$d_6$) δ ppm 1.37-1.52 (m, 11H) 1.67-1.76 (m, 2H) 2.36 (s, 3H): 2.40-2.48 (m, 1H) 2.68-2.90 (m, 2H) 3.96 (br d, 2H) 7.29 (d, 2H) 7.75-7.79 (m, 2H) 9.87 (br s, 1H) 10.23 (br s, 1H).

Intermediate 168

4-[5-(4-methylphenyl)-1,3,4-oxadiazol-2-yl]piperidine

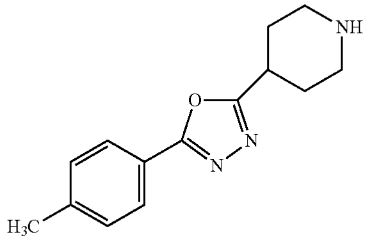 [SMILES: Cc1ccc(-c2nnc(C3CCNCC3)o2)cc1]

To a solution of 2.8 g tert-butyl 4-[2-(4-methylbenzoyl)hydrazinecarbonyl]piperidine-1-carboxylate (intermediate 167) in 60 mL acetonitrile was added 10.8 mL phosphoryl chloride. The reaction mixture was stirred at 100° C. for 10 h. The reaction mixture was poured into water and treated with solid sodium carbonate until pH>7. The mixture was extracted with ethyl acetate (3×) and the combined organic layers were washed with brine and water. The organic layer was dried and the solvents removed in vacuo. 1.7 g of the title compound were obtained.

$^1$H NMR (400 MHz, DMSO-d6) δ ppm 1.56-1.75 (m, 2H) 1.88-2.01 (m, 2H) 2.37-2.42 (m, 3H): 2.55-2.65 (m, 2H) 2.91-3.03 (m, 2H) 3.03-3.15 (m, 1H) 7.34-7.45 (m, 2H) 7.82-7.91 (m, 2H).

Intermediate 169

Tert-Butyl 4-[2-(3-methylbenzoyl)hydrazinecarbonyl]piperidine-1-carboxylate

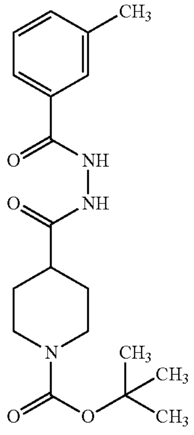 [SMILES: Cc1cccc(C(=O)NNC(=O)C2CCN(C(=O)OC(C)(C)C)CC2)c1]

The reaction was carried out in analogy to intermediate 165 by using 2 g 1-(tert-butoxycarbonyl)piperidine-4-carboxylic acid (2.00 g, 8.72 mmol) and 1.44 g 4-methylbenzohydrazide (9.60 mmol). 3 g of the title compound were obtained.

$^1$H NMR (400 MHz, DMSO-$d_6$) δ ppm 1.37-1.53 (m, 11H) 1.68-1.75 (m, 2H) 2.35-2.38 (m, 3H) 2.41-2.47 (m, 1H) 2.70-2.89 (m, 2H) 3.94 (br s, 2H) 7.34-7.40 (m, 2H) 7.61-7.67 (m, 1H) 7.67-7.73 (m, 1H) 9.84-9.95 (m, 1H) 10.19-10.33 (m, 1H).

Intermediate 170

4-[5-(3-methylphenyl)-1,3,4-oxadiazol-2-yl]piperidine

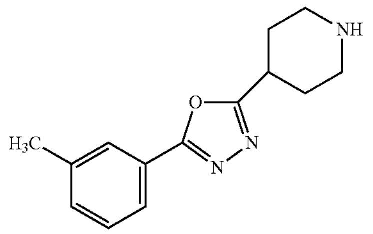 [SMILES: Cc1cccc(-c2nnc(C3CCNCC3)o2)c1]

To a solution of 3 g tert-butyl 4-[2-(3-methylbenzoyl)hydrazinecarbonyl]piperidine-1-carboxylate (intermediate 169) in 83 mL acetonitrile was added 7.7 mL phosphoryl chloride. The reaction mixture was stirred at 110° C. for 30 h. The reaction mixture was poured into water and treated with solid sodium carbonate until pH>7. The mixture was extracted with ethyl acetate (3×) and the combined organic layers were washed with brine and water. The organic layer was dried and the solvents removed in vacuo. 350 mg of the title compound were obtained.

$^1$H NMR (400 MHz, DMSO-$d_6$) δ ppm 1.58-1.71 (m, 2H) 1.92-2.01 (m, 2H) 2.40 (s, 3H) 2.55-2.64 (m, 2H) 2.90-3.05 (m, 2H) 3.09 (s, 1H) 7.40-7.45 (m, 1H) 7.45-7.51 (m, 1H) 7.76-7.80 (m, 1H) 7.80-7.84 (m, 1H).

Intermediate 171

Tert-Butyl 4-[2-(3-chlorobenzoyl)hydrazinecarbonyl]piperidine-1-carboxylate

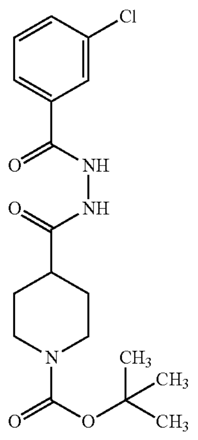

The reaction was carried out in analogy to intermediate 165 by using 2 g 1-(tert-butoxycarbonyl)piperidine-4-carboxylic acid (8.72 mmol) and 1.64 g 3-chlorobenzohydrazide (9.6 mmol). 2.8 g of the title compound were obtained.

$^1$H NMR (400 MHz, DMSO-d6) δ ppm 1.35-1.42 (m, 10H) 1.42-1.54 (m, 2H) 1.67-1.77 (m, 2H) 2.41-2.48 (m, 1H) 3.90-4.01 (m, 2H) 7.51-7.57 (m, 1H) 7.62-7.68 (m, 1H) 7.80-7.85 (m, 1H) 7.88-7.91 (m, 1H).

Intermediate 172

4-[5-(3-chlorophenyl)-1,3,4-oxadiazol-2-yl]piperidine

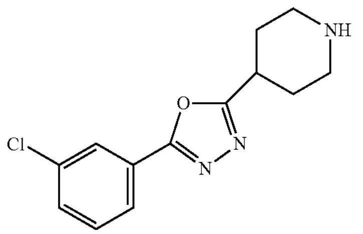 [SMILES: Clc1cccc(-c2nnc(C3CCNCC3)o2)c1]

To a solution of 2.5 g tert-butyl 4-[2-(3-chlorobenzoyl)hydrazinecarbonyl]piperidine-1-carboxylate (intermediate 171) in 25 mL acetonitrile was added 6.1 mL phosphoryl chloride. The reaction mixture was stirred at 105° C. for 10 h. The reaction mixture was poured into water and treated with solid sodium carbonate until pH>7. The mixture was extracted with ethyl acetate (3×) and the combined organic layers were washed with brine and water. The organic layer was dried and the solvents removed in vacuo. 700 mg of the title compound were obtained.

$^1$H NMR (400 MHz, DMSO-d6) δ ppm 1.88-1.99 (m, 3H) 2.12-2.22 (m, 2H) 2.89-3.00 (m, 2H): 3.20-3.26 (m, 3H) 3.34-3.37 (m, 1H) 7.61-7.68 (m, 1H) 7.69-7.75 (m, 1H) 7.91-8.02 (m, 2H).

Intermediate 173

Tert-Butyl 4-[2-(3-chlorobenzoyl)hydrazinecarbonyl]-4-methylpiperidine-1-carboxylate

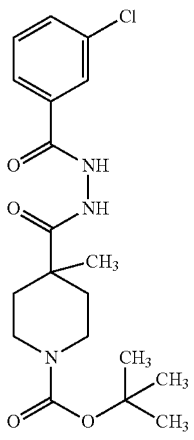 [SMILES: CC(C)(C)OC(=O)N1CCC(C)(C(=O)NNC(=O)c2cccc(Cl)c2)CC1]

The reaction was carried out in analogy to intermediate 165 by using 2 g 1-(tert-butoxycarbonyl)-4-methylpiperidine-4-carboxylic acid (8.22 mmol) and 1.54 g 3-chlorobenzohydrazide (9.04 mmol). 3.5 g of the title compound were obtained.

$^1$H NMR (400 MHz, DMSO-d6) δ ppm 1.18-1.23 (m, 3H) 1.37-1.51 (m, 10H) 2.00-2.12 (m, 2H) 3.00-3.20 (m, 3H) 3.53-3.68 (m, 2H) 7.49-7.60 (m, 1H) 7.63-7.72 (m, 1H) 7.80-7.95 (m, 2H) 9.61-9.85 (m, 1H) 10.35-10.49 (m, 1H).

Intermediate 174

4-[5-(3-chlorophenyl)-1,3,4-oxadiazol-2-yl]-4-methylpiperidine

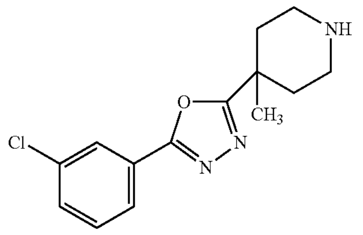 [SMILES: CC1(c2nnc(-c3cccc(Cl)c3)o2)CCNCC1]

To a solution of 3.5 g tert-butyl 4-[2-(3-chlorobenzoyl) hydrazinecarbonyl]-4-methylpiperidine-1-carboxylate (intermediate 173) in 34 mL acetonitrile was added 8.2 mL phosphoryl chloride. The reaction mixture was stirred at 105° C. for 10 h. The reaction mixture was poured into water and treated with solid sodium carbonate until pH>7. The mixture was extracted with dichloromethane (3×) and the combined organic layers were washed with brine and water. The organic layer was dried and the solvents removed in vacuo. 150 mg of the title compound were obtained.

LC-MS Method 2): $R_t$=1.01 min; MS (ESIpos): m/z=277 $[M+H]^+$

Intermediate 175

Tert-Butyl 4-(3,3-dimethyl-2,3-dihydro-1H-indol-5-yl)piperidine-1-carboxylate

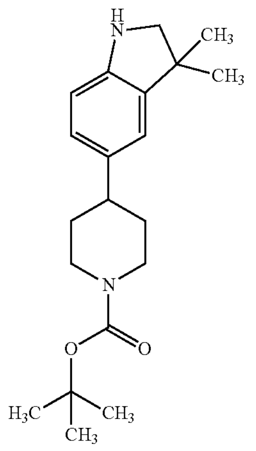 [SMILES: CC(C)(C)OC(=O)N1CCC(c2ccc3c(c2)C(C)(C)CN3)CC1]

Reaction was performed in analogy to intermediate 159 using 150 mg tert-butyl 4-(4,4,5,5-tetramethyl-1,3,2-dioxaborolan-2-yl)-3,6-dihydropyridine-1(2H)-carboxylate (485 μmol) and 110 mg 5-bromo-3,3-dimethyl-2,3-dihydro-1H-indole (485 μmol). The product was purified by RP-HPLC and obtained in 28% yield (53 mg).

$^1$H-NMR (400 MHz, DMSO-d6): δ [ppm]=1.18 (s, 6H), 1.32-1.47 (m, 11H), 1.68 (br d, 2H), 2.63-2.89 (m, 2H), 3.14 (d, 2H), 4.03 (br d, 2H), 5.34 (s, 1H), 6.33 (d, 1H), 6.41 (dd, 1H), 6.86 (d, 1H).

LC-MS Method 2): $R_t$=1.45 min; MS (ESIpos): m/z=331 $[M+H]^+$

Intermediate 176

3,3-dimethyl-5-(piperidin-4-yl)-2,3-dihydro-1H-indole

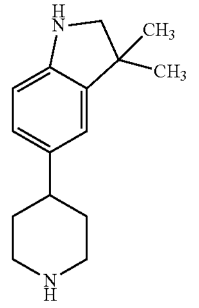 [SMILES: CC1(C)CNc2ccc(C3CCNCC3)cc21]

To a solution of 50 mg tert-butyl 4-(3,3-dimethyl-2,3-dihydro-1H-indol-5-yl)piperidine-1-carboxylate (151 μmol, intermediate 175) in 1.5 mL dichloromethane was added 0.12 mL trifluoroacetic acid (1.5 mmol). The mixture was stirred overnight at room temperature until complete conversion of starting material. The reaction mixture was concentrated under reduced pressure and directly used in the next step.

LC-MS Method 2): $R_t$=1.15 min; MS (ESIpos): m/z=231 $[M+H]^+$

Intermediate 177

Tert-Butyl 4-[2-methyl-2,3-dihydro-1-benzofuran-5-yl]piperidine-1-carboxylate

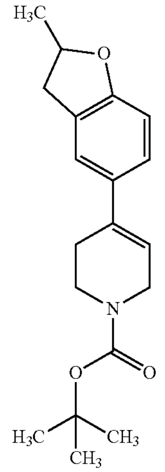

100 mg tert-butyl 4-(4,4,5,5-tetramethyl-1,3,2-dioxaborolan-2-yl)-3,6-dihydropyridine-1(2H)-carboxylate (0.323 mmol), 69 mg 5-bromo-2-methyl-2,3-dihydro-1-benzofuran (0.323 mmol), 69 mg sodium carbonate (0.65 mmol) and 24 mg (1,1-bis(diphenylphosphino)ferrocene)-dichloropalladium(II) (32.3 μmol; CAS 72287-26-4) were placed in a MW-Vial and flushed with Nitrogen-gas. 1.4 mL 1,4-dioxane and 0.26 mL water were added and the mixture stirred 2 h at 80° C.

The reaction mixture was evaporated, 1 mL water and dichloromethane was added to the residue and the aqueous layer was extracted with dichloromethane (3×).

The combined organic layers was washed with brine, filtered over a water-resistant filter and evaporated. The product was purified by RP-HPLC and used with some impurities in the next step.

$^1$H NMR (400 MHz, DMSO-$d_6$) δ ppm 1.33-1.41 (m, 6H) 1.42 (s, 9H) 2.40 (br d, 2H) 2.76 (dd, 1H) 3.24-3.31 (m, 1H) 3.50 (br t, 2H) 3.91-4.00 (m, 2H) 4.84-4.95 (m, 1H) 5.97 (br s, 1H): 6.67 (d, 1H) 7.14 (dd, 1H) 7.27 (d, 1H).

Intermediate 178

Tert-Butyl 4-[2-methyl-2,3-dihydro-1-benzofuran-5-yl]piperidine-1-carboxylate

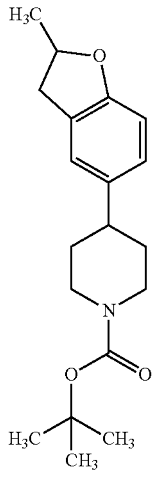

To a solution of 100 mg tert-butyl 4-[2-methyl-2,3-dihydro-1-benzofuran-5-yl]-3,6-dihydropyridine-1(2H)-carboxylate (317 μmol, intermediate 177) in 6.5 mL methanol was added 34 mg 10% Pd/C (32 μmol) under argon. The atmosphere was replaced with hydrogen and it was stirred at room temperature for 4.5 h. The reaction mixture was filtered over celite and washed with ethanol. The solvent were evaporated and the crude product was purified by column chromatography using dichloromethane:ethanol 100:0-dichloromethane:ethanol 90:10. The product was used in the next step.

Intermediate 179

4-[2-methyl-2,3-dihydro-1-benzofuran-5-yl]piperidine, Salt with Trifluoroacetic Acid

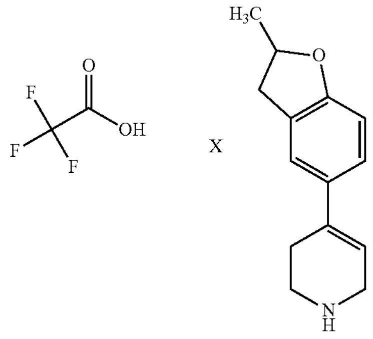

0.3 mL TFA was added to a solution of tert-butyl 4-[2-methyl-2,3-dihydro-1-benzofuran-5-yl]piperidine-1-carboxylate (50.0 mg including impurities, intermediate 178) in 0.81 mL dichloromethane and stirred for 3 h at room temperature. The reaction mixture was evaporated under reduced pressure and the crude product was directly used in the next step.

LC-MS Method 2): $R_t$=1.23 min; MS (ESIpos): m/z=218 $[M+H]^+$

Intermediate 180

Tert-Butyl 4-(1,3,3-trimethyl-2-oxo-2,3-dihydro-1H-indol-5-yl)piperidine-1-carboxylate

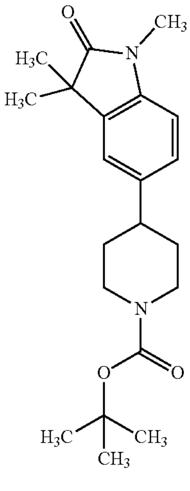 [SMILES: CN1C(=O)C(C)(C)c2cc(C3CCN(C(=O)OC(C)(C)C)CC3)ccc21]

Prepared in analogy to intermediate 159 by using 100 mg tert-butyl 4-(4,4,5,5-tetramethyl-1,3,2-dioxaborolan-2-yl)-3,6-dihydropyridine-1(2H)-carboxylate (0.32 mmol) and 82 mg 5-bromo-1,3,3-trimethyl-1,3-dihydro-2H-indol-2-one (0.32 mmol, CAS 72451-22-0).

The product was obtained in 84% yield (109 mg).

$^1$H NMR (400 MHz, DMSO-$d_6$) δ ppm 1.24 (s, 6H) 1.41 (s, 9H) 1.45-1.55 (m, 2H) 1.72 (br d, 2H) 2.58-2.69 (m, 1H) 2.78 (br s, 2H) 3.10 (s, 3H) 4.02-4.13 (m, 2H) 6.90 (d, 1H) 7.12 (dd, 1H) 7.26 (d, 1H).

Intermediate 181

1,3,3-trimethyl-5-(piperidin-4-yl)-1,3-dihydro-2H-indol-2-one, Salt with Trifluoroacetic Acid

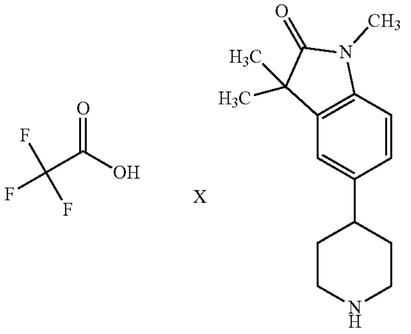

TFA was added to a solution of 105 mg tert-butyl 4-(1,3,3-trimethyl-2-oxo-2,3-dihydro-1H-indol-5-yl)piperidine-1-carboxylate (0.3 mmol, intermediate 180) in 1.5 mL dichloromethane and stirred 1.5 h at room temperature.

The mixture was concentrated under reduced pressure. and the resulting crude product was directly used in the next step.

Intermediate 182

Tert-Butyl 4-(2-hydroxy-2,3-dihydro-1H-inden-5-yl) piperidine-1-carboxylate

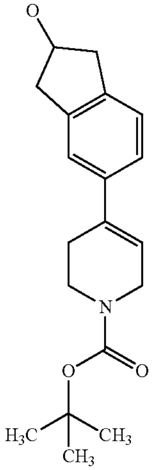

Prepared in analogy to intermediate 159 by using 100 mg tert-butyl 4-(4,4,5,5-tetramethyl-1,3,2-dioxaborolan-2-yl)-3,6-dihydropyridine-1(2H)-carboxylate (0.323 mmol) and 69 mg 5-bromo-2,3-dihydro-1H-inden-2-ol (0.323 mmol). Reduction of the double bond did not take place and was reduced in the next step.

Purified by column chromatography (dichloromethane 100→dichloromethane:EtOH 90:10).

The product was obtained in 75% yield (72 mg).

Intermediate 183

Tert-Butyl 4-(2-hydroxy-2,3-dihydro-1H-inden-5-yl) piperidine-1-carboxylate

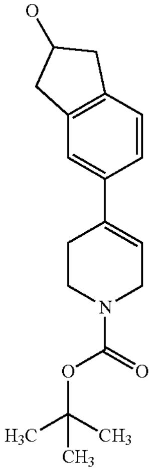

Pd/C was added under nitrogen to 85 mg tert-butyl 4-(2-hydroxy-2,3-dihydro-1H-inden-5-yl)-3,6-dihydropyridine-1(2H)-carboxylate (269 μmol, intermediate 182) in 5 mL methanol. The mixture was evacuated and backfilled with hydrogen and stirred 3.5 h under hydrogen at RT. Pd/C was added again under nitrogen and the mixture stirred 4 h under hydrogen. The reaction mixture was filtered over celite, washed with MeOH and evaporated. The product was obtained in 76% yield (72 mg).

$^{1}$H NMR (400 MHz, DMSO-$d_6$) δ ppm 1.37-1.52 (m, 11H) 1.70 (br d, 2H) 2.56-2.72 (m, 3H): 2.72-2.88 (m, 2H) 2.94-3.05 (m, 2H) 3.99-4.11 (m, 2H) 4.43-4.52 (m, 1H) 4.82 (br d, 1H): 6.97 (d, 1H) 7.04-7.08 (m, 1H) 7.08-7.13 (m, 1H).

Intermediate 184

5-(piperidin-4-yl)-2,3-dihydro-1H-inden-2-ol, Salt with Trifluoroacetic Acid

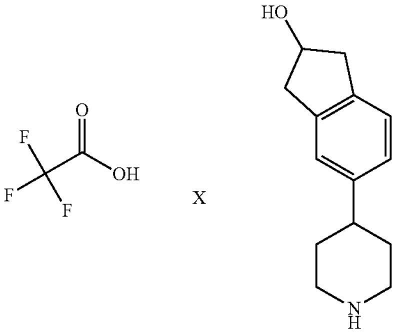

0.42 mL TFA was added to a solution of 70 mg tert-butyl 4-(2-hydroxy-2,3-dihydro-1H-inden-5-yl)piperidine-1-carboxylate (221 μmol, intermediate 183) in 1.1 mL dichloromethane and stirred over night at room temperature. After complete consumption of starting material the reaction mixture was evaporated under reduced pressure and the crude product (166 mg) was directly used in the next step.

$^1$H NMR (400 MHz, DMSO-$d_6$) δ ppm 1.68-1.84 (m, 2H) 1.90 (br s, 2H) 2.76-2.87 (m, 1H): 2.94-3.15 (m, 4H) 3.30-3.44 (m, 4H) 5.74 (s, 1H) 7.03-7.09 (m, 1H) 7.12-7.17 (m, 1H): 7.21-7.29 (m, 1H) 7.95 (s, 1H) 8.24-8.44 (m, 1H).

Intermediate 185

Tert-Butyl 4-(2,2-dimethyl-2H-1,3-benzodioxol-5-yl)-3,6-dihydropyridine-1(2H)-carboxylate

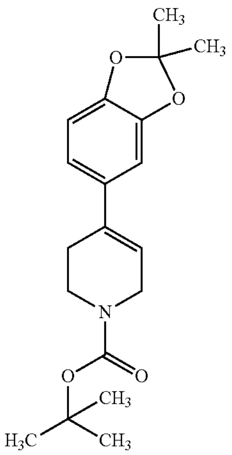 [SMILES: CC(C)(C)OC(=O)N1CC=C(c2ccc3c(c2)OC(C)(C)O3)CC1]

Prepared in analogy to intermediate 159 using 285 mg tert-butyl 4-(4,4,5,5-tetramethyl-1,3,2-dioxaborolan-2-yl)-3,6-dihydropyridine-1(2H)-carboxylate (0.92 mmol) and 201 mg 5-bromo-2,2-dimethyl-2H-1,3-benzodioxole (0.88 mmol). Hydrogenation of double bond did not take place and was performed with the crude product (198 mg) in the next step.

LC-MS Method 2): $R_t$=1.52 min; MS (ESIneg): m/z=331 [M]

Intermediate 186

Tert-Butyl 4-(2,2-dimethyl-2H-1,3-benzodioxol-5-yl)piperidine-1-carboxylate

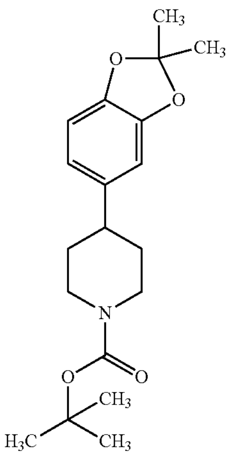 [SMILES: CC(C)(C)OC(=O)N1CCC(c2ccc3c(c2)OC(C)(C)O3)CC1]

Prepared in analogy to intermediate 188 with 198 mg tert-butyl 4-(2,2-dimethyl-2H-1,3-benzodioxol-5-yl)-3,6-dihydropyridine-1(2H)-carboxylate (0.6 mmol, intermediate 185). The crude product (183 mg) was directly used in the next step.

LC-MS Method 2): $R_t$=1.50 min; MS (ESIpos): m/z=334 $[M+H]^+$

Intermediate 187

4-(2,2-dimethyl-2H-1,3-benzodioxol-5-yl)piperidine

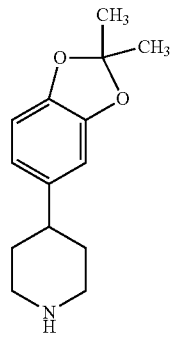 [SMILES: CC1(C)Oc2ccc(C3CCNCC3)cc2O1]

To a solution of 183 mg tert-butyl 4-(2,2-dimethyl-2H-1,3-benzodioxol-5-yl)piperidine-1-carboxylate (0.55 mmol) in 0.8 mL methanol was added chlorotrimethylsilane (350 µl, 2.7 mmol). The mixture was stirred at room temperature for 3 h. The mixture was concentrated under reduced pressure and dried overnight under high vacuum.

Purification crude product was purified by RP-HPLC. The product was obtained in 49% yield (90 mg, 70% purity).

LC-MS Method 2): $R_t$=1.22 min; MS (ESIpos): m/z=234 $[M+H]^+$

Intermediate 188

Tert-Butyl 4-(2'-oxo-1',2'-dihydrospiro[cyclobutane-1,3'-indol]-5'-yl)piperidine-1-carboxylate

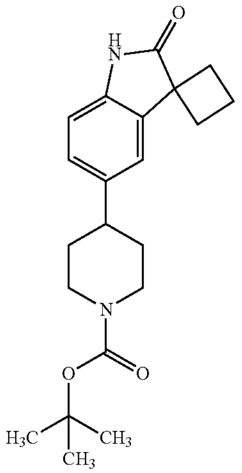

Prepared in analogy to intermediate 159 using 150 mg tert-butyl 4-(4,4,5,5-tetramethyl-1,3,2-dioxaborolan-2-yl)-

3,6-dihydropyridine-1(2H)-carboxylate (0.49 μmmol) and 122 mg 5'-bromospiro[cyclobutane-1,3'-indol]-2'(1'H)-one (0.49 mmol).

The product was purified by RP-HPLC and obtained 109 mg.

1H-NMR (400 MHz, DMSO-d6): δ [ppm]=1.36-1.50 (m, 11H), 1.72 (br d, 2H), 2.10-2.29 (m, 4H), 2.34-2.43 (m, 2H), 2.59-2.69 (m, 1H), 2.78 (br s, 2H), 4.05 (br d, 2H), 6.62 (d, 1H), 6.86 (dd, 1H), 7.44 (d, 1H), 10.17 (s, 1H).

LC-MS Method 2): $R_t$=1.31 min; MS (ESIpos): m/z=357 $[M+H]^+$

Intermediate 189

5'-(piperidin-4-yl)spiro[cyclobutane-1,3'-indol]-2'(1'H)-one

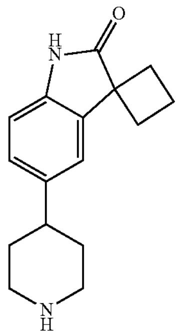

Prepared in analogy to intermediate 187 using intermediate 188. The crude product (75 mg) was directly used in the next step.

LC-MS Method 2): $R_t$=0.96 min; MS (ESIpos): m/z=257 $[M+H]^+$

Intermediate 190

Tert-Butyl 4-(1,3-dimethyl-2-oxo-2,3-dihydro-1H-benzimidazol-5-yl)-3,6-dihydropyridine-1(2H)-carboxylate

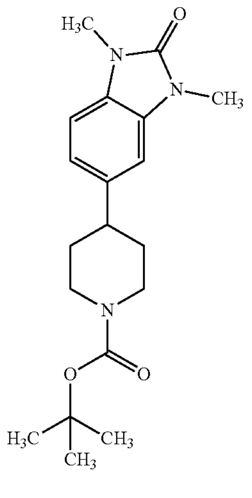 [SMILES: Cn1c(=O)n(C)c2cc(C3CCN(C(=O)OC(C)(C)C)CC3)ccc21]

Prepared in analogy to intermediate 159 using 80 mg tert-butyl 4-(4,4,5,5-tetramethyl-1,3,2-dioxaborolan-2-yl)-3,6-dihydropyridine-1(2H)-carboxylate (0.49 μmmol) and 50 mg 5-bromo-1,3-dimethyl-1,3-dihydro-2H-benzimidazol-2-one (207 μmol).

The crude product was directly used in the next step (88 mg).

Intermediate 191

1,3-dimethyl-5-(piperidin-4-yl)-1,3-dihydro-2H-benzimidazol-2-one

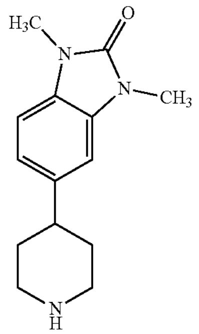 [SMILES: Cn1c(=O)n(C)c2cc(C3CCNCC3)ccc21]

To a solution of 86 mg tert-butyl 4-(1,3-dimethyl-2-oxo-2,3-dihydro-1H-benzimidazol-5-yl)piperidine-1-carboxylate (0.25 mmol) in 0.26 mL methanol was added 0.31 mL 4N HCl in dioxan. The mixture was stirred 2 days at room temperature. After full consumption of starting material the mixture was concentrated under reduced pressure. The product was purified by RP-HPLC and the product was obtained in 65% yield (44 mg).

1H-NMR (400 MHz, DMSO-d6): δ [ppm]=1.66-1.90 (m, 4H), 2.73-2.92 (m, 3H), 3.26 (br d, 2H), 3.32 (s, 3H), 6.93 (dd, 1H), 7.00 (d, 1H), 7.07 (d, 1H), 8.35 (s, 1H).

LC-MS (Method 1): $R_t$=0.49 min; MS (ESIpos): m/z=246 $[M+H]^+$

Intermediate 192

Tert-Butyl 4-{[(1,3-dioxo-1,3-dihydro-2H-isoindol-2-yl)oxy]carbonyl}-4-methylpiperidine-1-carboxylate

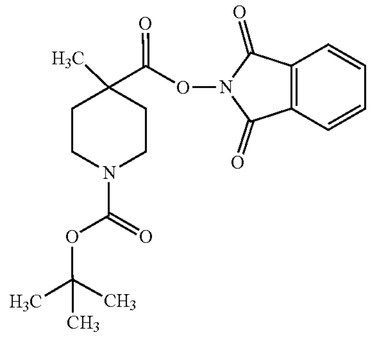 [SMILES: CC(C)(C)OC(=O)N1CCC(C)(C(=O)ON2C(=O)c3ccccc3C2=O)CC1]

To a vigorously stirring suspension of 500 mg 1-(tert-butoxycarbonyl)-4-methylpiperidine-4-carboxylic acid (2.06 mmol), 369 mg 2-hydroxy-1H-isoindole-1,3(2H)-dione (2.26 mmol) and 25 mg 4-dimethylaminopyridine (0.2 mmol) in 15 mL dichloromethane was added dropwise 0.35 mL DIC (2.3 mmol) at room temperature. The reaction mixture was stirred 1 h at room temperature (checked by TLC hexane/ethyl acetate 4:1). The suspension was filtered and washed with dichloromethane. The filtrate was concentrated under reduced pressure and the crude product was purified by column chromatography. The product was obtained as a white solid in 97% yield (808 mg).

$^1$H NMR (400 MHz, DMSO-$d_6$) δ ppm 1.38-1.47 (m, 12H) 1.55 (ddd, 2H) 2.07 (br d, 2H) 3.01 (br s, 2H) 3.71-3.84 (m, 2H) 7.91-8.05 (m, 4H):

Intermediate 193

Tert-Butyl 4-methyl-4-(4-methylquinolin-2-yl)piperidine-1-carboxylate

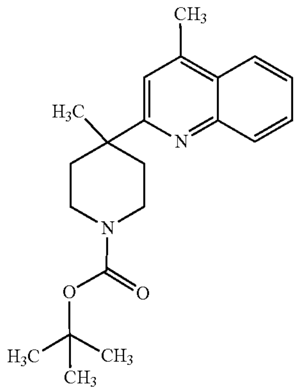 [SMILES: Cc1cc(C2(C)CCN(C(=O)OC(C)(C)C)CC2)nc2ccccc12]

A MW-vial was charged with 100 mg tert-butyl 4-{[(1,3-dioxo-1,3-dihydro-2H-isoindol-2-yl)oxy]carbonyl}-4-methylpiperidine-1-carboxylate (257 μmol), 9 mg triphenylphosphine (34 μmol) and 2.6 mg sodium iodide (17.2 μmol). The atmosphere was replaced with argon. The solvents were added and the mixture was sparged with argon for 5 min. 23 μl 4-methylquinoline (170 μmol) and 13 μl TFA (170 μmol) were added afterwards.

The MW-vial was placed in a Hepatochem-reactor were it was irradiated by a 40 W Kessil Blue LED lamp for 16 h. Water was added and the mixture was extracted with ethyl acetate for three times. The combined organic layers were filtered over a hydrophobic filter and the solvent was evaporated under reduced pressure. The crude product was purified by column chromatography and obtained as a colourless oil (50 mg, 56% yield).

$^1$H NMR (400 MHz, DMSO-$d_6$) δ ppm 1.28 (s, 3H) 1.38 (s, 9H) 1.64 (ddd, 2H) 2.29-2.38 (m, 2H) 2.68 (d, 3H) 3.14 (br s, 2H) 3.55 (ddd, 2H) 7.53 (d, 1H) 7.57 (ddd, 1H) 7.71 (ddd, 1H): 7.93 (dd, 1H) 8.04 (dd, 1H):

LC-MS (Method 1): $R_t$=1.35 min; MS (ESIpos): m/z=341 $[M+H]^+$

Intermediate 194

4-methyl-4-(4-methylquinolin-2-yl)piperidin-1-ium trifluoroacetate

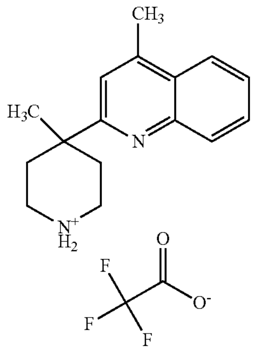

50 mg tert-butyl 4-methyl-4-(4-methylquinolin-2-yl)piperidine-1-carboxylate (147 μmol) was dissolved in 0.94 mL dichloromethane and 0.34 mL TFA (4.4 mmol) was added. The mixture was stirred for 16 h at room temperature. The solvent was evaporated under reduced pressure and used crude in the next step.

LC-MS Method 2): $R_t$=1.34 min; MS (ESIpos): m/z=241 [M]

Intermediate 195

Tert-Butyl 4-(4-fluoro-1-methyl-1H-indol-6-yl)piperidine-1-carboxylate

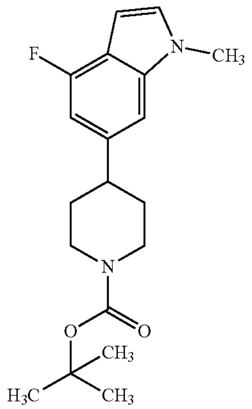 [SMILES: Cn1ccc2c(F)cc(C3CCN(C(=O)OC(C)(C)C)CC3)cc21]

Prepared in analogy to intermediate 159 by using 200 mg tert-butyl 4-(4,4,5,5-tetramethyl-1,3,2-dioxaborolan-2-yl)-3,6-dihydropyridine-1(2H)-carboxylate (0.65 mmol) and 140 mg 6-bromo-4-fluoro-1-methyl-1H-indole (0.61 mmol). The crude product (270 mg) was directly used in the next step.

$^1$H-NMR (400 MHz, DMSO-d6): δ [ppm]=1.42 (s, 9H), 1.57 (qd, 2H), 1.80 (br d, 2H), 2.71-2.94 (m, 3H), 3.77 (s, 3H), 4.04-4.17 (m, 2H), 6.40 (dd, 1H), 6.73 (dd, 1H), 7.16 (s, 1H), 7.30 (d, 1H).

LC-MS Method 2): $R_t$=1.49 min; MS (ESIneg): m/z=331 $[M-H]^-$

Intermediate 196

4-fluoro-1-methyl-6-(piperidin-4-yl)-1H-indole, Salt with Trifluoroacetic Acid

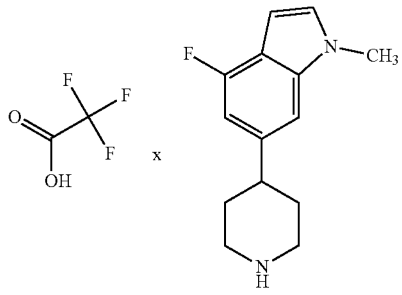 [SMILES: O=C(O)C(F)(F)F ; Cn1ccc2c(F)cc(C3CCNCC3)cc21]

To a solution of 270 mg tert-butyl 4-(4-fluoro-1-methyl-1H-indol-6-yl)piperidine-1-carboxylate (0.81 mmol) in 5.2 mL dichloromethane was added 0.63 mL TFA (8.1 mmol). The mixture stirred over night at room temperature. The mixture was concentrated under reduced pressure and evaporated 3× with toluene. The crude product (346 mg) was directly used in the next step without purification.

Intermediate 197

Tert-Butyl 4-[(2E)-3-(dimethylamino)prop-2-enoyl]piperidine-1-carboxylate

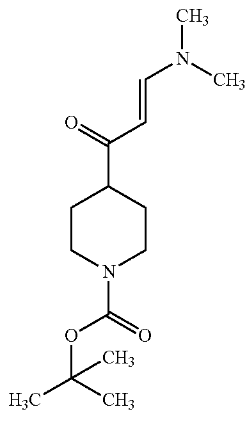 [SMILES: CN(C)/C=C/C(=O)C1CCN(C(=O)OC(C)(C)C)CC1]

A solution of 700 mg tert-butyl 4-acetylpiperidine-1-carboxylate (3.08 mmol) in 10 mL 1,1-dimethoxy-N,N-dimethylmethanamine was stirred at 110° C. for 2 days. The reaction mixture was concentrated under reduced pressure and the crude product (1 g) was directly used in the next step.

Intermediate 198

Tert-Butyl 4-(1H-pyrazol-3-yl)piperidine-1-carboxylate

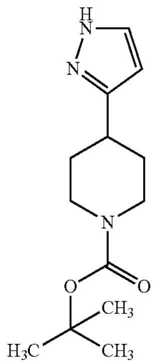

0.23 mL hydrazine monohydrate (4.8 mmol, CAS 7803-57-8) was added to a solution of 900 mg tert-butyl 4-[(2E)-3-(dimethylamino)prop-2-enoyl]piperidine-1-carboxylate (3.19 mmol, intermediate 197) in 18 mL ethanol at 15° C. The reaction mixture stirred over night at 85° C. and reaction progess was monitored by TCL (dichloromethane:ethanol 9:1; stained with potassium permanganate). The reaction mixture was evaporated and the crude product was purified by column chromatography (dichloromethane 100→dichloromethane:ethanol 90:10). The product was obtained in 78% yield (624 mg).

$^1$H NMR (400 MHz, DMSO-$d_6$) δ ppm 1.40 (s, 9H) 1.44 (dd, 2H) 1.84 (br d, 2H) 2.72-2.96 (m, 3H) 3.96 (br d, 2H) 6.05 (br d, 1H) 7.22-7.68 (m, 1H) 12.50 (br d, 1H).

Intermediate 199

Tert-Butyl 4-[1-(3-methylphenyl)-1H-pyrazol-3-yl]piperidine-1-carboxylate

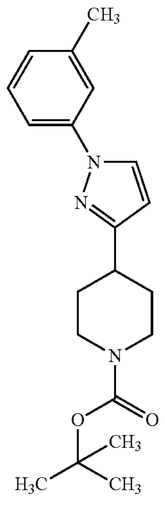 [SMILES: Cc1cccc(-n2ccc(C3CCN(C(=O)OC(C)(C)C)CC3)n2)c1]

50 mg tert-butyl 4-(1H-pyrazol-3-yl)piperidine-1-carboxylate (0.2 mmol, intermediate 198), 54 mg (3-methylphenyl)boronic acid (0.4 mmol), 54 mg Cu(II)acetate (298

μmol; CAS 142-71-2), and 150 mg activated molecular sieves were placed in a flask A solution of 32 μl pyridine (400 μmol) in 2.4 mL dichloromethane was added and the mixture stirred for 2 days under oxygen. The mixture was filtered over celite and it was washed with MeOH and some dichloromethane. The filtrate was evaporated and the crude product was purified by column chromatography (hexane 100→hexane:ethyl acetate 50:50) The product was obtained in 88% yield (63 mg).

$^{1}$H NMR (400 MHz, DMSO-$d_6$) δ ppm 1.41 (s, 9H) 1.45-1.58 (m, 2H) 1.90 (br dd, 2H) 2.36 (s, 3H) 2.84 (m, 3H) 3.95-4.01 (m, 2H) 6.40 (d, 1H) 7.07 (d, 1H) 7.33 (t, 1H) 7.54-7.60 (m, 1H): 7.63 (s, 1H) 8.35 (d, 1H).

Intermediate 200

4-[1-(3-methylphenyl)-1H-pyrazol-3-yl]piperidine, Salt with Trifluoroacetic Acid

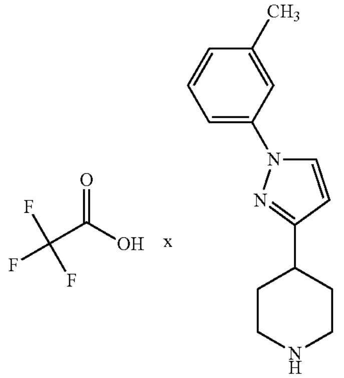 [SMILES: O=C(O)C(F)(F)F ; Cc1cccc(-n2ccc(C3CCNCC3)n2)c1]

To a solution of 60 mg tert-butyl 4-[1-(3-methylphenyl)-1H-pyrazol-3-yl]piperidine-1-carboxylate (176 μmol, intermediate 199) in 0.9 mL dichloromethane was added 0.34 mL TFA. The reaction mixture was stirred at room temperature until complete consumption of starting material. The crude product (99 mg) was directly used in the next step.

LC-MS (Method 1): $R_t$=1.45 min; MS (ESIpos): m/z=342 [M+H]$^+$

Intermediate 201

Tert-Butyl 4-[1-(3-chlorophenyl)-1H-pyrazol-3-yl]piperidine-1-carboxylate

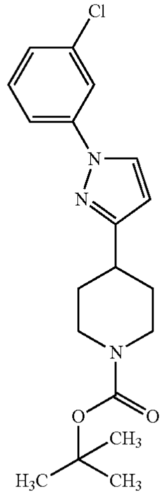 [SMILES: CC(C)(C)OC(=O)N1CCC(c2ccn(-c3cccc(Cl)c3)n2)CC1]

Prepared in analogy to intermediate 199 by using 70 mg tert-butyl 4-(1H-pyrazol-3-yl)piperidine-1-carboxylate (279 μmol, intermediate 198) and 87 mg (3-chlorophenyl)boronic acid (0.56 mmol). The product was purified by column chromatography (hexane 100→hexane:ethyl acetate 50:50) and the product was obtained in 92% yield (95 mg).

$^{1}$H NMR (400 MHz, DMSO-$d_6$) δ ppm 1.41 (s, 9H) 1.45-1.59 (m, 2H) 1.90 (br dd, 2H) 2.79-2.97 (m, 3H) 4.00 (br d, 2H) 6.46 (d, 1H) 7.31 (ddd, 1H) 7.49 (t, 1H) 7.79 (ddd, 1H) 7.89 (t, 1H) 8.47 (d, 1H).

Intermediate 202

4-[1-(3-chlorophenyl)-1H-pyrazol-3-yl]piperidine, Salt with Trifluoroacetic Acid

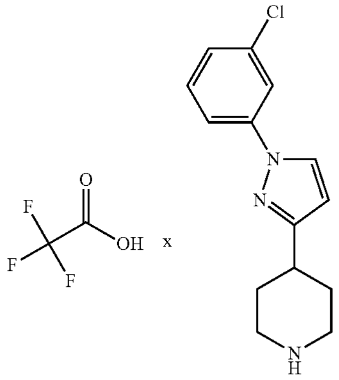 [SMILES: O=C(O)C(F)(F)F ; Clc1cccc(-n2ccc(C3CCNCC3)n2)c1]

Prepared in analogy to intermediate 200 by using 90 mg tert-butyl 4-[1-(3-chlorophenyl)-1H-pyrazol-3-yl]piperidine-1-carboxylate (249 μmol, intermediate 201). The crude product (170 mg): was used directly in the next step.

LC-MS (Method 1): $R_t$=1.52 min; MS (ESIpos): m/z=362 [M+H]$^+$

Intermediate 203

Tert-Butyl 4-[l-(4-chlorophenyl)-1H-pyrazol-3-yl]piperidine-1-carboxylate

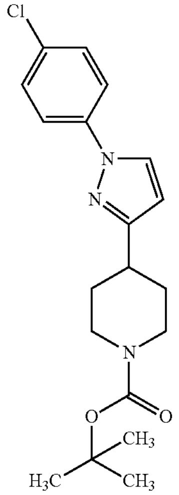 [SMILES: CC(C)(C)OC(=O)N1CCC(c2ccn(-c3ccc(Cl)cc3)n2)CC1]

Prepared in analogy to intermediate 199 by using 70 mg tert-butyl 4-(1H-pyrazol-3-yl)piperidine-1-carboxylate (279 μmol, intermediate 198) and 87 mg (4-chlorophenyl)boronic acid (0.56 mmol). The product was purified by column chromatography (hexane 100→hexane:ethyl acetate 50:50) and the product was obtained in 55% yield (62 mg).

$^1$H NMR (400 MHz, DMSO-$d_6$) δ ppm 1.41 (s, 9H) 1.45-1.59 (m, 2H) 1.90 (br dd, 2H) 2.78-2.96 (m, 3H) 3.99 (br d, 2H) 6.45 (d, 1H) 7.50-7.55 (m, 2H) 7.80-7.84 (m, 2H) 8.41 (d, 1H).

Intermediate 204

4-[1-(4-chlorophenyl)-1H-pyrazol-3-yl]piperidine, Salt with Trifluoroacetic Acid

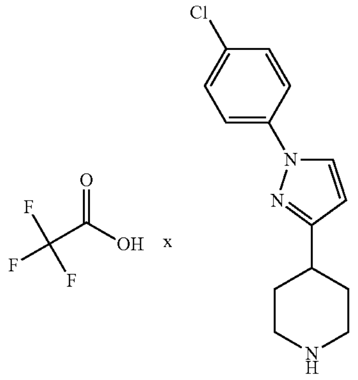 [SMILES: O=C(O)C(F)(F)F ; Clc1ccc(-n2ccc(C3CCNCC3)n2)cc1]

Prepared in analogy to intermediate 200 by using 60 mg tert-butyl 4-[1-(4-chlorophenyl)-1H-pyrazol-3-yl]piperidine-1-carboxylate (166 μmol, intermediate 203). The crude product (105 mg): was used directly in the next step.

LC-MS (Method 1): $R_t$=1.50 min; MS (ESIpos): m/z=362 $[M+H]^+$

Intermediate 205

Tert-Butyl 4-[({(Z)-[amino(pyridin-3-yl)methylidene]amino}oxy)carbonyl]piperidine-1-carboxylate

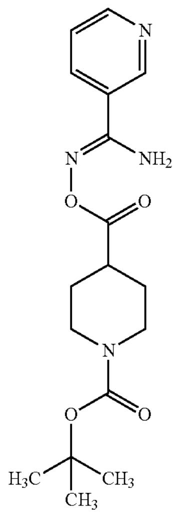 [SMILES: CC(C)(C)OC(=O)N1CCC(C(=O)O/N=C(\N)c2cccnc2)CC1]

To a suspension of 500 mg N'-hydroxypyridine-3-carboximidamide (3.65 mmol) and 820 mg 1-(tert-butoxycarbonyl) piperidine-4-carboxylic acid (3.57 mmol) in 10 mL dichloromethane was added dropwise 0.86 mL N-(3-dimethylaminopropyl)-N'-ethylcarbodiimide (3.9 mmol). The reaction mixture was stirred for 2 h at room temperature. The reaction mixture was washed with brine and the organic layer was separated, dried (waterresistant filter) and concentrated under reduced pressure. The crude product (2.2 g) was used in the next step.

LC-MS Method 2): $R_t$=0.95 min; MS (ESIneg): m/z=347 $[M-H]^-$

Intermediate 206

Tert-Butyl 4-[3-(pyridin-3-yl)-1,2,4-oxadiazol-5-yl] piperidine-1-carboxylate

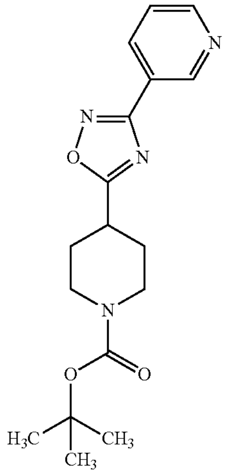 [SMILES: CC(C)(C)OC(=O)N1CCC(c2nc(-c3cccnc3)no2)CC1]

To a solution of 2.2 g tert-butyl 4-[({(Z)-[amino(pyridin-3-yl)methylidene]amino}oxy)-carbonyl]piperidine-1-carboxylate (6.31 mmol, intermediate 205) in toluene was added 10 μl sulfuric acid (190 μmol). The reaction mixture was stirred overnight at reflux. The mixture was concentrated under reduced pressure. The residue was partioned between dichloromethane and brine. The aqueous layer was extracted 2× with dichloromethane. The combined organic layers were dried (waterresistant filter) and concentrated under reduced pressure. The crude product was purified by column chromatography (Hexan/ethyl acetate 9:1→hexane/ethyl acetate 3:7) and the combined fractions were concentrated under reduced pressure. The product was obtained in 23% yield (539 mg).

1H-NMR (400 MHz, DMSO-d6): 5 [ppm]=1.41 (s, 9H), 1.61-1.75 (m, 2H), 2.09 (br dd, 2H), 2.99 (br s, 2H), 3.38 (tt, 1H), 3.95 (br d, 2H), 7.61 (ddd, 1H), 8.35 (dt, 1H), 8.78 (dd, 1H), 9.16 (dd, 1H).

LC-MS Method 2): $R_t$=1.22 min; MS (ESIpos): m/z=331 $[M+H]^+$

Intermediate 207

3-[5-(piperidin-4-yl)-1,2,4-oxadiazol-3-yl]pyridine

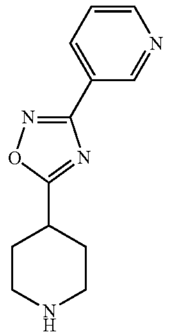 [SMILES: c1cncc(-c2noc(C3CCNCC3)n2)c1]

To a solution of 539 mg tert-butyl 4-[3-(pyridin-3-yl)-1,2,4-oxadiazol-5-yl]piperidine-1-carboxylate (1.63 mmol) in 10 mL dichloromethane was added at 0° C. 1.3 mL TFA (16 mmol). The reaction mixture was stirred overnight at room temperature. Due to incomplete conversion additional 10 eq of TFA were added and it was stirred for further 2 h. The reaction mixture was first neutralised with sat. aqueous sodium bicarbonate solution and then basified with 1 N sodium hydroxide solution. The layers were separated and the aqueous layer was extracted 2× with dichloromethane. The combined organic layers were washed with water and brine, dried (waterresistant filter) and concentrated under reduced pressure. The product (356 mg, 94% yield) was of sufficient purity to be used for the next step without further purification.

$^1$H-NMR (400 MHz, DMSO-d6): δ [ppm]=1.61-1.75 (m, 2H), 1.98 (br dd, 2H), 2.17 (br s, 1H), 2.60 (td, 2H), 2.99 (dt, 2H), 3.22 (tt, 1H), 7.61 (ddd, 1H), 8.35 (dt, 1H), 8.78 (dd, 1H), 9.13-9.18 (m, 1H).

LC-MS Method 2): $R_t$=0.70 min; MS (ESIpos): m/z=231 $[M+H]^+$

Intermediate 208

Tert-Butyl 4-(2-methylquinolin-6-yl)-3,6-dihydro-pyridine-1(2H)-carboxylate

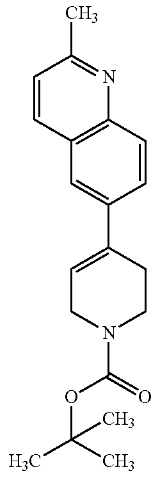

A mixture of 812 mg 6-bromo-2-methylquinoline, 41 mg Xphos Pd G2 (CAS 1310584-14-5), 1.17 g tetrahydroxydiboron and 1.28 g potassium actetate in 73 ml ethanol was heated for 3 hours at 80° C. under an Argon atmosphere. To this mixture, a mixture of 6.5 ml potassium carbonate solution (aqueous, 2M) and 1.1 g tert-butyl 4-[(1,1,2,2,3,3,4,4,4-nonafluorobutane-1-sulfonyl)oxy]-3,6-dihydropyridine-1(2H)-carboxylate in 5 ml ethanol were added and stirred for an additional 2 hours at 80° C. and 145 hours at RT. The reaction was poured into water and extracted with dichloromethane. The organic layer was washed with brine and water and dried with sodium sulfate. 880 mg of crude title compound was obtained and used directly in the next step.

LC-MS Method 2): $R_t$=1.29 min; MS (ESIpos): m/z=324 $[M+H]^+$

Intermediate 209

Tert-Butyl 4-(2-methylquinolin-6-yl)piperidine-1-carboxylate

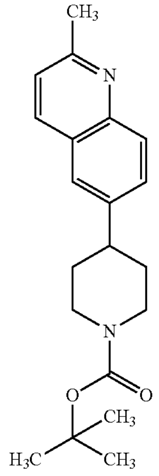

A mixture of 190 mg tert-butyl 4-(2-methylquinolin-6-yl)-3,6-dihydropyridine-1(2H)-carboxylate (intermediate 208), 740 mg ammonium formate and 80 mg palladium on charcoal (10%) in 71 ml dioxane and 8 ml methanol was stirred 3 hours at 60° C. The reaction was filtered and diluted with dichloromethane. The organic layer was washed with water and evaporated in vacuo. 180 mg of the title compound were obtained.

$^1$H NMR (400 MHz, DMSO-$d_6$) δ ppm 1.42 (s, 9H) 1.50-1.64 (m, 2H) 1.79-1.89 (m, 2H) 2.63 (s, 3H) 2.78-2.93 (m, 3H) 3.53-3.59 (m, 1H) 4.04-4.17 (m, 2H) 7.34-7.41 (m, 1H) 7.56-7.65 (m, 1H) 7.72-7.76 (m, 1H) 7.80-7.87 (m, 1H) 8.10-8.21 (m, 1H).

Intermediate 210

2-methyl-6-(piperidin-4-yl)quinoline

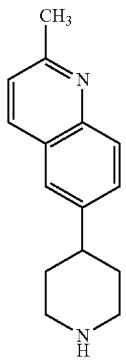 [SMILES: Cc1ccc2cc(C3CCNCC3)ccc2n1]

A solution of 190 mg tert-butyl 4-(2-methylquinolin-6-yl)piperidine-1-carboxylate (intermediate 209) and 1.1 ml trifluoroacetic acid in 6.3 ml dichloromethane was stirred for 2 hours at RT. The solvent was evaporated in vacuo and toluene was added and evaporated 2 times in vacuo. 165 mg of the title compound were obtained.

1H NMR (400 MHz, DMSO-d6) δ ppm 1.78-1.97 (m, 2H) 2.03-2.13 (m, 2H) 2.88 (s, 3H) 3.01-3.20 (m, 3H) 3.39-3.50 (m, 2H) 7.79-7.88 (m, 1H) 7.91-7.98 (m, 1H) 8.02-8.07 (m, 1H): 8.11-8.17 (m, 1H) 8.83-8.92 (m, 1H):

Intermediate 211

Tert-Butyl 4-[4-(3-methoxyphenyl)-1,3-thiazol-2-yl] piperidine-1-carboxylate

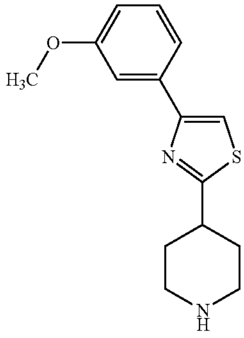 [SMILES: COc1cccc(-c2csc(C3CCNCC3)n2)c1]

A mixture of 150 mg 2-bromo-1-(3-methoxyphenyl) ethan-1-one (655 μmol) and 160 mg tert-butyl 4-carbamothioylpiperidine-1-carboxylate (655 μmol) in 2 mL of ethanol were stirred for 2 h at 90° C. The reaction mixture was cooled to room temperature and the resulting suspension was filtered and washed with ethanol. The solid was dried and the crude product (203 mg) was used directly in the next step.

1H-NMR (400 MHz, DMSO-d6): δ [ppm]=1.85-2.01 (m, 2H), 2.25 (br dd, 2H), 3.08 (br t, 2H), 3.36-3.50 (m, 3H), 3.81 (s, 3H), 6.93 (ddd, 1H), 7.36 (t, 1H), 7.46-7.57 (m, 2H), 8.08 (s, 1H), 8.24-8.46 (m, 1H), 8.62 (br s, 1H).

Intermediate 212

Tert-Butyl 4-[4-(2-methoxyphenyl)-1,3-thiazol-2-yl] piperidine-1-carboxylate

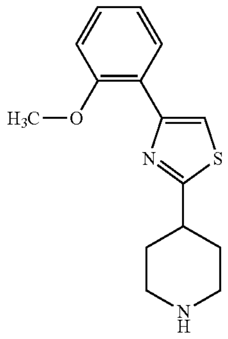 [SMILES: COc1ccccc1-c1csc(C2CCNCC2)n1]

A mixture of 150 mg 2-bromo-1-(2-methoxyphenyl) ethan-1-one (655 μmol) and 160 mg tert-butyl 4-carbamothioylpiperidine-1-carboxylate (655 μmol) in 2 mL of ethanol were stirred for 2 h at 90° C. The reaction mixture was cooled to room temperature, the solvent was evaporated and the crude product was purified by RP-HPLC. The product was obtained in 92% yield (197 mg).

$^1$H NMR (400 MHz, DMSO-$d_6$) δ ppm 1.81-1.97 (m, 2H) 2.22 (br dd, 2H) 3.02 (td, 2H) 3.29-3.45 (m, 3H) 3.92 (s, 3H) 7.04 (td, 1H) 7.14 (dd, 1H) 7.34 (ddd, 1H) 7.99 (s, 1H) 8.13 (dd, 1H).

Intermediate 213

Tert-Butyl 4-[4-(4-methylphenyl)-1,3-thiazol-2-yl] piperidine-1-carboxylate

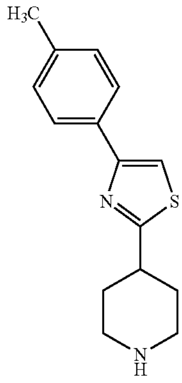 [SMILES: Cc1ccc(-c2csc(C3CCNCC3)n2)cc1]

A mixture of 150 mg 2-bromo-1-(4-methylphenyl)ethan-1-one (704 μmol) and 172 mg tert-butyl 4-carbamothioylpiperidine-1-carboxylate (704 μmol) in 2 mL of ethanol was stirred for 2 h at 90° C. The reaction mixture was cooled to room temperature and the solvent was evaporated. The crude product was purified by RP-HPLC and obtained in 96% yield (210 mg).

$^1$H NMR (400 MHz, DMSO-$d_6$) δ ppm 1.80-1.95 (m, 2H) 2.20 (br dd, 2H) 2.33 (s, 3H) 2.99 (td, 2H) 3.27-3.41 (m, 4H) 7.25 (d, 2H) 7.83 (d, 2H) 7.95 (s, 1H).

Intermediate 214

5-methoxy-2-(piperidin-4-yl)-1,3-benzoxazole

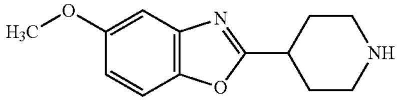 [SMILES: COc1ccc2oc(C3CCNCC3)nc2c1]

A MW-vial was charged with 150 mg 5-bromo-2-(piperidin-4-yl)-1,3-benzoxazole, 12 mg RockPhos ligand, 22 mg RockPhos Pd G3 and 243 mg cesium carbonate and flushed with nitrogen. 2 mL Degassed toluene and 216 μl methanol were added and the mixture was stirred 14 h at 60° C. under a nitrogen atmosphere. The mixture was diluted with dichloromethane, filtered over celite, washed with dichloromethane and the filtrate was evaporated. The residue was purified by RP-HPLC (column: X-Bridge C18 5 μm 100×30 mm, mobile phase:acetonitrile/water (0.2 vol. % ammonia 32%)-gradient) to obtain 23 mg of the title compound.

$^1$H NMR (400 MHz, DMSO-d6) δ ppm 1.58-1.86 (m, 2H) 2.02-2.18 (m, 3H) 2.57-2.66 (m, 1H): 2.86-3.10 (m, 4H) 3.79 (d, 3H) 6.92 (dd, 1H) 7.25 (s, 1H) 7.52-7.58 (m, 1H).

Intermediate 215

5-[(oxolan-2-yl)methoxy]-2-(piperidin-4-yl)-1,3-benzoxazole

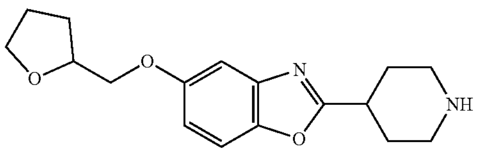 [SMILES: c1cc2oc(C3CCNCC3)nc2cc1OCC1CCCO1]

A MW-vial was charged with 100 mg 5-bromo-2-(piperidin-4-yl)-1,3-benzoxazole, 8 mg RockPhos ligand, 15 mg RockPhos Pd G3 and 162 mg cesium carbonate and flushed with nitrogen. 1.5 mL Degassed toluene and 340 μl tetrahydrofuranyl alcohol were added and the mixture was stirred 14 h at 80° C. under a nitrogen atmosphere. The mixture was diluted with dichloromethane, filtered over celite, washed with dichloromethane and the filtrate was evaporated. The residue was purified by RP-HPLC (column: X-Bridge C18 5 μm 100×30 mm, mobile phase:acetonitrile/water (0.2 vol. % ammonia 32%)-gradient) to obtain 30 mg of the title compound.

$^1$H NMR (400 MHz, DMSO-d6) δ ppm 1.57-1.74 (m, 3H) 1.75-1.92 (m, 2H) 1.77-1.91 (m, 2H): 1.92-2.06 (m, 3H) 2.54-2.65 (m, 2H) 2.93-3.08 (m, 3H) 3.62-3.72 (m, 1H)

3.74-3.83 (m, 1H) 3.89-4.02 (m, 2H) 4.11-4.21 (m, 1H) 6.84-6.96 (m, 1H) 7.25 (d, 1H) 7.54 (d, 1H).

Intermediate 216

Tert-Butyl 4-[6-(oxetan-3-yl)-1,3-benzoxazol-2-yl]piperidine-1-carboxylate

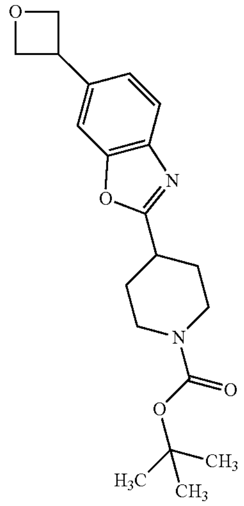 [SMILES: CC(C)(C)OC(=O)N1CCC(c2nc3ccc(C4COC4)cc3o2)CC1]

A mixture of 150 3-bromooxetane (1.8 mmol), 150 mg tert-butyl 4-(6-bromo-1,3-benzoxazol-2-yl)piperidine-1-carboxylat (0.4 mmol), 120 μL 1,1,1,3,3,3-hexamethyl-2-(trimethylsilyl)trisilane (0.4 mmol), 9 mg bis{3,5-difluoro-2-[5-(trifluoromethyl)pyridin-2-yl]phenyl}iridium-(I) hexafluorophosphate (8 μmol), 5.3 mg 4,4'-di-tert-butyl-2,2'-bipyridine (20 μmol), 57 mg Lithium hydroxide, 4.3 mg 1,2-dimethoxyethane-dichloronickel (1:1) (6.97 μmol) was stirred in 6.8 mL 1,2-dimethoxyethane and degassed under argon. The reaction was stirred and irradiated by two Kessil LED Aquarium lights (each 40 W) 455 nm for 12 h at 35° C. The mixture was concentrated under reduced pressure, water was added and the aqueous phase was extracted with ethyl acetate two times. The combined organic phases were washed with an aqueous solution of sodium bicarbonate and water, dried over sodium sulfate and the filtrate was concentrated under reduced pressure. Purification: The residue was purified by RP-HPLC (column: X-Bridge C18 5 μm 100×30 mm, mobile phase: acetonitrile/water (0.2 vol. % ammonia 32%)-gradient) to obtain 95 mg of the title compound.

$^1$H NMR (400 MHz, DMSO-d6) δ ppm 1.41 (s, 10H) 1.60-1.75 (m, 2H) 2.02-2.12 (m, 2H): 3.19-3.28 (m, 1H) 3.89-4.00 (m, 2H) 4.33-4.44 (m, 1H) 4.65 (dd, 2H) 4.96 (dd, 2H) 7.37 (dd, 1H) 7.67 (d, 1H) 7.74-7.77 (m, 1H).

Intermediate 217

6-(oxetan-3-yl)-2-(piperidin-4-yl)-1,3-benzoxazole

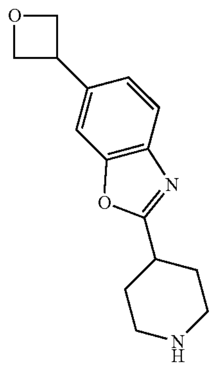 [SMILES: c1cc2nc(C3CCNCC3)oc2cc1C1COC1]

95 mg tert-butyl 4-[6-(oxetan-3-yl)-1,3-benzoxazol-2-yl]piperidine-1-carboxylate (intermediate 216) and 0.41 ml trifluoroacetic acid in 3 ml dichloromethane were stirred for 4 hours at RT. The solvent was evaporated in vacuo and toluene was added and evaporated 2 times in vacuo. 130 mg of the title compound were obtained.

LC-MS Method 2): $R_t$=0.79 min; MS (ESIpos): m/z=258 $[M+H]^+$

Intermediate 218

Tert-Butyl 4-(1,3-benzoxazol-2-yl)-4-hydroxypiperidine-1-carboxylate

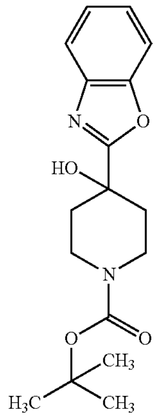 [SMILES: CC(C)(C)OC(=O)N1CCC(O)(c2nc3ccccc3o2)CC1]

To a solution of 179 mg 1,3-benzoxazole (12 mmol) in 8 mL THF at −78° C. was added 8.8 mL n-Butyllithium (2.5 M in hexane, 12 mmol) and it was stirred for 30 min. Then 3.1 g magnesiumbromid-diethylether-complex (12 mmol, CAS 29858-07-9) in 3 mL THF was added and it was stirred for 30 min at −78° C.

800 mg tert-butyl 4-oxopiperidine-1-carboxylate (4 mmol) was added and the solution was allowed to warm up to room temperature and stirred for 3.5 h. The mixture was carefully quenched with water and extracted 3× with ethyl acetate. The org. layer was filtered over a waterresistant-filter and concentrated under reduced pressure. The crude product was purified by column chromatography using hexanes→hexanes:ethyl acetate 60:40. The product was obtained in 30% yield (433 mg).

$^1H$ NMR (400 MHz, DMSO-$d_6$) δ ppm 1.40 (s, 9H) 1.89-1.96 (m, 2H) 1.99-2.09 (m, 2H) 3.23-3.33 (m, 2H) 3.58-3.67 (m, 2H) 6.01 (s, 1H) 7.39 (quind, 2H) 7.71-7.77 (m, 2H).

Intermediate 219

Tert-Butyl 4-(1,3-benzoxazol-2-yl)-4-fluoropiperidine-1-carboxylate

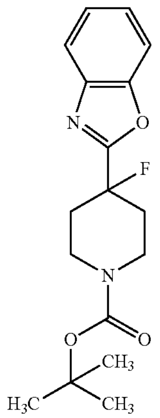 [SMILES: CC(C)(C)OC(=O)N1CCC(F)(c2nc3ccccc3o2)CC1]

A solution of 520 μl 2-methoxy-N-(2-methoxyethyl)-N-(trifluoro-lambda$^4$-sulfanyl)ethan-1-amine (50% in THF, 1.4 mmol) in 1.5 mL dichloromethane was cooled to −15° C. Then a solution of 150 mg tert-butyl 4-(1,3-benzoxazol-2-yl)-4-hydroxypiperidine-1-carboxylate (471 μmol, intermediate 218) in 3 mL dichloromethane was added dropwise and stirred 3.5 h at −15° C. Due to incomplete conversion another 3 equivalents of 2-methoxy-N-(2-methoxyethyl)-N-(trifluoro-lambda$^4$-sulfanyl)ethan-1-amine was added at −15° C. and it was stirred for 2 h. The reaction mixture was quenched with water, basified with sat. aq. Sodium bicarbonate and extracted 3× with dichloromethane.

The org. layer was filtered over a waterresistant-filter and concentrated under reduced pressure.

The crude product was purified by column chromatography using hexane 100→hexane:ethyl acetate 60:40. The product was obtained in 78% yield (122 mg).

$^1H$ NMR (400 MHz, DMSO-$d_6$) δ ppm 1.42 (s, 9H) 2.14-2.25 (m, 1H) 2.26-2.35 (m, 3H) 3.21-3.32 (m, 2H) 3.74-3.83 (m, 2H) 7.41-7.53 (m, 2H) 7.79-7.87 (m, 2H).

Intermediate 220

2-(4-fluoropiperidin-4-yl)-1,3-benzoxazole, Salt with Trifluoroacetic Acid

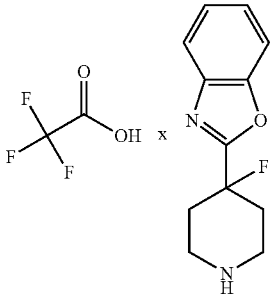

To a solution of 155 mg tert-butyl 4-(1,3-benzoxazol-2-yl)-4-fluoropiperidine-1-carboxylate (484 µmol, intermediate 219) in 2.5 mL dichloromethane was added 0.93 mL TFA and it was stirred for 2 h at room temperature. The mixture was concentrated under reduced pressure and the crude (225 mg) product was directly used in the next step.

LC-MS Method 2): $R_t$=0.61 min; MS (ESIpos): m/z=220 $[M+H]^+$

Intermediate 221

Tert-Butyl 4-(1,3-benzoxazol-2-yl)-4-methoxypiperidine-1-carboxylate

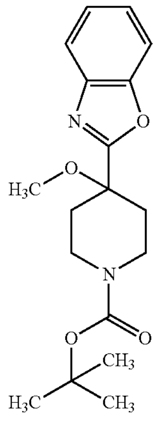 [SMILES: COC1(c2nc3ccccc3o2)CCN(C(=O)OC(C)(C)C)CC1]

28 mg sodium hydride (60% suspension in mineral oil, 707 µmol, CAS 7646-69-7) was added to a solution of 150 mg tert-butyl 4-(1,3-benzoxazol-2-yl)-4-hydroxypiperidine-1-carboxylate (471 µmol) in 3 mL DMF and stirred for 5 min. 59 µl iodomethane (940 µmol) was then added to the reaction mixture and it was stirred for 2 h at room temperature. The reaction mixture was diluted with water and extracted 3× with ethyl acetate. The org. layer was filtered over a waterresistant-filter and concentrated under reduced pressure. The crude product was purified by column chromatography using hexanes 100→hexanes:ethyl acetate 70:30. The product was obtained in quantitative yield (182 mg).

$^1$H NMR (400 MHz, DMSO-$d_6$) δ ppm 1.40 (s, 9H) 2.02-2.17 (m, 4H) 3.07 (s, 3H) 3.21-3.32 (m, 2H) 3.58 (br dt, 2H) 7.37-7.47 (m, 2H) 7.75-7.83 (m, 2H).

Intermediate 222

2-(4-methoxypiperidin-4-yl)-1,3-benzoxazole, Salt with Trifluoroacetic Acid

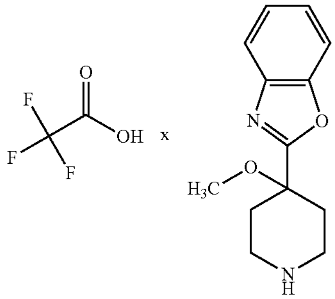

1 mL TFA was added to a solution of 180 mg tert-butyl 4-(1,3-benzoxazol-2-yl)-4-methoxypiperidine-1-carboxylate (542 µmol, intermediate 221) in 2.8 mL dichloromethane and stirred 3 h at room temperature. After full consumption of starting material the mixture was concentrated under reduced pressure and the crude product was directly used in the next step.

LC-MS (Method 1): $R_t$=0.61 min; MS (ESIpos): m/z=233 $[M+H]^+$

Intermediate 223

5-bromo-2-(4-methylpiperidin-4-yl)-1,3-benzoxazole

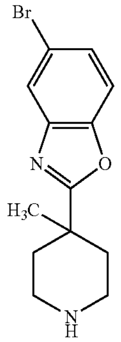 [SMILES: CC1(c2nc3cc(Br)ccc3o2)CCNCC1]

Polyphosphoric acid was heated up to 180° C. and stir red. 1 g 4-methylpiperidine-4-carboxylic acid (6.98 mmol) and 1.3 g 2-amino-4-bromophenol (6.98 mmol) were added afterwards and the black mixture was stirred for 45 min at 180° C. The hot mixture was poured onto ice and basified with solid potassium hydroxide. The mixture was extracted with ethyl acetate three times and the combined organic layers were washed with brine, filtered over a hydrophobic filter and the solvent was evaporated under reduced pressure. The product (950 mg) was used crude in the next step.

Intermediate 224

Tert-Butyl 4-(5-bromo-1,3-benzoxazol-2-yl)-4-methylpiperidine-1-carboxylate

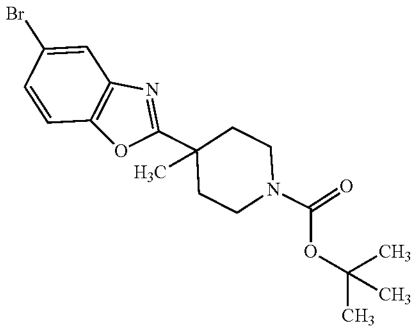 [SMILES: CC(C)(C)OC(=O)N1CCC(C)(c2nc3cc(Br)ccc3o2)CC1]

1.58 g 5-bromo-2-(4-methylpiperidin-4-yl)-1,3-benzoxazole (5.35 mmol, intermediate 223) was dissolved in 24 mL dichloromethane and 4.7 mL di-isopropylethylamine(27 mmol) and catalytic amounts of 4-dimethylaminopyridine were added. 2.3 g Di-tert-butyldicarbonat (11 mmol) was dissolved in 3 mL dichloromethane and slowly added to the mixture.

The mixture was stirred for 16 h at room temperature. Water was added and the mixture was extracted with dichloromethane 3×. The combined organic layers were filtered over a hydrophobic filter and the solvent was evaporated under reduced pressure. The product was purified by column chromatography and obtained in 37% yield (848 mg).

$^1$H NMR (400 MHz, DMSO-$d_6$) δ ppm 1.39 (s, 12H) 1.64 (ddd, 2H) 2.15-2.23 (m, 2H) 3.09 (br s, 2H) 3.65 (br dt, 2H) 7.54 (dd, 1H) 7.70 (d, 1H) 7.98 (dd, 1H).

Intermediate 225

Tert-Butyl 4-[5-(methoxymethyl)-1,3-benzoxazol-2-yl]-4-methylpiperidine-1-carboxylate

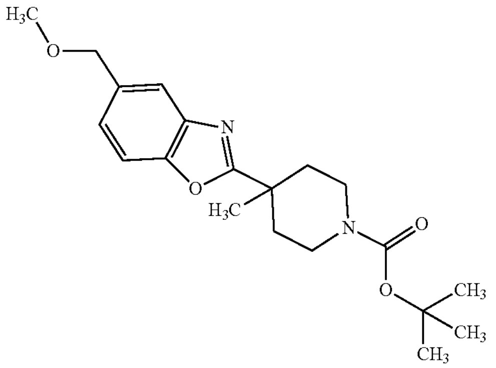 [SMILES: COCc1ccc2oc(C3(C)CCN(C(=O)OC(C)(C)C)CC3)nc2c1]

The reaction was carried out in three separate MW-Vials. 300 mg tert-butyl 4-(5-bromo-1,3-benzoxazol-2-yl)-4-methylpiperidine-1-carboxylate (759 μmol, intermediate 224), 231 mg potassium trifluorido(methoxymethyl)borate(1-) (1.52 mmol), then 161 mg sodium carbonate (1.52 mmol) and 17 mg [Ir(dF($CF_3$)$ppy_2$)$_2$(dtbbpy)]$PF_6$ (15 μmol, CAS 870987-63-6) were dissolved in 12 mL 1,4-dioxane and split onto 3 reaction vials. In a separate vial, 5 mg nickel(II): chloride ethylene glycol dimer (22.8 μmol, CAS 29046-78-4) and 4,4'-di-tert-butyl-2,2'-bipyridine (6.11 mg, 22.8 μmol; CAS 72914-19-3) were dissolved in 3 mL N,N-dimethylacetamide followed by stirring for 5 min. The catalyst solution was syringed and distributed to the sealed reaction vials and degassed for 5 minutes with argon. 230 μl Tris(trimethylsilyl)silan (760 μmol; CAS 1873-77-4) was added afterwards by distribution amond the three vials. The MW-vials were placed in a waterbath where they were subsequently irradiated by two 40 W Kessil LED Aquarium lamps.

Water was added and the mixture was extracted with ethyl acetate 3×. The combined organic layers were filtered over a hydrophobic filter and the solvent was evaporated under reduced pressure. The product was purified by column chromatography and the product was obtained as a yellow oil in 52% yield (158 mg).

$^1$H NMR (400 MHz, DMSO-$d_6$) δ ppm 1.36-1.42 (m, 12H) 1.64 (ddd, 2H) 2.21 (br dt, 2H) 3.08 (br s, 2H) 3.28 (s, 3H) 3.66 (dt, 2H) 4.50 (s, 2H) 7.33 (dd, 1H) 7.63-7.68 (m, 2H).

LC-MS Method 2): $R_t$=1.37 min; MS (ESIpos): m/z=361 $[M+H]^+$

Intermediate 226

5-(methoxymethyl)-2-(4-methylpiperidin-4-yl)-1,3-benzoxazole

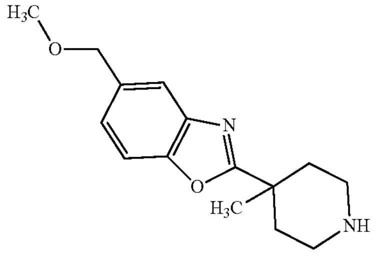 [SMILES: COCc1ccc2oc(C3(C)CCNCC3)nc2c1]

A solution of 150 mg tert-butyl 4-[5-(methoxymethyl)-1,3-benzoxazol-2-yl]-4-methylpiperidine-1-carboxylate (416 μmol, intermediate 225) in 5 mL dichloromethane was treated with 0.64 mL TFA and stirred at room temperature for 4 h. The reaction mixture was evaporated and co-evaporated with toluene 2×. The crude product (135 mg) was directly used in the next step. 1H NMR (400 MHz, DMSO-d6) δ ppm 1.43 (s, 3H) 1.82-1.97 (m, 2H) 2.35-2.46 (m, 2H) 2.91-3.11 (m, 2H) 3.29 (s, 5H) 4.51 (s, 2H) 7.29-7.40 (m, 1H) 7.68 (s, 2H) 8.33-8.56 (m, 2H).

Intermediate 227

6-bromo-2-(4-methylpiperidin-4-yl)-1,3-benzoxazole

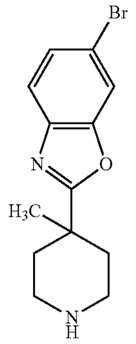

6 mL Polyphosphoric acid (CAS 8017-16-1) was heated up to 180° C. and stirred. 1 g 4-methylpiperidine-4-carboxylic acid (6.98 mmol) and 1.3 g 2-amino-5-bromophenol (6.98 mmol): were added afterwards and the black mixture was stirred for 30 min at 180° C. The hot mixture was poured over ice and basified with solid potassium hydroxide. The mixture was extracted with ethyl acetate for 3×. The combined organic layers were washed with brine, filtered over a hydrophobic filter and the solvent was evaporated under reduced pressure. The crude product was obtained as a brown solid and directly used in the next step.

$^1$H NMR (400 MHz, DMSO-$d_6$) δ ppm 1.35 (s, 3H) 1.51-1.63 (m, 2H) 2.17 (br dt, 2H) 2.53-2.61 (m, 2H) 2.77-2.84 (m, 2H) 7.52 (dd, 1H) 7.66-7.70 (m, 1H) 8.03 (dd, 1H).

Intermediate 228

Tert-Butyl 4-(6-bromo-1,3-benzoxazol-2-yl)-4-methylpiperidine-1-carboxylate

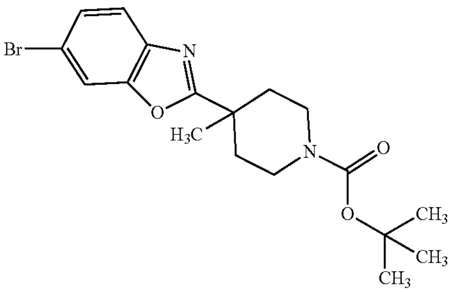 [SMILES: CC(C)(C)OC(=O)N1CCC(C)(c2nc3ccc(Br)cc3o2)CC1]

To a solution of 660 mg 6-bromo-2-(4-methylpiperidin-4-yl)-1,3-benzoxazole (2.24 mmol) in 9.8 mL dichloromethane were added 1.9 mL di-isopropylethylamine (11 mmol) and catalytic amounts of 4-dimethylaminopyridine. A solution of 0.98 g di-tert-butyldicarbonate (4.5 mmol) in 2 mL dichloromethane was slowly added to the mixture and it was stirred at room temperature for 16 hours. Water was added and the mixture was extracted with dichloromethane 3×. The combined organic layers were filtered over a waterresistant filter and the solvent was evaporated under reduced pressure. The product was purified by column chromatography and obtained as a brown oil (260 mg, 28% yield).

LC-MS Method 2): $R_t$=1.56 min; MS (ESIpos): m/z=339 [M+H—tert Butyl]$^+$

Intermediate 229

Tert-Butyl 4-[6-(methoxymethyl)-1,3-benzoxazol-2-yl]-4-methylpiperidine-1-carboxylate

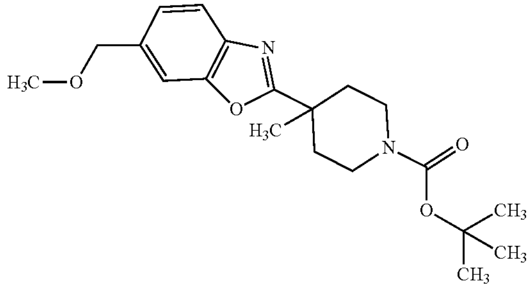 [SMILES: COCc1ccc2nc(C3(C)CCN(C(=O)OC(C)(C)C)CC3)oc2c1]

Prepared according to intermediate 225 by using 300 mg tert-butyl 4-(6-bromo-1,3-benzoxazol-2-yl)-4-methylpiperidine-1-carboxylate (0.76 mmol, intermediate 228) and lithium carbonate (112 mg, 1.52 mmol) as a based instead of sodium carbonate. The product was obtained as a brown oil in 62% yield (173 mg).

LC-MS Method 2): $R_t$=1.18 min; MS (ESIpos): m/z=361 [M+H]$^+$

Intermediate 230

6-(methoxymethyl)-2-(4-methylpiperidin-4-yl)-1,3-benzoxazole

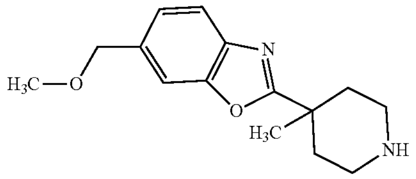 [SMILES: COCc1ccc2nc(C3(C)CCNCC3)oc2c1]

A solution of 170 mg tert-butyl 4-[6-(methoxymethyl)-1,3-benzoxazol-2-yl]-4-methylpiperidine-1-carboxylate (472 μmol, intermediate 229) in 5 mL dichloromethane was treated with 730 μl TFA (9.4 mmol) and stirred at room temperature for 4 h. After consumption of starting material the reaction mixture was evaporated and the product was obtained as the TFA salt (180 mg). 1H NMR (400 MHz, DMSO-d6) δ ppm 1.43 (s, 3H) 1.89 (s, 2H) 2.34-2.45 (m, 2H) 2.92-3.08 (m, 2H) 3.29 (s, 5H) 4.52 (s, 2H) 7.30-7.38 (m, 1H) 7.61-7.67 (m, 1H) 7.69 (s, 1H).

Intermediate 231

Tert-Butyl 4-hydroxy-4-(5-methoxy-1,3-benzoxazol-2-yl)piperidine-1-carboxylate

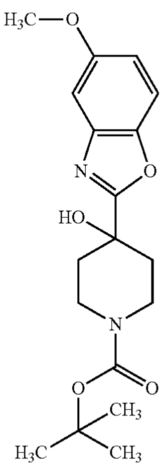 [SMILES: COc1ccc2oc(C3(O)CCN(C(=O)OC(C)(C)C)CC3)nc2c1]

A dry flask was charged with 852 mg tert-butyl 4-oxopiperidine-1-carboxylate (4.3 mmol) in 1.8 mL THF and flushed with nitrogen. 10.2 mL diiodidomagnesium-bis(5-methoxy-1,3-benzoxazol-2-yl)zinc (2/1) (0.42 M, 4.3 mmol, prepared according to A. Metzger et al. *Angew. Chem. Int. Ed.* 2010, 49, 4665-4668) was added dropwise and the reaction mixture was stirred for 2 h at room temperature. Another equivalent of tert-butyl 4-oxopiperidine-1-carboxylate was added and stirring was continued over night at room temperature. The reaction mixture was quenched with aq. ammonium chloride and extracted 3× with ethyl acetate. The organic layers were filtered over water-resistant filter and the solvents were evaporated. The crude product was purified by column chromatography (hexanes 100%→ethyl acetate 100%) and by RP-HPLC. The product was obtained in 7% yield (109 mg).

$^1$H NMR (400 MHz, DMSO-$d_6$) δ ppm 1.40 (s, 9H) 1.86-1.96 (m, 2H) 1.97-2.06 (m, 2H) 3.23-3.32 (m, 2H) 3.61 (dt, 2H) 3.80 (s, 3H) 5.98 (s, 1H) 6.98 (dd, 1H) 7.30 (d, 1H) 7.62 (d, 1H).

Intermediate 232

Tert-Butyl 4-fluoro-4-(5-methoxy-1,3-benzoxazol-2-yl)piperidine-1-carboxylate

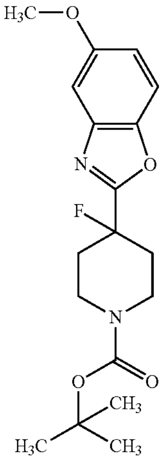 [SMILES: COc1ccc2oc(C3(F)CCN(C(=O)OC(C)(C)C)CC3)nc2c1]

A solution of 0.33 mL 2-methoxy-N-(2-methoxyethyl)-N-(trifluoro-lambda$^4$-sulfanyl)ethan-1-amine (2.7 M, 0.9 μmol) in 3 mL dichloromethane was cooled to −15° C. A solution of 105 mg tert-butyl 4-hydroxy-4-(5-methoxy-1,3-benzoxazol-2-yl)piperidine-1-carboxylate (301 μmol, intermediate 231) in 6 mL dichloromethane was added dropwise and it was stirred 2 h at −15° C.

The mixture was quenched with some water, basified with aq. Sodium bicarbonate and the aqueous layer was extracted 3× with dichloromethane.

The org. layer was filtered over a water-resistant filter and concentrated under reduced pressure. The crude product was purified by column chromatography using hexane 100→hexane:ethyl acetate 60:40. The product was obtained in 84% yield (91 mg).

$^1$H NMR (400 MHz, DMSO-$d_6$) δ ppm 1.42 (s, 9H) 2.13-2.31 (m, 4H) 3.23-3.32 (m, 2H) 3.77 (br dt, 2H) 3.81 (s, 3H) 7.06 (dd, 1H) 7.39 (d, 1H) 7.70 (d, 1H).

Intermediate 233

2-(4-fluoropiperidin-4-yl)-5-methoxy-1,3-benzoxazole, Salt with Trifluoroacetic Acid

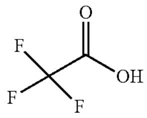

x

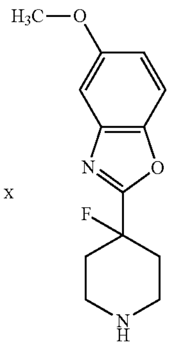

TFA was added to a solution of 90 mg tert-butyl 4-fluoro-4-(5-methoxy-1,3-benzoxazol-2-yl)piperidine-1-carboxylate (257 μmol) in 1.3 mL dichloromethane and stirred 2 h at room temperature. The mixture was concentrated under reduced pressure and the product was obtained as the TFA salt (131 mg).

LC-MS (Method 1): $R_t$=0.64 min; MS (ESIpos): m/z=251 $[M+H]^+$

Intermediate 234

5-bromo-2-(piperidin-4-yl)-1,3-benzoxazole

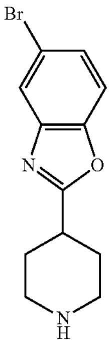 [SMILES: Brc1ccc2oc(C3CCNCC3)nc2c1]

Polyphosphoric acid (7.1 ml; CAS 8017-16-1) was heated up to 180° C., followed by the addition of piperidine-4-carboxylic acid (1.06 g, 8.21 mmol) and 2-amino-4-bromophenol (1.54 g, 8.21 mmol), and the mixture was stirred for 30 min at 180° C. The hot mixture was poured onto ice and basified with solid potassium hydroxide. The mixture was extracted with ethyl acetate three times, the combined organic layers were washed with saturated NaCl-solution, filtered over a hydrophobic filter and the solvent was evaporated under reduced pressure, yielding the title compound as a brown solid (2.08 g, 95% purity, 86% yield).

$^1$H NMR (400 MHz, DMSO-$d_6$) δ ppm 1.60-1.71 (m, 2H) 1.94-2.01 (m, 3H) 2.59 (td, 2H) 2.95-3.02 (m, 2H) 3.08 (s, 1H) 7.52 (dd, 1H) 7.67 (d, 1H) 7.94 (d, 1H):

LC-MS (Method 2): Rt=1.02 min; MS (ESIpos): m/z=281.1 [M+H]$^+$

Intermediate 235

Tert-Butyl 4-(5-bromo-1,3-benzoxazol-2-yl)piperidine-1-carboxylate

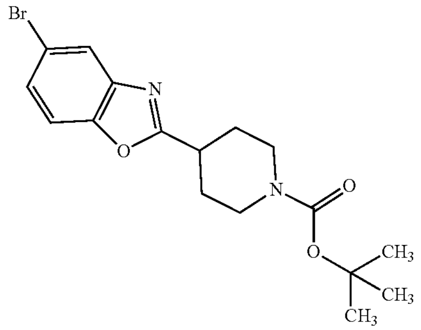 [SMILES: CC(C)(C)OC(=O)N1CCC(c2nc3cc(Br)ccc3o2)CC1]

5-Bromo-2-(piperidin-4-yl)-1,3-benzoxazole (1.30 g, 4.62 mmol, Intermediate 234) was dissolved in dichloromethane (15 ml), N,N-diisopropylethylamine (4.0 ml, 23 mmol; CAS 7087-68-5) a small quantity of 4-Dimethylaminopyridine were added, followed by the addition of di-tert-butylcarbonate (2.1 ml, 9.2 mmol; CAS 24424-99-5) in dichloromethane (5 ml). The mixture was stirred overnight at RT, following which water was added followed by extraction with dichloromethane, the phases separated, the organic phase washed with water and brine, filtered and the solvent removed under reduced pressure. Purification by silica gel column chromatography (25 g silica, dichloromethane: methanol 0% to 3%) yielded the title compound (1.3 g, 95% purity, 70% yield).

$^1$H NMR (400 MHz, DMSO-$d_6$) δ ppm 1.41 (s, 9H) 1.61-1.71 (m, 2H) 2.07 (br dd, 2H) 2.88-3.09 (m, 2H) 3.25 (s, 1H) 3.92 (br s, 2H) 7.53 (dd, 1H) 7.69 (d, 1H) 7.96 (d, 1H):

LC-MS (Method 2): $R_t$=1.45 min; MS (381.3): m/z=[M+H]$^+$

Intermediate 236

Tert-Butyl 4-(5-cyclopropyl-1,3-benzoxazol-2-yl)piperidine-1-carboxylate

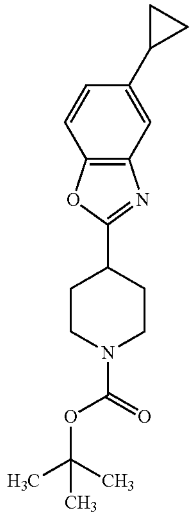 [SMILES: CC(C)(C)OC(=O)N1CCC(c2nc3cc(C4CC4)ccc3o2)CC1]

tert-Butyl 4-(5-bromo-1,3-benzoxazol-2-yl)piperidine-1-carboxylate (100 mg, 262 μmol, Intermediate 235) and Di-μ-iodobis(tri-t-butylphosphino)dipalladium(1) (22.9 mg, 26.2 μmol; CAS 166445-62-1) were sealed in a vessel and were flushed with Ar. Toluene, pre-flushed with argon, (500 μl) was added. Cyclopropylzinc bromide (0.5 M in THF, 2.6 ml, 1.3 mmol; CAS 126403-68-7) was added dropwise under argon and the mixture was stirred at RT for 1 hour. The mixture was diluted in dichloromethane/methanol (9:1) and was filtered, followed by purification with basic HPLC, yielding the title compound (42.8 mg, 98% purity, 39% yield).

1H NMR (400 MHz, DMSO-d6) δ ppm 0.66-0.72 (m, 2H) 0.92-0.98 (m, 2H) 1.41 (s, 9H) 1.56-1.70 (m, 2H) 1.99-2.09 (m, 3H) 2.52-2.54 (m, 1H) 2.86-3.07 (m, 2H) 3.09-3.31 m, 1H): 3.93 (br d, J=13.18 Hz, 2H) 7.10 (dd, J=8.36, 1.77 Hz, 1H) 7.37 (d, 1H) 7.52 (d, 1H):

LC-MS (Method 2): Rt=1.41 min; MS (ESIpos): m/z=342.98 [M+H]+

Intermediate 237

5-cyclopropyl-2-(piperidin-4-yl)-1,3-benzoxazole

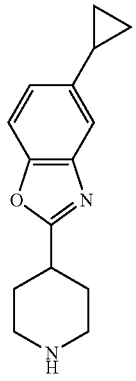 [SMILES: c1cc2oc(C3CCNCC3)nc2cc1C1CC1]

0.4 mL HCl in dioxane (1.6 mmol) was added to 42 mg tert-butyl 4-(5-cyclopropyl-1,3-benzoxazol-2-yl)piperidine-1-carboxylate (123 μmol, intermediate 239) and it was stirred 2.5 h at room temperature.

The reaction mixture was evaporated and the product was obtained as the hydrogen chloride salt (41 mg).

LC-MS Method 2): $R_t$=1.11 min; MS (ESIpos): m/z=243 $[M+H]^+$

Intermediate 238

6-bromo-2-(piperidin-4-yl)-1,3-benzoxazole

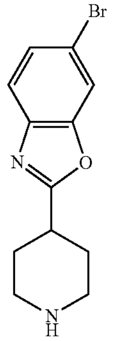 [SMILES: Brc1ccc2nc(C3CCNCC3)oc2c1]

Polyphosphoric acid (6.8 ml; CAS-RN:[8017-16-1]) was heated up to 180° C., followed by the addition of piperidine-4-carboxylic acid (1.02 g, 7.9 mmol) and 2-amino-5-bromophenol (1.48 g, 7.90 mmol), and the mixture was stirred for 30 min at 180° C. The hot mixture was poured onto ice and basified with solid potassium hydroxide. The mixture was extracted with ethyl acetate three times, the combined organic layers were washed with saturated sodium chloride solution, filtered over a hydrophobic filter and the solvent was evaporated under reduced pressure, yielding the title compound as a brown solid (1.88 g, 85% purity, 85% yield).

$^1$H NMR (400 MHz, DMSO-$d_6$) δ ppm 1.57-1.72 (m, 2H) 1.93-2.03 (m, 2H) 2.55-2.65 (m, 2H): 2.93-3.04 (m, 2H) 3.07 (s, 1H) 7.51 (dd, 1H) 7.64-7.68 (m, 1H) 8.02 (d, 1H).

LC-MS (Method 2): $R_t$=1.03 min; MS (281.1): m/z=[M+H]+

Intermediate 239

Tert-Butyl 4-(6-bromo-1,3-benzoxazol-2-yl)piperidine-1-carboxylate

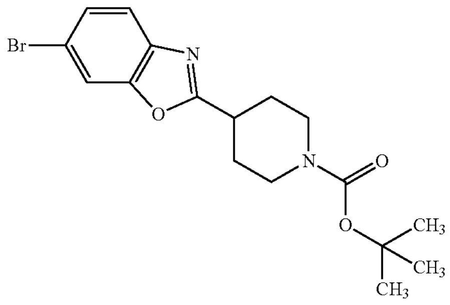 [SMILES: CC(C)(C)OC(=O)N1CCC(c2nc3ccc(Br)cc3o2)CC1]

6-bromo-2-(piperidin-4-yl)-1,3-benzoxazole (1.78 g, 6.3 mmol, Intermediate 238) was dissolved in dichloromethane (2.7 ml), N,N-diisopropylethylamine (310 μl, 1.8 mmol; CAS-RN:[7087-68-5]) and a small quantity of 4-Dimethylaminopyridine were added, followed by the addition of di-tert-butylcarbonate (0.16 g, 710 μmol; CAS-RN:[24424-99-5]). The mixture was stirred for 16 hours at RT, following which water was added followed by extraction with dichloromethane, the phases separated, the organic phase washed with water and brine, filtered and the solvent removed under reduced pressure. Purification by silica gel column chromatography (55 g NH silica, Hexane:ethyl acetate) yielded the title compound (1.41 g, 95% purity, 56% yield).

$^1$H NMR (400 MHz, DMSO-$d_6$) δ ppm 1.40-1.42 (m, 9H) 1.60-1.73 (m, 2H) 2.04-2.12 (m, 2H): 2.90-3.08 (m, 2H) 3.24 (s, 1H) 3.89-3.99 (m, 2H) 7.52 (dd, 1H) 7.65-7.69 (m, 1H) 8.03 (d, 1H).

LC-MS (Method 2): $R_t$=1.43 min; MS (381.1): m/z=[M+H]+

Intermediate 240

Tert-Butyl 4-(6-cyclopropyl-1,3-benzoxazol-2-yl) piperidine-1-carboxylate

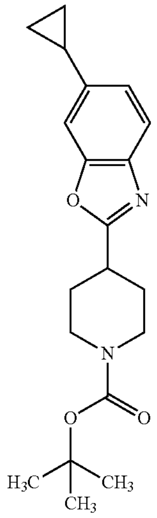 [SMILES: CC(C)(C)OC(=O)N1CCC(c2nc3ccc(C4CC4)cc3o2)CC1]

tert-Butyl 4-(6-bromo-1,3-benzoxazol-2-yl)piperidine-1-carboxylate (75.0 mg, 197 μmol, Intermediate 239) and Di-μ-iodobis(tri-t-butylphosphino)dipalladium(1) (17.1 mg, 19.7 μmol; CAS 166445-62-1) were sealed in a vessel and were flushed with Ar. Toluene, pre-flushed with argon, (500 μl) was added. Cyclopropylzinc bromide (2.0 ml, 0.50 M, 980 μmol; CAS 126403-68-7) was added dropwise under argon and the mixture was stirred at RT for 1 hour. The mixture was diluted in dichloromethane/methanol (9:1) and was filtered, followed by purification with basic HPLC, yielding the title compound (5.50 mg; 99% purity, 8% yield).

$^1$H NMR (400 MHz, DMSO-$d_6$) δ ppm 0.68-0.76 (m, 2H) 0.93-1.02 (m, 2H) 1.41 (s, 9H) 1.58-1.71 (m, 2H) 2.01-2.09 (m, 3H) 2.88-3.08 (m, 2H) 3.15-3.24 (m, 1H) 3.93 (br d, 2H) 7.10 (dd, 1H) 7.35 (d, 1H) 7.53 (d, 1H).

LC-MS (Method 2): $R_t$=1.41 min; MS (343.0): m/z=$[M+H]^+$

Intermediate 241

6-cyclopropyl-2-(piperidin-4-yl)-1,3-benzoxazole, Salt with Hydrochloric Acid

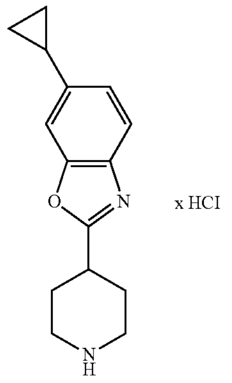 [SMILES: c1cc2nc(C3CCNCC3)oc2cc1C1CC1]

0.24 mL HCl in dioxane (4 M, 1 mmol) was added to 9 mg tert-butyl 4-(5-cyclopropyl-1,3-benzoxazol-2-yl)piperidine-1-carboxylate (26 μmol, intermediate 240) and it was stirred 2.5 h at room temperature.

The reaction mixture was evaporated and the product was obtained as the hydrogen chloride salt (9 mg).

LC-MS Method 2): $R_t$=1.12 min; MS (ESIpos): m/z=243 $[M+H]^+$

Intermediate 242

4-[4-fluoro-4-(5-methyl-1,3-benzoxazol-2-yl)piperidin-1-yl]-7-hydroxy-1-methyl-2-oxo-1,2-dihydroquinoline-3-carbonitrile

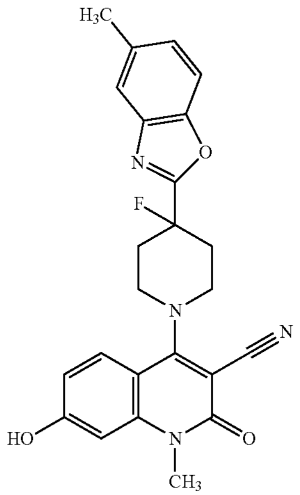 [SMILES: Cc1ccc2oc(C3(F)CCN(c4c(C#N)c(=O)n(C)c5cc(O)ccc45)CC3)nc2c1]

To a solution auf 100 mg 4-chloro-7-hydroxy-1-methyl-2-oxo-1,2-dihydroquinoline-3-carbonitrile (426 μmol, intermediate 136) and 148 mg of the salt of trifluoroacetic acid with 2-(4-fluoropiperidin-4-yl)-5-methyl-1,3-benzoxazole (426 μmol) in 5 mL 2-propanol was added 0.24 mL triethylamine (1.7 mmol) and stirred 4 h at 90° C. The reaction mixture was cooled to room temperature and the product was purified by RP-HPLC. The product was obtained in 18% yield (36 mg).

LC-MS (Method 1): $R_t$=1.15 min; MS (ESIpos): m/z=433 $[M+H]^+$

Intermediate 243

Tert-Butyl 4-{2-[3-(trifluoromethyl)benzoyl]hydrazinecarbonyl}piperidine-1-carboxylate

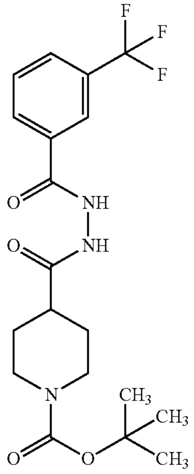 [SMILES: CC(C)(C)OC(=O)N1CCC(C(=O)NNC(=O)c2cccc(C(F)(F)F)c2)CC1]

To a solution of 1.5 g 1-(tert-butoxycarbonyl)piperidine-4-carboxylic acid (6.54 mmol) in 25 mL DMF was added 3.4 mL Di-isopropylethylamine (20 mmol), 3.73 g HATU (9.8 mmol, CAS 148893-10-1) and 1.47 g 3-(trifluoromethyl) benzohydrazide (7.2 mmol). The reaction mixture was stirred at room temperature overnight. The reaction mixture was diluted with ethyl acetate and water, the layer were separated and the aqueous layer was extracted with ethyl acetate (2×). The combined organic layers were evaporated and 2.9 g of the crude product (75% purity): were obtained.

LC-MS Method 2): $R_t$=0.84 min; MS (ESIpos): m/z=415 $[M+H]^+$

Intermediate 244

4-{5-[3-(trifluoromethyl)phenyl]-1,3,4-oxadiazol-2-yl}piperidine

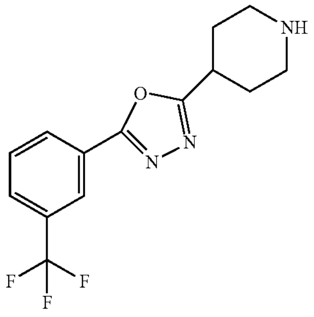 [SMILES: FC(F)(F)c1cccc(-c2nnc(C3CCNCC3)o2)c1]

To a solution of 2.9 g tert-butyl 4-{2-[3-(trifluoromethyl) benzoyl]hydrazinecarbonyl}piperidine-1-carboxylate (crude, 75 5 purity intermediate 243) in 70 mL acetonitrile was added 6.5 mL phosphoryl chloride (70 mmol, 10025-87-3). The reaction mixture was stirred at 100° C. for 7 h. The reaction mixture was poured over water and treated with solid sodium carbonate until pH>7. The mixture was extracted with ethyl acetate (3×) and the combined organic layers were washed with brine and water. The organic layer was dried and the solvents removed in vacuo. 310 mg of the title compound were obtained.

$^1$H NMR (400 MHz, DMSO-d6) δ ppm 1.64-1.78 (m, 2H) 1.95-2.07 (m, 2H) 2.59-2.74 (m, 2H): 2.98-3.08 (m, 2H) 3.11-3.23 (m, 1H) 7.80-7.90 (m, 1H) 7.97-8.03 (m, 1H) 8.20-8.25 (m, 1H) 8.27-8.33 (m, 1H).

Intermediate 245

Tert-Butyl 4-(3-phenyl-1,2,4-oxadiazol-5-yl)piperidine-1-carboxylate

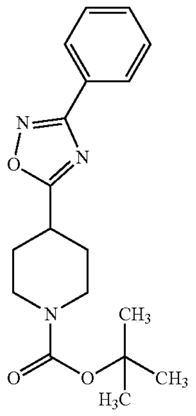 [SMILES: CC(C)(C)OC(=O)N1CCC(c2nc(-c3ccccc3)no2)CC1]

A mixture of 2.0 g 1-(tert-butoxycarbonyl)piperidine-4-carboxylic acid, 792 mg N-hydroxybenzenecarboximidamide, 2.4 ml triethylamine and 2.6 ml T3P in 40 ml ethyl acetate were stirred at 80° C. for 7 hours. The reaction was diluted with ethyl acetate and extracted with brine and water, dried and evaporated in vacuo. The residue was purified by flash chromatography (silica, dichloromethane/methanol gradient 0-2%). 1 g of the title compound was obtained.

$^1$H NMR (400 MHz, DMSO-d6) δ ppm 1.36-1.47 (m, 9H) 1.57-1.79 (m, 2H) 2.02-2.20 (m, 2H): 2.87-3.09 (m, 2H) 3.28-3.41 (m, 5H) 3.81-4.07 (m, 2H) 7.40-7.72 (m, 3H) 7.95-8.07 (m, 2H).

Intermediate 246

4-(3-phenyl-1,2,4-oxadiazol-5-yl)piperidine

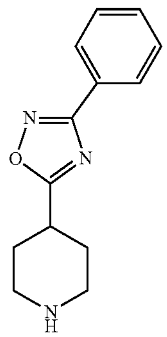 [SMILES: c1ccc(-c2noc(C3CCNCC3)n2)cc1]

A solution of 1 g tert-butyl 4-(3-phenyl-1,2,4-oxadiazol-5-yl)piperidine-1-carboxylate (3 mmol, intermediate 245) in 20 mL dichloromethane was treated with 2.3 mL TFA and stirred at room temperature for 4 hours. The reaction mixture was evaporated and co-evaporated with toluene 2×. 1.1 g crude title compound were obtained and used directly in the next step.

$^1$H NMR (400 MHz, DMSO-d6) δ ppm 1.91-2.08 (m, 2H) 2.23-2.33 (m, 2H) 2.98-3.19 (m, 2H): 3.32-3.44 (m, 2H) 3.46-3.66 (m, 1H) 7.41-7.71 (m, 3H) 7.89-8.11 (m, 2H).

Intermediate 247

Tert-Butyl 4-[3-(2-methylphenyl)-1,2,4-oxadiazol-5-yl]piperidine-1-carboxylate

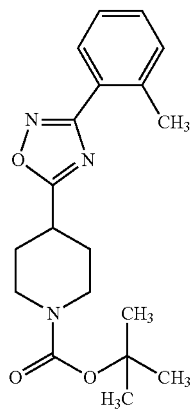 [SMILES: Cc1ccccc1-c1noc(C2CCN(C(=O)OC(C)(C)C)CC2)n1]

A mixture of 1.66 g 1-(tert-butoxycarbonyl)piperidine-4-carboxylic acid, 723 mg N-hydroxy-2-methylbenzene-1-carboximidamide, 2.0 ml triethylamine and 4.3 ml T3P in 33 ml ethyl acetate were stirred at 80° C. for 5 hours. The reaction was diluted with ethyl acetate and extracted with brine and water, dried and evaporated in vacuo. The residue was purified by flash chromatography (silica, dichloromethane/methanol gradient 0-2%). 680 mg of the title were obtained.

$^{1}$H NMR (400 MHz, DMSO-d6) δ ppm 1.18-1.59 (m, 9H) 1.62-1.93 (m, 2H) 2.06-2.24 (m, 3H): 2.93-3.22 (m, 3H) 3.24-3.47 (m, 8H) 3.81-4.23 (m, 2H) 7.23-7.71 (m, 3H) 7.76-8.14 (m, 1H).

Intermediate 248

4-[3-(2-methylphenyl)-1,2,4-oxadiazol-5-yl]piperidine

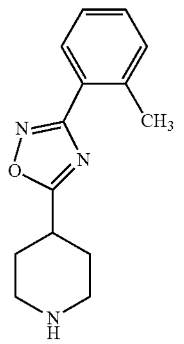 [SMILES: Cc1ccccc1-c1noc(C2CCNCC2)n1]

A solution of 650 mg tert-butyl 4-[3-(2-methylphenyl)-1,2,4-oxadiazol-5-yl]piperidine-1-carboxylate (1.89 mmol, intermediate 247) in 12 mL dichloromethane was treated with 1.5 mL TFA and stirred at room temperature for 14 hours. The reaction mixture was evaporated and co-evaporated with toluene 2×. 560 mg crude title compound were obtained and used directly in the next step.

$^{1}$H NMR (400 MHz, DMSO-d6) δ ppm 1.88-2.05 (m, 2H) 2.19-2.32 (m, 2H) 2.52-2.59 (m, 3H): 3.00-3.19 (m, 2H) 3.30-3.45 (m, 4H) 7.31-7.54 (m, 3H) 7.87-7.96 (m, 1H) 8.38-8.58 (m, 1H) 8.63-8.80 (m, 1H).

Intermediate 249

Tert-Butyl 4-(2-benzoylhydrazinecarbonyl)piperidine-1-carboxylate

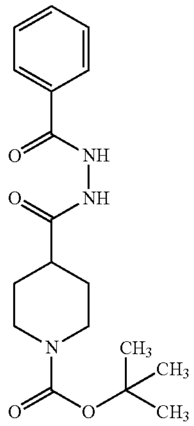 [SMILES: CC(C)(C)OC(=O)N1CCC(C(=O)NNC(=O)c2ccccc2)CC1]

To a solution of 3 g 1-(tert-butoxycarbonyl)piperidine-4-carboxylic acid (13.1 mmol) in 50 mL DMF was added 6.8 mL Di-isopropylethylamine (39 mmol), 7.46 g HATU (19.6 mmol, CAS 148893-10-1) and 1.96 g benzohydrazide (14.4 mmol). The reaction mixture was stirred at room temperature overnight. The reaction mixture was diluted with ethyl acetate and water and extracted with brine and water. The organic layer were evaporated and 6 g of the crude product were obtained.

LC-MS Method 2): $R_t$=0.80 min; MS (ESIpos): m/z=347 $[M+H]^+$

Intermediate 250

4-(5-phenyl-1,3,4-oxadiazol-2-yl)piperidine

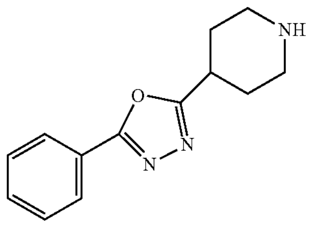 [SMILES: c1ccc(-c2nnc(C3CCNCC3)o2)cc1]

To a solution of 5 g crude tert-butyl 4-(2-benzoylhydrazinecarbonyl)piperidine-1-carboxylate (intermediate 249) in 140 mL acetonitrile was added 10.3 mL phosphoryl chloride (70 mmol, 10025-87-3). The reaction mixture was stirred at 100° C. for 7 h. The reaction mixture was poured over water and treated with solid sodium carbonate until pH>7. The mixture was extracted with ethyl acetate (3×) and the combined organic layers were washed with brine and water. The organic layer was dried and the solvents removed in vacuo. 1.65 g of the title compound were obtained.

LC-MS Method 2): $R_t$=0.80 min; MS (ESIpos): m/z=229 $[M+H]^+$

Intermediate 251

6-bromo-7-methoxy-1-methyl-4-{4-[5-(2-methylphenyl)-1,3,4-oxadiazol-2-yl]piperidin-1-yl}-2-oxo-1,2-dihydroquinoline-3-carbonitrile

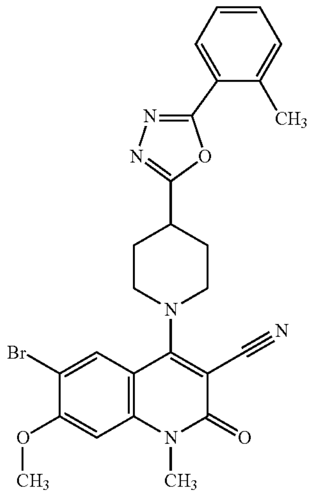 [SMILES: COc1cc2c(cc1Br)c(N1CCC(c3nnc(-c4ccccc4C)o3)CC1)c(C#N)c(=O)n2C]

A solution of 300 mg 6-bromo-4-chloro-7-methoxy-1-methyl-2-oxo-1,2-dihydroquinoline-3-carbonitrile (intermediate 264), 446 mg 4-[5-(2-methylphenyl)-1,3,4-oxadiazol-2-yl]piperidine (intermediate 166) and 0.26 mL triethylamine (1.8 mmol) in 16 mL 2-propanol was stirred for 5 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). 350 mg of the title compound were obtained.

$^1$H NMR (400 MHz, DMSO-d6) δ ppm 2.02-2.15 (m, 2H) 2.27-2.39 (m, 2H) 2.61-2.65 (m, 3H): 3.43-3.54 (m, 1H) 3.55-3.67 (m, 5H) 3.72-3.86 (m, 2H) 3.99-4.10 (m, 3H) 6.99-7.06 (m, 1H) 7.37-7.57 (m, 4H) 7.86-8.00 (m, 2H).

Intermediate 252

4-chloro-1-methyl-2-oxo-1,2-dihydroquinoline-3-carboxamide

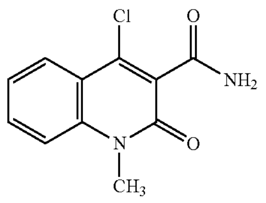 [SMILES: Cn1c(=O)c(C(N)=O)c(Cl)c2ccccc21]

To a suspension of 100 mg 4-chloro-1-methyl-2-oxo-1,2-dihydroquinoline-3-carbonitrile (457 μmol) was added 0.14 mL N-[(1E)-ethylidene]hydroxylamine (2.3 mmol, CAS 107-29-9) and 26 mg palladium(II)acetate (114 μmol). The mixture was heated for 4 h at 80° C. The mixture filtered over celite and washed with dichloromethane/ethanol 1:1. The filtrate was concentrated under reduced pressure and the crude product was purified by RP-HPLC. The product was obtained in 61% yield (69 mg).

$^1$H-NMR (400 MHz, DMSO-$d_6$): δ [ppm]=3.62-3.67 (m, 3H), 7.43 (ddd, 1H), 7.62-7.71 (m, 2H), 7.77 (ddd, 1H), 7.87 (br s, 1H), 8.02 (dd, 1H).

LC-MS Method 2): $R_t$=0.65 min; MS (ESIpos): m/z=237 $[M+H]^+$

Intermediate 253

Tert-Butyl 4-(1-benzothiophen-2-yl)-4-hydroxypiperidine-1-carboxylate

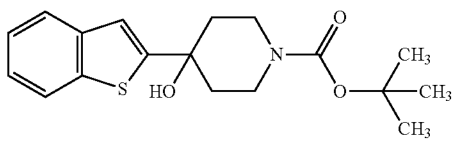

To a solution of 500 mg 1-benzothiophene (3.73 mmol) in 15 mL tetrahydrofuran at −78° C. was added a solution of 5.4 mL n-butyllithium (1.6 M in hexanes, 8.6 mmol). The solution was warmed to 0° C. for one hour and then cooled to −78° C. A solution of 817 mg tert-butyl 4-oxopiperidine-1-carboxylate (4.10 mmol, CAS 79099-07-3) in 4 mL tetrahydrofuran was added dropwise, and the mixture was warmed to 20° C. After stirring over night at 20° C., the mixture was diluted with brine and extracted 3× with ethyl acetate. The combined organic layers were dried over sodium sulfate, then filtered and evaporated. The residue was purified using silica gel chromatography (hexane→hexane/40 percent ethyl acetate gradient eluent), the combined fractions were concentrated under reduced pressure.

$^1$H-NMR (400 MHz, DMSO-d6): 5 [ppm]=1.38 (s, 9H), 1.81-1.91 (m, 4H), 3.55-3.65 (m, 2H), 3.76-3.89 (m, 2H), 7.25-7.37 (m, 3H), 7.75 (dd, 1H), 7.90 (dd, 1H).

Intermediate 254

4-(1-benzothiophen-2-yl)piperidin-4-ol

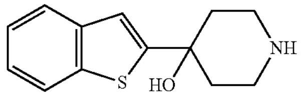 [SMILES: OC1(c2cc3ccccc3s2)CCNCC1]

To a solution of 690 mg tert-butyl 4-(1-benzothiophen-2-yl)-4-hydroxypiperidine-1-carboxylate (2.07 mmol, intermediate 264) in 2.2 mL methanol was added a solution of 2.6 mL 4N HCl in dioxane (10 mmol). The reaction mixture stirred 2 h at room temperature. Then the mixture was cooled to 0° C. with an ice/waterbath and 4N aqu. Sod ium hydroxide solution (3.7 mL) was added, and the mixture was extracted with ethyl acetate. The extract was washed with brine, dried (waterresistant filter) and concentrated under reduced pressure. The crude product was purified by RP-HPLC and a mixture of intermediate 254 (6%, 30 mg) and intermediate 255 (74 mg, 14% yield).

1H-NMR (400 MHz, DMSO-d6): 5 [ppm]=1.69-1.80 (m, 2H), 1.81-1.92 (m, 2H), 2.68-2.78 (m, 2H), 2.89 (td, 2H), 5.46 (s, 1H), 7.23 (s, 1H), 7.24-7.37 (m, 2H), 7.75 (dd, 1H), 7.88 (dd, 1H).

LC-MS Method 2): $R_t$=0.87 min; MS (ESIpos): m/z=234 $[M+H]^+$

Intermediate 255

4-(1-benzothiophen-2-yl)-4-methoxypiperidine

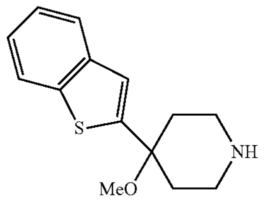 [SMILES: COC1(c2cc3ccccc3s2)CCNCC1]

Product was obtained as a byproduct in the synthesis of intermediate 254.

1H-NMR (400 MHz, DMSO-d6): δ [ppm]=1.84-2.05 (m, 4H), 2.68-2.87 (m, 4H), 2.99 (s, 3H), 7.30-7.38 (m, 3H), 7.78-7.82 (m, 1H), 7.90-7.94 (m, 1H).

Intermediate 256

Methyl 3-cyano-1-methyl-4-[4-(5-methyl-1,3-benzoxazol-2-yl)piperidin-1-yl]-2-oxo-1,2-dihydroquinoline-6-carboxylate

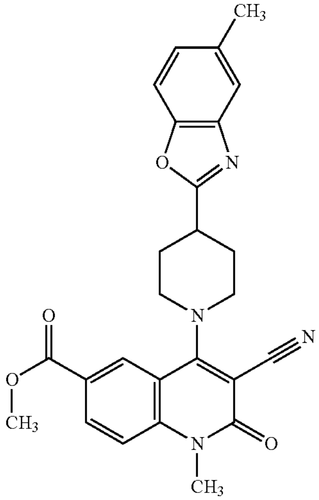 [SMILES: COC(=O)c1ccc2c(c1)c(N1CCC(c3nc4cc(C)ccc4o3)CC1)c(C#N)c(=O)n2C]

A solution of 1 g 6-bromo-1-methyl-4-[4-(5-methyl-1,3-benzoxazol-2-yl)piperidin-1-yl]-2-oxo-1,2-dihydroquinoline-3-carbonitrile (Example 396) and 171 mg 1,1'-bis(diphenylphosphino)ferrocene-Palladium(II)dichloride dichloromethane complex (CAS 95464-05-4) in 33 ml methanol, 0.58 ml triethylamine and 3.4 ml THF was stirred for 22 hours at 80° C. under an atmosphere of carbonmonoxy. The react ion mixture was evaporated in vacuo and the residue was re-suspended in ethyl acetate. The organic layer was washed with water and brine, dried and evaporated in vacuo. The residue was purified by flash chromatography (silica, dichloromethane/methanol gradient 0-1%). 40 mg of the title compound were obtained.

$^1$H NMR (400 MHz, DMSO-d6) δ ppm 1.84-1.99 (m, 2H) 2.19-2.30 (m, 2H) 3.53-3.68 (m, 5H): 3.75-3.86 (m, 2H) 3.87-3.95 (m, 3H) 4.76-4.94 (m, 1H) 7.17 (d, 2H) 7.31 (s, 2H) 7.68 (d, 1H) 8.13-8.27 (m, 1H) 8.44 (s, 1H).

Intermediate 257

3-cyano-1-methyl-4-[4-(5-methyl-1,3-benzoxazol-2-yl)piperidin-1-yl]-2-oxo-1,2-dihydroquinoline-6-carboxylic Acid

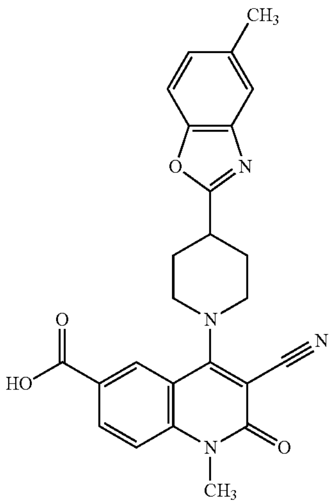 [SMILES: Cc1ccc2oc(C3CCN(c4c(C#N)c(=O)n(C)c5ccc(C(=O)O)cc45)CC3)nc2c1]

A solution of 35 mg methyl 3-cyano-1-methyl-4-[4-(5-methyl-1,3-benzoxazol-2-yl)piperidin-1-yl]-2-oxo-1,2-dihydroquinoline-6-carboxylate (intermediate 256) and 9.2 mg lithium hydroxyd in 1 ml THF and 0.1 ml water was stirred for 82 hours at RT. The reaction was poured into water, extracted with ethyl acetate and the organic layer was separated. The aqueous phase was treated with hydrochloric acid (1 N) to get a pH<2 and was extracted with ethyl acetate (2×). This organic layer was washed with brine, dried with sodium sulfate and evaporated in vacuo. 20 mg of the title compound was obtained.

1H NMR (400 MHz, DMSO-d6) δ ppm 2.05-2.18 (m, 2H) 2.32-2.38 (m, 2H) 2.34-2.38 (m, 1H) 2.39-2.46 (m, 3H) 3.46-3.54 (m, 1H) 3.58-3.72 (m, 5H) 3.83-3.93 (m, 2H) 7.16-7.22 (m, 1H) 7.51-7.56 (m, 1H) 7.57-7.62 (m, 1H) 7.63-7.69 (m, 1H) 7.70-7.72 (m, 1H) 8.16-8.23 (m, 1H) 8.44-8.49 (m, 1H):

Intermediate 258

2-amino-4-bromo-5-methylbenzoic Acid

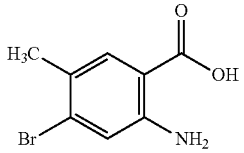

1 g 4-bromo-5-methyl-2-nitrobenzoic acid (3.85 mmol) and 2.6 g tin(II) chloride dihydrate (11-5 mmol, CAS 10025-69-1) was suspended in 7.6 mL water, 7.6 mL hydrochloric acid (35%) was added and it was stirred 1 h at 90° C. The mixture w as cooled to room temperature and the precipitate was filtered off and washed with water. The product was obtained in 54% yield (574 mg).

$^1$H NMR (400 MHz, DMSO-$d_6$) δ ppm 2.18 (s, 3H) 7.03 (s, 1H) 7.60 (s, 1H):

Intermediate 259

7-bromo-6-methyl-2H-3,1-benzoxazine-2,4(1H)-dione

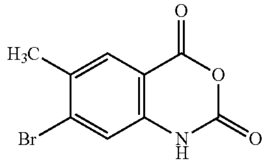

1,1'-Carbonyldiimidazole (343 mg, 2.12 mmol) was added to a suspension of 2-amino-4-bromo-5-methylbenzoic acid-hydrogen chloride (1/1) (470 mg, 1.76 mmol, intermediate 258) in 2.9 mL THF and stirred over night at room temperature. The reaction mixture was quenched with water, the precipitate was filtered off and dried. The product was obtained in quantitative yield (457 mg).

$^1$H NMR (400 MHz, DMSO-$d_6$) δ ppm 2.37 (s, 3H) 7.34 (s, 1H) 7.88 (s, 1H) 11.74 (br s, 1H):

Intermediate 260

7-bromo-1,6-dimethyl-2H-3,1-benzoxazine-2,4(1H)-dione

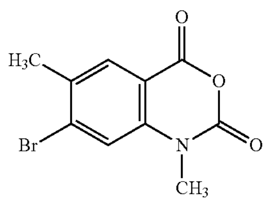

Methyl iodide (1.15 mL, 18.5 mmol; CAS 74-88-4) was added to a solution of 1.6 g 7-bromo-6-methyl-2H-3,1-benzoxazine-2,4(1H)-dione (6.2 mmol) and 2.2 mL di-isopropylethylamine (12.3 mmol) in 42 mL DMF and stirred 2 h at room temperature. The reaction was quenched with ice and stirred until the ice melted. The precipitate was filtered off, washed with water and dried (1.4 g, 83%).

$^1$H NMR (400 MHz, DMSO-$d_6$) δ ppm 2.40 (s, 3H) 3.44 (s, 3H) 7.72 (s, 1H) 7.96 (d, 1H):

Intermediate 261

7-bromo-4-hydroxy-1,6-dimethyl-2-oxo-1,2-dihydroquinoline-3-carbonitrile

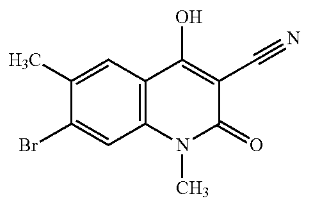

7-bromo-1,6-dimethyl-2H-3,1-benzoxazine-2,4(1H)-dione (250 mg, 926 μmol, intermediate 260) was solved in 1.9 mL THF, 1 mL triethylamine (7.4 mmol) and ethyl 0.39 mL cyanoacetate (3.7 mmol) were added and the mixture stirred over night at 70° C. The reaction mixture was evaporated. Water was added to the residue and the solution was acidified with 2N hydrochloric acid to pH=1. The precipitate was filtered off, washed with water and dried (232 mg, 86% yield).

$^1$H NMR (400 MHz, DMSO-$d_6$) δ ppm 2.40 (s, 3H) 3.47 (s, 3H) 7.68 (s, 1H) 7.96 (s, 1H).

Intermediate 262

7-bromo-4-chloro-1,6-dimethyl-2-oxo-1,2-dihydroquinoline-3-carbonitrile

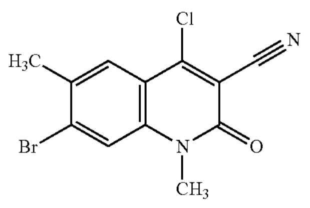 [SMILES: Cc1cc2c(Cl)c(C#N)c(=O)n(C)c2cc1Br]

7-Bromo-4-hydroxy-1,6-dimethyl-2-oxo-1,2-dihydroquinoline-3-carbonitrile (1.2 g, 4.2 mmol, intermediate 261) was stirred in 7.8 mL phosphoryl chloride (84 mmol) 2 h at 90° C. The mixture was poured carefully in ice-water and stirred till the ice was melted. The solution was added to ice-water and basified with sodium carbonat (strong gas evolution!). The precipitate was filtered, washed with water and dried. The product was purified by column chromatography and obtained in 87% yield (1.3 g).

$^1$H NMR (400 MHz, DMSO-$d_6$) δ ppm 2.48 (s, 3H) 3.64 (s, 3H) 7.98 (s, 1H) 8.01 (d, 1H).

Intermediate 263

7-bromo-1,6-dimethyl-4-[4-(5-methyl-1,3-benzoxazol-2-yl)piperidin-1-yl]-2-oxo-1,2-dihydroquinoline-3-carbonitrile

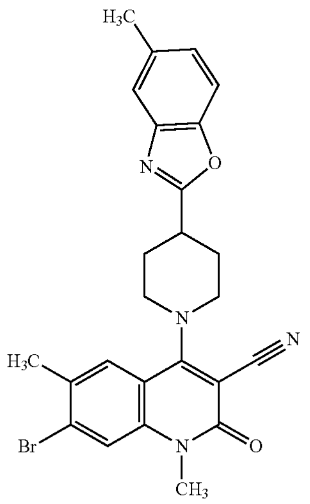 [SMILES: Cc1ccc2oc(C3CCN(c4c(C#N)c(=O)n(C)c5cc(Br)c(C)cc45)CC3)nc2c1]

N,N-diisopropylethylamine (130 μl, 720 μmol) and 63 mg 5-methyl-2-(piperidin-4-yl)-1,3-benzoxazole (289 μmol) were added to a suspension of 75 mg 7-bromo-4-chloro-1,6-dimethyl-2-oxo-1,2-dihydroquinoline-3-carbonitrile (241 μmol, intermediate 273) in 2.1 mL 2-propanol and stirred over night at 90° C. The precipitate was filtered off, washed with ethanol and dried (78 mg, 64%).

$^1$H NMR (400 MHz, CDCl3) δ ppm 2.16-2.32 (m, 2H) 2.38-2.47 (m, 3H) 2.48 (d, 6H) 3.29 (tt, 1H) 3.58-3.69 (m, 6H) 3.82-3.91 (m, 2H) 7.15 (dd, 1H) 7.40 (d, 1H) 7.49-7.51 (m, 1H): 7.57 (s, 1H) 7.65 (s, 1H).

Intermediate 264

6-bromo-4-chloro-7-methoxy-1-methyl-2-oxo-1,2-dihydroquinoline-3-carbonitrile

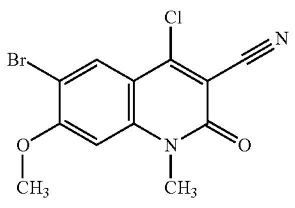 [SMILES: COc1cc2c(cc1Br)c(Cl)c(C#N)c(=O)n2C]

NBS (11.2 g, 62.8 mmol) was added to a solution of 6.25 g 4-chloro-7-methoxy-1-methyl-2-oxo-1,2-dihydroquinoline-3-carbonitrile (25.1 mmol, intermediate 135) in 55 mL DMF and stirred 2 h at 60° C.

The reaction mixture was poured into ice-water and the precipitate was filtered off and dried (7.5 g, 88% yield).

$^1H$ NMR (400 MHz, DMSO-$d_6$) δ ppm 3.69 (s, 3H) 4.10 (s, 3H) 7.12 (s, 1H) 8.15 (s, 1H).

Intermediate 265

Tert-Butyl 4-hydroxy-4-(5-methyl-1,3-benzoxazol-2-yl)piperidine-1-carboxylate

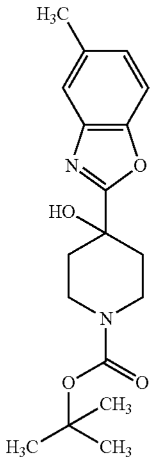 [SMILES: Cc1ccc2oc(C3(O)CCN(C(=O)OC(C)(C)C)CC3)nc2c1]

Cerium(III) chloride (1.36 g, 5.52 mmol; CAS 7790-86-5) was added to tert-butyl 4-oxopiperidine-1-carboxylate (1.00 g, 5.02 mmol) in 1 mL THF and stirred 1 h at RT under nitrogen. In a separate flask, n-butyllithium (9.4 ml, 1.6 M in hexanes, 15 mmol) was added to a solution of 5-methyl-1,3-benzoxazole (1.34 g, 10.0 mmol) in 10 mL THF at −78° C. under and stirred for 30 min. Then magnesiumbromid-diethylether-complex (3.89 g, 15.1 mmol; CAS 29858-07-9) in 30 mL THF was added and it was stirred for 30 min at −78° C. The ketone-Cerium(II) chloride-solution was then cooled to −78° C. and added to the benzoxazole solution. The reaction mixture was allowed to warm to room temperature and it was stirred at room temperature for 3 h. The mixture was carefully quenched with water and extracted 3× with ethyl acetate. The organic layer was filtered over a water-resistant filter and concentrated under reduced pressure. The crude product was purified by column chromatography and the product was obtained in 9% yield.

$^1H$ NMR (400 MHz, DMSO-$d_6$) δ ppm 1.40 (s, 10H) 1.87-1.95 (m, 2H) 2.00-2.06 (m, 1H): 2.42 (s, 3H) 3.57-3.66 (m, 2H) 5.98 (s, 1H) 7.19-7.23 (m, 1H) 7.52-7.55 (m, 1H) 7.59 (d, 1H).

Intermediate 266

Tert-Butyl 4-fluoro-4-(5-methyl-1,3-benzoxazol-2-yl)piperidine-1-carboxylate

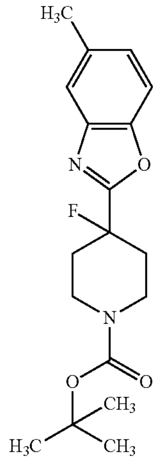 [SMILES: Cc1ccc2oc(C3(F)CCN(C(=O)OC(C)(C)C)CC3)nc2c1]

Deoxofluor (530 μl, 2.7 M in THF, 1.4 mmol) was added to 3 mL dichloromethane and cooled to −15° C. Then a solution of tert-butyl 4-hydroxy-4-(5-methyl-1,3-benzoxazol-2-yl)piperidine-1-carboxylate (160 mg, 481 μmol, intermediate 265) in 6 mL dichloromethane was added dropwise and stirred 3 h at −15° C. and over night at room temperature. The reaction mixture was quenched with some water, basified with aq. Sodium bicarbonate and extracted 3× with dichloromethane. The org. layer was filtered over a water-resistant-filter and concentrated under reduced pressure. The crude product was purified by column chromatography (hexane 100→hexane:ethyl acetate 60:40) obtained in 545 yield (91 mg).

$^1H$-NMR (400 MHz, DMSO-$d_6$): δ [ppm]=1.42 (s, 9H), 2.13-2.31 (m, 4H), 2.44 (s, 3H), 3.30 (br d, 2H), 3.72-3.82 (m, 2H), 7.30 (dd, 1H), 7.63 (d, 1H), 7.67 (d, 1H).

Intermediate 267

2-(4-fluoropiperidin-4-yl)-5-methyl-1,3-benzoxazole, Salt with Trifluoroacetic Acid

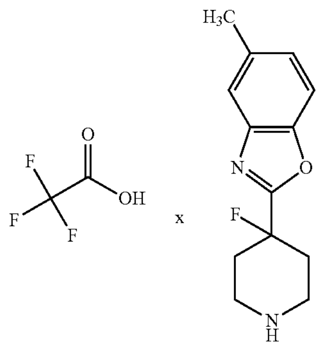

TFA was added to a solution of tert-butyl 4-fluoro-4-(5-methyl-1,3-benzoxazol-2-yl)piperidine-1-carboxylate (190 mg, 568 μmol, intermediate 266) in 3 mL dichloromethane and stirred 1.5 h at room temperature. After complete consumption of starting material the mixture was concentrated under reduced pressure and the product was used crude in the next step.

LC-MS Method 2): $R_t$=0.69 min; MS (ESIpos): m/z=235 $[M+H]^+$

Intermediate 268

4-chloro-1,6-dimethyl-7-nitro-2-oxo-1,2-dihydroquinoline-3-carbonitrile

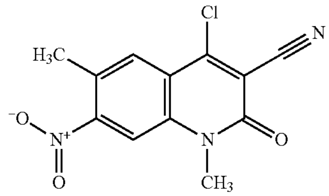

A solution of 500 mg 4-chloro-1,6-dimethyl-2-oxo-1,2-dihydroquinoline-3-carbonitrile (intermediate 92) in 10 ml concentrated sulfuric acid was cooled to 0° C. and treated with 9.14 ml nitric acid (65%). The reaction was stirred for 2 hours at 0° C. and poured into sodium bicarbonate solution. The solution was extracted with ethyl acetate (2×) and the combined organic layers were washed with brine, dried and evaporated in vacuo. The residue was purified by flash chromatography (silica, dichloromethane/methanol gradient 0-1%). 240 mg of the title compound were obtained.

$^1$H NMR (400 MHz, DMSO-d6) δ ppm 3.29-3.32 (m, 3H) 8.20-8.24 (m, 1H) 8.26-8.30 (m, 1H).

Intermediate 269

(rac)-4-chloro-1-methyl-2-oxo-7-(tetrahydrofuran-3-yloxy)-1,2-dihydroquinoline-3-carbonitrile

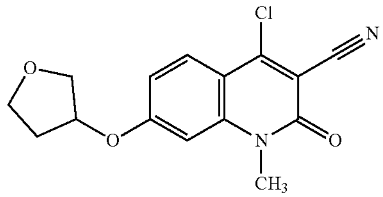 [SMILES: Cn1c(=O)c(C#N)c(Cl)c2ccc(OC3CCOC3)cc21]

Diisopropyl azodicarboxylate (1.1 ml, 5.6 mmol) was added to a solution of 870 mg 4-chloro-7-hydroxy-1-methyl-2-oxo-1,2-dihydroquinoline-3-carbonitrile (3.71 mmol, intermediate 136), 0.59 mL (3RS)-tetrahydrofuran-3-ol and 1.46 g triphenylphosphine (5.56 mmol) in 21 mL dichloromethane at 0° C. The mixture was stirred for 7 h at 40° C. And another set of reagents was added due to incomplete conversion and stirring was continued overnight. The reaction mixture was evaporated and the crude product was purified by column chromatography using (hexane:ethyl acetate 50:50→ethyl acetate 100→ethyl acetate:ethanol 80:20) and by RP-HPLC.

product fraction were combined $^1$H NMR (400 MHz, DMSO-$d_6$) δ ppm 1.97-2.07 (m, 1H) 2.29-2.40 (m, 1H) 3.64 (s, 3H) 3.79 (br td, 1H) 3.84-3.91 (m, 2H) 3.92-3.98 (m, 1H) 5.38 (br dd, 1H) 7.05 (d, 1H) 7.13 (dd, 1H): 8.00 (d, 1H).

Intermediate 270

(rac)-6-bromo-4-chloro-1-methyl-2-oxo-7-[(oxolan-3-yl)oxy]-1,2-dihydroquinoline-3-carbonitrile

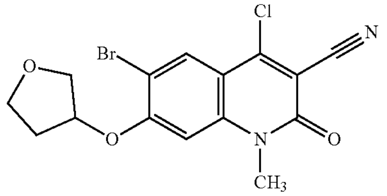 [SMILES: Cn1c(=O)c(C#N)c(Cl)c2cc(Br)c(OC3CCOC3)cc21]

N-Bromosuccinimide was added to a solution of 100 mg (rac)-4-chloro-1-methyl-2-oxo-7-(tetrahydrofuran-3-yloxy)-1,2-dihydroquinoline-3-carbonitrile (263 μmol, intermediate 269) in 0.62 mL DMF and stirred over night at 60° C. The re action mixture was poured to ice-water, the precipitate was filtered off, washed with water and dried. The product was obtained in 75% yield (101 mg).

$^1$H-NMR (400 MHz, DMSO-$d_6$): δ [ppm]=2.01-2.12 (m, 1H), 2.33-2.42 (m, 1H), 3.68 (s, 3H), 3.77-3.94 (m, 3H), 3.96-4.02 (m, 1H), 5.55 (dd, 1H), 7.09-7.13 (m, 1H), 8.18-8.21 (m, 1H).

Intermediate 271

(rac)-6-bromo-4-[4-fluoro-4-(5-methyl-1,3-benzoxazol-2-yl)piperidin-1-yl]-1-methyl-2-oxo-7-[(oxolan-3-yl)oxy]-1,2-dihydroquinoline-3-carbonitrile

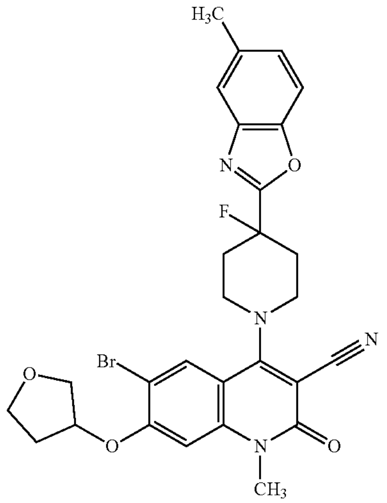 [SMILES: Cc1ccc2oc(C3(F)CCN(c4c(C#N)c(=O)n(C)c5cc(OC6CCOC6)c(Br)cc45)CC3)nc2c1]

To a suspension of 100 mg 2-(4-fluoropiperidin-4-yl)-5-methyl-1,3-benzoxazole (287 μmol, intermediate 267) and 147 mg (rac)-6-bromo-4-chloro-1-methyl-2-oxo-7-[(oxolan-3-yl)oxy]-1,2-dihydroquinoline-3-carbonitrile (287 μmol, intermediate 270) in 2.3 mL 2-propanol was added 0.2 mL di-isopropylethylamine (1.1 mmol) and it was stirred 3 h at 90° C. The reaction mixture was evaporated and the crude product was purified by column chromatography (dichloromethane→dichloromethane:ethanol 90:10) and by RP-HPLC. The product was obtained in 33% yield (55 mg).

LC-MS (Method 1): $R_t$=1.37 min; MS (ESIpos): m/z=581 $[M+H]^+$

Intermediate 272

(rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile

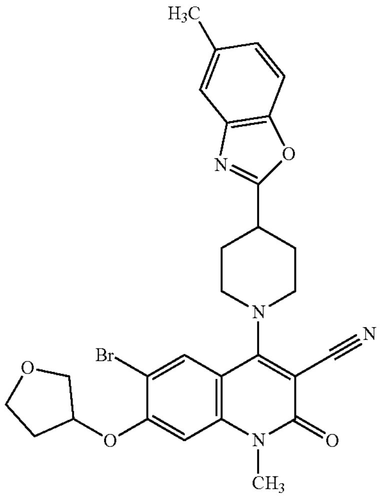 [SMILES: Cc1ccc2oc(C3CCN(c4c(C#N)c(=O)n(C)c5cc(OC6CCOC6)c(Br)cc45)CC3)nc2c1]

A flask was charged with 500 mg 6-bromo-7-hydroxy-1-methyl-4-[4-(5-methyl-1,3-benzoxazol-2-yl)piperidin-1-yl]-2-oxo-1,2-dihydroquinoline-3-carbonitrile (1.01 mmol, example 422) and 991 mg cesium carbonate (3.04 mmol) the atmosphere was replaced with argon. 15 mL anhydrous DMF and 190 μl 3-bromooxolane (2.0 mmol) were added and the reaction mixture was heated to 100° C. under argon. Water was added and the mixture was extracted with ethyl acetate 3×. The combined organic layers were washed with brine and filtered over a hydrophobic filter. The filtrate was concentrated under reduced pressure. To the residue was added water and this mixture was stirred overnight at room temperature, then filtered and washed with water. The solid was dried and the product was obtained in 92% yield (558 mg).

$^1$H NMR (400 MHz, DMSO-$d_6$) δ ppm 1.98-2.16 (m, 3H) 2.27-2.37 (m, 3H) 2.42 (s, 3H) 3.37-3.47 (m, 1H) 3.54-3.64 (m, 5H) 3.75-3.84 (m, 3H) 3.85-3.93 (m, 2H) 3.95-4.01 (m, 1H): 5.46 (br dd, 1H) 6.99 (s, 1H) 7.19 (dd, 1H) 7.51-7.54 (m, 1H) 7.58 (d, 1H) 7.96 (s, 1H).

LC-MS Method 2): $R_t$=1.39 min; MS (ESIpos): m/z=563 $[M+H]^+$

Intermediate 273

4-chloro-1-methyl-2-oxo-1,2-dihydroquinoline-3-carboxylic Acid

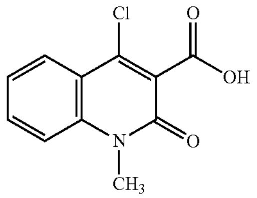 [SMILES: Cn1c(=O)c(C(=O)O)c(Cl)c2ccccc21]

To a solution of 100 mg ethyl 4-chloro-1-methyl-2-oxo-1,2-dihydroquinoline-3-carboxylate (376 μmol, CAS 75483-04-4) in 1.1 mL THF was added 1 mL water and 90 mg lithiumhydroxid (3.76 mmol). The reaction mixture was stirred at 100° C. for 1 h. the reaction mixture was cooled to room temperature and extracted 3× with dichloromethane. The aqueous layer was acidified with 2N aq. hydrochloric acid and then filtered. The solid was washed with water and dried. The product was obtained in 56% yield (66 mg).

$^1$H-NMR (400 MHz, DMSO-d6): 5 [ppm]=3.67 (s, 3H), 7.46 (ddd, 1H), 7.69 (d, 1H), 7.78-7.84 (m, 1H), 8.03 (dd, 1H), 13.78 (br s, 1H).

LC-MS (Method 1): $R_t$=0.74 min; MS (ESIpos): m/z=238 $[M+H]^+$

Intermediate 274

4-chloro-N,1-dimethyl-2-oxo-1,2-dihydroquinoline-3-carboxamide

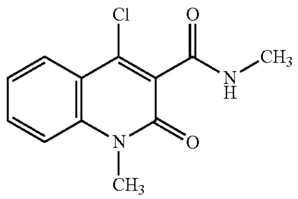 [SMILES: CNC(=O)c1c(Cl)c2ccccc2n(C)c1=O]

To a solution of 384 mg 4-chloro-1-methyl-2-oxo-1,2-dihydroquinoline-3-carboxylic acid (1.62 mmol, intermediate 273) in 6 mL DMF at 0° C. under a nitrogen atmosphere was added 800 mg HATU (2.10 mmol), 340 μl di-isopropylethylamine (1.9 mmol) and 890 μl methylamine (2.0 M, 1.8 mmol, CAS 74-89-5). The reaction mixture was stirred 30 min at 0° C. then warmed to room temperature and purified by RP-HPLC. The product was obtained in 35% yield (151 mg).

1H-NMR (400 MHz, DMSO-d6): 5 [ppm]=2.75 (d, 3H), 3.66 (s, 3H), 7.44 (ddd, 1H), 7.67 (d, 1H), 7.74-7.82 (m, 1H), 8.02 (dd, 1H), 8.37 (br d, 1H).

Intermediate 275

6-cyano-7-hydroxy-1-methyl-4-[4-methyl-4-(5-methyl-1,3-benzoxazol-2-yl)piperidin-1-yl]-2-oxo-1,2-dihydroquinoline-3-carboxamide

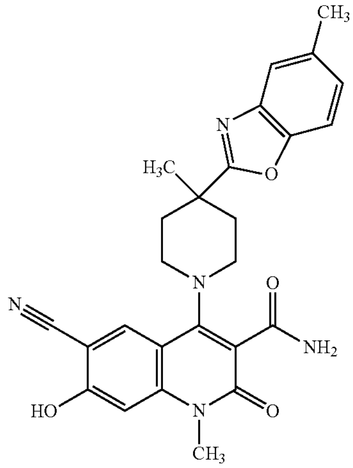 [SMILES: Cc1ccc2oc(C3(C)CCN(c4c(C(N)=O)c(=O)n(C)c5cc(O)c(C#N)cc45)CC3)nc2c1]

A flask was charged with 120 mg 6-bromo-7-hydroxy-1-methyl-4-[4-methyl-4-(5-methyl-1,3-benzoxazol-2-yl)piperidin-1-yl]-2-oxo-1,2-dihydroquinoline-3-carboxamide (228 μmol, example 512), 11.8 mg $[Pd(cinnamyl)Cl]_2$ (22.8 μmol, CAS 12131-44-1), 12.7 mg 1,1'-bis(diphenylphosphanyl)ferrocene (22.8 μmol; CAS 12150-46-8) and 40.2 mg zinc cyanide (343 μmol; CAS 557-21-1) and the contained was flushed with argon. 1 mL N,N-dimethylacetamide (pre-flushed with Ar) and 80 μl Di-isopropylethylamine (460 μmol) were added subsequently.

The mixture was stirred at 80° C. over night.

The reaction mixture was cooled to room temperature and was diluted with dichloromethane. Sat. sodium bicarbonate solution was added, the layers were separated and the aqueous layer was extracted twice with dichloromethane.

The combined org. layers were filtered via a water-repellent filter and were concentrated in vacuo. The crude product was purified by column chromatography and was obtained in 92% yield (104 mg).

$^1$H NMR (400 MHz, DMSO-$d_6$) δ ppm 1.45 (s, 3H) 1.95-2.05 (m, 2H) 2.42 (s, 3H) 2.44-2.48 (m, 2H) 3.01-3.12 (m, 2H) 3.20-3.30 (m, 2H) 3.47 (s, 3H) 6.89 (s, 1H) 7.16-7.21 (m, 1H): 7.41 (br s, 1H) 7.51-7.61 (m, 3H) 8.05 (s, 1H).

Intermediate 276

Tert-Butyl 4-methyl-4-{[(4,5,6,7-tetrachloro-1,3-dioxo-1,3-dihydro-2H-isoindol-2-yl)oxy]carbonyl}piperidine-1-carboxylate

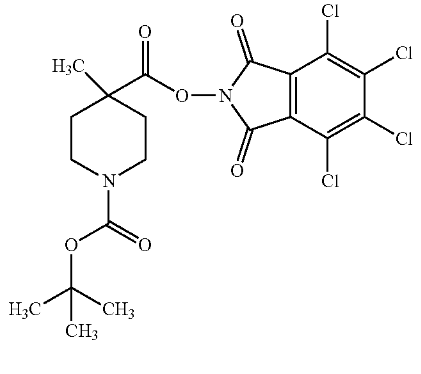 [SMILES: CC(C)(C)OC(=O)N1CCC(C)(C(=O)ON2C(=O)c3c(Cl)c(Cl)c(Cl)c(Cl)c3C2=O)CC1]

To a vigorously stirring suspension of 500 mg 1-(tert-butoxycarbonyl)-4-methylpiperidine-4-carboxylic acid, 680 mg 4,5,6,7-tetrachloro-2-hydroxy-1H-isoindole-1,3(2H)-dione and 25 mg 4-Dimethylaminopyridine in 15 ml dichloromethane were added dropwise 0.35 ml N,N'-disiopropylcarbodiimde at RT. The reaction mixture was stirred 1 h at RT. The suspension was filtered and washed with dichloromethane. The filtrate was concentrated under reduced pressure and the residue was purified by flash chromatography (silica, hexanes/ethyl acetate gradient 0-20%). 1.06 g of the title compound were obtained.

$^1$H-NMR (400 MHz, CDCl3): δ [ppm]=1.36-1.61 (m, 14H), 2.24 (br d, 2H), 3.09 (br s, 2H), 3.95 (br s, 2H).

Intermediate 277

Tert-Butyl 4-(1-benzothiophen-2-yl)-4-methylpiperidine-1-carboxylate

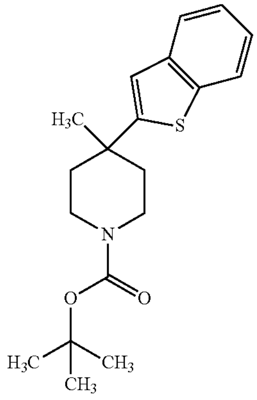 [SMILES: CC(C)(C)OC(=O)N1CCC(C)(c2cc3ccccc3s2)CC1]

To a solution of 1 g 2-iodo-1-benzothiophene (CAS 36748-89-7) in solvent 6 ml THF] was added at −20° C. 2.96 ml isopropylmagnesium chloride-lithium chloride complex solution (1.3M sol. in THF) dropwise. The reaction mixture stirred 30 min at −20° C. and 1 h at 0° C. A flask was dried under vacuum with a heat gun. Upon cooling the flask was backfilled with nitrogen gas, and 433 mg zinc dibromide was added. The flask was placed under vacuum and heated with a heat gun again. After cooling to RT, the flask was backfilled with nitrogen gas and 1.5 mL of THF. The mixture was vigorously stirred until nearly all zinc dibromide was dissolved (milky solution). The zinc dibromide solution was added to the grignard mixture at −20° C. The mixture was stirred 10 minutes at −20° C. and 20 min at 0° C. to obtain bis(1-benzothiophen-2-yl)zinc solution (ca. 0.21 M). A flask was charged with zinc dibromide and heated with a heatgun under vacuum. After cooling down to RT the flask was flushed with nitrogen gas. Then 440 mg tert-butyl 4-methyl-4-{[(4,5,6,7-tetrachloro-1,3-dioxo-1,3-dihydro-2H-isoindol-2-yl)oxy]carbonyl}piperidine-1-carboxylate (intermediate 276) and 178 mg bis(2,2,6,6-tetramethyl-3,5-heptanedionato)Nickel(II) and 4 mL of THF were added. Then 10 ml of bis(1-benzothiophen-2-yl)zinc solution were added at 0° C. The mixture was stirred further 2 minutes at 0° C. an d was then allowed to warm up to rt. The mixture was stirred overnight at RT. The mixture was diluted with ethyl acetate. The layers were separated and the aqueous layer was extracted with ethyl acetate (2×). The combined organic layers were washed with sat. aqu. Ammonium chloride solution, dried (waterresistant filter) and concentrated under reduced pressure. The residue was purified by flash chromatography (silica, hexanes/ethyl acetate gradient 0-20%). 117 mg of the crude title compound were obtained.

LC-MS Method 2): $R_t$=1.61 min; MS (ESIpos): m/z=332 $[M+H]^+$

Intermediate 278

4-(1-benzothiophen-2-yl)-4-methylpiperidine

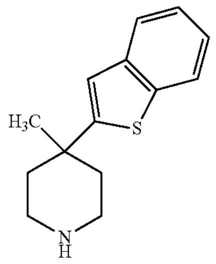 [SMILES: CC1(c2cc3ccccc3s2)CCNCC1]

To a solution of 117 mg crude tert-butyl 4-(1-benzothiophen-2-yl)-4-methylpiperidine-1-carboxylate (intermediate 277) 0.37 ml in methanol in methanol was added 0.44 ml (4N in dioxane). The reaction mixture stirred 4 hours at RT and was then concentrated under vacuo. 97 mg of the crude title compound were obtained.

LC-MS Method 2): $R_t$=1.24 min; MS (ESIpos): m/z=232 $[M+H]^+$

Intermediate 279

Tert-Butyl 4-[1-(2-methylphenyl)-1H-pyrazol-3-yl] piperidine-1-carboxylate

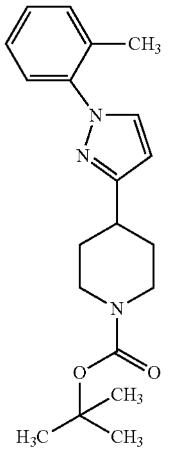 [SMILES: Cc1ccccc1-n1ccc(C2CCN(C(=O)OC(C)(C)C)CC2)n1]

70 mg tert-butyl 4-(1H-pyrazol-3-yl)piperidine-1-carboxylate (intermediate 198), 76 mg (2-methylphenyl)boronic acid, 76 mg copper(II) acetate (CAS 142-71-2), and 150 mg activated molecular sieves were placed in a flask A solution of 45 μl pyridine in 3.4 mL dichloromethane was added and the mixture stirred for 2 days. The mixture was filtered over celite and it was washed with methanol and some dichloromethane. The filtrate was evaporated and the crude product was purified by flash chromatography (silica, hexanes/ethyl acetate gradient 0-50%). 83 mg of the title compound were obtained.

$^1H$ NMR (400 MHz, DMSO-$d_6$) δ ppm 1.37-1.44 (m, 10H) 1.44-1.57 (m, 2H) 1.91 (br dd, 2H): 2.21 (s, 3H) 2.78-2.99 (m, 3H) 3.33 (s, 4H) 3.97 (br d, 2H) 6.35 (d, 1H) 7.29-7.38 (m, 4H): 7.90 (d, 1H).

Intermediate 280

4-[1-(2-methylphenyl)-1H-pyrazol-3-yl]piperidine, Salt with Trifluoroacetic Acid

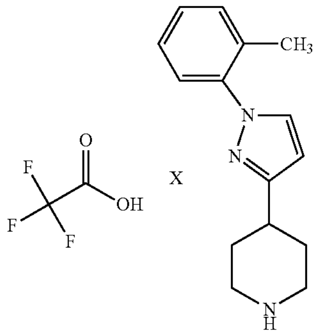

To a solution of 80 mg tert-butyl 4-[1-(2-methylphenyl)-1H-pyrazol-3-yl]piperidine-1-carboxylate (intermediate 279) in 1.2 mL dichloromethane was added 0.45 mL trifluoroacetic acid. The reaction mixture was stirred at room temperature until complete consumption of starting material. The crude product (160 mg) was directly used in the next step.

$^1H$ NMR (400 MHz, DMSO-$d_6$) δ ppm 1.75-1.88 (m, 2H) 2.08-2.16 (m, 2H) 2.21 (s, 3H) 2.96-3.09 (m, 3H) 3.33 (br d, 2H) 6.36 (d, 4H) 7.30-7.39 (m, 7H) 7.95 (d, 1H):

Intermediate 281

6-bromo-7-methoxy-1-methyl-4-[4-(5-methyl-1,3-benzoxazol-2-yl)piperidin-1-yl]-2-oxo-1,2-dihydroquinoline-3-carbonitrile

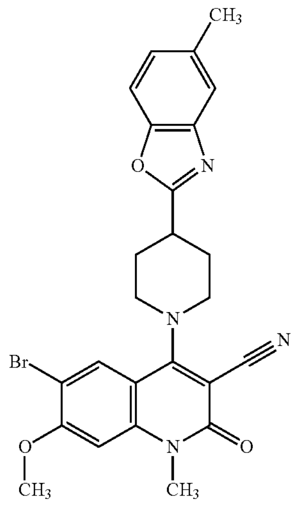 [SMILES: COc1cc2c(cc1Br)c(N1CCC(c3nc4cc(C)ccc4o3)CC1)c(C#N)c(=O)n2C]

A solution of 1.51 g 6-bromo-4-chloro-7-methoxy-1-methyl-2-oxo-1,2-dihydroquinoline-3-carbonitrile (intermediate 264), 1.0 g 5-methyl-2-(piperidin-4-yl)-1,3-benzoxazole (CAS 199292-77-8) and 2.4 mL N,N-diisopropylethylamine in 15 mL ethanol was stirred for 2 h at 100° C. After this time, the reaction was cooled to RT and stirred for 1 h. The resulting suspension was filtered and the solid product was washed with ethanol. 1.86 g of the title compound were.

1H-NMR (400 MHz, DMSO-d6): 5 [ppm]=2.00-2.15 (m, 2H), 2.25-2.34 (m, 2H), 2.42 (s, 3H), 3.38-3.48 (m, 1H), 3.53-3.64 (m, 5H), 3.79 (br d, 2H), 4.05 (s, 3H), 7.02 (s, 1H), 7.19 (dd, 1H), 7.50-7.55 (m, 1H), 7.58 (d, 1H), 7.95 (s, 1H). shows slight impurities LC-MS (Method 1): $R_t$=1.38 min; MS (ESIpos): m/z=507 $[M+H]^+$ Intermediate 282

(rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide

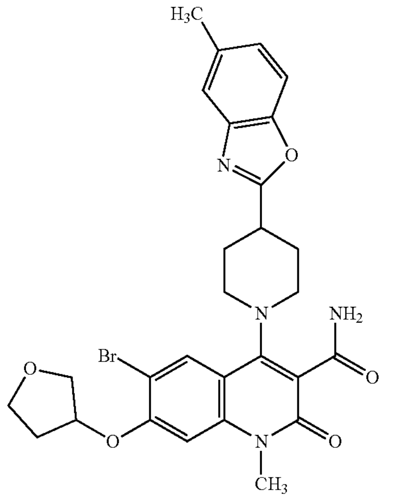 [SMILES: Cc1ccc2oc(C3CCN(c4c(C(N)=O)c(=O)n(C)c5cc(OC6CCOC6)c(Br)cc45)CC3)nc2c1]

A solution of 540 mg (rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (Example 424) was reacted with 1.06 g acetaldoxime and 80 mg chloridotris(triphenylphosphine)rhodium(I) (CAS 14694-95-2) in 26 ml toluene for 15 hours at 110° C. The reaction mixture was evaporated in vacuo and the residue was dissolved in dichloromethane and washed with water. The water phase was extracted with dichloromethane (2×) and the combined organic layers were washed with brine and concentrated under reduced pressure. The residue was purified by flash chromatography (silica, dichloromethane/ethanol gradient 0-10%) to obtain 333 mg of the title compound.

$^1$H NMR (400 MHz, DMSO-$d_6$) δ ppm 1.97-2.10 (m, 3H) 2.19-2.27 (m, 2H) 2.28-2.40 (m, 1H): 2.42 (s, 3H) 3.12-3.26 (m, 3H) 3.33-3.39 (m, 2H) 3.59 (s, 3H) 3.78-3.85 (m, 1H) 3.85-3.92 (m, 2H) 3.95-4.01 (m, 1H) 5.38-5.44 (m, 1H) 7.00 (s, 1H) 7.18 (dd, 1H) 7.47-7.51 (m, 1H) 7.51-7.54 (m, 1H) 7.55-7.61 (m, 1H) 7.65-7.70 (m, 1H) 7.98 (s, 1H).

LC-MS (Method 1): $R_t$=1.21 min; MS (ESIpos): m/z=583 $[M+H]^+$

Intermediate 283

(rac)-6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile

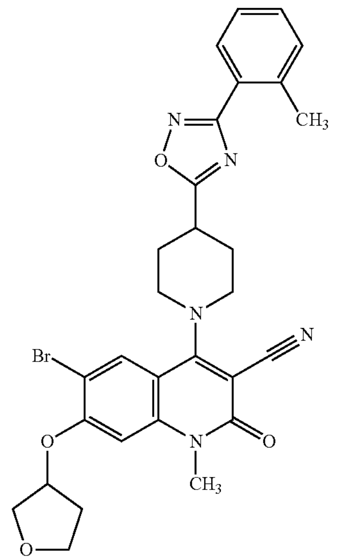 [SMILES: Cc1ccccc1-c1noc(C2CCN(c3c(C#N)c(=O)n(C)c4cc(OC5CCOC5)c(Br)cc34)CC2)n1]

A solution of 150 mg (rac)-6-bromo-4-chloro-1-methyl-2-oxo-7-[(oxolan-3-yl)oxy]-1,2-dihydroquinoline-3-carbonitrile (intermediate 270), 196 mg 4-[3-(2-methylphenyl)-1,2,4-oxadiazol-5-yl]piperidine (intermediate 248) and 0.2 mL N,N-diisopropylethylamine in 4 mL ethanol was stirred for 2 h at 90° C. After cooling down to RT, the mixture was filtered and the residue was washed with ethanol to deliver 150 mg of the title compound.

$^1$H-NMR (400 MHz, DMSO-$d_6$): δ [ppm]=2.00-2.17 (m, 3H), 2.29-2.37 (m, 3H), 2.57 (s, 3H), 3.53-3.64 (m, 6H), 3.76-3.84 (m, 3H), 3.85-3.93 (m, 2H), 3.95-4.02 (m, 1H), 5.47 (br t, 1H), 7.00 (s, 1H), 7.36-7.44 (m, 2H), 7.45-7.51 (m, 1H), 7.91-7.99 (m, 2H).

LC-MS (Method 1): $R_t$=1.43 min; MS (ESIpos): m/z=592 $[M+H]^+$

Intermediate 284

7-bromo-1,6-dimethyl-4-{4-[3-(2-methylphenyl)-1,2,4-oxadiazol-5-yl]piperidin-1-yl}-2-oxo-1,2-dihydroquinoline-3-carbonitrile

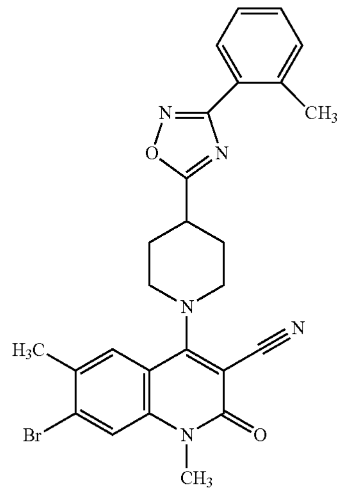

A solution of 1 g 7-bromo-4-chloro-1,6-dimethyl-2-oxo-1,2-dihydroquinoline-3-carbonitrile (intermediate 262), 1.15 mg 4-[3-(2-methylphenyl)-1,2,4-oxadiazol-5-yl]piperidine (intermediate 248) and 1.7 mL N,N-diisopropylethylamine in 10 mL ethanol was stirred for 2 h at 80° C. After cooling down to RT, the mixture was filtered and the residue was washed with ethanol to deliver 1.22 mg of the title compound.

$^1$H-NMR (400 MHz, DMSO-d6): 5 [ppm]=2.11-2.24 (m, 2H), 2.29-2.38 (m, 2H), 2.44 (s, 3H), 2.58 (s, 3H), 3.51-3.65 (m, 6H), 3.83 (br d, 2H), 7.36-7.45 (m, 2H), 7.45-7.51 (m, 1H), 7.75 (s, 1H), 7.80 (s, 1H), 7.95 (dd, 1H).

LC-MS (Method 1): $R_t$=1.54 min; MS (ESIpos): m/z=520 $[M+H]^+$

Intermediate 285

6-bromo-7-fluoro-1-methyl-2H-3,1-benzoxazine-2,4(1H)-dione

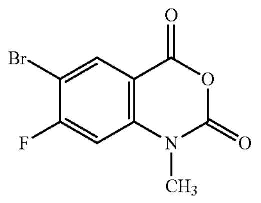

Methyl iodide (7.2 mL, 120 mmol; CAS 74-88-4) was added to a solution of 10 g 6-bromo-7-fluoro-2H-3,1-benzoxazine-2,4(1H)-dione (38.5 mmol) and 13 mL di-isopropylethylamine (77 mmol) in 100 mL DMF and stirred 3 h at room temperature. The reaction was quenched with ice and stirred until the ice melted. The precipitate was filtered off, washed with water and dried to obtain 10 g of the title compound.

$^1$H NMR (400 MHz, DMSO-d6) δ ppm 3.43 (s, 3H) 7.62 (d, 1H) 8.26 (d, 1H).

Intermediate 286

6-bromo-7-fluoro-4-hydroxy-1-methyl-2-oxo-1,2-dihydroquinoline-3-carbonitrile

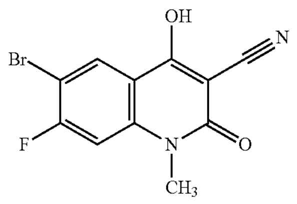

10 g 6-bromo-7-fluoro-1-methyl-2H-3,1-benzoxazine-2,4(1H)-dione (36.5 mmol, intermediate 285) was dissolved in 100 mL dioxane, 61 mL triethylamine (440 mmol) and ethyl 31 mL cyanoacetate (290 mmol) were added and the mixture stirred over night at 90° C. The reaction mixture was evaporated to a small volume. 300 ml water was added to the residue and the solution was acidified with 1 N hydrochloric acid to pH=1. The precipitate was filtered off, washed with water and dried at 60° C. to obtain 11 g of the title compound.

$^1$H NMR (400 MHz, DMSO-d6) δ ppm 3.40 (s, 5H) 7.41 (d, 1H) 8.16 (d, 1H).

Intermediate 287

6-bromo-4-chloro-7-fluoro-1-methyl-2-oxo-1,2-dihydroquinoline-3-carbonitrile

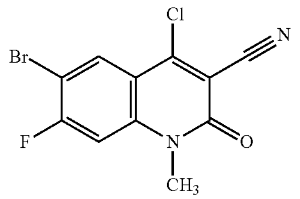 [SMILES: Cn1c(=O)c(C#N)c(Cl)c2cc(Br)c(F)cc21]

11 g 6-bromo-7-fluoro-4-hydroxy-1-methyl-2-oxo-1,2-dihydroquinoline-3-carbonitrile (31.8 mmol, intermediate 286) was stirred in 89 mL phosphoryl chloride (960 mmol) 26 h at 90° C. The mixture was poured carefully in ice-water and stirred till the ice was melted. The solution was added to ice-water and basified with sodium carbonat (strong gas evolution!). The precipitate was filtered, washed with water and dried. The product was purified by column chromatography and obtained in 6.2 g of the title compound.

$^1$H NMR (400 MHz, DMSO-d6) δ ppm 3.62 (s, 4H) 7.87 (d, 1H) 8.34 (d, 1H).

Intermediate 288

6-bromo-7-fluoro-1-methyl-4-[4-(5-methyl-1,3-benzoxazol-2-yl)piperidin-1-yl]-2-oxo-1,2-dihydroquinoline-3-carbonitrile

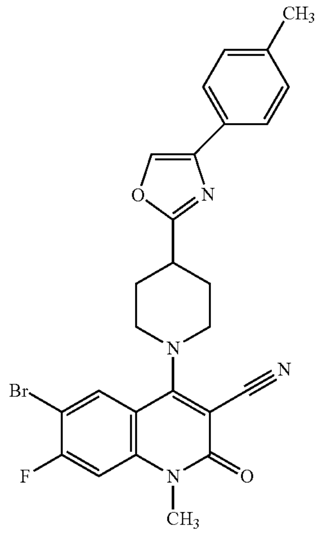 [SMILES: Cc1ccc(-c2coc(C3CCN(c4c(C#N)c(=O)n(C)c5cc(F)c(Br)cc45)CC3)n2)cc1]

A solution of 2.19 g 6-bromo-4-chloro-7-fluoro-1-methyl-2-oxo-1,2-dihydroquinoline-3-carbonitrile (6.9 mmol, intermediate 287), 1.5 g 2-(4-methylpiperidin-4-yl)-1,3-benzoxazole (intermediate 1, 6.9 mmol) and 2.9 mL triethylamine (21 mmol) in 40 mL 2-propanol was stirred for 4 h at 90° C. After this time, water and ethyl acetate were added. The respective solid was filtered and washed to obtain 2.8 g of the title compound.

$^1$H NMR (400 MHz, DMSO-d6) δ ppm 2.04-2.15 (m, 2H) 2.26-2.32 (m, 1H) 2.41 (s, 3H) 3.52 (s, 4H) 3.56-3.64 (m, 3H) 3.78-3.85 (m, 2H) 7.16-7.21 (m, 1H) 7.50-7.53 (m, 1H) 7.55-7.59 (m, 1H) 7.62-7.67 (m, 1H) 8.01-8.06 (m, 1H):

Intermediate 289

6-chloro-7-methoxy-2H-3,1-benzoxazine-2,4(1H)-dione

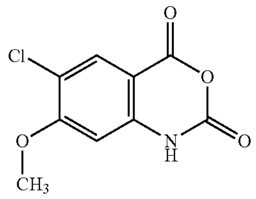

A mixture of 1.9 g 2-amino-5-chloro-4-methoxybenzoic acid (9.42 mmol; CAS-79025-82-4) and 3.06 g di-(1H-imidazol-1-yl)methanone (18.8 mmol; CAS-530-62-1) in 80 ml THF was stirred at RT for 14 hours. Water was added and the residue was filtered off. The residue was washed with water and dried at 60° C. to obtain 2 g crude product of the title compound that was used without further purification.

Intermediate 290

6-chloro-7-methoxy-1-methyl-2H-3,1-benzoxazine-2,4(1H)-dione

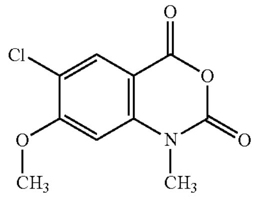 [SMILES: COc1cc2c(cc1Cl)c(=O)oc(=O)n2C]

1.6 ml Methyl iodide (26 mmol; CAS 74-88-4) was added to a solution of 2 g crude 6-chloro-7-methoxy-2H-3,1-benzoxazine-2,4(1H)-dione (intermediate 289) and 3.1 mL di-isopropylethylamine in 70 mL DMF and stirred 2.5 h at room temperature. The reaction was quenched with ice and stirred until the ice melted. The precipitate was filtered off, washed with water and dried to obtain 1.4 g of the title compound.

$^1$H NMR (400 MHz, DMSO-d6) δ ppm 3.51 (s, 3H) 4.07 (s, 3H) 6.95-6.99 (m, 1H) 7.95 (s, 1H).

Intermediate 291

6-chloro-4-hydroxy-7-methoxy-1-methyl-2-oxo-1,2-dihydroquinoline-3-carbonitrile

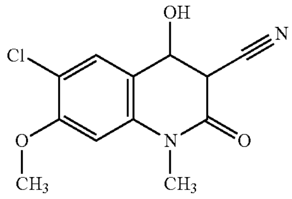

1.4 g 6-chloro-7-methoxy-1-methyl-2H-3,1-benzoxazine-2,4(1H)-dione (5.79 mmol, intermediate 290) was dissolved in 20 mL THF, 6.5 mL triethylamine (46 mmol) and ethyl 2.5 mL cyanoacetate (23 mmol) were added and the mixture stirred for 64 h at 70° C. The reaction mixture was evaporated to a small volume. Water was added to the residue and the solution was acidified with 1 N hydrochloric acid to pH=1. The resulting precipitate was filtered off, washed with water and dried at 60° C. to obtain 680 mg of the title compound.

$^1$H NMR (400 MHz, DMSO-d6) δ ppm 3.56 (s, 3H) 4.03 (s, 3H) 6.99 (s, 1H) 8.06 (s, 1H).

LC-MS (Method 1): $R_t$=0.72 min; MS (ESIpos): m/z=265 $[M+H]^+$

Intermediate 292

4,6-dichloro-7-methoxy-1-methyl-2-oxo-1,2-dihydroquinoline-3-carbonitrile

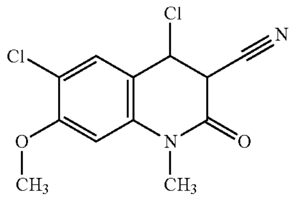 [SMILES: COc1cc2c(cc1Cl)C(Cl)C(C#N)C(=O)N2C]

680 mg 6-chloro-4-hydroxy-7-methoxy-1-methyl-2-oxo-1,2-dihydroquinoline-3-carbonitrile (2.57 mmol, intermediate 291) was stirred in 4.8 mL phosphoryl chloride (51 mmol) 14 h at 90° C. The mixture was poured carefully in ice-water and stirred till the ice was melted. The solution was added to ice-water and basified with sodium carbonat (strong gas evolution!). The precipitate was filtered, washed with water and dried. The product was purified by column chromatography and obtained in 640 mg of the title compound.

$^1$H NMR (400 MHz, DMSO-d6) δ ppm 3.69 (s, 3H) 4.11 (s, 3H) 7.17 (s, 1H) 8.04 (s, 1H):

LC-MS (Method 1): $R_t$=1.15 min; MS (ESIpos): m/z=283 $[M+H]^+$

Intermediate 293

Tert-Butyl 4-[1-(2-methylphenyl)-1H-1,2,3-triazol-4-yl]piperidine-1-carboxylate

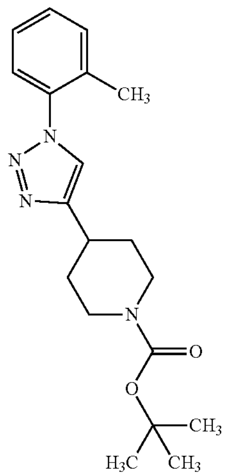 [SMILES: Cc1ccccc1-n1cc(C2CCN(C(=O)OC(C)(C)C)CC2)nn1]

A mixture of 78 mg sodium azide, 136 mg (2-methylphenyl)boronic acid and 16 mg Copper(II)sulfate were reacted in 3 ml methanol at rt for 5 h. 3 ml water, 230 mg tert-butyl 4-ethynylpiperidine-1-carboxylate and 99 mg sodium (2R)-2-[(1S)-1,2-dihydroxyethyl]-4-hydroxy-5-oxo-2,5-dihydrofuran-3-olate (sodium ascorbate) were added and the mixture was stirred for 14 h at RT. The mixture was evaporated to remove methanol. The aqueous residue was extracted 3× with dichloromethane. The combined organic layers were dried (using a waterresistant filter) and concentrated under reduced pressure. The residue was purified by column chromatography (silica; hexanes/ethyl acetate gradient 0-50%) to get 240 mg of the title compound.

1H-NMR (400 MHz, DMSO-d6): δ [ppm]=1.41 (s, 9H), 1.46-1.60 (m, 2H), 1.94-2.03 (m, 2H), 2.10-2.18 (m, 3H), 2.82-3.02 (m, 3H), 3.93-4.06 (m, 2H), 7.38-7.42 (m, 2H), 7.45-7.49 (m, 2H), 8.26-8.29 (m, 1H).

Intermediate 294

4-[1-(2-methylphenyl)-1H-1,2,3-triazol-4-yl]piperidine, Salt with Trifluoroacetic Acid

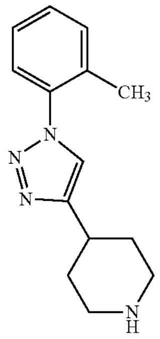

x $CF_3COOH$ 1.3 mL TFA was added to a solution of 240 mg tert-butyl 4-[1-(2-methylphenyl)-1H-1,2,3-triazol-4-yl]piperidine-1-carboxylate (intermediate 293, 0.7 mmol) in 4.5 mL dichloromethane and stirred 14 h at room temperature. The mixture was concentrated under reduced pressure and the crude product (342 mg) was directly used in the next step.

LC-MS (Method 2): $R_t$=0.98 min; MS (ESIpos): m/z=244 $[M+H]^+$

Intermediate 295

4-bromo-1-(2-methylphenyl)-1H-pyrazole

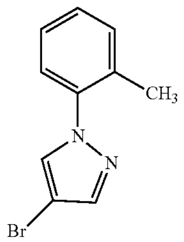

A mixture of 1.0 g 4-bromo-1H-pyrazole, 1.3 ml 1-iodo-2-methylbenzene, 2.22 g cesium carbonate and 97 mg Copper(II)oxide in 17 ml DMF was stirred for 14 hours at 110° C. After cooling down, the solid was allowed to settle. The liquid of the settled suspension was decanted and concentrated. The residue was diluted with water and extracted 3× with dichloromethane. The combined organic layers were concentrated under reduced pressure and the residue was purified by column chromatography (silica; hexanes/dichloromethane gradient 0-100%) to get 596 mg of the title compound.

$^1$H-NMR (400 MHz, DMSO-d6): δ [ppm]=2.19 (s, 3H), 7.33-7.42 (m, 4H), 7.82-7.86 (m, 1H), 8.33-8.36 (m, 1H).

LC-MS (Method 2): $R_t$=1.24 min; MS (ESIpos): m/z=239 $[M+H]^+$

Intermediate 296

Tert-Butyl 4-[1-(2-methylphenyl)-1H-pyrazol-4-yl]-3,6-dihydropyridine-1(2H)-carboxylate

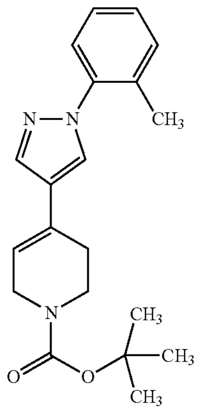 [SMILES: Cc1ccccc1-n1cc(C2=CCN(C(=O)OC(C)(C)C)CC2)cn1]

To a solution of tert-butyl 4-(4,4,5,5-tetramethyl-1,3,2-dioxaborolan-2-yl)-3,6-dihydropyridine-1(2H)-carboxylate (CAS-286961-14-6) in 11 ml dioxane was added 590 mg 4-bromo-1-(2-methylphenyl)-1H-pyrazole (intermediate 295). The mixture was sparkled 5 min with argon. Then 144 mg tertakis(triphenylphosphine)Palladium(0), 1.03 g potassium carbonate and 1.1 ml water were added. The reaction mixture was stirred for 14 hours at 80° C. The reaction mixture was diluted with water and extracted 3× with ethyl acetate. The combined organic layers were washed with water and brine, dried and concentrated under reduced pressure. The residue was purified by column chromatography (silica; hexanes/dichloromethane gradient 0-100%) to get 705 mg of the title compound (purity ca. 35%) that was used without further purification.

Intermediate 297

Tert-Butyl 4-[1-(2-methylphenyl)-1H-pyrazol-4-yl] piperidine-1-carboxylate

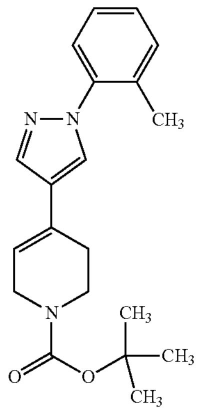 [SMILES: Cc1ccccc1-n1cc(C2=CCN(C(=O)OC(C)(C)C)CC2)cn1]

To a solution of 700 mg tert-butyl 4-[1-(2-methylphenyl)-1H-pyrazol-4-yl]-3,6-dihydropyridine-1(2H)-carboxylate (intermediate 296, purity ca. 35%) in 5 ml dichloromethane and 5 ml methanol was added 66 mg palladium on carbon (10%). The mixture was flushed with hydrogen and stirred 5 h at RT. The reaction mixture was filtered through Celite and washed with dichlormethane. The filtrate was concentrated under reduced pressure to obtain 680 mg of the title compound (purity ca. 30%).

LC-MS (Method 2): $R_t$=1.39 min; MS (ESIpos): m/z=342 $[M+H]^+$

Intermediate 298

4-[1-(2-methylphenyl)-1H-pyrazol-4-yl]piperidine, Salt with Trifluoroacetic Acid

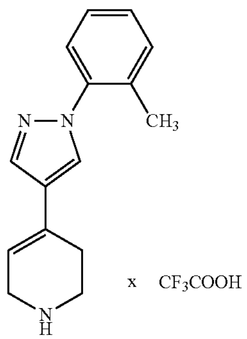 [SMILES: Cc1ccccc1-n1cc(C2=CCNCC2)cn1 ; "CF3COOH"]

0.92 mL TFA was added to a solution of 680 tert-butyl 4-[1-(2-methylphenyl)-1H-pyrazol-4-yl]piperidine-1-carboxylate (intermediate 297, purity ca. 30%) in 5 mL dichloromethane and stirred 14 h at room temperature. The mixture was concentrated under reduced pressure and the crude product (933 mg) was directly used in the next step.

Intermediate 299

2-amino-4-bromo-5-methylbenzoic Acid

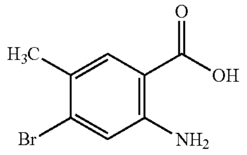

A mixture of 20 g 4-bromo-5-methyl-2-nitrobenzoic acid and 51.1 g tin(II)chloride hydrate in 150 ml water was treated with 150 ml hydrochloric acid (36%). After stirring for 1 hour at 90° C., the heating was removed and the mixture colled to RT. The resulting residue was collected by filtration and washed with water. The residue was dried at 50° C. to obtain 13.2 g of the title compound.

$^1$H NMR (400 MHz, DMSO-d6) δ ppm 2.18 (s, 3H) 7.03 (s, 1H) 7.59-7.63 (m, 1H).

LC-MS (Method 1): $R_t$=1.01 min; MS (ESIpos): m/z=229 $[M+H]^+$

Intermediate 300

7-bromo-6-methyl-2H-3,1-benzoxazine-2,4(1H)-dione

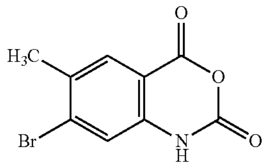

A mixture of 13.2 g 2-amino-4-bromo-5-methylbenzoic acid (intermediate 299) and 16.1 g di-(1H-imidazol-1-yl) methanone (99 mmol; CAS-530-62-1) in 80 ml THF was stirred at RT for 2 hours. Water was added and the residue was filtered off. The residue was washed with water and dried at 60° C. to obtain 13 g of the title compo und.

$^1$H NMR (400 MHz, DMSO-d6) δ ppm 2.36 (s, 3H) 3.33 (s, 6H) 7.34 (s, 1H) 7.88 (s, 1H) 11.68-11.81 (m, 1H).

Intermediate 301

7-bromo-1,6-dimethyl-2H-3,1-benzoxazine-2,4(1H)-dione

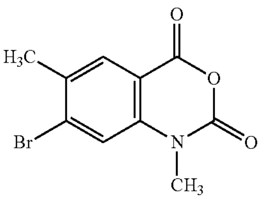

9.5 ml Methyl iodide (150 mmol; CAS 74-88-4) was added to a solution of 13 g 7-bromo-6-methyl-2H-3,1-benzoxazine-2,4(1H)-dione (intermediate 300) and 18 mL di-isopropylethylamine in 300 mL DMF and stirred 2.5 h at room temperature. The reaction was quenched with ice and stirred until the ice melted. The precipitate was filtered off, washed with water and dried to obtain 11.4 g of the title compound.

$^1$H NMR (400 MHz, DMSO-d6) δ ppm 2.40 (s, 3H) 3.44 (s, 3H) 7.71 (s, 1H) 7.96 (s, 1H):

LC-MS (Method 1): $R_t$=1.08 min; MS (ESIpos): m/z=269 $[M+H]^+$

Intermediate 302

7-bromo-4-hydroxy-1,6-dimethyl-2-oxo-1,2-dihydroquinoline-3-carbonitrile

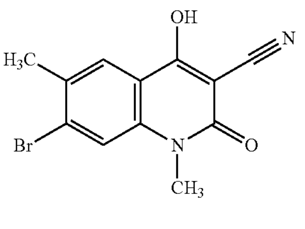 [SMILES: Cc1cc2c(O)c(C#N)c(=O)n(C)c2cc1Br]

11.4 g 7-bromo-1,6-dimethyl-2H-3,1-benzoxazine-2,4(1H)-dione (intermediate 301) was dissolved in 96 mL THF, 95 mL triethylamine and ethyl 18 mL cyanoacetate (170 mmol) were added and the mixture stirred for 5 days at 70° C. The reaction mixture was evaporated to a small volume. Water was added to the residue and the solution was acidified with 1 N hydrochloric acid to pH=1. The resulting precipitate was filtered off, washed with water and dried at 60° C. to obtain 13.6 g of the title compound.

$^1$H-NMR (400 MHz, DMSO-d6): 5 [ppm]=2.40 (s, 3H), 3.49 (s, 3H), 7.68-7.73 (m, 1H), 7.96-8.00 (m, 1H). OH-proton exchange with water LC-MS (Method 2): $R_t$=0.67 min; MS (ESIpos): m/z=295 $[M+H]^+$ Intermediate 303

7-bromo-4-chloro-1,6-dimethyl-2-oxo-1,2-dihydroquinoline-3-carbonitrile

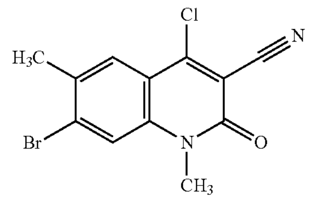 [SMILES: Cc1cc2c(Cl)c(C#N)c(=O)n(C)c2cc1Br]

13.6 g 7-bromo-4-hydroxy-1,6-dimethyl-2-oxo-1,2-dihydroquinoline-3-carbonitrile (intermediate 302) were stirred in 76 mL phosphoryl chloride 14 h at 90° C. The mixture was poured carefully in ice-water and stirred till the ice was melted. The solution was added to ice-water and basified with sodium carbonat (strong gas evolution!). The precipitate was filtered, washed with water and dried. The product was purified by column chromatography and obtained in 12.7 g of the title compound.

$^1$H-NMR (400 MHz, DMSO-d6): 5 [ppm]=2.47 (s, 3H), 3.63 (s, 3H), 7.96-7.98 (s, 1H), 7.99 (s, 1H).

EXPERIMENTAL SECTION—EXAMPLES

Example 1

4-[4-(1,3-benzoxazol-2-yl)-4-methylpiperidin-1-yl]-1-methyl-2-oxo-1,2-dihydroquinoline-3-carbonitrile

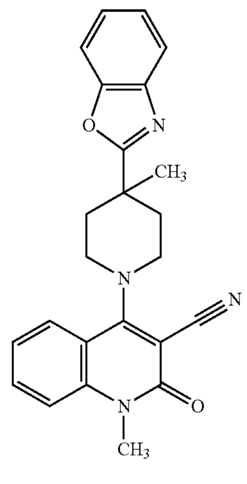 [SMILES: Cn1c(=O)c(C#N)c(N2CCC(C)(c3nc4ccccc4o3)CC2)c2ccccc21]

A solution of 116 mg 4-chloro-1-methyl-2-oxo-1,2-dihydroquinoline-3-carbonitrile (0.5 mmol, CAS 150617-68-8, synthesis described in WO2012009649, example 1—compound III), 230 mg 2-(4-methylpiperidin-4-yl)-1,3-benzoxazole (intermediate 1, 1.0 mmol) and 0.15 mL triethylamine (1 mmol) in 6 mL 2-propanol was stirred for 2 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). 100 mg of the title compound were obtained (98% purity, 46% yield).

$^1$H-NMR (400 MHz, DMSO-d6) δ[ppm]: 1.51 (s, 3H); 2.04-2.12 (m, 2H); 2.5-2.57 (m, signal below DMSO); 3.47-3.57 (m+s, 5H); 3.72-3.77 (m, 2H); 7.31-7.42, (m, 3H); 7.56 (dd, 1H); 7.70-7.80 (m, 3H); 7.90 (dd, 1H).

LC-MS (Method 2): $R_t$=1.26 min; MS (ESIpos): m/z=399.3 $[M+H]^+$

Example 2

4-[4-(1,3-benzoxazol-2-yl)piperidin-1-yl]-1-methyl-2-oxo-1,2-dihydroquinoline-3-carbonitrile

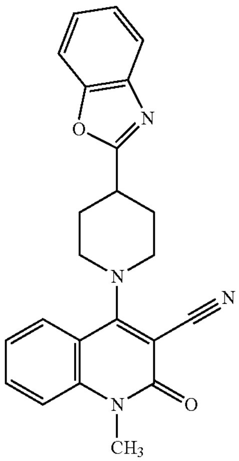 [SMILES: Cn1c(=O)c(C#N)c(N2CCC(c3nc4ccccc4o3)CC2)c2ccccc21]

A solution of 180 mg 4-chloro-1-methyl-2-oxo-1,2-dihydroquinoline-3-carbonitrile (0.8 mmol, CAS 150617-68-8), 500 mg 2-(piperidin-4-yl)-1,3-benzoxazole (2.5 mmol, CAS 51784-03-3) and 0.34 mL triethylamine (2.5 mmol) in 4.6 mL 2-propanol was stirred for 3 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). 250 mg of the title compound were obtained (95% purity, 75% yield).

$^1$H-NMR (400 MHz, DMSO-d6) δ[ppm]: 2.16 (dq, 2H); 2.28-2.37 (m, 2H); 3.48 (tt, 1H); 3.55-3.65 (s+m, 5H); 3.80-3.88 (m, 2H); 7.32-7.42 (m, 3H); 7.58 (d, 1H); 7.70-7.77 (m, 3H); 7.89 (dd, 1H).

LC-MS (Method 2): $R_t$=1.18 min; MS (ESIpos): m/z=385.6 $[M+H]^+$

Example 3

4-[4-(7-fluoro-1,3-benzoxazol-2-yl)piperidin-1-yl]-1-methyl-2-oxo-1,2-dihydroquinoline-3-carbonitrile

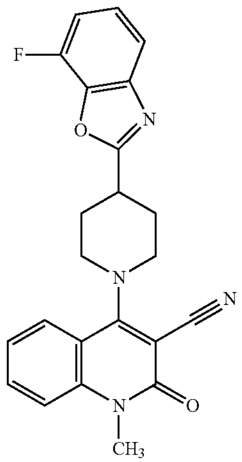 [SMILES: Cn1c(=O)c(C#N)c(N2CCC(c3nc4cccc(F)c4o3)CC2)c2ccccc21]

A solution of 70 mg 4-chloro-1-methyl-2-oxo-1,2-dihydroquinoline-3-carbonitrile (0.3 mmol, CAS 150617-68-8) 210 mg 7-fluoro-2-(piperidin-4-yl)-1,3-benzoxazole (0.95 mmol, intermediate 5) and 0.13 mL triethylamine (0.95 mmol) in 2.1 mL 2-propanol was stirred for 4 h at 90° C. After this time, water was added and the reaction was extracted with ethyl acetate. The organic phase was washed with water and brine and dried over sodium sulfate. After evaporation of the solvent, the residue was purified by RP-HPLC (column: X-Bridge C18 5 µm 100×30 mm, mobile phase: acetonitrile/water (0.2 vol. % ammonia 32%)-gradient). 9 mg of the title compound were obtained (95% purity, 6% yield).

$^1$H-NMR (400 MHz, DMSO-d6) δ[ppm]: 2.12-2.23 (m, 2H); 2.30-2.39 (m, 2H); 3.48. 3.66 (m+s, 6H); 3.80-3.89 (m, 2H); 7.30-7.42 (m, 3H); 7.57 (d, 1H); 7.60 (d, 1H); 7.71-7.77 (m, 1H); 7.89 (d, 1H).

LC-MS (Method 2): $R_t$=1.23 min; MS (ESIpos): m/z=403.6 $[M+H]^+$

Example 4

4-[4-(6-fluoro-1,3-benzoxazol-2-yl)piperidin-1-yl]-1-methyl-2-oxo-1,2-dihydroquinoline-3-carbonitrile

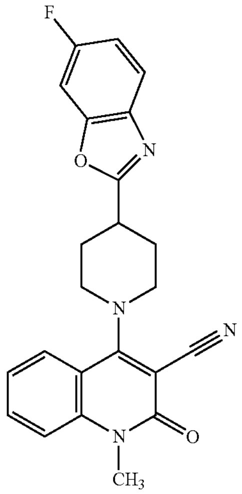 [SMILES: Cn1c(=O)c(C#N)c(N2CCC(c3nc4ccc(F)cc4o3)CC2)c2ccccc21]

A solution of 14 mg 4-chloro-1-methyl-2-oxo-1,2-dihydroquinoline-3-carbonitrile (0.06 mmol, CAS 150617-68-8), 42 mg 6-fluoro-2-(piperidin-4-yl)-1,3-benzoxazole (0.2 mmol, intermediate 2) and 0.03 mL triethylamine (0.2 mmol) in 0.35 mL 2-propanol was stirred for 4 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). 15 mg of the title compound were obtained (95% purity, 56% yield).

$^1$H-NMR (400 MHz, DMSO-d6) δ[ppm]: 2.09-2.20 (m, 2H); 2.28-2.36 (m, 2H); 3.43-3.52 (m, 1H); 3.57-3.64 (m+s, 5H); 3.80-3.88 (m, 2H); 7.25 (ddd, 1H); 7.32-7.38 (m, 1H); 7.58 (dd, 1H); 7.71-7.79 (m, 3H); 7.88 (dd, 1H).

LC-MS (Method 2): $R_t$=1.21 min; MS (ESIpos): m/z=403.5 [M+H]$^+$

Example 5

1-methyl-4-[4-(5-methyl-1,3-benzoxazol-2-yl)piperidin-1-yl]-2-oxo-1,2-dihydroquinoline-3-carbonitrile

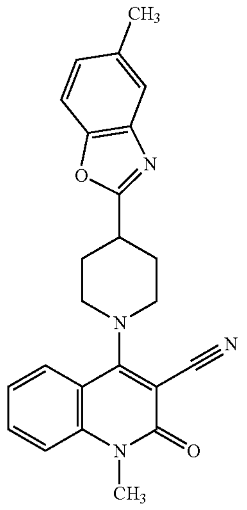 [SMILES: Cc1ccc2oc(C3CCN(c4c(C#N)c(=O)n(C)c5ccccc45)CC3)nc2c1]

A solution of 162 mg 4-chloro-1-methyl-2-oxo-1,2-dihydroquinoline-3-carbonitrile (0.74 mmol, CAS 150617-68-8), 480 mg 5-methyl-2-(piperidin-4-yl)-1,3-benzoxazole (2.2 mmol, CAS 199292-77-8) and 0.31 mL triethylamine (2.2 mmol) in 4.1 mL 2-propanol was stirred for 4 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). 220 mg of the title compound were obtained (95% purity, 71% yield).

$^1$H NMR (400 MHz, DMSO-$d_6$) δ ppm 2.09-2.22 (m, 2H) 2.27-2.33 (m, 2H) 2.42-2.45 (m, 3H): 3.40-3.50 (m, 1H) 3.53-3.69 (m, 5H) 3.78-3.89 (m, 2H) 7.16-7.23 (m, 1H) 7.30-7.40 (m, 1H) 7.49-7.64 (m, 3H) 7.70-7.79 (m, 1H) 7.85-7.94 (m, 1H).

LC-MS (Method 2): $R_t$=1.26 min; MS (ESIpos): m/z=399.7 [M+H]$^+$

Example 6

4-[4-(5-fluoro-1,3-benzoxazol-2-yl)piperidin-1-yl]-1-methyl-2-oxo-1,2-dihydroquinoline-3-carbonitrile

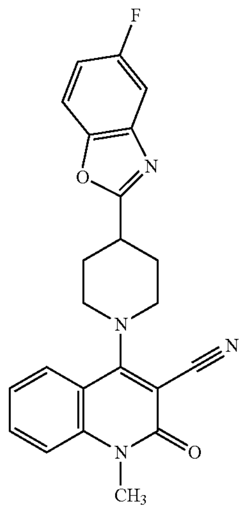 [SMILES: Cn1c(=O)c(C#N)c(N2CCC(c3nc4cc(F)ccc4o3)CC2)c2ccccc21]

A solution of 100 mg 4-chloro-1-methyl-2-oxo-1,2-dihydroquinoline-3-carbonitrile (0.45 mmol, CAS 150617-68-8), 302 mg 5-fluoro-2-(piperidin-4-yl)-1,3-benzoxazole (1.4 mmol, intermediate 3) and 0.19 mL triethylamine (1.4 mmol) in 3 mL 2-propanol was stirred for 4 h at 90° C. After this time, water was added and the reaction was extracted with ethyl acetate. The organic phase was washed with water and brine and dried over sodium sulfate. Upon evaporation of the solvent, a residue precipitated from the solution which was filtered off and dried in an air stream. 117 mg of the title compound were obtained (95% purity, 60% yield).

$^1$H-NMR (400 MHz, DMSO-d6) δ[ppm]: 2.09-2.21 (m, 2H); 2.27-2.36 (m, 2H); 3.44-3.53 (m, 1H); 3.55-3.65 (m+s, 5H); 3.79-3.88 (m, 2H); 7.22-7.29 (m, 1H); 7.32-7.38 (m, 1H); 7.58 (d, 1H); 7.63 (dd, 1H); 7.71-7.79 (m, 2H); 7.88 (dd, 1H).

LC-MS (Method 2): $R_t$=1.21 min; MS (ESIpos): m/z=403.7 [M+H]$^+$

Example 7

1-methyl-4-[4-(6-methyl-1,3-benzoxazol-2-yl)piperidin-1-yl]-2-oxo-1,2-dihydroquinoline-3-carbonitrile

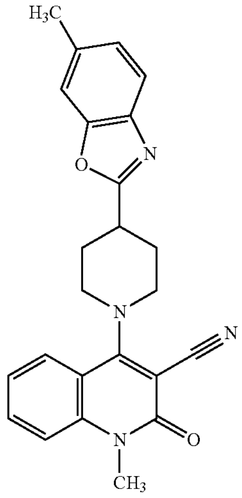 [SMILES: Cc1ccc2nc(C3CCN(c4c(C#N)c(=O)n(C)c5ccccc45)CC3)oc2c1]

A solution of 100 mg 4-chloro-1-methyl-2-oxo-1,2-dihydroquinoline-3-carbonitrile (0.43 mmol, CAS 150617-68-8), 99 mg 6-methyl-2-(piperidin-4-yl)-1,3-benzoxazole (0.43 mmol, CAS 951921-15-6) and 0.12 mL triethylamine (0.87 mmol) in 3 mL 2-propanol was stirred for 2 h at 90° C. After this time, water was added and the reaction was extracted with ethyl acetate. The precipitate that was generated by this procedure was collected by filtration and dried in vacuum. 100 mg of the title compound were obtained (93% purity, 53% yield).

$^1$H-NMR (400 MHz, DMSO-d6) δ[ppm]: 2.13 (dq, 2H); 2.26-2.35 (m, 2H); 2.44 (s, 3H); 3.44 (tt, 1H); 3.54-3.65 (s+m, 5H); 3.78-3.88 (m, 2H); 7.16-7.20 (m, 1H); 7.32-7.38 (m, 1H); 7.51-7.54 (m, 1H); 7.55-7.61 (m, 2H); 7.71-7.77 (m, 1H); 7.88 (dd, 1H).

LC-MS (Method 2): $R_t$=1.27 min; MS (ESIpos): m/z=399.5 $[M+H]^+$

Example 8

1-methyl-2-oxo-4-{4-[5-(propan-2-yl)-1,3-benzoxazol-2-yl]piperidin-1-yl}-1,2-dihydroquinoline-3-carbonitrile

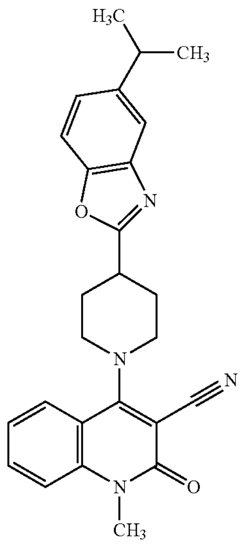 [SMILES: CC(C)c1ccc2oc(C3CCN(c4c(C#N)c(=O)n(C)c5ccccc45)CC3)nc2c1]

A solution of 90 mg 4-chloro-1-methyl-2-oxo-1,2-dihydroquinoline-3-carbonitrile (0.39 mmol, CAS 150617-68-8), 100 mg 2-(piperidin-4-yl)-5-(propan-2-yl)-1,3-benzoxazole (0.39 mmol, intermediate 6) and 0.11 mL triethylamine (0.78 mmol) in 5 mL 2-propanol was stirred for 2 h at 90° C. After this time, water was added and the reaction was extracted with ethyl acetate. The organic phase was washed with water and brine and dried over sodium sulfate. After evaporation of the solvent, the residue was purified by RP-HPLC (column: X-Bridge C18 5 μm 100×30 mm, mobile phase: acetonitrile/water (0.2 vol. % ammonia 32%)-gradient). 105 mg of the title compound were obtained (98% purity, 62% yield).

$^1$H-NMR (400 MHz, DMSO-d6) δ[ppm]: 1.25 (d, 6H); 2.14 (dq, 2H); 2.26-2.35 (m, 2H); 3.03 (spt, 1H); 3.55-3.65 (s+m, 5H); 3.79-3.88 (m, 2H); 7.26 (dd, 1H); 7.36 (dt, 1H); 7.56-7.63 (m, 3H); 7.74 (dt, 1H); 7.89 (dd, 1H).

LC-MS (Method 2): $R_t$=1.41 min; MS (ESIpos): m/z=427.6 $[M+H]^+$

Example 9

4-[4-(6-chloro-1,3-benzoxazol-2-yl)piperidin-1-yl]-1-methyl-2-oxo-1,2-dihydroquinoline-3-carbonitrile

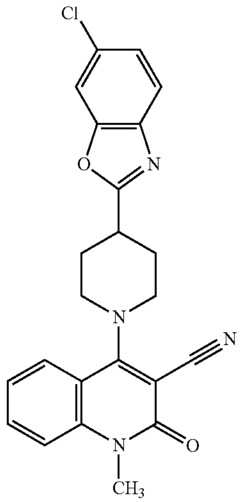 [SMILES: Cn1c(=O)c(C#N)c(N2CCC(c3nc4ccc(Cl)cc4o3)CC2)c2ccccc21]

A solution of 111 mg 4-chloro-1-methyl-2-oxo-1,2-dihydroquinoline-3-carbonitrile (0.5 mmol, CAS 150617-68-8), 120 mg 6-chloro-2-(piperidin-4-yl)-1,3-benzoxazole (0.5 mmol, intermediate 7) and 0.14 mL triethylamine (1.0 mmol) in 8 mL 2-propanol was stirred for 2 h at 90° C. After this time, water was added and the reaction was extracted with ethyl acetate. The precipitate that was generated by this procedure was collected by filtration and dried in vacuum. 165 mg of the title compound were obtained (95% purity, 74% yield).

$^1$H NMR (400 MHz, DMSO-$d_6$) δ [ppm]: 2.15 (m, 2H), 2.31 (m, 2H), 3.49 (m, 1H), 3.60 (m, 5H), 3.84 (m, 2H), 7.35 (m, 1H), 7.43 (m, 1H), 7.58 (m, 1H), 7.75 (m, 2H), 7.88 (dd, 1H), 7.95 (d, 1H).

LC-MS (Method 2): $R_t$=1.31 min; MS (ESIpos): m/z=419.3 $[M+H]^+$

Example 10

4-[4-(5-bromo-1,3-benzoxazol-2-yl)piperidin-1-yl]-1-methyl-2-oxo-1,2-dihydroquinoline-3-carbonitrile

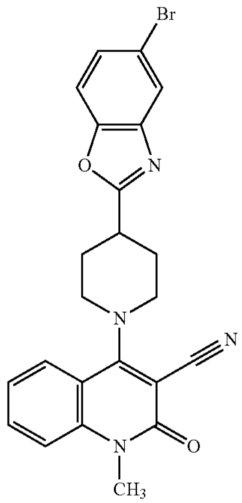 [SMILES: Cn1c(=O)c(C#N)c(N2CCC(c3nc4cc(Br)ccc4o3)CC2)c2ccccc21]

A solution of 78 mg 4-chloro-1-methyl-2-oxo-1,2-dihydroquinoline-3-carbonitrile (0.36 mmol, CAS 150617-68-8), 100 mg 5-bromo-2-(piperidin-4-yl)-1,3-benzoxazole (0.36 mmol, intermediate 8) and 0.2 mL triethylamine (1.4 mmol) in 7 mL 2-propanol was stirred for 3.5 h at 90° C. After this time, water was added and the reaction was extracted with ethyl acetate. The precipitate that was generated by this procedure was collected by filtration and dried in vacuum. 160 mg of the title compound were obtained (85% purity, 83% yield).

$^1$H-NMR (400 MHz, DMSO-d6) δ[ppm]: 2.08-2.21 (m, 2H); 2.26-2.37 (m, 2H); 3.49 (tt, 1H); 3.55-3.66 (s+m, 5H); 3.79-3.88 (m, 2H); 7.32-7.38 (m, 1H); 7.54-7.60 (m, 2H); 7.71-7.75 (m, 2H); 7.88 (dd, 1H); 7.99 (d, 1H).

LC-MS (Method 2): $R_t$=1.33 min; MS (ESIpos): m/z=464.4 [M+H]$^+$

Example 11

4-[4-(5-chloro-1,3-benzoxazol-2-yl)piperidin-1-yl]-1-methyl-2-oxo-1,2-dihydroquinoline-3-carbonitrile

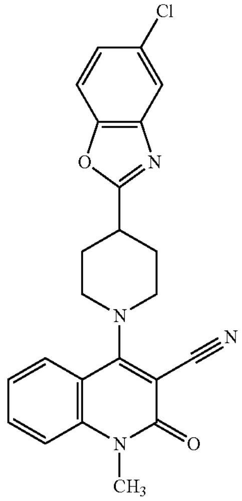 [SMILES: Cn1c(=O)c(C#N)c(N2CCC(c3nc4cc(Cl)ccc4o3)CC2)c2ccccc21]

A suspension of 92 mg 4-chloro-1-methyl-2-oxo-1,2-dihydroquinoline-3-carbonitrile (0.42 mmol, CAS 150617-68-8), 100 mg 5-chloro-2-(piperidin-4-yl)-1,3-benzoxazole (0.42 mmol, intermediate 9) and 0.12 mL triethylamine (0.85 mmol) in 6 mL 2-propanol was stirred for 2 h at 90° C. Some ethyl acetate was added and the reaction was further stirred for 10 min. at 90° C. After this time, water was added and the reaction was extracted with ethyl acetate. The precipitate that was generated by this procedure was collected by filtration and dried in vacuum. 115 mg of the title compound were obtained (90% purity, 58% yield).

$^1$H-NMR (400 MHz, DMSO-d6) δ[ppm]: 2.09-2.21 (m, 2H); 2.28-2.36 (m, 2H); 3.49 (tt, 1H); 3.55-5.66 (s+m, 5H); 3.80-3.88 (m, 2H); 7.32-7.38 (m, 1H); 7.44 (dd, 1H); 7.58 (dd, 1H); 7.71-7.80 (m, 2H); 7.86-7.91 (m, 2H).

LC-MS (Method 2): $R_t$=1.30 min; MS (ESIpos): m/z=419.3 [M+H]$^+$

Example 12

4-[4-(1,3-benzothiazol-2-yl)piperidin-1-yl]-1-methyl-2-oxo-1,2-dihydroquinoline-3-carbonitrile

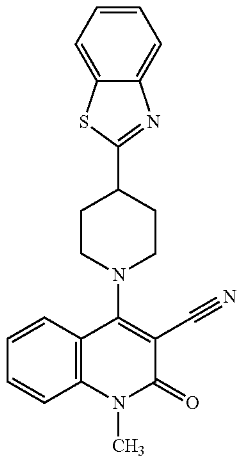 [SMILES: Cn1c(=O)c(C#N)c(N2CCC(c3nc4ccccc4s3)CC2)c2ccccc21]

A suspension of 2 g 4-chloro-1-methyl-2-oxo-1,2-dihydroquinoline-3-carbonitrile (9.1 mmol, CAS 150617-68-8), 3 g 2-(piperidin-4-yl)-1,3-benzothiazole (13.7 mmol, CAS 51784-73-7) and 3.8 mL triethylamine (27.4 mmol) in 47 mL 2-propanol was stirred for 6 h at 90° C. After this time, water and ethyl acetate were added and the reaction was stirred. The precipitate that was generated by this procedure was collected by filtration and dried in vacuum. 2.6 g of the title compound were obtained (95% purity, 67% yield).

$^1$H-NMR (400 MHz, DMSO-d6) δ[ppm]: 2.15 (dq, 2H); 2.28-2.38 (m, 2H); 3.52-3.66 (m, 6H); 3.82-3.92 (m, 2H); 7.33-7.39 (m, 1H); 7.40-7.46 (m, 1H); 7.49-7.55 (m, 1H); 7.56-7.60 (m, 1H); 7.71-7.78 (m, 1H); 7.90 (dd, 1H); 7.97-8.01 (m, 1H); 8.08-8.12 (m, 1H).

LC-MS (Method 2): $R_t$=1.25 min; MS (ESIpos): m/z=401.5 [M+H]$^+$

Example 13

4-[4-(5-fluoro-1,3-benzothiazol-2-yl)piperidin-1-yl]-1-methyl-2-oxo-1,2-dihydroquinoline-3-carbonitrile

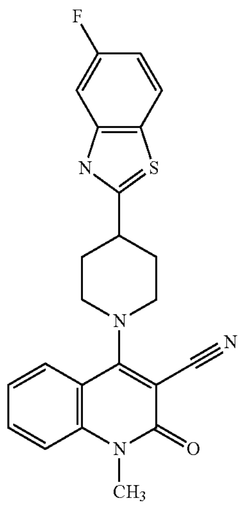

To 100 mg 1-(3-cyano-1-methyl-2-oxo-1,2-dihydroquinolin-4-yl)piperidine-4-carboxylic acid (321 μmol, intermediate 16) and 46 mg 2-amino-4-fluorobenzene-1-thiol (321 μmol, CAS 131105-89-0) were added 84 μL N,N-diisopropylethylamine (480 μmol) and 190 μL T3P (50% purity in ethyl acetate, 320 μmol) and the mixture was stirred for 20 min. at 100° C. in the microwave. The mixture was cooled down to rt and was concentrated under reduced pressure. The residue was purified by flash chromatography (basic silica, dichloromethane/ethanol gradient 0-9%). The impure product was purified by preparative TLC (dichloromethane/ethanol; 95:5) to give 61.5 mg of the title compound (43% yield, 95% purity).

$^1$H NMR (400 MHz, DMSO-$d_6$) δ ppm 2.07-2.20 (m, 2H) 2.26-2.36 (m, 2H) 3.53-3.66 (m, 6H): 3.82-3.93 (m, 2H) 7.31-7.40 (m, 2H) 7.54-7.61 (m, 1H) 7.69-7.78 (m, 1H) 7.81-7.92 (m, 2H) 8.10-8.20 (m, 1H).

LC-MS (Method 3): $R_t$=1.24 min; MS (ESIpos): m/z=419.1 [M+H]$^+$

Example 14

4-[4-(6-bromo-1,3-benzothiazol-2-yl)piperidin-1-yl]-1-methyl-2-oxo-1,2-dihydroquinoline-3-carbonitrile

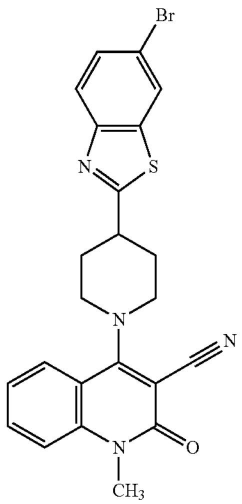 [SMILES: Cn1c(=O)c(C#N)c(N2CCC(c3nc4ccc(Br)cc4s3)CC2)c2ccccc21]

To 100 mg 1-(3-cyano-1-methyl-2-oxo-1,2-dihydroquinolin-4-yl)piperidine-4-carboxylic acid (321 μmol, intermediate 16) and 92 mg 2-amino-5-bromobenzene-1-thiol (450 μmol, CAS 23451-95-8) were added 140 μL N,N-diisopropylethylamine (800 μmol) and 380 μL T3P (50% purity in ethyl acetate, 640 μmol) and the mixture was stirred for 20 min. at 100° C. in the microwave. The mixture was cooled down to rt, water was added and the mixture was extracted with dichloromethane. The combined organic phases were washed with brine, filtered (using a waterresistant filter) and concentrated under reduced pressure. The residue was purified by flash chromatography (silica, hexane/ethyl acetate gradient 0-100%). The impure product was stirred in ethanol, the precipitate was collected by filtration and dried in vacuum. 17 mg of the title compound were obtained (10.5% yield, 95% purity).

$^1$H NMR (400 MHz, DMSO-$d_6$) δ [ppm]: 2.14 (m, 2H), 2.32 (m, 2H), 3.61 (m, 6H), 3.86 (m, 2H), 7.36 (m, 1H), 7.57 (m, 1H), 7.66 (m, 1H), 7.74 (m, 1H), 7.90 (m, 2H), 8.42 (m, 1H).

LC-MS (Method 1): $R_t$=1.42 min; MS (ESIpos): m/z=479.3 [M+H]$^+$

Example 15

1-methyl-4-[4-(7-methyl-1,3-benzoxazol-2-yl)piperi-din--yl]-2-oxo-1,2-dihydroquinoline-3-carbonitrile

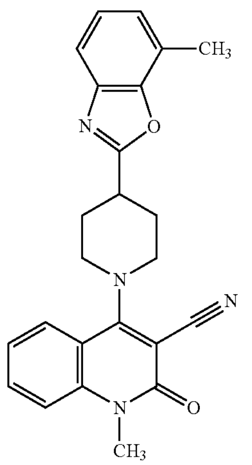 [SMILES: Cc1cccc2nc(C3CCN(c4c(C#N)c(=O)n(C)c5ccccc45)CC3)oc12]

A solution of 100 mg 1-(3-cyano-1-methyl-2-oxo-1,2-dihydroquinolin-4-yl)piperidine-4-carboxylic acid (321 μmol, intermediate 16), 51.3 mg 2-amino-6-methylphenole (321 μmol, CAS 17672-22-9), 190 μL T3P (50% purity in ethyl acetate, 320 μmol) and 150 μL N,N-diisopropylethyl-amine (840 μmol) in 1.0 mL ethyl acetate was stirred for 72 h at 100° C. The mixture was cooled down to rt and was concentrated under reduced pressure. The residue was purified by flash chromatography (basic silica, dichloromethane/ethanol gradient 0-10%). The impure product was purified by preparative TLC (dichloromethane/ethanol; 95:5) to give 44.2 mg of the title compound (33% yield, 95% purity).

$^1$H NMR (400 MHz, DMSO-$d_6$) δ ppm 2.08-2.22 (m, 2H) 2.27-2.38 (m, 2H) 3.41-3.54 (m, 1H): 3.56-3.67 (m, 5H) 3.85 (br d, 2H) 7.16-7.30 (m, 2H) 7.32-7.40 (m, 1H) 7.50-7.60 (m, 2H) 7.69-7.77 (m, 1H) 7.86-7.92 (m, 1H).

LC-MS (Method 3): Rt=1.22 min; MS (ESIpos): m/z=399.2 [M+H]+

Example 16

4-[4-(1,3-benzothiazol-2-yl)-4-fluoropiperidin-1-yl]-1-methyl-2-oxo-1,2-dihydroquinoline-3-carbonitrile

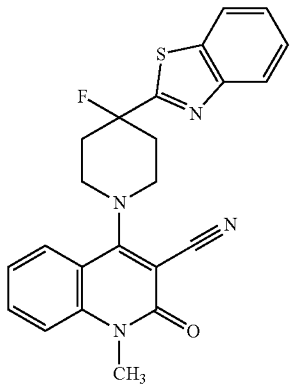 [SMILES: Cn1c(=O)c(C#N)c(N2CCC(F)(c3nc4ccccc4s3)CC2)c2ccccc21]

A solution of 150 mg 1-(3-cyano-1-methyl-2-oxo-1,2-dihydroquinolin-4-yl)-4-fluoropiperidine-4-carboxylic acid (455 μmol, intermediate 18), 58 μL 2-aminobenzene-1-thiol (550 μmol, CAS 137-07-5), 410 μL T3P (50% purity in ethyl acetate, 680 μmol) and 240 μL N,N-diisopropylethylamine (1.4 mmol) in 1.5 mL N,N-dimethylacetamide was stirred for 2 h at 100° C. in the microwave. The mixture was cooled down to rt and was concentrated under reduced pressure. The residue was purified by RP-HPLC (column: Chromatorex 125×30 mm, 10 μm mobile phase: water (0.1 vol. % formic acid)/acetonitrile 40-80%) to give 82.5 mg of the title compound (41% yield, 95% purity).

$^1$H NMR (400 MHz, DMSO-$d_6$) δ [ppm]: 2.42 (m, 2H), 2.67 (m, 2H), 3.60 (s, 3H), 3.81 (m, 4H), 7.38 (m, 1H), 7.57 (m, 3H), 7.76 (m, 1H), 7.97 (m, 1H), 8.10 (m, 1H), 8.22 (m, 1H).

LC-MS (Method 1): $R_t$=1.32 min; MS (ESIpos): m/z=419 $[M+H]^+$

Example 17

1-methyl-4-[4-(4-methyl-1,3-benzoxazol-2-yl)piperi-din-1-yl]-2-oxo-1,2-dihydroquinoline-3-carbonitrile

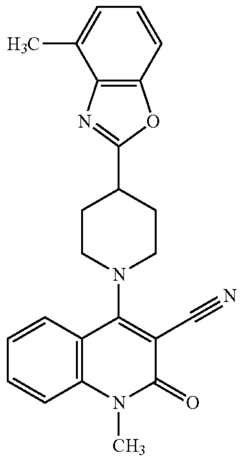 [SMILES: Cc1cccc2oc(C3CCN(c4c(C#N)c(=O)n(C)c5ccccc45)CC3)nc12]

A solution of 100 mg 1-(3-cyano-1-methyl-2-oxo-1,2-dihydroquinolin-4-yl)piperidine-4-carboxylic acid (321 μmol, intermediate 16), 39.6 mg 2-amino-3-methylphenol (321 μmol, CAS 2835-97-4), 191 μL T3P (50% purity in ethyl acetate, 320 μmol) and 84 μL N,N-diisopropylethyl-amine (480 μmol) in 1 mL ethyl acetate was stirred for 72 h at 100° C. The mixture was cooled down to rt and was concentrated under reduced pressure. The residue was purified by flash chromatography (basic silica, dichloromethane/ethanol gradient 0-10%). The impure product was purified by preparative TLC (dichloromethane/ethanol; 95:5) to give 45.7 mg of the title compound (34% yield, 95% purity).

$^1$H NMR (400 MHz, DMSO-$d_6$) δ ppm 2.07-2.21 (m, 2H) 2.27-2.36 (m, 2H) 2.53-2.55 (m, 3H): 3.40-3.51 (m, 1H) 3.55-3.67 (m, 5H) 3.81-3.90 (m, 2H) 7.15-7.20 (m, 1H) 7.23-7.30 (m, 1H) 7.32-7.41 (m, 1H) 7.48-7.55 (m, 1H) 7.56-7.61 (m, 1H) 7.70-7.81 (m, 1H) 7.86-7.95 (m, 1H).

LC-MS (Method 3): Rt=1.25 min; MS (ESIpos): m/z=399.2 [M+H]+

Example 18

4-[4-(5-chloro-1,3-benzothiazol-2-yl)piperidin-1-yl]-1-methyl-2-oxo-1,2-dihydroquinoline-3-carbonitrile

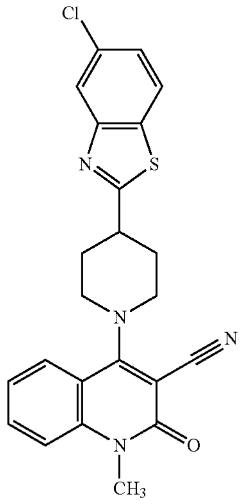 [SMILES: Cn1c(=O)c(C#N)c(N2CCC(c3nc4cc(Cl)ccc4s3)CC2)c2ccccc21]

To 100 mg 1-(3-cyano-1-methyl-2-oxo-1,2-dihydroquinolin-4-yl)piperidine-4-carboxylic acid (321 μmol, intermediate 16) and 51.3 mg 2-amino-4-chlorobenzene-1-thiol (321 μmol, CAS 1004-00-8) were added 140 μL N,N-diisopropylethylamine (800 μmol) and 380 μL T3P (50% purity in ethyl acetate, 640 μmol) and the mixture was stirred for 10 min. at 100° C. in the microwave. The mixture was cooled down to rt, water was added and the mixture was extracted with dichloromethane. The combined organic phases were washed with brine, filtered (using a waterresistant filter) and concentrated under reduced pressure. The residue was purified by flash chromatography (silica, dichloromethane/ethanol gradient 0-5%). The impure product was stirred in ethanol, the precipitate was collected by filtration and dried in vacuum. The impure product was stirred in DMSO, the precipitate was collected by filtration and dried in vacuum. 39.0 mg of the title compound were obtained (27% yield, 95% purity).

$^{1}$H NMR (400 MHz, DMSO-$d_6$) δ [ppm]: 2.14 (m, 2H), 2.33 (m, 2H), 3.60 (m, 6H), 3.89 (m, 2H), 7.36 (m, 1H), 7.53 (m, 2H), 7.74 (m, 1H), 7.91 (m, 1H), 8.14 (m, 2H).

LC-MS (Method 1): $R_t$=1.39 min; MS (ESIpos): m/z=435 $[M+H]^+$

Example 19

4-[4-(5-chloro[1,3]thiazolo[5,4-b]pyridin-2-yl)piperidin-1-yl]-1-methyl-2-oxo-1,2-dihydroquinoline-3-carbonitrile

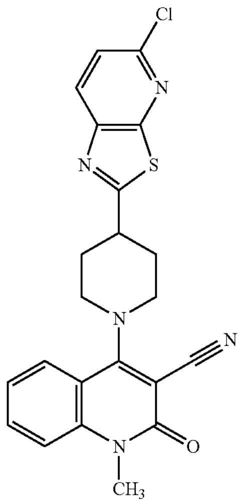 [SMILES: Cn1c(=O)c(C#N)c(N2CCC(c3nc4ccc(Cl)nc4s3)CC2)c2ccccc21]

To 100 mg 1-(3-cyano-1-methyl-2-oxo-1,2-dihydroquinolin-4-yl)piperidine-4-carboxylic acid (321 μmol, intermediate 16) and 51.6 mg 3-amino-6-chloropyridine-2-thiol (321 μmol, CAS 27467-92-1) were added 140 μL N,N-diisopropylethylamine (800 μmol) and 380 μL T3P (50% purity in ethyl acetate, 640 μmol) and the mixture was stirred for 10 min. at 100° C. in the microwave. The mixture was cooled down to rt and was concentrated under reduced pressure. The residue was purified by RP-HPLC (column: X-Bridge C18 5μ 150×50 mm; mobile phase: water (0.1 vol. % formic acid)/acetonitrile 50-95%) to give 10.0 mg of the title compound (6% yield, 85% purity).

$^{1}$H NMR (400 MHz, DMSO-$d_6$) δ ppm 2.08-2.22 (m, 2H) 2.29-2.34 (m, 2H) 3.55-3.64 (m, 6H): 3.81-3.94 (m, 2H) 7.34-7.38 (m, 1H) 7.56-7.61 (m, 1H) 7.67-7.71 (m, 1H) 7.72-7.76 (m, 1H) 7.87-7.92 (m, 1H) 8.42-8.50 (m, 1H).

LC-MS (Method 3): Rt=1.22 min; MS (ESIpos): m/z=436.0 [M+H]+

Example 20

1-methyl-4-{4-methyl-4-[6-(trifluoromethoxy)-1,3-benzoxazol-2-yl]piperidin-1-yl}-2-oxo-1,2-dihydroquinoline-3-carbonitrile

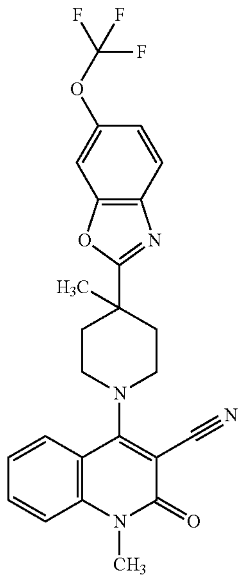 [SMILES: Cn1c(=O)c(C#N)c(N2CCC(C)(c3nc4ccc(OC(F)(F)F)cc4o3)CC2)c2ccccc21]

A solution of 100 mg 4-chloro-1-methyl-2-oxo-1,2-dihydroquinoline-3-carbonitrile (0.46 mmol, CAS 150617-68-8), 137 mg 2-(4-methylpiperidin-4-yl)-6-(trifluoromethoxy)-1,3-benzoxazole (0.46 mmol, intermediate 10) and 0.25 mL triethylamine (1.8 mmol) in 6 mL 2-propanol was stirred for 3 h at 90° C. After this time, water was added and the reaction was extracted with ethyl acetate. The organic phase was washed with water and brine and dried over sodium sulfate. After evaporation of the solvent, the residue was purified by RP-HPLC (column: X-Bridge C18 5 μm 100×30 mm, mobile phase: acetonitrile/water (0.2 vol. % ammonia 32%)-gradient). 112 mg of the title compound were obtained (54% yield, 99% purity).

$^1$H-NMR (400 MHz, DMSO-d6) δ[ppm]: 1.52 (s, 3H); 2.03-2.13 (m, 2H); 2H below DMSO signal; 3.49-3.59 (s+m, 5H); 3.74 (td, 2H); 7.30-7.36 (m, 1H); 7.40-7.45 (m, 1H); 7.56 (dd, 1H); 7.70-7.77 (m, 1H); 7.87-7.92 (m, 2H); 7.95-7.98 (m, 1H).

LC-MS (Method 2): Rt=1.40 min; MS (ESIpos): m/z=483.5 [M+H]+

Example 21

1-methyl-4-{4-methyl-4-[5-(propan-2-yl)-1,3-benzoxazol-2-yl]piperidin-1-yl}-2-oxo-1,2-dihydroquinoline-3-carbonitrile

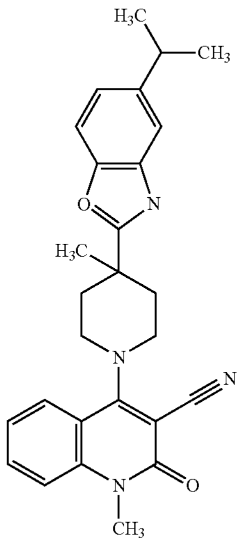

A solution of 173 mg 4-chloro-1-methyl-2-oxo-1,2-dihydroquinoline-3-carbonitrile (0.75 mmol, CAS 150617-68-8), 204 mg 2-(4-methylpiperidin-4-yl)-5-(propan-2-yl)-1,3-benzoxazole (0.75 mmol, intermediate 11) and 0.21 mL triethylamine (1.5 mmol) in 4.9 mL 2-propanol was stirred for 2 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). The impure product was purified by RP-HPLC (column: X-Bridge C18 5 μm 100×30 mm, mobile phase: acetonitrile/water (0.2 vol. % ammonia 32%)-gradient) to give 135 mg of the title compound (40% yield, 99% purity).

$^1$H-NMR (400 MHz, DMSO-d6) δ[ppm]: 1.25 (d, 6H); 1.49 (s, 3H); 2.01-2.12 (m, 2H); 2H below DMSO; 3.03 (spt, 1H); 3.45-3.59 (m, s+m, 5H); 3.69-3.78 (m, 2H); 7.28 (dd, 1H); 7.30-7.36 (m, 1H); 7.56 (d, 1H); 7.60-7.65 (m, 2H); 7.70-7.77 (m, 1H); 7.89 (dd, 1H).

LC-MS (Method 2): Rt=1.46 min; MS (ESIpos): m/z=441.6 [M+H]+

Example 22

4-[4-(5,6-difluoro-1,3-benzoxazol-2-yl)piperidin-1-yl]-1-methyl-2-oxo-1,2-dihydroquinoline-3-carbonitrile

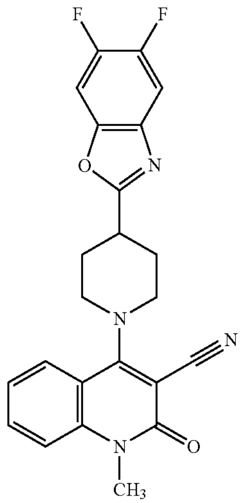 [SMILES: Cn1c(=O)c(C#N)c(N2CCC(c3nc4cc(F)c(F)cc4o3)CC2)c2ccccc21]

A suspension of 100 mg 4-chloro-1-methyl-2-oxo-1,2-dihydroquinoline-3-carbonitrile (0.46 mmol, CAS 150617-68-8), 109 mg 5,6-difluoro-2-(piperidin-4-yl)-1,3-benzoxazole (0.46 mmol, intermediate 12) and 0.25 mL triethylamine (1.8 mmol) in 6 mL 2-propanol was stirred for 3.5 h at 90° C. After this time, water and ethyl acetate w ere added and the reaction was stirred. The precipitate that was generated by this procedure was collected by filtration and dried in vacuum. 180 mg of the title compound were obtained (84% yield, 90% purity).

$^1$H-NMR (400 MHz, DMSO-d6) δ[ppm]: 2.07-2.20 (m, 2H); 2.27-2.36 (m, 2H); 3.49 (tt, 1H); 3.55-3.66 (s+m, 5H); 3.79-3.88 (m, 2H); 7.32-7.38 (m, 1H); 7.58 (d, 1H); 7.71-7.77 (m, 1H); 7.88 (dd, 1H); 7.93 (dd, 1H); 8.05 (dd, 1H).

LC-MS (Method 2): Rt=1.25 min; MS (ESIpos): m/z=421.5 [M+H]+

Example 23

1-methyl-2-oxo-4-{4-[5-(trifluoromethyl)-1,3-benzothiazol-2-yl]piperidin-1-yl}-1,2-dihydroquinoline-3-carbonitrile

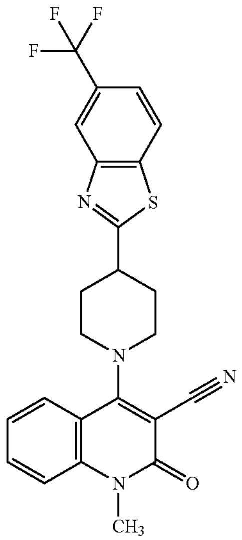 [SMILES: Cn1c(=O)c(C#N)c(N2CCC(c3nc4cc(C(F)(F)F)ccc4s3)CC2)c2ccccc21]

To 100 mg 1-(3-cyano-1-methyl-2-oxo-1,2-dihydroquinolin-4-yl)piperidine-4-carboxylic acid (321 μmol, intermediate 16) and 73.8 mg 2-amino-4-(trifluoromethyl)benzene-1-thiol hydrogen chloride salt (1:1) (321 μmol, CAS 4274-38-8) were added 140 μL N,N-diisopropylethylamine (800 μmol) and 380 μL T3P (50% purity in ethyl acetate, 640 μmol) and the mixture was stirred for 10 min. at 100° C. in the microwave. The mixture was cooled down to rt, water was added and the mixture was extracted with dichloromethane. The combined organic phases were washed with brine, filtered (using a waterresistant filter) and concentrated under reduced pressure. The residue was purified by flash chromatography (silica, dichloromethane 100%). The impure product was stirred in ethanol, the precipitate was collected by filtration and dried in vacuum. 56.0 mg of the title compound were obtained (35% yield, 95% purity).

$^1$H NMR (400 MHz, DMSO-$d_6$) δ ppm 2.09-2.26 (m, 2H) 2.30-2.39 (m, 2H) 3.54-3.70 (m, 6H): 3.83-3.94 (m, 2H) 7.30-7.41 (m, 1H) 7.53-7.63 (m, 1H) 7.71-7.80 (m, 2H) 7.86-7.93 (m, 1H) 8.34-8.42 (m, 2H).

LC-MS (Method 3): Rt=1.36 min; MS (ESIpos): m/z=469.1 [M+H]+

Example 24

4-[4-(5-tert-butyl-1,3-benzoxazol-2-yl)-4-methylpiperidin-1-yl]-1-methyl-2-oxo-1,2-dihydroquinoline-3-carbonitrile

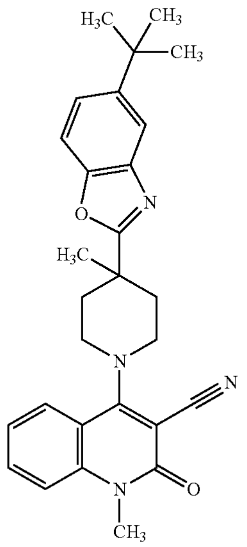 [SMILES: Cn1c(=O)c(C#N)c(N2CCC(C)(c3nc4cc(C(C)(C)C)ccc4o3)CC2)c2ccccc21]

A solution of 50 mg 4-chloro-1-methyl-2-oxo-1,2-dihydroquinoline-3-carbonitrile (0.21 mmol, CAS 150617-68-8), 93 mg 5-tert-butyl-2-(4-methylpiperidin-4-yl)-1,3-benzoxazole (0.32 mmol, intermediate 13) and 0.06 mL triethylamine (0.43 mmol) in 1.4 mL 2-propanol was stirred for 7 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). 24 mg of the title compound were obtained (23% yield, 95% purity).

$^1$H-NMR (400 MHz, DMSO-d6) δ[ppm]: 1.35 (s, 9H); 1.49 (s, 3H); 2.01-2.13 (m, 2H); 2H below DMSO; 3.45-3.59 (s+m, 5H); 3.70-3.80 (m, 2H); 7.30-7.36 (m, 1H); 7.45 (dd, 1H); 7.56 (dd, 1H); 7.63 (d, 1H); 7.70-7.77 (m, 2H); 7.89 (dd, 1H).

LC-MS (Method 2): Rt=1.52 min; MS (ESIpos): m/z=455.8 [M+H]+

Example 25

4-{4-[5-(methanesulfonyl)-1,3-benzoxazol-2-yl]-4-methylpiperidin-1-yl}-1-methyl-2-oxo-1,2-dihydroquinoline-3-carbonitrile

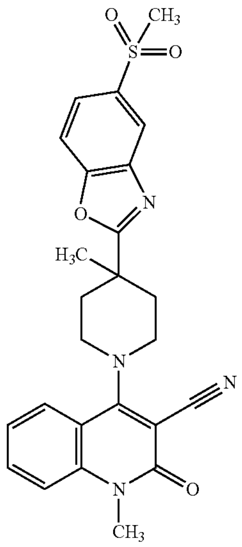 [SMILES: Cn1c(=O)c(C#N)c(N2CCC(C)(c3nc4cc(S(C)(=O)=O)ccc4o3)CC2)c2ccccc21]

A solution of 50 mg 4-chloro-1-methyl-2-oxo-1,2-dihydroquinoline-3-carbonitrile (0.21 mmol, CAS 150617-68-8), 100 mg 5-(methanesulfonyl)-2-(4-methylpiperidin-4-yl)-1,3-benzoxazole (0.32 mmol, intermediate 14) and 0.06 mL triethylamine (0.43 mmol) in 1.4 mL 2-propanol was stirred for 7 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). 78 mg of the title compound were obtained (72% yield, 95% purity).

$^1$H-NMR (400 MHz, DMSO-d6) δ[ppm]: 1.54 (s, 3H); 2.05-2.16 (m, 2H); 2H partially below DMSO; 3.29 (s, 3H); 3.48-3.59 (s+m, 5H); 3.71-3.80 (m, 2H); 7.31-7.37 (m, 1H); 7.56 (d, 1H); 7.71-7.77 (m, 1H); 7.89 (dd, 1H); 7.98 (dd, 1H); 8.04 (dd, 1H); 8.34 (d, 1H).

LC-MS (Method 2): Rt=1.08 min; MS (ESIpos): m/z=477.8 [M+H]+

Example 26

4-[4-(4-fluoro-1,3-benzoxazol-2-yl)piperidin-1-yl]-1-methyl-2-oxo-1,2-dihydroquinoline-3-carbonitrile

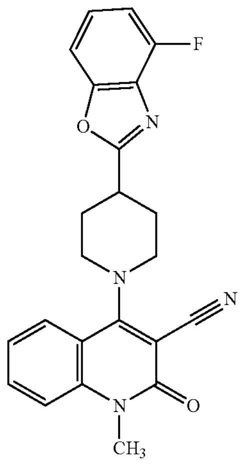 [SMILES: Cn1c(=O)c(C#N)c(N2CCC(c3nc4c(F)cccc4o3)CC2)c2ccccc21]

A solution of 100 mg 4-chloro-1-methyl-2-oxo-1,2-dihydroquinoline-3-carbonitrile (0.46 mmol, CAS 150617-68-8), 302 mg 4-fluoro-2-(piperidin-4-yl)-1,3-benzoxazole (1.4 mmol, intermediate 4) and 0.19 mL triethylamine (1.4 mmol) in 3 mL 2-propanol was stirred for 6 h at 90° C. After this time, water was added and the reaction was extracted with ethyl acetate. The organic phase was washed with water and brine and dried over sodium sulfate. Upon evaporation of the solvent, a residue precipitated from the solution which was filtered off and dried in an air stream. 60 mg of the title compound were obtained (31% yield, 95% purity).

$^1$H-NMR (400 MHz, DMSO-d6) δ[ppm]: 2.11-2.23 (m, 2H); 2.30-2.36 (m, 2H); 3.46-3.55 (m, 1H); 3.55-3.66 (m+s, 5H); 3.80-3.88 (m, 2H); 7.26 (dd, 1H); 7.33-7.38 (m, 1H); 7.41 (dt, 1H); 7.58 (d, 1H); 7.62 (dd, 1H); 7.75 (ddd, 1H); 7.89 (dd, 1H).

LC-MS (Method 2): Rt=1.22 min; MS (ESIpos): m/z=403.7 [M+H]+

Example 27

4-[4-(1,3-benzoxazol-2-yl)piperidin-1-yl]-7-bromo-1-methyl-2-oxo-1,2-dihydroquinoline-3-carbonitrile

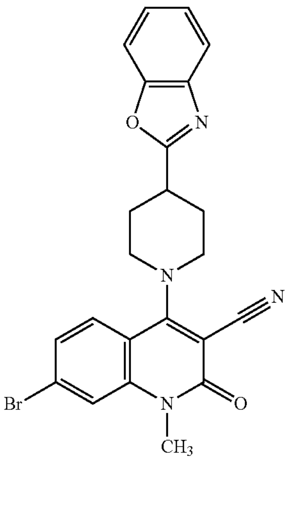

A suspension of 100 mg 7-bromo-4-chloro-1-methyl-2-oxo-1,2-dihydroquinoline-3-carbonitrile (336 μmol, intermediate 21), 81.6 mg 2-(piperidin-4-yl)-1,3-benzoxazole (403 μmol, CAS 51784-03-3) and 180 μL N,N-diisopropylethylamine (1.0 mmol) in 2.0 mL 2-propanol was stirred for 2 h at 90° C. The mixture was cooled down to rt, water was added, the precipitate was collected by filtration, washed with ethanol and dried in vacuum. 136 mg of the title compound were obtained (83% yield, 95% purity).

$^1$H NMR (400 MHz, DMSO-$d_6$) δ ppm 2.07-2.22 (m, 2H) 2.26-2.36 (m, 2H) 3.42-3.52 (m, 1H): 3.52-3.66 (m, 5H) 3.74-3.89 (m, 2H) 7.32-7.44 (m, 2H) 7.48-7.56 (m, 1H) 7.69-7.85 (m, 4H).

LC-MS (Method 3): Rt=1.27 min; MS (ESIpos): m/z=463.0 & 465.0 [M+H]+

Example 28

7-bromo-1-methyl-4-{4-methyl-4-[6-(trifluoromethoxy)-1,3-benzoxazol-2-yl]piperidin-1-yl}-2-oxo-1,2-dihydroquinoline-3-carbonitrile

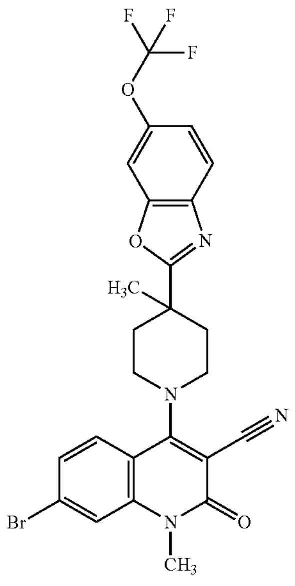 [SMILES: Cn1c(=O)c(C#N)c(N2CCC(C)(c3nc4ccc(OC(F)(F)F)cc4o3)CC2)c2ccc(Br)cc21]

A suspension of 99 mg 7-bromo-4-chloro-1-methyl-2-oxo-1,2-dihydroquinoline-3-carbonitrile (0.33 mmol, intermediate 21), 100 mg 2-(4-methylpiperidin-4-yl)-6-(trifluoromethoxy)-1,3-benzoxazole (0.33 mmol, intermediate 10) and 0.19 mL triethylamine (1.3 mmol) in 6 mL 2-propanol was stirred for 3 h at 90° C. After this ti me, water and ethyl acetate were added and the reaction was stirred. The mixture was extracted with ethyl acetate. The organic phase was washed with water and brine and dried over sodium sulfate. After evaporation of the solvent, the residue was purified by RP-HPLC (column: X-Bridge C18 5 μm 100×30 mm, mobile phase: acetonitrile/water (0.2 vol. % ammonia 32%)-gradient) to give 120 mg of the title compound (63% yield, 98% purity).

$^1$H-NMR (400 MHz, DMSO-d6) δ[ppm]: 1.51 (s, 3H); 2.01-2.11 (m, 2H); 2H below DMSO; 3.48-3.59 (s+m, 5H); 3.69 3.78 (m, 2H); 7.40-7.44 (m, 1H); 7.48 (dd, 1H); 7.75-7.80 (m, 2H); 7.89 (d, 1H); 7.96 (d, 1H).

LC-MS (Method 2): Rt=1.50 min; MS (ESIpos): m/z=562.4 [M+H]+

Example 29

7-bromo-4-[4-(5-chloro-1,3-benzoxazol-2-yl)piperidin-1-yl]-1-methyl-2-oxo-1,2-dihydroquinoline-3-carbonitrile

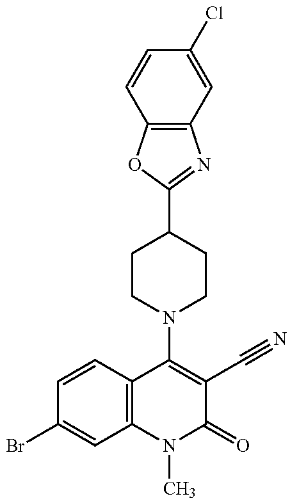 [SMILES: Cn1c(=O)c(C#N)c(N2CCC(c3nc4cc(Cl)ccc4o3)CC2)c2ccc(Br)cc21]

A suspension of 120 mg 7-bromo-4-chloro-1-methyl-2-oxo-1,2-dihydroquinoline-3-carbonitrile (0.38 mmol, intermediate 21), 96 mg 5-chloro-2-(piperidin-4-yl)-1,3-benzoxazole (0.38 mmol, intermediate 9) and 0.11 mL triethylamine (0.76 mmol) in 6 mL 2-propanol was stirred for 2 h at 90° C. After this time, water and ethyl acetate were added and the reaction was stirred. The precipitate that was generated by this procedure was collected by filtration and dried in vacuum. 170 mg of the title compound were obtained (85% yield, 95% purity).

$^1$H-NMR (400 MHz, DMSO-d6) δ[ppm]: 2.06-2.20 (m, 2H); 2.26-2.35 (m, 2H); 3.49 (tt, 1H); 3.53-3.64 (s+m, 5H); 3.77-3.86 (m, 2H); 7.44 (dd, 1H); 7.51 (dd, 1H); 7.75-7.80 (m, 3H); 7.86 (d, 1H).

LC-MS (Method 2): Rt=1.42 min; MS (ESIpos): m/z=496.2 [M+H]+

Example 30

7-bromo-1-methyl-2-oxo-4-{4-[5-(propan-2-yl)-1,3-benzoxazol-2-yl]piperidin-1-yl}-1,2-dihydroquinoline-3-carbonitrile

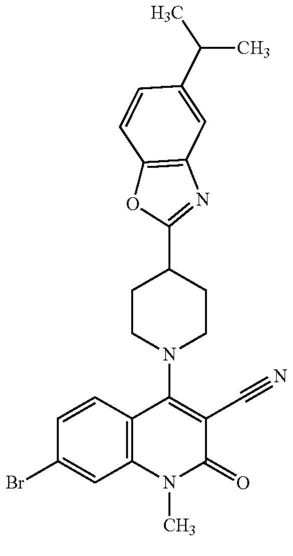 [SMILES: CC(C)c1ccc2oc(C3CCN(c4c(C#N)c(=O)n(C)c5cc(Br)ccc45)CC3)nc2c1]

A suspension of 120 mg 7-bromo-4-chloro-1-methyl-2-oxo-1,2-dihydroquinoline-3-carbonitrile (0.39 mmol, intermediate 21), 96 mg 5-chloro-2-(piperidin-4-yl)-1,3-benzoxazole (0.39 mmol, intermediate 6) and 0.11 mL triethylamine (0.78 mmol) in 6 mL 2-propanol was stirred for 2 h at 90° C. After this time, water and ethyl acetate were added and the reaction was stirred. The precipitate that was generated by this procedure was collected by filtration and dried in vacuum to give 50 mg of the title compound. The ethyl acetate phase was further washed with brine and dried over sodium sulfate. After evaporation of the solvent, the residue was purified by RP-HPLC (column: X-Bridge C18 5 μm 100×30 mm, mobile phase: acetonitrile/water (0.2 vol. % ammonia 32%)-gradient). 35 mg of the title compound were obtained (18% yield, 98% purity).

$^1$H-NMR (400 MHz, DMSO-d6) δ[ppm]: 1.25 (d, 6H); 2.06-2.20 (m, 2H); 2.25-2.33 (m, 2H); 3.03 (spt, 1H); 3.45 (tt, 1H); 3.53-3.64 (s+m, 5H); 3.77-3.85 (m, 2H); 7.26 (dd, 1H); 7.51 (dd, 1H); 7.58 (d, 1H); 7.60 (d, 1H); 7.76-7.80 (m, 2H).

LC-MS (Method 2): Rt=1.51 min; MS (ESIpos): m/z=506.5 [M+H]+

Example 31

7-bromo-4-[4-(5,6-difluoro-1,3-benzoxazol-2-yl)piperidin-1-yl]-1-methyl-2-oxo-1,2-dihydroquinoline-3-carbonitrile

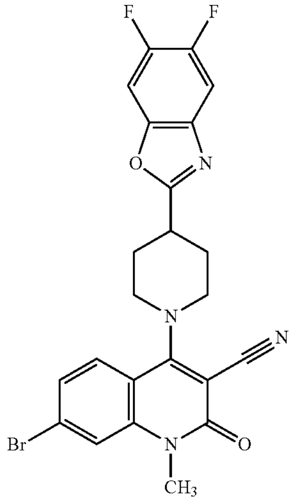 [SMILES: Cn1c(=O)c(C#N)c(N2CCC(c3nc4cc(F)c(F)cc4o3)CC2)c2ccc(Br)cc21]

A suspension of 120 mg 7-bromo-4-chloro-1-methyl-2-oxo-1,2-dihydroquinoline-3-carbonitrile (0.38 mmol, intermediate 21), 96 mg 5,6-difluoro-2-(piperidin-4-yl)-1,3-benzoxazole (0.38 mmol, intermediate 12) and 0.11 mL triethylamine (0.76 mmol) in 6 mL 2-propanol was stirred for 2 h at 90° C. After this time, water and ethyl acetate w ere added and the reaction was stirred. The precipitate that was generated by this procedure was collected by filtration and dried in vacuum. 170 mg of the title compound were obtained (86% yield, 97% purity).

$^1$H-NMR (400 MHz, DMSO-d6) δ[ppm]: 2.05-2.19 (m, 2H); 2.25-2.35 (m, 2H); 3.48 (tt, 1H); 3.53-3.64 (s+m, 5H); 3.76-3.86 (m, 2H); 7.50 (dd, 1H); 7.74-7.80 (m, 2H); 7.92 (dd, 1H); 8.05 (dd, 1H).

LC-MS (Method 2): Rt=1.36 min; MS (ESIpos): m/z=500.4 [M+H]+

Example 32

7-bromo-4-[4-(6-chloro-1,3-benzoxazol-2-yl)piperidin-1-yl]-1-methyl-2-oxo-1,2-dihydroquinoline-3-carbonitrile

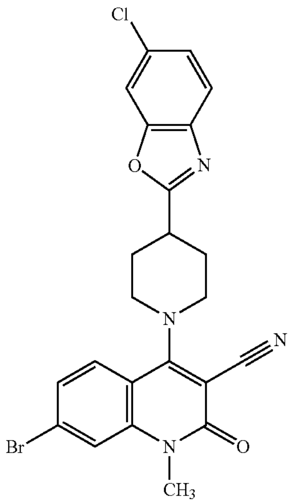 [SMILES: Cn1c(=O)c(C#N)c(N2CCC(c3nc4ccc(Cl)cc4o3)CC2)c2ccc(Br)cc21]

A suspension of 151 mg 7-bromo-4-chloro-1-methyl-2-oxo-1,2-dihydroquinoline-3-carbonitrile (0.48 mmol, intermediate 21), 120 mg 6-chloro-2-(piperidin-4-yl)-1,3-benzoxazole (0.48 mmol, intermediate 7) and 0.13 mL triethylamine (0.96 mmol) in 7.5 mL 2-propanol was stirred for 2 h at 90° C. After this time, water and ethyl acetate w ere added and the reaction was stirred. The precipitate that was generated by this procedure was collected by filtration and dried in vacuum. 220 mg of the title compound were obtained (83% yield, 90% purity).

$^1$H-NMR (400 MHz, DMSO-d6) δ[ppm]: 2.07-2.19 (m, 2H); 2.26-2.35 (m, 2H); 3.48 (tt, 1H); 3.53-3.54 (s+m, 5H); 3.77-3.86 (m, 2H); 7.63 (dd, 1H); 7.51 (dd, 1H); 7.74-7.80 (m, 3H); 7.95 (d, 1H).

LC-MS (Method 2): Rt=1.43 min; MS (ESIpos): m/z=497.3 [M+H]+

Example 33

4-[4-(1,3-benzothiazol-2-yl)piperidin-1-yl]-7-bromo-1-methyl-2-oxo-1,2-dihydroquinoline-3-carbonitrile

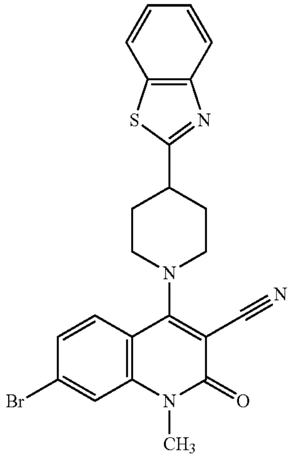

A suspension of 100 mg 7-bromo-4-chloro-1-methyl-2-oxo-1,2-dihydroquinoline-3-carbonitrile (336 μmol, intermediate 21), 88.1 mg 2-(piperidin-4-yl)-1,3-benzothiazole (403 μmol) and 180 μL N,N-diisopropylethylamine (1.0 mmol) in 2.0 mL 2-propanol was stirred for 2 h at 90° C. The mixture was cooled down to rt, water was added, the precipitate was collected by filtration, washed with ethanol and dried in vacuum. 149 mg of the title compound were obtained (88% yield, 95% purity).

$^1$H NMR (400 MHz, DMSO-$d_6$) δ ppm 2.05-2.21 (m, 2H) 2.28-2.36 (m, 2H) 3.38-3.49 (m, 1H): 3.50-3.66 (m, 5H) 3.79-3.93 (m, 2H) 7.39-7.58 (m, 3H) 7.76-7.84 (m, 2H) 7.95-8.02 (m, 1H) 8.05-8.17 (m, 1H).

LCMS (Method 3): Rt=1.34 min; MS (ESIpos): m/z=479.0 & 481.0 [M+H]+

Example 34

7-bromo-1-methyl-4-{4-methyl-4-[5-(propan-2-yl)-1,3-benzoxazol-2-yl]piperidin-1-yl}-2-oxo-1,2-dihydroquinoline-3-carbonitrile

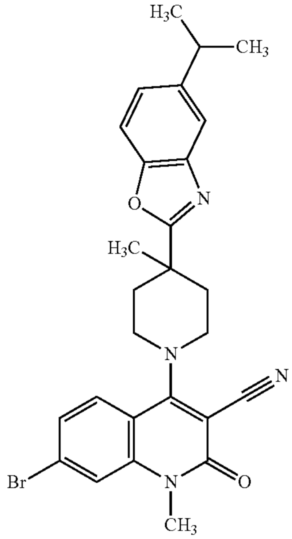 [SMILES: CC(C)c1ccc2oc(C3(C)CCN(c4c(C#N)c(=O)n(C)c5cc(Br)ccc45)CC3)nc2c1]

A suspension of 173 mg 7-bromo-4-chloro-1-methyl-2-oxo-1,2-dihydroquinoline-3-carbonitrile (0.55 mmol, intermediate 21), 150 mg 2-(4-methylpiperidin-4-yl)-5-(propan-2-yl)-1,3-benzoxazole (0.55 mmol, intermediate 11) and 0.15 mL triethylamine (1.1 mmol) in 6 mL 2-propanol was stirred for 2 h at 90° C. After this ti me, water and ethyl acetate were added and the reaction was stirred for 15 min. at 90° C. The precipitate that was generated by this procedure was collected by filtration and dried in vacuum to give 12 mg of the title compound. The ethyl acetate phase was further washed with brine and dried over sodium sulfate. After evaporation of the solvent, the residue was stirred in DMSO, the precipitate that was generated by this procedure was collected by filtration and dried in vacuum to give 200 mg of the title compound were obtained (68% yield, 98% purity).

$^1$H-NMR (400 MHz, DMSO-d6) δ[ppm]: 1.25 (d, 6H); 1.48 (s, 3H); 1.99-2.10 (m, 2H); 2H below DMSO signal; 3.03 (spt, 1H); 3.44-3.57 (s+m, 5H); 3.68-3.77 (m, 2H); 7.27 (dd, 1H); 7.48 (dd, 1H); 7.60-7.65 (m, 2H); 7.75-7.81 (m, 2H).

LC-MS (Method 2): Rt=1.58 min; MS (ESIpos): m/z=520.4 [M+H]+

Example 35

4-[4-(1,3-benzoxazol-2-yl)piperidin-1-yl]-1-methyl-2-oxo-7-(2-oxopyrrolidin-1-yl)-1,2-dihydroquinoline-3-carbonitrile

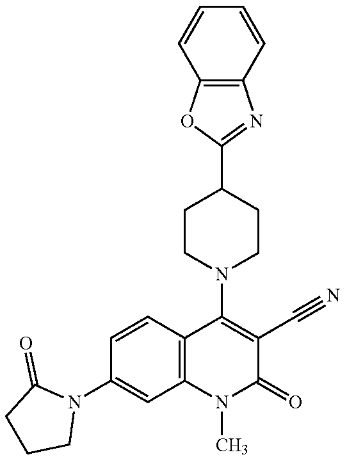

A suspension of 203 mg 4-[4-(1,3-benzoxazol-2-yl)piperidin-1-yl]-7-bromo-1-methyl-2-oxo-1,2-dihydroquinoline-3-carbonitrile (438 μmol, example 27), 74.6 mg pyrrolidin-2-one (876 μmol, CAS 616-45-5), 190 μL N,N'-dimethylethane-1,2-diamine (1.8 mmol), 16.7 mg copper(I) iodide (87.6 μmol) and 133 mg dipotassium carbonate (964 μmol) in 7.5 mL toluene was stirred overnight at 110° C. The mixture was cooled down to rt, water was added and the mixture was extracted with dichloromethane. The combined organic phases were washed with brine, filtered (using a waterresistant filter) and concentrated under reduced pressure. The residue was purified by flash chromatography (silica, dichloromethane/ethanol gradient 0-10%). The impure product was stirred in ethanol, the precipitate was collected by filtration and dried in vacuum. 156 mg of the title compound were obtained (72% yield, 95% purity).

$^1$H NMR (400 MHz, DMSO-$d_6$) δ [ppm]: 2.13 (m, 4H), 2.32 (m, 2H), 2.60 (t, 2H), 3.47 (m, 1H), 3.61 (m, 5H), 3.83 (m, 2H), 3.98 (t, 2H), 7.38 (m, 2H), 7.71 (m, 3H), 7.87 (m, 2H).

LC-MS (Method 3): $R_t$=1.07 min; MS (ESIpos): m/z=468 $[M+H]^+$

Example 36

4-[4-(1,3-benzothiazol-2-yl)piperidin-1-yl]-1-methyl-2-oxo-7-(2-oxopyrrolidin-1-yl)-1,2-dihydroquinoline-3-carbonitrile

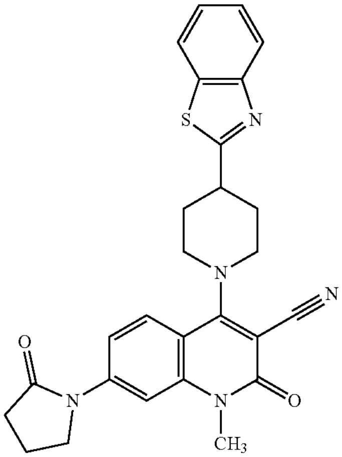 [SMILES: Cn1c(=O)c(C#N)c(N2CCC(c3nc4ccccc4o3)CC2)c2ccc(N3CCCC3=O)cc21]

A suspension of 200 mg 4-[4-(1,3-benzothiazol-2-yl)piperidin-1-yl]-7-bromo-1-methyl-2-oxo-1,2-dihydroquinoline-3-carbonitrile (417 μmol, example 33), 71.0 mg pyrrolidin-2-one (834 μmol, CAS 616-45-5), 180 μL N,N'-dimethylethane-1,2-diamine (1.7 mmol), 15.9 mg copper(I) iodide (83.4 μmol) and 127 mg dipotassium carbonate (918 μmol) in 7.1 mL toluene was stirred overnight at 110° C. The mixture was cooled down to rt, water was added and the mixture was extracted with dichloromethane. The combined organic phases were washed with brine, filtered (using a waterresistant filter) and concentrated under reduced pressure. The residue was purified by flash chromatography (silica, dichloromethane/ethanol gradient 0-10%). The impure product was stirred in ethanol, the precipitate was collected by filtration and dried in vacuum. 170 mg of the title compound were obtained (80% yield, 95% purity).

$^1$H NMR (400 MHz, DMSO-$d_6$) δ [ppm]: 2.13 (m, 4H), 2.32 (m, 2H), 2.59 (t, 2H), 3.56 (m, 6H), 3.87 (m, 2H), 3.97 (m, 2H), 7.47 (m, 2H), 7.69 (m, 1H), 7.86 (m, 2H), 7.99 (m, 1H), 8.11 (m, 1H).

LC-MS (Method 1): $R_t$=1.20 min; MS (ESIpos): m/z=484 $[M+H]^+$

Example 37

1-methyl-2-oxo-4-{4-[4-(2,2,2-trifluoroethoxy)phenyl]piperidin-1-yl}-1,2-dihydroquinoline-3-carbonitrile

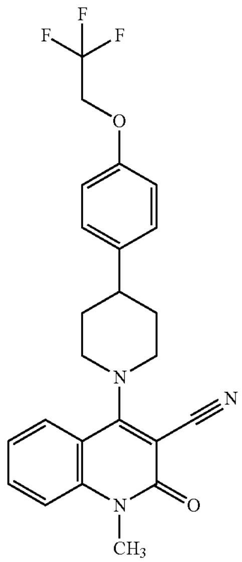 [SMILES: Cn1c(=O)c(C#N)c(N2CCC(c3ccc(OCC(F)(F)F)cc3)CC2)c2ccccc21]

A solution of 81 mg 4-chloro-1-methyl-2-oxo-1,2-dihydroquinoline-3-carbonitrile (0.37 mmol, CAS 150617-68-8), 125 mg 4-[4-(2,2,2-trifluoroethoxy)phenyl]piperidine (0.48 mmol, intermediate 23) and 0.1 mL triethylamine (0.74 mmol) in 2.4 mL 2-propanol was stirred for 16 h at 90° C. After this time, water was added and the reaction was extracted with ethyl acetate. The organic phase was washed with water and brine and dried over sodium sulfate. After evaporation of the solvent, the residue was concentrated and purified by flash chromatography (silica, dichloromethane/methanol gradient 0-3%). The obtained material was purified by RP-HPLC (column: X-Bridge C18 5 μm 100×30 mm, mobile phase: acetonitrile/water (0.2 vol. % ammonia 32%)-gradient). 30 mg of the title compound were obtained (17% yield, 95% purity).

$^1$H NMR (400 MHz, DMSO-$d_6$) δ [ppm]: 1.94 (m, 4H), 2.86 (m, 1H), 3.50 (m, 2H), 3.58 (s, 3H), 3.84 (m, 2H), 4.74 (q, 2H), 7.03 (m, 2H), 7.34 (m, 3H), 7.56 (m, 1H), 7.74 (m, 1H), 7.98 (m, 1H).

LC-MS (Method 2): Rt=1.34 min; MS (ESIpos): m/z=442.5 [M+H]+

Example 38

1-methyl-2-oxo-4-(4-{4-[(propan-2-yl)oxy]phenyl}piperidin-1-yl)-1,2-dihydroquinoline-3-carbonitrile

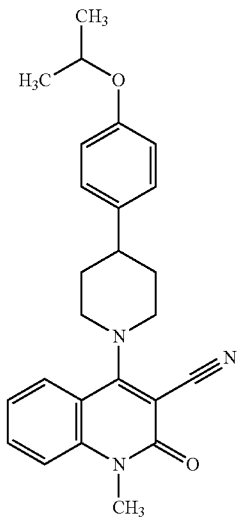 [SMILES: CC(C)Oc1ccc(C2CCN(c3c(C#N)c(=O)n(C)c4ccccc34)CC2)cc1]

A solution of 100 mg 4-chloro-1-methyl-2-oxo-1,2-dihydroquinoline-3-carbonitrile (0.46 mmol, CAS 150617-68-8), 120 mg 4-{4-[(propan-2-yl)oxy]phenyl}piperidine (0.55 mmol, intermediate 25) and 0.13 mL triethylamine (0.9 mmol) in 3 mL 2-propanol was stirred for 5 h at 90° C. After this time, water was added and the reaction was extracted with ethyl acetate. The organic phase was washed with water and brine and dried over sodium sulfate. After evaporation of the solvent, the residue was purified by RP-HPLC (column: X-Bridge C18 5 μm 100×30 mm, mobile phase: acetonitrile/water (0.2 vol. % ammonia 32%)-gradient). The obtained material was purified by flash chromatography (silica, dichloromethane/methanol gradient 0-1%). 22 mg of the title compound were obtained (11% yield, 95% purity).

$^1$H NMR (400 MHz, DMSO-$d_6$) δ [ppm]: 1.25 (d, 6H), 1.93 (m, 4H), 2.83 (m, 1H), 3.49 (m, 2H), 3.58 (s, 3H), 3.85 (m, 2H), 4.57 (spt, 1H), 6.87 (m, 2H), 7.24 (m, 2H), 7.35 (m, 1H), 7.57 (m, 1H), 7.74 (m, 1H), 7.95 (m, 1H).

LC-MS (Method 2): Rt=1.40 min; MS (ESIpos): m/z=402.5 [M+H]+

Example 39

4-[4-(4-ethoxyphenyl)piperidin-1-yl]-1-methyl-2-oxo-1,2-dihydroquinoline-3-carbonitrile

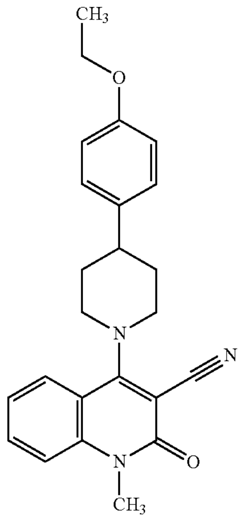 [SMILES: CCOc1ccc(C2CCN(c3c(C#N)c(=O)n(C)c4ccccc34)CC2)cc1]

A solution of 152 mg 4-chloro-1-methyl-2-oxo-1,2-dihydroquinoline-3-carbonitrile (0.69 mmol, CAS 150617-68-8), 185 mg 4-(4-ethoxyphenyl)piperidine (0.9 mmol, CAS 760150-51-4) and 0.19 mL triethylamine (1.4 mmol) in 4.6 mL 2-propanol was stirred for 5.5 h at 90° C. After this time, water was added and the reaction was extracted with ethyl acetate. The organic phase was washed with water and brine and dried over sodium sulfate. After evaporation of the solvent, the residue was purified by RP-HPLC (column: X-Bridge C18 5 μm 100×30 mm, mobile phase: acetonitrile/water (0.2 vol. % ammonia 32%)-gradient). 40 mg of the title compound were obtained (14% yield, 95% purity).

$^1$H NMR (400 MHz, DMSO-$d_6$) δ [ppm]: 1.32 (m, 3H), 1.93 (m, 4H), 2.82 (m, 1H), 3.49 (m, 2H), 3.58 (s, 3H), 3.83 (m, 2H), 4.02 (m, 2H), 6.88 (m, 2H), 7.26 (m, 2H), 7.35 (m, 1H), 7.58 (m, 1H), 7.73 (m, 1H), 7.92 (m, 1H).

LC-MS (Method 2): Rt=1.40 min; MS (ESIpos): m/z=402.5 [M+H]+

Example 40

4-[4-(4-cyclopropylphenyl)piperidin-1-yl]-1-methyl-2-oxo-1,2-dihydroquinoline-3-carbonitrile

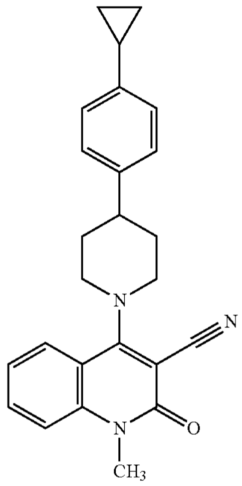 [SMILES: Cn1c(=O)c(C#N)c(N2CCC(c3ccc(C4CC4)cc3)CC2)c2ccccc21]

To a stirred solution of 100 mg 4-[4-(4-bromophenyl)piperidin-1-yl]-1-methyl-2-oxo-1,2-dihydroquinoline-3-carbonitrile (237 μmol, example 88) in 4.0 mL degassed THF were added 79.6 mg 2-cyclopropyl-4,4,5,5-tetramethyl-1,3,2-dioxaborolane (474 μmol, CAS 126689-01-8), 1.2 mL potassium phosphate (0.50 M in water, 590 μmol) and 27.9 mg chloro(2-dicyclohexylphosphino-2,4,6-triisopropyl-1,1-biphenyl)[2-(2-amino-1,1-biphenyl)]palladium(II): (35.5 μmol). The mixture was stirred overnight at 70° C. After this time, water was added and the reaction was extracted with dichloromethane (2×). The organic phase dried over sodium sulfate and concentrated under reduced pressure. The residue was purified by RP-HPLC (column: X-Bridge C18 5 μm 100×30 mm, mobile phase: acetonitrile/water (0.1 vol. % formic acid)-gradient). The impure product was purified by preparative TLC (hexane/ethyl acetate; 4:6) to give 6.5 mg of the title compound (95% purity, 7% yield).

$^1$H NMR (400 MHz, DMSO-$d_6$) δ ppm 0.57-0.70 (m, 2H) 0.87-0.99 (m, 2H) 1.83-2.05 (m, 5H): 2.76-2.91 (m, 1H) 3.44-3.64 (m, 5H) 3.79-3.91 (m, 2H) 7.00-7.08 (m, 2H) 7.19-7.25 (m, 2H) 7.32-7.40 (m, 1H) 7.55-7.60 (m, 1H) 7.68-7.81 (m, 1H) 7.89-8.00 (m, 1H).

LC-MS (Method 1): $R_t$=1.46 min; MS (ESIpos): m/z=385 $[M+H]^+$

Example 41

4-[4-(4-methoxyphenyl)piperidin-1-yl]-1-methyl-2-oxo-1,2-dihydroquinoline-3-carbonitrile

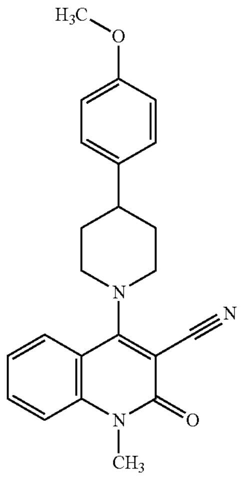

A solution of 1.76 g 4-chloro-1-methyl-2-oxo-1,2-dihydroquinoline-3-carbonitrile (8.0 mmol, CAS 150617-68-8), 2 g 4-(4-methoxyphenyl)piperidine (10.4 mmol, CAS 67259-62-5) and 2.24 mL triethylamine (16 mmol) in 53 mL 2-propanol was stirred for 8 h at 90° C. After this time, water was added and the reaction was extracted with ethyl acetate. The organic phase was washed with water and brine. A solid precipitated was isolated by filtration to give a first crop of 1.5 g of the title compound (95% purity, 47% yield). The solution was dried over sodium sulfate and the solvent was evaporated in vacuum to a smaller amount. A second crop of material was isolated by filtration from this suspension to give further 171 mg of the title compound (95% purity, 5% yield).

$^1$H NMR (400 MHz, DMSO-$d_6$) δ [ppm]: 1.91 (m, 4H), 2.82 (m, 1H), 3.50 (m, 2H), 3.58 (s, 3H), 3.73 (s, 3H), 3.83

(m, 2H), 6.89 (m, 2H), 7.25 (m, 2H), 7.36 (m, 1H), 7.57 (m, 1H), 7.74 (m, 1H), 7.93 (m, 1H).

LC-MS (Method 2): $R_t$=1.26 min; MS (ESIpos): m/z=374.5 $[M+H]^+$

Example 42

1-methyl-2-oxo-4-[4-(4-propoxyphenyl)piperidin-1-yl]-1,2-dihydroquinoline-3-carbonitrile

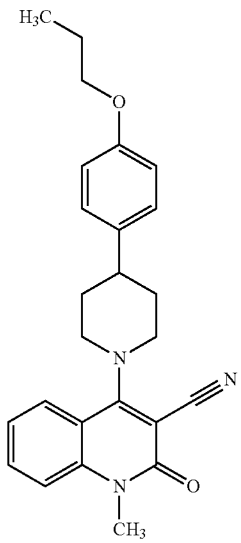 [SMILES: CCCOc1ccc(C2CCN(c3c(C#N)c(=O)n(C)c4ccccc34)CC2)cc1]

To an 8 mL vial was added 100 mg 4-(4-bromopiperidin-1-yl)-1-methyl-2-oxo-1,2-dihydroquinoline-3-carbonitrile (289 μmol, intermediate 26), 62.1 mg 1-bromo-4-propoxy-benzene (289 μmol, CAS 39969-56-7), 2.9 mg photocatalyst bis{3,5-difluoro-2-[5-(trifluoromethyl)pyridin-2-yl] phenyl}iridium(I)hexafluorophosphate-4,4-di-tert-butyl-2, 2-bipyridine (1:1:1) (2.89 μmol, CAS 870987-63-6), 71.6 mg 1,1,1,3,3,3-hexamethyl-2-(trimethylsilyl)trisilane (289 μmol) and 61.2 mg anhydrous sodium carbonate (578 μmol). The vial was sealed and placed under nitrogen before 4 mL 1,2-dimethoxyethane was added. To a separate vial were added 1.02 mg 1,2-dimethoxyethane-dibromonickel (1:1) (2.89 μmol) and 770 μg 4, 4-di-tert-butyl-2-2-bi-pyridine (2.9 μmol). The catalyst vial was sealed, purged with nitrogen then it was added 2 mL 1,2-dimethoxyethane. The pre-catalyst solution was stirred for 15 min, after that, the 2 mL solution was added into the first vial by a syringe. The resulting mixture was stirred and irradiated with a 34 W blue LED lamp (7 cm away, 1.4 Å, keep the reaction temperature at 25° C.) for 16 hours. Upon completion of the reaction, the solid was removed by filtration and the filtrate was concentrated under vacuum. The residue was purified by RP-HPLC [mobile phase A: water (0.1% ammonium formate), mobile phase B: acetonitrile; gradient: 68% B to 95% B in 8 min] to give 20.9 mg (18% yield) of the product as an white solid.

1H-NMR (400 MHz, DMSO-d6): 5 [ppm]=0.96 (t, 3H), 1.68-1.76 (m, 2H), 1.91-1.98 (m, 4H), 2.79-2.87 (m, 1H), 3.47-3.54 (m, 2H), 3.58 (s, 3H), 3.81-3.84 (m, 2H), 3.90 (t, 2H), 6.89 (d, 2H), 7.25 (d, 2H), 7.35 (t, 1H), 7.57 (d, 1H), 7.74 (t, 1H), 7.93 (d, 1H).

Example 43

1-methyl-2-oxo-4-{4-[4-(trifluoromethoxy)phenyl] piperidin-1-yl}-1,2-dihydroquinoline-3-carbonitrile

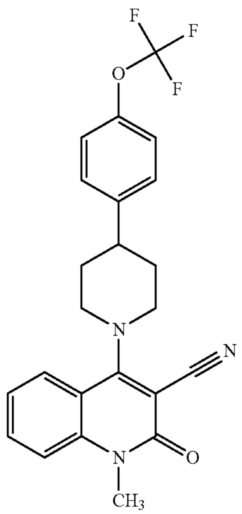 [SMILES: Cn1c(=O)c(C#N)c(N2CCC(c3ccc(OC(F)(F)F)cc3)CC2)c2ccccc21]

To an 8 mL vial equipped with a stir bar was added 100 mg intermediate 26 (0.29 mmol), 76.0 mg 1-(benzyloxy)-4-bromobenzene (0.29 mmol, CAS 407-14-7), 2.9 mg photocatalyst bis{3,5-difluoro-2-[5-(trifluoromethyl)pyridin-2-yl]phenyl}iridium(I)hexafluorophosphate-4,4-di-tert-butyl-2,2-bipyridine (1:1:1) (0.003 mmol, CAS 870987-63-6), 71.6 mg 1,1,1,3,3,3-hexamethyl-2-(trimethylsilyl)trisilane (0.29 mmol) and 61.2 mg anhydrous sodium carbonate (0.58 mmol). The vial was sealed and placed under nitrogen before 4 mL of 1,2-dimethoxyethane was added. To a separate vial was added 1.02 mg 1,2-dimethoxyethane-dibromonickel (1:1) (0.006 mmol) and 0.77 mg 4,4-di-tert-butyl-2-2-bi-pyridine (0.003 mmol). The catalyst vial was sealed, purged with nitrogen, then to it was added 2 mL of 1,2-dimethoxyethane. The precatalyst solution was stirred for 15 min., after that, the 2 mL solution was syringed into the first vial. The solution was degassed by sparging with nitrogen while stirring for 10 min. before sealing with parafilm. The result mixture was stirred and irradiated with a 34 W blue LED lamp (7 cm away, 1.4 A, keep the reaction temperature at 25° C.) for 16 h. Upon completion of the reaction, the solid was removed by filtration and the filtrate was concentrated under vacuum. The residue was purified by RP-HPLC [mobile phase A: water (0.1% ammonium formate), mobile phase B: acetonitrile; gradient: 35% B to 75% B in 8 min] to give 18.9 mg (15% yield) of the product as a white solid.

$^1$H NMR (400 MHz, DMSO-$d_6$) δ ppm 1.92-2.04 (m, 4H) 2.90-3.06 (m, 1H) 3.48-3.63 (m, 5H): 3.84 (br d, 1H) 3.84-3.85 (m, 1H) 7.25-7.39 (m, 3H) 7.44-7.65 (m, 3H) 7.69-7.82 (m, 1H) 7.88-8.00 (m, 1H).

Example 44

N-{4-[1-(3-cyano-1-methyl-2-oxo-1,2-dihydroquinolin-4-yl)piperidin-4-yl]phenyl}benzenesulfonamide

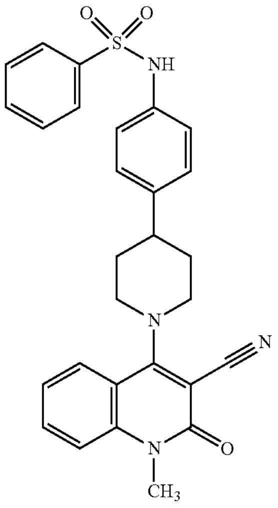 [SMILES: Cn1c(=O)c(C#N)c(N2CCC(c3ccc(NS(=O)(=O)c4ccccc4)cc3)CC2)c2ccccc21]

A suspension of 100 mg 4-[4-(4-bromophenyl)piperidin-1-yl]-1-methyl-2-oxo-1,2-dihydroquinoline-3-carbonitrile (237 μmol, example 88), 48.4 mg benzenesulfonamide (308 μmol, CAS 98-10-2), 10 μL N,N'-dimethylethane-1,2-diamine (95 μmol), 18.04 mg copper(I)iodide (94.8 μmol) and 121 mg potassium phosphate (568 μmol) in 2 mL toluene was stirred for 48 h at 110° C. The mixture was cooled d own to rt and was concentrated under reduced pressure. The residue was purified by RP-HPLC (column: X-Bridge C18 5 μm 100×30 mm, mobile phase: acetonitrile/water (0.1 vol. % formic acid)-gradient) to give 65.0 mg of the title compound (95% purity, 52% yield).

$^{1}H$ NMR (400 MHz, DMSO-$d_6$) δ ppm 1.80-1.93 (m, 4H) 2.73-2.85 (m, 1H) 3.43-3.52 (m, 2H): 3.53-3.61 (m, 3H) 3.75-3.85 (m, 2H) 7.02-7.09 (m, 2H) 7.18-7.27 (m, 2H) 7.30-7.37 (m, 1H) 7.49-7.66 (m, 4H) 7.69-7.82 (m, 3H) 7.86-7.93 (m, 1H) 9.95-10.56 (m, 1H).

LC-MS (Method 1): $R_t$=1.21 min; MS (ESIpos): m/z=500 $[M+H]^+$

Example 45

4-[4-(3-cyclopropylphenyl)piperidin-1-yl]-1-methyl-2-oxo-1,2-dihydroquinoline-3-carbonitrile

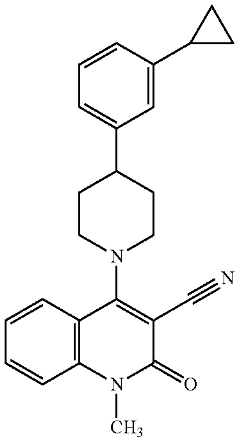 [SMILES: Cn1c(=O)c(C#N)c(N2CCC(c3cccc(C4CC4)c3)CC2)c2ccccc21]

100 mg 4-(4-bromopiperidin-1-yl)-1-methyl-2-oxo-1,2-dihydroquinoline-3-carbonitrile (289 μmol, intermediate 26), 6.48 mg bis{3,5-difluoro-2-[5-(trifluoromethyl)pyridin-2-yl]phenyl}iridium(I)hexafluorophosphate-4,4'-di-tert-butyl-2,2'-bipyridine (1:1:1) (5.78 μmol, CAS 870987-63-6) and 61.2 mg disodium carbonate (578 μmol) were dissolved in the reaction vial in 5.8 mL 1,2-dimethoxyethane. In a separate vial the Ni-catalyst was prepared by dissolving 320 μg 1,2-dimethoxyethane-dichloronickel (1:1) (1.4 μmol) and 388 μg 4,4-di-tert-butyl-2,2-bipyridine (1.4 μmol) in 1,2-dimethoxyethane (100-fold amount in 10 ml) followed by stirring for 5 min. The catalyst solution (0.1 ml) was syringed to the sealed reaction vial and argon was buddle through the solution for 5 min., then 82 μL 1-bromo-3-cyclopropylbenzene (580 μmol, CAS 1798-85-2) and 89 μL 1,1,1,3,3,3-hexamethyl-2-(trimethylsilyl)trisilane (290 μmol) was added. The vial was placed in a water bath (to keep the temp. below 35° C.) and was subsequently irradiated by two 40 W Kessil LED Aquarium lamps for 23 h. The reaction was quenched with half sat. sodium bicarbonate solution, extracted with ethyl acetate (3×), dried over sodium sulphate and concentrated in vacuum. The crude material was purified by RP-HPLC (instrument: Waters Autopurificationsystem; column: YMC-Triart C18 5μ 100×30 mm; eluent A: water (0.2 vol. % aq. ammonia 32%), eluent B: acetonitrile; gradient: 0.00-0.50 min. 31% B (25→70 ml/min), 0.51-5.50 min. 62-74% B (70 ml/min), DAD scan: 210-400 nm) to give 20 mg of the title compound (17% yield, 95% purity).

$^{1}H$ NMR (400 MHz, DMSO-$d_6$) δ [ppm]: 0.69 (m, 2H), 0.94 (m, 2H), 1.96 (m, 5H), 2.84 (m, 1H), 3.51 (m, 2H), 3.59 (s, 3H), 3.84 (m, 2H), 6.90 (d, 1H), 7.10 (m, 2H), 7.21 (m, 1H), 7.36 (m, 1H), 7.58 (m, 1H), 7.74 (m, 1H), 7.94 (m, 1H).

LC-MS (Method 2): $R_t$=1.43 min; MS (ESIpos): m/z=384.4 $[M+H]^+$

Example 46

4-{4-[4-(dimethylamino)phenyl]piperidin-1-yl}-1-methyl-2-oxo-1,2-dihydroquinoline-3-carbonitrile

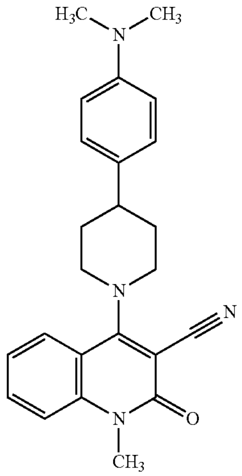 [SMILES: CC(C)c1ccc(C2CCN(c3c(C#N)c(=O)n(C)c4ccccc34)CC2)cc1]

80 mg 4-(4-bromopiperidin-1-yl)-1-methyl-2-oxo-1,2-dihydroquinoline-3-carbonitrile (231 μmol, intermediate 26), 92.5 mg 4-bromo-N,N-dimethylaniline (462 μmol, CAS 586-77-6), 5.18 mg bis{3,5-difluoro-2-[5-(trifluoromethyl)

pyridin-2-yl]phenyl}iridium(I)hexafluorophosphate-4,4-di-tert-butyl-2,2-bipyridine (1:1:1) (4.62 μmol, CAS 870987-63-6) and 49 mg disodium carbonate (462 μmol) were dissolved in the reaction vial in 4.6 mL 1,2-dimethoxyethane. In a separate vial the Ni-catalyst was prepared by dissolving 250 μg 1,2-dimethoxyethane-dichloronickel (1:1) (1.2 μmol) and 250 μg 4,4-di-tert-butyl-2,2-bipyridine (1.2 μmol) in 1,2-dimethoxyethane (100-fold amount in 10 ml) followed by stirring for 5 min. The catalyst solution (0.1 ml) was syringed to the sealed reaction vial and argon was buddle through the solution for 5 min., then 71 μL 1,1,1,3,3,3-hexamethyl-2-(trimethylsilyl)trisilane (230 μmol) was added. The vial was placed in a water bath (to keep the temp. below 35° C.) and was subsequently irradiated by two 40 W Kessil LED Aquarium lamps for 23 h. The reaction was quenched with half sat. sodium bicarbonate solution, extracted with ethyl acetate (3×), dried over sodium sulphate and concentrated in vacuum. The crude material was purified by RP-HPLC (instrument: Waters Autopurificationsystem; column: YMC-Triart C18 5μ 100×30 mm; eluent A: water (0.2 vol. % aq. ammonia 32%), eluent B: acetonitrile; gradient: 0.00-0.50 min. 28% B (25→70 ml/min), 0.51-5.50 min. 56-64% B (70 ml/min), DAD scan: 210-400 nm) to give 9 mg of the title compound (10% yield, 95% purity).

$^1$H NMR (400 MHz, DMSO-$d_6$) δ [ppm]: 1.90 (m, 4H), 2.76 (m, 1H), 2.86 (s, 6H), 3.49 (m, 2H), 3.58 (s, 3H), 3.83 (m, 2H), 6.70 (m, 2H), 7.17 (m, 2H), 7.36 (m, 1H), 7.58 (m, 1H), 7.73 (m, 1H), 7.93 (m, 1H).

LC-MS (Method 2): $R_t$=1.33 min; MS (ESIpos): m/z=387 [M+H]$^+$

Example 47

1-methyl-2-oxo-4-{4-[4-(propan-2-yl)phenyl]piperidin-1-yl}-1,2-dihydroquinoline-3-carbonitrile

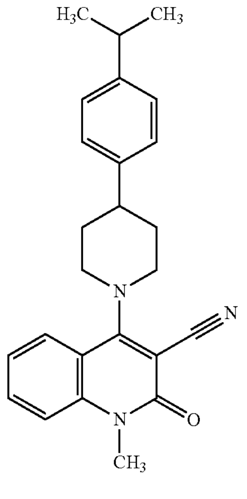

A solution of 47.9 mg 4-chloro-1-methyl-2-oxo-1,2-dihydroquinoline-3-carbonitrile (219 μmol, CAS 150617-68-8), 53.4 mg 4-[4-(propan-2-yl)phenyl]piperidine (263 μmol, intermediate 28) and 61 μL triethylamine (440 μmol) in 1.4 mL 2-propanol was stirred for 6 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). The impure product was purified by RP-HPLC (column: X-Bridge C18 5 μm 100×30 mm, mobile phase: acetonitrile/water (0.2 vol. % ammonia 32%)-gradient) to give 15 mg of the title compound (95% purity, 17% yield).

$^1$H NMR (400 MHz, DMSO-$d_6$) δ [ppm]: 1.20 (d, 6H), 1.96 (m, 4H), 2.86 (m, 2H), 3.51 (m, 2H), 3.58 (s, 3H), 3.84 (m, 2H), 7.21 (m, 2H), 7.27 (m, 2H), 7.36 (m, 1H), 7.57 (m, 1H), 7.74 (ddd, 1H), 7.93 (dd, 1H).

LC-MS (Method 2): $R_t$=1.52 min; MS (ESIpos): m/z=386.5 [M+H]$^+$

Example 48

4-{4-[4-(benzyloxy)phenyl]piperidin-1-yl}-1-methyl-2-oxo-1,2-dihydroquinoline-3-carbonitrile

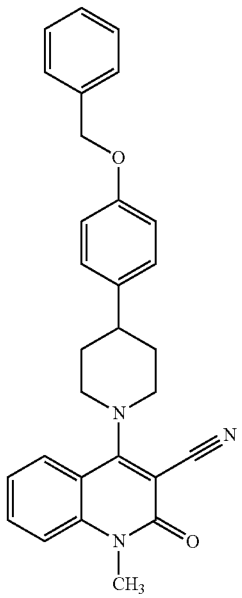 [SMILES: Cn1c(=O)c(C#N)c(N2CCC(c3ccc(OCc4ccccc4)cc3)CC2)c2ccccc21]

To a 8 mL vial equipped with a stir bar was added 100 mg 4-(4-bromopiperidin-1-yl)-1-methyl-2-oxo-1,2-dihydroquinoline-3-carbonitrile (0.29 mmol, intermediate 26), 76.0 mg (bromomethyl)benzene (0.29 mmol, CAS 100-39-0), 2.9 mg photocatalyst bis{3,5-difluoro-2-[5-(trifluoromethyl)pyridin-2-yl]phenyl}iridium(I)hexafluorophosphate-4,4-di-tert-butyl-2,2-bipyridine (1:1:1) (3 μmol, CAS 870987-63-6), 71.6 mg 1,1,1,3,3,3-hexamethyl-2-(trimethylsilyl)trisilane (0.29 mmol) and 61.2 mg anhydrous sodium carbonate (0.58 mmol). The vial was sealed and placed under nitrogen before 4 mL 1,2-dimethoxyethane was added. To a separate vial was added 1.02 mg 1,2-dimethoxyethane-dibromonickel (1:1) (0.006 mmol) and 0.77 mg 4, 4-di-tert-butyl-2-2-bi-pyridine (0.003 mmol). The catalyst vial was sealed, purged with nitrogen then to it was added 2 mL 1,2-dimethoxyethane. The pre-catalyst solution was stirred for 15 min., after which, the 2 mL solution was syringed into the first vial. The resulting mixture was stirred and irradiated with a 34 W blue LED lamp (7 cm away, 1.4 Å, keep the reaction temperature at 25° C.) for 16 h. Upon completion of the reaction, the solid was removed by filtration and the filtrate was concentrated in vacuum. The residue was purified by RP-HPLC [mobile phase A: water (0.1% ammonium formate), mobile phase B: acetonitrile; gradient: 68% B to 95% B in 8 min] to give 3 mg (2.3% yield) of the product as a white solid.

$^1$H-NMR (400 MHz, DMSO-$d_6$): δ [ppm]: 1.92-1.96 (m, 4H), 2.82-2.84 (m, 1H), 3.47-3.54 (m, 2H), 3.58 (s, 3H), 3.81-3.84 (m, 2H), 5.09 (s, 2H), 6.98 (d, 2H), 7.27 (d, 2H), 7.31-7.41 (m, 4H), 7.45 (d, 2H), 7.57 (d, 1H), 7.74 (t, 1H), 7.93 (d, 1H).

Example 49

N-{4-[1-(3-cyano-1-methyl-2-oxo-1,2-dihydroquinolin-4-yl)piperidin-4-yl]phenyl}benzamide

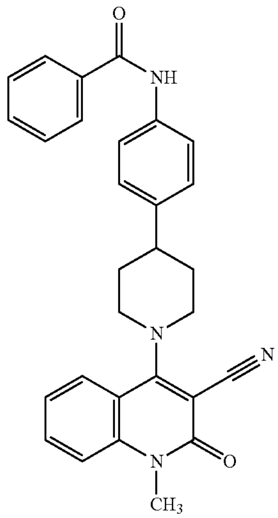 [SMILES: Cn1c(=O)c(C#N)c(N2CCC(c3ccc(NC(=O)c4ccccc4)cc3)CC2)c2ccccc21]

A suspension of 100 mg 4-[4-(4-bromophenyl)piperidin-1-yl]-1-methyl-2-oxo-1,2-dihydroquinoline-3-carbonitrile (237 μmol, example 88), 37.3 mg benzamide (308 μmol, CAS 55-21-0), 10 μL N,N'-dimethylethane-1,2-diamine (95 μmol), 18.04 mg copper(I)iodide (94.8 μmol): and 121 mg potassium phosphate (568 μmol) in 4 mL toluene was stirred for 48 h at 110° C. The mixture was cooled down to rt and was concentrated under reduced pressure. The residue was stirred in ethanol, the precipitate was collected by filtration and dried in vacuum. The impure product was solved in dichloromethane/ethanol, after evaporation of dichloromethane the precipitate was collected by filtration and dried in vacuum. 57.4 mg of the title compound were obtained (50% yield, 95% purity).

$^1$H NMR (400 MHz, DMSO-$d_6$) δ ppm 1.90-2.08 (m, 4H) 2.81-2.99 (m, 1H) 3.47-3.63 (m, 5H): 3.79-3.95 (m, 2H) 7.29-7.42 (m, 3H) 7.49-7.63 (m, 4H) 7.69-7.80 (m, 3H) 7.90-8.00 (m, 3H) 10.16-10.35 (m, 1H).

LC-MS (Method 1): $R_t$=1.23 min; MS (ESIpos): m/z=464 $[M+H]^+$

Example 50

1-methyl-4-[4-(1-methyl-1H-indol-5-yl)piperidin-1-yl]-2-oxo-1,2-dihydroquinoline-3-carbonitrile

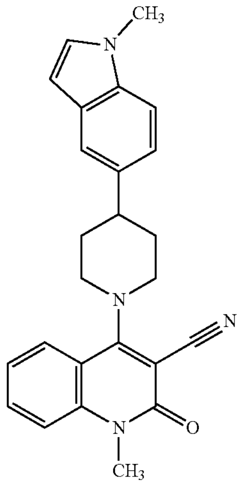 [SMILES: Cn1ccc2cc(C3CCN(c4c(C#N)c(=O)n(C)c5ccccc45)CC3)ccc21]

A solution of 157 mg 4-chloro-1-methyl-2-oxo-1,2-dihydroquinoline-3-carbonitrile (718 μmol, CAS 150617-68-8), 200 mg 1-methyl-5-(piperidin-4-yl)-1H-indole (933 μmol, intermediate 30): and 200 μL triethylamine (1.4 mmol) in 4.7 mL 2-propanol was stirred for 6 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%). The impure product was purified by RP-HPLC (instrument: Labomatic HD5000, Labocord-5000; Gilson GX-241, Labcol Vario 4000, column: YMC Cellulose SB 5μ 250×30 mm; eluent: methanol+0.1 vol. % diethylamine (99%)/ethanol 50:50%; flow 40.0 ml/min.; UV 254 nm) to give 25 mg of the title compound (95% purity, 8% yield).

$^1$H NMR (400 MHz, DMSO-$d_6$) δ [ppm]: 2.02 (m, 4H), 2.95 (m, 1H), 3.55 (m, 5H), 3.77 (m, 3H), 3.87 (m, 2H), 6.39 (m, 1H), 7.16 (m, 1H), 7.28 (m, 1H), 7.37 (m, 2H), 7.50 (m, 1H), 7.58 (m, 1H), 7.74 (m, 1H), 7.96 (m, 1H).

LC-MS (Method 2): $R_t$=1.32 min; MS (ESIpos): m/z=397.5 $[M+H]^+$

Example 51

4-[4-(3-fluoro-5-methylphenyl)piperidin-1-yl]-1-methyl-2-oxo-1,2-dihydroquinoline-3-carbonitrile

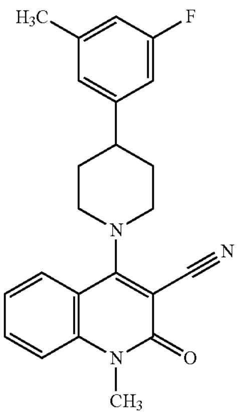

15 mg 4-(4-bromopiperidin-1-yl)-1-methyl-2-oxo-1,2-dihydroquinoline-3-carbonitrile (43.3 μmol, intermediate 26), 650 μg bis{3,5-difluoro-2-[5-(trifluoromethyl)pyridin-2-yl] phenyl}iridium(I)hexafluorophosphate-4,4-di-tert-butyl-2,2-bipyridine (1:1:1) (0.58 μmol, CAS 870987-63-6), 1.38 mg lithium hydroxide (57.8 μmol) and 8.9 μL 1,1,1,3,3,3-hexamethyl-2-(trimethylsilyl)trisilane (29 μmol) were dissolved in the reaction vial in 570 μL 1,2-dimethoxyethane. In a separate vial the Ni-catalyst was prepared by dissolving 32 μg 1,2-dimethoxyethane-dichloronickel (1:1) (0.14 μmol) and 39 μg 4,4-di-tert-butyl-2,2-bipyridine (0.14 μmol) in 1,2-dimethoxyethane (100-fold amount in 10 ml) followed by stirring for 5 min. (if necessary heated to 50° C.). The catalyst solution (0.1 ml) was syringed to the sealed reaction vial and argon was buddle through the solution for 5 min., then 3.6 μL 1-bromo-3-fluoro-5-methylbenzene (29 μmol, CAS 202865-83-6) was added. The vial was placed in a water bath (to keep the temp. below 35° C.) and was subsequently irradiated by two 40 W Kessil LED Aquarium lamps for 2 h. The reaction was concentrated in vacuum and purified by RP-HPLC (column: Chromatorex 125×30 mm, 10 μm mobile phase: water (0.2 vol. % ammonia 32%)/acetonitrile)-gradient) to give 3 mg of the title compound (18% yield, 95% purity).

$^1$H NMR (400 MHz, DMSO-$d_6$) δ [ppm]: 1.95 (m, 4H), 2.30 (s, 3H), 2.86 (m, 1H), 3.55 (m, 5H), 3.83 (m, 2H), 6.87 (m, 1H), 7.00 (m, 2H), 7.34 (m, 1H), 7.56 (m, 1H), 7.71 (m, 1H), 7.93 (m, 1H).

LC-MS (Method 2): $R_t$=1.38 min; MS (ESIpos): m/z=376.4 [M+H]$^+$

Example 52

4-[4-(2-methoxyphenyl)piperidin-1-yl]-1-methyl-2-oxo-1,2-dihydroquinoline-3-carbonitrile

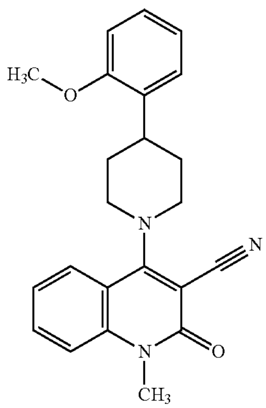 [SMILES: COc1ccccc1C1CCN(c2c(C#N)c(=O)n(C)c3ccccc23)CC1]

A suspension of 120 mg 4-chloro-1-methyl-2-oxo-1,2-dihydroquinoline-3-carbonitrile (494 μmol, CAS 150617-68-8) and 283 mg 4-(2-methoxyphenyl)piperidine (1.48 mmol, CAS 58333-75-8) in 2.4 mL 2-propanol was stirred for 2 h under reflux. The mixture was cooled down to rt, water was added, the precipitate was collected by filtration and dried in vacuum. 177 mg of the title compound were obtained (92% yield, 96% purity).

$^1$H NMR (400 MHz, DMSO-$d_6$) δ ppm 1.86-2.05 (m, 4H) 3.18-3.29 (m, 1H) 3.46-3.62 (m, 5H): 3.80-3.90 (m, 5H) 6.93-7.03 (m, 2H) 7.18-7.26 (m, 1H) 7.28-7.40 (m, 2H) 7.54-7.62 (m, 1H) 7.70-7.81 (m, 1H) 7.90-7.97 (m, 1H).

LC-MS (Method 2): $R_t$=1.34 min; MS (ESIpos): m/z=374.6 [M+H]$^+$

Example 53

4-[4-([1,1'-biphenyl]-4-yl)piperidin-1-yl]-1-methyl-2-oxo-1,2-dihydroquinoline-3-carbonitrile

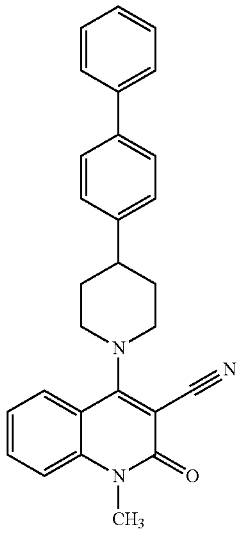 [SMILES: Cn1c(=O)c(C#N)c(N2CCC(c3ccc(-c4ccccc4)cc3)CC2)c2ccccc21]

To an 8 mL vial equipped with a stir bar was added 100 mg 4-(4-bromopiperidin-1-yl)-1-methyl-2-oxo-1,2-dihydroquinoline-3-carbonitrile (0.29 mmol, intermediate 26), 67.3 mg 4-bromobiphenyl (0.29 mmol, CAS 92-66-0), 2.9 mg photocatalyst bis{3,5-difluoro-2-[5-(trifluoromethyl)pyridin-2-yl]phenyl}iridium(I)hexafluorophosphate-4,4-di-tert-butyl-2,2-bipyridine (1:1:1) (2.89 μmol, CAS 870987-63-6), 71.6 mg 1,1,1,3,3,3-hexamethyl-2-(trimethylsilyl)trisilane (289 μmol) and 61.2 mg anhydrous sodium carbonate (0.58 mmol). The vial was sealed and placed under nitrogen before 4 mL 1,2-dimethoxyethane was added. To a separate vial was added 1.02 mg 1,2-dimethoxyethane-dibromonickel (1:1) (0.003 mmol) and 0.77 mg 4,4-di-tert-butyl-2-2-bi-pyridine (0.003 mmol). The catalyst vial was sealed, purged with nitrogen then to it was added 2 mL 1,2-dimethoxyethane. The precatalyst solution was stirred for 15 min., after that, the solution (2 ml) was syringed into the first vial. The resulting mixture was stirred and irradiated with a 34 W blue LED lamp (7 cm away, 1.4 Å, keep the reaction temperature at 25° C.) for 16 h. Upon completion of the reaction, the solid was removed by filtration and the filtrate was concentrated in vacuum. The residue was purified by RP-HPLC [mobile phase A: water (0.1% ammonium formate), mobile phase B: acetonitrile; gradient: 68% B to 95% B in 8 min] to give 28.8 mg (22% yield) of the product as a white solid.

$^1$H-NMR (400 MHz, DMSO-$d_6$): δ [ppm]: 1.99-2.05 (m, 4H), 2.92-3.00 (m, 1H), 3.52-3.55 (m, 2H), 3.59 (s, 3H), 3.85-3.88 (m, 2H), 7.34-7.39 (m, 2H), 7.45-7.49 (m, 4H), 7.58 (d, 1H), 7.63-7.67 (m, 4H), 7.74 (t, 1H), 7.96 (d, 1H).

Example 54

4-[4-(4-chlorophenyl)piperidin-1-yl]-1-methyl-2-oxo-1,2-dihydroquinoline-3-carbonitrile

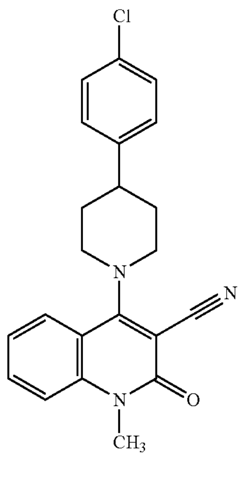

To a solution of 120 mg 4-chloro-1-methyl-2-oxo-1,2-dihydroquinoline-3-carbonitrile (0.55 mmol, CAS 150617-68-8) and 0.29 mL N,N-diisopropylethylamine (1.65 mmol) in 2.7 mL 2-propanol was added 153 mg 4-(4-chlorophenyl) piperidine hydrogen chloride salt (1:1) (0.66 mmol, CAS 6652-06-8) and the reaction was stirred under reflux for 2 h. The reaction was allowed to cool to ambient temperature and poured into water. The precipitate was filtered off and dried in vacuum. The title compound was obtained in 82% yield (172 mg, 99% purity).

$^1$H NMR (400 MHz, DMSO-$d_6$) δ ppm 1.86-2.10 (m, 4H) 2.83-3.00 (m, 1H) 3.43-3.63 (m, 5H): 3.76-3.92 (m, 2H) 7.31-7.43 (m, 5H) 7.54-7.60 (m, 1H) 7.70-7.79 (m, 1H) 7.90-7.97 (m, 1H).

LC-MS (Method 3): Rt=1.37 min; MS (ESIpos): m/z=378.1 [M+H]+

Example 55

4-[4-(3-methoxyphenyl)piperidin-1-yl]-1-methyl-2-oxo-1,2-dihydroquinoline-3-carbonitrile

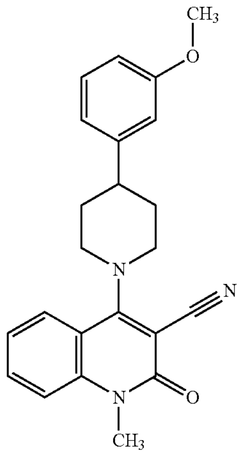 [SMILES: COc1cccc(C2CCN(c3c(C#N)c(=O)n(C)c4ccccc34)CC2)c1]

To a solution of 120 mg 4-chloro-1-methyl-2-oxo-1,2-dihydroquinoline-3-carbonitrile (549 μmol, CAS 150617-68-8) and 290 μL N,N-diisopropylethylamine (1.6 mmol) in 2.6 mL 2-propanol was added 150 mg 4-(3-methoxyphenyl) piperidine hydrogen chloride salt (1:1) (659 μmol, CAS 325808-20-6) and the reaction was stirred under reflux for 2 h. The reaction was allowed to cool to ambient temperature and poured into water. The precipitate was filtered off and dried in vacuum. The title compound was obtained in 69% yield (143 mg, 99% purity).

$^1$H NMR (400 MHz, DMSO-$d_6$) δ ppm 1.88-2.08 (m, 4H) 2.76-2.94 (m, 1H) 3.43-3.62 (m, 5H): 3.73-3.91 (m, 5H) 6.77-6.84 (m, 1H) 6.88-6.98 (m, 2H) 7.20-7.39 (m, 2H) 7.52-7.62 (m, 1H) 7.68-7.80 (m, 1H) 7.89-8.03 (m, 1H).

LC-MS (Method 3): $R_t$=1.25 min; MS (ESIpos): m/z=374.2 $[M+H]^+$

Example 56

1-methyl-2-oxo-4-[4-(4-phenoxyphenyl)piperidin-1-yl]-1,2-dihydroquinoline-3-carbonitrile

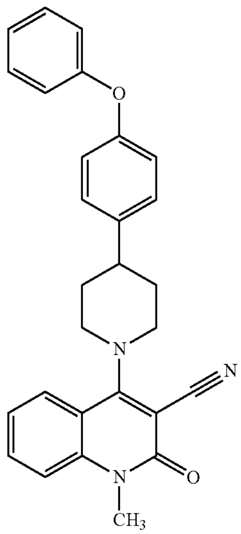 [SMILES: Cn1c(=O)c(C#N)c(N2CCC(c3ccc(Oc4ccccc4)cc3)CC2)c2ccccc21]

To an 8 mL vial equipped with a stir bar was added 100 mg 4-(4-bromopiperidin-1-yl)-1-methyl-2-oxo-1,2-dihydroquinoline-3-carbonitrile (0.29 mmol, intermediate 26), 71.9 mg 1-bromo-4-phenoxybenzene (289 μmol, CAS 101-55-3), 2.9 mg photocatalyst bis{3,5-difluoro-2-[5-(trifluoromethyl)pyridin-2-yl]phenyl}iridium(I)hexafluorophosphate-4,4-di-tert-butyl-2,2-bipyridine (1:1:1) (2.89 μmol, CAS 870987-63-61), 71.6 mg 1,1,3,3,3-hexamethyl-2-(trimethylsilyl)trisilane (289 μmol) and 61.2 mg anhydrous sodium carbonate (0.58 mmol). The vial was sealed and placed under nitrogen before 4 mL 1,2-dimethoxyethane was added. To a separate vial was added 1.02 mg 1,2-dimethoxyethane-dibromonickel (1:1) (2.89 μmol) and 0.77 mg 4,4-di-tert-butyl-2,2-bi-pyridine (0.003 mmol). The catalyst vial was sealed, purged with nitrogen then to it was added 2 mL 1,2-dimethoxyethane. The pre-catalyst solution was stirred for 15 min., after which, the solution (2 ml) was syringed into the first vial. The resulting mixture was stirred and irradiated with a 34 W blue LED lamp (7 cm away, 1.4 Å, keep the reaction temperature at 25° C.) for 16 h. Upon completion of the reaction, the solid was removed by filtration and the filtrate was concentrated under vacuum. The residue was purified by RP-HPLC [mobile phase A: water (0.1% ammonium formate), mobile phase B: acetonitrile; gradient: 35% B to 75% B in 8 min] to give 61.5 mg (49% yield) of the product as a white solid.

$^1$H-NMR (400 MHz, DMSO-$d_6$): δ [ppm]: 1.97-2.02 (m, 4H), 2.87-2.95 (m, 1H), 3.49-3.56 (m, 2H), 3.58 (s, 3H), 3.83-3.86 (m, 2H), 6.99-7.01 (m, 4H), 7.13 (t, 1H), 7.34-7.41 (m, 5H), 7.57 (d, 1H), 7.75 (t, 1H), 7.94 (d, 1H).

TABLE 5

Following examples of table 5 were prepared from assigned starting materials and according to the procedure stated in the table.

| Example | Structure | IUPAC-Name | Reference, Starting materials | Analytics |
|---|---|---|---|---|
| 57 | 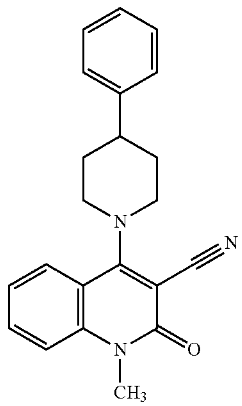 [SMILES: Cn1c(=O)c(C#N)c(N2CCC(c3ccccc3)CC2)c2ccccc21] | 1-methyl-2-oxo-4-(4-phenylpiperidin-1-yl)-1,2-dihydroquinoline-3-carbonitrile | in analogy to example 52 with 4-chloro-1-methyl-2-oxo-1,2-dihydroquinoline-3-carbonitrile (CAS 150617-68-8) and 4-phenylpiperidine (CAS 771-99-3) | $^1$H NMR (400 MHz, DMSO-$d_6$) δ [ppm]: 1.97 (m, 4 H), 2.89 (m, 1 H), 3.54 (m, 5 H), 3.85 (m, 2 H), 7.23 (m, 1 H), 7.35 (m, 5 H), 7.58 (m, 1 H), 7.76 (m, 1 H), 7.93 (m, 1 H). LC-MS (Method 2): $R_t$ = 1.31 min; MS (ESIpos): m/z = 344.5 $[M + H]^+$ |

TABLE 5-continued

Following examples of table 5 were prepared from assigned starting materials and according to the procedure stated in the table.

| Example | Structure | IUPAC-Name | Reference, Starting materials | Analytics |
|---|---|---|---|---|
| 58 | 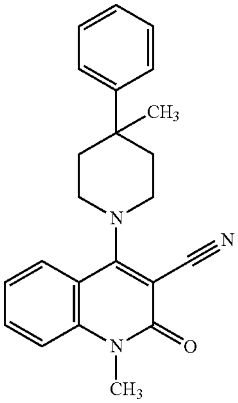 [SMILES: Cn1c(=O)c(C#N)c(N2CCC(C)(c3ccccc3)CC2)c2ccccc21] | 1-methyl-4-(4-methyl-4-phenylpiperidin-1-yl)-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8) and 4-methyl-4-phenylpiperidine (CAS 160132-91-2) | $^1$H NMR (400 MHz, DMSO-$d_6$) δ [ppm]: 1.31 (m, 3 H), 2.00 (m, 2 H), 2.33 (m, 2 H), 3.54 (m, 5 H), 3.69 (m, 2 H), 7.23 (m, 1 H), 7.36 (m, 3 H), 7.47 (m, 2 H), 7.55 (m, 1 H), 7.73 (m, 1 H), 7.87 (m, 1 H). LC-MS (Method 2): $R_t$ = 1.33 min; MS (ESIpos): m/z = 358.6 $[M + H]^+$ |
| 59 | 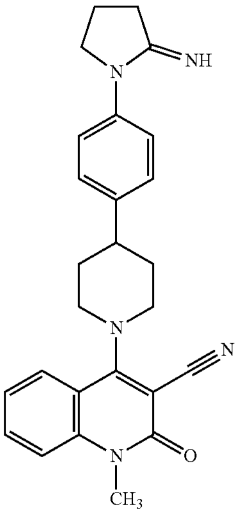 [SMILES: Cn1c(=O)c(C#N)c(N2CCC(c3ccc(N4CCCC4=N)cc3)CC2)c2ccccc21] | 1-methyl-2-oxo-4-{4-[4-(2-oxopyrrolidin-1-yl)phenyl]piperidin-1-yl}-1,2-dihydroquinoline-3-carbonitrile | in analogy to example 35 with 4-[4-(4-bromophenyl)piperidin-1-yl]-1-methyl-2-oxo-1,2-dihydroquinoline-3-carbonitrile (example 88) and pyrrolidin-2-one (CAS 616-45-5) | $^1$H NMR (400 MHz, DMSO-$d_6$) δ ppm 1.89-2.12 (m, 6 H) 2.46 (s, 2 H) 2.80-3.00 (m, 1 H) 3.47-3.63 (m, 5 H) 3.77-3.92 (m, 4 H) 7.29-7.42 (m, 3 H) 7.50-7.65 (m, 3 H) 7.69-7.81 (m, 1 H) 7.88-8.05 (m, 1 H). LC-MS (Method 3): Rt = 1.05 min; MS (ESIpos): m/z = 427.2 [M + H]+ |
| 60 | 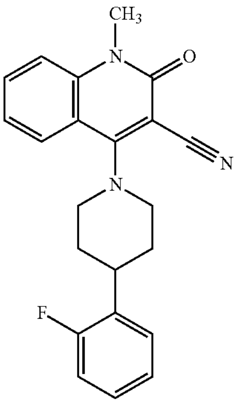 [SMILES: Cn1c(=O)c(C#N)c(N2CCC(c3ccccc3F)CC2)c2ccccc21] | 4-[4-(2-fluorophenyl)piperidin-1-yl]-1-methyl-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(2-fluorophenyl)piperidine (CAS 180161-17-5) and with 1-methylpyrrolidin-2-one as solvent | LC-MS (Method 1): Rt = 1.27 min; MS (ESIpos): m/z = 362.1 [M + H]+ |

TABLE 5-continued

Following examples of table 5 were prepared from assigned starting materials and according to the procedure stated in the table.

| Example | Structure | IUPAC-Name | Reference, Starting materials | Analytics |
| --- | --- | --- | --- | --- |
| 61 | 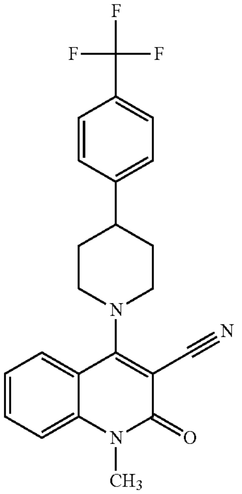 [SMILES: Cn1c(=O)c(C#N)c(N2CCC(c3ccc(C(F)(F)F)cc3)CC2)c2ccccc21] | 1-methyl-2-oxo-4-{4-[4-(trifluoromethyl)phenyl]piperidin-1-yl}-1,2-dihydroquinoline-3-carbonitrile | in analogy to example 42 with intermediate 26 and 1-bromo-4-(trifluoromethyl)benzene (CAS 402-43-7) | $^1$H-NMR (400 MHz, DMSO-$d_6$): δ [ppm] = 2.00-2.08 (m, 4H), 3.01-3.07 (m, 1H), 3.49-3.57 (m, 2H), 3.59 (s, 3H), 3.84-3.87 (m, 2H), 7.36 (t, 1H), 7.57-7.63 (m, 3H), 7.70-7.77 (m, 3H), 7.96 (d, 1H). |
| 62 | 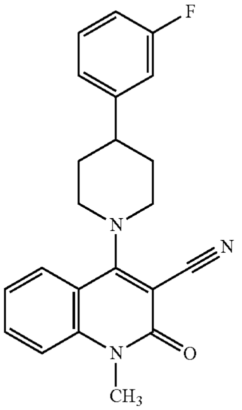 [SMILES: Cn1c(=O)c(C#N)c(N2CCC(c3cccc(F)c3)CC2)c2ccccc21] | 4-[4-(3-fluorophenyl)piperidin-1-yl]-1-methyl-2-oxo-1,2-dihydroquinoline-3-carbonitrile | in analogy to example 41 with 4-chloro-1-methyl-2-oxo-1,2-dihydroquinoline-3-carbonitrile (CAS 150617-68-8) and 4-(3-fluorophenyl)piperidine (CAS 104774-94-9) | $^1$H NMR (400 MHz, DMSO-$d_6$) δ [ppm]: 1.99 (m, 4 H), 2.94 (m, 1 H), 3.55 (m, 5 H), 3.82 (m, 2 H), 7.06 (m, 1 H), 7.23 (m, 2 H), 7.38 (m, 2 H), 7.57 (m, 1 H), 7.76 (m, 1 H), 7.96 (m, 1 H). LC-MS (Method 2): Rt = 1.31 min; MS (ESIpos): m/z = 362.5 [M + H]+ |
| 63 | 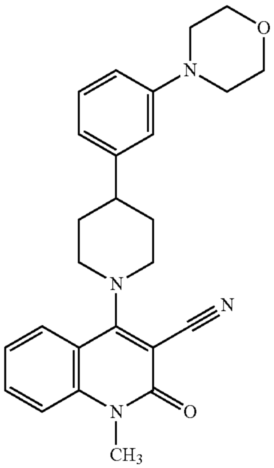 [SMILES: Cn1c(=O)c(C#N)c(N2CCC(c3cccc(N4CCOCC4)c3)CC2)c2ccccc21] | 1-methyl-4-(4-3-(morpholin-4-yl)phenyl]piperidin-1-yl}-2-oxo-1,2-dihydroquinoline-3-carbonitrile | in analogy to example 92 with example 85 and morpholine (CAS 110-91-8) | $^1$H NMR (400 MHz, DMSO-$d_6$) δ ppm 1.87-2.09 (m, 4 H) 2.75-2.90 (m, 1 H) 3.04-3.19 (m, 4 H) 3.42-3.64 (m, 5 H) 3.68-3.78 (m, 4 H) 3.79-3.90 (m, 2 H) 6.75-6.86 (m, 2 H) 6.89-6.99 (m, 1 H) 7.14-7.23 (m, 1 H) 7.31-7.42 (m, 1 H) 7.55-7.61 (m, 1 H) 7.70-7.81 (m, 1 H) 7.88- 8.00 (m, 1 H). LC-MS (Method 1): Rt = 1.23 min; MS (ESIpos): m/z = 429.7 [M + H]+ |

TABLE 5-continued

| Following examples of table 5 were prepared from assigned starting materials and according to the procedure stated in the table. | | | | |
|---|---|---|---|---|
| Example | Structure | IUPAC-Name | Reference, Starting materials | Analytics |
| 64 | 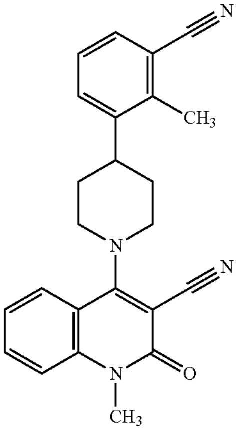 [SMILES: Cc1c(C#N)cccc1C1CCN(c2c(C#N)c(=O)n(C)c3ccccc23)CC1] | 4-[4-(3-cyano-2-methylphenyl) piperidin-1-yl]-1-methyl-2-oxo-1,2-dihydroquinoline-3-carbonitrile | in analogy to example 45 with intermediate 26 and 3-bromo-2-methylbenzonitrile (CAS 52780-15-1) | $^{1}H$ NMR (400 MHz, DMSO-$d_6$) δ [ppm]: 1.95 (m, 4H), 2.58 (s, 3 H), 3.19 (m, 1 H), 3.56 (m, 5 H), 3.83 (m, 2 H), 7.39 (m, 2 H), 7.56 (m, 1 H), 7.66 (m, 1 H), 7.75 (m, 2 H), 7.96 (m, 1 H). LC-MS (Method 2): Rt = 1.23 min; MS (ESIpos): m/z = 383 [M + H]+ |
| 65 | 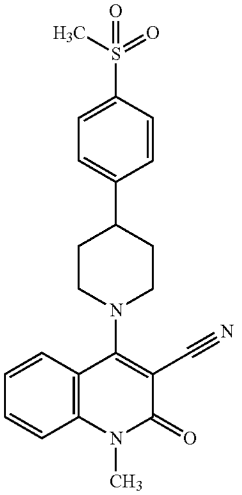 [SMILES: Cn1c(=O)c(C#N)c(N2CCC(c3ccc(S(C)(=O)=O)cc3)CC2)c2ccccc21] | 4-{4-[4-(methanesulfonyl) phenyl] piperidin-1-yl}-1-methyl-2-oxo-1,2-dihydroquinoline-3-carbonitrile | in analogy to example 164 with example 88 | $^{1}H$ NMR (400 MHz, DMSO-$d_6$) δ ppm 1.92-2.10 (m, 4 H) 2.99-3.12 (m, 1 H) 3.21 (s, 3 H) 3.47-3.64 (m, 5H) 3.85 (br d, 2 H) 7.33-7.40 (m, 1 H) 7.55-7.60 (m, 1 H) 7.63-7.70 (m, 2 H) 7.71-7.80 (m, 1 H) 7.86-8.02 (m, 3 H). LC-MS (Method 3): Rt = 0.96 min; MS (ESIpos): m/z = 422.1 [M + H]+ |
| 66 | 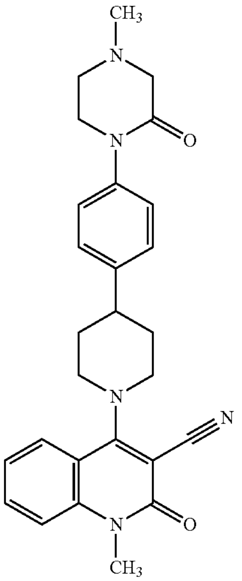 [SMILES: CN1CCN(c2ccc(C3CCN(c4c(C#N)c(=O)n(C)c5ccccc45)CC3)cc2)C(=O)C1] | 1-methyl-4-(4-4-(4-methyl-2-oxopiperazin-1-yl)phenyl] piperidin-1-yl}-2-oxo-1,2-dihydroquinoline-3-carbonitrile | in analogy to example 35 with 4-[4-(4-bromophenyl) piperidin-1-yl]-1-methyl-2-oxo-1,2-dihydroquinoline-3-carbonitrile (example 88) and 4-methylpiperazin-2-one (CAS 34770-60-0) | $^{1}H$ NMR (400 MHz, DMSO-$d_6$) δ ppm 1.89-2.08 (m, 4 H) 2.24-2.31 (m, 3 H) 2.69-2.77 (m, 2 H) 2.85-3.01 (m, 1 H) 3.05-3.19 (m, 2 H) 3.47-3.61 (m, 5 H) 3.62-3.71 (m, 2 H) 3.80-3.92 (m, 2 H) 7.25-7.44 (m, 5 H) 7.53-7.66 (m, 1 H) 7.71-7.81 (m, 1 H) 7.93-7.99 (m, 1 H). LC-MS (Method 3): Rt = 0.66 min; MS (ESIpos): m/z = 456.2 [M + H]+ |

TABLE 5-continued

| Example | Structure | IUPAC-Name | Reference, Starting materials | Analytics |
|---|---|---|---|---|
| Following examples of table 5 were prepared from assigned starting materials and according to the procedure stated in the table. | | | | |
| 67 | 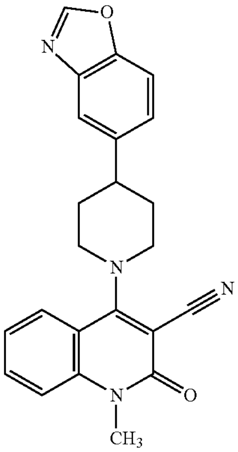 [SMILES: Cn1c(=O)c(C#N)c(N2CCC(c3ccc4ocnc4c3)CC2)c2ccccc21] | 4-[4-(1,3-benzoxazol-5-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8)and intermediate 41 | $^1$H NMR (400 MHz, DMSO-$d_6$) δ [ppm]: 1.19 (d, 6 H), 1.95 (m, 4 H), 2.86 (m, 2 H), 3.54 (m, 5 H), 3.86 (m, 2 H), 7.23 (m, 4 H), 7.36 (m, 1 H), 7.57 (m, 1 H), 7.75 (m, 1 H), 7.92 (m, 1 H). LC-MS (Method 2): Rt = 1.52 min; MS (ESIpos): m/z = 386.5 [M + H]+ |
| 68 | 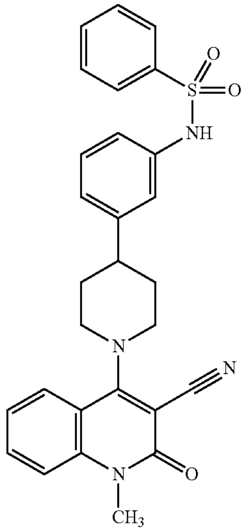 [SMILES: Cn1c(=O)c(C#N)c(N2CCC(c3cccc(NS(=O)(=O)c4ccccc4)c3)CC2)c2ccccc21] | N-{3-[1-(3-cyano-1-methyl-2-oxo-1,2-dihydroquinolin-4-yl)piperidin-4-yl]phenyl}benzenesulfonamide | in analogy to example 35 with 4-[4-(3-bromophenyl)piperidin-1-yl]-1-methyl-2-oxo-1,2-dihydroquinoline-3-carbonitrile (example 85) and benzenesulfonamide (CAS 98-10-2) | $^1$H NMR (400 MHz, DMSO-$d_6$) δ ppm 1.74-1.92 (m, 4 H) 2.74-2.86 (m, 1 H) 3.43-3.63 (m, 5 H) 3.73-3.91 (m, 2 H) 6.89 (br dd, 1 H) 6.99-7.07 (m, 2 H) 7.12-7.20 (m, 1 H) 7.33-7.40 (m, 1 H) 7.51-7.64 (m, 4 H) 7.71-7.82 (m, 3 H) 7.84-7.92 (m, 1 H) 10.17-10.32 (m, 1 H). LC-MS (Method 3): Rt = 1.16 min; MS (ESIpos): m/z = 499.1 [M + H]+ |
| 69 | 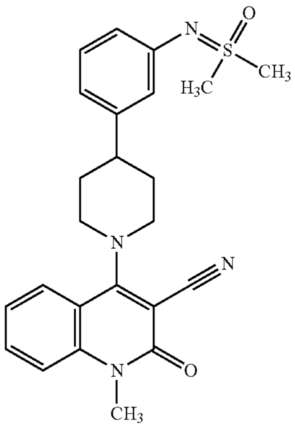 [SMILES: Cn1c(=O)c(C#N)c(N2CCC(c3cccc(N=S(C)(C)=O)c3)CC2)c2ccccc21] | 4-[4-(3-{[dimethyl(oxo)-λ$^6$-sulfanylidene]amino}phenyl)piperidin-1-yl]-1-methyl-2-oxo-1,2-dihydroquinoline-3-carbonitrile | in analogy to example 95 with 4-[4-(3-bromophenyl)piperidin-1-yl]-1-methyl-2-oxo-1,2-dihydroquinoline-3-carbonitrile (example 85) and (methylsulfonimidoyl)methane (CAS 1520-31-6) | $^1$H NMR (400 MHz, DMSO-$d_6$) δ [ppm]: 1.94 (m, 4 H), 2.80 (m, 1 H), 3.20 (s, 6H), 3.56 (m, 5 H), 3.85 (m,2H), 6.86 (m, 3 H), 7.12 (m, 1 H), 7.35 (m, 1 H), 7.62 (br d, 1 H), 7.75 (m, 1 H), 7.94 (m, 1 H). LC-MS (Method 1): Rt = 1.02 min; MS (ESIpos): m/z = 435.7 [M + H]+ |

TABLE 5-continued

Following examples of table 5 were prepared from assigned starting materials and according to the procedure stated in the table.

| Example | Structure | IUPAC-Name | Reference, Starting materials | Analytics |
|---|---|---|---|---|
| 70 | 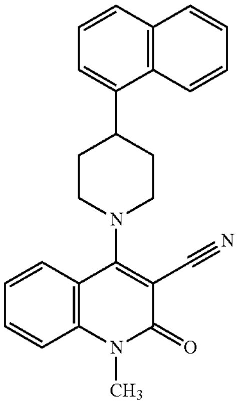 | 1-methyl-4-[4-(naphthalen-1-yl)piperidin-1-yl]-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and intermediate 42 | $^1$H NMR (400 MHz, DMSO-$d_6$) δ [ppm]: 2.09 (m, 4 H), 3.07 (m, 1 H), 3.58 (m, 5 H), 3.89 (m, 2 H), 7.36 (m, 1 H), 7.48 (m, 2 H), 7.59 (m, 2 H), 7.77 (m, 1 H), 7.87 (m, 4 H), 7.99 (m, 1 H). LC-MS (Method 2): Rt = 1.42 min; MS (ESIpos): m/z = 494.5 [M + H]+ |
| 71 | 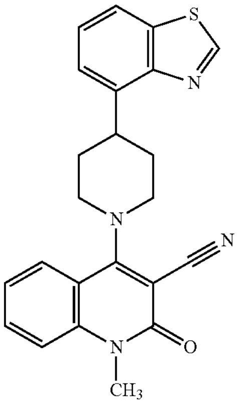 [SMILES: Cn1c(=O)c(C#N)c(N2CCC(c3cccc4scnc34)CC2)c2ccccc21] | 4-[4-(1,3-benzothiazol-4-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8)and intermediate 43 | $^1$H NMR (400 MHz, DMSO-$d_6$) δ [ppm]: 2.11 (m, 2 H), 2.21 (m, 2 H), 3.61 (m, 5 H), 3.87 (m, 3 H), 7.36 (m, 1 H), 7.54 (m, 3 H), 7.74 (m, 1 H), 8.01 (m, 2 H), 9.42 (s, 1 H). LC-MS (Method 2): Rt = 1.26 min; MS (ESIpos): m/z = 401.5 [M + H]+ |
| 72 | 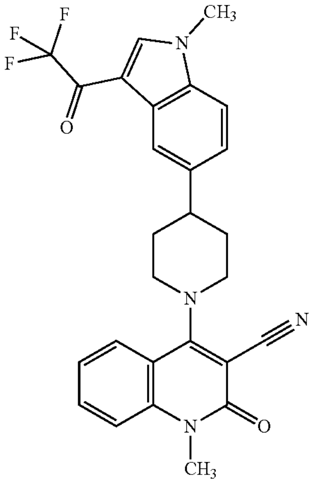 [SMILES: Cn1cc(C(=O)C(F)(F)F)c2cc(C3CCN(c4c(C#N)c(=O)n(C)c5ccccc45)CC3)ccc21] | 1-methyl-4-{4-[1-methyl-3-(trifluoroacetyl)-1H-indol-5-yl]piperidin-1-yl}-2-oxo-1,2-dihydroquinoline-3-carbonitrile | example 72 was isolated as a by-productin example 50. The respective (3-trifluoroacetyl-1H-indol-5-yl)piperidin was already formed in the synthesis of intermediate 29 | $^1$H NMR (400 MHz, DMSO-$d_6$) δ [ppm]: 2.03 (m, 4 H), 3.07 (m, 1 H), 3.58 (m, 5 H), 3.91 (m, 5H), 7.36 (m, 1H), 7.45 (m, 1H), 7.57 (m, 1H), 7.65 (m, 1H), 7.77 (m, 1H), 7.94 (m, 1H), 8.16 (m, 1H), 8.53 (m, 1 H). LC-MS (Method 1): Rt = 1.33 min; MS (ESIpos): m/z = 493.5 [M + H]+ |

TABLE 5-continued

Following examples of table 5 were prepared from assigned starting materials and according to the procedure stated in the table.

| Example | Structure | IUPAC-Name | Reference, Starting materials | Analytics |
|---|---|---|---|---|
| 73 | 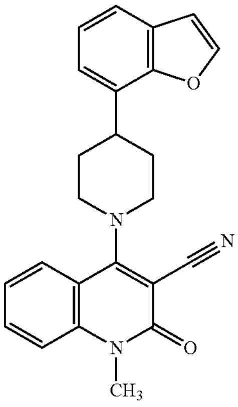 [SMILES: Cn1c(=O)c(C#N)c(N2CCC(c3cccc4ccoc34)CC2)c2ccccc21] | 4-[4-(1-benzofuran-7-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8) and intermediate 44 | $^1$H NMR (400 MHz, DMSO-$d_6$) δ [ppm]: 2.16 (m, 4 H), 3.41 (m, 1 H), 3.60 (m, 5 H), 3.91 (m, 2H), 6.98 (d, 1 H), 7.31 (m, 3 H), 7.57 (m, 2 H), 7.74 (m, 1 H), 7.95 (m, 1 H), 8.03 (m, 1 H). LC-MS (Method 2): Rt = 1.32 min; MS (ESIpos): m/z = 384.5 [M + H]+ |
| 74 | 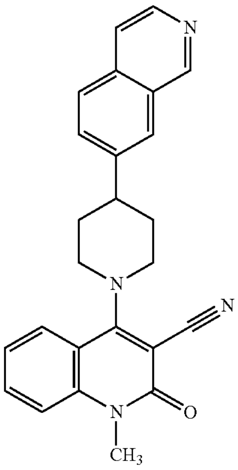 [SMILES: Cn1c(=O)c(C#N)c(N2CCC(c3ccc4ccncc4c3)CC2)c2ccccc21] | 4-[4-(isoquinolin-7-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8) and intermediate 49 | $^1$H NMR (400 MHz, DMSO-$d_6$) δ [ppm]: 2.10 (m, 4 H), 3.15 (m, 1 H), 3.57 (m, 5 H), 3.89 (m, 2 H), 7.38 (m, 1 H), 7.60 (m, 1 H), 7.80 (m, 3 H), 7.99 (m, 2 H), 8.07 (m, 1 H), 8.46 (m, 1 H), 9.30 (m, 1 H). LC-MS (Method 2): Rt = 1.12 min; MS (ESIpos): m/z = 395.6 [M + H]+ |
| 75 | 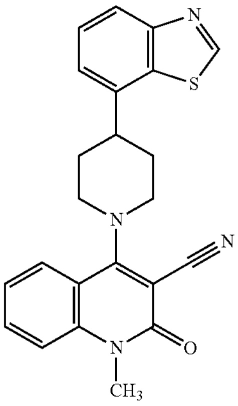 [SMILES: Cn1c(=O)c(C#N)c(N2CCC(c3cccc4ncsc34)CC2)c2ccccc21] | 4-[4-(1,3-benzothiazol-7-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8) and intermediate 45 | $^1$H NMR (400 MHz, DMSO-$d_6$) δ [ppm]: 2.17 (m, 4 H), 3.18 (m, 1 H), 3.62 (m, 5 H), 3.89 (m, 2 H), 7.36 (m, 1 H), 7.58 (m, 3 H), 7.77 (m, 1 H), 7.99 (m, 2 H), 9.43 (m, 1 H). LC-MS (Method 2): Rt = 1.15 min; MS (ESIpos): m/z = 401.5 [M + H]+ |

TABLE 5-continued

Following examples of table 5 were prepared from assigned starting materials and according to the procedure stated in the table.

| Example | Structure | IUPAC-Name | Reference, Starting materials | Analytics |
|---|---|---|---|---|
| 76 | 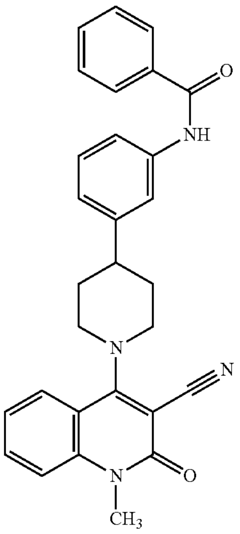 [SMILES: Cn1c(=O)c(C#N)c(N2CCC(c3cccc(NC(=O)c4ccccc4)c3)CC2)c2ccccc21] | N-{3-[1-(3-cyano-1-methyl-2-oxo-1,2-dihydroquinolin-4-yl)piperidin-4-yl]phenyl}benzamide | in analogy to example 35 with 4-[4-(3-bromophenyl)piperidin-1-yl]-1-methyl-2-oxo-1,2-dihydroquinoline-3-carbonitrile (example 85) and benzamide (CAS 55-21-0) | $^{1}$H NMR (400 MHz, DMSO-$d_6$) δ [ppm]: 1.97 (m, 4 H), 2.91 (m, 1 H), 3.56 (m, 5 H), 3.86 (m, 2 H), 7.11 (m, 1 H), 7.34 (m, 2 H), 7.56 (m, 4 H), 7.73 (m, 3 H), 7.94 (m, 3 H), 10.25 (s, 1 H). LC-MS (Method 1): Rt = 1.24 min; MS (ESIpos): m/z = 463.5 [M + H]+ |
| 77 | 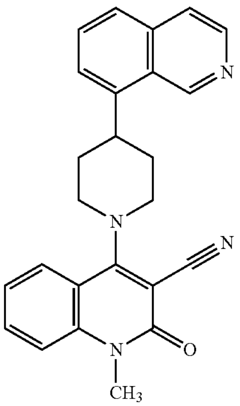 [SMILES: Cn1c(=O)c(C#N)c(N2CCC(c3cccc4ccncc34)CC2)c2ccccc21] | 4-[4-(isoquinolin-8-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8) and intermediate 46 | $^{1}$H NMR (400 MHz, DMSO-$d_6$) δ [ppm]: 2.16 (m, 4 H), 3.59 (m, 3 H), 3.77 (m, 2 H), 3.91 (m, 2 H), 4.05 (m, 1 H), 7.39 (m, 1 H), 7.58 (m, 1 H), 7.76 (m, 3 H), 7.87 (m, 2 H), 7.98 (m, 1 H), 8.54 (m, 1 H), 9.75 (m, 1 H). LC-MS (Method 2): Rt = 1.15 min; MS (ESIpos): m/z = 395.8 [M + H]+ |
| 78 | 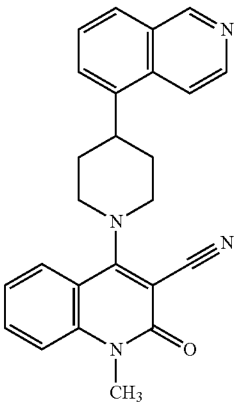 [SMILES: Cn1c(=O)c(C#N)c(N2CCC(c3cccc4cnccc34)CC2)c2ccccc21] | 4-[4-(isoquinolin-5-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8) and intermediate 47 | $^{1}$H NMR (400 MHz, DMSO-$d_6$) δ [ppm]: 2.09 (m, 4 H), 3.59 (s, 3 H), 3.76 (m, 3 H), 3.89 (m, 2 H), 7.36 (m, 1 H), 7.58 (m, 1 H), 7.72 (m, 2 H), 7.86 (m, 1 H), 7.99 (m, 2 H), 8.19 (m, 1 H), 8.56 (d, 1 H), 9.33 (s, 1 H). LC-MS (Method 2): Rt = 1.12 min; MS (ESIpos): m/z = 395.5 [M + H]+ |

TABLE 5-continued

Following examples of table 5 were prepared from assigned starting materials and according to the procedure stated in the table.

| Example | Structure | IUPAC-Name | Reference, Starting materials | Analytics |
|---|---|---|---|---|
| 79 | 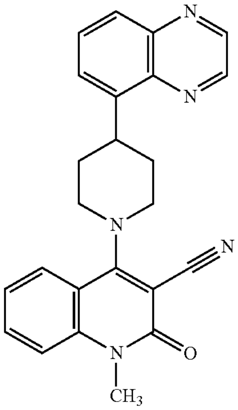 [SMILES: Cn1c(=O)c(C#N)c(N2CCC(c3cccc4nccnc34)CC2)c2ccccc21] | 1-methyl-2-oxo-4-[4-(quinoxalin-5-yl)piperidin-1-yl]-1,2-dihydroquinoline-3-carbonitrile | in analogy to example 47 with 4-chloro-1-methyl-2-oxo-1,2-dihydroquinoline-3-carbonitrile (CAS 150617-68-8) and intermediate 48 | $^1$H NMR (400 MHz, DMSO-$d_6$) δ [ppm]: 2.14 (m, 4 H), 3.59 (s, 3 H), 3.67 (br t, 2 H), 3.91 (m, 2 H), 4.22 (m, 1 H), 7.37 (m, 1 H), 7.57 (m, 1 H), 7.75 (m, 1 H), 7.90 (m, 2 H), 8.00 (m, 2 H), 9.01 (m, 2 H). LC-MS (Method 2): Rt = 1.15 min; MS (ESIpos): m/z = 396.6 [M + H]+ |
| 80 | 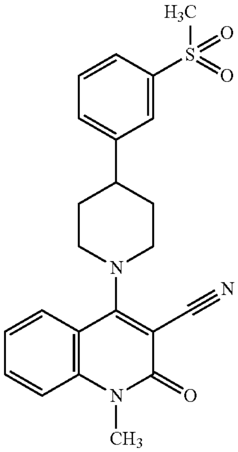 [SMILES: Cn1c(=O)c(C#N)c(N2CCC(c3cccc(S(C)(=O)=O)c3)CC2)c2ccccc21] | 4-{4-[3-(methanesulfonyl)phenyl]piperidin-1-yl}-1-methyl-2-oxo-1,2-dihydroquinoline-3-carbonitrile | in analogy to example 164 with 4-[4-(3-bromophenyl)piperidin-1-yl]-1-methyl-2-oxo-1,2-dihydroquinoline-3-carbonitrile (example 85) | $^1$H NMR (400 MHz, DMSO-$d_6$) δ [ppm]: 1.20 (t, 3H), 1.94 (m, 2 H), 2.83 (m, 1 H), 3.48 (m, 2 H), 3.74 (m, 3 H), 3.83 (m, 2 H), 4.24 (m, 2 H), 6.90 (m, 2 H), 7.26 (m, 2 H), 7.34 (m, 1 H), 7.61 (m, 1 H), 7.73 (m, 1 H), 7.93 (m, 1 H). LC-MS (Method 1): Rt = 1.07 min; MS (ESIpos): m/z = 422 [M + H]+ |
| 81 | 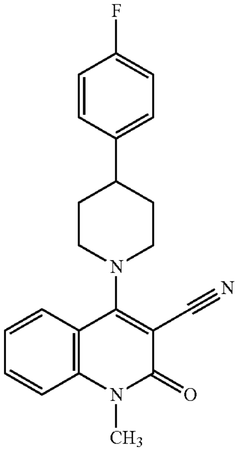 | 4-[4-(4-fluorophenyl)piperidin-1-yl]-1-methyl-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(4-fluorophenyl)piperidine hydrogen chloride salt (1:1) (CAS 6716-98-9) | $^1$H NMR (400 MHz, DMSO-$d_6$) δ [ppm]: 1.95 (m, 4 H), 2.91 (m, 1 H), 3.50 (m, 2H), 3.58 (s, 3 H), 3.83 (br d, 2 H), 7.17 (m, 2 H), 7.39 (m, 3 H), 7.58 (m, 1 H), 7.76 (m, 1 H), 7.96 (m, 1 H). LC-MS (Method 2): Rt = 1.07 min; MS (ESIpos): m/z = 462.3 [M + H]+ |

TABLE 5-continued

Following examples of table 5 were prepared from assigned starting materials and according to the procedure stated in the table.

| Example | Structure | IUPAC-Name | Reference, Starting materials | Analytics |
|---|---|---|---|---|
| 82 | 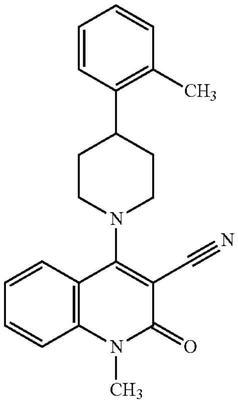 [SMILES: Cc1ccccc1C1CCN(c2c(C#N)c(=O)n(C)c3ccccc23)CC1] | 1-methyl-4-[4-(2-methylphenyl)piperidin-1-yl]-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(2-methylphenyl)piperidine hydrogen chloride salt (1:1) (CAS 82212-02-0) | $^1$H NMR (400 MHz, DMSO-$d_6$) δ [ppm]: 1.95 (m,4H), 2.38 (s, 3 H), 3.10 (m, 1 H), 3.57 (m, 5 H),3.93 (s, 2H), 7.17 (m, 3 H), 7.36 (m, 2 H), 7.58 (m, 1 H), 7.75 (m, 1 H), 7.95 (m, 1 H). LC-MS (Method 2): Rt = 1.39 min; MS (ESIpos): m/z = 358.5 [M + H]+ |
| 83 | 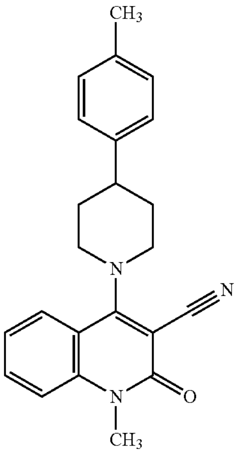 [SMILES: Cc1ccc(C2CCN(c3c(C#N)c(=O)n(C)c4ccccc34)CC2)cc1] | 1-methyl-4-[4-(4-methylphenyl)piperidin-1-yl]-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(4-methylphenyl)piperidine (CAS 59083-39-5) | $^1$H NMR (400 MHz, DMSO-$d_6$) δ [ppm]: 1.94 (m, 4H), 2.27 (s, 3 H), 2.85 (m, 1 H), 3.51 (m, 2 H), 3.58 (s, 3 H), 3.84 (m, 2 H), 7.14 (d, 2 H), 7.24 (m, 2 H), 7.35 (m, 1 H), 7.57 (m, 1 H), 7.74 (m, 1 H), 7.93 (m, 1 H). LC-MS (Method 2): Rt = 1.41 min; MS (ESIpos): m/z = 358.4 [M + H]+ |
| 84 | 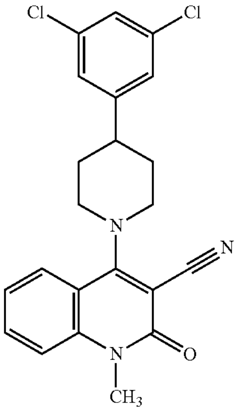 [SMILES: Cn1c(=O)c(C#N)c(N2CCC(c3cc(Cl)cc(Cl)c3)CC2)c2ccccc21] | 4-[4-(3,5-dichlorophenyl)piperidin-1-yl]-1-methyl-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(3,5-dichlorophenyl)piperidine (CAS 475653-05-5) | $^1$H NMR (400 MHz, DMSO-$d_6$) δ [ppm]: 1.99 (m, 4 H), 2.96 (m, 1 H), 3.47 (br t, 2 H), 3.59 (s, 3 H), 3.80 (m, 2 H), 7.35 (m, 1 H), 7.49 (m, 3 H), 7.58 (m, 1 H), 7.75 (m, 1 H), 7.98 (m, 1 H). LC-MS (Method 2): Rt = 1.49 min; MS (ESIpos): m/z = 412.3 [M + H]+ |

TABLE 5-continued

Following examples of table 5 were prepared from assigned starting materials and according to the procedure stated in the table.

| Example | Structure | IUPAC-Name | Reference, Starting materials | Analytics |
|---|---|---|---|---|
| 85 | 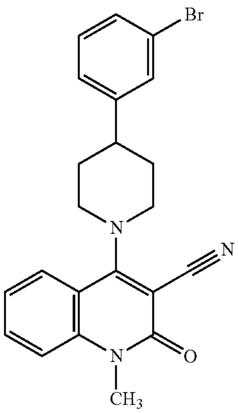 [SMILES: Cn1c(=O)c(C#N)c(N2CCC(c3cccc(Br)c3)CC2)c2ccccc21] | 4-[4-(3-bromophenyl) piperidin-1-yl]-1-methyl-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(3-bromophenyl) piperidine (CAS 351534-36-6) | $^{1}$H NMR (400 MHz, DMSO-$d_6$) δ [ppm]: 1.99 (m, 4 H), 2.92 (m, 1 H), 3.50 (m, 2 H), 3.59 (s, 3 H), 3.83 (br d, 2 H), 7.36 (m, 4 H), 7.59 (m, 2 H), 7.75 (m, 1 H), 7.96 (m, 1 H). LC-MS (Method 1): Rt = 1.41 min; MS (ESIpos): m/z = 422.3 [M + H]+ |
| 86 | 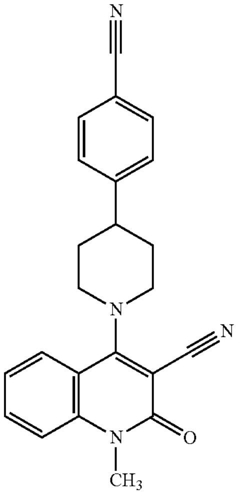 [SMILES: Cn1c(=O)c(C#N)c(N2CCC(c3ccc(C#N)cc3)CC2)c2ccccc21] | 4-[4-(4-cyanophenyl) piperidin-1-yl]-1-methyl-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(piperidin-4-yl)benzonitrile (CAS 149554-06-3) | $^{1}$H NMR (400 MHz, DMSO-$d_6$) δ [ppm]: 2.00 (m, 4 H), 3.02 (m, 1 H), 3.57 (m, 5 H), 3.86 (m, 2 H), 7.36 (m, 1 H), 7.59 (m, 3 H), 7.79 (m, 3 H), 7.97 (m, 1 H). LC-MS (Method 2): Rt = 1.18 min; MS (ESIpos): m/z = 369.4 [M + H]+ |
| 87 | 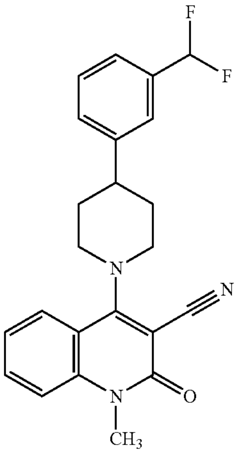 [SMILES: Cn1c(=O)c(C#N)c(N2CCC(c3cccc(C(F)F)c3)CC2)c2ccccc21] | 4-{4-[3-(difluoromethyl) phenyl] piperidin-1-yl}-1-methyl-2-oxo-1,2-dihydroquinoline-3-carbonitrile | in analogy to example 45 with intermediate 26 and 1-bromo-3-(difluoromethyl) benzene (CAS 29848-59-7) | $^{1}$H NMR (500 MHz, DMSO-$d_6$) δ [ppm]: 2.00 (m, 4 H), 2.99 (m, 1 H), 3.52 (m, 2 H), 3.58 (s, 3 H), 3.87 (m, 2 H), 7.04 (t, 1 H), 7.36 (m, 1 H), 7.51 (m, 5 H), 7.75 (ddd, 1 H), 7.95 (dd, 1 H). LC-MS (Method 2): Rt = 1.29 min; MS (ESIpos): m/z = 394.3 [M + H]+ |

TABLE 5-continued

| Following examples of table 5 were prepared from assigned starting materials and according to the procedure stated in the table. | | | | |
|---|---|---|---|---|
| Example | Structure | IUPAC-Name | Reference, Starting materials | Analytics |
| 88 | 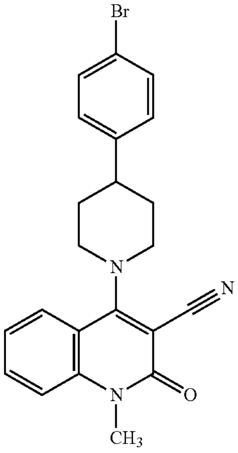 [SMILES: Cn1c(=O)c(C#N)c(N2CCC(c3ccc(Br)cc3)CC2)c2ccccc21] | 4-[4-(4-bromophenyl) piperidin-1-yl]-1-methyl-2-oxo-1,2-dihydroquinoline-3-carbonitrile | in analogy to example 33 with 4-chloro-1-methyl-2-oxo-1,2-dihydroquinoline-3-carbonitrile (CAS 150617-68-8) and 4-(4-bromophenyl) piperidine hydrogen chloride salt (1:1) (CAS 769944-79-8) | $^1$H NMR (400 MHz, DMSO-$d_6$) δ [ppm]: 1.97 (m, 4 H), 2.89 (m, 1 H), 3.56 (m, 5 H), 3.83 (m, 2 H), 7.35 (m, 3 H), 7.55 (m, 3 H), 7.74 (m, 1 H), 7.94 (m, 1 H). LC-MS (Method 1): Rt = 1.43 min; MS (ESIpos): m/z = 422.3 [M + H]+ |

Example 89

7-bromo-4-[4-(4-methoxyphenyl)piperidin-1-yl]-1-methyl-2-oxo-1,2-dihydroquinoline-3-carbonitrile

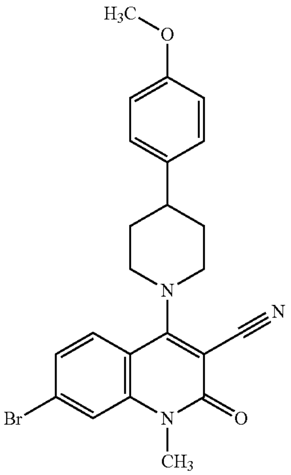 [SMILES: COc1ccc(C2CCN(c3c(C#N)c(=O)n(C)c4cc(Br)ccc34)CC2)cc1]

To a suspension of 1.30 g 7-bromo-4-chloro-1-methyl-2-oxo-1,2-dihydroquinoline-3-carbonitrile (4.37 mmol, intermediate 21) and 2.3 mL N,N-diisopropylethylamine (13 mmol) in 18 mL 2-propanol was added 1.00 g 4-(4-methoxyphenyl)piperidine (5.24 mmol, CAS 67259-62-5) and the reaction was stirred for 2 h at 90° C. The react ion was allowed to cool to rt and poured into water. The precipitate was filtered off, washed with ethanol and dried in vacuum. The title compound was obtained in 91% yield (1.90 g, 95% purity).

$^1$H NMR (400 MHz, DMSO-$d_6$) δ ppm 1.82-2.02 (m, 4H) 2.72-2.90 (m, 1H) 3.44-3.59 (m, 5H): 3.72 (s, 3H) 3.77-3.85 (m, 2H) 6.83-6.94 (m, 2H) 7.21-7.30 (m, 2H) 7.44-7.56 (m, 1H): 7.74-7.91 (m, 2H).

LC-MS (Method 1): $R_t$=1.41 min; MS (ESIpos): m/z=452 $[M+H]^+$

Example 90

7-bromo-1-methyl-2-oxo-4-(4-phenylpiperidin-1-yl)-1,2-dihydroquinoline-3-carbonitrile

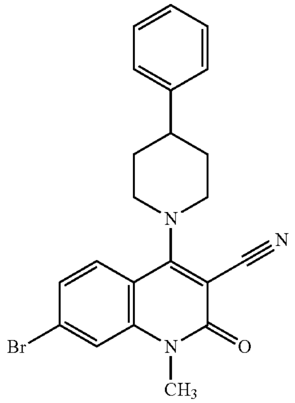 [SMILES: Cn1c(=O)c(C#N)c(N2CCC(c3ccccc3)CC2)c2ccc(Br)cc21]

To a suspension of 100 mg 7-bromo-4-chloro-1-methyl-2-oxo-1,2-dihydroquinoline-3-carbonitrile (336 μmol, intermediate 21) and 180 μL N,N-diisopropylethylamine (1.0 mmol) in 2.0 mL 2-propanol was added 65.0 mg 4-phenylpiperidine (403 μmol, CAS 771-99-3) and the reaction was stirred for 2 h at 90° C. The reaction was allowed to cool to rt and poured into water. The precipitate was filtered off, washed with ethanol and dried in vacuum. The title compound was obtained in 83% yield (125 mg, 95% purity).

$^1$H NMR (400 MHz, DMSO-$d_6$) δ ppm 1.90-2.04 (m, 4H) 2.81-2.97 (m, 1H) 3.43-3.65 (m, 5H): 3.76-3.89 (m, 2H) 7.18-7.26 (m, 1H) 7.29-7.38 (m, 4H) 7.47-7.53 (m, 1H) 7.75-7.79 (m, 1H) 7.80-7.86 (m, 1H).

LC-MS (Method 3): Rt=1.39 min; MS (ESIpos): m/z=422.0 & 424.0 [M+H]+

Example 91

4-[4-(4-methoxyphenyl)piperidin-1-yl]-1,7-dimethyl-2-oxo-1,2-dihydroquinoline-3-carbonitrile

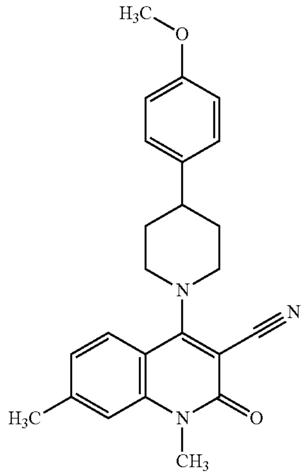 [SMILES: COc1ccc(C2CCN(c3c(C#N)c(=O)n(C)c4cc(C)ccc34)CC2)cc1]

To a stirred solution of 110 mg 7-bromo-4-[4-(4-methoxyphenyl)piperidin-1-yl]-1-methyl-2-oxo-1,2-dihydroquinoline-3-carbonitrile (243 μmol, example 89) in 4.0 mL degassed THF were added 69.1 mg 2,4,4,5,5-pentamethyl-1,3,2-dioxaborolane (486 μmol, CAS 94242-85-0), 1.2 mL potassium phosphate (0.50 M in water, 610 μmol) and 28.7 mg chloro(2-dicyclohexylphosphino-2,4,6-triisopropyl-1,1-biphenyl)[2-(2-amino-1,1-biphenyl)]palladium(II) (36.5 μmol, CAS 1310584-14-5). The mixture was stirred overnight at 70° C. After this time, water was added and the reaction was extracted with dichloromethane (2×). The organic phase filtered (using a waterresistant filter) and concentrated under reduced pressure. The residue was purified by RP-HPLC (column: X-Bridge C18 5 μm 100×30 mm, mobile phase: acetonitrile/water (0.2 vol. % ammonia 32%)-gradient) to give 22 mg of the title compound (95% purity, 22% yield).

$^1$H NMR (400 MHz, DMSO-$d_6$) δ ppm 1.83-2.05 (m, 4H) 2.47 (s, 3H) 2.92 (ddd, 1H) 3.42-3.61 (m, 5H) 3.73 (s, 3H) 3.82 (br d, 2H) 6.86-6.96 (m, 2H) 7.14-7.22 (m, 1H) 7.22-7.33 (m, 2H) 7.36-7.44 (m, 1H) 7.74-7.84 (m, 1H).

LC-MS (Method 1): $R_t$=1.36 min; MS (ESIpos): m/z=388 $[M+H]^+$

Example 92

4-[4-(4-methoxyphenyl)piperidin-1-yl]-1-methyl-2-oxo-7-phenyl-1,2-dihydroquinoline-3-carbonitrile

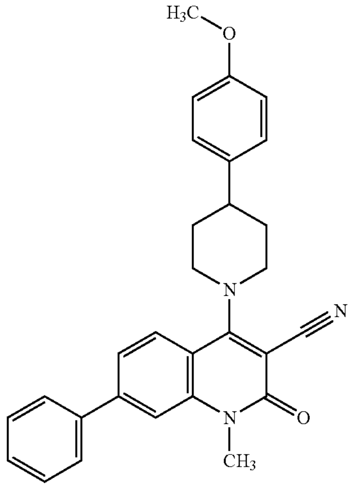 [SMILES: COc1ccc(C2CCN(c3c(C#N)c(=O)n(C)c4cc(-c5ccccc5)ccc34)CC2)cc1]

To a stirred solution of 100 mg 7-bromo-4-[4-(4-methoxyphenyl)piperidin-1-yl]-1-methyl-2-oxo-1,2-dihydroquinoline-3-carbonitrile (221 μmol, example 89) in 3.5 mL degassed THF were added 32.3 mg phenylboronic acid (265 μmol, CAS 98-80-6), 800 μL potassium phosphate (0.50 M in water, 400 μmol) and 26.1 mg chloro(2-dicyclohexylphosphino-2,4,6-triisopropyl-1,1-biphenyl)[2-(2-amino-1,1-biphenyl)]palladium(II) (33.2 μmol, CAS 1310584-14-5). The mixture was stirred overnight at 70° C. After this time, water was added and the reaction was extracted with dichloromethane (2×). The organic phase filtered (using a waterresistant filter) and concentrated under reduced pressure. The residue was purified by RP-HPLC (column: X-Bridge C18 5 μm 100×30 mm, mobile phase: acetonitrile/water (0.1 vol. % formic acid)-gradient) to give 70 mg of the title compound (95% purity, 67% yield).

$^1$H NMR (400 MHz, DMSO-$d_6$) δ ppm 1.87-2.05 (m, 4H) 2.77-2.95 (m, 1H) 3.47-3.60 (m, 2H): 3.69 (s, 3H) 3.74 (s, 3H) 3.83-3.96 (m, 2H) 6.88-7.00 (m, 2H) 7.24-7.34 (m, 2H) 7.42-7.51 (m, 1H) 7.53-7.60 (m, 2H) 7.63-7.70 (m, 1H) 7.71-7.78 (m, 1H) 7.83-7.91 (m, 2H): 7.95-8.04 (m, 1H).

LC-MS (Method 1): $R_t$=1.50 min; MS (ESIpos): m/z=450.5 $[M+H]^+$

Example 93

4-[4-(4-methoxyphenyl)piperidin-1-yl]-1-methyl-2-oxo-1,2-dihydroquinoline-3,7-dicarbonitrile

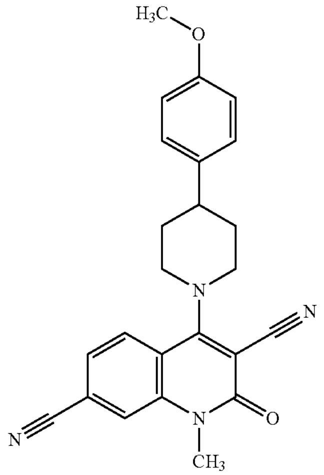 [SMILES: COc1ccc(C2CCN(c3c(C#N)c(=O)n(C)c4cc(C#N)ccc34)CC2)cc1]

To 100 mg 7-bromo-4-[4-(4-methoxyphenyl)piperidin-1-yl]-1-methyl-2-oxo-1,2-dihydroquinoline-3-carbonitrile (221 μmol, example 89) in 2.5 mL DMF was added 99.0 mg copper(I)cyanide (1.11 mmol) and the mixture was stirred for 12 h at 150° C. in the microwave. The mixture was cooled down to rt, water was added, the precipitate was collected by filtration, washed with ethanol and DMSO and dried in vacuum. The impure product was stirred in dichloromethane/ethanol. The precipitate was collected by filtration and the filtrate was concentrated under reduced pressure to give 32.0 mg of the title compound (95% purity, 35% yield).

$^1$H NMR (400 MHz, DMSO-$d_6$) δ ppm 1.84-2.01 (m, 4H) 2.77-2.92 (m, 1H) 3.47-3.61 (m, 5H): 3.72 (s, 3H) 3.78-3.89 (m, 2H) 6.97 (s, 2H) 7.20-7.32 (m, 2H) 7.67-7.74 (m, 1H) 8.00-8.17 (m, 2H).

LC-MS (Method 1): $R_t$=1.26 min; MS (ESIpos): m/z=399 [M+H]$^+$

Example 94

7-cyclopropyl-4-[4-(4-methoxyphenyl)piperidin-1-yl]-1-methyl-2-oxo-1,2-dihydroquinoline-3-carbonitrile

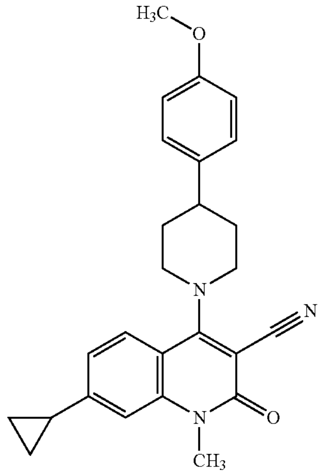 [SMILES: COc1ccc(C2CCN(c3c(C#N)c(=O)n(C)c4cc(C5CC5)ccc34)CC2)cc1]

To a solution of 150 mg 7-bromo-4-[4-(4-methoxyphenyl)piperidin-1-yl]-1-methyl-2-oxo-1,2-dihydroquinoline-3-carbonitrile (332 μmol, example 89) in 1.0 mL water and 4.0 mL DMSO were added 83.6 mg 2-cyclopropyl-4,4,5,5-tetramethyl-1,3,2-dioxaborolane (497 μmol, CAS 126689-01-8), 211 mg potassium phosphate (995 μmol) and 27.1 mg [1,1-Bis(diphenylphosphino)ferrocene]dichloropalladium (II)-complex with dichloromethane (33.2 μmol, CAS 95464-05-4). The mixture was stirred overnight at 100° C. The water was evaporated, the residue was stirred in DMSO, the precipitate was collected by filtration, washed with ethanol and dried in vacuum. 49.0 mg of the title compound were obtained (95% purity, 34% yield).

$^1$H NMR (400 MHz, DMSO-$d_6$) δ [ppm]: 0.88 (m, 2H), 1.10 (m, 2H), 1.91 (m, 4H), 2.12 (m, 1H), 2.82 (m, 1H), 3.48 (m, 2H), 3.57 (s, 3H), 3.73 (s, 3H), 3.80 (br d, 2H), 6.90 (d, 2H), 6.98 (dd, 1H), 7.26 (m, 3H), 7.78 (d, 1H).

LC-MS (Method 1): $R_t$=1.42 min; MS (ESIpos): m/z=415 [M+H]$^+$

Example 95

7-(2,2-dimethyl-2λ$^6$-diazathia-1,2-dien-1-yl)-4-[4-(4-methoxyphenyl)piperidin-1-yl]-1-methyl-2-oxo-1,2-dihydroquinoline-3-carbonitrile

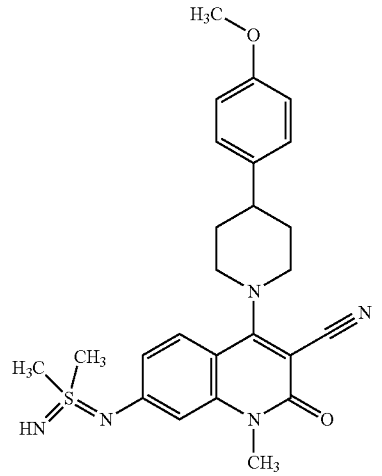 [SMILES: COc1ccc(C2CCN(c3c(C#N)c(=O)n(C)c4cc(N=S(C)(C)=N)ccc34)CC2)cc1]

To a solution of 100 mg 7-bromo-4-[4-(4-methoxyphenyl)piperidin-1-yl]-1-methyl-2-oxo-1,2-dihydroquinoline-3-carbonitrile (example 89, 221 μmol) in 2.3 mL 1,4-dioxane, 24.4 mg 2,2-dimethyl-2λ-diazathia-1,2-diene (265 μmol, CAS 13904-95-5), 14.2 mg tris(dibenzylideneacetone)dipalladium(0) (15 μmol), 13.2 mg 2-(di-tert-butylphosphino)biphenyl (44.2 μmol) and 29.7 mg sodium-tert-butoxide (310 mmol) were added and the mixture was stirred 4.5 h at 80° C. in the microwave. The suspension was filtered and the filtrate was purified by RP-HPLC (column: X-Bridge C18 5 μm 100×30 mm, mobile phase: acetonitrile/water (0.2 vol. % ammonia 32%)-gradient) to give 40.0 mg of the title compound (95% purity, 37% yield).

$^1$H NMR (400 MHz, DMSO-$d_6$) δ ppm 1.83-1.97 (m, 4H) 2.74-2.86 (m, 1H) 3.37 (s, 6H) 3.42-3.50 (m, 5H) 3.69-3.83 (m, 5H) 6.85-6.92 (m, 2H) 6.97-7.05 (m, 2H) 7.24-7.28 (m, 2H) 7.64-7.73 (m, 1H).

LC-MS (Method 1): $R_t$=0.98 min; MS (ESIpos): m/z=465 [M+H]$^+$

TABLE 6

Following examples of table 6 were prepared from assigned starting materials and according to the procedure stated in the table.

| Example | Structure | IUPAC-Name | | Analytics |
|---|---|---|---|---|
| 96 | 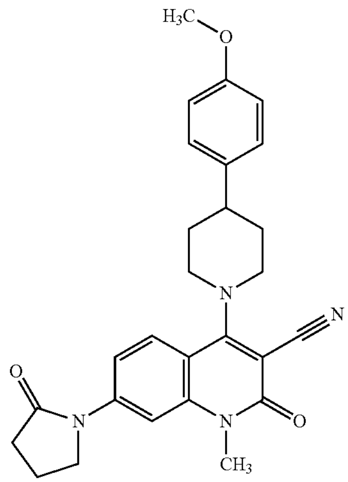 [SMILES: COc1ccc(C2CCN(c3c(C#N)c(=O)n(C)c4cc(N5CCCC5=O)ccc34)CC2)cc1] | 4-[4-(4-methoxyphenyl)piperidin-1-yl]-2-methyl-2-oxo-7-(2-oxopyrrolidin-1-yl)-1,2-dihydroquinoline-3-carbonitrile | in analogy to example 35 with 7-bromo-4-[4-(4-methoxyphenyl) piperidin-1-yl]-1-methyl-2-oxo-1,2-dihydroquinazoline-3-carbontrile (example 89) and pyrrolidin-2-one (CAS 616-45-5) | $^1$H NMR (400 MHz, DMSO-$d_6$) δ [ppm]: 1.93 (m, 4 H), 2.12 (m, 2 H), 2.60 (m, 2 H), 2.83 (m, 1 H), 3.52 (m, 5 H), 3.72 (s, 3 H), 3.82 (m, 2 H), 3.97 (m, 2 H), 6.90 (d, 2 H), 7.27 (d, 2 H), 7.70 (dd, 1 H), 7.79 (d, 1 H), 7.91 (d, 1 H). LC-MS (Method 1): $R_t$ = 1.21 min; MS (ESIpos): m/z = 457 [M + H]$^+$ |
| 97 | 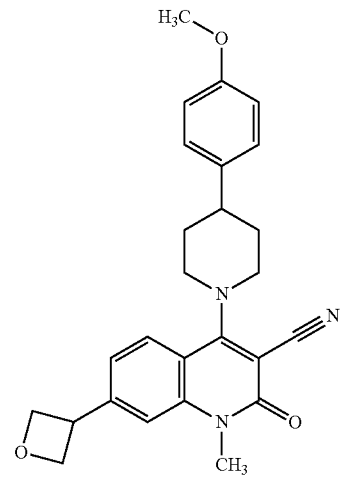 [SMILES: COc1ccc(C2CCN(c3c(C#N)c(=O)n(C)c4cc(C5COC5)ccc34)CC2)cc1] | 4-[4-(4-methoxyphenyl)piperidin-1-yl]-1-methyl-7-(oxetan-3-yl)-2-oxo-1,2-dihydroquinoline-3-carbonitrile | in analogy to example 45 with 7-bromo-4-[4-(4-methoxyphenyl) piperidin-1-yl]-1-methyl-2-oxo-1,2-dihydroquinoline-3-carbonitrile (example 89) and 3-bromooxetane (CAS 39267-79-3) | $^1$H NMR (400 MHz, DMSO-$d_6$) δ [ppm]: 1.93 (m, 4 H), 2.83 (m, 1 H), 3.50 (m, 2 H), 3.59 (s, 3 H), 3.74 (s, 3 H), 3.84 (m, 2 H), 4.44 (m, 1 H), 4.70 (m, 2 H), 4.99 (m, 2 H), 6.91 (m, 2 H), 7.26 (m, 2 H), 7.47 (m, 2 H), 7.94 (m, 1 H). LC-MS (Method 1): $R_t$ = 1.20 min; MS (ESIpos): m/z = 430.7 [M + H]$^+$ |
| 98 | 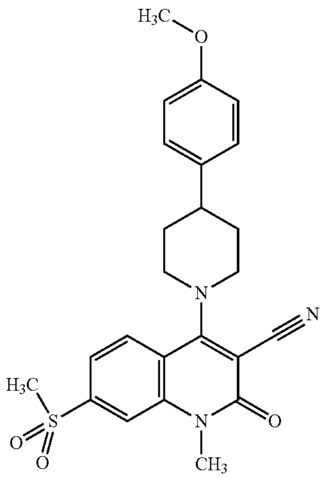 [SMILES: COc1ccc(C2CCN(c3c(C#N)c(=O)n(C)c4cc(S(C)(=O)=O)ccc34)CC2)cc1] | 7-(methanesulfonyl)-4-[4-(4-methoxyphenyl)piperidin-1-yl]-1-methyl-2-oxo-1,2-dihydroquinoline-3-carbonitrile | in analogy to example 164 with 7-bromo-4-[4-(4-methoxyphenyl) piperidin-1-yl]-1-methyl-2-oxo-1,2-dihydroquinoline-3-carbonitrile (example 89) | $^1$H NMR (400 MHz, DMSO-$d_6$) δ [ppm]: 1.96 (m, 4 H), 2.84 (m, 1 H), 3.35 (s, 3 H), 3.53 (m, 2 H), 3.66 (m, 3 H), 3.75 (m, 3 H), 3.85 (m, 2 H), 6.91 (m, 2 H), 7.27 (m, 2 H), 7.81 (dd, 1 H), 7.96 (d, 1 H), 8.15 (d, 1 H). LC-MS (Method 1): $R_t$ = 1.16 min; MS (ESIpos): m/z = 451.1 [M + H]$^+$ |

TABLE 6-continued

Following examples of table 6 were prepared from assigned starting materials and according to the procedure stated in the table.

| Example | Structure | IUPAC-Name | | Analytics |
|---|---|---|---|---|
| 99 | 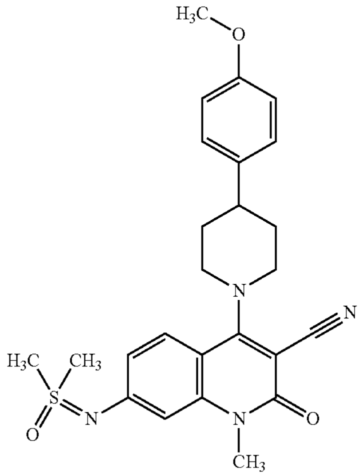 [SMILES: COc1ccc(C2CCN(c3c(C#N)c(=O)n(C)c4cc(N=S(C)(C)=O)ccc34)CC2)cc1] | 7-{[dimethyl(oxo)-λ6-sulfanylidene]amino]-4-[4-(4-methoxyphenyl)piperidin-1-yl]-1-methyl-2-oxo-1,2-dihydroquinoline-3-carbonitrile | in analogy to example 95 with 7-bromo-4-[4-(4-methoxyphenyl)piperidin-1-yl]-1-methyl-2-oxo-1,2-dihydroquinoline-3-carbonitrile (example 89) and (methylsulfonimidoyl)methane (CAS 1520-31-6) | $^1$H NMR (400 MHz, DMSO-$d_6$) δ [ppm]: 1.90 (m, 4 H), 2.81 (m, 1 H), 3.38 (s, 6 H), 3.48 (m, 5 H), 3.78 (m, 5 H), 6.91 (m, 4 H), 7.28 (m, 2 H), 7.73 (m, 1 H). LC-MS (Method 1): Rt = 1.21 min; MS (ESIpos): m/z = 465 $[M + H]^+$ |
| 100 | 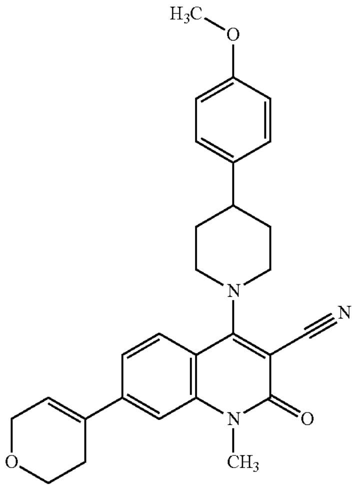 [SMILES: COc1ccc(C2CCN(c3c(C#N)c(=O)n(C)c4cc(C5=CCOCC5)ccc34)CC2)cc1] | 7-(3,6-dihydro-2H-pyran-4-yl)-4-[4-(4-methoxyphenyl)piperidin-1-yl]-1-methyl-2-oxo-1,2-dihydroquinoline-3-carbonitrile | in analogy to example 40 with 7-bromo-4-[4-(4-methoxyphenyl)piperidin-1-yl]-1-methyl-2-oxo-1,2-dihydroquinoline-3-carbonitrile (example 89) and 4-(4,4,5,5-tetramethyl-1,3,2-dioxaborolan-2-yl)-3,6-dihydro-2H-pyran (CAS 287944-16-5) | $^1$H NMR (400 MHz, DMSO-$d_6$) δ [ppm]: 1.93 (m, 4 H), 2.58 (m, 2 H), 2.83 (m, 1 H), 3.51 (m, 2 H), 3.61 (m, 3 H), 3.74 (m, 3 H), 3.85 (m, 4 H), 4.28 (m, 2 H), 6.59 (m, 1 H), 6.90 (m, 2 H), 7.26 (m, 2 H), 7.47 (m, 2 H), 7.87 (m, 1 H). LC-MS (Method 1): $R_t$ = 1.34 min; MS (ESIpos): m/z = 456.5 $[M + H]^+$ |
| 101 | 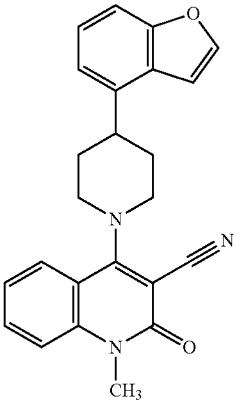 [SMILES: Cn1c(=O)c(C#N)c(N2CCC(c3cccc4occc34)CC2)c2ccccc21] | 4-[4-(1-benzofuran-4-yl)piperidin-1-yl]-1-methyl-2-oxo-1,2-dihydroquinoline-3-carbonitrile | in analogy to example 47 with 4-chloro-1-methyl-2-oxo-1,2-dihydroquinoline-3-carbonitrile (CAS 150617-68-8) and intermediate 50 | $^1$H NMR (400 MHz, DMSO-$d_6$) δ [ppm]: 2.07 (m, 4 H), 3.36 (m, 1 H), 3.62 (m, 5 H), 3.88 (m, 2 H), 7.33 (m, 4 H), 7.46 (m, 1 H), 7.58 (m, 1 H), 7.76 (m, 1 H), 7.99 (m, 2 H). LC-MS (Method 2): Rt = 1.32 min; MS (ESIpos): m/z = 384.5 $[M + H]^+$ |

Example 102

1-methyl-2-oxo-4-(4-{4-[(propan-2-yl)oxy] phenyl}piperidin-1-yl)-1,2-dihydroquinoline-3-carboxamide

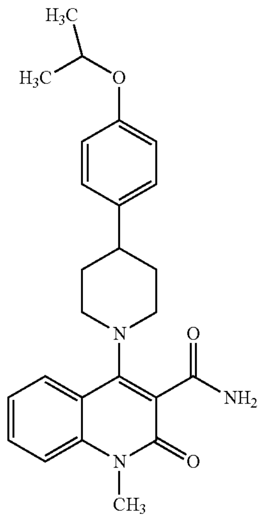 [SMILES: CC(C)Oc1ccc(C2CCN(c3c(C(N)=O)c(=O)n(C)c4ccccc34)CC2)cc1]

46 mg 1-methyl-2-oxo-4-[4-{4-[(propan-2-yl)oxy]phenyl}-3,6-dihydropyridin-1(2H)-yl]-1,2-dihydroquinoline-3-carbonitrile (example 38, 109 µmol), 6.14 mg palladium(II) acetate (27.3 µmol) and 64.6 mg acetaldoxime (1.49 mmol) were stirred in 5.0 mL ethanol for 4 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 µm 100×30 mm, mobile phase: acetonitrile/water (0.2 vol. % ammonia 32%)-gradient) to give 30 mg of the title compound (99% purity, 65% yield).

$^1$H NMR (400 MHz, DMSO-$d_6$) 5 [ppm]: 1.25 (d, 6H) 1.77-1.96 (m, 4H) 2.56-2.66 (m, 1H) 3.10-3.21 (m, 2H) 3.35-3.43 (m, 2H) 3.59 (s, 3H) 4.51-4.62 (m, 1H) 6.83-6.90 (m, 2H) 7.21-7.27 (m, 2H) 7.28-7.36 (m, 1H) 7.43-7.48 (m, 1H) 7.49-7.55 (m, 1H) 7.59-7.66 (m, 1H) 7.66-7.72 (m, 1H) 7.97 (dd, 1H).

Example 103

1-methyl-4-{4-methyl-4-[5-(propan-2-yl)-1,3-benzoxazol-2-yl]piperidin-1-yl}-2-oxo-1,2-dihydroquinoline-3-carboxamide

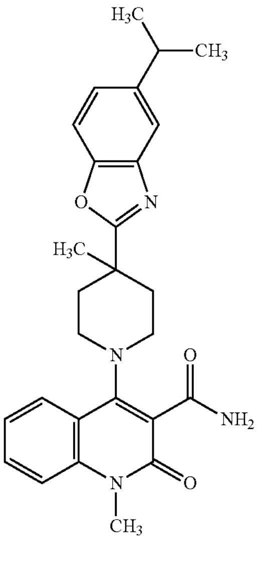 [SMILES: CC(C)c1ccc2oc(C3(C)CCN(c4c(C(N)=O)c(=O)n(C)c5ccccc45)CC3)nc2c1]

50 mg 1-methyl-4-{4-methyl-4-[5-(propan-2-yl)-1,3-benzoxazol-2-yl]piperidin-1-yl}-2-oxo-1,2-dihydroquinoline-3-carbonitrile (example 21, 108 µmol), 6.05 mg palladium (II)acetate (27.3 µmol) and 31.8 mg acetaldoxime (539 µmol) were stirred in 5.0 mL ethanol for 4 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 µm 100×30 mm, mobile phase: acetonitrile/water (0.2 vol. % ammonia 32%)-gradient) to give 25 mg of the title compound (98% purity, 50% yield).

$^1$H NMR (400 MHz, DMSO-$d_6$) 5 [ppm]: 1.26 (d, 6H) 1.45 (s, 3H) 1.94-2.06 (m, 2H) 2.42-2.49 (m, 2H) 2.96-3.16 (m, 3H) 3.29 (br d, 2H) 3.56 (s, 3H) 7.24-7.28 (m, 1H) 7.29-7.35 (m, 1H) 7.39-7.45 (m, 1H) 7.49-7.53 (m, 1H) 7.54-7.59 (m, 1H) 7.59-7.67 (m, 3H) 7.94 (dd, 1H).

Example 104

4-[4-(1,3-benzoxazol-2-yl)piperidin-1-yl]-7-bromo-1-methyl-2-oxo-1,2-dihydroquinoline-3-carboxamide

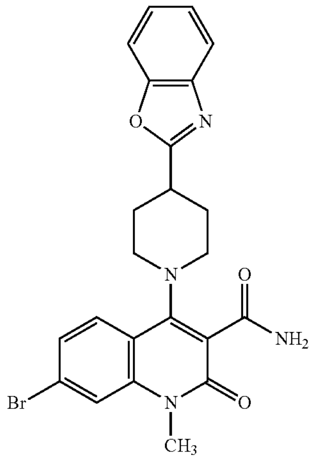

50 mg 4-[4-(1,3-benzoxazol-2-yl)piperidin-1-yl]-7-bromo-1-methyl-2-oxo-1,2-dihydroquinoline-3-carbonitrile (example 27, 103 µmol), 5.75 mg palladium(II)acetate (25.6 µmol) and 60.6 mg acetaldoxime (1.88 mmol) were stirred in 5.0 mL ethanol for 4 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 µm 100×30 mm, mobile phase: acetonitrile/water (0.2 vol. % ammonia 32%)-gradient) to give 29 mg of the title compound (95% purity, 56% yield).

$^1$H NMR (400 MHz, DMSO-$d_6$) 5 [ppm]: 2.02-2.16 (m, 2H) 2.23 (br dd, 2H) 3.14-3.29 (m, 3H) 3.34-3.42 (m, 2H) 3.58 (s, 3H) 7.34-7.41 (m, 2H) 7.48 (dd, 1H) 7.53 (br d, 1H) 7.69-7.75 (m, 4H) 7.84 (d, 1H).

Example 105

4-[4-(1,3-benzoxazol-2-yl)-4-methylpiperidin-1-yl]-1-methyl-2-oxo-1,2-dihydroquinoline-3-carboxamide

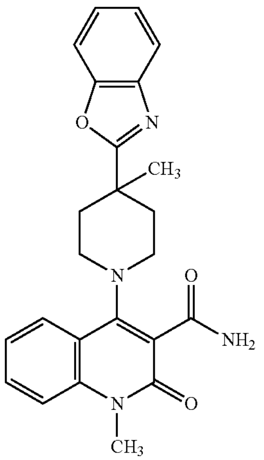 [SMILES: Cn1c(=O)c(C(N)=O)c(N2CCC(C)(c3nc4ccccc4o3)CC2)c2ccccc21]

50 mg 4-[4-(1,3-benzoxazol-2-yl)-4-methylpiperidin-1-yl]-1-methyl-2-oxo-1,2-dihydroquinoline-3-carbonitrile (example 1, 119 μmol), 6.69 mg palladium(II)acetate (29.8 μmol) and 70.4 mg acetaldoxime (1.92 mmol) were stirred in 5.0 mL ethanol for 4 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 28 mg of the title compound (95% purity, 54% yield).

$^1$H NMR (400 MHz, DMSO-$d_6$) δ ppm 1.47 (s, 3H), 1.96-2.06 (m, 2H), 2.43-2.49 (m, 2H), 3.06-3.17 (m, 2H), 3.30 (br d, 2H), 3.57 (s, 3H), 7.29-7.34 (m, 1H), 7.35-7.45 (m, 3H), 7.49-7.53 (m, 1H), 7.55-7.59 (m, 1H), 7.60-7.66 (m, 1H), 7.71-7.78 (m, 2H), 7.95 (dd, 1H).

Example 106

4-[4-(1,3-benzoxazol-2-yl)-4-ethylpiperidin-1-yl]-1-methyl-2-oxo-1,2-dihydroquinoline-3-carbonitrile

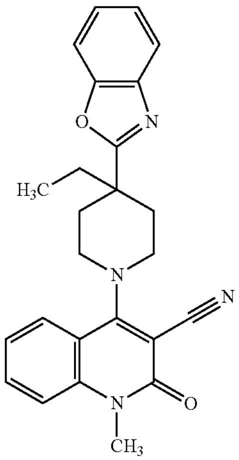 [SMILES: CCC1(c2nc3ccccc3o2)CCN(c2c(C#N)c(=O)n(C)c3ccccc23)CC1]

100 mg 4-chloro-1-methyl-2-oxo-1,2-dihydroquinoline-3-carbonitrile (434 μmol, CAS 150617-68-8), 100 mg 2-(4-ethylpiperidin-4-yl)-1,3-benzoxazole (434 μmol, intermediate 51) and 120 μL triethylamine (870 μmol) were stirred in 3.0 mL 2-propanol for 2 h at 90° C. The reaction mixture was diluted with water and ethyl acetate (1:1), the organic layer was washed with brine, filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 115 mg of the title compound (99% purity, 64% yield).

$^1$H NMR (400 MHz, DMSO-$d_6$) δ ppm 0.72 (t, 3H), 1.88 (q, 2H), 2.00-2.11 (m, 2H), 2.52-2.62 (m, 2H), 3.40-3.53 (m, 2H), 3.55 (s, 3H), 3.75 (br d, 2H), 7.27-7.35 (m, 1H), 7.35-7.44 (m, 2H), 7.52-7.58 (m, 1H), 7.70-7.81 (m, 3H), 7.88 (dd, 1H).

Example 107

1-methyl-4-[4-(5-methyl-1,3-benzoxazol-2-yl)piperidin-1-yl]-2-oxo-1,2-dihydroquinoline-3-carboxamide

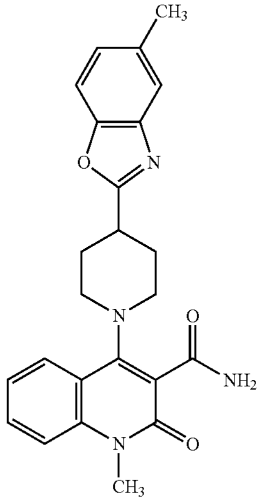 [SMILES: Cc1ccc2oc(C3CCN(c4c(C(N)=O)c(=O)n(C)c5ccccc45)CC3)nc2c1]

50 mg 1-methyl-4-[4-(5-methyl-1,3-benzoxazol-2-yl)piperidin-1-yl]-2-oxo-1,2-dihydroquinoline-3-carbonitrile (example 5, 119 μmol), 6.69 mg palladium(II)acetate (29.8 μmol) and 70.4 mg acetaldoxime (1.92 mmol) were stirred in 5.0 mL ethanol for 4 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 35 mg of the title compound (95% purity, 67% yield).

$^1$H NMR (400 MHz, DMSO-$d_6$) δ ppm 2.02-2.16 (m, 2H), 2.16-2.26 (m, 2H), 2.41-2.47 (m, 3H), 3.14-3.28 (m, 3H), 3.39 (br d, 2H), 3.59 (s, 3H), 7.18 (dd, 1H), 7.29-7.34 (m, 1H), 7.48-7.65 (m, 5H), 7.68 (s, 1H), 7.93 (dd, 1H).

Example 108

1-methyl-2-oxo-4-{4-[4-(trifluoromethoxy)phenyl] piperidin-1-yl}-1,2-dihydroquinoline-3-carboxamide

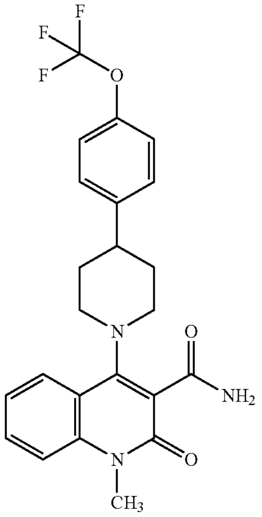 [SMILES: Cn1c(=O)c(C(N)=O)c(N2CCC(c3ccc(OC(F)(F)F)cc3)CC2)c2ccccc21]

200 mg 1-methyl-2-oxo-4-{4-[4-(trifluoromethoxy)phenyl]piperidin-1-yl}-1,2-dihydroquinoline-3-carbonitrile (example 43, 445 μmol), 24.9 mg palladium(II)acetate (111 μmol) and 131 mg acetaldoxime (2.22 mmol) were stirred in 10.0 mL ethanol for 2 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichloromethane/methanol 0-3%) to give 115 mg of the title compound (95% purity, 55% yield).

$^1$H NMR (400 MHz, DMSO-$d_6$) δ ppm 1.81-2.00 (m, 4H), 2.71-2.83 (m, 1H), 3.12-3.22 (m, 2H), 3.35-3.44 (m, 2H), 3.59 (s, 3H), 7.29-7.35 (m, 3H), 7.46-7.55 (m, 4H), 7.60-7.66 (m, 1H), 7.69 (s, 1H), 7.99 (dd, 1H).

Example 109

4-[4-(5,6-difluoro-1,3-benzoxazol-2-yl)piperidin-1-yl]-1-methyl-2-oxo-1,2-dihydroquinoline-3-carboxamide

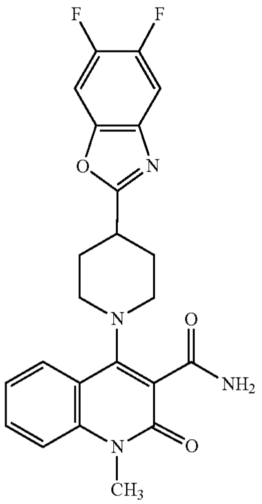 [SMILES: Cn1c(=O)c(C(N)=O)c(N2CCC(c3nc4cc(F)c(F)cc4o3)CC2)c2ccccc21]

170 mg 4-[4-(5,6-difluoro-1,3-benzoxazol-2-yl)piperidin-1-yl]-1-methyl-2-oxo-1,2-dihydroquinoline-3-carbonitrile (example 22, 384 μmol), 21.6 mg palladium(II)acetate (96 μmol) and 226 mg acetaldoxime (3.84 mmol) were stirred in 6.0 mL ethanol for 5 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 20 mg of the title compound (98% purity, 12% yield).

$^1$H NMR (400 MHz, DMSO-$d_6$) δ ppm 2.02-2.16 (m, 2H), 2.17-2.28 (m, 2H), 3.14-3.32 (m, 3H), 3.35-3.44 (m, 2H), 3.59 (s, 3H), 7.28-7.35 (m, 1H), 7.46-7.56 (m, 2H), 7.59-7.66 (m, 1H), 7.67-7.72 (m, 1H), 7.88-7.97 (m, 2H), 8.05 (dd, 1H).

Example 110

7-bromo-1-methyl-4-[4-methyl-4-(5-methyl-1,3-benzoxazol-2-yl)piperidin-1-yl]-2-oxo-1,2-dihydroquinoline-3-carbonitrile

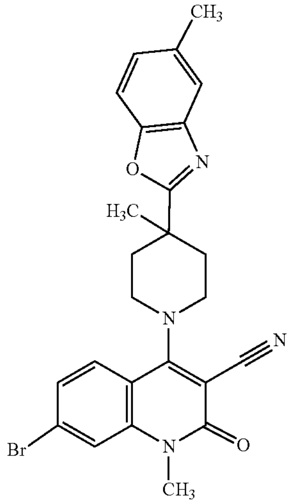 [SMILES: Cc1ccc2oc(C3(C)CCN(c4c(C#N)c(=O)n(C)c5cc(Br)ccc45)CC3)nc2c1]

1.03 g 7-bromo-4-chloro-1-methyl-2-oxo-1,2-dihydroquinoline-3-carbonitrile (3.30 mmol, intermediate 21), 800 mg 5-methyl-2-(4-methylpiperidin-4-yl)-1,3-benzoxazole (3.30 mmol, intermediate 52) and 920 μL triethylamine (6.6 mmol) were stirred in 15 mL 2-propanol for 2 h at 90° C. The reaction mixture was diluted with water and ethyl acetate (1:1), the organic layer was washed with brine, filtered through a waterresistant filter and the filtrate was concentrated under reduced pressure to give 1.35 g of the title compound (93% purity, 77% yield).

$^1$H NMR (400 MHz, DMSO-$d_6$) δ ppm 1.49 (s, 3H), 2.00-2.11 (m, 2H), 2.43 (s, 3H), 3.43-3.58 (m, 5H), 3.68-3.77 (m, 2H), 7.20 (dd, 1H), 7.49 (dd, 1H), 7.54-7.57 (m, 1H), 7.60 (d, 1H), 7.75-7.80 (m, 2H).

Example 111

1-methyl-4-[3-methyl-4-(5-methyl-1,3-benzoxazol-2-yl)piperidin-1-yl]-2-oxo-1,2-dihydroquinoline-3-carbonitrile, Mixture of Stereoisomers

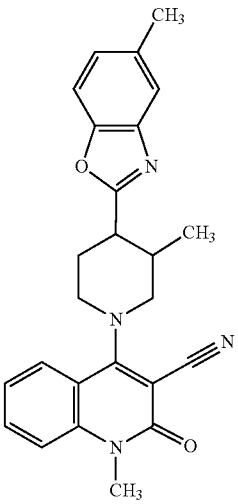 [SMILES: Cc1ccc2oc(C3CCN(c4c(C#N)c(=O)n(C)c5ccccc45)CC3C)nc2c1]

100 mg 4-chloro-1-methyl-2-oxo-1,2-dihydroquinoline-3-carbonitrile (434 μmol, CAS 150617-68-8), 105 mg 5-methyl-2-(3-methylpiperidin-4-yl)-1,3-benzoxazole (434 μmol, intermediate 53) and 120 μL triethylamine (870 μmol) were stirred in 3.0 mL 2-propanol for 2 h at 90° C. The reaction mixture was diluted with water and ethyl acetate (1:1), the organic layer was washed with brine, filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 90 mg of the title compound (99% purity, 50% yield).

$^1$H NMR (400 MHz, DMSO-$d_6$) δ ppm 0.83-0.90 (m, 3H), 2.08-2.22 (m, 2H), 2.29-2.45 (m, 4H), 3.02-3.12 (m, 1H), 3.22-3.30 (m, 1H), 3.43-3.53 (m, 1H), 3.53-3.70 (m, 4H), 3.78-4.02 (m, 2H), 7.19 (dd, 1H), 7.35-7.41 (m, 1H), 7.52-7.61 (m, 3H), 7.72-7.77 (m, 1H), 7.86-7.92 (m, 1H).

Example 112

4-[4-(4-methoxyphenyl)piperidin-1-yl]-1-methyl-2-oxo-1,2-dihydroquinoline-3-carboxamide

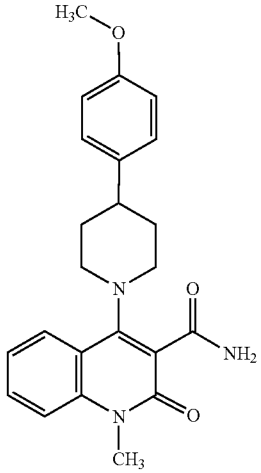 [SMILES: COc1ccc(C2CCN(c3c(C(N)=O)c(=O)n(C)c4ccccc34)CC2)cc1]

500 mg 4-[4-(4-methoxyphenyl)piperidin-1-yl]-1-methyl-2-oxo-1,2-dihydroquinoline-3-carbonitrile (example 41, 1.34 mmol), 75.1 mg palladium(II)acetate (335 μmol) and 395 mg acetaldoxime (6.69 mmol) were stirred in 15 mL ethanol for 2 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichloromethane/methanol gradient 0-3%) to give 360 mg of the title compound (99% purity, 68% yield).

$^1$H NMR (400 MHz, DMSO-$d_6$) δ ppm 1.77-1.97 (m, 4H), 2.58-2.67 (m, 1H), 3.10-3.21 (m, 2H), 3.35-3.43 (m, 2H), 3.59 (s, 3H), 3.74 (s, 3H), 6.85-6.92 (m, 2H), 7.24-7.37 (m, 3H), 7.43-7.48 (m, 1H), 7.52 (d, 1H), 7.59-7.66 (m, 1H), 7.68 (d, 1H), 7.98 (dd, 1H).

Example 113

4-[4-(1,3-benzothiazol-2-yl)piperidin-1-yl]-1-methyl-2-oxo-1,2-dihydroquinoline-3-carboxamide

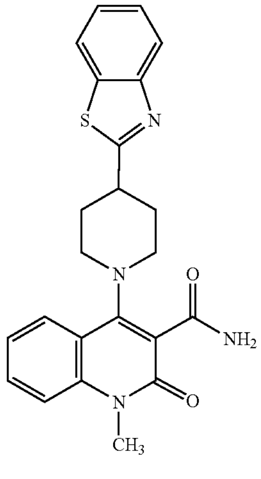 [SMILES: Cn1c(=O)c(C(N)=O)c(N2CCC(c3nc4ccccc4s3)CC2)c2ccccc21]

395 mg 4-[4-(1,3-benzothiazol-2-yl)piperidin-1-yl]-1-methyl-2-oxo-1,2-dihydroquinoline-3-carbonitrile (example 12, 986 μmol), 110.8 mg palladium(II)acetate (670 μmol) and 582 mg acetaldoxime (9.86 mmol) were stirred in 10 mL ethanol for 2 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichloromethane/methanol 0-3%) to give 155 mg of the title compound (95% purity, 36% yield).

$^1H$ NMR (400 MHz, DMSO-$d_6$) δ ppm 2.04-2.17 (m, 3H), 2.18-2.29 (m, 2H), 3.17-3.28 (m, 2H), 3.38-3.47 (m, 2H), 3.60 (s, 3H), 7.29-7.37 (m, 1H), 7.40-7.46 (m, 1H), 7.47-7.56 (m, 3H), 7.60-7.66 (m, 1H), 7.70 (s, 1H), 7.95 (dd, 1H), 7.99 (dd, 1H), 8.10 (dd, 1H).

Example 114

1-methyl-2-oxo-4-(4-phenylpiperidin-1-yl)-1,2-dihydroquinoline-3-carboxamide

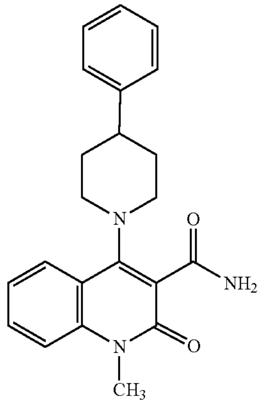 [SMILES: Cn1c(=O)c(C(N)=O)c(N2CCC(c3ccccc3)CC2)c2ccccc21]

A mixture of 100 mg 1-methyl-2-oxo-4-(4-phenylpiperidin-1-yl)-1,2-dihydroquinoline-3-carbonitrile (291 μmol, example 57) and 10 mL toluene, 68 mg chlororhodium-triphenylphosphine (1:3) (72.8 μmol) and 172 mg acetaldoxime (2.91 μmol) were added and the mixture was stirred at 110° C. for 6 h. The solution was cooled to rt and filtered through a pad of celite. The pad was washed with THF and the filtrate was evaporated under reduced pressure. The residue was purified by RP-HPLC (15-65% acetonitrile in ammonium bicarbonate aqueous buffer) to give 72 mg of the title compound (63% yield).

$^1$HNMR (400 MHz, d6-DMSO) δ [ppm]: 1.82-2.04 (m, 4H); 2.68-2.79 (m, 1H); 3.22 (t, 2H); 3.44 (d, 2H); 3.64 (s, 3H); 7.26 (t, 1H); 7.34-7.44 (m, 3H); 7.50 (s, 1H); 7.56 (d, 1H); 7.64-7.74 (m, 2H); 8.03 (d, 1H).

Example 115

4-[4-(4-methoxyphenyl)piperidin-1-yl]-1-methyl-7-(oxetan-3-yl)-2-oxo-1,2-dihydroquinoline-3-carboxamide

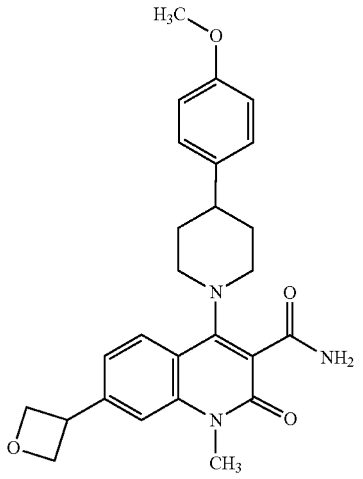 [SMILES: COc1ccc(C2CCN(c3c(C(N)=O)c(=O)n(C)c4cc(C5COC5)ccc34)CC2)cc1]

58 mg 4-[4-(4-methoxyphenyl)piperidin-1-yl]-1-methyl-7-(oxetan-3-yl)-2-oxo-1,2-dihydroquinoline-3-carbonitrile (example 97, 122 μmol), 6.82 mg palladium(II)acetate (30.4 μmol) and 71.8 mg acetaldoxime (1.36 mmol) were stirred in 1 mL ethanol for 7 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichloromethane/methanol gradient 0-3%) to give 35 mg of the title compound (90% purity, 58% yield).

$^1H$ NMR (400 MHz, DMSO-$d_6$) δ ppm 1.77-1.96 (m, 4H), 2.58-2.66 (m, 1H), 3.10-3.20 (m, 2H), 3.38 (br d, 2H), 3.61 (s, 3H), 3.74 (s, 3H), 4.37-4.48 (m, 1H), 4.70-4.74 (m, 2H), 4.99 (dd, 2H), 6.85-6.93 (m, 2H), 7.24-7.31 (m, 2H), 7.39-7.49 (m, 3H), 7.67 (br d, 1H), 7.98 (d, 1H).

Example 116

4-[4-(1,3-benzothiazol-2-yl)piperidin-1-yl]-1-methyl-2-oxo-7-(2-oxopyrrolidin-1-yl)-1,2-dihydroquinoline-3-carboxamide

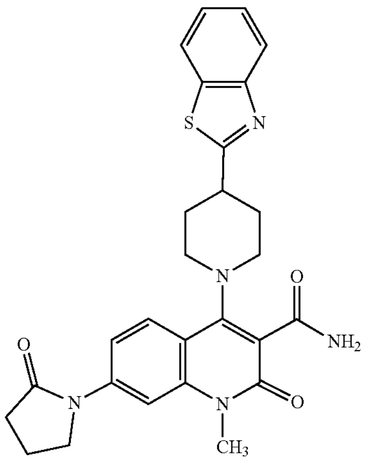 [SMILES: Cn1c(=O)c(C(N)=O)c(N2CCC(c3nc4ccccc4s3)CC2)c2ccc(N3CCCC3=O)cc21]

50 mg 4-[4-(1,3-benzothiazol-2-yl)piperidin-1-yl]-1-methyl-2-oxo-7-(2-oxopyrrolidin-1-yl)-1,2-dihydroquinoline-3-carbonitrile (example 36, 98.2 μmol), 5.51 mg palladium(II)acetate (24.6 μmol) and 58 mg acetaldoxime (1.36 mmol) were stirred in 5 mL ethanol for 7 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 17 mg of the title compound (95% purity, 33% yield).

$^1$H NMR (400 MHz, DMSO-$d_6$) δ ppm 2.04-2.17 (m, 4H), 2.18-2.28 (m, 2H), 2.54-2.62 (m, 2H), 3.22 (br t, 2H), 3.34-3.47 (m, 3H), 3.57 (s, 3H), 3.96 (t, 2H), 7.39-7.55 (m, 3H), 7.61 (dd, 1H), 7.68 (s, 1H), 7.86-7.93 (m, 2H), 7.97-8.00 (m, 1H), 8.10 (dd, 1H).

Example 117

(rac)-1-methyl-2-oxo-4-{4-[4-(propan-2-yl)phenyl]azepan-1-yl}-1,2-dihydroquinoline-3-carbonitrile

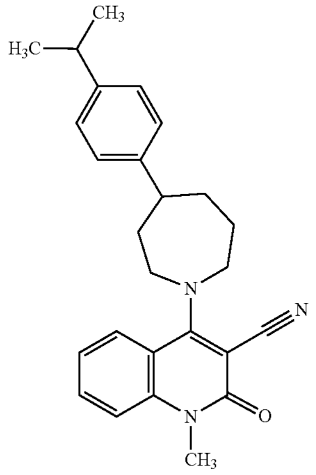 [SMILES: CC(C)c1ccc(C2CCCN(c3c(C#N)c(=O)n(C)c4ccccc34)CC2)cc1]

A solution of 108 mg 4-chloro-1-methyl-2-oxo-1,2-dihydroquinoline-3-carbonitrile (0.495 mmol, CAS 150617-68-8), 140 mg 4-[4-(propan-2-yl)phenyl]azepane (intermediate 55, 1.0 mmol) and 0.14 mL triethylamine (1 mmol) in 3.3 mL 2-propanol was stirred for 4.5 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%) and by RP-HPLC (column: X-Bridge C18 5 μm 100×30 mm, mobile phase: acetonitrile/water (0.2 vol. % ammonia 32%)-gradient). 51 mg of the title compound were obtained (24% yield).

$^1$H NMR (400 MHz, DMSO-$d_6$) δ ppm 1.19 (d, 6H), 1.75-2.11 (m, 6H), 2.80-2.93 (m, 2H), 3.58 (s, 3H), 3.65-3.76 (m, 2H), 3.93-4.00 (m, 2H), 7.15-7.23 (m, 4H), 7.34 (ddd, 1H), 7.57 (dd, 1H), 7.71-7.76 (m, 1H), 8.04 (dd, 1H).

The title compound (48 mg) was separated into enantiomers by preparative chiral HPLC to give enantiomer 1 (15 mg, see example 118) and enantiomer 2 (12 mg, see example 119).

Preparative Chiral HPLC Method:

Instrument: PrepCon Labomatic HPLC; column: Chiralpak IA 5μ 250×30; eluent A: 2-methoxy-2-methylpropane; eluent B: ethanol; isocratic: 90% A+10% B; flow: 50 ml/min; temperature: 25° C.; UV: 254 nm Analytical Chiral HPLC Method:

Instrument: Agilent 1260 HPLC; column: Chiralpak IA 3μ 100×4.6; eluent A: 2-methoxy-2-methylpropane+0.1% diethylamine; eluent B: ethanol; isocratic: 90% A+10% B; flow: 1.4 ml/min; temperature: 60° C.; UV: 254 nm Example 118

1-methyl-2-oxo-4-{4-[4-(propan-2-yl)phenyl]azepan-1-yl}-1,2-dihydroquinoline-3-carbonitrile, Enantiomer 1

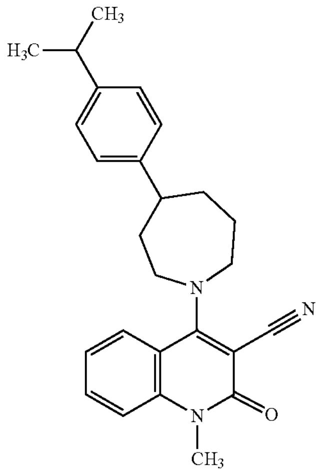 [SMILES: CC(C)c1ccc(C2CCCN(c3c(C#N)c(=O)n(C)c4ccccc34)CC2)cc1]

For the preparation of the racemic title compound see example 117. Separation of enantiomers by preparative chiral HPLC (method see example 117) to give 15 mg of the title compound (95% purity, 7% yield).

Analytical chiral HPLC (method see example 117): $R_t$=2.44 min.

Optical rotation:$[\alpha]_D$=+267° (c=6 mg/ml, chloroform)

$^1$H NMR (400 MHz, DMSO-$d_6$) δ ppm 1.19 (d, 6H), 1.75-2.11 (m, 6H), 2.80-2.93 (m, 2H), 3.58 (s, 3H), 3.65-3.76 (m, 2H), 3.93-4.00 (m, 2H), 7.15-7.23 (m, 4H), 7.34 (ddd, 1H), 7.57 (dd, 1H), 7.71-7.76 (m, 1H), 8.04 (dd, 1H).

Example 119

1-methyl-2-oxo-4-{4-[4-(propan-2-yl)phenyl]azepan-1-yl}-1,2-dihydroquinoline-3-carbonitrile, Enantiomer 2

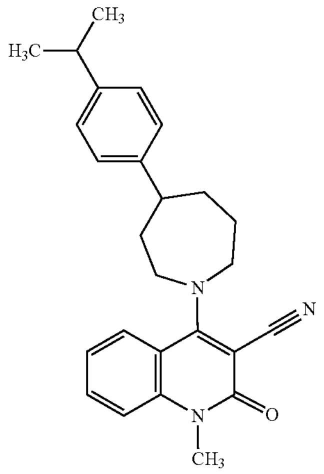 [SMILES: CC(C)c1ccc(C2CCCN(c3c(C#N)c(=O)n(C)c4ccccc34)CC2)cc1]

For the preparation of the racemic title compound see example 117. Separation of enantiomers by preparative chiral HPLC (method see example 117) to give 12 mg of the title compound (95% purity, 6% yield).

Analytical chiral HPLC (method see example 117): $R_t$=3.22 min.

Optical rotation:$[\alpha]_D$=−248° (c=5 mg/ml, chloroform)

$^1$H NMR (400 MHz, DMSO-$d_6$) δ ppm 1.19 (d, 6H), 1.75-2.11 (m, 6H), 2.80-2.93 (m, 2H), 3.58 (s, 3H), 3.65-3.76 (m, 2H), 3.93-4.00 (m, 2H), 7.15-7.23 (m, 4H), 7.34 (ddd, 1H), 7.57 (dd, 1H), 7.71-7.76 (m, 1H), 8.04 (dd, 1H).

Example 120

(rac)-4-[4-(1,3-benzoxazol-2-yl)azepan-1-yl]-1-methyl-2-oxo-1,2-dihydroquinoline-3-carbonitrile

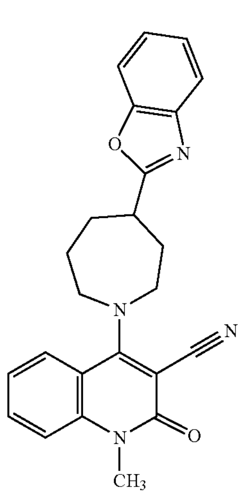 [SMILES: Cn1c(=O)c(C#N)c(N2CCCC(c3nc4ccccc4o3)CC2)c2ccccc21]

312 mg 4-chloro-1-methyl-2-oxo-1,2-dihydroquinoline-3-carbonitrile (1.35 mmol, CAS 150617-68-8), 370 mg 2-(azepan-4-yl)-1,3-benzoxazole (1.63 mmol, intermediate 56) and 380 μL triethylamine (2.7 mmol) were stirred in 18 mL 2-propanol for 3.5 h at 90° C. The reaction mixture was diluted with ethyl acetate, washed with water and brine, dried over sodium sulfate, filtered and the filtrate was concentrated under reduced pressure. The residue was purified by flash chromatography (silica, dichloromethane/ethanol gradient 0-3%) to give 450 mg of the title compound (95% purity, 79% yield).

$^1$H NMR (400 MHz, DMSO-$d_6$) δ ppm 1.93-2.19 (m, 3H), 2.20-2.31 (m, 1H), 2.31-2.47 (m, 2H), 3.46-3.56 (m, 1H), 3.58 (s, 3H), 3.63-3.73 (m, 1H), 3.74-3.84 (m, 2H), 3.84-3.95 (m, 1H), 7.28-7.39 (m, 3H), 7.58 (d, 1H), 7.68-7.76 (m, 3H), 7.97 (dd, 1H).

Example 121

(rac)-1-methyl-2-oxo-4-[4-{4-[(propan-2-yl)oxy]phenyl}azepan-1-yl]-1,2-dihydroquinoline-3-carbonitrile

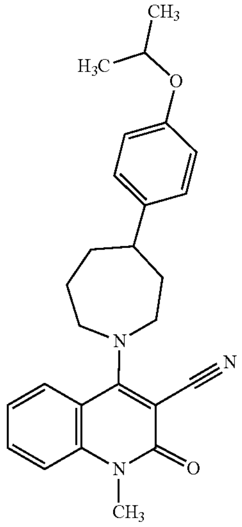 [SMILES: CC(C)Oc1ccc(C2CCCN(c3c(C#N)c(=O)n(C)c4ccccc34)CC2)cc1]

183 mg 4-chloro-1-methyl-2-oxo-1,2-dihydroquinoline-3-carbonitrile (796 μmol, CAS 150617-68-8), 284 mg 4-{4-[(propan-2-yl)oxy]phenyl}azepane (intermediate 58, 1.04 mmol) and 220 μL triethylamine (1.6 mmol) were stirred in 8 mL 2-propanol for 5 h at 90° C. The reaction mixture was diluted with ethyl acetate, washed with water and brine, dried over sodium sulfate, filtered and the filtrate was concentrated under reduced pressure. The residue was purified by flash chromatography (silica, dichloromethane/ethanol gradient 0-3%) to give 180 mg of the title compound (95% purity, 52% yield).

$^1$H NMR (400 MHz, DMSO-$d_6$) δ ppm 1.24 (d, 6H), 1.72-2.10 (m, 6H), 2.79-2.91 (m, 1H), 3.57 (s, 3H), 3.63-3.75 (m, 2H), 3.91-4.00 (m, 2H), 4.51-4.59 (m, 1H), 6.82-6.86 (m, 2H), 7.16-7.21 (m, 2H), 7.34 (ddd, 1H), 7.57 (dd, 1H), 7.70-7.76 (m, 1H), 8.03 (dd, 1H).

Example 122

(rac)-4-[4-(4-methoxyphenyl)azepan-1-yl]-1-methyl-2-oxo-1,2-dihydroquinoline-3-carbonitrile

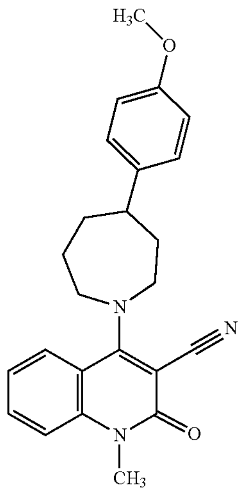 [SMILES: COc1ccc(C2CCCN(c3c(C#N)c(=O)n(C)c4ccccc34)CC2)cc1]

250 mg 4-chloro-1-methyl-2-oxo-1,2-dihydroquinoline-3-carbonitrile (1.14 mmol, CAS 150617-68-8), 282 mg 4-(4-methoxyphenyl)azepane (1.37 mmol, intermediate 62) and 320 μL triethylamine (2.3 mmol) were stirred in 7.5 mL 2-propanol for 2.5 h at 90° C. The reaction mixture was diluted with ethyl acetate, washed with water and brine, dried over sodium sulfate, filtered and the filtrate was concentrated under reduced pressure. The residue was purified by flash chromatography (silica, dichloromethane/ethanol gradient 0-1%) and by RP-HPLC (column: X-Bridge C18 5 μm 100×30 mm, mobile phase: acetonitrile/water (0.2 vol. % ammonia 32%)-gradient) to give 315 mg of the title compound (95% purity, 68% yield).

$^1$H NMR (400 MHz, DMSO-$d_6$) δ ppm 1.73-2.12 (m, 6H), 3.58 (s, 3H), 3.64-3.75 (m, 5H), 3.92-4.00 (m, 2H), 6.85-6.89 (m, 2H), 7.19-7.24 (m, 2H), 7.34 (ddd, 1H), 7.55-7.59 (m, 1H), 7.73 (ddd, 1H), 8.04 (dd, 1H).

The title compound (315 mg) was separated into enantiomers by preparative chiral HPLC to give enantiomer 1 (68 mg, see example 124) and enantiomer 2 (64 mg, see example 123).

Preparative Chiral HPLC Method:

Instrument: PrepCon Labomatic HPLC; column: Chiralpak IA 5μ 250×30; eluent A: 2-methoxy-2-methylpropane; eluent B: ethanol; isocratic: 90% A+10% B; flow: 50 ml/min; temperature: 25° C.; UV: 254 nm Analytical Chiral HPLC Method:

Instrument: Agilent 1260 HPLC; column: Chiralpak IA 3μ 100×4.6; eluent A: 2-methoxy-2-methylpropane+0.1% diethylamine; eluent B: ethanol; isocratic: 90% A+10% B; flow: 1.4 ml/min; temperature: 60° C.; UV: 254 nm Example 123

4-[4-(4-methoxyphenyl)azepan-1-yl]-1-methyl-2-oxo-1,2-dihydroquinoline-3-carbonitrile, Enantiomer 1

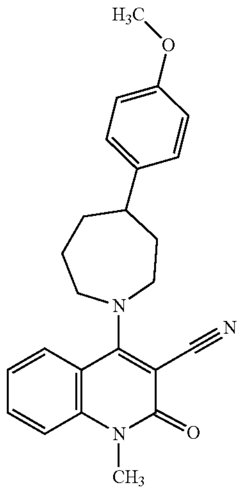 [SMILES: COc1ccc(C2CCCN(c3c(C#N)c(=O)n(C)c4ccccc34)CC2)cc1]

For the preparation of the racemic title compound see example 122. Separation of enantiomers by preparative chiral HPLC (method see example 122) to give 64 mg of the title compound (95% purity, 14% yield).

Analytical chiral HPLC (method see example 122): $R_t$=3.26 min.

Specific optical rotation: −255.9° (c=10 mg/ml, chloroform)

$^1$H NMR (400 MHz, DMSO-$d_6$) δ ppm 1.73-2.12 (m, 6H), 3.58 (s, 3H), 3.64-3.75 (m, 5H), 3.92-4.00 (m, 2H), 6.85-6.89 (m, 2H), 7.19-7.24 (m, 2H), 7.34 (ddd, 1H), 7.55-7.59 (m, 1H), 7.73 (ddd, 1H), 8.04 (dd, 1H).

Example 124

4-[4-(4-methoxyphenyl)azepan-1-yl]-1-methyl-2-oxo-1,2-dihydroquinoline-3-carbonitrile, Enantiomer 2

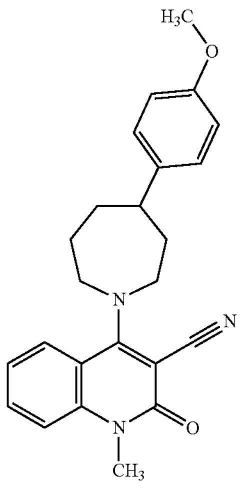 [SMILES: COc1ccc(C2CCCN(c3c(C#N)c(=O)n(C)c4ccccc34)CC2)cc1]

For the preparation of the racemic title compound see example 122. Separation of enantiomers by preparative chiral HPLC (method see example 122) to give 68 mg of the title compound (95% purity, 15% yield).

Analytical chiral HPLC (method see example 122): $R_t$=2.78 min.

Specific optical rotation: +319.4° (c=10 mg/ml, chloroform)

$^1$H NMR (400 MHz, DMSO-$d_6$) δ ppm 1.73-2.12 (m, 6H), 3.58 (s, 3H), 3.64-3.75 (m, 5H), 3.92-4.00 (m, 2H), 6.85-6.89 (m, 2H), 7.19-7.24 (m, 2H), 7.34 (ddd, 1H), 7.55-7.59 (m, 1H), 7.73 (ddd, 1H), 8.04 (dd, 1H).

Example 125

(rac)-4-[4-(1,3-benzoxazol-2-yl)azepan-1-yl]-7-bromo-1-methyl-2-oxo-1,2-dihydroquinoline-3-carbonitrile

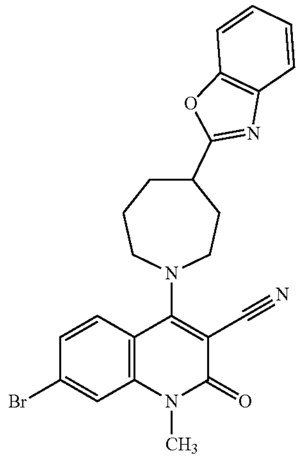 [SMILES: Cn1c(=O)c(C#N)c(N2CCCC(c3nc4ccccc4o3)CC2)c2ccc(Br)cc21]

100 mg 7-bromo-4-chloro-1-methyl-2-oxo-1,2-dihydroquinoline-3-carbonitrile (319 μmol, intermediate 21), 87.2 mg 2-(azepan-4-yl)-1,3-benzoxazole (383 μmol, intermediate 56) and 89 μL triethylamine (640 μmol) were stirred in 3.2 mL 2-propanol for 3 h at 90° C. The reaction mixture was diluted with ethyl acetate, washed with water and brine, dried over sodium sulfate, filtered and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 67 mg of the title compound (95% purity, 42% yield).

$^1$H NMR (400 MHz, DMSO-$d_6$) δ ppm 1.92-2.17 (m, 3H), 2.19-2.30 (m, 1H), 2.31-2.46 (m, 2H), 3.45-3.54 (m, 1H), 3.54-3.59 (m, 3H), 3.63-3.72 (m, 1H), 3.73-3.84 (m, 2H), 3.84-3.94 (m, 1H), 7.32-7.40 (m, 2H), 7.46 (dd, 1H), 7.66-7.74 (m, 2H), 7.78 (d, 1H), 7.87 (d, 1H).

The title compound (67 mg) was separated into enantiomers by preparative chiral HPLC to give enantiomer 1 (16 mg, see example 127) and enantiomer 2 (16 mg, see example 126).

Preparative Chiral HPLC Method:

Instrument: Labomatic HD5000, Labocord-5000; Gilson GX-241, Labcol Vario 4000, column: YMC Cellulose SB 5μ 250×30 mm; eluent A: hexane+0.1 vol. % diethylamine; eluent B: ethanol; isocratic: 50% B; flow 40.0 ml/min; UV 254 nm Analytical Chiral HPLC Method:

Instrument: Agilent HPLC 1260; column: YMC Cellulose SB 3μ 100×4.6 mm; eluent A: hexane+0.1 vol. % diethylamine; eluent B: ethanol; gradient: 20-50% B in 7 min.; flow 1.4 ml/min; temperature: 25° C.; DAD 254 nm Example 126

4-[4-(1,3-benzoxazol-2-yl)azepan-1-yl]-7-bromo-1-methyl-2-oxo-1,2-dihydroquinoline-3-carbonitrile, Enantiomer 1

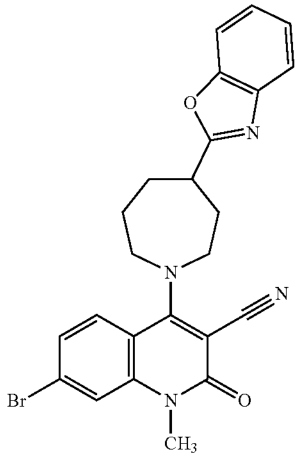 [SMILES: Cn1c(=O)c(C#N)c(N2CCCC(c3nc4ccccc4o3)CC2)c2ccc(Br)cc21]

For the preparation of the racemic title compound see example 125. Separation of enantiomers by preparative chiral HPLC (method see example 125) to give 16 mg of the title compound (95% purity, 10% yield).

Analytical chiral HPLC (method see example 125): $R_t$=4.83 min.

Specific optical rotation: +79.7° (c=10 mg/ml, chloroform)

$^1$H NMR (400 MHz, DMSO-$d_6$) δ ppm 1.92-2.17 (m, 3H), 2.19-2.30 (m, 1H), 2.31-2.46 (m, 2H), 3.45-3.54 (m, 1H), 3.54-3.59 (m, 3H), 3.63-3.72 (m, 1H), 3.73-3.84 (m, 2H), 3.84-3.94 (m, 1H), 7.32-7.40 (m, 2H), 7.46 (dd, 1H), 7.66-7.74 (m, 2H), 7.78 (d, 1H), 7.87 (d, 1H).

Example 127

4-[4-(1,3-benzoxazol-2-yl)azepan-1-yl]-7-bromo-1-methyl-2-oxo-1,2-dihydroquinoline-3-carbonitrile, Enantiomer 2

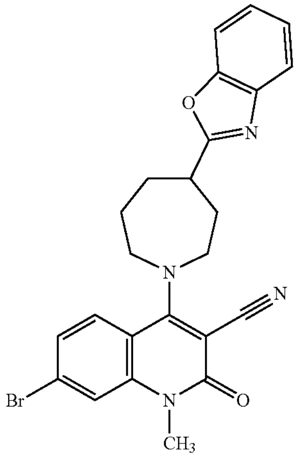 [SMILES: Cn1c(=O)c(C#N)c(N2CCCC(c3nc4ccccc4o3)CC2)c2ccc(Br)cc21]

For the preparation of the racemic title compound see example 125. Separation of enantiomers by preparative chiral HPLC (method see example 125) to give 16 mg of the title compound (95% purity, 10% yield).

Analytical chiral HPLC (method see example 125): $R_t$=4.09 min.

Specific optical rotation: −94.6° (c=10 mg/ml, chloroform)

$^1$H NMR (400 MHz, DMSO-$d_6$) δ ppm 1.92-2.17 (m, 3H), 2.19-2.30 (m, 1H), 2.31-2.46 (m, 2H), 3.45-3.54 (m, 1H), 3.54-3.59 (m, 3H), 3.63-3.72 (m, 1H), 3.73-3.84 (m, 2H), 3.84-3.94 (m, 1H), 7.32-7.40 (m, 2H), 7.46 (dd, 1H), 7.66-7.74 (m, 2H), 7.78 (d, 1H), 7.87 (d, 1H).

Example 128

(rac)-4-[4-(4-chlorophenyl)azepan-1-yl]-1-methyl-2-oxo-1,2-dihydroquinoline-3-carbonitrile

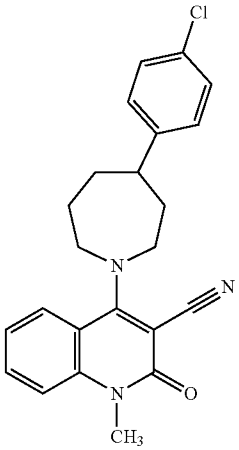 [SMILES: Cn1c(=O)c(C#N)c(N2CCCC(c3ccc(Cl)cc3)CC2)c2ccccc21]

100 mg 4-chloro-1-methyl-2-oxo-1,2-dihydroquinoline-3-carbonitrile (436 μmol, CAS 150617-68-8), 140 mg 4-(4-chlorophenyl)azepane (567 μmol, intermediate 65) and 120 μL triethylamine (870 μmol) were stirred in 4.4 mL 2-propanol for 7 h at 90° C. The reaction mixture was diluted with ethyl acetate, washed with water and brine, dried over sodium sulfate, filtered and the filtrate was concentrated under reduced pressure. The residue was purified by flash chromatography (silica, dichloromethane/methanol gradient 0-3%) to give 127 mg of the title compound (95% purity, 71% yield).

$^1$H NMR (400 MHz, DMSO-$d_6$) δ ppm 1.75-2.13 (m, 7H), 2.89-3.00 (m, 1H), 3.58 (s, 3H), 3.69 (br d, 2H), 3.91-4.00 (m, 2H), 7.30-7.39 (m, 5H), 7.57 (dd, 1H), 7.74 (ddd, 1H), 8.03 (dd, 1H).

The title compound (127 mg) was separated into enantiomers by preparative chiral HPLC to give enantiomer 1 (25 mg, see example 130) and enantiomer 2 (25 mg, see example 129).

Preparative Chiral HPLC Method:

Instrument: PrepCon Labomatic HPLC; column: YMC Amylose SA 5μ 250×30; eluent A: 2-methoxy-2-methylpropane; eluent B: ethanol; isocratic: 90% A+10% B; flow: 50 ml/min; temperature: 25° C.; UV: 254 nm Analytical Chiral HPLC Method:

Instrument: Agilent 1260 HPLC; column: YMC Amylose SA 3μ 100×4.6; eluent A: 2-methoxy-2-methylpropane+0.1% diethylamine; eluent B: ethanol; isocratic: 90% A+10% B; flow: 1.4 ml/min; temperature: 25° C.; UV: 254 nm Example 129

4-[4-(4-chlorophenyl)azepan-1-yl]-1-methyl-2-oxo-1,2-dihydroquinoline-3-carbonitrile, Enantiomer 1

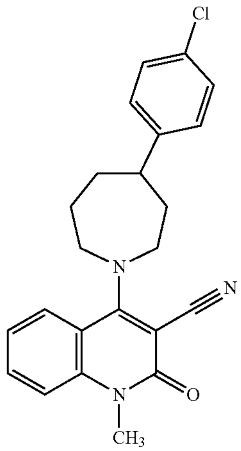 [SMILES: Cn1c(=O)c(C#N)c(N2CCCC(c3ccc(Cl)cc3)CC2)c2ccccc21]

For the preparation of the racemic title compound see example 128. Separation of enantiomers by preparative chiral HPLC (method see example 128) to give 25 mg the title compound (95% purity, 14% yield).

Analytical chiral HPLC (method see example 128): $R_t$=5.74 min.

Specific optical rotation: −260.7° (c=10 mg/ml, chloroform)

$^1$H NMR (400 MHz, DMSO-$d_6$) δ ppm 1.75-2.13 (m, 7H), 2.89-3.00 (m, 1H), 3.58 (s, 3H), 3.69 (br d, 2H), 3.91-4.00 (m, 2H), 7.30-7.39 (m, 5H), 7.57 (dd, 1H), 7.74 (ddd, 1H), 8.03 (dd, 1H).

Example 130

4-[4-(4-chlorophenyl)azepan-1-yl]-1-methyl-2-oxo-1,2-dihydroquinoline-3-carbonitrile, Enantiomer 2

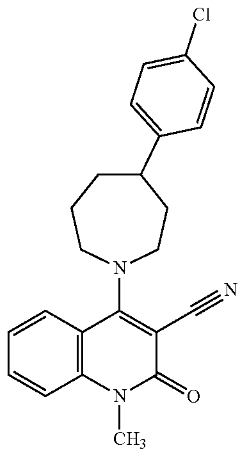 [SMILES: Cn1c(=O)c(C#N)c(N2CCCC(c3ccc(Cl)cc3)CC2)c2ccccc21]

For the preparation of the racemic title compound see example 128. Separation of enantiomers by preparative chiral HPLC (method see example 128) to give 25 mg the title compound (95% purity, 14% yield).

Analytical chiral HPLC (method see example 128): $R_t$=2.67 min.

Specific optical rotation: +227.6° (c=10 mg/ml, chloroform)

$^1$H NMR (400 MHz, DMSO-$d_6$) δ ppm 1.75-2.13 (m, 7H), 2.89-3.00 (m, 1H), 3.58 (s, 3H), 3.69 (br d, 2H), 3.91-4.00 (m, 2H), 7.30-7.39 (m, 5H), 7.57 (dd, 1H), 7.74 (ddd, 1H), 8.03 (dd, 1H).

Example 131

(rac)-1-methyl-2-oxo-4-[4-phenylazepan-1-yl]-1,2-dihydroquinoline-3-carbonitrile

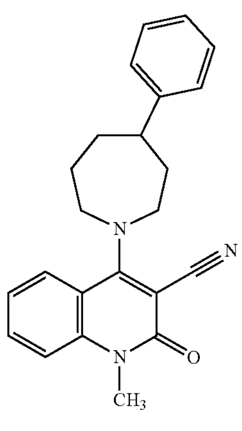 [SMILES: Cn1c(=O)c(C#N)c(N2CCCC(c3ccccc3)CC2)c2ccccc21]

100 mg 4-chloro-1-methyl-2-oxo-1,2-dihydroquinoline-3-carbonitrile (457 μmol, CAS 150617-68-8), 145 mg 4-phenylazepane (686 μmol, CAS 73252-01-4) and 130 μL triethylamine (910 μmol) were stirred in 3.0 mL 2-propanol for 6 h at 90° C. The reaction mixture was diluted with ethyl acetate, washed with water and brine, dried over sodium sulfate, filtered and the filtrate was concentrated under reduced pressure. The residue was purified by flash chromatography (silica, dichloromethane/methanol gradient 0-3%) to give 108 mg of the title compound (95% purity, 63% yield).

$^1$H NMR (400 MHz, DMSO-$d_6$) δ ppm 1.78-2.15 (m, 7H), 2.92 (tt, 1H), 3.58 (s, 3H), 3.65-3.75 (m, 2H), 3.92-4.01 (m, 2H), 7.10-7.28 (m, 1H), 7.28-7.36 (m, 5H), 7.55-7.59 (m, 1H), 7.74 (ddd, 1H), 8.04 (dd, 1H).

Example 132

(rac)-7-bromo-1-methyl-2-oxo-4-[4-phenylazepan-1-yl]-1,2-dihydroquinoline-3-carbonitrile

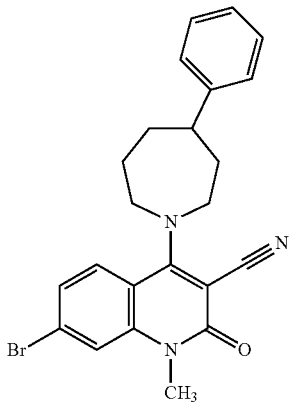 [SMILES: Cn1c(=O)c(C#N)c(N2CCCC(c3ccccc3)CC2)c2ccc(Br)cc21]

817 mg 7-bromo-4-chloro-1-methyl-2-oxo-1,2-dihydroquinoline-3-carbonitrile (intermediate 21, 2.75 mmol), 727 mg 4-phenylazepane (3.43 mmol, CAS 73252-01-4) and 770 μL triethylamine (5.5 mmol) were stirred in 18.0 mL 2-propanol for 6 h at 90° C. The reaction mixture was diluted with dichloromethanol, washed with water and brine, dried over sodium sulfate, filtered and the filtrate was concentrated under reduced pressure. The residue was purified by flash chromatography (silica, dichloromethane/methanol gradient 0-3%) to give 410 mg of the title compound (95% purity, 32% yield).

$^1$H NMR (400 MHz, DMSO-$d_6$) δ ppm 2.01 (br d, 7H), 2.84-2.96 (m, 1H), 3.56 (s, 3H), 3.65-3.77 (m, 2H), 3.91-4.02 (m, 2H), 7.19 (s, 1H), 7.27-7.35 (m, 4H), 7.49 (dd, 1H), 7.77 (d, 1H), 7.94 (s, 1H).

Example 133

(rac)-1-methyl-7-(oxetan-3-yl)-2-oxo-4-[4-phenylazepan-1-yl]-1,2-dihydroquinoline-3-carbonitrile

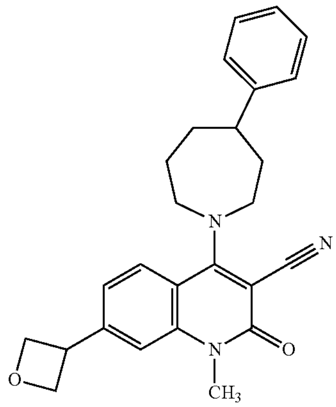 [SMILES: Cn1c(=O)c(C#N)c(N2CCCC(c3ccccc3)CC2)c2ccc(C3COC3)cc21]

124 mg 7-bromo-4-[4-(4-chlorophenoxy)piperidin-1-yl]-1-methyl-2-oxo-1,2-dihydroquinoline-3-carbonitrile (285 μmol, example 132), 6.4 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (5.7 μmol, CAS 870987-63-6) and 199 μL 2,6-dimethylpyridine (1.7 mmol) were dissolved in the reaction vial in 2.5 mL N,N-dimethylacetamide and 6.5 mL trifluorotoluene. In a separate vial the Ni-catalyst was prepared by dissolving 0.3 mg 1,2-dimethoxyethane-dichloronickel (1:1) (1.4 μmol) and 0.4 mg 4,4-di-tert-butyl-2,2-bipyridine (1.4 μmol) in 1.9 mL 1,2-dimethoxyethane followed by stirring for 5 min. The catalyst solution was syringed to the sealed reaction vial and was degassed with argon for 5 min., then 50 μL 3-bromooxetane (570 μmol, CAS 39267-79-3) and 88 μL 1,1,1,3,3,3-hexamethyl-2-(trimethylsilyl)trisilane (285 μmol) was added. The vial was placed in a water bath (to keep the temperature below 35° C.) and was subsequently irradiated by two 40 W Kessil LED Aquarium lamps for 20 h. The reaction was quenched with water, extracted with ethyl acetate (3×), dried over sodium sulfate and concentrated in vacuum. The crude material was purified by flash chromatography (silica, dichloromethane/methanol gradient 0-3%). 5 mg of the title compound were obtained (95% purity, 5% yield).

$^1$H NMR (400 MHz, DMSO-d$_6$) δ ppm 1.78-2.14 (m, 5H), 2.86-2.98 (m, 1H), 3.60 (s, 3H), 3.64-3.77 (m, 3H), 3.91-4.04 (m, 2H), 4.39-4.49 (m, 1H), 4.71 (br d, 2H), 4.99 (dd, 2H), 7.16-7.24 (m, 1H), 7.26-7.36 (m, 5H), 7.42-7.47 (m, 1H), 7.47-7.52 (m, 1H), 8.04 (s, 1H).

Example 134

(rac)-1-methyl-7-(morpholin-4-yl)-2-oxo-4-[4-phenylazepan-1-yl]-1,2-dihydroquinoline-3-carbonitrile

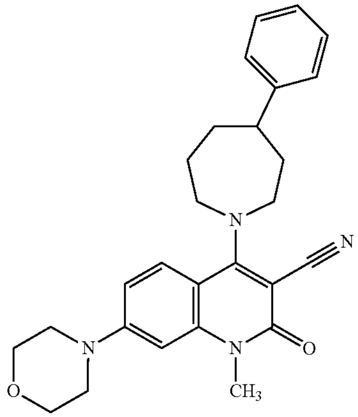 [SMILES: Cn1c(=O)c(C#N)c(N2CCCC(c3ccccc3)CC2)c2ccc(N3CCOCC3)cc21]

To a stirred solution of 100 mg 7-bromo-1-methyl-2-oxo-4-(4-phenylazepan-1-yl)-1,2-dihydroquinoline-3-carbonitrile (218 μmol, example 132) in 640 μL 1,4-dioxane were added 22.8 mg morpholine (261 μmol, CAS 110-91-8), 142 mg cesium carbonate (435 μmol) and 17.1 mg chloro(2-dicyclohexylphosphino-2,4,6-triisopropyl-1,1-biphenyl)[2-(2-amino-1,1-biphenyl)]palladium(II) (21.8 μmol, CAS 1310584-14-5). The mixture was stirred 5 h at 110° C. The reaction mixture was diluted with water and the aqueous phase was extracted with dichloromethane two times. The combined organic phases were filtered (using a waterresistant filter) and concentrated under reduced pressure. The residue was purified by flash chromatography (silica, dichloromethane/methanol gradient 0-3%) to give 41 mg of the title compound (95% purity, 40% yield).

$^1$H NMR (400 MHz, DMSO-d$_6$) δ ppm 1.77-2.12 (m, 6H), 2.85-2.98 (m, 1H), 3.38-3.47 (m, 4H), 3.54 (s, 3H), 3.57-3.68 (m, 2H), 3.70-3.80 (m, 4H), 3.81-3.94 (m, 2H), 6.65-6.74 (m, 1H), 6.97-7.03 (m, 1H), 7.15-7.24 (m, 1H), 7.26-7.37 (m, 4H), 7.83 (d, 1H).

Example 135

(rac)-1-methyl-2-oxo-7-(2-oxopyrrolidin-1-yl)-4-[4-phenylazepan-1-yl]-1,2-dihydroquinoline-3-carbonitrile

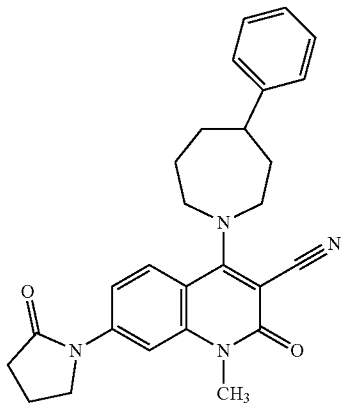 [SMILES: Cn1c(=O)c(C#N)c(N2CCCC(c3ccccc3)CC2)c2ccc(N3CCCC3=O)cc21]

200 mg 7-bromo-1-methyl-2-oxo-4-(4-phenylazepan-1-yl)-1,2-dihydroquinoline-3-carbonitrile (435 μmol, example 132), 74.1 mg pyrrolidin-2-one (871 μmol, CAS 616-45-5), 132 mg potassium carbonate (958 μmol), 16.6 mg copper (I)iodide (87.1 μmol) and 154 mg N,N-dimethylethylenediamine (1.74 mmol) were stirred in 10 mL toluene and the mixture was heated for 11 h at 110° C. The reaction mixture was diluted with water and the aqueous phase was extracted with ethyl acetate three times. The combined organic phases were filtered (using a waterresistant filter) and concentrated under reduced pressure. The residue was purified by flash chromatography (silica, dichloromethane/methanol gradient 0-3%) to give 135 mg of the title compound (95% purity, 67% yield).

$^1$H NMR (400 MHz, DMSO-$d_6$) δ ppm 1.77-2.16 (m, 8H), 2.59 (t, 2H), 2.86-2.96 (m, 1H), 3.55 (s, 3H), 3.63-3.76 (m, 2H), 3.91-4.01 (m, 4H), 7.15-7.23 (m, 1H), 7.29-7.33 (m, 4H), 7.68 (dd, 1H), 7.80 (d, 1H), 8.03 (d, 1H).

Example 136

(rac)-7-(1,1-dioxo-1λ$^6$-thiomorpholin-4-yl)-1-methyl-2-oxo-4-[4-phenylazepan-1-yl]-1,2-dihydroquinoline-3-carbonitrile

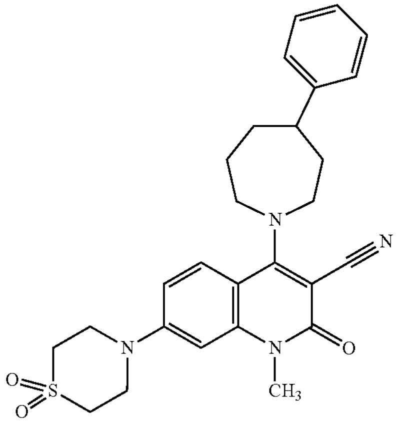 [SMILES: Cn1c(=O)c(C#N)c(N2CCCC(c3ccccc3)CC2)c2ccc(N3CCS(=O)(=O)CC3)cc21]

90 mg 7-bromo-1-methyl-2-oxo-4-(4-phenylazepan-1-yl)-1,2-dihydroquinoline-3-carbonitrile (196 μmol, example 32) in 570 μL 1,4-dioxane were added 31.8 mg 1λ$^6$-thiomorpholine-1,1-dione (235 μmol, CAS 39093-93-1), 128 mg cesium carbonate (392 μmol) and 15.4 mg chloro(2-dicyclohexylphosphino-2,4,6-triisopropyl-1,1-biphenyl)[2-(2-amino-1,1-biphenyl)]palladium(II) (19.6 μmol, CAS 1310584-14-5). The mixture was stirred 8 h at 110° C. The reaction mixture was diluted with water and the aqueous phase was extracted with ethyl acetate three times. The combined organic phases were filtered (using a waterresistant filter) and concentrated under reduced pressure. The residue was purified by flash chromatography (silica, dichloromethane/methanol gradient 0-1%) to give 10 mg of the title compound (95% purity, 10% yield).

$^1$H NMR (400 MHz, DMSO-$d_6$) δ ppm 1.79-2.08 (m, 6H), 2.86-2.96 (m, 1H), 3.19 (br s, 4H), 3.55-3.69 (m, 5H), 3.81-3.93 (m, 2H), 4.05 (br s, 4H), 6.79 (d, 1H), 7.07 (dd, 1H), 7.15-7.24 (m, 1H), 7.26-7.34 (m, 4H), 7.85 (d, 1H).

Example 137

(rac)-7-bromo-1-methyl-2-oxo-4-[4-phenylazepan-1-yl]-1,2-dihydroquinoline-3-carboxamide

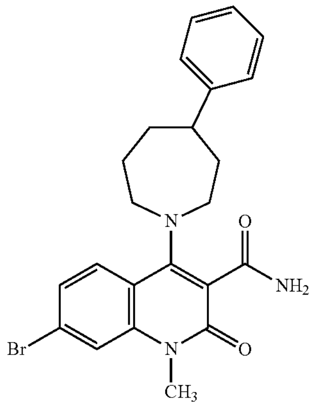 [SMILES: Cn1c(=O)c(C(N)=O)c(N2CCCC(c3ccccc3)CC2)c2ccc(Br)cc21]

150 mg 7-bromo-1-methyl-2-oxo-4-(4-phenylazepan-1-yl)-1,2-dihydroquinoline-3-carbonitrile (344 μmol, example 132), 19.3 mg palladium(II)acetate (85.9 μmol) and 102 mg acetaldoxime (1.72 mmol) were stirred in 5 mL ethanol for 6 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichlorormethane/methanol gradient 0-3%) to give 80 mg of the title compound (95% purity, 49% yield).

$^1$H NMR (400 MHz, DMSO-$d_6$) δ ppm 1.77-2.03 (m, 6H), 2.82-2.94 (m, 1H), 3.27-3.49 (m, 4H, partially below water signal), 3.59 (s, 3H), 7.13-7.23 (m, 1H), 7.27-7.32 (m, 4H), 7.47-7.58 (m, 2H), 7.66 (s, 1H), 7.74 (d, 1H), 7.91 (d, 1H).

The title compound (80 mg) was separated into enantiomers by preparative chiral HPLC to give enantiomer 1 (35 mg, see example 138) and enantiomer 2 (36 mg, see example 139).

Preparative Chiral HPLC Method:

Instrument: Labomatic HD5000, Labocord-5000; Gilson GX-241, Labcol Vario 4000, column: Chiralpak IG 5μ 250×30 mm; eluent: acetonitrile/ethanol 90:10; flow 60.0 ml/min; UV 254 nm Analytical Chiral HPLC Method:

Instrument: Agilent HPLC 1260; column: Chiralpak IG 3μ 100×4.6 mm; eluent: acetonitrile+0.1 vol. % diethylamine/ethanol 85:15; flow 1.4 ml/min; temperature: 25° C.; DAD 254 nm Example 138

7-bromo-1-methyl-2-oxo-4-[4-phenylazepan-1-yl]-1, 2-dihydroquinoline-3-carboxamide, Enantiomer 1

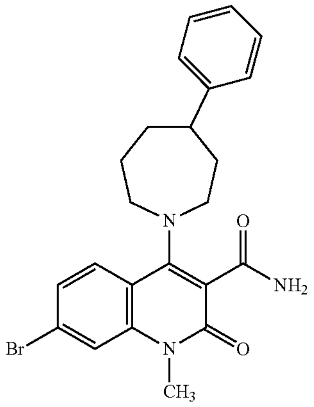 [SMILES: Cn1c(=O)c(C(N)=O)c(N2CCCC(c3ccccc3)CC2)c2ccc(Br)cc21]

For the preparation of the racemic title compound see example 137. Separation of enantiomers by preparative chiral HPLC (method see example 137) to give 35 mg the title compound (99% purity, 22% yield).

Analytical chiral HPLC (method see example 137): $R_t$=3.39 min.

Specific optical rotation: −126.1° (c=2.5 mg/ml, methanol)

$^1$H NMR (400 MHz, DMSO-$d_6$) δ ppm 1.77-2.03 (m, 6H), 2.82-2.94 (m, 1H), 3.27-3.49 (m, 4H, partially below water signal), 3.59 (s, 3H), 7.13-7.23 (m, 1H), 7.27-7.32 (m, 4H), 7.47-7.58 (m, 2H), 7.66 (s, 1H), 7.74 (d, 1H), 7.91 (d, 1H).

Example 139

7-bromo-1-methyl-2-oxo-4-[4-phenylazepan-1-yl]-1, 2-dihydroquinoline-3-carboxamide, Enantiomer 2

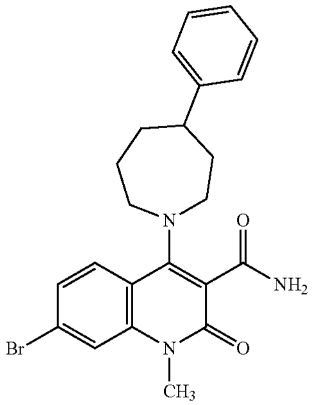 [SMILES: Cn1c(=O)c(C(N)=O)c(N2CCCC(c3ccccc3)CC2)c2ccc(Br)cc21]

For the preparation of the racemic titled compound see example 137. Separation of enantiomers by preparative chiral HPLC (method see example 137) to give 36 mg the title compound (99% purity, 23% yield).

Analytical chiral HPLC (method see example 137): $R_t$=5.93 min.

Specific optical rotation: 137.0° (c=2.2 mg/ml, m ethanol)

$^1$H NMR (400 MHz, DMSO-$d_6$) δ ppm 1.77-2.03 (m, 6H), 2.82-2.94 (m, 1H), 3.27-3.49 (m, 4H, partially below water signal), 3.59 (s, 3H), 7.13-7.23 (m, 1H), 7.27-7.32 (m, 4H), 7.47-7.58 (m, 2H), 7.66 (s, 1H), 7.74 (d, 1H), 7.91 (d, 1H).

Example 140

4-[4-ethyl-4-(5-methyl-1,3-benzoxazol-2-yl)piperidin-1-yl]-1-methyl-2-oxo-1,2-dihydroquinoline-3-carbonitrile

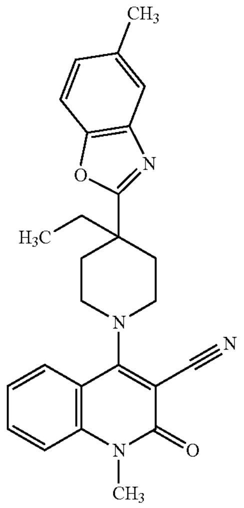 [SMILES: CCC1(c2nc3cc(C)ccc3o2)CCN(c2c(C#N)c(=O)n(C)c3ccccc23)CC1]

100 g 4-chloro-1-methyl-2-oxo-1,2-dihydroquinoline-3-carbonitrile (457 mmol, CAS 150617-68-8), 112 g 2-(4-ethylpiperidin-4-yl)-5-methyl-1,3-benzoxazole (457 mmol, intermediate 66) and 130 mL triethylamine (910 mmol) were stirred in 3 mL 2-propanol for 2 h at 90° C. The reaction mixture was diluted with ethyl acetate, washed with water and brine, dried over sodium sulfate, filtered and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 110 g of the title compound (99% purity, 56% yield).

$^1$H NMR (400 MHz, DMSO-$d_6$) δ ppm 0.71 (t, 3H), 1.87 (q, 2H), 1.98-2.09 (m, 2H), 2.43 (s, 3H), 2.51-2.59 (m, 2H), 3.42 (br t, 2H), 3.55 (s, 3H), 3.74 (br d, 2H), 7.18-7.22 (m, 1H), 7.30-7.36 (m, 1H), 7.52-7.58 (m, 2H), 7.61 (d, 1H), 7.73 (ddd, 1H), 7.88 (dd, 1H).

Example 141

7-bromo-4-[4-ethyl-4-(5-methyl-1,3-benzoxazol-2-yl)piperidin-1-yl]-1-methyl-2-oxo-1,2-dihydroquinoline-3-carbonitrile

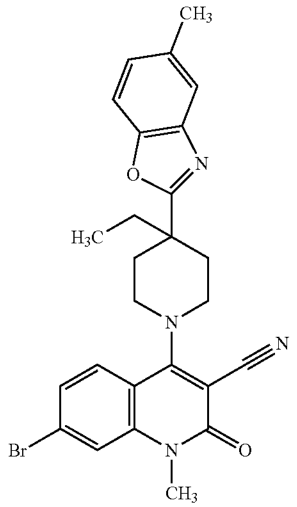 [SMILES: CCC1(c2nc3cc(C)ccc3o2)CCN(c2c(C#N)c(=O)n(C)c3cc(Br)ccc23)CC1]

200 mg 7-bromo-4-chloro-1-methyl-2-oxo-1,2-dihydroquinoline-3-carbonitrile (672 μmol, intermediate 21), 164 mg 2-(4-ethylpiperidin-4-yl)-5-methyl-1,3-benzoxazole (672 mmol, intermediate 66) and 190 μL triethylamine (1.3 mmol) were stirred in 5.0 mL 2-propanol for 1.5 h at 90° C. The reaction mixture was diluted with water and ethyl acetate, washed with water and brine, dried over sodium sulfate, filtered and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 105 g of the title compound (99% purity, 31% yield).

$^1H$ NMR (400 MHz, DMSO-$d_6$) δ ppm 0.71 (t, 3H), 1.81-1.91 (m, 2H), 1.97-2.08 (m, 2H), 2.51-2.58 (m, 2H), 3.37-3.47 (m, 2H), 3.50-3.58 (m, 3H), 3.68-3.78 (m, 2H), 7.20 (dd, 1H), 7.47 (dd, 1H), 7.55-7.58 (m, 1H), 7.58-7.63 (m, 1H), 7.74-7.81 (m, 2H).

Example 142

4-[4-(6-methoxypyridin-3-yl)piperidin-1-yl]-1-methyl-2-oxo-1,2-dihydroquinoline-3-carbonitrile

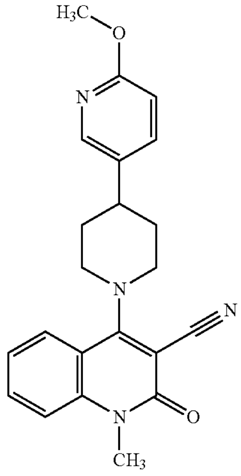 [SMILES: COc1ccc(C2CCN(c3c(C#N)c(=O)n(C)c4ccccc34)CC2)cn1]

25 mg 4-(6-methoxy-3',6'-dihydro[3,4'-bipyridin]-1'(2'H)-yl)-1-methyl-2-oxo-1,2-dihydroquinoline-3-carbonitrile (63.8 μmol, intermediate 70) was dissolved in 3 mL methanol, 2.5 mg palladium on carbon (10%, 23.5 μmol) was added and the mixture was stirred under hydrogen atmosphere for 7 h at rt. The reaction mixture was filtered through celite (celite pad prewashed with water), the filter cake was washed with methanol. The filtrate was concentrated under reduced pressure and the residue was purified by flash chromatography (silica, dichlorormethane/methanol gradient 0-3%) to give 20 mg of the title compound (95% purity, 84% yield).

$^1H$ NMR (400 MHz, DMSO-$d_6$) δ ppm 1.88-2.05 (m, 4H), 2.83-2.96 (m, 1H), 3.47-3.56 (m, 2H), 3.58 (s, 3H), 3.80-3.86 (m, 5H), 6.81 (d, 1H), 7.35 (s, 1H), 7.55-7.60 (m, 1H), 7.75 (dt, 2H), 7.94 (dd, 1H), 8.14 (d, 1H).

Example 143

1-methyl-4-[4-(6-methylpyridin-3-yl)piperidin-1-yl]-2-oxo-1,2-dihydroquinoline-3-carbonitrile

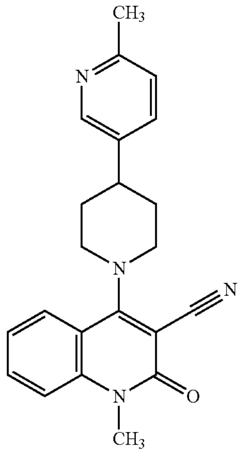 [SMILES: Cc1ccc(C2CCN(c3c(C#N)c(=O)n(C)c4ccccc34)CC2)cn1]

30 mg 1-methyl-4-(6-methyl-3',6'-dihydro[3,4'-bipyridin]-1'(2'H)-yl)-2-oxo-1,2-dihydroquinoline-3-carbonitrile (80.0 μmol, intermediate 73) was dissolved in 3 mL methanol, 3.0 mg palladium on carbon (10%, 28.2 μmol) was added and the mixture was stirred under hydrogen atmosphere for 8 h at rt. The reaction mixture was filtered through celite (celite pad prewashed with water), the filter cake was washed with methanol. The filtrate was concentrated under reduced and the residue was purified by flash chromatography (silica, dichlorormethane/methanol gradient 0-3%) to give 20 mg of the title compound (95% purity, 66% yield).

$^1H$ NMR (400 MHz, DMSO-$d_6$) δ ppm 1.88-2.07 (m, 4H), 2.44 (s, 3H), 2.87-2.97 (m, 1H), 3.47-3.56 (m, 2H), 3.57-3.61 (m, 3H), 3.82 (br s, 2H), 7.22 (d, 1H), 7.35 (s, 1H), 7.58 (d, 1H), 7.75 (s, 1H), 7.93-7.97 (m, 1H), 8.44 (d, 1H).

Example 144

1-methyl-2-oxo-4-[4-(pyridin-3-yl)piperidin-1-yl]-1,2-dihydroquinoline-3-carbonitrile

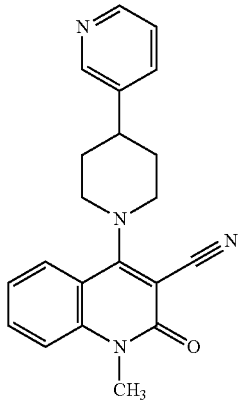 [SMILES: Cn1c(=O)c(C#N)c(N2CCC(c3cccnc3)CC2)c2ccccc21]

55 mg 4-(3',6'-dihydro[3,4'-bipyridin]-1'(2'H)-yl)-1-methyl-2-oxo-1,2-dihydroquinoline-3-carbonitrile (137 μmol, intermediate 76) was dissolved in 4 mL methanol, 5.5 mg palladium on carbon (10%, 51.7 μmol) was added and the mixture was stirred under hydrogen atmosphere for 8 h at rt. The reaction mixture was filtered through celite (celite pad prewashed with water), the filter cake was washed with less methanol three times. The filtrate was concentrated under reduced pressure and the residue was purified by flash chromatography (silica, dichloromethane/methanol gradient 0-3%) to give 34 mg of the title compound (95% purity, 69% yield).

$^1$H NMR (400 MHz, DMSO-$d_6$) δ ppm 1.93-2.10 (m, 4H), 2.91-3.03 (m, 1H), 3.47-3.63 (m, 6H), 3.85 (br d, 2H), 7.31-7.41 (m, 2H), 7.55-7.62 (m, 1H), 7.75 (ddd, 1H), 7.81 (dt, 1H), 7.96 (dd, 1H), 8.46 (d, 1H), 8.60 (d, 1H).

Example 145

4-[4-(1,3-benzothiazol-2-yl)piperidin-1-yl]-N,1-dimethyl-2-oxo-1,2-dihydroquinoline-3-carboxamide

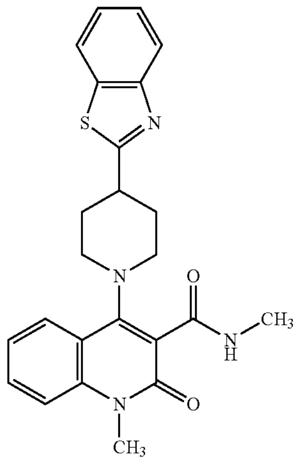 [SMILES: CNC(=O)c1c(N2CCC(c3nc4ccccc4s3)CC2)c2ccccc2n(C)c1=O]

50 mg 4-[4-(1,3-benzothiazol-2-yl)piperidin-1-yl]-1-methyl-2-oxo-1,2-dihydroquinoline-3-carboxylic acid (119 μmol, intermediate 80) was dissolved in 1.0 mL dichloromethane, 120 μL methanamine (2.0 M in THF, 240 μmol, CAS 74-89-5), 83 μL N,N-diisopropylethylamine (480 μmol) and 66.6 mg PyBOP (143 μmol) were added and the mixture was stirred overnight at rt. The reaction mixture was concentrated under reduced pressure and the residue was purified by RP-HPLC (column: Chromatorex 125×30 mm, 10 μm mobile phase: acetonitrile/water (0.1 vol. % formic acid)-acetonitrile 15-55%) to give 4.9 mg of the title compound (95% purity, 9% yield).

$^1$H NMR (400 MHz, DMSO-$d_6$) δ ppm 2.01-2.15 (m, 2H) 2.16-2.27 (m, 2H) 2.75 (d, 3H) 3.05-3.16 (m, 2H) 3.34-3.43 (m, 3H) 3.56-3.63 (m, 3H) 7.29-7.37 (m, 1H) 7.39-7.47 (m, 1H) 7.47-7.57 (m, 2H) 7.59-7.67 (m, 1H) 7.91-8.03 (m, 2H) 8.06-8.13 (m, 1H) 8.14-8.25 (m, 1H).

LC-MS (Method 3): $R_t$=1.08 min; MS (ESIpos): m/z=433 $[M+H]^+$

Example 146

4-[4-(1,3-benzothiazol-2-yl)piperidin-1-yl]-N,N,1-trimethyl-2-oxo-1,2-dihydroquinoline-3-carboxamide

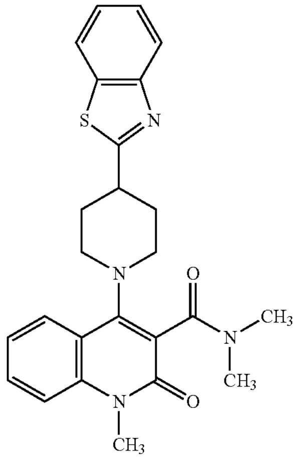 [SMILES: CN(C)C(=O)c1c(N2CCC(c3nc4ccccc4s3)CC2)c2ccccc2n(C)c1=O]

100 mg 4-[4-(1,3-benzothiazol-2-yl)piperidin-1-yl]-3-bromo-1-methylquinolin-2(1H)-one (220 μmol, intermediate 78) was suspended in 5.0 mL N-methylmethanamine (2.0 M in THF, 9.9 mmol), 18 mg 1,1-bis(diphenylphosphino)ferrocene-palladium(II)dichloride-dichloromethane complex (22.0 μmol, CAS 95464-05-4) and 61 μL triethylamie (440 μmol) were added and the mixture was stirred 22 h at 100° C. (15 bar) under carbon monooxide atmosphere. The reaction mixture was cooled down to rt and atmospheric pressure. The mixture was concentrated under reduced pressure and the residue was purified by RP-HPLC (column: X-Bridge C18 5 μm 100×30 mm, mobile phase: acetonitrile/water (0.1 vol. % formic acid)-gradient) to give 15.1 mg of the title compound (95% purity, 15% yield).

$^1$H NMR (400 MHz, DMSO-$d_6$) δ ppm 1.93-2.08 (m, 1H) 2.15-2.29 (m, 3H) 2.91 (s, 3H) 2.99 (s, 4H) 3.09-3.20 (m, 2H) 3.48 (br d, 1H) 3.61 (s, 3H) 7.31-7.38 (m, 1H) 7.40-7.45 (m, 1H) 7.47-7.58 (m, 2H) 7.60-7.70 (m, 1H) 7.93-8.03 (m, 2H) 8.07-8.13 (m, 1H).

LC-MS (Method 1): $R_t$=1.22 min; MS (ESIpos): m/z=448 $[M+H]^+$

Example 147

1-methyl-4-[4-(1-methyl-1H-benzimidazol-2-yl) piperidin-1-yl]-2-oxo-1,2-dihydroquinoline-3-carbonitrile

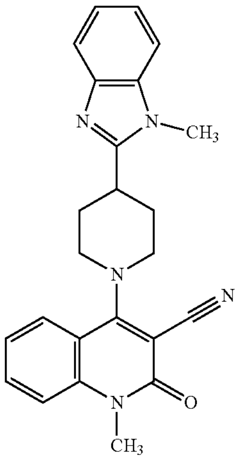 [SMILES: Cn1c(C2CCN(c3c(C#N)c(=O)n(C)c4ccccc34)CC2)nc2ccccc21]

120 mg 4-chloro-1-methyl-2-oxo-1,2-dihydroquinoline-3-carbonitrile (549 μmol, CAS 150617-68-8) was dissolved in 2.6 mL 2-propanol, 142 mg 1-methyl-2-(piperidin-4-yl)-1H-benzimidazole (659 μmol, CAS 180160-86-5) and 290 μL N,N-diisopropylethylamine (1.6 mmol) were added and the mixture was heated for 2 h under reflux. The reaction mixture was cooled down to rt, diluted with water, the resulting solid was filtered off and dried in vacuum to give 197 mg of the title compound (96% purity, 87% yield).

$^1$H NMR (400 MHz, DMSO-$d_6$) δ ppm 2.00-2.27 (m, 3H) 2.06-2.24 (m, 1H) 3.39-3.52 (m, 1H) 3.53-3.72 (m, 5H) 3.79-3.95 (m, 5H) 7.12-7.28 (m, 2H) 7.33-7.44 (m, 1H) 7.45-7.64 (m, 3H) 7.70-7.80 (m, 1H) 7.84-7.97 (m, 1H).

Example 148

1-methyl-2-oxo-4-[4-(3-propyl-1,2,4-oxadiazol-5-yl) piperidin-1-yl]-1,2-dihydroquinoline-3-carbonitrile

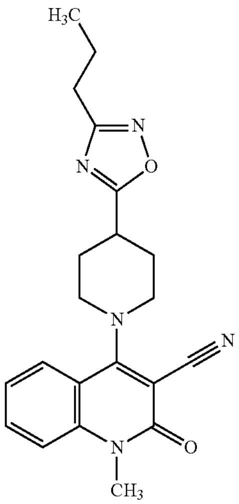 [SMILES: CCCc1noc(C2CCN(c3c(C#N)c(=O)n(C)c4ccccc34)CC2)n1]

120 mg 4-chloro-1-methyl-2-oxo-1,2-dihydroquinoline-3-carbonitrile (549 μmol, CAS 150617-68-8) was dissolved in 2.6 mL 2-propanol, 246 mg 4-(3-propyl-1,2,4-oxadiazol-5-yl)piperidine (1.26 mmol, CAS92837-03-0) was added and the mixture was stirred for 45 min. at 100° C. in the microwave. The reaction mixture was cooled down to rt, diluted with water, the resulting solid was filtered off and dried in vacuum to give 142 mg of the title compound (98% purity, 67% yield).

$^1$H NMR (400 MHz, DMSO-$d_6$) δ ppm 0.94 (t, 3H) 1.62-1.79 (m, 2H) 1.97-2.15 (m, 2H) 2.18-2.28 (m, 2H) 2.63-2.76 (m, 2H) 3.45 (ddt, 1H) 3.51-3.65 (m, 5H) 3.72-3.86 (m, 2H) 7.31-7.38 (m, 1H) 7.51-7.63 (m, 1H) 7.67-7.76 (m, 1H) 7.81-7.90 (m, 1H).

Example 149

1-methyl-4-[4-(1-methyl-1H-pyrazol-5-yl)piperidin-1-yl]-2-oxo-1,2-dihydroquinoline-3-carbonitrile

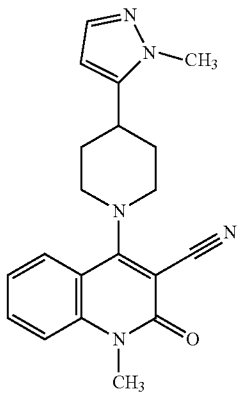 [SMILES: Cn1nccc1C1CCN(c2c(C#N)c(=O)n(C)c3ccccc23)CC1]

150 mg 4-chloro-1-methyl-2-oxo-1,2-dihydroquinoline-3-carbonitrile (686 μmol, CAS 150617-68-8) was dissolved in 4.5 mL 2-propanol, 136 mg 4-(1-methyl-1H-pyrazol-5-yl)piperidine (823 μmol, CAS 640270-01-5) and 190 μL triethylamine (1.4 mmol) were added and the mixture was heated for 3.5 h at 90° C. The reaction mixture was cooled down to rt, ethyl acetate was added and the suspension was filtered. The filter cake was washed and dried in vacuum to give 80 mg of the title compound (95% purity, 32% yield).

$^1$H NMR (400 MHz, DMSO-$d_6$) δ ppm 1.80-1.94 (m, 2H), 1.99-2.08 (m, 2H), 3.07-3.17 (m, 1H), 3.49-3.57 (m, 2H), 3.58 (s, 3H), 3.77-3.86 (m, 5H), 6.17 (d, 1H), 7.31-7.39 (m, 2H), 7.56-7.60 (m, 1H), 7.75 (s, 1H), 7.89 (dd, 1H).

Example 150

1-methyl-2-oxo-4-[4-(pyrazin-2-yl)piperidin-1-yl]-1,2-dihydroquinoline-3-carbonitrile

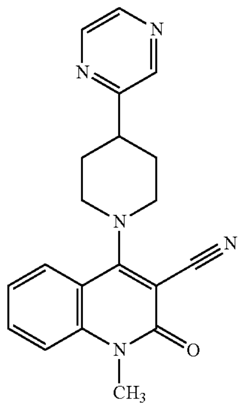 [SMILES: Cn1c(=O)c(C#N)c(N2CCC(c3cnccn3)CC2)c2ccccc21]

200 mg 4-chloro-1-methyl-2-oxo-1,2-dihydroquinoline-3-carbonitrile (915 μmol, CAS 150617-68-8) was dissolved in 6.0 mL 2-propanol, 179 mg 2-(piperidin-4-yl)pyrazine (1.10 mmol, CAS 736134-74-0) and 250 μL triethylamine (1.8 mmol) were added and the mixture was heated for 6 h at 90° C. The reaction mixture was cooled down to rt, diluted with water and the aqueous phase was extracted with ethyl acetate. The combined organic layers were washed with water and brine, filtered through a waterresistant filter and the filtrate was concentrated under reduced pressure. The residue was purified by flash chromatography (silica, dichloromethane/methanol gradient 0-3%) to give 181 mg of the title compound (95% purity, 54% yield).

$^1$H NMR (400 MHz, DMSO-$d_6$) δ ppm 2.01-2.17 (m, 4H), 3.13-3.25 (m, 1H), 3.50-3.63 (m, 5H), 3.87 (br d, 2H), 7.36 (t, 1H), 7.58 (d, 1H), 7.71-7.77 (m, 1H), 7.88-7.92 (m, 1H), 8.54 (d, 1H), 8.63 (dd, 1H), 8.72 (d, 1H).

Example 151

4-[4-(4-chlorophenyl)-4-hydroxypiperidin-1-yl]-1-methyl-2-oxo-1,2-dihydroquinoline-3-carbonitrile

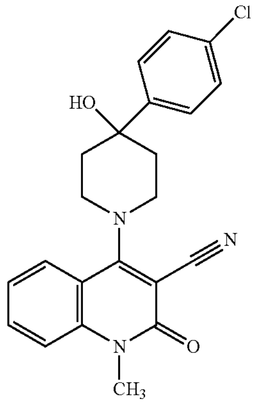 [SMILES: Cn1c(=O)c(C#N)c(N2CCC(O)(c3ccc(Cl)cc3)CC2)c2ccccc21]

100 mg 4-chloro-1-methyl-2-oxo-1,2-dihydroquinoline-3-carbonitrile (457 μmol, CAS 150617-68-8) was dissolved in 2.2 mL 2-propanol, 116 mg 4-(4-chlorophenyl)piperidin-4-ol (549 μmol, CAS 39512-49-7) and 240 μL N,N-diisopropylethylamine (1.4 mmol) were added and the mixture was heated for 2 h under reflux. The reaction mixture was cooled down to rt, diluted with water, the resulting solid was filtered off and dried in vacuum to give 117 mg of the title compound (98% purity, 64% yield).

$^1$H NMR (400 MHz, DMSO-$d_6$) δ ppm 1.78 (br d, 2H) 2.19-2.36 (m, 2H) 3.53-3.70 (m, 5H) 3.77-3.90 (m, 2H) 5.39 (s, 1H) 7.32-7.39 (m, 1H) 7.39-7.48 (m, 2H) 7.55-7.65 (m, 3H) 7.69-7.78 (m, 1H) 7.94-8.01 (m, 1H).

Example 152

4-{4-hydroxy-4-[3-(trifluoromethyl)phenyl]piperidin-1-yl}-1-methyl-2-oxo-1,2-dihydroquinoline-3-carbonitrile

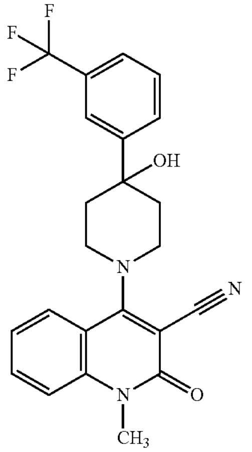 [SMILES: Cn1c(=O)c(C#N)c(N2CCC(O)(c3cccc(C(F)(F)F)c3)CC2)c2ccccc21]

100 mg 4-chloro-1-methyl-2-oxo-1,2-dihydroquinoline-3-carbonitrile (457 μmol, CAS 150617-68-8) was dissolved in 2.0 mL 2-propanol, 155 mg 4-[3-(trifluoromethyl)phenyl]piperidin-4-ol hydrogen chloride salt (1:1) (549 μmol, CAS 2249-28-7) and 240 μL N,N-diisopropylethylamine (1.4 mmol) were added and the mixture was heated for 2 h at 90° C. The reaction mixture was cooled down to rt, diluted with water, the resulting solid was filtered off, washed with ethanol and dried in vacuum at 100° C. to give 173 mg of the title compound (95% purity, 84% yield).

$^1$H NMR (400 MHz, DMSO-$d_6$) δ ppm 1.77-1.84 (m, 2H) 2.29-2.41 (m, 2H) 3.54-3.70 (m, 5H) 3.78-3.90 (m, 2H) 5.53 (s, 1H) 7.28-7.40 (m, 1H) 7.54-7.68 (m, 3H) 7.70-7.79 (m, 1H) 7.86-8.06 (m, 3H).

LC-MS (Method 1): $R_t$=1.24 min; MS (ESIpos): m/z=428 [M+H]$^+$

Example 153

8-fluoro-4-[4-(4-methoxyphenyl)piperidin-1-yl]-1-methyl-2-oxo-1,2-dihydroquinoline-3-carbonitrile

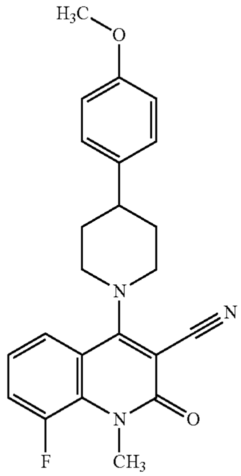 [SMILES: COc1ccc(C2CCN(c3c(C#N)c(=O)n(C)c4c(F)cccc34)CC2)cc1]

A solution of 100 mg 4-chloro-8-fluoro-1-methyl-2-oxo-1,2-dihydroquinoline-3-carbonitrile (423 μmol, intermediate 83), 105 mg 4-(4-methoxyphenyl)piperidine (549 μmol, CAS 67259-62-5) and 120 μL triethylamine (850 μmol) in 2.8 mL 2-propanol was stirred for 3.5 h at 90° C. After this time, water was added and the reaction was extracted with ethyl acetate. The organic phase was washed with water and brine and the solvent was removed in vacuum. The residue was purified by flash chromatography (silica, dichloromethane/methanol gradient 0-3%) to obtain 80 mg of the title compound (95% purity, 46% yield).

$^1$H NMR (400 MHz, DMSO-$d_6$) δ ppm 1.85-2.01 (m, 4H), 2.76-2.90 (m, 1H), 3.43-3.57 (m, 2H), 3.67-3.75 (m, 6H), 3.76-3.86 (m, 2H), 6.87-6.94 (m, 2H), 7.23-7.29 (m, 2H), 7.29-7.37 (m, 1H), 7.61 (ddd, 1H), 7.75 (d, 1H).

Example 154

4-[4-(1,3-benzothiazol-2-yl)piperidin-1-yl]-8-fluoro-1-methyl-2-oxo-1,2-dihydroquinoline-3-carbonitrile

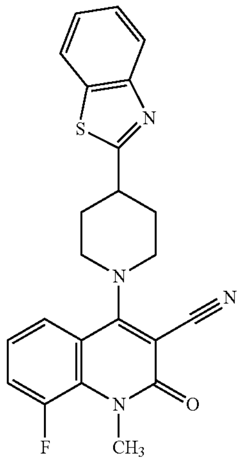 [SMILES: Cn1c(=O)c(C#N)c(N2CCC(c3nc4ccccc4s3)CC2)c2cccc(F)c21]

A solution of 100 mg 4-chloro-8-fluoro-1-methyl-2-oxo-1,2-dihydroquinoline-3-carbonitrile (423 μmol, intermediate 83), 120 mg 2-(piperidin-4-yl)-1,3-benzothiazole (549 μmol, CAS 51784-73-7) and 120 μL triethylamine (850 μmol) in 2.8 mL 2-propanol was stirred for 4 h at 90° C. After this time, water was added and the reaction was extracted with ethyl acetate. The organic phase was washed with water and brine and the solvent was removed in vacuum. The residue was purified by flash chromatography (silica, dichloromethane/methanol gradient 0-3%) to obtain 122 mg of the title compound (95% purity, 66% yield).

$^1$H NMR (400 MHz, DMSO-$d_6$) δ ppm 2.07-2.21 (m, 2H), 2.27-2.38 (m, 2H), 3.50-3.66 (m, 3H), 3.71 (d, 3H), 3.80-3.90 (m, 2H), 7.29-7.38 (m, 1H), 7.40-7.47 (m, 1H), 7.48-7.55 (m, 1H), 7.62 (ddd, 1H), 7.71 (d, 1H), 7.99 (d, 1H), 8.10 (d, 1H).

TABLE 7

Following examples of table 7 were prepared from assigned starting materials and according to the procedure of example 153.

| Example | Structure | IUPAC-Name | Starting Materials | Analytics |
|---|---|---|---|---|
| 155 | 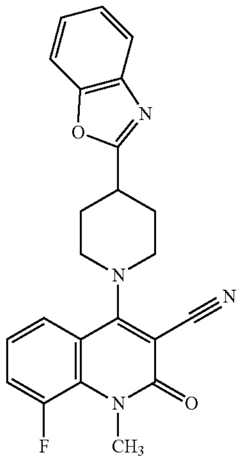 [SMILES: Cn1c(=O)c(C#N)c(N2CCC(c3nc4ccccc4o3)CC2)c2cccc(F)c21] | 4-[4-(1,3-benzoxazol-2-yl)piperidin-1-yl]-8-fluoro-1-methyl-2-oxo-1,2-dihydroquinoline-3-carbonitrile | intermediate 83 and 2-(piperidin-4-yl)-1,3-benzoxazole (CAS 51784-03-3) | $^1$H NMR (400 MHz, DMSO-$d_6$) δ ppm 2.08-2.22 (m, 2 H), 2.27-2.37 (m, 2 H), 3.42-3.53 (m, 1 H), 3.54-3.65 (m, 2 H), 3.71 (d, 3 H), 3.77-3.86 (m, 2 H), 7.29-7.42 (m, 3 H), 7.57-7.66 (m, 1 H), 7.68-7.77 (m, 3 H). |

TABLE 7-continued

Following examples of table 7 were prepared from assigned starting materials and according to the procedure of example 153.

| Example | Structure | IUPAC-Name | Starting Materials | Analytics |
|---|---|---|---|---|
| 156 | 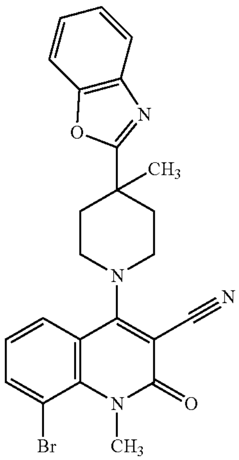 [SMILES: Cn1c(=O)c(C#N)c(N2CCC(C)(c3nc4ccccc4o3)CC2)c2cccc(Br)c21] | 4-[4-(1,3-benzoxazol-2-yl)-4-methylpiperidin-1-yl]-8-bromo-1-methyl-2-oxo-1,2-dihydroquinoline-3-carbonitrile | intermediate 86 and intermediate 1 | $^1$H NMR (400 MHz, DMSO-$d_6$) δ ppm 1.45-1.55 (m, 3 H), 2.07 (ddd, 2 H), 3.52 (br t, 2 H), 3.68 (s, 3 H), 3.70-3.80 (m, 2 H), 7.23 (s, 1 H), 7.34-7.44 (m, 2 H), 7.71-7.80 (m, 2 H), 7.87 (dd, 1 H), 7.97-8.01 (m, 1 H). |
| 157 | 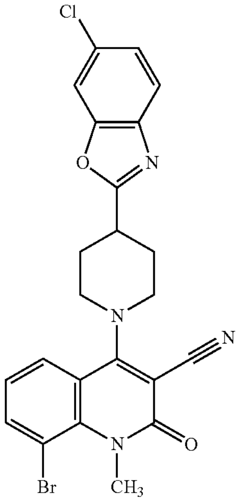 [SMILES: Cn1c(=O)c(C#N)c(N2CCC(c3nc4ccc(Cl)cc4o3)CC2)c2cccc(Br)c21] | 8-bromo-4-[4-(6-chloro-1,3-benzoxazol-2-yl)piperidin-1-yl]-1-methyl-2-oxo-1,2-dihydroquinoline-3-carbonitrile | intermediate 86 and intermediate 7 | $^1$H NMR (400 MHz, DMSO-$d_6$) δ ppm 2.07-2.21 (m, 2 H), 2.26-2.35 (m, 2 H), 3.43-3.54 (m, 1 H), 3.60 (s, 2 H), 3.7 (s, 3 H), 3.79-3.88 (m, 2 H), 7.26 (s, 1 H), 7.41-7.48 (m, 1 H), 7.76 (d, 1 H), 7.84-7.89 (m, 1 H), 7.95 (d, 1 H), 8.01 (dd, 1 H). |
| 158 | 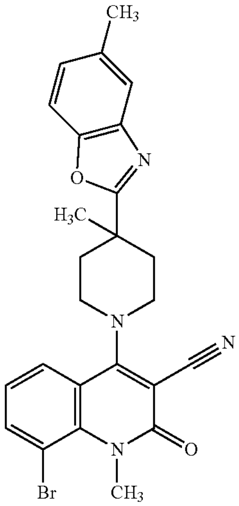 [SMILES: Cc1ccc2oc(C3(C)CCN(c4c(C#N)c(=O)n(C)c5c(Br)cccc45)CC3)nc2c1] | 8-bromo-1-methyl-4-[4-methyl-4-(5-methyl-1,3-benzoxazol-2-yl)piperidin-1-yl]-2-oxo-1,2-dihydroquinoline-3-carbonitrile | intermediate 86 and intermediate 52 | $^1$H NMR (400 MHz, DMSO-$d_6$) δ ppm 1.49 (s, 3 H), 2.00-2.12 (m, 2 H), 2.43 (s, 3 H), 3.44-3.56 (m, 2 H), 3.65-3.78 (m + s, 5 H), 7.17-7.28 (m, 2 H), 7.54-7.57 (m, 1 H), 7.58-7.63 (m, 1 H), 7.87 (dd, 1 H), 8.00 (dd, 1 H). |

TABLE 7-continued

Following examples of table 7 were prepared from assigned starting materials and according to the procedure of example 153.

| Example | Structure | IUPAC-Name | Starting Materials | Analytics |
|---|---|---|---|---|
| 159 | 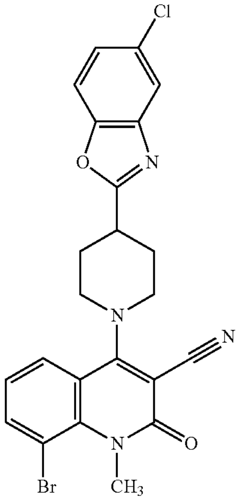 [SMILES: Cn1c(=O)c(C#N)c(N2CCC(c3nc4cc(Cl)ccc4o3)CC2)c2cccc(Br)c21] | 8-bromo-4-[4-(5-chloro-1,3-benzoxazol-2-yl)piperidin-1-yl]-1-methyl-2-oxo-1,2-dihydroquinoline-3-carbontrile | intermediate 86 and intermediate 9 | $^1$H NMR (400 MHz, DMSO-$d_6$) δ ppm 2.08-2.21 (m, 2 H), 2.26-2.36 (m, 2 H), 3.44-3.54 (m, 1 H), 3.54-3.65 (m, 2 H), 3.70 (s, 3 H), 3.79-3.87 (m, 2 H), 7.26 (s, 1 H), 7.43-7.46 (m, 1 H), 7.78 (d, 1 H), 7.83-7.89 (m, 2 H), 8.01 (dd, 1 H). |
| 160 | 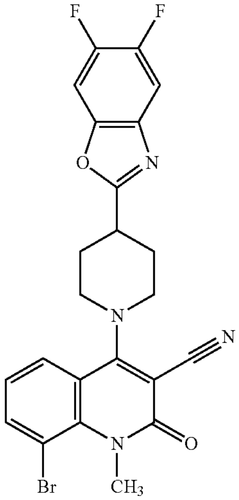 [SMILES: Cn1c(=O)c(C#N)c(N2CCC(c3nc4cc(F)c(F)cc4o3)CC2)c2cccc(Br)c21] | 8-bromo-4-[4-(5,6-difluoro-1,3-benzoxazol-2-yl)piperidin-1-yl]-1-methyl-2-oxo-1,2-dihydroquinoline-3-carbonitrile | intermediate 86 and intermediate 12 | $^1$H NMR (500 MHz, DMSO-$d_6$) δ ppm 2.07-2.19 (m, 2 H), 2.26-2.34 (m, 2 H), 3.44-3.53 (m, 1 H), 3.55-3.65 (m, 2 H), 3.70 (s, 3 H), 3.79-3.87 (m, 2 H), 7.26 (t, 1 H), 7.86 (dd, 1 H), 7.93 (dd, 1 H), 8.01 (dd, 1 H), 8.05 (dd, 1 H). |
| 161 | 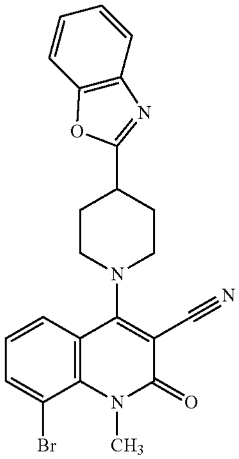 [SMILES: Cn1c(=O)c(C#N)c(N2CCC(c3nc4ccccc4o3)CC2)c2cccc(Br)c21] | 4-[4-(1,3-benzoxazol-2-yl)piperidin-1-yl] 8-bromo-1-methyl-2-oxo-1,2-dihydroquinoline-3-carbonitrile | intermediate 86 and 2-(piperidin-4-yl)-1,3-benzoxazole (CAS 51784-03-3) | $^1$H NMR (400 MHz, DMSO-$d_6$) δ ppm 2.07-2.22 (m, 2 H), 2.25-2.36 (m, 2 H), 3.42-3.53 (m, 1 H), 3.55-3.67 (m, 2 H), 3.70 (s, 3 H), 3.78-3.90 (m, 2 H), 7.26 (t, 1 H), 7.33-7.43 (m, 2 H), 7.68-7.77 (m, 2 H), 7.87 (dd, 1 H), 8.01 (dd, 1 H). |

TABLE 7-continued

Following examples of table 7 were prepared from assigned starting materials and according to the procedure of example 153.

| Example | Structure | IUPAC-Name | Starting Materials | Analytics |
|---|---|---|---|---|
| 162 | 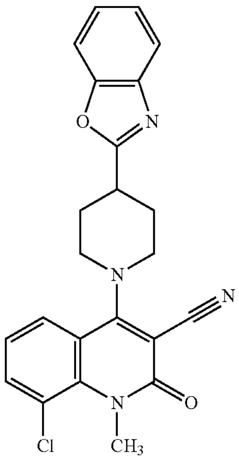 [SMILES: Cn1c(=O)c(C#N)c(N2CCC(c3nc4ccccc4o3)CC2)c2cccc(Cl)c21] | 4-[4-(1,3-benzoxazol-2-yl)piperidin-1-yl]-8-chloro-1-methyl-2-oxo-1,2-dihydroquinoline-3-carbonitrile | intermediate 89 and 2-(piperidin-4-yl)-1,3-benzoxazole (CAS 51784-03-3) | $^1$H NMR (400 MHz, DMSO-$d_6$) δ ppm 2.09-2.22 (m, 2 H), 2.27-2.37 (m, 2 H), 3.43-3.53 (m, 1 H), 3.55-3.66 (m, 2 H), 3.71 (s, 3 H), 3.79-3.89 (m, 2 H), 7.31-7.42 (m, 3 H), 7.69-7.76 (m, 2 H), 7.80-7.86 (m, 2 H). |

Example 163

1-methyl-4-[4-methyl-4-(5-methyl-1,3-benzoxazol-2-yl)piperidin-1-yl]-2-oxo-1,2-dihydroquinoline-3,8-dicarbonitrile

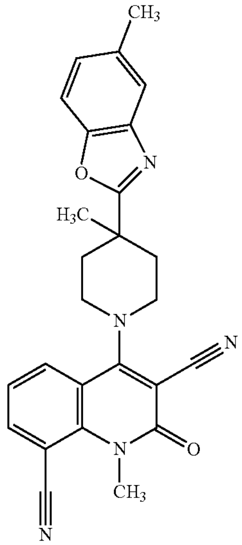 [SMILES: Cc1ccc2oc(C3(C)CCN(c4c(C#N)c(=O)n(C)c5c(C#N)cccc45)CC3)nc2c1]

A solution of 50 mg 8-bromo-1-methyl-4-[4-methyl-4-(5-methyl-1,3-benzoxazol-2-yl)piperidin-1-yl]-2-oxo-1,2-dihydroquinoline-3-carbonitrile (102 μmol, example 158), 2.6 mg palladium(1-phenylallyl)chloride dimer (5.1 μmol, CAS 12131-44-1), 2.8 mg 1,1-bis(diphenylphosphino)ferrocene (5.1 μmol, CAS 12150-46-8), 14.3 mg zinc cyanide (122 μmol, CAS 557-21-1) and 35 μL N,N-diisopropylethylamine (200 μmol) in 1 mL N,N-dimethylacetamide was flushed with argon and stirred for 14 hours at 80° C. Saturated aqueous sodium bicarbonate solution was added and the mixture was extracted with dichloromethane (3×). The combined organic layers were filtered with a water-repellent filter and concentrated in vacuum. The residue was purified by RP-HPLC (column: YMC Triart C18 5 μm 150×50 mm, mobile phase: acetonitrile/water (0.1 vol. % formic acid); gradient: 0.00-0.50 min. 56% B, 0.51-8.50 min. 56-86% B) to give 14.5 mg of the title compound (99% purity, 32% yield).

$^1$H NMR (400 MHz, DMSO-$d_6$) δ ppm 1.43-1.55 (m, 3H), 1.99-2.13 (m, 2H), 2.42 (s, 3H), 3.44-3.59 (m, 2H), 3.71 (br d, 2H), 3.88 (s, 3H), 7.15-7.25 (m, 1H), 7.38-7.47 (m, 1H), 7.52-7.65 (m, 2H), 8.17 (br t, 2H).

Example 164

8-(methanesulfonyl)-1-methyl-4-[4-methyl-4-(5-methyl-1,3-benzoxazol-2-yl)piperidin-1-yl]-2-oxo-1,2-dihydroquinoline-3-carbonitrile

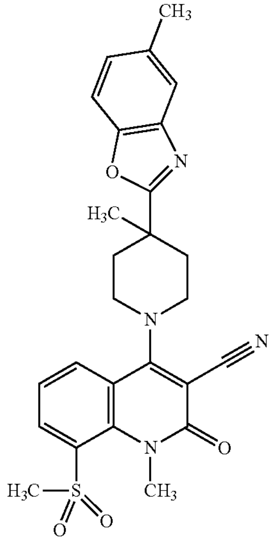 [SMILES: Cc1ccc2oc(C3(C)CCN(c4c(C#N)c(=O)n(C)c5c(S(C)(=O)=O)cccc45)CC3)nc2c1]

A solution of 100 mg 8-bromo-1-methyl-4-[4-methyl-4-(5-methyl-1,3-benzoxazol-2-yl)piperidin-1-yl]-2-oxo-1,2-dihydroquinoline-3-carbonitrile (193 μmol, example 158) in 1.5 mL DMSO was degassed with argon. To the mixture was added 31.2 mg sodium methanesulfinate (290 μmol, CAS 20277-69-4), 79 μL (1S,2S)-cyclohexane-1,2-diamine (9.5 μmol, CAS 1121-22-8) and 9.7 mg copper(I)trifluoromethanesulfonate-benzene (2:2:1) (19.3 μmol). The reaction was stirred for overnight at 110° C. The mixture was filtered an d the residue was purified by RP-HPLC (column: X-Bridge C18 5μ 100×30 mm; mobile phase: water (0.2 vol. % aq. ammonia 32%)/acetonitrile) to give 10 mg of the title compound (95% purity, 11% yield).

$^1$H NMR (400 MHz, DMSO-$d_6$) δ ppm 1.49 (s, 3H), 2.00-2.13 (m, 3H), 2.43 (s, 3H), 3.48-3.58 (m+s, 5H), 3.58-3.64 (m, 3H), 3.68-3.79 (m, 2H), 7.20 (dd, 1H), 7.41 (t, 1H), 7.54-7.57 (m, 1H), 7.58-7.63 (m, 1H), 8.10 (dd, 1H), 8.40 (dd, 1H).

Example 165

4-[4-(1,3-benzoxazol-2-yl)piperidin-1-yl]-1,6-dimethyl-2-oxo-1,2-dihydroquinoline-3-carbonitrile

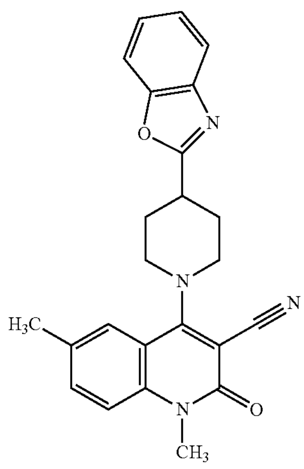 [SMILES: Cc1ccc2c(c1)c(N1CCC(c3nc4ccccc4o3)CC1)c(C#N)c(=O)n2C]

A solution of 150 mg 4-chloro-1,6-dimethyl-2-oxo-1,2-dihydroquinoline-3-carbonitrile (0.61 mmol, intermediate 92), 175 mg 2-(piperidin-4-yl)-1,3-benzoxazole (0.74 mmol, CAS 51784-03-3) and 0.17 mL triethylamine (1.2 mmol) in 6.2 mL 2-propanol was stirred for 4 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%) to obtain 135 mg of the title compound (95% purity, 53% yield).

$^1$H NMR (400 MHz, DMSO-$d_6$) δ ppm 2.09-2.22 (m, 2H), 2.30-2.39 (m, 2H), 2.41 (s, 3H), 3.41-3.52 (m, 1H), 3.53-3.66 (m, 5H), 3.79-3.88 (m, 2H), 7.35-7.41 (m, 2H), 7.47-7.51 (m, 1H), 7.56 (d, 1H), 7.64 (s, 1H), 7.71-7.76 (m, 2H).

Example 166

1,6-dimethyl-4-[4-(5-methyl-1,3-benzoxazol-2-yl)piperidin-1-yl]-2-oxo-1,2-dihydroquinoline-3-carbonitrile

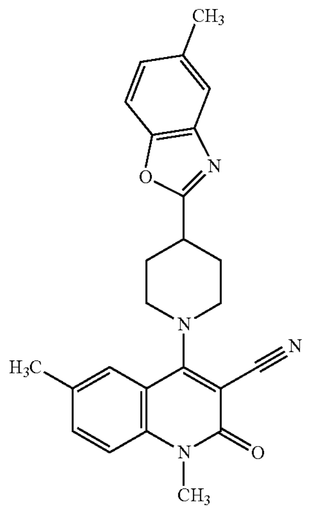 [SMILES: Cc1ccc2oc(C3CCN(c4c(C#N)c(=O)n(C)c5ccc(C)cc45)CC3)nc2c1]

A solution of 150 mg 4-chloro-1,6-dimethyl-2-oxo-1,2-dihydroquinoline-3-carbonitrile (0.61 mmol, intermediate 92), 167 mg 5-methyl-2-(piperidin-4-yl)-1,3-benzoxazole (0.74 mmol, CAS 199292-77-8) and 0.17 mL triethylamine (1.2 mmol) in 6.2 mL 2-propanol was stirred for 3 h at 90° C. After this time, water was added and the reaction was extracted with ethyl acetate. The organic phase was washed with water and brine and dried over sodium sulfate. After evaporation of the solvent, the residue was purified by flash chromatography (silica, dichloromethane/methanol gradient 0-3%) to obtain 185 mg of the title compound (95% purity, 70% yield).

$^1$H NMR (400 MHz, DMSO-$d_6$) δ ppm 2.07-2.20 (m, 2H), 2.26-2.36 (m, 2H), 2.41 (s, 3H), 2.44 (s, 3H), 3.37-3.48 (m, 1H), 3.53-3.65 (m+s, 5H), 3.78-3.88 (m, 2H), 7.16-7.22 (m, 1H), 7.45-7.51 (m, 1H), 7.51-7.54 (m, 1H), 7.55-7.62 (m, 2H), 7.62-7.67 (m, 1H).

Example 167

6-bromo-4-[4-(4-methoxyphenyl)piperidin-1-yl]-1-methyl-2-oxo-1,2-dihydroquinoline-3-carbonitrile

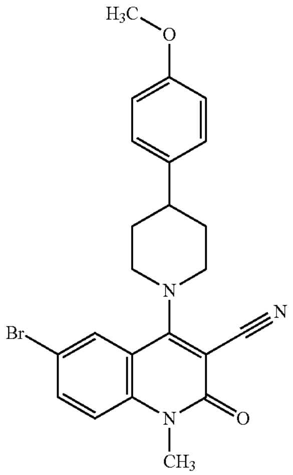 [SMILES: COc1ccc(C2CCN(c3c(C#N)c(=O)n(C)c4ccc(Br)cc34)CC2)cc1]

1.30 g 6-bromo-4-chloro-1-methyl-2-oxo-1,2-dihydroquinoline-3-carbonitrile (4.37 mmol, intermediate 95) was dissolved in 25 mL 2-propanol, 1 g 4-(4-methoxyphenyl) piperidine (5.24 mmol, CAS 67259-62-5) and 2.3 mL N,N-diisopropylethylamine (13 mmol) were added and the mixture was heated for 2 h at 90° C. The reaction mixture was cooled down to rt, diluted with water, the resulting solid was filtered off and dried in vacuum to give 1.82 g of the title compound (95% purity, 87% yield).

$^1$H NMR (400 MHz, DMSO-$d_6$) δ ppm 1.81-2.00 (m, 4H) 2.78-2.92 (m, 1H) 3.49-3.62 (m, 5H) 3.74 (s, 3H) 3.79-3.88 (m, 2H) 6.86-6.94 (m, 2H) 7.22-7.32 (m, 2H) 7.48-7.61 (m, 1H) 7.84-8.02 (m, 2H).

LC-MS (Method 1): $R_t$=1.41 min; MS (ESIpos): m/z=452 $[M+H]^+$

TABLE 8

Following examples of table 8 were prepared from assigned starting materials and according to the procedure stated in the table.

| Example | Structure | IUPAC-Name | Starting Materials | Analytics |
|---|---|---|---|---|
| 168 | 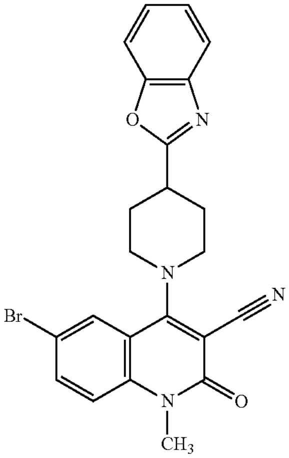 [SMILES: Cn1c(=O)c(C#N)c(N2CCC(c3nc4ccccc4o3)CC2)c2cc(Br)ccc21] | 4-[4-(1,3-benzoxazol-2-yl)piperidin-1-yl]-6-bromo-1-methyl-2-oxo-1,2-dihydroquinoline-3-carbonitrile | in analogy to example 167 with intermediate 95 and 2-(piperidin-4-yl)-1,3-benzoxazole (CAS 51784-03-3) | $^1$H NMR (400 Mhz, DMSO-$d_6$) δ ppm 2.04-2.22 (m, 2 H) 2.27-2.41 (m, 2 H) 3.42-3.51 (m, 1 H) 3.53-3.70 (m, 5 H) 3.79-3.88 (m, 2 H) 7.30-7.43 (m, 2 H) 7.49-7.61 (m, 1 H) 7.65-7.82 (m, 2 H) 7.85-8.00 (m, 2 H). |
| 169 | 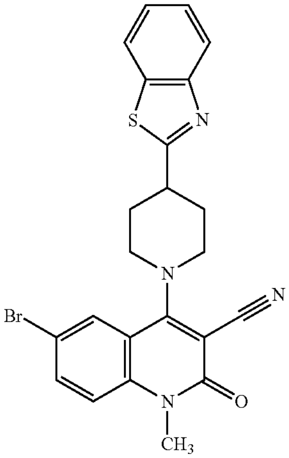 [SMILES: Cn1c(=O)c(C#N)c(N2CCC(c3nc4ccccc4s3)CC2)c2cc(Br)ccc21] | 4-[4-(1,3-benzothiazol-2-yl)piperidin-1-yl]-6-bromo-1-methyl-2-oxo-1,2-dihydroquinoline-3-carbonitrile | in analogy to example 167 with intermediate 95 and 2-(piperidin-4-yl)-1,3-benzthiazole (CAS 51784-73-7) | $^1$H NMR (400 MHz, DMSO-$d_6$) δ ppm 2.05-2.18 (m, 2 H) 2.29-2.41 (m, 2 H) 3.52-3.70 (m, 6 H) 3.81-3.92 (m, 2 H) 7.40-7.47 (m, 1 H) 7.48-7.59 (m, 2 H) 7.86-7.91 (m, 1 H) 7.92-7.96 (m, 1 H) 7.98-8.03 (m, 1 H) 8.07-8.13 (m, 1 H). |

TABLE 8-continued

| Example | Structure | IUPAC-Name | Starting Materials | Analytics |
|---|---|---|---|---|
| | | Following examples of table 8 were prepared from assigned starting materials and according to the procedure stated in the table. | | |
| 170 | 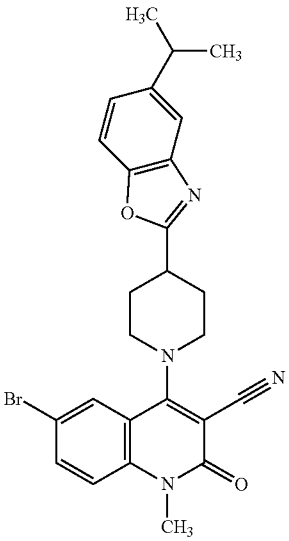 [SMILES: CC(C)c1ccc2oc(C3CCN(c4c(C#N)c(=O)n(C)c5ccc(Br)cc45)CC3)nc2c1] | 6-bromo-1-methyl-2-oxo-4-{4-[5-(propan-2-yl)-1,3-benzoxazol-2-yl]piperidin-1-yl}-1,2-dihydroquinoline-3-carbonitrile | in analogy to example 153 with intermediate 95 and intermediate 6 | $^{1}H$ NMR (400 MHz, DMSO-$d_6$) δ ppm 1.25 (d, 6 H), 2.04-2.17 (m, 2 H), 2.27-2.35 (m, 2 H), 2.97-3.09 (m, 1 H), 3.40-3.50 (m, 1 H), 3.54-3.67 (m, 5 H), 3.78-3.87 (m, 2 H), 7.27 (dd, 1 H), 7.55 (d, 1 H), 7.64 (br d, 2 H), 7.87-7.95 (m, 2 H). |
| 171 | 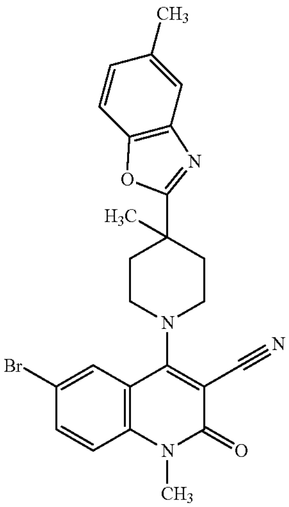 [SMILES: Cc1ccc2oc(C3(C)CCN(c4c(C#N)c(=O)n(C)c5ccc(Br)cc45)CC3)nc2c1] | 6-bromo-1-methyl-4-[4-methyl-4-(5-methyl-1,3-benzoxazol-2-yl)piperidin-1-yl]-2-oxo-1,2-dihydroquinoline-3-carbonitrile | in analogy to example 153 with intermediate 95 and intermediate 52 | $^{1}H$ NMR (400 MHz, DMSO-$d_6$) δ ppm 1.50 (s, 3 H), 1.98-2.10 (m, 2 H), 2.43 (s, 3 H), 3.45-3.57 (m, 5 H), 3.68-3.78 (m, 2 H), 7.20 (dd, 1 H), 7.50-7.54 (m, 1 H), 7.55-7.58 (m, 1 H), 7.59-7.63 (m, 1 H), 7.88 (dd, 1 H), 7.95 (d, 1 H). |

Example 172

4-[4-(4-methoxyphenyl)piperidin-1-yl]-1,6-dimethyl-2-oxo-1,2-dihydroquinoline-3-carbonitrile

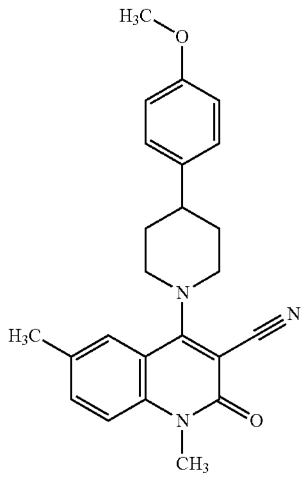 [SMILES: COc1ccc(C2CCN(c3c(C#N)c(=O)n(C)c4ccc(C)cc34)CC2)cc1]

To a stirred solution of 100 mg 6-bromo-4-[4-(4-methoxyphenyl)piperidin-1-yl]-1-methyl-2-oxo-1,2-dihydroquinoline-3-carbonitrile (221 μmol, example 167) in 3.5 mL degassed THF were added 37.7 mg 2,4,4,5,5-pentamethyl-1,3,2-dioxaborolane (265 μmol, CAS 94242-85-0), 800 μL potassium phosphate (0.50 M in water, 400 μmol) and 26.1 mg chloro(2-dicyclohexylphosphino-2,4,6-triisopropyl-1,1-biphenyl)[2-(2-amino-1,1-biphenyl)]palladium (II) (33.2 μmol, CAS1310584-14-5). The mixture was stirred overnight at 70° C. After this time, water was added and the reaction was extracted with dichloromethane (2×). The organic phase dried over sodium sulfate and concentrated under reduced pressure. The residue was purified by RP-HPLC (column: X-Bridge C18 5 μm 100×30 mm, mobile phase: acetonitrile/water (0.1 vol. % formic acid)-gradient) to give 26.4 mg of the title compound (95% purity, 29% yield).

LC-MS (Method 1): $R_t$=1.36 min; MS (ESIpos): m/z=389 $[M+H]^+$ $^1$H NMR (400 MHz, DMSO-$d_6$) δ ppm 1.85-1.99 (m, 4H) 2.42 (s, 3H) 2.83 (dt, 1H) 3.45-3.54 (m, 2H) 3.56 (s, 3H) 3.74 (s, 3H) 3.77-3.88 (m, 2H) 6.85-6.95 (m, 2H) 7.22-7.32 (m, 2H) 7.46-7.53 (m, 1H) 7.54-7.62 (m, 1H) 7.64-7.72 (m, 1H).

Example 173

4-[4-(4-methoxyphenyl)piperidin-1-yl]-1-methyl-2-oxo-1,2-dihydroquinoline-3,6-dicarbonitrile

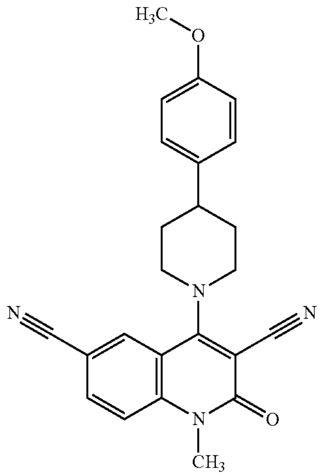 [SMILES: COc1ccc(C2CCN(c3c(C#N)c(=O)n(C)c4ccc(C#N)cc34)CC2)cc1]

To 100 mg 6-bromo-4-[4-(4-methoxyphenyl)piperidin-1-yl]-1-methyl-2-oxo-1,2-dihydroquinoline-3-carbonitrile (221 μmol, example 167) in 2 mL N,N-dimethylacetamide was added 99.0 mg copper(I)cyanide (1.11 mmol) and the mixture was stirred for 12 h at 150° C. in the microwave. The mixture was cooled down to rt, filtered and was purified by RP-HPLC (column: X-Bridge C18 5 μm 100×30 mm, mobile phase: acetonitrile/water (0.1 vol. % formic acid)-gradient). The impure product was crystallized from ethanol. The precipitate was collected by filtration and dried in vacuum to give 5.7 mg of the title compound (90% purity, 5% yield).

$^1$H NMR (400 MHz, DMSO-$d_6$) δ ppm 1.80-2.03 (m, 4H) 2.75-2.90 (m, 1H) 3.50-3.63 (m, 5H) 3.74 (s, 3H) 3.86 (br d, 2H) 6.86-6.95 (m, 2H) 7.28 (d, 2H) 7.69-7.76 (m, 1H) 8.06-8.16 (m, 1H) 8.23-8.31 (m, 1H).

LC-MS (Method 1): $R_t$=1.23 min; MS (ESIpos): m/z=399 $[M+H]^+$

TABLE 9

Following examples of table 9 were prepared from assigned starting materials and according to the procedure stated in the table.

| Example | Structure | IUPAC-Name | Starting Materials | Analyticals |
| --- | --- | --- | --- | --- |
| 174 | 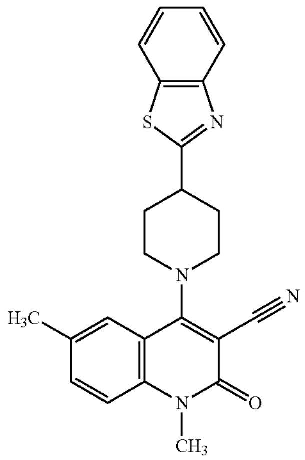 [SMILES: Cc1ccc2c(c1)c(N1CCC(c3nc4ccccc4s3)CC1)c(C#N)c(=O)n2C] | 4-[4-(1,3-benzothiazol-2-yl)piperidin-1-yl]-1,6-dimethyl-2-oxo-1,2-dihydroquinoline-3-carbonitrile | In analogy to example 172 with example 169 | $^1$H NMR (400 MHz, DMSO-$d_6$) δ ppm 2.04-2.21 (m, 2 H) 2.29-2.35 (m, 2 H) 2.41 (s, 3 H) 3.51-3.67 (m, 6 H) 3.81-3.94 (m, 2 H) 7.39-7.70 (m, 5 H) 7.95-8.07 (m, 1 H) 8.06-8.17 (m, 1 H). |
| 175 | 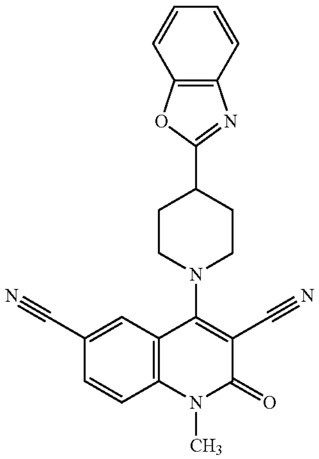 [SMILES: Cn1c(=O)c(C#N)c(N2CCC(c3nc4ccccc4o3)CC2)c2cc(C#N)ccc21] | 4-[4-(1,3-benzoxazol-2-yl)piperidin-1-yl]-1-methyl-2-oxo-1,2-dihydroquinazoline-3,6-dicarbonitrile | In analogy to example 173 with example 168 | $^1$H NMR (400 MHz, DMSO-$d_6$) δ ppm 2.13-2.26 (m, 2 H) 2.32-2.34 (m, 2 H) 3.42-3.52 (m, 1 H) 3.57-3.60 (m, 3 H) 3.61-3.71 (m, 2 H) 3.83-3.92 (m, 2 H) 7.36-7.43 (m, 2 H) 7.70-7.77 (m, 3 H) 8.08-8.17 (m, 1 H) 8.23-8.27 (m, 1 H). LC-MS (Method 3): $R_t$ = 1.08 min; MS (ESIpos): m/z = 410 $[M + H]^+$ |
| 176 | 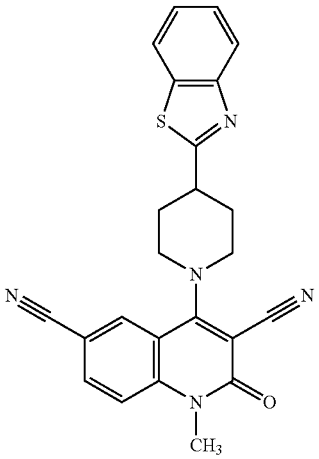 [SMILES: Cn1c(=O)c(C#N)c(N2CCC(c3nc4ccccc4s3)CC2)c2cc(C#N)ccc21] | 4-[4-(1,3-benzothiazol-2-yl)piperidin-1-yl]-1-methyl-2-oxo-1,2-dihydroquinoline-3,6-dicarbonitrile | In analogy to example 173 with example 169 | $^1$H NMR (400 MHz, DMSO-$d_6$) δ ppm 2.12-2.25 (m, 2 H) 2.30-2.35 (m, 2 H) 3.51-3.61 (m, 4 H) 3.62-3.72 (m, 2 H) 3.84-3.96 (m, 2 H) 7.39-7.46 (m, 1 H) 7.47-7.57 (m, 1 H) 7.67-7.77 (m, 1 H) 7.97-8.05 (m, 1 H) 8.09-8.14 (m, 2 H) 8.21-8.31 (m, 1 H). |

Example 177

6-cyclopropyl-4-[4-(4-methoxyphenyl)piperidin-1-yl]-1-methyl-2-oxo-1,2-dihydroquinoline-3-carbonitrile

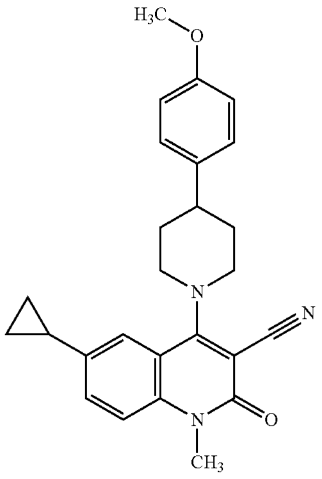 [SMILES: COc1ccc(C2CCN(c3c(C#N)c(=O)n(C)c4ccc(C5CC5)cc34)CC2)cc1]

To a stirred solution of 100 mg 6-bromo-4-[4-(4-methoxyphenyl)piperidin-1-yl]-1-methyl-2-oxo-1,2-dihydroquinoline-3-carbonitrile (221 μmol, example 167) in 4.0 mL degassed THF were added 74.3 mg 2-cyclopropyl-4,4,5,5-tetramethyl-1,3,2-dioxaborolane (442 μmol, CAS 126689-01-8), 1.1 mL potassium phosphate (0.50 M in water, 550 μmol) and 26.1 mg chloro(2-dicyclohexylphosphino-2,4,6-triisopropyl-1,1-biphenyl)[2-(2-amino-1,1-biphenyl)]palladium(II) (33.2 μmol). The mixture was stirred overnight at 70° C. After this time, water was added and the reaction was extracted with dichloromethane (2×). The organic phase was dried over sodium sulfate and concentrated under reduced pressure. The residue was purified by RP-HPLC (column: X-Bridge C18 5 μm 100×30 mm, mobile phase: acetonitrile/water (0.1 vol. % formic acid)-gradient) to give 38.9 mg of the title compound (95% purity, 40% yield).

LC-MS (Method 1): $R_t$=1.42 min; MS (ESIpos): m/z=415 $[M+H]^+$ $^1$H NMR (400 MHz, DMSO-$d_6$) δ ppm 0.68-0.74 (m, 2H) 0.98-1.06 (m, 2H) 1.83-2.01 (m, 4H) 2.03-2.15 (m, 1H) 2.77-2.92 (m, 1H) 3.46-3.58 (m, 5H) 3.74 (s, 3H) 3.77-3.88 (m, 2H) 6.85-6.96 (m, 2H) 7.24-7.30 (m, 2H) 7.40-7.51 (m, 2H) 7.51-7.57 (m, 1H).

Example 178

6-(methanesulfonyl)-4-[4-(4-methoxyphenyl)piperidin-1-yl]-1-methyl-2-oxo-1,2-dihydroquinoline-3-carbonitrile

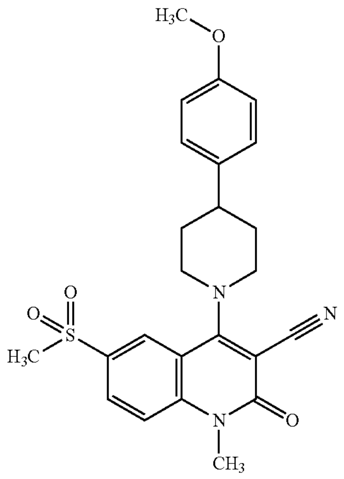 [SMILES: COc1ccc(C2CCN(c3c(C#N)c(=O)n(C)c4ccc(S(C)(=O)=O)cc34)CC2)cc1]

A solution of 100 mg 6-bromo-4-[4-(4-methoxyphenyl)piperidin-1-yl]-1-methyl-2-oxo-1,2-dihydroquinoline-3-carbonitrile (221 μmol, example 167) in 4 mL DMSO was degassed with argon. To the mixture was added 33.9 mg sodium methanesulfinate (332 μmol, CAS 20277-69-4), 11 μL (1S,2S)-cyclohexane-1,2-diamine (91 μmol, CAS 1121-22-8) and 4.2 mg copper(I)trifluoromethanesulfonate-benzene (2:2:1) (22.1 μmol). The reaction was stirred for overnight at 110° C. The mixture was filtered and the residue was purified by RP-HPLC (column: X-Bridge C18 5 μm 100×30 mm, mobile phase: acetonitrile/water (0.1 vol. % formic acid)-gradient) to give 36 mg of the title compound (95% purity, 34% yield).

LC-MS (Method 1): $R_t$=1.10 min; MS (ESIpos): m/z=452 $[M+H]^+$ $^1$H NMR (400 MHz, DMSO-$d_6$) δ ppm 1.82-2.03 (m, 4H) 2.82-2.97 (m, 1H) 3.29 (s, 3H) 3.52-3.64 (m, 5H) 3.74 (s, 3H) 3.86-3.95 (m, 2H) 6.90-6.95 (m, 2H) 7.20-7.27 (m, 2H) 7.77-7.84 (m, 1H) 8.17-8.22 (m, 1H) 8.32-8.37 (m, 1H).

Example 179

4-[4-(4-methoxyphenyl)piperidin-1-yl]-1-methyl-6-(oxetan-3-yl)-2-oxo-1,2-dihydroquinoline-3-carbonitrile

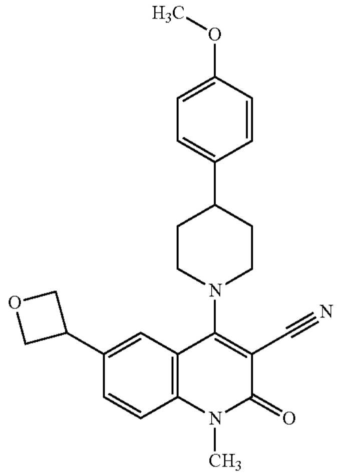 [SMILES: COc1ccc(C2CCN(c3c(C#N)c(=O)n(C)c4ccc(C5COC5)cc34)CC2)cc1]

100 mg 6-bromo-4-[4-(4-methoxyphenyl)piperidin-1-yl]-1-methyl-2-oxo-1,2-dihydroquinoline-3-carbonitrile (221 μmol, example 167), 4.96 mg bis{3,5-difluoro-2-[5-(trifluoromethyl)pyridin-2-yl]phenyl}iridium(I)hexafluorophosphate (4.42 μmol), 68 μL tris(trimethylsilyl)silan (220 μmol) and 141 mg sodium carbonate (1.33 mmol) was suspended in 4.0 mL trifluorotoluene. In a separate vial, the 240 μg nickel(II)chloride dimethoxyethane adduct (1.1 μmol) and 300 μg 4,4'di-tert-butyl-2,2'bipyridine (1.1 μmol) were solubilised in 2.0 mL N,N-dimethylacetamide, and stirred for 5 min. The catalyst solution was syringed to the sealed reaction vial and argon was bubbled through the solution for another 5 min. Then 83 μL 3-bromooxetane (990 μmol, CAS 39267-79-3) was added. The microwave vial was subsequently irradiated for 20 h by two 40 W Kessil LED Aquarium lights (40 W each, 4 cm distance) placed in a water bath to keep the temperature below 35° C. The reaction mixture was purified by RP-HPLC (column: X-Bridge C18 5μ 100×30 mm; mobile phase: water (0.2 vol. % aq. ammonia 32%)/acetonitrile)-gradient) to give 44.1 mg of the title compound (95% purity, 44% yield).

LC-MS (Method 1): $R_t$=1.20 min; MS (ESIpos): m/z=431 $[M+H]^+$ $^1$H NMR (400 MHz, DMSO-$d_6$) δ ppm 1.85-2.01 (m, 4H) 2.80-2.92 (m, 1H) 3.48-3.62 (m, 5H) 3.74 (s, 3H) 3.86 (br d, 2H) 4.30-4.43 (m, 1H) 4.61 (t, 2H) 5.01 (dd, 2H) 6.86-6.95 (m, 2H) 7.21-7.31 (m, 2H) 7.53-7.65 (m, 1H) 7.78-7.94 (m, 2H).

Example 180

6-(3,6-dihydro-2H-pyran-4-yl)-4-[4-(4-methoxyphenyl)piperidin-1-yl]-1-methyl-2-oxo-1,2-dihydroquinoline-3-carbonitrile

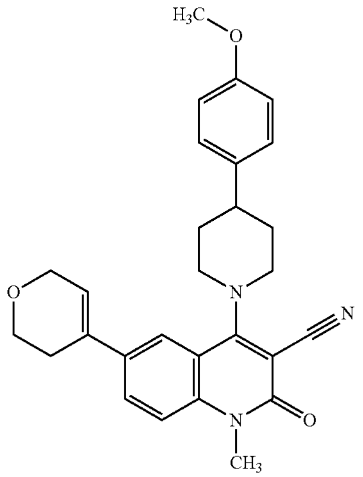 [SMILES: COc1ccc(C2CCN(c3c(C#N)c(=O)n(C)c4ccc(C5=CCOCC5)cc34)CC2)cc1]

To a stirred solution of 100 mg 6-bromo-4-[4-(4-methoxyphenyl)piperidin-1-yl]-1-methyl-2-oxo-1,2-dihydroquinoline-3-carbonitrile (221 μmol, example 167) in 3.5 mL degassed THF were added 55.7 mg 4-(4,4,5,5-tetramethyl-1,3,2-dioxaborolan-2-yl)-3,6-dihydro-2H-pyran (265 μmol, CAS 287944-16-5), 800 μL potassium phosphate (0.50 M in water, 400 μmol) and 26.1 mg chloro(2-dicyclohexylphosphino-2',4',6'-triisopropyl-1,1'-biphenyl)[2-(2'-amino-1,1'-biphenyl)]palladium(II) (33.2 μmol, CAS 1310584-14-5). The mixture was stirred overnight at rt. Water was added and the reaction was extracted with dichloromethane (2×). The organic phase was dried over sodium sulfate and concentrated under reduced pressure. The residue was purified by preparative TLC (silica, dichloromethane/ethanol; 95:5) to give 14 mg of the title compound (95% purity, 14% yield).

LC-MS (Method 1): $R_t$=1.28 min; MS (ESIpos): m/z=456 $[M+H]^+$ $^1$H NMR (400 MHz, DMSO-$d_6$) δ ppm 1.83-2.03 (m, 4H) 2.52-2.56 (m, 2H) 2.80-2.92 (m, 1H) 3.48-3.62 (m, 5H) 3.74 (s, 3H) 3.82-3.92 (m, 4H) 4.21-4.31 (m, 2H) 6.36-6.47 (m, 1H) 6.86-6.95 (m, 2H) 7.21-7.31 (m, 2H) 7.53-7.60 (m, 1H) 7.77-7.84 (m, 1H) 7.86-7.96 (m, 1H).

Example 181

4-[4-(4-methoxyphenyl)piperidin-1-yl]-1-methyl-2-oxo-6-phenyl-1,2-dihydroquinoline-3-carbonitrile

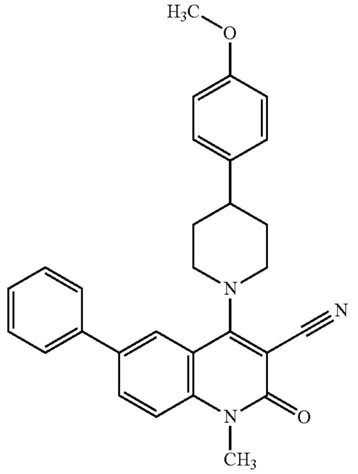 [SMILES: COc1ccc(C2CCN(c3c(C#N)c(=O)n(C)c4ccc(-c5ccccc5)cc34)CC2)cc1]

To a stirred solution of 100 mg 6-bromo-4-[4-(4-methoxyphenyl)piperidin-1-yl]-1-methyl-2-oxo-1,2-dihydroquinoline-3-carbonitrile (221 μmol, example 167) in 3.5 mL degassed THF were added 32.3 mg phenylboronic acid (265 μmol; CAS 98-80-6), 800 μL potassium phosphate (0.50 M in water, 400 μmol) and 26.1 mg chloro(2-dicyclohexylphosphino-2',4',6'-triisopropyl-1,1'-biphenyl)[2-(2'-amino-1,1'-biphenyl)]palladium(II) (33.2 μmol, CAS 1310584-14-5). The mixture was stirred overnight at 70° C. After this time, water was added and the reaction was extracted with dichloromethane (2×). The organic phase was dried over sodium sulfate and concentrated under reduced pressure. The residue was purified by preparative TLC (silica, hexane/ethyl acetate; 4:6) to give 42 mg of the title compound (95% purity, 41% yield).

LC-MS (Method 1): $R_t$=1.44 min; MS (ESIpos): m/z=450 $[M+H]^+$ $^1$H NMR (400 MHz, DMSO-$d_6$) δ ppm 1.85-2.04 (m, 4H) 2.81-2.93 (m, 1H) 3.52-3.65 (m, 5H) 3.73 (s, 3H) 3.91-3.99 (m, 2H) 6.85-6.96 (m, 2H) 7.23-7.30 (m, 2H) 7.36-7.44 (m, 1H) 7.48-7.55 (m, 2H) 7.64-7.69 (m, 1H) 7.70-7.76 (m, 2H) 8.03-8.12 (m, 2H).

Example 182

6-(methanesulfonyl)-1-methyl-4-[4-methyl-4-(5-methyl-1,3-benzoxazol-2-yl)piperidin-1-yl]-2-oxo-1,2-dihydroquinoline-3-carbonitrile

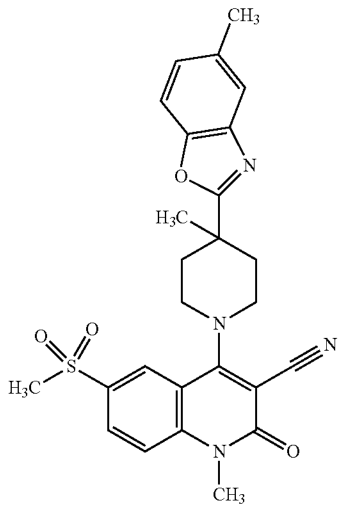 [SMILES: Cc1ccc2oc(C3(C)CCN(c4c(C#N)c(=O)n(C)c5ccc(S(C)(=O)=O)cc45)CC3)nc2c1]

A solution of 100 mg 6-bromo-1-methyl-4-[4-methyl-4-(5-methyl-1,3-benzoxazol-2-yl)piperidin-1-yl]-2-oxo-1,2-dihydroquinoline-3-carbonitrile (193 μmol, example 171) in 1.5 mL DMSO was degassed with argon. To the mixture was added 31.2 mg sodium methanesulfinate (290 μmol, CAS 20277-69-4), 79 μL (1 S,2S)-cyclohexane-1,2-diamine (9.5 μmol, CAS 1121-22-8) and 9.7 mg copper(I)trifluoromethanesulfonate-benzene (2:2:1) (19.3 μmol). The reaction was stirred overnight at 110° C. The mixture was filtered and the residue was purified by RP-HPLC (column: X-Bridge C18 5 μm 100×30 mm, mobile phase: acetonitrile/water (0.2 vol. % ammonia 32%)-gradient) to give 30 mg of the title compound (98% purity, 31% yield).

$^1$H NMR (400 MHz, DMSO-$d_6$) δ ppm 1.50 (s, 3H), 1.96-2.10 (m, 2H), 2.41 (s, 3H), 3.29 (s, 3H), 3.51-3.64 (m+s, 5H), 3.76-3.88 (m, 2H), 7.18-7.24 (m, 1H), 7.55-7.64 (m, 2H), 7.79 (d, 1H), 8.18 (dd, 1H), 8.29 (d, 1H).

Example 183

4-[4-(6-chloro-1,3-benzoxazol-2-yl)piperidin-1-yl]-1,6-dimethyl-2-oxo-1,2-dihydroquinoline-3-carbonitrile

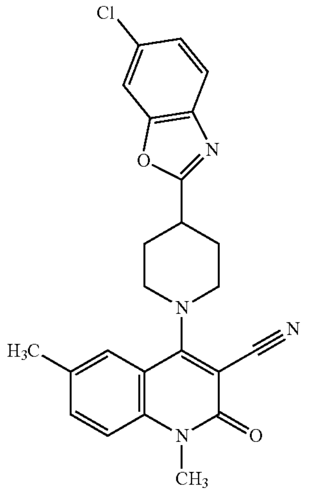 [SMILES: Cc1ccc2c(c1)c(N1CCC(c3nc4ccc(Cl)cc4o3)CC1)c(C#N)c(=O)n2C]

A solution of 120 mg 4-chloro-1,6-dimethyl-2-oxo-1,2-dihydroquinoline-3-carbonitrile (0.49 mmol, intermediate 92), 146 mg 6-chloro-2-(piperidin-4-yl)-1,3-benzoxazole (0.59 mmol, intermediate 7) and 0.14 mL triethylamine (0.98 mmol) in 4.9 mL 2-propanol was stirred for 4 h at 90° C. After this time, water was added and the reaction was extracted with ethyl acetate. The organic phase was washed with water and brine, dried over sodium sulfate and evaporated in vacuum. The residue was purified by RP-HPLC (column: X-Bridge C18 5 μm 100×30 mm, mobile phase: acetonitrile/water (0.2 vol. % ammonia 32%)-gradient) to give 58 mg of the title compound (95% purity, 26% yield).

$^1$H NMR (400 MHz, DMSO-$d_6$) δ ppm 2.08-2.21 (m, 2H), 2.28-2.37 (m, 2H), 2.41 (s, 3H), 3.43-3.53 (m, 1H), 3.53-3.65 (m+s, 5H), 3.83 (br d, 2H), 7.41-7.46 (m, 1H), 7.46-7.52 (m, 1H), 7.55-7.60 (m, 1H), 7.63 (s, 1H), 7.76 (d, 1H), 7.95 (d, 1H).

TABLE 10

Following examples of table 10 were prepared from assigned starting materials and according to the procedure stated in example 183.

| Example | Structure | IUPAC-Name | Starting Materials | Analytics |
|---|---|---|---|---|
| 184 | 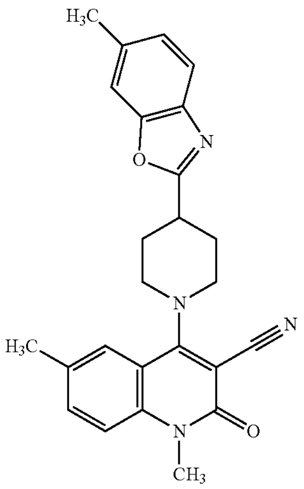 [SMILES: Cc1ccc2nc(C3CCN(c4c(C#N)c(=O)n(C)c5ccc(C)cc45)CC3)oc2c1] | 1,6-dimethyl-4-[4-(6-methyl-1,3-benzoxazol-2-yl)piperidin-1-yl]-2-oxo-1,2-dihydroquinoline-3-carbonitrile | intermediate 92 and 6-methyl-2-(piperidin-4-yl)-1,3-benzoxazole (CAS 951921-15-6) | $^1$H NMR (400 MHz, DMSO-$d_6$) δ ppm 2.07-2.20 (m, 2 H), 2.72-2.36 (m, 2 H), 2.41 (s, 3 H), 2.44 (s, 3 H), 3.37-3.48 (m, 1 H), 3.52-3.64 (m + s, 5 H), 3.77-3.88 (m, 2 H), 7.18 (dd, 1 H), 7.45-7.51 (m, 1 H), 7.51-7.54 (m, 1 H), 7.55-7.65 (m, 3 H). |
| 185 | 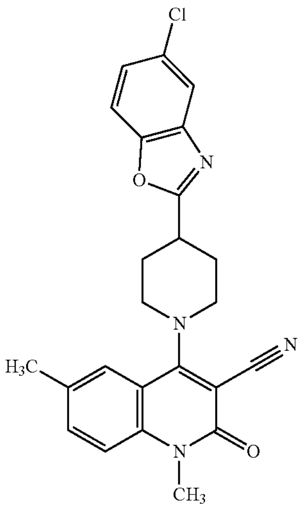 [SMILES: Cc1ccc2c(c1)c(N1CCC(c3nc4cc(Cl)ccc4o3)CC1)c(C#N)c(=O)n2C] | 4-[4-(5-chloro-1,3-benzoxazol-2-yl)piperidin-1-yl]-1,6-dimethyl-2-oxo-1,2-dihydroquinoline-3-carbonitrile | intermediate 92 and intermediate 9 | $^1$H NMR (400 MHz, DMSO-$d_6$) δ ppm 2.08-2.21 (m, 2 H), 2.30-2.38 (m, 2 H), 2.41 (s, 3 H), 3.43-3.53 (m, 1 H), 3.53-3.65 (m, + s, 5 H), 3.78-3.88 (m, 2 H), 7.42-7.46 (m, 1 H), 7.46-7.51 (m, 1 H), 7.55-7.60 (m, 1 H), 7.63 (s, 1 H), 7.78 (d, 1 H), 7.87 (d, 1 H). |

TABLE 10-continued

Following examples of table 10 were prepared from assigned starting materials and according to the procedure stated in example 183.

| Example | Structure | IUPAC-Name | Starting Materials | Analytics |
|---|---|---|---|---|
| 186 | 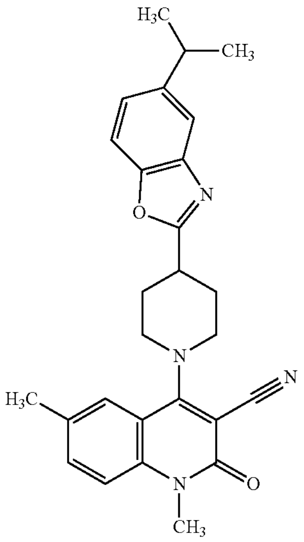 [SMILES: Cc1ccc2c(c1)c(N1CCC(c3nc4cc(C(C)C)ccc4o3)CC1)c(C#N)c(=O)n2C] | 1,6-dimethyl-2-oxo-4-{4-[5-(propan-2-yl)-1,3-benzoxazol-2-yl]piperidin-1-yl}-1,2-dihydroquinoline-3-carbonitrile | intermediate 92 and intermediate 6 | $^1$H NMR (400 MHz, DMSO-$d_6$) δ ppm 1.25 (d, 6 H), 2.08-2.21 (m, 2 H), 2.26-2.36 (m, 2 H), 2.41 (s, 3 H), 2.97-3.09 (m, 1 H), 3.39-3.49 (m, 1 H), 3.53-3.65 (m + s, 5 H), 3.78-3.88 (m, 2 H), 7.27 (dd, 1 H), 7.47-7.50 (m, 1 H), 7.56-7.64 (m, 4 H). |
| 187 | 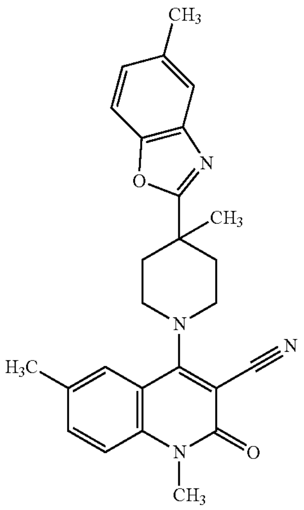 [SMILES: Cc1ccc2oc(C3(C)CCN(c4c(C#N)c(=O)n(C)c5ccc(C)cc45)CC3)nc2c1] | 1,6-dimethyl-4-[4-methyl-4-(5-methyl-1,3-benzoxazol-2-yl)piperidin-1-yl]-2-oxo-1,2-dihydroquinoline-3-carbonitrile | intermediate 92 and intermediate 52 | $^1$H NMR (400 MHz, DMSO-$d_6$) δ ppm 1.50 (s, 3 H), 2.00-2.12 (m, 2 H), 2.41 (s, 3 H), 2.43 (s, 3 H), 3.44-3.57 (m + s, 5 H), 3.68-3.79 (m, 2 H), 7.20 (dd, 1 H), 7.47 (d, 1 H), 7.53-7.58 (m, 2 H), 7.60 (d, 1 H), 7.64 (s, 1 H). |

TABLE 10-continued

| Following examples of table 10 were prepared from assigned starting materials and according to the procedure stated in example 183. | | | | |
|---|---|---|---|---|
| Example | Structure | IUPAC-Name | Starting Materials | Analytics |
| 188 | 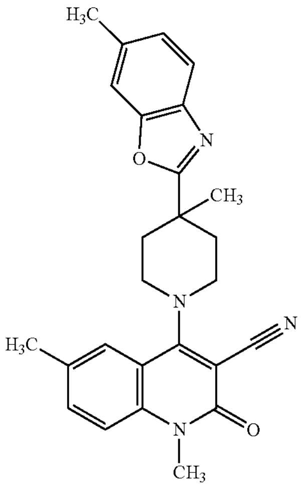 [SMILES: Cc1ccc2nc(C3(C)CCN(c4c(C#N)c(=O)n(C)c5ccc(C)cc45)CC3)oc2c1] | 1,6-dimethyl-4-[4-methyl-4-(6-methyl-1,3-benzoxazol-2-yl)piperidin-1-yl]-2-oxo-1,2-dihydroquinoline-3-carbonitrle | intermediate 92 and intermediate 96 | $^{1}$H NMR (400 MHz, DMSO-$d_6$) δ ppm 1.50 (s, 3 H), 2.02-2.12 (m, 3 H), 2.41 (s, 3 H), 2.44 (s, 3 H), 3.44-3.57 (m, 5 H), 3.68-3.78 (m, 2 H), 7.17-7.22 (m, 1 H), 7.44-7.49 (m, 1 H), 7.54-7.65 (m, 4 H). |
| 189 | 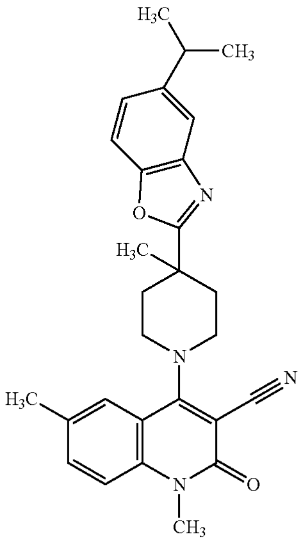 [SMILES: Cc1ccc2c(c1)c(N1CCC(C)(c3nc4cc(C(C)C)ccc4o3)CC1)c(C#N)c(=O)n2C] | 1,6-dimethyl-4-{4-methyl-4-[5-(propan-2-yl)-1,3-benzoxazol-2-yl]piperidin-1-yl}-2-oxo-1,2-dihydroquinoline-3-carbonitrile | intermediate 92 and intermediate 11 | $^{1}$H NMR (400 MHz, DMSO-$d_6$) δ ppm 1.25 (d, 6 H), 1.49 (s, 3 H), 2.06 (br s, 2 H), 2.41 (s, 3 H), 2.97-3.09 (m, 1 H), 3.45-3.57 (m + s, 5 H), 3.69-3.79 (m, 2 H), 7.28 (dd, 1 H), 7.45-7.49 (m, 1 H), 7.53-7.59 (m, 1 H), 7.60-7.67 (m, 3 H). |

Example 190

6-methoxy-1-methyl-4-[4-(6-methyl-1,3-benzoxazol-2-yl)piperidin-1-yl]-2-oxo-1,2-dihydroquinoline-3-carbonitrile

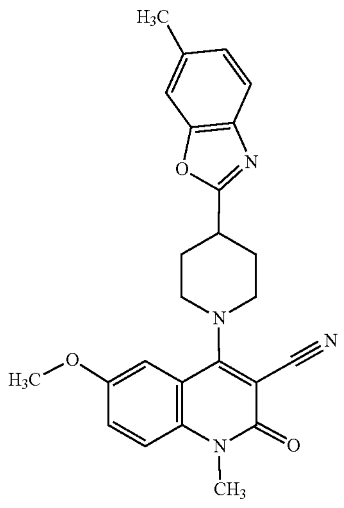 [SMILES: COc1ccc2c(c1)c(N1CCC(c3nc4ccc(C)cc4o3)CC1)c(C#N)c(=O)n2C]

A solution of 100 mg 4-chloro-6-methoxy-1-methyl-2-oxo-1,2-dihydroquinoline-3-carbonitrile (0.4 mmol, intermediate 99), 104 mg 6-methyl-2-(piperidin-4-yl)-1,3-benzoxazole (0.48 mmol, CAS 951921-15-6) and 0.11 mL triethylamine (0.8 mmol) in 5.7 mL 2-propanol was stirred for 5 h at 90° C. After this time, water was added and the reaction was extracted with ethyl acetate. The organic phase was washed with water and brine, dried over sodium sulfate and evaporated in vacuum. The residue was purified by RP-HPLC (column: X-Bridge C18 5 μm 100×30 mm, mobile phase: acetonitrile/water (0.2 vol. % ammonia 32%)-gradient) to give 72 mg of the title compound (95% purity, 40% yield).

$^1$H NMR (400 MHz, DMSO-d$_6$) δ ppm 2.03-2.18 (m, 2H), 2.30-2.38 (m, 2H), 2.44 (s, 3H), 3.39-3.49 (m, 1H), 3.54-3.64 (m+s, 5H), 3.78-3.89 (m+s, 5H), 7.18 (dd, 1H), 7.24 (d, 1H), 7.38-7.42 (m, 1H), 7.51-7.57 (m, 2H), 7.57-7.63 (m, 1H).

Example 191

6-methoxy-1-methyl-4-[4-methyl-4-(6-methyl-1,3-benzoxazol-2-yl)piperidin-1-yl]-2-oxo-1,2-dihydroquinoline-3-carbonitrile

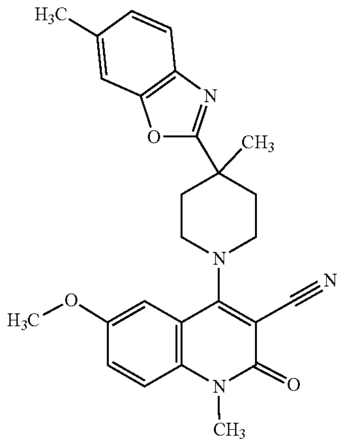 [SMILES: COc1ccc2c(c1)c(N1CCC(C)(c3nc4ccc(C)cc4o3)CC1)c(C#N)c(=O)n2C]

A solution of 100 mg 4-chloro-6-methoxy-1-methyl-2-oxo-1,2-dihydroquinoline-3-carbonitrile (0.4 mmol, intermediate 99), 111 mg 6-methyl-2-(4-methylpiperidin-4-yl)-1,3-benzoxazole (0.48 mmol, intermediate 95) and 0.11 mL triethylamine (0.8 mmol) in 5.7 mL 2-propanol was stirred for 4 h at 90° C. After this time, water was added and the reaction was extracted with ethyl acetate. The organic phase was washed with water and brine, dried over sodium sulfate and evaporated in vacuum. The residue was purified by RP-HPLC (column: X-Bridge C18 5 μm 100×30 mm, mobile phase: acetonitrile/water (0.2 vol. % ammonia 32%)-gradient) to give 12 mg of the title compound (95% purity, 6% yield).

$^1$H NMR (400 MHz, DMSO-d$_6$) δ ppm 1.50 (s, 3H), 2.00-2.11 (m, 2H), 2.44 (s, 3H), 3.41-3.52 (m, 2H), 3.53-3.59 (m, 3H), 3.68-3.78 (m, 2H), 3.87 (s, 3H), 7.17-7.22 (m, 1H), 7.23-7.29 (m, 1H), 7.40 (dd, 1H), 7.52-7.55 (m, 2H), 7.63 (d, 1H).

Example 192

6-chloro-1-methyl-4-[4-methyl-4-(6-methyl-1,3-benzoxazol-2-yl)piperidin-1-yl]-2-oxo-1,2-dihydro-quinoline-3-carbonitrile

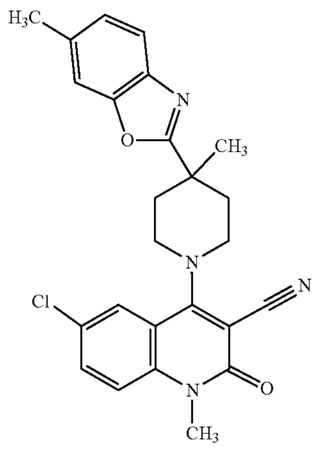 [SMILES: Cc1ccc2nc(C3(C)CCN(c4c(C#N)c(=O)n(C)c5ccc(Cl)cc45)CC3)oc2c1]

A solution of 90 mg 4,6-dichloro-1-methyl-2-oxo-1,2-dihydroquinoline-3-carbonitrile (0.36 mmol, intermediate 100), 98 mg 6-methyl-2-(4-methylpiperidin-4-yl)-1,3-benzoxazole (0.43 mmol, intermediate 95) and 0.1 mL triethylamine (0.7 mmol) in 5 mL 2-propanol was stirred for 3 h at 90° C. After this time, water was added and the reaction was extracted with ethyl acetate. The organic phase was washed with water and brine, dried over sodium sulfate and evaporated in vacuum. The residue was stirred in DMSO and a precipitate appeared after 24 h that was collected by filtration and washed with ethyl acetate to give 60 mg of the title compound (95% purity, 36% yield).

$^1$H NMR (400 MHz, DMSO-$d_6$) δ ppm 1.51 (s, 3H), 2.02-2.14 (m, 2H), 2.45 (s, 3H), 3.52-3.64 (m, 2H), 3.81-3.91 (m, 2H), 3.95 (s, 3H), 7.20 (dd, 1H), 7.30 (d, 1H), 7.52-7.56 (m, 2H), 7.63 (d, 1H), 7.83 (d, 1H).

Example 193

4-[4-(1,3-benzoxazol-2-yl)piperidin-1-yl]-1,6-dimethyl-2-oxo-1,2-dihydroquinoline-3-carboxamide

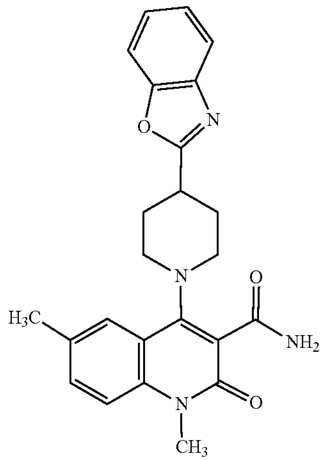 [SMILES: Cc1ccc2c(c1)c(N1CCC(c3nc4ccccc4o3)CC1)c(C(N)=O)c(=O)n2C]

75 mg 4-[4-(1,3-benzoxazol-2-yl)piperidin-1-yl]-1,6-dimethyl-2-oxo-1,2-dihydroquinoline-3-carbonitrile (example 165, 179 µmol), 10 mg palladium(II)acetate (45 µmol) and 117.2 mg acetaldoxime (1.72 mmol) were stirred in 10 mL ethanol for 4 h at 80° C. The reaction mixture was diluted with water, extracted with ethyl acetate two times, the combined organic layers were washed with brine, dried over sodium sulfate and the solvent was removed in vacuum. The residue was purified by RP-HPLC (column: X-Bridge C18 5 µm 100×30 mm, mobile phase: acetonitrile/water (0.2 vol. % ammonia 32%)-gradient) to give 38 mg of the title compound (95% purity, 48% yield).

$^1$H NMR (400 MHz, DMSO-$d_6$) δ ppm 2.04-2.17 (m, 2H), 2.20-2.29 (m, 2H), 2.41 (s, 3H), 3.11-3.29 (m, 3H), 3.36-3.44 (m, 2H), 3.57 (s, 3H), 7.34-7.42 (m, 2H), 7.42-7.51 (m, 3H), 7.66-7.77 (m, 4H).

Example 194

1,6-dimethyl-4-[4-(5-methyl-1,3-benzoxazol-2-yl)piperidin-1-yl]-2-oxo-1,2-dihydroquinoline-3-carboxamide

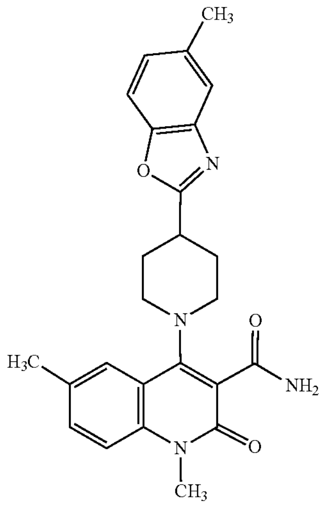 [SMILES: Cc1ccc2oc(C3CCN(c4c(C(N)=O)c(=O)n(C)c5ccc(C)cc45)CC3)nc2c1]

90 mg 1,6-dimethyl-4-[4-(5-methyl-1,3-benzoxazol-2-yl)piperidin-1-yl]-2-oxo-1,2-dihydroquinoline-3-carbonitrile (example 166, 207 µmol), 11.6 mg palladium(II)acetate (52 µmol) and 122.4 mg acetaldoxime (2.08 mmol) were stirred in 11 mL ethanol for 4 h at 80° C. The reaction mixture was diluted with water, extracted with ethyl acetate two times, the combined organic layers were washed with brine, dried over sodium sulfate and the solvent was removed in vacuum. The residue was purified by RP-HPLC (column: X-Bridge C18 5 µm 100×30 mm, mobile phase: acetonitrile/water (0.2 vol. % ammonia 32%)-gradient) to give 100 mg of the title compound (95% purity).

$^1$H NMR (400 MHz, DMSO-$d_6$) δ ppm 2.02-2.15 (m, 2H), 2.19-2.27 (m, 2H), 2.41 (s, 3H), 2.44 (s, 3H), 3.14-3.26 (m, 3H), 3.35-3.35 (m, 1H), 3.35-3.43 (m, 2H), 3.57 (s, 3H), 7.16-7.21 (m, 1H), 7.41-7.49 (m, 3H), 7.52 (d, 1H), 7.59 (d, 1H), 7.68 (s, 2H).

Example 195

4-[4-(1,3-benzoxazol-2-yl)-4-methylpiperidin-1-yl]-1,6-dimethyl-2-oxo-1,2-dihydroquinoline-3-carboxamide

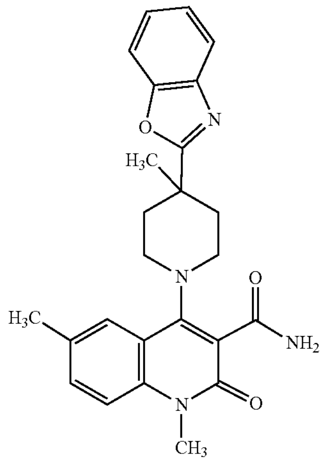 [SMILES: Cc1ccc2c(c1)c(N1CCC(C)(c3nc4ccccc4o3)CC1)c(C(N)=O)c(=O)n2C]

70 mg 4-[4-(1,3-benzoxazol-2-yl)-4-methylpiperidin-1-yl]-1,6-dimethyl-2-oxo-1,2-dihydroquinoline-3-carbonitrile (example 214, 161 μmol), 9 mg palladium(II)acetate (40 μmol) and 95 mg acetaldoxime (1.6 mmol) were stirred in 8.9 mL ethanol for 4 h at 80° C. The reaction mixture was diluted with water, extracted with ethyl acetate two times, the combined organic layers were washed with brine, dried over sodium sulfate and the solvent was removed in vacuum. The residue was purified by RP-HPLC (column: X-Bridge C18 5 μm 100×30 mm, mobile phase: acetonitrile/water (0.2 vol. % ammonia 32%)-gradient) to give 42 mg of the title compound (95% purity, 57% yield).

$^1$H NMR (400 MHz, DMSO-$d_6$) δ ppm 1.47 (s, 3H), 2.02 (br d, 2H), 2.43 (s, 3H), 3.05-3.16 (m, 2H), 3.54 (s, 3H), 7.34-7.48 (m, 5H), 7.53-7.60 (m, 1H), 7.70 (s, 1H), 7.71-7.82 (m, 2H).

Example 196

1,6-dimethyl-4-[4-(6-methyl-1,3-benzoxazol-2-yl)piperidin-1-yl]-2-oxo-1,2-dihydroquinoline-3-carboxamide

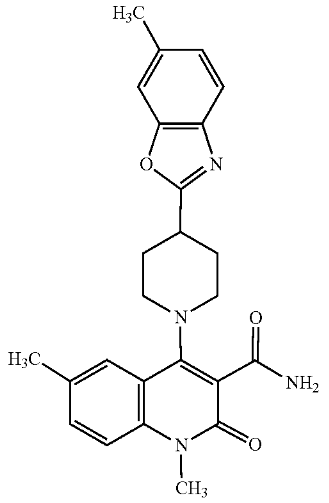 [SMILES: Cc1ccc2nc(C3CCN(c4c(C(N)=O)c(=O)n(C)c5ccc(C)cc45)CC3)oc2c1]

170 mg 1,6-dimethyl-4-[4-(6-methyl-1,3-benzoxazol-2-yl)piperidin-1-yl]-2-oxo-1,2-dihydroquinoline-3-carbonitrile (example 184, 392 μmol), 22 mg palladium(II)acetate (98 μmol) and 232 mg acetaldoxime (4 mmol) were stirred in 22 mL ethanol for 4 h at 80° C. The reaction mixture was diluted with water, extracted with ethyl acetate two times, the combined organic layers were washed with brine, dried over sodium sulfate and the solvent was removed in vacuum. The residue was purified by RP-HPLC (column: X-Bridge C18 5 μm 100×30 mm, mobile phase: acetonitrile/water (0.2 vol. % ammonia 32%)-gradient) to give 75 mg of the title compound (95% purity, 42% yield).

$^1$H NMR (500 MHz, DMSO-$d_6$) δ ppm 2.04-2.13 (m, 2H), 2.23 (br dd, 2H), 2.40-2.43 (m, 3H), 2.44 (s, 3H), 3.15-3.24 (m, 3H), 3.38 (br d, 2H), 3.56 (s, 3H), 7.18 (dd, 1H), 7.41-7.48 (m, 3H), 7.51-7.53 (m, 1H), 7.59 (d, 1H), 7.68 (s, 2H).

Example 197

1,6-dimethyl-4-[4-methyl-4-(6-methyl-1,3-benzoxazol-2-yl)piperidin-1-yl]-2-oxo-1,2-dihydroquinoline-3-carboxamide

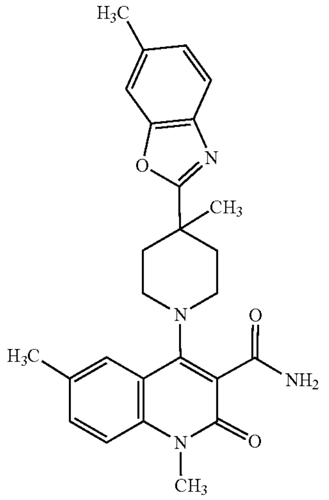 [SMILES: Cc1ccc2nc(C3(C)CCN(c4c(C(N)=O)c(=O)n(C)c5ccc(C)cc45)CC3)oc2c1]

170 mg 1,6-dimethyl-4-[4-methyl-4-(6-methyl-1,3-benzoxazol-2-yl)piperidin-1-yl]-2-oxo-1,2-dihydroquinoline-3-carbonitrile (example 188, 379 μmol), 21 mg palladium(II) acetate (95 μmol) and 224 mg acetaldoxime (3.8 mmol) were stirred in 21 mL ethanol for 4 h at 80° C. The reaction mixture was diluted with water, extracted with ethyl acetate two times, the combined organic layers were washed with brine, dried over sodium sulfate and the solvent was removed in vacuum. The residue was purified by RP-HPLC (column: X-Bridge C18 5 μm 100×30 mm, mobile phase: acetonitrile/water (0.2 vol. % ammonia 32%)-gradient) to give 130 mg of the title compound (95% purity, 73% yield).

$^1$H NMR (500 MHz, DMSO-$d_6$) δ ppm 1.45 (s, 3H), 1.95-2.04 (m, 2H), 2.41-2.48 (m+2s, 8H), 3.09 (br s, 2H), 3.23-3.32 (m, 2H), 3.54 (s, 3H), 7.16-7.21 (m, 1H), 7.37-7.40 (m, 1H), 7.40-7.43 (m, 1H), 7.43-7.47 (m, 1H), 7.53-7.57 (m, 2H), 7.61 (d, 1H), 7.69 (s, 1H).

Example 198

1,6-dimethyl-4-[4-methyl-4-(5-methyl-1,3-benzoxazol-2-yl)piperidin-1-yl]-2-oxo-1,2-dihydroquinoline-3-carboxamide

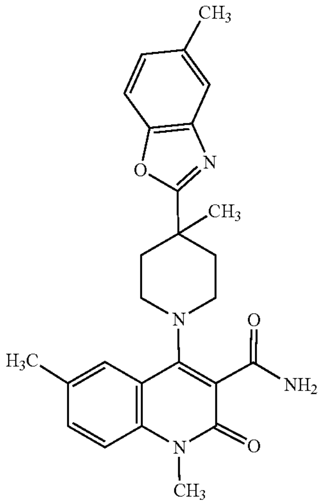 [SMILES: Cc1ccc2oc(C3(C)CCN(c4c(C(N)=O)c(=O)n(C)c5ccc(C)cc45)CC3)nc2c1]

140 mg 1,6-dimethyl-4-[4-methyl-4-(5-methyl-1,3-benzoxazol-2-yl)piperidin-1-yl]-2-oxo-1,2-dihydroquinoline-3-carbonitrile (example 187, 312 μmol), 17.5 mg palladium (II)acetate (78 μmol) and 184 mg acetaldoxime (3.1 mmol) were stirred in 17 mL ethanol for 4 h at 80° C. The reaction mixture was diluted with water, extracted with ethyl acetate two times, the combined organic layers were washed with brine, dried over sodium sulfate and the solvent was removed in vacuum. The residue was purified by RP-HPLC (column: X-Bridge C18 5 μm 100×30 mm, mobile phase: acetonitrile/water (0.2 vol. % ammonia 32%)-gradient) to give 45 mg of the title compound (95% purity, 31% yield).

$^1$H NMR (400 MHz, DMSO-$d_6$) δ ppm 1.45 (s, 3H), 1.99 (br s, 2H), 2.43 (m+s, 8H), 3.09 (br s, 2H), 3.23-3.32 (m, 2H), 3.54 (s, 3H), 7.17-7.21 (m, 1H), 7.37-7.40 (m, 1H), 7.40-7.43 (m, 1H), 7.43-7.47 (m, 1H), 7.51-7.57 (m, 2H), 7.57-7.62 (m, 1H), 7.69 (s, 1H).

TABLE 11

Following examples of table 11 were prepared from assigned starting materials and according to the procedure stated in the table.

| Example | Structure | IUPAC-Name | Starting Materials | Analytics |
|---|---|---|---|---|
| 199 | 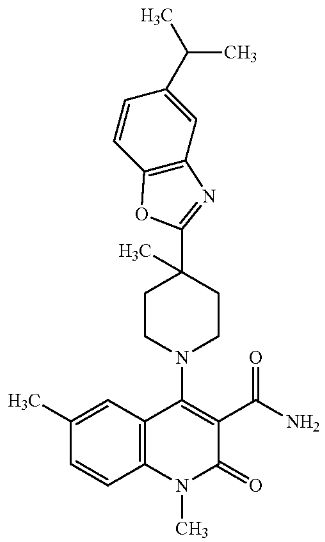 [SMILES: Cc1ccc2c(c1)c(N1CCC(C)(c3nc4cc(C(C)C)ccc4o3)CC1)c(C(N)=O)c(=O)n2C] | 1,6-dimethyl-4-{4-methyl-4-[5-(propan-2-yl)-1,3-benzoxazol-2-yl]piperidin-1-yl}-2-oxo-1,2-dihydroquinoline-3-carboxamide | in analogy to example 198 with example 189 | $^1$H NMR (400 MHz, DMSO-$d_6$) δ ppm 1.26 (d, 6 H), 1.45 (s, 3 H), 1.95-2.06 (m, 2 H), 2.40-2.49 (m + s, 5 H, partially below DMSO), 3.15 (s, 3 H), 3.25-3.32 (m, 2 H), 3.54 (s, 3 H), 7.26 (dd, 1 H), 7.37-7.43 (m, 2 H), 7.43-7.48 (m, 1 H), 7.54-7.59 (m, 1 H), 7.59-7.64 (m, 2 H), 7.69 (s, 1 H). |

TABLE 11-continued

Following examples of table 11 were prepared from assigned starting materials and according to the procedure stated in the table.

| Example | Structure | IUPAC-Name | Starting Materials | Analytics |
|---|---|---|---|---|
| 200 | 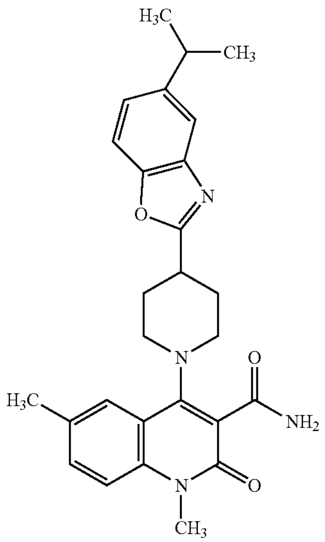 [SMILES: Cc1ccc2c(c1)c(N1CCC(c3nc4cc(C(C)C)ccc4o3)CC1)c(C(N)=O)c(=O)n2C] | 1,6-dimethyl-2-oxo-4-{4-[5-(propan-2-yl)-1,3-benzoxazol-2-yl]piperidin-1-yl}-1,2-dihydroquinoline-3-carboxamide | in analogy to example 198 with example 186 | $^1$H NMR (400 MHz, DMSO-$d_6$) δ ppm 1.25 (d, 6 H), 2.03-2.16 (m, 2 H), 2.18-2.28 (m, 2 H), 2.42 (s, 3 H), 2.97-3.08 (m, 1 H), 3.15-3.26 (m, 3 H), 3.35-3.43 (m, 2 H), 3.57 (s, 3 H), 7.24-7.29 (m, 1 H), 7.41-7.48 (m, 3 H), 7.58-7.61 (m, 2 H), 7.68 (s, 2 H). |
| 201 | 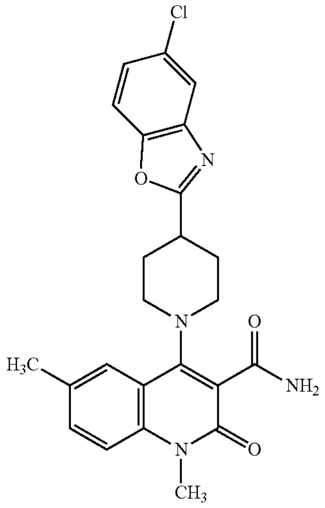 [SMILES: Cc1ccc2c(c1)c(N1CCC(c3nc4cc(Cl)ccc4o3)CC1)c(C(N)=O)c(=O)n2C] | 4-[4-(5-chloro-1,3-benzoxazol-2-yl)piperidin-1-yl]-1,6-dimethyl-2-oxo-1,2-dihydroquinoline-3-carboxamide | in analogy to example 198 with example 185 | $^1$H NMR (400 MHz, DMSO-$d_6$) δ ppm 2.04-2.17 (m, 2 H), 2.20-2.29 (m, 2 H), 2.41 (s, 3 H), 3.14-3.31 (m, 3 H), 3.35-3.43 (m, 2 H), 3.57 (s, 3 H), 7.41-7.49 (m, 4 H), 7.68 (br s, 2 H), 7.77 (d, 1 H), 7.86 (d, 1 H). |

TABLE 11-continued

Following examples of table 11 were prepared from assigned starting materials and according to the procedure stated in the table.

| Example | Structure | IUPAC-Name | Starting Materials | Analytics |
|---|---|---|---|---|
| 202 | 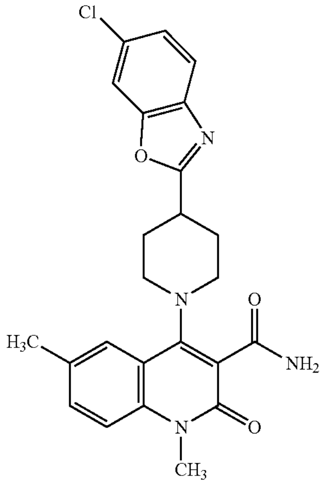 [SMILES: Cc1ccc2c(c1)c(N1CCC(c3nc4ccc(Cl)cc4o3)CC1)c(C(N)=O)c(=O)n2C] | 4-[4-(6-chloro-1,3-benzoxazol-2-yl)piperidin-1-yl]-1,6-dimethyl-2-oxo-1,2-dihydroquinoline-3-carboxamide | in analogy to example 198 with example 183 | $^1$H NMR (400 MHz, DMSO-$d_6$) δ ppm 2.04-2.16 (m, 2 H), 2.20-2.28 (m, 2 H), 2.41 (s, 3 H), 3.14-3.30 (m, 3 H), 3.35-3.43 (m, 2 H), 3.57 (s, 3 H), 7.41-7.48 (m, 4 H), 7.68 (s, 2 H), 7.76 (d, 1 H), 7.94 (d, 1 H). |
| 203 | 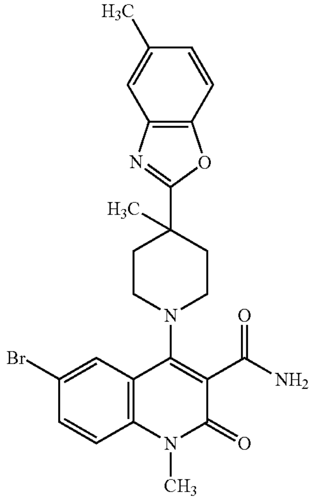 [SMILES: Cc1ccc2oc(C3(C)CCN(c4c(C(N)=O)c(=O)n(C)c5ccc(Br)cc45)CC3)nc2c1] | 6-bromo-1-methyl-4-[4-methyl-4-(5-methyl-1,3-benzoxazol-2-yl)piperidin-1-yl]-2-oxo-1,2-dihydroquinoline-3-carboxamide | in analogy to example 198 with example 171 | $^1$H NMR (500 MHz, DMSO-$d_6$) δ ppm 1.45 (s, 3 H), 1.92-2.02 (m, 2 H), 2.40-2.48 (m + s, 5 H), 3.04-3.13 (m, 2 H), 3.24-3.31 (m, 2 H), 3.55 (s, 3 H), 7.17-7.22 (m, 1 H), 7.45-7.48 (m, 1 H), 7.48-7.51 (m, 1 H), 7.53-7.55 (m, 1 H), 7.57-7.64 (m, 2 H), 7.76 (s, 1 H), 7.97 (d, 1 H). |
| 204 | 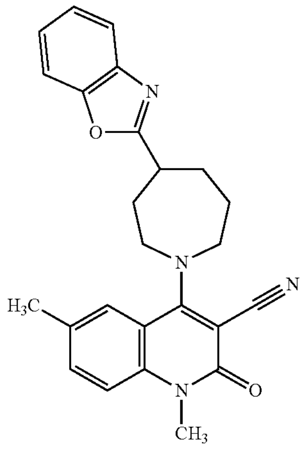 [SMILES: Cc1ccc2c(c1)c(N1CCCC(c3nc4ccccc4o3)CC1)c(C#N)c(=O)n2C] | 4-[4-(1,3-benoxazol-2-yl)azepan-1-yl]-1,6-dimethyl-2-oxo-1,2-dihydroquinoline-3-carbonitrile | in analogy to example 183 with intermediate 92 and intermediate 56 | $^1$H NMR (400 MHz, DMSO-$d_6$) δ ppm 1.93-2.18 (m, 3 H), 2.20-2.31 (m, 1 H), 2.34-2.46 (m, 5 H), 3.46-3.54 (m, 1 H), 3.54-3.58 (m, 3 H), 3.62-3.70 (m, 1 H), 3.73-3.86 (m, 2 H), 3.86-3.96 (m, 1 H), 7.32-7.40 (m, 2 H), 7.46-7.50 (m, 1 H), 7.54-7.58 (m, 1 H), 7.66-7.74 (m, 2 H), 7.74-7.78 (m, 1 H). |

TABLE 11-continued

Following examples of table 11 were prepared from assigned starting materials and according to the procedure stated in the table.

| Example | Structure | IUPAC-Name | Starting Materials | Analytics |
|---|---|---|---|---|
| 205 | 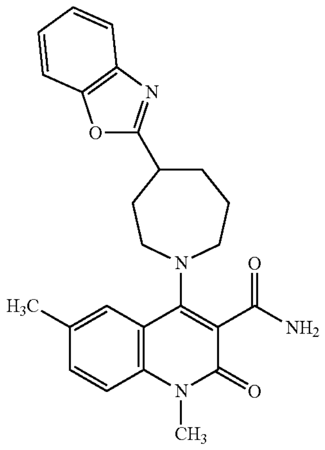 [SMILES: Cc1ccc2c(c1)c(N1CCCC(c3nc4ccccc4o3)CC1)c(C(N)=O)c(=O)n2C] | 4-[4-(1,3-benzoxazol-2-yl)azepan-1-yl]-1,6-dimethyl-2-oxo-1,2-dihydroquinoline-3-carboxamide | in analogy to example 198 with example 204 | $^1$H NMR (400 MHz, DMSO-$d_6$) δ ppm 1.86-1.98 (m, 2 H), 2.04-2.24 (m, 2 H), 2.25-2.36 (m, 3 H), 2.38-2.42 (m, 3 H), 3.39-3.51 (m, 3 H), 3.58 (s, 3 H), 7.31-7.40 (m, 2 H), 7.43-7.48 (m, 3 H), 7.63 (br d, 1 H), 7.67-7.75 (m, 3 H). |

Example 206

4-[4-(1,3-benzoxazol-2-yl)piperidin-1-yl]-6-fluoro-1-methyl-2-oxo-1,2-dihydroquinoline-3-carbonitrile

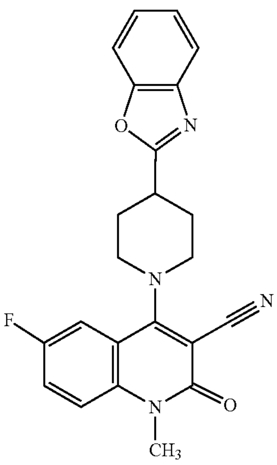 [SMILES: Cn1c(=O)c(C#N)c(N2CCC(c3nc4ccccc4o3)CC2)c2cc(F)ccc21]

120 mg 4-chloro-6-fluoro-1-methyl-2-oxo-1,2-dihydroquinoline-3-carbonitrile (507 μmol, intermediate 103) was solved in 3.4 mL 2-propanol, 260 μL N,N-diisopropylethylamine (1.5 mmol) and 130 mg 2-(piperidin-4-yl)-1,3-benzoxazole (609 μmol, CAS 51784-03-3) were added and the mixture was stirred for 2 h at 90° C. The re action mixture was cooled down to rt and the suspension was diluted with water and stirred for 15 min. The solid was filtered off and washed with water, less ethanol and hexane to give 203 mg of the title compound (100% purity, 99% yield).

LC-MS (Method 1): $R_t$=1.23 min; MS (ESIpos): m/z=403 $[M+H]^+$ $^1$H NMR (400 MHz, DMSO-$d_6$) δ ppm 2.07-2.23 (m, 3H) 2.27-2.37 (m, 3H) 3.37-3.53 (m, 2H) 3.58 (s, 5H) 3.60-3.67 (m, 2H) 3.77-3.89 (m, 3H) 7.33-7.42 (m, 3H) 7.54-7.61 (m, 2H) 7.61-7.70 (m, 3H) 7.70-7.78 (m, 3H).

Example 207

1-methyl-4-[4-methyl-4-(5-methyl-1,3-benzoxazol-2-yl)piperidin-1-yl]-2-oxo-1,2-dihydroquinoline-3,6-dicarbonitrile

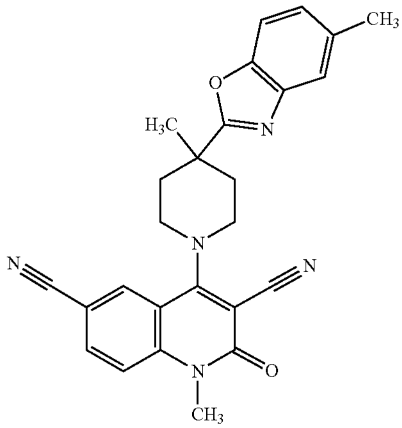 [SMILES: Cc1ccc2oc(C3(C)CCN(c4c(C#N)c(=O)n(C)c5ccc(C#N)cc45)CC3)nc2c1]

A solution of 50 mg 6-bromo-1-methyl-4-[4-methyl-4-(5-methyl-1,3-benzoxazol-2-yl)piperidin-1-yl]-2-oxo-1,2-dihydroquinoline-3-carbonitrile (102 μmol, example 171), 2.6 mg palladium(1-phenylallyl)chloride dimer (5.1 μmol, CAS 12131-44-1), 2.8 mg 1,1-bis(diphenylphosphino)ferrocene (5.1 μmol, CAS 12150-46-8), 14.3 mg zinc cyanide (122 μmol, CAS 557-21-1) and 35 μL N,N-diisopropylethylamine (200 μmol) in 1 mL N,N-dimethylacetamide was flushed with argon and stirred overnight at 80° C. Saturated aqueous sodium bicarbonate solution was added and the mixture was extracted dichloromethane (3×). The combined organic layers were filtered via a water repellent filter and concentrated in vacuum. The residue was purified by RP-HPLC (column: X-Bridge C18 5 μm 100×30 mm, mobile phase: acetonitrile/water (0.1 vol. % formic acid)-gradient) to give 18.2 mg of the title compound (99% purity, 40% yield).

$^1$H NMR (400 MHz, ACETONITRILE-$d_3$) δ ppm 1.31 (s, 3H), 1.82-1.91 (m, 2H), 2.24 (s, 3H), 2.36 (br d, 2H), 3.31-3.42 (m+s, 5H), 3.50-3.57 (m, 2H), 6.98 (dd, 1H), 7.23-7.28 (m, 1H), 7.29-7.32 (m, 1H), 7.32-7.37 (m, 1H), 7.70 (dd, 1H), 7.95 (d, 1H).

Example 208

6-cyano-1-methyl-4-[4-methyl-4-(5-methyl-1,3-benzoxazol-2-yl)piperidin-1-yl]-2-oxo-1,2-dihydroquinoline-3-carboxamide

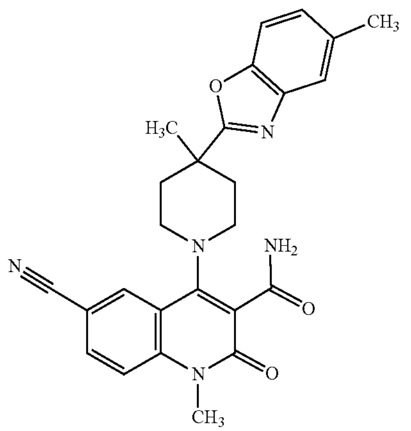 [SMILES: Cc1ccc2oc(C3(C)CCN(c4c(C(N)=O)c(=O)n(C)c5ccc(C#N)cc45)CC3)nc2c1]

A solution of 30 mg 6-bromo-1-methyl-4-[4-methyl-4-(5-methyl-1,3-benzoxazol-2-yl)piperidin-1-yl]-2-oxo-1,2-dihydroquinoline-3-carboxamide (59 μmol, example 203), 1.5 mg palladium(1-phenylallyl)chloride dimer (2.9 μmol, CAS 12131-44-1), 1.6 mg 1,1-bis(diphenylphosphino)ferrocene (2.9 μmol, CAS 12150-46-8), 8.3 mg zinc cyanide (71 μmol, CAS 557-21-1) and 21 μL N,N-diisopropylethylamine (120 μmol) in 0.5 mL N,N-dimethylacetamide was flushed with argon and stirred overnight at 80° C. Saturated aqueous sodium bicarbonate solution was added and the mixture was extracted with dichloromethane (3×). The combined organic layers were filtered via a water repellent filter and concentrated in vacuum. The residue was purified by RP-HPLC (column: X-Bridge C18 5 μm 100×30 mm, mobile phase: acetonitrile/water (0.1 vol. % formic acid)-gradient) to give 13.5 mg of the title compound (99% purity, 50% yield).

$^1$H NMR (400 MHz, ACETONITRILE-$d_3$) δ ppm 1.48 (s, 3H), 1.98-2.08 (m, 2H), 2.43-2.46 (m, 3H), 2.47-2.58 (m, 2H), 3.09-3.22 (m, 2H), 3.26-3.36 (m, 2H), 3.58 (s, 3H), 6.09 (br s, 1H), 6.54 (br s, 1H), 7.18 (dd, 1H), 7.43-7.47 (m, 1H), 7.48-7.50 (m, 1H), 7.53 (d, 1H), 7.86 (dd, 1H), 8.28 (d, 1H).

Example 209

6-(3,3-difluorocyclobutyl)-1-methyl-4-[4-methyl-4-(5-methyl-1,3-benzoxazol-2-yl)piperidin-1-yl]-2-oxo-1,2-dihydroquinoline-3-carbonitrile

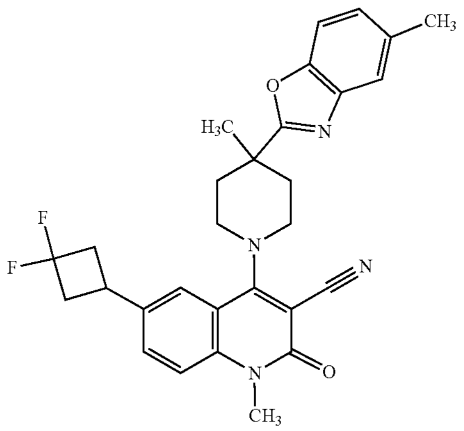 [SMILES: Cc1ccc2oc(C3(C)CCN(c4c(C#N)c(=O)n(C)c5ccc(C6CC(F)(F)C6)cc45)CC3)nc2c1]

80 mg 6-bromo-1-methyl-4-[4-methyl-4-(5-methyl-1,3-benzoxazol-2-yl)piperidin-1-yl]-2-oxo-1,2-dihydroquinoline-3-carbonitrile (163 μmol, example 171), 3.7 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (3.3 μmol, CAS 870987-63-6) and 110 μL 2,6-dimethylpyridine (1 mmol) were dissolved in the reaction vial in 2 mL 1,2-dimethoxyethan. In a separate vial the Ni-catalyst was prepared by dissolving 1.8 mg 1,2-dimethoxyethane-dichloronickel (1:1) (8.1 μmol) and 2.2 mg 4,4-di-tert-butyl-2,2-bipyridine (8.1 μmol) in 1 mL 1,2-dimethoxyethan followed by stirring for 5 min. The catalyst solution was syringed to the sealed reaction vial and was degassed with argon for 5 min., then 89 μL 3-bromo-1,1-difluorocyclobutane (730 μmol, CAS 1310729-91-9) and 50 μL 1,1,1,3,3,3-hexamethyl-2-(trimethylsilyl)trisilane (160 μmol) was added. The vial was placed in a water bath (to keep the temperature below 35° C.) and was subsequently irradiated by two 40 W Kessil LED Aquarium lamps for 20 h. The reaction was quenched with water, extracted with ethyl acetate (3×), dried over sodium sulfate and concentrated in vacuum. The crude material was purified by flash chromatography (silica, dichloromethane/methanol gradient 0-3%) to give 12 mg of the title compound (95% purity, 14% yield).

$^1$H NMR (400 MHz, DMSO-$d_6$) δ ppm 1.50 (s, 3H), 2.01-2.12 (m, 2H), 2.43 (s, 3H), 2.68-2.82 (m, 2H), 3.00-3.14 (m, 2H), 3.45-3.61 (m, 5H), 3.70-3.80 (m, 2H), 7.05 (s, 1H), 7.21 (dd, 1H), 7.51-7.58 (m, 2H), 7.58-7.64 (m, 1H), 7.68-7.74 (m, 2H).

Example 210

6-cyclopropyl-1-methyl-4-[4-methyl-4-(5-methyl-1,3-benzoxazol-2-yl)piperidin-1-yl]-2-oxo-1,2-dihydroquinoline-3-carbonitrile

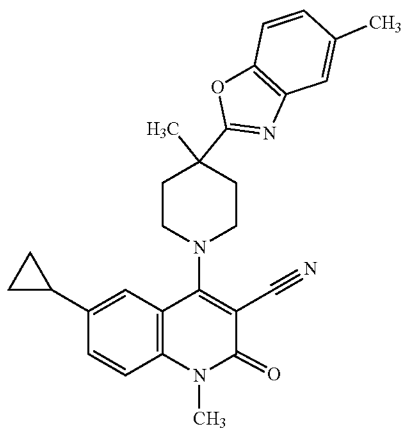 [SMILES: Cc1ccc2oc(C3(C)CCN(c4c(C#N)c(=O)n(C)c5ccc(C6CC6)cc45)CC3)nc2c1]

A solution of 50 mg 6-bromo-1-methyl-4-[4-methyl-4-(5-methyl-1,3-benzoxazol-2-yl)piperidin-1-yl]-2-oxo-1,2-dihydroquinoline-3-carbonitrile (102 μmol, example 171), 8.8 mg di-μ-iodobis(tri-t-butylphosphino)dipalladium(I) (10 μmol, CAS 166445-62-1) and 1 mL of toluene (pre flushed with argon) was added to a reaction vessel, the vessel sealed and the mixture stirred for 10 min. at rt. 610 μL of cyclopropylzinc bromide (0.5 M in THF, 305 μmol, CAS 126403-68-7) was added dropwise and the mixture stirred at rt for 1 h. The mixture was filtered through a silica plug, washed with dichloromethane/methanol (9:1), the organic phases were concentrated in vacuum. The residue was purified by RP-HPLC (column: X-Bridge C18 5 μm 100×30 mm, mobile phase: acetonitrile/water (0.1 vol. % formic acid)-gradient) to give 29.8 mg of the title compound (100% purity, 65% yield).

$^1$H NMR (400 MHz, ACETONITRILE-$d_3$) δ ppm 0.69-0.74 (m, 2H), 0.97-1.05 (m, 2H), 1.51 (s, 3H), 1.97-2.11 (m, 3H), 2.44 (s, 3H), 2.53-2.62 (m, 2H), 3.49-3.58 (m, 5H), 3.68-3.76 (m, 2H), 7.19 (dd, 1H), 7.32-7.36 (m, 1H), 7.36-7.40 (m, 1H), 7.43-7.48 (m, 1H), 7.49-7.51 (m, 1H), 7.52-7.55 (m, 1H).

Example 211

6-(butan-2-yl)-1-methyl-4-[4-methyl-4-(5-methyl-1,3-benzoxazol-2-yl)piperidin-1-yl]-2-oxo-1,2-dihydroquinoline-3-carbonitrile

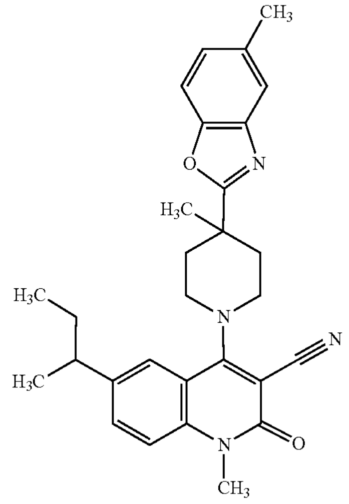 [SMILES: CCC(C)c1ccc2c(c1)c(N1CCC(C)(c3nc4cc(C)ccc4o3)CC1)c(C#N)c(=O)n2C]

80 mg 6-bromo-1-methyl-4-[4-methyl-4-(5-methyl-1,3-benzoxazol-2-yl)piperidin-1-yl]-2-oxo-1,2-dihydroquinoline-3-carbonitrile (163 μmol, example 171), 3.7 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (3.3 μmol, CAS 870987-63-6) and 110 μL 2,6-dimethylpyridine (1 mmol) were dissolved in the reaction vial in 2 mL 1,2-dimethoxyethan. In a separate vial the Ni-catalyst was prepared by dissolving 1.8 mg 1,2-dimethoxyethane-dichloronickel (1:1) (8.1 μmol) and 2.2 mg 4,4-di-tert-butyl-2,2-bipyridine (8.1 μmol) in 1 mL 1,2-dimethoxyethan followed by stirring for 5 min. The catalyst solution was syringed to the sealed reaction vial and was degassed with argon for 5 min., then 80 μL 2-bromobutane (730 μmol, CAS 78-76-2) and 50 μL 1,1,1,3,3,3-hexamethyl-2-(trimethylsilyl)trisilane (160 μmol) was added. The vial was placed in a water bath (to keep the temperature below 35° C.) and was subsequently irradiated by two 40 W Kessil LED Aquarium lamps for 6 h. The reaction was quenched with water, extracted with ethyl acetate (3×), dried over sodium sulfate and concentrated in vacuum. The crude material was purified by RP-HPLC (column: X-Bridge C18 5 μm 100×30 mm, mobile phase: acetonitrile/water (0.2 vol. % ammonia 32%)-gradient) to obtain 20 mg of the title compound (92% purity, 24% yield).

$^1$H NMR (400 MHz, DMSO-$d_6$) δ ppm 0.79 (t, 3H), 1.24 (d, 3H), 1.50 (s, 3H), 1.53-1.69 (m, 2H), 2.00-2.12 (m, 2H), 2.43 (s, 3H), 2.69-2.81 (m, 1H), 3.44-3.57 (m, 5H), 3.69-3.79 (m, 2H), 7.20 (dd, 1H), 7.50 (d, 1H), 7.55-7.58 (m, 1H), 7.58-7.65 (m, 3H).

Example 212

7-(methoxymethyl)-1-methyl-4-[4-methyl-4-(5-methyl-1,3-benzoxazol-2-yl)piperidin-1-yl]-2-oxo-1,2-dihydroquinoline-3-carbonitrile

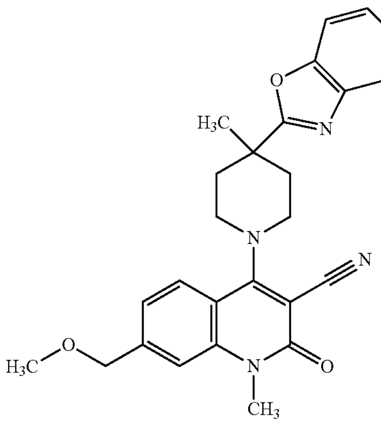

60 mg 7-bromo-1-methyl-4-[4-methyl-4-(5-methyl-1,3-benzoxazol-2-yl)piperidin-1-yl]-2-oxo-1,2-dihydroquinoline-3-carbonitrile (122 μmol, example 110), 2.7 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (2.4 μmol, CAS 870987-63-6) and 5.7 mg dipotassium hydrogenphosphat (33 μmol) were dissolved in the reaction vial in 0.6 mL N,N-dimethylacetamide. In a separate vial the Ni-catalyst was prepared by dissolving 0.8 mg 1,2-dimethoxyethane-dichloronickel (1:1) (3.6 μmol) and 0.9 mg 4,4-di-tert-butyl-2,2-bipyridine (3.6 μmol) in 2.4 mL dioxane followed by stirring for 5 min. The catalyst solution was syringed to the sealed reaction vial and was degassed with argon for 5 min., then 33 mg potassium trifluorido(methoxymethyl)borate (220 μmol, CAS 910251-11-5) was added. The vial was placed in a water bath (to keep the temperature below 35° C.) and was subsequently irradiated by two 40 W Kessil LED Aquarium lamps for 16 h. The reaction was quenched with water, extracted with ethyl acetate (3×), dried over sodium sulfate and concentrated in vacuum. The crude material was purified by flash chromatography (silica, dichloromethane/methanol gradient 0-3%). 20 mg of the title compound were obtained (95% purity, 35% yield).

$^1$H NMR (400 MHz, DMSO-$d_6$) δ ppm 1.50 (s, 3H), 1.99-2.12 (m, 2H), 2.43 (s, 3H), 3.36 (s, 3H), 3.43-3.59 (m+s, 5H), 3.67-3.80 (m, 2H), 4.57 (s, 2H), 7.20 (dd, 1H), 7.27 (dd, 1H), 7.46 (s, 1H), 7.53-7.58 (m, 1H), 7.60 (d, 1H), 7.85 (s, 1H).

Example 213

6-(methoxymethyl)-1-methyl-4-[4-methyl-4-(5-methyl-1,3-benzoxazol-2-yl)piperidin-1-yl]-2-oxo-1,2-dihydroquinoline-3-carbonitrile

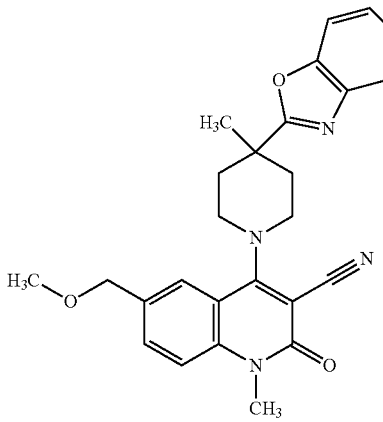

60 mg 6-bromo-1-methyl-4-[4-methyl-4-(5-methyl-1,3-benzoxazol-2-yl)piperidin-1-yl]-2-oxo-1,2-dihydroquinoline-3-carbonitrile (122 μmol, example 171), 2.7 mg bis{3,5-difluoro-2-[5-(trifluoromethyl)pyridin-2-yl]phenyl}iridium(I)hexafluorophosphate-4,4-di-tert-butyl-2,2-bipyridine (1:1:1) (2.4 μmol, CAS 870987-63-6) and 26 mg sodium carbonate (244 μmol) were dissolved in the reaction vial in 0.6 mL N,N-dimethylacetamide. In a separate vial the Ni-catalyst was prepared by dissolving 0.8 mg 1,2-dimethoxyethane-dichloronickel (1:1) (3.6 μmol) and 1 mg 4,4-di-tert-butyl-2,2-bipyridine (3.7 μmol) in 2.4 mL dioxane followed by stirring for 5 min. The catalyst solution was syringed to the sealed reaction vial and was degassed with argon for 5 min., then 33 mg potassium trifluorido(methoxymethyl)borate (220 μmol, CAS 910251-11-5) was added. The vial was placed in a water bath (to keep the temperature below 35° C.) and was subsequently irradiated by two 40 W Kessil LED Aquarium lamps for 16 h. The reaction was quenched with water, extracted with ethyl acetate (3×), dried over sodium sulfate and concentrated in vacuum. The crude material was purified by flash chromatography (silica, dichloromethane/methanol gradient 0-3%). 30 mg of the title compound were obtained (95% purity, 51% yield).

$^1$H NMR (400 MHz, DMSO-$d_6$) δ ppm 1.50 (s, 3H), 1.99-2.11 (m, 2H), 2.43 (s, 3H), 3.32 (s, 3H), 3.46-3.59 (m+s, 5H), 3.70-3.80 (m, 2H), 4.52 (s, 2H), 7.18-7.23 (m, 1H), 7.53-7.58 (m, 2H), 7.58-7.63 (m, 1H), 7.65-7.71 (m, 1H), 7.78 (d, 1H).

Example 214

4-[4-(1,3-benzoxazol-2-yl)-4-methylpiperidin-1-yl]-1,6-dimethyl-2-oxo-1,2-dihydroquinoline-3-carbonitrile

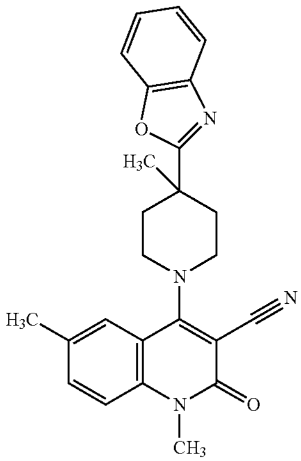 [SMILES: Cc1ccc2c(c1)c(N1CCC(C)(c3nc4ccccc4o3)CC1)c(C#N)c(=O)n2C]

A solution of 100 mg 4-chloro-1,6-dimethyl-2-oxo-1,2-dihydroquinoline-3-carbonitrile (0.41 mmol, intermediate 92), 125 mg 2-(4-methylpiperidin-4-yl)-1,3-benzoxazole (0.49 mmol, intermediate 1) and 0.11 mL triethylamine (0.8 mmol) in 4.1 mL 2-propanol was stirred for 4 h at 90° C. After this time, water was added and the reaction was extracted with ethyl acetate. The organic phase was washed with water and brine, dried over sodium sulfate and evaporated in vacuum. The residue was purified by flash chromatography (silica, dichloromethane/methanol gradient 0-3%) to give 110 mg of the title compound (95% purity, 62% yield).

$^1$H NMR (400 MHz, DMSO-$d_6$) δ ppm 1.51 (s, 3H), 2.01-2.14 (m, 3H), 2.41 (s, 3H), 2.51-2.57 (m, 2H), 3.46-3.58 (m+s, 5H), 3.69-3.80 (m, 2H), 7.35-7.43 (m, 2H), 7.44-7.49 (m, 1H), 7.54-7.59 (m, 1H), 7.65 (s, 1H), 7.72-7.81 (m, 2H).

Example 215

6-fluoro-1-methyl-4-[4-methyl-4-(5-methyl-1,3-benzoxazol-2-yl)piperidin-1-yl]-2-oxo-1,2-dihydroquinoline-3-carbonitrile

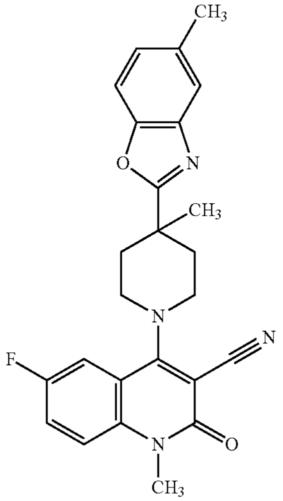 [SMILES: Cc1ccc2oc(C3(C)CCN(c4c(C#N)c(=O)n(C)c5ccc(F)cc45)CC3)nc2c1]

75 mg 4-chloro-6-fluoro-1-methyl-2-oxo-1,2-dihydroquinoline-3-carbonitrile (317 μmol, intermediate 103) was suspended in 2.5 mL 2-propanol, 170 μL N,N-diisopropylethylamine (950 μmol) and 87.6 mg 5-methyl-2-(4-methylpiperidin-4-yl)-1,3-benzoxazole (380 μmol, intermediate 52) were added and the mixture was stirred for 2 h at 90° C. The reaction mixture was cooled down to rt and the suspension was diluted with water and stirred for 15 min. The solid was filtered off and washed with water and ethanol to give 116 mg of the title compound (100% purity, 85% yield).

$^1$H NMR (400 MHz, DMSO-$d_6$) δ ppm 1.49 (s, 3H) 2.01-2.12 (m, 2H) 2.41-2.44 (m, 3H) 2.51-2.53 (m, 2H) 3.44-3.53 (m, 2H) 3.56 (s, 3H) 3.71 (br d, 2H) 7.16-7.27 (m, 1H) 7.53-7.74 (m, 5H).

LC-MS (Method 2): $R_t$=1.38 min; MS (ESIpos): m/z=331.5 $[M+H]^+$

Example 216

4-[4-(1,3-benzoxazol-2-yl)-4-methylpiperidin-1-yl]-6-fluoro-1-methyl-2-oxo-1,2-dihydroquinoline-3-carbonitrile

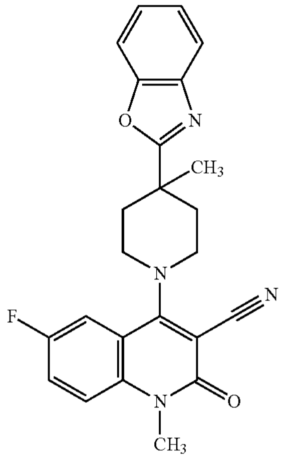 [SMILES: Cn1c(=O)c(C#N)c(N2CCC(C)(c3nc4ccccc4o3)CC2)c2cc(F)ccc21]

100 mg 4-chloro-6-fluoro-1-methyl-2-oxo-1,2-dihydroquinoline-3-carbonitrile (423 μmol, intermediate 103) was suspended in 3 mL 2-propanol, 220 μL N,N-diisopropylethylamine (1.3 mmol) and 115 mg 2-(4-methylpiperidin-4-yl)-1,3-benzoxazole (507 μmol, intermediate 1) were added and the mixture was stirred for 2 h at 90° C. The reaction mixture was cooled down to rt and the suspension was diluted with water and stirred for 15 min. The solid was filtered off and washed with water, less ethanol and less hexane to give 169 mg of the title compound (100% purity, 96% yield).

$^1$H NMR (400 MHz, DMSO-$d_6$) δ ppm 1.51 (s, 3H) 2.08 (ddd, 2H) 2.51-2.55 (m, 2H) 3.46-3.55 (m, 2H) 3.56 (s, 3H) 3.68-3.78 (m, 2H) 7.35-7.43 (m, 2H) 7.58-7.69 (m, 3H) 7.71-7.80 (m, 2H).

LC-MS (Method 1): $R_t$=1.30 min; MS (ESIpos): m/z=417.4 $[M+H]^+$

Example 217

6-fluoro-1-methyl-4-[4-(5-methyl-1,3-benzoxazol-2-yl)piperidin-1-yl]-2-oxo-1,2-dihydroquinoline-3-carbonitrile

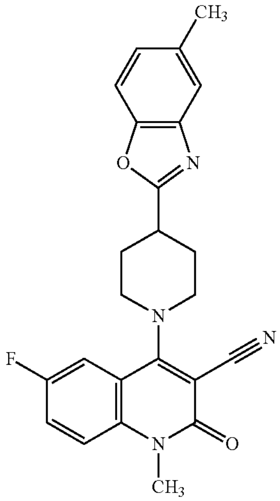 [SMILES: Cc1ccc2oc(C3CCN(c4c(C#N)c(=O)n(C)c5ccc(F)cc45)CC3)nc2c1]

80 mg 4-chloro-6-fluoro-1-methyl-2-oxo-1,2-dihydroquinoline-3-carbonitrile (338 µmol, intermediate 103) was suspended in 2.5 mL 2-propanol, 180 µL N,N-diisopropylethylamine (1.0 mmol) and 87.7 mg 5-methyl-2-(piperidin-4-yl)-1,3-benzoxazole (406 µmol, CAS 199292-77-8) were added and the mixture was stirred for 2 h at 90° C. The reaction mixture was cooled down to rt and the suspension was diluted with water and stirred for 15 min. The solid was filtered off and washed with water and ethanol to give 127 mg of the title compound (98% purity, 88% yield).

$^1$H NMR (400 MHz, DMSO-$d_6$) δ ppm 2.07-2.19 (m, 2H) 2.27-2.35 (m, 2H) 2.44 (s, 3H) 3.43 (tt, 1H) 3.55-3.64 (m, 5H) 3.81 (br d, 2H) 7.18 (dd, 1H) 7.53 (d, 1H) 7.54-7.61 (m, 2H) 7.61-7.70 (m, 2H).

LC-MS (Method 2): $R_t$=1.32 min; MS (ESIpos): m/z=417.4 [M+H]$^+$

Example 218

4-[4-(1,3-benzoxazol-2-yl)-4-methylpiperidin-1-yl]-1,7-dimethyl-2-oxo-1,2-dihydroquinoline-3-carbonitrile

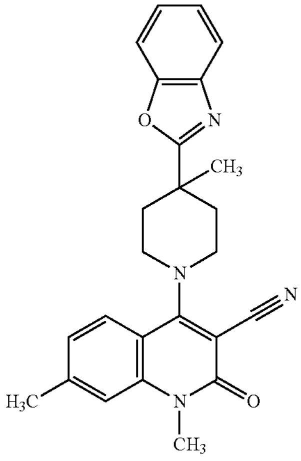 [SMILES: Cc1ccc2c(N3CCC(C)(c4nc5ccccc5o4)CC3)c(C#N)c(=O)n(C)c2c1]

75 mg 4-chloro-1,7-dimethyl-2-oxo-1,2-dihydroquinoline-3-carbonitrile (306 µmol, intermediate 106) was suspended in 2.5 mL 2-propanol, 160 µL N,N-diisopropylethylamine (920 µmol) and 83.7 mg 2-(4-methylpiperidin-4-yl)-1,3-benzoxazole (367 µmol, intermediate 1) were added and the mixture was stirred for 2 h at 90° C. The reaction mixture was cooled down to rt and the suspension was diluted with water and stirred for 15 min. The solid was filtered off and washed with water and ethanol to give 129 mg of the title compound (100% purity, 102% yield).

$^1$H NMR (400 MHz, DMSO-$d_6$) δ ppm 1.51 (s, 3H) 2.06 (ddd, 2H) 2.46 (s, 3H) 2.51-2.56 (m, 2H) 3.45-3.57 (m, 5H) 3.69-3.78 (m, 2H) 7.16 (dd, 1H) 7.36-7.43 (m, 3H) 7.71-7.80 (m, 3H).

LC-MS (Method 2): $R_t$=1.35 min; MS (ESIpos): m/z=413.5 [M+H]$^+$

Example 219

4-[4-(1,3-benzoxazol-2-yl)piperidin-1-yl]-1,7-dimethyl-2-oxo-1,2-dihydroquinoline-3-carbonitrile

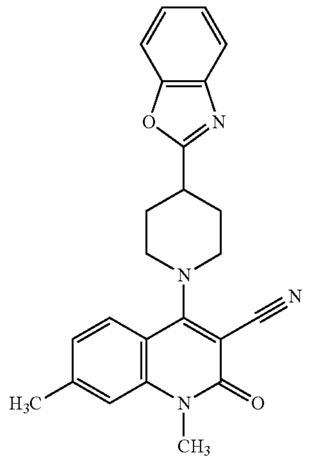 [SMILES: Cc1ccc2c(N3CCC(c4nc5ccccc5o4)CC3)c(C#N)c(=O)n(C)c2c1]

75 mg 4-chloro-1,7-dimethyl-2-oxo-1,2-dihydroquinoline-3-carbonitrile (306 µmol, intermediate 106) was suspended in 2.5 mL 2-propanol, 160 µL N,N-diisopropylethylamine (920 µmol) and 78.2 mg 2-(piperidin-4-yl)-1,3-benzoxazole (367 µmol, CAS 51784-03-3) were added and the mixture was stirred for 2 h at 90° C. The reaction mixture was cooled down to rt and the suspension was diluted with water and stirred for 15 min. The solid was filtered off and washed with water and ethanol to give 124 mg of the title compound (100% purity, 101% yield).

$^1$H NMR (400 MHz, DMSO-$d_6$) δ ppm 2.08-2.21 (m, 2H) 2.27-2.36 (m, 2H) 2.47 (s, 3H) 3.41-3.52 (m, 1H) 3.54-3.64 (m, 5H) 3.82 (br d, 2H) 7.18 (d, 1H) 7.34-7.42 (m, 3H) 7.69-7.79 (m, 3H).

LC-MS (Method 2): $R_t$=1.28 min; MS (ESIpos): m/z=399.5 [M+H]$^+$

Example 220

1,7-dimethyl-4-[4-methyl-4-(5-methyl-1,3-benzoxazol-2-yl)piperidin-1-yl]-2-oxo-1,2-dihydroquinoline-3-carbonitrile

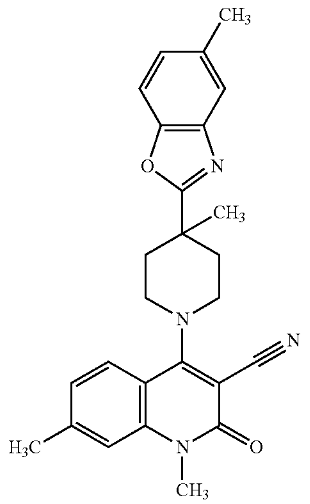 [SMILES: Cc1ccc2oc(C3(C)CCN(c4c(C#N)c(=O)n(C)c5cc(C)ccc45)CC3)nc2c1]

75 mg 4-chloro-1,7-dimethyl-2-oxo-1,2-dihydroquinoline-3-carbonitrile (306 μmol, intermediate 106) was suspended in 2.5 mL 2-propanol, 160 μL N,N-diisopropylethylamine (920 μmol) and 84.6 mg 5-methyl-2-(4-methylpiperidin-4-yl)-1,3-benzoxazole (367 μmol, intermediate 52) were added and the mixture was stirred for 2 h at 90° C. The reaction mixture was cooled down to rt and the suspension was diluted with water and stirred for 15 min. The solid was filtered off and washed with water and ethanol to give 135 mg of the title compound (100% purity, 103% yield).

$^1$H NMR (400 MHz, DMSO-$d_6$) δ ppm 1.49 (s, 3H) 1.99-2.10 (m, 2H) 2.42 (s, 3H) 2.46 (s, 3H) 2.51-2.53 (m, 2H) 3.48 (br t, 2H) 3.54 (s, 3H) 3.67-3.76 (m, 2H) 7.16 (dd, 1H) 7.18-7.23 (m, 1H) 7.39 (s, 1H) 7.54-7.57 (m, 1H) 7.60 (d, 1H) 7.76 (d, 1H).

LC-MS (Method 2): $R_t$=1.42 min; MS (ESIpos): m/z=427.5 $[M+H]^+$

Example 221

1,7-dimethyl-4-[4-(5-methyl-1,3-benzoxazol-2-yl)piperidin-1-yl]-2-oxo-1,2-dihydroquinoline-3-carbonitrile

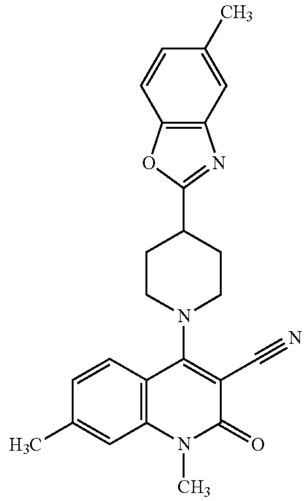 [SMILES: Cc1ccc2oc(C3CCN(c4c(C#N)c(=O)n(C)c5cc(C)ccc45)CC3)nc2c1]

75 mg 4-chloro-1,7-dimethyl-2-oxo-1,2-dihydroquinoline-3-carbonitrile (306 μmol, intermediate 106) was suspended in 2.5 mL 2-propanol, 160 μL N,N-diisopropylethylamine (920 μmol) and 83.7 mg 5-methyl-2-(piperidin-4-yl)-1,3-benzoxazole (367 μmol, CAS 199292-77-8) were added and the mixture was stirred for 2 h at 90° C. The re action mixture was cooled down to rt and the suspension was diluted with water and stirred for 15 min. The solid was filtered off and washed with water and ethanol to give 126 mg of the title compound (100% purity, 99% yield).

$^1$H NMR (400 MHz, DMSO-$d_6$) δ ppm 2.06-2.19 (m, 2H) 2.26-2.34 (m, 2H) 2.42 (s, 3H) 2.47 (s, 3H) 3.43 (tt, 1H) 3.54-3.62 (m, 5H) 3.81 (br d, 2H) 7.16-7.21 (m, 2H) 7.40 (s, 1H) 7.51-7.54 (m, 1H) 7.58 (d, 1H) 7.76 (d, 1H).

LC-MS (Method 2): $R_t$=1.35 min; MS (ESIpos): m/z=413.5 $[M+H]^+$

Example 222

4-[4-(1,3-benzothiazol-2-yl)piperidin-1-yl]-1,7-dimethyl-2-oxo-1,2-dihydroquinoline-3-carbonitrile

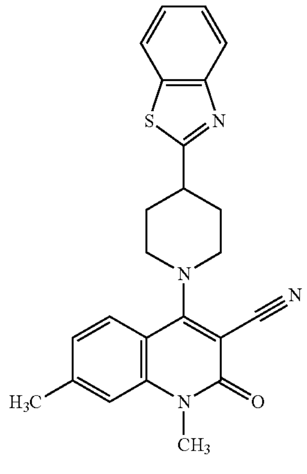 [SMILES: Cc1ccc2c(N3CCC(c4nc5ccccc5s4)CC3)c(C#N)c(=O)n(C)c2c1]

30 mg of 4-[4-(1,3-Benzothiazol-2-yl)piperidin-1-yl]-7-bromo-1-methyl-2-oxo-1,2-dihydro-quinoline-3-carbonitrile (62.6 µmol, example 33), 18.7 mg methylboronic acid (313 µmol, CAS 13061-96-6), 25.9 mg potassium carbonate (188 µmol, CAS 584-08-7), 5.11 mg [1,1'-Bis(diphenylphosphino)ferrocene]dichloropalladium(II), complex with dichloromethane (6.26 µmol, CAS 95464-05-4) were added to a reaction vessel, the vessel was sealed and flushed with argon. 600 µl 1,4-dioxane and 300 µl water (both pre-flushed with argon) were added and the mixture was stirred at 130° C. for 1 h. The mixture was filtered via a water-repellent filter and the filter was washed twice with dichloromethane. The filtrate was concentrated under reduced pressure, with further purification achieved by preparative HPLC using a Waters Auto purification system with a YMC Triart C18 5µ 150×50 mm column; eluent A: water+0.1 Vol-% formic acid (99%) and eluent B: acetonitrile; with the following gradient: 0.00-0.50 min 55% B (40→100 mL/min), 0.51-8.50 min 55-85% B (100 mL/min) yielding 4 mg of the title compound (95% purity, 15% yield).

$^1H$ NMR (400 MHz, ACETONITRILE-$d_3$) δ ppm 2.17-2.25 (m, 2H) 2.32-2.40 (m, 2H) 2.48 (s, 3H) 3.40-3.66 (m, 1H) 3.47-3.65 (m, 5H) 3.89 (br d, 2H) 7.14 (d, 1H) 7.32 (s, 1H) 7.39-7.46 (m, 1H) 7.50 (td, 1H) 7.80 (d, 1H) 7.94-8.01 (m, 2H) LC-MS (Method 1): $R_t$=1.31 min; MS (ESIpos): m/z=415.24 $[M+H]^+$

TABLE 12

Following examples of table 12 were prepared from assigned starting materials and according to the procedure stated in the table.

| Example | Structure | IUPAC-Name | Starting Materials | Analytics |
|---|---|---|---|---|
| 223 | 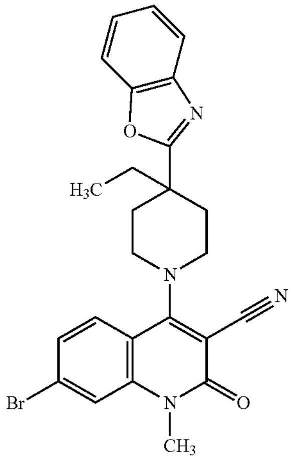 [SMILES: CCC1(c2nc3ccccc3o2)CCN(c2c(C#N)c(=O)n(C)c3cc(Br)ccc23)CC1] | 4-[4-(1,3-benzoxazol-2-yl)-4-ethylpiperidin-1-yl]-7-bromo-1-methyl-2-oxo-1,2-dihydroquinoline-3-carbonitrile | in analogy to example 191 with 7-bromo-4-chloro-1-methyl-2-oxo-1,2-dihydroquinoline-3-carbonitrile (intermediate 21) and 2-(4-ethylpiperidin-4-yl)-1,3-benzoxazole (intermediate 51) | $^1H$ NMR (400 MHz, DMSO-$d_6$) δ ppm 0.72 (t, 3 H) 1.88 (q, 2 H) 1.98-2.10 (m, 2 H) 2.53-2.59 (m, 2 H) 3.39-3.50 (m, 2 H) 3.54 (s, 3 H) 3.73 (br s, 2 H) 7.35-7.50 (m, 3 H) 7.70-7.85 (m, 4 H). LC-MS (Method 2): $R_t$ = 1.44 min; MS (ESIpos): m/z = 493.4 $[M + H]^+$ |
| 224 | 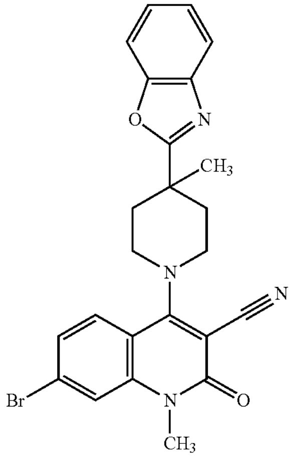 | 4-[4-(1,3-benzoxazol-2-yl)-4-methylpiperidin-1-yl]-7-bromo-1-methyl-2-oxo-1,2-dihydroquinoline-3-carbonitrile | in analogy to example 149 with 7-bromo-4-chloro-1-methyl-2-oxo-1,2-dihydroquinoline-3-carbonitrile (intermediate 21) and 2-(4-methylpiperidin-4-yl)-1,3-benzoxazole (intermediate 1) | $^1H$ NMR (400 MHz, DMSO-$d_6$) δ ppm 1.50 (s, 3 H) 2.00-2.12 (m, 2 H) 2.52 (br d, 2 H) 3.45-3.59 (m, 5 H) 3.65-3.80 (m, 2 H) 7.29-7.43 (m, 2H) 7.46-7.52 (m, 1 H) 7.68-7.86 (m, 4 H). LC-MS (Method 2): $R_t$ = 1.38 min; MS (ESIpos): m/z = 479.5 $[M + H]^+$ |

TABLE 12-continued

Following examples of table 12 were prepared from assigned starting materials and according to the procedure stated in the table.

| Example | Structure | IUPAC-Name | Starting Materials | Analytics |
|---|---|---|---|---|
| 225 | 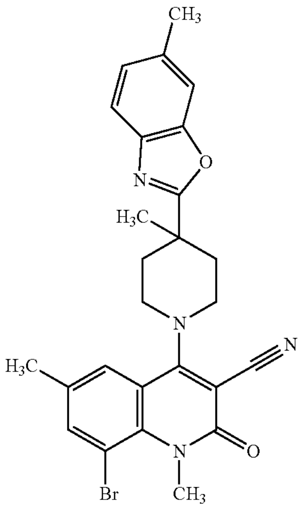 [SMILES: Cc1ccc2nc(C3(C)CCN(c4c(C#N)c(=O)n(C)c5c(Br)cc(C)cc45)CC3)oc2c1] | 8-bromo-1,6-dimethyl-4-[4-methyl-4-(6-methyl-1,3-benzoxazol-2-yl)piperidin-1-yl]-2-oxo-1,2-dihydroquinoline-3-carbonitrile | in analogy to example 214 with 8-bromo-4-chloro-1,6-dimethyl-2-oxo-1,2-dihydroquinoline-3-carbonitrile (intermediate 109) and 6-methyl-2-(4-methylpiperidin-4-yl)-1,3-benzoxazole (intermediate 95) | $^1$H NMR (400 MHz, DMSO-$d_6$) δ ppm 1.48 (s, 3 H) 2.04 (ddd, 2 H) 2.37 (s, 3 H) 2.41-2.49 (m ,5 H) 3.45-3.56 (m, 2 H) 3.66 (s, 3 H) 3.70-3.78 (m, 2 H) 7.14-7.23 (m, 1 H) 7.50-7.57 (m, 1 H) 7.59-7.68 (m, 2 H) 7.80-7.92 (m, 1 H). LC-MS (Method 2): $R_t$ = 1.51 min; MS (ESIpos): m/z = 507.5 $[M + H]^+$ |
| 226 | 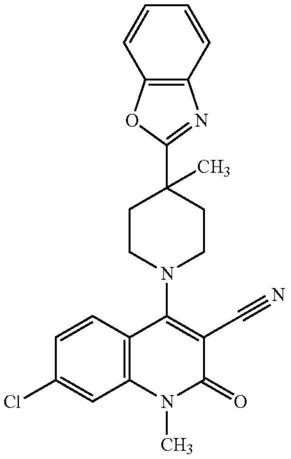 [SMILES: Cn1c(=O)c(C#N)c(N2CCC(C)(c3nc4ccccc4o3)CC2)c2ccc(Cl)cc21] | 4-[4-(1,3-benzoxazol-2-yl)-4-methylpiperidni-1-yl]-7-chloro-1-methyl-2-oxo-1,2-dihydroquinoline-3-carbonitrile | in analogy to example 221 with 4,7-dichloro-1-methyl-2-oxo-1,2-dihydroquinoline-3-carbonitrile (intermediate 112) and 2-(4-methylpiperidin-4-yl)-1,3-benzoxazole (intermediate 1) | $^1$H NMR (400 MHz, DMSO-$d_6$) δ ppm 1.51 (s, 3 H) 2.06 (ddd, 2 H) 2.52 (br d, 2 H) 3.54 (s, 5 H) 3.73 (br d, 2 H) 7.33-7.43 (m, 3 H) 7.62-7.67 (m, 1 H) 7.72-7.80 (m, 2 H) 7.84-7.90 (m, 1 H). LC-MS (Method 1): $R_t$ = 1.38 min; MS (ESIpos): m/z = 433.4 $[M + H]^+$ |
| 227 | 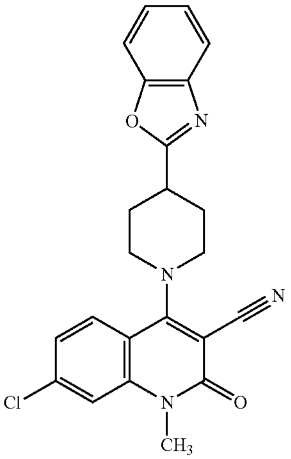 [SMILES: Cn1c(=O)c(C#N)c(N2CCC(c3nc4ccccc4o3)CC2)c2ccc(Cl)cc21] | 4-[4-(1,3-benzoxazol-2-yl)piperidin-1-yl]-7-chloro-1-methyl-2-oxo-1,2-dihydroquinoline-3-carbonitrile | in analogy to example 221 with 4,7-dichloro-1-methyl-2-oxo-1,2-dihydroquinoline-3-carbonitrile (intermediate 112) and 2-(piperidin-4-yl)-1,3-benzoxazole (CAS 51784-03-3) | $^1$H NMR (400 MHz, DMSO-$d_6$) δ ppm 2.08-2.21 (m, 2 H) 2.27-2.36 (m, 2 H) 3.42-3.53 (m, 1 H) 3.53-3.64 (m, 5 H) 3.82 (br d, 2 H) 7.34-7.42 (m, 3 H) 7.66 (d, 1 H) 7.69-7.77 (m, 2 H) 7.87 (d, 1 H). LC-MS (Method 1): $R_t$ = 1.31 min; MS (ESIpos): m/z = 419.4 $[M + H]^+$ |

TABLE 12-continued

| Example | Structure | IUPAC-Name | Starting Materials | Analytics |
|---|---|---|---|---|
| Following examples of table 12 were prepared from assigned starting materials and according to the procedure stated in the table. | | | | |
| 228 | 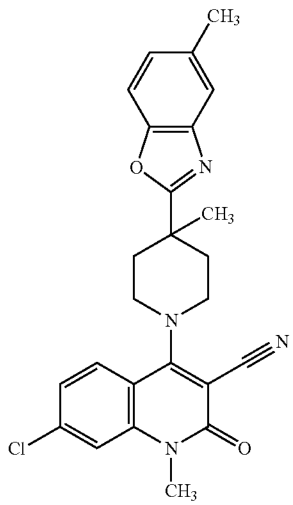 [SMILES: Cc1ccc2oc(C3(C)CCN(c4c(C#N)c(=O)n(C)c5cc(Cl)ccc45)CC3)nc2c1] | 7-chloro-1-methyl-4-[4-methyl-4-(5-methyl-1,3-benzoxazol-2-yl)piperidin-1-yl]-2-oxo-1,2-dihydroquinoline-3-carbonitrile | in analogy to example 221 with 4,7-dichloro-1-methyl-2-oxo-1,2-dihydroquinoline-3-carbonitrile (intermediate 112) and 5-methyl-2-(4-methylpiperidin-4-yl)-1,3-benzoxazole (intermediate 52) | $^1$H NMR (400 MHz, DMSO-$d_6$) δ ppm 1.49 (s, 3 H) 2.00-2.10 (m, 2 H) 2.43 (s, 3 H) 2.45-2.49 (m, 2 H) 3.44-3.53 (m, 2 H) 3.54 (s, 3 H) 3.67-3.77 (m, 2 H) 7.20 (dd, 1 H) 7.36 (dd, 1 H) 7.54-7.58 (m, 1 H) 7.60 (d, 1 H) 7.64 (d, 1 H) 7.87 (d, 1 H). LC-MS (Method 2): $R_t$ = 1.45 min; MS (ESIpos): m/z = 447.5 $[M + H]^+$ |
| 229 | 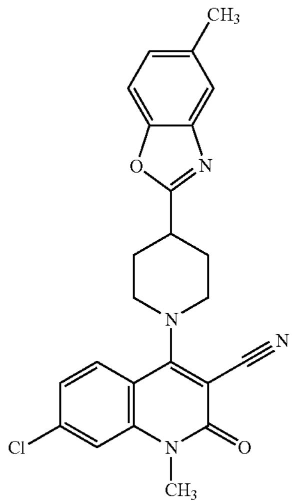 [SMILES: Cc1ccc2oc(C3CCN(c4c(C#N)c(=O)n(C)c5cc(Cl)ccc45)CC3)nc2c1] | 7-chloro-1-methyl-4-[4-(5-methyl-1,3-benzoxazol-2-yl)piperidin-1-yl]-2-oxo-1,2-dihydroquinoline-3-carbonnitrile | in analogy to example 221 with 4,7-dichloro-1-methyl-2-oxo-1,2-dihydroquinoline-3-carbonitrile (intermediate 112) and 5-methyl-2-(piperidin-4-yl)-1,3-benzoxazole (CAS 199292-77-8) | $^1$H NMR (400 MHz, DMSO-$d_6$) δ ppm 2.07-2.19 (m, 2 H) 2.25-2.34 (m, 2 H) 2.44 (s, 3 H) 3.39-3.48 (m, 1 H) 3.54-3.63 (m, 5 H) 3.81 (br d, 2 H) 7.18 (dd, 1 H) 7.38 (dd, 1 H) 7.52 (d, 1 H) 7.59 (d, 1 H) 7.66 (d, 1 H) 7.87 (d, 1 H). LC-MS (Method 2): $R_t$ = 1.39 min; MS (ESIpos): m/z = 433.4 $[M + H]^+$ |
| 230 | 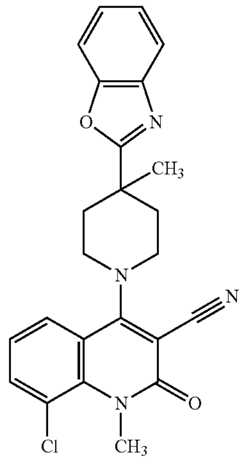 [SMILES: Cn1c(=O)c(C#N)c(N2CCC(C)(c3nc4ccccc4o3)CC2)c2cccc(Cl)c21] | 4-[4-(1,3-benzoxazol-2-yl)-4-methylpiperidni-1-yl]-8-chloro-1-methyl-2-oxo-1,2-dihydroquinoline-3-carbonitrile | in analogy to example 221 with 4,8-dichloro-1-methyl-2-oxo-1,2-dihydroquinoline-3-carbonitrile (intermediate 88) and 2-(4-methylpiperidin-4-yl)-1,3-benzoxazole (intermediate 1) | $^1$H NMR (400 MHz, DMSO-$d_6$) δ ppm 1.50 (s, 3 H) 2.07 (ddd, 2 H) 2.52 (br s, 2 H) 3.47-3.58 (m, 2 H) 3.69 (s, 3 H) 3.71-3.79 (m, 2 H) 7.32 (t, 1 H) 7.35-7.43 (m, 2 H) 7.73-7.79 (m, 2 H) 7.82 (ddd, 2 H). LC-MS (Method 1): $R_t$ = 1.37 min; MS (ESIpos): m/z = 433.4 $[M + H]^+$ |

TABLE 12-continued

| Following examples of table 12 were prepared from assigned starting materials and according to the procedure stated in the table. | | | | |
|---|---|---|---|---|
| Example | Structure | IUPAC-Name | Starting Materials | Analytics |
| 231 | 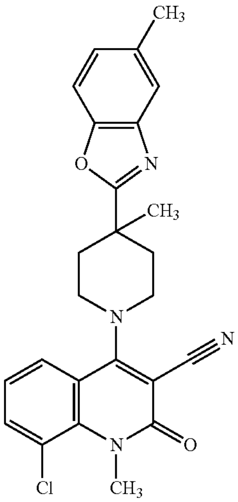 [SMILES: Cc1ccc2oc(C3(C)CCN(c4c(C#N)c(=O)n(C)c5c(Cl)cccc45)CC3)nc2c1] | 8-chloro-1-methyl-4-[4-methyl-4-(5-methyl-1,3-benzoxazol-2-yl)piperidin-1-yl]-2-oxo-1,2-dihydroquinoline-3-carbonitrile | in analogy to example 221 with 4,8-dichloro-1-methyl-2-oxo-1,2-dihydroquinoline-3-carbonitrile (intermediate 88) and 5-methyl-2-(4-methylpiperidin-4-yl)-1,3-benzoxazole (intermediate 52) | $^1$H NMR (400 MHz, DMSO-$d_6$) δ ppm 1.49 (s, 3 H) 2.00-2.10 (m, 2 H) 2.43 (s, 3 H) 2.45-2.49 (m, 2 H) 3.45-3.55 (m, 2 H) 3.69 (s, 3 H) 3.70-3.78 (m, 2 H) 7.18-7.23 (m, 1 H) 7.32 (t, 1 H) 7.54-7.57 (m, 1 H) 7.60 (d, 1 H) 7.82 (ddd, 2 H). LC-MS (Method 2): $R_t$ = 1.44 min; MS (ESIpos): m/z = 447.5 $[M + H]^+$ |
| 232 | 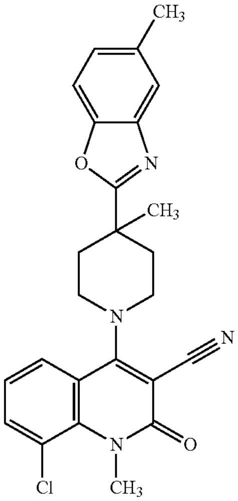 | 8-chloro-1-methyl-4-[4-(5-methyl-1,3-benzoxazol-2-yl)piperidin-1-yl]-2-oxo-1,2-dihydroquinoline-3-carbonitrile | in analogy to example 221 with 4,8-dichloro-1-methyl-2-oxo-1,2-dihydroquinoline-3-carbonitrile (intermeidate 88) and 5-methyl-2-(piperidin-4-yl)-1,3-benzoxazole (CAS 199292-77-8) | $^1$H NMR (400 MHz, DMSO-$d_6$) δ ppm 2.07-2.19 (m, 2 H) 2.26-2.34 (m, 2 H) 2.44 (s, 3 H) 3.39-3.49 (m, 1 H) 3.55-3.64 (m, 2 H) 3.71 (s, 3 H) 3.82 (br d, 2 H) 7.18 (dd, 1 H) 7.34 (t, 1 H) 7.52 (d, 1 H) 7.59 (d, 1 H) 7.82 (td, 2 H). LC-MS (Method 2): $R_t$ = 1.38 min; MS (ESIpos): m/z = 433.4 $[M + H]^+$ |

Example 233

8-bromo-1-methyl-4-{4-methyl-4-[5-methyl-4-(trifluoromethyl)-1,3-benzoxazol-2-yl]piperidin-1-yl}-2-oxo-1,2-dihydroquinoline-3-carbonitrile

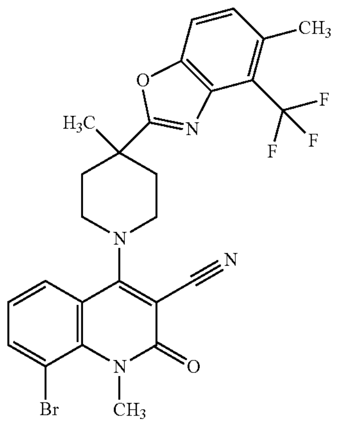 [SMILES: Cc1ccc2oc(C3(C)CCN(c4c(C#N)c(=O)n(C)c5c(Br)cccc45)CC3)nc2c1C(F)(F)F]

150 mg of 8-bromo-1-methyl-4-[4-methyl-4-(5-methyl-1,3-benzoxazol-2-yl)piperidin-1-yl]-2-oxo-1,2-dihydroquinoline-3-carbonitrile (305 μmol, example 158), 381 mg sodium trifluoromethanesulfinate (2.44 mmol, CAS 2926-29-6) and 22.1 mg copper trifluoromethanesulfonate (61.1 μmol, CAS 34946-82-2), were added to a 5 ml reaction vessel, the vessel was sealed and flushed with argon. 2.0 ml of acetonitrile (pre-flushed with argon) was added and 290 μl tert-butylhydroperoxide (70% in water, 3.1 mmol, CAS 75-91-2) was added over 30 minutes. The mixture was stirred for 2 hours at RT, followed by stirring at 40° C. for 30 minutes. The mixture was filtered through a 2 g silica column, the column flushed with a dichloromethane:methanol mixture (9:1), and the solvent removed under reduced pressure, purification achieved by preparative HPLC using a Waters Auto purification system with a YMC Triart C18 5μ 150×50 mm column; eluent A: water+0.1 Vol-% formic acid (99%) and eluent B: acetonitrile; with the following gradient: 0.00-0.50 min 75% B (50→100 mL/min), 0.51-8.50 min 75-95% B (100 mL/min), yielding 1 mg of the title compound (90% purity, 1% yield).

$^1$H NMR (400 MHz, ACETONITRILE-$d_3$) δ ppm 1.58 (s, 3H) 2.11 (m, 2H) 2.53-2.64 (m, 5H) 3.55-3.69 (m, 2H) 3.72-3.83 (m, 5H) 7.18 (t, 1H) 7.38 (d, 1H) 7.42-7.42 (m, 1H) 7.70-7.80 (m, 1H) 7.87 (dd, 1H) 7.91-7.96 (m, 1H)

LC-MS (Method 2): $R_t$=1.54 min; MS (ESIpos): m/z=559.14 $[M+H]^+$

Example 234

1-methyl-4-[(2S,4S)-2-methyl-4-(5-methyl-1,3-benzoxazol-2-yl)piperidin-1-yl]-2-oxo-1,2-dihydroquinoline-3-carbonitrile

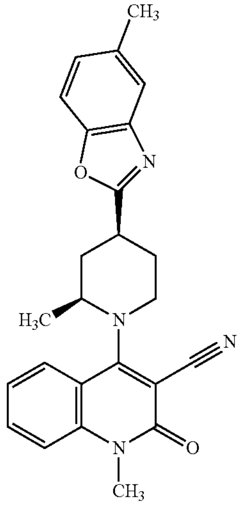 [SMILES: Cc1ccc2oc([C@H]3CCN(c4c(C#N)c(=O)n(C)c5ccccc45)[C@@H](C)C3)nc2c1]

A solution of 100 mg 4-chloro-1-methyl-2-oxo-1,2-dihydroquinoline-3-carbonitrile (434 μmol, CAS 150617-68-8), 105 mg 5-methyl-2-[(2S,4S)-2-methylpiperidin-4-yl]-1,3-benzoxazole (434 μmol, intermediate 113) and 0.12 mL triethylamine (0.87 mmol) in 3 mL 2-propanol was stirred for 2 h at 90° C. After this time, water was added and the reaction was extracted with ethyl acetate. The organic phase was washed with water and brine, dried over sodium sulfate and evaporated in vacuum. The residue was purified by RP-HPLC (column: X-Bridge C18 5 μm 100×30 mm, mobile phase: acetonitrile/water (0.2 vol. % ammonia 32%)-gradient) to give 25 mg of the title compound (95% purity, 13% yield).

$^1$H NMR (400 MHz, DMSO-$d_6$) δ ppm 1.30 (d, 3H) 1.85-1.99 (m, 1H) 2.07-2.18 (m, 1H) 2.27-2.36 (m, 1H) 2.41-2.45 (m, 3H) 3.37-3.48 (m, 2H) 3.54-3.74 (m, 4H) 4.05 (td, 1H) 4.21-4.32 (m, 1H) 7.15-7.22 (m, 1H) 7.30-7.41 (m, 1H) 7.48-7.54 (m, 1H) 7.54-7.63 (m, 2H) 7.75 (ddd, 1H) 7.90 (dd, 1H).

Example 235

4-[4-(1,3-benzoxazol-2-yl)-4-methylpiperidin-1-yl]-7-fluoro-1-methyl-2-oxo-1,2-dihydroquinoline-3-carbonitrile

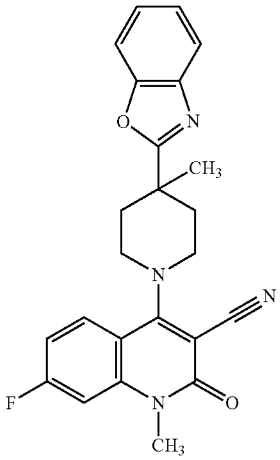 [SMILES: Cn1c(=O)c(C#N)c(N2CCC(C)(c3nc4ccccc4o3)CC2)c2ccc(F)cc21]

100 mg 4-chloro-7-fluoro-1-methyl-2-oxo-1,2-dihydroquinoline-3-carbonitrile (406 μmol, intermediate 116) was suspended in 3 mL 2-propanol, 210 μL N,N-diisopropylethylamine (1.2 mmol) and 111 mg 2-(4-methylpiperidin-4-yl)-1,3-benzoxazole (487 μmol, intermediate 1) were added and the mixture was stirred for 2 h at 90° C. The reaction mixture was cooled down to rt and the suspension was diluted with water and stirred for 15 min. The solid was filtered off and washed with water, less ethanol and hexane to give 164 mg of the title compound (99% purity, 96% yield).

$^{1}$H NMR (400 MHz, DMSO-$d_6$) δ ppm 1.51 (s, 3H) 2.07 (ddd, 2H) 2.51-2.57 (m, 2H) 3.46-3.57 (m, 5H) 3.68-3.78 (m, 2H) 7.19 (ddd, 1H) 7.35-7.48 (m, 3H) 7.71-7.80 (m, 2H) 7.94 (dd, 1H).

LC-MS (Method 1): $R_t$=1.30 min; MS (ESIpos): m/z=417.4 $[M+H]^+$

Example 236

4-[4-(1,3-benzoxazol-2-yl)piperidin-1-yl]-7-fluoro-1-methyl-2-oxo-1,2-dihydroquinoline-3-carbonitrile

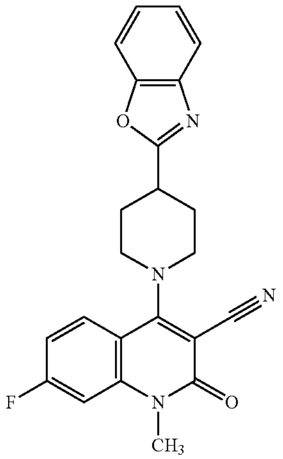 [SMILES: Cn1c(=O)c(C#N)c(N2CCC(c3nc4ccccc4o3)CC2)c2ccc(F)cc21]

120 mg 4-chloro-7-fluoro-1-methyl-2-oxo-1,2-dihydroquinoline-3-carbonitrile (487 μmol, intermediate 116) was suspended in 3.2 mL 2-propanol, 250 μL N,N-diisopropylethylamine (1.5 mmol) and 124 mg 2-(piperidin-4-yl)-1,3-benzoxazole (584 μmol, CAS 51784-03-3) were added and the mixture was stirred for 2 h at 90° C. The re action mixture was cooled down to rt and the suspension was diluted with water and stirred for 15 min. The solid was filtered off and washed with water, less ethanol and hexane to give 185 mg of the title compound (98% purity, 93% yield).

$^{1}$H NMR (400 MHz, DMSO-$d_6$) δ ppm 2.09-2.21 (m, 2H) 2.27-2.36 (m, 2H) 3.47 (tt, 1H) 3.54 (s, 3H) 3.56-3.65 (m, 2H) 3.82 (br d, 2H) 7.21 (ddd, 1H) 7.34-7.42 (m, 2H) 7.46 (dd, 1H) 7.70-7.76 (m, 2H) 7.94 (dd, 1H).

LC-MS (Method 1): $R_t$=1.23 min; MS (ESIpos): m/z=403.4 $[M+H]^+$

Example 237

7-fluoro-1-methyl-4-[4-methyl-4-(5-methyl-1,3-benzoxazol-2-yl)piperidin-1-yl]-2-oxo-1,2-dihydroquinoline-3-carbonitrile

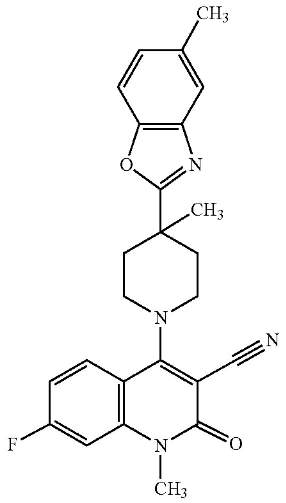

75 mg 4-chloro-7-fluoro-1-methyl-2-oxo-1,2-dihydroquinoline-3-carbonitrile (304 μmol, intermediate 116) was suspended in 2.5 mL 2-propanol, 160 μL N,N-diisopropylethylamine (910 μmol) and 84.1 mg 5-methyl-2-(4-methylpiperidin-4-yl)-1,3-benzoxazole (365 μmol, intermediate 52) were added and the mixture was stirred for 2 h at 90° C. The reaction mixture was cooled down to rt and the suspension was diluted with water and stirred for 15 min. The solid was filtered off and washed with water and ethanol to give 121 mg of the title compound (100% purity, 93% yield).

$^{1}$H NMR (400 MHz, DMSO-$d_6$) δ ppm 1.49 (s, 3H) 2.00-2.10 (m, 2H) 2.42 (s, 3H) 2.45-2.49 (m, 2H) 3.43-3.56 (m, 5H) 3.67-3.76 (m, 2H) 7.15-7.23 (m, 2H) 7.44 (dd, 1H) 7.54-7.57 (m, 1H) 7.60 (d, 1H) 7.94 (dd, 1H).

LC-MS (Method 2): $R_t$=1.37 min; MS (ESIpos): m/z=431.5 $[M+H]^+$

Example 238

7-fluoro-1-methyl-4-[4-(5-methyl-1,3-benzoxazol-2-yl)piperidin-1-yl]-2-oxo-1,2-dihydroquinoline-3-carbonitrile

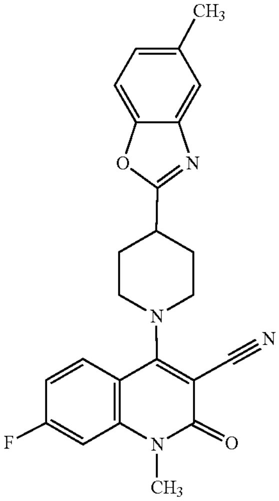 [SMILES: Cc1ccc2oc(C3CCN(c4c(C#N)c(=O)n(C)c5cc(F)ccc45)CC3)nc2c1]

80 mg 4-chloro-7-fluoro-1-methyl-2-oxo-1,2-dihydroquinoline-3-carbonitrile (325 μmol, intermediate 116) was suspended in 2.5 mL 2-propanol, 170 μL N,N-diisopropylethylamine (970 μmol) and 84.2 mg 5-methyl-2-(piperidin-4-yl)-1,3-benzoxazole (389 μmol, CAS 199292-77-8) were added and the mixture was stirred for 2 h at 90° C. The reaction mixture was cooled down to rt and the suspension was diluted with water and stirred for 15 min. The solid was filtered off and washed with water and ethanol to give 115 mg of the title compound (96% purity, 82% yield).

$^1$H NMR (400 MHz, DMSO-$d_6$) δ ppm 2.06-2.19 (m, 2H) 2.25-2.34 (m, 2H) 2.44 (s, 3H) 3.44 (tt, 1H) 3.52-3.63 (m, 5H) 3.81 (br d, 2H) 7.16-7.24 (m, 2H) 7.46 (dd, 1H) 7.51-7.54 (m, 1H) 7.59 (d, 1H) 7.93 (dd, 1H).

LC-MS (Method 2): $R_t$=1.32 min; MS (ESIpos): m/z=417.4 $[M+H]^+$

Example 239

7-[(1-hydroxycyclopropyl)methoxy]-1-methyl-4-[4-methyl-4-(5-methyl-1,3-benzoxazol-2-yl)piperidin-1-yl]-2-oxo-1,2-dihydroquinoline-3-carbonitrile

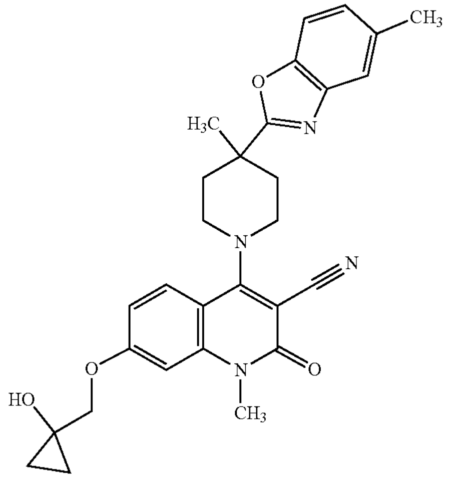 [SMILES: Cc1ccc2oc(C3(C)CCN(c4c(C#N)c(=O)n(C)c5cc(OCC6(O)CC6)ccc45)CC3)nc2c1]

50 mg of 7-bromo-1-methyl-4-[4-methyl-4-(5-methyl-1,3-benzoxazol-2-yl)piperidin-1-yl]-2-oxo-1,2-dihydroquinoline-3-carbonitrile (102 μmol, example 110), 8.5 mg [(2-di-tert-butyl-phosphino-3-methoxy-6-methyl-2',4',6'-triisopropyl-1,1'-biphenyl)-2-(2-aminobiphenyl)]-palladium (II) methanesulfonate (10.2 μmol), 4.8 mg 2-di(tert-butyl) phosphino-2',4',6'-triisopropyl-3-methoxy-6-methylbiphenyl (10.2 μmol, CAS 1262046-34-3) and 46.4 mg caesiumcarbonate (142 μmol, CAS 534-17-8) were added to a 5 ml reaction vessel, the vessel sealed and flushed with argon. 660 μl degassed toluene and 89.6 mg 1-(hydroxymethyl)cyclopropanol (1.02 mmol, CAS 42082-92-8) were added and the mixture was stirred at 80° C. overnight. The mixture was filtered through a 2 g silica column, the column flushed with a dichloromethane:methanol mixture (9:1), and the solvent removed under reduced pressure, purification achieved by preparative HPLC using a Waters Auto purification system with a XBrigde C18 5μ 100×30 mm; eluent A: water+0.1 Vol-% formic acid (99%) and eluent B: acetonitrile; with the following gradient: Gradient: 0.00 to 0.50 min 43% B (25 to 70 mL/min), 0.51-5.50 min 43-63% B (70 mL/min), yielding 11.8 mg of the title compound (90% purity, 1% yield).

$^1$H NMR (400 MHz, ACETONITRILE-$d_3$) δ ppm 0.67-0.71 (m, 2H) 0.74-0.82 (m, 2H) 1.50 (s, 3H) 2.04 (ddd, 2H) 2.44 (s, 3H) 2.52-2.58 (m, 2H) 3.49-3.57 (m, 5H) 3.67-3.78 (m, 2H) 4.13 (s, 2H) 6.83-6.89 (m, 2H) 7.17-7.21 (m, 1H) 7.44-7.51 (m, 3H) 7.80 (d, 1H)

LC-MS (Method 1): $R_t$=1.25 min; MS (ESIpos): m/z=499.28 $[M+H]^+$

Example 240

4-[4-(1,3-benzothiazol-2-yl)piperidin-1-yl]-7-methoxy-1-methyl-2-oxo-1,2-dihydroquinoline-3-carbonitrile

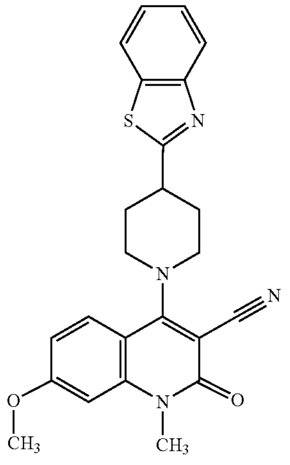 [SMILES: COc1ccc2c(N3CCC(c4nc5ccccc5s4)CC3)c(C#N)c(=O)n(C)c2c1]

30 mg of 4-[4-(1,3-benzothiazol-2-yl)piperidin-1-yl]-7-bromo-1-methyl-2-oxo-1,2-dihydroquinoline-3-carbonitrile (62.6 μmol, example 33), 5.4 mg [(2-Di-tert-butylphosphino-3,6-dimethoxy-2',4',6'-triisopropyl-1,1'-biphenyl)-2-(2'-amino-1,1'-biphenyl)]palladium(II) methanesulfonate (6.26 μmol, CAS 1536473-72-9), 3 mg 2-(di-tert-butylphosphino)-2',4',6'-triisopropyl-3,6-dimethoxy-1,1'-biphenyl (6.26 μmol, CAS 1160861-53-9), 28.5 mg caesiumcarbonate (87.6 μmol, CAS 534-17-8) were added to a 5 ml reaction vessel, the vessel sealed and flushed with argon. 1 ml of degassed toluene and 25 μl methanol (630 μmol) were added and the mixture was stirred at 80° C. overnight. The mixture was filtered through a 2 g silica column, the column flushed with a dichloromethane:methanol mixture (9:1), and the solvent removed under reduced pressure. Purification was achieved by RP-HPLC (column: X-Bridge C18 5 μm 100×30 mm, mobile phase: acetonitrile/water (0.2 vol. % ammonia 32%)-gradient) to give 2.6 mg of the title compound (93% purity, 9% yield).

$^1$H NMR (400 MHz, ACETONITRILE-$d_3$) δ ppm 1.95-2.03 (m, 2H) 2.14 (br dd, 2H) 3.24-3.42 (m, 6H) 3.65 (br d, 2H) 3.72 (s, 3H) 6.64-6.70 (m, 2H) 7.18-7.23 (m, 1H) 7.29 (ddd, 1H) 7.63 (d, 1H) 7.73-7.80 (m, 2H)

LC-MS (Method 2): $R_t$=1.29 min; MS (ESIpos): m/z=431.3 $[M+H]^+$

Example 241

1-methyl-4-[4-methyl-4-(5-methyl-1,3-benzoxazol-2-yl)piperidin-1-yl]-7-[(oxetan-3-yl)oxy]-2-oxo-1,2-dihydroquinoline-3-carbonitrile

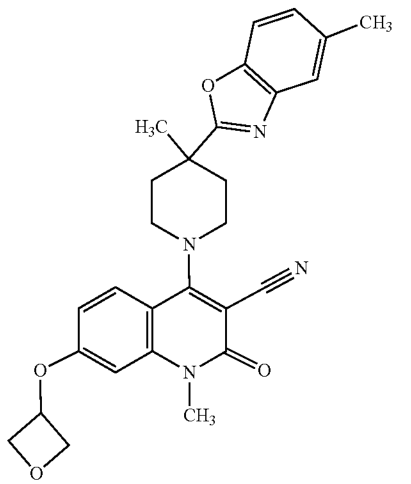 [SMILES: Cc1ccc2oc(C3(C)CCN(c4c(C#N)c(=O)n(C)c5cc(OC6COC6)ccc45)CC3)nc2c1]

The title compound (5.0 mg, 95% purity, 10% yield) was prepared using an analogous procedure used to prepare example 239, from example 110 using 68 μl of 3-Hydroxyoxetane (1.0 mmol, CAS 7748-36-9) with purification by RP-HPLC (column: X-Bridge C18 5 μm 100×30 mm, mobile phase: acetonitrile/water (0.2 vol. % ammonia 32%)-gradient).

1H NMR (400 MHz, ACETONITRILE-d3) δ ppm 1.50 (s, 3H) 2.00-2.08 (m, 2H) 2.44 (s, 3H) 2.55 (br d, 2H) 3.46-3.58 (m, 5H) 3.70 (dt, 2H) 4.60-4.65 (m, 2H) 4.99 (m, 2H) 5.33-5.44 (m, 1H) 6.61 (d, 1H) 6.71 (dd, 1H) 7.19 (d, 1H) 7.45 (d, 1H) 7.50 (s, 1H) 7.80 (d, 1H) LC-MS (Method 2): $R_t$=1.27 min; MS (ESIpos): m/z=485.34 [M+H]+

Example 242

6-hydroxy-1-methyl-4-[4-methyl-4-(5-methyl-1,3-benzoxazol-2-yl)piperidin-1-yl]-2-oxo-1,2-dihydroquinoline-3-carbonitrile

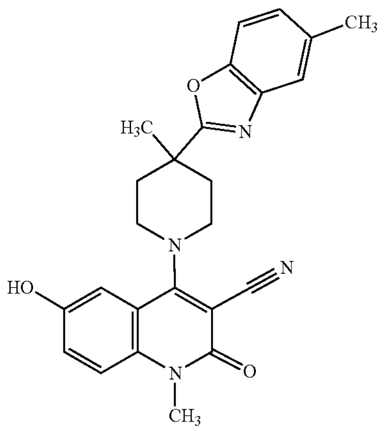 [SMILES: Cc1ccc2oc(C3(C)CCN(c4c(C#N)c(=O)n(C)c5ccc(O)cc45)CC3)nc2c1]

The title compound (0.9 mg, 70% purity, 1.3% yield) was prepared using an analogous procedure used to prepare example 239, from example 171 using 66 μl of 3-Hydroxypropionitrile (1.0 mmol, CAS 109-78-4) with purification by RP-HPLC (column: X-Bridge C18 5 μm 100×30 mm, mobile phase: acetonitrile/water (0.2 vol. % ammonia 32%)-gradient). 1H NMR (400 MHz, ACETONITRILE-d3) δ ppm 1.52 (s, 3H) 2.04-2.12 (m, 2H) 2.45 (s, 3H) 2.53-2.62 (m, 2H) 3.49-3.60 (m, 5H) 3.66-3.78 (m, 2H) 7.16-7.24 (m, 2H) 7.26 (d, 1H) 7.35 (d, 1H) 7.46 (d, 1H) 7.51 (d, 1H) 8.10-8.18 (m, 1H)

LC-MS (Method 2): $R_t$=0.93 min; MS (ESIpos): m/z=429.29 $[M+H]^+$

Example 243

4-[4-(1,3-benzoxazol-2-yl)piperidin-1-yl]-7-methoxy-1-methyl-2-oxo-1,2-dihydroquinoline-3-carbonitrile

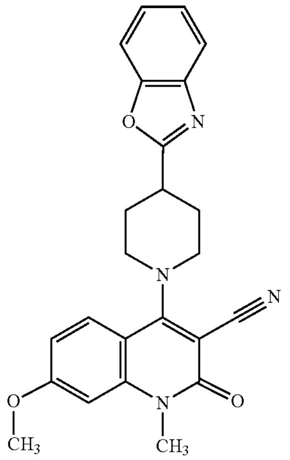 [SMILES: COc1ccc2c(N3CCC(c4nc5ccccc5o4)CC3)c(C#N)c(=O)n(C)c2c1]

The title compound (16.2 mg, 94% purity, 57% yield) was prepared using an analogous procedure used to prepare example 240, from 30 mg of example 27 (65 μmol) using 26 μl of methanol (0.65 mmol, CAS 67-56-1) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 2.16-2.25 (m, 2H) 2.31-2.39 (m, 2H) 3.30-3.41 (m, 1H) 3.53-3.63 (m, 5H) 3.77-3.87 (m, 2H) 3.92 (s, 3H) 6.84-6.86 (m, 1H) 6.86-6.92 (m, 1H) 7.30-7.40 (m, 2H) 7.55-7.60 (m, 1H) 7.64-7.71 (m, 1H) 7.79-7.85 (m, 1H)

LC-MS (Method 2): $R_t$=1.22 min; MS (ESIpos): m/z=415.3 $[M+H]^+$

Example 244

7-(cyclopropyloxy)-1-methyl-4-[4-methyl-4-(5-methyl-1,3-benzoxazol-2-yl)piperidin-1-yl]-2-oxo-1,2-dihydroquinoline-3-carbonitrile

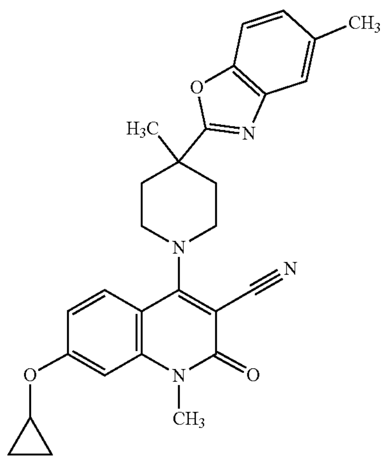 [SMILES: Cc1ccc2oc(C3(C)CCN(c4c(C#N)c(=O)n(C)c5cc(OC6CC6)ccc45)CC3)nc2c1]

The title compound (10.1 mg, 95% purity, 21% yield) was prepared using an analogous procedure used to prepare example 239, from example 110 using 49 μl of cyclopropanol (1.0 mmol, CAS 16545-68-9) with purification by RP-HPLC (column: X-Bridge C18 5 μm 100×30 mm, mobile phase: acetonitrile/water (0.1 vol. % formic acid)-gradient).

$^1$H NMR (400 MHz, ACETONITRILE-$d_3$) δ ppm 0.68-0.81 (m, 2H) 0.81-0.94 (m, 2H) 1.50 (s, 3H) 1.96-2.09 (m, 2H) 2.44 (s, 3H) 2.49 (s, 1H) 2.55 (br d, 2H) 3.55 (br d, 5H) 3.63-3.74 (m, 2H) 3.94 (dt, 1H) 6.97 (dd, 1H) 7.03 (d, 1H) 7.19 (d, 1H) 7.45 (d, 1H) 7.50 (s, 1H) 7.80 (d, 1H)

LC-MS (Method 1): $R_t$=1.47 min; MS (ESIpos): m/z=469.32 $[M+H]^+$

Example 245

1-methyl-4-[4-methyl-4-(5-methyl-1,3-benzoxazol-2-yl)piperidin-1-yl]-8-(oxetan-3-yl)-2-oxo-1,2-dihydroquinoline-3-carbonitrile

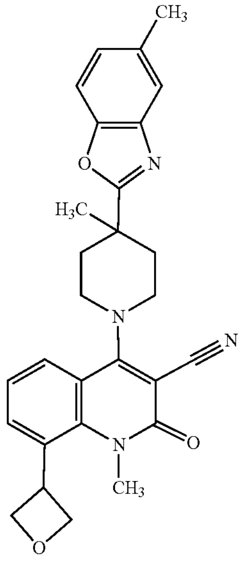 [SMILES: Cc1ccc2oc(C3(C)CCN(c4c(C#N)c(=O)n(C)c5c(C6COC6)cccc45)CC3)nc2c1]

80 mg 8-bromo-1-methyl-4-[4-methyl-4-(5-methyl-1,3-benzoxazol-2-yl)piperidin-1-yl]-2-oxo-1,2-dihydroquinoline-3-carbonitrile (163 μmol, example 158), 3.7 mg bis{3,5-difluoro-2-[5-(trifluoromethyl)pyridin-2-yl]phenyl}iridium(I)hexafluorophosphate-4,4'-di-tert-butyl-2,2'-bipyridine (1:1:1) (3.3 μmol, CAS 870987-63-6) and 110 μL 2,6-dimethylpyridine (980 μmol) were dissolved in the reaction vial in 3 mL 1,2-dimethoxyethane. In a separate vial the Ni-catalyst was prepared by dissolving 1.8 mg 1,2-dimethoxyethane-dichloronickel (1:1) (8.1 μmol) and 2.2 mg 4,4'-di-tert-butyl-2,2'-bipyridine (8.1 μmol) in 3 mL 1,2-dimethoxyethane followed by stirring for 5 min. The catalyst solution was syringed to the sealed reaction vial and was degassed with argon for 5 min., then 61 μL 3-bromooxetane (730 μmol, CAS 39267-79-3) and 50 μL 1,1,1,3,3,3-hexamethyl-2-(trimethylsilyl)trisilane (160 μmol) was added. The vial was placed in a water bath (to keep the temperature below 35° C.) and was subsequently irradiated by two 40 W Kessil LED Aquarium lamps for 4 h. The reaction was concentrated in vacuum. The crude material was purificated by flash chromatography (silica, dichloromethane/methanol gradient 0-2%). 20 mg of the title compound were obtained (95% purity, 25% yield).

$^1$H NMR (400 MHz, DMSO-$d_6$) δ ppm 1.49 (s, 3H) 2.00-2.11 (m, 2H) 2.42 (s, 3H) 2.51-2.53 (m, 2H) 3.31 (s, 3H) 3.42-3.54 (m, 2H) 3.65-3.80 (m, 2H) 4.57-4.69 (m, 2H) 4.70-4.86 (m, 1H) 4.93-5.04 (m, 2H) 7.18-7.24 (m, 1H) 7.33-7.42 (m, 1H) 7.52-7.62 (m, 2H) 7.74-7.83 (m, 1H) 7.87-7.93 (m, 1H).

LC-MS (Method 2): $R_t$=1.28 min; MS (ESIpos): m/z=469.5 $[M+H]^+$

Example 246

6-methoxy-1-methyl-4-[4-methyl-4-(5-methyl-1,3-benzoxazol-2-yl)piperidin-1-yl]-2-oxo-1,2-dihydro-quinoline-3-carbonitrile

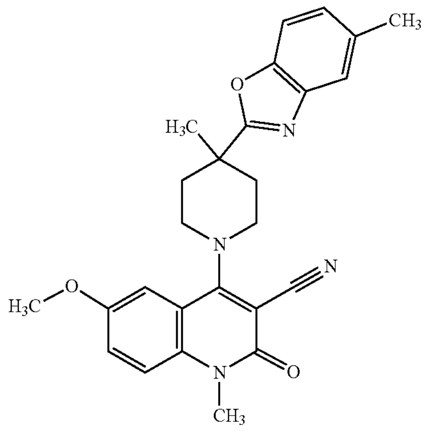

The title compound (4 mg, 95% purity, 9% yield) was prepared using an analogous procedure used to prepare example 239, from example 171 using 41 μl of methanol (1.0 mmol, CAS 67-56-1) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 1.29-1.33 (m, 3H) 1.79-1.90 (m, 2H) 2.25 (s, 3H) 2.33-2.42 (m, 2H) 3.29-3.39 (m, 5H) 3.47-3.58 (m, 2H) 3.67 (s, 3H) 6.95-7.02 (m, 1H) 7.07-7.14 (m, 2H) 7.20-7.24 (m, 1H) 7.24-7.27 (m, 1H) 7.29-7.34 (m, 1H)

LC-MS (Method 2): $R_t$=1.31 min; MS (ESIpos): m/z=443.28 [M+H]$^+$

Example 247

7-(cyclobutyloxy)-1-methyl-4-[4-methyl-4-(5-methyl-1,3-benzoxazol-2-yl)piperidin-1-yl]-2-oxo-1,2-dihydroquinoline-3-carbonitrile

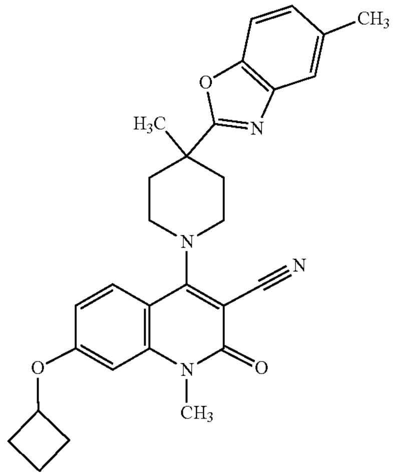 [SMILES: Cc1ccc2oc(C3(C)CCN(c4c(C#N)c(=O)n(C)c5cc(OC6CCC6)ccc45)CC3)nc2c1]

The title compound (21.8 mg, 95% purity, 44% yield) was prepared using an analogous procedure used to prepare example 239, from 50 mg of example 110 (0.102 mmol) using 80 μl of cyclobutanol (1.0 mmol, CAS 2919-23-5) with purification by RP-HPLC (column: X-Bridge C18 5 μm 100×30 mm, mobile phase: acetonitrile/water (0.1 vol. % formic acid)-gradient).

$^1$H NMR (400 MHz, ACETONITRILE-$d_3$) δ ppm 1.50 (s, 3H) 1.65-1.78 (m, 1H) 1.81-1.91 (m, 1H) 2.03 (m, 2H) 2.08-2.20 (m, 2H) 2.43-2.57 (m, 7H) 3.46-3.59 (m, 5H) 3.69 (m, 2H) 4.81-4.88 (m, 1H) 6.71 (d, 1H) 6.77 (dd, 1H) 7.18 (d, 1H) 7.45 (d, 1H) 7.49 (dt, 1H) 7.77 (d, 1H)

LC-MS (Method 1): $R_t$=1.54 min; MS (ESIpos): m/z=483.33 [M+H]$^+$

Example 248

7-methoxy-1-methyl-4-[4-methyl-4-(5-methyl-1,3-benzoxazol-2-yl)piperidin-1-yl]-2-oxo-1,2-dihydro-quinoline-3-carbonitrile

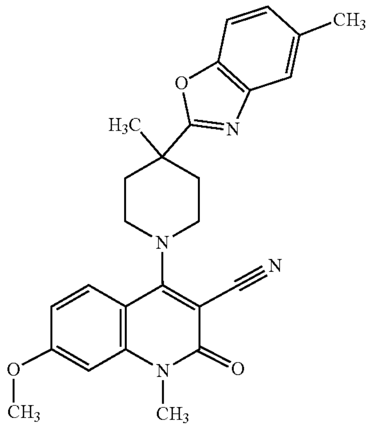 [SMILES: COc1ccc2c(N3CCC(C)(c4nc5cc(C)ccc5o4)CC3)c(C#N)c(=O)n(C)c2c1]

The title compound (3 mg, 95% purity, 7% yield) was prepared using an analogous procedure used to prepare example 239, from 50 mg of example 110 (1.02 mmol) using 41 μl of methanol (1.0 mmol, CAS 67-56-1) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 1.51 (s, 3H) 2.04 (m, 2H) 2.45 (s, 3H) 2.55 (br d, 2H) 3.50-3.58 (m, 5H) 3.63-3.78 (m, 2H) 3.92 (s, 3H) 6.83-6.84 (m, 1H) 6.87 (d, 1H) 7.16-7.23 (m, 1H) 7.46 (d, 1H) 7.51 (s, 1H) 7.80 (d, 1H)

LC-MS (Method 2): $R_t$=1.33 min; MS (ESIpos): m/z=443.3 [M+H]$^+$

Example 249

1-methyl-4-[4-methyl-4-(5-methyl-1,3-benzoxazol-2-yl)piperidin-1-yl]-2-oxo-1,2-dihydroquinoline-3,7-dicarbonitrile

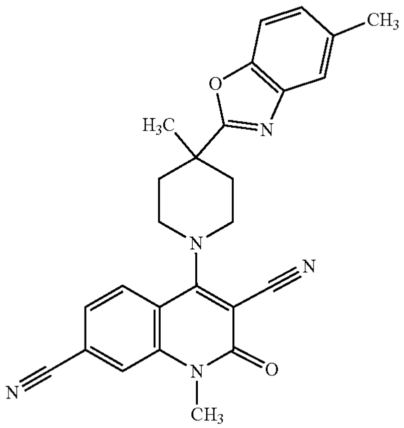 [SMILES: Cc1ccc2oc(C3(C)CCN(c4c(C#N)c(=O)n(C)c5cc(C#N)ccc45)CC3)nc2c1]

The title compound (1.9 mg, 95% purity, 4% yield) was prepared using an analogous procedure used to prepare example 208, from 50 mg of example 110 (0.102 mmol) with purification by RP-HPLC (column: X-Bridge C18 5 μm 100×30 mm, mobile phase: acetonitrile/water (0.1 vol. % formic acid)-gradient).

$^1$H NMR (400 MHz, ACETONITRILE-$d_3$) δ ppm 1.54 (s, 3H) 2.06-2.14 (m, 2H) 2.48 (s, 3H) 2.60 (br d, 2H) 3.54-3.63 (m, 5H) 3.76 (dt, 2H) 7.23 (dd, 1H) 7.49 (d, 1H) 7.52-7.55 (m, 1H) 7.57 (dd, 1H) 7.87 (d, 1H) 8.01 (d, 1H)

LC-MS (Method 1): $R_t$=1.30 min; MS (ESIpos): m/z=438.31 [M+H]$^+$

Example 250

7-cyclopropyl-1-methyl-4-[4-methyl-4-(5-methyl-1,3-benzoxazol-2-yl)piperidin-1-yl]-2-oxo-1,2-dihydroquinoline-3-carbonitrile

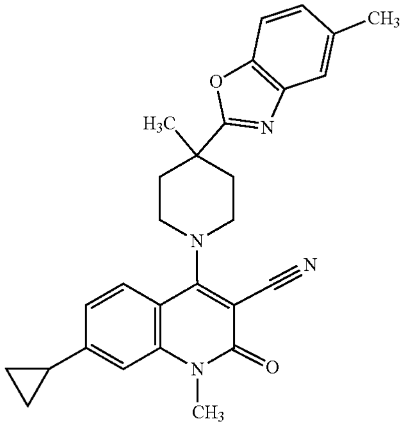 [SMILES: Cc1ccc2oc(C3(C)CCN(c4c(C#N)c(=O)n(C)c5cc(C6CC6)ccc45)CC3)nc2c1]

The title compound (31.6 mg, 94% purity, 65% yield) was prepared using an analogous procedure used to prepare example 210, from 50 mg of example 110 (0.102 mmol) with purification by RP-HPLC (column: X-Bridge C18 5 μm 100×30 mm, mobile phase: acetonitrile/water (0.1 vol. % formic acid)-gradient).

$^1$H NMR (400 MHz, ACETONITRILE-$d_3$) δ ppm 0.81-0.87 (m, 2H) 1.05-1.13 (m, 2H) 1.49 (s, 3H) 1.98-2.08 (m, 3H) 2.14 (s, 3H) 2.44 (s, 3H) 2.53 (br d, 2H) 3.46-3.56 (m, 5H) 3.63-3.75 (m, 2H) 6.91 (dd, 1H) 7.11 (s, 1H) 7.13-7.15 (m, 1H) 7.17 (d, 1H) 7.44 (d, 1H) 7.46-7.47 (m, 1H) 7.49 (s, 1H) 7.72 (d, 1H)

LC-MS (Method 2): $R_t$=1.17 min; MS (ESIpos): m/z=453.35 [M+H]$^+$

Example 251

7-[(1-cyanocyclopropyl)methoxy]-1-methyl-4-[4-methyl-4-(5-methyl-1,3-benzoxazol-2-yl)piperidin-1-yl]-2-oxo-1,2-dihydroquinoline-3-carbonitrile

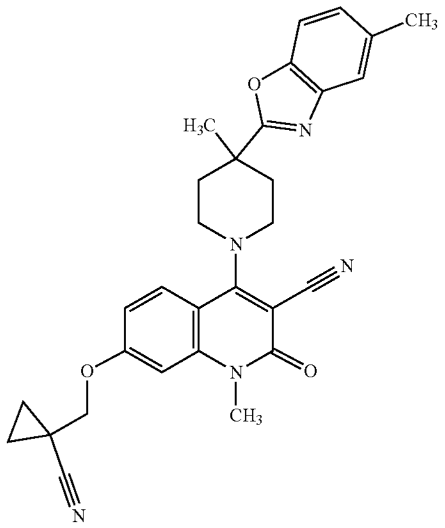 [SMILES: Cc1ccc2oc(C3(C)CCN(c4c(C#N)c(=O)n(C)c5cc(OCC6(C#N)CC6)ccc45)CC3)nc2c1]

The title compound (31.6 mg, 94% purity, 65% yield) was prepared using an analogous procedure used to prepare example 239, from 50 mg of example 110 (0.102 mmol) with 98.8 μl of 1-(hydroxymethyl)cyclopropanecarbonitrile (1.02 mmol, CAS 98730-77-9) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 1.12-1.23 (m, 2H) 1.35-1.45 (m, 2H) 1.51 (s, 3H) 2.04 (m, 2H) 2.45 (s, 3H) 2.55 (br d, 2H) 3.49-3.57 (m, 5H) 3.70 (dt, 2H) 4.13 (s, 2H) 6.83 (s, 1H) 6.86 (d, 1H) 7.19 (d, 1H) 7.46 (d, 1H) 7.47-7.48 (m, 1H) 7.50 (s, 1H) 7.81 (d, 1H)

LC-MS (Method 2): $R_t$=1.31 min; MS (ESIpos): m/z=508.31 [M+H]$^+$

Example 252

7-(3,3-difluorocyclobutyl)-1-methyl-4-[4-methyl-4-(5-methyl-1,3-benzoxazol-2-yl)piperidin-1-yl]-2-oxo-1,2-dihydroquinoline-3-carbonitrile

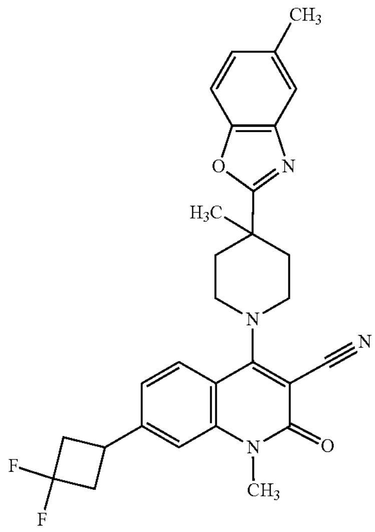 [SMILES: Cc1ccc2oc(C3(C)CCN(c4c(C#N)c(=O)n(C)c5cc(C6CC(F)(F)C6)ccc45)CC3)nc2c1]

80 mg 7-bromo-1-methyl-4-[4-methyl-4-(5-methyl-1,3-benzoxazol-2-yl)piperidin-1-yl]-2-oxo-1,2-dihydroquinoline-3-carbonitrile (163 μmol, example 110), 3.7 mg bis{3,5-difluoro-2-[5-(trifluoromethyl)pyridin-2-yl]phenyl}iridium(I)hexafluorophosphate-4,4'-di-tert-butyl-2,2'-bipyridine (1:1:1) (3.3 μmol, CAS 870987-63-6) and 114 μL 2,6-dimethylpyridine (977 μmol) were dissolved in the reaction vial in 3 mL 1,2-dimethoxyethane. In a separate vial the Ni-catalyst was prepared by dissolving 1.8 mg 1,2-dimethoxyethane-dichloronickel (1:1) (8.1 μmol) and 2.2 mg 4,4'-di-tert-butyl-2,2'-bipyridine (8.1 μmol) in 3 mL 1,2-dimethoxyethane followed by stirring for 5 min. The catalyst solution was syringed to the sealed reaction vial and was degassed with argon for 5 min., then 89 μL 3-bromo-1,1-difluorocyclobutane (733 μmol, CAS 1310729-91-9) and 50 μL 1,1,1,3,3,3-hexamethyl-2-(trimethylsilyl)trisilane (163 μmol) was added. The vial was placed in a water bath (to keep the temperature below 35° C.) and was subsequently irradiated by two 40 W Kessil LED Aquarium lamps for 5 h. The reaction was concentrated in vacuum. The crude material was purificated by flash chromatography (silica, dichloromethane/methanol gradient 0-3%). 40 mg of the title compound were obtained (95% purity, 46% yield).

$^1$H NMR (400 MHz, DMSO-$d_6$) δ ppm 1.49 (s, 3H) 1.99-2.11 (m, 2H) 2.42 (s, 3H) 2.76-2.93 (m, 2H) 2.98-3.17 (m, 2H) 3.43-3.54 (m, 2H) 3.54-3.63 (m, 4H) 3.67-3.79 (m, 2H) 7.17-7.23 (m, 1H) 7.27-7.33 (m, 1H) 7.40-7.47 (m, 1H) 7.53-7.64 (m, 2H) 7.80-7.89 (m, 1H).

LC-MS (Method 2): $R_t$=1.44 min; MS (ESIpos): m/z=503.6 $[M+H]^+$

Example 253

1-methyl-4-[4-methyl-4-(5-methyl-1,3-benzoxazol-2-yl)piperidin-1-yl]-8-[(oxetan-3-yl)oxy]-2-oxo-1,2-dihydroquinoline-3-carbonitrile

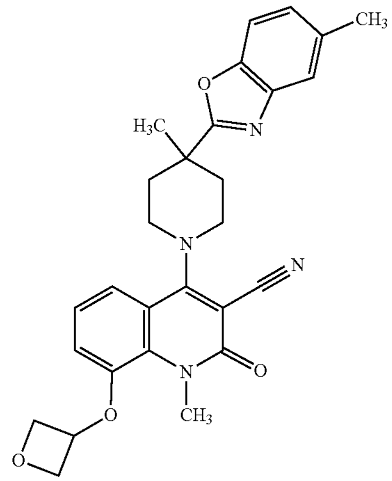 [SMILES: Cc1ccc2oc(C3(C)CCN(c4c(C#N)c(=O)n(C)c5c(OC6COC6)cccc45)CC3)nc2c1]

The title compound (2.8 mg, 97% purity, 7% yield) was prepared using an analogous procedure used to prepare example 239, from 40 mg of example 158 (0.081 mmol) with 54 μl of Oxetan-3-ol (1.02 mmol, CAS 16545-68-9) with purification by RP-HPLC (column: YMC Triart C18 5μ 150×50 mm, mobile phase: acetonitrile/water (0.1 vol. % formic acid 99%)-gradient).

$^1$H NMR (400 MHz, ACETONITRILE-$d_3$) δ ppm 1.49 (s, 3H) 2.03 (m, 2H) 2.44 (s, 3H) 2.54 (br d, 2H) 3.51 (m, 2H) 3.69 (dt, 3H) 3.82 (s, 3H) 4.68-4.73 (m, 2H) 4.92-4.97 (m, 2H) 5.24-5.30 (m, 1H) 6.75 (dd, 1H) 7.11-7.21 (m, 2H) 7.43-7.51 (m, 3H)

LC-MS (Method 1): $R_t$=1.28 min; MS (ESIpos): m/z=485.28 $[M+H]^+$

Example 254

4-[4-(5,6-difluoro-1,3-benzoxazol-2-yl)piperidin-1-yl]-7-methoxy-1-methyl-2-oxo-1,2-dihydroquinoline-3-carbonitrile

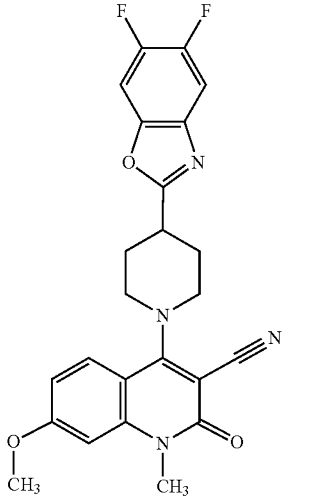 [SMILES: COc1ccc2c(N3CCC(c4nc5cc(F)c(F)cc5o4)CC3)c(C#N)c(=O)n(C)c2c1]

The title compound (2.1 mg, 95% purity, 7% yield) was prepared using an analogous procedure used to prepare example 240, from 30 mg of example 160 (0.060 mmol) using 24 μl of methanol (0.60 mmol, CAS 67-56-1) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 2.09-2.22 (m, 2H) 2.33 (br dd, 2H) 3.32-3.55-3.62 (m, 5H) 3.83 (dt, 2H) 3.93 (s, 3H) 6.85-6.91 (m, 2H) 7.56-7.64 (m, 2H) 7.82 (d, 1H)

LC-MS (Method 2): $R_t$=1.38 min; MS (ESIpos): m/z=451.22 [M+H]$^+$

Example 255

1,7-dimethyl-2-oxo-4-(4-phenylpiperidin-1-yl)-1,2-dihydroquinoline-3-carbonitrile

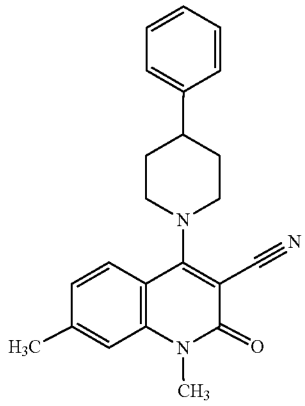 [SMILES: Cc1ccc2c(N3CCC(c4ccccc4)CC3)c(C#N)c(=O)n(C)c2c1]

The title compound (12.1 mg, 95% purity, 48% yield) was prepared using an analogous procedure used to prepare example 222, from 30 mg of example 90 (0.060 mmol) with purification by RP-HPLC (column: YMC Triart C18 5μ 150×50 mm, mobile phase: acetonitrile/water (0.1 vol. % formic acid 99%)-gradient).

$^1$H NMR (400 MHz, ACETONITRILE-$d_3$) δ ppm 1.91-2.08 (m, 4H) 2.49 (s, 3H) 2.91 (tt, 1H) 3.51-3.61 (m, 5H) 3.87 (br d, 2H) 7.14 (d, 1H) 7.22-7.38 (m, 6H) 7.84 (d, 1H)

LC-MS (Method 1): $R_t$=1.36 min; MS (ESIpos): m/z=358.17 [M+H]$^+$

Example 256

7-methoxy-1-methyl-2-oxo-4-(4-phenylpiperidin-1-yl)-1,2-dihydroquinoline-3-carbonitrile

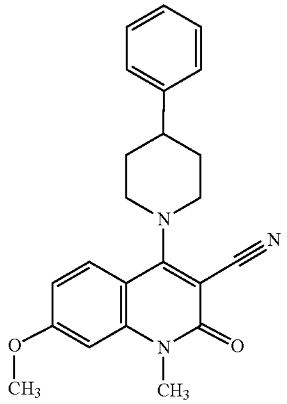 [SMILES: COc1ccc2c(N3CCC(c4ccccc4)CC3)c(C#N)c(=O)n(C)c2c1]

The title compound (15.4 mg, 95% purity, 58% yield) was prepared using an analogous procedure used to prepare example 240, from 30 mg of example 90 (0.071 mmol) using 29 μl of methanol (0.71 mmol, CAS 67-56-1) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 1.92-2.03 (m, 4H) 2.85-2.94 (m, 1H) 3.50-3.60 (m, 5H) 3.76-3.87 (m, 2H) 3.93 (s, 3H) 6.85 (s, 1H) 6.88 (d, 1H) 7.21-7.27 (m, 1H) 7.35 (d, 4H) 7.87 (d, 1H)

LC-MS (Method 2): $R_t$=1.43 min; MS (ESIpos): m/z=374.20 [M+H]$^+$

Example 257

1-methyl-4-[4-methyl-4-(5-methyl-1,3-benzoxazol-2-yl)piperidin-1-yl]-2-oxo-7-propoxy-1,2-dihydroquinoline-3-carbonitrile

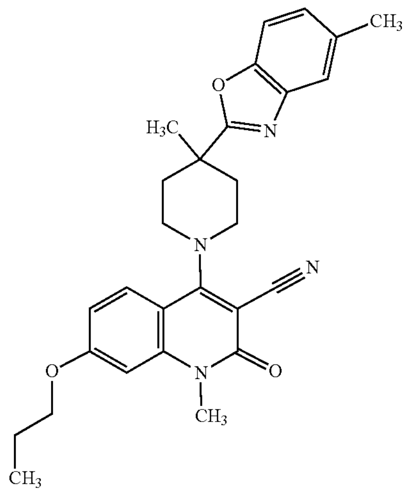 [SMILES: CCCOc1ccc2c(N3CCC(C)(c4nc5cc(C)ccc5o4)CC3)c(C#N)c(=O)n(C)c2c1]

The title compound (9.2 mg, 95% purity, 19% yield) was prepared using an analogous procedure used to prepare example 239, from 50 mg of example 110 (0.102 mmol) using 76 μl of 1-propanol (1.02 mmol, CAS 71-23-8) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 1.04 (t, 3H) 1.51 (s, 3H) 1.82 (sxt, 2H) 2.01-2.09 (m, 2H) 2.45 (s, 3H) 2.55 (br d, 2H) 3.49-3.57 (m, 5H) 3.71 (dt, 2H) 4.09 (t, 2H) 6.81-6.87 (m, 2H) 7.19 (dd, 1H) 7.46 (d, 1H) 7.49-7.53 (m, 1H) 7.79 (d, 1H)

LC-MS (Method 2): $R_t$=1.49 min; MS (ESIpos): m/z=471.33 [M+H]$^+$

Example 258

4-[4-(6-chloro-1,3-benzoxazol-2-yl)piperidin-1-yl]-7-methoxy-1-methyl-2-oxo-1,2-dihydroquinoline-3-carbonitrile

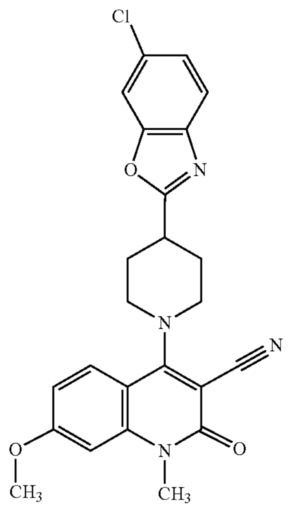 [SMILES: COc1ccc2c(N3CCC(c4nc5ccc(Cl)cc5o4)CC3)c(C#N)c(=O)n(C)c2c1]

The title compound (3.8 mg, 90% purity, 13% yield) was prepared using an analogous procedure used to prepare example 240, from 30 mg of example 32 (0.060 mmol) using 24 μl of methanol (0.70 mmol, CAS 67-56-1) with purification by RP-HPLC (column: X-Bridge C18 5 μm 100×30 mm, mobile phase: acetonitrile/water (0.2 vol. % ammonia 32%)-gradient).

$^1$H NMR (400 MHz, ACETONITRILE-$d_3$) δ ppm 2.17-2.24 (m, 4H) 2.27-2.40 (m, 3H) 3.54-3.63 (m, 5H) 3.79-3.88 (m, 2H) 3.93 (s, 3H) 6.83-6.92 (m, 2H) 7.35-7.41 (m, 1H) 7.63-7.70 (m, 2H) 7.79-7.85 (m, 1H)

LC-MS (Method 2): $R_t$=1.46 min; MS (ESIpos): m/z=449.19 [M+H]$^+$

TABLE 13

Following examples of table 13 were prepared from assigned starting materials and according to the procedure stated in the table.

| Example | Structure | IUPAC-Name | Starting Materials | Analytics |
|---|---|---|---|---|
| 259 | 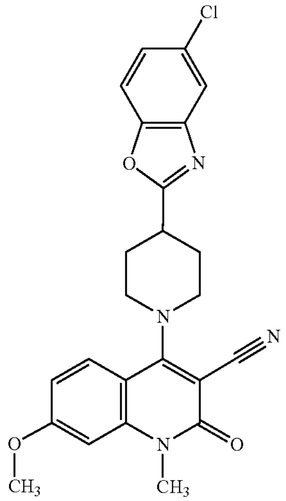 [SMILES: COc1ccc2c(N3CCC(c4nc5cc(Cl)ccc5o4)CC3)c(C#N)c(=O)n(C)c2c1] | 4-[4-(5-chloro-1,3-benzoxazol-2-yl)piperidin-1-yl]-7-methoxy-1-methyl-2-oxo-1,2-dihydroquinoline-3-carbonitrile | In analogy to example 240, from 7-bromo-4-[4-(5-chloro-1,3-benzoxazol-2-yl)piperidin-1-yl]-1-methyl-2-oxo-1,2-dihydroquinoline-3-carbonitrile (example 29) and methanol | $^1$H NMR (400 MHz, ACETONITRILE-$d_3$) δ ppm 2.17-2.24 (m, 2 H) 2.29-2.36 (m, 2 H) 3.55-3.63 (m, 5 H) 3.80-3.87 (m, 2 H) 3.92-3.95 (m, 3 H) 6.85-6.87 (m, 1 H) 6.88-6.92 (m, 1 H) 7.37 (dd, 1 H) 7.57 (d, 1 H) 7.72-7.75 (m, 1 H) 7.80-7.84 (m, 1 H) LC-MS (Method 2): $R_t$ = 1.34 min; MS (ESIpos): m/z = 449.3 [M + H]$^+$ |
| 260 | 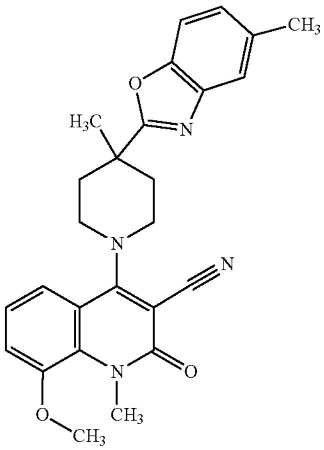 [SMILES: COc1cccc2c(N3CCC(C)(c4nc5cc(C)ccc5o4)CC3)c(C#N)c(=O)n(C)c12] | 8-methoxy-1-methyl-4-[4-methyl-4-(5-methyl-1,3-benzoxazol-2-yl)piperidin-1-yl]-2-oxo-1,2-dihydroquinoline-3-carbonitrile | In analogy to example 240, from 8-bromo-1-methyl-4-[4-methyl-4-(5-methyl-1,3-benzoxazol-2-yl)piperidin-1-yl]-2-oxo-1,2-dihydroquinoline-3-carbonitrile (example 158) and methanol | $^1$H NMR (400 MHz, ACETONITRILE-$d_3$) δ ppm 1.29 (s, 3 H) 1.78-1.87 (m, 2 H) 2.24 (s, 3 H) 2.30-2.37 (m, 2 H) 3.30 (m, 2 H) 3.46-3.55 (m, 5 H) 3.67 (s, 3 H) 6.96-7.06 (m, 3 H) 7.23-7.30 (m, 3 H) LC-MS (Method 2): $R_t$ = 1.39 min; MS (ESIpos): m/z = 443.4 [M + H]$^+$ |

TABLE 13-continued

Following examples of table 13 were prepared from assigned starting materials and according to the procedure stated in the table.

| Example | Structure | IUPAC-Name | Starting Materials | Analytics |
| --- | --- | --- | --- | --- |
| 261 | 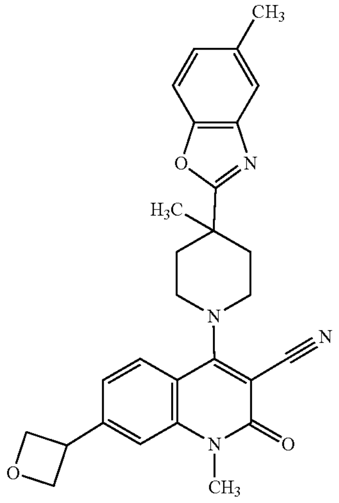 [SMILES: Cc1ccc2oc(C3(C)CCN(c4c(C#N)c(=O)n(C)c5cc(C6COC6)ccc45)CC3)nc2c1] | 1-methyl-4-[4-methyl-4-(5-methyl-1,3-benzoxazol-2-yl)piperidin-1-yl]-7-(oxetan-3-yl)-2-oxo-1,2-dihydroquinoline-3-carbonitrile | in analogy to example 252 with 7-bromo-1-methyl-4-[4-methyl-4-(5-methyl-1,3-benzoxazol-2-yl)piperidin-1-yl]-2-oxo-1,2-dihydroquinoline-3-carbonitrile (example 110) and and 3-bromooxetane (CAS 39267-79-3) | $^1$H NMR (400 MHz, DMSO-$d_6$) δ ppm 1.50 (s, 3 H) 1.99-2.15 (m, 2 H) 2.43 (s, 3 H) 2.52 (br s, 2 H) 3.44-3.54 (m, 2 H) 3.58 (s, 3 H) 3.69-3.79 (m, 2 H) 4.37-4.50 (m, 1 H) 4.70 (t, 2 H) 4.99 (dd, 2 H) 7.16-7.24 (m, 1 H) 7.39-7.52 (m, 2 H) 7.54-7.64 (m, 2 H) 7.86-7.96 (m, 1 H). LC-MS (Method 2): $R_t$ = 1.27 min; MS (ESIpos): m/z = 469.6 $[M + H]^+$ |
| 262 | 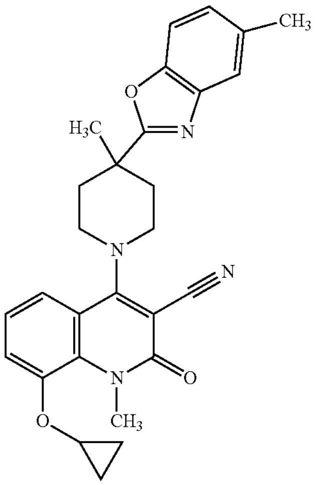 [SMILES: Cc1ccc2oc(C3(C)CCN(c4c(C#N)c(=O)n(C)c5c(OC6CC6)cccc45)CC3)nc2c1] | 8-(cyclopropyloxy)-1-methyl-4-[4-methyl-4-(5-methyl-1,3-benzoxazol-2-yl)piperidin-1-yl]-2-oxo-1,2-dihydroquinoline-3-carbonitrile | In analogy to example 239, from 8-bromo-1-methyl-4-[4-methyl-4-(5-methyl-1,3-benzoxazol-2-yl)piperidin-1-yl]-2-oxo-1,2-dihydroquinoline-3-carbonitrile (example 158) and cyclopropanol (CAS 16545-68-9) | $^1$H NMR (400 MHz, ACETONITRILE-$d_3$) δ ppm 0.76-0.85 (m, 4 H) 1.50 (s, 3 H) 1.98-2.08 (m, 2 H) 2.44 (s, 3 H) 2.49-2.58 (m, 2 H) 3.51 (m, 2H) 3.65-3.74 (m, 5 H) 3.87 (tt, 1 H) 7.14-7.25 (m, 2 H) 7.39-7.50 (m, 4 H) 7.59 (d, 1 H) LC-MS (Method 2): $R_t$ = 1.48 min; MS (ESIpos): m/z = 469.4 $[M + H]^+$ |
| 263 | 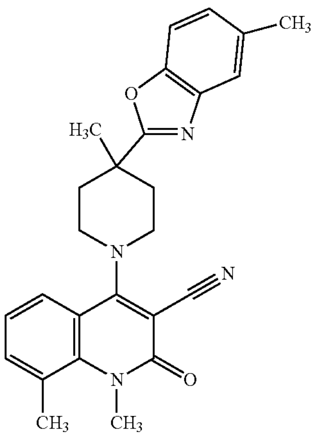 [SMILES: Cc1ccc2oc(C3(C)CCN(c4c(C#N)c(=O)n(C)c5c(C)cccc45)CC3)nc2c1] | 1,8-dimethyl-4-[4-methyl-4-(5-methyl-1,3-benzoxazol-2-yl)piperidin-1-yl]-2-oxo-1,2-dihydroquinoline-3-carbonitrile | In analogy to example 222, from 8-bromo-1-methyl-4-[4-methyl-4-(5-methyl-1,3-benzoxazol-2-yl)piperidin-1-yl]-2-oxo-1,2-dihydroquinoline-3-carbonitrile (example 158) | $^1$H NMR (400 MHz, ACETONITRILE-$d_3$) δ ppm 1.51 (s, 3 H) 2.00-2.10 (m, 2 H) 2.45 (s, 3 H) 2.53-2.63 (m, 5 H) 3.47-3.60 (m, 2 H) 3.61-3.74 (m, 5 H) 7.15-7.22 (m, 2 H) 7.40-7.53 (m, 3 H) 7.73 (d, 1 H) LC-MS (Method 2): $R_t$ = 1.38 min; MS (ESIpos): m/z = 427.5 $[M + H]^+$ |

TABLE 13-continued

Following examples of table 13 were prepared from assigned starting materials and according to the procedure stated in the table.

| Example | Structure | IUPAC-Name | Starting Materials | Analytics |
|---|---|---|---|---|
| 264 | 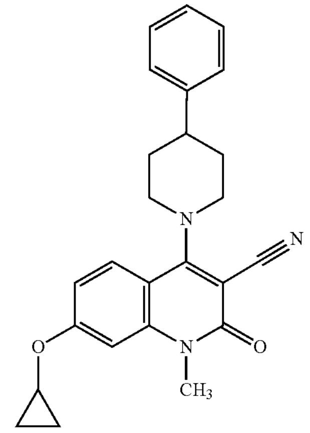 [SMILES: Cn1c(=O)c(C#N)c(N2CCC(c3ccccc3)CC2)c2ccc(OC3CC3)cc21] | 7-(cyclopropyloxy)-1-methyl-2-oxo-4-(4-phenylpiperidin-1-yl)-1,2-dihydroquinoline-3-carbonitrile | In analogy to example 239, from 7-bromo-1-methyl-2-oxo-4-(4-phenylpiperidin-1-yl)-1,2-dihydroquinoline-3-carbonitrile (example 90) and cyclopropanol (CAS 16545-68-9) | $^1$H NMR (400 MHz, ACETONITRILE-$d_3$) δ ppm 0.51-0.61 (m, 2 H) 0.61-0.73 (m, 2 H) 1.75-1.88 (m, 4H) 2.63-2.73 (m, 1 H) 3.29-3.38 (m, 5 H) 3.59-3.66 (m, 2 H) 3.75 (tt, 1 H) 6.78 (d, 1 H) 6.83 (s, 1 H) 6.98-7.07 (m, 1 H) 7.14 (d, 4H) 7.66 (d, 1 H) LC-MS (Method 2): $R_t$ = 1.48 min; MS (ESIpos): m/z = 400.24 [M + H]$^+$ |
| 265 | 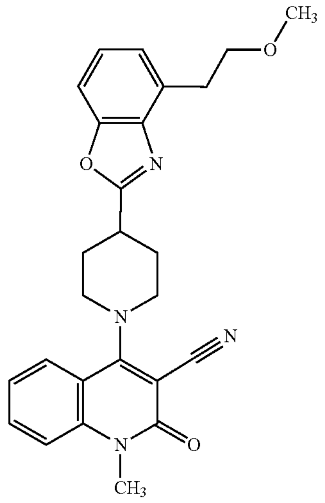 [SMILES: COCCc1cccc2oc(C3CCN(c4c(C#N)c(=O)n(C)c5ccccc45)CC3)nc12] | 4-{4-[4-(2-methoxyethyl)-1,3-benzoxazol-2-yl]piperidin-1-yl}-1-methyl-2-oxo-1,2-dihydroquinoline-3-carbonitrile | in analogy to example 214 with 4-chloro-1-methyl-2-oxo-1,2-dihydroquinoline-3-carbonitrile (CAS 150617-68-8) and and 4-(2-methoxyethyl)-2-(piperidin-4-yl)-1,3-benzoxazole (intermediate 120) | $^1$H NMR (400 MHz, DMSO-$d_6$) δ ppm 2.09-2.23 (m, 2 H) 2.26-2.37 (m, 2 H) 3.11-3.19 (m, 2 H) 3.26 (s, 3 H) 3.42-3.53 (m, 1 H) 3.55-3.65 (m, 5 H) 3.66-3.74 (m, 2 H) 3.81-3.94 (m, 2 H) 7.20-7.42 (m, 3 H) 7.51-7.62 (m, 2 H) 7.69-7.79 (m, 1 H) 7.84-7.97 (m, 1 H). LC-MS (Method 2): $R_t$ = 1.25 min; MS (ESIpos): m/z = 443.7 [M + H]$^+$ |
| 266 | 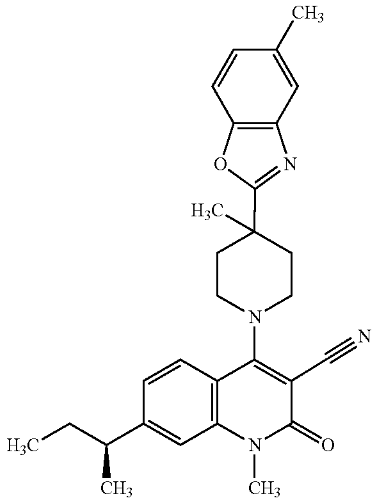 [SMILES: CC[C@H](C)c1ccc2c(N3CCC(C)(c4nc5cc(C)ccc5o4)CC3)c(C#N)c(=O)n(C)c2c1] | 7-[(2S)-butan-2-yl]-1-methyl-4-[4-methyl-4-(5-methyl-1,3-benzoxazol-2-yl)piperidin-1-yl]-2-oxo-1,2-dihydroquinoline-3-carbonitrile | in analogy to example 252 with 7-bromo-1-methyl-4-[4-methyl-4-(5-methyl-1,3-benzoxazol-2-yl)piperidin-1-yl]-2-oxo-1,2-dihydroquinoline-3-carbonitrile (example 110) and and 3-bromo-1,1-difluoro cyclobutane (CAS 1310729-91-9) | $^1$H NMR (400 MHz, DMSO-$d_6$) δ ppm 0.80 (t, 3 H) 1.25 (d,3 H) 1.49 (s, 3 H) 1.58-1.69 (m, 2 H) 1.98-2.15 (m, 2 H) 2.42 (s, 3 H) 2.52 (br s, 2 H) 2.73-2.85 (m, 1 H) 3.43-3.53 (m, 2 H) 3.56 (s, 3 H) 3.66-3.81 (m, 2 H) 7.15-7.26 (m, 2 H) 7.28-7.38 (m, 1 H) 7.51-7.64 (m, 2 H) 7.79-7.87 (m, 1 H). LC-MS (Method 2): Rt = 1.57 min; MS (ESIpos): m/z = 469.6 [M + H]$^+$ |

TABLE 13-continued

Following examples of table 13 were prepared from assigned starting materials and according to the procedure stated in the table.

| Example | Structure | IUPAC-Name | Starting Materials | Analytics |
|---|---|---|---|---|
| 267 | 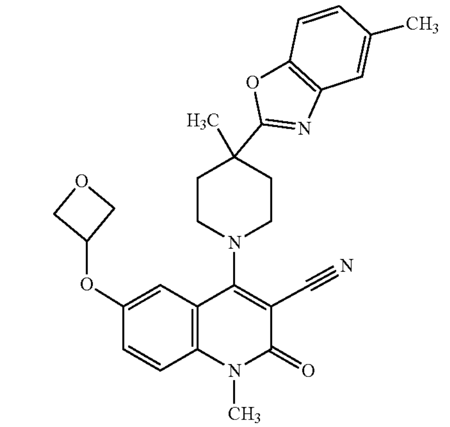 [SMILES: Cc1ccc2oc(C3(C)CCN(c4c(C#N)c(=O)n(C)c5ccc(OC6COC6)cc45)CC3)nc2c1] | 1-methyl-4-[4-methyl-4-(5-methyl-1,3-benzoxazol-2-yl)piperidin-1-yl]-6-[(oxetan-3-yl)oxy]-2-oxo-1,2-dihydroquinoline-3-carbonitrile | In analogy to example 239, from 6-bromo-1-methyl-4-[4-methyl-4-(5-methyl-1,3-benzoxazol-2-yl)piperidin-1-yl]-2-oxo-1,2-dihydroquinoline-3-carbonitrile (example 171) and 3-hydroxyoxetane (CAS 7748-36-9) | $^1$H NMR (400 MHz, ACETONITRILE-$d_3$) δ ppm 1.52-1.54 (m, 3 H) 1.98-2.07 (m, 2 H) 2.42-2.47 (m, 3 H) 2.53-2.62 (m, 2 H) 3.47-3.57 (m, 5 H) 3.62-3.72 (m, 2 H) 4.61-4.66 (m, 2 H) 4.94-5.02 (m, 2 H) 5.28-5.37 (m, 1 H) 7.03 (d, 1 H) 7.17-7.23 (m, 2 H) 7.40-7.51 (m, 3 H) LC-MS (Method 1): $R_t$ = 1.25 min; MS (ESIpos): m/z = 485.31 $[M + H]^+$ |
| 268 | 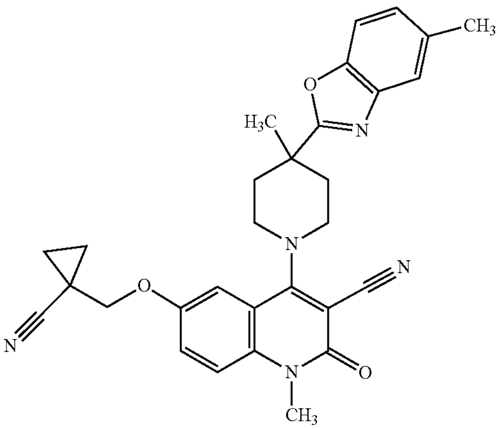 [SMILES: Cc1ccc2oc(C3(C)CCN(c4c(C#N)c(=O)n(C)c5ccc(OCC6(C#N)CC6)cc45)CC3)nc2c1] | 6-1(1-cyanocyclopropyl) methoxy]-1-methyl-4-[4-methyl-4-(5-methyl-1,3-benzoxazol-2-yl)piperidin-1-yl]-2-oxo-1,2-dihydroquinoline-3-carbonitrile | In analogy to example 239, from 6-bromo-1-methyl-4-[4-methyl-4-(5-methyl-1,3-benzoxazol-2-yl)piperidin-1-yl]-2-oxo-1,2-dihydroquinoline-3-carbonitrile (example 171) and 1-(hydroxymethyl)cyclo propanecarbonitrile (CAS 98730-77-9) | $^1$H NMR (400 MHz, ACETONITRILE-$d_3$) δ ppm 1.11-1.17 (m, 2 H) 1.31-1.44 (m, 2 H) 1.51 (s, 3 H) 2.01-2.08 (m, 2 H) 2.45 (s, 3 H) 2.57 (br d, 2 H) 3.49-3.59 (m, 5 H) 3.72 (m, 2 H) 4.06 (s, 2 H) 7.19 (br d, 1 H) 7.27 (d, 1 H) 7.31-7.37 (m, 1 H) 7.39-7.51 (m, 3 H) LC-MS (Method 1): $R_t$ = 1.30 min; MS (ESIpos): m/z = 508.33 $[M + H]^+$ |
| 269 | 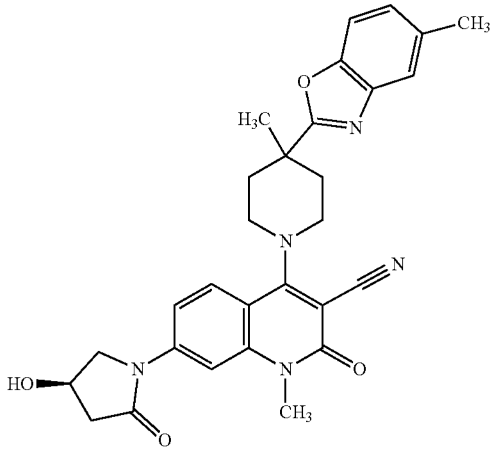 [SMILES: Cc1ccc2oc(C3(C)CCN(c4c(C#N)c(=O)n(C)c5cc(N6C[C@H](O)CC6=O)ccc45)CC3)nc2c1] | 7-[(4R)-4-hydroxy-2-oxopyrrolidin-1-yl]-1-methyl-4-[4-methyl-4-(5-methyl-1,3-benzoxazol-2-yl)piperidin-1-yl]-2-oxo-1,2-dihydroquinoline-3-carbonitrile | In analogy to example 239, from 7-bromo-1-methyl-4-[4-methyl-4-(5-methyl-1,3-benzoxazol-2-yl)piperidin-1-yl]-2-oxo-1,2-dihydroquinoline-3-carbonitrile (example 110)and4-hydroxypyrrolidin-2-one (CAS 22677-21-0) | $^1$H NMR (400 MHz, ACETONITRILE-$d_3$) δ ppm 1.50 (s, 3 H) 1.95-2.02 (m, 2 H) 2.45 (s, 3H) 2.50-5.60 (m, 2H) 2.83-2.92 (m, 1 H) 3.46-3.60 (m, 6 H) 4.12-1.16 (m, 1H) 3.72-3.78 (m, 3H) 4.49-4.54 (m, 1 H) 7.16-7.22 (m, 1 H) 7.45 (d, 1 H) 7.50 (d, 1 H) 7.56-7.61 (m, 1 H) 7.79 (d, 1 H) 7.86 (d, 1 H) LC-MS (Method 2): $R_t$ = 1.09 min; MS (ESIpos): m/z = 512.30 $[M + H]^+$ |

TABLE 13-continued

Following examples of table 13 were prepared from assigned starting materials and according to the procedure stated in the table.

| Example | Structure | IUPAC-Name | Starting Materials | Analytics |
|---|---|---|---|---|
| 270 | 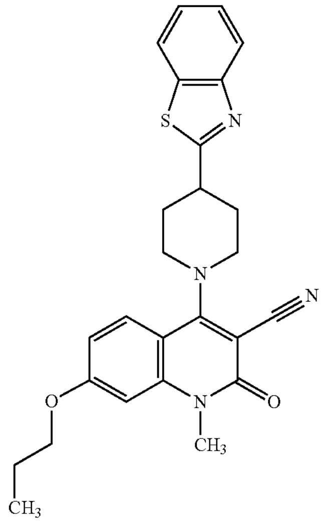 [SMILES: CCCOc1ccc2c(N3CCC(c4nc5ccccc5s4)CC3)c(C#N)c(=O)n(C)c2c1] | 4-[4-(1,3-benzothiazol-2-yl)piperidin-1-yl]-1-methyl-2-oxo-7-propoxy-1,2-dihydroquinoline-3-carbonitrile | In analogy to example 239, from 4-[4-(1,3-benzothiazol-2-yl)piperidin-1-yl]-7-bromo-1-methyl-2-oxo-1,2-dihydroquinoline-3-carbonitrile (example 33) and 1-propanol | $^1$H NMR (400 MHz, ACETONITRILE-$d_3$) δ ppm 1.03 (t, 3 H) 1.77-1.87 (m, 2 H) 2.16-2.23 (m, 2 H) 2.30-2.38 (m, 2 H) 3.56-3.62 (m, 5 H) 3.86 (br d, 2 H) 4.09 (t, 2 H) 6.83 (s, 1 H) 6.87 (d, 1 H) 7.41 (t, 1 H) 7.45-7.53 (m, 1 H) 7.49 (t, 1 H) 7.82 (d, 1 H) 7.93-8.00 (m, 2 H) LC-MS (Method 1): $R_t$ = 1.47 min; MS (ESIpos): m/z = 459.26 [M + H]$^+$ |
| 271 | 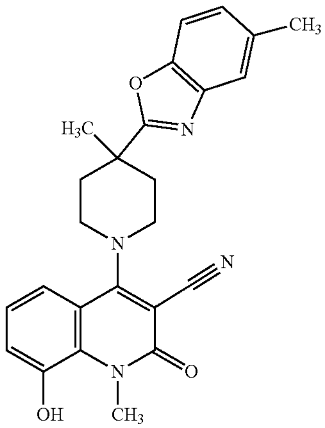 [SMILES: Cc1ccc2oc(C3(C)CCN(c4c(C#N)c(=O)n(C)c5c(O)cccc45)CC3)nc2c1] | 8-hydroxy-1-methyl-4-[4-methyl-4-(5-methyl-1,3-benzoxazol-2-yl)piperidin-1-yl]-2-oxo-1,2-dihydroquinoline-3-carbonitrile | In analogy to example 239, from 8-bromo-1-methyl-4-[4-methyl-4-(5-methyl-1,3-benzoxazol-2-yl)piperidin-1-yl]-2-oxo-1,2-dihydroquinoline-3-carbonitrile (example 158) and 3-hydroxypropionitrile (CAS 16545-68-9) | $^1$H NMR (400 MHz, ACETONITRILE-$d_3$) δ ppm 1.50 (s, 3 H) 2.00-2.07 (m, 2 H) 2.45 (s, 3 H) 2.51-2.58 (m, 2 H) 3.51 (m, 2 H) 3.69 (dt, 2 H) 3.80 (s, 3 H) 7.07-7.13 (m, 2 H) 7.19 (dd, 1 H) 7.41 (dd, 1 H) 7.46 (d, 1 H) 7.48-7.52 (m, 1 H) LC-MS (Method 2): $R_t$ = 0.96 min; MS (ESIpos): m/z = 427.29 [M + H]$^+$ |
| 272 | 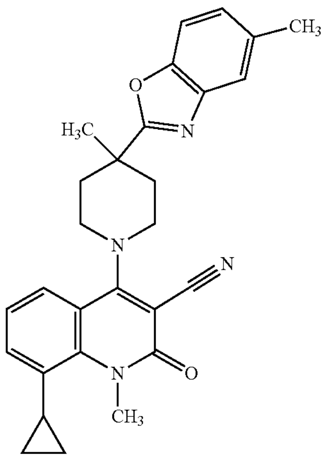 [SMILES: Cc1ccc2oc(C3(C)CCN(c4c(C#N)c(=O)n(C)c5c(C6CC6)cccc45)CC3)nc2c1] | 8-cyclopropyl-1-methyl-4-[4-methyl-4-(5-methyl-1,3-benzoxazol-2-yl)piperidin-1-yl]-2-oxo-1,2-dihydroquinoline-3-carbonitrile | In analogy to example 210, from 8-bromo-1-methyl-4-[4-methyl-4-(5-methyl-1,3-benzoxazol-2-yl)piperidin-1-yl]-2-oxo-1,2-dihydroquinoline-3-carbonitrile (example 158) | $^1$H NMR (400 MHz, ACETONITRILE-$d_3$) δ ppm 0.65-0.69 (m, 2 H) 0.98-1.07 (m, 2 H) 1.51 (s, 3H) 2.01-2.08 (m, 2 H) 2.30-2.39 (m, 1 H) 2.45 (s, 3 H) 2.52-2.59 (m, 2 H) 3.49-3.55 (m, 2 H) 3.66-3.72 (m, 2 H) 3.75 (s, 1 H) 3.82 (s, 3 H) 7.14-7.21 (m, 2 H) 7.46 (d, 1 H) 7.48-7.54 (m, 2 H) 7.72 (dd, 1 H) LC-MS (Method 1): $R_t$ = 1.46 min; MS (ESIpos): m/z = 453.28 [M + H]$^+$ |

TABLE 13-continued

| Following examples of table 13 were prepared from assigned starting materials and according to the procedure stated in the table. | | | | |
|---|---|---|---|---|
| Example | Structure | IUPAC-Name | Starting Materials | Analytics |
| 273 | 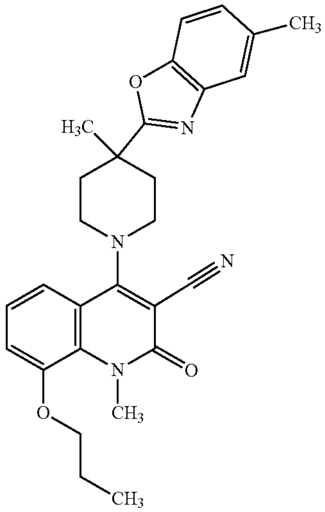 [SMILES: CCCOc1cccc2c(N3CCC(C)(c4nc5cc(C)ccc5o4)CC3)c(C#N)c(=O)n(C)c12] | 1-methyl-4-[4-methyl-4-(5-methyl-1,3-benzoxazol-2-yl)piperidin-1-yl]-2-oxo-8-propoxy-1,2-dihydroquinoline-3-carbonitrile | In analogy to example 239, from 8-bromo-1-methyl-4-[4-methyl-4-(5-methyl-1,3-benzoxazol-2-yl)piperidin-1-yl]-2-oxo-1,2-dihydroquinoline-3-carbonitrile (example 158) and 1-propanol (CAS 71-23-8) | $^{1}$H NMR (400 MHz, ACETONITRILE-$d_3$) δ ppm 1.05 (t, 3 H) 1.51 (s, 3 H) 1.82-1.92 (m, 2 H) 2.01-2.08 (m, 2 H) 2.45 (s, 3 H) 2.55 (br d, 2 H) 3.48-3.55 (m, 2 H) 3.68-3.72 (m, 2 H) 3.79 (s, 3 H) 4.02 (t, 2 H) 7.17-7.25 (m, 3 H) 7.42-7.48 (m, 2 H) 7.50 (s, 1 H) LC-MS (Method 2): $R_t$ = 1.62 min; MS (ESIpos): m/z = 471.34 [M + H]$^+$ |
| 274 | 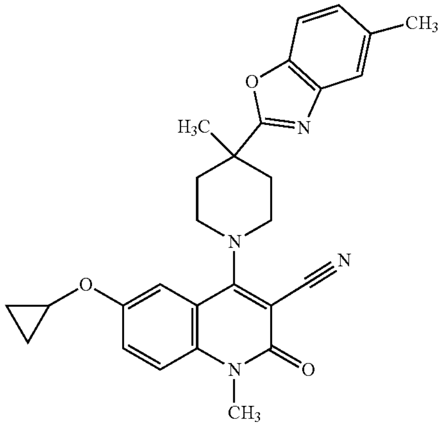 [SMILES: Cc1ccc2oc(C3(C)CCN(c4c(C#N)c(=O)n(C)c5ccc(OC6CC6)cc45)CC3)nc2c1] | 6-(cyclopropyloxy)-1-methyl-4-[4-methyl-4-(5-methyl-1,3-benzoxazol-2-yl)piperidin-1-yl]-2-oxo-1,2-dihydroquinoline-3-carbonitrile | In analogy to example 239, from 6-bromo-1-methyl-4-[4-methyl-4-(5-methyl-1,3-benzoxazol-2-yl)piperidin-1-yl]-2-oxo-1,2-dihydroquinoline-3-carbonitrile (example 171) and cyclopropanol | 1H NMR (400 MHz, ACETONITRILE-$d_3$) δ ppm 0.72-0.78 (m, 2 H) 0.83-0.90 (m, 2 H) 1.52 (s, 3H) 2.02-2.09 (m, 2 H) 2.45 (s, 3 H) 2.60 (br. d, 2H) 3.52-3.60 (m, 5 H) 3.75 (dt, 2 H) 3.89 (tt, 1 H) 7.19(d, 1 H) 7.30-7.37 (m, 1 H) 7.38-7.52 (m, 3 H) 7.56 (d, 1 H) LC-MS (Method 1): $R_t$ = 1.40 min; MS (ESIpos): m/z = 469.33 [M + H]$^+$ |
| 275 | 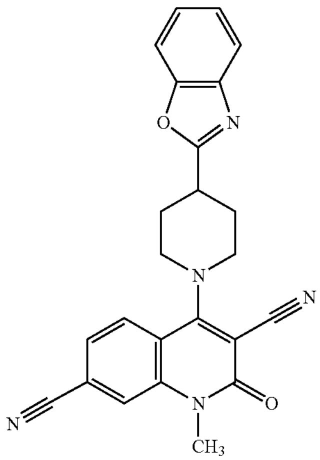 [SMILES: Cn1c(=O)c(C#N)c(N2CCC(c3nc4ccccc4o3)CC2)c2ccc(C#N)cc21] | 4-[4-(1,3-benzoxazol-2-yl)piperidin-1-yl]-1-methyl-2-oxo-1,2-dihydroquinoline-3,7-dicarbonitrile | In analogy to example 208, from 4-[4-(1,3-benzoxazol-2-yl)piperidin-1-yl]-7-bromo-1-methyl-2-oxo-1,2-dihydroquinoline-3-carbonitrile (example 27) | $^{1}$H NMR (400 MHz, ACETONITRILE-$d_3$) δ ppm 2.19-2.29 (m, 2 H) 2.32-2.41 (m, 2 H) 3.35-3.44 (m, 1 H) 3.57-3.66 (m, 5 H) 3.82-3.91 (m, 2 H) 7.33-7.41 (m, 2 H) 7.53-7.64 (m, 3 H) 7.69 (dt, 1 H) 7.87 (d, 1 H) 8.01 (d, 1 H) LC-MS (Method 1): $R_t$ = 1.21 min; MS (ESIpos): m/z = 410.20 [M + H]$^+$ |

TABLE 13-continued

Following examples of table 13 were prepared from assigned starting materials and according to the procedure stated in the table.

| Example | Structure | IUPAC-Name | Starting Materials | Analytics |
|---|---|---|---|---|
| 276 | 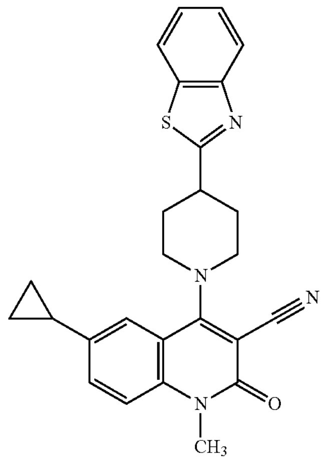 [SMILES: Cn1c(=O)c(C#N)c(N2CCC(c3nc4ccccc4s3)CC2)c2cc(C3CC3)ccc21] | 4-[4-(1,3-benzothiazol-2-yl)piperidin-1-yl]-6-cyclopropyl-1-methyl-2-oxo-1,2-dihydroquinoline-3-carbonitrile | In analogy to example 210, from 4-[4-(1,3-benzothiazol-2-yl)piperidin-1-yl]-6-bromo-1-methyl-2-oxo-1,2-dihydroquinoline-3-carbonitrile (example 169) | $^1$H NMR (400 MHz, ACETONITRILE-$d_3$) δ ppm 0.69-0.77 (m, 2 H) 0.95-1.08 (m, 2 H) 1.98-2.06 (m, 1 H) 2.17-2.25 (m, 2 H) 2.35-2.43 (m, 2 H) 3.46-3.65 (m, 6 H) 3.84-3.92 (m, 2 H) 7.36-7.46 (m, 3 H) 7.50 (ddd, 1 H) 7.56 (d, 1 H) 7.94-8.02 (m, 2 H) LC-MS (Method 1): $R_t$ = 1.43 min; MS (ESIpos): m/z = 441.25 $[M + H]^+$ |
| 277 | 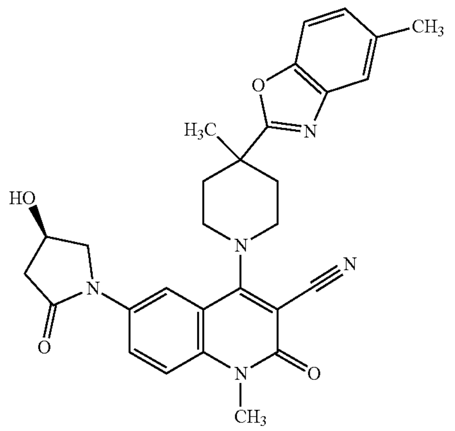 [SMILES: Cc1ccc2oc(C3(C)CCN(c4c(C#N)c(=O)n(C)c5ccc(N6C[C@H](O)CC6=O)cc45)CC3)nc2c1] | 6-[(4R)-4-hydroxy-2-oxopyrrolidin-1-yl]-1-methyl-4-[4-methyl-4-(5-methyl-1,3-benzoxazol-2-yl)piperidin-1-yl]-2-oxo-1,2-dihydroquinoline-3-carbonitrile | In analogy to example 239, from 6-bromo-1-methyl-4-[4-methyl-4-(5-methyl-1,3-benzoxazol-2-yl)piperidin-1-yl]-2-oxo-1,2-dihydroquinoline-3-carbonitrile (example 171) and 4-hydroxypyrrolidin-2-one (CAS 22677-21-0) | $^1$H NMR (400 MHz, ACETONITRILE-$d_3$) δ ppm 1.52 (s, 3 H) 2.06-2.12 (m, 2 H) 2.42 (dd, 1 H) 2.46 (s, 3 H) 2.55-2.62 (m, 2 H) 2.85 (dd, 1 H) 3.46-3.62 (m, 6 H) 3.70-3.82 (m, 3 H) 4.14 (dd, 1 H) 4.53 (brs, 1 H) 7.20 (dd, 1 H) 7.44-7.50 (m, 2 H) 7.51 (d, 1 H) 7.84 (dd, 1 H) 8.34 (d, 1 H) LC-MS (Method 2): $R_t$ = 1.03 min; MS (ESIpos): m/z = 512.32 $[M + H]^+$ |
| 278 | 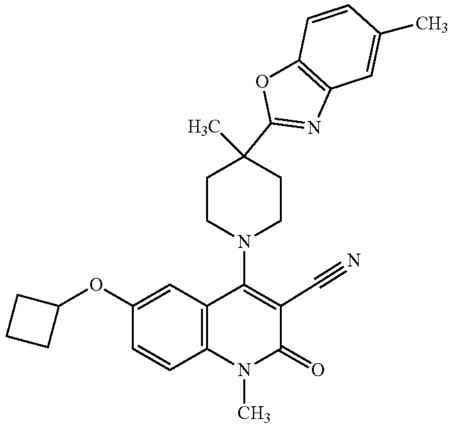 [SMILES: Cc1ccc2oc(C3(C)CCN(c4c(C#N)c(=O)n(C)c5ccc(OC6CCC6)cc45)CC3)nc2c1] | 6-(cyclobutyloxy)-1-methyl-4-[4-methyl-4-(5-methyl-1,3-benzoxazol-2-yl)piperidin-1-yl]-2-oxo-1,2-dihydroquinoline-3-carbonitrile | In analogy to example 239, from 6-bromo-1-methyl-4-[4-methyl-4-(5-methyl-1,3-benzoxazol-2-yl)piperidin-1-yl]-2-oxo-1,2-dihydroquinoline-3-carbonitrile (example 171) and cyclobutanol (CAS 2919-23-5) | 1H NMR (400 MHz, ACETONITRILE-$d_3$) δ ppm 1.54 (s, 3 H) 1.70-1.79 (m, 1 H) 1.83-1.92 (m, 1 H) 2.01-2.18 (m, 4 H) 2.44-2.53 (m, 5 H) 2.56-2.63 (m, 2 H) 3.51-3.58 (m, 5 H) 3.68-3.73 (m, 2 H) 4.78 (quin, 1 H) 7.18-7.26 (m, 3 H) 7.40 (d, 1 H) 7.46 (d, 1 H) 7.51 (s, 1 H) LC-MS (Method 1): $R_t$ = 1.52 min; MS (ESIpos): m/z = 483.32 $[M + H]^+$ |

TABLE 13-continued

Following examples of table 13 were prepared from assigned starting materials and according to the procedure stated in the table.

| Example | Structure | IUPAC-Name | Starting Materials | Analytics |
|---|---|---|---|---|
| 279 | 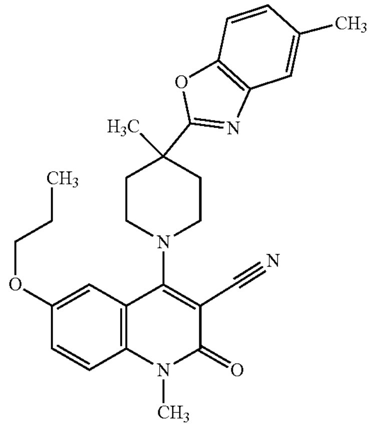 [SMILES: CCCOc1ccc2c(c1)c(N1CCC(C)(c3nc4cc(C)ccc4o3)CC1)c(C#N)c(=O)n2C] | 1-methyl-4-[4-methyl-4-(5-methyl-1,3-benzoxazol-2-yl)piperidin-1-yl]-2-oxo-6-propoxy-1,2-dihydroquinoline-3-carbonitrile | In analogy to example 239, from 6-bromo-1-methyl-4-[4-methyl-4-(5-methyl-1,3-benzoxazol-2-yl)piperidin-1-yl]-2-oxo-1,2-dihydroquinoline-3-carbonitrile (example 171) and 1-propanol | $^1$H NMR (400 MHz, ACETONITRILE-$d_3$) δ ppm 1.04 (t, 3 H) 1.52 (s, 3 H) 1.75-1.87 (m, 2 H) 2.05 (ddd, 2 H) 2.14 (s, 4 H) 2.45 (s, 3 H) 2.58 (br d, 2H) 3.51-3.58 (m, 5 H) 3.73 (dt, 2 H) 4.03 (t, 2 H) 7.19 (dd, 1 H) 7.26-7.31 (m, 2 H) 7.38-7.43 (m, 1 H) 7.46 (d, 1 H) 7.49-7.52 (m, 1 H) LC-MS (Method 2): $R_t$ = 1.46 min; MS (ESIpos): m/z = 471.32 [M + H]$^+$ |
| 280 | 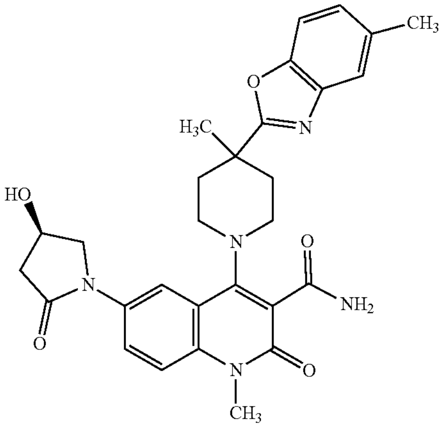 [SMILES: Cc1ccc2oc(C3(C)CCN(c4c(C(N)=O)c(=O)n(C)c5ccc(N6C[C@H](O)CC6=O)cc45)CC3)nc2c1] | 6-[(4R)-4-hydroxy-2-oxopyrrolidin-1-yl]-1-methyl-4-[4-methyl-4-(5-methyl-1,3-benzoxazol-2-yl)piperidin-1-yl]-2-oxo-1,2-dihydroquinoline-3-carboxamide | In analogy to example 239, from 6-bromo-1-methyl-4-[4-methyl-4-(5-methyl-1,3-benzoxazol-2-yl)piperidin-1-yl]-2-oxo-1,2-dihydroquinoline-3-carboxamide (example 277) and 4-hydroxypyrrolidin-2-one (CAS 22677-21-0) | $^1$H NMR (400 MHz, ACETONITRILE-$d_3$) δ ppm 1.48 (s, 3 H) 1.99-2.09 (m, 3 H) 2.41 (dd, 1 H) 2.45 (s, 3 H) 2.47-2.55 (m, 2 H) 2.84 (dd, 1 H) 3.13-3.22 (m, 2 H) 3.30-3.42 (m, 2 H) 3.42-3.48 (m, 1 H) 3.59 (s, 3 H) 3.70-3.75 (m, 1 H) 4.16 (dd, 1 H) 4.50-4.54 (m, 1 H) 5.99-6.06 (m, 1 H) 6.61-6.68 (m, 1 H) 7.18 (dd, 1 H) 7.42-7.50 (m, 3H) 7.82 (dd, 1 H) 8.38 (d, 1 H) LC-MS (Method 2): $R_t$ = 0.86 min; MS (ESIpos): m/z = 530.28 [M + H]$^+$ |

Example 281

7-bromo-1-methyl-4-[4-(5-methyl-1,3-benzoxazol-2-yl)piperidin-1-yl]-2-oxo-1,2-dihydroquinoline-3-carbonitrile

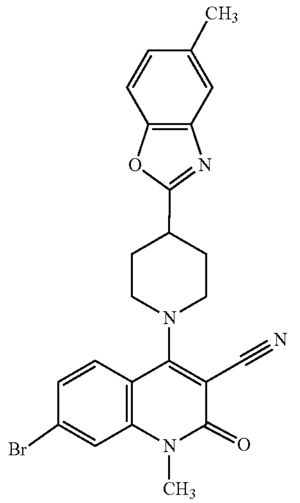 [SMILES: Cc1ccc2oc(C3CCN(c4c(C#N)c(=O)n(C)c5cc(Br)ccc45)CC3)nc2c1]

A solution of 700 mg 7-bromo-4-chloro-1-methyl-2-oxo-1,2-dihydroquinoline-3-carbonitrile (2.35 mmol, intermediate 21), 509 mg 5-methyl-2-(piperidin-4-yl)-1,3-benzoxazole (2.35 mmol, CAS 199292-77-8) and 0.66 mL triethylamine (4.7 mmol) in 30 mL 2-propanol was stirred for 2 h at 90° C. and 70 h at rt. After this time, water and eth yl acetate were added and the solid was filtered off, washed with water and ethanol to give 860 mg of the title compound (99% purity, 76% yield).

$^1$H NMR (400 MHz, DMSO-$d_6$) δ ppm 2.07-2.19 (m, 2H) 2.26-2.34 (m, 2H) 2.42 (s, 3H) 3.36-3.50 (m, 1H) 3.54-3.65 (m, 5H) 3.81 (br d, 2H) 7.19 (dd, 1H) 7.49-7.59 (m, 3H) 7.78 (dd, 2H).

LC-MS (Method 2): $R_t$=1.41 min; MS (ESIpos): m/z=479.3 [M+H]$^+$

Example 282

7-(dimethylphosphoryl)-1-methyl-4-[4-(5-methyl-1,3-benzoxazol-2-yl)piperidin-1-yl]-2-oxo-1,2-dihydroquinoline-3-carbonitrile

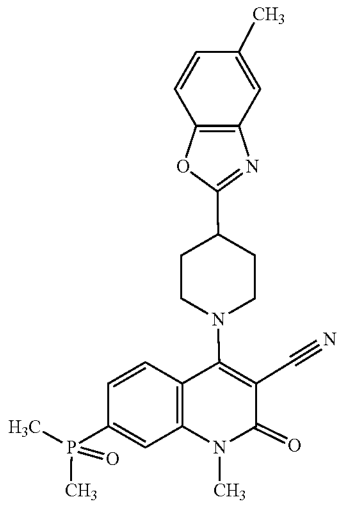 [SMILES: Cc1ccc2oc(C3CCN(c4c(C#N)c(=O)n(C)c5cc(P(C)(C)=O)ccc45)CC3)nc2c1]

To a suspension of 360 mg 7-bromo-1-methyl-4-[4-(5-methyl-1,3-benzoxazol-2-yl)piperidin-1-yl]-2-oxo-1,2-dihydroquinoline-3-carbonitrile (754 μmol, example 281), 26.2 mg (9,9-dimethyl-9H-xanthene-4,5-diyl)bis(diphenylphosphine) (45 μmol), 8.47 mg palladium(II) diacetate (38 μmol) and 176 mg tripotassium phosphate (830 μmol) in 12 mL DMF was added 64.7 mg dimethylphosphine oxide (830 μmol, CAS 7211-39-4) and the mixture was stirred for 6 h at 130° C. Water was added, and the reaction was extracted with ethyl acetate (2×). The organic phase was washed with water and brine and dried over sodium sulfate. After evaporation of the solvent, the residue was purified by flash chromatography (silica, dichloromethane/methanol gradient 0-5%). The impure product was stirred in hexane for 1 h. The solid that precipitated from this procedure was collected by filtration and dried. 150 mg of the title compound were obtained (85% purity, 36% yield).

$^1$H NMR (400 MHz, DMSO-$d_6$) δ ppm 1.74 (d, 6H) 2.12-2.22 (m, 2H) 2.26-2.33 (m, 2H) 2.42 (s, 3H) 3.39-3.52 (m, 1H) 3.56-3.69 (m, 5H) 3.79-3.89 (m, 2H) 7.15-7.22 (m, 1H) 7.50-7.56 (m, 1H) 7.57-7.61 (m, 1H) 7.69 (ddd, 1H) 7.80-7.86 (m, 1H) 7.94-8.05 (m, 1H).

LC-MS (Method 2): $R_t$=1.03 min; MS (ESIpos): m/z=475.6 [M+H]$^+$

Example 283

4-{4-[5-(2-methoxyethyl)-1,3-benzoxazol-2-yl]piperidin-1-yl}-1-methyl-2-oxo-1,2-dihydroquinoline-3-carbonitrile

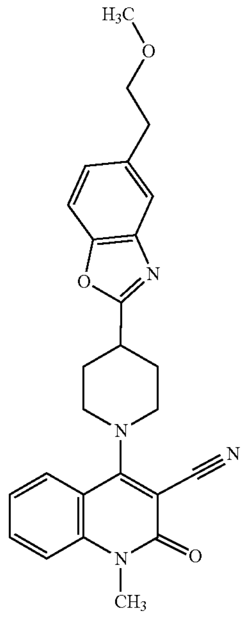 [SMILES: COCCc1ccc2oc(C3CCN(c4c(C#N)c(=O)n(C)c5ccccc45)CC3)nc2c1]

54.6 mg 4-chloro-1-methyl-2-oxo-1,2-dihydroquinoline-3-carbonitrile (250 μmol, CAS 150617-68-8) was dissolved in 3 mL 2-propanol, 65 mg 5-(2-methoxyethyl)-2-(piperidin-4-yl)-1,3-benzoxazole (250 μmol, intermediate 123) and 70 μL triethylamine (500 μmol) were added and the mixture was heated for 3 h at 90° C. The reaction mixture was cooled down to rt, diluted with water and the aqueous phase was extracted with ethyl acetate. The combined organic layers were washed with water and brine, filtered through a waterresistant filter and the filtrate was concentrated under reduced pressure. The residue was purified by flash chromatography (silica, dichloromethane/methanol gradient 0-3%) to give 90 mg of the title compound (98% purity, 80% yield).

$^1$H NMR (400 MHz, DMSO-$d_6$) δ ppm 2.08-2.21 (m, 2H) 2.31 (br d, 2H) 2.88-2.96 (m, 2H) 3.24 (s, 3H) 3.40-3.51 (m, 1H) 3.53-3.66 (m, 7H) 3.78-3.90 (m, 2H) 7.20-7.27 (m, 1H) 7.29-7.39 (m, 1H) 7.53-7.65 (m, 3H) 7.72-7.81 (m, 1H) 7.89 (dd, 1H).

LC-MS (Method 2): $R_t$=1.20 min; MS (ESIpos): m/z=443.3 $[M+H]^+$

Example 284

4-{4-[6-(2-methoxyethyl)-1,3-benzoxazol-2-yl]piperidin-1-yl}-1-methyl-2-oxo-1,2-dihydroquinoline-3-carbonitrile

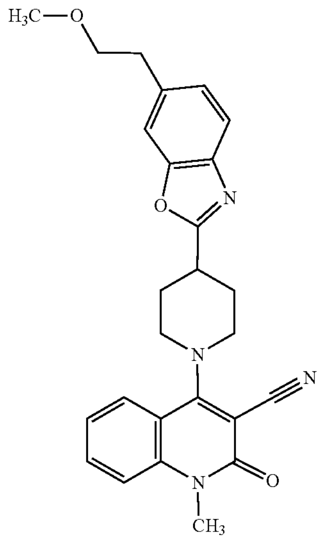 [SMILES: COCCc1ccc2nc(C3CCN(c4c(C#N)c(=O)n(C)c5ccccc45)CC3)oc2c1]

58.8 mg 4-chloro-1-methyl-2-oxo-1,2-dihydroquinoline-3-carbonitrile (269 μmol, CAS 150617-68-8) was dissolved in 3 mL 2-propanol, 70 mg 6-(2-methoxyethyl)-2-(piperidin-4-yl)-1,3-benzoxazole (269 μmol, intermediate 127) and 75 μL triethylamine (540 μmol) were added and the mixture was heated for 3 h at 90° C. The reaction mixture was cooled down to rt, ethyl acetate and water were added and the suspension was filtered. The filter cake was washed and dried in vacuum to give 85 mg of the title compound (96% purity, 69% yield).

$^1$H NMR (400 MHz, DMSO-$d_6$) δ ppm 2.06-2.20 (m, 2H) 2.26-2.33 (m, 2H) 2.94 (t, 2H) 3.24 (s, 3H) 3.40-3.51 (m, 1H) 3.54-3.65 (m, 7H) 3.84 (br d, 2H) 7.24 (dd, 1H) 7.32-7.39 (m, 1H) 7.55-7.64 (m, 3H) 7.70-7.78 (m, 1H) 7.89 (dd, 1H).

LC-MS (Method 2): $R_t$=1.21 min; MS (ESIpos): m/z=443.3 $[M+H]^+$

Example 285

1-methyl-4-[4-methyl-4-(5-methyl-1,3-benzoxazol-2-yl)piperidin-1-yl]-7-[(oxetan-3-yl)methyl]-2-oxo-1,2-dihydroquinoline-3-carbonitrile

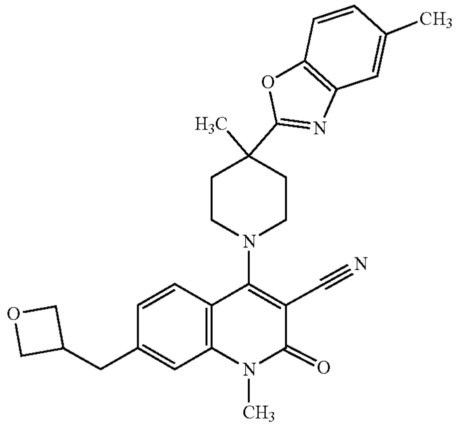 [SMILES: Cc1ccc2oc(C3(C)CCN(c4c(C#N)c(=O)n(C)c5cc(CC6COC6)ccc45)CC3)nc2c1]

80 mg 7-bromo-1-methyl-4-[4-methyl-4-(5-methyl-1,3-benzoxazol-2-yl)piperidin-1-yl]-2-oxo-1,2-dihydroquinoline-3-carbonitrile (163 μmol, example 110), 3.7 mg bis{3,5-difluoro-2-[5-(trifluoromethyl)pyridin-2-yl] phenyl}iridium(I)hexafluorophosphate-4,4'-di-tert-butyl-2,2'-bipyridine (1:1:1) (3.3 μmol, CAS 870987-63-6) and 110 μL 2,6-dimethylpyridine (980 μmol) were dissolved in the reaction vial in 3 mL 1,2-dimethoxyethane. In a separate vial the Ni-catalyst was prepared by dissolving 1.8 mg 1,2-dimethoxyethane-dichloronickel (1:1) (8.1 μmol) and 2.2 mg 4,4'-di-tert-butyl-2,2'-bipyridine (8.1 μmol) in 3 mL 1,2-dimethoxyethane followed by stirring for 5 min. The catalyst solution was syringed to the sealed reaction vial and was degassed with argon for 5 min., then 74 μL 3-(bromomethyl)oxetane (730 μmol, CAS 1374014-30-8) and 50 μL 1,1,1,3,3,3-hexamethyl-2-(trimethylsilyl)trisilane (160 μmol) was added. The vial was placed in a water bath (to keep the temperature below 35° C.) and was subsequently irradiated by two 40 W Kessil LED Aquarium lamps for 5 h. The reaction was concentrated in vacuum. The crude material was purificated by flash chromatography (silica, dichloromethane/methanol gradient 0-2%). 30 mg of the title compound were obtained (99% purity, 38% yield).

$^1$H NMR (400 MHz, DMSO-$d_6$) δ ppm 1.49 (s, 3H) 1.97-2.10 (m, 2H) 2.42 (s, 3H) 3.08-3.16 (m, 2H) 3.29-3.32 (m, 1H) 3.42-3.52 (m, 2H) 3.55 (s, 3H) 3.65-3.77 (m, 2H) 4.38 (t, 2H) 4.63 (dd, 2H) 7.12-7.25 (m, 2H) 7.36-7.44 (m, 1H) 7.52-7.64 (m, 2H) 7.70-7.84 (m, 1H).

LC-MS (Method 2): $R_t$=1.28 min; MS (ESIpos): m/z=483.6 $[M+H]^+$

Example 286

1-methyl-4-[4-methyl-4-(5-methyl-1,3-benzoxazol-2-yl)piperidin-1-yl]-6-[(oxetan-3-yl)methyl]-2-oxo-1,2-dihydroquinoline-3-carbonitrile

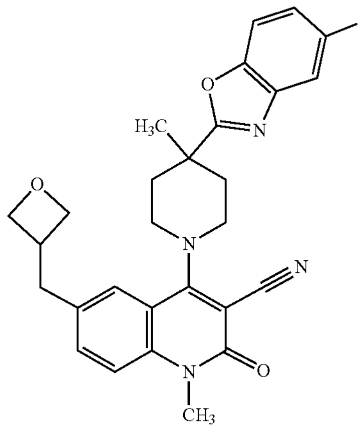

80 mg 6-bromo-1-methyl-4-[4-methyl-4-(5-methyl-1,3-benzoxazol-2-yl)piperidin-1-yl]-2-oxo-1,2-dihydroquinoline-3-carbonitrile (163 μmol, example 171), 3.7 mg bis{3,5-difluoro-2-[5-(trifluoromethyl)pyridin-2-yl]phenyl}iridium(I)hexafluorophosphate-4,4'-di-tert-butyl-2,2'-bipyridine (1:1:1) (3.3 μmol, CAS 870987-63-6) and 110 μL 2,6-dimethylpyridine (980 μmol) were dissolved in the reaction vial in 3 mL 1,2-dimethoxyethane. In a separate vial the Ni-catalyst was prepared by dissolving 1.8 mg 1,2-dimethoxyethane-dichloronickel (1:1) (8.1 μmol) and 2.2 mg 4,4'-di-tert-butyl-2,2'-bipyridine (8.1 μmol) in 3 mL 1,2-dimethoxyethane followed by stirring for 5 min. The catalyst solution was syringed to the sealed reaction vial and was degassed with argon for 5 min., then 74 μL 3-(bromomethyl)oxetane (730 μmol, CAS 1374014-30-8) and 50 μL 1,1,1,3,3,3-hexamethyl-2-(trimethylsilyl)trisilane (160 μmol) was added. The vial was placed in a water bath (to keep the temperature below 35° C.) and was subsequently irradiated by two 40 W Kessil LED Aquarium lamps for 6 h. Water was added, and the reaction was extracted with ethyl acetate. The organic phase was washed and dried over sodium sulfate. After evaporation of the solvent, the residue was purified by flash chromatography (silica, dichloromethane/methanol gradient 0-8%). 4 mg of the title compound were obtained (95% purity, 5% yield).

$^1$H NMR (400 MHz, DMSO-$d_6$) δ ppm 1.54 (s, 3H) 2.03-2.16 (m, 2H) 2.45 (s, 3H) 3.10 (d, 2H) 3.26-3.35 (m, 1H) 3.46-3.62 (m, 5H) 3.69-3.82 (m, 2H) 4.33-4.45 (m, 2H) 4.67 (dd, 2H) 7.18-7.30 (m, 1H) 7.46-7.55 (m, 1H) 7.55-7.68 (m, 4H).

LC-MS (Method 2): $R_t$=1.44 min; MS (ESIpos): m/z=483.5 [M+H]$^+$

Example 287

1-methyl-4-{4-[5-(oxetan-3-yl)-1,3-benzoxazol-2-yl]piperidin-1-yl}-2-oxo-1,2-dihydroquinoline-3-carbonitrile

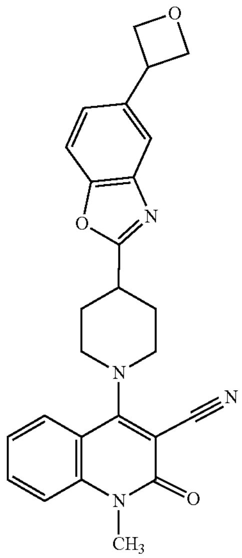 [SMILES: Cn1c(=O)c(C#N)c(N2CCC(c3nc4cc(C5COC5)ccc4o3)CC2)c2ccccc21]

A solution of 30.5 mg 4-chloro-1-methyl-2-oxo-1,2-dihydroquinoline-3-carbonitrile (139 μmol, CAS 150617-68-8), 36 mg 5-(oxetan-3-yl)-2-(piperidin-4-yl)-1,3-benzoxazole (139 μmol, intermediate 129) and 39 μL triethylamine (280 μmol) in 2 mL 2-propanol was stirred for 3 h at 90° C. After this time, water was added and the reaction was extracted with ethyl acetate. The organic phase was washed with water and brine, filtered and evaporated in vacuum. The residue was purified by flash chromatography (silica, dichloromethane/methanol gradient 0-3%) to give 15 mg of the title compound (95% purity, 23% yield).

$^1$H NMR (400 MHz, DMSO-$d_6$) δ ppm 2.10-2.23 (m, 2H) 2.26-2.35 (m, 2H) 3.39-3.52 (m, 1H) 3.54-3.67 (m, 5H) 3.80-3.92 (m, 2H) 4.33-4.46 (m, 1H) 4.62-4.70 (m, 2H) 4.94-5.02 (m, 2H) 7.31-7.47 (m, 2H) 7.54-7.62 (m, 1H) 7.69-7.82 (m, 3H) 7.86-7.94 (m, 1H).

LC-MS (Method 2): $R_t$=1.09 min; MS (ESIpos): m/z=441.5 [M+H]$^+$

Example 288

1-methyl-4-[4-methyl-4-(5-methyl-1,3-benzoxazol-2-yl)piperidin-1-yl]-2-oxo-1,2-dihydroquinoline-3-carbonitrile

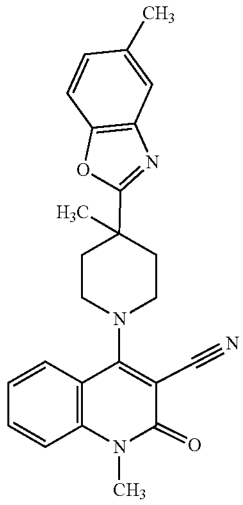 [SMILES: Cc1ccc2oc(C3(C)CCN(c4c(C#N)c(=O)n(C)c5ccccc45)CC3)nc2c1]

800 mg 4-chloro-1-methyl-2-oxo-1,2-dihydroquinoline-3-carbonitrile (3.66 mmol, CAS 150617-68-8) was dissolved in 15 mL 2-propanol, 1.06 g 5-methyl-2-(4-methylpiperidin-4-yl)-1,3-benzoxazole (4.39 mmol, intermediate 52) and 1 mL triethylamine (7.3 mmol) were added and the mixture was heated for 2 h at 90° C. The suspension was cooled down to rt and was stirred for 72 h. ethyl acetate was added and the mixture was heated for 15 min. under reflux. Water was added and the suspension was filtered. The filter cake was washed and dried in vacuum to give 1.2 g of the title compound (95% purity, 76% yield).

$^1$H NMR (400 MHz, DMSO-$d_6$) δ ppm 1.50 (s, 3H) 1.99-2.10 (m, 2H) 2.43 (s, 3H) 2.51-2.54 (m, 2H) 3.38-3.58 (m, 5H) 3.67-3.77 (m, 2H) 7.20 (dd, 1H) 7.34 (t, 1H) 7.54-7.62 (m, 3H) 7.73 (ddd, 1H) 7.89 (dd, 1H).

LC-MS (Method 2): $R_t$=1.36 min; MS (ESIpos): m/z=413.4 $[M+H]^+$

Example 289

1-methyl-4-[4-(5-methyl-1,3-benzoxazol-2-yl)piperidin-1-yl]-2-oxo-7-(trifluoromethyl)-1,2-dihydroquinoline-3-carbonitrile

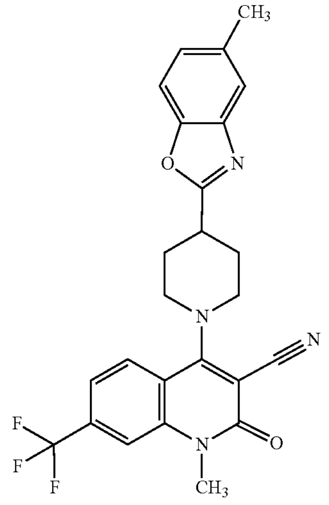 [SMILES: Cc1ccc2oc(C3CCN(c4c(C#N)c(=O)n(C)c5cc(C(F)(F)F)ccc45)CC3)nc2c1]

75 mg 4-chloro-1-methyl-2-oxo-7-(trifluoromethyl)-1,2-dihydroquinoline-3-carbonitrile (249 μmol, intermediate 132) was suspended in 2 mL 2-propanol, 130 μL N,N-diisopropylethylamine (750 μmol) and 67.9 mg 5-methyl-2-(piperidin-4-yl)-1,3-benzoxazole (298 μmol, CAS 199292-77-8) were added and the mixture was stirred for 2 h at 90° C. The reaction mixture was cooled down to rt and the suspension was diluted with water and stirred for 15 min. The solid was filtered off and washed with water and ethanol to give 120 mg of the title compound (100% purity, 103% yield).

$^1$H NMR (400 MHz, DMSO-$d_6$) δ ppm 2.09-2.22 (m, 2H) 2.27-2.35 (m, 2H) 2.42 (s, 3H) 3.41-3.52 (m, 1H) 3.57-3.67 (m, 5H) 3.85 (br d, 2H) 7.19 (dd, 1H) 7.53 (s, 1H) 7.58 (d, 1H) 7.65 (dd, 1H) 7.83 (s, 1H) 8.08 (d, 1H).

LC-MS (Method 2): $R_t$=1.42 min; MS (ESIpos): m/z=467.4 $[M+H]^+$

Example 290

1-methyl-4-[4-methyl-4-(5-methyl-1,3-benzoxazol-2-yl)piperidin-1-yl]-2-oxo-7-(trifluoromethyl)-1,2-dihydroquinoline-3-carbonitrile

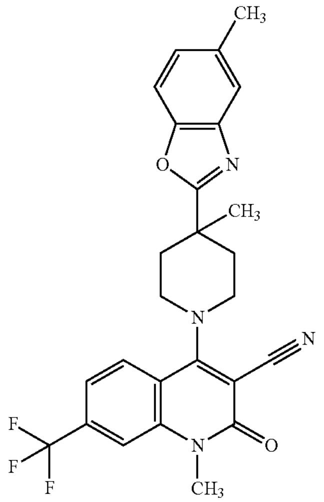 [SMILES: Cc1ccc2oc(C3(C)CCN(c4c(C#N)c(=O)n(C)c5cc(C(F)(F)F)ccc45)CC3)nc2c1]

65 mg 4-chloro-1-methyl-2-oxo-7-(trifluoromethyl)-1,2-dihydroquinoline-3-carbonitrile (215 μmol, intermediate 132) was suspended in 2 mL 2-propanol, 110 μL N,N-diisopropylethylamine (650 μmol) and 59.5 mg 5-methyl-2-(4-methylpiperidin-4-yl)-1,3-benzoxazole (259 μmol, intermediate 52) were added and the mixture was stirred for 2 h at 90° C. The reaction mixture was cooled down to rt and the suspension was diluted with water and stirred for 15 min. The solid was filtered off and washed with water and ethanol to give 104 mg of the title compound (100% purity, 100% yield).

$^1$H NMR (400 MHz, DMSO-$d_6$) δ ppm 1.50 (s, 3H) 2.07 (ddd, 2H) 2.43 (s, 3H) 2.52 (m, 2H) 3.52 (br t, 2H) 3.62 (s, 3H) 3.70-3.81 (m, 2H) 7.21 (dd, 1H) 7.54-7.58 (m, 1H) 7.58-7.65 (m, 2H) 7.81 (s, 1H) 8.08 (d, 1H).

LC-MS (Method 2): $R_t$=1.48 min; MS (ESIpos): m/z=481.5 [M+H]$^+$

Example 291

4-[4-(1,3-benzoxazol-2-yl)piperidin-1-yl]-1-methyl-2-oxo-7-(trifluoromethyl)-1,2-dihydroquinoline-3-carbonitrile

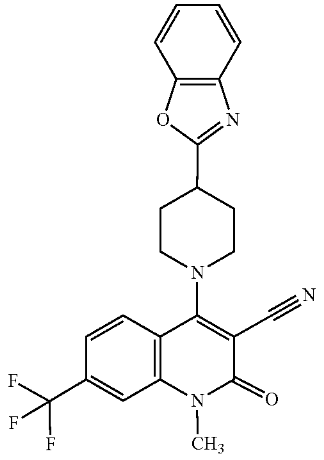 [SMILES: Cn1c(=O)c(C#N)c(N2CCC(c3nc4ccccc4o3)CC2)c2ccc(C(F)(F)F)cc21]

75 mg 4-chloro-1-methyl-2-oxo-7-(trifluoromethyl)-1,2-dihydroquinoline-3-carbonitrile (249 μmol, intermediate 132) was suspended in 2 mL 2-propanol, 130 μL N,N-diisopropylethylamine (750 μmol) and 63.5 mg 2-(piperidin-4-yl)-1,3-benzoxazole (298 μmol, CAS 51784-03-3) were added and the mixture was stirred for 2 h at 90° C. The reaction mixture was cooled down to rt and the suspension was diluted with water and stirred for 15 min. The solid was filtered off and washed with water and ethanol to give 119 mg of the title compound (100% purity, 106% yield).

$^1$H NMR (400 MHz, DMSO-$d_6$) δ ppm 2.11-2.23 (m, 2H) 2.29-2.38 (m, 2H) 3.45-3.55 (m, 1H) 3.58-3.67 (m, 5H) 3.86 (br d, 2H) 7.34-7.42 (m, 2H) 7.62-7.68 (m, 1H) 7.70-7.77 (m, 2H) 7.83 (s, 1H) 8.08 (d, 1H).

LC-MS (Method 2): $R_t$=1.35 min; MS (ESIpos): m/z=453.4 [M+H]$^+$

Example 292

4-[4-(1,3-benzoxazol-2-yl)-4-methylpiperidin-1-yl]-1-methyl-2-oxo-7-(trifluoromethyl)-1,2-dihydroquinoline-3-carbonitrile

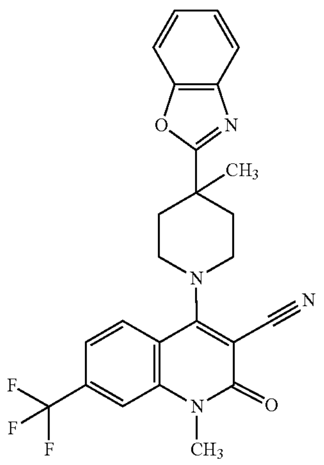 [SMILES: Cn1c(=O)c(C#N)c(N2CCC(C)(c3nc4ccccc4o3)CC2)c2ccc(C(F)(F)F)cc21]

75 mg 4-chloro-1-methyl-2-oxo-7-(trifluoromethyl)-1,2-dihydroquinoline-3-carbonitrile (249 μmol, intermediate 132) was suspended in 2 mL 2-propanol, 130 μL N,N-diisopropylethylamine (750 μmol) and 67.9 mg 2-(4-methylpiperidin-4-yl)-1,3-benzoxazole (298 μmol, intermediate 1) were added and the mixture was stirred for 2 h at 90° C. The reaction mixture was cooled down to rt and the suspension was diluted with water and stirred for 15 min. The solid was filtered off and washed with water and ethanol to give 119 mg of the title compound (100% purity, 103% yield).

$^1$H NMR (400 MHz, DMSO-$d_6$) δ ppm 1.52 (s, 3H) 2.08 (ddd, 2H) 2.52-2.59 (m, 2H) 3.55 (br t, 2H) 3.62 (s, 3H) 3.71-3.83 (m, 2H) 7.35-7.43 (m, 2H) 7.59-7.64 (m, 1H) 7.72-7.80 (m, 2H) 7.81 (s, 1H) 8.08 (d, 1H).

LC-MS (Method 2): $R_t$=1.42 min; MS (ESIpos): m/z=467.4 [M+H]$^+$

Example 293

7-hydroxy-1-methyl-4-[4-(5-methyl-1,3-benzoxazol-2-yl)piperidin-1-yl]-2-oxo-1,2-dihydroquinoline-3-carbonitrile

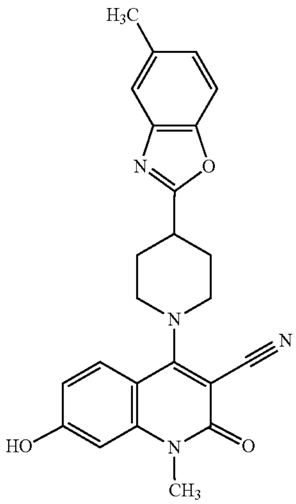 [SMILES: Cc1ccc2oc(C3CCN(c4c(C#N)c(=O)n(C)c5cc(O)ccc45)CC3)nc2c1]

A solution of 2.22 g 4-chloro-7-hydroxy-1-methyl-2-oxo-1,2-dihydroquinoline-3-carbonitrile (9.45 mmol, intermediate 136), 2.04 g 5-methyl-2-(piperidin-4-yl)-1,3-benzoxazole (9.45 mmol, CAS 199292-77-8) and 2.6 mL triethylamine (19 mmol) in 120 mL 2-propanol was stirred for 6 h at 90° C. After this time, water was added and the reaction was extracted with ethyl acetate. The precipitate that was generated by this procedure was collected by filtration and dried in vacuum. 2.25 g of the title compound were obtained (95% purity, 55% yield).

$^1$H NMR (400 MHz, DMSO-$d_6$) δ ppm 2.05-2.16 (m, 2H) 2.28 (br d, 2H) 2.42 (s, 3H) 3.40-3.46 (m, 2H) 3.48 (s, 3H) 3.54 (br t, 2H) 3.76 (br d, 2H) 6.76 (s, 1H) 6.79 (d, 1H) 7.19 (dd, 1H) 7.52 (s, 1H) 7.58 (d, 1H) 7.71 (d, 1H).

LC-MS (Method 2): $R_t$=0.70 min; MS (ESIpos): m/z=415.5 [M+H]$^+$

Example 294

4-[4-(6-bromo-1,3-benzoxazol-2-yl)piperidin-1-yl]-1-methyl-2-oxo-1,2-dihydroquinoline-3-carbonitrile

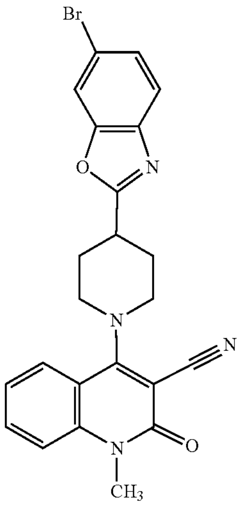 [SMILES: Cn1c(=O)c(C#N)c(N2CCC(c3nc4ccc(Br)cc4o3)CC2)c2ccccc21]

A solution of 100 mg 4-chloro-1-methyl-2-oxo-1,2-dihydroquinoline-3-carbonitrile (457 μmol, CAS 150617-68-8), 257 mg 6-bromo-2-(piperidin-4-yl)-1,3-benzoxazole (915 μmol, intermediate 124) and 250 μL triethylamine (1.8 mmol) in 5 mL 2-propanol was stirred for 3.5 h at 90° C. The suspension was cooled down to rt and was stirred for 72 h. Water was added and the reaction was extracted with ethyl acetate. The precipitate that was generated by this procedure was collected by filtration and dried in vacuum. The impure product was purified by flash chromatography (silica, dichloromethane/methanol gradient 0-2%) to give 90 mg of the title compound (99% purity, 42% yield).

$^1$H NMR (400 MHz, DMSO-$d_6$) δ ppm 2.09-2.20 (m, 2H) 2.28-2.33 (m, 2H) 3.48 (tt, 1H) 3.56-3.66 (m, 5H) 3.84 (br d, 2H) 7.35 (t, 1H) 7.54-7.60 (m, 2H) 7.69-7.77 (m, 2H) 7.88 (dd, 1H) 8.08 (d, 1H).

LC-MS (Method 2): $R_t$=1.34 min; MS (ESIpos): m/z=465.4 [M+H]$^+$

Example 295

4-{4-[5-(2-methoxyethyl)-1,3-benzoxazol-2-yl]piperidin-1-yl}-1-methyl-2-oxo-1,2-dihydroquinoline-3-carboxamide

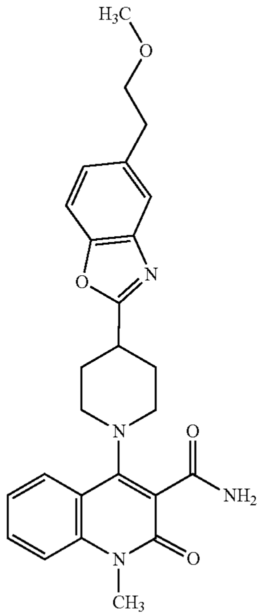 [SMILES: COCCc1ccc2oc(C3CCN(c4c(C(N)=O)c(=O)n(C)c5ccccc45)CC3)nc2c1]

60 mg 4-{4-[5-(2-methoxyethyl)-1,3-benzoxazol-2-yl]piperidin-1-yl}-1-methyl-2-oxo-1,2-dihydroquinoline-3-carbonitrile (136 μmol, example 283), 15.2 mg palladium(II) acetate (67.8 μmol) and 80 mg acetaldoxime (1.36 mmol) were stirred in 4 mL ethanol for 3 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichlorormethane/methanol gradient 0-5%) to give 55 mg of the title compound (99% purity, 87% yield).

$^1$H NMR (400 MHz, DMSO-$d_6$) δ ppm 2.05-2.17 (m, 2H) 2.17-2.25 (m, 2H) 2.92 (t, 2H) 3.16-3.27 (m, 6H) 3.36-3.44

(m, 2H) 3.54-3.61 (m, 5H) 7.24 (d, 1H) 7.32 (t, 1H) 7.47-7.70 (m, 6H) 7.93 (dd, 1H).

LC-MS (Method 2): $R_t$=1.07 min; MS (ESIpos): m/z=461.7 $[M+H]^+$

Example 296

4-[4-(1,3-benzoxazol-2-yl)-4-methylpiperidin-1-yl]-6-fluoro-1-methyl-2-oxo-1,2-dihydroquinoline-3-carboxamide

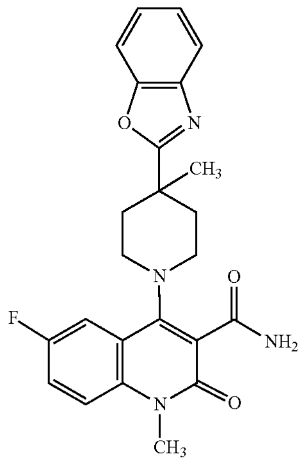 [SMILES: Cn1c(=O)c(C(N)=O)c(N2CCC(C)(c3nc4ccccc4o3)CC2)c2cc(F)ccc21]

126 mg 4-[4-(1,3-benzoxazol-2-yl)-4-methylpiperidin-1-yl]-6-fluoro-1-methyl-2-oxo-1,2-dihydroquinoline-3-carbonitrile (303 μmol, example 216), 17 mg palladium(II)acetate (75.6 μmol) and 179 mg acetaldoxime (3.02 mmol) were stirred in 2.5 mL ethanol for 4 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 78.5 mg of the title compound (100% purity, 60% yield).

$^1$H NMR (400 MHz, DMSO-$d_6$) δ ppm 1.46 (s, 3H) 1.96-2.06 (m, 2H) 2.41-2.48 (m, 2H) 3.04-3.14 (m, 2H) 3.26 (br s, 2H) 3.57 (s, 3H) 7.34-7.42 (m, 2H) 7.47 (br s, 1H) 7.50-7.58 (m, 2H) 7.58-7.66 (m, 2H) 7.70-7.78 (m, 2H).

LC-MS (Method 2): $R_t$=1.12 min; MS (ESIpos): m/z=435.4 $[M+H]^+$

Example 297

4-[4-(1,3-benzoxazol-2-yl)-4-methylpiperidin-1-yl]-7-chloro-1-methyl-2-oxo-1,2-dihydroquinoline-3-carboxamide

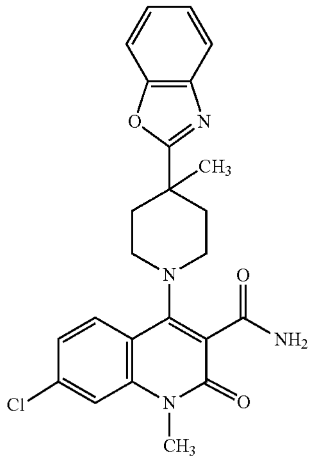 [SMILES: Cn1c(=O)c(C(N)=O)c(N2CCC(C)(c3nc4ccccc4o3)CC2)c2ccc(Cl)cc21]

96 mg 4-[4-(1,3-benzoxazol-2-yl)-4-methylpiperidin-1-yl]-7-chloro-1-methyl-2-oxo-1,2-dihydroquinoline-3-carbonitrile (222 μmol, example 226), 12.4 mg palladium(II) acetate (55.4 μmol) and 131 mg acetaldoxime (2.22 mmol) were stirred in 2 mL ethanol for 4 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 50 mg of the title compound (100% purity, 54% yield).

$^1$H NMR (400 MHz, DMSO-$d_6$) δ ppm 1.46 (s, 3H) 2.00 (br t, 2H) 2.38-2.47 (m, 2H) 3.09 (br t, 2H) 3.23-3.31 (m, 2H) 3.55 (s, 3H) 7.31-7.42 (m, 3H) 7.46 (br s, 1H) 7.59 (br s, 2H) 7.74 (br t, 2H) 7.92 (br d, 1H).

LC-MS (Method 2): $R_t$=1.20 min; MS (ESIpos): m/z=451.4 $[M+H]^+$

Example 298

6-fluoro-1-methyl-4-[4-(5-methyl-1,3-benzoxazol-2-yl)piperidin-1-yl]-2-oxo-1,2-dihydroquinoline-3-carboxamide

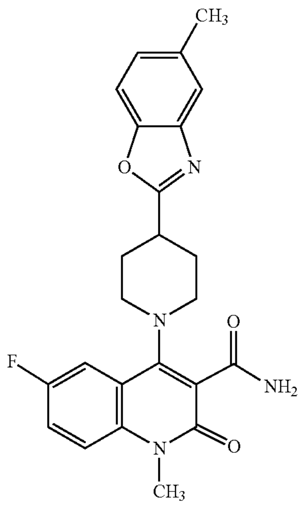 [SMILES: Cc1ccc2oc(C3CCN(c4c(C(N)=O)c(=O)n(C)c5ccc(F)cc45)CC3)nc2c1]

68 mg 6-fluoro-1-methyl-4-[4-(5-methyl-1,3-benzoxazol-2-yl)piperidin-1-yl]-2-oxo-1,2-dihydroquinoline-3-carbonitrile (160 μmol, example 217), 9 mg palladium(II)acetate (40 μmol) and 142 mg acetaldoxime (2.4 mmol) were stirred in 1.5 mL ethanol for 5 h at 80° C. The reaction mixture was diluted with water, extracted with ethyl acetate two times, the combined organic layers were filtered through a water-resistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 41.4 mg of the title compound (100% purity, 60% yield).

$^1$H NMR (400 MHz, DMSO-$d_6$) δ ppm 2.02-2.15 (m, 2H) 2.17-2.26 (m, 2H) 2.44 (s, 3H) 3.13-3.25 (m, 3H) 3.35-3.43 (m, 2H) 3.59 (s, 3H) 7.18 (d, 1H) 7.47-7.63 (m, 6H) 7.73 (br s, 1H).

LC-MS (Method 2): $R_t$=1.17 min; MS (ESIpos): m/z=435.4 [M+H]$^+$

Example 299

4-[4-(1,3-benzoxazol-2-yl)piperidin-1-yl]-6-fluoro-1-methyl-2-oxo-1,2-dihydroquinoline-3-carboxamide

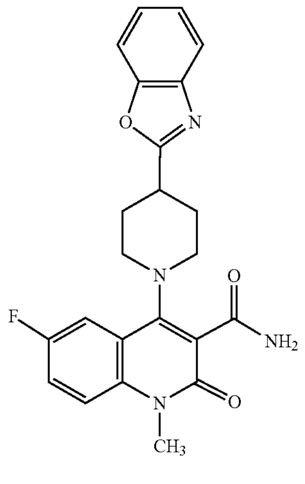 [SMILES: Cn1c(=O)c(C(N)=O)c(N2CCC(c3nc4ccccc4o3)CC2)c2cc(F)ccc21]

70 mg 4-[4-(1,3-benzoxazol-2-yl)piperidin-1-yl]-6-fluoro-1-methyl-2-oxo-1,2-dihydroquinoline-3-carbonitrile (174 μmol, example 206), 9.8 mg palladium(II)acetate (43.5 μmol) and 154.2 mg acetaldoxime (2.6 mmol) were stirred in 1.5 mL ethanol for 27 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: Chromatorex 125×30 mm, 10 μm mobile phase: acetonitrile/water (0.2 vol. % ammonia 32%)-gradient) to give 26.8 mg of the title compound (100% purity, 37% yield).

$^1$H NMR (400 MHz, DMSO-$d_6$) δ ppm 2.04-2.18 (m, 2H) 2.19-2.29 (m, 2H) 3.13-3.30 (m, 3H) 3.35 (br s, 2H) 3.60 (s, 3H) 7.34-7.41 (m, 2H) 7.50-7.62 (m, 4H) 7.69-7.76 (m, 3H).

LC-MS (Method 2): $R_t$=1.07 min; MS (ESIpos): m/z=421.4 [M+H]$^+$

Example 300

4-[4-(1,3-benzoxazol-2-yl)piperidin-1-yl]-7-chloro-1-methyl-2-oxo-1,2-dihydroquinoline-3-carboxamide

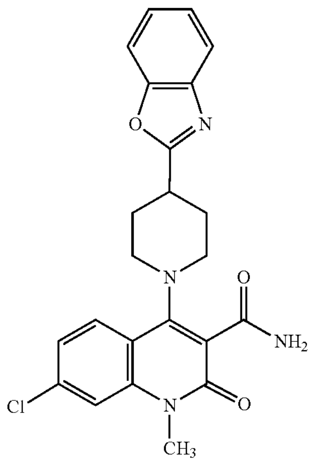 [SMILES: Cn1c(=O)c(C(N)=O)c(N2CCC(c3nc4ccccc4o3)CC2)c2ccc(Cl)cc21]

70 mg 4-[4-(1,3-benzoxazol-2-yl)piperidin-1-yl]-7-chloro-1-methyl-2-oxo-1,2-dihydroquinoline-3-carbonitrile (159 μmol, example 227), 8.9 mg palladium(II)acetate (39.7 μmol) and 140.7 mg acetaldoxime (2.4 mmol) were stirred in 1.5 mL ethanol for 27 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: Chromatorex 125×30 mm, 10 μm mobile phase: acetonitrile/water (0.2 vol. % ammonia 32%)-gradient) to give 25.8 mg of the title compound (100% purity, 37% yield).

$^1$H NMR (400 MHz, DMSO-$d_6$) δ ppm 2.04-2.17 (m, 2H) 2.19-2.27 (m, 2H) 3.14-3.30 (m, 3H) 3.36 (br s, 2H) 3.58 (s, 3H) 7.33-7.41 (m, 3H) 7.53 (br d, 1H) 7.61 (d, 1H) 7.69-7.76 (m, 3H) 7.91 (d, 1H).

LC-MS (Method 2): $R_t$=1.16 min; MS (ESIpos): m/z=437.4 [M+H]$^+$

Example 301

7-chloro-1-methyl-4-[4-(5-methyl-1,3-benzoxazol-2-yl)piperidin-1-yl]-2-oxo-1,2-dihydroquinoline-3-carboxamide

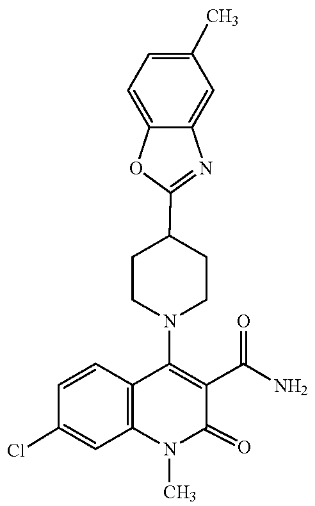 [SMILES: Cc1ccc2oc(C3CCN(c4c(C(N)=O)c(=O)n(C)c5cc(Cl)ccc45)CC3)nc2c1]

68 mg 7-chloro-1-methyl-4-[4-(5-methyl-1,3-benzoxazol-2-yl)piperidin-1-yl]-2-oxo-1,2-dihydroquinoline-3-carbonitrile (143 μmol, example 229), 8.0 mg palladium(II) acetate (35.7 μmol) and 126.6 mg acetaldoxime (2.14 mmol) were stirred in 1.5 mL ethanol for 5 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 13.4 mg of the title compound (100% purity, 21% yield).

$^1$H NMR (400 MHz, DMSO-$d_6$) δ ppm 2.02-2.15 (m, 2H) 2.16-2.25 (m, 2H) 2.44 (s, 3H) 3.13-3.27 (m, 3H) 3.36-3.42 (m, 2H) 3.57 (s, 3H) 7.18 (dd, 1H) 7.35 (dd, 1H) 7.49-7.55 (m, 2H) 7.56-7.62 (m, 2H) 7.71 (s, 1H) 7.91 (d, 1H).

LC-MS (Method 2): $R_t$=1.24 min; MS (ESIpos): m/z=451.4 $[M+H]^+$

Example 302

1-methyl-4-[4-methyl-4-(5-methyl-1,3-benzoxazol-2-yl)piperidin-1-yl]-2-oxo-1,2-dihydroquinoline-3-carboxamide

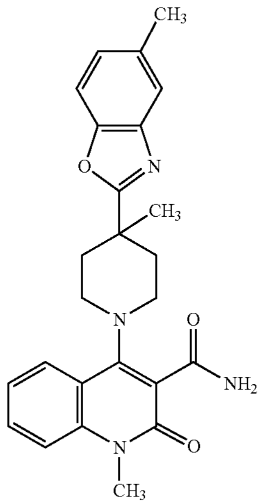 [SMILES: Cc1ccc2oc(C3(C)CCN(c4c(C(N)=O)c(=O)n(C)c5ccccc45)CC3)nc2c1]

800 mg 1-methyl-4-[4-methyl-4-(5-methyl-1,3-benzoxazol-2-yl)piperidin-1-yl]-2-oxo-1,2-dihydroquinoline-3-carbonitrile (1.94 mmol, example 288), 109 mg palladium(II) acetate (485 μmol) and 1.15 g acetaldoxime (19.4 mmol) were stirred in 80 mL ethanol for 5 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichlorormethane/methanol gradient 0-10%) to give 210 mg of the title compound (92% purity, 23% yield).

$^1$H NMR (400 MHz, DMSO-$d_6$) δ ppm 1.45 (s, 3H) 1.94-2.03 (m, 2H) 2.43 (s, 3H) 2.44-2.48 (m, 2H) 3.04-3.15 (m, 2H) 3.25-3.32 (m, 2H) 3.57 (s, 3H) 7.19 (dd, 1H) 7.32 (t, 1H) 7.40 (br s, 1H) 7.49-7.65 (m, 5H) 7.95 (s, 1H).

LC-MS (Method 2): $R_t$=1.17 min; MS (ESIpos): m/z=431.6 $[M+H]^+$

Example 303

4-[4-(1,3-benzoxazol-2-yl)-4-methylpiperidin-1-yl]-7-fluoro-1-methyl-2-oxo-1,2-dihydroquinoline-3-carboxamide

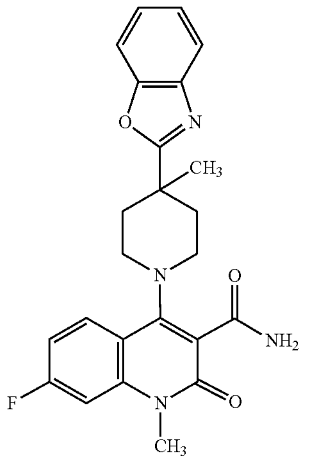 [SMILES: Cn1c(=O)c(C(N)=O)c(N2CCC(C)(c3nc4ccccc4o3)CC2)c2ccc(F)cc21]

118 mg 4-[4-(1,3-benzoxazol-2-yl)-4-methylpiperidin-1-yl]-7-fluoro-1-methyl-2-oxo-1,2-dihydroquinoline-3-carbonitrile (281 μmol, example 235), 15.7 mg palladium(II) acetate (70.1 μmol) and 166 mg acetaldoxime (2.8 mmol) were stirred in 2.5 mL ethanol for 4 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 70 mg of the title compound (100% purity, 57% yield).

$^1$H NMR (400 MHz, DMSO-$d_6$) δ ppm 1.46 (s, 3H) 2.00 (br t, 2H) 2.41-2.48 (m, 2H) 3.10 (br t, 2H) 3.25-3.32 (m, 2H) 3.53 (s, 3H) 7.12-7.21 (m, 1H) 7.38 (br dd, 3H) 7.44 (br s, 1H) 7.58 (br s, 1H) 7.69-7.79 (m, 2H) 7.97 (dd, 1H).

LC-MS (Method 2): $R_t$=1.13 min; MS (ESIpos): m/z=435.4 $[M+H]^+$

Example 304

7-fluoro-1-methyl-4-[4-(5-methyl-1,3-benzoxazol-2-yl)piperidin-1-yl]-2-oxo-1,2-dihydroquinoline-3-carboxamide

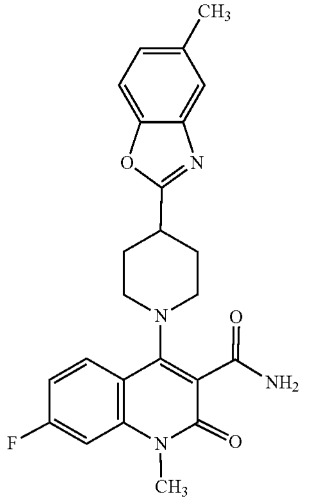 [SMILES: Cc1ccc2oc(C3CCN(c4c(C(N)=O)c(=O)n(C)c5cc(F)ccc45)CC3)nc2c1]

68 mg 7-fluoro-1-methyl-4-[4-(5-methyl-1,3-benzoxazol-2-yl)piperidin-1-yl]-2-oxo-1,2-dihydroquinoline-3-carbonitrile (157 μmol, example 238), 8.8 mg palladium(II)acetate (39.2 μmol) and 139 mg acetaldoxime (2.4 mmol) were stirred in 1.5 mL ethanol for 5 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 32.6 mg of the title compound (100% purity, 48% yield).

$^1$H NMR (400 MHz, DMSO-$d_6$) δ ppm 2.03-2.16 (m, 2H) 2.17-2.26 (m, 2H) 2.44 (s, 3H) 3.12-3.27 (m, 3H) 3.36-3.44 (m, 2H) 3.56 (s, 3H) 7.12-7.21 (m, 2H) 7.39 (dd, 1H) 7.51 (br s, 2H) 7.58 (d, 1H) 7.69 (br s, 1H) 7.95 (dd, 1H).

LC-MS (Method 2): $R_t$=1.17 min; MS (ESIpos): m/z=435.4 $[M+H]^+$

Example 305

4-[4-(1,3-benzoxazol-2-yl)piperidin-1-yl]-7-fluoro-1-methyl-2-oxo-1,2-dihydroquinoline-3-carboxamide

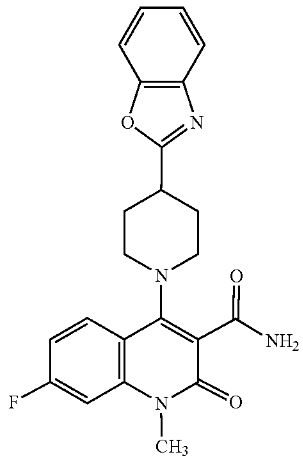 [SMILES: Cn1c(=O)c(C(N)=O)c(N2CCC(c3nc4ccccc4o3)CC2)c2ccc(F)cc21]

70 mg 4-[4-(1,3-benzoxazol-2-yl)piperidin-1-yl]-7-fluoro-1-methyl-2-oxo-1,2-dihydroquinoline-3-carbonitrile (170 μmol, example 236), 9.57 mg palladium(II)acetate (42.6 μmol) and 151 mg acetaldoxime (2.6 mmol) were stirred in 1.5 mL ethanol for 27 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: Chromatorex 125×30 mm, 10 μm mobile phase: acetonitrile/water (0.2 vol. % ammonia 32%)-gradient) to give 36.1 mg of the title compound (100% purity, 50% yield).

$^1$H NMR (400 MHz, DMSO-$d_6$) δ ppm 2.05-2.17 (m, 2H) 2.18-2.27 (m, 2H) 3.15-3.30 (m, 3H) 3.35-3.43 (m, 2H) 3.56 (s, 3H) 7.17 (td, 1H) 7.33-7.43 (m, 3H) 7.51 (d, 1H) 7.67-7.76 (m, 3H) 7.96 (dd, 1H).

LC-MS (Method 2): $R_t$=1.08 min; MS (ESIpos): m/z=421.5 $[M+H]^+$

Example 306

4-[4-(1,3-benzoxazol-2-yl)-4-methylpiperidin-1-yl]-1-methyl-2-oxo-7-(trifluoromethyl)-1,2-dihydroquinoline-3-carboxamide

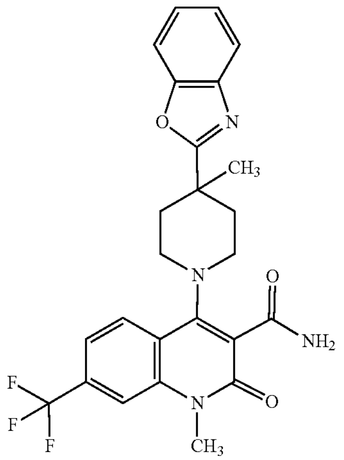 [SMILES: Cn1c(=O)c(C(N)=O)c(N2CCC(C)(c3nc4ccccc4o3)CC2)c2ccc(C(F)(F)F)cc21]

75 mg 4-[4-(1,3-benzoxazol-2-yl)-4-methylpiperidin-1-yl]-1-methyl-2-oxo-7-(trifluoromethyl)-1,2-dihydroquinoline-3-carbonitrile (161 μmol, example 292), 9.02 mg palladium(II)acetate (40.2 μmol) and 47.5 mg acetaldoxime (804 μmol) were stirred in 2 mL ethanol for 2 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 45.5 mg of the title compound (100% purity, 58% yield).

$^1$H NMR (400 MHz, DMSO-$d_6$) δ ppm 1.47 (s, 3H) 1.97-2.07 (m, 2H) 2.43-2.49 (m, 2H) 3.12 (br t, 2H) 3.26-3.33 (m, 2H) 3.63 (s, 3H) 7.34-7.43 (m, 2H) 7.52 (br s, 1H) 7.59-7.64 (m, 1H) 7.66 (br s, 1H) 7.71-7.79 (m, 3H) 8.13 (d, 1H).

LC-MS (Method 2): $R_t$=1.27 min; MS (ESIpos): m/z=485.5 $[M+H]^+$

Example 307

1-methyl-4-[4-(5-methyl-1,3-benzoxazol-2-yl)piperidin-1-yl]-2-oxo-7-(trifluoromethyl)-1,2-dihydroquinoline-3-carboxamide

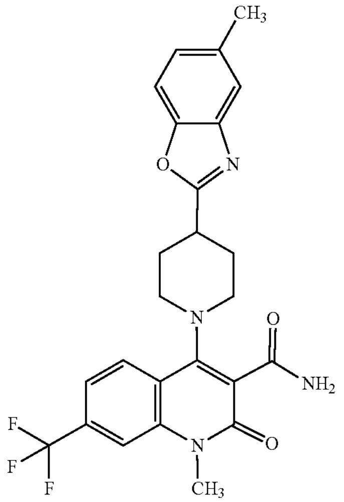 [SMILES: Cc1ccc2oc(C3CCN(c4c(C(N)=O)c(=O)n(C)c5cc(C(F)(F)F)ccc45)CC3)nc2c1]

75 mg 1-methyl-4-[4-(5-methyl-1,3-benzoxazol-2-yl)piperidin-1-yl]-2-oxo-7-(trifluoromethyl)-1,2-dihydroquinoline-3-carbonitrile (161 μmol, example 289), 9.02 mg palladium(II)acetate (40.2 μmol) and 142.5 mg acetaldoxime (2.4 mmol) were stirred in 2 mL ethanol for 8 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 40.6 mg of the title compound (100% purity, 52% yield).

$^1$H NMR (400 MHz, DMSO-$d_6$) δ ppm 2.05-2.18 (m, 2H) 2.18-2.27 (m, 2H) 2.42 (s, 3H) 3.15-3.29 (m, 3H) 3.37-3.44 (m, 2H) 3.65 (s, 3H) 7.18 (dd, 1H) 7.52 (s, 1H) 7.57 (d, 2H) 7.63 (dd, 1H) 7.78 (br s, 2H) 8.12 (d, 1H).

LC-MS (Method 2): $R_t$=1.28 min; MS (ESIpos): m/z=485.5 [M+H]$^+$

Example 308

4-[4-(1,3-benzoxazol-2-yl)piperidin-1-yl]-1-methyl-2-oxo-7-(trifluoromethyl)-1,2-dihydroquinoline-3-carboxamide

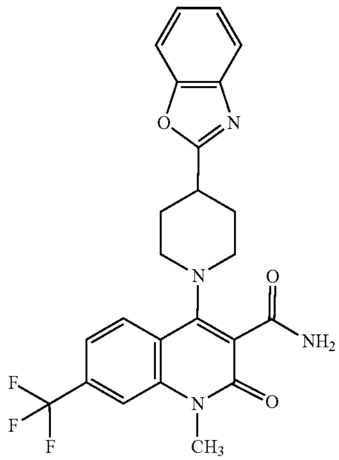 [SMILES: Cn1c(=O)c(C(N)=O)c(N2CCC(c3nc4ccccc4o3)CC2)c2ccc(C(F)(F)F)cc21]

75 mg 4-[4-(1,3-benzoxazol-2-yl)piperidin-1-yl]-1-methyl-2-oxo-7-(trifluoromethyl)-1,2-dihydroquinoline-3-carbonitrile (166 μmol, example 291), 9.3 mg palladium(II) acetate (41.4 μmol) and 147 mg acetaldoxime (2.5 mmol) were stirred in 2 mL ethanol for 9 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 48.8 mg of the title compound (100% purity, 63% yield).

$^1$H NMR (400 MHz, DMSO-$d_6$) δ ppm 2.08-2.19 (m, 2H) 2.20-2.29 (m, 2H) 3.16-3.31 (m, 3H) 3.38-3.45 (m, 2H) 3.65 (s, 3H) 7.33-7.42 (m, 2H) 7.59 (br s, 1H) 7.63 (br d, 1H) 7.69-7.75 (m, 2H) 7.78 (br s, 2H) 8.12 (d, 1H).

LC-MS (Method 2): $R_t$=1.21 min; MS (ESIpos): m/z=471.5 [M+H]$^+$

Example 309

4-[4-(1,3-benzoxazol-2-yl)piperidin-1-yl]-8-chloro-1-methyl-2-oxo-1,2-dihydroquinoline-3-carboxamide

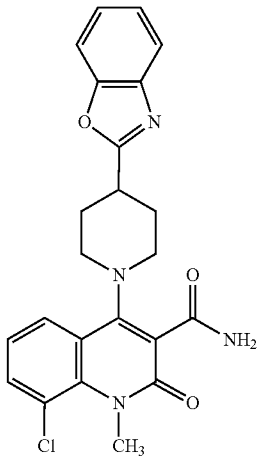 [SMILES: Cn1c(=O)c(C(N)=O)c(N2CCC(c3nc4ccccc4o3)CC2)c2cccc(Cl)c21]

70 mg 4-[4-(1,3-benzoxazol-2-yl)piperidin-1-yl]-8-chloro-1-methyl-2-oxo-1,2-dihydroquinoline-3-carbonitrile (159 μmol, example 162), 8.91 mg palladium(II)acetate (39.7 μmol) and 140.7 mg acetaldoxime (2.38 mmol) were stirred in 1.5 mL ethanol for 27 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: Chromatorex 125×30 mm, 10 μm mobile phase: acetonitrile/water (0.2 vol. % ammonia 32%)-gradient) to give 6.6 mg of the title compound (100% purity, 10% yield).

$^1$H NMR (400 MHz, DMSO-$d_6$) δ ppm 2.05-2.17 (m, 2H) 2.19-2.27 (m, 2H) 3.19 (s, 3H) 3.36-3.42 (m, 2H) 3.74 (s, 3H) 7.32 (t, 1H) 7.34-7.41 (m, 2H) 7.55 (d, 1H) 7.68-7.76 (m, 4H) 7.92 (dd, 1H).

LC-MS (Method 2): $R_t$=1.14 min; MS (ESIpos): m/z=437.4 [M+H]$^+$

Example 310

4-[4-(1,3-benzoxazol-2-yl)-4-methylpiperidin-1-yl]-8-chloro-1-methyl-2-oxo-1,2-dihydroquinoline-3-carboxamide

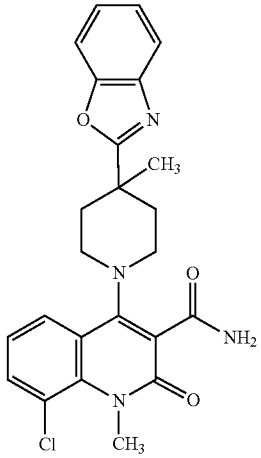 [SMILES: Cn1c(=O)c(C(N)=O)c(N2CCC(C)(c3nc4ccccc4o3)CC2)c2cccc(Cl)c21]

117 mg 4-[4-(1,3-benzoxazol-2-yl)-4-methylpiperidin-1-yl]-8-chloro-1-methyl-2-oxo-1,2-dihydroquinoline-3-carbonitrile (265 μmol, example 230), 14.9 mg palladium(II) acetate (66.2 μmol) and 156 mg acetaldoxime (2.64 mmol) were stirred in 2.5 mL ethanol for 4 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 44.7 mg of the title compound (100% purity, 37% yield).

$^1$H NMR (400 MHz, DMSO-$d_6$) δ ppm 1.46 (s, 3H) 1.95-2.06 (m, 2H) 2.40-2.47 (m, 2H) 3.10 (br t, 2H) 3.24-3.32 (m, 2H) 3.71 (s, 3H) 7.32 (t, 1H) 7.35-7.43 (m, 2H) 7.48 (br s, 1H) 7.62 (br s, 1H) 7.68-7.79 (m, 3H) 7.93 (d, 1H).

LC-MS (Method 2): $R_t$=1.19 min; MS (ESIpos): m/z=451.4 [M+H]$^+$

Example 311

4-[4-(1,3-benzoxazol-2-yl)-4-methylpiperidin-1-yl]-1,7-dimethyl-2-oxo-1,2-dihydroquinoline-3-carboxamide

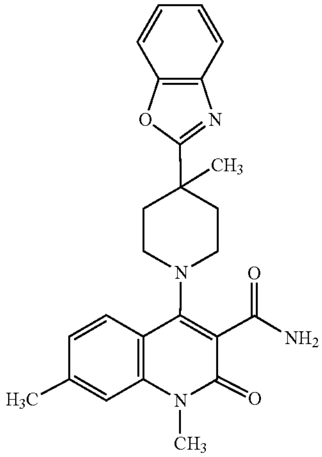 [SMILES: Cc1ccc2c(N3CCC(C)(c4nc5ccccc5o4)CC3)c(C(N)=O)c(=O)n(C)c2c1]

80 mg 4-[4-(1,3-benzoxazol-2-yl)-4-methylpiperidin-1-yl]-1,7-dimethyl-2-oxo-1,2-dihydro-quinoline-3-carbonitrile (194 μmol, example 218), 10.9 mg palladium(II)acetate (48.5 μmol) and 115 mg acetaldoxime (1.94 mmol) were stirred in 2.5 mL ethanol for 4 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 54 mg of the title compound (100% purity, 65% yield).

$^1$H NMR (400 MHz, DMSO-$d_6$) δ ppm 1.46 (s, 3H) 1.94-2.04 (m, 2H) 2.43-2.48 (m, 5H) 3.05-3.14 (m, 2H) 3.26-3.32 (m, 2H) 3.55 (s, 3H) 7.14 (dd, 1H) 7.33 (s, 1H) 7.35-7.42 (m, 3H) 7.55 (br s, 1H) 7.74 (ddt, 2H) 7.82 (d, 1H).

LC-MS (Method 2): $R_t$=1.18 min; MS (ESIpos): m/z=431.5 [M+H]$^+$

Example 312

1,7-dimethyl-4-[4-methyl-4-(5-methyl-1,3-benzoxazol-2-yl)piperidin-1-yl]-2-oxo-1,2-dihydroquinoline-3-carboxamide

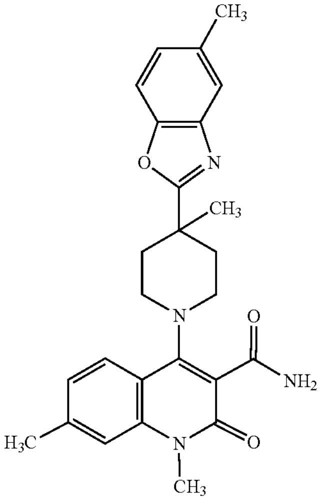 [SMILES: Cc1ccc2oc(C3(C)CCN(c4c(C(N)=O)c(=O)n(C)c5cc(C)ccc45)CC3)nc2c1]

80 mg 1,7-dimethyl-4-[4-methyl-4-(5-methyl-1,3-benzoxazol-2-yl)piperidin-1-yl]-2-oxo-1,2-dihydroquinoline-3-carbonitrile (188 μmol, example 220), 10.5 mg palladium (II)acetate (46.9 μmol) and 110.8 mg acetaldoxime (1.87 mmol) were stirred in 2.5 mL ethanol for 4 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 52 mg of the title compound (100% purity, 62% yield).

$^1$H NMR (400 MHz, DMSO-$d_6$) δ ppm 1.45 (s, 3H) 1.92-2.02 (m, 2H) 2.44 (d, 8H) 3.03-3.12 (m, 2H) 3.24-3.32 (m, 2H) 3.55 (s, 3H) 7.14 (dd, 1H) 7.19 (dd, 1H) 7.33 (s, 1H) 7.37 (br s, 1H) 7.51-7.56 (m, 2H) 7.59 (d, 1H) 7.81 (d, 1H).

LC-MS (Method 2): $R_t$=1.27 min; MS (ESIpos): m/z=445.5 [M+H]$^+$

Example 313

1,7-dimethyl-4-[4-(5-methyl-1,3-benzoxazol-2-yl)piperidin-1-yl]-2-oxo-1,2-dihydroquinoline-3-carboxamide

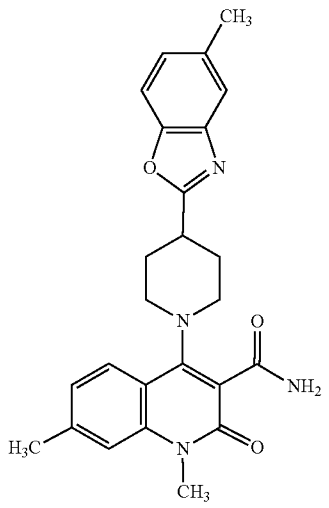 [SMILES: Cc1ccc2oc(C3CCN(c4c(C(N)=O)c(=O)n(C)c5cc(C)ccc45)CC3)nc2c1]

80 mg 1,7-dimethyl-4-[4-(5-methyl-1,3-benzoxazol-2-yl)piperidin-1-yl]-2-oxo-1,2-dihydro-quinoline-3-carbonitrile (194 μmol, example 221), 10.9 mg palladium(II)acetate (48.5 μmol) and 114.6 mg acetaldoxime (1.94 mmol) were stirred in 2.5 mL ethanol for 4 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 33 mg of the title compound (100% purity, 40% yield).

$^1$H NMR (400 MHz, DMSO-$d_6$) δ ppm 2.01-2.14 (m, 2H) 2.16-2.25 (m, 2H) 2.42 (s, 3H) 2.46 (s, 3H) 3.13-3.27 (m, 3H) 3.38 (br d, 2H) 3.57 (s, 3H) 7.14 (dd, 1H) 7.18 (dd, 1H) 7.35 (s, 1H) 7.45 (d, 1H) 7.50-7.53 (m, 1H) 7.57 (d, 1H) 7.66 (s, 1H) 7.80 (d, 1H).

LC-MS (Method 2): $R_t$=1.22 min; MS (ESIpos): m/z=431.4 $[M+H]^+$

Example 314

4-[4-(1,3-benzoxazol-2-yl)piperidin-1-yl]-1,7-dimethyl-2-oxo-1,2-dihydroquinoline-3-carboxamide

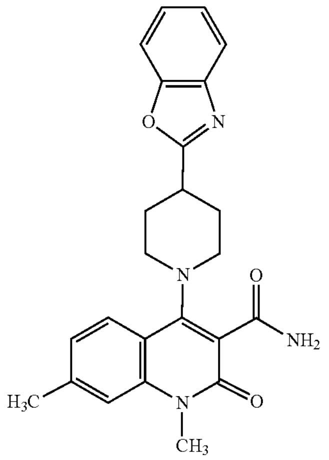 [SMILES: Cc1ccc2c(N3CCC(c4nc5ccccc5o4)CC3)c(C(N)=O)c(=O)n(C)c2c1]

80 mg 4-[4-(1,3-benzoxazol-2-yl)piperidin-1-yl]-1,7-dimethyl-2-oxo-1,2-dihydroquinoline-3-carbonitrile (201 μmol, example 219), 11.3 mg palladium(II)acetate (20.2 μmol) and 118.6 mg acetaldoxime (2.0 mmol) were stirred in 2.5 mL ethanol for 4 h at 80° C. The reaction mixture was diluted with water, extracted with ethyl acetate two times, the combined organic layers were filtered through a water-resistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 45 mg of the title compound (100% purity, 54% yield).

$^1$H NMR (400 MHz, DMSO-$d_6$) δ ppm 2.04-2.16 (m, 2H) 2.18-2.26 (m, 2H) 2.46 (s, 3H) 3.15-3.29 (m, 3H) 3.39 (br d, 2H) 3.57 (s, 3H) 7.14 (dd, 1H) 7.35 (d, 1H) 7.36-7.41 (m, 2H) 7.43-7.49 (m, 1H) 7.67 (br d, 1H) 7.69-7.75 (m, 2H) 7.80 (d, 1H).

LC-MS (Method 2): $R_t$=1.13 min; MS (ESIpos): m/z=417.4 $[M+H]^+$

Example 315

4-{4-[4-(2-methoxyethyl)-1,3-benzoxazol-2-yl]piperidin-1-yl}-1-methyl-2-oxo-1,2-dihydroquinoline-3-carboxamide

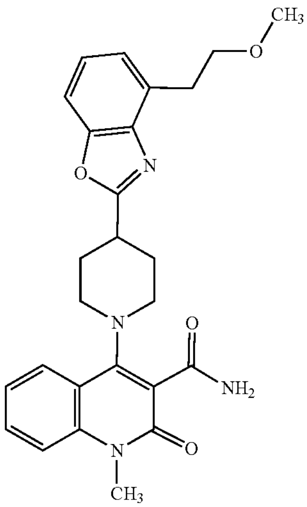 [SMILES: COCCc1cccc2oc(C3CCN(c4c(C(N)=O)c(=O)n(C)c5ccccc45)CC3)nc12]

100 mg 4-{4-[4-(2-methoxyethyl)-1,3-benzoxazol-2-yl]piperidin-1-yl}-1-methyl-2-oxo-1,2-dihydroquinoline-3-carbonitrile (226 μmol, example 265), 12.7 mg palladium (II)acetate (56.5 μmol) and 133.4 mg acetaldoxime (2.26 mmol) were stirred in 3 mL ethanol for 4 h at 90° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichlorormethane/methanol gradient 0-5%) to give 80 mg of the title compound (99% purity, 80% yield).

$^1$H NMR (400 MHz, DMSO-$d_6$) δ ppm 2.05-2.17 (m, 2H) 2.19-2.26 (m, 2H) 3.14-3.27 (m, 8H) 3.36-3.46 (m, 2H) 3.59 (s, 3H) 3.68 (t, 2H) 7.21-7.35 (m, 3H) 7.48-7.57 (m, 3H) 7.60-7.73 (m, 2H) 7.94 (dd, 1H).

LC-MS (Method 2): $R_t$=1.11 min; MS (ESIpos): m/z=461.5 [M+H]$^+$

Example 316

4-[4-(1,3-benzoxazol-2-yl)piperidin-1-yl]-1-methyl-2-oxo-1,2-dihydroquinoline-3-carboxamide

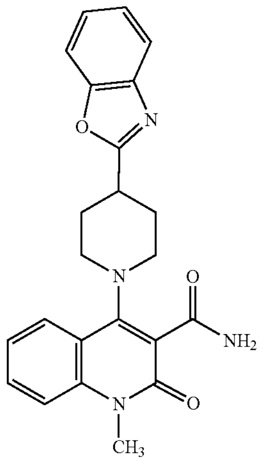 [SMILES: Cn1c(=O)c(C(N)=O)c(N2CCC(c3nc4ccccc4o3)CC2)c2ccccc21]

130 mg 4-[4-(1,3-benzoxazol-2-yl)piperidin-1-yl]-1-methyl-2-oxo-1,2-dihydroquinoline-3-carbonitrile (338 μmol, example 2), 19 mg palladium(II)acetate (84.5 μmol) and 200 mg acetaldoxime (3.38 mmol) were stirred in 15 mL ethanol for 9 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 μm 100×30 mm, mobile phase: acetonitrile/water (0.2 vol. % ammonia 32%)-gradient) to give 74 mg of the title compound.

$^1$H NMR (400 MHz, DMSO-$d_6$) δ ppm 2.06-2.18 (m, 2H) 2.20-2.32 (m, 2H) 3.17-3.31 (m, 3H) 3.35-3.44 (m, 2H) 3.59 (s, 3H) 7.30-7.41 (m, 3H) 7.47-7.55 (m, 2H) 7.61-7.75 (m, 4H) 7.93 (dd, 1H).

LC-MS (Method 2): $R_t$=1.03 min; MS (ESIpos): m/z=403.8 [M+H]$^+$

Example 317

4-{4-[6-(2-methoxyethyl)-1,3-benzoxazol-2-yl]piperidin-1-yl}-1-methyl-2-oxo-1,2-dihydroquinoline-3-carboxamide

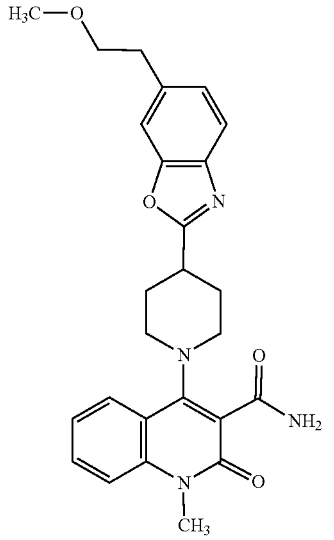 [SMILES: COCCc1ccc2nc(C3CCN(c4c(C(N)=O)c(=O)n(C)c5ccccc45)CC3)oc2c1]

80 mg 4-{4-[6-(2-methoxyethyl)-1,3-benzoxazol-2-yl]piperidin-1-yl}-1-methyl-2-oxo-1,2-dihydroquinoline-3-carbonitrile (181 µmol, example 284), 20.2 mg palladium(II) acetate (90.2 µmol) and 106.8 mg acetaldoxime (1.8 mmol) were stirred in 5 mL ethanol for 3 h at 80° C. The reaction mixture was diluted with water, extracted with ethyl acetate two times, the combined organic layers were washed with brine, filtered through a waterresistant filter and the filtrate was concentrated under reduced pressure. The residue was purified by flash chromatography (silica, dichlorormethane/methanol gradient 0-5%) to give 60 mg of the title compound (95% purity, 68% yield).

$^1$H NMR (400 MHz, DMSO-$d_6$) δ ppm 2.04-2.16 (m, 2H) 2.18-2.25 (m, 2H) 2.94 (t, 2H) 3.16-3.29 (m, 6H) 3.35-3.43 (m, 2H) 3.55-3.61 (m, 5H) 7.23 (dd, 1H) 7.32 (t, 1H) 7.47-7.70 (m, 6H) 7.93 (dd, 1H).

LC-MS (Method 2): $R_t$=0.86 min; MS (ESIpos): m/z=461.6 $[M+H]^+$

Example 318

4-[4-(1,3-benzoxazol-2-yl)piperidin-1-yl]-1-methyl-2-oxo-7-(2-oxopyrrolidin-1-yl)-1,2-dihydroquinoline-3-carboxamide

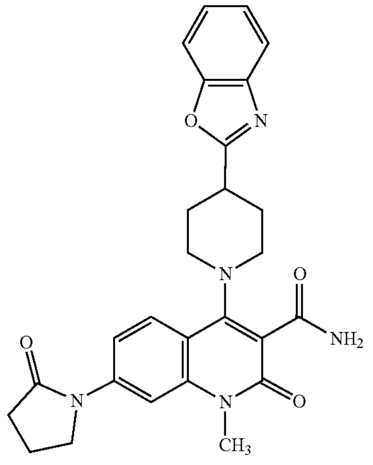

50 mg 4-[4-(1,3-benzoxazol-2-yl)piperidin-1-yl]-1-methyl-2-oxo-7-(2-oxopyrrolidin-1-yl)-1,2-dihydroquinoline-3-carbonitrile (102 µmol, example 35), 5.7 mg palladium(II)acetate (25.4 µmol) and 60 mg acetaldoxime (1.01 mmol) were stirred in 5 mL ethanol for 15 h at 80° C. The reaction mixture was diluted with water, extracted with ethyl acetate two times, the combined organic layers were washed with brine, filtered through a waterresistant filter and the filtrate was concentrated under reduced pressure. The residue was purified by RP-HPLC (column: X-Bridge C18 5 µm 100×30 mm, mobile phase: acetonitrile/water (0.2 vol. % ammonia 32%)-gradient) to give 10 mg of the title compound (95% purity, 19% yield).

$^1$H NMR (400 MHz, DMSO-$d_6$) δ ppm 2.06-2.17 (m, 4H) 2.19-2.27 (m, 2H) 2.53-2.59 (m, 2H) 3.16-3.30 (m, 3H) 3.35-3.43 (m, 2H) 3.56 (s, 3H) 3.96 (t, 2H) 7.34-7.41 (m, 2H) 7.47 (s, 1H) 7.60 (dd, 1H) 7.66-7.75 (m, 3H) 7.86 (s, 1H) 7.90 (d, 1H).

LC-MS (Method 2): $R_t$=0.98 min; MS (ESIpos): m/z=486.6 $[M+H]^+$

Example 319

8-chloro-1-methyl-4-[4-(5-methyl-1,3-benzoxazol-2-yl)piperidin-1-yl]-2-oxo-1,2-dihydroquinoline-3-carboxamide

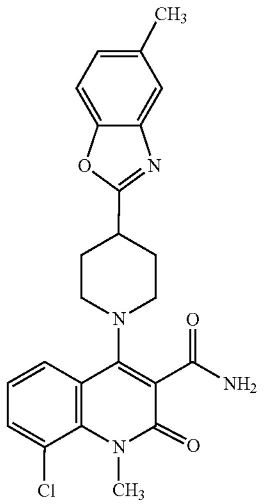 [SMILES: Cc1ccc2oc(C3CCN(c4c(C(N)=O)c(=O)n(C)c5c(Cl)cccc45)CC3)nc2c1]

68 mg 8-chloro-1-methyl-4-[4-(5-methyl-1,3-benzoxazol-2-yl)piperidin-1-yl]-2-oxo-1,2-dihydroquinoline-3-carbonitrile (154 µmol, example 232), 8.64 mg palladium(II) acetate (38.5 µmol) and 136.5 mg acetaldoxime (2.31 mmol) were stirred in 1.5 mL ethanol for 5 h at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: X-Bridge C18 5 µm 100×30 mm, mobile phase: acetonitrile/water (0.2 vol. % ammonia 32%)-gradient) to give 18 mg of the title compound (100% purity, 26% yield).

$^1$H NMR (400 MHz, DMSO-$d_6$) δ ppm 2.02-2.15 (m, 2H) 2.16-2.25 (m, 2H) 2.44 (s, 3H) 3.14-3.27 (m, 3H) 3.35-3.42 (m, 2H) 3.74 (s, 3H) 7.18 (d, 1H) 7.32 (t, 1H) 7.51 (s, 1H) 7.53-7.62 (m, 2H) 7.68-7.76 (m, 2H) 7.88-7.94 (m, 1H).

LC-MS (Method 2): $R_t$=1.23 min; MS (ESIpos): m/z=451.4 $[M+H]^+$

TABLE 14

| Compounds were prepared as referenced | | | | |
|---|---|---|---|---|
| Example | Structure | IUPAC-Name | Starting Materials | Analytics |
| 320 | 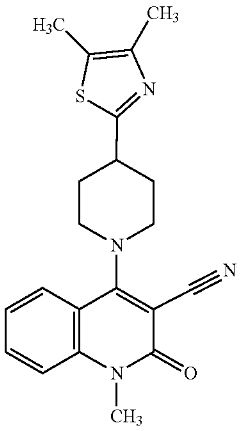 | 4-[4-(4,5-dimethyl-1,3-thiazol-2-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and 4-(4,5-dimethyl-1,3-thiazol-2-yl)piperidine (CAS 1004527-71-2) | $^1$H NMR (400 MHz, DMSO-$d_6$) δ ppm 1.91-2.02 (m, 2 H), 2.13-2.20 (m, 2H), 2.24 (d, 3 H), 2.31 (s, 3 H), 3.22-3.30 (m, 1 H), 3.50-3.58 (m, 5 H), 3.81 (br d, 2 H), 7.35 (ddd, 1 H), 7.55-7.58 (m, 1 H), 7.73 (ddd, 1 H), 7.86 (dd, 1 H). LC-MS (method 2): $R_t$ = 1.23 min; MS (ESIpos): m/z = 523 [M + H]$^+$ |
| 321 | 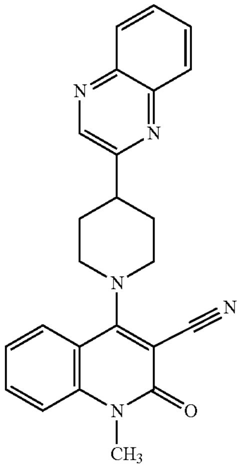 [SMILES: Cn1c(=O)c(C#N)c(N2CCC(c3cnc4ccccc4n3)CC2)c2ccccc21] | 1-methyl-2-oxo-4-[4-(quinoxalin-2-yl)piperidin-1-yl]-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 138 | $^1$H NMR (400 MHz, DMSO-$d_6$) δ ppm 2.16-2.27 (m, 4 H), 3.38-3.50 (m, 1 H), 3.56-3.68 (m, 5 H), 3.92 (br d, 2 H), 7.38 (s, 1 H), 7.59 (d, 1 H), 7.73-7.80 (m, 1 H), 7.84 (td, 2 H), 7.94 (dd, 1 H), 8.07-8.12 (m, 2 H), 9.07 (s, 1 H). LC-MS (method 2): $R_t$ = 1.15 min; MS (ESIpos): m/z = 396 [M + H]$^+$ |
| 322 | 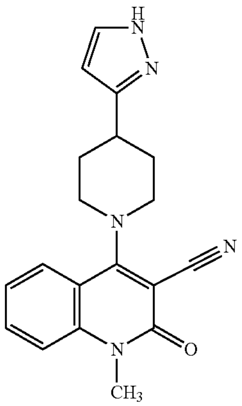 [SMILES: Cn1c(=O)c(C#N)c(N2CCC(c3cc[nH]n3)CC2)c2ccccc21] | 1-methyl-2-oxo-4-[4-(1H-pyrazol-3-yl)piperidin-1-yl]-1,2-dihydroquinoline-3-carbonitrile | In analogy to example 52 with 4-chloro-1-methyl-2-oxo-1,2-dihydroquinoline-3-carbonitrile (CAS 150617-68-8) and 4-(1H-pyrazol-5-yl)piperidine (CAS 278798-08-6) | $^1$H-NMR (400 MHz, DMSO-$d_6$): δ [ppm] = 1.86-2.00 (m, 2H), 2.03-2.15 (m, 2H), 3.00 (m, 1H), 3.47-3.55 (m, 2H), 3.57 (s, 3H), 3.80 (br d, 2H), 6.16 (br s, 1H), 7.34 (ddd, 1H), 7,40-7.67 (m, 1H), 7.57 (dd, 1H), 7.73 (ddd, 1H), 7.88 (dd, 1H), 12.45-12.74 (m, 1H). LC-MS (Method 1): $R_t$ = 0.92 min; MS (ESIpos): m/z = 334 [M + H]$^+$ |

TABLE 14-continued

| Compounds were prepared as referenced | | | | |
|---|---|---|---|---|
| Example | Structure | IUPAC-Name | Starting Materials | Analytics |
| 323 | 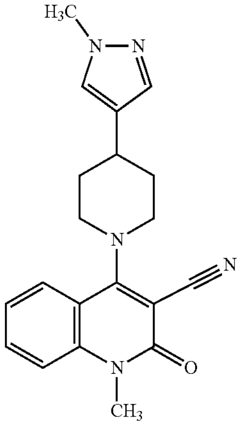 [SMILES: Cn1cc(C2CCN(c3c(C#N)c(=O)n(C)c4ccccc34)CC2)cn1] | 1-methyl-4-[4-(1-methyl-1H-pyrazol-4-yl)piperidin-1-yl]-2-oxo-1,2-dihydroquinoline-3-carbonitrile | Prepared from from intermediate 141. | $^1$H-NMR (400 MHz, DMSO-$d_6$): δ [ppm] = 1.75-1.87 (m, 2H), 2.04 (br d, 2H), 2.81 (tt, 1H), 3.49 (br t, 2H), 3.57 (s, 3H), 3.73-3.79 (br d, 2H), 3.79 (s, 3H), 7.31-7.38 (m, 2H), 7.55-7.58 (m, 1H), 7.58 (s, 1H), 7.73 (ddd, 1H), 7.87 (dd, 1H). LC-MS (Method 1): $R_t$ = 0.98 min; MS (ESIpos): m/z = 348 $[M + H]^+$ |
| 324 | 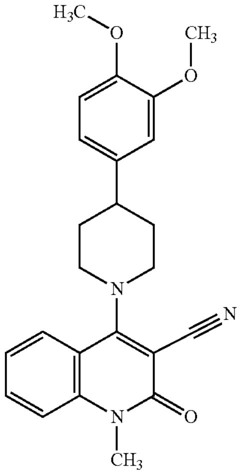 [SMILES: COc1ccc(C2CCN(c3c(C#N)c(=O)n(C)c4ccccc34)CC2)cc1OC] | 4-[4-(3,4-dimethoxyphenyl) piperidin-1-yl]-1-methyl-2-oxo-1,2-dihydroquinoline-3-carbonitrile | Prepared from from intermediate 144. | $^1$H-NMR (400 MHz, DMSO-$d_6$): δ [ppm] = 1.91-2.03 (m,4H), 2.77-2.88 (m, 1H), 3.45-3.55 (m, 2H), 3.58 (s, 3H), 3.73 (s, 3H), 3.78 (s, 3H), 3.84 (br d, 2H), 6.83-6.88 (m, 1H), 6.89-6.93 (m, 1H), 6.96 (d, 1H), 7.36 (ddd, 1H), 7.57 (dd, 1H), 7.75 (ddd, 1H), 7.94 (dd, 1H). LC-MS (Method 1): $R_t$ = 1.20 min; MS (ESIpos): m/z = 404 $[M + H]^+$ |
| 325 | 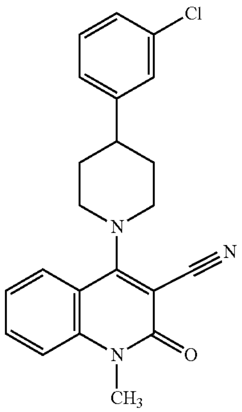 [SMILES: Cn1c(=O)c(C#N)c(N2CCC(c3cccc(Cl)c3)CC2)c2ccccc21] | 4-[4-(3-chlorophenyl) piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and 4-(3-4-(3-chlorophenyl) piperidine hydrochloride (CAS 99329-70-1) | $^1$H NMR (400 MHz, DMSO-$d_6$) δ ppm 1.88-2.09 (m, 4 H) 2.94 (s, 1 H) 3.45-3.55 (m, 2 H) 3.58 (s, 3 H) 3.72-3.89 (m, 2 H) 7.27-7.32 (m, 1 H) 7.32-7.41 (m, 3H) 7.44-7.48 (m, 1 H) 7.54-7.62 (m, 1 H) 7.70-7.80 (m, 1 H) 7.92-7.99 (m, 1 H). LC-MS (Method 2): $R_t$ = 1.38 min; MS (ESIpos): m/z = 378 $[M + H]^+$ |

TABLE 14-continued

| Compounds were prepared as referenced | | | | |
|---|---|---|---|---|
| Example | Structure | IUPAC-Name | Starting Materials | Analytics |
| 326 | 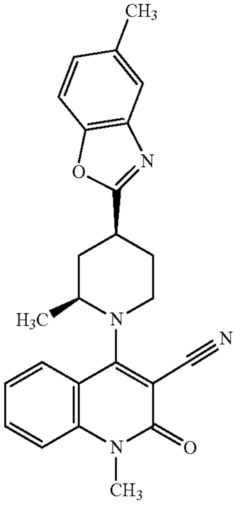 [SMILES: Cc1ccc2oc([C@H]3CCN(c4c(C#N)c(=O)n(C)c5ccccc45)[C@@H](C)C3)nc2c1] | 1-methyl-4-[(2S,4S)-2-methyl-4-(5-methyl-1,3-benzoxazol-2-yl)-1-piperidyl]-2-oxo-quinoline-3-carbonitrile | In analogy to example 52 with 4-chloro-1-methyl-2-oxo-1,2-dihydroquinoline-3-carbonitrile (CAS 150617-68-8) and intermediate 145 | $^1$H NMR (400 MHz, DMSO-$d_6$) δ ppm 0.99-1.06 (m, 3 H), 1.74-1.86 (m, 1 H), 2.09-2.25 (m, 2 H), 2.38-2.45 (m, 4 H), 3.20-3.46 (m, 123 H), 3.61-3.68 (m, 3 H), 3.87-3.98 (m, 1 H), 7.16-7.23 (m, 1 H), 7.36-7.45 (m, 1 H), 7.52 (s, 1 H), 7.55-7.60 (m, 1 H), 7.61-7.66 (m, 1 H), 7.77-7.84 (m, 1 H), 8.12-8.19 (m, 1 H). LC-MS (Method 2): $R_t$ = 1.33 min; MS (ESIpos): m/z = 413 [M + H]$^+$ |
| 327 | 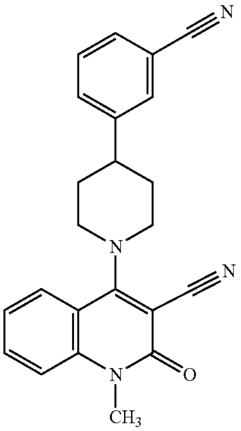 [SMILES: Cn1c(=O)c(C#N)c(N2CCC(c3cccc(C#N)c3)CC2)c2ccccc21] | 4-[4-(3-cyanophenyl) piperidin-1-yl]-1-methyl-2-oxo-1,2-dihydroquinoline-3-carbonitrile | Prepared from intermediate 148. | 1H-NMR (400 MHz, DMSO-$d_6$): δ [ppm] = 1.91-2.12 (m, 4H), 3.00 (tt, 1H), 3.51 (br t, 2H), 3.58 (s, 3H), 3.83 (br d, 2H), 7.32-7.39 (m, 1H), 7.53-7.61 (m, 2H), 7.69-7.79 (m, 3H), 7.90 (s, 1H), 7.97 (dd, 1H). LC-MS (Method 2): $R_t$ = 1.14 min; MS (ESIpos): m/z = 369 [M + H]$^+$ |
| 328 | 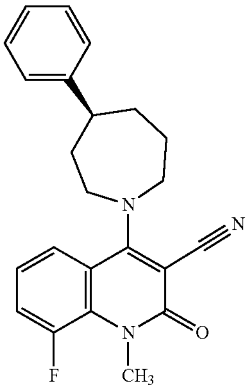 [SMILES: Cn1c(=O)c(C#N)c(N2CCC[C@H](c3ccccc3)CC2)c2cccc(F)c21] | 8-fluoro-1-methyl-2-oxo-4-[(4S)-4-phenylazepan-1-yl]-1,2-dihydroquinoline-3-carbonitrile | Prepared from intermediate 82 and 4-phenylazepane hydrochloride (CAS 7500-45-5) in analogy to example 52. | $^1$H NMR (400 MHz, DMSO-$d_6$) δ ppm 1.75-2.12 (m, 6 H), 2.91 (tt, 1 H), 3.65-3.77 (m, 5 H), 3.89-3.99 (m, 2 H), 7.15-7.24 (m, 1 H), 7.27-7.35 (m, 5 H), 7.56-7.65 (m, 1 H), 7.84 (s, 1 H). LC-MS (Method 2): $R_t$ = 1.39 min; MS (ESIpos): m/z = 376 [M + H]$^+$ |

TABLE 14-continued

| Compounds were prepared as referenced | | | | |
|---|---|---|---|---|
| Example | Structure | IUPAC-Name | Starting Materials | Analytics |
| 329 | 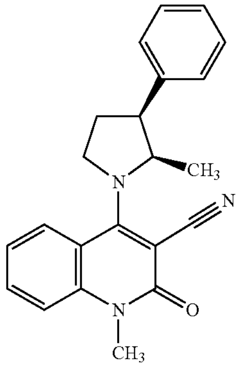 [SMILES: C[C@@H]1[C@H](c2ccccc2)CCN1c1c(C#N)c(=O)n(C)c2ccccc12] | 1-methyl-4-[rac-(2R,3S)-2-methyl-3-phenylpyrrolidin-1-yl]-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and rel-(2R,3S)-2-methyl-3-phenylpyrrolidine (135762-31-1). | 1H NMR (400 MHz, DMSO-$d_6$, mixture of stereoisomers A + B) δ ppm 0.83 (d, 3 H, A), 1.14-1.19 (m, 3 H, B), 2.10-2.36 (m, 3 H), 3.09-3.18 (m, 1 H), 3.51-3.54 (m, 3 H), 3.55 (s, 3 H), 3.67-3.77 (m, 3 H), 4.35-4.50 (m, 2 H), 4.81-4.90 (m, 1 H, A), 5.02 (t, 1 H, B), 7.25-7.41 (m, 12 H), 7.52 (ddd, 2 H), 7.68-7.73 (m, 2 H), 8.07 (dd, 1 H, A), 8.14 (dd, 1 H, B). LC-MS (Method 2): $R_t$ = 1.25 min; MS (ESIpos): m/z = 344 $[M + H]^+$ |
| 330 | 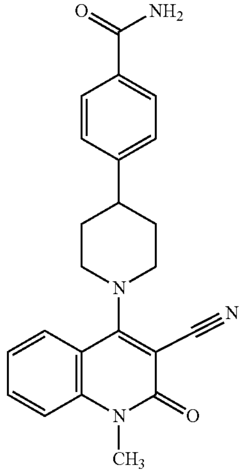 [SMILES: Cn1c(=O)c(C#N)c(N2CCC(c3ccc(C(N)=O)cc3)CC2)c2ccccc21] | 4-[1-(3-cyano-1-methyl-2-oxo-1,2-dihydroquinolin-4-yl)piperidin-4-yl]benzamide | In analogy to example 52 with 4-chloro-1-methyl-2-oxo-1,2-dihydroquinoline-3-carbonitrile (CAS 150617-68-8) and 4-(piperidin-4-yl)benzamide (CAS 886362-49-8). | $^1$H NMR (400 MHz, DMSO-$d_6$) δ ppm 1.91-2.07 (m, 4 H), 2.90-3.03 (m, 1 H), 3.47-3.62 (m, 5 H), 3.80-3.90 (m, 2 H), 7.26-7.41 (m, 2 H), 7.44 (d, 2 H), 7.57 (d, 1 H), 7.70-7.82 (m, 1 H), 7.85 (d, 2 H), 7.90-7.99 (m, 2H). |
| 331 | 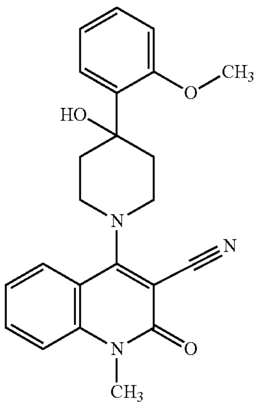 [SMILES: COc1ccccc1C1(O)CCN(c2c(C#N)c(=O)n(C)c3ccccc23)CC1] | 4-[4-hydroxy-4-(2-methoxyphenyl) piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and 4-(2-methoxyphenyl) piperidin-4-ol (CAS 81950-85-8). | $^1$H NMR (400 MHz, DMSO-$d_6$) δ ppm 1.63 (br d, 2 H) 2.72-2.87 (m, 2 H) 3.58 (s, 5 H) 3.84 (s, 5 H) 5.04-5.22 (m, 1 H) 6.90-7.09 (m, 2H) 7.19-7.32 (m, 1 H) 7.34-7.42 (m, 1 H) 7.52-7.67 (m, 2 H) 7.69-7.79 (m, 1 H) 7.86-7.96 (m, 1 H). LC-MS (Method 2): $R_t$ = 1.13 min; MS (ESIpos): m/z = 390 $[M + H]^+$ |

TABLE 14-continued

Compounds were prepared as referenced

| Example | Structure | IUPAC-Name | Starting Materials | Analytics |
|---|---|---|---|---|
| 332 | 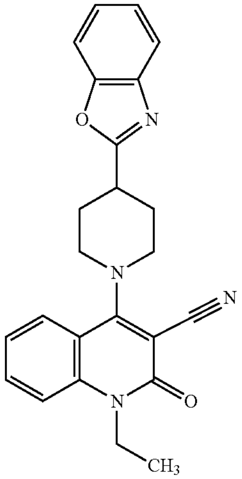 [SMILES: CCn1c(=O)c(C#N)c(N2CCC(c3nc4ccccc4o3)CC2)c2ccccc21] | 4-[4-(1,3-benzoxazol-2-yl)piperidin-1-yl]-1-ethyl-2-oxo-1,2-dihydroquinoline-3-carbonitrile | Prepared in analogy to example 52 with intermediate 151 and 2-(piperidin-4-yl)-1,3-benzoxazole (51784-03-3). | $^1H$ NMR (400 MHz, DMSO-$d_6$) δ ppm 1.20 (t, 3 H), 2.09-2.23 (m, 2 H), 2.32 (ddd, 2 H), 3.42-3.53 (m, 1 H), 3.55-3.66 (m, 2 H), 3.83 (br d, 2 H), 4.21-4.29 (m, 2 H), 7.32-7.41 (m, 3 H), 7.63 (d, 1 H), 7.68-7.79 (m, 3 H), 7.90 (dd, 1 H). LC-MS (Method 1): $R_t$ = 1.24 min; MS (ESIpos): m/z = 399 $[M + H]^+$ |
| 333 | 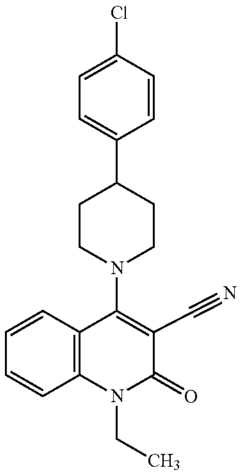 [SMILES: CCn1c(=O)c(C#N)c(N2CCC(c3ccc(Cl)cc3)CC2)c2ccccc21] | 4-[4-(4-chlorophenyl) piperidin-1-yl]-1-ethyl-2-oxo-1,2-dihydroquinoline-3-carbonitrile | Prepared in analogy to example 52 with intermediate 151 and 4-(4-chloro-phenyl)piperidine (26905-02-2). | $^1H$ NMR (400 MHz, DMSO-$d_6$) δ ppm 1.20 (t, 3 H), 1.87-2.02 (m, 4 H), 2.92 (br s, 1 H), 3.43-3.56 (m, 2 H), 3.82 (br d, 2H), 4.25 (q, 2 H), 7.31-7.37 (m, 1 H), 7.40 (s, 4 H), 7.63 (d, 1 H), 7.71-7.79 (m, 1 H), 7.95 (dd, 1 H). LC-MS (Method 1): $R_t$ = 1.43 min; MS (ESIpos): m/z = 392 $[M + H]^+$ |
| 334 | 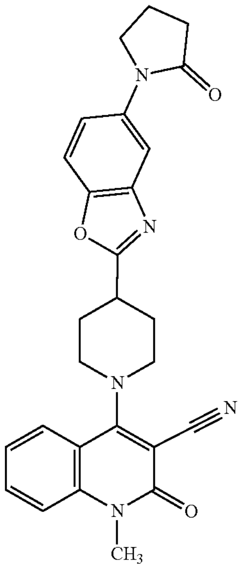 [SMILES: Cn1c(=O)c(C#N)c(N2CCC(c3nc4cc(N5CCCC5=O)ccc4o3)CC2)c2ccccc21] | 1-methyl-2-oxo-4-{4-[5-(2-oxopyrrolidin-1-yl)-1,3-benzoxazol-2-yl]piperidin-1-yl}-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 153. | $^1H$ NMR (400 MHz, DMSO-$d_6$) δ ppm 2.10 (br d, 4 H) 2.27-2.37 (m, 2 H) 3.42-3.53 (m, 1 H) 3.55-3.64 (m, 5 H) 3.79-3.87 (m, 2 H) 3.90 (t, 2H) 7.27-7.38 (m, 1 H) 7.54-7.61 (m, 1 H) 7.67-7.78 (m, 3H) 7.86-7.91 (m, 1 H) 7.94-7.98 (m, 1 H). LC-MS (Method 2): $R_t$ = 1.04 min; MS (ESIpos): m/z = 468 $[M + H]^+$ |

TABLE 14-continued

| Compounds were prepared as referenced | | | | |
| --- | --- | --- | --- | --- |
| Example | Structure | IUPAC-Name | Starting Materials | Analytics |
| 335 | 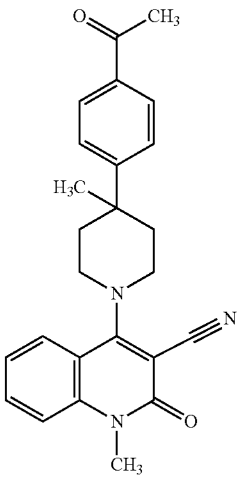 [SMILES: CC(=O)c1ccc(C2(C)CCN(c3c(C#N)c(=O)n(C)c4ccccc34)CC2)cc1] | 4-[4-(4-acetylphenyl)-4-methylpiperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 155. | $^1$H NMR (400 MHz, DMSO-$d_6$) δ ppm 1.31-1.34 (m, 1 H) 1.34 (s, 2 H) 2.00-2.10 (m, 2 H) 2.33-2.41 (m, 2H) 2.58 (s, 3 H) 3.49 (br d, 2 H) 3.56 (s, 3 H) 3.66-3.75 (m, 2 H) 7.30-7.36 (m, 1 H) 7.55 (d, 1 H) 7.63 (d, 2 H) 7.73 (ddd, 1 H) 7.86-7.88 (m, 1 H) 7.86-7.86 (m, 1 H) 7.88 (dd, 1 H) 7.97 (d, 2 H). |
| 336 | 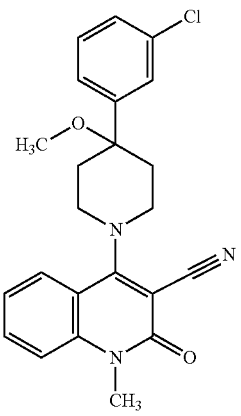 [SMILES: COC1(c2cccc(Cl)c2)CCN(c2c(C#N)c(=O)n(C)c3ccccc23)CC1] | 4-[4-(3-chlorophenyl)-4-methoxypiperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 158. | 1H NMR (400 MHz, DMSO-d6) δ ppm 2.14-2.31 (m, 4 H) 2.98 (s, 3 H) 3.58 (s, 3 H) 3.59-3.67 (m, 2 H) 3.68-3.78 (m, 2 H) 7.29-7.36 (m, 1 H) 7.39-7.44 (m, 1 H) 7.45-7.49 (m, 2H)7.52 (d, 1 H) 7.57 (d, 1 H) 7.74 (ddd, 1 H) 7.95 (dd, 1 H). LC-MS (Method 1): $R_t$ = 1.33 min; MS (ESIpos): m/z = 408 $[M + H]^+$ |

Example 337

6-(dimethylphosphoryl)-1-methyl-4-[4-methyl-4-(5-methyl-1,3-benzoxazol-2-yl)piperidin-1-yl]-2-oxo-1,2-dihydroquinoline-3-carbonitrile

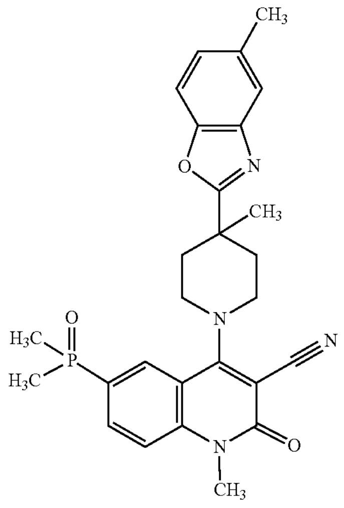 [SMILES: Cc1ccc2oc(C3(C)CCN(c4c(C#N)c(=O)n(C)c5ccc(P(C)(C)=O)cc45)CC3)nc2c1]

To a suspension of 950 mg 6-bromo-1-methyl-4-[4-methyl-4-(5-methyl-1,3-benzoxazol-2-yl)piperidin-1-yl]-2-oxo-1,2-dihydroquinoline-3-carbonitrile (1.93 mmol, example 171), 67.1 mg (9,9-dimethyl-9H-xanthene-4,5-diyl)bis(diphenylphosphine) (116 μmol), 21.7 mg palladium (II) diacetate (97 μmol) and 451 mg tripotassium phosphate (2.13 mmol) in 40 mL DMF was added 178 mg dimethylphosphine oxide (2.13 mmol, CAS 7211-39-4) and the mixture was stirred for 2 h at 80° C. Water was added, and the reaction was extracted with dichloromethane (2×). The organic phase was washed with water and brine and dried over sodium sulfate. After evaporation of the solvent, the residue was purified by flash chromatography (silica, dichloromethane/methanol gradient 0-5%) 630 mg of the title compound were obtained (95% purity, 66% yield).

$^1$H-NMR (400 MHz, DMSO-d6) δ[ppm]: 1.50 (s, 3H) 1.71 (d, 6H) 1.93-2.13 (m, 2H) 2.43 (s, 3H) 3.58 (s, 5H) 3.71-3.89 (m, 2H) 7.12-7.26 (m, 1H) 7.52-7.63 (m, 2H) 7.65-7.72 (m, 1H) 7.98-8.11 (m, 1H) 8.15-8.24 (m, 1H).

LC-MS Method 2): $R_t$=1.04 min; MS (ESIpos): m/z=489 $[M+H]^+$

Example 338

6-(dimethylphosphoryl)-1-methyl-4-[4-(5-methyl-1,3-benzoxazol-2-yl)piperidin-1-yl]-2-oxo-1,2-dihydroquinoline-3-carbonitrile

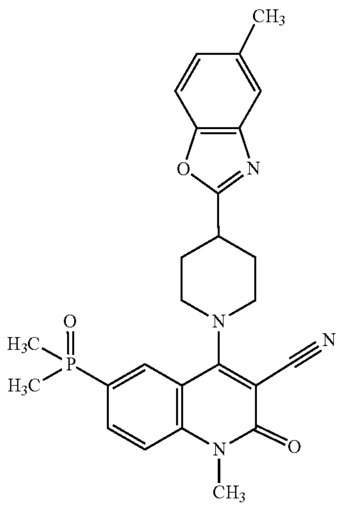 [SMILES: Cc1ccc2oc(C3CCN(c4c(C#N)c(=O)n(C)c5ccc(P(C)(C)=O)cc45)CC3)nc2c1]

To a suspension of 400 mg 6-bromo-1-methyl-4-[4-(5-methyl-1,3-benzoxazol-2-yl)piperidin-1-yl]-2-oxo-1,2-dihydroquinoline-3-carbonitrile (838 μmol, example 396), 29.1 mg (9,9-dimethyl-9H-xanthene-4,5-diyl)bis(diphenylphosphine) (50.3 μmol), 9.41 mg palladium(II) diacetate (41.9 μmol) and 196 mg tripotassium phosphate (922 μmol) in 20 mL DMF was added 77.8 mg dimethylphosphine oxide (922 μmol, CAS 7211-39-4) and the mixture was stirred for 2 h at 80° C. Water was added, and the reaction was extracted with dichloromethane (2×). The organic phase was washed with water and brine and dried over sodium sulfate. After evaporation of the solvent, the residue was purified by flash chromatography (silica, dichloromethane/methanol gradient 0-10%) 165 mg of the title compound were obtained (95% purity, 41% yield).

$^1$H-NMR (400 MHz, DMSO-d6) δ[ppm]: 1.70 (d, J=13.43 Hz, 6H) 2.05-2.22 (m, 2H) 2.28-2.38 (m, 2H) 2.42 (s, 3H) 3.40-3.52 (m, 1H) 3.60 (s, 5H) 3.80-3.94 (m, 2H) 7.10-7.25 (m, 1H) 7.47-7.62 (m, 2H) 7.64-7.73 (m, 1H) 8.00-8.11 (m, 1H) 8.18-8.29 (m, 1H).

LC-MS Method 2): $R_t$=0.99 min; MS (ESIpos): m/z=475 $[M+H]^+$

Example 339

6-(methanesulfonyl)-1-methyl-4-[4-(5-methyl-1,3-benzoxazol-2-yl)piperidin-1-yl]-2-oxo-1,2-dihydroquinoline-3-carbonitrile

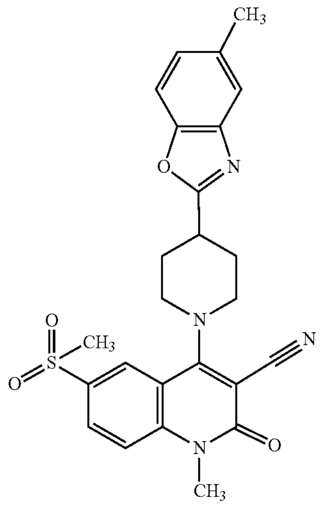 [SMILES: Cc1ccc2oc(C3CCN(c4c(C#N)c(=O)n(C)c5ccc(S(C)(=O)=O)cc45)CC3)nc2c1]

120 mg Sodium methanesulfinate (1.17 mmol), 47 µl (1S,2S)-cyclohexane-1,2-diamine (350 µmol) and 401 mg copper(I) trifluoromethanesulfonate benzene complex (117 µmol, CAS 42152-46-5) were added to a $N_2$-degassed solution of 280 mg 6-bromo-1-methyl-4-[4-(5-methyl-1,3-benzoxazol-2-yl)piperidin-1-yl]-2-oxo-1,2-dihydroquinoline-3-carbonitrile (587 µmol, example 396) in 5.1 mL DMSO. It was first stirred 4.5 h at 110° C. and then over night at room temperature. The reaction mixture was filtered and the crude product was purified by column chromatography (dichloromethane 100→dichloromethane:ethanol 80:20) and by RP-HPLC. The product was obtained in 2% yield (6 mg).

$^1$H NMR (400 MHz, DMSO-$d_6$) δ ppm 2.07-2.18 (m, 2H) 2.30-2.38 (m, 2H) 2.42 (s, 3H) 3.29 (s, 3H) 3.44-3.53 (m, 1H) 3.62 (s, 3H) 3.63-3.69 (m, 2H) 3.89 (br d, 2H) 7.19 (dd, 1H) 7.54 (s, 1H) 7.59 (d, 1H) 7.80 (d, 1H) 8.20 (dd, 1H) 8.30 (d, 1H).

Example 340

4-[4-(1-benzothiophen-2-yl)-4-hydroxypiperidin-1-yl]-1-methyl-2-oxo-1,2-dihydroquinoline-3-carbonitrile

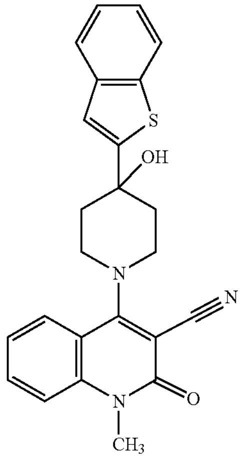 [SMILES: Cn1c(=O)c(C#N)c(N2CCC(O)(c3cc4ccccc4s3)CC2)c2ccccc21]

To a suspension of 27 mg 4-chloro-1-methyl-2-oxo-1,2-dihydroquinoline-3-carbonitrile (124 µmol) in 1.24 mL ethanol was added 52 µl triethylamine (370 µmol) and 29 mg 4-(1-benzothiophen-2-yl)piperidin-4-ol (124 µmol, intermediate 254). The mixture was stirred 5 h at 90° C. and overnight at room temperature. The reaction mixture was filtered and washed with ethanol. The product was obtained in 52% yield (28 mg).

$^1$H-NMR (400 MHz, DMSO-d6): δ [ppm]=2.03-2.13 (m, 2H), 2.33-2.43 (m, 2H), 3.58 (s, 3H), 3.65 (br d, 2H), 3.77-3.88 (m, 2H), 5.99 (s, 1H), 7.28-7.39 (m, 3H), 7.41 (s, 1H), 7.58 (d, 1H), 7.75 (ddd, 1H), 7.80 (dd, 1H), 7.91-7.99 (m, 1H).

LC-MS Method 2): $R_t$=1.21 min; MS (ESIpos): m/z=416 $[M+H]^+$

Example 341

4-[4-(1-benzothiophen-2-yl)-4-methoxypiperidin-1-yl]-1-methyl-2-oxo-1,2-dihydroquinoline-3-carbonitrile

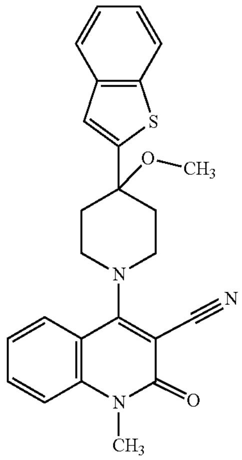 [SMILES: COC1(c2cc3ccccc3s2)CCN(c2c(C#N)c(=O)n(C)c3ccccc23)CC1]

To a suspension of 62 mg 4-chloro-1-methyl-2-oxo-1,2-dihydroquinoline-3-carbonitrile (283 μmol) in 2.8 mL ethanol was added 120 μl triethylamine (850 μmol) and 70 mg 4-(1-benzothiophen-2-yl)-4-methoxypiperidine (283 μmol, intermediate 255). The mixture was stirred 5 h at 90° C. and overnight at room temperature. The reaction mixture was filtered and the solid was washed with ethanol and dried. The product was obtained in 73% yield (98 mg).

$^1$H-NMR (400 MHz, DMSO-d6): 5 [ppm]=2.34-2.41 (m, 4H), 3.12 (s, 3H), 3.58 (s, 3H), 3.61-3.81 (m, 4H), 7.30-7.42 (m, 3H), 7.50 (s, 1H), 7.57 (dd, 1H), 7.74 (ddd, 1H), 7.82-7.88 (m, 1H), 7.90-8.00 (m, 2H).

Example 342

4-[4-(1-benzothiophen-2-yl)-4-methylpiperidin-1-yl]-1-methyl-2-oxo-1,2-dihydroquinoline-3-carbonitrile

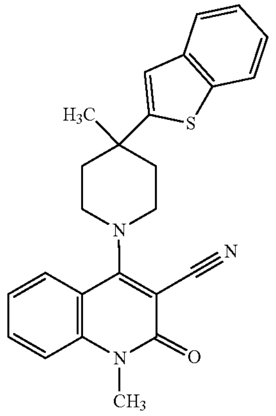 [SMILES: Cn1c(=O)c(C#N)c(N2CCC(C)(c3cc4ccccc4s3)CC2)c2ccccc21]

To a suspension of 40 mg 4-chloro-1-methyl-2-oxo-1,2-dihydroquinoline-3-carbonitrile (181 μmol) in 1.8 mL ethanol was added 76 μl triethylamine (540 μmol) and 97 mg of the salt of 4-(1-benzothiophen-2-yl)-4-methylpiperidine with hydrochloric acid (50% purity, 181 μmol, intermediate 278). The reaction mixture was stirred overnight at 90° C. The reaction mixture was cooled to room temperature and then concentrated under reduced pressure. Purification by prep HPLC gave the product in 16% yield (13.5 mg).

$^1$H-NMR (400 MHz, DMSO-d6): 5 [ppm]=1.48 (s, 3H), 2.04-2.14 (m, 2H), 2.31-2.41 (m, 2H), 3.53-3.64 (m, 5H), 3.72 (ddd, 2H), 7.28-7.41 (m, 4H), 7.56 (dd, 1H), 7.70-7.81 (m, 2H), 7.91 (ddd, 2H).

LC-MS Method 2): $R_t$=1.46 min; MS (ESIpos): m/z=414 $[M+H]^+$

Example 343

4-[4-(6-methoxynaphthalen-2-yl)piperidin-1-yl]-1-methyl-2-oxo-1,2-dihydroquinoline-3-carbonitrile

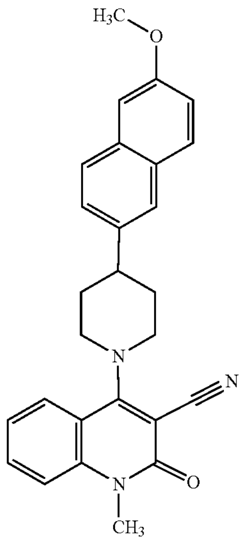 [SMILES: COc1ccc2cc(C3CCN(c4c(C#N)c(=O)n(C)c5ccccc45)CC3)ccc2c1]

The reaction was carried out in two separate MW-Vials. 100 mg 4-(4-bromopiperidin-1-yl)-1-methyl-2-oxo-1,2-dihydroquinoline-3-carbonitrile (289 μmol, intermediate 26), 308 mg 2-bromo-6-methoxynaphthalene (1.30 mmol), then 0.2 mL 2,6-dimethylpyridine (1.7 mmol, CAS 108-48-5) and 6.5 mg $[Ir(dF(CF_3)ppy_2)_2(dtbbpy)]PF_6$ (5.8 μmol, CAS 870987-63-6) were dissolved in 4 mL 1,2-dimethoxyethane and split onto 2 reaction vials. In a separate vial, 3.2 mg nickel(II) chloride ethylene glycol dimer (14 μmol, CAS 29046-78-4) and 4,4'-di-tert-butyl-2,2'-bipyridine (3.9 mg, 14 μmol; CAS 72914-19-3) were dissolved in 2 mL 1,2-dimethoxyethane followed by stirring for 5 min. The catalyst solution was syringed and distributed to the sealed reaction vials and degassed for 5 minutes with argon. 89 μl tris (trimethylsilyl)silan (290 μmol, CAS 1873-77-4) was added afterwards by distribution amond the two vials. The MW-vials were placed in a waterbath where they were subsequently irradiated by two 40 W Kessil LED Aquarium lamps. Water was added and the mixture was extracted with ethyl acetate 3×. The combined organic layers were filtered over a hydrophobic filter and the solvent was evaporated under reduced pressure. The product was purified by column chromatography and the product was obtained as a yellow oil in 26% yield (34 mg).

$^1$H NMR (400 MHz, DMSO-$d_6$) ppm 1.98-2.14 (m, 4H) 2.97-3.07 (m, 1H) 3.52-3.64 (m, 5H) 3.83-3.92 (h, 5H) 7.15 (dd, 1H) 7.30 (d, 1H) 7.33-7.40 (m, 1H) 7.51 (dd, 1H) 7.58 (d, 1H) 7.72-7.84 (m, 4H) 7.97 (dd, 1H).

LC-MS (Method 1): $R_t$=1.36 min; MS (ESIpos): m/z=424 $[M+H]^+$

TABLE 15

| Compounds were prepared as referenced | | | | |
|---|---|---|---|---|
| Example | Structure | IUPAC-Name | Starting Materials | Analytics |
| 344 | 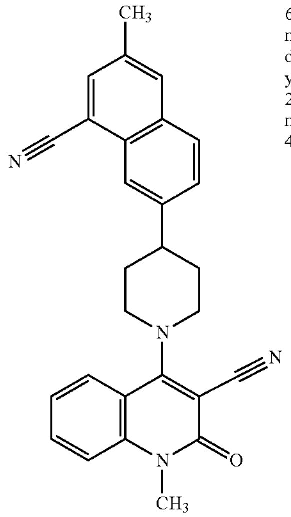 | 6-[1-(3-cyano-1-methyl-2-oxo-1,2-dihydroquinolin-4-yl)piperidin-4-yl]-2-methylquinoline-4-carbonitrile | Prepared in analogy to example 343 using intermediate 26 and 6-bromo-2-methylquinoline-4-carbonitrile (CAS 1416439-30-9). | $^1$H NMR (400 MHz, DMSO-$d_6$) δ ppm 2.05-2.16 (m, 4 H) 2.70-2.74 (m, 3 H) 3.25 (brs, 1 H) 3.59 (s, 5 H) 3.90 (br d, 2H) 7.34-7.40 (m, 1 H) 7.58 (d, 1 H) 7.75 (ddd, 1 H) 7.95 (d, 1 H) 8.01 (br d, 2 H) 8.03-8.11 (m, 2 H). LC-MS (method 1): $R_t$ = 1.22 min; MS (ESIpos): m/z = 434 $[M + H]^+$ |
| 345 | 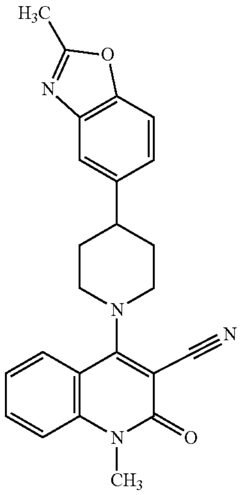 [SMILES: Cc1nc2cc(C3CCN(c4c(C#N)c(=O)n(C)c5ccccc45)CC3)ccc2o1] | 1-methyl-4-[4-(2-methyl-1,3-benzoxazol-5-yl)piperidin-1-yl]-2-oxo-1,2-dihydroquinoline-3-carbonitrile | Prepared in analogy to example 343 using intermediate 26 and 5-bromo-2-methyl-1,3-benzoxazole (CAS 5676-56-2). | $^1$H NMR (400 MHz, DMSO-$d_6$) δ ppm 1.94-2.12 (m, 4 H) 2.60 (s, 3 H) 2.98-3.07 (m, 1 H) 3.48-3.58 (m, 2H) 3.59 (s, 3 H) 3.85 (br d, 2 H) 7.32-7.41 (m, 2H) 7.55-7.63 (m, 2 H) 7.66 (d, 1 H) 7.75 (ddd, 1 H) 7.98 (dd, 1 H). LC-MS (Method 1): $R_t$ = 1.16 min; MS (ESIpos): m/z = 399 $[M + H]^+$ |

TABLE 15-continued

Compounds were prepared as referenced

| Example | Structure | IUPAC-Name | Starting Materials | Analytics |
|---|---|---|---|---|
| 346 | 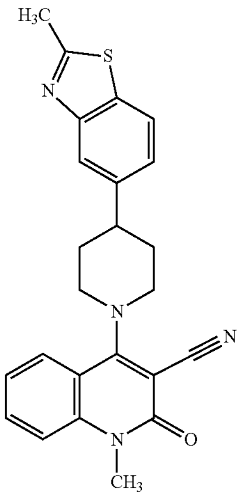 [SMILES: Cc1nc2cc(C3CCN(c4c(C#N)c(=O)n(C)c5ccccc45)CC3)ccc2s1] | 1-methyl-4-[4-(2-methyl-1,3-benzothiazol-5-yl)piperidin-1-yl]-2-oxo-1,2-dihydroquinoline-3-carbonitrile | Prepared in analogy to example 343 using intermediate 26 and 5-bromo-2-methyl-1,3-benzothiazole (CAS 63837-11-6) and lithiumcarbonate (6 equiv) as a base instead of 2,6-dimethylpyridine. | $^1$H NMR (400 MHz, DMSO-$d_6$) δ ppm 1.99-2.13 (m, 4 H) 2.80 (s, 3 H) 3.00-3.11 (m, 1 H) 3.50-3.57 (m, 2 H) 3.59 (s, 3 H) 3.87 (br d, 2 H) 7.33-7.39 (m, 1 H) 7.43 (dd, 1 H) 7.58 (d, 1 H) 7.75 (br ddd, 1 H) 7.91 (d, 1 H) 7.98 (d, 2 H). LC-MS (Method 1): $R_t$ = 1.23 min; MS (ESIpos): m/z = 415 $[M + H]^+$ |
| 347 | 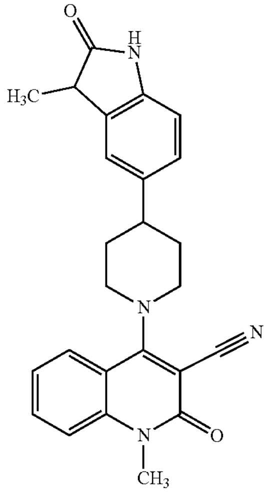 [SMILES: CC1C(=O)Nc2ccc(C3CCN(c4c(C#N)c(=O)n(C)c5ccccc45)CC3)cc21] | (rac)-1-methyl-4-[4-(3-methyl-2-oxo-2,3-dihydro-1 H-indol-5-yl)piperidin-1-yl]-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 160. | $^1$H-NMR (400 MHz, DMSO-$d_6$): δ [ppm] = 1.05 (t, 1H), 1.34 (d, 3H), 1.86-2.04 (m, 4H), 2.78-2.91 (m, 1H), 3.46-3.56 (m, 2H), 3.58 (s, 3H), 3.84 (br d, 2H), 6.78 (d, 1H), 7.14 (d, 1H), 7.28 (s, 1H), 7.32-7.40 (m, 1H), 7.58 (d, 1H), 7.75 (ddd, 1H), 7.94 (dd, 1H), 10.28 (s, 1H). LC-MS (Method 2): $R_t$ = 1.02 min; MS (ESIpos): m/z = 413 $[M + H]^+$ |

Example 348

1-methyl-4-{4-[3-(2-methylphenyl)-1,2,4-oxadiazol-5-yl]piperidin-1-yl}-2-oxo-1,2-dihydroquinoline-3-carbonitrile

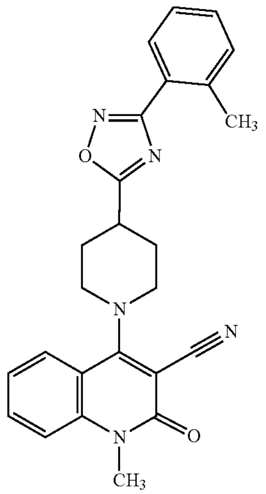 [SMILES: Cc1ccccc1-c1noc(C2CCN(c3c(C#N)c(=O)n(C)c4ccccc34)CC2)n1]

A suspension of 250 mg 4-chloro-1-methyl-2-oxo-1,2-dihydroquinoline-3-carbonitrile (1.14 mmol), 306 mg 4-[3-(2-methylphenyl)-1,2,4-oxadiazol-5-yl]piperidine (1.26 mmol, intermediate 248) and 0.48 mL triethylamine (3.4 mmol) in 20 mL 2-propanol was stirred for 6 h at 90° C. After this time, water and ethyl acetate were added and the reaction was stirred. The precipitate that was generated by this procedure was collected by filtration and dried in vacuum. 240 mg of the title compound were obtained (47% yield, 95% purity).

$^1$H-NMR (400 MHz, DMSO-d6) δ[ppm]: 2.08-2.24 (m, 2H) 2.31-2.39 (m, 2H) 2.55-2.60 (m, 3H) 3.30-3.32 (m, 1H) 3.58-3.69 (m, 5H) 3.79-3.91 (m, 2H) 7.32-7.44 (m, 3H) 7.45-7.51 (m, 1H) 7.56-7.62 (m, 1H) 7.70-7.78 (m, 1H) 7.86-7.92 (m, 1H) 7.92-7.98 (m, 1H).

LC-MS Method 2): $R_t$=1.33 min; MS (ESIpos): m/z=426 $[M+H]^+$

TABLE 16

Compounds were prepared as referenced

| Example | Structure | IUPAC-Name | Starting Materials | Analytics |
|---|---|---|---|---|
| 349 | 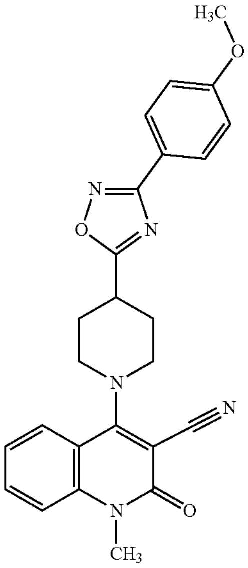 [SMILES: COc1ccc(-c2noc(C3CCN(c4c(C#N)c(=O)n(C)c5ccccc45)CC3)n2)cc1] | 4-{4-[3-(4-methoxyphenyl)-1,2,4-oxadiazol-5-yl]piperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 162. | $^1$H NMR (400 MHz, DMSO-$d_6$) δ ppm 2.04-2.21 (m, 2 H) 2.25-2.37 (m, 3 H) 2.59-2.75 (m, 1 H) 3.58 (s, 6 H) 3.84 (s, 5 H) 7.12 (d, 2 H) 7.25-7.42 (m, 1 H) 7.58 (dd, 1 H) 7.75 (ddd, 1 H) 7.89 (dd, 1 H) 7.93-8.01 (m, 2 H). LC-MS (Method 2): $R_t$ = 1.24 min; MS (ESIpos): m/z = 442 $[M + H]^+$ |

TABLE 16-continued

| Compounds were prepared as referenced | | | | |
|---|---|---|---|---|
| Example | Structure | IUPAC-Name | Starting Materials | Analytics |
| 350 | 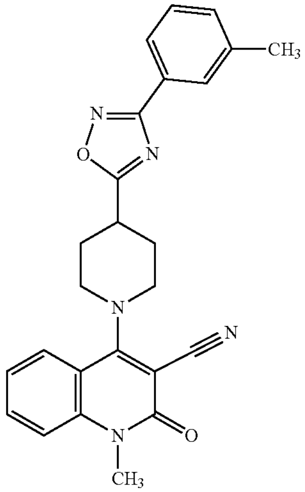 [SMILES: Cc1cccc(-c2noc(C3CCN(c4c(C#N)c(=O)n(C)c5ccccc45)CC3)n2)c1] | 1-methyl-4-{4-[3-(3-methylphenyl)-1,2,4-oxadiazol-5-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 164. | $^1$H NMR (400 MHz, DMSO-$d_6$) δ ppm 2.08-2.21 (m, 2 H) 2.29-2.34 (m, 2 H) 2.39-2.44 (m, 3 H) 3.51-3.65 (m, 6 H) 3.79-3.90 (m, 2H) 7.31-7.39 (m, 1 H) 7.39-7.51 (m, 2H) 7.55-7.62 (m, 1 H) 7.72-7.78 (m, 1 H) 7.80-7.92 (m, 3 H). |
| 351 | 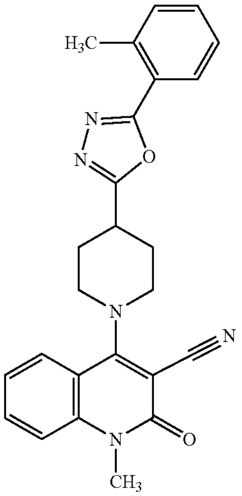 [SMILES: Cc1ccccc1-c1nnc(C2CCN(c3c(C#N)c(=O)n(C)c4ccccc34)CC2)o1] | 1-methyl-4-{4-[5-(2-methylphenyl)-1,3,4-oxadiazol-2-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 166. | $^1$H NMR (400 MHz, DMSO-$d_6$) δ ppm 2.08-2.22 (m, 2 H) 2.27-2.37 (m, 2 H) 2.60-2.66 (m, 3 H) 3.47-3.55 (m, 1 H) 3.56-3.65 (m, 5H) 3.79-3.91 (m, 2 H) 7.32-7.38 (m, 1 H) 7.39-7.48 (m, 2 H) 7.48-7.54 (m, 1 H) 7.55-7.60 (m, 1 H) 7.69-7.80 (m, 1 H) 7.86-7.95 (m, 2H). |
| 352 | 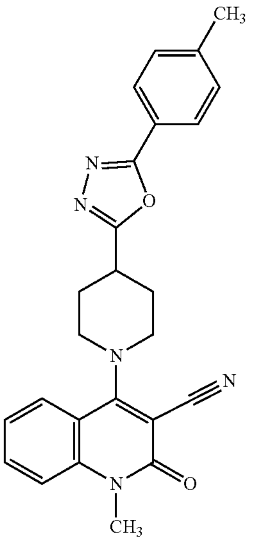 [SMILES: Cc1ccc(-c2nnc(C3CCN(c4c(C#N)c(=O)n(C)c5ccccc45)CC3)o2)cc1] | 1-methyl-4-{4-[5-(4-methylphenyl)-1,3,4-oxadiazol-2-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 168. | $^1$H NMR (400 MHz, DMSO-$d_6$) δ ppm 2.10-2.20 (m, 2 H) 2.26-2.36 (m, 2 H) 2.38-2.45 (m, 3 H) 3.45-3.54 (m, 1 H) 3.56-3.65 (m, 5H) 3.78-3.90 (m, 2 H) 7.33-7.39 (m, 1 H) 7.39-7.46 (m, 2 H) 7.56-7.61 (m, 1 H) 7.71-7.79 (m, 1 H) 7.85-7.96 (m, 3H). |

TABLE 16-continued

Compounds were prepared as referenced

| Example | Structure | IUPAC-Name | Starting Materials | Analytics |
|---|---|---|---|---|
| 353 | 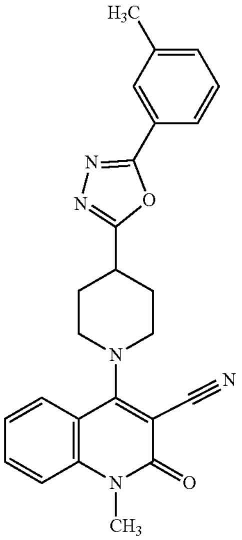 [SMILES: Cc1cccc(-c2nnc(C3CCN(c4c(C#N)c(=O)n(C)c5ccccc45)CC3)o2)c1] | 1-methyl-4-{4-[5-(3-methylphenyl)-1,3,4-oxadiazol-2-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 170. | $^1$H NMR (400 MHz, DMSO-$d_6$) δ ppm 2.10-2.21 (m, 2 H) 2.27-2.36 (m, 2 H) 2.39-2.44 (m, 3 H) 3.46-3.54 (m, 1 H) 3.55-3.66 (m, 5 H) 3.80-3.88 (m, 2 H) 7.32-7.38 (m, 1 H) 7.43-7.47 (m, 1 H) 7.47-7.53 (m, 1 H) 7.56-7.60 (m, 1 H) 7.72-7.78 (m, 1 H) 7.81-7.87 (m, 2 H) 7.87-7.91 (m, 1 H). |
| 354 | 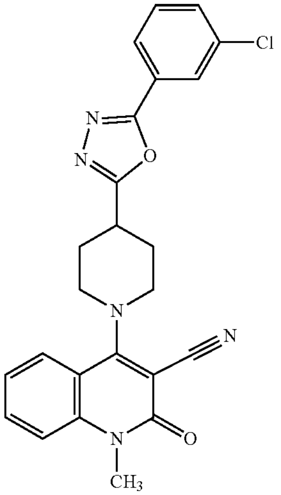 [SMILES: Cn1c(=O)c(C#N)c(N2CCC(c3nnc(-c4cccc(Cl)c4)o3)CC2)c2ccccc21] | 4-{4-[5-(3-chlorophenyl)-1,3,4-oxadiazol-2-yl]piperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 172. | $^1$H NMR (400 MHz, DMSO-$d_6$) δ ppm 2.09-2.22 (m, 2 H) 2.29-2.36 (m, 2 H) 3.47-3.55 (m, 1 H) 3.55-3.68 (m, 5 H) 3.78-3.88 (m, 2H) 7.32-7.38 (m, 1 H) 7.55-7.61 (m, 1 H) 7.62-7.69 (m, 1 H) 7.69-7.78 (m, 2H) 7.86-7.92 (m, 1 H) 7.97-8.06 (m, 2 H). |
| 355 | 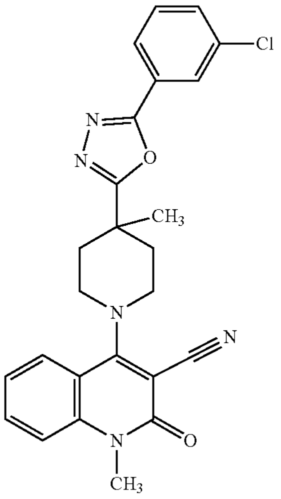 [SMILES: Cn1c(=O)c(C#N)c(N2CCC(C)(c3nnc(-c4cccc(Cl)c4)o3)CC2)c2ccccc21] | 4-{4-[5-(3-chlorophenyl)-1,3,4-oxadiazol-2-yl]-4-methylpiperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 174. | $^1$H NMR (400 MHz, DMSO-$d_6$) δ ppm 1.50-1.56 (m, 3 H) 2.04-2.13 (m, 2 H) 2.45-2.49 (m, 2 H) 3.51-3.65 (m, 5 H) 3.68-3.79 (m, 2H) 7.29-7.38 (m, 1 H) 7.54-7.60 (m, 1 H) 7.62-7.69 (m, 1 H) 7.71-7.77 (m, 2H) 7.87-7.92 (m, 1 H) 8.00-8.09 (m, 2H). |

TABLE 16-continued

| Compounds were prepared as referenced | | | | |
|---|---|---|---|---|
| Example | Structure | IUPAC-Name | Starting Materials | Analytics |
| 356 | 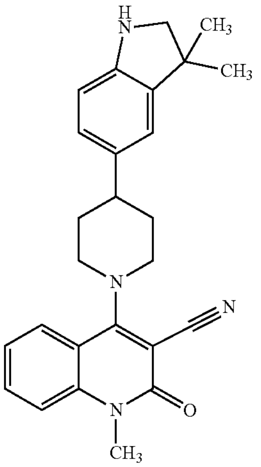 [SMILES: Cn1c(=O)c(C#N)c(N2CCC(c3ccc4c(c3)C(C)(C)CN4)CC2)c2ccccc21] | 4-[4-(3,3-dimethyl-2,3-dihydro-1 H-indol-5-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 176. | $^1$H-NMR (400 MHz, DMSO-$d_6$): δ [ppm] = 1.20 (s, 6H), 1.85-1.96 (m, 4H), 2.69-2.80 (m, 1H), 3.16 (d,2H), 3.45-3.55 (m, 2H), 3.58 (s, 3H), 3.83 (br d, 2H), 5.40 (s, 1H), 6.47 (d, 1H), 6.53 (dd, 1H), 6.91 (d, 1H), 7.31-7.40 (m, 1H), 7.57 (dd, 1H), 7.74 (ddd, 1H), 7.91 (dd, 1H). LC-MS (Method 2): $R_t$ = 1.34 min; MS (ESIpos): m/z = 413 $[M + H]^+$ |
| 357 | 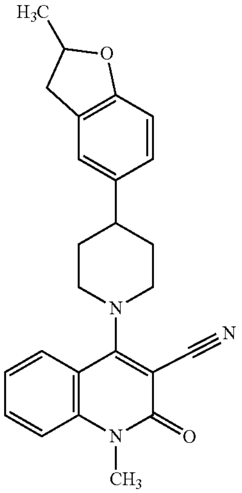 [SMILES: CC1Cc2cc(C3CCN(c4c(C#N)c(=O)n(C)c5ccccc45)CC3)ccc2O1] | 1-methyl-4-{4-[(2R)-2-methyl-2,3-dihydro-1-benzofuran-5-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 179. | $^1$H NMR (400 MHz, DMSO-$d_6$) δ ppm 1.37 (d, J = 6.34 Hz, 3 H) 1.85-2.00 (m, 4 H) 2.73-2.85 (m, 2 H) 3.23-3.32 (m, 1 H) 3.44-3.54 (m, 2 H) 3.58 (s, 3 H) 3.82 (br d, 2 H) 4.82-4.93 (m, 1 H) 6.67 (d, 1 H) 7.04 (dd, 1 H) 7.19 (s, 1 H) 7.31-7.40 (m, 1 H) 7.57 (d, 1 H) 7.74 (ddd, 1 H) 7.93 (dd, 1 H). LC-MS (Method 2): $R_t$ = 1.35 min; MS (ESIpos): m/z = 399 $[M + H]^+$ |
| 358 | 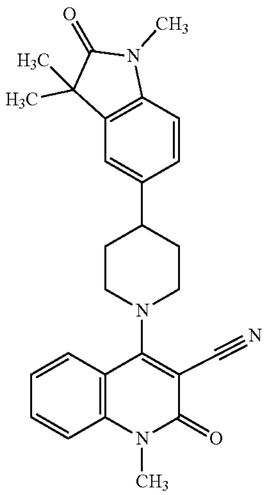 [SMILES: CN1C(=O)C(C)(C)c2cc(C3CCN(c4c(C#N)c(=O)n(C)c5ccccc45)CC3)ccc21] | 1-methyl-2-oxo-4-[4-(1,3,3-trimethyl-2-oxo-2,3-dihydro-1 H-indol-5-yl)piperidin-1-yl]-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 181. | $^1$H NMR (400 MHz, DMSO-$d_6$) δ ppm 1.28 (s, 6 H) 1.90-2.06 (m, 5 H) 2.82-2.92 (m, 1 H) 3.13 (s, 3 H) 3.46-3.56 (m, 2 H) 3.58 (s, 3 H) 3.85 (br d, 2 H) 6.96 (d, 1 H) 7.25 (dd, 1 H) 7.33-7.41 (m, 2 H) 7.58 (dd, 1 H) 7.75 (ddd, 1 H) 7.95 (dd, 1 H). LC-MS (Method 2): $R_t$ = 1.18 min; MS (ESIpos): m/z = 441 $[M + H]^+$ |

TABLE 16-continued

Compounds were prepared as referenced

| Example | Structure | IUPAC-Name | Starting Materials | Analytics |
|---|---|---|---|---|
| 359 | 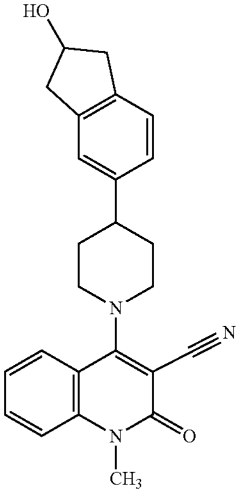 | 4-[4-(2-hydroxy-2,3-dihydro-1H-inden-5-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 184. | $^1$H NMR (400 MHz, DMSO-$d_6$) δ ppm 1.86-2.04 (m, 4 H) 2.72 (s, 2 H) 2.79-2.90 (m, 1 H) 2.98-3.09 (m, 2H) 3.44-3.55 (m, 2 H) 3.58 (s, 3 H) 3.83 (br d, 2 H) 4.46-4.54 (m, 1 H) 4.84 (d, 1 H) 7.07-7.12 (m, 1 H) 7.13-7.17 (m, 1 H) 7.20 (s, 1 H) 7.32-7.39 (m, 1 H) 7.57 (dd, 1 H) 7.74 (ddd, 1 H) 7.94 (dd, 1 H) LC-MS (Method 2): $R_t$ = 1.09 min; MS (ESIpos): m/z = 400 [M + H]$^+$ |
| 360 | 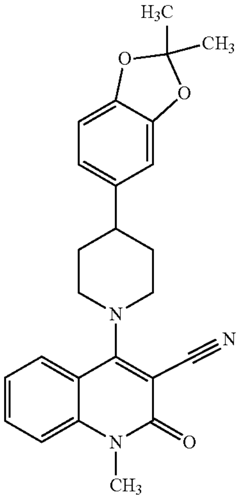 [SMILES: Cn1c(=O)c(C#N)c(N2CCC(c3ccc4c(c3)OC(C)(C)O4)CC2)c2ccccc21] | 4-[4-(2,2-dimethyl-2H-1,3-benzodioxol-5-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 187. | $^1$H-NMR (400 MHz, DMSO-$d_6$): δ [ppm] = 1.63 (s, 6H), 1.86-2.02 (m, 4H), 2.74-2.86 (m, 1H), 3.43-3.54 (m, 2H), 3.58 (s, 3H), 3.81 (br d, 2H), 6.74-6.77 (m, 2H), 6.87 (s, 1H), 7.31-7.39 (m, 1H), 7.57 (dd, 1H), 7.74 (ddd, 1H), 7.94 (dd, 1H). LC-MS (Method 2): $R_t$ = 1.38 min; MS (ESIpos): m/z = 416 [M + H]$^+$ |
| 361 | 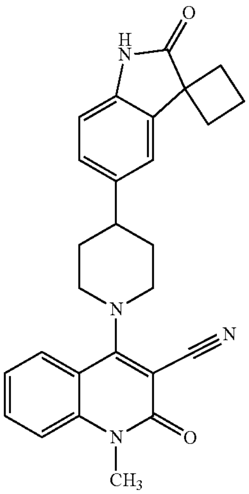 [SMILES: Cn1c(=O)c(C#N)c(N2CCC(c3ccc4c(c3)C3(CCC3)C(=O)N4)CC2)c2ccccc21] | 1-methyl-2-oxo-4-[4-(2'-oxo-1',2'-dihydrospiro[cyclobutane-1,3'-indol]-5'-yl)piperidin-1-yl]-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 189. | $^1$H NMR (400 MHz, DMSO-$d_6$) δ ppm 1.86-2.02 (m, 4H) 2.13-2.31 (m, 4 H) 2.36-2.46 (m, 2 H) 2.82-2.93 (m, 1 H) 3.47-3.56 (m, 2H) 3.58 (s, 3 H) 3.84 (br d, 2 H) 6.75 (d, 1 H) 6.99 (dd, 1 H) 7.33-7.38 (m, 1 H) 7.50 (d, 1 H) 7.55-7.60 (m, 1 H) 7.74 (td, 1 H) 7.93 (dd, 1 H) 10.22 (s, 1 H). LC-MS (Method 1): $R_t$ = 1.18 min; MS (ESIpos): m/z = 439 [M + H]$^+$ |

TABLE 16-continued

| Compounds were prepared as referenced | | | | |
|---|---|---|---|---|
| Example | Structure | IUPAC-Name | Starting Materials | Analytics |
| 362 | 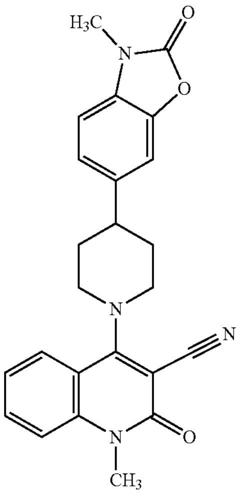 [SMILES: Cn1c(=O)oc2cc(C3CCN(c4c(C#N)c(=O)n(C)c5ccccc45)CC3)ccc21] | 1-methyl-4-[4-(3-methyl-2-oxo-2,3-dihydro-1,3-benzoxazol-6-yl)piperidin-1-yl]-2-oxo-1,2-dihydroquinoline-3-carbonitrile | Prepared in analogy to example 343 using intermediate 26 and 6-bromo-3-methyl-1,3-benzoxazol-2(3H)-one (CAS 67927-44-0) and Lithiumcarbonate (6 equiv) as a base instead of 2,6-dimethylpyridine. | $^1$H NMR (400 MHz, CDCl3) δ ppm 1.93-2.14 (m, 4 H) 2.90 (br tt, 1 H) 3.41 (s, 3 H) 3.54-3.66 (m, 2 H) 3.69 (s, 3 H) 3.90 (br d, 2 H) 6.94 (d, 1 H) 7.14 (dd, 1 H) 7.18 (d, 1 H) 7.27-7.32 (m, 1 H) 7.38 (d, 1 H) 7.61-7.70 (m, 1 H) 7.86 (dd, 1 H). LC-MS (Method 1): $R_t$ = 1.10 min; MS (ESIpos): m/z = 415 [M + H]$^+$ |
| 363 | 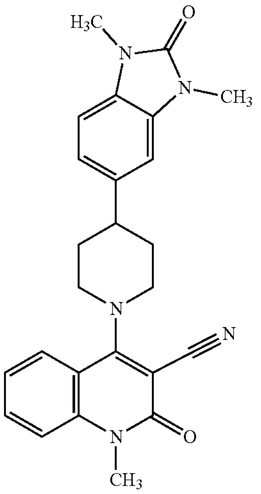 | 4-[4-(1,3-dimethyl-2-oxo-2,3-dihydro-1H-benzimidazol-5-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 191. | $^1$H NMR (400 MHz, CDCl3) δ ppm 1.98-2.15 (m, 4H) 2.85-2.97 (m, 1 H) 3.43 (s, 3 H) 3.46 (s, 3 H) 3.57-3.67 (m, 2 H) 3.70 (s, 3 H) 3.93 (br d, 2 H) 6.90 (d, 1 H) 6.95 (d, 1 H) 7.05 (dd, 1 H) 7.27-7.31 (m, 1 H) 7.38 (d, 1 H) 7.66 (br ddd, 1 H) 7.89 (dd, 1 H). LC-MS (Method 1): $R_t$ = 1.06 min; MS (ESIpos): m/z = 472 [M + H]$^+$ |
| 364 | 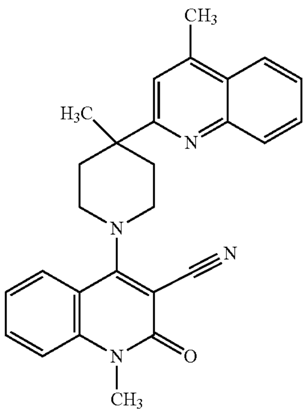 [SMILES: Cc1cc(C2(C)CCN(c3c(C#N)c(=O)n(C)c4ccccc34)CC2)nc2ccccc12] | 1-methyl-4-[4-methyl-4-(4-methylquinolin-2-yl)piperidin-1-yl]-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 194. | $^1$H-NMR (400 MHz, DMSO-$d_6$): δ [ppm] = 1.40 (s, 3H), 2.00-2.13 (m, 2H), 2.61-2.77 (m, 5H), 3.47-3.60 (m, 5H), 3.68-3.79 (m, 2H), 7.29-7.37 (m, 1H), 7.52-7.66 (m, 3H), 7.68-7.78 (m, 2H), 7.89 (dd, 1H), 7.97 (dd, 1H), 8.08 (dd, 1H). LC-MS (Method 2): $R_t$ = 1.41 min; MS (ESIpos): m/z = 423 [M + H]$^+$ |

TABLE 16-continued

| Compounds were prepared as referenced | | | | |
|---|---|---|---|---|
| Example | Structure | IUPAC-Name | Starting Materials | Analytics |
| 365 | 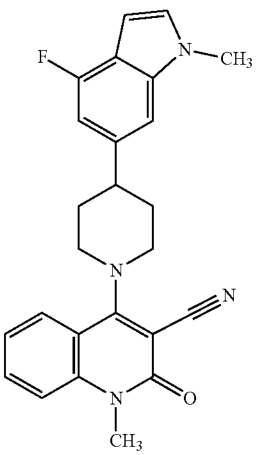 [SMILES: Cn1ccc2c(F)cc(C3CCN(c4c(C#N)c(=O)n(C)c5ccccc45)CC3)cc21] | 4-[4-(4-fluoro-1-methyl-1H-indol-6-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 196. | $^1$H-NMR (400 MHz, DMSO-$d_6$): δ [ppm] = 1.96-2.15 (m, 4H), 2.96-3.06 (m, 1H), 3.48-3.62 (m, 5H), 3.79-3.91 (m, 5H), 6.40-6.45 (m, 1H), 6.88 (d, 1H), 7.27 (s, 1H), 7.31-7.41 (m, 2H), 7.58 (d, 1H), 7.75 (ddd, 1H), 7.98 (dd, 1H). LC-MS (Method 2): $R_t$ = 1.35 min; MS (ESIpos): m/z = 415 $[M + H]^+$ |
| 366 | 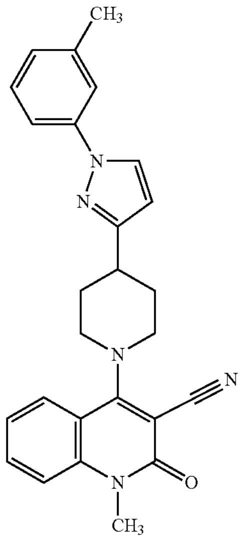 [SMILES: Cc1cccc(-n2ccc(C3CCN(c4c(C#N)c(=O)n(C)c5ccccc45)CC3)n2)c1] | 1-methyl-4-{4-[1-(3-methylphenyl)-1H-pyrazol-3-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 200. | $^1$H NMR (400 MHz, DMSO-$d_6$) δ ppm 1.92-2.06 (m, 2 H) 2.16 (br dd, 2 H) 3.02-3.14 (m, 1 H) 3.49-3.56 (m, 2H) 3.58 (s, 3 H) 3.84 (br d, 2 H) 6.57 (d, 1 H) 7.31-7.39 (m, 2 H) 7.51 (t, 1 H) 7.57 (d, 1 H) 7.74 (br ddd, 1 H) 7.83 (ddd, 1 H) 7.88-7.92 (m, 1 H) 7.93 (t, 1 H) 8.53 (d, 1 H). LC-MS (Method 1): $R_t$ = 1.38 min; MS (ESIpos): m/z = 424 $[M + H]^+$ |
| 367 | 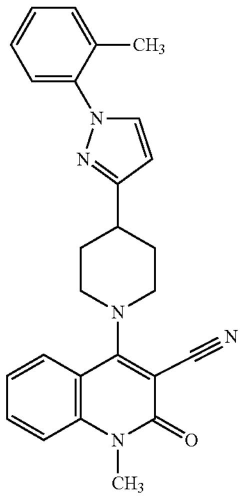 [SMILES: Cc1ccccc1-n1ccc(C2CCN(c3c(C#N)c(=O)n(C)c4ccccc34)CC2)n1] | 1-methyl-4-{4-[1-(2-methylphenyl)-1H-pyrazol-3-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 280 | $^1$H NMR (400 MHz, DMSO-$d_6$) δ ppm 1.93-2.06 (m, 2 H) 2.17 (br dd, 2 H) 2.24 (s, 3 H) 3.06 (tt, 1 H) 3.50-3.56 (m, 1 H) 3.58 (s, 3 H) 3.83 (br d, 2 H) 6.45 (d, 1 H) 7.30-7.41 (m, 4H) 7.57 (d, 1 H) 7.71-7.76 (m, 1 H) 7.90 (dd, 1 H) 7.95 (d, 1 H). LC-MS (Method 1): $R_t$ = 1.32 min; MS (ESIpos): m/z = 424 $[M + H]^+$ |

TABLE 16-continued

Compounds were prepared as referenced

| Example | Structure | IUPAC-Name | Starting Materials | Analytics |
|---|---|---|---|---|
| 368 | 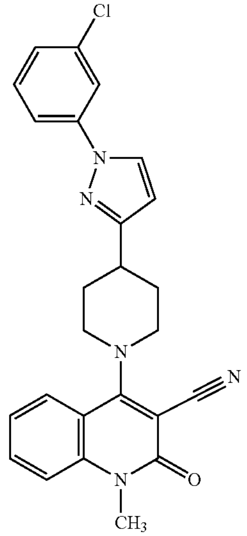 [SMILES: Cn1c(=O)c(C#N)c(N2CCC(c3ccn(-c4cccc(Cl)c4)n3)CC2)c2ccccc21] | 4-{4-[1-(3-chlorophenyl)-1H-pyrazol-3-yl]piperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 202. | $^1$H NMR (400 MHz, DMSO-$d_6$) δ ppm 1.94-2.07 (m, 2 H) 2.16 (br dd, 2 H) 2.38 (s, 3 H) 3.01-3.12(m, 1 H) 3.50-3.56 (m, 2 H) 3.59 (s, 3 H) 3.84 (br d, 2 H) 6.51 (d, 1 H) 7.09 (d, 1 H) 7.35 (t, 2 H) 7.55-7.63 (m, 2 H) 7.66 (s, 1 H) 7.74 (br ddd, 7.22, 1.52 Hz, 1 H) 7.91 (dd, 1 H) 8.41 (d, 1 H). LC-MS (Method 1): $R_t$ = 1.38 min; MS (ESIpos): m/z = 444 $[M + H]^+$ |
| 369 | 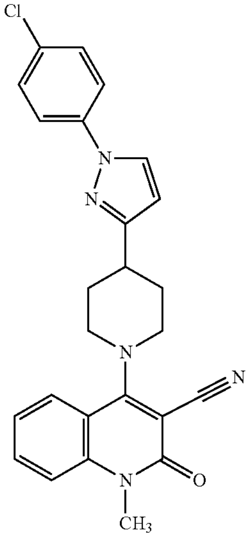 [SMILES: Cn1c(=O)c(C#N)c(N2CCC(c3ccn(-c4ccc(Cl)cc4)n3)CC2)c2ccccc21] | 4-{4-[1-(4-chlorophenyl)-1H-pyrazol-3-yl]piperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 204. | $^1$H NMR (600 MHz, DMSO-$d_6$) δ ppm 1.96-2.05 (m, 2 H) 2.13-2.19 (m, 2 H) 3.07 (br tt, 1 H) 3.52-3.56 (m, 2H) 3.58 (s, 3 H) 3.84 (br d, 2 H) 6.55 (d, 1 H) 7.33-7.37 (m, 1 H) 7.53-7.56 (m, 2 H) 7.57 (d, 1 H) 7.74 (br ddd, 1 H) 7.84-7.88 (m, 2 H) 7.90 (dd, 1 H) 8.47 (d, 1 H). LC-MS (Method 1): $R_t$ = 1.19 min; MS (ESIpos): m/z = 444 $[M + H]^+$ |

TABLE 16-continued

| Compounds were prepared as referenced | | | | |
|---|---|---|---|---|
| Example | Structure | IUPAC-Name | Starting Materials | Analytics |
| 370 | 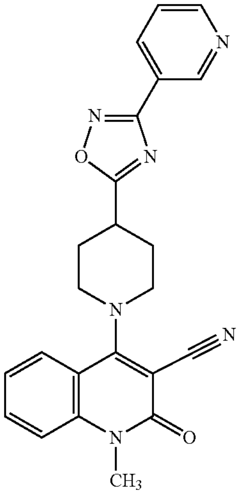 [SMILES: Cn1c(=O)c(C#N)c(N2CCC(c3nc(-c4cccnc4)no3)CC2)c2ccccc21] | 1-methyl-2-oxo-4-{4-[3-(pyridin-3-yl)-1,2,4-oxadiazol-5-yl]piperidin-1-yl}-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 207. | $^{1}$H-NMR (400 MHz, DMSO-$d_6$): δ [ppm] = 2.11-2.22 (m, 2H), 2.30-2.37 (m, 2H), 3.56-3.67 (m, 6H), 3.85 (br d, 2H), 7.35 (t, 1H), 7.58 (d, 1H), 7.61-7.65 (m, 1H), 7.89 (dd, 1H), 8.39 (dt, 1H), 8.80 (dd, 1H), 9.18-9.23 (m, 1H), 9.19 (dd, 1H). LC-MS (Method 2): $R_t$ = 1.03 min; MS (ESIpos): m/z = 413 $[M + H]^+$ |
| 371 | 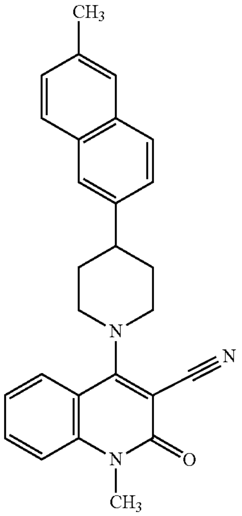 [SMILES: Cc1ccc2cc(C3CCN(c4c(C#N)c(=O)n(C)c5ccccc45)CC3)ccc2c1] | 1-methyl-4-[4-(2-methylquinolin-6-yl)piperidin-1-yl]-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 210. | $^{1}$H NMR (400 MHz, DMSO-$d_6$) δ ppm 2.02-2.13 (m, 4 H) 2.65 (s, 3 H) 3.03-3.15 (m, 1 H) 3.59 (s, 5 H) 3.83-3.94 (m, 2 H) 7.32-7.44 (m, 2H) 7.56-7.62 (m, 1 H) 7.72-7.79 (m, 2H) 7.83-7.87 (m, 1 H) 7.87-7.93 (m, 1 H) 7.95-8.01 (m, 1 H) 8.19-8.26 (m, 1 H). |
| 372 | 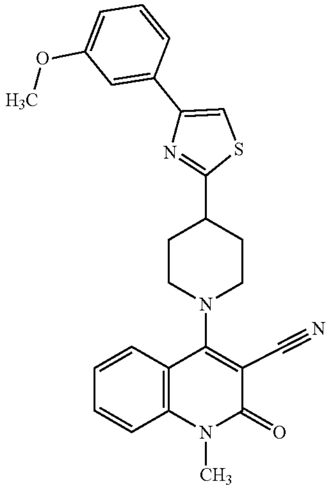 [SMILES: COc1cccc(-c2csc(C3CCN(c4c(C#N)c(=O)n(C)c5ccccc45)CC3)n2)c1] | 4-{4-[4-(3-methoxyphenyl)-1,3-thiazol-2-yl]piperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 216. | $^{1}$H-NMR (400 MHz, DMSO-$d_6$): δ [ppm] = 2.02-2.16 (m, 2H), 2.27-2.36 (m, 2H), 3.48 (tt, 1H), 3.56-3.65 (m, 5H), 3.82 (s, 3H), 3.87 (br d, 2H), 6.89-6.95 (m, 1H), 7.36 (t, 2H), 7.51-7.54 (m, 1H), 7.55-7.61 (m, 2H), 7.75 (ddd, 1H), 7.90 (dd, 1H), 8.08 (s, 1H). LC-MS (Method 2): $R_t$ = 1.33 min; MS (ESIpos): m/z = 457 $[M + H]^+$ |

TABLE 16-continued

Compounds were prepared as referenced

| Example | Structure | IUPAC-Name | Starting Materials | Analytics |
|---|---|---|---|---|
| 373 | 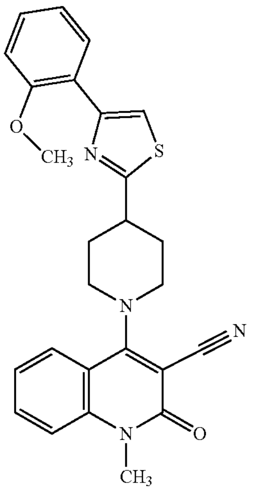 [SMILES: COc1ccccc1-c1csc(C2CCN(c3c(C#N)c(=O)n(C)c4ccccc34)CC2)n1] | 4-{4-[4-(2-methoxyphenyl)-1,3-thiazol-2-yl]piperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 212. | $^1$H-NMR (400 MHz, DMSO-$d_6$): δ [ppm] = 2.03-2.16 (m, 2H), 2.27-2.35 (m, 2H), 3.41-3.52 (m, 1H), 3.54-3.65 (m, 5H), 3.87 (br d, 2H), 3.93 (s, 3H), 7.05 (td, 1H), 7.15 (dd, 1H), 7.30-7.40 (m, 2H), 7.55-7.62 (m, 1H), 7.74 (ddd, 1H), 7.90 (dd, 1H), 8.02 (s, 1H), 8.20 (dd, 1H). LC-MS (Method 2): $R_t$ = 1.38 min; MS (ESIpos): m/z = 457 $[M + H]^+$ |
| 374 | 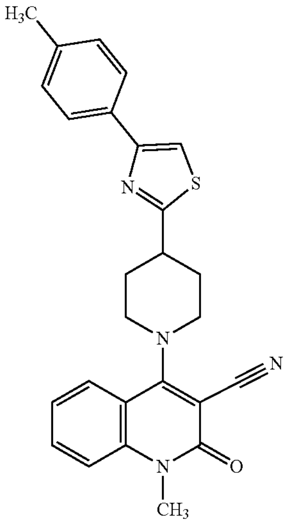 [SMILES: Cc1ccc(-c2csc(C3CCN(c4c(C#N)c(=O)n(C)c5ccccc45)CC3)n2)cc1] | 1-methyl-4-{4-[4-(4-methylphenyl)-1,3-thiazol-2-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 213. | $^1$H NMR (400 MHz, DMSO-$d_6$) δ ppm 2.02-2.15 (m, 2 H) 2.26-2.37 (m, 6 H) 3.42-3.52 (m, 1 H) 3.54-3.65 (m, 5 H) 3.87 (br d, 2 H) 7.25 (d, 2 H) 7.36 (ddd, 1 H) 7.58 (d, 1 H) 7.75 (ddd, 1 H) 7.85-7.89 (m, 2H) 7.90 (dd, 1 H) 7.96 (s, 1 H). LC-MS (Method 2): $R_t$ = 1.42 min; MS (ESIpos): m/z = 441 $[M + H]^+$ |

Example 375

4-[4-(1,3-dimethyl-1H-indazol-5-yl)piperidin-1-yl]-1-methyl-2-oxo-1,2-dihydroquinoline-3-carbonitrile

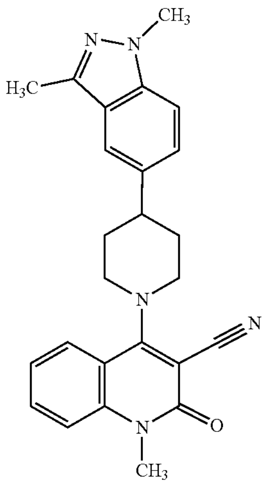 [SMILES: Cc1nn(C)c2ccc(C3CCN(c4c(C#N)c(=O)n(C)c5ccccc45)CC3)cc12]

The reaction was carried out in two separate MW-Vials. 150 mg 4-(4-bromopiperidin-1-yl)-1-methyl-2-oxo-1,2-dihydroquinoline-3-carbonitrile (433 µmol, intermediate 26), 439 mg 5-bromo-1,3-dimethyl-1H-indazole (1.95 mmol), then 0.3 mL 2,6-dimethylpyridine (2.6 mmol, CAS 108-48-5) and 9.7 mg $[Ir(dF(CF_3)ppy_2)_2(dtbbpy)]PF_6$ (8.7 µmol, CAS 870987-63-6) were dissolved in 6 mL 1,2-dimethoxyethane and split onto 2 reaction vials. In a separate vial, 4.8 mg nickel(II) chloride ethylene glycol dimer (22 µmol, CAS 29046-78-4) and 5.8 mg 4,4'-di-tert-butyl-2,2'-bipyridine (22 µmol; CAS 72914-19-3) were dissolved in 3 mL 1,2-dimethoxyethane followed by stirring for 5 min. The catalyst solution was syringed and distributed to the sealed reaction vials and degassed for 5 minutes with argon. 130 µl tris(trimethylsilyl)silan (430 µmol; CAS 1873-77-4) was added afterwards by distribution amond the two vials. The MW-vials were placed in a waterbath where they were subsequently irradiated by two 40 W Kessil LED Aquarium lamps. Water was added and the mixture was extracted with ethyl acetate 3×. The combined organic layers were filtered over a hydrophobic filter and the solvent was evaporated under reduced pressure. The product was purified by column chromatography and the product was obtained in 34% yield (62 mg).

$^1$H NMR (400 MHz, DMSO-$d_6$) δ ppm 1.95-2.12 (m, 4H) 2.48 (s, 3H) 2.95-3.06 (m, 1H) 3.49-3.57 (m, 2H) 3.59 (s, 3H) 3.87 (br d, 2H) 3.94 (s, 3H) 7.35-7.43 (m, 2H) 7.49-7.53 (m, 1H) 7.58 (dd, 1H) 7.62 (s, 1H) 7.75 (ddd, 1H) 7.98 (dd, 1H).

LC-MS (Method 1): $R_t$=1.24 min; MS (ESIpos): m/z=413 $[M+H]^+$

TABLE 17

Compounds were prepared as referenced

| Example | Structure | IUPAC-Name | Starting Materials | Analytics |
|---|---|---|---|---|
| 376 | 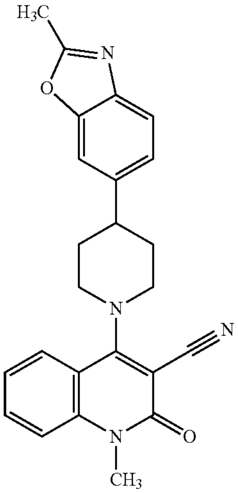 [SMILES: Cc1nc2ccc(C3CCN(c4c(C#N)c(=O)n(C)c5ccccc45)CC3)cc2o1] | 1-methyl-4-[4-(2-methyl-1,3-benzoxazol-6-yl)piperidin-1-yl]-2-oxo-1,2-dihydroquinoline-3-carbonitrile | Prepared in analogy to example 343 using intermediate 26 and 6-bromo-2-methyl-1,3-benzoxazole (CAS 151230-42-1) and Lithiumcarbonate (6 equiv) as a base instead of 2,6-dimethylpyridine. | $^1$H NMR (400 MHz, DMSO-$d_6$) δ ppm 1.95-2.12 (m, 4 H) 2.60 (s, 3 H) 2.98-3.09 (m, 1 H) 3.48-3.57 (m, 2 H) 3.59 (s, 3 H) 3.85 (br d, 2 H) 7.32-7.39 (m, 2 H) 7.56-7.63 (m, 2 H) 7.68 (d, 1 H) 7.75 (br ddd, 1 H) 7.97 (dd, 1 H). LC-MS (Method 1): $R_t$ = 1.11 min; MS (ESIpos): m/z = 399 $[M + H]^+$ |

TABLE 17-continued

| Compounds were prepared as referenced | | | | |
|---|---|---|---|---|
| Example | Structure | IUPAC-Name | Starting Materials | Analytics |
| 377 | 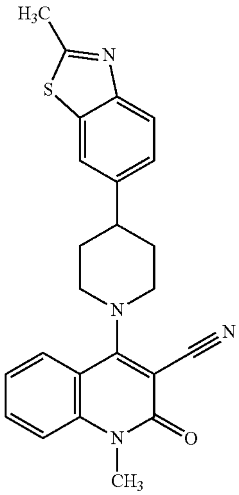 [SMILES: Cc1nc2ccc(C3CCN(c4c(C#N)c(=O)n(C)c5ccccc45)CC3)cc2s1] | 1-methyl-4-[4-(2-methyl-1,3-benzothiazol-6-yl) piperidin-1-yl]-2-oxo-1,2-dihydroquinoline-3-carbonitrile | Prepared in analogy to example 343 using intermediate 26 and 6-bromo-2-methyl-1,3-benzothiazole (CAS 5304-21-2). | $^{1}$H NMR (400 MHz, DMSO-$d_6$) δ ppm 1.97-2.13 (m, 4 H) 2.79 (s, 3 H) 3.04 (br s, 1 H) 3.55 (br s, 2 H) 3.59 (s, 4 H) 3.86 (br d, 2 H) 7.33-7.39 (m, 1 H) 7.49 (dd, 1 H) 7.58 (d, 1 H) 7.75 (ddd, 1 H) 7.87 (d, 1 H) 7.97 (dd, 1 H) 8.03 (d, 1 H). LC-MS (Method 1): $R_t$ = 1.21 min; MS (ESIpos): m/z = 415 $[M + H]^+$ |
| 378 | 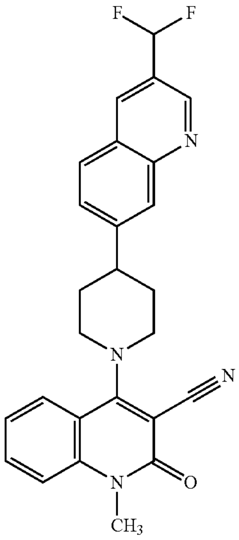 [SMILES: Cn1c(=O)c(C#N)c(N2CCC(c3ccc4cc(C(F)F)cnc4c3)CC2)c2ccccc21] | 4-{4-[3-(difluoromethyl) quinolin-7-yl] piperidin-1-yl}-1-methyl-2-oxo-1,2-dihydroquinoline-3-carbonitrile | Prepared in analogy to example 343 using intermediate 26 and 7-bromo-3-(difluoromethyl) quinoline (CAS 1207747-91-8). | $^{1}$H NMR (400 MHz, DMSO-$d_6$) δ ppm 2.08-2.22 (m, 4 H) 3.15-3.25 (m, 1 H) 3.54-3.65 (m, 5 H) 3.90 (br d, 2 H) 7.16-7.50 (m, 1 H) 7.35-7.41 (m, 1 H) 7.59 (d, 1 H) 7.71-7.84 (m, 2 H) 8.01 (dd, 1 H) 8.06 (s, 1 H) 8.13 (d, 1 H) 8.63 (s, 1 H) 9.05 (d, 1 H). LC-MS (Method 1): $R_t$ = 1.15 min; MS (ESIpos): m/z = 445 $[M + H]^+$ |

Example 379

(rac)-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile

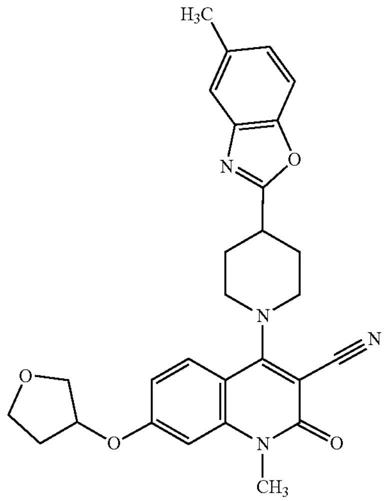 [SMILES: Cc1ccc2oc(C3CCN(c4c(C#N)c(=O)n(C)c5cc(OC6CCOC6)ccc45)CC3)nc2c1]

A mixture of 1.1 g 7-hydroxy-1-methyl-4-[4-(5-methyl-1,3-benzoxazol-2-yl)piperidin-1-yl]-2-oxo-1,2-dihydroquinoline-3-carbonitrile (example 293), 2.6 g cesium carbonate and 801 mg 3-bromooxolane in 40 mL DMF was stirred for 5 hours at 100° C. under argon. Water was added and the mixture was extracted with ethyl acetate (3×). The combined organic layers were washed with brine, the solvent was evaporated under reduced pressure and the crude product was purified by flash chromatography (silica, dichloromethane/methanol gradient 0-3%) to give 870 mg of the title compound.

$^1$H NMR (400 MHz, DMSO-d6) δ ppm 1.95-2.20 (m, 3H) 2.22-2.38 (m, 3H) 2.40-2.44 (m, 3H) 2.53-2.55 (m, 1H) 3.38-3.48 (m, 1H) 3.51-3.61 (m, 5H) 3.73-4.00 (m, 6H) 5.24-5.34 (m, 1H) 6.87-6.93 (m, 1H) 6.93-7.01 (m, 1H) 7.14-7.23 (m, 1H) 7.49-7.54 (m, 1H) 7.55-7.63 (m, 1H) 7.74-7.86 (m, 1H).

Example 380

1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile, Enantiomer 1

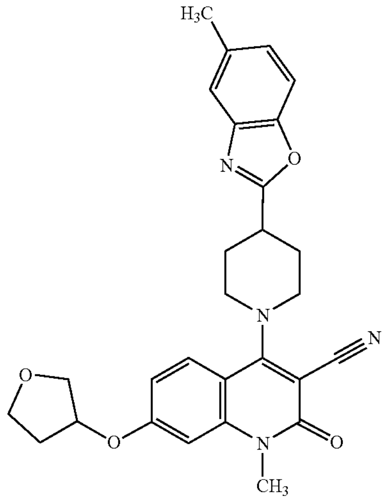 [SMILES: Cc1ccc2oc(C3CCN(c4c(C#N)c(=O)n(C)c5cc(OC6CCOC6)ccc45)CC3)nc2c1]

860 mg 1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (Example 379) were separated by chiral HPLC: Instrument: Labomatic HD5000, Labocord-5000; Gilson GX-241, Labcol Vario 4000, Säule: Amylose SA 5μ 250×30 mm; Eluent A: Hexane+0.1 Vol-% Diethylamine (99%);

Eluent B: Ethanol; Isocratic 50% A+50% B; Flow 50.0 ml/min; UV 254 nm. 152 mg of the title compound were obtained.

$^1$H NMR (400 MHz, DMSO-d6) δ ppm 1.95-2.20 (m, 3H) 2.22-2.38 (m, 3H) 2.40-2.44 (m, 3H) 2.53-2.55 (m, 1H) 3.38-3.48 (m, 1H) 3.51-3.61 (m, 5H) 3.73-4.00 (m, 6H) 5.24-5.34 (m, 1H) 6.87-6.93 (m, 1H) 6.93-7.01 (m, 1H) 7.14-7.23 (m, 1H) 7.49-7.54 (m, 1H) 7.55-7.63 (m, 1H) 7.74-7.86 (m, 1H).

Analytical chiral HPLC: $R_t$=4.82 min

Instrument: Agilent HPLC 1260; Säule: Amylose SA 3μ 100×4.6 mm;

Eluent A: Hexane+0.1 Vol-% Diethylamine (99%); Eluent B: Ethanol; Isocratic: 50% A+50% B; Flow 1.4 ml/min; Temperature: 25° C.; DAD 254 nm.

Example 381

1-methyl-4-[4-(5-methyl-1,3-benzoxazol-2-yl)piperidin-1-yl]-2-oxo-7[(oxolan-3-yl)oxy]-1,2-dihydroquinoline-3-carbonitrile, Enantiomer 2

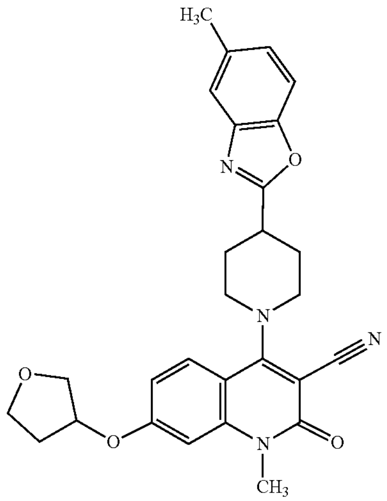 [SMILES: Cc1ccc2oc(C3CCN(c4c(C#N)c(=O)n(C)c5cc(OC6CCOC6)ccc45)CC3)nc2c1]

With the chiral separation of 860 mg 1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (Example 379) described in example 380, 120 mg of the title compound were obtained.

$^1$H NMR (400 MHz, DMSO-d6) δ ppm 1.95-2.20 (m, 3H) 2.22-2.38 (m, 3H) 2.40-2.44 (m, 3H) 2.53-2.55 (m, 1H) 3.38-3.48 (m, 1H) 3.51-3.61 (m, 5H) 3.73-4.00 (m, 6H) 5.24-5.34 (m, 1H) 6.87-6.93 (m, 1H) 6.93-7.01 (m, 1H) 7.14-7.23 (m, 1H) 7.49-7.54 (m, 1H) 7.55-7.63 (m, 1H) 7.74-7.86 (m, 1H).

Analytical chiral HPLC: $R_t$=6.53 min

Instrument: Agilent HPLC 1260; Säule: Amylose SA 3μ 100×4.6 mm;

Eluent A: Hexane+0.1 Vol-% Diethylamine (99%); Eluent B: Ethanol; Isocratic: 50% A+50% B; Flow 1.4 ml/min; Temperature: 25° C.; DAD 254 nm.

TABLE 18

| Compounds were prepared in analogy to the synthesis of example 1 | | | | |
|---|---|---|---|---|
| Example | Structure | IUPAC-Name | Starting Materials | Analytics |
| 382 | 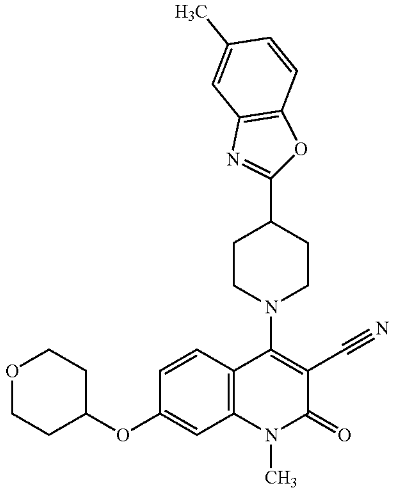 [SMILES: Cc1ccc2oc(C3CCN(c4c(C#N)c(=O)n(C)c5cc(OC6CCOCC6)ccc45)CC3)nc2c1] | 1-methyl-4-[4-(5-methyl-1,3-benzoxazol-2-yl) piperidin-1-yl]-7-[(oxan-4-yl)oxy]-2-oxo-1,2-dihydroquinoline-3-carbonitrile | Prepared in analogy to example 380 using example 293 and 4-bromotetrahydro-2H-pyran (CAS 25637-16-5). | $^1$H NMR (400 MHz, DMSO-$d_6$) δ ppm 1.55-1.72 (m, 2 H) 2.00-2.17 (m, 6 H) 2.24-2.32 (m, 2 H) 2.37-2.46 (m, 3H) 3.42 (br t, 1 H) 3.48-3.63 (m, 7 H) 3.78 (br d, 2 H) 3.87 (dt, 2 H) 4.77-4.92 (m, 1 H) 6.91-7.07 (m, 2 H) 7.13-7.23(m, 1 H) 7.49-7.54 (m, 1 H) 7.55-7.66 (m, 1 H) 7.75-7.83 (m, 1 H). |
| 383 | 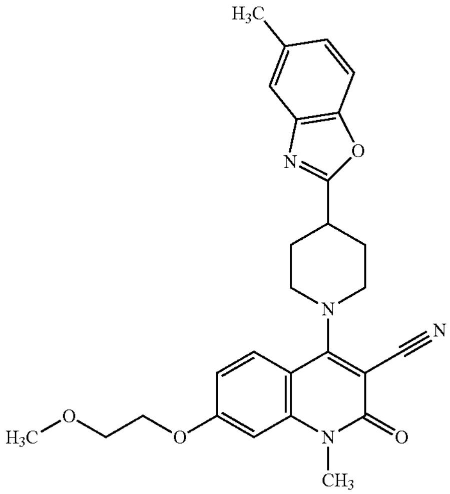 [SMILES: COCCOc1ccc2c(N3CCC(c4nc5cc(C)ccc5o4)CC3)c(C#N)c(=O)n(C)c2c1] | 7-(2-methoxyethoxy)-1-methyl-4-[4-(5-methyl-1,3-benzoxazol-2-yl)piperidin-1-yl]-2-oxo-1,2-dihydroquinoline-3-carbonitrile | Prepared in analogy to example 380 using example 293 and 1-bromo-2-methoxyethane (CAS 6482-24-2) in DMF at 100° C. | $^1$H NMR (400 MHz, DMSO-$d_6$) δ ppm 2.04-2.19 (m, 2 H) 2.24-2.35 (m, 2 H) 2.39-2.43 (m, 3 H) 3.37-3.49 (m, 1 H) 3.51-3.62 (m, 5 H) 3.67-3.74 (m, 2 H) 3.74-3.85 (m, 2 H) 4.22-4.38 (m, 2 H) 6.85-7.01 (m, 2 H) 7.16-7.23 (m, 1 H) 7.51-7.55 (m, 1 H) 7.55-7.61 (m, 1 H) 7.73-7.84 (m, 1 H). |

TABLE 18-continued

Compounds were prepared in analogy to the synthesis of example 1

| Example | Structure | IUPAC-Name | Starting Materials | Analytics |
|---|---|---|---|---|
| 384 | 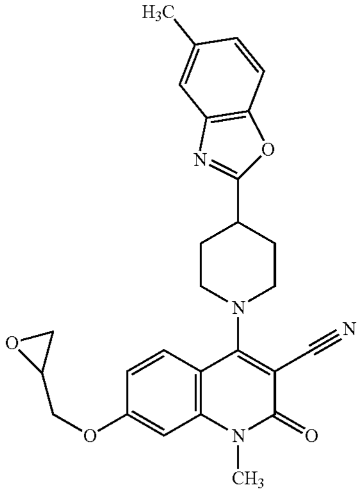 [SMILES: Cc1ccc2oc(C3CCN(c4c(C#N)c(=O)n(C)c5cc(OCC6CO6)ccc45)CC3)nc2c1] | 1-methyl-4-[4-(5-methyl-1,3-benzoxazol-2-yl) piperidin-1-yl]-7-{[oxiran-2-yl] methoxy}-2-oxo-1,2-dihydroquinoline-3-carbonitrile | Prepared in analogy to example 380 using example 293 and 2-(bromomethyl) oxirane (CAS 3132-64-7) in DMF at 100° C. | $^{1}$H NMR (400 MHz, DMSO-$d_6$) δ ppm 2.07-2.17 (m, 3 H) 2.25-2.36 (m, 2 H) 2.40-2.45 (m, 3 H) 2.74-2.81 (m, 1 H) 2.85-2.96 (m, 1 H) 3.36-3.48 (m, 3 H) 3.51-3.63 (m, 5 H) 3.73-3.86 (m, 2 H) 3.95-4.11 (m, 1 H) 4.49-4.62 (m, 1 H) 6.93-7.04 (m, 2 H) 7.14-7.23 (m, 1 H) 7.49-7.55 (m, 1 H) 7.55-7.61 (m, 1 H) 7.78-7.85 (m, 1 H) |
| 385 | 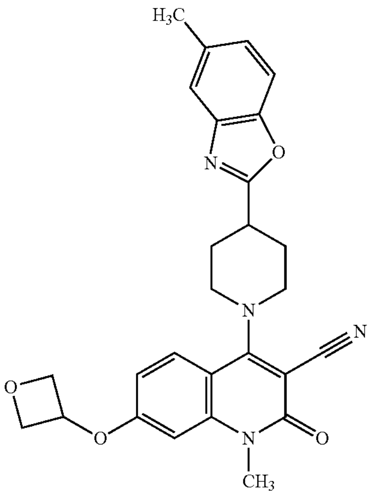 [SMILES: Cc1ccc2oc(C3CCN(c4c(C#N)c(=O)n(C)c5cc(OC6COC6)ccc45)CC3)nc2c1] | 1-methyl-4-[4-(5-methyl-1,3-benzoxazol-2-yl) piperidin-1-yl]-7-[(oxetan-3-yl) oxy]-2-oxo-1,2-dihydroquinoline-3-carbonitrile | Prepared in analogy to example 380 using Example 293 and 3-bromooxetane (CAS 39267-79-3). | $^{1}$H NMR (400 MHz, DMSO-$d_6$) δ ppm 2.03-2.17 (m, 2 H) 2.23-2.31 (m, 2 H) 2.40-2.45 (m, 3 H) 3.37-3.48 (m, 1 H) 3.50-3.65 (m, 5 H) 3.72-3.88 (m, 2 H) 4.46-4.77 (m, 2 H) 4.92-5.10 (m, 2 H) 5.45-5.59 (m, 1 H) 6.71-6.79 (m, 1 H) 6.79-6.89 (m, 1 H) 7.12-7.25 (m, 1 H) 7.49-7.54 (m, 1 H) 7.55-7.66 (m, 1 H) 7.76-7.87 (m, 1 H). |

TABLE 19

| Compounds were prepared in analogy to the synthesis of example 1 | | | | |
|---|---|---|---|---|
| Example | Structure | IUPAC-Name | Starting Materials | Analytics |
| 386 | 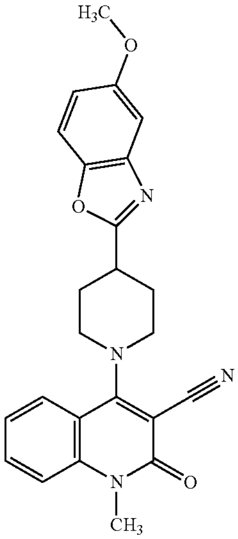 [SMILES: COc1ccc2oc(C3CCN(c4c(C#N)c(=O)n(C)c5ccccc45)CC3)nc2c1] | 4-[4-(5-methoxy-1,3-benzoxazol-2-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 219. | $^1$H NMR (400 MHz, DMSO-$d_6$) δ ppm 3.82 (br s, 1 H) 2.07-2.21 (m, 2 H) 2.25-2.33 (m, 2 H) 3.39-3.49 (m, 1 H) 3.58 (s, 5 H) 3.80 (s, 4 H) 6.96 (dd, 1 H) 7.29 (d, 1 H) 7.32-7.39 (m, 1 H) 7.55-7.63 (m, 2 H) 7.71-7.77 (m, 1 H) 7.86-7.91 (m, 1 H). |
| 387 | 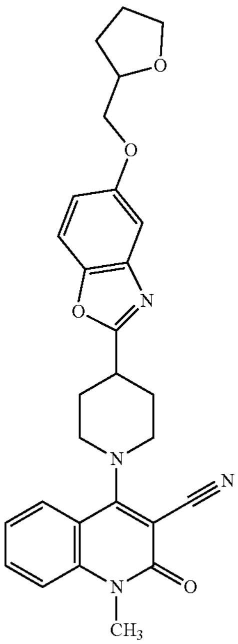 [SMILES: Cn1c(=O)c(C#N)c(N2CCC(c3nc4cc(OCC5CCCO5)ccc4o3)CC2)c2ccccc21] | 1-methyl-2-oxo-4-(4-{5-[(oxolan-2-yl)methoxy]-1,3-benzoxazol-2-yl}piperidin-1-yl)-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 220. | $^1$H NMR (400 MHz, DMSO-$d_6$) δ ppm 1.62-1.74 (m, 1 H) 1.76-1.95 (m, 2 H) 1.96-2.07 (m, 1 H) 2.08-2.22 (m, 2 H) 2.24-2.33 (m, 2 H) 3.39-3.49 (m, 1 H) 3.58 (s, 5 H) 3.64-3.73 (m, 1 H) 3.75-3.88 (m, 3 H) 3.92-4.04 (m, 2 H) 4.12-4.21 (m, 1 H) 6.92-7.00 (m, 1 H) 7.29 (d, 1 H) 7.31-7.39 (m, 1 H) 7.55-7.62 (m, 2 H) 7.70-7.77 (m, 1 H) 7.84-7.92 (m, 1 H). |

TABLE 19-continued

| Compounds were prepared in analogy to the synthesis of example 1 | | | | |
|---|---|---|---|---|
| Example | Structure | IUPAC-Name | Starting Materials | Analytics |
| 388 | 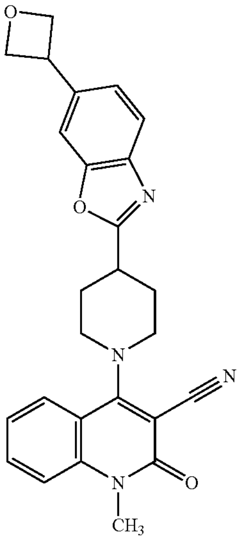 [SMILES: Cn1c(=O)c(C#N)c(N2CCC(c3nc4ccc(C5COC5)cc4o3)CC2)c2ccccc21] | 1-methyl-4-{4-[6-(oxetan-3-yl)-1,3-benzoxazol-2-yl]piperidin-1-yl}-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 217. | $^{1}H$ NMR (400 MHz, DMSO-$d_6$) δ ppm 0.98-8.58 (m, 1 H) 2.08-2.21 (m, 2 H) 2.26-2.32 (m, 1 H) 3.42-3.52 (m, 1 H) 3.58 (s, 5 H) 3.79-3.91 (m, 2 H) 4.33-4.45 (m, 1 H) 4.62-4.73 (m, 2 H) 4.92-5.04 (m, 2 H) 7.28-7.43 (m, 2 H) 7.54-7.61 (m, 1 H) 7.66-7.83 (m, 3 H) 7.85-7.94 (m, 1 H) |
| 389 | 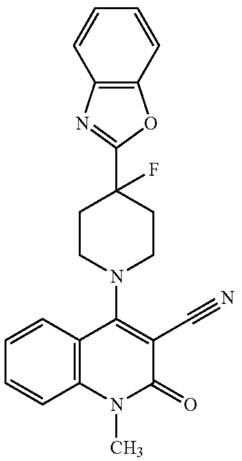 [SMILES: Cn1c(=O)c(C#N)c(N2CCC(F)(c3nc4ccccc4o3)CC2)c2ccccc21] | 4-[4-(1,3-benzoxazol-2-yl)-4-fluoropiperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 220. | $^{1}H$ NMR (400 MHz, DMSO-$d_6$) δ ppm 2.55-2.68 (m, 3 H) 2.69-2.80 (m, 1 H) 3.59 (s, 3 H) 3.71-3.86 (m, 4 H) 7.32-7.37 (m, 1 H) 7.45-7.50 (m, 1 H) 7.50-7.55 (m, 1 H) 7.59 (dd, 1 H) 7.76 (br ddd, 1 H) 7.84-7.91 (m, 2 H) 7.94 (dd, 1 H). LC-MS (Method 2): $R_t$ = 1.21 min; MS (ESIpos): m/z = 403 $[M + H]^+$ |

TABLE 19-continued

| Compounds were prepared in analogy to the synthesis of example 1 | | | | |
|---|---|---|---|---|
| Example | Structure | IUPAC-Name | Starting Materials | Analytics |
| 390 | 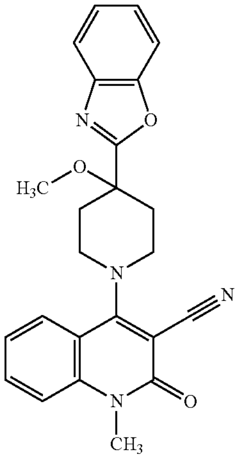 [SMILES: COC1(c2nc3ccccc3o2)CCN(c2c(C#N)c(=O)n(C)c3ccccc23)CC1] | 4-[4-(1,3-benzoxazol-2-yl)-4-methoxypiperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 222. | $^1$H NMR (400 MHz, DMSO-$d_6$) δ ppm 2.50 (m, 4 H) 3.16 (s, 3 H) 3.57 (s, 3 H) 3.59-3.67 (m, 2 H) 3.72-3.82 (m, 2 H) 7.30-7.36 (m, 1 H) 7.41-7.50 (m, 2 H) 7.57 (d, 1 H) 7.74 (ddd, 1 H) 7.79-7.86 (m, 2 H) 7.90 (dd, 1 H) LC-MS (Method 1): $R_t$ = 1.18 min; MS (ESIpos): m/z = 415 [M + H]$^+$ |
| 391 | 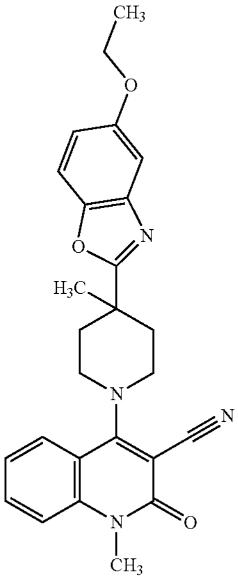 [SMILES: CCOc1ccc2oc(C3(C)CCN(c4c(C#N)c(=O)n(C)c5ccccc45)CC3)nc2c1] | 4-{4-[5-(methoxymethyl)-1,3-benzoxazol-2-yl]-4-methylpiperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 226. | $^1$H NMR (400 MHz, DMSO-$d_6$) δ ppm 1.51 (s, 3 H) 2.01-2.12 (m, 2 H) 3.30 (s, 3 H) 3.56 (s, 5 H) 3.68-3.80 (m, 2H) 4.52 (s, 2 H) 7.27-7.39 (m, 2 H) 7.53-7.60 (m, 1 H) 7.70 (s, 3 H) 7.84-7.93 (m, 1 H). |

TABLE 19-continued

Compounds were prepared in analogy to the synthesis of example 1

| Example | Structure | IUPAC-Name | Starting Materials | Analytics |
|---|---|---|---|---|
| 392 | 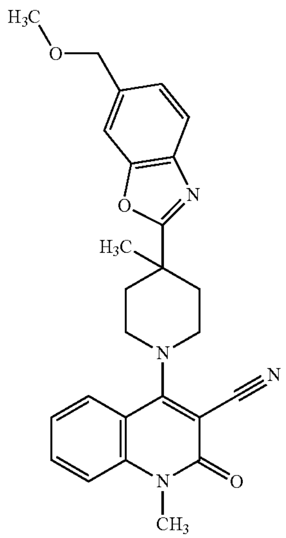 [SMILES: COCc1ccc2nc(C3(C)CCN(c4c(C#N)c(=O)n(C)c5ccccc45)CC3)oc2c1] | 4-{4-[6-(methoxymethyl)-1,3-benzoxazol-2-yl]-4-methylpiperidin-1-yl}-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 230. | $^1$H NMR (400 MHz, DMSO-$d_6$) δ ppm 1.51 (s, 3 H) 1.99-2.14 (m, 2 H) 3.30 (s, 3 H) 3.56 (s, 5 H) 3.68-3.81 (m, 2 H) 4.48-4.56 (m, 2 H) 7.34 (d , 2 H) 7.57 (s, 1 H) 7.65-7.69 (m, 1 H) 7.72 (s, 2 H) 7.86-7.94 (m, 1 H). |
| 393 | 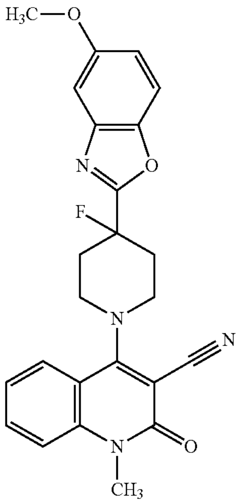 [SMILES: COc1ccc2oc(C3(F)CCN(c4c(C#N)c(=O)n(C)c5ccccc45)CC3)nc2c1] | 4-[4-fluoro-4-(5-methoxy-1,3-benzoxazol-2-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 233. | $^1$H NMR (400 MHz, DMSO-$d_6$) δ ppm 2.55-2.78 (m, 5 H) 3.59 (s, 3 H) 3.69-3.81 (m, 4 H) 3.83 (s, 4H) 7.10 (dd, 1 H) 7.31-7.37 (m, 1 H) 7.42 (d, 1 H) 7.59 (d, 1 H) 7.72-7.78 (m, 2 H) 7.94 (dd, 1 H). LC-MS (Method 1): $R_t$ = 1.20 min; MS (ESIpos): m/z = 433 [M + H]$^+$ |

TABLE 19-continued

| Example | Structure | IUPAC-Name | Starting Materials | Analytics |
|---|---|---|---|---|
| Compounds were prepared in analogy to the synthesis of example 1 | | | | |
| 394 | 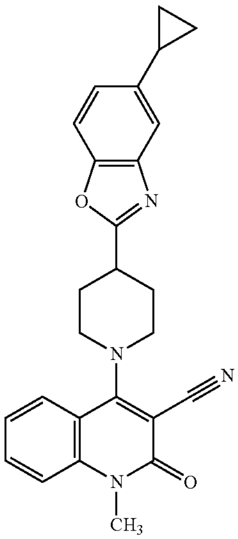 | 4-[4-(5-cyclopropyl-1,3-benzoxazol-2-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 237. | $^1$H NMR (400 MHz, DMSO-$d_6$) δ ppm 0.68-0.76 (m, 2 H) 0.92-1.02 (m, 2 H) 2.01-2.08 (m, 1 H) 2.11-2.20 (m, 2 H) 2.30 (br dd, 2 H) 3.38-3.48 (m, 1 H) 3.58 (s, 3 H) 3.58-3.64 (m, 2 H) 3.83 (br d, 2 H) 7.12 (dd, 1 H) 7.35 (t, 1 H) 7.41 (d, 1 H) 7.57 (dd, 2 H) 7.70-7.79 (m, 1 H) 7.85-7.92 (m, 1 H). LC-MS (Method 1): $R_t$ = 1.14 min; MS (ESIpos): m/z = 443 [M + H]$^+$ |
| 395 | 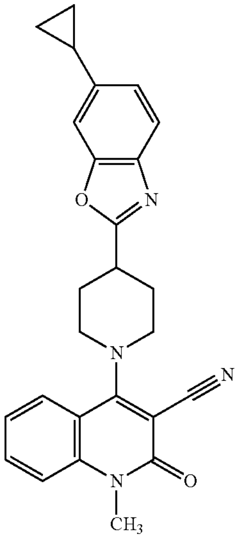 [SMILES: Cn1c(=O)c(C#N)c(N2CCC(c3nc4ccc(C5CC5)cc4o3)CC2)c2ccccc21] | 4-[4-(6-cyclopropyl-1,3-benzoxazol-2-yl)piperidin-1-yl]-1-methyl-2-oxo-1,2-dihydroquinoline-3-carbonitrile | In analogy to example 52 with 4-chloro-1-methyl-2-oxo-1,2-dihydroquinoline-3-carbonitrile (CAS 150617-68-8) and intermediate 241. | $^1$H NMR (400 MHz, DMSO-$d_6$) δ ppm 0.70-0.77 (m, 2 H) 1.00 (s, 2 H) 2.01-2.19 (m, 3 H) 2.24-2.35 (m, 2 H) 3.38-3.49 (m, 1 H) 3.54-3.66 (m, 5 H) 3.77-3.87 (m, 2 H) 7.12 (dd, 1 H) 7.35 (t, 1 H) 7.40 (d, 1 H) 7.57 (d, 2 H) 7.70-7.78 (m, 1 H) 7.88 (dd, 1 H). LC-MS (Method 1): $R_t$ = 1.32 min; MS (ESIpos): m/z = 425 [M + H]$^+$ |

Example 396

6-bromo-1-methyl-4-[4-(5-methyl-1,3-benzoxazol-2-yl)piperidin-1-yl]-2-oxo-1,2-dihydroquinoline-3-carbonitrile

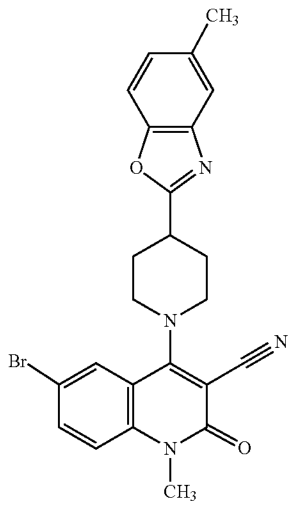 [SMILES: Cc1ccc2oc(C3CCN(c4c(C#N)c(=O)n(C)c5ccc(Br)cc45)CC3)nc2c1]

A solution of 2.2 g 6-bromo-4-chloro-1-methyl-2-oxo-1,2-dihydroquinoline-3-carbonitrile (intermediate 95), 1.6 g 5-methyl-2-(piperidin-4-yl)-1,3-benzoxazole (CAS 199292-77-8) and 2.1 mL triethylamine in 100 mL 2-propanol was stirred for 5 h at 90° C. After this time, water and ethyl acetate were added. The precipitate was filtered off and washed with ethyl acetate to generate a first crop of 1.7 g of the title compound. The combined organic layers were washed with water and brine and dried over sodium sulfate. After evaporation of the solvent, the residue was purified by flash chromatography (silica, dichloromethane/methanol gradient 0-1%). Further 620 mg of the title compound were obtained.

$^1$H-NMR (400 MHz, DMSO-d6) δ[ppm]: 1.99-2.18 (m, 2H) 2.26-2.34 (m, 2H) 2.42 (s, 3H) 3.37-3.50 (m, 1H) 3.56 (s, 5H) 3.77-3.89 (m, 2H) 7.15-7.23 (m, 1H) 7.54 (s, 3H) 7.82-7.96 (m, 2H).

Example 397

8-bromo-1-methyl-4-[4-(5-methyl-1,3-benzoxazol-2-yl)piperidin-1-yl]-2-oxo-1,2-dihydroquinoline-3-carbonitrile

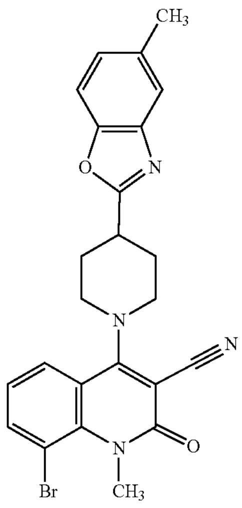 [SMILES: Cc1ccc2oc(C3CCN(c4c(C#N)c(=O)n(C)c5c(Br)cccc45)CC3)nc2c1]

A solution of 1.0 g 8-bromo-4-chloro-1-methyl-2-oxo-1,2-dihydroquinoline-3-carbonitrile (intermediate 86), 727 mg 5-methyl-2-(piperidin-4-yl)-1,3-benzoxazole (CAS 199292-77-8) and 0.94 mL triethylamine in 40 mL 2-propanol was stirred for 4 h at 90° C. After this time, water and ethyl acetate were added. The precipitate was filtered off and washed with ethyl acetate to obtain 1.1 g of the title compound.

$^1$H-NMR (400 MHz, DMSO-d6) δ[ppm]: 2.03-2.20 (m, 2H) 2.25-2.33 (m, 2H) 2.42 (s, 3H) 3.39-3.51 (m, 1H) 3.53-3.65 (m, 2H) 3.70 (s, 3H) 3.77-3.88 (m, 2H) 7.14-7.22 (m, 1H) 7.22-7.33 (m, 1H) 7.48-7.63 (m, 2H) 7.80-7.91 (m, 1H) 8.00 (d, 1H).

Example 398

1-methyl-4-[4-(5-methyl-1,3-benzoxazol-2-yl)piperidin-1-yl]-7-[methyl(oxetan-3-yl)amino]-2-oxo-1,2-dihydroquinoline-3-carbonitrile

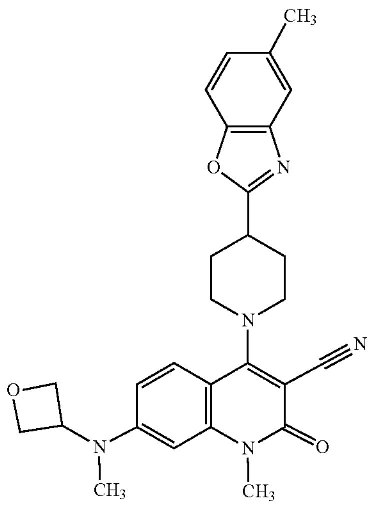 [SMILES: Cc1ccc2oc(C3CCN(c4c(C#N)c(=O)n(C)c5cc(N(C)C6COC6)ccc45)CC3)nc2c1]

A suspension of 300 mg 7-bromo-1-methyl-4-[4-(5-methyl-1,3-benzoxazol-2-yl)piperidin-1-yl]-2-oxo-1,2-dihydroquinoline-3-carbonitrile (example 281), 400 mg tripotassium phosphate and 66 mg N-methyloxetan-3-amine in 10 ml dioxane was purged with Argon for 10 min, 49 mg XPhos Pd G2 (CAS 1310584-14-5) were added and this mixture stirred for 2 hours at 11° C. The reaction mixture was diluted with water and extracted with ethyl acetate (3×). The combined organic layers were dried over sodium sulfate and concentrated under reduced pressure. The residue was purified by flash chromatography (silica, dichloromethane/methanol gradient 0-3%) to obtain 75 mg of the title compound.

$^1$H-NMR (400 MHz, DMSO-d6) δ[ppm]: 2.02-2.16 (m, 2H) 2.20-2.31 (m, 2H) 2.42 (s, 3H) 3.10 (s, 3H) 3.36-3.45 (m, 1H) 3.53 (s, 6H) 3.68-3.79 (m, 2H) 4.62-4.73 (m, 2H) 4.80-4.90 (m, 2H) 5.02-5.15 (m, 1H) 6.38 (d, 1H) 6.71-6.79 (m, 1H) 7.03-7.08 (m, 1H) 7.13-7.22 (m, 1H) 7.30-7.32 (m, 1H) 7.49-7.54 (m, 1H) 7.56-7.60 (m, 1H) 7.63-7.70 (m, 1H).

TABLE 20

Compounds were prepared in analogy to example 398.

| Example | Structure | IUPAC-Name | Starting Materials | Analytics |
|---|---|---|---|---|
| 399 | 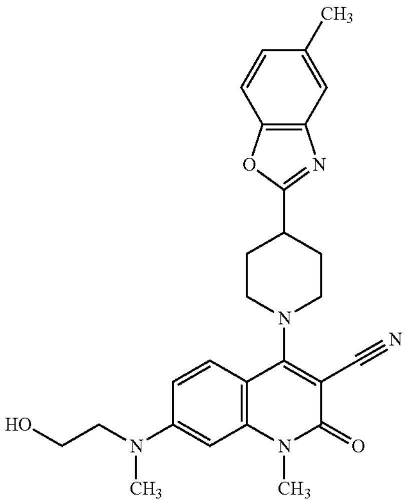 [SMILES: Cc1ccc2oc(C3CCN(c4c(C#N)c(=O)n(C)c5cc(N(C)CCO)ccc45)CC3)nc2c1] | 7-[(2-hydroxyethyl)(methyl)amino]-1-methyl-4-[4-(5-methyl-1,3-benzoxazol-2-yl)piperidin-1-yl]-2-oxo-1,2-dihydroquinoline-3-carbonitrile | Prepared in analogy to example 398 by using 2-(methylamino)ethanol (CAS 109-83-1). | $^1$H NMR (400 MHz, DMSO-$d_6$) δ ppm 2.01-2.16 (m, 2 H) 2.22-2.31 (m, 2 H) 2.42 (s, 4 H) 3.11 (s, 3 H) 3.36-3.45 (m, 1 H) 3.52 (s, 10 H) 3.69-3.80 (m, 2 H) 4.75-4.84 (m, 1 H) 6.35-6.43 (m, 1 H) 6.76-6.85 (m, 1 H) 7.12-7.22 (m, 1 H) 7.48-7.55 (m, 1 H) 7.55-7.69 (m, 2 H). |
| 400 | 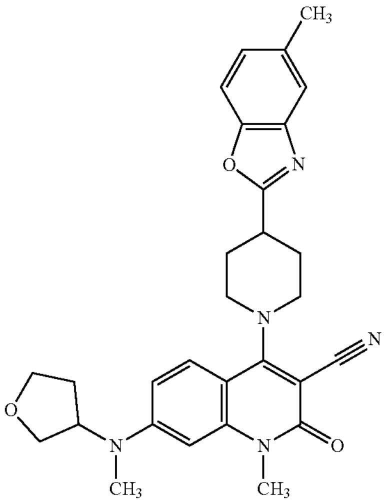 [SMILES: Cc1ccc2oc(C3CCN(c4c(C#N)c(=O)n(C)c5cc(N(C)C6CCOC6)ccc45)CC3)nc2c1] | (rac)-1-methyl-4-[4-(5-methyl-1,3-benzoxazol-2-yl)piperidin-1-yl]-7-[methyl(oxolan-3-yl)amino]-2-oxo-1,2-dihydroquinoline-3-carbonitrile | Prepared in analogy to example 398 by using N-methyltetrahydrofuran-3-amine (CAS 2439-56-7) and 0.05 equiv (1E,4E)-1,5-diphenylpenta-1,4-dien-3-one-palladium (3:2) (CAS 51364-51-3) and 0.05 equiv (9,9-dimethyl-9H-xanthene-4,5-diyl)bis(diphenylphosphane) (CAS 161265-03-8) | $^1$H NMR (400 MHz, DMSO-$d_6$) δ ppm 1.78-1.93 (m, 1 H) 2.02-2.17 (m, 2 H) 2.26-2.34 (m, 2 H) 2.38-2.45 (m, 3 H) 2.91-3.00 (m, 3 H) 3.37-3.45 (m, 1 H) 3.48-3.59 (m, 5 H) 3.60-3.67 (m, 1 H) 3.69-3.85 (m, 4 H) 3.93-4.10 (m, 1 H) 4.72-4.91 (m, 1 H) 6.44-6.59 (m, 1 H) 6.82-7.00 (m, 1 H) 7.14-7.23 (m, 1 H) 7.48-7.54 (m, 1 H) 7.55-7.60 (m, 1 H) 7.61-7.69 (m, 1 H). |

TABLE 20-continued

| Compounds were prepared in analogy to example 398. | | | | |
|---|---|---|---|---|
| Example | Structure | IUPAC-Name | Starting Materials | Analytics |
| 401 | 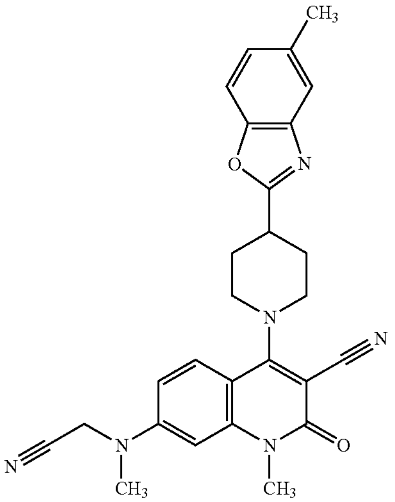 [SMILES: Cc1ccc2oc(C3CCN(c4c(C#N)c(=O)n(C)c5cc(N(C)CC#N)ccc45)CC3)nc2c1] | 7-[(cyanomethyl)(methyl)amino]-1-methyl-4-[4-(5-methyl-1,3-benzoxazol-2-yl)piperidin-1-yl]-2-oxo-1,2-dihydroquinoline-3-carbonitrile | Prepared in analogy to example 398 by using (methylamino) acetonitrile (CAS 5616-32-0). | $^1$H NMR (400 MHz, DMSO-$d_6$) δ ppm 2.04-2.17 (m, 2 H), 2.24-2.32 (m, 2 H), 2.42 (s, 3 H), 3.14 (s, 3 H), 3.37-3.47 (m, 1 H), 3.51-3.63 (m, 5 H), 3.78 (br d, 2 H), 4.78 (s, 2 H), 6.65 (d, 1 H), 6.96 (dd, 1 H), 7.16-7.22 (m, 1 H), 7.50-7.54 (m, 1 H), 7.61 (br d, 1 H), 7.75 (d, 1 H). |

Example 402

6-methoxy-1-methyl-4-[4-(5-methyl-1,3-benzoxazol-2-yl)piperidin-1-yl]-2-oxo-1,2-dihydroquinoline-3-carbonitrile

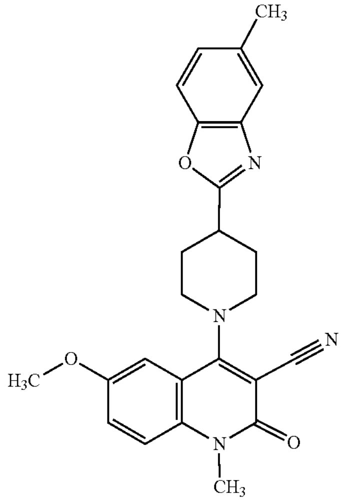 [SMILES: COc1ccc2c(c1)c(N1CCC(c3nc4cc(C)ccc4o3)CC1)c(C#N)c(=O)n2C]

A solution of 270 mg 4-chloro-6-methoxy-1-methyl-2-oxo-1,2-dihydroquinoline-3-carbonitrile (intermediate 99), 235 mg 5-methyl-2-(piperidin-4-yl)-1,3-benzoxazole (CAS 199292-77-8) and 0.3 mL triethylamine in 20 mL 2-propanol was stirred for 5 h at 90° C. After this time, water and ethyl acetate were added. The precipitate was filtered off and washed with ethyl acetate to generate a first crop of 290 mg of the title compound. The combined organic layers were washed with water and brine and dried over sodium sulfate. After evaporation of the solvent, the residue was purified by flash chromatography (silica, dichloromethane/methanol gradient 0-3%). Further 105 mg of the title compound were obtained.

$^1$H-NMR (400 MHz, DMSO-d6) δ[ppm]: 2.06-2.19 (m, 2H) 2.31-2.39 (m, 2H) 2.40-2.44 (m, 3H) 3.40-3.50 (m, 1H) 3.58-3.64 (m, 2H) 3.79-3.87 (m, 5H) 3.85-3.87 (m, 3H) 7.17-7.21 (m, 1H) 7.22-7.27 (m, 1H) 7.38-7.43 (m, 1H) 7.51-7.56 (m, 2H) 7.51-7.55 (m, 2H) 7.56-7.61 (m, 1H).

Example 403

1-methyl-4-[4-(5-methyl-1,3-benzoxazol-2-yl)piperidin-1-yl]-2-oxo-1,2-dihydroquinoline-3,6-dicarbonitrile

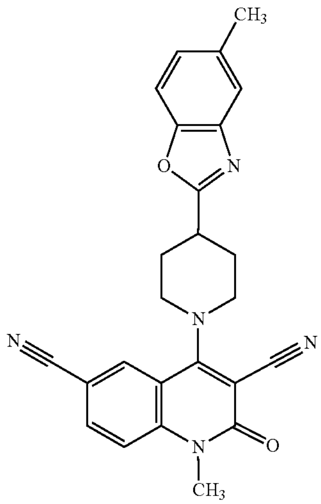 [SMILES: Cc1ccc2oc(C3CCN(c4c(C#N)c(=O)n(C)c5ccc(C#N)cc45)CC3)nc2c1]

A mixture of 300 mg 6-bromo-1-methyl-4-[4-(5-methyl-1,3-benzoxazol-2-yl)piperidin-1-yl]-2-oxo-1,2-dihydroquinoline-3-carbonitrile (example 396), 16.3 mg palladium(π-cinnamyl) chloride dimer (CAS 12131-44-1), 56 mg zinc cyanide (CAS 557-21-1), 17.4 mg 1,1'-bis(diphenylphosphanyl)ferrocene and 0.22 ml N,N-diisopropylethylamine in 15 ml N,N-dimethylacetamide were stirred at 120° C. for 9 hours. After this time, water was added and it was extracted with ethyl acetate (2×). The combined organic layers were washed with water and brine and dried over sodium sulfate. After evaporation of the solvent, the residue was purified by flash chromatography (silica, dichloromethane/methanol gradient 0-1%) to obtain 105 mg of the title compound.

$^1$H-NMR (400 MHz, DMSO-d6) δ[ppm]: 2.12-2.25 (m, 2H) 2.26-2.37 (m, 3H) 2.41-2.45 (m, 3H) 3.40-3.49 (m, 1H) 3.55-3.71 (m, 5H) 3.81-3.92 (m, 2H) 7.16-7.22 (m, 1H) 7.51-7.55 (m, 1H) 7.56-7.61 (m, 1H) 7.69-7.75 (m, 1H) 8.08-8.14 (m, 1H) 8.23-8.27 (m, 1H).

Example 404

3-cyano-1-methyl-4-[4-(5-methyl-1,3-benzoxazol-2-yl)piperidin-1-yl]-2-oxo-1,2-dihydroquinoline-6-carboxamide

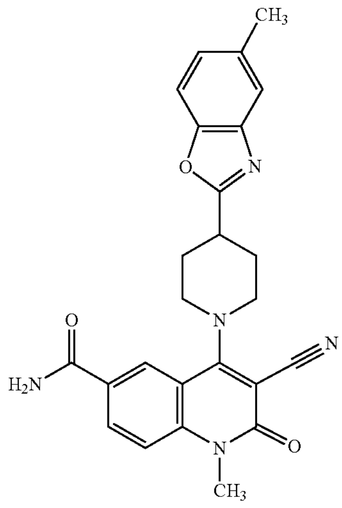 [SMILES: Cc1ccc2oc(C3CCN(c4c(C#N)c(=O)n(C)c5ccc(C(N)=O)cc45)CC3)nc2c1]

A solution of 10 mg 3-cyano-1-methyl-4-[4-(5-methyl-1,3-benzoxazol-2-yl)piperidin-1-yl]-2-oxo-1,2-dihydroquinoline-6-carboxylic acid (intermediate 257), 0.11 ml aqueous ammonia (2M), 12 μL N,N-diisopropylethylamine and 12.9 mg HATU in 0.22 ml DMF were stirred at RT for 14 hours. After this time, water was added and it was extracted with ethyl acetate (2×) ethyl acetate. The combined organic layers were washed with water and brine and dried over sodium sulfate. After evaporation of the solvent, the residue was purified by flash chromatography (silica, dichloromethane/methanol gradient 0-3%) to obtain 4 mg of the title compound.

$^1$H-NMR (400 MHz, DMSO-d6) δ[ppm]: 1.12-1.16 (m, 1H) 1.21-1.29 (m, 2H) 2.12-2.24 (m, 2H) 2.29-2.37 (m, 2H) 2.40-2.46 (m, 3H) 3.42-3.54 (m, 1H) 3.56-3.72 (m, 5H) 3.82-3.95 (m, 2H) 7.15-7.24 (m, 1H) 7.47-7.56 (m, 2H) 7.57-7.68 (m, 2H) 8.08-8.23 (m, 2H) 8.32-8.42 (m, 1H).

Example 405

6-ethoxy-1-methyl-4-[4-(5-methyl-1,3-benzoxazol-2-yl)piperidin-1-yl]-2-oxo-1,2-dihydroquinoline-3-carbonitrile

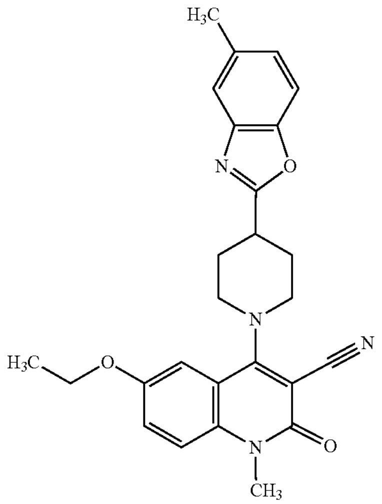 [SMILES: CCOc1ccc2c(c1)c(N1CCC(c3nc4cc(C)ccc4o3)CC1)c(C#N)c(=O)n2C]

6-bromo-1-methyl-4-[4-(5-methyl-1,3-benzoxazol-2-yl)piperidin-1-yl]-2-oxo-1,2-dihydroquinoline-3-carbonitrile (135 mg, 283 μmol, Example 396), 2-(di-tert-butylphosphino)-2',4',6'-triisopropyl-3,6-dimethoxy-1,1'-biphenyl (13.7 mg, 28.3 μmol; CAS 1160861-53-9), [(2-di-tert-butylphosphino-3,6-dimethoxy-2',4',6'-triisopropyl-1,1'-biphenyl)-2-(2'-amino-1,1'-biphenyl)]palladium(II) methanesulfonate (24.2 mg, 28.3 μmol; CAS 1536473-72-9), Cesium carbonate (129 mg, 396 μmol; CAS 534-17-8) were added to a 5 ml reaction vessel, the vessel was crimp sealed and flushed with argon. Toluene (anhydrous, degassed, 1.5 ml) and ethanol (160 μl, 2.83 mmol) were added and the mixture stirred at 80° C. overnight. The mixture was filtered through a column of Isolute (2 g, 1 cm diameter), the Isolute was washed with a mixture of dichloromethane:methanol (9:1) and the filtrate concentrated under reduced pressure. Purification by silica gel column chromatography (10 g, SNAP ultra, Hexane:ethyl acetate 50:50 to 100) yielded the title compound (35 mg, 95% purity, 36% yield).

$^1$H NMR (400 MHz, $CDCl_3$) δ ppm 1.46 (t, 3H) 2.18-2.30 (m, 2H) 2.41-2.48 (m, 2H) 3.28 (tt, 1H) 3.59-3.71 (m, 5H) 3.83-3.91 (m, 2H) 7.13-7.18 (m, 1H) 7.24-7.28 (m, 2H) 7.29-7.33 (m, 1H) 7.38-7.43 (m, 1H) 7.48-7.52 (m, 1H)

LC-MS (Method 1): $R_t$=1.32 min; MS (443.3): m/z=[M+H]+

Example 406

6-(2,2-difluoropropoxy)-1-methyl-4-[4-(5-methyl-1,3-benzoxazol-2-yl)piperidin-1-yl]-2-oxo-1,2-dihydroquinoline-3-carbonitrile

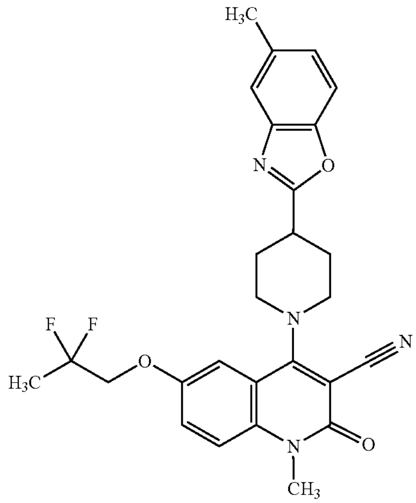 [SMILES: Cc1ccc2oc(C3CCN(c4c(C#N)c(=O)n(C)c5ccc(OCC(C)(F)F)cc45)CC3)nc2c1]

The title compound (21 mg, 90% purity, 15% yield) was produced using an analogue procedure used to produce 6-ethoxy-1-methyl-4-[4-(5-methyl-1,3-benzoxazol-2-yl)piperidin-1-yl]-2-oxo-1,2-dihydroquinoline-3-carbonitrile (Example 405), from 6-bromo-1-methyl-4-[4-(5-methyl-1,3-benzoxazol-2-yl)piperidin-1-yl]-2-oxo-1,2-dihydroquinoline-3-carbonitrile (135 mg, 283 μmol, example 396) and 2,2-Difluoropropanol (230 μl, 2.8 mmol; CAS 33420-52-9).

$^1$H NMR (400 MHz, $CDCl_3$) δ ppm 1.80-1.80 (m, 1H) 2.19-2.32 (m, 2H) 2.40-2.50 (m, 5H) 3.30 (tt, 1H) 3.59-3.72 (m, 5H) 3.81-3.90 (m, 2H) 4.18 (t, 2H) 7.12-7.17 (m, 1H) 7.30-7.36 (m, 3H) 7.40 (d, 1H) 7.47-7.51 (m, 1H) LC-MS (Method 1): $R_t$=1.32 min; MS (493.3): m/z=[M+H]+

Example 407

6-(2,2-difluoroethoxy)-1-methyl-4-[4-(5-methyl-1,3-benzoxazol-2-yl)piperidin-1-yl]-2-oxo-1,2-dihydroquinoline-3-carbonitrile

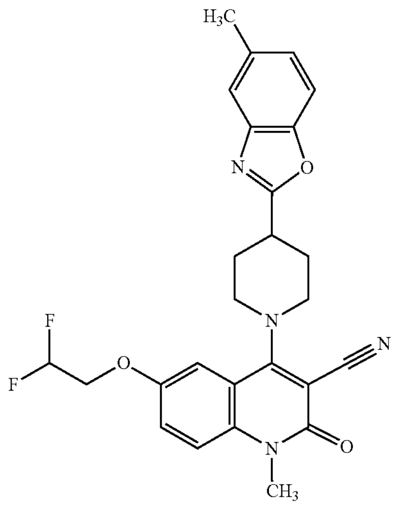 [SMILES: Cc1ccc2oc(C3CCN(c4c(C#N)c(=O)n(C)c5ccc(OCC(F)F)cc45)CC3)nc2c1]

The title compound (36 mg, 80% purity, 26% yield) was produced using an analogue procedure used to produce 6-ethoxy-1-methyl-4-[4-(5-methyl-1,3-benzoxazol-2-yl)piperidin-1-yl]-2-oxo-1,2-dihydroquinoline-3-carbonitrile (Example 405), from 6-bromo-1-methyl-4-[4-(5-methyl-1,3-benzoxazol-2-yl)piperidin-1-yl]-2-oxo-1,2-dihydroquinoline-3-carbonitrile (135 mg, 283 μmol, Example 396) and 2,2-Difluoroethanol (180 μl, 2.8 mmol; CAS 359-13-7).

$^1$H NMR (400 MHz, $CDCl_3$) δ ppm 1.57 (s, 3H) 2.19-2.32 (m, 2H) 2.40-2.50 (m, 5H) 2.41-2.48 (m, 2H) 3.30 (tt, 1H) 3.60-3.71 (m, 5H) 3.81-3.89 (m, 2H) 4.25 (td, 2H) 6.13 (tt, 1H) 7.13-7.18 (m, 1H) 7.28-7.37 (m, 3H) 7.38-7.42 (m, 1H) 7.48-7.52 (m, 1H)

LC-MS (Method 1): $R_t$=1.26 min; MS (479.3): m/z=[M+H]+

Example 408

6-(cyclopropylmethoxy)-1-methyl-4-[4-(5-methyl-1,3-benzoxazol-2-yl)piperidin-1-yl]-2-oxo-1,2-dihydroquinoline-3-carbonitrile

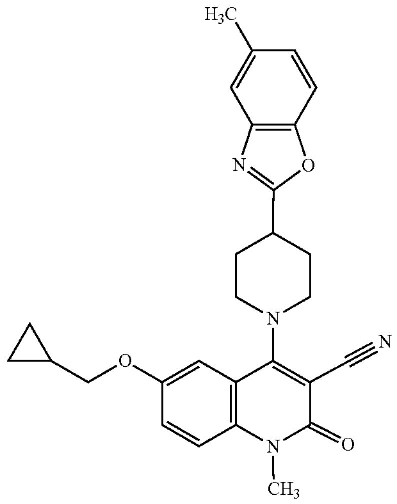 [SMILES: Cc1ccc2oc(C3CCN(c4c(C#N)c(=O)n(C)c5ccc(OCC6CC6)cc45)CC3)nc2c1]

The title compound (57 mg, 90% purity, 43% yield) was produced using an analogue procedure used to produce 6-ethoxy-1-methyl-4-[4-(5-methyl-1,3-benzoxazol-2-yl)piperidin-1-yl]-2-oxo-1,2-dihydroquinoline-3-carbonitrile (Example 405), from 6-bromo-1-methyl-4-[4-(5-methyl-1,3-benzoxazol-2-yl)piperidin-1-yl]-2-oxo-1,2-dihydroquinoline-3-carbonitrile (135 mg, 283 μmol, Example 396) and cyclopropanemethanol (230 μl, 2.8 mmol; CAS 2516-33-8).

$^1$H NMR (400 MHz, $CDCl_3$) δ ppm 0.35-0.42 (m, 2H) 0.64-0.72 (m, 2H) 1.20-1.37 (m, 2H) 2.19-2.31 (m, 2H) 2.39-2.46 (m, 1H) 2.40-2.46 (m, 2H) 2.48 (s, 3H) 3.29 (tt, 1H) 3.59-3.70 (m, 5H) 3.82-3.90 (m, 4H) 7.13-7.18 (m, 1H) 7.27-7.33 (m, 3H) 7.40 (d, 1H) 7.49-7.52 (m, 1H).

LC-MS (Method 1): $R_t$=1.38 min; MS (469.3): m/z=[M+H]+

Example 409

6-cyclobutyl-1-methyl-4-[4-(5-methyl-1,3-benzoxazol-2-yl)piperidin-1-yl]-2-oxo-1,2-dihydroquinoline-3-carbonitrile

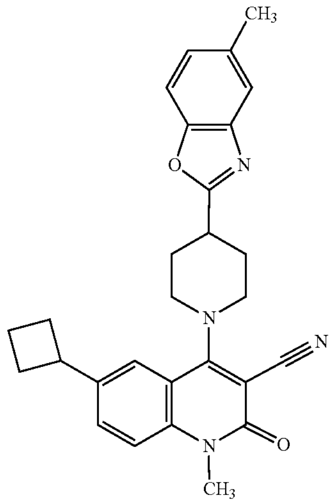 [SMILES: Cc1ccc2oc(C3CCN(c4c(C#N)c(=O)n(C)c5ccc(C6CCC6)cc45)CC3)nc2c1]

A MW-Vial was charged with 200 mg 6-bromo-1-methyl-4-[4-(5-methyl-1,3-benzoxazol-2-yl)piperidin-1-yl]-2-oxo-1,2-dihydroquinoline-3-carbonitrile (419 μmol, example 396) and $[Ir(dF(CF_3)ppy_2)_2(dtbbpy)]PF_6$ (9.40 mg, 8.38 μmol, CAS 870987-63-6). In a separate vial, the Ni-catalyst was prepared by dissolving 4.6 mg nickel(II) chloride ethylene glycol dimer (8.4 μmol, CAS 29046-78-4) and the 4,4'-di-tert-butyl-2,2'-bipyridine (5.6 mg, 21 μmol; CAS 72914-19-3) in 8.4 mL 1,2-dimethoxyethan followed by stirring for 5 min. The catalyst solution was syringed to the sealed reaction vial and degassed for 5 minutes with argon. 130 μl Tris(trimethylsilyl)silan (420 μmol; CAS 1873-77-4), 0.29 mL 2,6-dimethylpyridine (2.5 mmol) and 0.18 mmol bromocyclobutane (1.9 mmol) were added afterwards. The MW-vial was placed in a Hepatochem-reactor were it was subsequently irradiated by a 40 W Kessil LED aquarium lamp. After 16 h water was added and the mixture was extracted with ethyl acetate three times. The combined organic layers were filtered over a hydrophobic filter and the solvent was evaporated under reduced pressure. The crude product was purified by column chromatography and the product was obtained as a yellow solid in 41% yield (87 mg).

$^1H$ NMR (400 MHz, DMSO-$d_6$) δ ppm 1.78-1.89 (m, 1H) 1.93-2.03 (m, 1H) 2.04-2.19 (m, 4H) 2.29-2.38 (m, 4H) 2.42 (s, 3H) 3.41-3.50 (m, 1H) 3.57 (s, 3H) 3.58-3.69 (m, 4H) 3.78-3.88 (m, 2H) 7.19 (dd, 1H) 7.50-7.55 (m, 2H) 7.56-7.66 (m, 3H).

LC-MS (Method 1): $R_t$=1.47 min; MS (ESIpos): m/z=453 $[M+H]^+$

Example 410

6-[2,2-dimethylcyclobutyl]-1-methyl-4-[4-(5-methyl-1,3-benzoxazol-2-yl)piperidin-1-yl]-2-oxo-1,2-dihydroquinoline-3-carbonitrile

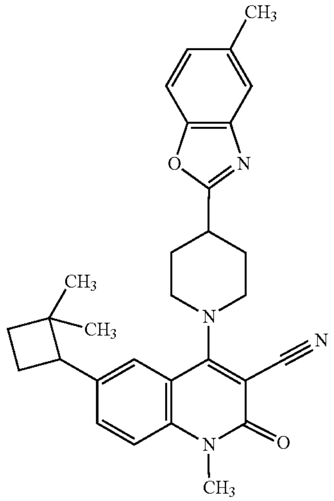 [SMILES: Cc1ccc2oc(C3CCN(c4c(C#N)c(=O)n(C)c5ccc(C6CCC6(C)C)cc45)CC3)nc2c1]

Prepared according to example 409 by using 200 mg 6-bromo-1-methyl-4-[4-(5-methyl-1,3-benzoxazol-2-yl)piperidin-1-yl]-2-oxo-1,2-dihydroquinoline-3-carbonitrile (419 μmol, example 396) and 307 mg 2-bromo-1,1-dimethylcyclobutane (250 μl, 1.9 mmol) and by using a mixture of N,N-dimethylacetamide (1.7 mL) and benzotrifluoride (6.7 mL) as a solvent. The product was purified by column chromatography and obtained in 12% yield (26 mg).

$^1H$ NMR (400 MHz, DMSO-$d_6$) δ ppm 1.47 (d, 3H) 1.61 (d, 3H) 2.07-2.19 (m, 2H) 2.25-2.37 (m, 4H) 2.42 (s, 3H) 2.72 (t, 2H) 3.40-3.49 (m, 1H) 3.56 (s, 3H) 3.57-3.64 (m, 2H) 3.82 (br d, 2H) 5.13 (tt, 1H) 7.19 (dd, 1H) 7.47-7.54 (m, 2H) 7.55-7.64 (m, 3H).

LC-MS (Method 1): $R_t$=1.55 min; MS (ESIpos): m/z=481 $[M+H]^+$

Example 411

1-methyl-4-[4-(5-methyl-1,3-benzoxazol-2-yl)piperidin-1-yl]-2-oxo-6-(3,3,3-trifluoroprop-1-en-2-yl)-1,2-dihydroquinoline-3-carbonitrile

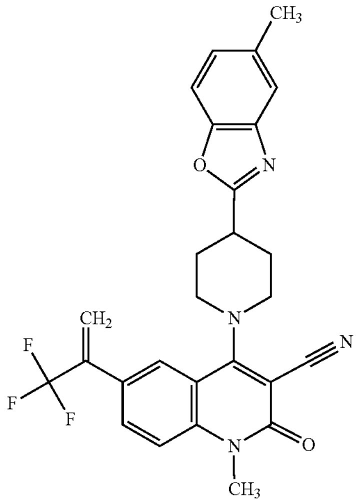 [SMILES: C=C(c1ccc2c(c1)c(N1CCC(c3nc4cc(C)ccc4o3)CC1)c(C#N)c(=O)n2C)C(F)(F)F]

6-Bromo-1-methyl-4-[4-(5-methyl-1,3-benzoxazol-2-yl)piperidin-1-yl]-2-oxo-1,2-dihydroquinoline-3-carbonitrile (100 mg, 209 μmol, example 396), 93 mg 4,4,5,5-tetramethyl-2-(3,3,3-trifluoroprop-1-en-2-yl)-1,3,2-dioxaborolane (90 μl, 420 μmol, CAS 1055881-27-0) and XPhos Pd G4 (9.01 mg, 10.5 μmol) were dissolved in 4 mL 1,4-dioxane followed by the addition of 0.27 mL 2M sodium carbonate. The reaction mixture was degased by sparging with argon while sonication for 10 min and subsequently stirred at 100° C. for 4 h. Water was added and the mixture was extracted with ethyl acetate three times. The combined organic layers were filtered over a hydrophobic filter and the solvent was evaporated under reduced pressure. Purification by column chromatography gave the product in 65% yield (71 mg) as a yellow solid.

$^1$H NMR (400 MHz, DMSO-$d_6$) δ ppm 2.03-2.15 (m, 2H) 2.28-2.37 (m, 2H) 2.42 (s, 3H) 3.41-3.51 (m, 1H) 3.55-3.67 (m, 5H) 3.84 (br d, 2H) 6.15-6.20 (m, 1H) 6.23-6.28 (m, 1H) 7.19 (dd, 1H) 7.50-7.55 (m, 1H) 7.58 (d, 1H) 7.67 (d, 1H) 7.88-7.93 (m, 2H).

LC-MS (Method 1): $R_t$=1.41 min; MS (ESIpos): m/z=493 $[M+H]^+$

Example 412

1-methyl-4-[4-(5-methyl-1,3-benzoxazol-2-yl)piperidin-1-yl]-2-oxo-6-[1-(trifluoromethyl)cyclopropyl]-1,2-dihydroquinoline-3-carbonitrile

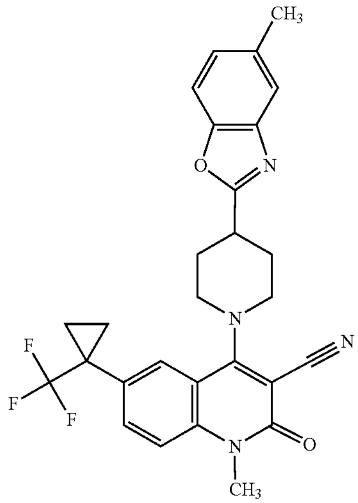 [SMILES: Cc1ccc2oc(C3CCN(c4c(C#N)c(=O)n(C)c5ccc(C6(C(F)(F)F)CC6)cc45)CC3)nc2c1]

This compound was prepared with a method from the literature: J. P. Phelan et al. *J. Am. Chem. Soc.* 2018, 140, 8037-8047.

1-Methyl-4-[4-(5-methyl-1,3-benzoxazol-2-yl)piperidin-1-yl]-2-oxo-6-(3,3,3-trifluoroprop-1-en-2-yl)-1,2-dihydroquinoline-3-carbonitrile (60.0 mg, 122 μmol, example 411), 119 mg N,N-diethylethanaminium bis[benzene-1,2-diolato (2-)-kappa$^2$O$^1$,O$^2$](iodomethyl)silicate(1-) (244 μmol) and 4.8 mg 2,4,5,6-tetra(9H-carbazol-9-yl)isophthalonitrile (6.09 μmol, CAS 1416881-52-1) were dissolved in solvent 2.4 mL DMSO and degased with argon for 5 min. The MW-vial was placed in a water bath (to keep the temp. below 35° C.) and was subsequently irradiated by two 40 W Kessil LED aquarium lamps for 12 h. A 1M sodium hydroxide solution was added and the mixture was extracted three times with ethyl acetate. The combined organic layers were washed with 1M sodium hydroxide solution and brine, filtered over a hydrophobic filter and the solvent was evaporated under reduced pressure. Purification by column chromatography gave the product as a yellow solid (25 mg, 38% yield).

$^1$H NMR (400 MHz, DMSO-$d_6$) δ ppm 1.20-1.26 (m, 2H) 1.38-1.44 (m, 2H) 2.04-2.16 (m, 2H) 2.29-2.38 (m, 2H) 2.42 (s, 3H) 3.43-3.52 (m, 1H) 3.57 (s, 3H) 3.59-3.67 (m, 2H) 3.84 (br d, 2H) 7.20 (dd, 1H) 7.54 (s, 1H) 7.59 (d, 2H) 7.79 (dd, 1H) 7.86-7.91 (m, 1H).

Example 413

2-({3-cyano-1-methyl-4-[4-(5-methyl-1,3-benzoxazol-2-yl)piperidin-1-yl]-2-oxo-1,2-dihydroquinolin-7-yl}oxy)acetamide

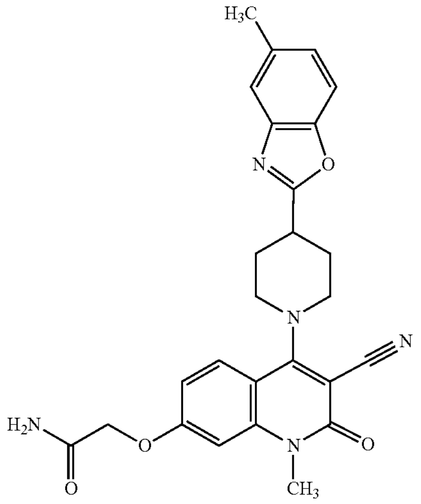 [SMILES: Cc1ccc2oc(C3CCN(c4c(C#N)c(=O)n(C)c5cc(OCC(N)=O)ccc45)CC3)nc2c1]

A solution of 460 mg ({3-cyano-1-methyl-4-[4-(5-methyl-1,3-benzoxazol-2-yl)piperidin-1-yl]-2-oxo-1,2-dihydroquinolin-7-yl}oxy)acetic acid (Example 416 in 23 ml THF was treated slowly with 492 mg 4-methylmorpholine and 528 mg ethyl chloroformate at −20° C. After further stirring for 30 minutes at −20° C., 1.5 ml aqueous ammonia were added dropwise. After completion, the temperature was raised to RT and it was stirred for further 30 min. The reaction mixture was diluted with water and extracted with ethyl acetate (2×). The combined organic layers were dried over sodium sulfate and concentrated under reduced pressure. The residue was purified by flash chromatography (silica, dichloromethane/methanol gradient 0-3%) to obtain 300 mg of the title compound.

$^1$H NMR (400 MHz, DMSO-d6) δ ppm 2.06-2.21 (m, 3H) 2.25-2.36 (m, 2H) 2.40-2.46 (m, 3H) 3.37-3.49 (m, 1H) 3.51-3.67 (m, 5H) 3.72-3.87 (m, 2H) 4.57-4.72 (m, 2H) 5.70-5.80 (m, 1H) 5.70-5.80 (m, 1H) 6.94-7.04 (m, 2H) 7.13-7.24 (m, 1H) 7.43-7.62 (m, 3H) 7.63-7.74 (m, 1H) 7.77-7.88 (m, 1H).

TABLE 21

| Example | Structure | IUPAC-Name | Starting Materials | Analytics |
|---|---|---|---|---|
| | Compounds were prepared as referenced | | | |
| 414 | 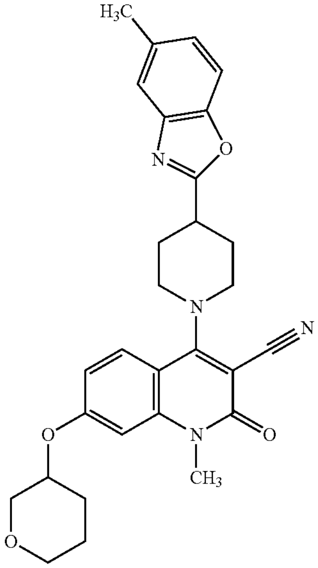 [SMILES: Cc1ccc2oc(C3CCN(c4c(C#N)c(=O)n(C)c5cc(OC6CCCOC6)ccc45)CC3)nc2c1] | 1-methyl-4-[4-(5-methyl-1,3-benzoxazol-2-yl) piperidin-1-yl]-7-{[oxan-3-yl]oxy}-2-oxo-1,2-dihydroquinoline-3-carbonitrile | Prepared according to example 379 by using 3-bromotetrahydro-2H-pyran (CAS 13047-01-3). | $^1$H NMR (400 MHz, DMSO-$d_6$) δ ppm 1.47-1.67 (m, 1 H) 1.69-1.88 (m, 2 H) 2.01-2.20 (m, 3 H) 2.24-2.31 (m, 2 H) 2.40-2.44 (m, 3 H) 3.38-3.48 (m, 1 H) 3.52-3.68 (m, 8 H) 3.75-3.89 (m, 3 H) 4.64-4.74 (m, 1 H) 6.92-7.05 (m, 2 H) 7.15-7.24 (m, 1 H) 7.49-7.55 (m, 1 H) 7.56-7.63 (m, 1 H) 7.76-7.85 (m, 1 H). |
| 415 | 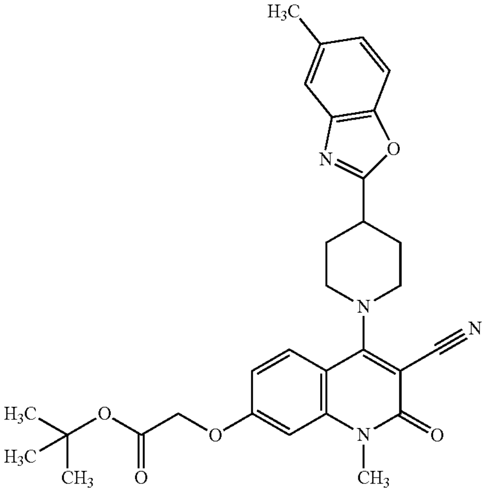 [SMILES: Cc1ccc2oc(C3CCN(c4c(C#N)c(=O)n(C)c5cc(OCC(=O)OC(C)(C)C)ccc45)CC3)nc2c1] | (rac)-tert-butyl ({3-cyano-1-methyl-4-[4-(5-methyl-1,3-benzoxazol-2-yl)piperidin-1-yl]-2-oxo-1,2-dihydroquinolin-7-yl} oxy)acetate | Prepared in analogy to example 379 by using tert-butyl bromoacetate (CAS 5292-43-3) | $^1$H NMR (400 MHz, DMSO-$d_6$) δ ppm 1.39-1.50 (m, 10 H) 2.03-2.20 (m, 2 H) 2.23-2.32 (m, 2 H) 2.39-2.45 (m, 3 H) 3.38-3.49 (m, 1 H) 3.51-3.64 (m, 5 H) 3.72-3.86 (m, 2 H) 4.77-5.00 (m, 2 H) 6.83-7.02 (m, 2 H) 7.14-7.24 (m, 1 H) 7.50-7.54 (m, 1 H) 7.55-7.65 (m, 1 H) 7.75-7.87 (m, 1 H). |
| 416 | 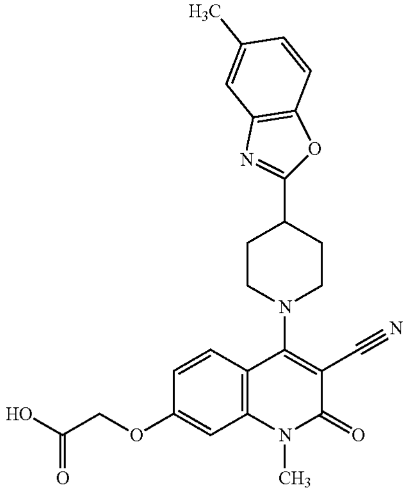 [SMILES: Cc1ccc2oc(C3CCN(c4c(C#N)c(=O)n(C)c5cc(OCC(=O)O)ccc45)CC3)nc2c1] | ({3-cyano-1-methyl-4-[4-(5-methyl-1,3-benzoxazol-2-yl)piperidin-1-yl]-2-oxo-1,2-dihydroquinolin-7-yl}oxy)acetic acid | Prepared from example 415 by treatment with 30 equiv. TFA (CAS 76-05-1) in dichloromethane (0.1 M) for 16 h at RT. | $^1$H NMR (400 MHz, DMSO-$d_6$) δ ppm 2.06-2.20 (m, 2 H) 2.22-2.34 (m, 2 H) 2.38-2.45 (m, 3 H) 3.30-3.47 (m, 1 H) 3.50-3.66 (m, 5 H) 3.72-3.86 (m, 2 H) 4.84-4.95 (m, 2 H) 6.89-7.03 (m, 3 H) 7.14-7.23 (m, 1 H) 7.48-7.54 (m, 1 H) 7.55-7.62 (m, 1 H) 7.74-7.86 (m, 1 H). |

TABLE 21-continued

Compounds were prepared as referenced

| Example | Structure | IUPAC-Name | Starting Materials | Analytics |
|---|---|---|---|---|
| 417 | 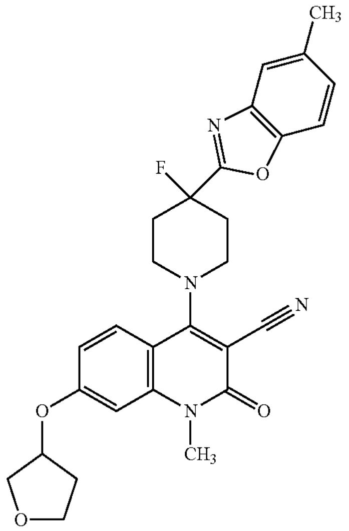 [SMILES: Cc1ccc2oc(C3(F)CCN(c4c(C#N)c(=O)n(C)c5cc(OC6CCOC6)ccc45)CC3)nc2c1] | (rac)-4-[4-fluoro-4-(5-methyl-1,3-benzoxazol-2-yl)piperidin-1-yl]-1-methyl-2-oxo-7-(tetrahydrofuran-3-yloxy)-1 2-dihydroquinoline-3-carbonitrile | Prepared from intermediate 242 in analogy to 379. | $^1$H NMR (400 MHz, DMSO-$d_6$) δ ppm 1.95-2.06 (m, 1 H) 2.24-2.36 (m, 1 H) 2.46 (s, 3 H) 2.53-2.74 (m, 4 H) 3.56 (s, 3 H) 3.66-3.81 (m, 5 H) 3.82-3.90 (m, 2 H) 3.91-3.97 (m, 1 H) 5.27-5.33 (m, 1 H) 6.90-6.97 (m, 2 H) 7.33 (dd, 1 H) 7.65-7.68 (m, 1 H) 7.71 (d, 1 H) 7.86 (d, 1 H). LC-MS (Method 1): $R_t$ = 1.26 min; MS (ESIpos): m/z = 503 $[M + H]^+$ |

Example 418

7-(cyclopropylamino)-1-methyl-4-[4-methyl-4-(5-methyl-1,3-benzoxazol-2-yl)piperidin-1-yl]-2-oxo-1,2-dihydroquinoline-3-carbonitrile

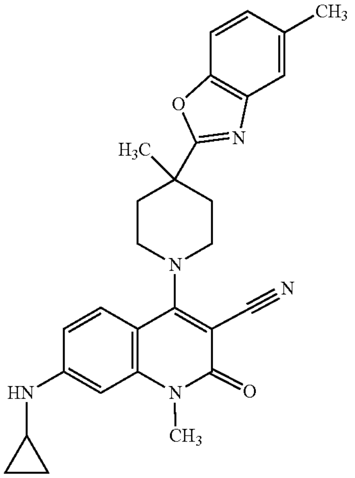 [SMILES: Cc1ccc2oc(C3(C)CCN(c4c(C#N)c(=O)n(C)c5cc(NC6CC6)ccc45)CC3)nc2c1]

7-bromo-1-methyl-4-[4-methyl-4-(5-methyl-1,3-benzoxazol-2-yl)piperidin-1-yl]-2-oxo-1,2-dihydroquinoline-3-carbonitrile (50.0 mg, 102 μmol, example 110), Xantphos (11.8 mg, 20.4 μmol; CAS 161265-03-8) Di-μ-chlorobis[(1, 2,3-n)-1-phenyl-2-propenyl]dipalladium(II) (5.27 mg, 10.2 μmol; CAS 12131-44-1) cesium carbonate (99.5 mg, 305 μmol; CAS 534-17-8) were added to a 5 ml vessel and were flushed with Argon. Tert-amyl alcohol (pre-sparged with argon) (500 μl) and cyclopropylamine (14 μl, 200 μmol; CAS 765-30-0) were added, the vessel crimp sealed, and the mixture was stirred at 95° C. overnight. The mixture was filtered through a 2 g Isolute column. The column was washed thrice with dichloromethane/methanol (9:1). The filtrate was concentrated under reduced pressure with subsequent purification by acidic preperative HPLC yielding the title compound (7.5 mg, 95% purity, 15% yield).

$^1$H NMR (400 MHz, ACETONITRILE-$d_3$) δ ppm 0.47-0.53 (m, 2H) 0.78-0.85 (m, 2H) 1.47-1.52 (m, 3H) 1.74-1.78 (m, 1H) 1.97-2.06 (m, 2H) 2.42-2.46 (m, 3H) 2.48-2.57 (m, 2H) 3.44-3.54 (m, 5H) 3.61-3.70 (m, 2H) 6.61 (d, 1H) 6.65 (dd, 1H) 7.18 (dd, 1H) 7.22-7.29 (m, 1H) 7.45 (d, 1H) 7.48-7.51 (m, 1H) 7.60-7.64 (m, 1H)

LC-MS (Method 1): $R_t$=1.38 min; MS (468.4): m/z=[M+H]+

Example 419

7-methoxy-1,6-dimethyl-4-[4-(5-methyl-1,3-benzoxazol-2-yl)piperidin-1-yl]-2-oxo-1,2-dihydroquinoline-3-carbonitrile

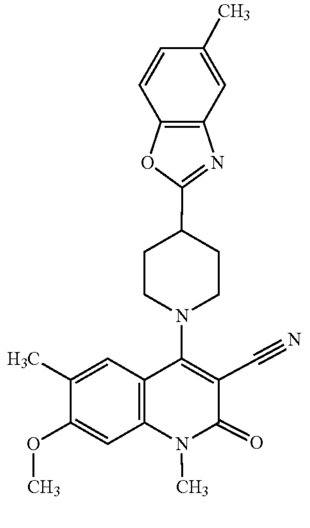 [SMILES: COc1cc2c(cc1C)c(N1CCC(c3nc4cc(C)ccc4o3)CC1)c(C#N)c(=O)n2C]

To a suspension of 200 mg 6-bromo-7-methoxy-1-methyl-4-[4-(5-methyl-1,3-benzoxazol-2-yl)piperidin-1-yl]-2-oxo-1,2-dihydroquinoline-3-carbonitrile (394 μmol, intermediate 263) in 1 mL dioxan and 50 μl water was added 61 μl trimethylboroxine (0.43 mmol, CAS 823-96-1), 321 mg cesium carbonate (0.98 mmol) and 29 mg [1,1'-bis (diphenylphosphino)ferrocene]-dichloropalladium(II) (39.4 μmol). The reaction mixture was purged for 5 min with nitrogen then heated at 90° C. for 2 h. The reaction mixture was concentrated under reduced pressure. The residue was diluted with water and extracted 3× with ethyl acetate. The product precipitated between the layers and so the extracts were filtered. The solid was purified by RP-HPLC and the product was obtained in 67% yield (140 mg)

$^1$H-NMR (400 MHz, DMSO-d6): δ [ppm]=2.07-2.20 (m, 2H), 2.22 (s, 3H), 2.29 (br s, 2H), 2.42 (s, 3H), 3.37-3.46 (m, 1H), 3.52-3.63 (m, 5H), 3.79 (br d, 2H), 3.99 (s, 3H), 6.90 (s, 1H), 7.19 (d, 1H), 7.53 (s, 1H), 7.56-7.61 (m, 2H).

LC-MS (Method 1): $R_t$=1.40 min; MS (ESIpos): m/z=443 $[M+H]^+$

Example 420

6-bromo-4-[4-fluoro-4-(5-methyl-1,3-benzoxazol-2-yl)piperidin-1-yl]-7-methoxy-1-methyl-2-oxo-1,2-dihydroquinoline-3-carbonitrile

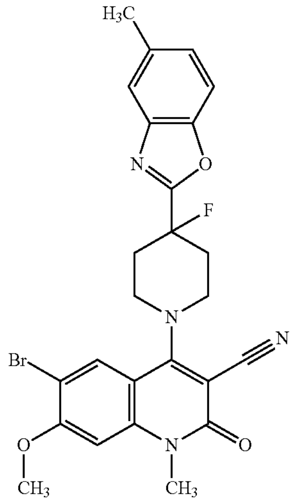 [SMILES: COc1cc2c(cc1Br)c(N1CCC(F)(c3nc4cc(C)ccc4o3)CC1)c(C#N)c(=O)n2C]

Triethylamine (360 μl, 2.6 mmol) was added to a suspension of 282 mg 6-bromo-4-chloro-7-methoxy-1-methyl-2-oxo-1,2-dihydroquinoline-3-carbonitrile (861 μmol, intermediate 264) and 300 mg 2-(4-fluoropiperidin-4-yl)-5-methyl-1,3-benzoxazole (300 mg, 861 μmol, intermediate 267) in 5.3 mL ethanol and stirred for 2 h at 90° C. After cooling down to room temperature, the suspension was filtered and washed with ethanol. The filtrate was evaporated and purified by RP-HPLC. The product was obtained in 4% yield.

1H-NMR (400 MHz, DMSO-d6): δ [ppm]=2.46 (s, 3H), 2.52-2.74 (m, 4H), 3.62 (s, 3H), 3.67-3.84 (m, 4H), 4.05 (s, 3H), 7.03 (s, 1H), 7.33 (dd, 1H), 7.67 (s, 1H), 7.72 (d, 1H), 8.02 (s, 1H).

LC-MS (Method 1): $R_t$=1.38 min; MS (ESIpos): m/z=527 $[M+H]^+$

Example 421

1,6-dimethyl-4-[4-(5-methyl-1,3-benzoxazol-2-yl)piperidin-1-yl]-7-nitro-2-oxo-1,2-dihydroquinoline-3-carbonitrile

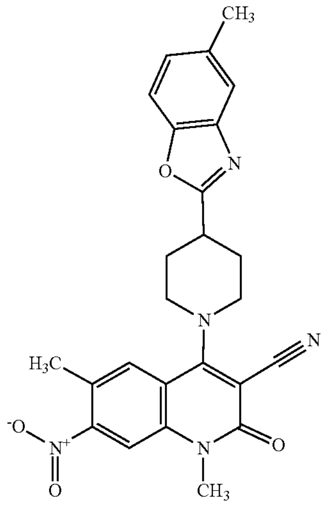

A solution of 230 mg 4-chloro-1,6-dimethyl-7-nitro-2-oxo-1,2-dihydroquinoline-3-carbonitrile (intermediate 279), 179 mg 5-methyl-2-(piperidin-4-yl)-1,3-benzoxazole (CAS 199292-77-8) and 0.23 mL triethylamine in 15 mL 2-propanol was stirred for 4 h at 90° C. After this time, water and ethyl acetate were added. The precipitate was filtered off and washed with ethyl acetate to generate a first crop of 220 mg of the title compound. The combined organic layers were washed with water and brine and dried over sodium sulfate. After evaporation of the solvent, the residue was purified by RP-HPLC (column: X-Bridge C18 5 μm 100×30 mm, mobile phase: acetonitrile/water (0.1 vol. % formic acid)-gradient) to give further 30 mg of the title compound.

$^1$H-NMR (400 MHz, DMSO-d6) δ[ppm]: 2.09-2.23 (m, 2H) 2.29-2.37 (m, 2H) 2.32-2.33 (m, 1H) 2.41-2.44 (m, 3H) 2.44-2.47 (m, 3H) 3.20-3.25 (m, 3H) 3.39-3.53 (m, 1H) 3.59-3.72 (m, 2H) 3.80-3.93 (m, 2H) 7.06-7.25 (m, 1H) 7.50-7.55 (m, 1H) 7.56-7.65 (m, 1H) 7.88-7.95 (m, 1H) 8.08-8.14 (m, 1H).

Example 422

6-bromo-7-hydroxy-1-methyl-4-[4-(5-methyl-1,3-benzoxazol-2-yl)piperidin-1-yl]-2-oxo-1,2-dihydro-quinoline-3-carbonitrile

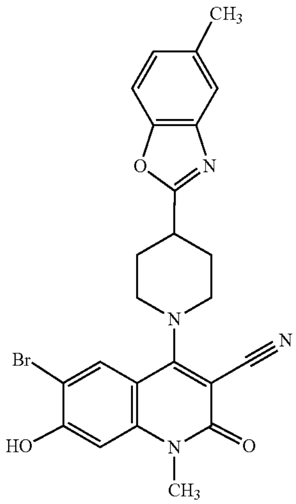 [SMILES: Cc1ccc2oc(C3CCN(c4c(C#N)c(=O)n(C)c5cc(O)c(Br)cc45)CC3)nc2c1]

Boron tribromide (18 ml, 1.0 M in dichloromethane, 18 mmol; CAS 10294-33-4) was added slowly to a suspension of 6-bromo-7-methoxy-1-methyl-4-[4-(5-methyl-1,3-benzo-xazol-2-yl)piperidin-1-yl]-2-oxo-1,2-dihydroquinoline-3-carbonitrile (1.86 g, 3.67 mmol, intermediate 281) in 38 mL dichloromethane at −78° C. under a nitrogen atmosphere. The mixture was allowed to warm to room temperature and stirred overnight.

The reaction mixture was poured into ice-water and stirred 1 h. The layers were separated and the organic layer was evaporated partially. The precipitate was filtered and dried and the product was obtain end in 71% yield.

$^{1}$H-NMR (400 MHz, DMSO-d6): 5 [ppm]=2.01-2.15 (m, 2H), 2.25-2.36 (m, 2H), 2.42 (s, 3H), 3.37-3.62 (m, 9H), 3.78 (br d, 2H), 6.94 (s, 1H), 7.19 (dd, 1H), 7.53 (s, 1H), 7.58 (d, 1H), 7.90 (s, 1H), 11.64 (s, 1H).

LC-MS Method 2): $R_t$=0.75 min; MS (ESIpos): m/z=493 $[M+H]^+$

Example 423

6-bromo-7-hydroxy-1-methyl-4-[4-methyl-4-(5-methyl-1,3-benzoxazol-2-yl)piperidin-1-yl]-2-oxo-1,2-dihydroquinoline-3-carbonitrile

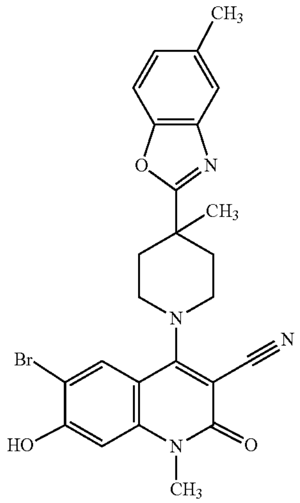 [SMILES: Cc1ccc2oc(C3(C)CCN(c4c(C#N)c(=O)n(C)c5cc(O)c(Br)cc45)CC3)nc2c1]

Boron tribromide (17 ml, 1.0 M in dichloromethane, 17 mmol; CAS 10294-33-4) was added slowly to a suspension of 6-bromo-7-methoxy-1-methyl-4-[4-methyl-4-(5-methyl-1,3-benz-oxazol-2-yl)piperidin-1-yl]-2-oxo-1,2-dihydroquinoline-3-carbonitrile (2.17 g, 4.16 mmol) was dissolved in 43 mL dichloromethane and cooled to −78° C. under a nitrogen atmosphere. The mixture was allowed to warm to room temperature and stirred overnight. The reaction mixture was poured into ice-water and stirred 1 h. The dichloromethane was evaporated and the aqueous layer was extracted 3× with ethyl acetate:methanol 9:1. The org. layers were filtered over a waterresistant-filter and concentrated under reduced pressure. The product was obtained in quantitative yield (2.38 g).

$^{1}$H NMR (400 MHz, DMSO-$d_6$) δ ppm 1.49 (s, 3H) 2.01 (ddd, 2H) 2.42 (s, 3H) 2.44-2.48 (m, 2H) 3.45 (s, 3H) 3.47-3.53 (m, 2H) 3.65-3.75 (m, 2H) 6.93 (s, 1H) 7.15-7.24 (m, 1H) 7.55-7.57 (m, 1H) 7.60 (d, 1H) 7.92 (s, 1H) 11.62 (br s, 1H).

Example 424

(rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile

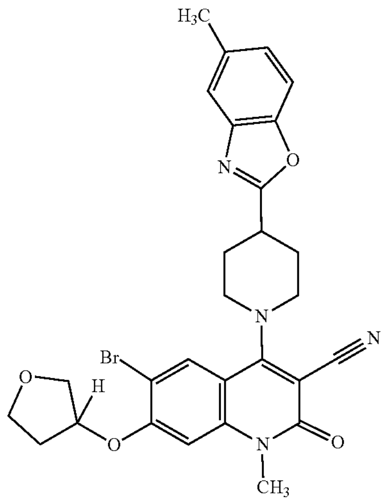 [SMILES: Cc1ccc2oc(C3CCN(c4c(C#N)c(=O)n(C)c5cc(OC6CCOC6)c(Br)cc45)CC3)nc2c1]

A MW vial charged with 6-bromo-7-hydroxy-1-methyl-4-[4-(5-methyl-1,3-benzoxazol-2-yl)piperidin-1-yl]-2-oxo-1,2-dihydroquinoline-3-carbonitrile (100 mg, 203 μmol, example 422), 198 mg cesium carbonate (608 μmol) was flushed with argon and 3.1 mL anhydrous DMF was added followed by 39 μl 3-bromooxolane (410 μmol). The reaction mixture was heated to 100° C. under argon. In case of incomplete conversion, more equivalents of 3-bromooxolane and cesium carbonate were added and it was stirred at 100° C. W ater was added and the mixture was extracted with ethyl acetate 3×. The combined organic layers were washed with saturated sodium chloride solution and filtered over a hydrophobic filter. The solvent was evaporated under reduced pressure and the crude product was purified by pHPLC. The product was obtained in 35% yield (41 mg).

$^1$H NMR (400 MHz, DMSO-$d_6$) δ ppm 2.01-2.14 (m, 3H) 2.26-2.37 (m, 3H) 2.42 (s, 3H) 3.38-3.47 (m, 1H) 3.59 (s, 5H) 3.76-3.84 (m, 3H) 3.85-3.93 (m, 2H) 3.94-4.01 (m, 1H) 5.43-5.49 (m, 1H) 6.99 (s, 1H) 7.16-7.22 (m, 1H) 7.19 (dd, 1H) 7.49-7.54 (m, 1H) 7.96 (s, 1H).

Example 425

(rac)-1-methyl-4-[4-(5-methyl-1,3-benzoxazol-2-yl)piperidin-1-yl]-2-oxo-7-[tetrahydrofuran-3-yloxy]-1,2-dihydroquinoline-3,6-dicarbonitrile

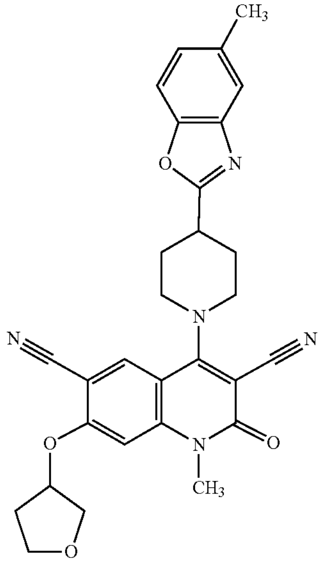 [SMILES: Cc1ccc2oc(C3CCN(c4c(C#N)c(=O)n(C)c5cc(OC6CCOC6)c(C#N)cc45)CC3)nc2c1]

A flask with 150 mg 6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (266 μmol, example 424), 13.8 mg di-chlorobis[(1,2,3-n)-1-phenyl-2-propenyl]dipalladium(II) (26.6 μmol; CAS 12131-44-1), 14.8 mg 1,1'-bis(diphenylphosphino)ferrocene (26.6 μmol; CAS 12150-46-8) and 46.9 mg zinc cyanide (399 μmol; CAS 557-21-1) was flushed with nitrogen. Then 1.9 ml N,N-dimethylacetamide and 93 μl di-isopropylethylamine (530 μmol) were added and the mixture was stirred 5.5 h under a nitrogen atmosphere at 80° C. The mixture was filtered over celite, washed with dichloromethane and the filtrate was evaporated. The crude product was purified by column chromatography (dichloromethane 100→dichloromethane:ethanol 90:10) and by RP-HPLC.

$^1$H NMR (400 MHz, DMSO-$d_6$) δ ppm 2.01-2.11 (m, 1H) 2.11-2.21 (m, 2H) 2.25-2.33 (m, 3H) 2.34-2.40 (m, 1H) 2.42 (s, 3H) 3.37-3.46 (m, 1H) 3.61-3.67 (m, 2H) 3.77-3.86 (m, 3H) 3.87-3.93 (m, 2H) 3.94-4.02 (m, 1H) 5.53 (td, 1H) 7.03 (s, 1H) 7.17-7.22 (m, 1H) 7.49-7.54 (m, 1H) 7.58 (d, 1H) 8.17 (s, 1H).

LC-MS (Method 1): $R_t$=1.20 min; MS (ESIpos): m/z=510 $[M+H]^+$

Example 426

7-hydroxy-1-methyl-4-[4-methyl-4-(5-methyl-1,3-benzoxazol-2-yl)piperidin-1-yl]-2-oxo-1,2-dihydroquinoline-3,6-dicarbonitrile

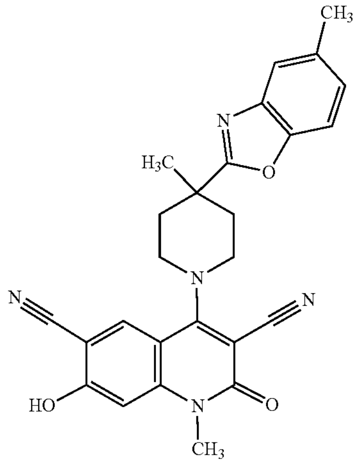 [SMILES: Cc1ccc2oc(C3(C)CCN(c4c(C#N)c(=O)n(C)c5cc(O)c(C#N)cc45)CC3)nc2c1]

A flask charged with 200 mg 6-bromo-7-hydroxy-1-methyl-4-[4-methyl-4-(5-methyl-1,3-benzoxazol-2-yl)piperidin-1-yl]-2-oxo-1,2-dihydroquinoline-3-carbonitrile (394 μmol, example 423), 20.4 mg [Pd(cinnamyl)$Cl_2$ (39.4 μmol, CAS 12131-44-1), 22 mg 1,1'-bis(diphenylphosphanyl)ferrocene (39.4 μmol, CAS 12150-46-8) and 69.4 mg zinc cyanide (591 μmol) was sealed and flushed with argon. 2 mL degassed N,N-dimethylacetamide and 140 μl di-isopropylethylamine were added subsequently. The mixture was stirred at 80° C. for 2 d. The crude product was purified by RP-HPLC and the product was obtained in 48% yield (91 mg).

1H-NMR (400 MHz, DMSO-d6): 5 [ppm]=1.48 (s, 3H), 1.97-2.08 (m, 2H), 2.40-2.47 (m, 5H), 3.40-3.54 (m, 5H), 3.65-3.75 (m, 2H), 6.73 (s, 1H), 7.20 (dd, 1H), 7.54-7.57 (m, 1H), 7.60 (d, 1H), 8.04 (s, 1H).

LC-MS (Method 1): $R_t$=1.21 min; MS (ESIpos): m/z=454 $[M+H]^+$

Example 427

(rac)-6-ethoxy-1-methyl-4-[4-(5-methyl-1,3-benzoxazol-2-yl)piperidin-1-yl]-2-oxo-7-[tetrahydrofuran-3-yloxy]-1,2-dihydroquinoline-3-carbonitrile

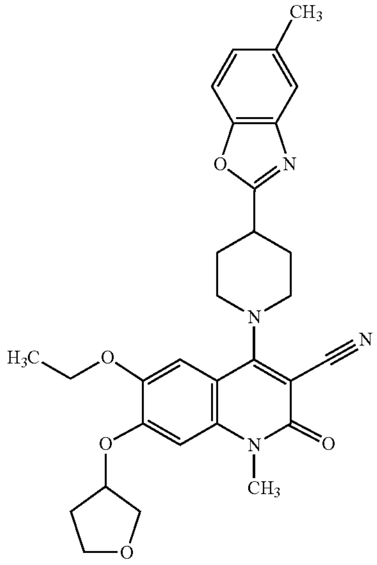 [SMILES: CCOc1cc2c(N3CCC(c4nc5cc(C)ccc5o4)CC3)c(C#N)c(=O)n(C)c2cc1OC1CCOC1]

A MW-vial was charged with 186 mg 6-bromo-1-methyl-4-[4-(5-methyl-1,3-benzoxazol-2-yl)piperidin-1-yl]-2-oxo-7-[tetrahydrofuran-3-yloxy]-1,2-dihydroquinoline-3-carbonitrile (330 μmol, example 424), 16 mg tBuBrettPhos ligand (33.0 μmol), 28 mg tBuBrettPhos Pd G3 (33.0 μmol) and 151 mg cesium carbonate (462 μmol) and flushed with nitrogen. 1.9 mL Degassed toluene and 190 μl ethanol were added and the mixture was stirred 4 h at 80° C. under a nitrogen atmosphere. The mixture was diluted with dichloromethane, filtered over celite, washed with dichloromethane and the filtrate was evaporated. The crude product was purified by column chromatography (dichloromethane 100→dichloromethane:ethanol 90:10) and by RP-HPLC. The product was obtained in 9% yield (15 mg).

$^1H$ NMR (400 MHz, DMSO-$d_6$) δ ppm 1.36 (t, 3H) 1.98-2.15 (m, 3H) 2.28-2.37 (m, 3H) 2.42 (s, 3H) 3.38-3.46 (m, 1H) 3.51-3.57 (m, 2H) 3.59 (s, 3H) 3.74-3.82 (m, 3H) 3.83-3.91 (m, 2H) 3.92-3.98 (m, 1H) 4.10 (q, 2H) 5.31-5.36 (m, 1H) 6.94 (s, 1H) 7.16-7.21 (m, 2H) 7.51-7.54 (m, 1H) 7.58 (d, 1H).

LC-MS (Method 1): $R_t$=1.28 min; MS (ESIpos): m/z=529 $[M+H]^+$

Example 428

7-hydroxy-1,6-dimethyl-4-[4-(5-methyl-1,3-benzoxazol-2-yl)piperidin-1-yl]-2-oxo-1,2-dihydroquinoline-3-carbonitrile

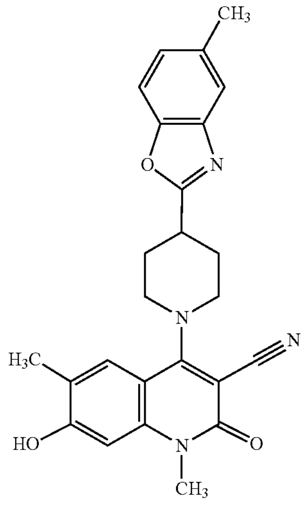 [SMILES: Cc1ccc2oc(C3CCN(c4c(C#N)c(=O)n(C)c5cc(O)c(C)cc45)CC3)nc2c1]

To a stirred suspension of 20 mg 7-methoxy-1,6-dimethyl-4-[4-(5-methyl-1,3-benzoxazol-2-yl)piperidin-1-yl]-2-oxo-1,2-dihydroquinoline-3-carbonitrile (37.5 μmol, example 419) in 0.4 mL dichloromethane at −78° C. was added 190 μl boron tri bromide (1.0 M in dichloromethane, 190 μmol) via a syringe. After 1 h the cooling bath was removed and the reaction mixture was allowed to warm to room temperature and stirred for 3 h. To the reaction mixture was added water and it was stirred until a suspension formed. The suspension was filtered and the solid was dried. The crude product was purified by RP-HPLC and the product was obtained in 87% yield.

1H-NMR (400 MHz, DMSO-d6): 5 [ppm]=2.05-2.17 (m, 2H), 2.19 (s, 3H), 2.26-2.32 (m, 2H), 2.42 (s, 3H), 3.36-3.44 (m, 1H), 3.47 (s, 3H), 3.55 (br t, 2H), 3.77 (br d, 2H), 6.80 (s, 1H), 7.19 (dd, 1H), 7.51-7.60 (m, 3H).

LC-MS (Method 1): $R_t$=1.21 min; MS (ESIpos): m/z=429 $[M+H]^+$

Example 429

(rac)-1,6-dimethyl-4-[4-(5-methyl-1,3-benzoxazol-2-yl)piperidin-1-yl]-2-oxo-7-[tetrahydrofuran-3-yloxy]-1,2-dihydroquinoline-3-carbonitrile

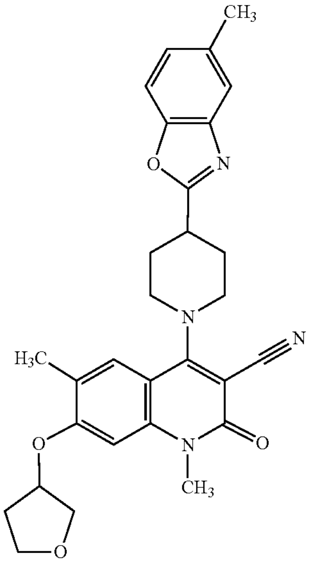 [SMILES: Cc1ccc2oc(C3CCN(c4c(C#N)c(=O)n(C)c5cc(OC6CCOC6)c(C)cc45)CC3)nc2c1]

To a suspension of 61 mg 7-hydroxy-1,6-dimethyl-4-[4-(5-methyl-1,3-benzoxazol-2-yl)piperidin 1-yl]-2-oxo-1,2-dihydroquinoline-3-carbonitrile (142 μmol, example 428) in 0.5 mL THF were added 17 μl 3-hydroxytetrahydrofuran (210 μmol), 75 mg triphenylphosphine (285 μmol) and 56 μl diisopropyl azodicarboxylate (280 μmol). The reaction mixture was stirred overnight at room temperature. To the reaction mixture was added 3 drops of water and the reaction mixture was concentrated under reduced pressure. The crude product was purified by RP-HPLC and prepTLC.

$^1$H NMR (400 MHz, DMSO-$d_6$) δ ppm 1.99-2.08 (m, 1H) 2.09-2.18 (m, 2H) 2.21 (s, 3H) 2.26-2.39 (m, 3H) 2.42 (s, 3H) 3.37-3.45 (m, 1H) 3.51-3.62 (m, 5H) 3.75-3.83 (m, 3H) 3.84-3.91 (m, 2H) 3.95-4.02 (m, 1H) 5.33-5.39 (m, 1H) 6.86 (s, 1H) 7.16-7.22 (m, 1H) 7.50-7.55 (m, 1H) 7.56-7.62 (m, 2H).

LC-MS Method 2): $R_t$=1.35 min; MS (ESIpos): m/z=499 $[M+H]^+$

Example 430

(rac)-6-(2,2-difluoroethoxy)-1-methyl-4-[4-(5-methyl-1,3-benzoxazol-2-yl)piperidin-1-yl]-2-oxo-7-[tetrahydrofuran-3-yloxy]-1,2-dihydroquinoline-3-carbonitrile

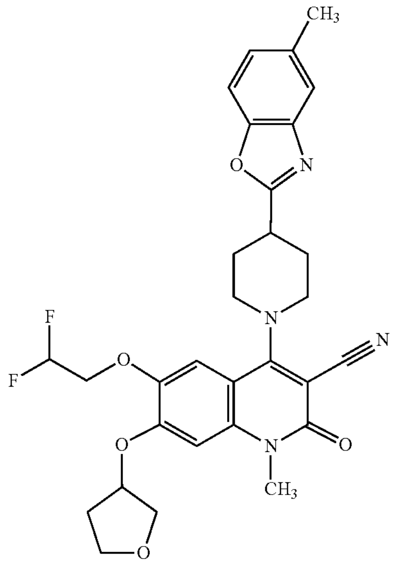 [SMILES: Cc1ccc2oc(C3CCN(c4c(C#N)c(=O)n(C)c5cc(OC6CCOC6)c(OCC(F)F)cc45)CC3)nc2c1]

A MW-vial was charged with 80 mg 6-bromo-1-methyl-4-[4-(5-methyl-1,3-benzoxazol-2-yl)piperidin-1-yl]-2-oxo-7-[tetrahydrofuran-3-yloxy]-1,2-dihydroquinoline-3-carbonitrile (80.0 mg, 142 μmol, example 424), 8 mg tBuBrettPhos ligand (14.0 μmol), 12 mg tBuBrettPhos Pd G3 (14.0 μmol) and 65 mg cesium carbonate (199 μmol) and flushed with nitrogen. 0.8 mL Degassed toluene and 86 μl 2,2-difluoroethanol were added and the mixture was stirred 4 h at 80° C. under a nitrogen atmosphere. The mixture was diluted with dichloromethane, filtered over celite, washed with dichloromethane and the filtrate was evaporated. The crude product was purified by RP-HPLC and the product was obtained in 22% yield.

$^1$H NMR (400 MHz, DMSO-$d_6$) δ ppm 2.00-2.18 (m, 3H) 2.26-2.37 (m, 3H) 2.42 (s, 3H) 3.41 (tt, 1H) 3.52-3.62 (m, 5H) 3.75-3.83 (m, 3H) 3.84-3.98 (m, 3H) 4.39 (td, 2H) 5.34-5.40 (m, 1H) 6.25-6.56 (m, 1H) 6.97 (s, 1H) 7.19 (dd, 1H) 7.30 (s, 1H) 7.51-7.54 (m, 1H) 7.58 (d, 1H).

Example 431

(rac)-4-[4-fluoro-4-(5-methyl-1,3-benzoxazol-2-yl)piperidin-1-yl]-6-methoxy-1-methyl-2-oxo-7-[tetrahydrofuran-3-yloxy]-1,2-dihydroquinoline-3-carbonitrile

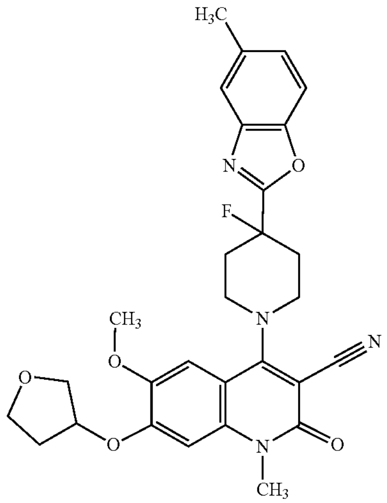 [SMILES: COc1cc2c(N3CCC(F)(c4nc5cc(C)ccc5o4)CC3)c(C#N)c(=O)n(C)c2cc1OC1CCOC1]

A MW-vial was charged with 50 mg 6-bromo-4-[4-fluoro-4-(5-methyl-1,3-benzoxazol-2-yl)piperidin-1-yl]-1-methyl-2-oxo-7-[(oxolan-3-yl)oxy]-1,2-dihydroquinoline-3-carbonitrile (86.0 μmol, intermediate 282), 4 mg tBuBrettPhos ligand (9.0 μmol), 7 mg tBuBrettPhos Pd G3 (8.6 μmol) and 39 mg cesium carbonate (120 μmol) and flushed with nitrogen. 0.48 mL Degassed toluene and 35 μl methanol were added and the mixture was stirred 22 h at 80° C. under a nitrogen atmosphere. The mixture was diluted with dichloromethane, filtered over celite, washed with dichloromethane and the filtrate was evaporated. The crude product was purified by RP-HPLC and the product was obtained in 3% yield (2 mg).

$^1$H NMR (400 MHz, DMSO-$d_6$) δ ppm 1.99-2.08 (m, 1H) 2.27-2.37 (m, 1H) 2.45 (s, 3H) 2.60 (br d, 3H) 2.64-2.72 (m, 1H) 3.60 (s, 3H) 3.67-3.82 (m, 5H) 3.83-3.90 (m, 5H) 3.92-3.98 (m, 1H) 5.33-5.39 (m, 1H) 6.94 (s, 1H) 7.20 (s, 1H) 7.33 (dd, 1H) 7.67 (s, 1H) 7.72 (d, 1H).

Example 432

(rac)-1-methyl-4-[4-methyl-4-(5-methyl-1,3-benzoxazol-2-yl)piperidin-1-yl]-2-oxo-7-[(oxolan-3-yl)oxy]-1,2-dihydroquinoline-3,6-dicarbonitrile

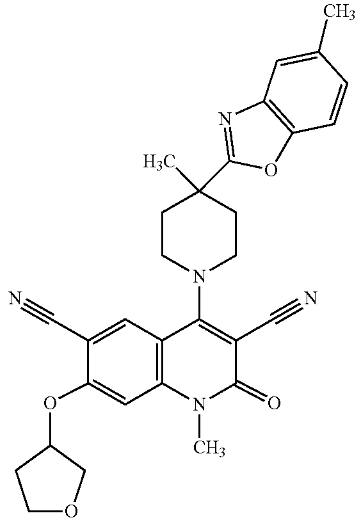 [SMILES: Cc1ccc2oc(C3(C)CCN(c4c(C#N)c(=O)n(C)c5cc(OC6CCOC6)c(C#N)cc45)CC3)nc2c1]

To a suspension of 30 mg 7-hydroxy-1-methyl-4-[4-methyl-4-(5-methyl-1,3-benzoxazol-2-yl)piperidin-1-yl]-2-oxo-1,2-dihydroquinoline-3,6-dicarbonitrile (example 426) and 26 mg Triphenylphosphin in 0.3 ml THF was added 26 µL diisopropyl azodicarboxylate and then 8 µL oxolan-3-ol. The reaction mixture was stirred for 14 hours at RT. To the reaction mixture was added 0.1 mL of water and then the mixture was concentrated under reduced pressure. The residue was purified by RP-HPLC (column: X-Bridge C18 5 µm 100×30 mm, mobile phase: acetonitrile/water (0.1 vol. % formic acid)-gradient) to obtain 37 mg of the title compound.

$^{1}$H-NMR (400 MHz, DMSO-d6): δ [ppm]=1.48 (s, 3H), 1.99-2.11 (m, 3H), 2.30-2.40 (m, 1H), 2.42 (s, 3H), 3.48-3.61 (m, 5H), 3.69-4.00 (m, 6H), 5.51 (br dd, 1H), 7.00 (s, 1H), 7.20 (dd, 1H), 7.54-7.58 (m, 1H), 7.60 (d, 1H), 8.19 (s, 1H). 2H-signals under DMSO-signal LC-MS Method 2): $R_t$=1.31 min; MS (ESIpos): m/z=524 $[M+H]^+$ Example 433

(rac)-1-methyl-4-[4-(5-methyl-1,3-benzoxazol-2-yl)piperidin-1-yl]-2-oxo-7-[(oxolan-3-yl)oxy]-6-(3,3,3-trifluoroprop-1-en-2-yl)-1,2-dihydroquinoline-3-carbonitrile

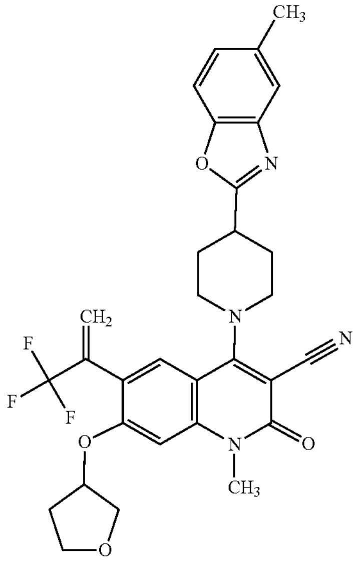 [SMILES: C=C(c1cc2c(N3CCC(c4nc5cc(C)ccc5o4)CC3)c(C#N)c(=O)n(C)c2cc1OC1CCOC1)C(F)(F)F]

A flask with a suspension of 100 mg (rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (177 µmol, intermediate 283) and 7.64 mg XPhos Pd G4 (8.87 µmol) were suspended in 3.4 mL 1,4-dioxan was flushed with nitrogen. A solution of sodium carbonate in water (230 µl, 2.0 M, 460 µmol) and 77 µl 4,4,5,5-tetramethyl-2-(3,3,3-trifluoroprop-1-en-2-yl)-1,3,2-dioxaborolane (350 µmol) were added and the mixture was stirred over night at 100° C. The reaction mixture was quenched with water and extracted 3× with ethyl acetate. The org. layer was washed with brine, filtered over a waterresistant-filter and evaporated. The crude product was purified by column chromatography (hexane:ethyl acetate 60:40→ethyl acetate 100→ethyl acetate:ethanol 90:10) and RP-HPLC. The product was obtained in 40% yield (41 mg).

$^{1}$H NMR (400 MHz, DMSO-d6) δ ppm 1.92-2.15 (m, 3H) 2.24-2.38 (m, 3H) 2.40-2.44 (m, 3H) 3.36-3.48 (m, 1H) 3.51-3.67 (m, 5H) 3.73-3.86 (m, 5H) 3.91-4.05 (m, 1H) 5.34-5.49 (m, 1H) 5.87-6.02 (m, 1H) 6.19-6.33 (m, 1H) 6.88-7.05 (m, 1H) 7.12-7.24 (m, 1H) 7.47-7.68 (m, 3H).

Example 434

(rac)-1-methyl-4-[4-(5-methyl-1,3-benzoxazol-2-yl)piperidin-1-yl]-2-oxo-7-[(oxolan-3-yl)oxy]-6-[1-(trifluoromethyl)cyclopropyl]-1,2-dihydroquinoline-3-carbonitrile

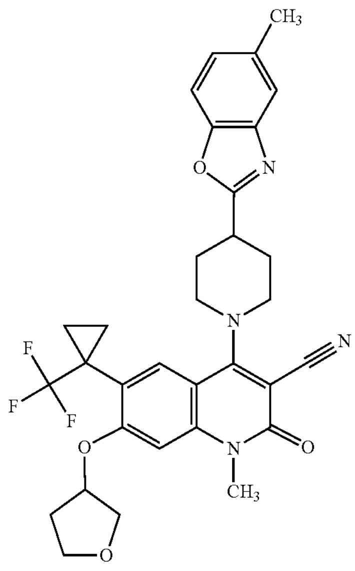 [SMILES: Cc1ccc2oc(C3CCN(c4c(C#N)c(=O)n(C)c5cc(OC6CCOC6)c(C6(C(F)(F)F)CC6)cc45)CC3)nc2c1]

This cyclopropanation method reaction was adapted from the literature: J. P. Phelan et al. *J. Am. Chem. Soc.* 2018, 140, 8037-8047.

55 mg 1-Methyl-4-[4-(5-methyl-1,3-benzoxazol-2-yl)piperidin-1-yl]-2-oxo-7-[(oxolan-3-yl)oxy]-6-(3,3,3-trifluoroprop-1-en-2-yl)-1,2-dihydroquinoline-3-carbonitrile (95.1 μmol, example 433), 93 mg N,N-diethylethanaminium bis[benzene-1,2-diolato(2-)-kappa$^2$O$^1$,O$^2$](iodomethyl)silicate (1-) (190 μmol, for preparation see *J. Am. Chem. Soc.* 2018, 140, 8037-8047) and 3.75 mg 2,4,5,6-tetra(9H-carbazol-9-yl)isophthalonitrile (4.75 μmol, CAS 1416881-52-1) were dissolved in 1.9 mL DMSO and degased with argon for 5 min. The MW-vial was placed in a water bath (to keep the temp. below 35° C.) and was subsequently irradiated by two 40 W Kessil LED Aquarium lamps for 12 h. 1M sodium hydroxide solution was added and the mixture was extracted with ethyl acetate 3×. The combined organic layers were washed with 1 M sodium hydroxide solution and brine, filtered over a hydrophobic filter and the solvent was evaporated under reduced pressure. The crude product was purified by column chromatography and the product was obtained in 49% yield (29 mg).

$^1$H NMR (400 MHz, DMSO-$d_6$) δ ppm 1.05-1.12 (m, 2H) 1.35-1.42 (m, 2H) 2.01-2.13 (m, 3H) 2.25-2.37 (m, 3H) 2.42 (s, 3H) 3.40-3.51 (m, 1H) 3.54-3.64 (m, 6H) 3.76-3.89 (m, 6H) 5.41-5.46 (m, 1H) 6.90 (s, 1H) 7.16-7.23 (m, 1H) 7.52-7.55 (m, 1H) 7.58 (d, 1H) 7.78 (s, 1H).

LC-MS Method 2): $R_t$=1.46 min; MS (ESIpos): m/z=593 [M+H]$^+$

TABLE 22

Compounds were prepared as referenced

| Example | Structure | IUPAC-Name | Starting Materials | Analytics |
|---|---|---|---|---|
| 435 | 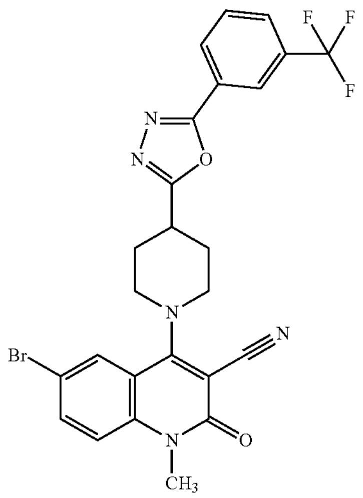 [SMILES: Cn1c(=O)c(C#N)c(N2CCC(c3nnc(-c4cccc(C(F)(F)F)c4)o3)CC2)c2cc(Br)ccc21] | 6-bromo-1-methyl-2-oxo-4-(4-{5-[3-(trifluoromethyl)phenyl]-1,3,4-oxadiazol-2-yl}piperidin-1-yl)-1,2-dihydroquinoline-3-carbonitrile | In analogy to example 421 but with intermediate 95 and intermediate 244. | $^1$H NMR (400 MHz, DMSO-$d_6$) δ ppm 2.04-2.21 (m, 2 H) 2.33-2.40 (m, 2 H) 3.48-3.55 (m, 1 H) 3.55-3.68 (m, 5 H) 3.79-3.89 (m, 2 H) 7.53-7.59 (m, 1 H) 7.85-7.95 (m, 3 H) 7.99-8.06 (m, 1 H) 8.26-8.30 (m, 1 H) 8.32-8.38 (m, 1 H). |

TABLE 22-continued

Compounds were prepared as referenced

| Example | Structure | IUPAC-Name | Starting Materials | Analytics |
| --- | --- | --- | --- | --- |
| 436 | 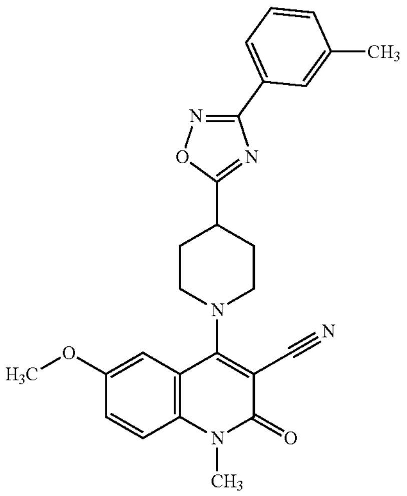 | 6-methoxy-1-methyl-4-{4-[3-(3-methylphenyl)-1,2,4-oxadiazol-5-yl]piperidin-1-yl}-2-oxo-1,2-dihydroquinoline-3-carbonitrile | In analogy to example 421 but with intermediate 99 and intermediate 169. | $^1$H NMR (400 MHz, DMSO-$d_6$) δ ppm 2.07-2.21 (m, 2 H) 2.32-2.43 (m, 5 H) 3.50-3.66 (m, 6 H) 3.79-3.89 (m, 5 H) 7.19-7.27 (m, 1 H) 7.37-7.49 (m, 3 H) 7.51-7.59 (m, 1 H) 7.79-7.89 (m, 2 H). |
| 437 | 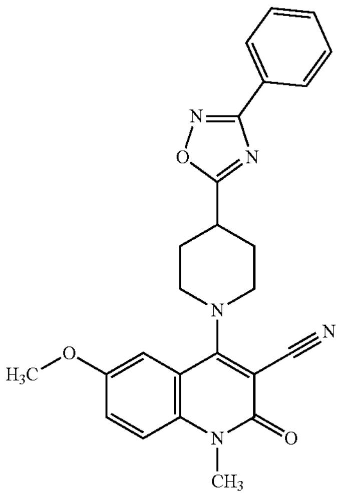 [SMILES: COc1ccc2c(c1)c(N1CCC(c3nc(-c4ccccc4)no3)CC1)c(C#N)c(=O)n2C] | 6-methoxy-1-methyl-2-oxo-4-[4-(3-phenyl-1,2,4-oxadiazol-5-yl)piperidin-1-yl]-1,2-dihydroquinoline-3-carbonitrile | In analogy to example 421 but with intermediate 99 and intermediate 246. | $^1$H NMR (400 MHz, DMSO-$d_6$) δ ppm 2.06-2.23 (m, 2 H) 2.32-2.39 (m, 2 H) 3.52-3.65 (m, 6 H) 3.78-3.91 (m, 5 H) 7.18-7.30 (m, 1 H) 7.36-7.44 (m, 1 H) 7.51-7.63 (m, 4 H) 8.00-8.07 (m, 2 H) |
| 438 | 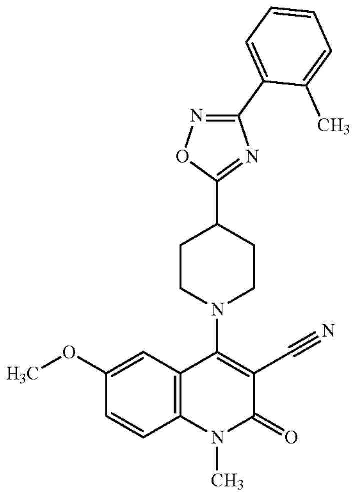 [SMILES: COc1ccc2c(c1)c(N1CCC(c3nc(-c4ccccc4C)no3)CC1)c(C#N)c(=O)n2C] | 6-methoxy-1-methyl-4-{4-[3-(2-methylphenyl)-1,2,4-oxadiazol-5-yl]piperidin-1-yl}-2-oxo-1,2-dihydroquinoline-3-carbonitrile | In analogy to example 421 but with intermediate 99 and intermediate 248 | $^1$H NMR (400 MHz, DMSO-$d_6$) δ ppm 2.06-2.22 (m, 2 H) 2.29-2.42 (m, 2 H) 2.55-2.61 (m, 3 H) 3.53-3.65 (m, 6 H) 3.78-3.93 (m, 5 H) 7.19-7.27 (m, 1 H) 7.33-7.52 (m, 4 H) 7.53-7.62 (m, 1 H) 7.90-8.01 (m, 1 H). |

TABLE 22-continued

Compounds were prepared as referenced

| Example | Structure | IUPAC-Name | Starting Materials | Analytics |
|---|---|---|---|---|
| 439 | 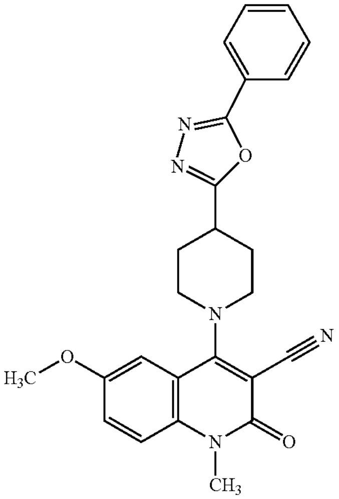 [SMILES: COc1ccc2c(c1)c(N1CCC(c3nnc(-c4ccccc4)o3)CC1)c(C#N)c(=O)n2C] | 6-methoxy-1-methyl-2-oxo-4-[4-(5-phenyl-1,3,4-oxadiazol-2-yl)piperidin-1-yl]-1,2-dihydroquinoline-3-carbonitrile | In analogy to example 421 but with intermediate 99 and intermediate 250. | $^{1}H$ NMR (400 MHz, DMSO-$d_6$) δ ppm 2.05-2.19 (m, 2 H), 2.31-2.39 (m, 2 H), 3.45-3.54 (m, 1 H), 3.55-3.65 (m, 5 H), 3.86 (s, 5 H), 7.24 (d, 1 H), 7.41 (dd, 1 H), 7.52-7.58 (m, 1 H), 7.58-7.68 (m, 3 H), 8.00-8.05 (m, 2 H). |
| 440 | 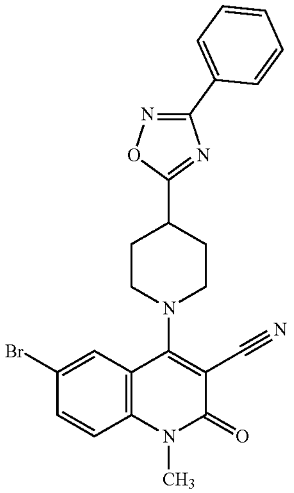 [SMILES: Cn1c(=O)c(C#N)c(N2CCC(c3nc(-c4ccccc4)no3)CC2)c2cc(Br)ccc21] | 6-bromo-1-methyl-2-oxo-4-[4-(3-phenyl-1,2,4-oxadiazol-5-yl)piperidin-1-yl]-1,2-dihydroquinoline-3-carbonitrile | In analogy to example 421 but with intermediate 95 and intermediate 246. | $^{1}H$ NMR (400 MHz, DMSO-$d_6$) δ ppm 2.06-2.19 (m, 2 H) 2.30-2.37(m, 2 H) 3.52-3.69 (m, 6 H) 3.79-3.88 (m, 2 H) 7.52-7.65 (m, 4 H) 7.87-7.92 (m, 1 H) 7.92-7.96 (m, 1 H) 8.01-8.06 (m, 2 H). |
| 441 | 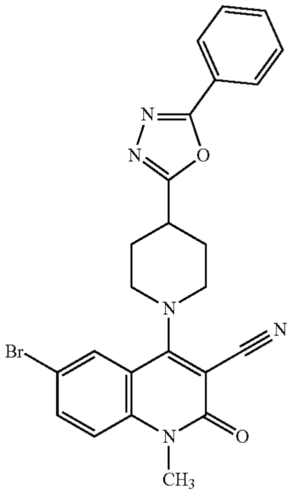 [SMILES: Cn1c(=O)c(C#N)c(N2CCC(c3nnc(-c4ccccc4)o3)CC2)c2cc(Br)ccc21] | 6-bromo-1-methyl-2-oxo-4-[4-(5-phenyl-1,3,4-oxadiazol-2-yl)piperidin-1-yl]-1,2-dihydroquinoline-3-carbonitrile | In analogy to example 421 but with intermediate 95 and intermediate 250. | $^{1}H$ NMR (400 MHz, DMSO-$d_6$) δ ppm 2.03-2.20 (m, 2 H) 2.27-2.35 (m, 2 H) 3.45-3.53 (m, 1 H) 3.54-3.68 (m, 5 H) 3.77-3.88 (m, 2 H) 7.51-7.58 (m, 1 H) 7.58-7.68 (m, 3 H) 7.87-7.95 (m, 2 H) 7.99-8.07 (m, 2 H). |

TABLE 22-continued

| Compounds were prepared as referenced | | | | |
|---|---|---|---|---|
| Example | Structure | IUPAC-Name | Starting Materials | Analytics |
| 442 | 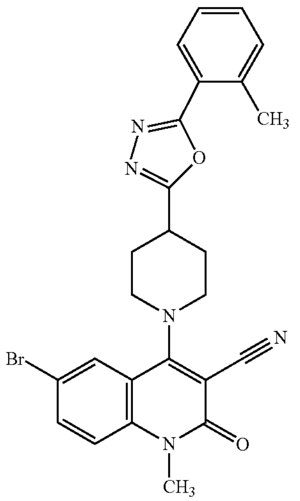 [SMILES: Cc1ccccc1-c1nnc(C2CCN(c3c(C#N)c(=O)n(C)c4ccc(Br)cc34)CC2)o1] | 6-bromo-1-methyl-4-{4-[5-(2-methylphenyl)-1,3,4-oxadiazol-2-yl]piperidin-1-yl}-2-oxo-1,2-dihydroquinoline-3-carbonitrile | In analogy to example 421 but with intermediate 95 and intermediate 166. | $^1$H NMR (400 MHz, DMSO-$d_6$) δ ppm 2.07-2.18 (m, 2 H) 2.30-2.38 (m, 2 H) 2.60-2.65 (m, 3 H) 3.45-3.55 (m, 1 H) 3.55-3.57 (m, 3 H) 3.58-3.68 (m, 2 H) 3.78-3.90 (m, 2 H) 7.37-7.48 (m, 2 H) 7.48-7.58 (m, 2 H) 7.85-7.97 (m, 3 H). |
| 443 | 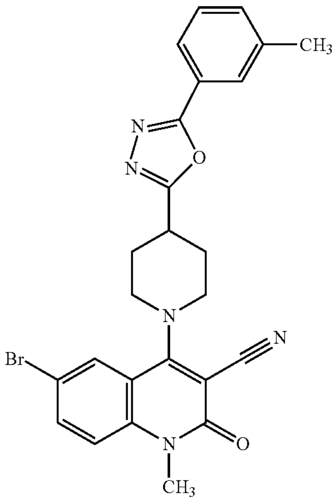 [SMILES: Cc1cccc(-c2nnc(C3CCN(c4c(C#N)c(=O)n(C)c5ccc(Br)cc45)CC3)o2)c1] | 6-bromo-1-methyl-4-{4-[5-(3-methylphenyl)-1,3,4-oxadiazol-2-yl]piperidin-1-yl}-2-oxo-1,2-dihydroquinoline-3-carbonitrile | In analogy to example 421 but with intermediate 95 and intermediate 177. | $^1$H NMR (400 MHz, DMSO-$d_6$) δ ppm 2.04-2.18 (m, 2 H) 2.26-2.39 (m, 2 H) 2.39-2.44 (m, 3 H) 3.44-3.54 (m, 1 H) 3.55-3.58 (m, 3 H) 3.57-3.67 (m, 2 H) 3.77-3.88 (m, 2 H) 7.39-7.59 (m, 3 H) 7.78-7.97 (m, 4 H). |

TABLE 22-continued

| Compounds were prepared as referenced | | | | |
|---|---|---|---|---|
| Example | Structure | IUPAC-Name | Starting Materials | Analytics |
| 444 | 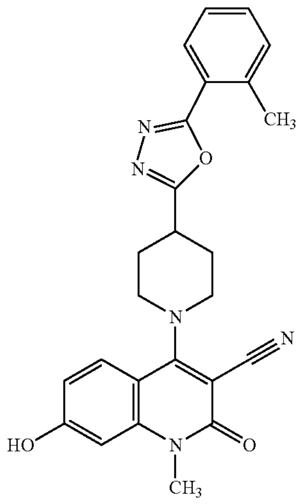 [SMILES: Cc1ccccc1-c1nnc(C2CCN(c3c(C#N)c(=O)n(C)c4cc(O)ccc34)CC2)o1] | 7-hydroxy-1-methyl-4-{4-[5-(2-methylphenyl)-1,3,4-oxadiazol-2-yl]piperidin-1-yl}-2-oxo-1,2-dihydroquinoline-3-carbonitrile | In analogy to example 421 but with intermediate 136 and intermediate 166. | $^{1}$H NMR (400 MHz, DMSO-$d_6$) δ ppm 2.04-2.18 (m, 2 H), 2.26-2.34 (m, 2 H), 2.63 (s, 3 H), 3.42-3.64 (m, 1 H), 3.58 (s, 1 H), 3.78 (br d, 2 H), 6.78-6.83 (m, 2 H), 7.38-7.48 (m, 2 H), 7.55 (s, 1 H), 7.73 (d, 1 H), 7.92 (dd, 1 H), 10.78 (bs, 1 H). |
| 445 | 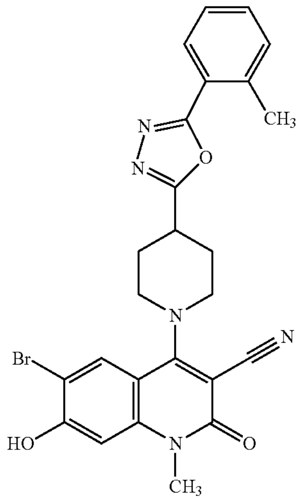 [SMILES: Cc1ccccc1-c1nnc(C2CCN(c3c(C#N)c(=O)n(C)c4cc(O)c(Br)cc34)CC2)o1] | 6-bromo-7-hydroxy-1-methyl-4-{4-[5-(2-methylphenyl)-1,3,4-oxadiazol-2-yl]piperidin-1-yl}-2-oxo-1,2-dihydroquinoline-3-carbonitrile | In analogy to example 428 using intermediate 251. | $^{1}$H NMR (400 MHz, DMSO-$d_6$) δ ppm 2.01-2.15 (m, 3 H), 2.26-2.37 (m, 3 H), 2.61-2.65 (m, 3 H), 3.42-3.53 (m, 4 H), 3.53-3.65 (m, 2 H), 3.84 (s, 2 H), 6.89-6.95 (m, 1 H), 7.38-7.48 (m, 2 H), 7.48-7.55 (m, 1 H), 7.88-7.95 (m, 2 H), 11.69 (s, 1 H). |

Example 446

(rac)-1-methyl-4-{4-[5-(2-methylphenyl)-1,3,4-oxadiazol-2-yl]piperidin-1-yl}-7-{[oxan-3-yl]oxy}-2-oxo-1,2-dihydroquinoline-3-carbonitrile

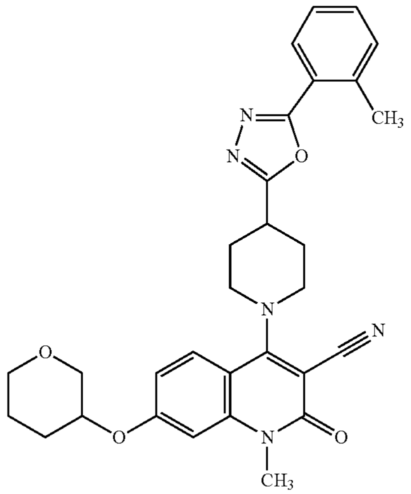 [SMILES: Cc1ccccc1-c1nnc(C2CCN(c3c(C#N)c(=O)n(C)c4cc(OC5CCCOC5)ccc34)CC2)o1]

A mixture of 260 mg 7-hydroxy-1-methyl-4-{4-[5-(2-methylphenyl)-1,3,4-oxadiazol-2-yl]piperidin-1-yl}-2-oxo-1,2-dihydroquinoline-3-carbonitrile (example 444), 49 mg sodium iodide, 576 mg cesium carbonate and 389 mg 3-bromooxane in 13 mL DMF was stirred for 20 hours at 120° C. under argon. Water was added and the mixture was extracted with ethyl acetate (2×). The combined organic layers were washed with brine, the solvent was evaporated under reduced pressure and the crude product was purified by flash chromatography (silica, dichloromethane/methanol gradient 0-2%) to give 45 mg of the title compound.

$^{1}$NMR (400 MHz, DMSO-d6) δ ppm 1.48-1.64 (m, 2H) 1.66-1.88 (m, 2H) 2.00-2.19 (m, 5H) 2.22-2.37 (m, 3H) 2.60-2.65 (m, 3H) 3.44-3.70 (m, 9H) 3.75-3.91 (m, 3H) 4.63-4.77 (m, 1H) 6.90-7.05 (m, 2H) 7.35-7.57 (m, 3H) 7.74-7.86 (m, 1H) 7.88-7.97 (m, 1H)

Example 447

4-[4-(1,3-benzoxazol-2-yl)piperidin-1-yl]-N,1-dimethyl-2-oxo-1,2-dihydroquinoline-3-carboxamide

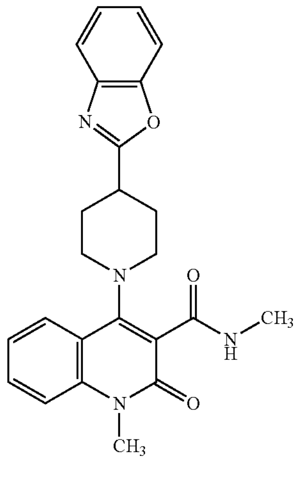 [SMILES: CNC(=O)c1c(N2CCC(c3nc4ccccc4o3)CC2)c2ccccc2n(C)c1=O]

To a suspension of 4-chloro-N,1-dimethyl-2-oxo-1,2-dihydroquinoline-3-carboxamide (42.0 mg, 168 μmol, intermediate 274) in 1 mL ethanol was added 58 μl Di-isopropylethylamine (340 μmol) an 34 mg 2-(piperidin-4-yl)-1,3-benzoxazole (168 μmol, CAS 51784-03-3). The reaction mixture stirred 3 h at 90° C. and at room temperature overnight. The resulting suspension was filtered and the solid was dried. The product was obtained in 63% yield.

1H-NMR (400 MHz, DMSO-d6): 5 [ppm]=2.03-2.15 (m, 2H), 2.17-2.26 (m, 2H), 2.74 (d, 3H), 3.09 (br t, 2H), 3.19-3.30 (m, 1H), 3.36 (br d, 2H), 3.59 (s, 3H), 7.29-7.41 (m, 3H), 7.50-7.55 (m, 1H), 7.60-7.67 (m, 1H), 7.69-7.75 (m, 2H), 7.93 (dd, 1H), 8.18 (q, 1H).

LC-MS (Method 1): $R_t$=1.05 min; MS (ESIpos): m/z=417 $[M+H]^+$

Example 448

N,1-dimethyl-4-[4-(5-methyl-1,3-benzoxazol-2-yl)piperidin-1-yl]-2-oxo-1,2-dihydroquinoline-3-carboxamide

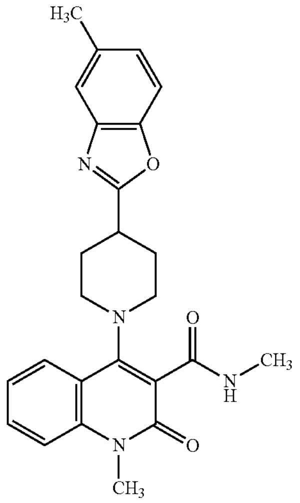 [SMILES: CNC(=O)c1c(N2CCC(c3nc4cc(C)ccc4o3)CC2)c2ccccc2n(C)c1=O]

To a suspension of 30 mg 4-chloro-N,1-dimethyl-2-oxo-1,2-dihydroquinoline-3-carboxamide (120 μmol, intermediate 274) in 1 mL 2-propanol was added 42 μl Di-isopropylethylamine (240 μmol) and 29 mg 5-methyl-2-(piperidin-4-yl)-1,3-benzoxazole (132 μmol, CAS 199292-77-8). The reaction mixture stirred 3 h at 90° C. The mixture was cooled to room temperature and concentrated under reduced pressure. The residue (68 mg) was diluted with DMSO, filtered and the filtrate was purified by RP-HPLC. The product was obtained in 76% yield (41 mg).

$^{1}$H-NMR (400 MHz, DMSO-d6): 5 [ppm]=2.01-2.13 (m, 2H), 2.15-2.24 (m, 2H), 2.42 (s, 3H), 2.73 (d, 3H), 3.08 (br t, 2H), 3.16-3.27 (m, 1H), 3.36 (br s, 2H), 3.59 (s, 3H), 7.15-7.21 (m, 1H), 7.29-7.35 (m, 1H), 7.50-7.59 (m, 3H), 7.60-7.67 (m, 1H), 7.92 (dd, 1H), 8.17 (q, 1H).

LC-MS (Method 2): $R_t$=1.13 min; MS (ESIneg): m/z=429 $[M-H]^-$

Example 449

4-[4-(1,3-benzoxazol-2-yl)-4-methylpiperidin-1-yl]-N,1-dimethyl-2-oxo-1,2-dihydroquinoline-3-carboxamide

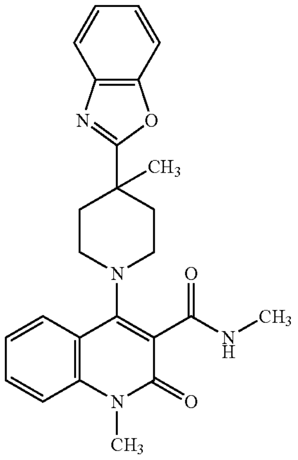 [SMILES: CNC(=O)c1c(N2CCC(C)(c3nc4ccccc4o3)CC2)c2ccccc2n(C)c1=O]

To a suspension of 30.0 mg 4-chloro-N,1-dimethyl-2-oxo-1,2-dihydroquinoline-3-carboxamide (120 μmol, intermediate 274) in 1 mL 2-propanol was added 42 μl di-isopropylethylamine (240 μmol) and 29 mg 2-(4-methylpiperidin-4-yl)-1,3-benzoxazole (132 μmol, intermediate 1). The reaction mixture stirred 3 h at 90° C. The mixture w as cooled to room temperature and concentrated under reduced pressure. The residue (70 mg) was diluted with DMSO, filtered and the filtrate purified by RP-HPLC. The product was obtained in 88% yield (47 mg).

$^1$H-NMR (400 MHz, DMSO-d6): 5 [ppm]=1.47 (s, 3H), 1.97 (ddd, 2H), 2.99-3.09 (m, 2H), 3.15-3.24 (m, 2H), 3.56 (s, 3H), 7.32 (td, 1H), 7.34-7.42 (m, 2H), 7.51 (dd, 1H), 7.60-7.67 (m, 1H), 7.69-7.79 (m, 2H), 7.95 (dd, 1H), 8.01 (br d, 1H). Protons (3H) from Methyl group on amid and Protons (2H) of the piperidinyl under the DMSO signal.

LC-MS (Method 2): $R_t$=1.11 min; MS (ESIneg): m/z=429 $[M-H]^-$

Example 450

1-methyl-2-oxo-4-{4-[5-(2-oxopyrrolidin-1-yl)-1,3-benzoxazol-2-yl]piperidin-1-yl}-1,2-dihydroquinoline-3-carboxamide

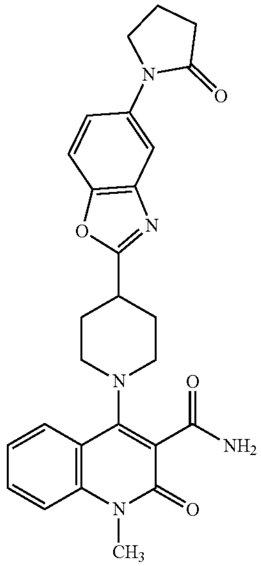 [SMILES: Cn1c(=O)c(C(N)=O)c(N2CCC(c3nc4cc(N5CCCC5=O)ccc4o3)CC2)c2ccccc21]

40 mg 1-methyl-2-oxo-4-{4-[5-(2-oxopyrrolidin-1-yl)-1,3-benzoxazol-2-yl]piperidin-1-yl}-1,2-dihydroquinoline-3-carbonitrile (example 334), 48 mg palladium(II)acetate and 25.3 mg acetaldoxime were stirred in 2 mL ethanol for 4 h at 90° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-5%) to obtain 20 mg of the title compound.

$^1$H-NMR (400 MHz, DMSO-d6) δ[ppm]: 2.02-2.17 (m, 4H) 2.19-2.28 (m, 2H) 3.14-3.30 (m, 3H) 3.36-3.46 (m, 2H) 3.56-3.63 (m, 3H) 3.86-3.95 (m, 2H) 7.32 (s, 1H) 7.54 (d, 2H) 7.59-7.73 (m, 4H) 7.89-7.98 (m, 2H).

Example 451

4-[4-(3-chlorophenyl)-4-methoxypiperidin-1-yl]-1-methyl-2-oxo-1,2-dihydroquinoline-3-carboxamide

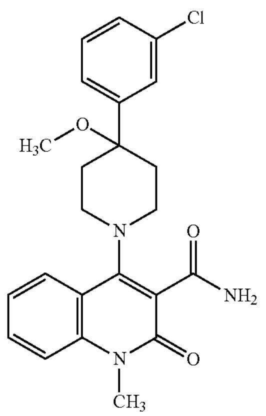 [SMILES: COC1(c2cccc(Cl)c2)CCN(c2c(C(N)=O)c(=O)n(C)c3ccccc23)CC1]

20 mg Pd(II)acetat (88.9 μmol) was added to a suspension of 145 mg 4-[4-(3-chlorophenyl)-4-methoxypiperidin-1-yl]-1-methyl-2-oxo-1,2-dihydroquinoline-3-carbonitrile (355 μmol, example 336) and 110 μl N-[(1E)-ethylidene]hydroxylamine (1.8 mmol, CAS 107-29-9) in 4.5 mL ethanol and stirred over night at 80° C. until complete conversion (more reagents were added in case no progess was observed). The mixture was cooled to room temperature, filtered over celite, washed with ethanol and the filtrate was concentrated under reduced pressure. The crude product was purified by RP-HPLC and the product was obtained in 45% yield (69 mg).

1H NMR (400 MHz, DMSO-d6) δ ppm 1.95-2.12 (m, 2H) 2.13-2.27 (m, 2H) 2.89-2.97 (m, 3H) 3.10-3.22 (m, 2H) 3.37-3.50 (m, 2H) 3.53-3.69 (m, 3H) 7.23-7.35 (m, 1H) 7.36-7.55 (m, 6H) 7.57-7.72 (m, 2H) 7.90-8.07 (m, 1H)

LC-MS (Method 2): $R_t$=1.21 min; MS (ESIpos): m/z=426 $[M+H]^+$

Example 452

6-(dimethylphosphoryl)-1-methyl-4-[4-methyl-4-(5-methyl-1,3-benzoxazol-2-yl)piperidin-1-yl]-2-oxo-1,2-dihydroquinoline-3-carboxamide

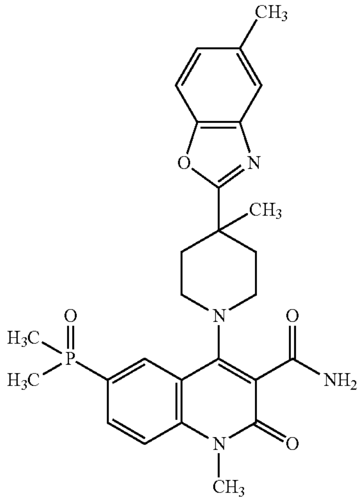 [SMILES: Cc1ccc2oc(C3(C)CCN(c4c(C(N)=O)c(=O)n(C)c5ccc(P(C)(C)=O)cc45)CC3)nc2c1]

300 mg 6-(dimethylphosphoryl)-1-methyl-4-[4-methyl-4-(5-methyl-1,3-benzoxazol-2-yl)piperidin-1-yl]-2-oxo-1,2-dihydroquinoline-3-carbonitrile (example 337), 35 mg palladium(II)acetate and 181 mg acetaldoxime were stirred in 30 mL ethanol for 4 h at 80° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-10%) to obtain 180 mg of the title compound.

$^1$H NMR (400 MHz, DMSO-d6) δ ppm 1.45 (s, 3H) 1.71 (d, J=13.43 Hz, 6H) 1.89-2.06 (m, 2H) 2.43 (s, 4H) 3.02-3.19 (m, 2H) 3.59 (s, 3H) 7.12-7.26 (m, 1H) 7.39-7.50 (m, 1H) 7.51-7.69 (m, 4H) 7.90-8.00 (m, 1H) 8.22-8.33 (m, 1H)

TABLE 23

Compounds were prepared as referenced

| Example | Structure | IUPAC-Name | Starting Materials | Analytics |
|---|---|---|---|---|
| 453 | 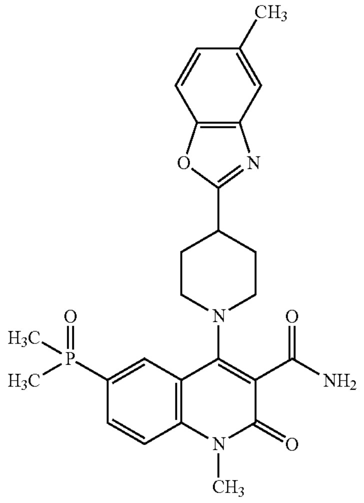 [SMILES: Cc1ccc2oc(C3CCN(c4c(C(N)=O)c(=O)n(C)c5ccc(P(C)(C)=O)cc45)CC3)nc2c1] | 6-(dimethylphosphoryl)-1-methyl-4-[4-(5-methyl-1,3-benzoxazol-2-yl)piperidin-1-yl]-2-oxo-1,2-dihydroquinoline-3-carboxamide | In analogy to example 450 from example 338. | $^1$H NMR (400 MHz, DMSO-$d_6$) δ ppm 1.69 (d, 6 H) 2.01-2.16 (m,2 H) 2.19-2.30 (m, 2 H) 2.42 (s, 3 H) 3.21 (br s, 3 H) 3.33 (s, 21 H) 3.37-3.51 (m, 2 H) 3.62 (s, 3 H) 7.11-7.26 (m, 1 H) 7.48-7.61 (m, 3 H) 7.65 (s, 1 H) 7.73 (d, 1 H) 7.95 (s, 1 H) 8.29 (dd, 1 H). |
| 454 | 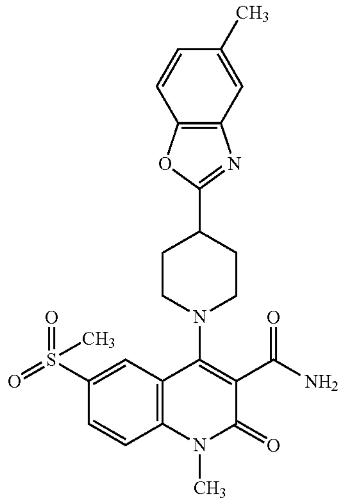 [SMILES: Cc1ccc2oc(C3CCN(c4c(C(N)=O)c(=O)n(C)c5ccc(S(C)(=O)=O)cc45)CC3)nc2c1] | 6-(methanesulfonyl)-1-methyl-4-[4-(5-methyl-1,3-benzoxazol-2-yl)piperidin-1-yl]-2-oxo-1,2-dihydroquinoline-3-carboxamide | Prepared from example 339 in analogy to example 450. | $^1$H NMR (400 MHz, DMSO-$d_6$) δ ppm 1.94-2.04 (m, 1 H) 2.05-2.15 (m, 2 H) 2.22-2.30 (m, 2 H) 2.43 (s, 3 H) 3.16-3.26 (m, 2 H) 3.27 (s, 3 H) 3.43 (br d, 2 H) 3.64 (s, 3 H) 7.19 (dd, 1 H) 7.54 (s, 1 H) 7.58 (d, 2 H) 7.74-7.82 (m, 2 H) 8.11 (dd, 1 H) 8.37 (d, 1 H). LC-MS (Method 2): $R_t$ = 0.94 min; MS (ESIpos): m/z = 495 [M + H]$^+$ |
| 455 | 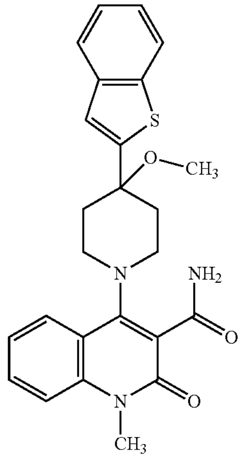 [SMILES: COC1(c2cc3ccccc3s2)CCN(c2c(C(N)=O)c(=O)n(C)c3ccccc23)CC1] | 4-[4-(1-benzothiophen-2-yl)-4-methoxypiperidin-1-yl]-1-methyl-2-oxo-1,2-dihydroquinoline-3-carboxamide | In analogy to example 450 from example 341. | $^1$H-NMR(400 MHz, DMSO-$d_6$): δ [ppm] = 2.20-2.38 (m,4H), 3.06 (s, 3H), 3.20 (br d, 2H), 3.37-3.48 (m, 2H), 3.59 (s, 3H), 7.26-7.32 (m, 1H), 7.33-7.42 (m, 2H), 7.46-7.54 (m, 3H), 7.59-7.69 (m, 1H), 7.84 (dd, 1H), 7.92-7.98 (m, 1H). LC-MS (Method 2): $R_t$ = 1.22 min; MS (ESIpos): m/z = 448 [M + H]$^+$ |

TABLE 23-continued

| Compounds were prepared as referenced | | | | |
|---|---|---|---|---|
| Example | Structure | IUPAC-Name | Starting Materials | Analytics |
| 456 | 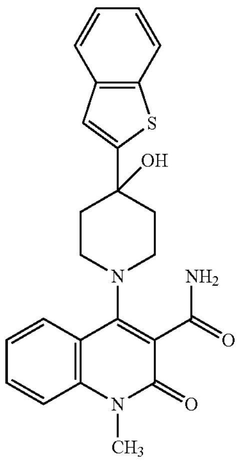 [SMILES: Cn1c(=O)c(C(N)=O)c(N2CCC(O)(c3cc4ccccc4s3)CC2)c2ccccc21] | 4-[4-(1-benzothiophen-2-yl)-4-hydroxypiperidin-1-yl]-1-methyl-2-oxo-1,2-dihydroquinoline-3-carboxamide | Prepared from example 340 in analogy to example 450. | $^{1}$H-NMR (400 MHz, DMSO-$d_6$): δ [ppm] = 1.98 (br d, 2H), 2.21-2.33 (m, 2H), 3.15-3.24 (m, 2H), 3.45-3.67 (m, 5H), 5.75 (br s, 1H), 7.26-7.42 (m, 4H), 7.46 (br s, 1H), 7.52 (d, 1H), 7.59-7.70 (m, 2H), 7.79 (d, 1H), 7.95 (dd, 2H). LC-MS (Method 2): $R_t$ = 1.10 min; MS (ESIpos): m/z = 434 [M + H]$^+$ |
| 457 | 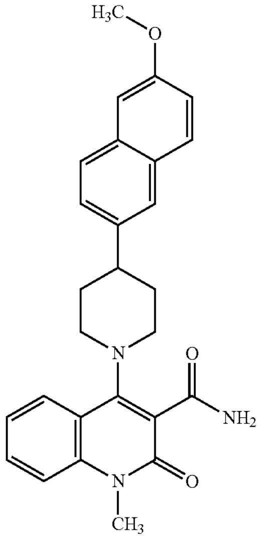 [SMILES: COc1ccc2cc(C3CCN(c4c(C(N)=O)c(=O)n(C)c5ccccc45)CC3)ccc2c1] | 4-[4-(6-methoxynaphthalen-2-yl)piperidin-1-yl]-1-methyl-2-oxo-1,2-dihydroquinoline-3-carboxamide | Prepared from example 343 in analogy to example 450. | $^{1}$H NMR (400 MHz, DMSO-$d_6$) δ ppm 1.94-2.06 (m, 5 H) 2.77-2.87 (m, 1 H) 3.18-3.26 (m, 2 H) 3.40-3.47 (m, 2 H) 3.60 (s, 3 H) 3.87 (s, 3 H) 7.12-7.18 (m, 1 H) 7.29 (s, 2 H) 7.47-7.55 (m, 3 H) 7.61-7.67 (m, 1 H) 7.68-7.73 (m, 1 H) 7.76-7.83 (m, 3 H) 8.02 (dd, 1 H). LC-MS (Method 2): $R_t$ = 1.23 min; MS (ESIpos): m/z = 442 [M + H]$^+$ |
| 458 | 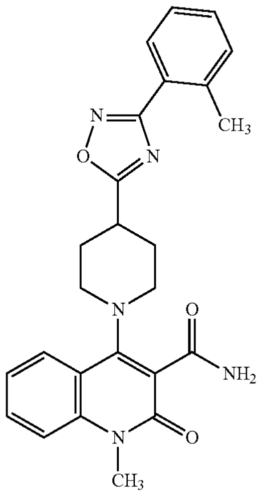 [SMILES: Cc1ccccc1-c1noc(C2CCN(c3c(C(N)=O)c(=O)n(C)c4ccccc34)CC2)n1] | 1-methyl-4-{4-[3-(2-methylphenyl)-1,2,4-oxadiazol-5-yl]piperidin-1-yl}-2-oxo-1,2-dihydroquinoline-3-carboxamide | Prepared from example 348 in analogy to example 450. | $^{1}$H NMR (400 MHz, DMSO-$d_6$) δ ppm 2.07-2.18 (m, 2 H) 2.19-2.29 (m, 2 H) 2.55-2.60 (m, 3 H) 3.15-3.27 (m, 2 H) 3.37-3.45 (m, 2 H) 3.55-3.66 (m, 3 H) 7.28-7.35 (m, 1 H) 7.36-7.45 (m, 2 H) 7.45-7.56 (m, 3 H) 7.60-7.67 (m, 1 H) 7.67-7.73 (m, 1 H) 7.88-7.98 (m, 2 H). |

TABLE 23-continued

| Example | Structure | IUPAC-Name | Starting Materials | Analytics |
|---|---|---|---|---|
| Compounds were prepared as referenced | | | | |
| 459 | 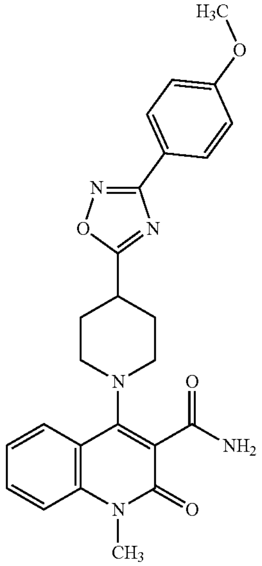 [SMILES: COc1ccc(-c2noc(C3CCN(c4c(C(N)=O)c(=O)n(C)c5ccccc45)CC3)n2)cc1] | 4-{4-[3-(4-methoxyphenyl)-1,2,4-oxadiazol-5-yl]piperidin-1-yl}-1-methyl-2-oxo-1,2-dihydroquinoline-3-carboxamide | Prepared from example 349 in analogy to example 450. | $^1$H NMR (400 MHz, DMSO-$d_6$) δ ppm 2.02-2.16 (m, 2 H) 2.18-2.27 (m, 2 H) 3.14-3.24 (m, 2 H) 3.39 (br d, 2 H) 3.59 (s, 3 H) 3.84 (s, 3H) 7.08-7.16 (m, 2 H) 7.28-7.36 (m, 1 H) 7.48-7.57 (m, 2 H) 7.60-7.66 (m, 1 H) 7.70 (d, 1 H) 7.88-8.01 (m, 3 H). LC-MS (Method 2): $R_t$ = 1.11 min; MS (ESIpos): m/z = 460 $[M + H]^+$ |
| 460 | 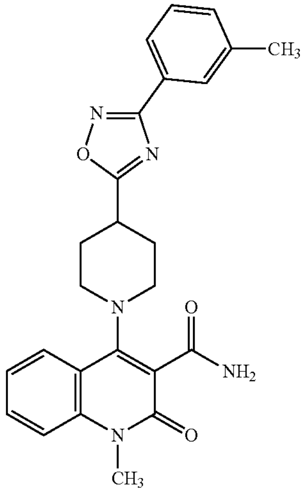 [SMILES: Cc1cccc(-c2noc(C3CCN(c4c(C(N)=O)c(=O)n(C)c5ccccc45)CC3)n2)c1] | 1-methyl-4-{4-[3-(3-methylphenyl)-1,2,4-oxadiazol-5-yl]piperidin-1-yl}-2-oxo-1,2-dihydroquinoline-3-carboxamide | Prepared from example 350 in analogy to example 450. | $^1$H NMR (400 MHz, DMSO-$d_6$) δ ppm 2.07-2.18 (m, 2 H) 2.19-2.28 (m, 2 H) 2.38-2.44 (m, 3 H) 3.12-3.25 (m, 2 H) 3.37-3.45 (m, 2 H) 3.55-3.64 (m, 3 H) 7.29-7.35 (m, 1 H) 7.39-7.47 (m, 2 H) 7.48-7.57 (m, 2 H) 7.61-7.67 (m, 1 H) 7.68-7.73 (m, 1 H) 7.80-7.88 (m, 2 H) 7.91-7.98 (m, 1 H). |
| 461 | 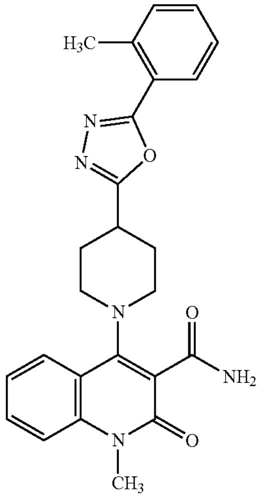 [SMILES: Cc1ccccc1-c1nnc(C2CCN(c3c(C(N)=O)c(=O)n(C)c4ccccc34)CC2)o1] | 1-methyl-4-{4-[5-(2-methylphenyl)-1,3,4-oxadiazol-2-yl]piperidin-1-yl}-2-oxo-1,2-dihydroquinoline-3-carboxamide | Prepared from example 351 in analogy to example 450. | $^1$H NMR (400 MHz, DMSO-$d_6$) δ ppm 2.03-2.16 (m, 2 H) 2.19-2.28 (m, 2 H) 2.61-2.65 (m, 3 H) 3.15-3.24 (m, 2 H) 3.24-3.31 (m, 1 H) 3.36-3.46 (m, 2 H) 3.56-3.64 (m, 3 H) 7.28-7.35 (m, 1 H) 7.38-7.57 (m, 5 H) 7.61-7.67 (m, 1 H) 7.67-7.73 (m, 1 H) 7.89-7.97 (m, 2 H). |

TABLE 23-continued

| Example | Structure | IUPAC-Name | Starting Materials | Analytics |
|---|---|---|---|---|
| Compounds were prepared as referenced | | | | |
| 462 | 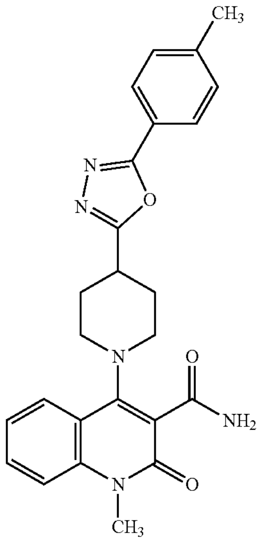 [SMILES: Cc1ccc(-c2nnc(C3CCN(c4c(C(N)=O)c(=O)n(C)c5ccccc45)CC3)o2)cc1] | 1-methyl-4-{4-[5-(4-methylphenyl)-1,3,4-oxadiazol-2-yl]piperidin-1-yl}-2-oxo-1,2-dihydroquinoline-3-carboxamide | Prepared from example 352 in analogy to example 450. | $^1$H NMR (400 MHz, DMSO-$d_6$) δ ppm 2.02-2.14 (m, 2 H) 2.17-2.27 (m, 2 H) 2.38-2.44 (m, 3 H) 3.14-3.23 (m, 2 H) 3.24-3.31 (m, 1 H) 3.36-3.46 (m, 2 H) 3.56-3.64 (m, 3 H) 7.28-7.36 (m, 1 H) 7.39-7.45 (m, 2 H) 7.48-7.58 (m, 2 H) 7.60-7.75 (m, 2 H) 7.89-7.97 (m, 3 H). |
| 463 | 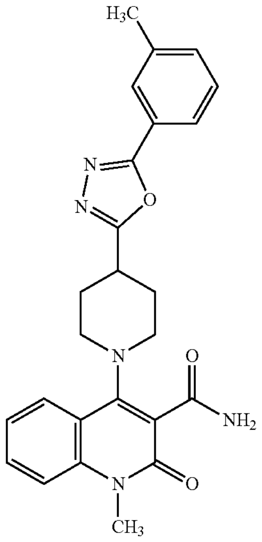 [SMILES: Cc1cccc(-c2nnc(C3CCN(c4c(C(N)=O)c(=O)n(C)c5ccccc45)CC3)o2)c1] | 1-methyl-4-{4-[5-(3-methylphenyl)-1,3,4-oxadiazol-2-yl]piperidin-1-yl}-2-oxo-1,2-dihydroquinoline-3-carboxamide | Prepared from example 353 in analogy to example 450. | $^1$H NMR (400 MHz, DMSO-$d_6$) δ ppm 2.00-2.15 (m, 2 H) 2.16-2.29 (m, 2 H) 2.38-2.45 (m, 3 H) 3.15-3.25 (m, 2 H) 3.26-3.32 (m, 1 H) 3.37-3.47 (m, 2 H) 3.54-3.64 (m, 3 H) 7.25-7.37 (m, 1 H) 7.41-7.58 (m, 4 H) 7.59-7.75 (m, 2 H) 7.80-7.89 (m, 2 H) 7.90-7.98 (m, 1 H). |

TABLE 23-continued

Compounds were prepared as referenced

| Example | Structure | IUPAC-Name | Starting Materials | Analytics |
|---|---|---|---|---|
| 464 | 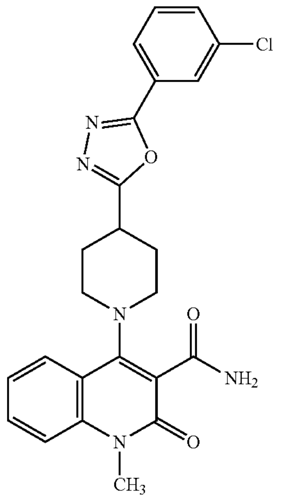 [SMILES: Cn1c(=O)c(C(N)=O)c(N2CCC(c3nnc(-c4cccc(Cl)c4)o3)CC2)c2ccccc21] | 4-{4-[5-(3-chlorophenyl)-1,3,4-oxadiazol-2-yl]piperidin-1-yl}-1-methyl-2-oxo-1,2-dihydroquinoline-3-carboxamide | Prepared from example 354 in analogy to example 450. | $^1$H NMR (400 MHz, DMSO-$d_6$) δ ppm 2.04-2.16 (m, 2 H) 2.19-2.27 (m, 2 H) 3.15-3.24 (m, 2 H) 3.26-3.31 (m, 1 H) 3.37-3.45 (m, 2 H) 3.54-3.62 (m, 3 H) 7.28-7.37 (m, 1 H) 7.45-7.56 (m, 2 H) 7.60-7.76 (m, 4 H) 7.90-7.96 (m, 1 H) 7.98-8.08 (m, 2H). |
| 465 | 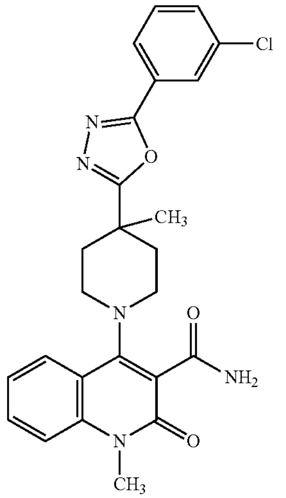 [SMILES: Cn1c(=O)c(C(N)=O)c(N2CCC(C)(c3nnc(-c4cccc(Cl)c4)o3)CC2)c2ccccc21] | 4-{4-[5-(3-chlorophenyl)-1,3,4-oxadiazol-2-yl]-4-methylpiperidin-1-yl}-1-methyl-2-oxo-1,2-dihydroquinoline-3-carboxamide | Prepared from example 355 in analogy to example 450. | $^1$H NMR (400 MHz, DMSO-$d_6$) δ ppm 1.44-1.58 (m, 3 H) 1.96-2.07 (m, 2 H) 2.36-2.44 (m, 2 H) 3.11-3.21 (m, 2 H) 3.25-3.33 (m, 3 H) 3.25-3.32 (m, 2 H) 3.54-3.65 (m, 3 H) 7.28-7.36 (m, 1 H) 7.42-7.48 (m, 1 H) 7.43-7.47 (m, 1 H) 7.49-7.55 (m, 1 H) 7.59-7.69 (m, 3 H) 7.69-7.77 (m, 1 H) 7.91-7.97 (m, 1 H) 8.01-8.06 (m, 1 H) 8.07-8.11 (m, 1 H). |
| 466 | 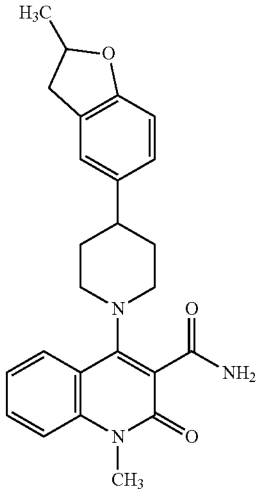 [SMILES: CC1Cc2cc(C3CCN(c4c(C(N)=O)c(=O)n(C)c5ccccc45)CC3)ccc2O1] | 1-methyl-4-{4-[2-methyl-2,3-dihydro-1-benzofuran-5-yl]piperidin-1-yl}-2-oxo-1,2-dihydroquinoline-3-carboxamide | Prepared from example 357 in analogy to example 450. | $^1$H NMR (400 MHz, DMSO-$d_6$) δ ppm 1.37 (d, 3 H) 1.74-1.83 (m, 2 H) 1.83-1.95 (m, 2 H) 2.55-2.64 (m, 1 H) 2.76 (dd, 1 H) 3.08-3.19 (m, 2 H) 3.24-3.31 (m, 1 H) 3.37 (br d, 2 H) 3.59 (s, 3 H) 4.87 (m, 1 H) 4.83-4.92 (m, 1 H) 6.65 (d, 1 H) 7.04 (dd, 1 H) 7.19 (s, 1 H) 7.28-7.34 (m, 1 H) 7.46 (d, 1 H) 7.51 (d, 1 H) 7.59-7.65 (m, 1 H) 7.68 (d, 1 H) 7.98 (dd, 1 H). LC-MS (Method 2): $R_t$ = 1.17 min; MS (ESIpos): m/z = 418 [M + H]$^+$ |

TABLE 23-continued

| Compounds were prepared as referenced | | | | |
|---|---|---|---|---|
| Example | Structure | IUPAC-Name | Starting Materials | Analytics |
| 467 | 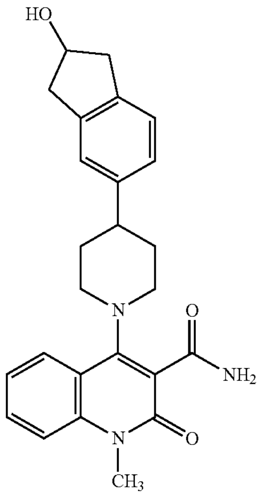 [SMILES: Cn1c(=O)c(C(N)=O)c(N2CCC(c3ccc4c(c3)CC(O)C4)CC2)c2ccccc21] | 4-[4-(2-hydroxy-2,3-dihydro-1H-inden-5-yl)piperidin-1-yl]-1-methyl-2-oxo-1,2-dihydroquinoline-3-carboxamide | Prepared from example 359 in analogy to example 450. | $^1$H NMR (400 MHz, DMSO-$d_6$) δ ppm 1.75-1.85 (m, 2 H) 1.85-1.99 (m, 2 H) 2.59-2.66 (m, 1 H) 2.66-2.77 (m, 2 H) 3.03 (ddd, 2 H) 3.10-3.20 (m, 2 H) 3.38 (br d, 2 H) 3.59 (s, 3 H) 4.49 (tq, 1 H) 4.84 (d, 1 H) 7.12 (q, 2 H) 7.20 (s, 1 H) 7.29-7.35 (m, 1 H) 7.46 (d, 1 H) 7.52 (d, 1H) 7.59-7.66 (m, 1 H) 7.68 (d, 1 H) 7.99 (dd, 1 H) LC-MS (Method 2): $R_t$ = 0.94 min; MS (ESIpos): m/z = 418 [M + H]$^+$ |
| 468 | 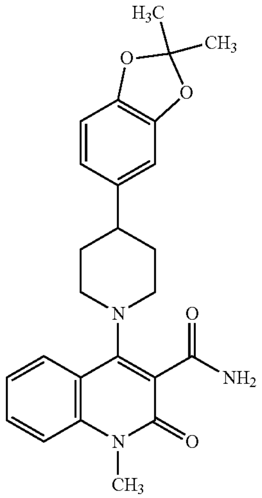 [SMILES: Cn1c(=O)c(C(N)=O)c(N2CCC(c3ccc4c(c3)OC(C)(C)O4)CC2)c2ccccc21] | 4-[4-(2,2-dimethyl-2H-1,3-benzodioxol-5-yl)piperidin-1-yl]-1-methyl-2-oxo-1,2-dihydroquinoline-3-carboxamide | Prepared from example 360 in analogy to example 450. | $^1$H-NMR (400 MHz, DMSO-$d_6$): δ [ppm] = 1.62 (s, 6H), 1.75-1.96 (m, 4H), 2.59 (tt, 1H), 3.08-3.17 (m, 2H), 3.36 (br d, 2H), 3.59 (s, 3H), 6.72-6.78 (m, 2H), 6.88 (s, 1H), 7.27-7.34 (m, 1H), 7.45 (d, 1H), 7.49-7.55 (m, 1H), 7.59-7.65 (m, 1H), 7.68 (d, 1H), 7.98 (dd, 1H). LC-MS (Method 1): $R_t$ = 1.23 min; MS (ESIpos): m/z = 435 [M + H]$^+$ |
| 469 | 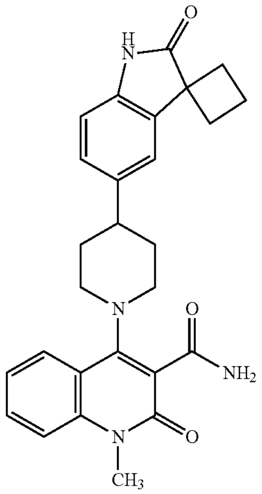 [SMILES: Cn1c(=O)c(C(N)=O)c(N2CCC(c3ccc4c(c3)C3(CCC3)C(=O)N4)CC2)c2ccccc21] | 1-methyl-2-oxo-4-[4-(2'-oxo-1',2'-dihydrospiro[cyclobutane-1,3'-indol]-5'-yl)piperidin-1-yl]-1,2-dihydroquinoline-3-carboxamide | Prepared from example 361 in analogy to example 450. | $^1$H-NMR (400 MHz, DMSO-$d_6$): δ [ppm] = 1.78-1.97 (m, 4H), 2.13-2.31 (m, 4H), 2.35-2.46 (m,2H), 2.61-2.72 (m, 1H), 3.11-3.22 (m, 2H), 3.39 (br d, 2H), 3.59 (s, 3H), 6.76 (d, 1H), 7.00 (dd, 1H), 7.29-7.37 (m, 1H), 7.43-7.56 (m, 3H), 7.60-7.66 (m, 1H), 7.68 (s, 1H), 7.97 (dd, 1H), 10.20 (s, 1H). LC-MS (Method 2): $R_t$ = 1.03 min; MS (ESIpos): m/z = 457 [M + H]$^+$ |

TABLE 23-continued

| Compounds were prepared as referenced | | | | |
|---|---|---|---|---|
| Example | Structure | IUPAC-Name | Starting Materials | Analytics |
| 470 | 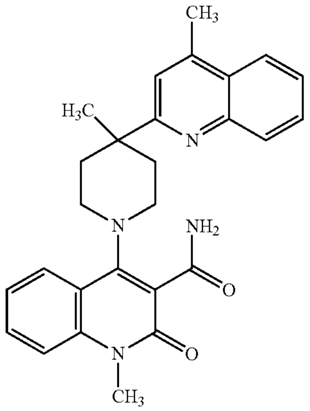 [SMILES: Cc1cc(C2(C)CCN(c3c(C(N)=O)c(=O)n(C)c4ccccc34)CC2)nc2ccccc12] | 1-methyl-4-[4-methyl-4-(4-methylquinolin-2-yl)piperidin-1-yl]-2-oxo-1,2-dihydroquinoline-3-carboxamide | Prepared from example 364 in analogy to example 450. | $^1$H-NMR (400 MHz, DMSO-$d_6$): δ [ppm] = 1.36 (s, 3H), 1.94-2.04 (m, 2H), 2.50-2.62 (m, 2H), 2.71 (s, 3H), 3.10-3.19 (m, 2H), 3.33 (s, 2H), 3.57 (s, 3H), 7.28-7.34 (m, 1H), 7.38 (br s, 1H), 7.48-7.65 (m, 5H), 7.72 (ddd, 1H), 7.93-7.99 (m, 2H), 8.04-8.09 (m, 1H). LC-MS (Method 2): $R_t$ = 1.24 min; MS (ESIpos): m/z = 441 $[M + H]^+$ |
| 471 | 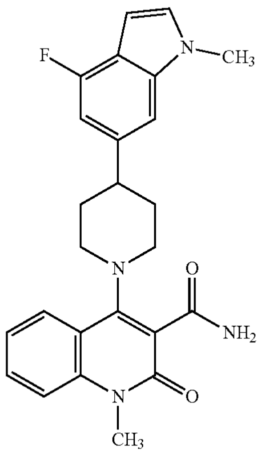 [SMILES: Cn1ccc2c(F)cc(C3CCN(c4c(C(N)=O)c(=O)n(C)c5ccccc45)CC3)cc21] | 4-[4-(4-fluoro-1-methyl-1 H-indol-6-yl)piperidin-1-yl]-1-methyl-2-oxo-1,2-dihydroquinoline-3-carboxamide | Prepared from example 365 in analogy to example 450. | $^1$H-NMR (400 MHz, DMSO-$d_6$): δ [ppm] = 1.85-2.11 (m, 4H), 2.75-2.85 (m, 1H), 3.14-3.26 (m, 2H), 3.42 (br d, 2H), 3.60 (s, 3H), 3.81 (s, 3H), 6.39-6.46 (m, 1H), 6.88 (dd, 1H), 7.25-7.38 (m, 3H), 7.45-7.57 (m, 2H), 7.60-7.75 (m, 2H), 8.03 (dd, 1H). LC-MS (Method 2): $R_t$ = 1.20 min; MS (ESIpos): m/z = 433 $[M + H]^+$ |
| 472 | 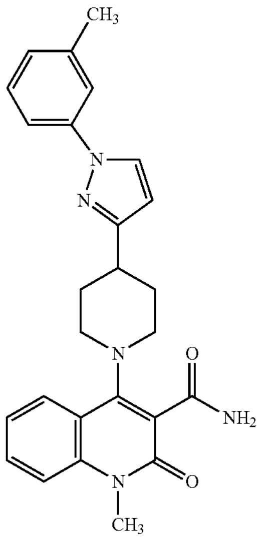 | 1-methyl-4-{4-[1-(3-methylphenyl)-1H-pyrazol-3-yl]piperidin-1-yl}-2-oxo-1,2-dihydroquinoline-3-carboxamide | Prepared from example 366 in analogy to example 450. | $^1$H NMR (600 MHz, DMSO-$d_6$) δ ppm 1.95 (qd, 2 H) 2.02-2.08 (m, 2 H) 2.38 (s, 3 H) 2.85 (br tt, 1 H) 3.15-3.21 (m, 2 H) 3.40 (br d, 2 H) 3.59 (s, 3 H) 6.50 (d, 1 H) 7.09 (d, 1 H) 7.32 (t, 1 H) 7.35 (t, 1 H) 7.48 (d1 H) 7.52 (d, 1 H) 7.58-7.65 (m, 2 H) 7.65-7.70 (m, 2 H) 7.95 (dd, 1 H) 8.39 (d, 1 H). LC-MS (Method 2): $R_t$ = 1.20 min; MS (ESIpos): m/z = 442 $[M + H]^+$ |

TABLE 23-continued

| Compounds were prepared as referenced | | | | |
|---|---|---|---|---|
| Example | Structure | IUPAC-Name | Starting Materials | Analytics |
| 473 | 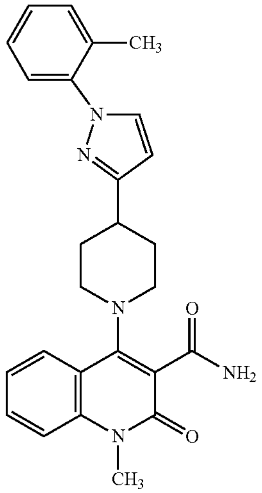 [SMILES: Cc1ccccc1-n1ccc(C2CCN(c3c(C(N)=O)c(=O)n(C)c4ccccc34)CC2)n1] | 1-methyl-4-{4-[1-(2-methylphenyl)-1H-pyrazol-3-yl]piperidin-1-yl}-2-oxo-1,2-dihydroquinoline-3-carboxamide | Prepared from example 367 in analogy to example 450. | $^1$H NMR (600 MHz, DMSO-$d_6$) δ ppm 1.94 (br qd, 2 H) 2.06 (br dd, 2 H) 2.24 (s, 3 H) 2.84 (tt, 1 H) 3.17 (td, 2 H) 3.40 (br d, 2 H) 3.59 (s, 3 H) 6.44 (d, 1 H) 7.29-7.39 (m, 5 H) 7.44-7.49 (m, 1 H) 7.52 (d, 1 H) 7.60-7.64 (m, 1 H) 7.67 (d, 1 H) 7.92-7.95 (m, 2 H). LC-MS (Method 2): $R_t$ = 1.14 min; MS (ESIpos): m/z = 442 [M + H]$^+$ |
| 474 | 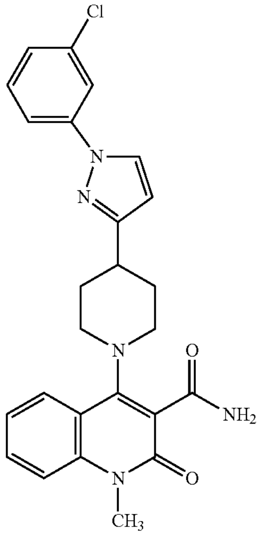 [SMILES: Cn1c(=O)c(C(N)=O)c(N2CCC(c3ccn(-c4cccc(Cl)c4)n3)CC2)c2ccccc21] | 4-{4-[1-(3-chlorophenyl)-1H-pyrazol-3-yl]piperidin-1-yl}-1-methyl-2-oxo-1,2-dihydroquinoline-3-carboxamide | Prepared from example 368 in analogy to example 450. | $^1$H NMR (500 MHz, DMSO-$d_6$) δ ppm 1.95 (qd, 2 H) 2.02-2.09 (m, 2 H) 2.81-2.90 (m, 1 H) 3.18 (td, 2 H) 3.40 (br d, 2 H) 3.60 (s, 3 H) 6.56 (d, 1 H) 7.29-7.35 (m, 2 H) 7.46-7.55 (m, 3 H) 7.60-7.65 (m, 1 H) 7.65-7.71 (m, 1 H) 7.83 (ddd, 1 H) 7.93 (t, 1 H) 7.95 (dd, 1 H) 8.51 (d, 1 H). LC-MS (Method 2): $R_t$ = 1.23 min; MS (ESIpos): m/z = 462 [M + H]$^+$ |
| 475 | 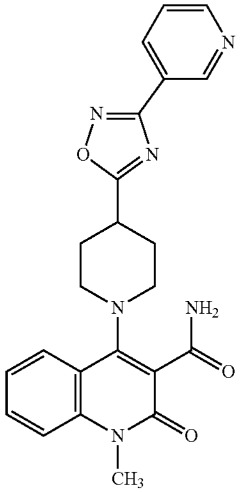 [SMILES: Cn1c(=O)c(C(N)=O)c(N2CCC(c3nc(-c4cccnc4)no3)CC2)c2ccccc21] | 1-methyl-2-oxo-4-{4-[3-(pyridin-3-yl)-1,2,4-oxadiazol-5-yl]piperidin-1-yl}-1,2-dihydroquinoline-3-carboxamide | Prepared from intermediate 207 and intermediate 252 in analogy to example 52. | $^1$H-NMR (400 MHz, DMSO-$d_6$): δ [ppm] = 2.03-2.21 (m, 2H , 2.21-2.28 (m, 2H), 3.21 (br t, 2H), 3.36-3.47 (m, 4H), 3.59 (s, 3H), 7.32 (t, 1H), 7.47-7.57 (m, 2H), 7.60-7.72 (m, 3H), 7.93 (dd, 1H), 8.39 (dt, 1H), 8.80 (dd, 1H), 9.20 (d, 1H). . LC-MS (Method 2): $R_t$ = 0.90 min; MS (ESIpos): m/z = 431 [M + H]$^+$ |

TABLE 23-continued

Compounds were prepared as referenced

| Example | Structure | IUPAC-Name | Starting Materials | Analytics |
|---|---|---|---|---|
| 476 | 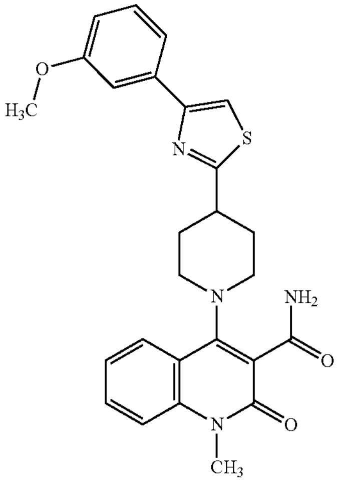 [SMILES: COc1cccc(-c2csc(C3CCN(c4c(C(N)=O)c(=O)n(C)c5ccccc45)CC3)n2)c1] | 4-{4-[4-(3-methoxyphenyl)-1,3-thiazol-2-yl]piperidin-1-yl}-1-methyl-2-oxo-1,2-dihydroquinoline-3-carboxamide | Prepared from intermediate 211 and intermediate 252 in analogy to example 52. | $^{1}$H-NMR (400 MHz, DMSO-$d_6$): δ [ppm] = 2.03 (qd, 2H), 2.22 (br d, 2H), 3.16-3.30 (m, 3H), 3.42 (br d, 2H), 3.59 (s, 3H), 3.82 (s, 3H), 6.92 (ddd, 1H), 7.29-7.41 (m, 2H), 7.47-7.59 (m, 4H), 7.60-7.66 (m, 1H), 7.69 (s, 1H), 7.94 (dd, 1H), 8.06 (s, 1H). LC-MS (Method 2): $R_t$ = 1.19 min; MS (ESIpos): m/z = 475 $[M + H]^+$ |
| 477 | 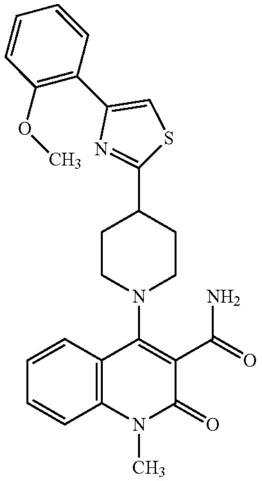 [SMILES: COc1ccccc1-c1csc(C2CCN(c3c(C(N)=O)c(=O)n(C)c4ccccc34)CC2)n1] | 4-{4-[4-(2-methoxyphenyl)-1,3-thiazol-2-yl]piperidin-1-yl}-1-methyl-2-oxo-1,2-dihydroquinoline-3-carboxamide | Prepared from intermediate 212 and intermediate 252 in analogy to example 52. | $^{1}$H-NMR (400 MHz, DMSO-$d_6$): δ [ppm] = 1.96-2.12 (m, 2H), 2.22 (br d, 2H), 3.16-3.29 (m, 3H), 3.42 (br d, 2H), 3.59 (s, 3H), 3.93 (s, 3H), 7.05 (td, 1H), 7.15 (dd, 1H), 7.29-7.38 (m, 2H), 7.46-7.57 (m, 2H), 7.60-7.67 (m, 1H), 7.69 (s, 1H), 7.94 (dd, 1H), 8.00 (s, 1H), 8.20 (dd, 1H). LC-MS (Method 2): $R_t$ = 1.23 min; MS (ESIpos): m/z = 475 $[M + H]^+$ |
| 478 | 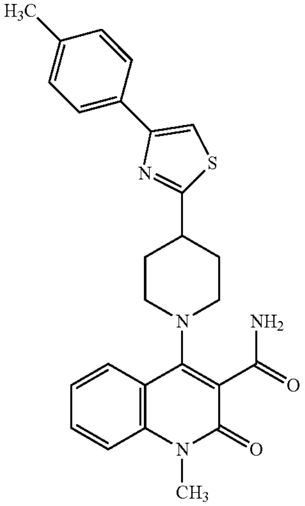 [SMILES: Cc1ccc(-c2csc(C3CCN(c4c(C(N)=O)c(=O)n(C)c5ccccc45)CC3)n2)cc1] | 1-methyl-4-{4-[4-(4-methylphenyl)-1,3-thiazol-2-yl]piperidin-1-yl}-2-oxo-1,2-dihydroquinoline-3-carboxamide | Prepared from intermediate 213 and intermediate 252 in analogy to example 52. | $^{1}$H-NMR (400 MHz, DMSO-$d_6$): δ [ppm] = 2.03 (qd, 2H), 2.21 (br d, 2H), 2.30-2.38 (m, 3H), 3.15-3.31 (m, 3H), 3.42 (br d, 2H), 3.59 (s, 3H), 7.25 (d, 2H), 7.29-7.36 (m, 1H), 7.47-7.55 (m, 2H), 7.60-7.67 (m, 1H), 7.69 (s, 1H), 7.84-7.90 (m, 2H), 7.92-7.97 (m, 1H). LC-MS (Method 2): $R_t$ = 1.28 min; MS (ESIpos): m/z = 459 $[M + H]^+$ |

TABLE 23-continued

Compounds were prepared as referenced

| Example | Structure | IUPAC-Name | Starting Materials | Analytics |
|---|---|---|---|---|
| 479 | 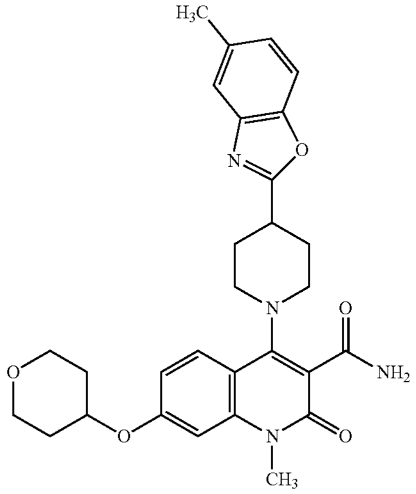 [SMILES: Cc1ccc2oc(C3CCN(c4c(C(N)=O)c(=O)n(C)c5cc(OC6CCOCC6)ccc45)CC3)nc2c1] | 1-methyl-4-[4-(5-methyl-1,3-benzoxazol-2-yl)piperidin-1-yl]-7-[(oxan-4-yl)oxy]-2-oxo-1,2-dihydroquinoline-3-carboxamide | Prepared from example 382 in analogy to example 450. | $^1$H NMR (400 MHz, DMSO-$d_6$) δ ppm 1.58-1.69 (m, 2 H) 1.99-2.14 (m, 4 H) 2.15-2.24 (m, 2 H) 2.40-2.46 (m, 3 H) 3.13-3.25 (m, 3 H) 3.35-3.41 (m, 2 H) 3.48-3.54 (m, 2 H) 3.54-3.54 (m, 1 H) 3.55-3.59 (m, 3 H) 3.82-3.93 (m, 2 H) 4.75-4.87 (m, 1 H) 6.92-7.07 (m, 2 H) 7.14-7.23 (m, 1 H) 7.36-7.47 (m, 1 H) 7.50-7.53 (m, 1 H) 7.55-7.60 (m, 1 H) 7.60-7.66 (m, 1 H) 7.79-7.85 (m, 1 H). |
| 480 | 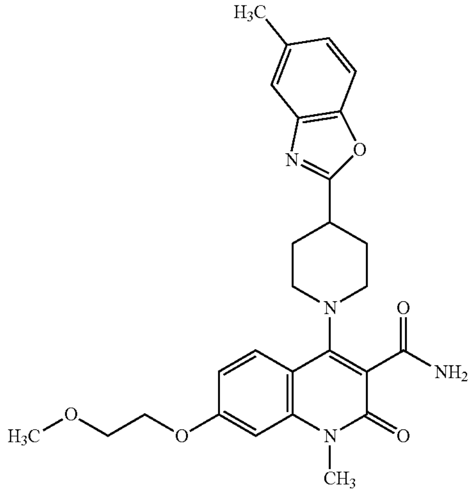 [SMILES: COCCOc1ccc2c(N3CCC(c4nc5cc(C)ccc5o4)CC3)c(C(N)=O)c(=O)n(C)c2c1] | 7-(2-methoxyethoxy)-1-methyl-4-[4-(5-methyl-1,3-benzoxazol-2-yl)piperidin-1-yl]-2-oxo-1,2-dihydroquinoline-3-carboxamide | Prepared from example 383 in analogy to example 450. | $^1$H NMR (400 MHz, DMSO-$d_6$) δ ppm 1.99-2.14 (m, 2 H) 2.15-2.26 (m, 2 H) 2.40-2.46 (m, 3 H) 3.11-3.26 (m, 3 H) 3.51-3.61 (m, 3 H) 3.67-3.74 (m, 2 H) 4.21-4.30 (m, 2 H) 6.88-7.00 (m, 2 H) 7.15-7.24 (m, 1 H) 7.37-7.47 (m, 1 H) 7.50-7.54 (m, 1 H) 7.54-7.60 (m, 1 H) 7.61-7.67 (m, 1 H) 7.77-7.86 (m, 1 H). |
| 481 | 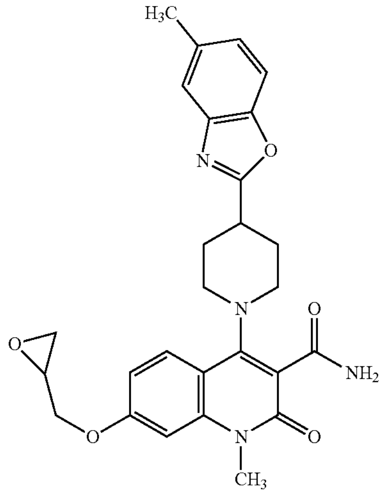 [SMILES: Cc1ccc2oc(C3CCN(c4c(C(N)=O)c(=O)n(C)c5cc(OCC6CO6)ccc45)CC3)nc2c1] | 1-methyl-4-[4-(5-methyl-1,3-benzoxazol-2-yl)piperidin-1-yl]-7-{[oxiran-2-yl]methoxy}-2-oxo-1,2-dihydroquinoline-3-carboxamide | Prepared from example 384 in analogy to example 450. | $^1$H NMR (400 MHz, DMSO-$d_6$) δ ppm 2.01-2.15 (m, 2 H) 2.15-2.27 (m, 2 H) 2.40-2.45 (m, 3 H) 2.73-2.81 (m, 1 H) 2.83-2.92 (m, 1 H) 3.11-3.24 (m, 3 H) 3.37-3.42 (m, 2 H) 3.53-3.59 (m, 3 H) 3.91-4.06 (m, 1 H) 4.46-4.54 (m, 1 H) 6.90-7.04 (m, 2 H) 7.11-7.24 (m, 1 H) 7.40-7.47 (m, 1 H) 7.49-7.54 (m, 1 H) 7.55-7.60 (m, 1 H) 7.61-7.71 (m, 1 H) 7.78-7.88 (m, 1 H). |

TABLE 23-continued

Compounds were prepared as referenced

| Example | Structure | IUPAC-Name | Starting Materials | Analytics |
|---|---|---|---|---|
| 482 | 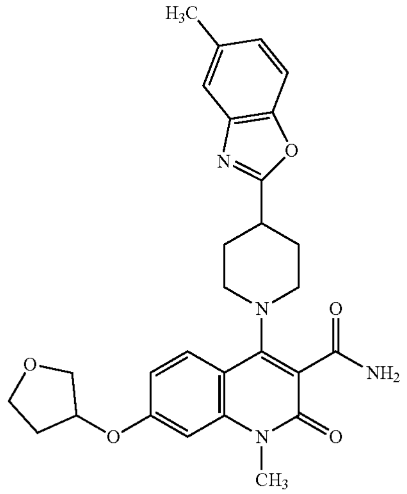 [SMILES: Cc1ccc2oc(C3CCN(c4c(C(N)=O)c(=O)n(C)c5cc(OC6CCOC6)ccc45)CC3)nc2c1] | (rac)-1-methyl-4-[4-(5-methyl-1,3-benzoxazol-2-yl)piperidin-1-yl]-2-oxo-7-[(oxolan-3-yl)oxy]-1 2-dihydroquinoline-3-carboxamide | Prepared from example 379 in analogy to example 450. | $^{1}$H NMR (400 MHz, DMSO-$d_6$) δ ppm 1.97-2.13 (m, 3 H) 2.14-2.24 (m, 2 H) 2.24-2.36 (m, 1 H) 2.41-2.45 (m, 3 H) 3.13-3.26 (m, 3 H) 3.51-3.61 (m, 3 H) 3.73-3.81 (m, 1 H) 3.82-3.91 (m, 2 H) 3.91-3.99 (m, 1 H) 5.18-5.34 (m, 1 H) 6.83-7.03 (m, 2 H) 7.12-7.25 (m, 1 H) 7.39-7.45 (m, 1 H) 7.49-7.54 (m, 1 H) 7.55-7.60 (m, 1 H) 7.60-7.70 (m, 1 H) 7.80-7.88 (m, 1 H). |
| 483 | 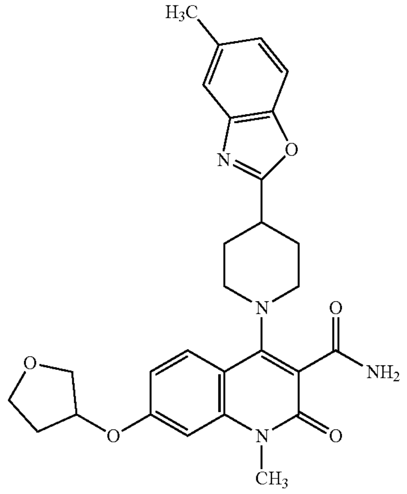 [SMILES: Cc1ccc2oc(C3CCN(c4c(C(N)=O)c(=O)n(C)c5cc(OC6CCOC6)ccc45)CC3)nc2c1] | (-)-1-methyl-4-[4-(5-methyl-1,3-benzoxazol-2-yl)piperidin-1-yl]-2-oxo-7-[(oxolan-3-yl)oxy]-1 2-dihydroquinoline-3-carboxamide, Enantiomer 1 | Prepared from example 380 in analogy to example 450. | $^{1}$H NMR (400 MHz, DMSO-$d_6$) δ ppm 1.97-2.32 (m, 6 H) 3.14-3.26 (m, 3 H) 3.51-3.61 (m, 3 H) 3.70-4.00 (m, 4 H) 5.18-5.31 (m, 1 H) 6.85-6.99 (m, 2 H) 7.14-7.23 (m, 1 H) 7.38-7.47 (m, 1 H) 7.49-7.54 (m, 1 H) 7.55-7.60 (m, 1 H) 7.60-7.68 (m, 1 H) 7.79-7.88 (m, 1 H). Optical rotation: $[\alpha]_D$ = −5.6° (c = 6 mg/ml, chloroform). |
| 484 | 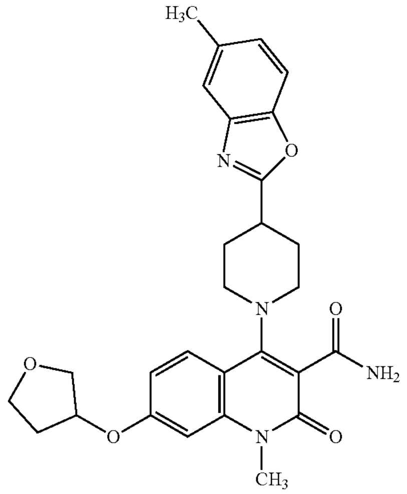 [SMILES: Cc1ccc2oc(C3CCN(c4c(C(N)=O)c(=O)n(C)c5cc(OC6CCOC6)ccc45)CC3)nc2c1] | (+)-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 2 | Prepared from example 381 in analogy to example 450. | $^{1}$H NMR (400 MHz, DMSO-$d_6$) δ ppm 1.97-2.32 (m, 6 H) 3.14-3.26 (m, 3 H) 3.51-3.61 (m, 3 H) 3.70-4.00 (m, 4 H) 5.18-5.31 (m, 1 H) 6.85-6.99 (m, 2 H) 7.14-7.23 (m, 1 H) 7.38-7.47 (m, 1 H) 7.49-7.54 (m, 1 H) 7.55-7.60 (m, 1 H) 7.60-7.68 (m, 1 H) 7.79-7.88 (m, 1 H). Optical rotation: $[\alpha]_D$ = +4.1° (c = 5 mg/ml, chloroform). |

TABLE 23-continued

| Compounds were prepared as referenced | | | | |
|---|---|---|---|---|
| Example | Structure | IUPAC-Name | Starting Materials | Analytics |
| 485 | 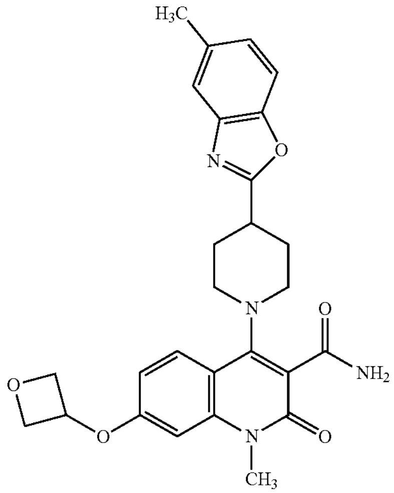 [SMILES: Cc1ccc2oc(C3CCN(c4c(C(N)=O)c(=O)n(C)c5cc(OC6COC6)ccc45)CC3)nc2c1] | 1-methyl-4-[4-(5-methyl-1,3-benzoxazol-2-yl)piperidin-1-yl]-7-[(oxetan-3-yl)oxy]-2-oxo-1,2-dihydroquinoline-3-carboxamide | Prepared from example 385 in analogy to 450. | $^1$H NMR (400 MHz, DMSO-$d_6$) δ ppm 2.00-2.14 (m, 3 H) 2.14-2.24 (m, 2 H) 2.38-2.45 (m, 3 H) 3.11-3.25 (m, 3 H) 3.47-3.64 (m, 3 H) 4.44-4.69 (m, 2 H) 4.73-5.06 (m, 2 H) 5.39-5.57 (m, 1 H) 6.67-6.92 (m, 2 H) 7.10-7.28 (m, 1 H) 7.37-7.46 (m, 1 H) 7.46-7.53 (m, 1 H) 7.54-7.60 (m, 1 H) 7.60-7.71 (m, 1 H) 7.77-7.91 (m, 1 H). |
| 486 | 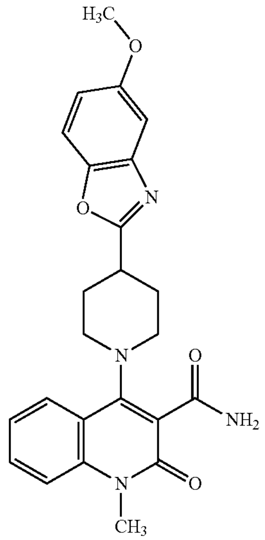 [SMILES: COc1ccc2oc(C3CCN(c4c(C(N)=O)c(=O)n(C)c5ccccc45)CC3)nc2c1] | 4-[4-(5-methoxy-1,3-benzoxazol-2-yl)piperidin-1-yl]-1-methyl-2-oxo-1,2-dihydroquinoline-3-carboxamide | Prepared from example 386 in analogy to example 450. | $^1$H NMR (400 MHz, DMSO-$d_6$) δ ppm 2.00-2.16 (m, 2 H) 2.17-2.27 (m, 2 H) 3.15-3.26 (m, 3 H) 3.37 (br s, 2 H) 3.59 (s, 3 H) 3.80 (s, 3H) 6.92-6.98 (m, 1 H) 7.23-7.35 (m, 2 H) 7.46-7.56 (m, 2 H) 7.57-7.72 (m, 3 H) 7.87-7.97 (m, 1 H). |

TABLE 23-continued

Compounds were prepared as referenced

| Example | Structure | IUPAC-Name | Starting Materials | Analytics |
|---|---|---|---|---|
| 487 | 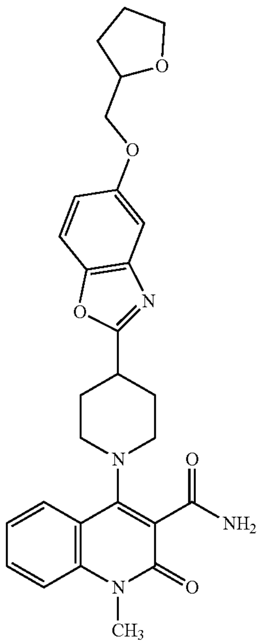 [SMILES: Cn1c(=O)c(C(N)=O)c(N2CCC(c3nc4cc(OCC5CCCO5)ccc4o3)CC2)c2ccccc21] | 1-methyl-2-oxo-4-(4-{5-[(oxolan-2-yl)methoxy]-1,3-benzoxazol-2-yl}piperidin-1-yl)-1,2-dihydroquinoline-3-carboxamide | Prepared from example 387 in analogy to example 450. | $^1$H NMR (400 MHz, DMSO-$d_6$) δ ppm 1.58-1.76 (m, 1 H) 1.77-1.95 (m, 2 H) 1.95-2.15 (m, 3 H) 2.16-2.26 (m, 2 H) 3.11-3.25 (m, 3 H) 3.35-3.44 (m, 2 H) 3.59 (s, 3 H) 3.64-3.73 (m, 1 H) 3.76-3.84 (m, 1 H) 3.91-4.04 (m, 2 H) 4.12-4.22 (m, 1 H) 6.90-6.99 (m, 1 H) 7.23-7.36 (m, 2 H) 7.44-7.55 (m, 2 H) 7.59 (d, 3 H) 7.89-7.97 (m, 1 H). |
| 488 | 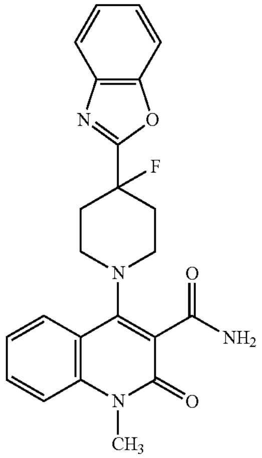 [SMILES: Cn1c(=O)c(C(N)=O)c(N2CCC(F)(c3nc4ccccc4o3)CC2)c2ccccc21] | 4-[4-(1,3-benzoxazol-2-yl)-4-fluoropiperidin-1-yl]-1-methyl-2-oxo-1,2-dihydroquinoline-3-carboxamide | Prepared from example 389 in analogy to example 450. | $^1$H NMR (400 MHz, DMSO-$d_6$) δ ppm 2.42-2.72 (m, 4 H) 3.23-3.32 (m, 1 H) 3.41-3.50 (m, 1 H) 3.60 (s, 1 H) 7.29-7.34 (m, 1 H) 7.42-7.49 (m, 1 H) 7.50-7.57 (m, 1 H) 7.61-7.67 (m, 1 H) 7.69-7.75 (m, 1 H) 7.83-7.89 (m, 1 H) 7.97 (dd, 1 H). LC-MS (Method 2): $R_t$ = 1.04 min; MS (ESIneg): m/z = 419[M − H]- |
| 489 | 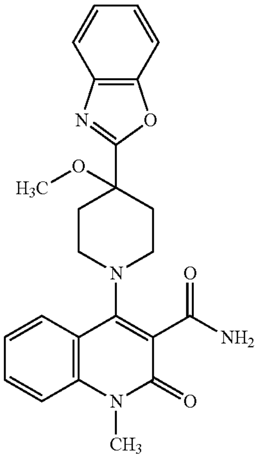 [SMILES: COC1(c2nc3ccccc3o2)CCN(c2c(C(N)=O)c(=O)n(C)c3ccccc23)CC1] | 4-[4-(1,3-benzoxazol-2-yl)-4-methoxypiperidin-1-yl]-1-methyl-2-oxo-1,2-dihydroquinoline-3-carboxamide | Prepared from example 390 in analogy to example 450. | $^1$H NMR (400 MHz, DMSO-$d_6$) δ ppm 2.29-2.38 (m, 2 H) 2.42-2.48 (m, 2 H) 3.11 (s, 3 H) 3.13-3.22 (m, 2 H) 3.37-3.45 (m, 2 H) 3.58 (s, 3H) 7.28-7.32 (m, 1 H) 7.41-7.53 (m,4H) 7.60-7.67 (m, 2 H) 7.79-7.85 (m, 2 H) 7.93 (dd, 1 H). LC-MS (Method 2): $R_t$ = 1.07 min; MS (ESIpos): m/z = 433 [M + H]$^+$ |

TABLE 23-continued

| Compounds were prepared as referenced | | | | |
|---|---|---|---|---|
| Example | Structure | IUPAC-Name | Starting Materials | Analytics |
| 490 | 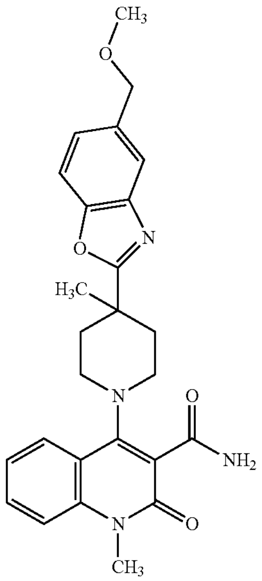 [SMILES: COCc1ccc2oc(C3(C)CCN(c4c(C(N)=O)c(=O)n(C)c5ccccc45)CC3)nc2c1] | 4-{4-[5-(methoxymethyl)-1,3-benzoxazol-2-yl]-4-methylpiperidin-1-yl}-1-methyl-2-oxo-1,2-dihydroquinoline-3-carboxamide | Prepared from example 391 in analogy to example 450. | $^1$H NMR (400 MHz, DMSO-$d_6$) δ ppm 1.47 (s, 3 H) 1.89-2.09 (m, 2 H) 3.03-3.17 (m, 2 H) 3.30 (s, 4 H) 3.57 (s, 3 H) 4.52 (s, 2 H) 7.25-7.37 (m, 2 H) 7.37-7.44 (m, 1 H) 7.48-7.53 (m, 1 H) 7.54-7.59 (m, 1 H) 7.69 (s, 3 H) 7.90-8.03 (m, 1 H). |
| 491 | 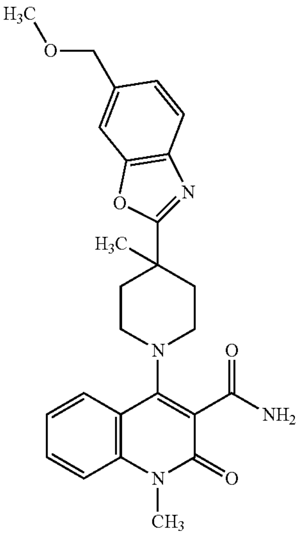 [SMILES: COCc1ccc2nc(C3(C)CCN(c4c(C(N)=O)c(=O)n(C)c5ccccc45)CC3)oc2c1] | 4-4-[6-(methoxymethyl)-1,3-benzoxazol-2-yl]-4-methylpiperidin-1-yl}-1-methyl-2-oxo-1,2-dihydroquinoline-3-carboxamide | Prepared from example 392 in analogy to example 450. | $^1$H NMR (400 MHz DMSO-$d_6$) δ ppm 1.42-1.50 (m, 3 H) 1.94-2.07 (m, 2 H) 3.05-3.17 (m, 2 H) 3.26-3.32 (m, 5 H) 3.57 (s, 3 H) 4.53 (s, 2 H) 7.25-7.36 (m, 2 H) 7.38-7.46 (m, 1 H) 7.52 (s, 1 H) 7.55-7.59 (m, 1 H) 7.66 (d, 2 H) 7.71 (d, 1 H) 7.93 (d, 1 H). |

Example 492

6-bromo-1-methyl-4-[4-(5-methyl-1,3-benzoxazol-2-yl)piperidin-1-yl]-2-oxo-1,2-dihydroquinoline-3-carboxamide

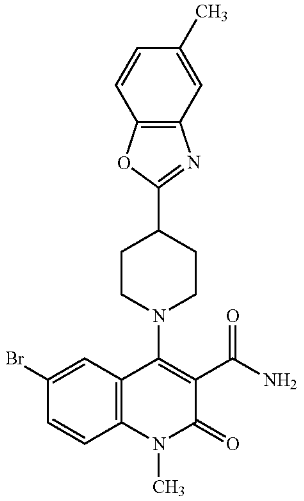 [SMILES: Cc1ccc2oc(C3CCN(c4c(C(N)=O)c(=O)n(C)c5ccc(Br)cc45)CC3)nc2c1]

350 mg 6-bromo-1-methyl-4-[4-(5-methyl-1,3-benzoxazol-2-yl)piperidin-1-yl]-2-oxo-1,2-dihydroquinoline-3-carbonitrile (example 396), 41 mg palladium(II)acetate and 217 mg acetaldoxime were stirred in 15 mL ethanol for 2 h at 80° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-10%) to obtain 130 mg of the title compound.

$^{1}$H-NMR (400 MHz, DMSO-d6) δ[ppm]: 1.96-2.12 (m, 2H) 2.18-2.28 (m, 2H) 2.42 (s, 3H) 3.09-3.27 (m, 3H) 3.57 (s, 3H) 7.10-7.22 (m, 1H) 7.45-7.61 (m, 4H) 7.71-7.82 (m, 2H) 7.93-8.01 (m, 1H).

Example 493

8-bromo-1-methyl-4-[4-(5-methyl-1,3-benzoxazol-2-yl)piperidin-1-yl]-2-oxo-1,2-dihydroquinoline-3-carboxamide

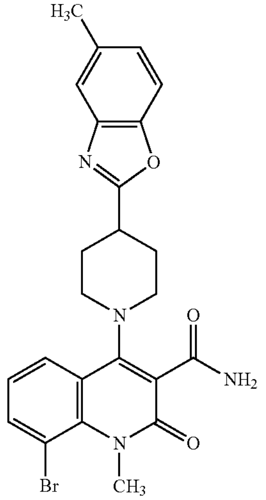 [SMILES: Cc1ccc2oc(C3CCN(c4c(C(N)=O)c(=O)n(C)c5c(Br)cccc45)CC3)nc2c1]

5.88 mg palladium(II)acetate (26.2 μmol) was added to a suspension of 50 mg 8-bromo-1-methyl-4-[4-(5-methyl-1,3-benzoxazol-2-yl)piperidin-1-yl]-2-oxo-1,2-dihydroquinoline-3-carbonitrile (105 μmol, example 397) and 64 μl acetaldoxime (1.0 mmol, CAS 107-29-9) in 1.6 mL ethanol and stirred over night under a nitrogen atmosphere at 80° C. Due to incomplete conversion another two sets of Pd(II) acetate and acetaldoxime were added and stirring was continued at 80° C. The reaction mixture was filtered over celite, washed with EtOH and evaporated. The crude product was purified by RP-HPLC and the product was obtained in 13% yield (6.6 mg).

$^{1}$H NMR (400 MHz, DMSO-$d_6$) δ ppm 2.03-2.15 (m, 2H) 2.17-2.25 (m, 2H) 2.42 (s, 3H) 3.13-3.27 (m, 3H) 3.34-3.40 (m, 2H) 3.73 (s, 3H) 7.18 (dd, 1H) 7.24 (t, 1H) 7.49-7.56 (m, 2H) 7.57 (d, 1H) 7.73 (d, 1H) 7.90 (dd, 1H) 7.94 (dd, 1H).

Example 494

1-methyl-4-[4-(5-methyl-1,3-benzoxazol-2-yl)piperidin-1-yl]-7-[methyl(oxetan-3-yl)amino]-2-oxo-1,2-dihydroquinoline-3-carboxamide

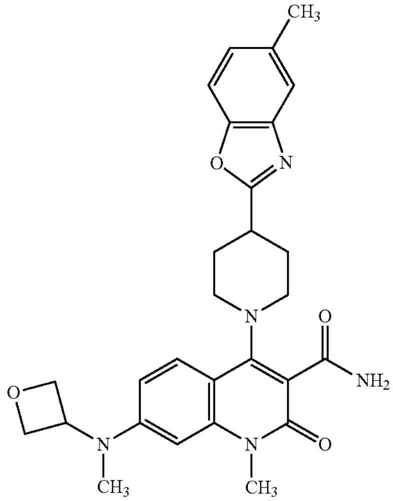 [SMILES: Cc1ccc2oc(C3CCN(c4c(C(N)=O)c(=O)n(C)c5cc(N(C)C6COC6)ccc45)CC3)nc2c1]

70 mg 1-methyl-4-[4-(5-methyl-1,3-benzoxazol-2-yl)piperidin-1-yl]-7-[methyl(oxetan-3-yl)amino]-2-oxo-1,2-dihydroquinoline-3-carbonitrile (example 398), 8 mg palladium (II)acetate and 43 mg acetaldoxime were stirred in 3 mL ethanol for 3 h at 90° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-10%) to obtain 50 mg of the title compound.

$^{1}$H NMR (400 MHz, DMSO-d6) δ ppm 1.98-2.11 (m, 2H) 2.13-2.26 (m, 2H) 2.42 (s, 3H) 3.03 (s, 3H) 3.09-3.22 (m, 3H) 3.54 (s, 3H) 4.66 (s, 2H) 4.84 (s, 2H) 4.90-5.02 (m, 1H) 6.36-6.45 (m, 1H) 6.66-6.73 (m, 1H) 7.14-7.21 (m, 1H) 7.32-7.38 (m, 1H) 7.47-7.54 (m, 1H) 7.54-7.60 (m, 2H) 7.64-7.73 (m, 1H)

Example 495

7-[(2-hydroxyethyl)(methyl)amino]-1-methyl-4-[4-(5-methyl-1,3-benzoxazol-2-yl)piperidin-1-yl]-2-oxo-1,2-dihydroquinoline-3-carboxamide

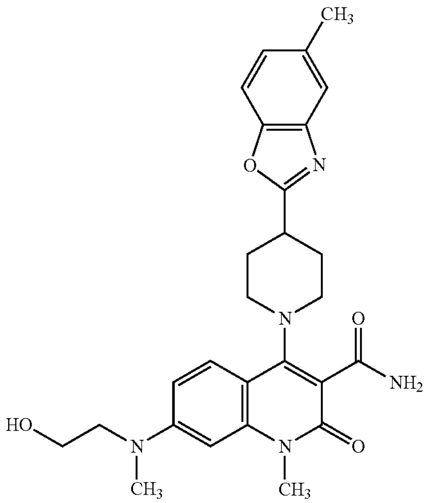 [SMILES: Cc1ccc2oc(C3CCN(c4c(C(N)=O)c(=O)n(C)c5cc(N(C)CCO)ccc45)CC3)nc2c1]

mg 7-[(2-hydroxyethyl)(methyl)amino]-1-methyl-4-[4-(5-methyl-1,3-benzoxazol-2-yl)piperidin-1-yl]-2-oxo-1,2-dihydroquinoline-3-carbonitrile (example 399), 4 mg palladium(II)acetate and 19 mg acetaldoxime were stirred in 3 mL ethanol for 4 h at 90° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-10%) to obtain 25 mg of the title compound.

$^1$H-NMR (400 MHz, DMSO-d6) δ[ppm]: 1.96-2.12 (m, 2H) 2.14-2.24 (m, 2H) 2.42 (s, 3H) 3.07 (s, 3H) 3.12-3.24 (m, 3H) 3.53 (s, 5H) 3.56-3.66 (m, 2H) 4.69-4.80 (m, 1H) 6.27-6.47 (m, 1H) 6.64-6.82 (m, 1H) 7.08-7.22 (m, 1H) 7.26-7.36 (m, 1H) 7.46-7.54 (m, 1H) 7.57 (d, J=8.11 Hz, 2H) 7.62-7.72 (m, 1H).

Example 496

1-methyl-4-[4-(5-methyl-1,3-benzoxazol-2-yl)piperidin-1-yl]-7-[methyl(oxolan-3-yl)amino]-2-oxo-1,2-dihydroquinoline-3-carboxamide, Enantiomer 1

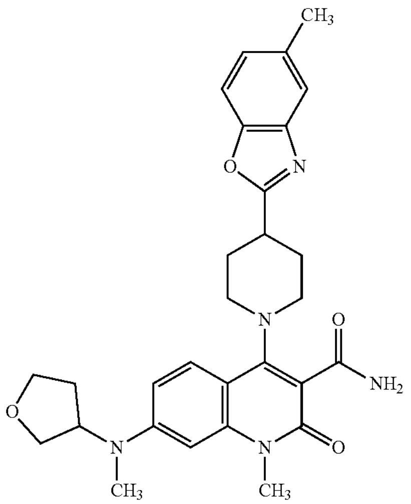 [SMILES: Cc1ccc2oc(C3CCN(c4c(C(N)=O)c(=O)n(C)c5cc(N(C)C6CCOC6)ccc45)CC3)nc2c1]

40 mg 1-methyl-4-[4-(5-methyl-1,3-benzoxazol-2-yl)piperidin-1-yl]-7-[methyl(oxolan-3-yl)amino]-2-oxo-1,2-dihydroquinoline-3-carbonitrile (example 400), 4.5 mg palladium(II)acetate and 48 mg acetaldoxime were stirred in 3.8 mL ethanol for 4 h at 90° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-10%) to obtain 18 mg racemic 1-methyl-4-[4-(5-methyl-1,3-benzoxazol-2-yl)piperidin-1-yl]-7-[methyl(oxolan-3-yl)amino]-2-oxo-1,2-dihydroquinoline-3-carboxamide. This material was subjected to chiral HPLC separation: Instrument: PrepCon Labomatic HPLC; Column: YMC Cellulose SB 5p, 250×30; eluent A: methyl tert-butyl ether+0.1 vol % diethylamine; eluent B: acetonitrile+0.1 vol % diethylamine; isocratic: 60% A+40% B; flow: 50 ml/min; temperature: 25° C.; UV: 254 nm. 6 mg of the title compound were obtained.

$^1$H NMR (400 MHz, DMSO-d6) δ ppm 1.80-1.92 (m, 1H) 2.00-2.13 (m, 2H) 2.14-2.24 (m, 2H) 2.39-2.45 (m, 3H) 2.85-2.96 (m, 3H) 3.11-3.27 (m, 3H) 3.34-3.40 (m, 2H) 3.53-3.58 (m, 3H) 3.59-3.72 (m, 1H) 3.74-3.86 (m, 2H) 3.92-4.04 (m, 1H) 4.68-4.85 (m, 1H) 6.46-6.62 (m, 1H) 6.82-6.96 (m, 1H) 7.12-7.25 (m, 1H) 7.27-7.39 (m, 1H) 7.48-7.63 (m, 3H) 7.64-7.74 (m, 1H).

Analytical chiral HPLC: $R_t$=5.05 min

Instrument: Waters Alliance 2695; Column: YMC Cellulose SB 3μ, 100×4.6; eluent A: methyl tert-butyl ether+0.1 vol % diethylamine; eluent B: acetonitrile; isocratic: 60% A+40% B; flow: 1.4 ml/min; temperature: 25° C.; UV: 254 nm Example 497

1-methyl-4-[4-(5-methyl-1,3-benzoxazol-2-yl)piperidin-1-yl]-7-[methyl(oxolan-3-yl)amino]-2-oxo-1,2-dihydroquinoline-3-carboxamide, enantiomer 2

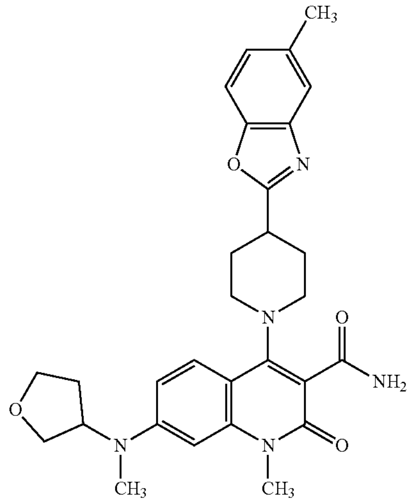 [SMILES: Cc1ccc2oc(C3CCN(c4c(C(N)=O)c(=O)n(C)c5cc(N(C)C6CCOC6)ccc45)CC3)nc2c1]

Chrial separation of 18 mg racemic 1-methyl-4-[4-(5-methyl-1,3-benzoxazol-2-yl)piperidin-1-yl]-7-[methyl(oxolan-3-yl)amino]-2-oxo-1,2-dihydroquinoline-3-carboxamide in example 496 delivered 3 mg of the title compound

$^1$H NMR (400 MHz, DMSO-d6) δ ppm 1.80-1.92 (m, 1H) 2.00-2.13 (m, 2H) 2.14-2.24 (m, 2H) 2.39-2.45 (m, 3H) 2.85-2.96 (m, 3H) 3.11-3.27 (m, 3H) 3.34-3.40 (m, 2H) 3.53-3.58 (m, 3H) 3.59-3.72 (m, 1H) 3.74-3.86 (m, 2H) 3.92-4.04 (m, 1H) 4.68-4.85 (m, 1H) 6.46-6.62 (m, 1H) 6.82-6.96 (m, 1H) 7.12-7.25 (m, 1H) 7.27-7.39 (m, 1H) 7.48-7.63 (m, 3H) 7.64-7.74 (m, 1H).

Analytical chiral HPLC: $R_t$=5.87 min

Instrument: Waters Alliance 2695; Column: YMC Cellulose SB 3μ, 100×4.6;

eluent A: methyl tert-butyl ether+0.1 vol % diethylamine; eluent B: acetonitrile; isocratic: 60% A+40% B; flow: 1.4 ml/min; temperature: 25° C.; UV: 254 nm

Example 498

6-cyano-1-methyl-4-[4-(5-methyl-1,3-benzoxazol-2-yl)piperidin-1-yl]-2-oxo-1,2-dihydroquinoline-3-carboxamide

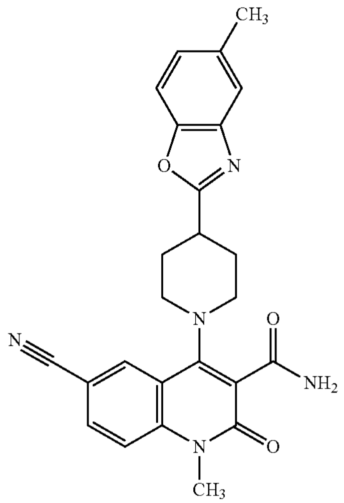 [SMILES: Cc1ccc2oc(C3CCN(c4c(C(N)=O)c(=O)n(C)c5ccc(C#N)cc45)CC3)nc2c1]

A mixture of 100 mg 6-bromo-1-methyl-4-[4-(5-methyl-1,3-benzoxazol-2-yl)piperidin-1-yl]-2-oxo-1,2-dihydroquinoline-3-carboxamide (example 492), 5.3 mg palladium(π-cinnamyl) chloride dimer (CAS 12131-44-1), 28.4 mg zinc cyanide (CAS 557-21-1), 5.6 mg 1,1'-bis(diphenylphosphanyl)ferrocene and 0.07 ml N,N-diisopropylethylamine in 3 ml N,N-dimethylacetamide were stirred at 120° C. for 9 hours. After this time, water was added and it was extracted with dichloromethane. The combined organic layers were washed with water and brine and dried over sodium sulfate. After evaporation of the solvent, the residue was purified by flash chromatography (silica, dichloromethane/methanol gradient 0-10%) to obtain 40 mg of the title compound.

$^1$H-NMR (400 MHz, DMSO-d6) δ[ppm]: 2.02-2.29 (m, 4H) 2.42 (s, 3H) 3.11-3.27 (m, 3H) 3.61 (s, 3H) 7.12-7.22 (m, 1H) 7.50-7.54 (m, 1H) 7.55-7.62 (m, 2H) 7.66-7.72 (m, 1H) 7.73-7.81 (m, 1H) 8.00-8.07 (m, 1H) 8.23 (d, 1H).

Example 499

1-methyl-4-[4-(5-methyl-1,3-benzoxazol-2-yl)piperidin-1-yl]-2-oxo-1,2-dihydroquinoline-3,6-dicarboxamide

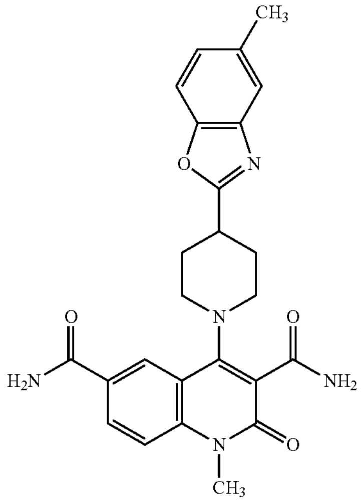 [SMILES: Cc1ccc2oc(C3CCN(c4c(C(N)=O)c(=O)n(C)c5ccc(C(N)=O)cc45)CC3)nc2c1]

52 mg 1-methyl-4-[4-(5-methyl-1,3-benzoxazol-2-yl)piperidin-1-yl]-2-oxo-1,2-dihydroquinoline-3,6-dicarbonitrile (example 403), 7 mg palladium(II)acetate and 72 mg acetaldoxime were stirred in 5 mL ethanol for 4 h at 90° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-3%) to obtain 20 mg of the title compound.

$^1$H-NMR (400 MHz, DMSO-d6) δ[ppm]: 2.09-2.29 (m, 4H) 2.42-2.45 (m, 3H) 3.16-3.28 (m, 3H) 3.39-3.48 (m, 2H) 3.57-3.65 (m, 3H) 7.10-7.29 (m, 1H) 7.39-7.48 (m, 1H) 7.49-7.66 (m, 4H) 7.68-7.78 (m, 1H) 8.04-8.17 (m, 2H) 8.39-8.46 (m, 1H).

TABLE 24

| Compounds were prepared as referenced | | | | |
|---|---|---|---|---|
| Example | Structure | IUPAC-Name | Starting Materials | Analytics |
| 500 | 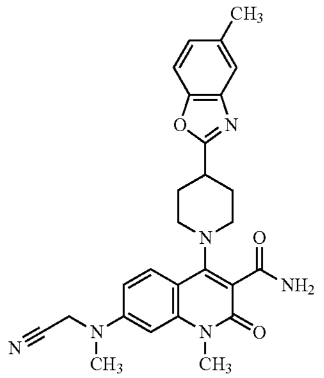 [SMILES: Cc1ccc2oc(C3CCN(c4c(C(N)=O)c(=O)n(C)c5cc(N(C)CC#N)ccc45)CC3)nc2c1] | 7-[(cyanomethyl)(methyl)amino]-1-methyl-4-[4-(5-methyl-1,3-benzoxazol-2-yl)piperidin-1-yl]-2-oxo-1,2-dihydroquinoline-3-carboxamide | Prepared from example 401 in analogy to example 450. | $^1H$ NMR (400 MHz, DMSO-$d_6$) δ ppm 2.03-2.16 (m, 2H), 2.23-2.31 (m, 2H), 2.42 (s, 3H), 3.15 (s, 3H), 3.48-3.59 (m, 6H), 3.70-3.79 (m, 2H), 4.09 (s, 2H), 6.37 (d, 1H), 6.69 (dd, 1H), 7.15-7.22 (m, 2H), 7.46-7.50 (m, 1H), 7.50-7.54 (m, 1H), 7.58 (d, 1H), 7.65 (d, 1H). |
| 501 | 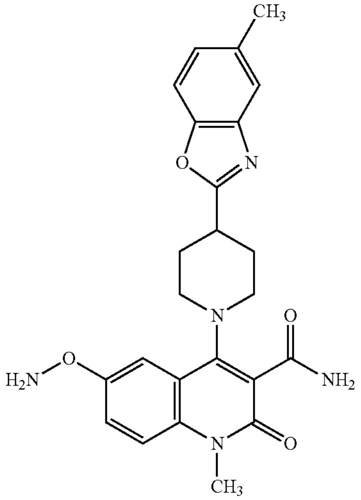 [SMILES: Cc1ccc2oc(C3CCN(c4c(C(N)=O)c(=O)n(C)c5ccc(ON)cc45)CC3)nc2c1] | 6-methoxy-1-methyl-4-[4-(5-methyl-1,3-benzoxazol-2-yl)piperidin-1-yl]-2-oxo-1,2-dihydroquinoline-3-carboxamide | Prepared from example 402 in analogy to example 450. | $^1H$ NMR (400 MHz, DMSO-$d_6$) δ ppm 1.99-2.14 (m, 2H), 2.19-2.30 (m, 2H), 2.42 (s, 3H), 3.14-3.27 (m, 3H), 3.36-3.45 (m, 2H), 3.57 (s, 3H), 3.84 (s, 3H), 7.15-7.21 (m, 1H), 7.27 (dd, 1H), 7.34 (d, 1H), 7.46-7.53 (m, 3H), 7.57 (d, 1H), 7.69 (br s, 1H) |
| 502 | 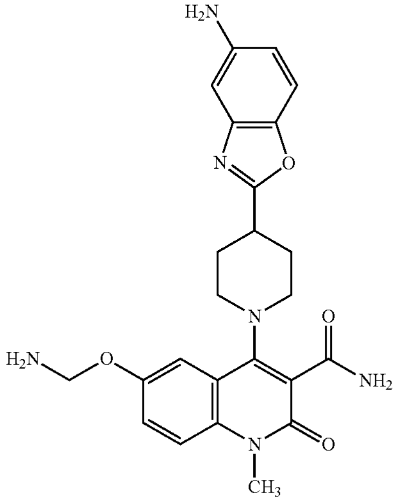 [SMILES: Cn1c(=O)c(C(N)=O)c(N2CCC(c3nc4cc(N)ccc4o3)CC2)c2cc(OCN)ccc21] | 6-ethoxy-1-methyl-4-[4-(5-methyl-1,3-benzoxazol-2-yl)piperidin-1-yl]-2-oxo-1,2-dihydroquinoline-3-carboxamide | Prepared from example 405 in analogy to example 450. | $^1H$ NMR (400 MHz, DMSO-$d_6$) δ ppm 1.37 (t, 3H) 1.94-2.11 (m, 2H) 2.24 (br dd, 2H) 2.42 (s, 3H) 3.12-3.27 (m, 3H) 3.35-3.45 (m, 2H) 3.57 (s, 3H) 4.10 (q, 2H) 7.18 (dd, 1H) 7.26 (dd, 1H) 7.33 (d, 1H) 7.47 (d, 2H) 7.50-7.55 (m, 1H) 7.58 (d, 1H) 7.68 (s, 1H). LC-MS (Method 2): $R_t$ = 1.18 min; MS (ESIpos): m/z = 461 $[M + H]^+$ |

TABLE 24-continued

Compounds were prepared as referenced

| Example | Structure | IUPAC-Name | Starting Materials | Analytics |
| --- | --- | --- | --- | --- |
| 503 | 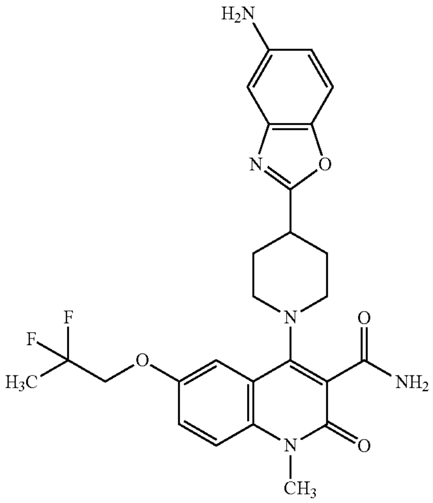 [SMILES: Cn1c(=O)c(C(N)=O)c(N2CCC(c3nc4cc(N)ccc4o3)CC2)c2cc(OCC(C)(F)F)ccc21] | 6-(2,2-difluoropropoxy)-1-methyl-4-[4-(5-methyl-1,3-benzoxazol-2-yl)piperidin-1-yl]-2-oxo-1,2-dihydroquinoline-3-carboxamide | Prepared from example 406 in Analogy to example 450. | $^1$H NMR (400 MHz, DMSO-$d_6$) δ ppm 1.76 (t, 3H) 2.02-2.15 (m, 2H) 2.19-2.28 (m, 2H) 2.42 (s, 3H) 3.14-3.26 (m, 3H) 3.39 (br d, 2H) 3.58 (s, 3H) 4.39 (t, 2H) 7.15-7.21 (m, 1H) 7.33-7.41 (m, 2H) 7.51 (d, 3H) 7.57 (d, 1H) 7.70 (br s, 1H). LC-MS (Method 2): $R_t$ = 1.20 min; MS (ESIpos): m/z = 511 $[M + H]^+$ |
| 504 | 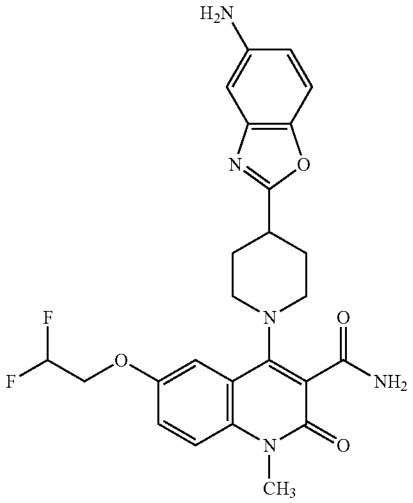 [SMILES: Cn1c(=O)c(C(N)=O)c(N2CCC(c3nc4cc(N)ccc4o3)CC2)c2cc(OCC(F)F)ccc21] | 6-(2,2-difluoroethoxy)-1-methyl-4-[4-(5-methyl-1,3-benzoxazol-2-yl)piperidin-1-yl]-2-oxo-1,2-dihydroquinoline-3-carboxamide | Prepared from example 407 in analogy to example 450. | $^1$H NMR (400 MHz, DMSO-$d_6$) δ ppm 2.01-2.14 (m, 2H) 2.20-2.28 (m, 2H) 2.42 (s, 3H) 3.13-3.26 (m, 3H) 3.39 (br d, 2H) 3.58 (s, 3H) 4.42 (td, 2H) 6.26-6.60 (m, 1H) 7.18 (dd, 1H) 7.33-7.40 (m, 2H) 7.51 (d, 3H) 7.57 (d, 1H) 7.70 (s, 1H). LC-MS (Method 2): $R_t$ = 1.14 min; MS (ESIpos): m/z = 497 $[M + H]^+$ |
| 505 | 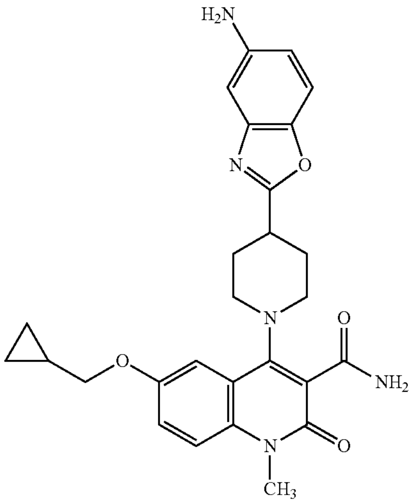 [SMILES: Cn1c(=O)c(C(N)=O)c(N2CCC(c3nc4cc(N)ccc4o3)CC2)c2cc(OCC3CC3)ccc21] | 6-(cyclopropylmethoxy)-1-methyl-4-[4-(5-methyl-1,3-benzoxazol-2-yl)piperidin-1-yl]-2-oxo-1,2-dihydroquinoline-3-carboxamide | Prepared from example 408 in analogy to example 450. | $^1$H NMR (400 MHz, DMSO-$d_6$) δ ppm 0.31-0.38 (m, 2H) 0.52-0.64 (m, 2H) 1.94-2.12 (m, 3H) 2.19-2.27 (m, 2H) 2.42 (s, 3H) 3.13-3.27 (m, 3H) 3.36-3.42 (m, 2H) 3.57 (s, 3H) 3.90 (d, 2H) 7.18 (dd, 1H) 7.28 (dd, 1H) 7.33 (d, 1H) 7.43-7.50 (m, 2H) 7.52 (s, 1H) 7.57 (d, 1H) 7.68 (br s, 1H). LC-MS (Method 2): $R_t$ = 1.25 min; MS (ESIpos): m/z = 487 $[M + H]^+$ |

TABLE 24-continued

| Compounds were prepared as referenced | | | | |
|---|---|---|---|---|
| Example | Structure | IUPAC-Name | Starting Materials | Analytics |
| 506 | 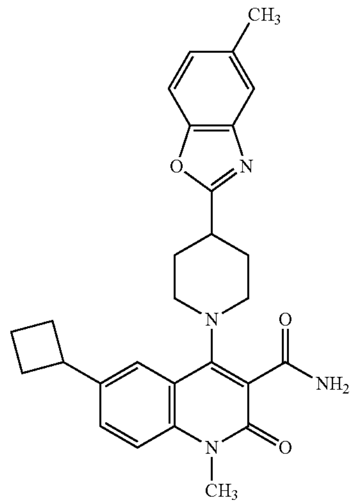 [SMILES: Cc1ccc2oc(C3CCN(c4c(C(N)=O)c(=O)n(C)c5ccc(C6CCC6)cc45)CC3)nc2c1] | 6-cyclobutyl-1-methyl-4-[4-(5-methyl-1,3-benzoxazol-2-yl)piperidin-1-yl]-2-oxo-1,2-dihydroquinoline-3-carboxamide | Prepared from example 409 in analogy to example 450. | $^{1}$H NMR (400 MHz, DMSO-$d_6$) δ ppm 1.85 (s, 1H) 1.93-2.07 (m, 2H) 2.08-2.17 (m, 3H) 2.21-2.28 (m, 2H) 2.31-2.40 (m, 2H) 2.43 (s, 3H) 3.15-3.28 (m, 3H) 3.40 (br d, 2H) 3.57 (s, 3H) 3.64 (quin, 1H) 7.19 (dd, 1H) 7.44-7.49 (m, 2H) 7.49-7.54 (m, 2H) 7.58 (d, 1H) 7.68 (s, 1H) 7.70 (d, 1H). LC-MS (Method 2): $R_t$ = 1.36 min; MS (ESIpos): m/z = 471 $[M + H]^+$ |
| 507 | 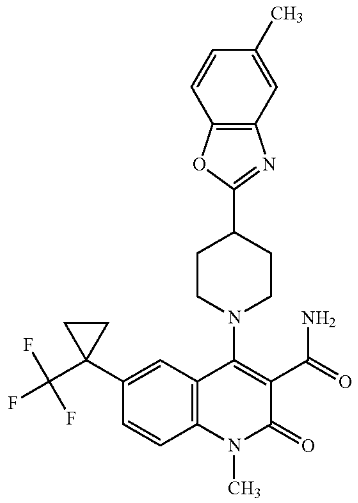 [SMILES: Cc1ccc2oc(C3CCN(c4c(C(N)=O)c(=O)n(C)c5ccc(C6(C(F)(F)F)CC6)cc45)CC3)nc2c1] | 1-methyl-4-[4-(5-methyl-1,3-benzoxazol-2-yl)piperidin-1-yl]-2-oxo-6-[1-(trifluoromethyl)cyclopropyl]-1,2-dihydroquinoline-3-carboxamide | Prepared from example 412 in analogy to example 450. | $^{1}$H NMR (400 MHz, DMSO-$d_6$) δ ppm 1.19 (br s, 2H) 1.38-1.44 (m, 2H) 1.99-2.11 (m, 2H) 2.26 (br dd, 2H) 2.43 (s, 3H) 3.15-3.27 (m, 3H) 3.40 (br d, 2H) 3.59 (s, 3H) 7.19 (dd, 1H) 7.48-7.56 (m, 3H) 7.58 (d, 1H) 7.64-7.71 (m, 2H) 7.96 (d, 1H). LC-MS (Method 2): $R_t$ = 1.31 min; MS (ESIpos): m/z = 525 $[M + H]^+$ |
| 508 | 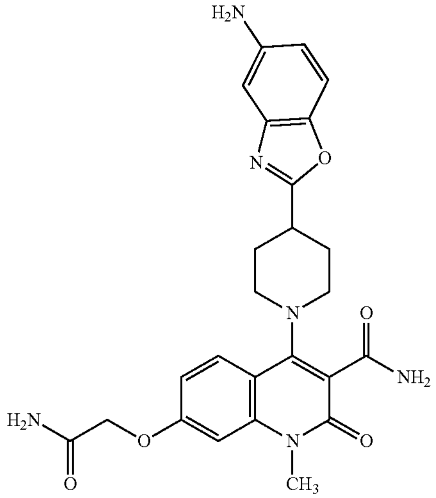 [SMILES: Cn1c(=O)c(C(N)=O)c(N2CCC(c3nc4cc(N)ccc4o3)CC2)c2ccc(OCC(N)=O)cc21] | 7-(2-amino-2-oxoethoxy)-1-methyl-4-[4-(5-methyl-1,3-benzoxazol-2-yl)piperidin-1-yl]-2-oxo-1,2-dihydroquinoline-3-carboxamide | Prepared from example 413 in analogy to example 450. | $^{1}$H NMR (400 MHz, DMSO-$d_6$) δ ppm 2.02-2.15 (m, 3H), 2.16-2.26 (m, 2H), 2.42 (s, 3H), 3.12-3.26 (m, 3H), 3.55 (s, 3H), 4.59 (s, 2H), 4.64-4.66 (m, 1H), 6.96 (dd, 1H), 6.99 (d, 1H), 7.15-7.21 (m, 1H), 7.40-7.49 (m, 2H), 7.50-7.54 (m, 1H), 7.57 (d, 1H),7.64 (bs, 2H), 7.84 (d, 1H). LC-MS (Method 2): $R_t$ = 0.92 min; MS (ESIpos): m/z = 490 $[M + H]^+$ |

TABLE 24-continued

| Compounds were prepared as referenced | | | | |
|---|---|---|---|---|
| Example | Structure | IUPAC-Name | Starting Materials | Analytics |
| 509 | 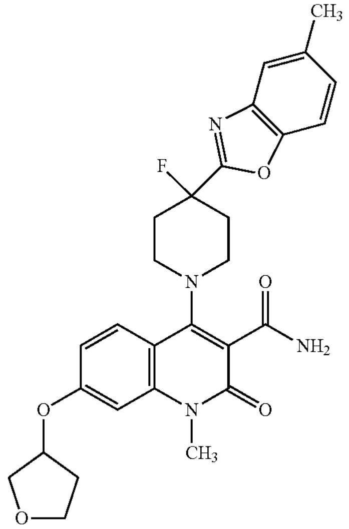 [SMILES: Cc1ccc2oc(C3(F)CCN(c4c(C(N)=O)c(=O)n(C)c5cc(OC6CCOC6)ccc45)CC3)nc2c1] | 4-[4-fluoro-4-(5-methyl-1,3-benzoxazol-2-yl)piperidin-1-yl]-1-methyl-2-oxo-7-[(oxolan-3-yl)oxy]-1,2-dihydroquinoline-3-carboxamide | Prepared from example 417 in analogy to example 450. | $^1$H NMR (400 MHz, DMSO-$d_6$) δ ppm 1.97-2.06 (m, 1H) 2.24-2.35 (m, 1H) 2.39-2.47 (m, 5H) 2.54-2.65 (m, 1H) 3.25 (br s, 2H) 3.43 (br s, 2H) 3.56 (s, 3H) 3.78 (br d, 1H) 3.82-3.91 (m, 2H) 3.93 (d, 1H) 5.25 (dd, 1H) 6.89-6.94 (m, 2H) 7.32 (dd, 1H) 7.47 (br s, 1H) 7.61-7.68 (m, 2H) 7.71 (d, 1H) 7.88 (d, 1H). LC-MS (Method 1): $R_t$ = 1.12 min; MS (ESIpos): m/z = 521 $[M + H]^+$ |
| 510 | 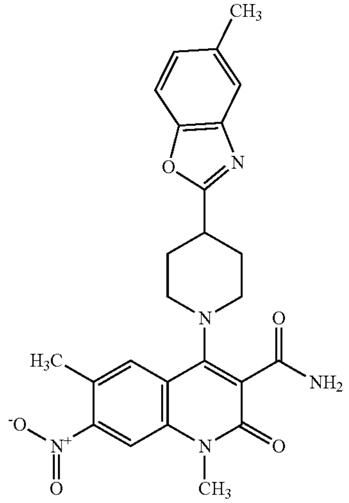 [SMILES: Cc1ccc2oc(C3CCN(c4c(C(N)=O)c(=O)n(C)c5cc([N+](=O)[O-])c(C)cc45)CC3)nc2c1] | 1,6-dimethyl-4-[4-(5-methyl-1,3-benzoxazol-2-yl)piperidin-1-yl]-7-nitro-2-oxo-1,2-dihydroquinoline-3-carboxamide | Prepared from example 421 in analogy to example 450. | $^1$H NMR (400 MHz, DMSO-$d_6$) δ ppm 2.06-2.18 (m, 2H), 2.19-2.29 (m, 2H), 2.43 (s, 3H), 2.47 (s, 3H), 3.17-3.28 (m, 6H), 3.35-3.43 (m, 2H), 7.19 (dd, 1H), 7.51-7.54 (m, 1H), 7.57 (d, 1H), 7.60-7.64 (m, 1H), 7.81 (br d, 1H), 7.94-7.99 (m, 2H). |
| 511 | 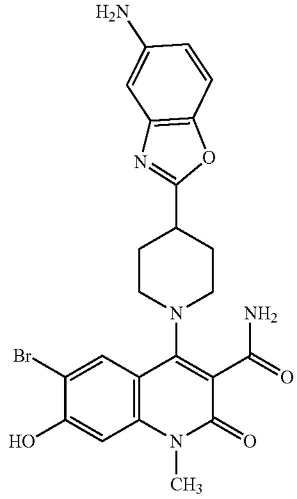 [SMILES: Cn1c(=O)c(C(N)=O)c(N2CCC(c3nc4cc(N)ccc4o3)CC2)c2cc(Br)c(O)cc21] | 6-bromo-7-hydroxy-1-methyl-4-[4-(5-methyl-1,3-benzoxazol-2-yl)piperidin-1-yl]-2-oxo-1,2-dihydroquinoline-3-carboxamide | Prepared from example 422 in analogy to example 450. | $^1$H NMR (400 MHz, DMSO-$d_6$) δ ppm 1.96-2.08 (m, 2H) 2.22 (br dd, 2H) 2.42 (s, 3H) 3.12-3.26 (m, 3H) 3.46-3.51 (m, 3H) 6.95 (s, 1H) 7.18 (dd, 1H) 7.45 (br s, 1H) 7.51-7.54 (m, 1H) 7.58 (d, 1H) 7.63-7.67 (m, 1H) 7.91 (s, 1H) 11.09-11.18 (m, 1H). LC-MS (Method 2): $R_t$ = 0.68 min; MS (ESIpos): m/z = 511 $[M + H]^+$ |

TABLE 24-continued

| Compounds were prepared as referenced | | | | |
|---|---|---|---|---|
| Example | Structure | IUPAC-Name | Starting Materials | Analytics |
| 512 | 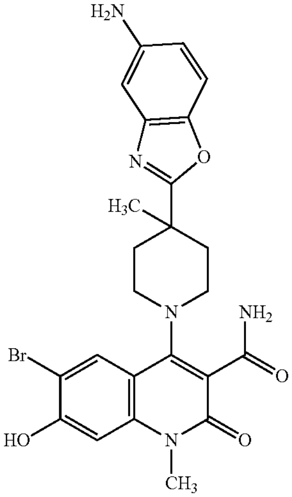 [SMILES: Cn1c(=O)c(C(N)=O)c(N2CCC(C)(c3nc4cc(N)ccc4o3)CC2)c2cc(Br)c(O)cc21] | 6-bromo-7-hydroxy-1-methyl-4-[4-methyl-4-(5-methyl-1,3-benzoxazol-2-yl)piperidin-1-yl]-2-oxo-1,2-dihydroquinoline-3-carboxamide | Prepared from example 423 in analogy to example 450. | $^{1}$H NMR (400 MHz, DMSO-$d_6$) δ ppm 1.45 (s, 3H) 1.85-2.00 (m, 2H) 2.37-2.47 (m, 5H) 3.07 (br t, 2H) 3.22-3.30 (m, 2H) 3.46 (s, 3H) 6.94 (s, 1H) 7.16-7.21 (m, 1H) 7.37 (br s, 1H) 7.54 (s, 2H) 7.59 (d, 1H) 7.92 (s, 1H) 11.12 (s, 1H). |
| 513 | 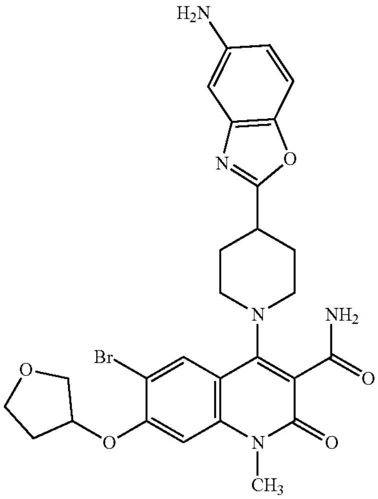 [SMILES: Cn1c(=O)c(C(N)=O)c(N2CCC(c3nc4cc(N)ccc4o3)CC2)c2cc(Br)c(OC3CCOC3)cc21] | (rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide | Prepared from example 424 in analogy to example 450. | $^{1}$H NMR (400 MHz, DMSO-$d_6$) δ ppm 2.00-2.10 (m, 3H) 2.17-2.26 (m, 2H) 2.33 (s, 2H) 2.42 (s, 4H) 3.13-3.25 (m, 3H) 3.60 (s, 3H) 3.78-3.85 (m, 1H) 3.85-3.92 (m, 2H) 3.95-4.04 (m, 1H) 5.39-5.44 (m, 1H) 7.01 (s, 1H) 7.18 (dd, 1H) 7.49 (s, 1H) 7.51-7.54 (m, 1H) 7.58 (d, 1H) 7.67 (br s, 1H) 7.98 (s, 1H). LC-MS (Method 1): $R_t$ = 1.21 min; MS (ESIpos): m/z = 581 $[M + H]^+$ |

Example 514

(rac)-6-cyano-1-methyl-4-[4-methyl-4-(5-methyl-1,3-benzoxazol-2-yl)piperidin-1-yl]-2-oxo-7-[(oxolan-3-yl)oxy]-1,2-dihydroquinoline-3-carboxamide

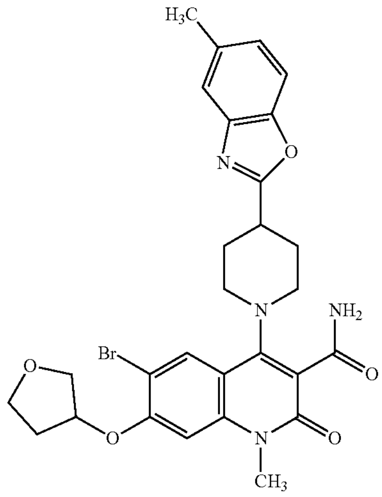 [SMILES: Cc1ccc2oc(C3CCN(c4c(C(N)=O)c(=O)n(C)c5cc(OC6CCOC6)c(Br)cc45)CC3)nc2c1]

23 μl 3-bromooxolane (240 μmol) was added to a suspension of 6-cyano-7-hydroxy-1-methyl-4-[4-methyl-4-(5-methyl-1,3-benzoxazol-2-yl)piperidin-1-yl]-2-oxo-1,2-dihydroquinoline-3-carboxamide (95.0 mg, 201 μmol, intermediate 286) and 131 mg cesium carbonate (403 μmol) in 3.3 mL DMF under a nitrogen atmosphere and stirred over night at 85° C. Due to incomplete conversion another 1.2 eq. of 3-bromooxolane was added and stirring was continued B at 85° C. Water and ethyl acetate were added and the aq. layer was extracted with ethyl acetate 3×. The org. layer was washed with brine, filtered over water-repellent filter and the solvents were evaporated. The crude product was purified by RP-HPLC and the product was obtained in 63 mg yield.

$^1$H NMR (400 MHz, DMSO-$d_6$) δ ppm 1.97-2.11 (m, 3H) 2.30-2.39 (m, 1H) 2.42 (s, 3H) 3.07 (br t, 2H) 3.23-3.30 (m, 2H) 3.59 (s, 3H) 3.81 (br td, 1H) 3.87-4.00 (m, 3H) 5.48 (br dd, 1H) 7.02 (s, 1H) 7.18 (dd, 1H) 7.45 (br s, 1H) 7.53 (s, 1H) 7.59 (d, 2H) 8.13 (s, 1H).

(Signals are partially overlapping the the DMSO signal).

LC-MS (Method 1): $R_t$=1.13 min; MS (ESIpos): m/z=542 $[M+H]^+$ 37 mg of the title compound was separated into enantiomers by preparative chiral HPLC:

Instrument: PrepCon Labomatic HPLC; Column: YMC Cellulose SC 10p, 250×50; eluent A: methyl tert-butyl ether+0.1 vol % diethylamine; eluent B: acetonitrile; gradient: flow: 150 mL/min; temperature: 25° C.; UV: 254 nm 13.7 mg of enantiomer 1 (Example 515) and 13.5 mg of enantiomer 2 (Example 516) were obtained.

Example 515

6-cyano-1-methyl-4-[4-methyl-4-(5-methyl-1,3-benzoxazol-2-yl)piperidin-1-yl]-2-oxo-7-[(oxolan-3-yl)oxy]-1,2-dihydroquinoline-3-carboxamide, enantiomer 1

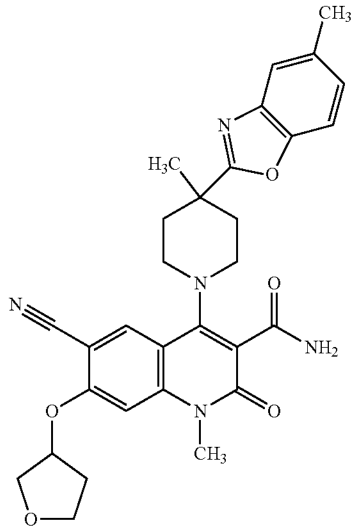 [SMILES: Cc1ccc2oc(C3(C)CCN(c4c(C(N)=O)c(=O)n(C)c5cc(OC6CCOC6)c(C#N)cc45)CC3)nc2c1]

For the preparation of the racemic title compound see example 514. Separation of enantiomers by preparative chiral HPLC (method see example 514) to give 13.7 mg the title compound.

Analytical chiral HPLC: $R_t$=5.32 min.

Instrument: Waters Alliance 2695; Column: YMC Cellulose SC 3μ, 100×4.6; eluent A: methyl tert-butyl ether+0.1 vol % diethylamine; eluent B: acetonitrile; gradient: flow: 1.4 ml/min; temperature: 25° C.; UV: 254 nm $^1$H NMR (400 MHz, DMSO-$d_6$) δ ppm 1.97-2.11 (m, 3H) 2.30-2.39 (m, 1H) 2.42 (s, 3H) 3.07 (br t, 2H) 3.23-3.30 (m, 2H) 3.59 (s, 3H) 3.81 (br td, 1H) 3.87-4.00 (m, 3H) 5.48 (br dd, 1H) 7.02 (s, 1H) 7.18 (dd, 1H) 7.45 (br s, 1H) 7.53 (s, 1H) 7.59 (d, 2H) 8.13 (s, 1H).

Example 516

6-cyano-1-methyl-4-[4-methyl-4-(5-methyl-1,3-benzoxazol-2-yl)piperidin-1-yl]-2-oxo-7-[(oxolan-3-yl)oxy]-1,2-dihydroquinoline-3-carboxamide, enantiomer 2

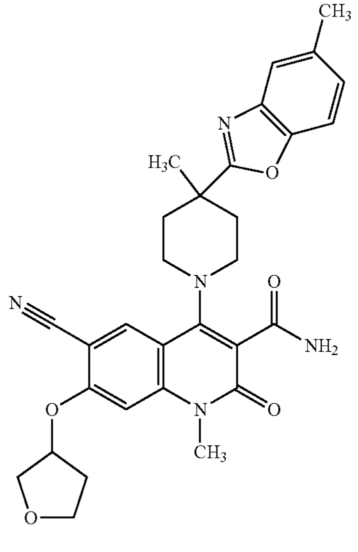 [SMILES: Cc1ccc2oc(C3(C)CCN(c4c(C(N)=O)c(=O)n(C)c5cc(OC6CCOC6)c(C#N)cc45)CC3)nc2c1]

For the preparation of the racemic title compound see example 514. Separation of enantiomers by preparative chiral HPLC (method see example 514) to give 13.5 mg the title compound.

Analytical chiral HPLC: $R_t$=6.23 min.

Instrument: Waters Alliance 2695; Column: YMC Cellulose SC 3μ, 100×4.6; eluent A: methyl tert-butyl ether+0.1 vol % diethylamine; eluent B: acetonitrile; gradient: flow: 1.4 ml/min; temperature: 25° C.; UV: 254 nm $^1$H NMR (400 MHz, DMSO-$d_6$) δ ppm 1.97-2.11 (m, 3H) 2.30-2.39 (m, 1H) 2.42 (s, 3H) 3.07 (br t, 2H) 3.23-3.30 (m, 2H) 3.59 (s, 3H) 3.81 (br td, 1H) 3.87-4.00 (m, 3H) 5.48 (br dd, 1H) 7.02 (s, 1H) 7.18 (dd, 1H) 7.45 (br s, 1H) 7.53 (s, 1H) 7.59 (d, 2H) 8.13 (s, 1H).

TABLE 25

Compounds were prepared as referenced

| Example | Structure | IUPAC-Name | Starting Materials | Analytics |
|---|---|---|---|---|
| 517 | 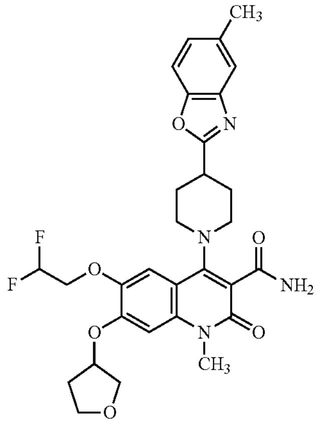 [SMILES: Cc1ccc2oc(C3CCN(c4c(C(N)=O)c(=O)n(C)c5cc(OC6CCOC6)c(OCC(F)F)cc45)CC3)nc2c1] | (rac)-6-(2,2-difluoroethoxy)-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide | Prepared from Example 430 in analogy to Example 450. | $^1$H NMR (400 MHz, DMSO-$d_6$) δ ppm 2.00-2.13 (m, 3H) 2.19-2.26 (m, 2H) 2.27-2.35 (m, 1H) 2.42 (s, 3H) 3.19 (br d, 3H) 3.38 (br d, 2H) 3.59 (s, 3H) 3.79 (br d, 1H) 3.85-3.91 (m, 2H) 3.93 (d, 1H) 4.35 (d, 2H) 5.28-5.35 (m, 1H) 6.24-6.55 (m, 1H) 6.98 (s, 1H) 7.18 (dd, 1H) 7.39 (s, 1H) 7.44 (br s, 1H) 7.52 (s, 1H) 7.57 (d, 1H) 7.63 (br s, 1H). LC-MS (Method 2): $R_t$ = 1.13 min; MS (ESIpos): m/z = 583 $[M + H]^+$ |
| 518 | 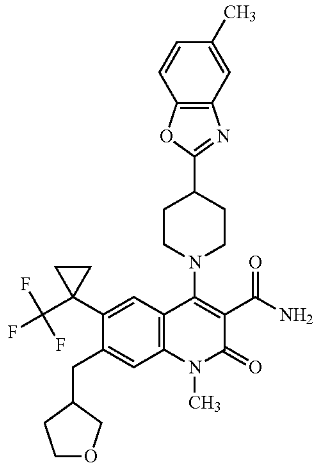 [SMILES: Cc1ccc2oc(C3CCN(c4c(C(N)=O)c(=O)n(C)c5cc(CC6CCOC6)c(C6(C(F)(F)F)CC6)cc45)CC3)nc2c1] | (rac)-1-methyl-4-[4-(5-methyl-1,3-benzoxazol-2-yl)piperidin-1-yl]-2-oxo-7-[(oxolan-3-yl)oxy]-6-[1-(trifluoromethyl)cyclopropyl]-1,2-dihydroquinoline-3-carboxamide | Prepared from example 434 in analogy to example 450. | $^1$H NMR (400 MHz, DMSO-$d_6$) δ ppm 1.07 (br s, 2H) 1.35-1.42 (m, 2H) 1.96-2.10 (m, 3H) 2.21-2.31 (m, 3H) 2.42 (s, 3H) 3.15-3.27 (m, 3H) 3.38 (br d, 2H) 3.59 (s, 3H) 3.80-3.88 (m, 3H) 4.02 (dd, 1H) 5.39 (br t, 1H) 6.88 (s, 1H) 7.19 (dd, 1H) 7.45 (br d, 1H) 7.53 (s, 1H) 7.58 (d, 1H) 7.63 (br s, 1H) 7.84 (s, 1H). LC-MS (Method 1): $R_t$ = 1.30 min; MS (ESIpos): m/z = 611 $[M + H]^+$ |
| 519 | 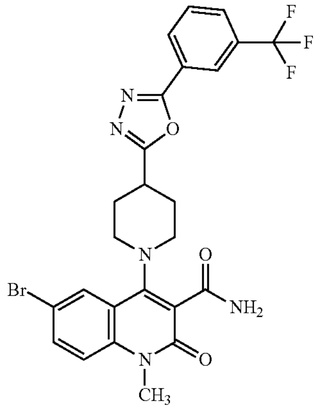 [SMILES: Cn1c(=O)c(C(N)=O)c(N2CCC(c3nnc(-c4cccc(C(F)(F)F)c4)o3)CC2)c2cc(Br)ccc21] | 6-bromo-1-methyl-2-oxo-4-(4-{5-[3-(trifluoromethyl)phenyl]-1,3,4-oxadiazol-2-yl}piperidin-1-yl)-1,2-dihydroquinoline-3-carboxamide | Prepared from example 435 in analogy to example 450. | $^1$H NMR (400 MHz, DMSO-$d_6$) δ ppm 1.99-2.08 (m, 2H) 2.21-2.31 (m, 2H) 3.12-3.25 (m, 2H) 3.34-3.44 (m, 4H) 3.35-3.44 (m, 2H) 3.36-3.41 (m, 2H) 3.58 (s, 3H) 7.51 (d, 1H) 7.56 (bs, 1H) 7.75 (bs, 1H) 7.79 (dd, 1H) 7.87 (t, 1H) 7.96 (d, 1H) 8.00-8.07 (m, 1H) 8.26-8.31 (m, 1H) 8.32-8.37 (m, 1H). |

TABLE 25-continued

| Compounds were prepared as referenced | | | | |
|---|---|---|---|---|
| Example | Structure | IUPAC-Name | Starting Materials | Analytics |
| 520 | 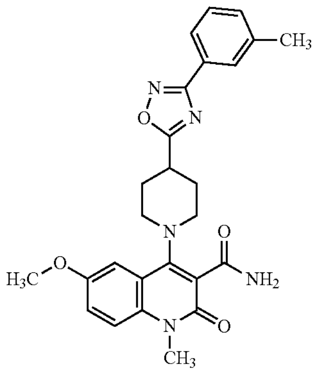 | 6-methoxy-1-methyl-4-{4-[3-(3-methylphenyl)-1,2,4-oxadiazol-5-yl]piperidin-1-yl}-2-oxo-1,2-dihydroquinoline-3-carboxamide | Prepared from example 436 in analogy to example 450. | $^1$H NMR (400 MHz, DMSO-$d_6$) δ ppm 2.00-2.14 (m, 2H), 2.22-2.31 (m, 2H), 2.41 (s, 3H), 3.14-3.25 (m, 2H), 3.34-3.44 (m, 3H), 3.58 (s, 3H), 3.84 (s, 3H), 7.28 (dd, 1H), 7.34 (d, 1H), 7.40-7.51 (m, 4H), 7.68-7.74 (m, 1H), 7.81-7.87 (m, 2H). |
| 521 | 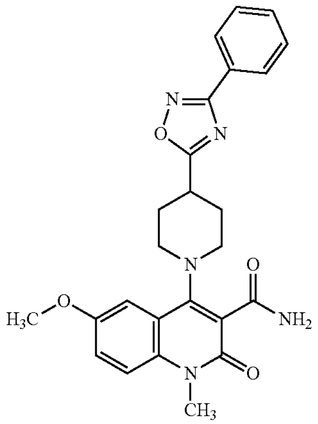 [SMILES: COc1ccc2c(c1)c(N1CCC(c3nc(-c4ccccc4)no3)CC1)c(C(N)=O)c(=O)n2C] | 6-methoxy-1-methyl-2-oxo-4-[4-(3-phenyl-1,2,4-oxadiazol-5-yl)piperidin-1-yl]-1,2-dihydroquinoline-3-carboxamide | Prepared from example 437 in analogy to example 450. | $^1$H NMR (400 MHz, DMSO-$d_6$) δ ppm 2.01-2.15 (m, 2H), 2.22-2.31 (m, 2H), 3.15-3.25 (m, 2H), 3.34-3.44 (m, 3H), 3.58 (s, 3H), 3.84 (s, 3H), 7.28 (dd, 1H), 7.34 (d, 1H), 7.49 (d, 2H), 7.55-7.63 (m, 3H), 7.70 (s, 1H), 8.02-8.06 (m, 2H). |
| 522 | 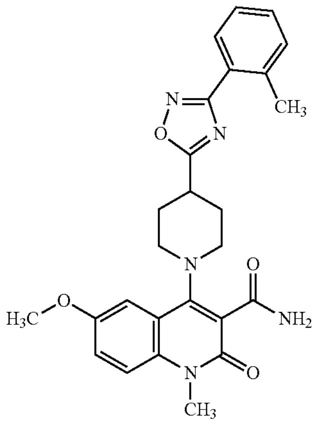 [SMILES: COc1ccc2c(c1)c(N1CCC(c3nc(-c4ccccc4C)no3)CC1)c(C(N)=O)c(=O)n2C] | 6-methoxy-1-methyl-4-{4-[3-(2-methylphenyl)-1,2,4-oxadiazol-5-yl]piperidin-1-yl}-2-oxo-1,2-dihydroquinoline-3-carboxamide | Prepared from example 438 in analogy to example 450. | $^1$H NMR (400 MHz, DMSO-$d_6$) δ ppm 2.01-2.15 (m, 2H), 2.22-2.31 (m, 2H), 2.57 (s, 3H), 3.15-3.26 (m, 2H), 3.34-3.45 (m, 3H), 3.57 (s, 3H), 3.84 (s, 3H), 7.28 (dd, 1H), 7.34 (d, 1H), 7.36-7.53 (m, 5H), 7.70 (s, 1H), 7.95 (dd, 1H). |

TABLE 25-continued

| Compounds were prepared as referenced | | | | |
|---|---|---|---|---|
| Example | Structure | IUPAC-Name | Starting Materials | Analytics |
| 523 | 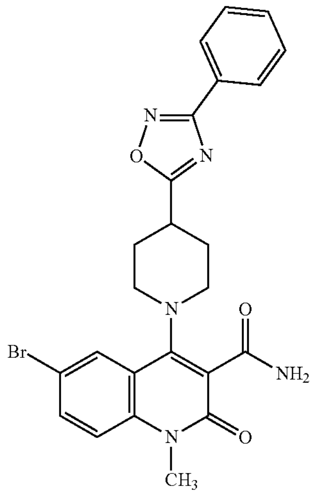 [SMILES: Cn1c(=O)c(C(N)=O)c(N2CCC(c3nc(-c4ccccc4)no3)CC2)c2cc(Br)ccc21] | 6-bromo-1-methyl-2-oxo-4-[4-(3-phenyl-1,2,4-oxadiazol-5-yl)piperidin-1-yl]-1,2-dihydroquinoline-3-carboxamide | Prepared from example 440 in analogy to example 450. | $^1$H NMR (400 MHz, DMSO-$d_6$) δ ppm 2.01-2.14 (m, 2H), 2.22-2.30 (m, 2H), 3.14-3.24 (m, 2H), 3.35-3.43 (m, 3H), 3.58 (s, 3H), 7.51 (d, 1H), 7.55-7.62 (m, 4H), 7.71-7.76 (m, 1H), 7.72-7.83 (m, 2H), 7.79 (dd, 1H), 7.97 (d, 1H), 8.04 (dd, 2H). |
| 524 | 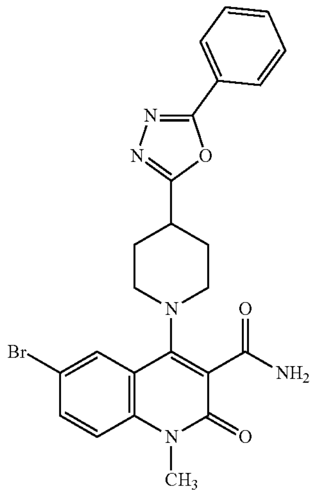 [SMILES: Cn1c(=O)c(C(N)=O)c(N2CCC(c3nnc(-c4ccccc4)o3)CC2)c2cc(Br)ccc21] | 6-bromo-1-methyl-2-oxo-4-[4-(5-phenyl-1,3,4-oxadiazol-2-yl)piperidin-1-yl]-1,2-dihydroquinoline-3-carboxamide | Prepared from example 441 in analogy to example 450. | $^1$H NMR (400 MHz, DMSO-$d_6$) δ ppm 1.98-2.11 (m, 2H), 2.20-2.30 (m, 2H), 3.14-3.23 (m, 2H), 3.24-3.31 (m, 1H), 3.34-3.43 (m, 2H), 3.58 (s, 3H), 7.51 (d, 1H), 7.54-7.58 (m, 1H), 7.58-7.67 (m, 3H), 7.73-7.76 (m, 1H), 7.79 (dd, 1H), 7.97 (d, 1H), 8.03 (dd, 2H). |
| 525 | 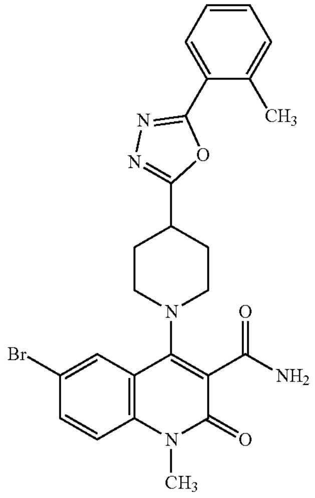 [SMILES: Cc1ccccc1-c1nnc(C2CCN(c3c(C(N)=O)c(=O)n(C)c4ccc(Br)cc34)CC2)o1] | 6-bromo-1-methyl-4-{4-[5-(2-methylphenyl)-1,3,4-oxadiazol-2-yl]piperidin-1-yl}-2-oxo-1,2-dihydroquinoline-3-carboxamide | Prepared from example 442 in analogy to example 450. | $^1$H NMR (400 MHz, DMSO-$d_6$) δ ppm 2.03-2.10 (m, 3H) 2.22-2.31 (m, 2H) 2.63 (s, 3H) 3.14-3.24 (m, 2H) 3.28-3.32 (m, 1H) 3.35-3.42 (m, 2H) 3.58 (s, 3H) 7.36-7.54 (m, 4H) 7.54-7.59 (m, 1H) 7.74 (bs, 1H) 7.78 (dd, 1H) 7.90-7.95 (m, 1H) 7.96 (d, 1H). |

TABLE 25-continued

Compounds were prepared as referenced

| Example | Structure | IUPAC-Name | Starting Materials | Analytics |
|---|---|---|---|---|
| 526 | 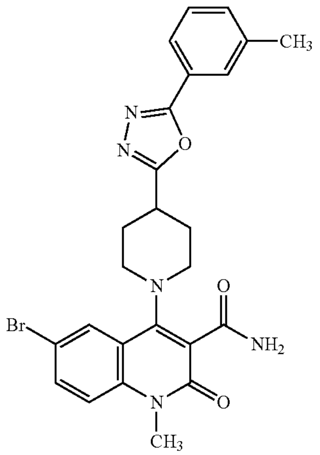 [SMILES: Cc1cccc(-c2nnc(C3CCN(c4c(C(N)=O)c(=O)n(C)c5ccc(Br)cc45)CC3)o2)c1] | 6-bromo-1-methyl-4-{4-[5-(3-methylphenyl)-1,3,4-oxadiazol-2-yl]piperidin-1-yl}-2-oxo-1,2-dihydroquinoline-3-carboxamide | Prepared from example 443 in analogy to example 450. | $^{1}$H NMR (400 MHz, DMSO-$d_6$) δ ppm 2.00-2.10 (m, 4H) 2.21-2.30 (m, 2H) 2.41 (s, 3H) 3.14-3.23 (m, 2H) 3.24-3.30 (m, 1H) 3.35-3.43 (m, 2H) 3.57 (s, 3H) 7.42-7.59 (m, 4H) 7.72-7.87 (m, 4H) 7.95-7.99 (m, 1H). |
| 527 | 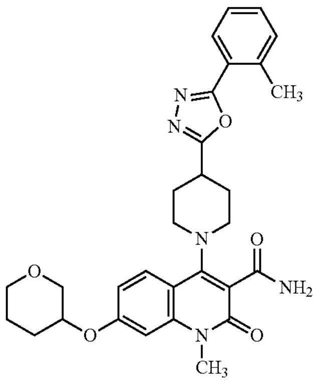 [SMILES: Cc1ccccc1-c1nnc(C2CCN(c3c(C(N)=O)c(=O)n(C)c4cc(OC5CCCOC5)ccc34)CC2)o1] | 1-methyl-4-{4-[5-(2-methylphenyl)-1,3,4-oxadiazol-2-yl]piperidin-1-yl}-7-[(oxan-3-yl)oxy]-2-oxo-1,2-dihydroquinoline-3-carboxamide, Enantiomer 1 | rac-1-methyl-4-{4-[5-(2-methylphenyl)-1,3,4-oxadiazol-2-yl]piperidin-1-yl}-7-{[oxan-3-yl]oxy}-2-oxo-1,2-dihydroquinoline-3-carboxamide reparedfrom example 446 in analogy to example 450. Chiral Separation: Instrument: PrepCon Labomatic HPLC; column: YMC Cellulose SB 5μ, 250 x 30; eluent A: methyl tert-butyl ether + 0.1 vol % diethylamine; eluent B: acetonitrile + 0.1 vol % diethylamine; isocratic: 70% A+30% B; flow: 50 ml/min; temperature: 25° C.; UV: 254 nm | $^{1}$H NMR (400 MHz, DMSO-$d_6$) δ ppm 1.99-2.13 (m, 3H), 2.16-2.26 (m, 2H), 2.63 (s, 3H), 3.13-3.23 (m, 2H), 3.23-3.30 (m, 1H), 3.34-3.43 (m, 3H), 3.51-3.60 (m, 5H), 3.60-3.68 (m, 1H), 3.85 (dd, 1H), 4.59-4.67 (m, 1H), 6.92-7.00 (m, 2H), 7.38-7.48 (m, 3H), 7.48-7.54 (m, 1H), 7.60-7.67 (m, 1H), 7.83 (d, 1H), 7.93 (dd, 1H) Chiral analytical HPLC: $R_t$ = 4.78 min, Instrument: Waters Alliance 2695; Column: YMC Cellulose SB 3μ, 100 x 4.6; eluent A: methyl tert-butyl ether + 0.1 vol % diethylamine; eluent B: acetonitrile; isocratic: 70% A + 30% B; flow: 1.4 ml/min; temperature: 25° C.; UV: 254 nm |
| 528 | 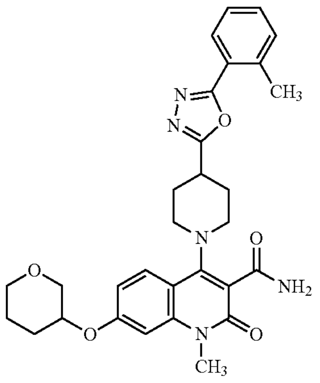 [SMILES: Cc1ccccc1-c1nnc(C2CCN(c3c(C(N)=O)c(=O)n(C)c4cc(OC5CCCOC5)ccc34)CC2)o1] | 1-methyl-4-{4-[5-(2-methylphenyl)-1,3,4-oxadiazol-2-yl]piperidin-1-yl}-7-[(oxan-3-yl)oxy]-2-oxo-1,2-dihydroquinoline-3-carboxamide, Enantiomer 2 | rac-1-methyl-4-{4-[5-(2-methylphenyl)-1,3,4-oxadiazol-2-yl]piperidin-1-yl}-7-{[oxan-3-yl]oxy}-2-oxo-1,2-dihydroquinoline-3-carboxamide repared from example 446 in analogy to example 450. Chiral Separation: Instrument: PrepCon Labomatic HPLC; column:YMC Cellulose SB 5μ, 250 x 30; eluent A: methyl tert-butyl ether + 0.1 vol % diethylamine; eluent B: acetonitrile + 0.1 vol % diethylamine; isocratic: 70% A + 30% B; flow: 50 ml/min; temperature: 25° C.; UV: 254 nm | $^{1}$H NMR (400 MHz, DMSO-$d_6$) δ ppm 1.99-2.13 (m, 3H), 2.16-2.26 (m, 2H), 2.63 (s, 3H), 3.13-3.23 (m, 2H), 3.23-3.30 (m, 1H), 3.34-3.43 (m, 3H), 3.51-3.60 (m, 5H), 3.60-3.68 (m, 1H), 3.85 (dd, 1H), 4.59-4.67 (m, 1H), 6.92-7.00 (m, 2H), 7.38-7.48 (m, 3H), 7.48-7.54 (m, 1H), 7.60-7.67 (m, 1H), 7.83 (d, 1H), 7.93 (dd, 1H) Chiral analytical HPLC: $R_t$ = 6.03 min, Instrument: Waters Alliance 2695; Column: YMC Cellulose SB 3μ, 100 x 4.6; eluent A: methyl tert-butyl ether + 0.1 vol % diethylamine; eluent B: acetonitrile; isocratic: 70% A + 30% B; flow: 1.4 ml/min; temperature: 25° C.; UV: 254 nm |

TABLE 25-continued

Compounds were prepared as referenced

| Example | Structure | IUPAC-Name | Starting Materials | Analytics |
| --- | --- | --- | --- | --- |
| 529 | 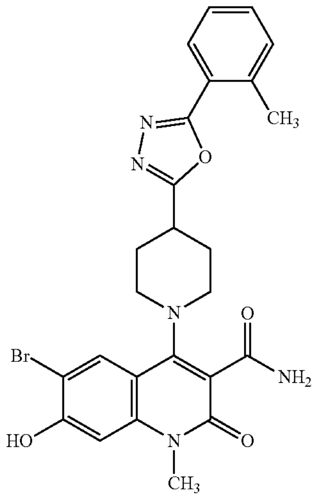 [SMILES: Cc1ccccc1-c1nnc(C2CCN(c3c(C(N)=O)c(=O)n(C)c4cc(O)c(Br)cc34)CC2)o1] | 6-bromo-7-hydroxy-1-methyl-4-{4-[5-(2-methylphenyl)-1,3,4-oxadiazol-2-yl]piperidin-1-yl}-2-oxo-1,2-dihydroquinoline-3-carboxamide | Prepared from example 445 in analogy to example 450. | $^1$H NMR (400 MHz, DMSO-$d_6$) δ ppm 1.99-2.09 (m, 2H) 2.19-2.29 (m, 2H) 2.62-2.63 (s, 3H) 3.13-3.23 (m, 3H) 3.47-3.54 (m + s, 4H) 6.91-6.99 (m, 1H) 7.38-7.56 (m, 5H) 7.62-7.68 (m, 1H) 7.89-7.97 (m, 2H). LC-MS (Method 2): $R_t$ = 0.64 min; MS (ESIpos): m/z = 538 $[M + H]^+$ |

Example 530

6-bromo-7-methoxy-1-methyl-4-{4-[3-(2-methylphenyl)-1,2,4-oxadiazol-5-yl]piperidin-1-yl}-2-oxo-1,2-dihydroquinoline-3-carbonitrile

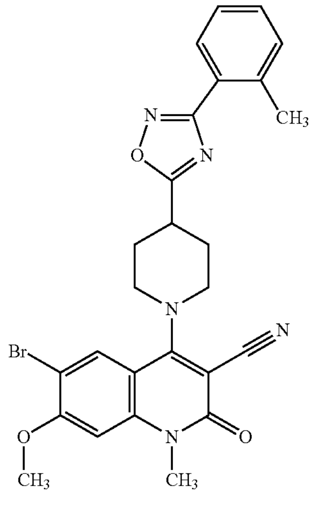 [SMILES: COc1cc2c(cc1Br)c(N1CCC(c3nc(-c4ccccc4C)no3)CC1)c(C#N)c(=O)n2C]

A solution of 500 mg 6-bromo-4-chloro-7-methoxy-1-methyl-2-oxo-1,2-dihydroquinoline-3-carbonitrile (intermediate 264), 545 mg of the salt of 4-[3-(2-methylphenyl)-1,2,4-oxadiazol-5-yl]piperidine with trifluoroacetic acid (intermediate 248) and 0.43 mL triethylamine in 27 mL 2-propanol was stirred for 5 h at 90° C. After this ti me, water was added and the reaction was extracted with dichloromethane. The organic phase was washed with water and brine and dried over sodium sulfate. After evaporation of the solvent, the residue was purified by flash chromatography (silica, dichloromethane/methanol gradient 0-3%). 160 mg of the title compound were obtained.

$^1$H NMR (400 MHz, DMSO-d6) δ ppm 2.04-2.17 (m, 5H) 2.27-2.36 (m, 2H) 2.54-2.60 (m, 3H) 3.48-3.69 (m, 6H) 3.73-3.90 (m, 2H) 3.98-4.13 (m, 3H) 6.89-7.12 (m, 1H) 7.24-7.59 (m, 3H) 7.86-8.01 (m, 2H)

Example 531

6-bromo-7-hydroxy-1-methyl-4-{4-[3-(2-methylphenyl)-1,2,4-oxadiazol-5-yl]piperidin-1-yl}-2-oxo-1,2-dihydroquinoline-3-carbonitrile

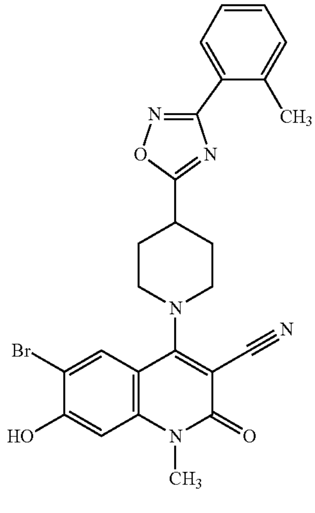 [SMILES: Cc1ccccc1-c1noc(C2CCN(c3c(C#N)c(=O)n(C)c4cc(O)c(Br)cc34)CC2)n1]

A solution of 460 mg 6-bromo-7-methoxy-1-methyl-4-{4-[3-(2-methylphenyl)-1,2,4-oxadiazol-5-yl]piperidin-1-yl}-2-oxo-1,2-dihydroquinoline-3-carbonitrile (Example 530) in 20 ml dichloromethane at −70° C. was added 8.6 ml boron tri bromide solution (1 M in dichloromethane). The temperature was raised to RT over 1 hour and stirred for further 14 hours at RT. The reaction was pred into aqueous bicarbonate solution and extracted with dichloromethane (2×). The combined organic layers were washed with water and brine and dried over sodium sulfate. After evaporation of the solvent, the residue was purified by flash chromatography (silica, dichloromethane/methanol gradient 0-2%). 220 mg of the title compound were obtained.

$^1$H NMR (400 MHz, DMSO-d6) δ ppm 2.05-2.15 (m, 2H) 2.29-2.35 (m, 2H) 2.55-2.61 (m, 3H) 3.44-3.47 (m, 3H) 3.51-3.65 (m, 4H) 3.72-3.82 (m, 2H) 6.83-6.90 (m, 1H) 7.33-7.54 (m, 3H) 7.86-7.91 (m, 1H) 7.92-7.97 (m, 1H)

Example 532

(rac)-6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile

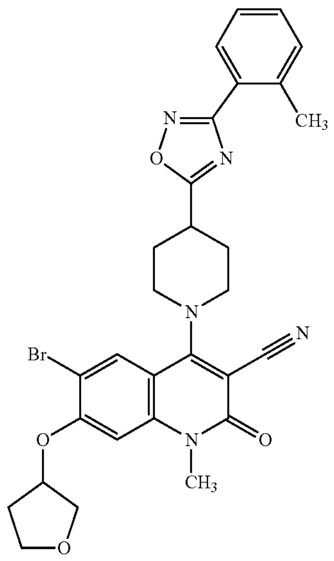 [SMILES: Cc1ccccc1-c1noc(C2CCN(c3c(C#N)c(=O)n(C)c4cc(OC5CCOC5)c(Br)cc34)CC2)n1]

A mixture of 420 mg 6-bromo-7-hydroxy-1-methyl-4-{4-[3-(2-methylphenyl)-1,2,4-oxadiazol-5-yl]piperidin-1-yl}-2-oxo-1,2-dihydroquinoline-3-carbonitrile (example 531), 789 mg cesium carbonate and 244 mg 3-bromooxolane in 15 mL DMF was stirred for 7.5 hours at 100° C. under argon. Water was added and the mixture was extracted with ethyl acetate (2×). The combined organic layers were washed with brine, the solvent was evaporated under reduced pressure and the crude product was purified by flash chromatography (silica, dichloromethane/methanol gradient 0-1%) to give 290 mg of the title compound.

$^1$H NMR (400 MHz, DMSO-d6) δ ppm 2.00-2.18 (m, H) 2.27-2.43 (m, 3H) 2.55-2.59 (m, 3H) 2.63-2.70 (m, 1H) 2.71-2.76 (m, 1H) 2.87-2.91 (m, 1H) 3.51-3.65 (m, 6H) 3.76-3.84 (m, 3H) 3.85-3.93 (m, 2H) 3.95-4.03 (m, 1H) 5.43-5.49 (m, 1H) 6.96-7.02 (m, 1H) 7.35-7.52 (m, 3H) 7.91-7.99 (m, 2H).

Example 533

(rac)-6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide

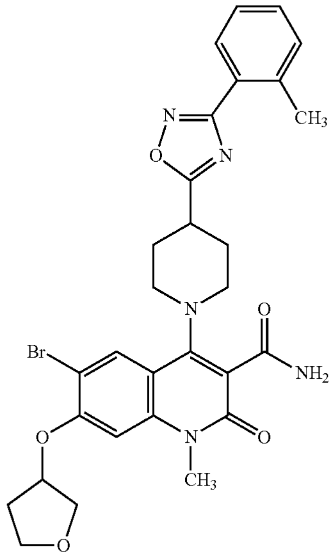 [SMILES: Cc1ccccc1-c1noc(C2CCN(c3c(C(N)=O)c(=O)n(C)c4cc(OC5CCOC5)c(Br)cc34)CC2)n1]

A solution of 51 mg 285 mg 6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile (example 532) was reacted with 285 mg acetaldoxime and 45 mg chloridotris(triphenylphosphine)rhodium(I) (CAS 14694-95-2) in 10 ml toluene for 20 hours at 110° C. The reaction mixture was diluted with water ethyl acetate (2×) and the combined organic layers were washed with brine and concentrated under reduced pressure. The residue was purified by flash chromatography (silica, dichloromethane/ethanol gradient 0-3%) to obtain 240 mg of the title compound.

$^1$H NMR (400 MHz, DMSO-d6) δ ppm 1.97-2.10 (m, 4H) 2.00-2.15 (m, 4H) 2.19-2.36 (m, 4H) 2.56-2.59 (m, 3H) 3.15-3.25 (m, 2H) 3.58-3.64 (m, 3H) 3.75-4.04 (m, 5H) 5.37-5.45 (m, 1H) 6.99-7.04 (m, 1H) 7.34-7.52 (m, 5H) 7.66-7.72 (m, 1H) 7.92-8.02 (m, 2H).

Example 534

(rac)-6-cyano-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide

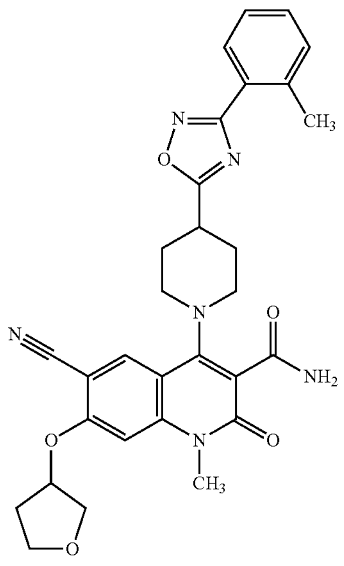 [SMILES: Cc1ccccc1-c1noc(C2CCN(c3c(C(N)=O)c(=O)n(C)c4cc(OC5CCOC5)c(C#N)cc34)CC2)n1]

A mixture of 235 mg 6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide (example 533), 9.5 mg palladium(π-cinnamyl) chloride dimer (CAS 12131-44-1), 51.7 mg zinc cyanide (CAS 557-21-1), 10.2 mg 1,1'-bis(diphenylphosphanyl)ferrocene and 0.13 ml N,N-diisopropylethylamine in 12 ml N,N-dimethylacetamide were stirred at 120° C. for 8 h ours. After this time, water was added and it was extracted with ethyl acetate (2×). The combined organic layers were washed with water and brine and dried over sodium sulfate. After evaporation of the solvent, the residue was purified by flash chromatography (silica, dichloromethane/methanol gradient 0-2%) to obtain 10 mg of the title compound.

$^1$H NMR (400 MHz, DMSO-d6) δ ppm 2.03-2.28 (m, 5H) 2.33-2.42 (m, 1H) 2.55-2.60 (m, 3H) 3.13-3.25 (m, 2H) 3.36-3.41 (m, 2H) 3.59-3.65 (m, 3H) 3.77-4.03 (m, 4H) 5.45-5.53 (m, 1H) 7.02-7.06 (m, 1H) 7.35-7.50 (m, 3H) 7.51-7.59 (m, 1H) 7.69-7.75 (m, 1H) 7.92-7.99 (m, 1H) 8.10-8.17 (m, 1H).

Example 535

6-cyano-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide, Enantiomer 1

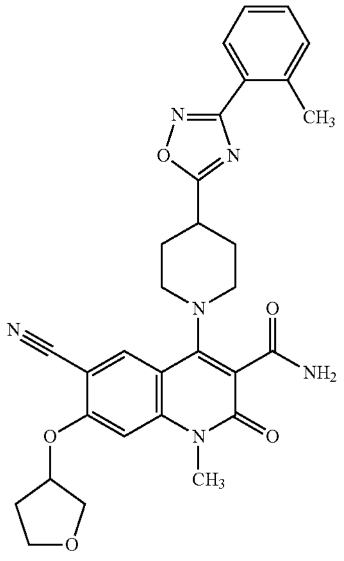 [SMILES: Cc1ccccc1-c1noc(C2CCN(c3c(C(N)=O)c(=O)n(C)c4cc(OC5CCOC5)c(C#N)cc34)CC2)n1]

350 mg 6-cyano-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide (Example 534) were separated by chiral HPLC: Instrument: PrepCon Labomatic HPLC-4; Column: YMC Cellulose SC 10p, 250×50; eluent A: methyl tert-butyl ether+0.1 vol % diethylamine; eluent B: methanol; isocratic: 30% A+70% B; flow: 130 mL/min; temperature: 25° C.; UV: 254 nm 140 mg of the title compound were obtained.

$^1$H NMR (400 MHz, DMSO-d6) δ ppm 2.08-2.08 (m, 1H) 2.08-2.19 (m, 2H) 2.20-2.28 (m, 2H) 2.57-2.60 (m, 3H) 3.14-3.24 (m, 2H) 3.47-3.54 (m, 3H) 6.85-6.92 (m, 1H) 7.36-7.54 (m, 4H) 7.66-7.73 (m, 1H) 7.93-8.00 (m, 1H) 8.01-8.08 (m, 1H).

Optical rotation:$[\alpha]_D$=5.17° (c=5 mg/ml, chloroform)

Analytical chiral HPLC: $R_t$=2.57 min

Instrument: Thermo Fisher UltiMate 3000; Column: YMC Cellulose SC 3μ, 100×4.6; eluent A: methyl tert-butyl ether+0.1 vol % diethylamine; eluent B: methanol; isocratic: 30% A+70% B; flow: 1.4 ml/min; temperature: 25° C.; UV: 254 nm.

Example 536

6-cyano-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide, Enantiomer 2

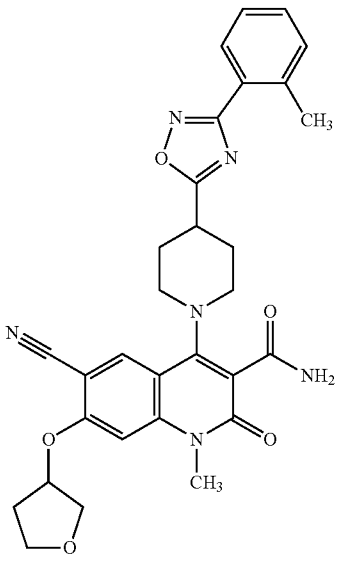 [SMILES: Cc1ccccc1-c1noc(C2CCN(c3c(C(N)=O)c(=O)n(C)c4cc(OC5CCOC5)c(C#N)cc34)CC2)n1]

With the chiral separation of 350 mg 6-cyano-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide (Example 534) described in example 535, 140 mg of the title compound were obtained.

$^1$H NMR (400 MHz, DMSO-d6) δ ppm 2.08-2.08 (m, 1H) 2.08-2.19 (m, 2H) 2.20-2.28 (m, 2H) 2.57-2.60 (m, 3H) 3.14-3.24 (m, 2H) 3.47-3.54 (m, 3H) 6.85-6.92 (m, 1H) 7.36-7.54 (m, 4H) 7.66-7.73 (m, 1H) 7.93-8.00 (m, 1H) 8.01-8.08 (m, 1H).

Optical rotation:$[\alpha]_D$=−3.4° (c=5 mg/ml, chloroform)

Analytical chiral HPLC: $R_t$=3.13 min

Instrument: Thermo Fisher UltiMate 3000; Column: YMC Cellulose SC 3μ, 100×4.6;

eluent A: methyl tert-butyl ether+0.1 vol % diethylamine; eluent B: methanol; isocratic: 30% A+70% B; flow: 1.4 ml/min; temperature: 25° C.; UV: 254 nm.

Example 537

(−)-6-bromo-1-methyl-4-[4-(5-methyl-1,3-benzoxazol-2-yl)piperidin-1-yl]-2-oxo-7-{[(3R)-oxolan-3-yl]oxy}-1,2-dihydroquinoline-3-carbonitrile

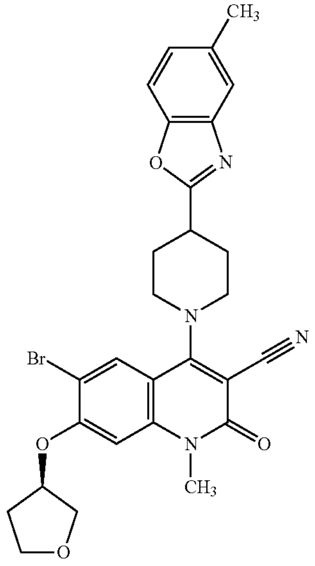 [SMILES: Cc1ccc2oc(C3CCN(c4c(C#N)c(=O)n(C)c5cc(O[C@@H]6CCOC6)c(Br)cc45)CC3)nc2c1]

To a suspension of 100 mg 6-bromo-7-hydroxy-1-methyl-4-[4-(5-methyl-1,3-benzoxazol-2-yl)piperidin-1-yl]-2-oxo-1,2-dihydroquinoline-3-carbonitrile (example 422) and 80 mg triphenylphosphin in 1.1 ml dichloromethane was added 60 μL diisopropyl azodicarboxylate and then 300 μL (3S)-oxolan-3-ol. The reaction mixture was stirred for 20 hours at RT. To the reaction mixture was added water and then the mixture was concentrated under reduced pressure. The residue was purified by RP-HPLC (column: X-Bridge C18 5 μm 100×30 mm, mobile phase: acetonitrile/water (0.1 vol. % formic acid)-gradient) to obtain 59 mg of the title compound.

$^1$H NMR (400 MHz, DMSO-$d_6$) δ ppm 2.00-2.15 (m, 3H) 2.27-2.38 (m, 3H) 2.42 (s, 3H) 3.38-3.48 (m, 1H) 3.54-3.65 (m, 5H) 3.75-3.84 (m, 3H) 3.85-3.93 (m, 2H) 3.95-4.02 (m, 1H) 5.44-5.49 (m, 1H) 7.00-7.00 (m, 1H) 7.17-7.21 (m, 1H) 7.51-7.55 (m, 1H) 7.56-7.61 (m, 1H) 7.96 (s, 1H)

Optical rotation:$[\alpha]_D$=−6.91° (c=10.2 mg/ml, chloroform).

Example 538

(rac)-6-cyano-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide

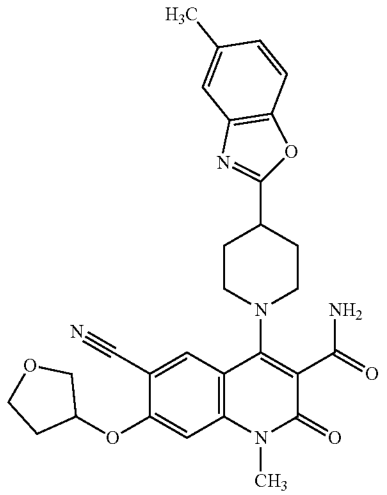 [SMILES: Cc1ccc2oc(C3CCN(c4c(C(N)=O)c(=O)n(C)c5cc(OC6CCOC6)c(C#N)cc45)CC3)nc2c1]

A mixture of 330 mg 6-bromo-1-methyl-4-[4-(5-methyl-1,3-benzoxazol-2-yl)piperidin-1-yl]-2-oxo-7-{[(3RS)-oxolan-3-yl]oxy}-1,2-dihydroquinoline-3-carboxamide (intermediate 282), 59 mg palladium(π-cinnamyl) chloride dimer (CAS 12131-44-1), 80 mg zinc cyanide (CAS 557-21-1), 63 mg 1,1'-bis(diphenylphosphanyl)ferrocene and 0.2 ml N,N-diisopropylethylamine in 5.6 ml N,N-dimethylacetamide were stirred at 80° C. for 14 h ours. After this time, water was added and it was extracted with ethyl acetate (3×). The combined organic layers were washed with water and brine and dried over sodium sulfate. After evaporation of the solvent, the residue was purified by RP-HPLC (column: X-Bridge C18 5 μm 100×30 mm, mobile phase: acetonitrile/water (0.1 vol. % formic acid)-gradient) to obtain 173 mg of the title compound.

$^1$H-NMR (400 MHz, DMSO-d6): δ [ppm]=2.02-2.26 (m, 5H), 2.29-2.39 (m, 1H), 2.42 (s, 3H), 3.12-3.26 (m, 3H), 3.34-3.40 (m, 2H), 3.61 (s, 3H), 3.81 (td, 1H), 3.86-4.02 (m, 3H), 5.46-5.52 (m, 1H), 7.04 (s, 1H), 7.18 (dd, 1H), 7.50-7.61 (m, 3H), 7.70 (s, 1H), 8.12 (s, 1H).

LC-MS (Method 1): $R_t$=1.08 min; MS (ESIpos): m/z=528 $[M+H]^+$

Example 539

6-cyano-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 1

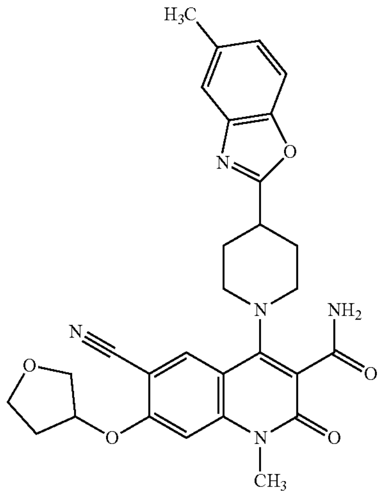 [SMILES: Cc1ccc2oc(C3CCN(c4c(C(N)=O)c(=O)n(C)c5cc(OC6CCOC6)c(C#N)cc45)CC3)nc2c1]

170 mg 6-cyano-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide (Example 538) were separated by chiral HPLC: Instrument: PrepCon Labomatic HPLC-2; Column: YMC Cellulose SC 10p, 250×50; eluent A: methyl tert-butyl ether+0.1 vol % diethylamine; eluent B: methanol; isocratic: 70% A+30% B; flow: 100 mL/min; temperature: 25° C.; UV: 254 nm.

66 mg of the title compound were obtained.

$^1$H-NMR (400 MHz, DMSO-d6): δ [ppm]=2.02-2.26 (m, 5H), 2.29-2.39 (m, 1H), 2.42 (s, 3H), 3.12-3.26 (m, 3H), 3.34-3.40 (m, 2H), 3.61 (s, 3H), 3.81 (td, 1H), 3.86-4.02 (m, 3H), 5.46-5.52 (m, 1H), 7.04 (s, 1H), 7.18 (dd, 1H), 7.50-7.61 (m, 3H), 7.70 (s, 1H), 8.12 (s, 1H).

Analytical chiral HPLC: $R_t$=4.99 min

Instrument: Thermo Fisher UltiMate 3000; Column: YMC Cellulose SC 3μ, 100×4.6; eluent A: methyl tert-butyl ether+0.1 vol % diethylamine; eluent B: methanol; isocratic: 70% A+30% B; flow: 1.4 ml/min; temperature: 25° C.; UV: 254 nm.

Example 540

6-cyano-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 2

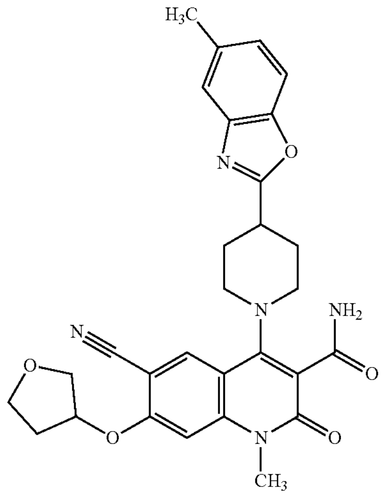 [SMILES: Cc1ccc2oc(C3CCN(c4c(C(N)=O)c(=O)n(C)c5cc(OC6CCOC6)c(C#N)cc45)CC3)nc2c1]

With the chiral separation of 170 mg 6-cyano-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide (Example 538) described in example 539, 61 mg of the title compound were obtained.

$^1$H-NMR (400 MHz, DMSO-d6): 5 [ppm]=2.02-2.26 (m, 5H), 2.29-2.39 (m, 1H), 2.42 (s, 3H), 3.12-3.26 (m, 3H), 3.34-3.40 (m, 2H), 3.61 (s, 3H), 3.81 (td, 1H), 3.86-4.02 (m, 3H), 5.46-5.52 (m, 1H), 7.04 (s, 1H), 7.18 (dd, 1H), 7.50-7.61 (m, 3H), 7.70 (s, 1H), 8.12 (s, 1H).

Analytical chiral HPLC: $R_t$=6.61 min

Instrument: Thermo Fisher UltiMate 3000; Column: YMC Cellulose SC 3μ, 100×4.6; eluent A: methyl tert-butyl ether+0.1 vol % diethylamine; eluent B: methanol; isocratic: 70% A+30% B; flow: 1.4 ml/min; temperature: 25° C.; UV: 254 nm.

Example 541

6-methoxy-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile, Enantiomer 1

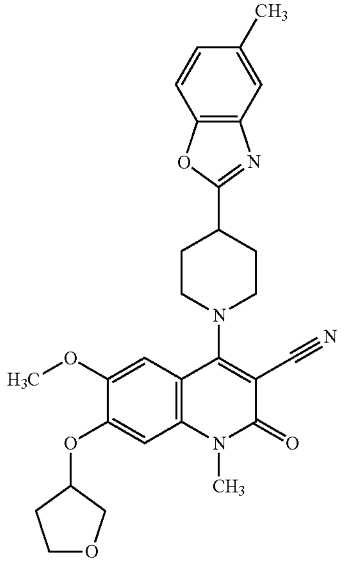 [SMILES: COc1cc2c(N3CCC(c4nc5cc(C)ccc5o4)CC3)c(C#N)c(=O)n(C)c2cc1OC1CCOC1]

A mixture of 260 mg 6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (example 424), 33.5 mg tBuBrettPhos Pd G3, 19 mg tBuBrettPhos and 179 mg caesium carbonate in 0.16 ml methanol and 2.2 ml toluene were heated in a closed vial for 2 hours at 80° C. under an Nitrogen atmosphere. The mixture was diluted with dichloromethane, filtered over celite, washed with dichloromethane and the combine organic layers were evaporated in vacuo. The residue was purified by flash chromatography (silica, dichloromethane/ethanol gradient 0-10%) to obtain 109 mg racemic 6-methoxy-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile. This material was separated into the enantiomers by chiral HPLC: Instrument: PrepCon Labomatic HPLC; Column: YMC Cellulose SC 10μ, 250×50; eluent A: methyl tert-butyl ether+0.1 vol % diethylamine; eluent B: acetonitrile; isocratic: 50% A+50% B; flow: 100 mL/min; temperature: 25° C.; UV: 254 nm 38 mg of the title compound were obtained from chiral HPLC separation.

$^1$H NMR (400 MHz, DMSO-$d_6$) δ ppm 1.98-2.18 (m, 3H) 2.27-2.39 (m, 3H) 2.42 (s, 3H) 3.37-3.47 (m, 1H) 3.51-3.63 (m, 5H) 3.74-3.90 (m, 8H) 3.91-3.99 (m, 1H) 5.35 (br dd, 1H) 6.93 (s, 1H) 7.16-7.20 (m, 2H) 7.50-7.54 (m, 1H) 7.58 (d, 1H).

Optical rotation:$[\alpha]_D$=+7.5 (c=9.8 mg/ml, chloroform)

Analytical chiral HPLC: $R_t$=3.2 min

Instrument: Waters Alliance 2695; Column: YMC Cellulose SC 3μ, 100×4.6; eluent A: methyl tert-butyl ether+0.1 vol % diethylamine; eluent B: acetonitrile; isocratic: 50% A+50% B; flow: 1.4 ml/min; temperature: 25° C.; UV: 254 nm Example 542

6-methoxy-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile, Enantiomer 2

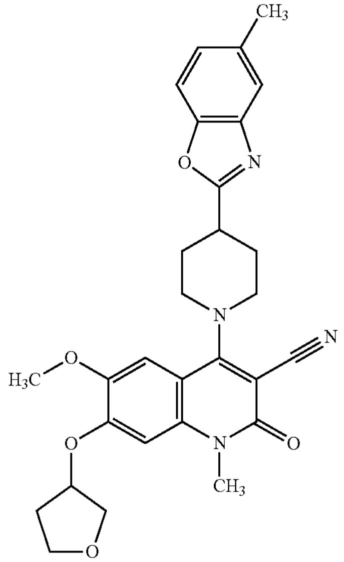 [SMILES: COc1cc2c(N3CCC(c4nc5cc(C)ccc5o4)CC3)c(C#N)c(=O)n(C)c2cc1OC1CCOC1]

The chiral separation described for example 541 delivered the second enantiomer as well. 38.4 mg of the title compound were obtained.

$^1$H NMR (400 MHz, DMSO-$d_6$) δ ppm 1.98-2.18 (m, 3H) 2.27-2.39 (m, 3H) 2.42 (s, 3H) 3.37-3.47 (m, 1H) 3.51-3.63 (m, 5H) 3.74-3.90 (m, 8H) 3.91-3.99 (m, 1H) 5.35 (br dd, 1H) 6.93 (s, 1H) 7.16-7.20 (m, 2H) 7.50-7.54 (m, 1H) 7.58 (d, 1H)

Optical rotation:$[\alpha]_D$=−7.79 (c=9.5 mg/ml, chloroform)

Analytical chiral HPLC: $R_t$=2.91 min

Instrument: Waters Alliance 2695; Column: YMC Cellulose SC 3μ, 100×4.6; eluent A: methyl tert-butyl ether+0.1 vol % diethylamine; eluent B: acetonitrile; isocratic: 50% A+50% B; flow: 1.4 ml/min; temperature: 25° C.; UV: 254 nm Example 543

6-methoxy-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 1

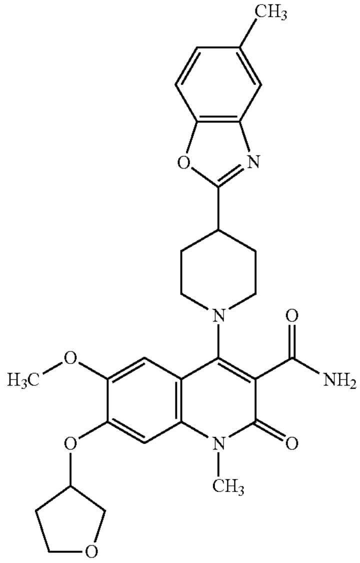 [SMILES: COc1cc2c(N3CCC(c4nc5cc(C)ccc5o4)CC3)c(C(N)=O)c(=O)n(C)c2cc1OC1CCOC1]

A mixture of 250 mg 6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (example 424), 37.9 mg tBuBrettPhos Pd G3, 21.5 mg tBuBrettPhos and 202 mg caesium carbonate in 0.18 ml methanol and 2.5 ml toluene were heated in a closed vial for 2 hours at 80° C. under an Nitrogen atmosphere. The mixture was diluted with dichloromethane, filtered over celite, washed with dichloromethane and the combine organic layers were evaporated in vacuo. The residue was purified by flash chromatography (silica, dichloromethane/ethanol gradient 0-10%) to obtain 181 mg racemic 6-methoxy-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile. This material was reacted with 230 μL acetaldoxime and 41.4 mg Palladium (II)acetate in 7.9 ml ethanol for 2.5 hours at 80° C. after this time, the same amounts of acetaldoxime and Palladium(II) acetate were added and it was stirred for further 3.5 hours at 80° C. The reaction mixture was diluted with water, extracted with ethyl acetate two times, the combined organic layers were filtered through a waterresistant filter and the filtrate was concentrated under reduced pressure. The residue was purified by RP-HPLC (column: Chromatorex 125×30 mm, 10 μm mobile phase: acetonitrile/water (0.2 vol. % ammonia 32%)-gradient) to give 149 mg of racemic 6-methoxy-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide. This material was separated into the enantiomers by chiral HPLC: Instrument: PrepCon Labomatic HPLC; Column: YMC Cellulose SC 10p, 250×50; eluent A: methyl tert-butyl ether; eluent B: methanol; isocratic: 70% A+30% B; flow: 150 mL/min; temperature: 25° C.; UV: 254 nm 61 mg of the title compound were obtained from chiral HPLC separation.

$^1$H NMR (400 MHz, DMSO-$d_6$) δ ppm 1.98-2.13 (m, 3H) 2.21-2.32 (m, 3H) 2.42 (s, 3H) 3.14-3.25 (m, 3H) 3.35-3.44

(m, 2H) 3.59 (s, 3H) 3.74-3.81 (m, 1H) 3.81-3.91 (m, 5H) 3.91-3.98 (m, 1H) 5.26-5.32 (m, 1H) 6.93 (s, 1H) 7.15-7.21 (m, 1H) 7.30 (s, 1H) 7.38-7.45 (m, 1H) 7.50-7.53 (m, 1H) 7.55-7.59 (m, 1H) 7.62 (br s, 1H)

Optical rotation:$[\alpha]_D$=−1.86 (c=10.2 mg/ml, chloroform)

Analytical chiral HPLC: $R_t$=4.87 min

Instrument: Waters Alliance 2695; Column: YMC Cellulose SC 3μ, 100×4.6; eluent A: methyl tert-butyl ether; eluent B: methanol; isocratic: 70% A+30% B; flow: 1.4 ml/min; temperature: 25° C.; UV: 254 nm Example 544

(rac)-1,6-dimethyl-4-[4-(5-methyl-1,3-benzoxazol-2-yl)piperidin-1-yl]-2-oxo-7-[(oxolan-3-yl)oxy]-1,2-dihydroquinoline-3-carboxamide

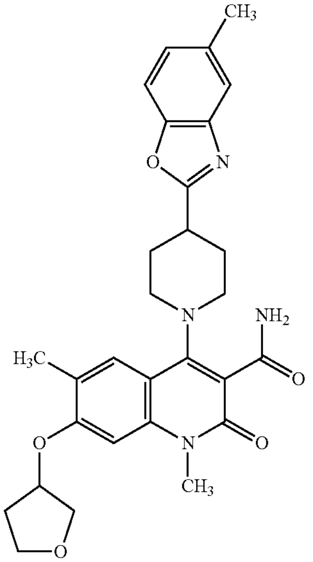 [SMILES: Cc1ccc2oc(C3CCN(c4c(C(N)=O)c(=O)n(C)c5cc(OC6CCOC6)c(C)cc45)CC3)nc2c1]

A solution of 570 mg 1,6-dimethyl-4-[4-(5-methyl-1,3-benzoxazol-2-yl)piperidin-1-yl]-2-oxo-7-[(oxolan-3-yl)oxy]-1,2-dihydroquinoline-3-carbonitrile (Example 429) was reacted with 700 μL acetaldoxime and 106 mg mg chloridotris(triphenylphosphine)rhodium(I) (CAS 14694-95-2) in 34 ml toluene for 72 hours at 110° C. The reaction mixture was diluted with water, extracted with ethyl acetate (3×), the combined organic layers were washed with brine and concentrated under reduced pressure. The residue was purified by flash chromatography (silica, dichloromethane/ethanol gradient 0-10%) to obtain 318 mg of the title compound.

$^1$H-NMR (400 MHz, DMSO-d6): δ [ppm]=1.99-2.15 (m, 3H), 2.22 (s, 5H), 2.25-2.35 (m, 1H), 2.42 (s, 3H), 3.13-3.25 (m, 3H), 3.36 (br d, 2H), 3.58 (s, 3H), 3.77-3.92 (m, 3H), 3.95-4.01 (m, 1H), 5.28-5.35 (m, 1H), 6.85 (s, 1H), 7.15-7.21 (m, 1H), 7.40 (s, 1H), 7.50-7.53 (m, 1H), 7.55-7.65 (m, 3H).

Example 545

1,6-dimethyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 1

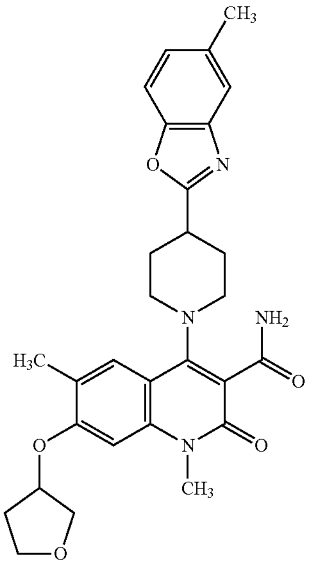 [SMILES: Cc1ccc2oc(C3CCN(c4c(C(N)=O)c(=O)n(C)c5cc(OC6CCOC6)c(C)cc45)CC3)nc2c1]

310 mg 1,6-dimethyl-4-[4-(5-methyl-1,3-benzoxazol-2-yl)piperidin-1-yl]-2-oxo-7-[(oxolan-3-yl)oxy]-1,2-dihydroquinoline-3-carboxamide (Example 544) were separated by chiral HPLC: Instrument: Sepiatec: Prep SFC100; Column: Chiralpak IA 5μ 250×30 mm; eluent A: CO2; eluent B: ethanol+0.2 vol % aqueous ammonia (32%); isocratic: 35% B; flow: 100 ml/min; temperature: 40° C.; BPR: 150 bar; UV: 254 nm. 121 mg of the title compound were obtained.

$^1$H-NMR (400 MHz, DMSO-d6): δ [ppm]=1.99-2.15 (m, 3H), 2.22 (s, 5H), 2.25-2.35 (m, 1H), 2.42 (s, 3H), 3.13-3.25 (m, 3H), 3.36 (br d, 2H), 3.58 (s, 3H), 3.77-3.92 (m, 3H), 3.95-4.01 (m, 1H), 5.28-5.35 (m, 1H), 6.85 (s, 1H), 7.15-7.21 (m, 1H), 7.40 (s, 1H), 7.50-7.53 (m, 1H), 7.55-7.65 (m, 3H).

Optical rotation:$[\alpha]_D$=−0.5° (c=9.7 mg/ml, chloroform)

Analytical chiral HPLC: $R_t$=2.81 min

Instrument: Agilent: 1260, Aurora SFC-Modul; Column: Chiralpak IA 5μ 100×4.6 mm; eluent A: CO2; eluent B: ethanol+0.2 vol % aqueous ammonia (32%); isocratic: 35% B; flow: 4 ml/min; temperature: 37.5° C.; BPR: 100 bar; UV: 254 nm Example 546

1,6-dimethyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 2

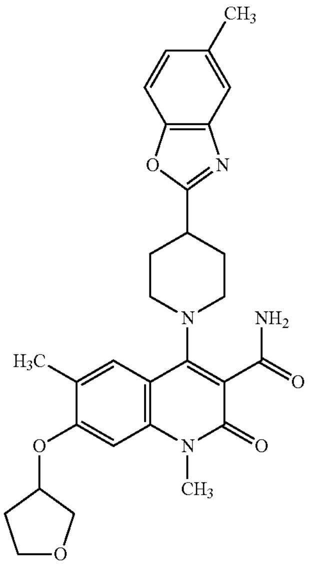 [SMILES: Cc1ccc2oc(C3CCN(c4c(C(N)=O)c(=O)n(C)c5cc(OC6CCOC6)c(C)cc45)CC3)nc2c1]

With the chiral separation of 310 mg 1,6-dimethyl-4-[4-(5-methyl-1,3-benzoxazol-2-yl)piperidin-1-yl]-2-oxo-7-[(oxolan-3-yl)oxy]-1,2-dihydroquinoline-3-carboxamide (Example 544) described in example 545, 119 mg of the title compound were obtained.

$^1$H-NMR (400 MHz, DMSO-d6): 5 [ppm]=1.99-2.15 (m, 3H), 2.22 (s, 5H), 2.25-2.35 (m, 1H), 2.42 (s, 3H), 3.13-3.25 (m, 3H), 3.36 (br d, 2H), 3.58 (s, 3H), 3.77-3.92 (m, 3H), 3.95-4.01 (m, 1H), 5.28-5.35 (m, 1H), 6.85 (s, 1H), 7.15-7.21 (m, 1H), 7.40 (s, 1H), 7.50-7.53 (m, 1H), 7.55-7.65 (m, 3H).

Optical rotation:$[\alpha]_D$=1.2° (c=9.3 mg/ml, chloroform)

Analytical chiral HPLC: $R_t$=5.05 min

Instrument: Agilent: 1260, Aurora SFC-Modul; Column: Chiralpak IA 5μ 100×4.6 mm; eluent A: CO2; eluent B: ethanol+0.2 vol % aqueous ammonia (32%); isocratic: 35% B; flow: 4 ml/min; temperature: 37.5° C.; BPR: 100 bar; UV: 254 nm Example 547

7-[(2-methoxyethyl)amino]-1,6-dimethyl-4-[4-(5-methyl-1,3-benzoxazol-2-yl)piperidin-1-yl]-2-oxo-1,2-dihydroquinoline-3-carbonitrile

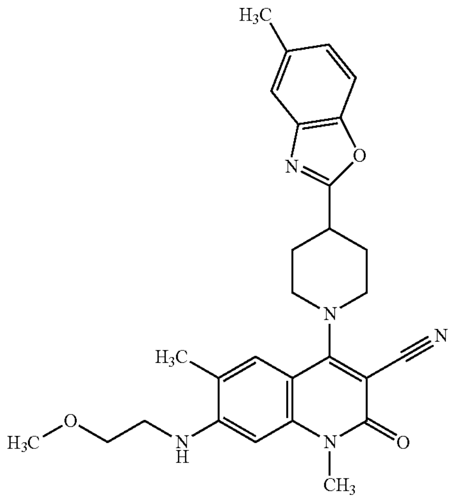 [SMILES: COCCNc1cc2c(cc1C)c(N1CCC(c3nc4cc(C)ccc4o3)CC1)c(C#N)c(=O)n2C]

A suspension of 500 mg 7-bromo-1,6-dimethyl-4-[4-(5-methyl-1,3-benzoxazol-2-yl)piperidin-1-yl]-2-oxo-1,2-dihydroquinoline-3-carbonitrile (Intermediate 263), 864 mg tripotassium phosphate and 153 mg 2-methoxyethan-1-amine in 19 ml THF was purged with Argon for 10 min, 80 mg XPhos Pd G2 (CAS 1310584-14-5) were added and this mixture stirred overnight at 100° C. The reaction mixture was diluted with dichloromethane/MeOH 9:1, filtered and washed with dichloromethane/MeOH 9:1. The filtrate was concentrated under reduced pressure. The residue was purified by flash chromatography (silica, dichloromethane/ethanol gradient 0-10%) to obtain 128 mg of the title compound.

$^1$H NMR (400 MHz, DMSO-$d_6$) δ ppm 2.04-2.15 (m, 2H) 2.16 (s, 4H) 2.25-2.32 (m, 2H) 2.42 (s, 3H) 3.28-3.32 (m, 3H) 3.35-3.43 (m, 1H) 3.44-3.56 (m, 7H) 3.56-3.61 (m, 2H) 3.71 (br d, 2H) 6.13 (s, 1H) 6.40 (s, 1H) 7.16-7.22 (m, 1H) 7.40 (s, 1H) 7.50-7.54 (m, 1H) 7.55-7.61 (m, 1H).

Example 548

7-(3-hydroxyazetidin-1-yl)-1,6-dimethyl-4-[4-(5-methyl-1,3-benzoxazol-2-yl)piperidin-1-yl]-2-oxo-1,2-dihydroquinoline-3-carbonitrile

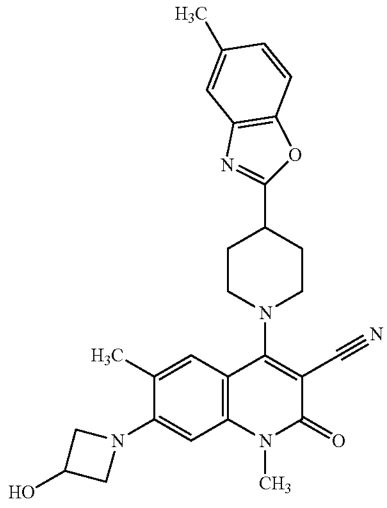 [SMILES: Cc1ccc2oc(C3CCN(c4c(C#N)c(=O)n(C)c5cc(N6CC(O)C6)c(C)cc45)CC3)nc2c1]

A suspension of 500 mg 7-bromo-1,6-dimethyl-4-[4-(5-methyl-1,3-benzoxazol-2-yl)piperidin-1-yl]-2-oxo-1,2-dihydroquinoline-3-carbonitrile (Intermediate 263), 1.51 g tripotassium phosphate and 223 mg azetidin-3-ol hydrogen chloride salt (1/1) in 20 ml THF was purged with Argon for 10 min, 80 mg XPhos Pd G2 (CAS 1310584-14-5) were added and this mixture stirred overnight at 100° C.

The reaction mixture was concentrated under reduced pressure. The residue was diluted with water and extracted 3× with dichloromethane/isopropanol 4:1. The combined organic layers were dried (waterresistant filter) and concentrated under reduced pressure. The residue was purified by flash chromatography (silica, dichloromethane/ethanol gradient 0-10%) to obtain 77 mg of the title compound.

$^1$H NMR (400 MHz, DMSO-$d_6$) δ ppm 2.04-2.17 (m, 2H) 2.22-2.32 (m, 5H) 2.42 (s, 3H) 3.36-3.43 (m, 1H) 3.48-3.59 (m, 5H) 3.69-3.78 (m, 2H) 3.83-3.90 (m, 2H) 4.35-4.43 (m, 2H) 4.52-4.61 (m, 1H) 5.72 (d, 1H) 6.10 (s, 1H) 7.16-7.21 (m, 1H) 7.38 (s, 1H) 7.50-7.54 (m, 1H) 7.56-7.60 (m, 1H)

LC-MS (Method 1): $R_t$=1.18 min; MS (ESIpos): m/z=485 $[M+H]^+$

Example 549

1,6-dimethyl-4-[4-(5-methyl-1,3-benzoxazol-2-yl)piperidin-1-yl]-7-[(oxetan-3-yl)amino]-2-oxo-1,2-dihydroquinoline-3-carbonitrile

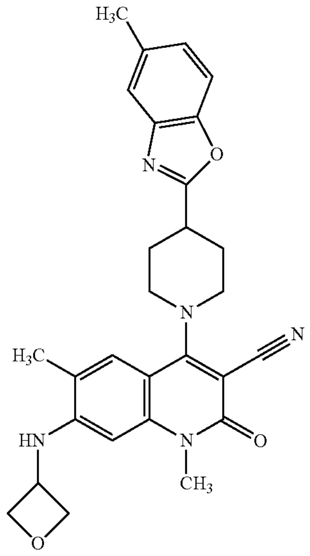 [SMILES: Cc1ccc2oc(C3CCN(c4c(C#N)c(=O)n(C)c5cc(NC6COC6)c(C)cc45)CC3)nc2c1]

A suspension of 250 mg 7-bromo-1,6-dimethyl-4-[4-(5-methyl-1,3-benzoxazol-2-yl)piperidin-1-yl]-2-oxo-1,2-dihydroquinoline-3-carbonitrile (Intermediate 263), 324 mg tripotassium phosphate and 223 mg oxetan-3-amine in 10 ml THF was purged with Argon for 10 min, 40 mg XPhos Pd G2 (CAS 1310584-14-5) were added and this mixture stirred overnight at 70° C. The reaction mixture was diluted with water and extracted 3× with ethyl acetate. The combined organic layers were dried (waterresistant filter) and concentrated under reduced pressure. The residue was purified by flash chromatography (silica, dichloromethane/ethanol gradient 0-10%). A further purification was done by RP-HPLC to obtain 62 mg of the title compound.

$^1$H-NMR (400 MHz, DMSO-d6): 5 [ppm]=2.05-2.15 (m, 2H), 2.21-2.32 (m, 5H), 2.42 (s, 3H), 3.36-3.44 (m, 1H), 3.44-3.57 (m, 5H), 3.72 (br d, 2H), 4.59-4.64 (m, 2H), 4.79-4.87 (m, 1H), 4.90-4.95 (m, 2H), 6.03 (s, 1H), 6.65 (d, 1H), 7.19 (dd, 1H), 7.44 (s, 1H), 7.52 (s, 1H), 7.58 (d, 1H).

LC-MS (Method 2): $R_t$=1.24 min; MS (ESIpos): m/z=484 $[M+H]^+$

Example 550

7-[(2-hydroxyethyl)amino]-1,6-dimethyl-4-[4-(5-methyl-1,3-benzoxazol-2-yl)piperidin-1-yl]-2-oxo-1,2-dihydroquinoline-3-carbonitrile

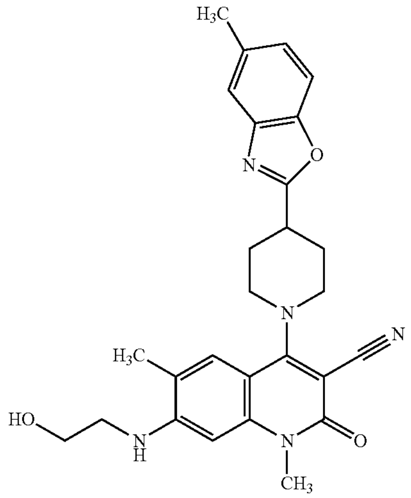 [SMILES: Cc1ccc2oc(C3CCN(c4c(C#N)c(=O)n(C)c5cc(NCCO)c(C)cc45)CC3)nc2c1]

A suspension of 250 mg 7-bromo-1,6-dimethyl-4-[4-(5-methyl-1,3-benzoxazol-2-yl)piperidin-1-yl]-2-oxo-1,2-dihydroquinoline-3-carbonitrile (Intermediate 263), 432 mg tripotassium phosphate and 62 mg 2-aminoethan-1-ol in 10 ml THF was purged with argon for 10 min, 40 mg XPhos Pd G2 (CAS 1310584-14-5) were added and this mixture stirred overnight at 70° C. The reaction mixture was diluted with water and extracted 3× with dichloromethane/Isopropanol 4:1. The combined organic layers were dried (waterresistant filter) and concentrated under reduced pressure. The residue was purified by flash chromatography (silica, dichloromethane/ethanol gradient 0-10%) to obtain 83 mg of the title compound.

$^1$H NMR (400 MHz, DMSO-$d_6$) δ ppm 2.04-2.16 (m, 2H) 2.17 (s, 3H) 2.24-2.34 (m, 2H) 2.42 (s, 3H) 3.34-3.42 (m, 3H) 3.47-3.57 (m, 5H) 3.61-3.67 (m, 2H) 3.68-3.76 (m, 2H) 4.86 (t, 1H) 6.05 (t, 1H) 6.38 (s, 1H) 7.16-7.22 (m, 1H) 7.39-7.42 (m, 1H) 7.50-7.54 (m, 1H) 7.56-7.60 (m, 1H).

LC-MS (Method 1): $R_t$=1.14 min; MS (ESIpos): m/z=473 [M+H]$^+$

Example 551

7-[(2-hydroxyethyl)(methyl)amino]-1,6-dimethyl-4-[4-(5-methyl-1,3-benzoxazol-2-yl)piperidin-1-yl]-2-oxo-1,2-dihydroquinoline-3-carbonitrile

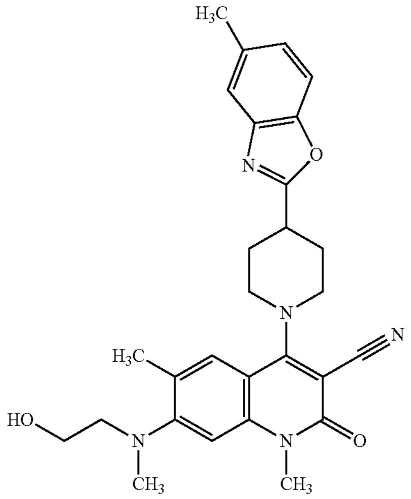 [SMILES: Cc1ccc2oc(C3CCN(c4c(C#N)c(=O)n(C)c5cc(N(C)CCO)c(C)cc45)CC3)nc2c1]

A suspension of 100 mg 7-bromo-1,6-dimethyl-4-[4-(5-methyl-1,3-benzoxazol-2-yl)piperidin-1-yl]-2-oxo-1,2-dihydroquinoline-3-carbonitrile (Intermediate 263), 130 mg tripotassium phosphate and 32 μL 2-(methylamino)ethanol in 4 ml THF was purged with Argon for 10 min, 16 mg XPhos Pd G2 (CAS 1310584-14-5) were added and this mixture stirred overnight at 70° C. The reaction mixture was diluted with water and extracted 3× with ethyl acetate. The combined organic layers were dried (waterresistant filter) and concentrated under reduced pressure. The residue was purified by RP-HPLC (column: X-Bridge C18 5 μm 100×30 mm, mobile phase: acetonitrile/water (0.2 vol. % ammonia 32%)-gradient) to obtain 2.2 mg of the title compound.

$^1$H-NMR (400 MHz, DMSO-d6): 5 [ppm]=2.04-2.18 (m, 2H), 2.25-2.36 (m, 5H), 2.42 (s, 3H), 2.92 (s, 3H), 3.19 (t, 2H), 3.36-3.46 (m, 1H), 3.50-3.66 (m, 7H), 3.79 (br d, 2H), 4.67 (t, 1H), 6.82 (s, 1H), 7.19 (dd, 1H), 7.52 (s, 2H), 7.58 (d, 1H).

LC-MS (Method 2): $R_t$=1.24 min; MS (ESIpos): m/z=486 [M+H]$^+$

Example 552

7-[(2-methoxyethyl)amino]-1,6-dimethyl-4-[4-(5-methyl-1,3-benzoxazol-2-yl)piperidin-1-yl]-2-oxo-1,2-dihydroquinoline-3-carboxamide

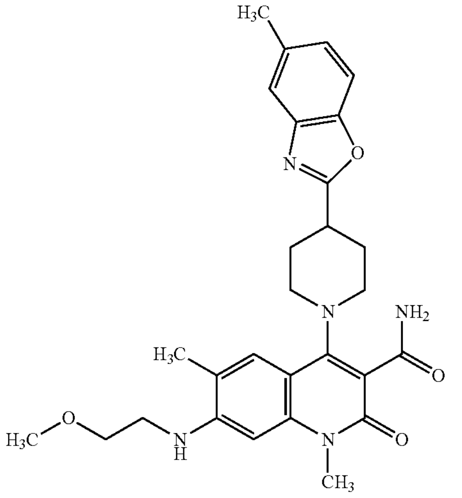 [SMILES: COCCNc1cc2c(cc1C)c(N1CCC(c3nc4cc(C)ccc4o3)CC1)c(C(N)=O)c(=O)n2C]

A solution of 175 mg 7-[(2-methoxyethyl)amino]-1,6-dimethyl-4-[4-(5-methyl-1,3-benzoxazol-2-yl)piperidin-1-yl]-2-oxo-1,2-dihydroquinoline-3-carbonitrile (Example 547) was reacted with 103 mg acetaldoxime and 16 mg chloridotris(triphenylphosphine)rhodium(I) (CAS 14694-95-2) in 4 ml toluene for 14 hours at 110° C. The reaction mixture was diluted with dichloromethane and washed with saturated aqueous ammonium chloride solution. The water phase was extracted with dichloromethane (2×) and the combined organic layers were washed with brine and concentrated under reduced pressure. The residue was purified by flash chromatography (silica, dichloromethane/ethanol gradient 0-10%) to obtain 16 mg of the title compound.

$^1$H NMR (400 MHz, DMSO-$d_6$) δ ppm 2.00-2.12 (m, 2H) 2.14-2.24 (m, 5H) 2.42 (s, 3H) 3.12-3.23 (m, 3H) 3.27-3.37 (m, 5H, partly in water signal) 3.40-3.47 (m, 2H) 3.53 (s, 3H) 3.56-3.63 (m, 2H) 5.57-5.63 (m, 1H) 6.41 (s, 1H) 7.15-7.21 (m, 1H) 7.29 (br s, 1H) 7.43-7.47 (m, 1H) 7.50-7.61 (m, 3H).

LC-MS (Method 1): $R_t$=1.16 min; MS (ESIneg): m/z=502 $[M-H]^-$

Example 553

7-(3-hydroxyazetidin-1-yl)-1,6-dimethyl-4-[4-(5-methyl-1,3-benzoxazol-2-yl)piperidin-1-yl]-2-oxo-1,2-dihydroquinoline-3-carboxamide

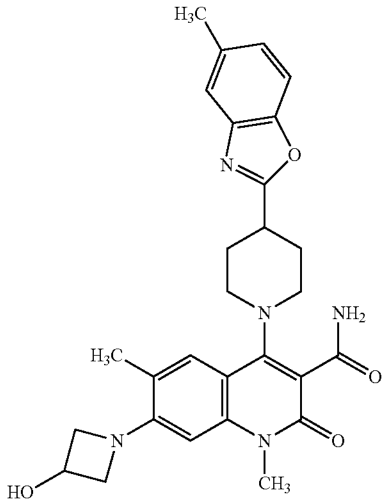 [SMILES: Cc1ccc2oc(C3CCN(c4c(C(N)=O)c(=O)n(C)c5cc(N6CC(O)C6)c(C)cc45)CC3)nc2c1]

A solution of 51 mg 7-(3-hydroxyazetidin-1-yl)-1,6-dimethyl-4-[4-(5-methyl-1,3-benzoxazol-2-yl)piperidin-1-yl]-2-oxo-1,2-dihydroquinoline-3-carbonitrile (Example 548) was reacted with 62 mg acetaldoxime and 20 mg chloridotris(triphenylphosphine)rhodium(I) (CAS 14694-95-2) in 3.8 ml toluene for 14 hours at 110° C. The reaction mixture was diluted with dichloromethane and washed with saturated aqueous ammonium chloride solution. The water phase was extracted with dichloromethane (2×) and the combined organic layers were washed with brine and concentrated under reduced pressure. The residue was purified by flash chromatography (silica, dichloromethane/ethanol gradient 0-10%) to obtain 65 mg of the title compound.

$^1$H-NMR (400 MHz, DMSO-d6): δ [ppm]=2.00-2.13 (m, 2H), 2.17-2.28 (m, 5H), 2.42 (s, 3H), 3.10-3.24 (m, 3H), 3.52 (s, 3H), 3.75 (dd, 2H), 4.30 (t, 2H), 4.51-4.63 (m, 1H), 5.65 (d, 1H), 6.20 (s, 1H), 7.18 (d, 1H), 7.34 (br s, 1H), 7.44 (s, 1H), 7.52 (s, 1H), 7.57 (d, 2H). →2 protons under the water signal LC-MS (Method 1): $R_t$=1.04 min; MS (ESIpos): m/z=503 $[M+H]^+$ Example 554

(rac)-1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile

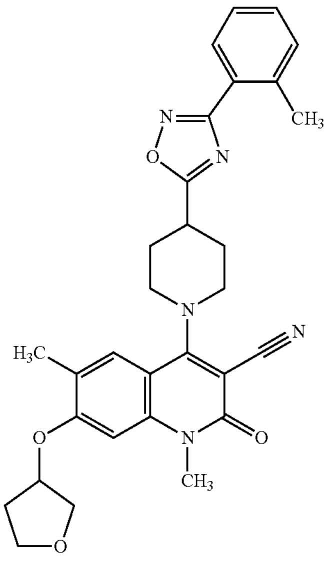 [SMILES: Cc1cc2c(N3CCC(c4nc(-c5ccccc5C)no4)CC3)c(C#N)c(=O)n(C)c2cc1OC1CCOC1]

To a suspension of 250 mg 6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile (intermediate 283) in 6.1 ml dioxan and 0.61 ml water was added 89 μL trimethylboroxine, 345 mg cesium carbonate and 31 mg [1,1'-bis(diphenylphosphino)ferrocene] dichloro-palladium(II) was purged for 5 min with nitrogen gas and heated at 90° C. for 2 h. The reaction mixture was diluted with water and extracted 3× with ethyl acetate. The combined organic layers were dried (waterresistant filter) and concentrated under reduced pressure. The residue was purified by flash chromatography (silica, dichloromethane/ethanol gradient 0-5%) to obtain 56 mg of the title compound.

$^1$H-NMR (400 MHz, DMSO-d6): δ [ppm]=1.99-2.23 (m, 6H), 2.27-2.37 (m, 3H), 2.57 (s, 3H), 3.50-3.63 (m, 6H), 3.74-3.92 (m, 5H), 3.95-4.01 (m, 1H), 5.33-5.40 (m, 1H), 6.86 (s, 1H), 7.35-7.51 (m, 3H), 7.60 (s, 1H), 7.95 (dd, 1H).

LC-MS (Method 2): $R_t$=1.40 min; MS (ESIpos): m/z=526 $[M+H]^+$

Example 555

1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile, Enantiomer 1

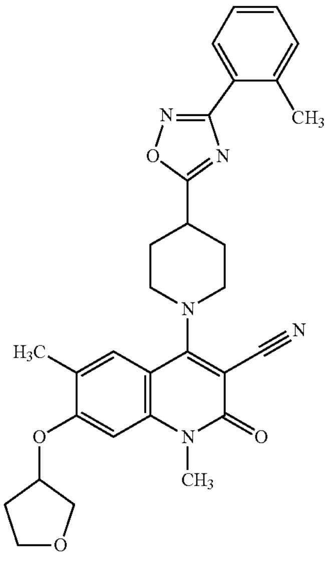 [SMILES: Cc1cc2c(N3CCC(c4nc(-c5ccccc5C)no4)CC3)c(C#N)c(=O)n(C)c2cc1OC1CCOC1]

54 mg 1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile (Example 554) were separated by chiral HPLC: Instrument: PrepCon Labomatic HPLC; Column: YMC Cellulose SB 5p, 250×30; eluent A: hexane+0.1 vol % diethylamine; eluent B: ethanol+0.1 vol % diethylamine; isocratic: 70% A+30% B; flow: 50 ml/min; temperature: 25° C.; UV: 254 nm. 13 mg of the title compound were obtained.

$^1$H-NMR (400 MHz, DMSO-d6): δ [ppm]=1.99-2.15 (m, 3H), 2.22 (s, 5H), 2.25-2.35 (m, 1H), 2.42 (s, 3H), 3.13-3.25 (m, 3H), 3.36 (br d, 2H), 3.58 (s, 3H), 3.77-3.92 (m, 3H), 3.95-4.01 (m, 1H), 5.28-5.35 (m, 1H), 6.85 (s, 1H), 7.15-7.21 (m, 1H), 7.40 (s, 1H), 7.50-7.53 (m, 1H), 7.55-7.65 (m, 3H).

Analytical chiral HPLC: $R_t$=11.62 min

Instrument: Waters Alliance 2695; Column: YMC Cellulose SB 3μ, 100×4.6; eluent A: hexane+0.1 vol % diethylamine; eluent B: ethanol; isocratic: 70% A+30% B; flow: 1.4 ml/min; temperature: 25° C.; UV: 254 nm.

Example 556

1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile, Enantiomer 2

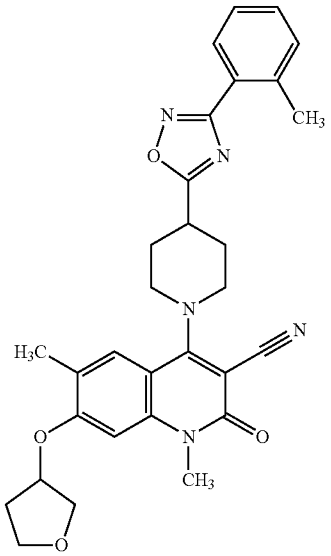 [SMILES: Cc1cc2c(N3CCC(c4nc(-c5ccccc5C)no4)CC3)c(C#N)c(=O)n(C)c2cc1OC1CCOC1]

With the chiral separation of 54 mg 1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile (Example 554) described in example 555, 9 mg of the title compound were obtained.

$^1$H-NMR (400 MHz, DMSO-d6): 5 [ppm]=1.99-2.15 (m, 3H), 2.22 (s, 5H), 2.25-2.35 (m, 1H), 2.42 (s, 3H), 3.13-3.25 (m, 3H), 3.36 (br d, 2H), 3.58 (s, 3H), 3.77-3.92 (m, 3H), 3.95-4.01 (m, 1H), 5.28-5.35 (m, 1H), 6.85 (s, 1H), 7.15-7.21 (m, 1H), 7.40 (s, 1H), 7.50-7.53 (m, 1H), 7.55-7.65 (m, 3H).

Analytical chiral HPLC: $R_t$=9.58 min

Instrument: Waters Alliance 2695; Column: YMC Cellulose SB 3μ, 100×4.6;

eluent A: hexane+0.1 vol % diethylamine; eluent B: ethanol; isocratic: 70% A+30% B; flow: 1.4 ml/min; temperature: 25° C.; UV: 254 nm.

Example 557

1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide, Enantiomer 1

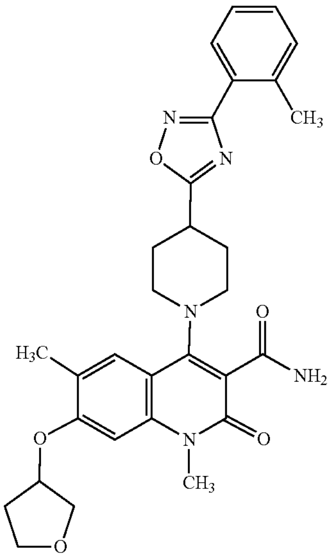 [SMILES: Cc1cc2c(N3CCC(c4nc(-c5ccccc5C)no4)CC3)c(C(N)=O)c(=O)n(C)c2cc1OC1CCOC1]

29.5 mg 1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile (example 554), 3.2 mg palladium(II)acetate and 10 μL acetaldoxime were stirred in 0.5 mL ethanol for 16 h at 90° C. The reaction mixture was diluted with water, extracted with dichloromethane (3×), the combined organic layers were dried with sodium sulfate and concentrated under reduced pressure. The residue was purified by flash chromatography (silica, hexanes/ethyl acetate gradient 0-20%) to obtain 11 mg racemic 1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide. This material was separated into the enantiomers by chiral HPLC: Instrument: PrepCon Labomatic HPLC; Column: YMC Amylose SA 5p, 250×30; eluent A: hexane; eluent B: ethanol; isocratic: 50% A+50% B; flow: 30 ml/min; temperature: 25° C.; UV: 220 nm.

4.8 mg of the title compound were obtained.

$^1$H NMR (400 MHz, DMSO-$d_6$) δ ppm 1.99-2.16 (m, 3H) 2.19-2.31 (m, 6H) 2.57 (s, 3H) 3.14-3.24 (m, 2H) 3.34-3.41 (m, 2H) 3.59 (s, 3H) 3.77-3.92 (m, 3H) 3.95-4.02 (m, 1H) 5.28-5.34 (m, 1H) 6.86 (s, 1H) 7.36-7.44 (m, 3H) 7.45-7.51 (m, 1H) 7.63 (s, 2H) 7.92-7.98 (m, 1H).

Analytical chiral HPLC: $R_t$=2.86 min

Instrument: Waters Alliance 2695; Column: YMC Amylose SA 3μ, 100×4.6; eluent A: hexane+0.1 vol % diethylamine; eluent B: ethanol; isocratic: 50% A+50% B; flow: 1.4 ml/min; temperature: 25° C.; UV: 220 nm.

Example 558

1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide, Enantiomer 2

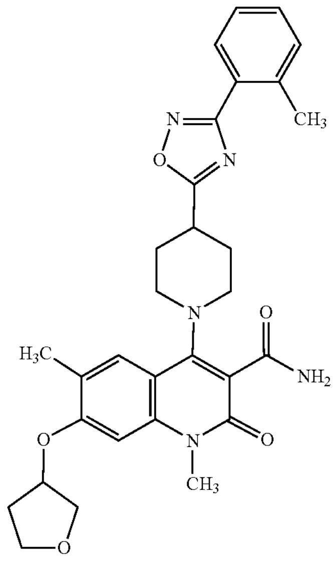 [SMILES: Cc1cc2c(N3CCC(c4nc(-c5ccccc5C)no4)CC3)c(C(N)=O)c(=O)n(C)c2cc1OC1CCOC1]

With the chiral separation of 11 mg racemic 1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide (synthesis in example 557) described in example 557, 6 mg of the title compound were obtained.

$^1$H NMR (400 MHz, DMSO-$d_6$) δ ppm 1.99-2.16 (m, 3H) 2.19-2.31 (m, 6H) 2.57 (s, 3H) 3.14-3.24 (m, 2H) 3.34-3.41 (m, 2H) 3.59 (s, 3H) 3.77-3.92 (m, 3H) 3.95-4.02 (m, 1H) 5.28-5.34 (m, 1H) 6.86 (s, 1H) 7.36-7.44 (m, 3H) 7.45-7.51 (m, 1H) 7.63 (s, 2H) 7.92-7.98 (m, 1H).

Analytical chiral HPLC: $R_t$=5.56 min

Instrument: Waters Alliance 2695; Column: YMC Amylose SA 3μ, 100×4.6; eluent A: hexane+0.1 vol % diethylamine; eluent B: ethanol; isocratic: 50% A+50% B; flow: 1.4 ml/min; temperature: 25° C.; UV: 220 nm.

Example 559

7-[(2-hydroxyethyl)amino]-1,6-dimethyl-4-{4-[3-(2-methylphenyl)-1,2,4-oxadiazol-5-yl]piperidin-1-yl}-2-oxo-1,2-dihydroquinoline-3-carbonitrile

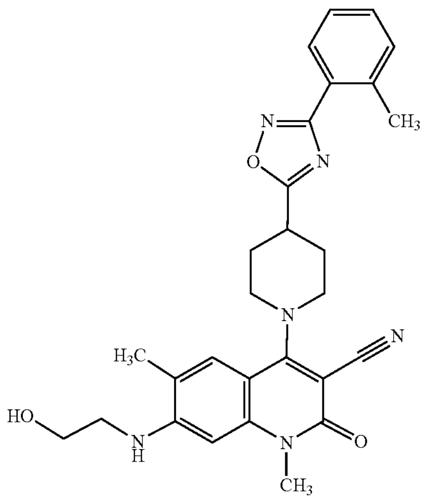 [SMILES: Cc1cc2c(N3CCC(c4nc(-c5ccccc5C)no4)CC3)c(C#N)c(=O)n(C)c2cc1NCCO]

A suspension of 100 mg 7-bromo-1,6-dimethyl-4-{4-[3-(2-methylphenyl)-1,2,4-oxadiazol-5-yl]piperidin-1-yl}-2-oxo-1,2-dihydroquinoline-3-carbonitrile (Intermediate 284), 287 mg tripotassium phosphate and 35 mg 2-aminoethan-1-ol in 4 ml THF was purged with Argon for 10 min, 15 mg XPhos Pd G2 (CAS 1310584-14-5) were added and this mixture stirred overnight at 70° C. The reaction mixture was diluted with water and extracted 3× with ethyl acetate. The combined organic layers were washed with brine, dried (waterresistant filter) and concentrated under reduced pressure. The residue was purified by flash chromatography (silica, dichloromethane/ethanol gradient 0-5%) to obtain 19 mg of the title compound.

$^1$H-NMR (400 MHz, DMSO-d6): δ [ppm]=7.89-8.00 (m, 1H), 7.33-7.53 (m, 4H), 6.34-6.41 (m, 1H), 6.01-6.10 (m, 1H), 4.86 (t, 1H), 3.67-3.77 (m, 2H), 3.62-3.67 (m, 2H), 3.47-3.57 (m, 6H), 3.34-3.39 (m, 2H), 2.58 (s, 3H), 2.26-2.34 (m, 2H), 2.18 (s, 3H), 2.07-2.16 (m, 2H).

LC-MS (Method 2): $R_t$=1.25 min; MS (ESIpos): m/z=499 $[M+H]^+$

Example 560

7-bromo-1,6-dimethyl-4-{4-[1-(2-methylphenyl)-1H-pyrazol-3-yl]piperidin-1-yl}-2-oxo-1,2-dihydroquinoline-3-carbonitrile

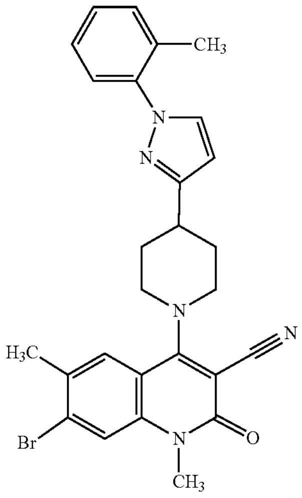 [SMILES: Cc1cc2c(N3CCC(c4ccn(-c5ccccc5C)n4)CC3)c(C#N)c(=O)n(C)c2cc1Br]

A suspension of 500 mg 7-bromo-4-chloro-1,6-dimethyl-2-oxo-1,2-dihydroquinoline-3-carbonitrile (1.60 mmol, Intermediate 262), 855 mg of the salt of 4-[1-(2-methylphenyl)-1H-pyrazol-3-yl]piperidine with trifluoroacetic acid (2.41 mmol, intermediate 280) and 1.4 mL N,N-diisopropylethylamine (8 mmol) in ethanol was stirred overnight at 100° C. After cooling to rt, the mixture was concentrated under reduced pressure. The residue was purified by flash chromatography (silica, dichloromethane/ethanol gradient 0-5%). The impure product was purified by flash chromatography (silica, hexane/ethyl acetate gradient 10-64%) to give 525 mg of the title compound (90% purity, 57% yield).

$^1$H-NMR (400 MHz, DMSO-$d_6$): δ [ppm]=1.91-2.05 (m, 2H), 2.12-2.21 (m, 2H), 2.22-2.30 (m, 3H), 2.42-2.46 (m, 3H), 3.00-3.12 (m, 1H), 3.49-3.62 (m, 5H), 3.78-3.89 (m, 2H), 6.43-6.49 (m, 1H), 7.28-7.41 (m, 4H), 7.74-7.76 (m, 1H), 7.78-7.81 (m, 1H), 7.96 (d, 1H).

LC-MS (Method 2): $R_t$=1.53 min; MS (ESIpos): m/z=518 $[M+H]^+$

Example 561

7-[(2-hydroxyethyl)amino]-1,6-dimethyl-4-{4-[1-(2-methylphenyl)-1H-pyrazol-3-yl]piperidin-1-yl}-2-oxo-1,2-dihydroquinoline-3-carbonitrile

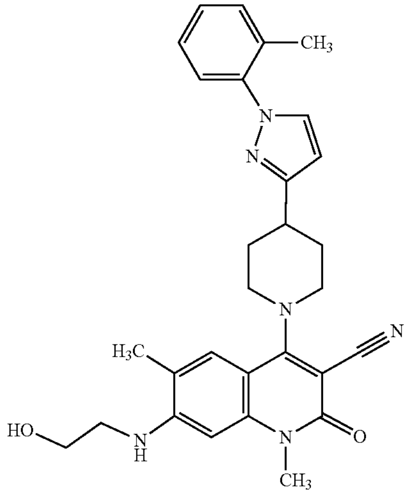 [SMILES: Cc1cc2c(N3CCC(c4ccn(-c5ccccc5C)n4)CC3)c(C#N)c(=O)n(C)c2cc1NCCO]

A suspension of 100 mg 7-bromo-1,6-dimethyl-4-{4-[1-(2-methylphenyl)-1H-pyrazol-3-yl]piperidin-1-yl}-2-oxo-1,2-dihydroquinoline-3-carbonitrile (194 μmol, example 583), 123 mg tripotassium phosphate (581 μmol) and 23.7 mg 2-aminoethan-1-ol (387 μmol; CAS 141-43-5) in 1 mL THF was purged with argon for 10 min, 30.5 mg chloro(2-dicyclohexylphosphino-2',4',6'-triisopropyl-1,1'-biphenyl)[2-(2'-amino-1,1'-biphenyl)]palladium(II) (38.7 μmol, CAS 1310584-14-5) were added and the mixture was stirred overnight at 70° C. The reaction mixture was diluted with water and extracted with dichloromethane (3×). The combined organic layers were dried (using a waterresistant filter) and concentrated under reduced pressure. The residue was purified preparative TLC (dichloromethane/methanol 9:1) to give 14 mg of the title compound (99% purity, 14% yield).

$^1$H-NMR (400 MHz, DMSO-$d_6$): δ [ppm]=1.87-2.01 (m, 2H), 2.10-2.20 (m, 5H), 2.24 (s, 3H), 2.94-3.06 (m, 1H), 3.34-3.39 (m, 2H), 3.43-3.53 (m, 5H), 3.64 (q, 2H), 3.71 (br d, 2H), 4.86 (t, 1H), 6.00-6.07 (m, 1H), 6.41 (br d, 1H), 6.45 (d, 1H), 7.31-7.40 (m, 4H), 7.42 (s, 1H), 7.92-7.97 (m, 1H).

LC-MS (Method 1): $R_t$=1.18 min; MS (ESIpos): m/z=497 $[M+H]^+$

Example 562

7-[(2-hydroxyethyl)amino]-1,6-dimethyl-4-{4-[1-(2-methylphenyl)-1H-pyrazol-3-yl]piperidin-1-yl}-2-oxo-1,2-dihydroquinoline-3-carboxamide

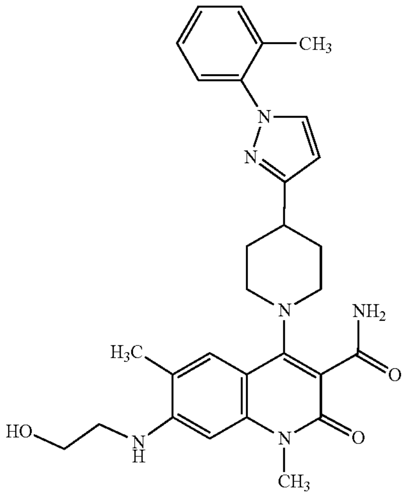 [SMILES: Cc1cc2c(N3CCC(c4ccn(-c5ccccc5C)n4)CC3)c(C(N)=O)c(=O)n(C)c2cc1NCCO]

To a suspension of 70 mg 7-[(2-hydroxyethyl)amino]-1,6-dimethyl-4-{4-[1-(2-methylphenyl)-1H-pyrazol-3-yl]piperidin-1-yl}-2-oxo-1,2-dihydroquinoline-3-carbonitrile (141 μmol, example 584) in 4.6 mL toluene were added 83.3 mg N-[(1E)-ethylidene]hydroxylamine (1.41 mmol, CAS 107-29-9) and 26.2 mg tris(triphenylphosphine)rhodium(I) chloride (28.2 μmol, CAS 14694-95-2). The mixture was stirred for 3 d at 110° C. The react ion mixture was concentrated under reduced pressure. The residue was diluted with water and extracted with dichloromethane (3×). The combined organic layers were washed with brine, dried (using a waterresistant filter) and concentrated under reduced pressure. The crude product was purified by flash chromatography (silica, dichloromethane/ethanol gradient 0-20%) to give 10 mg of the title compound (95% purity, 13% yield).

$^1$H-NMR (400 MHz, DMSO-$d_6$): 5 [ppm]=1.84-1.97 (m, 2H), 1.99-2.08 (m, 2H), 2.14-2.20 (m, 3H), 2.25 (s, 3H), 2.75-2.86 (m, 1H), 3.09-3.21 (m, 2H), 3.27-3.37 (m, 4H under water signal), 3.50-3.55 (m, 3H), 3.66 (q, 2H), 4.85 (t, 1H), 5.51 (t, 1H), 6.38 (s, 1H), 6.45 (d, 1H), 7.25-7.30 (m, 1H), 7.30-7.40 (m, 4H), 7.45-7.49 (m, 1H), 7.50-7.57 (m, 1H), 7.92-7.96 (m, 1H).

LC-MS (Method 1): $R_t$=1.02 min; MS (ESIpos): m/z=516 $[M+H]^+$

Example 563

6-bromo-7-fluoro-1-methyl-4-[4-(5-methyl-1,3-benzoxazol-2-yl)piperidin-1-yl]-2-oxo-1,2-dihydroquinoline-3-carboxamide

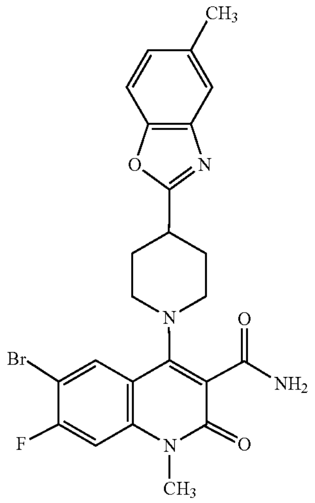 [SMILES: Cc1ccc2oc(C3CCN(c4c(C(N)=O)c(=O)n(C)c5cc(F)c(Br)cc45)CC3)nc2c1]

To a suspension of 2.8 g 6-bromo-7-fluoro-1-methyl-4-[4-(5-methyl-1,3-benzoxazol-2-yl)piperidin-1-yl]-2-oxo-1,2-dihydroquinoline-3-carbonitrile (5.56 mmol, intermediate 288) in 70 mL toluene were added 3.34 g N-[(1E)-ethylidene]hydroxylamine (56.5 mmol, CAS 107-29-9) and 150 mg tris(triphenylphosphine)rhodium(I) chloride (565 μmol, CAS 14694-95-2). The mixture was stirred for 20 hours at 110° C. The reaction mixture was concentrated under reduced pressure. The residue was diluted with water and extracted with dichloromethane (3×). The combined organic layers were washed with brine, dried (using a waterresistant filter) and concentrated under reduced pressure. The crude product was purified by flash chromatography (silica, dichloromethane/ethanol gradient 0-5%) to give 1.3 g of the title compound.

$^1$H NMR (400 MHz, DMSO-d6) δ ppm 1.99-2.12 (m, 2H) 2.19-2.27 (m, 2H) 2.42 (s, 3H) 3.18 (s, 3H) 3.55 (s, 3H) 7.17-7.21 (m, 1H) 7.51-7.53 (m, 1H) 7.53-7.60 (m, 2H) 7.61-7.65 (m, 1H) 7.71-7.76 (m, 1H) 8.02-8.08 (m, 1H).

LC-MS (Method 2): $R_t$=1.27 min; MS (ESIpos): m/z=513 $[M+H]^+$

Example 564

6-cyano-7-fluoro-1-methyl-4-[4-(5-methyl-1,3-benzoxazol-2-yl)piperidin-1-yl]-2-oxo-1,2-dihydroquinoline-3-carboxamide

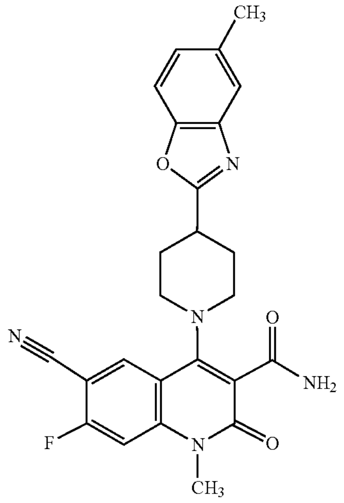 [SMILES: Cc1ccc2oc(C3CCN(c4c(C(N)=O)c(=O)n(C)c5cc(F)c(C#N)cc45)CC3)nc2c1]

A mixture of 1.3 g 6-bromo-7-fluoro-1-methyl-4-[4-(5-methyl-1,3-benzoxazol-2-yl)piperidin-1-yl]-2-oxo-1,2-dihydroquinoline-3-carboxamide (example 563), 65.6 mg palladium(π-cinnamyl) chloride dimer (CAS 12131-44-1), 357 mg zinc cyanide (CAS 557-21-1), 70.2 mg 1,1'-bis(diphenylphosphanyl)ferrocene and 5.3 ml N,N-diisopropylethylamine in 40 ml N,N-dimethylacetamide were stirred at 100° C. for 14 hours. After this time, sodium bicarbonate solution was added and it was extracted with dichloromethane (2×). The combined organic layers were washed with water and brine and dried over sodium sulfate. After evaporation of the solvent, the residue was purified by flash chromatography (silica, dichloromethane/methanol gradient 0-5%) to obtain 900 mg of the title compound.

$^1$H NMR (400 MHz, DMSO-d6) δ ppm 2.11-2.26 (m, 4H) 2.42 (s, 3H) 3.13-3.22 (m, 3H) 3.35-3.41 (m, 2H) 3.57 (s, 3H) 7.16-7.22 (m, 1H) 7.49-7.53 (m, 1H) 7.55-7.63 (m, 2H) 7.68-7.74 (m, 1H) 7.75-7.79 (m, 1H) 8.29 (d, 1H).

LC-MS (Method 1): $R_t$=1.14 min; MS (ESIpos): m/z=460 $[M+H]^+$

Example 565

(rac)-6-cyano-1-methyl-4-[4-(5-methyl-1,3-benzoxazol-2-yl)piperidin-1-yl]-2-oxo-7-{[(oxolan-3-yl)methyl]amino}-1,2-dihydroquinoline-3-carboxamide

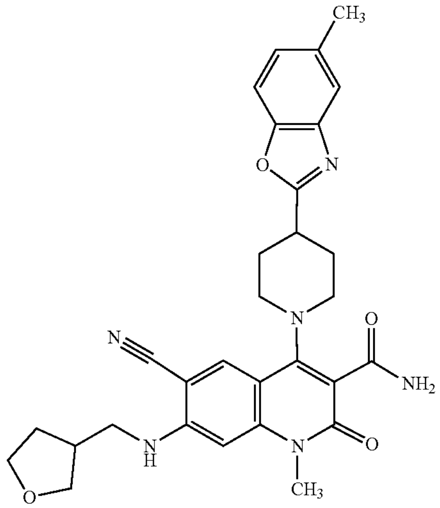 [SMILES: Cc1ccc2oc(C3CCN(c4c(C(N)=O)c(=O)n(C)c5cc(NCC6CCOC6)c(C#N)cc45)CC3)nc2c1]

A mixture of 400 mg 6-cyano-7-fluoro-1-methyl-4-[4-(5-methyl-1,3-benzoxazol-2-yl)piperidin-1-yl]-2-oxo-1,2-dihydroquinoline-3-carboxamide (example 564) and 106 mg 1-[(3RS)-oxolan-3-yl]methanamine in 8 ml DMA was heated for 20 hours at 140° C. in a closed reaction vial. After that, the solvent was removed at reduced pressure and the residue was purified by flash chromatography (silica, dichloromethane/methanol gradient 0-10%) to obtain 95 mg of the title compound.

$^1$H NMR (400 MHz, DMSO-d6) δ ppm 1.60-1.71 (m, 1H) 1.93-1.93 (m, 1H) 1.94-2.03 (m, 1H) 2.04-2.14 (m, 2H) 2.17-2.24 (m, 2H) 2.42 (s, 3H) 2.63-2.72 (m, 1H) 3.11-3.22 (m, 3H) 3.54 (s, 5H) 3.61-3.68 (m, 1H) 3.69-3.76 (m, 1H) 3.76-3.84 (m, 1H) 6.71-6.78 (m, 1H) 7.18 (dd, 1H) 7.40-7.46 (m, 1H) 7.50-7.54 (m, 1H) 7.58 (d, 1H) 7.61-7.66 (m, 1H) 7.90 (s, 1H).

LC-MS (Method 2): $R_t$=1.11 min; MS (ESIpos): m/z=541 $[M+H]^+$

Example 566

6-chloro-7-methoxy-1-methyl-4-[4-(5-methyl-1,3-benzoxazol-2-yl)piperidin-1-yl]-2-oxo-1,2-dihydro-quinoline-3-carbonitrile

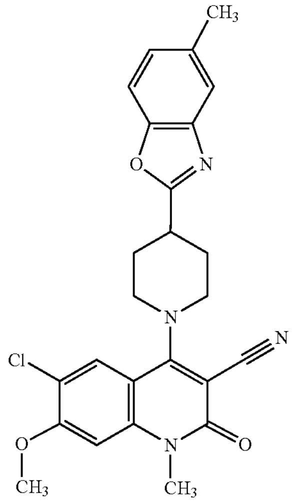 [SMILES: COc1cc2c(cc1Cl)c(N1CCC(c3nc4cc(C)ccc4o3)CC1)c(C#N)c(=O)n2C]

A solution of 150 mg 6-chloro-4-hydroxy-7-methoxy-1-methyl-2-oxo-1,2-dihydroquinoline-3-carbonitrile (intermediate 292), 135 mg 2-(4-methylpiperidin-4-yl)-1,3-benzoxazole (intermediate 1, 1.0 mmol) and 0.24 mL triethylamine (1 mmol) in 8 mL 2-propanol was stirred for 6 h at 90° C. After this time, water and ethyl acetate were was added and the reaction stirred vigorously. The resulting precipitate was collected by filtration to obtain 185 mg of the title compound.

$^1$H NMR (400 MHz, DMSO-d6) δ ppm 2.09 (br d, 2H) 2.26-2.35 (m, 2H) 2.42 (s, 3H) 3.38-3.46 (m, 1H) 3.56-3.64 (m, 5H) 3.79 (br d, 2H) 4.06 (s, 3H) 7.06 (s, 1H) 7.19 (dd, 1H) 7.51-7.60 (m, 2H) 7.80 (s, 1H).

LC-MS (Method 2): $R_t$=1.37 min; MS (ESIpos): m/z=463 $[M+H]^+$

Example 567

6-chloro-7-hydroxy-1-methyl-4-[4-(5-methyl-1,3-benzoxazol-2-yl)piperidin-1-yl]-2-oxo-1,2-dihydro-quinoline-3-carbonitrile

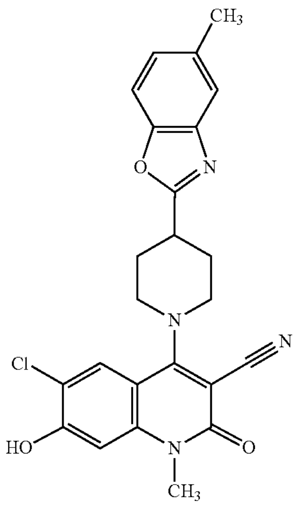 [SMILES: Cc1ccc2oc(C3CCN(c4c(C#N)c(=O)n(C)c5cc(O)c(Cl)cc45)CC3)nc2c1]

A solution of 180 mg 6-chloro-7-methoxy-1-methyl-4-[4-(5-methyl-1,3-benzoxazol-2-yl)piperidin-1-yl]-2-oxo-1,2-dihydroquinoline-3-carbonitrile (Example 566) in 5 ml dichloromethane at −70° C. was added 3.9 ml boron tribromide solution (1M in dichloromethane). The temperature was raised to RT over 1 hour and stirred for further 14 hours at RT. The reaction was poured into ice water and stirred vigorously. The precipitate was collected by filtration and dried at 40° C. to obtain 200 mg of the title compound.

$^1$H NMR (500 MHz, DMSO-d6) δ ppm 2.09 (br s, 2H) 2.29 (br s, 2H) 2.42 (s, 3H) 3.35-3.46 (m, 1H) 3.48 (s, 3H) 3.57 (s, 2H) 3.77 (br s, 2H) 6.98 (s, 1H) 7.19 (dd, 1H) 7.52 (s, 1H) 7.58 (d, 1H) 7.76 (s, 1H).

Example 568

(rac)-6-chloro-1-methyl-4-[4-(5-methyl-1,3-benzo-xazol-2-yl)piperidin-1-yl]-2-oxo-7-[(oxolan-3-yl)oxy]-1,2-dihydroquinoline-3-carbonitrile

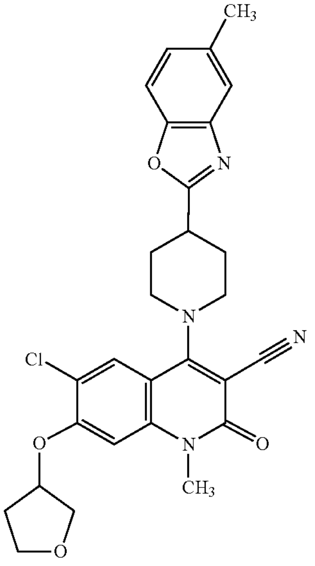 [SMILES: Cc1ccc2oc(C3CCN(c4c(C#N)c(=O)n(C)c5cc(OC6CCOC6)c(Cl)cc45)CC3)nc2c1]

A mixture of 185 mg 6-chloro-7-hydroxy-1-methyl-4-[4-(5-methyl-1,3-benzoxazol-2-yl)piperidin-1-yl]-2-oxo-1,2-dihydroquinoline-3-carbonitrile (example 567), 537 mg cesium carbonate and 77 μL 3-bromooxolane in 5 mL DMF was stirred for 14 hours at 100° C. under argon. Water was added and the mixture was extracted with ethyl acetate (2×). The combined organic layers were washed with brine, the solvent was evaporated under reduced pressure and the crude product was purified by flash chromatography (silica, dichloromethane/methanol gradient 0-3%) to give 70 mg of the title compound.

$^1$H NMR (400 MHz, DMSO-d6) δ ppm 2.01-2.16 (m, 3H) 2.33 (dt, 4H) 2.42 (s, 3H) 3.42 (br s, 1H) 3.60 (s, 5H) 3.75-3.84 (m, 3H) 3.89 (br d, 2H) 3.96 (d, 1H) 5.47 (br d, 1H) 7.03 (s, 1H) 7.19 (dd, 1H) 7.53 (s, 1H) 7.58 (d, 1H) 7.81 (s, 1H).

Example 569

(rac)-6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide

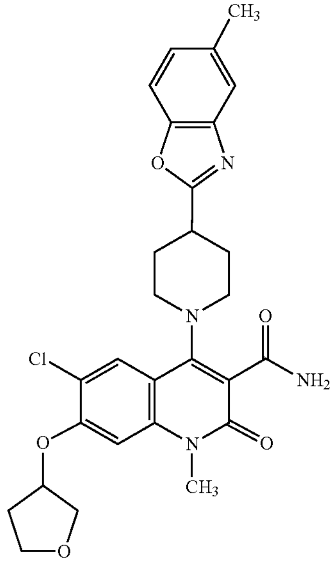 [SMILES: Cc1ccc2oc(C3CCN(c4c(C(N)=O)c(=O)n(C)c5cc(OC6CCOC6)c(Cl)cc45)CC3)nc2c1]

To a suspension of 65 mg (rac)-6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile (example 568) in 5 mL toluene were added 74 mg N-[(1E)-ethylidene]hydroxylamine (CAS 107-29-9) and 11.6 mg tris(triphenylphosphine)rhodium(I) chloride (CAS 14694-95-2). The mixture was stirred for 24 hours at 110° C. The reaction mixture was concentrated under reduced pressure. The residue was diluted with water and extracted with dichloromethane (3×). The combined organic layers were washed with brine, dried (using a waterresistant filter) and concentrated under reduced pressure. The crude product was purified by flash chromatography (silica, dichloromethane/ethanol gradient 0-10%) to give 60 mg of the title compound.

$^{1}$H NMR (400 MHz, DMSO-d6) δ ppm 1.99-2.11 (m, 3H) 2.18-2.28 (m, 2H) 2.33 (s, 1H) 2.42 (s, 3H) 3.19 (br d, 3H) 3.60 (s, 3H) 3.77-3.86 (m, 1H) 3.89 (d, 2H) 3.93-4.01 (m, 1H) 5.42 (br s, 1H) 7.04 (s, 1H) 7.18 (dd, 1H) 7.46-7.60 (m, 3H) 7.67 (s, 1H) 7.82 (s, 1H).

LC-MS (Method 2): $R_t$=1.21 min; MS (ESIpos): m/z=537 $[M+H]^+$

Example 570

6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 1

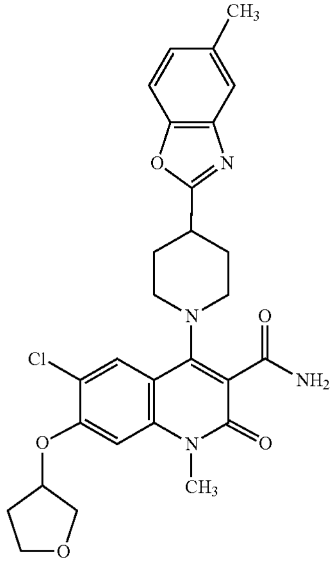 [SMILES: Cc1ccc2oc(C3CCN(c4c(C(N)=O)c(=O)n(C)c5cc(OC6CCOC6)c(Cl)cc45)CC3)nc2c1]

55 mg (rac)-6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide (Example 569) were separated by chiral HPLC: Instrument: Sepiatec: Prep SFC100; Column: Chiralpak IG 5μ 250×30 mm; eluent A: CO2; eluent B: ethanol+0.2 vol % aqueous ammonia (32%); isocratic: 45% B; flow: 100 ml/min; temperature: 40° C.; BPR: 150 bar; UV: 230 nm 21 mg of the title compound were obtained.

$^{1}$H NMR (400 MHz, DMSO-d6) δ ppm 1.99-2.11 (m, 3H) 2.18-2.28 (m, 2H) 2.33 (s, 1H) 2.42 (s, 3H) 3.19 (br d, 3H) 3.60 (s, 3H) 3.77-3.86 (m, 1H) 3.89 (d, 2H) 3.93-4.01 (m, 1H) 5.42 (br s, 1H) 7.04 (s, 1H) 7.18 (dd, 1H) 7.46-7.60 (m, 3H) 7.67 (s, 1H) 7.82 (s, 1H).

Optical rotation: $[\alpha]_D$=4.93° (c=6.4 mg/ml, chloroform)

Analytical chiral HPLC: $R_t$=3.06 min

Instrument: Agilent: 1260, Aurora SFC-Modul; Column: Chiralpak IG 5μ 100×4.6 mm; eluent A: CO2; eluent B: ethanol+0.2 vol % aqueous ammonia (32%); isocratic: 45% B; flow: 4 ml/min; temperature: 37.5° C.; BPR: 100 bar; UV: 230 nm Example 571

6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide, Enantiomer 2

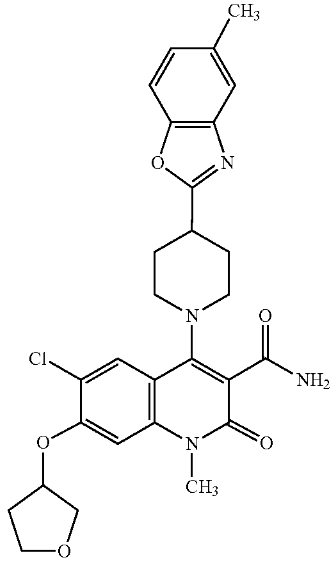 [SMILES: Cc1ccc2oc(C3CCN(c4c(C(N)=O)c(=O)n(C)c5cc(OC6CCOC6)c(Cl)cc45)CC3)nc2c1]

55 mg (rac)-6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide (Example 569) were separated by chiral HPLC: Instrument: Sepiatec: Prep SFC100; Column: Chiralpak IG 5μ 250×30 mm; eluent A: CO2; eluent B: ethanol+0.2 vol % aqueous ammonia (32%); isocratic: 45% B; flow: 100 ml/min; temperature: 40° C.; BPR: 150 bar; UV: 230 nm 15 mg of the title compound were obtained.

$^1$H NMR (400 MHz, DMSO-d6) δ ppm 1.99-2.11 (m, 3H) 2.18-2.28 (m, 2H) 2.33 (s, 1H) 2.42 (s, 3H) 3.19 (br d, 3H) 3.60 (s, 3H) 3.77-3.86 (m, 1H) 3.89 (d, 2H) 3.93-4.01 (m, 1H) 5.42 (br s, 1H) 7.04 (s, 1H) 7.18 (dd, 1H) 7.46-7.60 (m, 3H) 7.67 (s, 1H) 7.82 (s, 1H).

Optical rotation:$[\alpha]_D$=−6.69° (c=5.4 mg/ml, chloroform)

Analytical chiral HPLC: $R_t$=4.07 min

Instrument: Agilent: 1260, Aurora SFC-Modul; Column: Chiralpak IG 5μ 100×4.6 mm; eluent A: CO2; eluent B: ethanol+0.2 vol % aqueous ammonia (32%); isocratic: 45% B; flow: 4 ml/min; temperature: 37.5° C.; BPR: 100 bar; UV: 230 nm.

Example 572

(rac)-6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carbonitrile

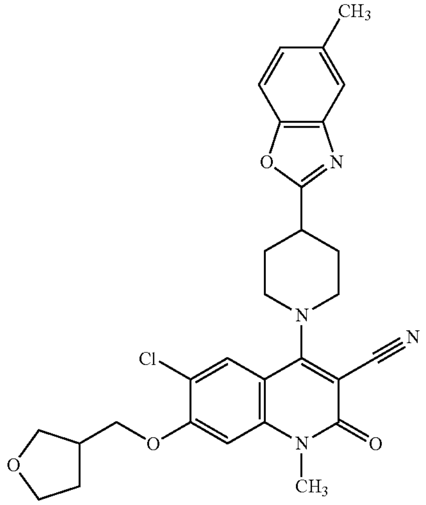 [SMILES: Cc1ccc2oc(C3CCN(c4c(C#N)c(=O)n(C)c5cc(OCC6CCOC6)c(Cl)cc45)CC3)nc2c1]

A mixture of 231 mg 6-chloro-7-hydroxy-1-methyl-4-[4-(5-methyl-1,3-benzoxazol-2-yl)piperidin-1-yl]-2-oxo-1,2-dihydroquinoline-3-carbonitrile (example 567), 504 mg cesium carbonate and 170 mg 3-(bromomethyl)oxolane in 8.1 mL DMF was stirred for 6.5 hours at 100° C. under argon. Water was added and the mixture was extracted with ethyl acetate (2×). The combined organic layers were washed with brine, the solvent was evaporated under reduced pressure and the crude product was purified by flash chromatography (silica, dichloromethane/methanol gradient 0-2%) to give 180 mg of the title compound.

$^1$H NMR (400 MHz, DMSO-d6) δ ppm 1.63-1.80 (m, 1H) 2.02-2.15 (m, 3H) 2.26-2.31 (m, 1H) 2.39-2.44 (m, 3H) 2.70-2.82 (m, 1H) 3.38-3.48 (m, 1H) 3.56-3.63 (m, 6H) 3.66-3.74 (m, 1H) 3.75-3.86 (m, 4H) 4.15-4.32 (m, 2H) 7.05-7.11 (m, 1H) 7.15-7.21 (m, 1H) 7.50-7.55 (m, 1H) 7.55-7.61 (m, 1H) 7.77-7.84 (m, 1H).

LC-MS (Method 2): $R_t$=1.42 min; MS (ESIpos): m/z=533 $[M+H]^+$

Example 573

(rac)-6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carboxamide

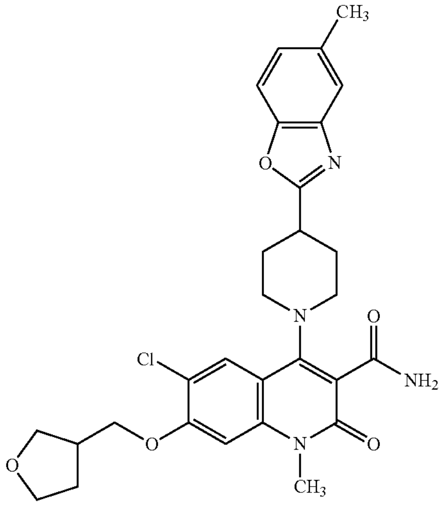 [SMILES: Cc1ccc2oc(C3CCN(c4c(C(N)=O)c(=O)n(C)c5cc(OCC6CCOC6)c(Cl)cc45)CC3)nc2c1]

90 mg (rac)-6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carbonitrile (example 572), 9.5 mg palladium(II)acetate and 100 mg acetaldoxime were stirred in 5.4 mL ethanol for 7 h at 90° C. The reaction mixture was diluted with water, extracted with ethyl acetate two times, the combined organic layers were dried with sodium sulfate and concentrated under reduced pressure. The residue was purified by flash chromatography (silica, dichloromethane/methanol gradient 0-3%) to obtain 110 mg of the title compound.

$^1$H NMR (400 MHz, DMSO-d6) δ ppm 1.68-1.80 (m, 2H) 1.99-2.07 (m, 2H) 2.18-2.27 (m, 2H) 2.41-2.45 (m, 3H) 2.70-2.83 (m, 1H) 3.12-3.26 (m, 3H) 3.35-3.40 (m, 1H) 3.58-3.64 (m, 4H) 3.65-3.75 (m, 1H) 3.77-3.87 (m, 2H) 4.10-4.29 (m, 2H) 7.07-7.12 (m, 1H) 7.15-7.22 (m, 1H) 7.46-7.50 (m, 1H) 7.51-7.54 (m, 1H) 7.55-7.62 (m, 1H) 7.64-7.71 (m, 1H) 7.79-7.85 (m, 1H).

LC-MS (Method 2): $R_t$=1.27 min; MS (ESIpos): m/z=552 $[M+H]^+$

Example 574

6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carboxamide, Enantiomer 1

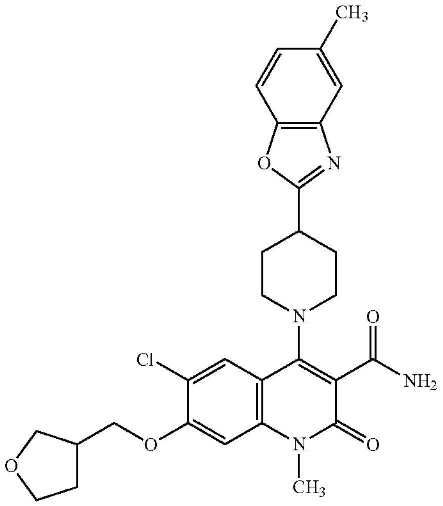 [SMILES: Cc1ccc2oc(C3CCN(c4c(C(N)=O)c(=O)n(C)c5cc(OCC6CCOC6)c(Cl)cc45)CC3)nc2c1]

85 mg (rac)-6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carboxamide (Example 573) were separated by chiral HPLC Instrument: PrepCon Labomatic HPLC-4; Column: YMC Cellulose SB 10µ, 250×50; eluent A: methyl tert-butyl ether+0.1 vol % diethylamine; eluent B: acetonitrile; isocratic: 60% A+40% B; flow: 100 mL/min; temperature: 25° C.; UV: 254 nm; 35 mg of the title compound were obtained.

$^1$H NMR (400 MHz, DMSO-d6) δ ppm 1.68-1.80 (m, 2H) 1.99-2.07 (m, 2H) 2.18-2.27 (m, 2H) 2.41-2.45 (m, 3H) 2.70-2.83 (m, 1H) 3.12-3.26 (m, 3H) 3.35-3.40 (m, 1H) 3.58-3.64 (m, 4H) 3.65-3.75 (m, 1H) 3.77-3.87 (m, 2H) 4.10-4.29 (m, 2H) 7.07-7.12 (m, 1H) 7.15-7.22 (m, 1H) 7.46-7.50 (m, 1H) 7.51-7.54 (m, 1H) 7.55-7.62 (m, 1H) 7.64-7.71 (m, 1H) 7.79-7.85 (m, 1H).

Analytical chiral HPLC: $R_t$=5.05 min

Instrument: Thermo Fisher UltiMate 3000; Column: YMC Cellulose SC 3µ, 100×4.6;

eluent A: methyl tert-butyl ether+0.1 vol % diethylamine; eluent B: methanol; isocratic: 30% A+70% B; flow: 1.4 ml/min; temperature: 25° C.; UV: 254 nm.

Example 575

6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carboxamide, Enantiomer 2

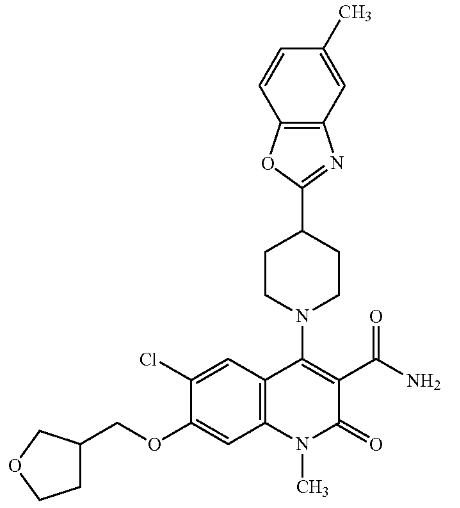 [SMILES: Cc1ccc2oc(C3CCN(c4c(C(N)=O)c(=O)n(C)c5cc(OCC6CCOC6)c(Cl)cc45)CC3)nc2c1]

85 mg (rac)-6-chloro-1-methyl-4-[4-(5-methyl-1,3-benzoxazol-2-yl)piperidin-1-yl]-2-oxo-7-[(oxolan-3-yl) methoxy]-1,2-dihydroquinoline-3-carboxamide (Example 573) were separated by chiral HPLC: Instrument: PrepCon Labomatic HPLC-4; Column: YMC Cellulose SB 10μ, 250×50; eluent A: methyl tert-butyl ether+0.1 vol % diethylamine; eluent B: acetonitrile; isocratic: 60% A+40% B; flow: 100 mL/min; temperature: 25° C.; UV: 254 nm; 35 mg of the title compound were obtained.

$^1$H NMR (400 MHz, DMSO-d6) δ ppm 1.68-1.80 (m, 2H) 1.99-2.07 (m, 2H) 2.18-2.27 (m, 2H) 2.41-2.45 (m, 3H) 2.70-2.83 (m, 1H) 3.12-3.26 (m, 3H) 3.35-3.40 (m, 1H) 3.58-3.64 (m, 4H) 3.65-3.75 (m, 1H) 3.77-3.87 (m, 2H) 4.10-4.29 (m, 2H) 7.07-7.12 (m, 1H) 7.15-7.22 (m, 1H) 7.46-7.50 (m, 1H) 7.51-7.54 (m, 1H) 7.55-7.62 (m, 1H) 7.64-7.71 (m, 1H) 7.79-7.85 (m, 1H).

Analytical chiral HPLC: $R_t$=2.85 min

Instrument: Thermo Fisher UltiMate 3000; Column: YMC Cellulose SB 3μ, 100×4.6; eluent A: methyl tert-butyl ether+0.1 vol % diethylamine; eluent B: acetonitrile; isocratic: 60% A+40% B; flow: 1.4 ml/min; temperature: 25° C.; UV: 254 nm.

Example 576

(rac)-6-bromo-1-methyl-2-oxo-7-[(oxolan-3-yl)oxy]-4-{4-[2-(pyridin-3-yl)-2H-1,2,3-triazol-4-yl]piperidin-1-yl}-1,2-dihydroquinoline-3-carbonitrile

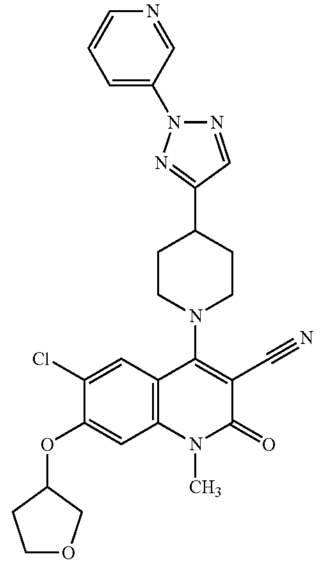 [SMILES: Cn1c(=O)c(C#N)c(N2CCC(c3cnn(-c4cccnc4)n3)CC2)c2cc(Cl)c(OC3CCOC3)cc21]

A solution of 250 mg (rac)-6-bromo-4-chloro-1-methyl-2-oxo-7-[(oxolan-3-yl)oxy]-1,2-dihydroquinoline-3-carbonitrile (intermediate 270), 173 mg 3-[4-(piperidin-4-yl)-2H-1,2,3-triazol-2-yl]pyridine (CAS 2360335-15-3) and 0.34 mL triethylamine in 4.2 mL 2-propanol was stirred for 2 h at 90° C. After this time, water and ethyl acetate were was added and the reaction stirred vigorously. The resulting precipitate was collected by filtration to obtain 380 mg of the title compound.

$^1$H-NMR (400 MHz, DMSO-d6): δ [ppm]=1.91-2.11 (m, 3H), 2.19-2.27 (m, 2H), 2.28-2.40 (m, 1H), 3.18-3.29 (m, 1H), 3.40-3.48 (m, 1H), 3.53-3.64 (m, 5H), 3.77-3.84 (m, 3H), 3.85-3.93 (m, 2H), 3.95-4.02 (m, 1H), 5.43-5.49 (m, 1H), 6.96-7.02 (m, 1H), 7.59-7.65 (m, 1H), 7.96-8.01 (m, 1H), 8.19-8.22 (m, 1H), 8.33-8.39 (m, 1H), 8.58-8.66 (m, 1H), 9.20-9.24 (m, 1H).

LC-MS (Method 1): $R_t$=1.24 min; MS (ESIpos): m/z=579 $[M+H]^+$

Example 577

(rac)-6-bromo-1-methyl-4-{4-[1-(2-methylphenyl)-1H-1,2,3-triazol-4-yl]piperidin-1-yl}-2-oxo-7-[(oxolan-3-yl)oxy]-1,2-dihydroquinoline-3-carbonitrile

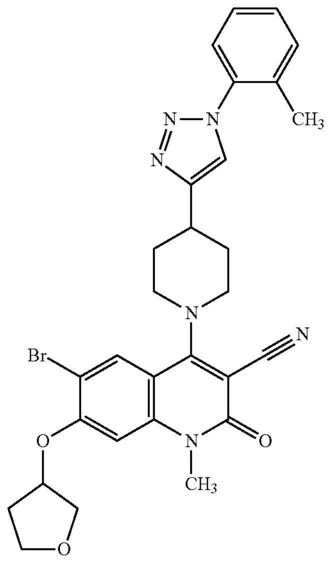 [SMILES: Cc1ccccc1-n1cc(C2CCN(c3c(C#N)c(=O)n(C)c4cc(OC5CCOC5)c(Br)cc34)CC2)nn1]

A solution of 240 mg (rac)-6-bromo-4-chloro-1-methyl-2-oxo-7-[(oxolan-3-yl)oxy]-1,2-dihydroquinoline-3-carbonitrile (intermediate 270), 318 mg 4-[1-(2-methylphenyl)-1H-1,2,3-triazol-4-yl]piperidine (intermediate 294) and 0.33 mL triethylamine in 4 mL ethanol was stirred for 2 h at 90° C. After this time, water and ethyl a were was added and the reaction stirred vigorously. The resulting precipitate was collected by filtration to obtain 360 mg of the title compound.

$^{1}$H-NMR (400 MHz, DMSO-d6): δ [ppm]=1.89-2.10 (m, 3H), 2.16-2.19 (m, 3H), 2.20-2.28 (m, 2H), 2.28-2.39 (m, 2H), 3.11-3.23 (m, 1H), 3.52-3.63 (m, 5H), 3.77-3.84 (m, 3H), 3.85-3.94 (m, 2H), 3.95-4.02 (m, 1H), 5.43-5.49 (m, 1H), 6.97-7.02 (m, 1H), 7.38-7.50 (m, 4H), 7.95-7.98 (m, 1H), 8.37-8.40 (m, 1H).

LC-MS (Method 2): $R_t$=1.26 min; MS (ESIpos): m/z=591 $[M+H]^+$

Example 578

(rac)-1,6-dimethyl-4-{4-[1-(2-methylphenyl)-1H-1,2,3-triazol-4-yl]piperidin-1-yl}-2-oxo-7-[(oxolan-3-yl)oxy]-1,2-dihydroquinoline-3-carbonitrile

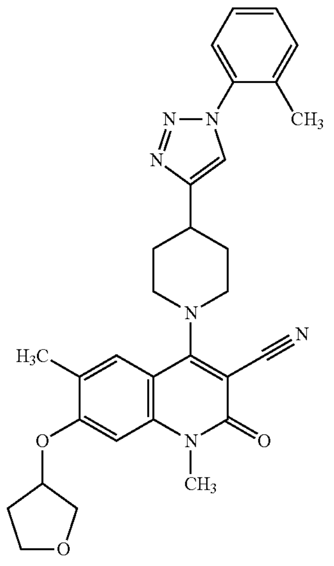 [SMILES: Cc1cc2c(N3CCC(c4cn(-c5ccccc5C)nn4)CC3)c(C#N)c(=O)n(C)c2cc1OC1CCOC1]

To a suspension of 160 mg (rac)-6-bromo-1-methyl-4-{4-[1-(2-methylphenyl)-1H-1,2,3-triazol-4-yl]piperidin-1-yl}-2-oxo-7-[(oxolan-3-yl)oxy]-1,2-dihydroquinoline-3-carbonitrile (example 577) in 0.7 ml dioxane and 0.04 ml water was added 42 μL trimethylboroxine, 221 mg cesium carbonate and 19.9 mg [1,1'-bis(diphenylphosphino)ferrocene] dichloro-palladium(II) was purged for 5 min with nitrogen gas and heated at 80° C. for 4 h. The re action mixture was diluted with water and extracted 3× with ethyl acetate. The combined organic layers were dried (waterresistant filter) and concentrated under reduced pressure. The residue was purified by flash chromatography (silica, hexanes/ethyl acetate (50:50)-ethyl acetate (100)-ethyl acetate/methanol (8:2), gradients) to obtain 78 mg of the title compound.

$^{1}$H-NMR (400 MHz, DMSO-d6): δ [ppm]=1.92-2.09 (m, 3H), 2.20 (d, 8H), 2.27-2.38 (m, 1H), 3.11-3.22 (m, 1H), 3.50-3.62 (m, 5H), 3.75-3.83 (m, 3H), 3.84-3.92 (m, 2H), 3.95-4.02 (m, 1H), 5.33-5.40 (m, 1H), 6.86 (s, 1H), 7.37-7.46 (m, 2H), 7.47-7.51 (m, 2H), 7.61 (s, 1H), 8.38 (s, 1H).

LC-MS (Method 1): $R_t$=1.26 min; MS (ESIpos): m/z=526 $[M+H]^+$

Example 579

7-bromo-1,6-dimethyl-4-{4-[1-(2-methylphenyl)-1H-pyrazol-4-yl]piperidin-1-yl}-2-oxo-1,2-dihydroquinoline-3-carbonitrile

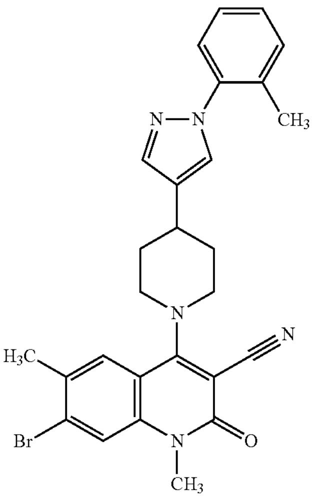 [SMILES: Cc1cc2c(N3CCC(c4cnn(-c5ccccc5C)c4)CC3)c(C#N)c(=O)n(C)c2cc1Br]

A solution of 245 mg 7-bromo-4-chloro-1,6-dimethyl-2-oxo-1,2-dihydroquinoline-3-carbonitrile (intermediate 303), 933 mg 4-[1-(2-methylphenyl)-1H-pyrazol-4-yl]piperidine (intermediate 298, purity ca. 30%) and 0.41 mL triethylamine in 4 mL 2-propanol was stirred for 14 h at 80° C. After this time, water and ethyl acetate were was added and the reaction stirred vigorously. The resulting precipitate was collected by filtration. This residue was purified by repeated flash chromatography (silica, dichloromethane/methanol gradient 0-3% and hexanes/ethyl acetate gradient 0-80%) to obtain 92 mg of the title compound.

$^1$H-NMR (400 MHz, DMSO-d6): δ [ppm]=1.85-1.98 (m, 2H), 2.10-2.18 (m, 2H), 2.24 (s, 3H), 2.45 (s, 3H), 2.87-2.98 (m, 1H), 3.47-3.57 (m, 5H), 3.77-3.85 (m, 2H), 7.31-7.41 (m, 4H), 7.71 (s, 1H), 7.76 (s, 1H), 7.79-7.81 (m, 1H), 7.96-7.98 (m, 1H).

LC-MS (Method 2): $R_t$=1.43 min; MS (ESIpos): m/z=518 $[M+H]^+$

Example 580

(rac)-1,6-dimethyl-4-{4-[1-(2-methylphenyl)-1H-pyrazol-4-yl]piperidin-1-yl}-2-oxo-7-[(oxolan-3-yl)oxy]-1,2-dihydroquinoline-3-carbonitrile

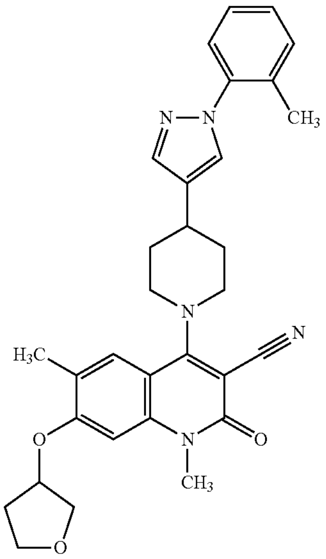 [SMILES: Cc1cc2c(N3CCC(c4cnn(-c5ccccc5C)c4)CC3)c(C#N)c(=O)n(C)c2cc1OC1CCOC1]

A mixture of 85 mg 7-bromo-1,6-dimethyl-4-{4-[1-(2-methylphenyl)-1H-pyrazol-4-yl]piperidin-1-yl}-2-oxo-1,2-dihydroquinoline-3-carbonitrile (example 579), 13.2 mg sodium hydride (60% in mineral oil) and 20 μL oxolan-3-ol (CAS 453-20-3) in 2 ml DMF was stirred at 80° C. for 3 hours. After cooling to rt, the mixture was diluted with water and extracted with dichloromethane (3×). The combined organic layers were washed with brine, filtered (using a water-resistant filter) and concentrated under reduced pressure. The aqueous layer was extracted again with diuchloromethane/2-propanol 4:1 (2×). The combined organic layers were filtered (using a water-resistant filter) and concentrated under reduced pressure. The residue was solved in 1 mL of DMSO and diluted with 30 mL water. The solid that precipitate was collected by filtration, washed with water and dried under vacuo. The residue was purified by RP-HPLC (column: X-Bridge C18 5 μm 100×30 mm, mobile phase: acetonitrile/water (0.2 vol. % ammonia 32%)-gradient). 9 mg of the title compound were obtained.

$^1$H-NMR (400 MHz, DMSO-d6): δ [ppm]=1.81-1.96 (m, 2H), 1.99-2.08 (m, 1H), 2.09-2.18 (m, 2H), 2.21-2.23 (m, 3H), 2.24 (s, 3H), 2.26-2.38 (m, 1H), 2.90 (tt, 1H), 3.45-3.54 (m, 2H), 3.58 (s, 3H), 3.72-3.91 (m, 5H), 3.96-4.01 (m, 1H), 5.32-5.39 (m, 1H), 6.85 (s, 1H), 7.29-7.41 (m, 4H), 7.62 (s, 1H), 7.71 (s, 1H), 7.96 (s, 1H).

LC-MS (Method 2): $R_t$=1.35 min; MS (ESIpos): m/z=525 $[M+H]^+$

Experimental Section—Biological Assays

Human DGKα Kinase Activity Inhibition Assay.

Human DGKα inhibitory activity of compounds of the present invention was quantified employing the human DGKα kinase activity assay as described in the following paragraphs. In essence, the enzyme activity was measured by quantification of the adenosine-di-phosphate (ADP) generated as a co-product of the enzyme reaction via the "ADP-Glo™ Kinase Assay" kit from the company Promega.

This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP, which subsequently generates in a luciferase-based reaction a glow-luminescence signal ("Kinase Detection Reagent").

C-terminally FLAG-tagged, recombinant full-length human DGKα (expressed in baculovirus infected insect cells, purified using anti-Flag pulldown and size exclusion chromatography as described below, DGKa_hu_1) was used as enzyme. As substrate for the kinase 1,2-dioleoyl-sn-glycerol, reconstituted in octyl-μ-D-glucopyranoside micelles, was used. For the preparation of the micelles, 1 volume of a 16.1 mM solution of 1,2-dioleoyl-sn-glycerol (Avanti, Cat. #08001-25G) in chloroform was slowly evaporated using a nitrogen stream. Subsequently, 22.55 volumes of a 510 mM solution of octyl-μ-D-glucopyranoside (Sigma-Aldrich, Cat. #08001-10G) in 50 mM MOPS buffer (pH 7.4) were added, and the mixture was sonicated in an ultrasonic bath for 20 s. Then 35 volumes of 50 mM MOPS buffer (pH 7.4) were added to yield a solution of 0.28 mM 1,2 dioleoyl-sn-glycerol and 200 mM octyl-μ-D-glucopyranoside, which was aliquoted, flash-frozen in liquid nitrogen, and stored at −20° C. until use. For each experiment, a fresh aliquot was quickly thawed and diluted 24-fold with aqueous assay buffer (described below) containing 95.7 μM adenosine triphosphate (Promega) to yield a 1.67-fold concentrated substrate solution.

For the assay 50 nl of a 100-fold concentrated solution of the test compound in dimethyl sulfoxide (DMSO, Sigma) was pipetted into either a white 1536-well or a white low-volume 384-well microtiter plate (both Greiner Bio-One, Frickenhausen, Germany). Subsequently, 2 μl of a solution of human DGKα in aqueous assay buffer [50 mM (3-(N-morpholino)propanesulfonic acid (MOPS, pH 7.4, Sigma-Aldrich), 1 mM dithiothreitol (DTT, Sigma-Aldrich), 100 mM NaCl (Sigma-Aldrich), 10 mM $MgCl_2$ (Sigma-Aldrich), 0.1% (w/v) bovine gamma globulin (BGG, Sigma-Aldrich), 1 μM $CaCl_2$ (Sigma-Aldrich)] were added to the wells, and the mixture was incubated for 15 min at 22° C. to allow pre-binding of the test compounds to the enzyme. The reaction was initiated by the addition of 3 μl of substrate solution [preparation described above; 11.7 μM 1,2-dioleoyl-sn-glycerol (=>final conc. in the 5 μl assay volume is 7 μM), 8.33 mM octyl-β-D-glucopyranoside (=>final conc. in 5 μl assay volume is 5 mM), and 91.67 μM adenosine triphosphate (=>final conc. in 5 μl assay volume is 55 μM) in assay buffer] and the resulting mixture was incubated for a reaction time of 20 min at 22° C. The concentration of DGK a was adjusted depending of the activity of the enzyme lot and was chosen appropriate to have the assay in the linear range, a typical concentration is about 0.1 nM. The reaction was stopped by the addition of 2.5 μl of "ADP-Glo-reagent" (1 to 1.5 diluted with water) and the resulting mixture was incubated at 22° C. for 1 h to convert the ATP no t consumed in the kinase reaction completely to cAMP. Subsequently 2.5 μl of the "kinase detection reagent" (1.2-fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the DGKa.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100-fold concentrated solutions in DMSO by serial dilutions, exact concentrations may vary depending pipettors used) in duplicate values for each concentration and $IC_{50}$ values were calculated using Genedata Screener™ software.

TABLE 26

$IC_{50}$ values of examples in in vitro human DGKα kinase activity inhibition assays.

| Example | $IC_{50}$ [nM] |
|---|---|
| 1 | 1.4 |
| 2 | 6.4 |
| 3 | 2.6 |
| 4 | 2.8 |
| 5 | 1.6 |
| 6 | 4.3 |
| 7 | 3.2 |
| 8 | 3.2 |
| 9 | 3.3 |
| 10 | 3.7 |
| 11 | 3.8 |
| 12 | 3.5 |
| 13 | 5.1 |
| 14 | 4.4 |
| 15 | 11 |
| 16 | 9.9 |
| 17 | 12 |
| 18 | 3.7 |
| 19 | 15 |
| 20 | 1.5 |
| 21 | 5.2 |
| 22 | 6 |
| 23 | 12 |
| 24 | 45 |
| 25 | 168 |
| 26 | 10 |
| 27 | 2 |
| 28 | 2.7 |
| 29 | 2.9 |
| 30 | 3.9 |
| 31 | 5.6 |
| 32 | 6 |
| 33 | 6.2 |
| 34 | 18 |
| 35 | 7.8 |
| 36 | 8.3 |
| 37 | 1.1 |
| 38 | 1.5 |
| 39 | 2 |
| 40 | 3.5 |
| 41 | 4.9 |
| 42 | 11 |
| 43 | 11 |
| 44 | 12 |
| 45 | 2.1 |
| 46 | 2.5 |
| 47 | 3 |
| 48 | 3 |
| 49 | 4.1 |
| 50 | 8.3 |
| 51 | 8.3 |
| 52 | 8.8 |
| 53 | 13 |
| 54 | 14 |
| 55 | 14 |
| 56 | 17 |
| 57 | 22 |
| 58 | 2.6 |
| 59 | 23 |
| 60 | 33 |
| 61 | 37 |

TABLE 26-continued

IC$_{50}$ values of examples in in vitro human DGKα kinase activity inhibition assays.

| Example | IC$_{50}$ [nM] |
|---|---|
| 62 | 38 |
| 63 | 39 |
| 64 | 73 |
| 65 | 74 |
| 66 | 78 |
| 67 | 85 |
| 68 | 99 |
| 69 | 105 |
| 70 | 21 |
| 71 | 23 |
| 72 | 30 |
| 73 | 33 |
| 74 | 48 |
| 75 | 49 |
| 76 | 50 |
| 77 | 64 |
| 78 | 104 |
| 79 | 104 |
| 80 | 333 |
| 81 | 14 |
| 82 | 11 |
| 83 | 4.4 |
| 84 | 52 |
| 85 | 54 |
| 86 | 54 |
| 87 | 7.1 |
| 88 | 47 |
| 89 | 2.1 |
| 90 | 5.5 |
| 91 | 3.1 |
| 92 | 9.8 |
| 93 | 11 |
| 94 | 12 |
| 95 | 19 |
| 96 | 20 |
| 97 | 33 |
| 98 | 35 |
| 99 | 64 |
| 100 | 2.3 |
| 101 | 12 |
| 102 | 0.3 |
| 103 | 0.6 |
| 104 | 0.6 |
| 105 | 1.9 |
| 106 | 0.9 |
| 107 | 2.3 |
| 108 | 1.8 |
| 109 | 2.1 |
| 110 | 2.6 |
| 111 | 3.2 |
| 112 | 4.5 |
| 113 | 3.5 |
| 114 | 15 |
| 115 | 20 |
| 116 | 36 |
| 117 | 7.7 |
| 118 | 6.8 |
| 119 | 7.9 |
| 120 | 7.7 |
| 121 | 5.7 |
| 122 | 15 |
| 123 | 10 |
| 124 | 12 |
| 125 | 1.2 |
| 126 | 2.6 |
| 127 | 3.4 |
| 128 | 18 |
| 129 | 16 |
| 130 | 23 |
| 131 | 26 |
| 132 | 17 |
| 133 | 23 |
| 134 | 12 |
| 135 | 88 |
| 136 | 482 |

TABLE 26-continued

IC$_{50}$ values of examples in in vitro human DGKα kinase activity inhibition assays.

| Example | IC$_{50}$ [nM] |
|---|---|
| 137 | 3 |
| 138 | 1.9 |
| 139 | 2.1 |
| 140 | 1.6 |
| 141 | 5.6 |
| 142 | 58 |
| 143 | 554 |
| 144 | 897 |
| 145 | 41 |
| 146 | 821 |
| 147 | 358 |
| 148 | 369 |
| 149 | 1100 |
| 150 | 1530 |
| 151 | 486 |
| 152 | 1070 |
| 153 | 45 |
| 154 | 34 |
| 155 | 60 |
| 156 | 182 |
| 157 | 252 |
| 158 | 304 |
| 159 | 383 |
| 160 | 544 |
| 161 | 1100 |
| 162 | 134 |
| 163 | 146 |
| 164 | 1.1 |
| 165 | 2.6 |
| 166 | 2.2 |
| 167 | 3.2 |
| 168 | 0.5 |
| 169 | 0.6 |
| 170 | 7.2 |
| 171 | 1.5 |
| 172 | 9.4 |
| 173 | 12 |
| 174 | 1.7 |
| 175 | 4.2 |
| 176 | 3 |
| 177 | 209 |
| 178 | 298 |
| 179 | 431 |
| 180 | 1510 |
| 181 | 150 |
| 182 | 47 |
| 183 | 1.5 |
| 184 | 1.5 |
| 185 | 2.9 |
| 186 | 9.1 |
| 187 | 2 |
| 188 | 2.6 |
| 189 | 15 |
| 190 | 5.7 |
| 191 | 7 |
| 192 | 1360 |
| 193 | 2.4 |
| 194 | 2.2 |
| 195 | 1.5 |
| 196 | 3.1 |
| 197 | 2.2 |
| 198 | 2.1 |
| 199 | 3.4 |
| 200 | 3.9 |
| 201 | 1.1 |
| 202 | 2.7 |
| 203 | 0.9 |
| 204 | 7 |
| 205 | 4.8 |
| 206 | 0.8 |
| 207 | 2.7 |
| 208 | 3.4 |
| 209 | 26 |
| 210 | 119 |
| 211 | 456 |

TABLE 26-continued $IC_{50}$ values of examples in in vitro human DGKα kinase activity inhibition assays.

| Example | $IC_{50}$ [nM] |
|---|---|
| 212 | 0.3 |
| 213 | 39 |
| 214 | 0.9 |
| 215 | 0.4 |
| 216 | 0.4 |
| 217 | 1.0 |
| 218 | 0.6 |
| 219 | 1.6 |
| 220 | 1.7 |
| 221 | 1.8 |
| 222 | 5.2 |
| 223 | 1.2 |
| 224 | 1.5 |
| 225 | 121 |
| 226 | 1.3 |
| 227 | 2.0 |
| 228 | 2.4 |
| 229 | 3.0 |
| 230 | 83 |
| 231 | 108 |
| 232 | 163 |
| 233 | 1270 |
| 234 | 1.8 |
| 235 | 2.9 |
| 236 | 4.3 |
| 237 | 5.0 |
| 238 | 12 |
| 239 | 0.6 |
| 240 | 2.5 |
| 241 | 2.5 |
| 242 | 2.7 |
| 243 | 3.5 |
| 244 | 4.6 |
| 245 | 5.9 |
| 246 | 6.5 |
| 247 | 6.9 |
| 248 | 6.9 |
| 249 | 7.2 |
| 250 | 9.1 |
| 251 | 9.3 |
| 252 | 13 |
| 253 | 14 |
| 254 | 15 |
| 255 | 18 |
| 256 | 25 |
| 257 | 26 |
| 258 | 29 |
| 259 | 29 |
| 260 | 35 |
| 261 | 35 |
| 262 | 36 |
| 263 | 42 |
| 264 | 49 |
| 265 | 49 |
| 266 | 53 |
| 267 | 64 |
| 268 | 65 |
| 269 | 71 |
| 270 | 72 |
| 271 | 105 |
| 272 | 113 |
| 273 | 119 |
| 274 | 152 |
| 275 | 172 |
| 276 | 216 |
| 277 | 243 |
| 278 | 480 |
| 279 | 1280 |
| 280 | 4740 |
| 281 | 8.9 |
| 282 | 872 |
| 283 | 6.8 |
| 284 | 9.3 |
| 285 | 10 |
| 286 | 374 |

TABLE 26-continued $IC_{50}$ values of examples in in vitro human DGKα kinase activity inhibition assays.

| Example | $IC_{50}$ [nM] |
|---|---|
| 287 | 22 |
| 288 | 3.8 |
| 289 | 8.3 |
| 290 | 10 |
| 291 | 11 |
| 292 | 3.2 |
| 293 | 2.1 |
| 294 | 12 |
| 295 | 9.5 |
| 296 | 0.5 |
| 297 | 0.6 |
| 298 | 0.5 |
| 299 | 1.0 |
| 300 | 1.2 |
| 301 | 1.4 |
| 302 | 1.1 |
| 303 | 1.9 |
| 304 | 2.1 |
| 305 | 4.5 |
| 306 | 4.1 |
| 307 | 5.7 |
| 308 | 6.4 |
| 309 | 101 |
| 310 | 34 |
| 311 | 1.2 |
| 312 | 0.7 |
| 313 | 1.5 |
| 314 | 1.7 |
| 315 | 46 |
| 316 | 6.5 |
| 317 | 17 |
| 318 | 48 |
| 319 | 74 |
| 320 | 32 |
| 321 | 75 |
| 322 | 239 |
| 323 | 326 |
| 324 | 14 |
| 325 | 26 |
| 326 | 34 |
| 327 | 85 |
| 328 | 144 |
| 329 | 152 |
| 330 | 217 |
| 331 | 861 |
| 332 | 17 |
| 333 | 172 |
| 334 | 100 |
| 335 | 2.3 |
| 336 | 80 |
| 337 | 2390 |
| 338 | 86 |
| 339 | 67 |
| 340 | 72 |
| 341 | 3.3 |
| 342 | 2.9 |
| 343 | 16 |
| 344 | 489 |
| 345 | 38 |
| 346 | 28 |
| 347 | 106 |
| 348 | 7.9 |
| 349 | 15 |
| 350 | 11 |
| 351 | 87 |
| 352 | 113 |
| 353 | 254 |
| 354 | 112 |
| 355 | 140 |
| 356 | 5.1 |
| 357 | 0.6 |
| 358 | 44 |
| 359 | 3.3 |
| 360 | 1.2 |
| 361 | 27 |

TABLE 26-continued

IC50 values of examples in in vitro human DGKα kinase activity inhibition assays.

| Example | $IC_{50}$ [nM] |
|---|---|
| 362 | 106 |
| 363 | 189 |
| 364 | 34 |
| 365 | 14 |
| 366 | 12 |
| 367 | 21 |
| 368 | 13 |
| 369 | 14 |
| 370 | 158 |
| 371 | 14 |
| 372 | 14 |
| 373 | 9.9 |
| 374 | 34 |
| 375 | 21 |
| 376 | 14 |
| 377 | 4.8 |
| 378 | 23 |
| 379 | 1.0 |
| 380 | 0.4 |
| 381 | 7.4 |
| 382 | 13 |
| 383 | 5.1 |
| 384 | 1.8 |
| 385 | 0.9 |
| 386 | 9.4 |
| 387 | 8.9 |
| 388 | 33 |
| 389 | 3.1 |
| 390 | 3.5 |
| 391 | 8.3 |
| 392 | 6.7 |
| 393 | 106 |
| 394 | 2.1 |
| 395 | 2.4 |
| 396 | 0.9 |
| 397 | 399 |
| 398 | 1.7 |
| 399 | 0.5 |
| 400 | 6.7 |
| 401 | 0.8 |
| 402 | 16 |
| 403 | 2.0 |
| 404 | 5.3 |
| 405 | 41 |
| 406 | 36 |
| 407 | 48 |
| 408 | 15 |
| 409 | 8.4 |
| 410 | 51 |
| 411 | 5.1 |
| 412 | 21 |
| 413 | 1.0 |
| 414 | 1.3 |
| 415 | 146 |
| 416 | 34 |
| 417 | 1.2 |
| 418 | 1.4 |
| 419 | 4.6 |
| 420 | 0.6 |
| 421 | 137 |
| 422 | 0.7 |
| 423 | 1.0 |
| 424 | 0.3 |
| 425 | 0.2 |
| 426 | 13 |
| 427 | 8.2 |
| 428 | 0.6 |
| 429 | 0.3 |
| 430 | 9.9 |
| 431 | 3.2 |
| 432 | 0.1 |
| 433 | 8.6 |
| 434 | 525 |
| 435 | 4.3 |
| 436 | 32 |

TABLE 26-continued

IC50 values of examples in in vitro human DGKα kinase activity inhibition assays.

| Example | $IC_{50}$ [nM] |
|---|---|
| 437 | 27 |
| 438 | 31 |
| 439 | 492 |
| 440 | 8.9 |
| 441 | 11 |
| 442 | 15 |
| 443 | 9.1 |
| 444 | 82 |
| 445 | 44 |
| 446 | 18 |
| 447 | 63 |
| 448 | 27 |
| 449 | 13 |
| 450 | 119 |
| 451 | 163 |
| 452 | 2570 |
| 453 | 598 |
| 454 | 373 |
| 455 | 1.9 |
| 456 | 41 |
| 457 | 6.8 |
| 458 | 4.3 |
| 459 | 9.8 |
| 460 | 3.5 |
| 461 | 77 |
| 462 | 121 |
| 463 | 113 |
| 464 | 123 |
| 465 | 175 |
| 466 | 0.5 |
| 467 | 3.9 |
| 468 | 0.7 |
| 469 | 33 |
| 470 | 13 |
| 471 | 3.9 |
| 472 | 6.7 |
| 473 | 23 |
| 474 | 4.6 |
| 475 | 224 |
| 476 | 7.1 |
| 477 | 3.9 |
| 478 | 9.4 |
| 479 | 59 |
| 480 | 9.8 |
| 481 | 2.0 |
| 482 | 3.1 |
| 483 | 1.8 |
| 484 | 15 |
| 485 | 2.0 |
| 486 | 5.6 |
| 487 | 13 |
| 488 | 1.6 |
| 489 | 7.5 |
| 490 | 7.8 |
| 491 | 9.1 |
| 492 | 1.5 |
| 493 | 80 |
| 494 | 6.2 |
| 495 | 1.4 |
| 496 | 19 |
| 497 | 80 |
| 498 | 3.1 |
| 499 | 74 |
| 500 | 0.7 |
| 501 | 21 |
| 502 | 120 |
| 503 | 2690 |
| 504 | 238 |
| 505 | 269 |
| 506 | 574 |
| 507 | 85 |
| 508 | 1.4 |
| 509 | 2.0 |
| 510 | 70 |
| 511 | 1.5 |

TABLE 26-continued

IC50 values of examples in in vitro human DGKα kinase activity inhibition assays.

| Example | $IC_{50}$ [nM] |
|---|---|
| 512 | 0.8 |
| 513 | 0.2 |
| 514 | 0.6 |
| 515 | 0.3 |
| 516 | 2.8 |
| 517 | 64 |
| 518 | 596 |
| 519 | 20 |
| 520 | 37 |
| 521 | 43 |
| 522 | 44 |
| 523 | 3.7 |
| 524 | 45 |
| 525 | 39 |
| 526 | 27 |
| 527 | 67 |
| 528 | 2920 |
| 529 | 46 |
| 530 | 1.8 |
| 531 | 8.1 |
| 532 | 1.0 |
| 533 | 1.9 |
| 534 | 2.0 |
| 535 | 0.8 |
| 536 | 6.7 |
| 537 | 0.2 |
| 538 | 0.5 |
| 539 | 0.2 |
| 540 | 2.8 |
| 541 | 29 |
| 542 | 2.5 |
| 543 | 7.5 |
| 544 | 0.3 |
| 545 | 0.2 |
| 546 | 0.9 |
| 547 | 0.6 |
| 548 | 0.3 |
| 549 | 0.6 |
| 550 | 0.2 |
| 551 | 0.1 |
| 552 | 1.6 |
| 553 | 1.1 |
| 554 | 1.6 |
| 555 | 1.1 |
| 556 | 20 |
| 557 | 3.6 |
| 558 | 72 |
| 559 | 1.7 |
| 560 | 105 |
| 561 | 1.4 |
| 562 | 13 |
| 563 | 1.7 |
| 564 | 3.3 |
| 565 | 3.0 |
| 566 | 0.3 |
| 567 | 2.0 |
| 568 | 0.3 |
| 569 | 0.1 |
| 570 | <0.07 |
| 571 | 0.7 |
| 572 | 1.5 |
| 573 | 1.5 |
| 574 | 0.4 |
| 575 | 5.6 |
| 576 | 1.4 |
| 577 | 2.9 |
| 578 | 4.2 |
| 579 | 61 |
| 580 | 1.3 |

Transactivation Assay in Jurkat IL2-Reporter Cell Line

Transactivation assays were carried out in Jurkat cells purchased from Promega (Promega, #CS187001) stably transfected with a firefly luciferase reporter gene construct under the control of the IL2-promoter. Cells were cultured as specified by the manufacturer. Bulk cells were harvested at a culture density of approx. 1E+06 cells/ml, suspended in cryo-storage medium (70% RPMI/20% FCS/10% DMSO), frozen at controlled rate of −1°/min in 1.8 ml cryo-vials with cell densities of 1E+07 to 1E+08 cells per vial, and stored at −150° C. or below until further use. Frozen cells were thawed and cultured in medium at a starting density of 3.5E+05 cells/ml for 6 days. On day 6 cells were centrifuged for 5 min at 300×g, medium was decanted and cell concentration was adjusted to 5.0E+06 cells/ml with fresh assay medium (500 ml RPMI (Gibco, #22400)+5 ml L-Glutamin (Sigma, #G7513)+5 ml Penicillin/Streptomycin (Sigma #P0781)+5 ml Non-essential amino acids (Invitrogen, #11140)+5 ml sodium-pyruvate (Gibco #1136088), 5 ml FBS (Biochrom, #S0615)). Cell working stock was split in two parts: neutral control and compounds with EC30 stimulation, high control with EC100 stimulation.

An antibody premix was prepared by diluting anti-CD3 (BD Pharmingen, #555329), anti-CD28 (BD Pharmingen, #555725) and goat anti mouse anti-IgG (ThermoFisher, #31160) antibodies at 1/1/4 ratio in assay medium at 2-fold of final concentration (final concentrations depend on cell batch, typically for neutral control 0.055/0.055/0.22 μg/ml, for high control 0.5/0.5/2 mg/ml). The premix solutions were added to the cells in 1+1 volume prior use.

Fifty nl of a 100-fold concentrated solution of the test compounds in DMSO were transferred into a white microtiter test plate (384, Greiner Bio-One, Germany). For this, either a Hummingbird liquid handler (Digilab, USA) or an Echo acoustic system (Labcyte, USA) was used. Five μl of the freshly prepared cell suspension was added to the wells of a test plate and incubated at 37° C. in a 5% $CO_2$ atmosphere. After completion of the incubation for 4 hours, 3 μl of Bio-Glo Luciferase assay reagent (Promega, #G7941, prepared as recommended by the supplier) were added to all wells. The test plate was incubated at 20° C. for 10 min before measurement of the luminescence in a microplate reader (typically Pherastar by BMG, Germany, or ViewLux by Perkin-Elmer, USA). Data were normalized (neutral control=0% effect, high control=100% effect). Compounds were tested in duplicates at up to 11 concentrations (typically 20 μM, 5.7 μM, 1.6 μM, 0.47 μM, 0.13 μM, 38 nM, 11 nM, 3.1 nM, 0.89 nM, 0.25 nM and 0,073 nM). Dilution series were made prior to the assay in a 100-fold concentrated form by serial dilution. $EC_{50}$ values were calculated by 4-Parameter fitting using a commercial software package (Genedata Analyzer, Switzerland).

Polyclonal Activation of Human PBMCs

To test the effect of DGKα compounds on IL-2 and IFN-γ secretion of human Peripheral Blood Mononuclear Cells (PBMCs) a 24 h human PBMC assay is performed as screening assay. For this, a 96 well flat bottom plate is coated with a suboptimal stimulation condition (EC 10-30) of human aCD3 (Invitrogen, clone OKT3) antibody in 50 μl PBS/well at 4° C. overnight. PBMCs isolated and frozen at liquid $N_2$ from leucapherese samples is thawed and resuspended in culture medium (X-Vivo-20). $4\times10^5$ cells/well are plated. Wells are treated with the respective compound concentrations (5-fold dilution steps from 10 μM to 3 nM) and the final DMSO concentration per well is 0.1%. Medium+ DMSO (0.1%) is used as baseline value. As positive controls 1000 ng/ml aCD3+aCD28 (1 μg/ml) and a DGKα reference compound is used. After 24 h the medium is collected and hIL-2 or hIFN-γ ELISA are performed. The following parameters are calculated: $EC_{50}$ value, concentration at 50% increase; max increase in % and respective concentration and maximum effect normalized to max concentration (10 μM) of a selected DGKα reference compound.

In Vitro Activation of Mouse OT-I Antigen-Specific T-Cells

To test the effect of DGKα compounds in murine antigen-specific T-cells, spleens and lymph nodes of OT-I mice are collected and mashed through a 40 μm cell strainer and incubated for 1 min in 1 ml ACK lysing buffer (Gibco)/spleen. 4×106 cells/ml are incubated in medium containing 0.05 ng/ml SIINFEKL in a 50 ml falcon at 37° C. for 30 min. Afterwards cells are centrifuged and 4×106 cells/ml are resuspended in fresh medium (DMEM; 10% FCS, 1% Pen/Strep, 0.1% μ-mercaptoethanol, 1% HEPES). 4×105 cells are plated per well in a 96-well round bottom plate. Wells are treated with respective compound concentrations (5-fold dilution steps from 10 μM to 3 nM) in a final DMSO concentration of 0.1%. Medium+DMSO (0.1%) is used as baseline value. As positive controls cells incubated with the 4×SIINFEKL concentration (0.2 ng/ml) and a DGKα reference compound are used. The plates are centrifuged to reduce the distance between T-cells and APCs before incubation. After 24 h the medium is collected and mIL-2 or mIFN-γ ELISAs are performed. The following parameters are calculated: $EC_{50}$ value, concentration at 50% increase; max increase in % and respective concentration and maximum effect normalized to max concentration (10 μM) of a selected DGKα reference compound.

DGKα Surface Plasmon Resonance Interaction Assay

The ability of the compounds described in this invention to bind to DGKα may be determined using surface plasmon resonance (SPR). This allows for the quantification of binding in terms of the equilibrium dissociation constant ($K_D$ [M]), as well as association and dissociation rate constants ($k_{on}$[1/Ms] and $k_{off}$ [1/s], respectively). The measurements may be performed using Biacore® T200, Biacore® S200 or Biacore® 8K (GE Healthcare).

All buffers described in this section were prepared with 10×HBS-P+ Buffer (GE Healthcare, #BR100671) supplemented with additional buffer components as indicated below, dithiothreitol (DTT from Sigma, #D0632-25G), Adenosine 5'-triphosphate (ATP from Sigma, #A26209-10G), $MgCl_2$ (Sigma, #M1028-100ML), dimethyl sulfoxide (DMSO from Biomol, #54686.500).

For SPR measurements, recombinant and biotinylated human DGKα (DGKa_hu_1Avi) was immobilized via the streptavidin-biotin interaction onto a Series S Sensor Chip SA (GE Healthcare, #BR-1005-31). Briefly, DGKα was diluted to a concentration of 19 μg/ml in Immobilization Buffer (10 mM HEPES, 150 mM NaCl, 0.05% v/v Surfactant P20, 2 mM $MgCl_2$, 1 mM DTT, pH 7.4) and captured on the SA Chip surface using a flow rate of 10 μl/min for 500 seconds at a temperature of 10° C. Immobilization levels of approximately 8000-10000 RU were typically achieved. The reference surface consisted of a streptavidin surface without immobilized protein. Compounds were diluted from 10 mM DMSO stock solution into Running Buffer (10 mM HEPES, 150 mM NaCl, 0.05% v/v Surfactant P20, 2 mM $MgCl_2$, 1 mM DTT, 0.2 mM ATP and 1% v/v DMSO, pH 7.4). For SPR-binding measurements serial dilutions (typically 1:3 dilutions resulting in 8 concentrations up to 2 μM or 20 μM) were injected over immobilized protein. Binding affinity and kinetics were measured at 18° C. and at a flow rate of 100 μl/min.

For regeneration of slowly dissociating compounds an additional regeneration step was included by injection of Regeneration Buffer without ATP (10 mM HEPES, 150 mM NaCl, 0.05% v/v Surfactant P20, 1 mM DTT and 1% v/v DMSO, pH 7.4) for 200 s at a flow rate of 30 μl/min The double-referenced sensorgrams were fit to a simple reversible Langmuir 1:1 reaction mechanism as implemented in the Biacore® T200, S200 and 8K evaluation software (Biacore T200 Evaluation Software version 2.0, Biacore S200 Evaluation Software version 1.0, Biacore 8K Evaluation Software v 1.1.1.7442, GE Healthcare).

Expression of DGKα in Insect Cells Using the Baculovirus System

Expression Constructs:

The cDNA encoding the full length sequence of human DGKα (Uniprot P23743) was optimized for expression in eukaryotic cells and synthesized by the GeneArt Technology at Life Technologies.

The DNA sequence encoded the following sequence:

Construct Dgka_Hu Amino Acid M1 to S735

Additionally the expression construct encoded: a Kozak DNA sequence for translation initiation (GCCACC), at the C-terminus a Flag (DYKDDDDK) sequence followed by two stop codons and additionally 5' and 3' att-DNA sequences for Gateway Cloning.

The DGKα construct was subcloned using the Gateway Technology into the Destination vector pD-INS. The vector pD-INS is a Baculovirus transfer vector (based on vector pVL1393, Pharmingen) which enables the expression of the DGK-Flag protein. The respective protein was named DNA_hu_1.

Additionally the DNA construct DGKa_hu with C-terminal Flag tag was also subcloned in to the Destination vector pD-INSA. This Baculovirus transfer vector is designed to fuse a His6 tag+Avi tag protein sequence to N-terminus of the DGKa_hu-Flag protein. The complete encoded protein was designated DGKa_hu_1Avi. The Avi-tag sequence enables a site-specific in-vitro biotinylation of the DGKα protein.

Generation of Recombinant Baculovirus

In separate approaches each of the two DGK transfer vectors was co-transfected in Sf9 cells with Baculovirus DNA (Flashbac Gold DNA, Oxford Expression Technologies) using Fugene HD (Roche). After 5 days the supernatant of the transfected cells containing the recombinant Baculovirus encoding the various DGK proteins was used for further infection of Sf9 cells for virus amplification whereby the virus titer was monitored using qPCR.

DGK Expression in Sf9 Cells Using Bioreactor

Sf9 cells cultured (Insect-xpress medium, Lonza, 27° C.) in a Wave-bioreactor with a disposable culture bag were infected at a cell density of $10^6$ cells/mL with one of the recombinant baculovirus stocks at a multiplicity of infection of 1 and incubated for 72. Subsequently the cells were harvested by centrifugation (800×g) and cell pellet frozen at −80° C.

To produce biotinylated DGKa_hu_1Avi the Sf9 cells in the bioreactor were co-infected with the Baculovirus encoding DGKa_hu_1Avi as well as with a Baculovirus encoding the biotinylation enzyme BirA.

Purification of the DGK-Flag Proteins:

Purification of the DGK-Flag proteins was achieved by a two-step chromatography procedure as follows.

The pelleted cells (from 8 L cell culture) were resuspended in Lysis-Buffer (50 mM Tris HCl 7.4; 150 mM NaCl; 10 mM $MgCl_2$; 1 μM $CaCl_2$; 1 mM DTT; 0.1% NP-40; 0.1% NP-40; Complete Protease Inhibitor Cocktail-(Roche)) and lysed by a freeze-thaw cycle followed by an incubation on ice for 60 min. The lysate was centrifuged at 63.000×g for 30 min. at 4° C. The soluble supernatant was than incubated with 25 mL anti-Flag M2 Agarose (Sigma) in a plastic flask rotating for 16 h at 4° C. for binding of the DGK-Fl ag proteins, subsequently rinsed with 10×25 mL Wash-Buffer (50 mM Tris HCl 7.4; 150 mM NaCl; 10 mM $MgCl_2$; 1 μM $CaCl_2$; 1 mM DTT) and finally the bound protein was eluted using Elusion-Buffer (Wash-Buffer with 300 μg/mL FLAG-Peptide, incubated 30 min. at 4° C. with 3×15 mL).

The elution fractions from the affinity chromatography were concentrated (using Amicon Ultra 15, Centrifugal Filters, 30 kDa MW cut-off; Millipore #UFC903024) to 10 mL and applied to a size exclusion chromatography column (S200 prep grade 26/60, GE Healthcare) and the resulting monomeric peak fraction was collected, pooled and again concentrated. Wash-buffer was used for size exclusion chromatography and the final concentrated sample. The final protein sample concentration was 5-10 mg/mL and the yield was 1-2 mg final protein per L cell culture. For DGKa_hu_1Avi a biotinylation level of 100% was demonstrated by mass spectromentry.

In Vivo Activation of Murine Antigen Specific OT1 T Cells

Oral Administration of compounds enhances antigen-specific T cell activation in vivo.

Direct detection of antigen-specific T cell proliferation in vivo is technically challenging, since it requires the presence of T cells specific for a cognate antigen and also a specific measurement procedure for cell proliferation. Both these requirements are fulfilled in the OT-1 transfer model, which utilizes the direct transfer of CD8 T cells transgenic for a T cell receptor recognizing an Ovalbumin-derived peptide as antigen. Before transfer, these cells are labeled with the fluorescent dye CFSE, which is diluted by every cell division and therefore allows detection of cell proliferation. After transfer of the CFSE-labeled T cells, mice are vaccinated with the Ovalbumin antigen OVA-30. Only transferred OT-1 cells are able to recognize the OVA-antigen presented by APC and only these transferred T cells then get activated. Flow cytometric analysis of CFSE-levels in the OT-1 cells can be combined with measurement of multiple activation markers like CD69, CD25 and PD1.

In particular, mice receive 2×10×6 CFSE-labeled OT-1 T cells and are vaccinated one day later by intravenous application of 2.5 μg OVA-30. Mice are then divided into groups which receive vehicle only, compound alone or in combination with other immune modulating agents. Mice are treated for 2 to 20 days and T cell composition (incl. transferred OT-1 cells) of spleen, blood and lymphodes are analysed by FACS.

In Vivo Syngeneic Tumor Models

Animals are assigned to a study at the age of 6-8 weeks. Animal husbandry, feeding and health conditions are according to animal welfare guidelines. Syngeinic tumor cell lines are cultivated with appropriate medium and splitted at least 3 times before inoculation. Female mice are inoculated with appropriate amount of tumor cells in medium or a medium/matrigel mixture s.c, i.v. or i.p depending on the model. After 4-10 days the animals are randomized and therapeutic treatment starts when tumors reach a size of approx. 40-70 mm2.

Tumor size is measured using calipers determining length (a) and width (b). Tumor volume is calculated according to:

$$v=(a\times b^2)/2$$

Significance of monotherapies and combination treatment is calculated versus control group as determined by 2-Way ANOVA analysis.

The invention claimed is:

1. A compound of general formula (I):

(I)

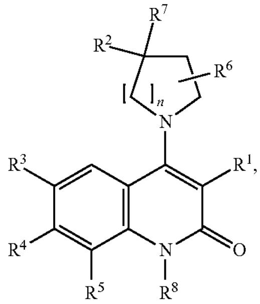

wherein:

$R^1$ is selected from the group consisting of cyano, —C(=O)$NH_2$, —C(=O)N(H)$CH_3$, —C(=O)N(H)$C_2H_5$, —C(=O)N$(CH_3)_2$, and —C(=O)$OR^{15}$;

$R^2$ is selected from the group consisting of phenyl, naphthyl, and 5- to 10-membered heteroaryl, wherein the 5- to 10-membered heteroaryl group is connected to the rest of the molecule via a carbon atom of said 5- to 10-membered heteroaryl group, wherein the phenyl, naphthyl, and 5- to 10-membered heteroaryl group each optionally substituted, one, two, three, or four times, wherein each substituent is independently selected from the group consisting of a halogen atom, $C_1$-$C_6$-alkyl, $C_3$-$C_6$-cycloalkyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_6$-haloalkoxy, $C_3$-$C_6$-cycloalkyloxy, phenoxy, —$SR^{14}$, —S(=O)$R^{14}$, —S(=O)$_2R^{14}$, —P(=O)$(R^{14})_2$, cyano, hydroxy, —N($R^9$)($R^{10}$), —C(=O)N($R^9$)($R^{10}$), —C(=O)$R^{11}$, —N($R^{12}$)C(=O)$R^{13}$, —N($R^{12}$)S(=O)$_2R^{14}$, —N=S(=NH)$(R^{14})_2$, —N=S(=O)$(R^{14})_2$, 4- to 7-membered heterocycloalkyl, 5- to 7-membered heterocycloalkenyl, (4- to 7-membered heterocycloalkyl)oxy, phenyl, and 5- or 6-membered heteroaryl, or two substituents of said phenyl group, when they are attached to adjacent ring atoms, are linked to one another in such a way that they jointly form a group selected from the group consisting of —$(CH_2)_3$—, —$CH_2$—CH(OH)—$CH_2$—, —$(CH_2)_4$—, —O—$(CH_2)_2$—, —$(CH_2)_2$—O—, —$CH_2$—CH($CH_3$)—O—, —$CH_2$—O—$CH_2$—, —O—$(CH_2)_3$—, —$(CH_2)_3$—O—, —$CH_2$—O—$(CH_2)_2$—, —$(CH_2)_2$—O—$CH_2$—, —O—$CH_2$—O—, —O—C$(CH_3)_2$—O—, —O—$(CH_2)_2$—O—, —N($R^{18}$)—C(=O)—(C($R^{18}$)($R^{19}$))$_m$—, —N($R^{18}$)—C(=O)—(C$(CH_3)_2$)—, —N($R^{18}$)—(C($R^{18}$)($R^{19}$))$_m$—, —N($R^{18}$)—C(=O)—O—, and —N($R^{18}$)—C(=O)—N($R^{18}$)—, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl and $C_1$-$C_6$-alkoxy groups are optionally substituted with a group selected from the group consisting of $C_3$-$C_4$-cycloalkyl, phenyl, and 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$), wherein the $C_3$-$C_4$-cycloalkyl group is optionally substituted, one or two times, wherein each substituent is independently selected from the group consisting of a halogen atom, cyano, and hydroxy, wherein said $C_3$-$C_6$-cycloalkyl group is optionally substituted, one or two times, wherein each substituent is independently a halogen atom or a $C_1$-$C_4$-alkyl group, and wherein said phenyl, phenoxy, and 5- or 6-membered heteroaryl group are optionally substituted, one or two times, each substituent independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N ($R^9$) ($R^{10}$);

$R^3$ is selected from the group consisting of a hydrogen atom, a halogen atom, $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, $C_3$-$C_6$-cycloalkyloxy, phenoxy, —$SR^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl, and 5- or 6-membered heteroaryl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl, $C_2$-$C_6$-alkenyl, $C_2$-$C_6$-alkynyl, and $C_1$-$C_6$-alkoxy groups are optionally substituted with a group selected from the group consisting of $C_3$-$C_4$-cycloalkyl, phenyl, and 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two, or three times, each substituent independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$), wherein the $C_3$-$C_4$-cycloalkyl group is optionally substituted, one or two times, each substituent independently selected from the group consisting of a halogen atom, cyano, and hydroxy, wherein said $C_2$-$C_6$-alkenyl group is optionally substituted with a $C_1$-$C_4$-haloalkyl group, wherein said $C_3$-$C_6$-cycloalkyl and $C_4$-$C_6$-cycloalkenyl groups are optionally substituted, one or two times, wherein each substituent is independently selected from the group consisting of a halogen atom, $C_1$-$C_4$-alkyl, and $C_1$-$C_4$-haloalkyl, wherein said phenyl, phenoxy, and 5- or 6-membered heteroaryl groups are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl and —N($R^9$)($R^{10}$);

$R^4$ is selected from the group consisting of a hydrogen atom, a halogen atom, $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_1$-$C_6$-alkoxy)-, $C_1$-$C_4$-haloalkoxy, —O—($C_1$-$C_4$-alkyl)-C(═O)$OR^{15}$, —O—($C_1$-$C_4$-alkyl)-C(═O)N($R^9$)($R^{10}$), $C_3$-$C_6$-cycloalkyloxy, —S(═O)$R^{14}$, —S(═O)$_2$ $R^{14}$, cyano, nitro, hydroxy, —N($R^9$)($R^{10}$), —N($R^{16}$)($R^{17}$), —N($R^{16}$)($R^{20}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl, and 5- or 6-membered heteroaryl, wherein said 4- to 7-membered heterocycloalkyl group and 5- to 7-membered heterocycloalkenyl group are connected to the rest of the molecule via a carbon atom of said 4- to 7-membered heterocycloalkyl group, or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl, $C_2$-$C_6$-alkenyl, $C_2$-$C_6$-alkynyl, and $C_1$-$C_6$-alkoxy groups are optionally substituted with $C_3$-$C_4$-cycloalkyl or 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the $C_3$-$C_4$-cycloalkyl group is optionally substituted, one or two times, wherein each substituent is independently selected from a halogen atom, cyano, and hydroxy, wherein said $C_1$-$C_6$-alkoxy group is optionally substituted with an oxiran-2-yl group, wherein said $C_3$-$C_6$-cycloalkyl and $C_4$-$C_6$-cycloalkenyl groups are optionally substituted, one or two times, wherein each substituent is independently a halogen atom or a $C_1$-$C_4$-alkyl group, wherein said phenyl and 5- or 6-membered heteroaryl groups are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^5$ is selected from the group consisting of a hydrogen atom, a halogen atom, $C_1$-$C_6$-alkyl, $C_2$-$C_6$-alkenyl, $C_2$-$C_6$-alkynyl, $C_3$-$C_6$-cycloalkyl, $C_4$-$C_6$-cycloalkenyl, $C_1$-$C_6$-hydroxyalkyl, $C_1$-$C_6$-haloalkyl, ($C_1$-$C_2$-alkoxy)-($C_1$-$C_6$-alkyl)-, $C_1$-$C_6$-alkoxy, ($C_1$-$C_2$ alkoxy)-($C_2$-$C_6$-alkoxy)-, $C_1$-$C_4$-haloalkoxy, $C_3$-$C_6$-cycloalkyloxy, phenoxy, —$SR^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl, and 5- or 6-membered heteroaryl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl, $C_2$-$C_6$-alkenyl, $C_2$-$C_6$-alkynyl, and $C_1$-$C_6$-alkoxy groups are optionally substituted with a group selected from the group consisting of $C_3$-$C_4$-cycloalkyl, phenyl, and 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two, or three times, wherein each substituent is independently selected from the group consisting of a halogen atom, —$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$), and wherein the $C_3$-$C_4$-cycloalkyl group is optionally substituted, one or two times, wherein each substituent is independently selected from the group consisting of a halogen atom, cyano, and hydroxy, wherein said $C_3$-$C_6$-cycloalkyl and $C_4$-$C_6$-cycloalkenyl groups are optionally substituted, one or two times, wherein each substituent is independently a halogen atom or a $C_1$-$C_4$-alkyl group, wherein said phenyl, phenoxy, and 5- or 6-membered heteroaryl groups are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^6$ is selected from the group consisting of a hydrogen atom, a fluorine atom, $C_1$-$C_4$-alkyl, $C_1$-$C_4$-hydroxyalkyl, $C_1$-$C_4$-alkoxy, hydroxy, and oxo;

$R^7$ is selected from the group consisting of a hydrogen atom, a halogen atom, $C_1$-$C_4$-alkyl, $C_1$-$C_4$-alkoxy, hydroxy, and cyano;

$R^8$ is methyl or ethyl;

$R^9$ and $R^{10}$ are each independently selected from the group consisting of a hydrogen atom, $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)-, $C_3$-$C_4$-cycloalkyl and $C_2$-$C_4$-haloalkyl, or $R^9$ and $R^{10}$ together with the nitrogen to which they are attached form a nitrogen containing 4- to 7-membered heterocycloalkyl group, wherein said nitrogen containing 4- to 7-membered heterocycloalkyl group is optionally substituted, one, two, or three times, wherein each substituent is independently selected from the group consisting of a halogen atom, $C_1$-$C_4$-alkyl, $C_3$-$C_4$-cycloalkyl, hydroxy and oxo, or two substituents, which are attached to the same carbon atom of said nitrogen containing 4- to 7-membered heterocycloalkyl group, together with the carbon atom to which they are attached, form a 4- to 7-membered heterocycloalkyl group, wherein said 4- to 7-membered heterocycloalkyl group is optionally substituted, one or two times, wherein each substituent is independently selected from the group consisting of a halogen atom, $C_1$-$C_4$-alkyl, $C_3$-$C_4$-cycloalkyl, $C_1$-$C_4$-haloalkyl, hydroxy, and oxo;

$R^{11}$ is selected from the group consisting of a hydrogen atom, $C_1$-$C_4$-alkyl, $C_1$-$C_4$-hydroxyalkyl, $C_1$-$C_4$-haloalkyl, phenyl, and 5- or 6-membered heteroaryl, wherein said phenyl group and 5- or 6-membered heteroaryl group are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^{12}$ is a hydrogen atom or a $C_1$-$C_4$-alkyl group;

$R^{13}$ is selected from the group consisting of a hydrogen atom, $C_1$-$C_6$-alkyl, phenyl, and 5- or 6-membered heteroaryl, wherein said phenyl group and 5- or 6-membered heteroaryl group are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^{14}$ is selected from the group consisting of $C_1$-$C_6$-alkyl, $C_1$-$C_6$-haloalkyl, $C_3$-$C_6$-cycloalkyl, phenyl, and 5- or 6-membered heteroaryl, wherein said phenyl group and 5- or 6-membered heteroaryl group are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^{15}$ is a hydrogen atom or a $C_1$-$C_4$-alkyl group;

$R^{16}$ is selected from the group consisting of a hydrogen atom, $C_1$-$C_4$-alkyl, $C_3$-$C_4$-cycloalkyl, and $C_2$-$C_4$-haloalkyl;

$R^{17}$ is a 4- to 7-membered heterocycloalkyl group, wherein said 4- to 7-membered heterocycloalkyl group is optionally substituted, one, two, or three times, wherein each substituent is independently selected from the group consisting of a halogen atom, $C_1$-$C_4$-alkyl, $C_3$-$C_4$-cycloalkyl, $C_1$-$C_4$-alkoxy, hydroxy and oxo, wherein said 4- to 7-membered heterocycloalkyl group is connected to the rest of the molecule via a carbon atom of the 4- to 7-membered heterocycloalkyl group;

$R^{18}$ is selected from the group consisting of a hydrogen atom, methyl, and ethyl;

$R^{19}$ is selected from the group consisting of a hydrogen atom, methyl, and ethyl;

$R^{20}$ is a (4- to 7-membered heterocycloalkyl)-($C_1$-$C_4$-alkyl)-group, wherein the (4- to 7-membered heterocycloalkyl) part of said group is optionally substituted, one, two, or three times, wherein each substituent is independently selected from the group consisting of a halogen atom, $C_1$-$C_4$-alkyl, $C_3$-$C_4$-cycloalkyl, $C_1$-$C_4$-alkoxy, hydroxy, and oxo;

m is 1, 2, or 3; and n is 1, 2, or 3, or a stereoisomer, a tautomer, an N-oxide, a hydrate, a solvate, or a salt thereof, or a mixture of any of the foregoing.

2. The compound according to claim 1, wherein:

$R^1$ is selected from the group consisting of cyano, —C(═O)$NH_2$, —C(═O)N(H)$CH_3$, —C(═O)N(H)$C_2H_5$, —C(═O)N$(CH_3)_2$, and —C(═O)$OR^{15}$;

$R^2$ is selected from the group consisting of phenyl, naphthyl, and 5-10-membered heteroaryl, wherein the 5- to 10-membered heteroaryl group is connected to the rest of the molecule via a carbon atom of said 5- to 10-membered heteroaryl group, wherein phenyl, naphthyl, and 5- to 10-membered heteroaryl groups are optionally substituted, one, two, three, or four times, wherein each substituent is independently selected from the group consisting of a halogen atom, $C_1$-$C_6$-alkyl, $C_3$-$C_5$-cycloalkyl, $C_1$-$C_6$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —$SR^{14}$, —S(═O)$R^{14}$, —S(═O)$_2R^{14}$, —P(═O)$(R^{14})_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$) S(═O)$_2R^{14}$, —N═S(═NH)$(R^{14})_2$, —N═S(═O)$(R^{14})_2$, 4- to 7-membered heterocycloalkyl, 5- to 7-membered heterocycloalkenyl, (4- to 7-membered heterocycloalkyl)oxy, phenyl, and 5- or 6-membered heteroaryl, or two substituents of said phenyl group, when they are attached to adjacent ring atoms, are linked to one another in such a way that they jointly form a group selected from the group consisting of $(CH_2)_3$—, —$CH_2$—CH(OH)—$CH_2$—, —$(CH_2)_4$—, —O—$(CH_2)_2$—, —$(CH_2)_2$—O—, —$CH_2$—CH($CH_3$)—O—, —$CH_2$—O—$CH_2$—, —O—$(CH_2)_3$—, —$(CH_2)_3$—O—, —$CH_2$—O—$(CH_2)_2$—, $(CH_2)_2$—O—$CH_2$—, —O—$CH_2$—O—, —O—C$(CH_3)_2$—O—, —O—$(CH_2)_2$—O—, —N($R^{18}$)—C(═O)—(C($R^{18}$)($R^{19}$))$_m$—, —N($R^{18}$)—C(═O)—(C$(CH_3)_2$)—, —N($R^{18}$)—(C($R^{18}$)($R^{19}$))$_m$—, —N($R^{18}$)—C(═O)—O—, and —N($R^{18}$)—C(═O)—N($R^{18}$)—, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl) oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl and $C_1$-$C_4$-alkoxy groups are optionally substituted with a group selected from the group consisting of $C_3$-$C_4$-cycloalkyl, phenyl, and 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$), wherein the $C_3$-$C_4$-cycloalkyl group is optionally substituted, one or two times, wherein each substituent is independently selected from the group consisting of a halogen atom, cyano, and hydroxy, wherein said $C_3$-$C_5$-cycloalkyl group is optionally substituted, one or two times, wherein each substituent is independently a halogen atom or a $C_1$-$C_4$-alkyl group, and wherein said phenyl, phenoxy, and 5- or 6-membered heteroaryl group are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^3$ is selected from the group consisting of a hydrogen atom, a halogen atom, $C_1$-$C_6$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, $C_3$-$C_5$-cycloalkyloxy, phenoxy, —$SR^{14}$, —S(═O)$R^{14}$, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)$(R^{14})_2$, —N═S(═O)$(R^{14})_2$, —P(═O)$(R^{14})_2$, 4- to 7-membered heterocycloalkyl, 5- to 7-membered heterocycloalkenyl, (4- to 7-membered heterocycloalkyl)oxy, phenyl, and 5- or 6-membered heteroaryl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, each substituent independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl, $C_2$-$C_4$-alkenyl, $C_2$-$C_4$-alkynyl, and $C_1$-$C_4$-alkoxy groups is optionally substituted with a group selected from the group consisting of $C_3$-$C_4$-cycloalkyl, phenyl, and 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two, or three times, each substituent independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$), wherein the $C_3$-$C_4$-cycloalkyl group is optionally substituted, one or two times, wherein each substituent is independently selected from the group consisting of a halogen atom, cyano, and hydroxy, wherein said $C_2$-$C_4$-alkenyl group is optionally substituted with a $C_1$-$C_4$-haloalkyl group, wherein said $C_3$-$C_5$-cycloalkyl and $C_4$-$C_5$-cycloalkenyl groups are optionally substituted, one or two times, wherein each substituent is independently selected from the group consisting of a halogen atom, $C_1$-$C_4$-alkyl, and $C_1$-$C_4$-haloalkyl, wherein said phenyl, phenoxy, and 5- or 6-membered heteroaryl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^4$ is selected from the group consisting of a hydrogen atom, a halogen atom, $C_1$-$C_6$-alkyl, $C_1$-$C_6$-haloalkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_5$-hydroxyalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, $C_1$-$C_4$-haloalkoxy, —O—($C_1$-$C_4$-alkyl)-C(═O)O$R^{15}$, —O—($C_1$-$C_4$-alkyl)-C(═O)N($R^9$)($R^{10}$), $C_3$-$C_5$-cycloalkyloxy, —S(═O)$R^{14}$, —S(═O)$_2$$R^{14}$, cyano, nitro, hydroxy, —N($R^9$)($R^{10}$), —N($R^{16}$)($R^{17}$), —N($R^{16}$)($R^{20}$), —C(═O)N($R^9$)($R^{10}$), —C(═O)$R^{11}$, —N($R^{12}$)C(═O)$R^{13}$, —N($R^{12}$)S(═O)$_2$$R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl, and 5- or 6-membered heteroaryl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl, $C_2$-$C_4$-alkenyl, $C_2$-$C_4$-alkynyl, and $C_1$-$C_4$-alkoxy groups are optionally substituted with a group selected from the group consisting of $C_3$-$C_4$-cycloalkyl and 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the $C_3$-$C_4$-cycloalkyl group is optionally substituted, one or two times, wherein each substituent is independently selected from the group consisting of a halogen atom, cyano, and hydroxy, wherein said $C_1$-$C_4$-alkoxy group is optionally substituted with an oxiran-2-yl group, wherein said $C_3$-$C_5$-cycloalkyl and $C_4$-$C_6$-cycloalkenyl groups are optionally substituted, one or two times, wherein each substituent is independently selected from the group consisting of a halogen atom and a $C_1$-$C_4$-alkyl group, and wherein said phenyl and 5- or 6-membered heteroaryl group are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^5$ is selected from the group consisting of a hydrogen atom, a halogen atom, $C_1$-$C_5$-alkyl, $C_2$-$C_4$-alkenyl, $C_2$-$C_4$-alkynyl, $C_3$-$C_5$-cycloalkyl, $C_4$-$C_5$-cycloalkenyl, $C_1$-$C_4$-hydroxyalkyl, $C_1$-$C_4$-haloalkyl, ($C_1$-$C_2$-alkoxy)-($C_1$-$C_4$-alkyl)-, $C_1$-$C_4$-alkoxy, ($C_1$-$C_2$ alkoxy)-($C_2$-$C_4$-alkoxy)-, $C_1$-$C_4$-haloalkoxy, $C_3$-$C_5$-cycloalkyloxy, phenoxy, —S$R^{14}$, —S(═O)$R^{14}$, —S(═O)$_2$$R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$$R^{14}$, —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, phenyl, and 5- or 6-membered heteroaryl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_5$-alkyl, $C_2$-$C_4$-alkenyl, $C_2$-$C_4$-alkynyl, and $C_1$-$C_4$-alkoxy group are optionally substituted with a group selected from the group consisting of $C_3$-$C_4$-cycloalkyl, phenyl, and 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two or three times, wherein each substituent is independently selected from a halogen atom or a group selected from the group consisting of $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$), wherein the $C_3$-$C_4$-cycloalkyl group is optionally substituted, one or two times, wherein each substituent is independently selected from the group consisting of a halogen atom, cyano, and hydroxy, wherein said $C_3$-$C_5$-cycloalkyl and $C_4$-$C_5$-cycloalkenyl groups are optionally substituted, one or two times, wherein each substituent is independently a halogen atom or a $C_1$-$C_4$-alkyl group, wherein said phenyl, phenoxy, and 5- or 6-membered heteroaryl groups are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^6$ is selected from the group consisting of a hydrogen atom, a fluorine atom, $C_1$-$C_4$-alkyl, $C_1$-$C_4$-hydroxyalkyl, $C_1$-$C_4$-alkoxy, hydroxy, and oxo;

$R^7$ is selected from the group consisting of a hydrogen atom, a halogen atom, $C_1$-$C_4$-alkyl, $C_1$-$C_4$-alkoxy, hydroxy, and cyano;

$R^8$ methyl or ethyl; $R^8$ $R^9$ and $R^{10}$ are each independently selected from the group consisting of a hydrogen atom, $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)-, $C_3$-$C_4$-cycloalkyl, and $C_2$-$C_4$-haloalkyl, or $R^9$ and $R^{10}$ together with the nitrogen to which they are attached form a nitrogen containing 4- to 7-membered heterocycloalkyl group, wherein said nitrogen containing 4- to 7-membered heterocycloalkyl group is optionally substituted, one, two, or three times, wherein each substituent is independently selected from the group consisting of a halogen atom, $C_1$-$C_4$-alkyl, $C_3$-$C_4$-cycloalkyl, hydroxy, and oxo, or two substituents, which are attached to the same carbon atom of said nitrogen containing 4- to 7-membered heterocycloalkyl group, together with the carbon atom to which they are attached, form a 4- to 7-membered heterocycloalkyl group, wherein said 4- to 7-membered heterocycloalkyl group is optionally substituted, one or two times, wherein each substituent is independently selected from the group consisting of a halogen atom, $C_1$-$C_4$-alkyl, $C_3$-$C_4$-cycloalkyl, $C_1$-$C_4$-haloalkyl, hydroxy, and oxo;

$R^{11}$ is selected from the group consisting of a hydrogen atom, $C_1$-$C_4$-alkyl, $C_1$-$C_4$-hydroxyalkyl, $C_1$-$C_4$-haloalkyl, phenyl, and 5- or 6-membered heteroaryl, wherein said phenyl group and 5- or 6-membered heteroaryl group are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^{12}$ is a hydrogen atom or a $C_1$-$C_4$-alkyl group;

$R^{13}$ is selected from the group consisting of a hydrogen atom, $C_1$-$C_4$-alkyl, phenyl, and 5- or 6-membered heteroaryl, wherein said phenyl group and 5- or 6-membered heteroaryl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^{14}$ is selected from the group consisting of $C_1$-$C_4$-alkyl, $C_1$-$C_4$-haloalkyl, $C_3$-$C_5$-cycloalkyl, phenyl, and 5- or 6-membered heteroaryl, wherein said phenyl group and 5- or 6-membered heteroaryl group are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^{15}$ is a hydrogen atom or a $C_1$-$C_4$-alkyl group;

$R^{16}$ is selected from the group consisting of a hydrogen atom, $C_1$-$C_4$-alkyl, $C_3$-$C_4$-cycloalkyl, and $C_2$-$C_4$-haloalkyl;

$R^{17}$ is a 4- to 7-membered heterocycloalkyl group, wherein said 4- to 7-membered heterocycloalkyl group is optionally substituted, one, two, or three times, wherein each substituent is independently selected from the group consisting of a halogen atom, $C_1$-$C_4$-alkyl, $C_3$-$C_4$-cycloalkyl, $C_1$-$C_4$-alkoxy, hydroxy, and oxo;

and wherein said 4- to 7-membered heterocycloalkyl group is connected to the rest of the molecule via a carbon atom of the 4- to 7-membered heterocycloalkyl group;

$R^{18}$ is selected from the group consisting of a hydrogen atom, methyl, and ethyl;

$R^{19}$ is selected from the group consisting of a hydrogen atom, methyl, and ethyl;

$R^{20}$ is a (4- to 7-membered heterocycloalkyl)-($C_1$-$C_4$-alkyl)-group, wherein the (4- to 7-membered heterocycloalkyl) part of said group is optionally substituted, one, two, or three times, each substituent independently selected from the group consisting of a halogen atom, $C_1$-$C_4$-alkyl, $C_3$-$C_4$-cycloalkyl, $C_1$-$C_4$-alkoxy, hydroxy, and oxo;

m is 1, 2, or 3; and n is 1, 2, or 3, or a stereoisomer, a tautomer, an N-oxide, a hydrate, a solvate, or a salt thereof, or a mixture of any of the foregoing.

3. The compound according to claim 1, wherein:

$R^1$ is selected from the group consisting of cyano, —C(═O)$NH_2$, —C(═O)N(H)$CH_3$, —C(═O)N(H)$C_2H_5$, —C(═O)N$(CH_3)_2$, and —C(═O)$OR^{15}$;

$R^2$ is selected from group consisting of phenyl, naphthyl, and 5- to 10-membered heteroaryl, which 5- to 10-membered heteroaryl group is connected to the rest of the molecule via a carbon atom of said 5- to 10-membered heteroaryl group, wherein phenyl, naphthyl, and 5- to 10-membered heteroaryl group is optionally substituted, one, two, three, or four times, wherein each substituent is independently selected from the group consisting of a halogen atom, $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(═O)$_2R^{14}$, —P(═O)$(R^{14})_2$, cyano, hydroxy, —N$(R^9)(R^{10})$, —C(═O)N$(R^9)(R^{10})$, —C(═O)$R^{11}$, —N$(R^{12})$C(═O)$R^{13}$, —N$(R^{12})$S(═O)$_2R^{14}$, —N═S(═O)$(R^{14})_2$, 4- to 7-membered heterocycloalkyl, phenyl, and 5- or 6-membered heteroaryl, or two substituents of said phenyl group, when they are attached to adjacent ring atoms, are linked to one another in such a way that they jointly form a group selected from the group consisting of —$CH_2$—CH(OH)—$CH_2$—, —$CH_2$—CH($CH_3$)—O—, —O—C$(CH_3)_2$—O—, —N$(R^{18})$—C(═O)—(C$(R^{18})(R^{19}))_m$—, —N$(R^{18})$—C(═O)—(C$(CH_3)_2$)—, —N$(R^{18})$—(C$(R^{18})(R^{19}))_m$—, —N$(R^{18})$—C(═O)—O—, and —N$(R^{18})$—C(═O)—N$(R^{18})$—, wherein said 4- to 7-membered heterocycloalkyl group is connected to the rest of the molecule via a carbon atom of said 4- to 7-membered heterocycloalkyl group, wherein said $C_1$-$C_4$-alkoxy group is optionally substituted with phenyl or 4- to 7-membered heterocycloalkyl, wherein said 4- to 7-membered heterocycloalkyl group is connected to the rest of the molecule via a carbon atom of said 4- to 7-membered heterocycloalkyl group, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N$(R^9)(R^{10})$, wherein said phenyl, phenoxy, and 5- or 6-membered heteroaryl groups are optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N$(R^9)(R^{10})$;

$R^3$ is selected from the group consisting of a hydrogen atom, a halogen atom, $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2R^{14}$, cyano, hydroxy, —N$(R^9)(R^{10})$, —C(═O)N$(R^9)(R^{10})$, —P(═O)$(R^{14})_2$, 4- to 7-membered heterocycloalkyl, 5- to 7-membered heterocycloalkenyl, (4- to 7-membered heterocycloalkyl)oxy, and phenyl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, and wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N$(R^9)(R^{10})$, and oxo, wherein said $C_1$-$C_6$-alkyl and $C_1$-$C_4$-alkoxy groups are optionally substituted with $C_3$-$C_4$-cycloalkyl or 4- to 7-membered heterocycloalkyl, wherein said 4- to 7-membered heterocycloalkyl group is connected to the rest of the molecule via a carbon atom of said 4- to 7-membered heterocycloalkyl group, and wherein said 4- to 7-membered heterocycloalkyl group is optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N$(R^9)(R^{10})$, and oxo, wherein $C_3$-$C_4$-cycloalkyl group is optionally substituted, one or two times, wherein each substituent is independently selected from a halogen atom, cyano, and hydroxy, wherein said $C_2$-$C_4$-alkenyl group is optionally substituted with a $C_1$-$C_4$-haloalkyl group, wherein said $C_3$-$C_5$-cycloalkyl group is optionally substituted, one or two times, wherein each substituent is independently selected from the group consisting of a halogen atom, $C_1$-$C_4$-alkyl, and $C_1$-$C_4$-haloalkyl;

$R^4$ is selected from the group consisting of a hydrogen atom, a halogen atom, $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—($C_1$-$C_4$-alkyl)-C(═O)$OR^{15}$, —O—($C_1$-$C_4$-alkyl)-C(═O)N$(R^9)(R^{10})$, $C_3$-$C_5$-cycloalkyloxy, —S(═O)$_2R^{14}$, cyano, nitro, hydroxy, —N$(R^9)(R^{10})$, —N$(R^{16})(R^{17})$, —N$(R^{16})(R^{20})$, —N═S(═NH)$(R^{14})_2$, —N═S(═O)$(R^{14})_2$, —P(═O)$(R^{14})_2$, 4- to 7-membered heterocycloalkyl, 5- to 7-membered heterocycloalkenyl, (4- to 7-membered heterocycloalkyl)oxy, and phenyl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_6$-alkyl and $C_1$-$C_4$-alkoxy group are optionally substituted with $C_3$-$C_4$-cycloalkyl or 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the $C_3$-$C_4$-cycloalkyl group is optionally substituted, one or two times, wherein each substituent is independently selected from the group consisting of a halogen atom, cyano, and hydroxy, wherein said $C_1$-$C_4$-alkoxy group is optionally substituted with an oxiran-2-yl group, wherein said $C_3$-$C_5$-cycloalkyl group is optionally substituted, one or two times, wherein each substituent is independently a halogen atom or a $C_1$-$C_4$-alkyl group, and wherein said phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^5$ is selected from the group consisting of a hydrogen atom, a halogen atom, $C_1$-$C_5$-alkyl, $C_3$-$C_5$-cycloalkyl, $C_1$-$C_4$-alkoxy, $C_3$-$C_5$-cycloalkyloxy, —S(═O)$_2R^{14}$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2$ $R^{14}$, —N═S(═NH)($R^{14}$)$_2$, —N═S(═O)($R^{14}$)$_2$, —P(═O)($R^{14}$)$_2$, 4- to 7-membered heterocycloalkyl, and (4- to 7-membered heterocycloalkyl)oxy, wherein said 4- to 7-membered heterocycloalkyl group is connected to the rest of the molecule via a carbon atom of said 4- to 7-membered heterocycloalkyl group, and wherein said 4- to 7-membered heterocycloalkyl group, 5- to 7-membered heterocycloalkenyl group, and (4- to 7-membered heterocycloalkyl)oxy group are optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein said $C_1$-$C_5$-alkyl and $C_1$-$C_4$-alkoxy groups are optionally substituted with a group selected from the group consisting of $C_3$-$C_4$-cycloalkyl, phenyl, and 4- to 7-membered heterocycloalkyl, wherein said 4- to 7-membered heterocycloalkyl group is connected to the rest of the molecule via a carbon atom of said 4- to 7-membered heterocycloalkyl group, wherein said 4- to 7-membered heterocycloalkyl group is optionally substituted, one, two, or three times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, —N($R^9$)($R^{10}$), and oxo, wherein the phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$), wherein the $C_3$-$C_4$-cycloalkyl group is optionally substituted, one or two times, wherein each substituent is independently selected from the group consisting of a halogen atom, cyano, and hydroxy, wherein said $C_3$-$C_5$-cycloalkyl group is optionally substituted, one or two times, wherein each substituent is independently a halogen atom or a $C_1$-$C_4$-alkyl group;

$R^6$ is selected from the group consisting of a hydrogen atom, $C_1$-$C_4$-alkyl, $C_1$-$C_4$-hydroxyalkyl, $C_1$-$C_4$-alkoxy, hydroxy, and oxo;

$R^7$ is selected from the group consisting of a hydrogen atom, a halogen atom, $C_1$-$C_4$-alkyl, $C_1$-$C_4$-alkoxy, and hydroxy;

$R^8$ is methyl or ethyl;

$R^9$ and $R^{10}$ are each independently selected from the group consisting of a hydrogen atom, $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)-, and $C_3$-$C_4$-cycloalkyl, or $R^9$ and $R^{10}$ together with the nitrogen to which they are attached form a nitrogen containing 4- to 7-membered heterocycloalkyl group, wherein said nitrogen containing 4- to 7-membered heterocycloalkyl group is optionally substituted, one, two, or three times, wherein each substituent is independently selected from the group consisting of a halogen atom, $C_1$-$C_4$-alkyl, $C_3$-$C_4$-cycloalkyl, hydroxy, and oxo, or two substituents, which are attached to the same carbon atom of said nitrogen containing 4- to 7-membered heterocycloalkyl group, together with the carbon atom to which they are attached, form a 4- to 7-membered heterocycloalkyl group, wherein said 4- to 7-membered heterocycloalkyl group is optionally substituted, one or two times, wherein each substituent is independently selected from the group consisting of a halogen atom, $C_1$-$C_4$-alkyl, $C_3$-$C_4$-cycloalkyl, $C_1$-$C_4$-haloalkyl, hydroxy, and oxo;

$R^{11}$ is selected from the group consisting of a hydrogen atom, $C_1$-$C_4$-alkyl, and $C_1$-$C_4$-haloalkyl;

$R^{12}$ is a hydrogen atom;

$R^{13}$ is a phenyl group;

$R^{14}$ is $C_1$-$C_4$-alkyl or phenyl, wherein said phenyl group is optionally substituted, one or two times, wherein each substituent is independently selected from the group consisting of a halogen atom, $C_1$-$C_2$-alkyl, $C_1$-$C_2$-haloalkyl, cyano, hydroxy, $C_1$-$C_2$-alkoxy, $C_3$-$C_4$-cycloalkyl, and —N($R^9$)($R^{10}$);

$R^{15}$ is a hydrogen atom or a $C_1$-$C_4$-alkyl group;

$R^{16}$ is a hydrogen atom or a $C_1$-$C_4$-alkyl group;

$R^{17}$ is a 4- to 7-membered heterocycloalkyl group, wherein said 4- to 7-membered heterocycloalkyl group is optionally substituted, one or two times, with a $C_1$-$C_4$-alkyl group, wherein said 4- to 7-membered heterocycloalkyl group is connected to the rest of the molecule via a carbon atom of the 4- to 7-membered heterocycloalkyl group;

$R^{18}$ is a hydrogen atom or a methyl group;

$R^{19}$ is a hydrogen atom or a methyl group;

$R^{20}$ is a (4- to 7-membered heterocycloalkyl)-($C_1$-$C_4$-alkyl)-group, wherein the (4- to 7-membered heterocycloalkyl) part of said group is optionally substituted, one or two times, with a $C_1$-$C_4$-alkyl group;

m 1 or 2;

and n is 1, 2, or 3, or a stereoisomer, a tautomer, an N-oxide, a hydrate, a solvate, or a salt thereof, or a mixture of any of the foregoing.

4. The compound according to claim 1, wherein:

$R^1$ is selected from the group consisting of cyano, —C(═O)$NH_2$, —C(═O)N(H)$CH_3$, and —C(═O) $N(CH_3)_2$;

$R^2$ selected from the group consisting of phenyl, naphthyl, and 5- to 10-membered heteroaryl, wherein the 5- to 10-membered heteroaryl group is connected to the rest of the molecule via a carbon atom of said 5- to 10-membered heteroaryl group, wherein phenyl, naphthyl, and 5- to 10-membered heteroaryl group is optionally substituted, one, two, three, or four times, wherein each substituent is independently selected from the group consisting of a halogen atom, $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(═O)$_2R^{14}$, —P(═O)$(R^{14})_2$, cyano, hydroxy, —N($R^9$)($R^{10}$), —C(═O)N($R^9$)($R^{10}$), —C(═O)$R^{11}$, —N($R^{12}$)C(═O)$R^{13}$, —N($R^{12}$)S(═O)$_2R^{14}$, —N═S(═O)$(R^{14})_2$, 4- to 7-membered heterocycloalkyl, phenyl, and 5- or 6-membered heteroaryl, or two substituents of said phenyl group, when they are attached to adjacent ring atoms, are linked to one another in such a way that they jointly form a group selected from the group consisting of —$CH_2$—CH (OH)—$CH_2$—, —$CH_2$—CH($CH_3$)—O—, —O—C $(CH_3)_2$—O—, —N($R^{18}$)—C(═O)—(C($R^{18}$) $(R^{19}))_m$—, —N($R^{18}$)—C(═O)—(C$(CH_3)_2$)—, —N($R^{18}$)—(C($R^{18}$)$(R^{19}))_m$—, —N($R^{18}$)—C (═O)—O—, and —N($R^{18}$)—C(═O)—N($R^{18}$)—, wherein said 4- to 7-membered heterocycloalkyl group is connected to the rest of the molecule via a carbon atom of said 4- to 7-membered heterocycloalkyl group, wherein said $C_1$-$C_4$-alkoxy group is optionally substituted with 4- to 7-membered heterocycloalkyl or phenyl, wherein said 4- to 7-membered heterocycloalkyl group is connected to the rest of the molecule via a carbon atom of said 4- to 7-membered heterocycloalkyl group, wherein said phenyl and 5- or 6-membered heteroaryl group is optionally substituted, one or two times, wherein each substituent is independently selected from the group consisting of a halogen atom, $C_1$-$C_2$-alkyl, $C_1$-$C_2$-haloalkyl, and $C_1$-$C_2$-alkoxy;

$R^3$ is selected from the group consisting of a hydrogen atom, a halogen atom, $C_1$-$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(═O)$_2R^{14}$, cyano, hydroxy, —N($R^9$)($R^{10}$), —C(═O)N($R^9$)($R^{10}$), —P(—O) $(R^{14})_2$, 4- to 7-membered heterocycloalkyl, 5- to 7-membered heterocycloalkenyl, (4- to 7-membered heterocycloalkyl)oxy, and phenyl, wherein said 4- to 7-membered heterocycloalkyl group and 5- to 7-membered heterocycloalkenyl group are connected to the rest of the molecule via a carbon atom of said 4- to 7-membered heterocycloalkyl group and 5- to 7-membered heterocycloalkenyl group, wherein said $C_1$-$C_6$-alkyl and $C_1$-$C_4$-alkoxy groups are optionally substituted with $C_3$-$C_4$-cycloalkyl or 4- to 7-membered heterocycloalkyl, wherein said 4- to 7-membered heterocycloalkyl group is connected to the rest of the molecule via a carbon atom of said 4- to 7-membered heterocycloalkyl group, wherein the $C_3$-$C_4$-cycloalkyl group is optionally substituted, one or two times, with a cyano group, wherein said $C_2$-$C_4$-alkenyl group is optionally substituted with a $C_1$-$C_4$-haloalkyl group, wherein said $C_3$-$C_5$-cycloalkyl group is optionally substituted, one or two times, wherein each substituent is independently selected from the group consisting of a halogen atom, $C_1$-$C_4$-alkyl, and $C_1$-$C_4$-haloalkyl;

$R^4$ is selected from the group consisting of a hydrogen atom, a halogen atom, $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—($C_1$-$C_4$-alkyl)-C(═O)O$R^{15}$, —O—($C_1$-$C_4$-alkyl)-C (═O)N($R^9$)($R^{10}$), $C_3$-$C_5$-cycloalkyloxy, —S(═O)$_2$ $R^{14}$, cyano, nitro, hydroxy, —N($R^9$)($R^{10}$), —N($R^{16}$) ($R^{17}$), —N($R^{16}$)($R^{20}$), —N═S(═NH)$(R^{14})_2$, —N═S (═O)$(R^{14})_2$, —P(═O)$(R^{14})_2$, 4- to 7-membered heterocycloalkyl, 5- to 7-membered heterocycloalkenyl, (4- to 7-membered heterocycloalkyl)oxy, and phenyl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said $C_1$-$C_6$-alkyl and $C_1$-$C_4$-alkoxy groups are optionally substituted with $C_3$-$C_4$-cycloalkyl or 4- to 7-membered heterocycloalkyl, wherein said 4- to 7-membered heterocycloalkyl group is connected to the rest of the molecule via a carbon atom of said 4- to 7-membered heterocycloalkyl group, wherein the $C_3$-$C_4$-cycloalkyl group is optionally substituted, one or two times, wherein each substituent is independently selected from the group consisting of a halogen atom, cyano, and hydroxy, wherein said $C_1$-$C_4$-alkoxy group is optionally substituted with an oxiran-2-yl group, wherein said $C_3$-$C_5$-cycloalkyl is optionally substituted, one or two times, wherein each substituent is independently a halogen atom or a $C_1$-$C_4$-alkyl group;

$R^5$ is selected from the group consisting of a hydrogen atom, a halogen atom, $C_1$-$C_5$-alkyl, $C_3$-$C_5$-cycloalkyl, $C_1$-$C_4$-alkoxy, $C_3$-$C_5$-cycloalkyloxy, —S(═O)$_2R^{14}$, cyano, hydroxy, —$N(R^9)(R^{10})$, 4- to 7-membered heterocycloalkyl, and (4- to 7-membered heterocycloalkyl)oxy, wherein said 4- to 7-membered heterocycloalkyl group is connected to the rest of the molecule via a carbon atom of said 4- to 7-membered heterocycloalkyl group;

$R^6$ is selected from the group consisting of a hydrogen atom, $C_1$-$C_4$-alkyl, and $C_1$-$C_4$-hydroxyalkyl;

$R^7$ is selected from the group consisting of a hydrogen atom, a halogen atom, $C_1$-$C_4$-alkyl, $C_1$-$C_4$-alkoxy, and hydroxy;

$R^8$ is methyl or ethyl;

$R^9$ and $R^{10}$ are each independently selected from the group consisting of a hydrogen atom, $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)-, and $C_3$-$C_4$-cycloalkyl, or $R^9$ and $R^{10}$ together with the nitrogen to which they are attached form a nitrogen containing 4- to 7-membered heterocycloalkyl group, wherein said nitrogen containing 4- to 7-membered heterocycloalkyl group is optionally substituted, one, two, or three times, wherein each substituent is independently selected from the group consisting of a halogen atom, $C_1$-$C_4$-alkyl, hydroxy, and oxo, or two substituents, which are attached to the same carbon atom of said nitrogen containing 4- to 7-membered heterocycloalkyl group, together with the carbon atom to which they are attached, form a 4- to 7-membered heterocycloalkyl group, wherein said 4- to 7-membered heterocycloalkyl group is optionally substituted, one or two times, with a $C_1$-$C_4$-alkyl group;

$R^{11}$ is $C_1$-$C_4$-alkyl or $C_1$-$C_4$-haloalkyl;

$R^{12}$ is a hydrogen atom;

$R^{13}$ is a phenyl group;

$R^{14}$ is $C_1$-$C_4$-alkyl or phenyl;

$R^{15}$ is a hydrogen atom or a $C_1$-$C_4$-alkyl group;

$R^{16}$ is a hydrogen atom or a $C_1$-$C_4$-alkyl group;

$R^{17}$ is a 4- to 7-membered heterocycloalkyl group, wherein said 4- to 7-membered heterocycloalkyl group is optionally substituted, one or two times, with a $C_1$-$C_4$-alkyl group, and wherein said 4- to 7-membered heterocycloalkyl group is connected to the rest of the molecule via a carbon atom of the 4- to 7-membered heterocycloalkyl group;

$R^{18}$ is a hydrogen atom or a methyl group;

$R^{19}$ is a hydrogen atom or a methyl group;

$R^{20}$ is a (4- to 7-membered heterocycloalkyl)-($C_1$-$C_4$-alkyl)-group, wherein the (4- to 7-membered heterocycloalkyl) part of said group is optionally substituted, one or two times, with a $C_1$-$C_4$-alkyl group;

m is 1 or 2; and n is 1, 2, or 3, or a stereoisomer, a tautomer, an N-oxide, a hydrate, a solvate, or a salt thereof, or a mixture of any of the foregoing.

5. The compound according to claim 1, wherein:

$R^1$ is selected from the group consisting of cyano, —C(=O)$NH_2$, —C(=O)N(H)$CH_3$ and —C(=O)N($CH_3$)$_2$;

$R^2$ is selected from the group consisting of phenyl, 1-naphthyl, 2-naphthyl, and 5- to 10-membered heteroaryl, wherein the 5- to 10-membered heteroaryl group is selected from pyrazolyl, 1,2,4-oxadiazol, 1,3,4-oxadiazol, 1H-1,2,3-triazolyl, 2H-1,2,3-triazolyl, 1,3-thiazolyl, pyridinyl, pyrazinyl, indolyl, benzothiophenyl, benzofuranyl, 1,3-benzoxazolyl, indazolyl, benzimidazolyl, 1,3-benzothiazolyl, pyrrolo[2,3-b]pyridinyl, quinolinyl, isoquinolinyl, quinoxalinyl, and 1,3-thiazolo[5,4-b]pyridinyl, wherein the 5- to 10-membered heteroaryl group is connected to the rest of the molecule via a carbon atom of said 5- to 10-membered heteroaryl group, wherein phenyl, 1-naphthyl, 2-naphthyl, and 5- to 10-membered heteroaryl group is optionally substituted, one, two, three, or four times, wherein each substituent is independently selected from the group consisting of a halogen atom, $C_1$-$C_6$-alkyl, $C_3$-$C_5$-cycloalkyl, $C_1$-$C_4$-haloalkyl, ($C_1$-$C_2$-alkoxy)-($C_1$-$C_2$-alkyl)-, $C_1$-$C_4$-alkoxy, $C_1$-$C_4$-haloalkoxy, phenoxy, —S(=O)$_2R^{14}$, —P(=O)($R^{14}$)$_2$, cyano, hydroxy, —$N(R^9)(R^{10})$, —C(=O)$N(R^9)(R^{10})$, —C(=O)$R^{11}$, —N($R^{12}$)C(=O)$R^{13}$, —N($R^{12}$)S(=O)$_2R^{14}$, —N=S(=O)($R^{14}$)$_2$, 4- to 7-membered heterocycloalkyl, phenyl, and pyridinyl, or two substituents of said phenyl group, when they are attached to adjacent ring atoms, are linked to one another in such a way that they jointly form a group selected from the group consisting of —$CH_2$—CH(OH)—$CH_2$—, —$CH_2$—CH($CH_3$)—O—, —O—C($CH_3$)$_2$—O—, —NH—C(=O)—CH($CH_3$)—, —N($CH_3$)—C(=O)—C($CH_3$)$_2$—, —NH—C(=O)—(C($CH_3$)$_2$)—, —NH—$CH_2$—C($CH_3$)$_2$—, —N($CH_3$)—C(=O)—O—, and —N($CH_3$)—C(=O)—N($CH_3$)—, wherein said 4- to 7-membered heterocycloalkyl group is connected to the rest of the molecule via a carbon atom of said 4- to 7-membered heterocycloalkyl group, wherein said $C_1$-$C_4$-alkoxy group is optionally substituted with 4- to 7-membered heterocycloalkyl or phenyl, wherein said 4- to 7-membered heterocycloalkyl group is connected to the rest of the molecule via a carbon atom of said 4- to 7-membered heterocycloalkyl group, wherein said phenyl group is optionally substituted, one or two times, wherein each substituent is independently selected from the group consisting of a halogen atom, $C_1$-$C_2$-alkyl, $C_1$-$C_2$-haloalkyl, and $C_1$-$C_2$-alkoxy;

$R^3$ is selected from the group consisting of a hydrogen atom, a halogen atom, —$C_6$-alkyl, $C_2$-$C_4$-alkenyl, $C_3$-$C_5$-cycloalkyl, ($C_1$-$C_2$-alkoxy)-($C_1$-$C_4$-alkyl)-, $C_1$-$C_4$-alkoxy, $C_1$-$C_4$-haloalkoxy, $C_3$-$C_5$-cycloalkyloxy, —S(=O)$_2R^{14}$, cyano, hydroxy, —$N(R^9)(R^{10})$, —C(=O)$N(R^9)(R^{10})$, —P(=O)($R^{14}$)$_2$, 4- to 7-membered heterocycloalkyl, 5- to 7-membered heterocycloalkenyl, (4- to 7-membered heterocycloalkyl)oxy, and phenyl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said $C_1$-$C_6$-alkyl and $C_1$-$C_4$-alkoxy groups are optionally substituted with $C_3$-$C_4$-cycloalkyl or 4- to 7-membered heterocycloalkyl, wherein said 4- to 7-membered heterocycloalkyl group is connected to the rest of the molecule via a carbon atom of said 4- to 7-membered heterocycloalkyl group, which $C_3$-$C_4$-cycloalkyl group is optionally substituted, one or two times, with a cyano group, wherein said $C_2$-$C_4$-alkenyl group is optionally substituted with a $C_1$-$C_4$-haloalkyl group, wherein said $C_3$-$C_5$-cycloalkyl group is optionally substituted, one or two times, with a halogen atom, $C_1$-$C_4$-alkyl, or $C_1$-$C_4$-haloalkyl;

$R^4$ is selected from the group consisting of a hydrogen atom, a halogen atom, $C_1$-$C_6$-alkyl, $C_1$-$C_6$-haloalkyl, $C_3$-$C_5$-cycloalkyl, ($C_1$-$C_2$-alkoxy)-($C_1$-$C_4$-alkyl)-, $C_1$-$C_4$-alkoxy, ($C_1$-$C_2$ alkoxy)-($C_1$-$C_4$-alkoxy)-, —O—$CH_2$—C(═O)O$R^{15}$, —O—$CH_2$—C(═O)N($R^9$)($R^{10}$), $C_3$-$C_5$-cycloalkyloxy, —S(═O)$_2R^{14}$, cyano, nitro, hydroxy, —N($R^9$)($R^{10}$), —N($R^{16}$)($R^{17}$), —N($R^{16}$) ($R^{20}$), —N═S(═NH)($R^{14}$)$_2$, —N═S(═O)($R^{14}$)$_2$, —P(═O)($R^{14}$)$_2$, 4- to 7-membered heterocycloalkyl, 5- to 7-membered heterocycloalkenyl, (4- to 7-membered heterocycloalkyl)oxy, and phenyl, wherein said 4- to 7-membered heterocycloalkyl group and 5- to 7-membered heterocycloalkenyl group are connected to the rest of the molecule via a carbon atom of said 4- to 7-membered heterocycloalkyl group or 5- to 7-membered heterocycloalkenyl group, wherein said $C_1$-$C_6$-alkyl and $C_1$-$C_4$-alkoxy groups are optionally substituted with $C_3$-$C_4$-cycloalkyl or 4- to 7-membered heterocycloalkyl, wherein said 4- to 7-membered heterocycloalkyl group is connected to the rest of the molecule via a carbon atom of said 4- to 7-membered heterocycloalkyl group, wherein the $C_3$-$C_4$-cycloalkyl group is optionally substituted, one or two times, wherein each substituent is independently selected from the group consisting of a halogen atom, cyano, and hydroxy, wherein said $C_1$-$C_4$-alkoxy group is optionally substituted with an oxiran-2-yl group, wherein said $C_3$-$C_5$-cycloalkyl group is optionally substituted, one or two times, wherein each substituent is a halogen atom or a $C_1$-$C_4$-alkyl group;

$R^5$ is selected from the group consisting of a hydrogen atom, a halogen atom, $C_1$-$C_5$-alkyl, $C_3$-$C_5$-cycloalkyl, $C_1$-$C_4$-alkoxy, $C_3$-$C_5$-cycloalkyloxy, —S(═O)$_2R^{14}$, cyano, hydroxy, —N($R^9$)($R^{10}$), 4- to 7-membered heterocycloalkyl, and (4- to 7-membered heterocycloalkyl)oxy, wherein said 4- to 7-membered heterocycloalkyl group is connected to the rest of the molecule via a carbon atom of said 4- to 7-membered heterocycloalkyl group;

$R^6$ is selected from the group consisting of a hydrogen atom, $C_1$-$C_4$-alkyl, and $C_1$-$C_4$-hydroxyalkyl;

$R^7$ is selected from the group consisting of a hydrogen atom, a halogen atom, $C_1$-$C_4$-alkyl, $C_1$-$C_4$-alkoxy, and hydroxy;

$R^8$ is methyl or ethyl;

$R^9$ and $R^{10}$ are each independently selected from the group consisting of a hydrogen atom, $C_1$-$C_4$-alkyl, $C_2$-$C_4$-hydroxyalkyl, N≡C—($C_1$-$C_4$-alkyl)-, ($C_1$-$C_4$-alkoxy)-($C_2$-$C_4$-alkyl)- and $C_3$-$C_4$-cycloalkyl, or $R^9$ and $R^{10}$ together with the nitrogen to which they are attached form a nitrogen containing 4- to 7-membered heterocycloalkyl group, wherein said nitrogen containing 4- to 7-membered heterocycloalkyl group is optionally substituted, one, two, or three times, wherein each substituent is independently selected from the group consisting of a halogen atom, $C_1$-$C_4$-alkyl, hydroxy, and oxo, or two substituents, which are attached to the same carbon atom of said nitrogen containing 4- to 7-membered heterocycloalkyl group, together with the carbon atom to which they are attached, form a 4- to 7-membered heterocycloalkyl group, wherein said 4- to 7-membered heterocycloalkyl group is optionally substituted, one or two times, with a $C_1$-$C_4$-alkyl group;

$R^{11}$ is $C_1$-$C_4$-alkyl or $C_1$-$C_4$-haloalkyl;

$R^{12}$ is a hydrogen atom;

$R^{13}$ is a phenyl group;

$R^{14}$ is $C_1$-$C_4$-alkyl or phenyl;

$R^{15}$ is a hydrogen atom or a $C_1$-$C_4$-alkyl group;

$R^{16}$ is a hydrogen atom or a $C_1$-$C_4$-alkyl group;

$R^{17}$ is a 4- to 7-membered heterocycloalkyl group, wherein said 4- to 7-membered heterocycloalkyl group is connected to the rest of the molecule via a carbon atom of the 4- to 7-membered heterocycloalkyl group;

$R^{20}$ is a (4- to 7-membered heterocycloalkyl)-($C_1$-$C_4$-alkyl)-group; and n is 1, 2, or 3, or a stereoisomer, a tautomer, an N-oxide, a hydrate, a solvate, or a salt thereof, or a mixture of any of the foregoing.

6. The compound according to claim 1, wherein:

$R^1$ is selected from the group consisting of cyano, —C(═O)$NH_2$, —C(═O)N(H)$CH_3$ and —C(═O)N($CH_3$)$_2$;

$R^2$ is selected from the group consisting of phenyl, 1-naphthyl, 2-naphthyl, 1H-pyrazol-3-yl, 1H-pyrazol-4-yl, 1H-pyrazol-5-yl, 1,2,4-oxadiazol-5-yl, 1,3,4-oxadiazol-2-yl, 1H-1,2,3-triazol-4-yl, 2H-1,2,3-triazol-4-yl, 1,3-thiazol-2-yl, pyridin-3-yl, pyrazin-2-yl, 1H-indol-5-yl, 1-benzofuran-4-yl, 1-benzofuran-7-yl, 1H-indol-6-yl, benzothiophen-2-yl, 1,3-benzoxazol-2-yl, 1,3-benzoxazol-5-yl, 1,3-benzoxazol-6-yl, 1,3-benzoxazol-7-yl, 1H-indazol-5-yl, 1H-benzimidazol-2-yl, 1H-benzimidazol-4-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1H-pyrrolo[2,3-b]pyridin-3-yl, quinolin-2-yl, quinolin-4-yl, quinolin-6-yl, quinolin-7-yl, isoquinolin-5-yl, isoquinolin-7-yl, isoquinolin-8-yl, quinoxalin-2-yl, quinoxalin-5-yl, and 1,3-thiazolo[5,4-b]pyridin-2-yl, wherein $R^2$ is optionally substituted, one or two times, wherein each substituent is independently selected from the group consisting of a fluorine atom, a chlorine atom, a bromine atom, methyl, propyl, isopropyl, tert-butyl, cyclopropyl, difluoromethyl, trifluoromethyl, methoxy, ethoxy, propoxy, (propan-2-yl)oxy, methoxymethyl, 2-methoxyethyl, benzyloxy, trifluormethoxy, 2,2,2-trifluoroethoxy, phenoxy, (oxolan-2-yl)methoxy, (tetrahydrofuran-2-yl)methoxy, methanesulfonyl, dimethylphosphoryl, cyano, hydroxy, dimethylamino, oxetan-3-yl, 2-oxopyrrolidin-1-yl, 4-methyl-2-oxopiperazin-1-yl, 4-methyl-3-oxopiperazin-1-yl, morpholino-4-yl, carbamoyl, acetyl, trifluoroacetyl, benzamido, benzenesulfonamido, [dimethyl(oxido)-$\lambda^6$-sulfanylidene]amino, phenyl, 3-chlorophenyl, 4-chlorophenyl, 2-methylphenyl, 3-methylphenyl, 4-methylphenyl, 3-trifluoromethylphenyl, 2-methoxyphenyl, 3-methoxyphenyl, 4-methoxyphenyl, and pyridin-3-yl, or two substituents of said phenyl group, when they are attached to adjacent ring atoms, are linked to one another in such a way that they jointly form a group selected from the group consisting of $—CH_2—CH(OH)—CH_2—$, $—CH_2—CH(CH_3)—O—$, $—O—C(CH_3)_2—O—$, $—NH—C(=O)—CH(CH_3)—$, $—N(CH_3)—C(=O)—C(CH_3)_2—$, $—NH—C(=O)—(C(CH_3)_2)—$, $—NH—CH_2—C(CH_3)_2—$, $—N(CH_3)—C(=O)—O—$, and $—N(CH_3)—C(=O)—N(CH_3)—$;

$R^3$ is selected from the group consisting of a hydrogen atom, a fluorine atom, a chlorine atom, a bromine atom, methyl, sec-butyl, (oxetan-3-yl)methyl, 3,3,3-trifluoroprop-1-en-2-yl, cyclopropyl, (trifluoromethyl)cyclopropyl, cyclobutyl, 2,2-dimethylcyclobutyl, 3,3-difluorocyclobutyl, methoxymethyl, methoxy, ethoxy, propoxy, 2,2-difluoroethoxy, 2,2-difluoropropoxy, cyclopropylmethoxy, (1-cyanocyclopropyl) methoxy, cyclopropyloxy, cyclobutyloxy, methanesulfonyl, cyano, hydroxy, 4-hydroxy-2-oxo-pyrrolidin-1-yl, carbamoyl, dimethylphosphoryl, oxetan-3-yl, 3,6-dihydro-2H-pyran-4-yl, (oxetan-3-yl)oxy, and phenyl, $R^4$ is selected from the group consisting of a hydrogen atom, a fluorine atom, a chlorine atom, a bromine atom, methyl, sec-butyl, (oxetan-3-yl)methyl, trifluoromethyl, cyclopropyl, 3,3-difluorocyclobutyl, methoxymethyl, methoxy, propoxy, 2-methoxyethoxy, (1-hydroxycyclopropyl) methoxy, (1-cyanocyclopropyl) methoxy, (oxiran-2-yl)methoxy, carboxymethoxy, 2-tert-butoxy-2-oxo-ethoxy, 2-amino-2-oxo-ethoxy, cyclopropyloxy, cyclobutyloxy, methanesulfonyl, dimethylphosphoryl, cyano, nitro, hydroxy, (cyanomethyl)(methyll)amino, (2-hydroxyethyl)amino, (2-hydroxyethyl)(methyl)amino, (2-methoxyethyl)amino, (2-methoxyethyl)(methyl)amino, cyclopropylamino, (oxetan-3-yl)amino, methyl(oxetan-3-yl)amino, methyl(oxolan-3-yl)amino, 3-hydroxyazetidin-1-yl, 2-oxopyrrolidin-1-yl, morpholino, 1,1-dioxidothiomorpholin-4-yl, 4-hydroxy-2-oxo-pyrrolidin-1-yl, 2,2-dimethyl-$2\lambda^6$-diazathia-1,2-dien-1-yl, [dimethyl(oxido)-$\lambda^6$-sulfanylidene]amino, methyl(tetrahydrofuran-3-yl)amino, tetrahydrofuran-3-ylmethoxy, (tetrahydrofuran-3-ylmethyl)amino, oxetan-3-yl, 3,6-dihydro-2H-pyran-4-yl, (oxetan-3-yl)oxy, (tetrahydrofuran-3-yl)oxy, (tetrahydro-2H-pyran-3-yl)oxy, (tetrahydro-2H-pyran-4-yl)oxy, and phenyl;

$R^5$ is selected from the group consisting of a hydrogen atom, a fluorine atom, a chlorine atom, a bromine atom, methyl, cyclopropyl, methoxy, propoxy, cyclopropyloxy, methanesulfonyl, cyano, hydroxy, oxetan-3-yl, and oxetan-3-yloxy;

$R^6$ is selected from the group consisting of a hydrogen atom, methyl, and hydroxymethyl;

$R^7$ is selected from the group consisting of a hydrogen atom, a fluorine atom, methyl, ethyl, methoxy, and hydroxy;

$R^8$ is methyl or ethyl; and n is 1, 2, or 3, or a stereoisomer, a tautomer, an N-oxide, a hydrate, a solvate, or a salt thereof, or a mixture of any of the foregoing.

7. The compound according to claim 1, wherein the compound is selected from the group consisting of:

4-[4-(1,3-benzoxazol-2-yl)-4-methylpiperidin-1-yl]-1-methyl-2-oxo-1,2-dihydroquinoline-3-carbonitrile;

4-[4-(1,3-benzoxazol-2-yl)piperidin-1-yl]-1-methyl-2-oxo-1,2-dihydroquinoline-3-carbonitrile;

4-[4-(7-fluoro-1,3-benzoxazol-2-yl)piperidin-1-yl]-1-methyl-2-oxo-1,2-dihydroquinoline-3-carbonitrile;

4-[4-(6-fluoro-1,3-benzoxazol-2-yl)piperidin-1-yl]-1-methyl-2-oxo-1,2-dihydroquinoline-3-carbonitrile;

1-methyl-4-[4-(5-methyl-1,3-benzoxazol-2-yl)piperidin-1-yl]-2-oxo-1,2-dihydroquinoline-3-carbonitrile;

4-[4-(5-fluoro-1,3-benzoxazol-2-yl)piperidin-1-yl]-1-methyl-2-oxo-1,2-dihydroquinoline-3-carbonitrile;

1-methyl-4-[4-(6-methyl-1,3-benzoxazol-2-yl)piperidin-1-yl]-2-oxo-1,2-dihydroquinoline-3-carbonitrile;

1-methyl-2-oxo-4-{4-[5-(propan-2-yl)-1,3-benzoxazol-2-yl]piperidin-1-yl}-1,2-dihydroquinoline-3-carbonitrile;

4-[4-(6-chloro-1,3-benzoxazol-2-yl)piperidin-1-yl]-1-methyl-2-oxo-1,2-dihydroquinoline-3-carbonitrile;

4-[4-(5-bromo-1,3-benzoxazol-2-yl)piperidin-1-yl]-1-methyl-2-oxo-1,2-dihydroquinoline-3-carbonitrile;

4-[4-(5-chloro-1,3-benzoxazol-2-yl)piperidin-1-yl]-1-methyl-2-oxo-1,2-dihydroquinoline-3-carbonitrile;

4-[4-(1,3-benzothiazol-2-yl)piperidin-1-yl]-1-methyl-2-oxo-1,2-dihydroquinoline-3-carbonitrile;

4-[4-(5-fluoro-1,3-benzothiazol-2-yl)piperidin-1-yl]-1-methyl-2-oxo-1,2-dihydroquinoline-3-carbonitrile;

4-[4-(6-bromo-1,3-benzothiazol-2-yl)piperidin-1-yl]-1-methyl-2-oxo-1,2-dihydroquinoline-3-carbonitrile;

1-methyl-4-[4-(7-methyl-1,3-benzoxazol-2-yl)piperidin-1-yl]-2-oxo-1,2-dihydroquinoline-3-carbonitrile;

4-[4-(1,3-benzothiazol-2-yl)-4-fluoropiperidin-1-yl]-1-methyl-2-oxo-1,2-dihydroquinoline-3-carbonitrile;

1-methyl-4-[4-(4-methyl-1,3-benzoxazol-2-yl)piperidin-1-yl]-2-oxo-1,2-dihydroquinoline-3-carbonitrile;

4-[4-(5-chloro-1,3-benzothiazol-2-yl)piperidin-1-yl]-1-methyl-2-oxo-1,2-dihydroquinoline-3-carbonitrile;

4-[4-(5-chloro[1,3]thiazolo[5,4-b]pyridin-2-yl)piperidin-1-yl]-1-methyl-2-oxo-1,2-dihydroquinoline-3-carbonitrile;

1-methyl-4-{4-methyl-4-[6-(trifluoromethoxy)-1,3-benzoxazol-2-yl]piperidin-1-yl}-2-oxo-1,2-dihydroquinoline-3-carbonitrile;

1-methyl-4-{4-methyl-4-[5-(propan-2-yl)-1,3-benzoxazol-2-yl]piperidin-1-yl}-2-oxo-1,2-dihydroquinoline-3-carbonitrile;

4-[4-(5,6-difluoro-1,3-benzoxazol-2-yl)piperidin-1-yl]-1-methyl-2-oxo-1,2-dihydroquinoline-3-carbonitrile;

1-methyl-2-oxo-4-{4-[5-(trifluoromethyl)-1,3-benzothiazol-2-yl]piperidin-1-yl}-1,2-dihydroquinoline-3-carbonitrile;

4-[4-(5-tert-butyl-1,3-benzoxazol-2-yl)-4-methylpiperidin-1-yl]-1-methyl-2-oxo-1,2-dihydroquinoline-3-carbonitrile;

4-{4-[5-(methanesulfonyl)-1,3-benzoxazol-2-yl]-4-methylpiperidin-1-yl}-1-methyl-2-oxo-1,2-dihydroquinoline-3-carbonitrile;

4-[4-(4-fluoro-1,3-benzoxazol-2-yl)piperidin-1-yl]-1-methyl-2-oxo-1,2-dihydroquinoline-3-carbonitrile;

4-[4-(1,3-benzoxazol-2-yl)piperidin-1-yl]-7-bromo-1-methyl-2-oxo-1,2-dihydroquinoline-3-carbonitrile;

7-bromo-1-methyl-4-{4-methyl-4-[6-(trifluoromethoxy)-1,3-benzoxazol-2-yl]piperidin-1-yl}-2-oxo-1,2-dihydroquinoline-3-carbonitrile;

7-bromo-4-[4-(5-chloro-1,3-benzoxazol-2-yl)piperidin-1-yl]-1-methyl-2-oxo-1,2-dihydroquinoline-3-carbonitrile;

7-bromo-1-methyl-2-oxo-4-{4-[5-(propan-2-yl)-1,3-benzoxazol-2-yl]piperidin-1-yl}-1,2-dihydroquinoline-3-carbonitrile;

7-bromo-4-[4-(5,6-difluoro-1,3-benzoxazol-2-yl)piperidin-1-yl]-1-methyl-2-oxo-1,2-dihydroquinoline-3-carbonitrile;

7-bromo-4-[4-(6-chloro-1,3-benzoxazol-2-yl)piperidin-1-yl]-1-methyl-2-oxo-1,2-dihydroquinoline-3-carbonitrile;

4-[4-(1,3-benzothiazol-2-yl)piperidin-1-yl]-7-bromo-1-methyl-2-oxo-1,2-dihydroquinoline-3-carbonitrile;

7-bromo-1-methyl-4-{4-methyl-4-[5-(propan-2-yl)-1,3-benzoxazol-2-yl]piperidin-1-yl}-2-oxo-1,2-dihydroquinoline-3-carbonitrile;

4-[4-(1,3-benzoxazol-2-yl)piperidin-1-yl]-1-methyl-2-oxo-7-(2-oxopyrrolidin-1-yl)-1,2-dihydroquinoline-3-carbonitrile;

4-[4-(1,3-benzothiazol-2-yl)piperidin-1-yl]-1-methyl-2-oxo-7-(2-oxopyrrolidin-1-yl)-1,2-dihydroquinoline-3-carbonitrile;

1-methyl-2-oxo-4-{4-[4-(2,2,2-trifluoroethoxy)phenyl]piperidin-1-yl}-1,2-dihydroquinoline-3-carbonitrile;

1-methyl-2-oxo-4-(4-{4-[(propan-2-yl)oxy]phenyl}piperidin-1-yl)-1,2-dihydroquinoline-3-carbonitrile;

4-[4-(4-ethoxyphenyl)piperidin-1-yl]-1-methyl-2-oxo-1,2-dihydroquinoline-3-carbonitrile;

4-[4-(4-cyclopropylphenyl)piperidin-1-yl]-1-methyl-2-oxo-1,2-dihydroquinoline-3-carbonitrile;

4-[4-(4-methoxyphenyl)piperidin-1-yl]-1-methyl-2-oxo-1,2-dihydroquinoline-3-carbonitrile;

1-methyl-2-oxo-4-[4-(4-propoxyphenyl)piperidin-1-yl]-1,2-dihydroquinoline-3-carbonitrile;

1-methyl-2-oxo-4-{4-[4-(trifluoromethoxy)phenyl]piperidin-1-yl}-1,2-dihydroquinoline-3-carbonitrile;

N-{4-[1-(3-cyano-1-methyl-2-oxo-1,2-dihydroquinolin-4-yl)piperidin-4-yl]phenyl}benzenesulfonamide;

4-[4-(3-cyclopropylphenyl)piperidin-1-yl]-1-methyl-2-oxo-1,2-dihydroquinoline-3-carbonitrile;

4-{4-[4-(dimethylamino)phenyl]piperidin-1-yl}-1-methyl-2-oxo-1,2-dihydroquinoline-3-carbonitrile;

1-methyl-2-oxo-4-{4-[4-(propan-2-yl)phenyl]piperidin-1-yl}-1,2-dihydroquinoline-3-carbonitrile;

4-{4-[4-(benzyloxy)phenyl]piperidin-1-yl}-1-methyl-2-oxo-1,2-dihydroquinoline-3-carbonitrile;

N-{4-[1-(3-cyano-1-methyl-2-oxo-1,2-dihydroquinolin-4-yl)piperidin-4-yl]phenyl}benzamide;

1-methyl-4-[4-(1-methyl-1H-indol-5-yl)piperidin-1-yl]-2-oxo-1,2-dihydroquinoline-3-carbonitrile;

4-[4-(3-fluoro-5-methylphenyl)piperidin-1-yl]-1-methyl-2-oxo-1,2-dihydroquinoline-3-carbonitrile;

4-[4-(2-methoxyphenyl)piperidin-1-yl]-1-methyl-2-oxo-1,2-dihydroquinoline-3-carbonitrile;

4-[4-([1,1'-biphenyl]-4-yl)piperidin-1-yl]-1-methyl-2-oxo-1,2-dihydroquinoline-3-carbonitrile;

4-[4-(4-chlorophenyl)piperidin-1-yl]-1-methyl-2-oxo-1,2-dihydroquinoline-3-carbonitrile;

4-[4-(3-methoxyphenyl)piperidin-1-yl]-1-methyl-2-oxo-1,2-dihydroquinoline-3-carbonitrile;

1-methyl-2-oxo-4-[4-(4-phenoxyphenyl)piperidin-1-yl]-1,2-dihydroquinoline-3-carbonitrile;

1-methyl-2-oxo-4-(4-phenylpiperidin-1-yl)-1,2-dihydroquinoline-3-carbonitrile;

1-methyl-4-(4-methyl-4-phenylpiperidin-1-yl)-2-oxo-1,2-dihydroquinoline-3-carbonitrile;

1-methyl-2-oxo-4-{4-[4-(2-oxopyrrolidin-1-yl)phenyl]piperidin-1-yl}-1,2-dihydroquinoline-3-carbonitrile;

4-[4-(2-fluorophenyl)piperidin-1-yl]-1-methyl-2-oxo-1,2-dihydroquinoline-3-carbonitrile, 1-methyl-2-oxo-4-{4-[4-(trifluoromethyl)phenyl]piperidin-1-yl}-1,2-dihydroquinoline-3-carbonitrile;

4-[4-(3-fluorophenyl)piperidin-1-yl]-1-methyl-2-oxo-1,2-dihydroquinoline-3-carbonitrile;

1-methyl-4-{4-[3-(morpholin-4-yl)phenyl]piperidin-1-yl}-2-oxo-1,2-dihydroquinoline-3-carbonitrile;

4-[4-(3-cyano-2-methylphenyl)piperidin-1-yl]-1-methyl-2-oxo-1,2-dihydroquinoline-3-carbonitrile;

4-{4-[4-(methanesulfonyl)phenyl]piperidin-1-yl}-1-methyl-2-oxo-1,2-dihydroquinoline-3-carbonitrile;

1-methyl-4-{4-[4-(4-methyl-2-oxopiperazin-1-yl)phenyl]piperidin-1-yl}-2-oxo-1,2-dihydroquinoline-3-carbonitrile;

4-[4-(1,3-benzoxazol-5-yl)piperidin-1-yl]-1-methyl-2-oxo-1,2-dihydroquinoline-3-carbonitrile;

N-{3-[1-(3-cyano-1-methyl-2-oxo-1,2-dihydroquinolin-4-yl)piperidin-4-yl]phenyl}benzenesulfonamide;

4-[4-(3-{[dimethyl(oxo)-λ6-sulfanylidene]amino}phenyl)piperidin-1-yl]-1-methyl-2-oxo-1,2-dihydroquinoline-3-carbonitrile;

1-methyl-4-[4-(naphthalen-1-yl)piperidin-1-yl]-2-oxo-1,2-dihydroquinoline-3-carbonitrile;

4-[4-(1,3-benzothiazol-4-yl)piperidin-1-yl]-1-methyl-2-oxo-1,2-dihydroquinoline-3-carbonitrile;

1-methyl-4-{4-[1-methyl-3-(trifluoroacetyl)-1H-indol-5-yl]piperidin-1-yl}-2-oxo-1,2-dihydroquinoline-3-carbonitrile;

4-[4-(1-benzofuran-7-yl)piperidin-1-yl]-1-methyl-2-oxo-1,2-dihydroquinoline-3-carbonitrile;

4-[4-(isoquinolin-7-yl)piperidin-1-yl]-1-methyl-2-oxo-1,2-dihydroquinoline-3-carbonitrile;

4-[4-(1,3-benzothiazol-7-yl)piperidin-1-yl]-1-methyl-2-oxo-1,2-dihydroquinoline-3-carbonitrile;

N-{3-[1-(3-cyano-1-methyl-2-oxo-1,2-dihydroquinolin-4-yl)piperidin-4-yl]phenyl}benzamide;

4-[4-(isoquinolin-8-yl)piperidin-1-yl]-1-methyl-2-oxo-1,2-dihydroquinoline-3-carbonitrile;

4-[4-(isoquinolin-5-yl)piperidin-1-yl]-1-methyl-2-oxo-1,2-dihydroquinoline-3-carbonitrile;

1-methyl-2-oxo-4-[4-(quinoxalin-5-yl)piperidin-1-yl]-1,2-dihydroquinoline-3-carbonitrile;

4-{4-[3-(methanesulfonyl)phenyl]piperidin-1-yl}-1-methyl-2-oxo-1,2-dihydroquinoline-3-carbonitrile;

4-[4-(4-fluorophenyl)piperidin-1-yl]-1-methyl-2-oxo-1,2-dihydroquinoline-3-carbonitrile;

1-methyl-4-[4-(2-methylphenyl)piperidin-1-yl]-2-oxo-1,2-dihydroquinoline-3-carbonitrile;

1-methyl-4-[4-(4-methylphenyl)piperidin-1-yl]-2-oxo-1,2-dihydroquinoline-3-carbonitrile;

4-[4-(3,5-dichlorophenyl)piperidin-1-yl]-1-methyl-2-oxo-1,2-dihydroquinoline-3-carbonitrile;

4-[4-(3-bromophenyl)piperidin-1-yl]-1-methyl-2-oxo-1,2-dihydroquinoline-3-carbonitrile;

4-[4-(4-cyanophenyl)piperidin-1-yl]-1-methyl-2-oxo-1,2-dihydroquinoline-3-carbonitrile;

4-{4-[3-(difluoromethyl)phenyl]piperidin-1-yl}-1-methyl-2-oxo-1,2-dihydroquinoline-3-carbonitrile;

4-[4-(4-bromophenyl)piperidin-1-yl]-1-methyl-2-oxo-1,2-dihydroquinoline-3-carbonitrile, 7-bromo-4-[4-(4-methoxyphenyl)piperidin-1-yl]-1-methyl-2-oxo-1,2-dihydroquinoline-3-carbonitrile;

7-bromo-1-methyl-2-oxo-4-(4-phenylpiperidin-1-yl)-1,2-dihydroquinoline-3-carbonitrile;

4-[4-(4-methoxyphenyl)piperidin-1-yl]-1,7-dimethyl-2-oxo-1,2-dihydroquinoline-3-carbonitrile;

4-[4-(4-methoxyphenyl)piperidin-1-yl]-1-methyl-2-oxo-7-phenyl-1,2-dihydroquinoline-3-carbonitrile;

4-[4-(4-methoxyphenyl)piperidin-1-yl]-1-methyl-2-oxo-1,2-dihydroquinoline-3,7-dicarbonitrile;

7-cyclopropyl-4-[4-(4-methoxyphenyl)piperidin-1-yl]-1-methyl-2-oxo-1,2-dihydroquinoline-3-carbonitrile;

7-(2,2-dimethyl-2λ6-diazathia-1,2-dien-1-yl)-4-[4-(4-methoxyphenyl)piperidin-1-yl]-1-methyl-2-oxo-1,2-dihydroquinoline-3-carbonitrile;

4-[4-(4-methoxyphenyl)piperidin-1-yl]-1-methyl-2-oxo-7-(2-oxopyrrolidin-1-yl)-1,2-dihydroquinoline-3-carbonitrile;

4-[4-(4-methoxyphenyl)piperidin-1-yl]-1-methyl-7-(oxetan-3-yl)-2-oxo-1,2-dihydroquinoline-3-carbonitrile;

7-(methanesulfonyl)-4-[4-(4-methoxyphenyl)piperidin-1-yl]-1-methyl-2-oxo-1,2-dihydroquinoline-3-carbonitrile;

7-{[dimethyl(oxo)-λ6-sulfanylidene]amino}-4-[4-(4-methoxyphenyl)piperidin-1-yl]-1-methyl-2-oxo-1,2-dihydroquinoline-3-carbonitrile;

7-(3,6-dihydro-2H-pyran-4-yl)-4-[4-(4-methoxyphenyl)piperidin-1-yl]-1-methyl-2-oxo-1,2-dihydroquinoline-3-carbonitrile;

4-[4-(1-benzofuran-4-yl)piperidin-1-yl]-1-methyl-2-oxo-1,2-dihydroquinoline-3-carbonitrile;

1-methyl-2-oxo-4-(4-{4-[(propan-2-yl)oxy]phenyl}piperidin-1-yl)-1,2-dihydroquinoline-3-carboxamide;

1-methyl-4-{4-methyl-4-[5-(propan-2-yl)-1,3-benzoxazol-2-yl]piperidin-1-yl}-2-oxo-1,2-dihydroquinoline-3-carboxamide;

4-[4-(1,3-benzoxazol-2-yl)piperidin-1-yl]-7-bromo-1-methyl-2-oxo-1,2-dihydroquinoline-3-carboxamide;

4-[4-(1,3-benzoxazol-2-yl)-4-methylpiperidin-1-yl]-1-methyl-2-oxo-1,2-dihydroquinoline-3-carboxamide;

4-[4-(1,3-benzoxazol-2-yl)-4-ethylpiperidin-1-yl]-1-methyl-2-oxo-1,2-dihydroquinoline-3-carbonitrile;

1-methyl-4-[4-(5-methyl-1,3-benzoxazol-2-yl)piperidin-1-yl]-2-oxo-1,2-dihydroquinoline-3-carboxamide;

1-methyl-2-oxo-4-{4-[4-(trifluoromethoxy)phenyl]piperidin-1-yl}-1,2-dihydroquinoline-3-carboxamide;

4-[4-(5,6-difluoro-1,3-benzoxazol-2-yl)piperidin-1-yl]-1-methyl-2-oxo-1,2-dihydroquinoline-3-carboxamide;

7-bromo-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[3-methyl-4-(5-methyl-1,3-benzoxazol-2-yl)piperidin-1-yl]-2-oxo-1,2-dihydroquinoline-3-carbonitrile, mixture of stereoisomers;

4-[4-(4-methoxyphenyl)piperidin-1-yl]-1-methyl-2-oxo-1,2-dihydroquinoline-3-carboxamide;

4-[4-(1,3-benzothiazol-2-yl)piperidin-1-yl]-1-methyl-2-oxo-1,2-dihydroquinoline-3-carboxamide;

1-methyl-2-oxo-4-(4-phenylpiperidin-1-yl)-1,2-dihydroquinoline-3-carboxamide;

4-[4-(4-methoxyphenyl)piperidin-1-yl]-1-methyl-7-(oxetan-3-yl)-2-oxo-1,2-dihydroquinoline-3-carboxamide;

4-[4-(1,3-benzothiazol-2-yl)piperidin-1-yl]-1-methyl-2-oxo-7-(2-oxopyrrolidin-1-yl)-1,2-dihydroquinoline-3-carboxamide;

(rac)-1-methyl-2-oxo-4-{4-[4-(propan-2-yl)phenyl]azepan-1-yl}-1,2-dihydroquinoline-3-carbonitrile;

1-methyl-2-oxo-4-{(4S)-4-[4-(propan-2-yl)phenyl]azepan-1-yl}-1,2-dihydroquinoline-3-carbonitrile;

1-methyl-2-oxo-4-{(4R)-4-[4-(propan-2-yl)phenyl]azepan-1-yl}-1,2-dihydroquinoline-3-carbonitrile;

(rac)-4-[4-(1,3-benzoxazol-2-yl)azepan-1-yl]-1-methyl-2-oxo-1,2-dihydroquinoline-3-carbonitrile;

1-methyl-2-oxo-4-[4-{4-[(propan-2-yl)oxy]phenyl}azepan-1-yl]-1,2-dihydroquinoline-3-carbonitrile;

(rac)-4-[4-(4-methoxyphenyl)azepan-1-yl]-1-methyl-2-oxo-1,2-dihydroquinoline-3-carbonitrile;

4-[(4R)-4-(4-methoxyphenyl)azepan-1-yl]-1-methyl-2-oxo-1,2-dihydroquinoline-3-carbonitrile;

4-[(4S)-4-(4-methoxyphenyl)azepan-1-yl]-1-methyl-2-oxo-1,2-dihydroquinoline-3-carbonitrile;

(rac)-4-[4-(1,3-benzoxazol-2-yl)azepan-1-yl]-7-bromo-1-methyl-2-oxo-1,2-dihydroquinoline-3-carbonitrile;

4-[(4R)-4-(1,3-benzoxazol-2-yl)azepan-1-yl]-7-bromo-1-methyl-2-oxo-1,2-dihydroquinoline-3-carbonitrile;

4-[(4S)-4-(1,3-benzoxazol-2-yl)azepan-1-yl]-7-bromo-1-methyl-2-oxo-1,2-dihydroquinoline-3-carbonitrile;

(rac)-4-[4-(4-chlorophenyl)azepan-1-yl]-1-methyl-2-oxo-1,2-dihydroquinoline-3-carbonitrile;

4-[(4R)-4-(4-chlorophenyl)azepan-1-yl]-1-methyl-2-oxo-1,2-dihydroquinoline-3-carbonitrile;

4-[(4SR)-4-(4-chlorophenyl)azepan-1-yl]-1-methyl-2-oxo-1,2-dihydroquinoline-3-carbonitrile;

(rac)-1-methyl-2-oxo-4-[4-phenylazepan-1-yl]-1,2-dihydroquinoline-3-carbonitrile;

(rac)-7-bromo-1-methyl-2-oxo-4-[4-phenylazepan-1-yl]-1,2-dihydroquinoline-3-carbonitrile;

(rac)-1-methyl-7-(oxetan-3-yl)-2-oxo-4-[4-phenylazepan-1-yl]-1,2-dihydroquinoline-3-carbonitrile;

(rac)-1-methyl-7-(morpholin-4-yl)-2-oxo-4-[4-phenylazepan-1-yl]-1,2-dihydroquinoline-3-carbonitrile;

(rac)-1-methyl-2-oxo-7-(2-oxopyrrolidin-1-yl)-4-[4-phenylazepan-1-yl]-1,2-dihydroquinoline-3-carbonitrile;

(rac)-7-(1,1-dioxo-1$\lambda^6$-thiomorpholin-4-yl)-1-methyl-2-oxo-4-[4-phenylazepan-1-yl]-1,2-dihydroquinoline-3-carbonitrile;

(rac)-7-bromo-1-methyl-2-oxo-4-[4-phenylazepan-1-yl]-1,2-dihydroquinoline-3-carboxamide;

7-bromo-1-methyl-2-oxo-4-[(4S)-4-phenylazepan-1-yl]-1,2-dihydroquinoline-3-carboxamide;

7-bromo-1-methyl-2-oxo-4-[(4S)-4-phenylazepan-1-yl]-1,2-dihydroquinoline-3-carboxamide;

4-[4-ethyl-4-(5-methyl-1,3-benzoxazol-2-yl)piperidin-1-yl]-1-methyl-2-oxo-1,2-dihydroquinoline-3-carbonitrile;

7-bromo-4-[4-ethyl-4-(5-methyl-1,3-benzoxazol-2-yl)piperidin-1-yl]-1-methyl-2-oxo-1,2-dihydroquinoline-3-carbonitrile;

4-[4-(6-methoxypyridin-3-yl)piperidin-1-yl]-1-methyl-2-oxo-1,2-dihydroquinoline-3-carbonitrile;

1-methyl-4-[4-(6-methylpyridin-3-yl)piperidin-1-yl]-2-oxo-1,2-dihydroquinoline-3-carbonitrile;

1-methyl-2-oxo-4-[4-(pyridin-3-yl)piperidin-1-yl]-1,2-dihydroquinoline-3-carbonitrile;

4-[4-(1,3-benzothiazol-2-yl)piperidin-1-yl]-N,1-dimethyl-2-oxo-1,2-dihydroquinoline-3-carboxamide;

4-[4-(1,3-benzothiazol-2-yl)piperidin-1-yl]-N,N,1-trimethyl-2-oxo-1,2-dihydroquinoline-3-carboxamide;

1-methyl-4-[4-(1-methyl-1H-benzimidazol-2-yl)piperidin-1-yl]-2-oxo-1,2-dihydroquinoline-3-carbonitrile;

1-methyl-2-oxo-4-[4-(3-propyl-1,2,4-oxadiazol-5-yl)piperidin-1-yl]-1,2-dihydroquinoline-3-carbonitrile;

1-methyl-4-[4-(1-methyl-1H-pyrazol-5-yl)piperidin-1-yl]-2-oxo-1,2-dihydroquinoline-3-carbonitrile;

1-methyl-2-oxo-4-[4-(pyrazin-2-yl)piperidin-1-yl]-1,2-dihydroquinoline-3-carbonitrile;

4-[4-(4-chlorophenyl)-4-hydroxypiperidin-1-yl]-1-methyl-2-oxo-1,2-dihydroquinoline-3-carbonitrile;

4-{4-hydroxy-4-[3-(trifluoromethyl)phenyl]piperidin-1-yl}-1-methyl-2-oxo-1,2-dihydroquinoline-3-carbonitrile;

8-fluoro-4-[4-(4-methoxyphenyl)piperidin-1-yl]-1-methyl-2-oxo-1,2-dihydroquinoline-3-carbonitrile;

4-[4-(1,3-benzothiazol-2-yl)piperidin-1-yl]-8-fluoro-1-methyl-2-oxo-1,2-dihydroquinoline-3-carbonitrile;

4-[4-(1,3-benzoxazol-2-yl)piperidin-1-yl]-8-fluoro-1-methyl-2-oxo-1,2-dihydroquinoline-3-carbonitrile;

4-[4-(1,3-benzoxazol-2-yl)-4-methylpiperidin-1-yl]-8-bromo-1-methyl-2-oxo-1,2-dihydroquinoline-3-carbonitrile;

8-bromo-4-[4-(6-chloro-1,3-benzoxazol-2-yl)piperidin-1-yl]-1-methyl-2-oxo-1,2-dihydroquinoline-3-carbonitrile;

8-bromo-1-methyl-4-[4-methyl-4-(5-methyl-1,3-benzoxazol-2-yl)piperidin-1-yl]-2-oxo-1,2-dihydroquinoline-3-carbonitrile;

8-bromo-4-[4-(5-chloro-1,3-benzoxazol-2-yl)piperidin-1-yl]-1-methyl-2-oxo-1,2-dihydroquinoline-3-carbonitrile;

8-bromo-4-[4-(5,6-difluoro-1,3-benzoxazol-2-yl)piperidin-1-yl]-1-methyl-2-oxo-1,2-dihydroquinoline-3-carbonitrile;

4-[4-(1,3-benzoxazol-2-yl)piperidin-1-yl]-8-bromo-1-methyl-2-oxo-1,2-dihydroquinoline-3-carbonitrile;

4-[4-(1,3-benzoxazol-2-yl)piperidin-1-yl]-8-chloro-1-methyl-2-oxo-1,2-dihydroquinoline-3-carbonitrile;

1-methyl-4-[4-methyl-4-(5-methyl-1,3-benzoxazol-2-yl)piperidin-1-yl]-2-oxo-1,2-dihydroquinoline-3,8-dicarbonitrile;

8-(methanesulfonyl)-1-methyl-4-[4-methyl-4-(5-methyl-1,3-benzoxazol-2-yl)piperidin-1-yl]-2-oxo-1,2-dihydroquinoline-3-carbonitrile;

4-[4-(1,3-benzoxazol-2-yl)piperidin-1-yl]-1,6-dimethyl-2-oxo-1,2-dihydroquinoline-3-carbonitrile;

1,6-dimethyl-4-[4-(5-methyl-1,3-benzoxazol-2-yl)piperidin-1-yl]-2-oxo-1,2-dihydroquinoline-3-carbonitrile;

6-bromo-4-[4-(4-methoxyphenyl)piperidin-1-yl]-1-methyl-2-oxo-1,2-dihydroquinoline-3-carbonitrile;

4-[4-(1,3-benzoxazol-2-yl)piperidin-1-yl]-6-bromo-1-methyl-2-oxo-1,2-dihydroquinoline-3-carbonitrile;

4-[4-(1,3-benzothiazol-2-yl)piperidin-1-yl]-6-bromo-1-methyl-2-oxo-1,2-dihydroquinoline-3-carbonitrile;

6-bromo-1-methyl-2-oxo-4-{4-[5-(propan-2-yl)-1,3-benzoxazol-2-yl]piperidin-1-yl}-1,2-dihydroquinoline-3-carbonitrile;

6-bromo-1-methyl-4-[4-methyl-4-(5-methyl-1,3-benzoxazol-2-yl)piperidin-1-yl]-2-oxo-1,2-dihydroquinoline-3-carbonitrile;

4-[4-(4-methoxyphenyl)piperidin-1-yl]-1,6-dimethyl-2-oxo-1,2-dihydroquinoline-3-carbonitrile;

4-[4-(4-methoxyphenyl)piperidin-1-yl]-1-methyl-2-oxo-1,2-dihydroquinoline-3,6-dicarbonitrile;

4-[4-(1,3-benzothiazol-2-yl)piperidin-1-yl]-1,6-dimethyl-2-oxo-1,2-dihydroquinoline-3-carbonitrile;

4-[4-(1,3-benzoxazol-2-yl)piperidin-1-yl]-1-methyl-2-oxo-1,2-dihydroquinoline-3,6-dicarbonitrile;

4-[4-(1,3-benzothiazol-2-yl)piperidin-1-yl]-1-methyl-2-oxo-1,2-dihydroquinoline-3,6-dicarbonitrile;

6-cyclopropyl-4-[4-(4-methoxyphenyl)piperidin-1-yl]-1-methyl-2-oxo-1,2-dihydroquinoline-3-carbonitrile;

6-(methanesulfonyl)-4-[4-(4-methoxyphenyl)piperidin-1-yl]-1-methyl-2-oxo-1,2-dihydroquinoline-3-carbonitrile;

4-[4-(4-methoxyphenyl)piperidin-1-yl]-1-methyl-6-(oxetan-3-yl)-2-oxo-1,2-dihydroquinoline-3-carbonitrile;

6-(3,6-dihydro-2H-pyran-4-yl)-4-[4-(4-methoxyphenyl)piperidin-1-yl]-1-methyl-2-oxo-1,2-dihydroquinoline-3-carbonitrile;

4-[4-(4-methoxyphenyl)piperidin-1-yl]-1-methyl-2-oxo-6-phenyl-1,2-dihydroquinoline-3-carbonitrile;

6-(methanesulfonyl)-1-methyl-4-[4-methyl-4-(5-methyl-1,3-benzoxazol-2-yl)piperidin-1-yl]-2-oxo-1,2-dihydroquinoline-3-carbonitrile;

4-[4-(6-chloro-1,3-benzoxazol-2-yl)piperidin-1-yl]-1,6-dimethyl-2-oxo-1,2-dihydroquinoline-3-carbonitrile;

1,6-dimethyl-4-[4-(6-methyl-1,3-benzoxazol-2-yl)piperidin-1-yl]-2-oxo-1,2-dihydroquinoline-3-carbonitrile;

4-[4-(5-chloro-1,3-benzoxazol-2-yl)piperidin-1-yl]-1,6-dimethyl-2-oxo-1,2-dihydroquinoline-3-carbonitrile;

1,6-dimethyl-2-oxo-4-{4-[5-(propan-2-yl)-1,3-benzoxazol-2-yl]piperidin-1-yl}-1,2-dihydroquinoline-3-carbonitrile;

1,6-dimethyl-4-[4-methyl-4-(5-methyl-1,3-benzoxazol-2-yl)piperidin-1-yl]-2-oxo-1,2-dihydroquinoline-3-carbonitrile;

1,6-dimethyl-4-[4-methyl-4-(6-methyl-1,3-benzoxazol-2-yl)piperidin-1-yl]-2-oxo-1,2-dihydroquinoline-3-carbonitrile;

1,6-dimethyl-4-{4-methyl-4-[5-(propan-2-yl)-1,3-benzoxazol-2-yl]piperidin-1-yl}-2-oxo-1,2-dihydroquinoline-3-carbonitrile;

6-methoxy-1-methyl-4-[4-(6-methyl-1,3-benzoxazol-2-yl)piperidin-1-yl]-2-oxo-1,2-dihydroquinoline-3-carbonitrile;

6-methoxy-1-methyl-4-[4-methyl-4-(6-methyl-1,3-benzoxazol-2-yl)piperidin-1-yl]-2-oxo-1,2-dihydroquinoline-3-carbonitrile;

6-chloro-1-methyl-4-[4-methyl-4-(6-methyl-1,3-benzoxazol-2-yl)piperidin-1-yl]-2-oxo-1,2-dihydroquinoline-3-carbonitrile;

4-[4-(1,3-benzoxazol-2-yl)piperidin-1-yl]-1,6-dimethyl-2-oxo-1,2-dihydroquinoline-3-carboxamide;

1,6-dimethyl-4-[4-(5-methyl-1,3-benzoxazol-2-yl)piperidin-1-yl]-2-oxo-1,2-dihydroquinoline-3-carboxamide;

4-[4-(1,3-benzoxazol-2-yl)-4-methylpiperidin-1-yl]-1,6-dimethyl-2-oxo-1,2-dihydroquinoline-3-carboxamide;

1,6-dimethyl-4-[4-(6-methyl-1,3-benzoxazol-2-yl)piperidin-1-yl]-2-oxo-1,2-dihydroquinoline-3-carboxamide;

1,6-dimethyl-4-[4-methyl-4-(6-methyl-1,3-benzoxazol-2-yl)piperidin-1-yl]-2-oxo-1,2-dihydroquinoline-3-carboxamide;

1,6-dimethyl-4-[4-methyl-4-(5-methyl-1,3-benzoxazol-2-yl)piperidin-1-yl]-2-oxo-1,2-dihydroquinoline-3-carboxamide;

1,6-dimethyl-4-{4-methyl-4-[5-(propan-2-yl)-1,3-benzoxazol-2-yl]piperidin-1-yl}-2-oxo-1,2-dihydroquinoline-3-carboxamide;

1,6-dimethyl-2-oxo-4-{4-[5-(propan-2-yl)-1,3-benzoxazol-2-yl]piperidin-1-yl}-1,2-dihydroquinoline-3-carboxamide;

4-[4-(5-chloro-1,3-benzoxazol-2-yl)piperidin-1-yl]-1,6-dimethyl-2-oxo-1,2-dihydroquinoline-3-carboxamide;

4-[4-(6-chloro-1,3-benzoxazol-2-yl)piperidin-1-yl]-1,6-dimethyl-2-oxo-1,2-dihydroquinoline-3-carboxamide;

6-bromo-1-methyl-4-[4-methyl-4-(5-methyl-1,3-benzoxazol-2-yl)piperidin-1-yl]-2-oxo-1,2-dihydroquinoline-3-carboxamide;

4-[4-(1,3-benzoxazol-2-yl)azepan-1-yl]-1,6-dimethyl-2-oxo-1,2-dihydroquinoline-3-carbonitrile;

4-[4-(1,3-benzoxazol-2-yl)azepan-1-yl]-1,6-dimethyl-2-oxo-1,2-dihydroquinoline-3-carboxamide;

4-[4-(1,3-benzoxazol-2-yl)piperidin-1-yl]-6-fluoro-1-methyl-2-oxo-1,2-dihydroquinoline-3-carbonitrile;

1-methyl-4-[4-methyl-4-(5-methyl-1,3-benzoxazol-2-yl)piperidin-1-yl]-2-oxo-1,2-dihydroquinoline-3,6-dicarbonitrile;

6-cyano-1-methyl-4-[4-methyl-4-(5-methyl-1,3-benzoxazol-2-yl)piperidin-1-yl]-2-oxo-1,2-dihydroquinoline-3-carboxamide;

6-(3,3-difluorocyclobutyl)-1-methyl-4-[4-methyl-4-(5-methyl-1,3-benzoxazol-2-yl)piperidin-1-yl]-2-oxo-1,2-dihydroquinoline-3-carbonitrile;

6-cyclopropyl-1-methyl-4-[4-methyl-4-(5-methyl-1,3-benzoxazol-2-yl)piperidin-1-yl]-2-oxo-1,2-dihydroquinoline-3-carbonitrile;

6-(butan-2-yl)-1-methyl-4-[4-methyl-4-(5-methyl-1,3-benzoxazol-2-yl)piperidin-1-yl]-2-oxo-1,2-dihydroquinoline-3-carbonitrile;

7-(methoxymethyl)-1-methyl-4-[4-methyl-4-(5-methyl-1,3-benzoxazol-2-yl)piperidin-1-yl]-2-oxo-1,2-dihydroquinoline-3-carbonitrile;

6-(methoxymethyl)-1-methyl-4-[4-methyl-4-(5-methyl-1,3-benzoxazol-2-yl)piperidin-1-yl]-2-oxo-1,2-dihydroquinoline-3-carbonitrile;

4-[4-(1,3-benzoxazol-2-yl)-4-methylpiperidin-1-yl]-1,6-dimethyl-2-oxo-1,2-dihydroquinoline-3-carbonitrile;

6-fluoro-1-methyl-4-[4-methyl-4-(5-methyl-1,3-benzoxazol-2-yl)piperidin-1-yl]-2-oxo-1,2-dihydroquinoline-3-carbonitrile;

4-[4-(1,3-benzoxazol-2-yl)-4-methylpiperidin-1-yl]-6-fluoro-1-methyl-2-oxo-1,2-dihydroquinoline-3-carbonitrile;

6-fluoro-1-methyl-4-[4-(5-methyl-1,3-benzoxazol-2-yl)piperidin-1-yl]-2-oxo-1,2-dihydroquinoline-3-carbonitrile;

4-[4-(1,3-benzoxazol-2-yl)-4-methylpiperidin-1-yl]-1,7-dimethyl-2-oxo-1,2-dihydroquinoline-3-carbonitrile;

4-[4-(1,3-benzoxazol-2-yl)piperidin-1-yl]-1,7-dimethyl-2-oxo-1,2-dihydroquinoline-3-carbonitrile;

1,7-dimethyl-4-[4-methyl-4-(5-methyl-1,3-benzoxazol-2-yl)piperidin-1-yl]-2-oxo-1,2-dihydroquinoline-3-carbonitrile;

1,7-dimethyl-4-[4-(5-methyl-1,3-benzoxazol-2-yl)piperidin-1-yl]-2-oxo-1,2-dihydroquinoline-3-carbonitrile;

4-[4-(1,3-benzothiazol-2-yl)piperidin-1-yl]-1,7-dimethyl-2-oxo-1,2-dihydroquinoline-3-carbonitrile;

4-[4-(1,3-benzoxazol-2-yl)-4-ethylpiperidin-1-yl]-7-bromo-1-methyl-2-oxo-1,2-dihydroquinoline-3-carbonitrile;

4-[4-(1,3-benzoxazol-2-yl)-4-methylpiperidin-1-yl]-7-bromo-1-methyl-2-oxo-1,2-dihydroquinoline-3-carbonitrile;

8-bromo-1,6-dimethyl-4-[4-methyl-4-(6-methyl-1,3-benzoxazol-2-yl)piperidin-1-yl]-2-oxo-1,2-dihydroquinoline-3-carbonitrile;

4-[4-(1,3-benzoxazol-2-yl)-4-methylpiperidin-1-yl]-7-chloro-1-methyl-2-oxo-1,2-dihydroquinoline-3-carbonitrile;

4-[4-(1,3-benzoxazol-2-yl)piperidin-1-yl]-7-chloro-1-methyl-2-oxo-1,2-dihydroquinoline-3-carbonitrile;

7-chloro-1-methyl-4-[4-methyl-4-(5-methyl-1,3-benzoxazol-2-yl)piperidin-1-yl]-2-oxo-1,2-dihydroquinoline-3-carbonitrile;

7-chloro-1-methyl-4-[4-(5-methyl-1,3-benzoxazol-2-yl)piperidin-1-yl]-2-oxo-1,2-dihydroquinoline-3-carbonitrile;

4-[4-(1,3-benzoxazol-2-yl)-4-methylpiperidin-1-yl]-8-chloro-1-methyl-2-oxo-1,2-dihydroquinoline-3-carbonitrile;

8-chloro-1-methyl-4-[4-methyl-4-(5-methyl-1,3-benzoxazol-2-yl)piperidin-1-yl]-2-oxo-1,2-dihydroquinoline-3-carbonitrile;

8-chloro-1-methyl-4-[4-(5-methyl-1,3-benzoxazol-2-yl)piperidin-1-yl]-2-oxo-1,2-dihydroquinoline-3-carbonitrile;

8-bromo-1-methyl-4-{4-methyl-4-[5-methyl-4-(trifluoromethyl)-1,3-benzoxazol-2-yl]piperidin-1-yl}-2-oxo-1,2-dihydroquinoline-3-carbonitrile;

1-methyl-4-[(2S,4S)-2-methyl-4-(5-methyl-1,3-benzoxazol-2-yl)piperidin-1-yl]-2-oxo-1,2-dihydroquinoline-3-carbonitrile;

4-[4-(1,3-benzoxazol-2-yl)-4-methylpiperidin-1-yl]-7-fluoro-1-methyl-2-oxo-1,2-dihydroquinoline-3-carbonitrile;

4-[4-(1,3-benzoxazol-2-yl)piperidin-1-yl]-7-fluoro-1-methyl-2-oxo-1,2-dihydroquinoline-3-carbonitrile;

7-fluoro-1-methyl-4-[4-methyl-4-(5-methyl-1,3-benzoxazol-2-yl)piperidin-1-yl]-2-oxo-1,2-dihydroquinoline-3-carbonitrile;

7-fluoro-1-methyl-4-[4-(5-methyl-1,3-benzoxazol-2-yl)piperidin-1-yl]-2-oxo-1,2-dihydroquinoline-3-carbonitrile;

7-[(1-hydroxycyclopropyl) methoxy]-1-methyl-4-[4-methyl-4-(5-methyl-1,3-benzoxazol-2-yl) piperidin-1-yl]-2-oxo-1,2-dihydroquinoline-3-carbonitrile;

4-[4-(1,3-benzothiazol-2-yl)piperidin-1-yl]-7-methoxy-1-methyl-2-oxo-1,2-dihydroquinoline-3-carbonitrile;

1-methyl-4-[4-methyl-4-(5-methyl-1,3-benzoxazol-2-yl)piperidin-1-yl]-7-[(oxetan-3-yl)oxy]-2-oxo-1,2-dihydroquinoline-3-carbonitrile;

6-hydroxy-1-methyl-4-[4-methyl-4-(5-methyl-1,3-benzoxazol-2-yl)piperidin-1-yl]-2-oxo-1,2-dihydroquinoline-3-carbonitrile;

4-[4-(1,3-benzoxazol-2-yl)piperidin-1-yl]-7-methoxy-1-methyl-2-oxo-1,2-dihydroquinoline-3-carbonitrile;

7-(cyclopropyloxy)-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-methyl-4-(5-methyl-1,3-benzoxazol-2-yl)piperidin-1-yl]-8-(oxetan-3-yl)-2-oxo-1,2-dihydroquinoline-3-carbonitrile;

6-methoxy-1-methyl-4-[4-methyl-4-(5-methyl-1,3-benzoxazol-2-yl)piperidin-1-yl]-2-oxo-1,2-dihydroquinoline-3-carbonitrile;

7-(cyclobutyloxy)-1-methyl-4-[4-methyl-4-(5-methyl-1,3-benzoxazol-2-yl)piperidin-1-yl]-2-oxo-1,2-dihydroquinoline-3-carbonitrile;

7-methoxy-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-methyl-4-(5-methyl-1,3-benzoxazol-2-yl)piperidin-1-yl]-2-oxo-1,2-dihydroquinoline-3,7-dicarbonitrile;

7-cyclopropyl-1-methyl-4-[4-methyl-4-(5-methyl-1,3-benzoxazol-2-yl)piperidin-1-yl]-2-oxo-1,2-dihydroquinoline-3-carbonitrile;

7-[(1-cyanocyclopropyl) methoxy]-1-methyl-4-[4-methyl-4-(5-methyl-1,3-benzoxazol-2-yl) piperidin-1-yl]-2-oxo-1,2-dihydroquinoline-3-carbonitrile;

7-(3,3-difluorocyclobutyl)-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-methyl-4-(5-methyl-1,3-benzoxazol-2-yl)piperidin-1-yl]-8-[(oxetan-3-yl)oxy]-2-oxo-1,2-dihydroquinoline-3-carbonitrile;

4-[4-(5,6-difluoro-1,3-benzoxazol-2-yl)piperidin-1-yl]-7-methoxy-1-methyl-2-oxo-1,2-dihydroquinoline-3-carbonitrile;

1,7-dimethyl-2-oxo-4-(4-phenylpiperidin-1-yl)-1,2-dihydroquinoline-3-carbonitrile;

7-methoxy-1-methyl-2-oxo-4-(4-phenylpiperidin-1-yl)-1,2-dihydroquinoline-3-carbonitrile;

1-methyl-4-[4-methyl-4-(5-methyl-1,3-benzoxazol-2-yl)piperidin-1-yl]-2-oxo-7-propoxy-1,2-dihydroquinoline-3-carbonitrile;

4-[4-(6-chloro-1,3-benzoxazol-2-yl)piperidin-1-yl]-7-methoxy-1-methyl-2-oxo-1,2-dihydroquinoline-3-carbonitrile;

4-[4-(5-chloro-1,3-benzoxazol-2-yl)piperidin-1-yl]-7-methoxy-1-methyl-2-oxo-1,2-dihydroquinoline-3-carbonitrile;

8-methoxy-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-methyl-4-(5-methyl-1,3-benzoxazol-2-yl)piperidin-1-yl]-7-(oxetan-3-yl)-2-oxo-1,2-dihydroquinoline-3-carbonitrile;

8-(cyclopropyloxy)-1-methyl-4-[4-methyl-4-(5-methyl-1,3-benzoxazol-2-yl)piperidin-1-yl]-2-oxo-1,2-dihydroquinoline-3-carbonitrile;

1,8-dimethyl-4-[4-methyl-4-(5-methyl-1,3-benzoxazol-2-yl)piperidin-1-yl]-2-oxo-1,2-dihydroquinoline-3-carbonitrile;

7-(cyclopropyloxy)-1-methyl-2-oxo-4-(4-phenylpiperidin-1-yl)-1,2-dihydroquinoline-3-carbonitrile;

4-{4-[4-(2-methoxyethyl)-1,3-benzoxazol-2-yl]piperidin-1-yl}-1-methyl-2-oxo-1,2-dihydroquinoline-3-carbonitrile;

7-[(2S)-butan-2-yl]-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-methyl-4-(5-methyl-1,3-benzoxazol-2-yl)piperidin-1-yl]-6-[(oxetan-3-yl)oxy]-2-oxo-1,2-dihydroquinoline-3-carbonitrile;

6-[(1-cyanocyclopropyl) methoxy]-1-methyl-4-[4-methyl-4-(5-methyl-1,3-benzoxazol-2-yl) piperidin-1-yl]-2-oxo-1,2-dihydroquinoline-3-carbonitrile;

7-[(4R)-4-hydroxy-2-oxopyrrolidin-1-yl]-1-methyl-4-[4-methyl-4-(5-methyl-1,3-benzoxazol-2-yl)piperidin-1-yl]-2-oxo-1,2-dihydroquinoline-3-carbonitrile;

4-[4-(1,3-benzothiazol-2-yl)piperidin-1-yl]-1-methyl-2-oxo-7-propoxy-1,2-dihydroquinoline-3-carbonitrile;

8-hydroxy-1-methyl-4-[4-methyl-4-(5-methyl-1,3-benzoxazol-2-yl)piperidin-1-yl]-2-oxo-1,2-dihydroquinoline-3-carbonitrile;

8-cyclopropyl-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-methyl-4-(5-methyl-1,3-benzoxazol-2-yl)piperidin-1-yl]-2-oxo-8-propoxy-1,2-dihydroquinoline-3-carbonitrile;

6-(cyclopropyloxy)-1-methyl-4-[4-methyl-4-(5-methyl-1,3-benzoxazol-2-yl)piperidin-1-yl]-2-oxo-1,2-dihydroquinoline-3-carbonitrile;

4-[4-(1,3-benzoxazol-2-yl)piperidin-1-yl]-1-methyl-2-oxo-1,2-dihydroquinoline-3,7-dicarbonitrile;

4-[4-(1,3-benzothiazol-2-yl)piperidin-1-yl]-6-cyclopropyl-1-methyl-2-oxo-1,2-dihydroquinoline-3-carbonitrile;

6-[(4R)-4-hydroxy-2-oxopyrrolidin-1-yl]-1-methyl-4-[4-methyl-4-(5-methyl-1,3-benzoxazol-2-yl)piperidin-1-yl]-2-oxo-1,2-dihydroquinoline-3-carbonitrile;

6-(cyclobutyloxy)-1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-methyl-4-(5-methyl-1,3-benzoxazol-2-yl)piperidin-1-yl]-2-oxo-6-propoxy-1,2-dihydroquinoline-3-carbonitrile;

6-[(4R)-4-hydroxy-2-oxopyrrolidin-1-yl]-1-methyl-4-[4-methyl-4-(5-methyl-1,3-benzoxazol-2-yl)piperidin-1-yl]-2-oxo-1,2-dihydroquinoline-3-carboxamide;

7-bromo-1-methyl-4-[4-(5-methyl-1,3-benzoxazol-2-yl)piperidin-1-yl]-2-oxo-1,2-dihydroquinoline-3-carbonitrile;

7-(dimethylphosphoryl)-1-methyl-4-[4-(5-methyl-1,3-benzoxazol-2-yl)piperidin-1-yl]-2-oxo-1,2-dihydroquinoline-3-carbonitrile;

4-{4-[5-(2-methoxyethyl)-1,3-benzoxazol-2-yl]piperidin-1-yl}-1-methyl-2-oxo-1,2-dihydroquinoline-3-carbonitrile;

4-{4-[6-(2-methoxyethyl)-1,3-benzoxazol-2-yl]piperidin-1-yl}-1-methyl-2-oxo-1,2-dihydroquinoline-3-carbonitrile;

1-methyl-4-[4-methyl-4-(5-methyl-1,3-benzoxazol-2-yl)piperidin-1-yl]-7-[(oxetan-3-yl)methyl]-2-oxo-1,2-dihydroquinoline-3-carbonitrile;

1-methyl-4-[4-methyl-4-(5-methyl-1,3-benzoxazol-2-yl)piperidin-1-yl]-6-[(oxetan-3-yl)methyl]-2-oxo-1,2-dihydroquinoline-3-carbonitrile;

1-methyl-4-{4-[5-(oxetan-3-yl)-1,3-benzoxazol-2-yl]piperidin-1-yl}-2-oxo-1,2-dihydroquinoline-3-carbonitrile;

1-methyl-4-[4-methyl-4-(5-methyl-1,3-benzoxazol-2-yl)piperidin-1-yl]-2-oxo-1,2-dihydroquinoline-3-carbonitrile;

1-methyl-4-[4-(5-methyl-1,3-benzoxazol-2-yl)piperidin-1-yl]-2-oxo-7-(trifluoromethyl)-1,2-dihydroquinoline-3-carbonitrile;

1-methyl-4-[4-methyl-4-(5-methyl-1,3-benzoxazol-2-yl)piperidin-1-yl]-2-oxo-7-(trifluoromethyl)-1,2-dihydroquinoline-3-carbonitrile;

4-[4-(1,3-benzoxazol-2-yl)piperidin-1-yl]-1-methyl-2-oxo-7-(trifluoromethyl)-1,2-dihydroquinoline-3-carbonitrile;

4-[4-(1,3-benzoxazol-2-yl)-4-methylpiperidin-1-yl]-1-methyl-2-oxo-7-(trifluoromethyl)-1,2-dihydroquinoline-3-carbonitrile;

7-hydroxy-1-methyl-4-[4-(5-methyl-1,3-benzoxazol-2-yl)piperidin-1-yl]-2-oxo-1,2-dihydroquinoline-3-carbonitrile;

4-[4-(6-bromo-1,3-benzoxazol-2-yl)piperidin-1-yl]-1-methyl-2-oxo-1,2-dihydroquinoline-3-carbonitrile;

4-{4-[5-(2-methoxyethyl)-1,3-benzoxazol-2-yl]piperidin-1-yl}-1-methyl-2-oxo-1,2-dihydroquinoline-3-carboxamide;

4-[4-(1,3-benzoxazol-2-yl)-4-methylpiperidin-1-yl]-6-fluoro-1-methyl-2-oxo-1,2-dihydroquinoline-3-carboxamide;
4-[4-(1,3-benzoxazol-2-yl)-4-methylpiperidin-1-yl]-7-chloro-1-methyl-2-oxo-1,2-dihydroquinoline-3-carboxamide;
6-fluoro-1-methyl-4-[4-(5-methyl-1,3-benzoxazol-2-yl)piperidin-1-yl]-2-oxo-1,2-dihydroquinoline-3-carboxamide;
4-[4-(1,3-benzoxazol-2-yl)piperidin-1-yl]-6-fluoro-1-methyl-2-oxo-1,2-dihydroquinoline-3-carboxamide;
4-[4-(1,3-benzoxazol-2-yl)piperidin-1-yl]-7-chloro-1-methyl-2-oxo-1,2-dihydroquinoline-3-carboxamide;
7-chloro-1-methyl-4-[4-(5-methyl-1,3-benzoxazol-2-yl)piperidin-1-yl]-2-oxo-1,2-dihydroquinoline-3-carboxamide;
1-methyl-4-[4-methyl-4-(5-methyl-1,3-benzoxazol-2-yl)piperidin-1-yl]-2-oxo-1,2-dihydroquinoline-3-carboxamide;
4-[4-(1,3-benzoxazol-2-yl)-4-methylpiperidin-1-yl]-7-fluoro-1-methyl-2-oxo-1,2-dihydroquinoline-3-carboxamide;
7-fluoro-1-methyl-4-[4-(5-methyl-1,3-benzoxazol-2-yl)piperidin-1-yl]-2-oxo-1,2-dihydroquinoline-3-carboxamide;
4-[4-(1,3-benzoxazol-2-yl)piperidin-1-yl]-7-fluoro-1-methyl-2-oxo-1,2-dihydroquinoline-3-carboxamide;
4-[4-(1,3-benzoxazol-2-yl)-4-methylpiperidin-1-yl]-1-methyl-2-oxo-7-(trifluoromethyl)-1,2-dihydroquinoline-3-carboxamide;
1-methyl-4-[4-(5-methyl-1,3-benzoxazol-2-yl)piperidin-1-yl]-2-oxo-7-(trifluoromethyl)-1,2-dihydroquinoline-3-carboxamide;
4-[4-(1,3-benzoxazol-2-yl)piperidin-1-yl]-1-methyl-2-oxo-7-(trifluoromethyl)-1,2-dihydroquinoline-3-carboxamide;
4-[4-(1,3-benzoxazol-2-yl)piperidin-1-yl]-8-chloro-1-methyl-2-oxo-1,2-dihydroquinoline-3-carboxamide;
4-[4-(1,3-benzoxazol-2-yl)-4-methylpiperidin-1-yl]-8-chloro-1-methyl-2-oxo-1,2-dihydroquinoline-3-carboxamide;
4-[4-(1,3-benzoxazol-2-yl)-4-methylpiperidin-1-yl]-1,7-dimethyl-2-oxo-1,2-dihydroquinoline-3-carboxamide;
1,7-dimethyl-4-[4-methyl-4-(5-methyl-1,3-benzoxazol-2-yl)piperidin-1-yl]-2-oxo-1,2-dihydroquinoline-3-carboxamide;
1,7-dimethyl-4-[4-(5-methyl-1,3-benzoxazol-2-yl)piperidin-1-yl]-2-oxo-1,2-dihydroquinoline-3-carboxamide;
4-[4-(1,3-benzoxazol-2-yl)piperidin-1-yl]-1,7-dimethyl-2-oxo-1,2-dihydroquinoline-3-carboxamide;
4-{4-[4-(2-methoxyethyl)-1,3-benzoxazol-2-yl]piperidin-1-yl}-1-methyl-2-oxo-1,2-dihydroquinoline-3-carboxamide;
4-[4-(1,3-benzoxazol-2-yl)piperidin-1-yl]-1-methyl-2-oxo-1,2-dihydroquinoline-3-carboxamide;
4-{4-[6-(2-methoxyethyl)-1,3-benzoxazol-2-yl]piperidin-1-yl}-1-methyl-2-oxo-1,2-dihydroquinoline-3-carboxamide;
4-[4-(1,3-benzoxazol-2-yl)piperidin-1-yl]-1-methyl-2-oxo-7-(2-oxopyrrolidin-1-yl)-1,2-dihydroquinoline-3-carboxamide;
8-chloro-1-methyl-4-[4-(5-methyl-1,3-benzoxazol-2-yl)piperidin-1-yl]-2-oxo-1,2-dihydroquinoline-3-carboxamide;
4-[4-(4,5-dimethyl-1,3-thiazol-2-yl)piperidin-1-yl]-1-methyl-2-oxo-1,2-dihydroquinoline-3-carbonitrile;
1-methyl-2-oxo-4-[4-(quinoxalin-2-yl)piperidin-1-yl]-1,2-dihydroquinoline-3-carbonitrile;
1-methyl-2-oxo-4-[4-(1H-pyrazol-3-yl)piperidin-1-yl]-1,2-dihydroquinoline-3-carbonitrile;
1-methyl-4-[4-(1-methyl-1H-pyrazol-4-yl)piperidin-1-yl]-2-oxo-1,2-dihydroquinoline-3-carbonitrile;
4-[4-(3,4-dimethoxyphenyl)piperidin-1-yl]-1-methyl-2-oxo-1,2-dihydroquinoline-3-carbonitrile;
4-[4-(3-chlorophenyl)piperidin-1-yl]-1-methyl-2-oxo-1,2-dihydroquinoline-3-carbonitrile;
1-methyl-4-[(2S,4S)-2-methyl-4-(5-methyl-1,3-benzoxazol-2-yl)-1-piperidyl]-2-oxo-quinoline-3-carbonitrile;
4-[4-(3-cyanophenyl)piperidin-1-yl]-1-methyl-2-oxo-1,2-dihydroquinoline-3-carbonitrile;
8-fluoro-1-methyl-2-oxo-4-[(4S)-4-phenylazepan-1-yl]-1,2-dihydroquinoline-3-carbonitrile;
1-methyl-4-[rac-(2R,3S)-2-methyl-3-phenylpyrrolidin-1-yl]-2-oxo-1,2-dihydroquinoline-3-carbonitrile;
4-[1-(3-cyano-1-methyl-2-oxo-1,2-dihydroquinolin-4-yl)piperidin-4-yl]benzamide;
4-[4-hydroxy-4-(2-methoxyphenyl)piperidin-1-yl]-1-methyl-2-oxo-1,2-dihydroquinoline-3-carbonitrile;
4-[4-(1,3-benzoxazol-2-yl)piperidin-1-yl]-1-ethyl-2-oxo-1,2-dihydroquinoline-3-carbonitrile;
4-[4-(4-chlorophenyl)piperidin-1-yl]-1-ethyl-2-oxo-1,2-dihydroquinoline-3-carbonitrile;
1-methyl-2-oxo-4-{4-[5-(2-oxopyrrolidin-1-yl)-1,3-benzoxazol-2-yl]piperidin-1-yl}-1,2-dihydroquinoline-3-carbonitrile;
4-[4-(4-acetylphenyl)-4-methylpiperidin-1-yl]-1-methyl-2-oxo-1,2-dihydroquinoline-3-carbonitrile;
4-[4-(3-chlorophenyl)-4-methoxypiperidin-1-yl]-1-methyl-2-oxo-1,2-dihydroquinoline-3-carbonitrile;
6-(dimethylphosphoryl)-1-methyl-4-[4-methyl-4-(5-methyl-1,3-benzoxazol-2-yl)piperidin-1-yl]-2-oxo-1,2-dihydroquinoline-3-carbonitrile;
6-(dimethylphosphoryl)-1-methyl-4-[4-(5-methyl-1,3-benzoxazol-2-yl)piperidin-1-yl]-2-oxo-1,2-dihydroquinoline-3-carbonitrile;
6-(methanesulfonyl)-1-methyl-4-[4-(5-methyl-1,3-benzoxazol-2-yl)piperidin-1-yl]-2-oxo-1,2-dihydroquinoline-3-carbonitrile;
4-[4-(1-benzothiophen-2-yl)-4-hydroxypiperidin-1-yl]-1-methyl-2-oxo-1,2-dihydroquinoline-3-carbonitrile;
4-[4-(1-benzothiophen-2-yl)-4-methoxypiperidin-1-yl]-1-methyl-2-oxo-1,2-dihydroquinoline-3-carbonitrile;
4-[4-(1-benzothiophen-2-yl)-4-methylpiperidin-1-yl]-1-methyl-2-oxo-1,2-dihydroquinoline-3-carbonitrile;
4-[4-(6-methoxynaphthalen-2-yl)piperidin-1-yl]-1-methyl-2-oxo-1,2-dihydroquinoline-3-carbonitrile;
6-[1-(3-cyano-1-methyl-2-oxo-1,2-dihydroquinolin-4-yl)piperidin-4-yl]-2-methylquinoline-4-carbonitrile;
1-methyl-4-[4-(2-methyl-1,3-benzoxazol-5-yl)piperidin-1-yl]-2-oxo-1,2-dihydroquinoline-3-carbonitrile;
1-methyl-4-[4-(2-methyl-1,3-benzothiazol-5-yl)piperidin-1-yl]-2-oxo-1,2-dihydroquinoline-3-carbonitrile;
(rac)-1-methyl-4-[4-(3-methyl-2-oxo-2,3-dihydro-1H-indol-5-yl)piperidin-1-yl]-2-oxo-1,2-dihydroquinoline-3-carbonitrile;
1-methyl-4-{4-[3-(2-methylphenyl)-1,2,4-oxadiazol-5-yl]piperidin-1-yl}-2-oxo-1,2-dihydroquinoline-3-carbonitrile;
4-{4-[3-(4-methoxyphenyl)-1,2,4-oxadiazol-5-yl]piperidin-1-yl}-1-methyl-2-oxo-1,2-dihydroquinoline-3-carbonitrile;

1-methyl-4-{4-[3-(3-methylphenyl)-1,2,4-oxadiazol-5-yl]piperidin-1-yl}-2-oxo-1,2-dihydroquinoline-3-carbonitrile;

1-methyl-4-{4-[5-(2-methylphenyl)-1,3,4-oxadiazol-2-yl]piperidin-1-yl}-2-oxo-1,2-dihydroquinoline-3-carbonitrile;

1-methyl-4-{4-[5-(4-methylphenyl)-1,3,4-oxadiazol-2-yl]piperidin-1-yl}-2-oxo-1,2-dihydroquinoline-3-carbonitrile;

1-methyl-4-{4-[5-(3-methylphenyl)-1,3,4-oxadiazol-2-yl]piperidin-1-yl}-2-oxo-1,2-dihydroquinoline-3-carbonitrile;

4-{4-[5-(3-chlorophenyl)-1,3,4-oxadiazol-2-yl]piperidin-1-yl}-1-methyl-2-oxo-1,2-dihydroquinoline-3-carbonitrile;

4-{4-[5-(3-chlorophenyl)-1,3,4-oxadiazol-2-yl]-4-methylpiperidin-1-yl}-1-methyl-2-oxo-1,2-dihydroquinoline-3-carbonitrile;

4-[4-(3,3-dimethyl-2,3-dihydro-1H-indol-5-yl)piperidin-1-yl]-1-methyl-2-oxo-1,2-dihydroquinoline-3-carbonitrile;

1-methyl-4-{4-[(2R)-2-methyl-2,3-dihydro-1-benzofuran-5-yl]piperidin-1-yl}-2-oxo-1,2-dihydroquinoline-3-carbonitrile;

1-methyl-2-oxo-4-[4-(1,3,3-trimethyl-2-oxo-2,3-dihydro-1H-indol-5-yl)piperidin-1-yl]-1,2-dihydroquinoline-3-carbonitrile;

4-[4-(2-hydroxy-2,3-dihydro-1H-inden-5-yl)piperidin-1-yl]-1-methyl-2-oxo-1,2-dihydroquinoline-3-carbonitrile;

4-[4-(2,2-dimethyl-2H-1,3-benzodioxol-5-yl)piperidin-1-yl]-1-methyl-2-oxo-1,2-dihydroquinoline-3-carbonitrile;

1-methyl-4-[4-(3-methyl-2-oxo-2,3-dihydro-1,3-benzoxazol-6-yl)piperidin-1-yl]-2-oxo-1,2-dihydroquinoline-3-carbonitrile;

4-[4-(1,3-dimethyl-2-oxo-2,3-dihydro-1H-benzimidazol-5-yl)piperidin-1-yl]-1-methyl-2-oxo-1,2-dihydroquinoline-3-carbonitrile;

1-methyl-4-[4-methyl-4-(4-methylquinolin-2-yl)piperidin-1-yl]-2-oxo-1,2-dihydroquinoline-3-carbonitrile;

4-[4-(4-fluoro-1-methyl-1H-indol-6-yl)piperidin-1-yl]-1-methyl-2-oxo-1,2-dihydroquinoline-3-carbonitrile;

1-methyl-4-{4-[1-(3-methylphenyl)-1H-pyrazol-3-yl]piperidin-1-yl}-2-oxo-1,2-dihydroquinoline-3-carbonitrile;

1-methyl-4-{4-[1-(2-methylphenyl)-1H-pyrazol-3-yl]piperidin-1-yl}-2-oxo-1,2-dihydroquinoline-3-carbonitrile;

4-{4-[1-(3-chlorophenyl)-1H-pyrazol-3-yl]piperidin-1-yl}-1-methyl-2-oxo-1,2-dihydroquinoline-3-carbonitrile;

4-{4-[1-(4-chlorophenyl)-1H-pyrazol-3-yl]piperidin-1-yl}-1-methyl-2-oxo-1,2-dihydroquinoline-3-carbonitrile;

1-methyl-2-oxo-4-{4-[3-(pyridin-3-yl)-1,2,4-oxadiazol-5-yl]piperidin-1-yl}-1,2-dihydroquinoline-3-carbonitrile;

1-methyl-4-[4-(2-methylquinolin-6-yl)piperidin-1-yl]-2-oxo-1,2-dihydroquinoline-3-carbonitrile;

4-{4-[4-(3-methoxyphenyl)-1,3-thiazol-2-yl]piperidin-1-yl}-1-methyl-2-oxo-1,2-dihydroquinoline-3-carbonitrile;

4-{4-[4-(2-methoxyphenyl)-1,3-thiazol-2-yl]piperidin-1-yl}-1-methyl-2-oxo-1,2-dihydroquinoline-3-carbonitrile;

1-methyl-4-{4-[4-(4-methylphenyl)-1,3-thiazol-2-yl]piperidin-1-yl}-2-oxo-1,2-dihydroquinoline-3-carbonitrile;

4-[4-(1,3-dimethyl-1H-indazol-5-yl)piperidin-1-yl]-1-methyl-2-oxo-1,2-dihydroquinoline-3-carbonitrile;

1-methyl-4-[4-(2-methyl-1,3-benzoxazol-6-yl)piperidin-1-yl]-2-oxo-1,2-dihydroquinoline-3-carbonitrile;

1-methyl-4-[4-(2-methyl-1,3-benzothiazol-6-yl)piperidin-1-yl]-2-oxo-1,2-dihydroquinoline-3-carbonitrile;

4-{4-[3-(difluoromethyl) quinolin-7-yl]piperidin-1-yl}-1-methyl-2-oxo-1,2-dihydroquinoline-3-carbonitrile;

(rac)-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile;

1-methyl-4-[4-(5-methyl-1,3-benzoxazol-2-yl)piperidin-1-yl]-2-oxo-7-{[(3R)-oxolan-3-yl]oxy}-1,2-dihydroquinoline-3-carbonitrile;

1-methyl-4-[4-(5-methyl-1,3-benzoxazol-2-yl)piperidin-1-yl]-2-oxo-7-{[(3S)-oxolan-3-yl]oxy}-1,2-dihydroquinoline-3-carbonitrile;

1-methyl-4-[4-(5-methyl-1,3-benzoxazol-2-yl)piperidin-1-yl]-7-[(oxan-4-yl)oxy]-2-oxo-1,2-dihydroquinoline-3-carbonitrile;

7-(2-methoxyethoxy)-1-methyl-4-[4-(5-methyl-1,3-benzoxazol-2-yl)piperidin-1-yl]-2-oxo-1,2-dihydroquinoline-3-carbonitrile;

1-methyl-4-[4-(5-methyl-1,3-benzoxazol-2-yl)piperidin-1-yl]-7-{[oxiran-2-yl]methoxy}-2-oxo-1,2-dihydroquinoline-3-carbonitrile;

1-methyl-4-[4-(5-methyl-1,3-benzoxazol-2-yl)piperidin-1-yl]-7-[(oxetan-3-yl)oxy]-2-oxo-1,2-dihydroquinoline-3-carbonitrile;

4-[4-(5-methoxy-1,3-benzoxazol-2-yl)piperidin-1-yl]-1-methyl-2-oxo-1,2-dihydroquinoline-3-carbonitrile;

1-methyl-2-oxo-4-(4-{5-[(oxolan-2-yl)methoxy]-1,3-benzoxazol-2-yl}piperidin-1-yl)-1,2-dihydroquinoline-3-carbonitrile;

1-methyl-4-{4-[6-(oxetan-3-yl)-1,3-benzoxazol-2-yl]piperidin-1-yl}-2-oxo-1,2-dihydroquinoline-3-carbonitrile;

4-[4-(1,3-benzoxazol-2-yl)-4-fluoropiperidin-1-yl]-1-methyl-2-oxo-1,2-dihydroquinoline-3-carbonitrile;

4-[4-(1,3-benzoxazol-2-yl)-4-methoxypiperidin-1-yl]-1-methyl-2-oxo-1,2-dihydroquinoline-3-carbonitrile;

4-{4-[5-(methoxymethyl)-1,3-benzoxazol-2-yl]-4-methylpiperidin-1-yl}-1-methyl-2-oxo-1,2-dihydroquinoline-3-carbonitrile;

4-{4-[6-(methoxymethyl)-1,3-benzoxazol-2-yl]-4-methylpiperidin-1-yl}-1-methyl-2-oxo-1,2-dihydroquinoline-3-carbonitrile;

4-[4-fluoro-4-(5-methoxy-1,3-benzoxazol-2-yl)piperidin-1-yl]-1-methyl-2-oxo-1,2-dihydroquinoline-3-carbonitrile;

4-[4-(5-cyclopropyl-1,3-benzoxazol-2-yl)piperidin-1-yl]-1-methyl-2-oxo-1,2-dihydroquinoline-3-carbonitrile;

4-[4-(6-cyclopropyl-1,3-benzoxazol-2-yl)piperidin-1-yl]-1-methyl-2-oxo-1,2-dihydroquinoline-3-carbonitrile;

6-bromo-1-methyl-4-[4-(5-methyl-1,3-benzoxazol-2-yl) piperidin-1-yl]-2-oxo-1,2-dihydroquinoline-3-carbonitrile;

8-bromo-1-methyl-4-[4-(5-methyl-1,3-benzoxazol-2-yl) piperidin-1-yl]-2-oxo-1,2-dihydroquinoline-3-carbonitrile;

1-methyl-4-[4-(5-methyl-1,3-benzoxazol-2-yl)piperidin-1-yl]-7-[methyl(oxetan-3-yl)amino]-2-oxo-1,2-dihydroquinoline-3-carbonitrile;

7-[(2-hydroxyethyl)(methyl)amino]-1-methyl-4-[4-(5-methyl-1,3-benzoxazol-2-yl)piperidin-1-yl]-2-oxo-1,2-dihydroquinoline-3-carbonitrile;

(rac)-1-methyl-4-[4-(5-methyl-1,3-benzoxazol-2-yl)piperidin-1-yl]-7-[methyl(oxolan-3-yl)amino]-2-oxo-1,2-dihydroquinoline-3-carbonitrile;

7-[(cyanomethyl)(methyl)amino]-1-methyl-4-[4-(5-methyl-1,3-benzoxazol-2-yl)piperidin-1-yl]-2-oxo-1,2-dihydroquinoline-3-carbonitrile;

6-methoxy-1-methyl-4-[4-(5-methyl-1,3-benzoxazol-2-yl)piperidin-1-yl]-2-oxo-1,2-dihydroquinoline-3-carbonitrile;

1-methyl-4-[4-(5-methyl-1,3-benzoxazol-2-yl)piperidin-1-yl]-2-oxo-1,2-dihydroquinoline-3,6-dicarbonitrile;

3-cyano-1-methyl-4-[4-(5-methyl-1,3-benzoxazol-2-yl) piperidin-1-yl]-2-oxo-1,2-dihydroquinoline-6-carboxamide;

6-ethoxy-1-methyl-4-[4-(5-methyl-1,3-benzoxazol-2-yl) piperidin-1-yl]-2-oxo-1,2-dihydroquinoline-3-carbonitrile;

6-(2,2-difluoropropoxy)-1-methyl-4-[4-(5-methyl-1,3-benzoxazol-2-yl)piperidin-1-yl]-2-oxo-1,2-dihydroquinoline-3-carbonitrile;

6-(2,2-difluoroethoxy)-1-methyl-4-[4-(5-methyl-1,3-benzoxazol-2-yl)piperidin-1-yl]-2-oxo-1,2-dihydroquinoline-3-carbonitrile;

6-(cyclopropylmethoxy)-1-methyl-4-[4-(5-methyl-1,3-benzoxazol-2-yl)piperidin-1-yl]-2-oxo-1,2-dihydroquinoline-3-carbonitrile;

6-cyclobutyl-1-methyl-4-[4-(5-methyl-1,3-benzoxazol-2-yl)piperidin-1-yl]-2-oxo-1,2-dihydroquinoline-3-carbonitrile;

6-[2,2-dimethylcyclobutyl]-1-methyl-4-[4-(5-methyl-1,3-benzoxazol-2-yl)piperidin-1-yl]-2-oxo-1,2-dihydroquinoline-3-carbonitrile;

1-methyl-4-[4-(5-methyl-1,3-benzoxazol-2-yl)piperidin-1-yl]-2-oxo-6-(3,3,3-trifluoroprop-1-en-2-yl)-1,2-dihydroquinoline-3-carbonitrile;

1-methyl-4-[4-(5-methyl-1,3-benzoxazol-2-yl)piperidin-1-yl]-2-oxo-6-[1-(trifluoromethyl)cyclopropyl]-1,2-dihydroquinoline-3-carbonitrile;

2- ({3-cyano-1-methyl-4-[4-(5-methyl-1,3-benzoxazol-2-yl)piperidin-1-yl]-2-oxo-1,2-dihydroquinolin-7-yl}oxy) acetamide;

1-methyl-4-[4-(5-methyl-1,3-benzoxazol-2-yl)piperidin-1-yl]-7-{[oxan-3-yl]oxy}-2-oxo-1,2-dihydroquinoline-3-carbonitrile;

(rac)-tert-butyl({3-cyano-1-methyl-4-[4-(5-methyl-1,3-benzoxazol-2-yl)piperidin-1-yl]-2-oxo-1,2-dihydroquinolin-7-yl}oxy)acetate;

({3-cyano-1-methyl-4-[4-(5-methyl-1,3-benzoxazol-2-yl) piperidin-1-yl]-2-oxo-1,2-dihydroquinolin-7-yl}oxy) acetic acid;

(rac)-4-[4-fluoro-4-(5-methyl-1,3-benzoxazol-2-yl)piperidin-1-yl]-1-methyl-2-oxo-7-(tetrahydrofuran-3-yloxy)-1,2-dihydroquinoline-3-carbonitrile;

7-(cyclopropylamino)-1-methyl-4-[4-methyl-4-(5-methyl-1,3-benzoxazol-2-yl)piperidin-1-yl]-2-oxo-1,2-dihydroquinoline-3-carbonitrile;

7-methoxy-1,6-dimethyl-4-[4-(5-methyl-1,3-benzoxazol-2-yl)piperidin-1-yl]-2-oxo-1,2-dihydroquinoline-3-carbonitrile;

6-bromo-4-[4-fluoro-4-(5-methyl-1,3-benzoxazol-2-yl) piperidin-1-yl]-7-methoxy-1-methyl-2-oxo-1,2-dihydroquinoline-3-carbonitrile;

1,6-dimethyl-4-[4-(5-methyl-1,3-benzoxazol-2-yl)piperidin-1-yl]-7-nitro-2-oxo-1,2-dihydroquinoline-3-carbonitrile;

6-bromo-7-hydroxy-1-methyl-4-[4-(5-methyl-1,3-benzoxazol-2-yl)piperidin-1-yl]-2-oxo-1,2-dihydroquinoline-3-carbonitrile;

6-bromo-7-hydroxy-1-methyl-4-[4-methyl-4-(5-methyl-1,3-benzoxazol-2-yl)piperidin-1-yl]-2-oxo-1,2-dihydroquinoline-3-carbonitrile;

(rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile;

(rac)-1-methyl-4-[4-(5-methyl-1,3-benzoxazol-2-yl)piperidin-1-yl]-2-oxo-7-[tetrahydrofuran-3-yloxy]-1,2-dihydroquinoline-3,6-dicarbonitrile;

7-hydroxy-1-methyl-4-[4-methyl-4-(5-methyl-1,3-benzoxazol-2-yl)piperidin-1-yl]-2-oxo-1,2-dihydroquinoline-3,6-dicarbonitrile;

(rac)-6-ethoxy-1-methyl-4-[4-(5-methyl-1,3-benzoxazol-2-yl)piperidin-1-yl]-2-oxo-7-[tetrahydrofuran-3-yloxy]-1,2-dihydroquinoline-3-carbonitrile;

7-hydroxy-1,6-dimethyl-4-[4-(5-methyl-1,3-benzoxazol-2-yl)piperidin-1-yl]-2-oxo-1,2-dihydroquinoline-3-carbonitrile;

(rac)-1,6-dimethyl-4-[4-(5-methyl-1,3-benzoxazol-2-yl) piperidin-1-yl]-2-oxo-7-[tetrahydrofuran-3-yloxy]-1,2-dihydroquinoline-3-carbonitrile;

(rac)-6-(2,2-difluoroethoxy)-1-methyl-4-[4-(5-methyl-1,3-benzoxazol-2-yl)piperidin-1-yl]-2-oxo-7-[tetrahydrofuran-3-yloxy]-1,2-dihydroquinoline-3-carbonitrile;

(rac)-4-[4-fluoro-4-(5-methyl-1,3-benzoxazol-2-yl)piperidin-1-yl]-6-methoxy-1-methyl-2-oxo-7-[tetrahydrofuran-3-yloxy]-1,2-dihydroquinoline-3-carbonitrile;

(rac)-1-methyl-4-[4-methyl-4-(5-methyl-1,3-benzoxazol-2-yl)piperidin-1-yl]-2-oxo-7-[(oxolan-3-yl)oxy]-1,2-dihydroquinoline-3,6-dicarbonitrile;

(rac)-1-methyl-4-[4-(5-methyl-1,3-benzoxazol-2-yl)piperidin-1-yl]-2-oxo-7-[(oxolan-3-yl)oxy]-6-(3,3,3-trifluoroprop-1-en-2-yl)-1,2-dihydroquinoline-3-carbonitrile;

(rac)-1-methyl-4-[4-(5-methyl-1,3-benzoxazol-2-yl)piperidin-1-yl]-2-oxo-7-[(oxolan-3-yl)oxy]-6-[1-(trifluoromethyl)cyclopropyl]-1,2-dihydroquinoline-3-carbonitrile;

6-bromo-1-methyl-2-oxo-4-(4-{5-[3-(trifluoromethyl) phenyl]-1,3,4-oxadiazol-2-yl}piperidin-1-yl)-1,2-dihydroquinoline-3-carbonitrile;

6-methoxy-1-methyl-4-{4-[3-(3-methylphenyl)-1,2,4-oxadiazol-5-yl]piperidin-1-yl}-2-oxo-1,2-dihydroquinoline-3-carbonitrile;

6-methoxy-1-methyl-2-oxo-4-[4-(3-phenyl-1,2,4-oxadiazol-5-yl)piperidin-1-yl]-1,2-dihydroquinoline-3-carbonitrile;

6-methoxy-1-methyl-4-{4-[3-(2-methylphenyl)-1,2,4-oxadiazol-5-yl]piperidin-1-yl}-2-oxo-1,2-dihydroquinoline-3-carbonitrile;

6-methoxy-1-methyl-2-oxo-4-[4-(5-phenyl-1,3,4-oxadiazol-2-yl)piperidin-1-yl]-1,2-dihydroquinoline-3-carbonitrile;

6-bromo-1-methyl-2-oxo-4-[4-(3-phenyl-1,2,4-oxadiazol-5-yl)piperidin-1-yl]-1,2-dihydroquinoline-3-carbonitrile;

6-bromo-1-methyl-2-oxo-4-[4-(5-phenyl-1,3,4-oxadiazol-2-yl)piperidin-1-yl]-1,2-dihydroquinoline-3-carbonitrile;

6-bromo-1-methyl-4-{4-[5-(2-methylphenyl)-1,3,4-oxadiazol-2-yl]piperidin-1-yl}-2-oxo-1,2-dihydroquinoline-3-carbonitrile;

6-bromo-1-methyl-4-{4-[5-(3-methylphenyl)-1,3,4-oxadiazol-2-yl]piperidin-1-yl}-2-oxo-1,2-dihydroquinoline-3-carbonitrile;

7-hydroxy-1-methyl-4-{4-[5-(2-methylphenyl)-1,3,4-oxadiazol-2-yl]piperidin-1-yl}-2-oxo-1,2-dihydroquinoline-3-carbonitrile;

6-bromo-7-hydroxy-1-methyl-4-{4-[5-(2-methylphenyl)-1,3,4-oxadiazol-2-yl]piperidin-1-yl}-2-oxo-1,2-dihydroquinoline-3-carbonitrile;

(rac)-1-methyl-4-{4-[5-(2-methylphenyl)-1,3,4-oxadiazol-2-yl]piperidin-1-yl}-7-{[oxan-3-yl]oxy}-2-oxo-1,2-dihydroquinoline-3-carbonitrile;

4-[4-(1,3-benzoxazol-2-yl)piperidin-1-yl]-N,1-dimethyl-2-oxo-1,2-dihydroquinoline-3-carboxamide;

N,1-dimethyl-4-[4-(5-methyl-1,3-benzoxazol-2-yl)piperidin-1-yl]-2-oxo-1,2-dihydroquinoline-3-carboxamide;

4-[4-(1,3-benzoxazol-2-yl)-4-methylpiperidin-1-yl]-N,1-dimethyl-2-oxo-1,2-dihydroquinoline-3-carboxamide;

1-methyl-2-oxo-4-{4-[5-(2-oxopyrrolidin-1-yl)-1,3-benzoxazol-2-yl]piperidin-1-yl}-1,2-dihydroquinoline-3-carboxamide;

4-[4-(3-chlorophenyl)-4-methoxypiperidin-1-yl]-1-methyl-2-oxo-1,2-dihydroquinoline-3-carboxamide;

6-(dimethylphosphoryl)-1-methyl-4-[4-methyl-4-(5-methyl-1,3-benzoxazol-2-yl)piperidin-1-yl]-2-oxo-1,2-dihydroquinoline-3-carboxamide;

6-(dimethylphosphoryl)-1-methyl-4-[4-(5-methyl-1,3-benzoxazol-2-yl)piperidin-1-yl]-2-oxo-1,2-dihydroquinoline-3-carboxamide;

6-(methanesulfonyl)-1-methyl-4-[4-(5-methyl-1,3-benzoxazol-2-yl)piperidin-1-yl]-2-oxo-1,2-dihydroquinoline-3-carboxamide;

4-[4-(1-benzothiophen-2-yl)-4-methoxypiperidin-1-yl]-1-methyl-2-oxo-1,2-dihydroquinoline-3-carboxamide;

4-[4-(1-benzothiophen-2-yl)-4-hydroxypiperidin-1-yl]-1-methyl-2-oxo-1,2-dihydroquinoline-3-carboxamide;

4-[4-(6-methoxynaphthalen-2-yl)piperidin-1-yl]-1-methyl-2-oxo-1,2-dihydroquinoline-3-carboxamide;

1-methyl-4-{4-[3-(2-methylphenyl)-1,2,4-oxadiazol-5-yl]piperidin-1-yl}-2-oxo-1,2-dihydroquinoline-3-carboxamide;

4-{4-[3-(4-methoxyphenyl)-1,2,4-oxadiazol-5-yl]piperidin-1-yl}-1-methyl-2-oxo-1,2-dihydroquinoline-3-carboxamide;

1-methyl-4-{4-[3-(3-methylphenyl)-1,2,4-oxadiazol-5-yl]piperidin-1-yl}-2-oxo-1,2-dihydroquinoline-3-carboxamide;

1-methyl-4-{4-[5-(2-methylphenyl)-1,3,4-oxadiazol-2-yl]piperidin-1-yl}-2-oxo-1,2-dihydroquinoline-3-carboxamide;

1-methyl-4-{4-[5-(4-methylphenyl)-1,3,4-oxadiazol-2-yl]piperidin-1-yl}-2-oxo-1,2-dihydroquinoline-3-carboxamide;

1-methyl-4-{4-[5-(3-methylphenyl)-1,3,4-oxadiazol-2-yl]piperidin-1-yl}-2-oxo-1,2-dihydroquinoline-3-carboxamide;

4-{4-[5-(3-chlorophenyl)-1,3,4-oxadiazol-2-yl]piperidin-1-yl}-1-methyl-2-oxo-1,2-dihydroquinoline-3-carboxamide;

4-{4-[5-(3-chlorophenyl)-1,3,4-oxadiazol-2-yl]-4-methylpiperidin-1-yl}-1-methyl-2-oxo-1,2-dihydroquinoline-3-carboxamide;

1-methyl-4-{4-[2-methyl-2,3-dihydro-1-benzofuran-5-yl]piperidin-1-yl}-2-oxo-1,2-dihydroquinoline-3-carboxamide;

4-[4-(2-hydroxy-2,3-dihydro-1H-inden-5-yl)piperidin-1-yl]-1-methyl-2-oxo-1,2-dihydroquinoline-3-carboxamide;

4-[4-(2,2-dimethyl-2H-1,3-benzodioxol-5-yl)piperidin-1-yl]-1-methyl-2-oxo-1,2-dihydroquinoline-3-carboxamide;

1-methyl-4-[4-methyl-4-(4-methylquinolin-2-yl)piperidin-1-yl]-2-oxo-1,2-dihydroquinoline-3-carboxamide;

4-[4-(4-fluoro-1-methyl-1H-indol-6-yl)piperidin-1-yl]-1-methyl-2-oxo-1,2-dihydroquinoline-3-carboxamide;

1-methyl-4-{4-[1-(3-methylphenyl)-1H-pyrazol-3-yl]piperidin-1-yl}-2-oxo-1,2-dihydroquinoline-3-carboxamide;

1-methyl-4-{4-[1-(2-methylphenyl)-1H-pyrazol-3-yl]piperidin-1-yl}-2-oxo-1,2-dihydroquinoline-3-carboxamide;

4-{4-[1-(3-chlorophenyl)-1H-pyrazol-3-yl]piperidin-1-yl}-1-methyl-2-oxo-1,2-dihydroquinoline-3-carboxamide;

1-methyl-2-oxo-4-{4-[3-(pyridin-3-yl)-1,2,4-oxadiazol-5-yl]piperidin-1-yl}-1,2-dihydroquinoline-3-carboxamide;

4-{4-[4-(3-methoxyphenyl)-1,3-thiazol-2-yl]piperidin-1-yl}-1-methyl-2-oxo-1,2-dihydroquinoline-3-carboxamide;

4-{4-[4-(2-methoxyphenyl)-1,3-thiazol-2-yl]piperidin-1-yl}-1-methyl-2-oxo-1,2-dihydroquinoline-3-carboxamide;

1-methyl-4-{4-[4-(4-methylphenyl)-1,3-thiazol-2-yl]piperidin-1-yl}-2-oxo-1,2-dihydroquinoline-3-carboxamide;

1-methyl-4-[4-(5-methyl-1,3-benzoxazol-2-yl)piperidin-1-yl]-7-[(oxan-4-yl)oxy]-2-oxo-1,2-dihydroquinoline-3-carboxamide;

7-(2-methoxyethoxy)-1-methyl-4-[4-(5-methyl-1,3-benzoxazol-2-yl)piperidin-1-yl]-2-oxo-1,2-dihydroquinoline-3-carboxamide;

1-methyl-4-[4-(5-methyl-1,3-benzoxazol-2-yl)piperidin-1-yl]-7-{[oxiran-2-yl]methoxy}-2-oxo-1,2-dihydroquinoline-3-carboxamide;

(rac)-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide;

(−)-1-methyl-4-[4-(5-methyl-1,3-benzoxazol-2-yl)piperidin-1-yl]-2-oxo-7-{[(3R)-oxolan-3-yl]oxy}-1,2-dihydroquinoline-3-carboxamide;

(+)-1-methyl-4-[4-(5-methyl-1,3-benzoxazol-2-yl)piperidin-1-yl]-2-oxo-7-{[(3S)-oxolan-3-yl]oxy}-1,2-dihydroquinoline-3-carboxamide;

1-methyl-4-[4-(5-methyl-1,3-benzoxazol-2-yl)piperidin-1-yl]-7-[(oxetan-3-yl)oxy]-2-oxo-1,2-dihydroquinoline-3-carboxamide;

4-[4-(5-methoxy-1,3-benzoxazol-2-yl)piperidin-1-yl]-1-methyl-2-oxo-1,2-dihydroquinoline-3-carboxamide;

1-methyl-2-oxo-4-(4-{5-[(oxolan-2-yl)methoxy]-1,3-benzoxazol-2-yl}piperidin-1-yl)-1,2-dihydroquinoline-3-carboxamide;

4-[4-(1,3-benzoxazol-2-yl)-4-fluoropiperidin-1-yl]-1-methyl-2-oxo-1,2-dihydroquinoline-3-carboxamide;

4-[4-(1,3-benzoxazol-2-yl)-4-methoxypiperidin-1-yl]-1-methyl-2-oxo-1,2-dihydroquinoline-3-carboxamide;

4-{4-[5-(methoxymethyl)-1,3-benzoxazol-2-yl]-4-methylpiperidin-1-yl}-1-methyl-2-oxo-1,2-dihydroquinoline-3-carboxamide;

4-{4-[6-(methoxymethyl)-1,3-benzoxazol-2-yl]-4-methylpiperidin-1-yl}-1-methyl-2-oxo-1,2-dihydroquinoline-3-carboxamide;

6-bromo-1-methyl-4-[4-(5-methyl-1,3-benzoxazol-2-yl)piperidin-1-yl]-2-oxo-1,2-dihydroquinoline-3-carboxamide;

8-bromo-1-methyl-4-[4-(5-methyl-1,3-benzoxazol-2-yl)piperidin-1-yl]-2-oxo-1,2-dihydroquinoline-3-carboxamide;

1-methyl-4-[4-(5-methyl-1,3-benzoxazol-2-yl)piperidin-1-yl]-7-[methyl(oxetan-3-yl)amino]-2-oxo-1,2-dihydroquinoline-3-carboxamide;

7-[(2-hydroxyethyl)(methyl)amino]-1-methyl-4-[4-(5-methyl-1,3-benzoxazol-2-yl)piperidin-1-yl]-2-oxo-1,2-dihydroquinoline-3-carboxamide;

1-methyl-4-[4-(5-methyl-1,3-benzoxazol-2-yl)piperidin-1-yl]-7-{methyl[(3R)-oxolan-3-yl]amino}-2-oxo-1,2-dihydroquinoline-3-carboxamide;

1-methyl-4-[4-(5-methyl-1,3-benzoxazol-2-yl)piperidin-1-yl]-7-{methyl[(3S)-oxolan-3-yl]amino}-2-oxo-1,2-dihydroquinoline-3-carboxamide;

6-cyano-1-methyl-4-[4-(5-methyl-1,3-benzoxazol-2-yl)piperidin-1-yl]-2-oxo-1,2-dihydroquinoline-3-carboxamide;

1-methyl-4-[4-(5-methyl-1,3-benzoxazol-2-yl)piperidin-1-yl]-2-oxo-1,2-dihydroquinoline-3,6-dicarboxamide;

7-[(cyanomethyl)(methyl)amino]-1-methyl-4-[4-(5-methyl-1,3-benzoxazol-2-yl)piperidin-1-yl]-2-oxo-1,2-dihydroquinoline-3-carboxamide;

6-methoxy-1-methyl-4-[4-(5-methyl-1,3-benzoxazol-2-yl)piperidin-1-yl]-2-oxo-1,2-dihydroquinoline-3-carboxamide;

6-ethoxy-1-methyl-4-[4-(5-methyl-1,3-benzoxazol-2-yl)piperidin-1-yl]-2-oxo-1,2-dihydroquinoline-3-carboxamide;

6-(2,2-difluoropropoxy)-1-methyl-4-[4-(5-methyl-1,3-benzoxazol-2-yl)piperidin-1-yl]-2-oxo-1,2-dihydroquinoline-3-carboxamide;

6-(2,2-difluoroethoxy)-1-methyl-4-[4-(5-methyl-1,3-benzoxazol-2-yl)piperidin-1-yl]-2-oxo-1,2-dihydroquinoline-3-carboxamide;

6-(cyclopropylmethoxy)-1-methyl-4-[4-(5-methyl-1,3-benzoxazol-2-yl)piperidin-1-yl]-2-oxo-1,2-dihydroquinoline-3-carboxamide;

6-cyclobutyl-1-methyl-4-[4-(5-methyl-1,3-benzoxazol-2-yl)piperidin-1-yl]-2-oxo-1,2-dihydroquinoline-3-carboxamide;

1-methyl-4-[4-(5-methyl-1,3-benzoxazol-2-yl)piperidin-1-yl]-2-oxo-6-[1-(trifluoromethyl)cyclopropyl]-1,2-dihydroquinoline-3-carboxamide;

7-(2-amino-2-oxoethoxy)-1-methyl-4-[4-(5-methyl-1,3-benzoxazol-2-yl)piperidin-1-yl]-2-oxo-1,2-dihydroquinoline-3-carboxamide;

4-[4-fluoro-4-(5-methyl-1,3-benzoxazol-2-yl)piperidin-1-yl]-1-methyl-2-oxo-7-[(oxolan-3-yl)oxy]-1,2-dihydroquinoline-3-carboxamide;

1,6-dimethyl-4-[4-(5-methyl-1,3-benzoxazol-2-yl)piperidin-1-yl]-7-nitro-2-oxo-1,2-dihydroquinoline-3-carboxamide;

6-bromo-7-hydroxy-1-methyl-4-[4-(5-methyl-1,3-benzoxazol-2-yl)piperidin-1-yl]-2-oxo-1,2-dihydroquinoline-3-carboxamide;

6-bromo-7-hydroxy-1-methyl-4-[4-methyl-4-(5-methyl-1,3-benzoxazol-2-yl)piperidin-1-yl]-2-oxo-1,2-dihydroquinoline-3-carboxamide;

(rac)-6-bromo-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide;

(rac)-6-cyano-1-methyl-4-[4-methyl-4-(5-methyl-1,3-benzoxazol-2-yl)piperidin-1-yl]-2-oxo-7-[(oxolan-3-yl)oxy]-1,2-dihydroquinoline-3-carboxamide;

6-cyano-1-methyl-4-[4-methyl-4-(5-methyl-1,3-benzoxazol-2-yl)piperidin-1-yl]-2-oxo-7-{[(3R)-oxolan-3-yl]oxy}-1,2-dihydroquinoline-3-carboxamide;

6-cyano-1-methyl-4-[4-methyl-4-(5-methyl-1,3-benzoxazol-2-yl)piperidin-1-yl]-2-oxo-7-{[(3S)-oxolan-3-yl]oxy}-1,2-dihydroquinoline-3-carboxamide;

(rac)-6-(2,2-difluoroethoxy)-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide;

(rac)-1-methyl-4-[4-(5-methyl-1,3-benzoxazol-2-yl)piperidin-1-yl]-2-oxo-7-[(oxolan-3-yl)oxy]-6-[1-(trifluoromethyl)cyclopropyl]-1,2-dihydroquinoline-3-carboxamide;

6-bromo-1-methyl-2-oxo-4-(4-{5-[3-(trifluoromethyl)phenyl]-1,3,4-oxadiazol-2-yl}piperidin-1-yl)-1,2-dihydroquinoline-3-carboxamide;

6-methoxy-1-methyl-4-{4-[3-(3-methylphenyl)-1,2,4-oxadiazol-5-yl]piperidin-1-yl}-2-oxo-1,2-dihydroquinoline-3-carboxamide;

6-methoxy-1-methyl-2-oxo-4-[4-(3-phenyl-1,2,4-oxadiazol-5-yl)piperidin-1-yl]-1,2-dihydroquinoline-3-carboxamide;

6-methoxy-1-methyl-4-{4-[3-(2-methylphenyl)-1,2,4-oxadiazol-5-yl]piperidin-1-yl}-2-oxo-1,2-dihydroquinoline-3-carboxamide;

6-bromo-1-methyl-2-oxo-4-[4-(3-phenyl-1,2,4-oxadiazol-5-yl)piperidin-1-yl]-1,2-dihydroquinoline-3-carboxamide;

6-bromo-1-methyl-2-oxo-4-[4-(5-phenyl-1,3,4-oxadiazol-2-yl)piperidin-1-yl]-1,2-dihydroquinoline-3-carboxamide;

6-bromo-1-methyl-4-{4-[5-(2-methylphenyl)-1,3,4-oxadiazol-2-yl]piperidin-1-yl}-2-oxo-1,2-dihydroquinoline-3-carboxamide;

6-bromo-1-methyl-4-{4-[5-(3-methylphenyl)-1,3,4-oxadiazol-2-yl]piperidin-1-yl}-2-oxo-1,2-dihydroquinoline-3-carboxamide;

1-methyl-4-{4-[5-(2-methylphenyl)-1,3,4-oxadiazol-2-yl]piperidin-1-yl}-7-{[(3R)-oxan-3-yl]oxy}-2-oxo-1,2-dihydroquinoline-3-carboxamide;

1-methyl-4-{4-[5-(2-methylphenyl)-1,3,4-oxadiazol-2-yl]piperidin-1-yl}-7-{[(3S)-oxan-3-yl]oxy}-2-oxo-1,2-dihydroquinoline-3-carboxamide;

6-bromo-7-hydroxy-1-methyl-4-{4-[5-(2-methylphenyl)-1,3,4-oxadiazol-2-yl]piperidin-1-yl}-2-oxo-1,2-dihydroquinoline-3-carboxamide;

6-bromo-7-methoxy-1-methyl-4-{4-[3-(2-methylphenyl)-1,2,4-oxadiazol-5-yl]piperidin-1-yl}-2-oxo-1,2-dihydroquinoline-3-carbonitrile;

6-bromo-7-hydroxy-1-methyl-4-{4-[3-(2-methylphenyl)-1,2,4-oxadiazol-5-yl]piperidin-1-yl}-2-oxo-1,2-dihydroquinoline-3-carbonitrile;

(rac)-6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile;

(rac)-6-bromo-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide;

(rac)-6-cyano-1-methyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carboxamide;

6-cyano-1-methyl-4-{4-[3-(2-methylphenyl)-1,2,4-oxadiazol-5-yl]piperidin-1-yl}-2-oxo-7-{[(3R)-oxolan-3-yl]oxy}-1,2-dihydroquinoline-3-carboxamide;

6-cyano-1-methyl-4-{4-[3-(2-methylphenyl)-1,2,4-oxadiazol-5-yl]piperidin-1-yl}-2-oxo-7-{[(3S)-oxolan-3-yl]oxy}-1,2-dihydroquinoline-3-carboxamide;

(−)-6-bromo-1-methyl-4-[4-(5-methyl-1,3-benzoxazol-2-yl)piperidin-1-yl]-2-oxo-7-{[(3R)-oxolan-3-yl]oxy}-1,2-dihydroquinoline-3-carbonitrile;

(rac)-6-cyano-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide;

6-cyano-1-methyl-4-[4-(5-methyl-1,3-benzoxazol-2-yl)piperidin-1-yl]-2-oxo-7-{[(3R)-oxolan-3-yl]oxy}-1,2-dihydroquinoline-3-carboxamide;

6-cyano-1-methyl-4-[4-(5-methyl-1,3-benzoxazol-2-yl)piperidin-1-yl]-2-oxo-7-{[(3S)-oxolan-3-yl]oxy}-1,2-dihydroquinoline-3-carboxamide;

6-methoxy-1-methyl-4-[4-(5-methyl-1,3-benzoxazol-2-yl)piperidin-1-yl]-2-oxo-7-{[(3R)-oxolan-3-yl]oxy}-1,2-dihydroquinoline-3-carbonitrile;

6-methoxy-1-methyl-4-[4-(5-methyl-1,3-benzoxazol-2-yl)piperidin-1-yl]-2-oxo-7-{[(3S)-oxolan-3-yl]oxy}-1,2-dihydroquinoline-3-carbonitrile;

6-methoxy-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide;

(rac)-1,6-dimethyl-4-[4-(5-methyl-1,3-benzoxazol-2-yl)piperidin-1-yl]-2-oxo-7-[(oxolan-3-yl)oxy]-1,2-dihydroquinoline-3-carboxamide;

1,6-dimethyl-4-[4-(5-methyl-1,3-benzoxazol-2-yl)piperidin-1-yl]-2-oxo-7-{[(3R)-oxolan-3-yl]oxy}-1,2-dihydroquinoline-3-carboxamide;

1,6-dimethyl-4-[4-(5-methyl-1,3-benzoxazol-2-yl)piperidin-1-yl]-2-oxo-7-{[(3S)-oxolan-3-yl]oxy}-1,2-dihydroquinoline-3-carboxamide;

7-[(2-methoxyethyl)amino]-1,6-dimethyl-4-[4-(5-methyl-1,3-benzoxazol-2-yl)piperidin-1-yl]-2-oxo-1,2-dihydroquinoline-3-carbonitrile;

7-(3-hydroxyazetidin-1-yl)-1,6-dimethyl-4-[4-(5-methyl-1,3-benzoxazol-2-yl)piperidin-1-yl]-2-oxo-1,2-dihydroquinoline-3-carbonitrile;

1,6-dimethyl-4-[4-(5-methyl-1,3-benzoxazol-2-yl)piperidin-1-yl]-7-[(oxetan-3-yl)amino]-2-oxo-1,2-dihydroquinoline-3-carbonitrile;

7-[(2-hydroxyethyl)amino]-1,6-dimethyl-4-[4-(5-methyl-1,3-benzoxazol-2-yl)piperidin-1-yl]-2-oxo-1,2-dihydroquinoline-3-carbonitrile;

7-[(2-hydroxyethyl)(methyl)amino]-1,6-dimethyl-4-[4-(5-methyl-1,3-benzoxazol-2-yl) piperidin-1-yl]-2-oxo-1,2-dihydroquinoline-3-carbonitrile;

7-[(2-methoxyethyl)amino]-1,6-dimethyl-4-[4-(5-methyl-1,3-benzoxazol-2-yl)piperidin-1-yl]-2-oxo-1,2-dihydroquinoline-3-carboxamide;

7-(3-hydroxyazetidin-1-yl)-1,6-dimethyl-4-[4-(5-methyl-1,3-benzoxazol-2-yl)piperidin-1-yl]-2-oxo-1,2-dihydroquinoline-3-carboxamide;

(rac)-1,6-dimethyl-4-{4-[3-(2-methylphenyl)-1,2,4-oxadiazol-5-yl]piperidin-1-yl}-2-oxo-7-[(oxolan-3-yl)oxy]-1,2-dihydroquinoline-3-carbonitrile;

1,6-dimethyl-4-{4-[3-(2-methylphenyl)-1,2,4-oxadiazol-5-yl]piperidin-1-yl}-2-oxo-7-{[(3R)-oxolan-3-yl]oxy}-1,2-dihydroquinoline-3-carbonitrile;

1,6-dimethyl-4-{4-[3-(2-methylphenyl)-1,2,4-oxadiazol-5-yl]piperidin-1-yl}-2-oxo-7-{[(3S)-oxolan-3-yl]oxy}-1,2-dihydroquinoline-3-carbonitrile;

1,6-dimethyl-4-{4-[3-(2-methylphenyl)-1,2,4-oxadiazol-5-yl]piperidin-1-yl}-2-oxo-7-{[(3R)-oxolan-3-yl]oxy}-1,2-dihydroquinoline-3-carboxamide;

1,6-dimethyl-4-{4-[3-(2-methylphenyl)-1,2,4-oxadiazol-5-yl]piperidin-1-yl}-2-oxo-7-{[(3S)-oxolan-3-yl]oxy}-1,2-dihydroquinoline-3-carboxamide;

7-[(2-hydroxyethyl)amino]-1,6-dimethyl-4-{4-[3-(2-methylphenyl)-1,2,4-oxadiazol-5-yl]piperidin-1-yl}-2-oxo-1,2-dihydroquinoline-3-carbonitrile;

7-bromo-1,6-dimethyl-4-{4-[1-(2-methylphenyl)-1H-pyrazol-3-yl]piperidin-1-yl}-2-oxo-1,2-dihydroquinoline-3-carbonitrile;

7-[(2-hydroxyethyl)amino]-1,6-dimethyl-4-{4-[1-(2-methylphenyl)-1H-pyrazol-3-yl]piperidin-1-yl}-2-oxo-1,2-dihydroquinoline-3-carbonitrile;

6-bromo-7-fluoro-1-methyl-4-[4-(5-methyl-1,3-benzoxazol-2-yl)piperidin-1-yl]-2-oxo-1,2-dihydroquinoline-3-carboxamide;

6-cyano-7-fluoro-1-methyl-4-[4-(5-methyl-1,3-benzoxazol-2-yl)piperidin-1-yl]-2-oxo-1,2-dihydroquinoline-3-carboxamide;

(rac)-6-cyano-1-methyl-4-[4-(5-methyl-1,3-benzoxazol-2-yl)piperidin-1-yl]-2-oxo-7-{[(oxolan-3-yl)methyl]amino}-1,2-dihydroquinoline-3-carboxamide;

6-cyano-1-methyl-4-[4-(5-methyl-1,3-benzoxazol-2-yl)piperidin-1-yl]-2-oxo-7-({[(3R)-oxolan-3-yl]methyl}amino)-1,2-dihydroquinoline-3-carboxamide;

6-cyano-1-methyl-4-[4-(5-methyl-1,3-benzoxazol-2-yl)piperidin-1-yl]-2-oxo-7-({[(3S)-oxolan-3-yl]methyl}amino)-1,2-dihydroquinoline-3-carboxamide;

6-chloro-7-methoxy-1-methyl-4-[4-(5-methyl-1,3-benzoxazol-2-yl)piperidin-1-yl]-2-oxo-1,2-dihydroquinoline-3-carbonitrile;

6-chloro-7-hydroxy-1-methyl-4-[4-(5-methyl-1,3-benzoxazol-2-yl)piperidin-1-yl]-2-oxo-1,2-dihydroquinoline-3-carbonitrile;

(rac)-6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carbonitrile;

(rac)-6-chloro-1-methyl-4-[4-(5-methyl-1,3-benzoxazol-2-yl)piperidin-1-yl]-2-oxo-7-[(oxolan-3-yl)oxy]-1,2-dihydroquinoline-3-carboxamide;

6-chloro-1-methyl-4-[4-(5-methyl-1,3-benzoxazol-2-yl)piperidin-1-yl]-2-oxo-7-{[(3R)-oxolan-3-yl]oxy}-1,2-dihydroquinoline-3-carboxamide;

6-chloro-1-methyl-4-[4-(5-methyl-1,3-benzoxazol-2-yl)piperidin-1-yl]-2-oxo-7-{[(3S)-oxolan-3-yl]oxy}-1,2-dihydroquinoline-3-carboxamide;

(rac)-6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carbonitrile;

(rac)-6-chloro-1-methyl-4-[4-(5-methyl-1,3-benzoxazol-2-yl)piperidin-1-yl]-2-oxo-7-[(oxolan-3-yl)methoxy]-1,2-dihydroquinoline-3-carboxamide;

6-chloro-1-methyl-4-[4-(5-methyl-1,3-benzoxazol-2-yl)piperidin-1-yl]-2-oxo-7-{[(3R)-oxolan-3-yl]methoxy}-1,2-dihydroquinoline-3-carboxamide;

6-chloro-1-methyl-4-[4-(5-methyl-1,3-benzoxazol-2-yl)piperidin-1-yl]-2-oxo-7-{[(3S)-oxolan-3-yl]methoxy}-1,2-dihydroquinoline-3-carboxamide;

(rac)-6-bromo-1-methyl-2-oxo-7-[(oxolan-3-yl)oxy]-4-{4-[2-(pyridin-3-yl)-2H-1,2,3-triazol-4-yl]piperidin-1-yl}-1,2-dihydroquinoline-3-carbonitrile;

(rac)-6-bromo-1-methyl-4-{4-[1-(2-methylphenyl)-1H-1,2,3-triazol-4-yl]piperidin-1-yl}-2-oxo-7-[(oxolan-3-yl)oxy]-1,2-dihydroquinoline-3-carbonitrile;

(rac)-1,6-dimethyl-4-{4-[1-(2-methylphenyl)-1H-1,2,3-triazol-4-yl]piperidin-1-yl}-2-oxo-7-[(oxolan-3-yl)oxy]-1,2-dihydroquinoline-3-carbonitrile;

7-bromo-1,6-dimethyl-4-{4-[1-(2-methylphenyl)-1H-pyrazol-4-yl]piperidin-1-yl}-2-oxo-1,2-dihydroquinoline-3-carbonitrile; and (rac)-1,6-dimethyl-4-{4-[1-(2-methylphenyl)-1H-pyrazol-4-yl]piperidin-1-yl}-2-oxo-7-[(oxolan-3-yl)oxy]-1,2-dihydroquinoline-3-carbonitrile, or a stereoisomer, a tautomer, an N-oxide, a hydrate, a solvate, or a salt thereof, or a mixture of any of the foregoing.

8. The compound of claim 1, wherein $R^1$ is selected from the group consisting of —C(═O)$NH_2$, —C(═O)N(H)$CH_3$, and —C(═O)N$(CH_3)_2$, or a stereoisomer, a tautomer, an N-oxide, a hydrate, a solvate, or a salt thereof, or a mixture of any of the foregoing.

9. A compound of formula (II):

(II)

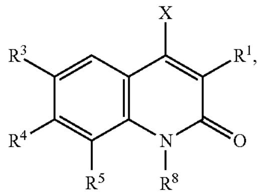

in which $R^1$ is selected from the group consisting of —C(═O)$NH_2$, —C(═O)N(H)$CH_3$, and —C(═O)N$(CH_3)_2$, $R^3$, $R^4$, $R^5$ and $R^8$ are as defined for the compound of formula (I) according to claim 1, and X is chloro or bromo.

10. A pharmaceutical composition comprising the compound of claim 1, or a pharmaceutically acceptable salt thereof, and one or more pharmaceutically acceptable excipients.

11. A pharmaceutical combination comprising:

one or more compounds of formula (I) according to claim 1, or a pharmaceutically acceptable salt thereof, and one or more further active ingredients.

12. The pharmaceutical combination of claim 11, wherein the one or more further active ingredients comprises an immune checkpoint inhibitor.

13. The pharmaceutical combination of claim 12, wherein the immune checkpoint inhibitor is a PD-1/L-1 axis antagonist.

14. The pharmaceutical combination of claim 12, wherein the immune checkpoint inhibitor is an inhibitor of DGK.

15. A method of preparing the compound of formula (I) according to claim 1, said method comprising reacting an intermediate compound of formula (II):

(II)

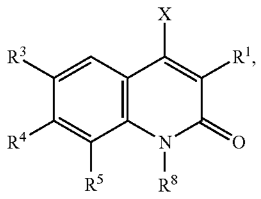

wherein $R^1$, $R^3$, $R^4$, $R^5$, and $R^8$ are as defined for the compound of formula (I), and X is chloro or bromo, with a compound of formula (III):

(III)

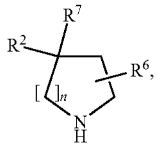

wherein $R^2$, $R^6$, $R^7$, and n are as defined for the compound of formula (I), to yield a compound of formula (I):

(I)

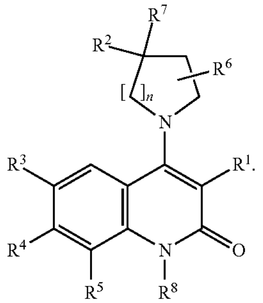

16. A method for treatment or prophylaxis of a disease, comprising administering a therapeutically effective amount of the compound of formula (I) according to claim 1, or a pharmaceutically acceptable salt thereof, to a mammal in need thereof.

17. The method of claim 16, wherein the disease is cancer, a condition with dysregulated immune response, or a disorder associated with aberrant DGKα signalling.

* * * * *

```
                              SEQUENCE LISTING

<160> NUMBER OF SEQ ID NOS: 5

<210> SEQ ID NO 1
<211> LENGTH: 743
<212> TYPE: PRT
<213> ORGANISM: Homo sapiens
<220> FEATURE:
<223> OTHER INFORMATION: human DGKa M1 to S735 plus C-terminal Flag-Tag

<400> SEQUENCE: 1

Met Ala Lys Glu Arg Gly Leu Ile Ser Pro Ser Asp Phe Ala Gln Leu
1               5                   10                  15

Gln Lys Tyr Met Glu Tyr Ser Thr Lys Lys Val Ser Asp Val Leu Lys
            20                  25                  30

Leu Phe Glu Asp Gly Glu Met Ala Lys Tyr Val Gln Gly Asp Ala Ile
        35                  40                  45

Gly Tyr Glu Gly Phe Gln Gln Phe Leu Lys Ile Tyr Leu Glu Val Asp
    50                  55                  60

Asn Val Pro Arg His Leu Ser Leu Ala Leu Phe Gln Ser Phe Glu Thr
65                  70                  75                  80

Gly His Cys Leu Asn Glu Thr Asn Val Thr Lys Asp Val Val Cys Leu
                85                  90                  95

Asn Asp Val Ser Cys Tyr Phe Ser Leu Leu Glu Gly Gly Arg Pro Glu
            100                 105                 110

Asp Lys Leu Glu Phe Thr Phe Lys Leu Tyr Asp Thr Asp Arg Asn Gly
        115                 120                 125

Ile Leu Asp Ser Ser Glu Val Asp Lys Ile Ile Leu Gln Met Met Arg
```

-continued

```
    130                 135                 140

Val Ala Glu Tyr Leu Asp Trp Asp Val Ser Glu Leu Arg Pro Ile Leu
145                 150                 155                 160

Gln Glu Met Met Lys Glu Ile Asp Tyr Asp Gly Ser Gly Ser Val Ser
                165                 170                 175

Gln Ala Glu Trp Val Arg Ala Gly Ala Thr Thr Val Pro Leu Leu Val
            180                 185                 190

Leu Leu Gly Leu Glu Met Thr Leu Lys Asp Asp Gly Gln His Met Trp
        195                 200                 205

Arg Pro Lys Arg Phe Pro Arg Pro Val Tyr Cys Asn Leu Cys Glu Ser
    210                 215                 220

Ser Ile Gly Leu Gly Lys Gln Gly Leu Ser Cys Asn Leu Cys Lys Tyr
225                 230                 235                 240

Thr Val His Asp Gln Cys Ala Met Lys Ala Leu Pro Cys Glu Val Ser
                245                 250                 255

Thr Tyr Ala Lys Ser Arg Lys Asp Ile Gly Val Gln Ser His Val Trp
            260                 265                 270

Val Arg Gly Gly Cys Glu Ser Gly Arg Cys Asp Arg Cys Gln Lys Lys
        275                 280                 285

Ile Arg Ile Tyr His Ser Leu Thr Gly Leu His Cys Val Trp Cys His
    290                 295                 300

Leu Glu Ile His Asp Asp Cys Leu Gln Ala Val Gly His Glu Cys Asp
305                 310                 315                 320

Cys Gly Leu Leu Arg Asp His Ile Leu Pro Pro Ser Ser Ile Tyr Pro
                325                 330                 335

Ser Val Leu Ala Ser Gly Pro Asp Arg Lys Asn Ser Lys Thr Ser Gln
            340                 345                 350

Lys Thr Met Asp Asp Leu Asn Leu Ser Thr Ser Glu Ala Leu Arg Ile
        355                 360                 365

Asp Pro Val Pro Asn Thr His Pro Leu Leu Val Phe Val Asn Pro Lys
    370                 375                 380

Ser Gly Gly Lys Gln Gly Gln Arg Val Leu Trp Lys Phe Gln Tyr Ile
385                 390                 395                 400

Leu Asn Pro Arg Gln Val Phe Asn Leu Leu Lys Asp Gly Pro Glu Ile
                405                 410                 415

Gly Leu Arg Leu Phe Lys Asp Val Pro Asp Ser Arg Ile Leu Val Cys
            420                 425                 430

Gly Gly Asp Gly Thr Val Gly Trp Ile Leu Glu Thr Ile Asp Lys Ala
        435                 440                 445

Asn Leu Pro Val Leu Pro Pro Val Ala Val Leu Pro Leu Gly Thr Gly
    450                 455                 460

Asn Asp Leu Ala Arg Cys Leu Arg Trp Gly Gly Gly Tyr Glu Gly Gln
465                 470                 475                 480

Asn Leu Ala Lys Ile Leu Lys Asp Leu Glu Met Ser Lys Val Val His
                485                 490                 495

Met Asp Arg Trp Ser Val Glu Val Ile Pro Gln Gln Thr Glu Glu Lys
            500                 505                 510

Ser Asp Pro Val Pro Phe Gln Ile Ile Asn Asn Tyr Phe Ser Ile Gly
        515                 520                 525

Val Asp Ala Ser Ile Ala His Arg Phe His Ile Met Arg Glu Lys Tyr
    530                 535                 540

Pro Glu Lys Phe Asn Ser Arg Met Lys Asn Lys Leu Trp Tyr Phe Glu
545                 550                 555                 560
```

```
Phe Ala Thr Ser Glu Ser Ile Phe Ser Thr Cys Lys Lys Leu Glu Glu
                565                 570                 575

Ser Leu Thr Val Glu Ile Cys Gly Lys Pro Leu Asp Leu Ser Asn Leu
            580                 585                 590

Ser Leu Glu Gly Ile Ala Val Leu Asn Ile Pro Ser Met His Gly Gly
        595                 600                 605

Ser Asn Leu Trp Gly Asp Thr Arg Arg Pro His Gly Asp Ile Tyr Gly
    610                 615                 620

Ile Asn Gln Ala Leu Gly Ala Thr Ala Lys Val Ile Thr Asp Pro Asp
625                 630                 635                 640

Ile Leu Lys Thr Cys Val Pro Asp Leu Ser Asp Lys Arg Leu Glu Val
                645                 650                 655

Val Gly Leu Glu Gly Ala Ile Glu Met Gly Gln Ile Tyr Thr Lys Leu
            660                 665                 670

Lys Asn Ala Gly Arg Arg Leu Ala Lys Cys Ser Glu Ile Thr Phe His
        675                 680                 685

Thr Thr Lys Thr Leu Pro Met Gln Ile Asp Gly Glu Pro Trp Met Gln
    690                 695                 700

Thr Pro Cys Thr Ile Lys Ile Thr His Lys Asn Gln Met Pro Met Leu
705                 710                 715                 720

Met Gly Pro Pro Pro Arg Ser Thr Asn Phe Phe Gly Phe Leu Ser Asp
                725                 730                 735

Tyr Lys Asp Asp Asp Asp Lys
            740


<210> SEQ ID NO 2
<211> LENGTH: 793
<212> TYPE: PRT
<213> ORGANISM: Homo sapiens
<220> FEATURE:
<223> OTHER INFORMATION: human DGKa M1 to S735 plus N-terminal Avi-Tag
      and C-terminal Flag-Tag, DGKa_hu_1Avi

<400> SEQUENCE: 2

Met Thr Ser His His His His His His Ser Ser Met Gly Ser Arg Gly
1               5                   10                  15

Ile Glu Gly Arg Gly Gly Leu Asn Asp Ile Phe Glu Ala Gln Lys Ile
            20                  25                  30

Glu Trp His Glu Gly Ser Arg Thr Ser Leu Tyr Lys Lys Ala Gly Ser
        35                  40                  45

Ala Thr Met Ala Lys Glu Arg Gly Leu Ile Ser Pro Ser Asp Phe Ala
    50                  55                  60

Gln Leu Gln Lys Tyr Met Glu Tyr Ser Thr Lys Lys Val Ser Asp Val
65                  70                  75                  80

Leu Lys Leu Phe Glu Asp Gly Glu Met Ala Lys Tyr Val Gln Gly Asp
                85                  90                  95

Ala Ile Gly Tyr Glu Gly Phe Gln Gln Phe Leu Lys Ile Tyr Leu Glu
            100                 105                 110

Val Asp Asn Val Pro Arg His Leu Ser Leu Ala Leu Phe Gln Ser Phe
        115                 120                 125

Glu Thr Gly His Cys Leu Asn Glu Thr Asn Val Thr Lys Asp Val Val
    130                 135                 140

Cys Leu Asn Asp Val Ser Cys Tyr Phe Ser Leu Leu Glu Gly Gly Arg
145                 150                 155                 160

Pro Glu Asp Lys Leu Glu Phe Thr Phe Lys Leu Tyr Asp Thr Asp Arg
```

-continued

```
                165                 170                 175

Asn Gly Ile Leu Asp Ser Ser Glu Val Asp Lys Ile Ile Leu Gln Met
            180                 185                 190

Met Arg Val Ala Glu Tyr Leu Asp Trp Asp Val Ser Glu Leu Arg Pro
        195                 200                 205

Ile Leu Gln Glu Met Met Lys Glu Ile Asp Tyr Asp Gly Ser Gly Ser
    210                 215                 220

Val Ser Gln Ala Glu Trp Val Arg Ala Gly Ala Thr Thr Val Pro Leu
225                 230                 235                 240

Leu Val Leu Leu Gly Leu Glu Met Thr Leu Lys Asp Asp Gly Gln His
                245                 250                 255

Met Trp Arg Pro Lys Arg Phe Pro Arg Pro Val Tyr Cys Asn Leu Cys
            260                 265                 270

Glu Ser Ser Ile Gly Leu Gly Lys Gln Gly Leu Ser Cys Asn Leu Cys
        275                 280                 285

Lys Tyr Thr Val His Asp Gln Cys Ala Met Lys Ala Leu Pro Cys Glu
    290                 295                 300

Val Ser Thr Tyr Ala Lys Ser Arg Lys Asp Ile Gly Val Gln Ser His
305                 310                 315                 320

Val Trp Val Arg Gly Gly Cys Glu Ser Gly Arg Cys Asp Arg Cys Gln
                325                 330                 335

Lys Lys Ile Arg Ile Tyr His Ser Leu Thr Gly Leu His Cys Val Trp
            340                 345                 350

Cys His Leu Glu Ile His Asp Asp Cys Leu Gln Ala Val Gly His Glu
        355                 360                 365

Cys Asp Cys Gly Leu Leu Arg Asp His Ile Leu Pro Pro Ser Ser Ile
    370                 375                 380

Tyr Pro Ser Val Leu Ala Ser Gly Pro Asp Arg Lys Asn Ser Lys Thr
385                 390                 395                 400

Ser Gln Lys Thr Met Asp Asp Leu Asn Leu Ser Thr Ser Glu Ala Leu
                405                 410                 415

Arg Ile Asp Pro Val Pro Asn Thr His Pro Leu Leu Val Phe Val Asn
            420                 425                 430

Pro Lys Ser Gly Gly Lys Gln Gly Gln Arg Val Leu Trp Lys Phe Gln
        435                 440                 445

Tyr Ile Leu Asn Pro Arg Gln Val Phe Asn Leu Leu Lys Asp Gly Pro
    450                 455                 460

Glu Ile Gly Leu Arg Leu Phe Lys Asp Val Pro Asp Ser Arg Ile Leu
465                 470                 475                 480

Val Cys Gly Gly Asp Gly Thr Val Gly Trp Ile Leu Glu Thr Ile Asp
                485                 490                 495

Lys Ala Asn Leu Pro Val Leu Pro Pro Val Ala Val Leu Pro Leu Gly
            500                 505                 510

Thr Gly Asn Asp Leu Ala Arg Cys Leu Arg Trp Gly Gly Gly Tyr Glu
        515                 520                 525

Gly Gln Asn Leu Ala Lys Ile Leu Lys Asp Leu Glu Met Ser Lys Val
    530                 535                 540

Val His Met Asp Arg Trp Ser Val Glu Val Ile Pro Gln Gln Thr Glu
545                 550                 555                 560

Glu Lys Ser Asp Pro Val Pro Phe Gln Ile Ile Asn Asn Tyr Phe Ser
                565                 570                 575

Ile Gly Val Asp Ala Ser Ile Ala His Arg Phe His Ile Met Arg Glu
            580                 585                 590
```

```
Lys Tyr Pro Glu Lys Phe Asn Ser Arg Met Lys Asn Lys Leu Trp Tyr
        595                 600                 605

Phe Glu Phe Ala Thr Ser Glu Ser Ile Phe Ser Thr Cys Lys Lys Leu
    610                 615                 620

Glu Glu Ser Leu Thr Val Glu Ile Cys Gly Lys Pro Leu Asp Leu Ser
625                 630                 635                 640

Asn Leu Ser Leu Glu Gly Ile Ala Val Leu Asn Ile Pro Ser Met His
                645                 650                 655

Gly Gly Ser Asn Leu Trp Gly Asp Thr Arg Arg Pro His Gly Asp Ile
            660                 665                 670

Tyr Gly Ile Asn Gln Ala Leu Gly Ala Thr Ala Lys Val Ile Thr Asp
        675                 680                 685

Pro Asp Ile Leu Lys Thr Cys Val Pro Asp Leu Ser Asp Lys Arg Leu
    690                 695                 700

Glu Val Val Gly Leu Glu Gly Ala Ile Glu Met Gly Gln Ile Tyr Thr
705                 710                 715                 720

Lys Leu Lys Asn Ala Gly Arg Arg Leu Ala Lys Cys Ser Glu Ile Thr
                725                 730                 735

Phe His Thr Thr Lys Thr Leu Pro Met Gln Ile Asp Gly Glu Pro Trp
            740                 745                 750

Met Gln Thr Pro Cys Thr Ile Lys Ile Thr His Lys Asn Gln Met Pro
        755                 760                 765

Met Leu Met Gly Pro Pro Pro Arg Ser Thr Asn Phe Phe Gly Phe Leu
    770                 775                 780

Ser Asp Tyr Lys Asp Asp Asp Asp Lys
785                 790


<210> SEQ ID NO 3
<211> LENGTH: 8
<212> TYPE: PRT
<213> ORGANISM: Homo sapiens
<220> FEATURE:
<223> OTHER INFORMATION: SIINFEKL amino acid sequence

<400> SEQUENCE: 3

Ser Ile Ile Asn Phe Glu Lys Leu
1               5


<210> SEQ ID NO 4
<211> LENGTH: 8
<212> TYPE: PRT
<213> ORGANISM: Homo sapiens
<220> FEATURE:
<223> OTHER INFORMATION: Flag-Tag sequence

<400> SEQUENCE: 4

Asp Tyr Lys Asp Asp Asp Asp Lys
1               5


<210> SEQ ID NO 5
<211> LENGTH: 30
<212> TYPE: PRT
<213> ORGANISM: Homo sapiens
<220> FEATURE:
<223> OTHER INFORMATION: OVA-30 peptide sequence
```

-continued

```
<400> SEQUENCE: 5

Ser Met Leu Val Leu Leu Pro Asp Glu Val Ser Gly Leu Glu Gln Leu
1               5                   10                  15

Glu Ser Ile Ile Asn Phe Glu Lys Leu Thr Glu Trp Thr Ser
            20                  25                  30
```